US011242525B2

(12) United States Patent
Friedland et al.

(10) Patent No.: US 11,242,525 B2
(45) Date of Patent: Feb. 8, 2022

(54) CRISPR/CAS-RELATED METHODS AND COMPOSITIONS FOR TREATING SICKLE CELL DISEASE

(71) Applicant: EDITAS MEDICINE, INC., Cambridge, MA (US)

(72) Inventors: Ari E. Friedland, Boston, MA (US); Morgan L. Maeder, Jamaica Plain, MA (US); G. Grant Welstead, Cambridge, MA (US); David A. Bumcrot, Belmont, MA (US)

(73) Assignee: EDITAS MEDICINE, INC., Cambridge, MA (US)

( * ) Notice: Subject to any disclaimer, the term of this patent is extended or adjusted under 35 U.S.C. 154(b) by 383 days.

(21) Appl. No.: 15/129,367

(22) PCT Filed: Mar. 26, 2015

(86) PCT No.: PCT/US2015/022856
§ 371 (c)(1),
(2) Date: Sep. 26, 2016

(87) PCT Pub. No.: WO2015/148863
PCT Pub. Date: Oct. 1, 2015

(65) Prior Publication Data
US 2017/0314015 A1 Nov. 2, 2017

Related U.S. Application Data

(60) Provisional application No. 61/970,588, filed on Mar. 26, 2014, provisional application No. 62/084,487, filed on Nov. 25, 2014.

(51) Int. Cl.
| | |
|---|---|
| *C12N 15/11* | (2006.01) |
| *C12N 9/22* | (2006.01) |
| *C12N 15/10* | (2006.01) |
| *A61K 48/00* | (2006.01) |
| *C12N 15/113* | (2010.01) |

(52) U.S. Cl.
CPC ............ *C12N 15/11* (2013.01); *A61K 48/005* (2013.01); *C12N 9/22* (2013.01); *C12N 15/1024* (2013.01); *C12N 15/113* (2013.01); *C12N 2310/10* (2013.01); *C12N 2310/20* (2017.05); *C12N 2320/34* (2013.01)

(58) Field of Classification Search
CPC ........ C12N 15/907; C12N 15/63; C12N 9/22; C12N 2310/20; A61K 48/00
See application file for complete search history.

(56) References Cited

U.S. PATENT DOCUMENTS

| | | | |
|---|---|---|---|
| 6,413,540 B1 | 7/2002 | Yaacobi | |
| 6,586,240 B1 | 7/2003 | Singer et al. | |
| 8,697,359 B1 * | 4/2014 | Zhang | C12N 15/63 435/6.1 |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,394 B2 | 11/2014 | Chalasani et al. | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 9,322,037 B2 | 4/2016 | Liu et al. | |
| 9,499,847 B2 | 11/2016 | Porter et al. | |
| 2003/0186238 A1 | 10/2003 | Allawi et al. | |
| 2007/0020627 A1 | 1/2007 | Barbas | |
| 2010/0055793 A1 | 3/2010 | Chandrasegaran et al. | |
| 2010/0055798 A1 | 3/2010 | Battersby | |
| 2010/0076057 A1 | 3/2010 | Sontheimer et al. | |
| 2011/0059502 A1 | 3/2011 | Chalasani | |
| 2011/0189776 A1 | 8/2011 | Terns et al. | |
| 2011/0223638 A1 | 9/2011 | Wiedenheft et al. | |
| 2011/0236894 A1 | 9/2011 | Rao et al. | |
| 2011/0301073 A1 | 12/2011 | Gregory et al. | |
| 2012/0270273 A1 | 10/2012 | Zhang et al. | |
| 2013/0130248 A1 | 5/2013 | Haurwitz et al. | |
| 2013/0253040 A1 | 9/2013 | Miller et al. | |
| 2014/0068797 A1 | 3/2014 | Doudna et al. | |
| 2014/0179770 A1 | 6/2014 | Zhang et al. | |
| 2014/0242699 A1 | 8/2014 | Zhang | |
| 2014/0309177 A1 | 10/2014 | Perez-Pinera et al. | |

(Continued)

FOREIGN PATENT DOCUMENTS

| | | | |
|---|---|---|---|
| WO | 2002/089767 A1 | 11/2002 | |
| WO | 2003/072788 A1 | 9/2003 | |

(Continued)

OTHER PUBLICATIONS

Bauer et al.; An Erythroid Enhancer of BCL11A Subject to Genetic Variation Determines Fetal Hemoglobin Level; Science; vol. 342, pp. 253-257, published Oct. 11, 2013 (Year: 2013).*
U.S. Appl. No. 61/652,086, filed May 25, 2012, Jinek et al.
U.S. Appl. No. 61/716,256, filed Oct. 19, 2012, Jinek et al.
U.S. Appl. No. 61/734,256, filed Dec. 6, 2012, Chen et al.
U.S. Appl. No. 61/736,527, filed Dec. 12, 2012, Zhang et al.
U.S. Appl. No. 61/738,355, filed Dec. 17, 2012, Church et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/779,169, filed Mar. 13, 2013, Mali et al.

(Continued)

Primary Examiner — Antonio Galisteo Gonzalez
(74) Attorney, Agent, or Firm — Perkins Coie LLP; Patrick D. Morris; Courtney Prochnow

(57) ABSTRACT

CRISPR/CAS-related compositions and methods for treatment of Sickle Cell Disease (SCD) are disclosed.

28 Claims, 45 Drawing Sheets

Specification includes a Sequence Listing.

(56) References Cited

U.S. PATENT DOCUMENTS

| | | |
|---|---|---|
| 2014/0315985 A1 | 10/2014 | May et al. |
| 2014/0335620 A1 | 11/2014 | Zhang et al. |
| 2014/0342456 A1 | 11/2014 | Mali et al. |
| 2014/0342457 A1 | 11/2014 | Mali et al. |
| 2014/0342458 A1 | 11/2014 | Mali et al. |
| 2014/0356958 A1 | 12/2014 | Mali et al. |
| 2015/0056705 A1* | 2/2015 | Conway ............ C12N 15/11 435/462 |
| 2015/0232833 A1 | 8/2015 | Mali et al. |
| 2015/0259704 A1 | 9/2015 | Church et al. |
| 2016/0281111 A1 | 9/2016 | Cotta-Ramusino et al. |
| 2016/0324987 A1 | 11/2016 | Wang et al. |
| 2016/0340661 A1* | 11/2016 | Cong ................ A61P 27/02 |
| 2017/0058298 A1 | 3/2017 | Kennedy et al. |
| 2018/0291370 A1 | 10/2018 | Gersbach et al. |

FOREIGN PATENT DOCUMENTS

| | | |
|---|---|---|
| WO | 2008/108989 A2 | 9/2008 |
| WO | 2010/054108 A9 | 5/2010 |
| WO | 2011/143124 A2 | 11/2011 |
| WO | 2011/146121 A1 | 11/2011 |
| WO | 2012/145601 A2 | 10/2012 |
| WO | 2012/164565 A8 | 12/2012 |
| WO | 2013/012674 A1 | 1/2013 |
| WO | 2013/066438 A2 | 5/2013 |
| WO | 2013/082519 A2 | 6/2013 |
| WO | 2013/098244 A1 | 7/2013 |
| WO | 2013/126794 A1 | 8/2013 |
| WO | 2013/141680 A1 | 9/2013 |
| WO | 2013/142578 A1 | 9/2013 |
| WO | 2013/163628 A2 | 10/2013 |
| WO | 2013/176772 A1 | 11/2013 |
| WO | 2013/181228 A1 | 12/2013 |
| WO | 2014/018423 A8 | 1/2014 |
| WO | 2014/022702 A2 | 2/2014 |
| WO | 2014/036219 A2 | 3/2014 |
| WO | 2014/059255 A1 | 4/2014 |
| WO | 2014/065596 A1 | 5/2014 |
| WO | 2014/089290 A1 | 6/2014 |
| WO | 2014/093479 A1 | 6/2014 |
| WO | 2014/093595 A1 | 6/2014 |
| WO | 2014/093622 A8 | 6/2014 |
| WO | 2014/093635 A9 | 6/2014 |
| WO | 2014/093655 A2 | 6/2014 |
| WO | 2014/093661 A2 | 6/2014 |
| WO | 2014/093694 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/099744 A1 | 6/2014 |
| WO | 2014/099750 A2 | 8/2014 |
| WO | 2014/124284 A1 | 8/2014 |
| WO | 2014/144288 A1 | 9/2014 |
| WO | 2014/144592 A2 | 9/2014 |
| WO | 2014/144761 A2 | 9/2014 |
| WO | 2014/152432 A2 | 9/2014 |
| WO | 2014/186585 A2 | 11/2014 |
| WO | 2014/197568 A2 | 12/2014 |
| WO | 2014/197748 A2 | 12/2014 |
| WO | 2014/204578 A1 | 12/2014 |
| WO | 2014/204725 A8 | 12/2014 |
| WO | 2015/006290 A1 | 1/2015 |
| WO | 2015/006294 A2 | 1/2015 |
| WO | 2015/006498 A2 | 1/2015 |
| WO | 2015/013583 A8 | 1/2015 |
| WO | 2015/021353 A1 | 2/2015 |
| WO | 2015/027134 A1 | 2/2015 |
| WO | 2015/035136 A8 | 3/2015 |
| WO | 2015/035139 A2 | 3/2015 |
| WO | 2015/035162 A2 | 3/2015 |
| WO | 2015/048577 A2 | 4/2015 |
| WO | 2015/048680 A1 | 4/2015 |
| WO | 2015/070083 A1 | 5/2015 |
| WO | 2015/071474 A9 | 5/2015 |
| WO | 2015/077290 A2 | 5/2015 |
| WO | 2015/077318 A1 | 5/2015 |
| WO | 2015/089406 A1 | 6/2015 |
| WO | 2015/089462 A1 | 6/2015 |
| WO | 2015/099850 A1 | 7/2015 |
| WO | 2015/138510 A8 | 9/2015 |
| WO | 2015/148860 | 10/2015 |
| WO | 2015/148863 A2 | 10/2015 |
| WO | 2015/188056 A1 | 12/2015 |
| WO | 2015/195621 A1 | 12/2015 |
| WO | 2016/011080 A2 | 1/2016 |
| WO | 2016/022363 A9 | 2/2016 |
| WO | 2016/073990 A2 | 5/2016 |
| WO | 2016/135557 A2 | 9/2016 |
| WO | 2016/135558 A2 | 9/2016 |
| WO | 2016/182959 A1 | 11/2016 |
| WO | 2016/186772 A2 | 11/2016 |
| WO | 2016/205749 A1 | 12/2016 |
| WO | 2017/035416 A2 | 3/2017 |
| WO | 2017/077394 A2 | 5/2017 |
| WO | 2017/060890 A1 | 9/2017 |
| WO | 2017/184768 | 10/2017 |
| WO | 2017/191503 A1 | 11/2017 |
| WO | 2018/009562 A1 | 1/2018 |
| WO | 2018/017754 A1 | 1/2018 |
| WO | 2018/026976 A1 | 2/2018 |
| WO | 2018/126176 A1 | 7/2018 |
| WO | 2018/142364 A1 | 8/2018 |
| WO | 2018/170184 A1 | 9/2018 |
| WO | 2018/209158 A2 | 11/2018 |
| WO | 2019/178416 A1 | 9/2019 |
| WO | 2019/178426 A1 | 9/2019 |

OTHER PUBLICATIONS

Ahern, E.J., et al., "The Prevalence of the Rarer Inherited Haemoglobin Defects in Adult Jamaicans," Br. J. Haematol. 25(4):437-444 (1973).

Akinbami, A.O., et al., "Hereditary Persistence of Fetal Hemoglobin Caused by Single Nucleotide Promoter Mutations in Sickle Cell Trait and Hb SC Disease," Hemoglobin 40(1):64-65 (2016).

Al-Attar, S., et al., "Clustered Regularly Interspaced Short Palindromic Repeats (CRISPRs) The Hallmark of an Ingenious Antiviral Defense Mechanism in Prokaryotes," Biol. Chem. 392:277-289 (2011).

Aliyu, Z.Y., et al., "Sickle Cell Disease and Pulmonary Hypertension in Africa: A Global Perspective and Review of Epidemiology, Pathophysiology, and Management," Am. J. Hematol. 83(1):63-70 (2008).

Altschul, S. F., et al., "Gapped BLAST and PSI-BLAST: A New Generation of Protein Database Search Programs," Nucleic Acids Res. 25(17):3389-3402 (1997).

Altschul, S. F et al., "Basic Local Alignment Search Tool," J. Mol. Biol. 215(3):403-410 (1990).

Anders, C., et al., "Structural Basis of PAM-Dependent Target DNA Recognition by the Cas9 Endonuclease," Nature 513(7519):569-573 (2014).

Andreas, S., et al., "Enhanced Efficiency Through Nuclear Localization Signal Fusion on Phage PhiC31-Integrase: Activity Comparison with Cre and FLPe Recombinase in Mammalian Cells," Nucleic Acids Res. 30(11):2299-2306 (2002).

Angastiniotis, M., et al., "Global Epidemiology of Hemoglobin Disorders," Ann. N.Y. Acad. Sci. 850:251-269 (1998).

Anonymous, Third Party Observation for EP13818570.7, Oct. 1, 2014, 15 pages.

Anonymous, Third Party Observation for EP13824232.6, Sep. 8, 2014, 48 pages.

Anonymous, Third Party Observation for EP13824232.6, Sep. 22, 2014, 19 pages.

Anonymous, Third Party Observation for EP13824232.6, Oct. 22, 2014, 7 pages.

Bae, S., et al., "Cas-OFFinder: A Fast and Versatile Algorithm that Searches for Potential Off-Target Sites of Cas9 RNA-Guided Endonucleases," Bioinformatics 30(10):1473-1475 (2014).

Baker, M., "Gene Editing at CRISPR Speed," Nat. Biotechnol. 32(4):309-312 (2014).

(56) References Cited

OTHER PUBLICATIONS

Barbosa, C.G., et al., "Promoter Region Sequence Differences in the A and G Gamma Globin Genes of Brazilian Sickle Cell Anemia Patients," Braz. J. Med. Biol. Res. 43(8):705-711 (2010).
Barker, C. S., et al., "Increased DNA Microarray Hybridization Specificity Using sscDNA Targets," BMC Genomics 6:57 (2005).
Baron-Benhamou, J., et al., "Using the LambdaN Peptide to Tether Proteins to RNAs," Methods Mol. Biol. 257:135-153 (2004).
Barrangou, R., "RNA-Mediated Programmable DNA Cleavage," Nat. Biotechnol. 30(9):836-838 (2012).
Barretina, J., et al., "The Cancer Cell Line Encyclopedia Enables Predictive Modeling of Anticancer Drug Sensitivity," Nature 483(7391):603-607 (2012).
Bassett, A. R., et al., "CRISPR/Cas9 and Genome Editing in Drosophila," J. Genet. Genom. 41:7-19(2014).
Bauer, D. E., et al., "Blood Journal: Fine-Mapping and Genome Editing Reveal an Essential Erythroid Enhancer at the HbF-Associated BCL11A Locus," Blood 122(21):437 (2013).
Bauer, D. E., et al., "An Erythroid Enhancer of BCL11A Subject to Genetic Variation Determines Fetal Hemoglobin Level," Science 342(6155):253-257 (2013).
Beerli, R. R., et al., "Toward Controlling Gene Expresion at Will: Specific Regulation of the erbB-2/HER-2 Promoter by Using Polydactyl Zinc Finger Proteins Constructed from Modular Building Blocks," Proc. Natl. Acad. Sci. 95:14628-14633 (1998).
Bhaya, D., et al., "CRISPR-Cas Systems in Bacteria and Archaea: Versatile Small RNAs for Adaptive Defense and Regulation," Annu. Rev. Genet. 45:273-297 (2011).
Bikard, D., et al., "Programmable Repression and Activation of Bacterial Gene Expression Using an Engineered CRISPR-Cas System," Nucl. Acids Res. 41(15):7429-7437 (2013).
Bitinaite, J., et al., "FokI Dimerization is Required for DNA Cleavage," Proc. Natl. Acad. Sci. 95:10570-10575 (1998).
Boch, J., et al., "Breaking the Code of DNA Binding Specificity of TAL-Type III Effectors," Science 326(5959):1509-1512 (2009).
Boch, J., et al., "Xanthomonas AvrBs3 Family-Type III Effectors: Discovery and Function," Annu. Rev. Phytopathol. 48:419-436 (2010).
Bouva, M. J., et al., "Known and New Delta Globin Gene Mutations and Their Diagnostic Significance," Haematologica 91(1):129-132 (2006).
Briner, A.E., et al., "Guide RNA Functional Modules Direct Cas9 Activity and Orthogonality," Mol. Cell 56(2):333-339 (2014).
Broad Institute, Communication Forwarding Declaration of Feng Zhang for U.S. Appl. No. 14/256,912, filed Nov. 24, 2014, 5 pages.
Broad Institute, Information Disclosure Statement submitted for U.S. Appl. No. 14/256,912, citing Electronic Mail from T. Kowalski to Examiner N. Leith which references Briner et al., Nov. 3, 2014, 8 pages.
Broad Institute, Request for Oral Examination for EP13818570.7, Oct. 27, 2014, 3 pages.
Broad Institute, Response to EP Examination Report for EP13824232.6, dated Dec. 31, 2014, 44 pages.
Broad Institute, Response to Third Party Observations and Request for Oral Hearing for EP13824232.6, Oct. 27, 2014, 9 pages.
Broad Institute, Response to Third Party Observations, with redlined and clean amended claims, for EP13818570.7, Oct. 16, 2014, 30 pages.
Broad Institute, Response to Third Party Observations, with redlined and clean amended claims, for EP13824232.6, Oct. 2, 2014, 16 pages.
Brousseau, D.C., et al., "The Number of People with Sickle-Cell Disease in the United States: National and State Estimates," Am. J. Hematol. 85(1):77-78 (2010).
Brummelkamp, T. R., et al., "A System for Stable Expression of Short Interfering RNAs in Mammalian Cells," Science 296(5567):550-553 (2002).
Caldecott, K.W., "Single-Strand Break Repair and Genetic Disease," Nat. Rev. Genet. 9(8):619-631 (2008).

Canver, M. C., "Evaluation of the Clinical Success of Ex Vivo and In Vivo Gene Therapy," Journal of Young Investitgators, http://www.hyi.org/issue/evaluation-of-the-clinical-success-of-ex-vivo-and-in-vivo-gene-therapy/, 9 pages (2009).
Carroll, D., "A CRISPR Approach to Gene Targeting," Mol. Ther. 20(9):1658-1660 (2012).
Cathomen, T., et al., "Zinc-Finger Nucleases: The Next Generation Emerges," Mol. Ther. 16:1200-1207 (2008).
Cermak, T., et al., "Efficient Design and Assembly of Custom TALEN and Other TAL Effector-Based Constructs for DNA Targeting," Nucl. Acids Res. 39(12):e82 (2011).
Chassanidis, C., et al., "The Hellenic Type of Nondeletional Hereditary Persistence of Fetal Hemoglobin Results from a Novel Mutation (g.-109G>T) in the HBG2 Gene Promoter," Ann. Hematol. 88(6):549-555 (2009).
Chen, X., et al., "Fusion Protein Linkers: Property, Design and Functionality," Adv. Drug Deliv. Rev. 65(10):1357-1369 (2013).
Cho, S. W., et al., Supplementary Information: Targeted Genome Engineering in Human Cells With the Cas9 RNA-Guided Endonuclease, Nature Biotechnology (Mar. 2013) vol. 31, No. 3, 11 pages.
Cho, S. W., et al., "Targeted Genome Engineering in Human Cells with the Cas9 RNA-Guided Endonuclease," Nat. Biotechnol. 31(3):230-232 (2013).
Christian, M., et al., "Targeting DNA Double-Strand Breaks With TAL Effector Nucleases," Genetics 186:757-761 (2010).
Christian, M., et al., "Targeting DNA Double-Strand Breaks With TAL Effector Nucleases," Genetics Supporting Information, 1SI-8SI (2010).
Chylinski, K., et al., "The TrackRNA and Cas9 Families of Type II CRISPR-Cas Immunity Systems," RNA Biol. 10(5):726-737 (2013).
Cong, L., et al., "Multiplex Genome Engineering Using CRISPR/Cas Systems," Science 339(6121):819-823 (2013).
Cong, L., et al., "Supplementary Material: Multiplex Genome Engineering Using CRISPR-Cas Systems," Science Express (Jul. 5, 2012).
Cong, L., et al., "Supplementary Material: Multiplex Genome Engineering Using CRISPR-Cas Systems," Science Express (Jan. 3, 2013).
Cornish-Bowden, A., "Nomenclature for Incompletely Specified Bases in Nucleic Acid Sequences: Recommendations 1984," Nucleic Acids Res. 13(9):3021-3030 (1985).
Cradick, T. J., et al., "CRISPR/Cas9 Systems Targeting Beta-Globin and CCR5 Genes Have Substantial Off-Target Activity," Nucleic Acids Res. 41(20):9584-9592 (2013).
Datsenko, K. A., et al., "Molecular Memory of Prior Infections Activates the CRISPR/Cas Adaptive Bacterial Immunity System," Nat. Commun. 3:945 (2012).
Davis, L., et al., "Homology-Directed Repair of DNA Nicks Via Pathways Distinct from Canonical Double-Strand Break Repair," PNAS 111(10):E924-932 (2014).
Deltcheva, E., et al., CRISPR RNA Maturation by Trans-Encoded Small RNA and Host Factor RNase III, Nature 471:602-607 (2011).
Deltcheva, E., et al., Supplementary Figures: CRISPR RNA Maturation by Trans-Encoded Small RNA and Host Factor RNase III. Downloaded from www.nature.com/nature, p. 1-35, 2011.
Deveau, H., et al., "Phage Response to CRISPR-Encoded Resistance in Streptococcus thermophilus," J. Bacteriol. 190(4):1390-1400 (2008).
Dicarlo, J. E., et al., "Genome Engineering in Saccharomyces cerevisiae Using CRISPR-Cas Systems," Nucl. Acids Res. 41(7):4336-43 (2013).
Dingwall, C., et al., "A Polypeptide Domain That Specifies Migration of Nucleoplasmin Into the Nucleus," Cell 30:449-458 (1982).
Dreszer, T. R., et al., "The UCSC Genome Browser Database: Extensions and Updates 2011," Nucl. Acids Res. 40:D918-D923 (2012).
Esvelt, K.M., et al., "A System for the Continuous Directed Evolution of Biomolecules," Nature 472(7344):499-503 (2011).
Esvelt, K. M., et al., "Orthogonal Cas9 Proteins for RNA-Guided Gene Regulation and Editing," Nat. Methods 10(11):1116-1121 (2013).

(56) References Cited

OTHER PUBLICATIONS

Fine, E.J., et al., "Trans-Spliced Cas9 Allows Cleavage of HBB and CCR5 Genes in Human Cells Using Compact Expression Cassettes," Sci. Rep. 5:10777 (2015).
Fonfara, I., et al., "Phylogeny of Cas9 Determines Functional Exchangeability of Dual-RNA and Cas9 Among Orthologous Type II CRISPR-Cas Systems," Nucl. Acids Res.42(4):2577-2590 (2014).
Friedland, A.E., et al., "Characterization of *Staphylococcus aureus* Cas9: A Smaller Cas9 for All-in-One Adeno-Associated Virus Delivery and Paired Nickase Applications," Genome Biol. 16:257 (2015).
Frit, P., et al., "Alternative End-Joining Pathway(s): Bricolage at DNA Breaks," DNA Repair (Amst) 17:81-97 (2014).
Fu, Y., et al., "High-Frequency Off-Target Mutagenesis Induced by CRISPR-Cas Nucleases in Human Cells," Nat. Biotechnol. 31:822-826 (2013).
Fu, Y., et al., "Improving CRISPR-Cas Nuclease Specificity Using Truncated Guide RNAs," Nat. Biotechnol. 32(3):279-284 (2014).
Gabriel, R., et al., "An Unbiased Genome-Wide Analysis of Zinc-Finger Nuclease Specificity," Nat. Biotechnol. 29:816-823 (2011).
Garneau, J. E., et al., "The CRISPR-Cas Bacterial Immune Systems Cleaves Bacteriophage and Plasmid DNA," Nature 468:67-71 (2010).
Gasiunas, G., et al., "Cas9-crRNA Ribonucleoprotein Complex Mediates Specific DNA Cleavage for Adaptive Immunity in Bacteria," Proc. Natl. Acad. Sci. 109(39):E2579-E2586 (2012).
Gilbert, L. A., et al., "CRISPR-Mediated Modular RNA-Guided Regulation of Transcription in Eukaryotes," Cell 154(2):442-451 (2013).
Goldfarb, D. S., et al., "Synthetic Peptides as Nuclear Localization Signals," Nature 322:641-644 (1986).
Gratz, S. J., et al., "Genome Engineering of *Drosophila* with the CRISPR RNA-Guided Cas9 Nuclease," Genetics 194(4):1029-1035 (2013).
Grieger, J. C., et al., "Production and Characterization of Adeno-Associated Viral Vectors," Nat. Protoc. 1(3):1412-1428 (2006).
Guilinger, J. P., et al., "Fusion of Catalytically Inactive Cas9 to FokI Nuclease Improves the Specificity of Genome Modification," Nat Biotechnol. 32(6):577-583 (2014).
Guo, X., et al., "RNA-Dependent Folding and Stabilization of C5 Protein During Assembly of the *E. coli* Rnase P Holoenzyme," J. Mol. Biol. 360:190-203 (2006).
Gustafsson, C., et al., "Codon Bias and Heterologous Protein Expression," Trends Biotechnol. 22(7):346-353 (2004).
Haft, D. H., et al., "A Guild of 45 CRISPR-Associated (Cas) Protein Families and Multiple CRISPR/Cas Subtypes Exist in Prokaryotic Genomes," PLoS Comput. Biol. 1(6):e60 (2005).
Hale, C. R., et al., "Essential Features and Rational Design of CRISPR RNAs That Function With the Cas RAMP Module Complex to Cleave RNAs," Mol. Cell 45(3):292-302 (2012).
Hatoum-Aslan, A., et al. "Mature Clustered Regularly Interspaced, Short Palindromic Repeats RNA 5,9,14 (crRNA) Length is Measured by a Ruler Mechanism Anchored at the Precursor Processing Site," Proc. Natl. Acad. Sci. 108(52):21218-21222 (2011).
Heigwer, F., et al., "E-CRISP: Fast CRISPR Target Site Identification," Nat. Methods 11(2):122-123 (2014).
Hockemeyer, D., et al., "Efficient Targeting of Expressed and Silent Genes in Human ESCs and iPSCs Using Zinc-Finger Nucleases," Nat. Biotechnol. 27(9):851-857 (2009).
Hockemeyer, D., et al., "Genetic Engineering of Human luripotent Cells Using TALE Nucleases," Nat. Biotechnol. 29:731-734 (2011).
Holt, N, et al., "Zinc Finger Nuclease-Mediated CCR5 Konockout Hematopoietic Stem Cell Transplantation Controls HIV-1 In Vivo," Nat. Biotechnol. 28(8):839-847 (2010).
Horvath, P., et al., "CRISPR/Cas, The Immune System of Bacteria and Archaea," Science 327(5962):167-170 (2010).
Horvath, P., et al., "RNA-Guided Genome Editing A La Carte," Cell Res. 23:733-734 (2013).
Hou, Z., et al., "Efficient Genome Engineering in Human Pluripotent Stem Cells Using Cas9 from Neisseria Meningitidis," Proc. Natl. Acad. Sci. U.S.A. 110(39):15644-15649 (2013).

Hsu, P.D., et al., "DNA Targeting Specificity of RNA-Guided Cas9 Nucleases," Nat. Biotechnol. 31(9): 827-832 (2013).
Hwang, W. Y., et al., "Heritable and Precise Zebrafish Genome Editing Using a CRISPR-Cas System," PLoS One 8(7):e68708 (2013).
Hwang, W. Y., et al., "Efficient Genome Editing in Zebrafish Using a CRISPR-Cas System," Nat. Biotechnol. 31(3):227-229 (2013).
Iyama, T., et al., "DNA Repair Mechanisms in Dividing and Non-Dividing Cells," DNA Repair (Amst.) 12(8):620-636 (2013).
Iyer, L. M., et al., "Prediction of Novel Families of Enzymes Involved in Oxidative and Other Complex Modifications of Bases in Nucleic Acids," Cell Cycle 8(11):1698-1710 (2009).
Jiang, W., et al., "RNA-Guided Editing of Bacterial Genomes Using CRISPR-Cas Systems," Nat. Biotechnol. 31(3):233-239 (2013).
Jinek, M., et al., "A Programmable Dual-RNA-Guided DNA Endonuclease in Adaptive Bacterial Immunity," Science 337(6096):816-821 (2012).
Jinek, M., et al., "Structures of Cas9 Endonucleases Reveal RNA-Mediated Conformational Activation," Science 343(6176):1247997 (2014).
Jinek, M., et al., "RNA-Programmed Genome Editing in Human Cells," eLife 2:e00471 (2013).
Kaiser, J., "The Gene Editor CRISPR Won't Fully Fix Sick People Anytime Soon. Here's Why," (May 3, 2016), Biol., Technol, CRISPR, DOI: 10.1126/science.aaf5689, 5 pages.
Karolchik, D., et al., "The UCSC Table Browser Data Retrieval Tool," Nucleic Acids Research 32:D493-496 (2004).
Kent, W. J., et al., "The Human Genome Browserat UCSC," Genome Research 12:996-1006 (2002).
Keryer-Bibens, C., et al., "Tethering of Proteins to RNAs by Bacteriophage Proteins," Biol. Cell, 100:125-138 (2008).
Khalil, A. S., et al., "Synthetic Biology: Applications Come of Age," Nat. Rev. Genet. 11(5):367-379 (2010).
Kim, Y.G., et al., "Hybrid Restriction Enzymes: Zinc Finger Fusions to Fok I Cleavage Domain," Proc. Natl. Acad. Sci. USA 93:1156-1160 (1996).
King, N. M.P., et al., "En Route to Ethical Recommendations for Gene Transfer Clinical Trials," Mol. Ther. 16(3):432-438 (2008).
Kleinstiver, B.P., et al., "Broadening the Targeting Range of *Staphylococcus aureus* CRISPR-Cas9 by Modifying PAM Recognition," Nat. Biotechnol. 33(12):1293-1298 (2015).
Kleinstiver, B.P., et al., "Engineered CRISPR-Cas9 Nucleases with Altered PAM Specificities," Nature 523(7561):481-485 (2015).
Kleinstiver, B.P., et al., "High-Fidelity CRISPR-Cas9 Nucleases with No Detectable Genome-Wide Off-Target Effects," Nature 529(7587):490-495 (2016).
Komor, A.C., et al., "Programmable Editing of a Target Base in Genomic DNA Without Double-Stranded DNA Cleavage," Nature 533(7603):420-424 (2016).
Kosuri, S., et al., "A Scalable Gene Synthesis Platform Using High-Fidelity DNA Microchips," Nat. Biotechnol. 28(12):1295-1299 (2010).
Lambowitz, A. M., et al., "Group II Introns: Mobile Ribozymes that Invade DNA," Cold Spring Harb. Perspect. Biol. 3:a003616 (2011).
Langmead, B., et al., "Ultrafast and Memory-Efficient Alignment of Short DNA Sequences to the Human Genome," Genome Biology 10(3):R25 (2009).
Lee, J.H., et al., "A Robust Approach to Identifying Tissue-Specific Gene Expression Regulatory Variants Using Personalized Human Induced Pluripotent Stem Cells," PLoS Genetics 5(11):e1000718 (2009).
Lee, J., et al., "Non-Endocytic Delivery of Functional Engineered Nanoparticles into the Cytoplasm of Live Cells Using a Novel, High-Throughput Microfluidic Device," Nano Lett. 12(12):6322-6327 (2012).
Li, G.M., "Mechanisms and Functions of DNA Mismatch Repair," Cell Res. 18(1):85-98 (2008).
Li, T., et al., "TAL Nucleases (TALNs): Hybrid Proteins Composed of TAL Effectors and Fokl DNA-Cleavage Domain," Nucl. Acids Res.39(1): 359-372 (2011).
Li, H., et al., "In Vivo Genome Editing Restores Hemostasis in a Mouse Model of Hemophilia," Nature 475(7355):217-221 (2011).

(56) References Cited

OTHER PUBLICATIONS

Li, T., et al., "Modularly Assembled Designer TAL Effector Nucleases for Targeted Gene Knockout and Gene Replacement in Eukaryotes," Nucl. Acids Res. 39(14):6315-6325 (2011).
Lombardo, A., et al., "Gene Editing in Human Stem Cells Using Xinc Finger Nucleases and Integrase-Defective Lentiviral Vector Delivery," Nat. Biotechnol. 25(11):1298-1306 (2007).
Lorenz, R., et al., "ViennaRNA Package 2.0," Algorithms for Molecular Biology 6:26 (2011).
Maeder, M. L., et al., "CRISPR RNA-Guided Activation of Endogenous Human Genes," Nat. Methods 10:977-979 (2013).
Maeder, M. L., et al., "Rapid "Open-Source" Engineering of Customized Zinc-Finger Nucleases for Highly Efficient Gene Modification," Mol. Cell 31(2):294-301 (2008).
Makarova, K. S., et al., "A Putative RNA-lnterference-Based Immune System in Prokaryotes Computational Analysis of the Predicted Enzymatic Machinery, Functional Analogies with Eukaryotic RNAi, and Hypothetical Mechanisms of Action," Biol. Direct. 1:7 (2006).
Makarova, K. S., et al., "Unification of Cas Protein Families and a Simple Scenario for the Origin and Evolution of CRISPR-Cas Systems," Biol. Direct 6:38 (2011).
Makarova, K.S., et al., "Evolution and Classification of the CRISPR-Cas Systems," Nat. Rev. Microbiol. 9(6):467-477 (2011).
Mali, P., et al., "CAS9 Transcriptional Activators for Target Specificity Screening and Paired Nickases for Cooperative Genome Engineering," Nat. Biotechnol. 31:833-838 (2013).
Mali, P., et al., "Cas9 as a Versatile Tool for Engineering Biology," Nat. Methods 10(10):957-963 (2013).
Mali, P., et al., "RNA-Guided Human Genome Engineering Via Cas9," Science 339(6121):823-826 (2013).
Mantovani, R., et al., "The Effects of HPFH Mutations in the Human Gamma-Globin Promoter on Binding of Ubiquitous and Erythroid Specific Nuclear Factors," Nucleic Acids Res. 16(16):7783-7797 (1988).
Marteijn, J.A., et al., "Understanding Nucleotide Excision Repair and Its Role in Cancer and Ageing," Nat. Rev. Mol. Cell Biol. 15(7):465-481 (2014).
Mathews, D. H., et al., "Expanded Sequence Dependence of Thermodynamic Parameters Improves Prediction of RNA Secondary Structure," J. Mol. Biol. 288:911-940 (1999).
Miller, J. C., et al., "An Improved Zinc-Finger Nuclease Architecture for Highly Specific Genome Editing," Nat. Biotechnol. 25:778-785 (2007).
Miller, J. C., et al., "A TALE Nuclease Architecture for Efficient Genome Editing," Nat. Biotechnol. 29(2):143-150 (2011).
Miyagishim M., et al., "U6 Promoter-Driven siRNAs with Four Uridine 3' Overhangs Efficiently Suppress Targeted Gene Expression in Mammalian Cells," Nat. Biotechnol. 20(5):497-500 (2002).
Moscou, M. J., et al., "A Simple Cipher Governs DNA Recognition by TAL Effectors," Science 326(5959):1501 (2009).
Myers, E. W., et al., "Optimal Alignments in Linear Space," Comput. Appl. Biosci. 4(1):11-17 (1988).
Nakamura, Y., et al., "Codon Usage Tabulated From International DNA Sequence Databases: Status for the Year 2000," Nucl. Acids Res. 28(1):292 (2000).
Needleman, S. B., et al., "A General Method Applicable to the Search for Similarities in the Amino Acid Sequence of Two Proteins," J. Mol. Biol. 48(3):443-453 (1970).
Nishimasu, H., et al., "Crystal Structure of Cas9 in Complex with Guide RNA and Target DNA," Cell 156(5):935-949 (2014).
Nishimasu, H., et al., "Crystal Structure of *Staphylococcus aureus* Cas9," Cell 162:1113-1126 (2015).
Pattanayak, V., et al., "High-Throughput Profiling of Off-Target DNA Cleavage Reveals RNA-Programmed Cas9 Nuclease Specificity," Nat. Biotechnol. 31:839-843 (2013).
Pattanayak, V., et al., "Revealing Off-Target Cleavage Specificities of Zinc-Finger Nucleases by In Vitro Selection," Nat. Methods 8:765-770 (2011).
Patterson, S. S., et al., "Codon Optimization of Bacterial Luciferase (lux) for Expression in Mammalian Cells," J. Ind. Microbio. Biotechnology 32:115-123 (2005).
Pearson, W. R., et al., "Improved Tools for Biological Sequence Comparison," Proc. Natl. Acad. Sci. U.S.A. 85(8):2444-2448 (1988).
Perez, E. E., et al., "Establishment of HIV-1 Resistance in CD4+ T Cells by Genome Editing Using Zinc-Finger Nucleases," Nat. Biotechnol. 26:808-816 (2008).
Porteus, M. H., et al., "Gene Targeting Using Zinc Finger Nucleases," Nat. Biotechnol. 23(8):967-973 (2005).
Pougach, K., et al., "Transcription, Processing and Function of CRISPR Cassettes in *Escherichia coli*," Mol. Microbiol. 77(6):1367-1379 (2010).
Pride, D. T., et al., "Analysis of *Streptococcal* CRISPRs from Human Saliva Reveals Substantial Sequence Diversity Within and Between Subjects Over Time," Genome Res. 21:126-136 (2011).
Purnick, P. E. M., et al., "The Second Wave of Synthetic Biology: From Modules to Systems," Nat. Rev. Mol. Cell Biol. 10(6):410-422 (2009).
Qi, L. S., et al., "Repurposing CRISPR as an RNA-Guided Platform for Sequence-Specific Control of Gene Expression," Cell 152:1173-1183 (2013).
Qi, L., et al., "RNA Processing Enables Predictable Programming of Gene Expression," Nat. Biotechnol. 30(10):1002-1007 (2012).
Quinlan, A. R., et al., "BEDTools: A Flexible Suite of Utilities for Comparing Genomic Features," Bioinformatics 26(6):841-842 (2010).
Ran, F.A., et al., "Double Nicking by RNA-Guided CRISPR Cas9 for Enhanced Genome Editing Specificity," Cell 154(6):1380-1389 (2013).
Rand, T. A., et al., "Argonaute2 Cleaves the Anti-Guide Strand of siRNA During RISC Activation," Cell 123:621-629 (2005).
Raymond, C. S., et al., "High-Efficiency FLP and PhiC31 Site-Specific Recombination in Mammalian Cells," PLoS One 2(1):e162 (2007).
Rebar, E. J., et al., "Zinc Finger Phage: Affinity Selection of Fingers with New DNA-Binding Specificities," Science 263(5147):671-673 (1994).
Rebar, E. J., et al., "Induction of Angiogenesis in a Mouse Model Using Engineered Transcription Factors," Nat. Med. 8(12):1427-1432 (2008).
Recht, M. I., et al., "Monitoring Assembly of Ribonucleoprotein Complexes by Isothermal Titration Calorimetry," Methods in Mol. Biol. 488:117-127 (2008).
Regalado, A., "Who Owns the Biggest Biotech Discovery of the Century?," MIT Technology Review, Dec. 4, 2014, http://www.technologyreview.com/featuredstory/532796/who-owns-the-biggest--biotech-discovery-of-the-century/.
Reyon, D., et al., "FLASH Assembly of TALENs for High-Throughput Genome Editing," Nat. Biotech. 30:460-465 (2012).
Rho, M., et al. "Diverse CRISPRs Evolving in Human Microbiomes." PLoS Genetics 8(6):e1002441 (2012).
Sander, J. D., et al., "Zinc Finger Targeter (ZiFiT): An Engineered Zinc Finger/Target Site Design Tool," Nucleic Acids Res. 35:W599-W605 (2007).
Sander, J. D., et al., "ZiFiT (Zinc Finger Targeter): An Updated Zinc Finger Engineering Tool," Nucleic Acids Res. 38:W462-468 (2010).
Sander, J. D., et al., "CRISPR-Cas Systems for Editing, Regulating and Targeting Genomes," Nat. Biotechnol. 32(4):347-355 (2014).
Sanders, R., "Cheap and Easy Technique to Snip DNA Could Revolutionize Gene Therapy", Berkeley News Online, pp. 1-3 (Jan. 7, 2013).
Sanjana, N. E., et al., "A Transcription Activator-Like Effector (TALE) Toolbox for Genome Engineering," Nat. Protoc. 7(1):171-192 (2012).
Sankaran, V. G., et al., "Human Fetal Hemoglobin Expression is Regulated by the Developmental Stage-Specific Repressor BCL11 A," Science 322(5909):1839-1842 (2008).
Sapranauskas, R., et al., "The *Streptococcus thermophilus* CRISPR-Cas System Provides Immunity in *Escherichia coli*," Nucl. Acids Res.39:9275-9282 (2011).
Schramm, L., et al., "Recruitment of RNA Polymerase III to Its Target Promoters," Genes Devel. 16:2593-2620 (2002).

(56) References Cited

OTHER PUBLICATIONS

Selleck, W., et al., "Biophysical Characterization and Direct Delivery of S. Pyogenes Cas9 Ribonucleoprotein Complexes," Editas Medicine, Apr. 27, 2015, retrieved from URL"http://www.editasmedicine.com/documents/ASGCT_poster_2015_Will.pdf.
Shanks, P., "Crispr Opportunities . . . For What? And for Whom?," Biopolitical Times, Dec. 4, 2014, http://www.biopoliticaltimes.org/article.php?id=8235.
Sharma, R., et al., "In Vivo Genome Editing of the Albumin Locus as a Platform for Protein Replacement Therapy," Blood 126(15):1777-1784 (2015).
Shayakhmetov, D. M., et al., "Analysis of Adenovirus Sequestration in the Liver, Transduction of Hepatic Cells, and Innate Toxicity after Injection of Fiber-Modified Vectors," J. Virol. 78(10):5368-5381 (2004).
Shen, B., et al., "Generation of Gene-Modified Mice via Cas9/RNA-Mediated Gene Targeting," Cell Res. 23:720-723 (2013).
Smith, T. F., et al., "Comparison of Biosequences," Adv. Appl. Math. 2(4):482-489 (1981).
Sontheimer, E., "Project 7: Establishing RNA-Directed DNA Targeting in Eukaryotic Cells Project dates: Nov. 16, 2011 to Dec. 31, 2012," Physical Sciences—Oncology Center (Feb. 4, 2012).
Sternberg, S.H., et al., "DNA Interrogation by the CRISPR RNA-Guided Endonuclease Cas9," Nature 507(7490):62-67 (2014).
Sugimoto, N., et al., "Thermodynamic Parameters to Predict Stability of RNA/DNA Hybrid Duplexes," Biochem. 34:11211-11216 (1995).
Sugimoto, N., et al., "Thermodynamics-Structure Relationship of Single Mismatches in RNA/DNA Duplexes," Biochem. 39(37):11270-11281 (2000).
Superti-Furga, G., et al., "The −117 Mutation in Greek HPFH Affects the Binding of Three Nuclear Factors to the CCAAT Region of the Gamma-Globin Gene," EMBO J. 7(10):3099-3107 (1988).
Szczepek, M., et al., "Structure-Based Redesign of the Dimerization Interface Reduces the Toxicity of Zinc-Finger Nucleases," Nat. Biotechnol. 25:786-793 (2007).
Terns, M. P., et al., "CRISPR-based Adaptive Immune Systems," Curr. Opin. Microbiol. 14:321-327 (2011).
Thein, S.L., et al., "Control of Fetal Hemoglobin: New Insights Emerging from Genomics and Clinical Implications," Hum. Mol. Genet. 18(R2):R216-R223 (2009).
Thurman, R. E., et al., "The Accessible Chromatin Landscape of the Human Genome," Nature 489(7414):75-82 (2012).
Tolia, N. H., et al., "Slicer and the Argonautes," Nat. Chem. Biol. 3(1):36-43 (2007).
Tolpin, Thomas W., Third Party Observation for EP13793997.1, Jan. 6, 2015, 50 pages.
Tsai, S. Q., et al., "Dimeric CRISPR RNA-Guided FokI Nucleases for Highly Specific Genome Editing," Nat. Biotechnol. 32(6):569-576 (2014).
Tsai, S.Q., et al., "Open-Source GuideSeq Software for Analysis of GUIDE-Seq Data," Nat. Biotechnol. 34(5):483 (2016).
Urnov, F. D., et al., "Highly Efficient Endogenous Human Gene Correction Using Designed Zinc-Finger Nucleases," Nature 435:646-651 (2005).
Van Der Oost, J., "New Tool for Genome Surgery," Science 336:768-768 (2013).
Van Der Ploeg, J. R., "Analysis of CRISPR in *Streptococcus* Mutans Suggests Frequent Occurrence of Acquired Immunity Against Infection by M102-Like Bacteriophages," Microbiology 155:1966-1976 (2009).
Waber, P.G., et al., "Concordance of a Point Mutation 5' to the A Gamma-Globin Gene with A Gamma Beta + Hereditary Persistence of Fetal Hemoglobin in Greeks," Blood 67(2):551-554 (1986).
Wang, H., et al., "One-Step Generation of Mice Carrying Mutations in Multiple Genes By CRISPR/Cas-Mediated Genome Engineering," Cell 153(4):910-918 (2013).
Wang, J., et al., "Homology-Driven Genome Editing in Hematopoietic Stem and Progenitor Cells Using ZFN mRNA and AAV6 Donors," Nat. Biotechnol. 33(12):1256-1263 (2015).

Wang, J., et al., "Highly Efficient Homology-Driven Genome Editing in Human T Cells by Combining Zinc-Finger Nuclease mRNA and AAV6 Donor Delivery," Nucleic Acids Res. 44(3):e30 (2016).
Wang, T., et al., "Genetic Screens in Human Cells Using the CRISPR-Cas9 System," Science 343(6166):80-84 (2013).
Wiedenheft, B., et al., "RNA-Guided Genetic Silencing Systems in Bacteria and Archaea," Nature 482:331-338 (2012).
Wu, X., et al., "Genome-Wide Binding of the CRISPR Endonuclease Cas9 in Mammalian Cells," Nat. Biotechnol. 32(7):670-676 (2014).
Wu, Y., et al., "Correction of a Genetic Disease in Mouse via Use of CRISPR-Cas9," Cell Stem Cell 13(6):659-662 (2013).
Xiao, A., et al., "CasOT: A Genome-Wide Cas9/gRNA Off-Target Searching Tool," Bioinformatics 30(8):1180-1182 (2014).
Xu, Q., et al., "Design of 240,000 Orthogonal 25mer DNA Barcode Probes," Proc. Natl. Acad. Sci.106(7):2289-2294 (2009).
Xu, J., et al., "Transcriptional Silencing of {Gamma}-Globin by BCL11A Involves Long-Range Interactions and Cooperation with SOX6," Genes Dev. 24(8):783-798 (2010).
Yang, H., et al., "One-Step Generation of Mice Carrying Reporter and Conditional Alleles by CRISPR/Cas-Mediated Genome Engineering," Cell 154(6):1370-1390 (2013).
Zetsche, B., et al., "A Split-Cas9 Architecture for Inducible Genome Editing and Transcription Modulation," Nat. Biotechnol. 33(2):139-142 (2015).
Zou, J., et al., "Gene Targeting of a Disease-Related Gene in Human Induced Pluripotent Stem and Embryonic Stem Cells," Cell Stem Cell 5(1):97-110 (2009).
Zou, J., et al., "Site-Specific Gene Correction of a Point Mutation in Human iPS Cells Derived from an Adult Patient with Sickle Cell Disease," Blood 118(17):4599-4608 (2011).
European Patent Office, International Search Report and Written Opinion dated Jun. 24, 2015 for PCT/US2015/019064.
European Patent Office, International Search Report and Written Opinion dated Jul. 1, 2015 for PCT/US2015/019790.
European Patent Office, International Search Report and Written Opinion dated Sep. 28, 2015 for PCT/US2015/022856.
European Patent Office, International Search Report and Written Opinion dated Jul. 31, 2015 for PCT/US2015/022851.
European Patent Office, International Search Report and Written Opinion dated Aug. 10, 2015 for PCT/US2015/023906.
European Patent Office, International Search Report and Written Opinion dated Jul. 28, 2016 for PCT/US2016/029252.
European Patent Office, Examination Report for EP 13824232.6, dated Dec. 16, 2014, 4 pages.
United States Patent and Trademark Office, International Search Report and Written Opinion for PCT/US2013/075317, dated Apr. 15, 2014, 12 pages.
United States Patent and Trademark Office, International Search Report and Written Opinion for PCT/US2013/075326, dated Aug. 22, 2014, 13 pages.
United States Patent and Trademark Office, International Search Report and Written Opinion for PCT/US2014/027335, dated Jul. 16, 2014, 13 pages.
United States Patent and Trademark Office, International Search Report and Written Opinion for PCT/US2014/028630, dated Jul. 24, 2014, 9 pages.
United States Patent and Trademark Office, Invitation to Pay Additional Fees and, Where Applicable, Protest Fee for PCT/US2014/029068, Aug. 20, 2014, 3 pages.
United States Patent and Trademark Office, Office Action for U.S. Appl. No. 14/319,380, dated Jan. 28, 2015, 47 pages.
United States Patent and Trademark Office, Office Action for U.S. Appl. No. 14/319,530, dated Apr. 1, 2015, 23 pages.
Bothmer, A., et al., "Characterization of the Interplay Between DNA Repair and CRISPR/Cas9-Induced DNA Lesions at an Endogenous Locus," Nat. Commun. 8:13905 (2017).
Canver, M. C., et al., "BCL11A Enancer Dissection by Cas9-Mediated In Situ Saturating Mutagenesis," Nature 527(7577):192-197 (2015).
Chang, K.H., et al., "Long-Term Engraftment and Fetal Globin Induction upon BCL11A Gene Editing in Bone-Marrow-Derived CD34+ Hematopoietic Stem and Progenitor Cells," Mol. Ther. Methods Clin. Dev. 4:137-148 (2017).

(56) References Cited

OTHER PUBLICATIONS

Chen, F., et al., "Targeted Activation of Diverse CRISPR-Cas Systems for Mammalian Genome Editing Via Proximal CRISPR Targeting," Nat. Commun. 8:14958 (2017).
Dever, D. P., et al., "CRISPR/Cas9 Beta-Globin Gene Targeting in Human Haematopoietic Stem Cells," Nature 539:384-389 (2016).
European Patent Office, International Search Report and Written Opinion dated May 29, 2017 for PCT/US2017/022377.
Hinz, J. M., et al., "Nucleosomes Selectively Inhibit Cas9 Off-Target Activity at a Site Located at the Nucleosome Edge," J. Biol. Chem. 291 (48):24851-24856 (2016).
Ran, F. A., et al., "In Vivo Genome Editing Using *Staphylococcus aureus* Cas9," Nature 520(7546):186-191 (2015).
Richardson, C. D., et al., "Enhancing Homology-Directed Genome Editing by Catalytically Active and Inactive CRISPR-Cas9 Using Asymmetric Donor DNA," Nat. Biotechnol. 34(3):339-344 (2016).
Traxler, E. A., et al., "A Genome-Editing Strategy to Treat Beta-Hemoglobinopathies that Recapitulates a Muation Associated with a Benign Genetic Condition," Nat. Med. 22(9):987-990 (2016).
Zetsche, B., et al., "Cpf1 Is a Single RNA-Guided Endonuclease of a Class 2 CRISPR-Cas System," Cell 163(3):759-771 (2015).
Joung, J., et al., "Genome-Scale CRISPR-Cas9 Knockout and Transcriptional Activation Screening," Nat. Protoc. 12(4):828-863 (2017).
Kurita, R., et al., "Establishment of Immortalized Human Erythroid Progenitor Cell Lines Able to Produce Enucleated Red Blood Cells," PLoS One 8(3):e59890 (2013).
Martyn, G.E., et al., "The Regulation of Human Globin Promoters by CCAAT Box Elements and the Recruitment of NF-Y," Biochim. Biophys. Acta 1860(5):525-536 (2017).
Koike-Yusa, H., et al., "Genome-Wide Recessive Genetic Screening in Mammalian Cells with a Lentiviral CRISPR-Guide RNA Library," Nat. Biotechnol. 32(3):267-273 (2014).
Shalem, O., et al., "Genome-Scale CRISPR-Cas9 Knockout Screening in Human Cells," Science 343:84 (2014).
Sather, B. D., et al., "Efficient Modification of CCR5 in Primary Human Hematopoietic Cells Using a Mega TAL Nuclease and AAV Donor Template," Sci. Trans. Med. 7(307):307ra156 (2015).
Shmakov, S., et al., "Discovery and Functional Characterization of Diverse Class 2 CRISPR-Cas Systems," Mol. Cell 60(3):385-397 (2015).
Smith, C., et al., "Efficient and Allele-Specific Genome Editing of Disease Loci in Human iPSCs," Mol. Ther. 23(3):570-577 (2015).
Traxler, E., et al., "Genome Editing Recreates Hereditary Persistence of Fetal Hemoglobin in Primary Human Erythroblasts," Blood J. 126(23):640 (2015).
Yamano, T., et al., "Crystal Structure of Cpf1 in Complex with Guide RNA and Target DNA," Cell 165(4):949-962 (2016).
European Patent Office, International Search Report and Written Opinion dated Jun. 12, 2017 for PCT/US2017/024163.
Amrani, N., et al., "NmeCas9 is an Intrinsically High-Fidelity Genome-Editing Platform," Genome Biol. 19:214 (2018).
Burstein, D., et al., "New CRISPR-Cas Systems from Uncultivated Microbes," Nature 542(7640):237-241 (2017).
Cassini, A., et al., "A Highly Specific SpCas9 Variant is Identified by In Vivo Screening in Yeast," Nat. Biotechnol. 36(3):265-271 (2018).
Chandrakasan, S., et al., "Gene Therapy for Hemoglobinopathies: The State of the Field and the Future," Hematol. Oncol. Clin. North Am. 28(2): 199-216 (2014).
Chen, J. S., et al., "Enhanced Proofreading Governs CRISPR-Cas9 Targeting Accuracy," Nature 550(7676):407-410 (2017).
Fu, Y., et al., "Targeted Genome Editing in Human Cells Using CRISPR/Cas Nucleases and Truncated Guide RNAs," Methods Enzymol. 546:21-45 (2014).
Giarratana, M. C., et al., "Proof of Principle for Transfusion of In Vitro-Generated Red Blood Cells," Blood 118(19):5071-5079 (2011).

Huang, X., et al., "Production of Gene-Corrected Adult Beta Globin Protein in Human Erythrocytes Differentiated from Patient iPSCs After Genome Editing of the Sickle Point Mutation," Stem Cells 33:1470-1479 (2015).
Hyun, P. S., et al., "Therapeutic CRISPR/Cas9 Genome Editing for Treating Sickle Cell Disease," Blood 128(22):4703 (2016).
Karvelis, T., et al., "crRNA and tracrRNA Guide Cas9-Mediated DNA Interference in *Streptococcus thermophilus*," RNA Biol. 10(5):841-851 (2013).
Kim, H.S., et al., "Problems Encountered in Detecting a Targeted Gene by the Polymerase Chain Reaction," Gene 103:227-233 (1991).
Kim, E., et al., "In Vivo Genome Editing with a Small Cas9 Orthologue Derived from Campylobacter Jejuni," Nat. Commun. 8:14500 (2017).
Lee, J. K., et al., "Directed evolution of CRISPR-Cas9 to Increase Its Specificity," Nat. Commun. 9:3048 (2018).
Liang, P., et al., "CRISPR/Cas9-Mediated Gene Editing in Human Tripronuclear Zygotes," Protein Cell 6(5):363-372 (2015).
Nishimasu, H., et al., "Engineered CRISPR-Cas9 Nuclease with Expanded Targeting Space," Science 361 (6408): 1259-1262 (2018).
Notta, F., et al., "Isolation of Single Human Hematopoietic Stem Cells Capable of Long-Term Multilineage Engraftment," Science 333(6039):218-221 (2011).
Ou, Z., et al., "The Combination of CRISPR/Cas9 and iPSC Technologies in the Gene Therapy of Human Beta-Thalassemia in Mice," Scientific Reports 6(1):32463 (2016).
Pellissier, L. P., et al., "Specific Tools for Targeting and Expression in Muller Glial Cells," Mol. Ther. Methods Clin. Dev. 1:14009 (2014).
Peng, R., et al., "Potential Pitfalls of CRISPR/Cas9-Mediated Genome Editing," FEBS J. 283:1218-1231 (2016).
Song, B., et al., "Improved Hematopoietic Differentiation Efficiency of Gene-Corrected Beta-Thalassemia Induced Pluripotent Stem Cells by CRISPR/Cas9 System," Stem Cells Devel. 24(9):1053-1065 (2015).
Strecker, J., et al., "Engineering of CRISPR-Cas12b for Human Genome Editing," Nat. Commun. 10:212 (2019).
Tang, L., et al., "CRISPR/Cas9-Mediated Gene Editing in Human Zygotes Using Cas9 Protein," Mol. Genet. Genom. 292(3):525-533 (2017).
Teng, F., et al., "Repurposing CRISPR-Cas12b for Mammalian Genome Engineering," Cell Discov. 4:63 (2018).
Thorpe, S. J., et al., "Immunochemical Estimation of Haemoglobin Types in Red Blood Cells by FACS Analysis," Br. J. Haematol. 87:125-132 (1994).
Truong, L. N., et al., "Microhomology-Mediated End Joining and Homologous Recombination Share the Initial End Resection Step to Repair DNA Double-Strand Breaks in Mammalian Cells," PNAS 110(19):7720-7725 (2013).
Van Overbeek, M., et al., "DNA Repair Profiling Reveals Nonrandom Outcomes at Cas9-Mediated Breaks," Mol. Cell 63:633-646 (2016).
Wang, J., et al., "xCas9 Expands the Scope of Genome Editing with Reduced Efficiency in Rice," Plant Biotechnol. J. 17:709-711 (2019).
Xu, P., et al., "Both TALENs and CRISPR/Cas9 Directly Target the HBB IVS2-654 (C>T) Mutation in Beta-Thalassemia-Derived iPSCs," Scientific Reports 5:12065 (2015).
Yan, W. X., et al., "Functionally Diversse Type V CRISPR-Cas Systems," Science 363:88-91 (2019).
European Patent Office, International Search Report and Written Opinion dated Aug. 20, 2018 for PCT/US2018/022516.
European Patent Office, International Search Report and Written Opinion dated Dec. 3, 2018 for PCT/US2018/032172.
European Patent Office, International Search Report and Written Opinion dated Mar. 13, 2019 for PCT/US2018/059700.
Cramer, M. L., et al., "Induction of T-Cell Infiltration and Programmed Death Ligand 2 Expression by Adeno-Associated Virus in Rhesus Macaque Skeletal Muscle and Modulation by Prednisone," Hum. Gene Ther. 28(6):493-509 (2017).
Ding, Q., et al., "Enhanced Efficiency of Human Pluripotent Stem Cell Genome Editing Through Replacing TALENs with CRISPRs," Cell Stem Cell 12:393-394 (2013).

(56) References Cited

OTHER PUBLICATIONS

Guo, Q., et al., "'Cold shock' increases the frequency of homology directed repair gene editing in induced pluripotent stem cells," Sci. Rep. 8(1):2080 (2018).
Heintze, J., et al., "A CRISPR CASe for High-Throughput Silencing," Front. Genet. 4(193):1-6 (2013).
Hoban, M. D., et al., "A genome editing primer for the hematologist," Blood 127(21):2525-2535 (2016).
Kumar, S. R.P., et al., "Clinical development of gene therapy: results and lessons from recent successes," Mol. Ther. Methods Clin. Dev. 3:16034 (2016).
Lederer, C. W., et al., "Beta Testing: Preclinical Genome Editing in Beta-Globin Disorders," Cell Gene Therapeutic Insights 1(2):231-242 (2015).
Lidonnici, M. R., et al., "Gene Therapy and Gene Editing Strategies for Hemoglobinopathies," Blood Cells, Molecules & Diseases 70:87-101 (2018).
Mukherjee-Clavin, B., et al., "Current Approaches for Efficient Genetic Editing in Human Pluripotent Stem Cells," Front. Biol. 8(5):461-467 (2013).
Sobrevals, L., et al., "AAV Vectors Transduce Hepatocytes In Vivo as Efficiently in Cirrhotic as in Healthy Rat Livers," Gene Ther. 19:411-417 (2012).
Wu, Y., et al., "Highly Efficient Therapeutic Gene Editing of Human Hematopoietic Stem Cells," Nat. Med. 25(5)776-783 (2019).
Zetsche, B., et al., "Multiplex Gene Editing by CRISPR-Cpf1 Through Autonomous Processing of a Single crRNA Array," Nat. Biotechnol. 35(1):31-34 (2017).
European Patent Office, International Search Report and Written Opinion dated Jul. 1, 2019 for PCT/US2019/022360.
Bothmer, A., et al., "Detection and Modulation of DNA Translocations During Multi-Gene Genome Editing in T Cells," The CRISPR Journal 3(3):177-187 (2020).
Cost, G. J., et al., Geneseq Accession No. BBD49192 (2014), 2 pages.
De Dreuzy, E., et al., "EDIT-301: An Experimental Autologous Cell Therapy Comprising Cas12a-RNP Modified mPB-CD34+ Cells for the Potential Treatment of SCD," Blood 134(Suppl. 1):4636 (2019).
De Dreuzy, E., et al., "Robust Pre-Clinical Results and Large-Scale Manufacturing Process for Edit-301: An Autologous Cell Therapy for the Potential Treatment of SCD," Blood 136(Suppl. 1):45-46 (2020).

Fu, B. X. H., et al., "Landscape of Target: Guide Homology Effects on Cas9-Mediated Cleavage," Nucl. Acids Res. 42(22): 13778-13787 (2014).
Giannoukos, G., et al., "UDiTaS™, a genome editing detection method for indels and genome rearrangements," BMC Genomics 19:212 (2018).
Giarratana, M. C., et al., "Ex vivo generation of fully mature human red blood cells from hematopoietic stem cells," Nat. Biotechnol. 23(1):69-74 (2005).
Heath, J., et al., "EDIT-301: An Autologous Cell Therapy to Promote Fetal Hemoglobin Expression for the Potential Treatment of Sickle Cell Disease," Hemasphere 4(S1):S292 (2020).
Hu, X., "CRISPR/Cas9 System and Its Applications in Human Hematopoietic Cells," Blood Cells, Molecules & Diseases 62:6-12 (2016).
Kleinstiver, B. P., et al., "Engineered CRISPR-Cas12a variants with increased activities and improved targeting ranges for gene, epigenetic and base editing," Nat. Biotechnol. 37(3):276-282 (2019).
Kosicki, M., et al., "Repair of Double-Strand Breaks Induced by CRISPR-Cas9 Leads to Large Deletions and Complex Rearrangements," Nat. Biotechnol. 36(8):765-771 (2018).
Krieg, A. M., et al., GeneSeq Accession No. BAY71542 (2013).
Metais, J.Y., et al., "Genome Editing of HBG1 and HBG2 to Induce Fetal Hemoglobin," Blood Adv. 3(21):3379-92 (2019).
Pausch, P., et al., "CRISPR-Casϕ from Huge Phages is a Hypercompact Genome Editor," Science ;369(6501):333-337 (2020).
Reeks, J., et al., "Structure of a Dimeric Crenarchaeal Cas6 Enzyme with an Atypical Active Site for CRISPR RNA Processing," Biochem. J. 452:223-230 (2013).
Strohkendl, I., et al., "Kinetic Basis for DNA Target Specificity of CRISPR-Cas12a," Mol Cell. 71(5):816-824 (2018).
Swarts, D. C., et al., "Cas9 Versus Cas12a/Cpf1: Structure-Function Comparisons and Implications for Genome Editing," WIREs RNA 9:e1481 (2018).
Vidigal, J. A., et al.,"Rapid and Efficient One-Step Generation of Paired gRNA CRISPR-Cas9 Libraries," Nat. Commun. 6:8083 (2015).
European Patent Office, International Search Report and Written Opinion dated Mar. 6, 2020 for PCT/US2019/063766, 12 pages.
European Patent Office, International Search Report and Written Opinion dated Apr. 13, 2021 for PCT/US2020/063854, 18 pages.

* cited by examiner

Fig. 1G

Alignment

S. pyogenes      5'-NNNNNNNNNNNNNNNNNNNNGUUUACAGCUAUGCUGUUUG-3'    (SEQ ID NO:50)
S. thermophilus  5'-NNNNNNNNNNNNNNNNNNNNGUUUAAGAGCUGUGUUGUUUCG-3'  (SEQ ID NO:51)
                    ********************      * *** *  *  ******  *

S. pyogenes      5'-GAACCAUUCAAAACAGCAUAGCAAGUUAAAAUAAGGCUAGUCCGUUAUCAACUUGAAAAAGUGGCACCGAGUCGGUGCUUUU-3'     (SEQ ID NO:52)
S. thermophilus  5'------GGCGAACAACACAGCGAGUUAAAAUAAGGCUUAGUCCGUACUCAACUUGAAAAGUGGCACCGAUUCGGUGUUUU---3'   (SEQ ID NO:53)
                        *    *   **  *************  ***** * ********* ******* ** **

S. pyogenes - cont
S. thermophilus - cont

```
SM   GNSDK--LIPRKTKKFYWDTKKYGGFDSPTVAYSILVIADIERGKSKKLKTVKALVGVTIM
SP   RNSDK--LIARKKD----WDPKKYGGFDSPTVAYSVLVVAKVEKGKSNKLSVRELLGITIM
ST   PNSNEMLVQAKEY----LDPKKYGGYAGISNSFTVLVEGTIEKGAKKITNVLEFQGISIL
LI   GNESK--LIPRKTN----WDPMKYGGLDSPNMAYAVVI--EYAKGRN-KLVFEKKITRVIIM
            *  :       *::* **    .: :.:       : :     :      ::
Motif: -NS---L--*----K----D---KYGG------------*----KG---K*-----**I-*

SM   EKMTFERDPVAFLEREGYRMVQEEHTIKLLPKYSLFKLEMGRKRLLAS------AKELQK
SP   ERGSFEKMPIDFLEAKGYREVKKDLIIKLLPKYSLFELEMGRRRMELAS-----AGELQK
ST   DRINTRKDKLNFLLERGYRDI---ELIIEILPKYSLFELSDGSRRMLASILSTNMRKGEIHK
LI   ERKAFEEDERAFLEEQGTRQP---RVLAKILPKYTLYECEEGRRRMELAS------ANEAQK
       :   :   ::          ::  :***:*     . *:                : :
Motif: *------L-------*---------*LPKY*L*----*Q--R*LAS-------R---*-K SM   GNEIVLPMHLGTLLYHAKNIHKV-------DEPKHLDYVDKHRDEFKELLQVVSNFSKKYT
SP   GNELALPSKYVNFLYLASHYEKLKGSPEDNEQRQL-FVEQHKHYLDEIIEQISEFSKRVI
ST   GNQIFLSQFVKLLVYHAKRISNT-------IMENHRKYVENHKKEFEELFYYILEFMEDYV
LI   GNQQVLPMHLVTLLHHAANCEVS-------DQKSLDYIESNREMFAELLAHVSEFAPKYT
     **    *  : ::                         :   :  *  :     *
Motif: GN*--*L---*--L-*-A-----------------*-------*---F-----*--*-

SM   LAEGNLEKIKELYAQHNGEDLKELASSFI-------NLLTTTAIGAPATPKFFDKNIDR
SP   LADANLDKVLSAYNKHRDKPIREQAEHII-------HLFTLTNLGAPAAPKYFDTIDR
ST   GAKNKGKILNSAPQSWQHSIDELCSSFIGPTGSERKGLFELTSRGSAADPEFLGVNIPR
LI   LAEANLNKIWQLFEQNREGDIKALAQSFV-------DLMAFNAMGAPASFKFFETTIER
      * :: : :  :    :     *  *          :         ** .*     *
Motif: -A--N---I---------------------------*-----G---A--F----*-I-R
```

Fig. 2G

```
SM   KR-YTSTTEILNATLIHQSITGLYETRIDLNKLGGD    (SEQ ID NO: 1)
SP   KR-YTSTKEVLDATLIHQSITGLYETRIDLSQLGGD    (SEQ ID NO: 2)
ST   YRDYIPSSLLKDATLIHQSVTGLYETRIDLAKLGEG    (SEQ ID NO: 3)
LI   KR-YNNLKELLNSTIYQSITGLYESRKRLD----D    (SEQ ID NO: 4)
        *  :  . : :*::*::***::*:  .

Motif: --R--Y------*--*-*T**I*QS*TGLYE*R---L-----
```

Fig. 3A

Alignment of the N terminal BarC-like Domains disclosed in Chylinski et al. (excluding sequence outliers).
CLUSTAL format alignment by MAFFT (v7.0xxb))

| # | Sequence | SEQ ID |
|---|---|---|
| 1 | DIGTNSYGMAVT | (SEQ ID NO: 54) |
| 12 | DIGTNSYGMAVT | (SEQ ID NO: 55) |
| 3 | DVGTNSYGMAVT | (SEQ ID NO: 56) |
| 20 | DVGTNSYGMAVT | (SEQ ID NO: 57) |
| 15 | DMGTNSYGMAVT | (SEQ ID NO: 58) |
| 4 | DVGTNSYGMAVT | (SEQ ID NO: 59) |
| 7 | DIGTASYGMAVT | (SEQ ID NO: 60) |
| 6 | DVGTGSYGMAVT | (SEQ ID NO: 61) |
| 9 | DIGTNSYGMAVT | (SEQ ID NO: 62) |
| 10 | DIGTNSYGMAVT | (SEQ ID NO: 63) |
| 11 | DLGTNSYGMAVL | (SEQ ID NO: 64) |
| 43 | DLATNSYGMAVV | (SEQ ID NO: 65) |
| 40 | DIGTNSYGMAI- | (SEQ ID NO: 66) |
| 42 | DIGTNSIGMALV | (SEQ ID NO: 67) |
| 13 | DIGTNSYGMCVT | (SEQ ID NO: 68) |
| 14 | DIGTSSVGMAVT | (SEQ ID NO: 69) |
| 5 | DMGTGSIGMAVI | (SEQ ID NO: 70) |
| 16 | DIGTASYGMAII | (SEQ ID NO: 71) |
| 8 | DLGTGSYGMAVV | (SEQ ID NO: 72) |
| 17 | DIGIASIGMAIV | (SEQ ID NO: 73) |
| 21 | DLGVGSYGMSIV | (SEQ ID NO: 74) |
| 24 | DLGIASVGMAII | (SEQ ID NO: 75) |
| 25 | DIGVASVGMSIV | (SEQ ID NO: 76) |
| 26 | DIGIASVGMAVV | (SEQ ID NO: 77) |
| 28 | DIGYASIGPAIV | (SEQ ID NO: 78) |
| 29 | DIGIGSIGMSVI | (SEQ ID NO: 79) |
| 32 | DLGVGSIGMSVI | (SEQ ID NO: 80) |
| 33 | DLGVASVGMSVI | (SEQ ID NO: 81) |
| 38 | DVGVGSVGMAVI | (SEQ ID NO: 82) |
| 34 | DIGVGSIGMAVI | (SEQ ID NO: 83) |
| 47 | DYGTNSLGMAIV | (SEQ ID NO: 84) |
| 50 | DLGTNSIGMCLL | (SEQ ID NO: 85) |
| 49 | DIGTDSLGMAVV | (SEQ ID NO: 86) |
| 18 | DIGSNSIGPAVV | (SEQ ID NO: 87) |
| 41 | DLAVGSIGVAVA | (SEQ ID NO: 88) |
| 45 | DLGIASGMGYPP | (SEQ ID NO: 89) |

Alignment of the HNH-like Domains disclosed in Chylinski et al.
(CLUSTAL format alignment by MAFFT (v7.058b))

| | | SEQ ID NO |
|---|---|---|
| 1 | YDIDHIYPRS-LIKD------DSF-DNLVLCERTAN | SEQ ID NO: 178 |
| 2 | -DIDHIYPRSKVIKD------DSF-DNLVLKMEN | SEQ ID NO: 179 |
| 3 | -DRDHIYPQS-KIKD------DSI-DNLVLVNKTYN | SEQ ID NO: 180 |
| 4 | -DIDHIYPRS-KIKD------DSI-TNRVLVEKDIN | SEQ ID NO: 181 |
| 6 | -DIDHIYPQS-KIKD------DSI-SNRVLVCSSCN | SEQ ID NO: 182 |
| 5 | -DIDHIYPQS-KTMD------DSL-SNRVLVKKNYN | SEQ ID NO: 183 |
| 7 | -DQDHIYPKS-KIYD------DSL-ENRVLVKKNLN | SEQ ID NO: 184 |
| 8 | -QIDHIYPQS-LVKD------DSF-DNRVLVVPSEN | SEQ ID NO: 185 |
| 9 | -DIDHIIPQA-FIKD------NSI-DNRVLTSSKEN | SEQ ID NO: 186 |
| 12 | -DIDHIIPQA-FLKD------NSI-DNRVLVSSASN | SEQ ID NO: 187 |
| 16 | -DIDHIIPQA-YTKD------NSI-DNRVLVSNTIN | SEQ ID NO: 188 |
| 11 | -DIDHIYPQS-FITD------MSI-DNRVLTSSAGN | SEQ ID NO: 189 |
| 10 | -DVDHIYPQS-FLKD------DSI-DNRVLTRSDKN | SEQ ID NO: 190 |
| 14 | -NIDHIYPQS-MVKD------DSL-DNRVLVQSEIN | SEQ ID NO: 191 |
| 18 | -DIDHILPQS-LIKD------DSL-DNRVLVNATIN | SEQ ID NO: 192 |
| 19 | -DIDHILPQS-FIKD------DSI-ENRVLVKKAVN | SEQ ID NO: 193 |
| 13 | -EVDHIFPRS-FIKD------DSI-DNRVLVIKMMN | SEQ ID NO: 194 |
| 15 | -EVDHIYPRS-YIKD------DSF-ENRVLVTREEN | SEQ ID NO: 195 |
| 17 | -DIDHIIPQA-VTQN------DSI-DNRVLVARAEN | SEQ ID NO: 196 |
| 22 | -EIDHIIPYS-ISFD------DSS-SNKLLVLAESN | SEQ ID NO: 197 |
| 24 | -EIDHIIPYS-LCPD------DSS-ANRVLVHKQSN | SEQ ID NO: 198 |
| 23 | -EIDHIIPYS-KSMD------DSY-SNRVLVLSGEN | SEQ ID NO: 199 |
| 63 | -DIDHIIPYS-RSPD------DSF-NNRVLVLAEEN | SEQ ID NO: 200 |
| 59 | -EIDHIIPYS-RSPD------DSY-NNRVLVLVFTKQN | SEQ ID NO: 201 |
| 65 | -EIDHALPFS-RTWD------DSY-MNRVLVLTDZN | SEQ ID NO: 202 |
| 64 | -EIDHALPFS-RSPD------DSL-SNKILVLGSEN | SEQ ID NO: 203 |
| 68 | -EIDHALPFS-RTWD------DSF-NNRVLVLGGSN | SEQ ID NO: 204 |
| 69 | -EIDHALPFS-RTWD------DSF-NNRVLVLAEEN | SEQ ID NO: 205 |
| 28 | -EIDHIIPIS-ISLD------DSI-NNRVLVLSAAN | SEQ ID NO: 206 |
| 30 | -EVDHALPYS-RSYD------DSI-TNRVLVTHREN | SEQ ID NO: 207 |
| 62 | -QVDHALPYS-RSYD------DSK-NNRVLVLTHEN | SEQ ID NO: 208 |
| 27 | -EVDHILPLS-ITFD------DSL-ANRVLVTATAN | SEQ ID NO: 209 |
| 26 | -EIDHIIPRS-ISPD------DAR-SNRVLVTREEN | SEQ ID NO: 210 |

```
72  EIDHIYPRS-LSKKHFGVIFNSE-VNLIYCSSQGN  (SEQ ID NO:249)
74  EIDHILPRS-HTLKIYGFVFNPE-GNLIYVHQKCN  (SEQ ID NO:250)
75  ELDHIIPRS-HKKY----GTLNDE-ANLICVTRGDN (SEQ ID NO:251)
34  ELEHIVPHS-FRQS------NAL-SSLVLTWPGVN  (SEQ ID NO:252)
     *:  * *                *           
```

Alignment of the MAM-like Domains disclosed in Chylinski et al. (excluding sequence outliers). (CLUSTAL format alignment by MAFFT (v7.058b))

| | | |
|---|---|---|
| (SEQ ID NO: 288) | (SEQ ID NO: 289) | |
| (SEQ ID NO: 289) | (SEQ ID NO: 290) | |
| (SEQ ID NO: 290) | (SEQ ID NO: 291) | |
| (SEQ ID NO: 291) | (SEQ ID NO: 292) | |
| (SEQ ID NO: 292) | (SEQ ID NO: 293) | |
| (SEQ ID NO: 293) | (SEQ ID NO: 294) | |
| (SEQ ID NO: 294) | (SEQ ID NO: 295) | |
| (SEQ ID NO: 295) | (SEQ ID NO: 296) | |
| (SEQ ID NO: 296) | (SEQ ID NO: 297) | |
| (SEQ ID NO: 297) | (SEQ ID NO: 298) | |
| (SEQ ID NO: 298) | (SEQ ID NO: 299) | |
| (SEQ ID NO: 299) | (SEQ ID NO: 300) | |
| (SEQ ID NO: 300) | (SEQ ID NO: 301) | |
| (SEQ ID NO: 301) | (SEQ ID NO: 302) | |

Fig. 6B

```
44  EIEHIVPKA-RVFDDS--FGNKFLLTPHRIN
20  DKDHIIPQS-MKKDDSIINNLVLVNKNAN
45  QVDHILPWS-RFCDDS-YLNKTLCTARSN
50  DIDHIVPLA-RCGRDS-LDNMVLCQSDAN
46  DMEHTIPKS-ISFDNS--DQNLTLCESYYN
47  DIEHTIPRS-AGGDST--RMNLTLCSSRFN
48  DIEHTIPRS-ISQDNS--QMNKFLCSLAFN
39  DIEHLFPIA-ESEDNC--RMNLVISHSACN
41  DVDHIIPRD-DTADNS-YGNKVVAHRQCN
40  DIEHTVPQS-LQGLST-DYNTTVTLKSVN
35  ELDHIVPRT-DGGSNR-HENLAITCCACN
36  EMDHIVPRKGVGSTNT-KTNFAAVCAEEN
37  BMDHIVPRKGVGSTNT-RVMLAAACAACN
38  EMDHIVPRAGQGSTNT-BENLVAVCHRCN
34  ELEHIVPHS-PRQSNA-LSSLVLTWPGVN
```

Fig. 7A

Sequence alignment between SpCas9 and NmCas9

```
                                                                    Y
NmCas9      MAAFKPNSINYILGLDIGIASVGWAMVEIDEEENPIRLID-------------LGVRVFE
SpCas9      -------MDKKYSIGLDIGTNSVGWAVITDEYKVPSKKFKVLGNTDRHSIKKNLIGALLFD
            ----------*Y-*GLDIG--SVGWA**---*-*-----**----------------*G---*F*

NmCas9      RAEVPKTGDSLAMARRLARSVRRLTRRRAHRLLRTRRLLKREGVLQAA-------------
SpCas9      SGET-------AEATRLKRTARRRYTRRKNRICYLQEIFSNEMAKVDDSFFHRLEESFLV
            --E---------A-A-RL-R*-RR---RR---R*----*-_**--E--------------

NmCas9      ---------------NFDENGLIKSLPNTPWQLRAAALDRK----LTPLEWSAVLLHLIKHR
SpCas9      EEDKKHERHPIFGNIVDEVAYHEKYP-TIYHLRKKLVDSTDKADLRLI-YLALAHMIKFR
            ----------------DE----*--P-T-**LR---*D---------L------L-H*IK-R

NmCas9      GYLSQRKNE----------------------------------GETA---------DKEL---
SpCas9      GHFLIEGDLNPDNSDVDKLFIQLVQTYNQLFEENPINASGVDAKAILSARLSKSRRLENL
            G**----*---------------------------G--A-----------*-L---

NmCas9      ------GALLKGVAGNAHALQTG----DFRTPAE-------LAL---NKFEKESGHIRNQ-RSD
SpCas9      IAQLPGEKKNGLFGNLIALSLGLTPNFKSNFDLAEDAKLQLSKDTYDDDLDNLLAQIGDQ
            -----G---*G*-GN--AL--G---*F**--*------L-L--*-**-*----*--Q---*

NmCas9      YSHTFSR--------------------------------------------KDLQA
SpCas9      YADLFLAAKNLSDAILLSDILRVNTEITKAPLSASMIKRYDEHHQDLTLLKALVRQQLPE
            Y*--F-----------------------------------------**L--

NmCas9      ELILLFEKQKEFGN-PHVSGGLK--------------EGIETL---------LMTQRPA
SpCas9      KYKEIFFDQSKNGYAGYIDGGASQEEFYKFIKPILEKMDGTEELLVKLNREDLLRKQRTF
            *----*F--Q-*-G-*-**-GG---------------*G-E-L---------L--QR--

NmCas9      LSGDAV-QKMLGH---------CTFEPAEP------------KAAKNTYTAERFIWL
SpCas9      DNGSIPHQIHLGELHAILRRQEDFYPFLKDNREKIEKILTFRIPYYVGPLARGNSRFAWM
            --G----Q--LG----------F-P------------------*-----RF-W*

NmCas9      TKLNNLRILEQGSERPLTD--------TERATLMDEPY------RKSKLTYAQAR-------
SpCas9      TRKSEETITPWNFEEVVDKGASAQSFIERMTNFDKNLPNEKVLPKHSLLYEYFTVYNELF
            T*---**--I-----E---*---------ER-T-*D*--------K--L-Y---------

NmCas9      ----KLLGLEDTAFFKGLRY---------GKDN--------------------AEA
SpCas9      KVKYVTEGMRKPAFLSGEQKKAIVDLLFKTNRKVTVKQLKEDYFKKIECFDSVEISGVED
            --------G*----AF*-G-*----------*-----------------------E-

NmCas9      STLMEMKAYHAISRALEKEGLKDKKSPLNLSPELQDEIGTAFSLFKTDEDITGRLKDRIQ
SpCas9      RFNASLGTYHDLLKIIKDKDFLDNEE----NEDILEDIVLTLTLFEDREMIEERLKTYAH
            -----*-*YH-*-*-**-*--D**-----**--**I---***LF*--E-I--RLK---*

NmCas9      P---EILEALLKHISFDKFVQISLKALRRIVPLMEQGKRYDEACAE----IYGDHYGKKNT
SpCas9      LFDDKVMKQLKRRRYTGWGRLSRKLI---------NGIRDKQSGKTILDFLKSDGFANRNF
            ----*-*---LK*---*---*-**S-K-*---------*G-R---**--------*--D-*-*-**N-

NmCas9      EEKI-------Y------------LPPIPADEIRNPVVLRALSQARKVINGVVRRYG-
SpCas9      MQLIHDDSLTFKEDIQKAQVSGQGDSLHEHIANLAGSPAIKKGILQTVKVVDELVKVMGR
            -*-I--------*--------------L----A*-----P-*-*-*-Q*-KV**-*V*--G-

NmCas9      -SPARIHIETARE VGKSFKDRKEIEKRQEENRKDREKAAAKFREYFPNF----VGEPKSK
SpCas9      HKPENIVIEMARE NQTTQKGQKNSRER-------NKRIEEGIKELGSQILKEHPVENTQL
            --P--I-IE-ARE---*-K-*K*--*R-----------**-----**E---**------E-
         B                                       G
NmCas9      DILKLRLYEQQHGKCLYSGKEINLGRLNEKGYVEIDHALPFSRTWDDSFNNKVLVLGSEN
SpCas9      QNEKLYLYYLQNGRDMYVDQELDINRLSD----YDVDHIVPQSFLKDDSIDNKVLTRSDKN
            *--KL-LY--Q-G*--Y--*E***-RL-*----**DH-*P-S--DDS**NKVL-----N

NmCas9      QNKGNQTPYEYFNGKDNSREWQEFKA-RVET-SRFP-RSKKQRILLQKFDEDGFKERNLN
SpCas9      RGKSDNVPSEEVVKKM-KNYWRQLLNAKLITQRKFDNLTKAERGGLSELDKAGFIKRQLV
            *-K--P-E-----K-------W*--**-T--*F----*K-*R--L-**D*-GF-*R*L-
```

Fig. 7B

```
NmCas9    DTRYVNRFLCQFVADRMRLTGKGKKRVF------ASNGQITNLLRGFWGLRKVRAENDRH
SpCas9    ETRQITKHVAQILDSRMNTKYDENDKLIREVKVITLKSKLVSDFRKDPQFYKVREINNYH
          *TR-*-*-*-Q**---RM------*-***------*-*-**---*R---*-*-KVR--N*-H

NmCas9    HALDAVVACSTVAMQQKI---TRFVRYKEMNAFDGKTID----KETGEVLHQKTHFPQP
SpCas9    HHAHDAYLNAVVGTALIKKYPKLESEFVYGDYKVYDVRKMIAKSEQEIGKATAKYFFYSNI
          HH-AD-*-A-----A*-*K---------Y-*-*-*D-*-*------*E-G*---*---*-*-

NmCas9    WEFFAQEVMIRVPGKPDGKPE-----------FEEADTLEKLRTLLAEKLSSRPEAVHEY
SpCas9    MNFFKTEITLA-NGEIRKRPLIETNGETGEIVWDKGRDFATVRKVLS-----MPQ-----
          -*FF--E*-*---G*----*P-----------***----*--R-*L*------P*------

NmCas9    VTPLFVSRAPNRKMSGQGHMETVKSAKRLDEGVSVLRVPLTQLKLKDLEKMVN--REREP
SpCas9    --------------------VNIVKKTEVQTGGFSKES-----ILPKRNSDKLIARKKDWDP
          ---------------------VK-----G-S--------L--**-*K----*P

NmCas9    KLYEALKARLEAHKDDPAKAFAEPFYKYDKAGNRTQQVKAVR---VEQVQKTGVWVRNH-
SpCas9    KKYGGFD--------SPTVAYSVLVVAKVEKGK-SKKLKSVKELLGITIMERSSFEKNPI
          K-Y--*---------P*-A**--------*-G*-****K*V*------*-*----*-*N--

NmCas9    ----NGIAD----------------NATMVRVDVFEKGDKYYLVPIY--------
SpCas9    DFLEAKGYKEVKKDLIIKLPKYSLFELENGRKRMLASAGELQKGNELALPSKYVNFLYLA
          -----*G--*-----------------*---*------KG--L---Y--------

NmCas9    -SWQVAKGILPDRAVVQGKDEEDWQLIDDS------FNFKFSLHPNDLVEVI--------
SpCas9    SHYEKLKGSPEDNEQKQLFVEQHKHYLDEIIEQISEFSKRVILADANLDKVLSAYNKHRD
          --**--KG---D----Q---E*---*-*D*-------F--*--L----*L--*V*---------

NmCas9    ------------------TKKARMFGYFASCHRGTGNINIRIHDLDHKIGKNGILEGIGV
SpCas9    KPIREQAENIIHLFTLTNLGAPAAFKYFDTTIDRKRYTS-TKEVLDATLIHQSI-------
          -----------------------F-YF-*--------LD--*-**-I-------

NmCas9    KTALSFQKYQIDELGKEIRPCRLKKRPPVR    (SEQ ID NO:6)
SpCas9    -TGLYETRIDLSQLGGD-----------    (SEQ ID NO:7)
          -T-L---*-*-**-*LG-*-----------
```

Percent Identity Matrix - created by Clustal2.1

Fig. 8

Sequence of the NmCas9 ORF with dual NLS and HA tags atg[gtgcctaagaagaagagaaaggtg]gctgccttcaaacctaattcaatcaactacatcctcggcctcgat
atcggcatcgcatccgtcggctgggcgatggtagaaattgacgaagaagaaacccccatccgcctgattgat
ttgggcgtgcgcgtatttgagcgtgccgaagtaccgaaaacaggcgactcccttgccatggcaaggcgtttg
gcgcgcagtgttcgccgcctgacccgccgtcgcgcccaccgcctgcttcggacccgccgcctattgaaacgc
gaaggcgtattacaagccgccaattttgacgaaaacggcttgattaaatccttaccgaatacaccatggcaa
cttcgcgcagccgcattagaccgcaaactgacgcctttagagtggtcggcagtcttgttgcatttaatcaaa
catcgcggctatttatcgaacgaaaaacgagggcgaaactgccgataaggagcttggcgctttgcttaaa
ggcgtagccggcaatgccatgccttacagacaggcgatttccgcacaccggccgaattggctttaaataaa
tttgagaaagaaagcggccatatccgcaatcagcgcagcgattattcgcatacgttcagccgcaaagattta
caggcggagctgattttgctgtttgaaaaacaaaagaatttggcaatccgcatgtttcaggcggccttaaa
gaaggtattgaaacccctactgatgacgcaacgccctgccctgtccggcgatgccgttcaaaaaatgttgggg
cattgcaccttcgaaccggcagagccgaaagccgctaaaaacacctacacagccgaacgtttcatctggctg
accaagctgaacaacctgcgtatttagagcaaggcagcgagcggccattgaccgataccgaacgcgccacg
cttatggacgagccatacagaaaatccaaactgacttacgcacaagcccgtaagctgctgggtttagaagat
accgccttttcaaaggcttgcgctatggtaaagacaatgccgaagcctcaacattgatggaaatgaaggcc
taccatgccatcagccgtgcactggaaaaagaaggattgaaagacaaaaaatcccccattaaacctttctccc
gaattacaagacgaaatcggcacggcattctccctgttcaaaaccgatgaagacattacaggccgtctgaaa
gaccgtatacagcccgaaatcttagaagcgctgttgaaacacatcagcttcgataagttcgtccaaatttcc
ttgaaagcattgcgccgaattgtgcctctaatggaacaaggcaaacgttacgatgaagcctgcgccgaaatc
tacggagaccattacggcaagaagaatacggaagaaaagatttatctgccgccgattcccgccgacgaaatc
cgcaaccccgtcgtcttgcgcgccttatctcaagcacgtaaggtcattaacggcgtggtacgccgttacggc
tccccagctcgtatccatattgaaactgcaagggaagtaggtaaatcgtttaaagaccgcaagaaattgag
aaacgccaagaagaaaaccgcaaagaccgggaaaagccgccgccaaattccgagagtatttccccaattttt
gtcggagaacccaaatccaaagatattctgaaactgcgcctgtacgagcaacaacacggcaaatgcctgtat
tcgggcaaagaaatcaacttaggccgtctgaacgaaaaaggctatgtcgaaatcgaccatgccctgccgttc
tcgcgcacatgggacgacagtttcaacaataaagtactggtattgggcagcgaaaaccaaaacaaaggcaat
caaaccccttacgaatacttcaacggcaaagacaacagccgcgaatggcaggaatttaaagcgcgtgtcgaa
accagccgtttcccgcgcagtaaaaaacaacggattctgctgcaaaaattcgatgaagacggctttaaagaa
cgcaatctgaacgacacgcgctacgtcaaccgtttcctgtgtcaatttgttgccgaccgtatgcggctgaca
ggtaaaggcaagaaacgtgtctttgcatccaacggacaaattaccaatctgttgcgcggcttttggggattg
cgcaaagtgcgtgcggaaaacgaccgccatcacgccttggacgccgtcgtcgttgcctgctcgaccgttgcc
atgcagcagaaaattacccgttttgtacgctataaagagatgaacgcgtttgacggtaaaaccatagacaaa
gaaacaggagaagtgctgcatcaaaaaacacacttcccacaaccttgggaatttttcgcacaagaagtcatg
attcgcgtcttcggcaaaccggacggcaaacccgaattcgaagaagccgataccctagaaaaactgcgcacg
ttgcttgccgaaaaattatcatctcgccccgaagccgtacacgaatacgttacgccactgtttgtttcacgc
gcgcccaatcggaagatgagcgggcaagggcatatggagaccgtcaaatccgccaaacgactggacgaaggc
gtcagcgtgttgcgcgtaccgctgacacagttaaaactgaaagacttggaaaaaatggtcaatcgggagcgc
gaacctaagctatacgaagcactgaaagcacggctggaagcacataaagacgatcctgccaaagccttgcc
gagccgttttacaaatacgataaagcaggcaaccgcacccaacaggtaaaagccgtacgcgtagagcaagta
cagaaaaccggcgtatgggtgcgcaaccataacggtattgccgacaacgcaaccatggtgcgcgtagatgtg
tttgagaaaggcgacaagtattatctggtaccgatttacagttggcaggtagcgaaagggattttgccggat
agggctgttgtacaagaaaagatgaagaagattggcaacttattgatgatagtttcaactttaaattctca
ttacaccctaatgatttagtcgaggttataacaaaaaagctagaatgtttggttactttgccagctgccat
cgaggcacaggtaatatcaatatacgcattcatgatcttgatcataaaattggcaaaaatggaatactggaa
ggtatcggcgtcaaaaccgccctttcattccaaaaataccaaattgacgaactgggcaaagaaatcagacca
tgccgtctgaaaaaacgcccgcctgtccgt[tacccatacgatgttccagattacgct]gcagctccagcagcg
[aagaaaaagaagctggat]taa (SEQ ID NO:303)

R: SV40 NLS, G: HA tag, O: synthetic NLS (1); all else NmCas9

Fig. 9A

Fig. 9B gRNA pair BCL11A-2983W and BCL11A-2981W Deletion Events

Deletion Sequence:

SEQ ID NO: 16301  AATAAAAGGCTGTTTTGGAATGTGTAGAGAGGCA....13.3kb....AACCCTGTGAATTGTATAAGTAGCACCAGTTCTG  SEQ ID NO: 16302

Deletion Length:

13,336 base pair deletion (~13.3kb)

SEQ ID NO: 16303  AATAAAAGGCTGTTTTGGAA————13.3kb————TGTATAAGTAGTAGCAC (x2) SEQ ID NO: 16304
SEQ ID NO: 16305  AATAAAAGGCTGTTTTGGAATGTA————13.3kb————AATTGTATAAGTAGCAC (x9) SEQ ID NO: 16306
SEQ ID NO: 16307  AATAAAAGGCTGTTTTGGAATGT————13.3kb————AATTGTATAAGTAGTAGCAC (x2) SEQ ID NO: 16308
SEQ ID NO: 16309  AATAAAAGGCTGTTTTGGAATGTA————13.3kb————AAGTAGCAC  SEQ ID NO: 16310
SEQ ID NO: 16311  AATAAAAGGCTGTTTTGGA————13.3kb————ATAAGTAGCAC  SEQ ID NO: 16312
SEQ ID NO: 16313  AATAAAAGGCTGTT————13.3kb————TGTATAAGTAGTAGCAC  SEQ ID NO: 16314

Fig. 12B gRNA Pair BCL11A-2995W and BCL11A-2984W Deletion Events

Deletion Sequence:

SEQ ID NO: 16317  CTGTTTTGGAATGTAGAGAGGCAGAGGGGC---13.3kb---TTACAGCCATAACAGGGTTCCAGTGAATTGTATAA  SEQ ID NO: 16318

Deletion Length:

13,327 base pair deletion (~13.3kb)

| SEQ ID NO: 16319 | CTGTTTTGGAA------13.3kb------TGTAT (x2) | SEQ ID NO: 16320 |
| SEQ ID NO: 16321 | CTGTTTTGGAATGTA------13.3kb------TGTAT | SEQ ID NO: 16322 |
| SEQ ID NO: 16323 | CTGTTTTGGAATGTA------13.3kb------AATTGTAT (x12) | SEQ ID NO: 16324 |
| SEQ ID NO: 16325 | CTGTTTTG------13.3kb------GAATTGTAT (x4) | SEQ ID NO: 16326 |
| SEQ ID NO: 16327 | CTGTTTTGGAATG------13.3kb------GAATTGTAT | SEQ ID NO: 16328 |
| SEQ ID NO: 16329 | CTGTTTTGGAATGTA------13.3kb------GTAT | SEQ ID NO: 16330 |

Fig. 13B

CRISPR/CAS-RELATED METHODS AND COMPOSITIONS FOR TREATING SICKLE CELL DISEASE

REFERENCE TO RELATED APPLICATIONS

The present application is a national phase of International Application No. PCT/US2015/022856, filed Mar. 26, 2015, which claims the benefit of U.S. Provisional Application No. 61/970,588, filed Mar. 26, 2014, and U.S. Provisional Application No. 62/084,487, filed Nov. 25, 2014, the contents of each of which are hereby incorporated by reference in their entirety.

SEQUENCE LISTING

This application contains a Sequence Listing, which was submitted in ASCII format via EFS-Web, and is hereby incorporated by reference in its entirety. The ASCII copy, created on Aug. 17, 2021, is named SupplementalSequenceListing.txt and is 3,998,410 bytes in size.

FIELD OF THE INVENTION

The invention relates to CRISPR/CAS-related methods and components for editing of a target nucleic acid sequence, or modulating expression of a target nucleic acid sequence, and applications thereof in connection with Sickle Cell Disease (SCD).

BACKGROUND

Sickle Cell Disease (SCD), also known as Sickle Cell Anemia (SCA), is a common inherited hematologic disease. It affects 80,000-90,000 people in the United States. It is common in people of African descent and in Hispanic-Americans with the prevalence of SCD being 1 in 500 and 1 in 1,000, respectively.

SCD is caused by a mutation in the beta-globin (HBB) gene. HBB is located on chromosome 11 within the HBB gene cluster, which includes genes encoding the delta globin chain, A gamma chain, G gamma chain. The alpha-globin gene is located on chromosome 16. A point mutation (e.g., GAG→GTG) results in the substitution of valine for glutamic acid at amino acid position 6 in exon 1 of the HBB gene. Beta hemoglobin chains with this mutation are expressed as HbS. The disease is inherited in an autosomal recessive manner, so that only patients with two HbS alleles have SCD. Subjects who have sickle cell trait (are heterozygous for HbS) only display a phenotype if they are severely dehydrated or oxygen deprived.

Normal adult hemoglobin (Hb) is composed of a tetramer made from two alpha-globin chains and two beta-globin chains. In SCD, the valine at position 6 of the beta-chain is hydrophobic and causes a change in conformation of the beta-globin protein when it is not bound to oxygen. HbS is more likely to polymerize and leads to the characteristic sickle shaped red blood cells (RBCs) found in SCD.

Sickle shape RBCs cause multiple manifestations of disease, which include, e.g., anemia, sickle cell crises, vasoocclusive crises, aplastic crises and acute chest syndrome. The disease has various manifestations, e.g., vaso-occlusive crisis, splenic sequestration crisis and anemia. Subjects may also suffer from acute chest crisis and infarcts of extremities, end organs and central nervous system. Treatment includes, e.g., hydration, transfusion and analgesics. Treatment of SCD also includes, e.g., the use of hydroxyurea, supplementation with folic acid, and penicillin prophylaxis during childhood. Bone marrow transplants have been demonstrated to cure SCD.

Thus, there remains a need for additional methods and compositions that can be used to treat SCD.

SUMMARY OF THE INVENTION

Methods and compositions discussed herein, provide for the treatment and prevention of Sickle Cell Disease (SCD), also known as Sickle Cell Anemia (SCA). SCD is an inherited hematologic disease.

In healthy individuals, two beta-globin molecules pair with two alpha-globin molecules to form normal hemoglobin (Hb). In SCD, mutations in the beta-globin (HBB) gene, e.g., a point mutation (GAG→GTG) that results in the substitution of valine for glutamic acid at amino acid position 6 of the beta-globin molecule, cause production of sickle hemoglobin (HbS). HbS is more likely to polymerize and leads to the characteristic sickle shaped red blood cells (RBCs). Sickle shaped RBCs give rise to multiple manifestations of disease, such as, anemia, sickle cell crises, vasoocclusive crises, aplastic crises and acute chest syndrome. Alpha-globin can also pair with fetal hemoglobin (HbF), which significantly moderates the severe anemia and other symptoms of SCD. However, the expression of HbF is negatively regulated by the BCL11A gene product.

Methods and compositions disclosed herein provide a number of approaches for treating SCD. As is discussed in more detail below, methods described herein provide for treating SCD by correcting a target position in the HBB gene to provide corrected, or functional, e.g., wild type, beta-globin. Methods and compositions discussed herein can be used to treat or prevent SCD by altering the BCL11A gene (also known as B-cell CLL/lymphoma 11A, BCL11A-L, BCL11A-S, BCL11A-XL, CTIP1, HBFQTL5 and ZNF). BCL11A encodes a zinc-finger protein that is involved in the regulation of globin gene expression. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating SCD disease phenotypes.

In one aspect, methods and compositions discussed herein, provide for the correction of the underlying genetic cause of SCD, e.g., the correction of a mutation at a target position in the HBB gene, e.g., correction of a mutation at amino acid position 6, e.g., an E6V substitution in the HBB gene.

Mutations in the HBB gene (also known as beta-globin and CD113t-C) have been shown to cause SCD. Mutations leading to SCD can be described based on their target positions in the HBB gene. In an embodiment, the target position is E6, e.g., E6V, in the HBB gene.

"SCD target point position", as used herein, refers to a target position in the HBB gene, typically a single nucleotide, which, if mutated, can result in a protein having a mutant amino acid and give rise to SCD. In an embodiment, the SCD target position is the target position at which a change can give rise to an E6 mutant protein, e.g., a protein having an E6V substitution.

While much of the disclosure herein is presented in the context of the mutation in the HBB gene that gives rise to an E6 mutant protein (e.g., E6V mutant protein), the methods and compositions herein are broadly applicable to any mutation, e.g., a point mutation or a deletion, in the HBB gene that gives rise to SCD.

While not wishing to be bound by theory, it is believed that, in an embodiment, a mutation at an SCD target point position in the HBB gene is corrected, e.g., by homology directed repair (HDR), as described herein.

In one aspect, methods and compositions discussed herein may be used to alter the BCL11A gene to treat or prevent SCD, by targeting the BCL11A gene, e.g., coding or non-coding regions of the BCL11A gene. Altering the BCL11A gene herein refers to reducing or eliminating (1) BCL11A gene expression, (2) BCL11A protein function, or (3) the level of BCL11A protein.

In an embodiment, the coding region (e.g., an early coding region) of the BCL11A gene is targeted for alteration. In an embodiment, a non-coding sequence (e.g., an enhancer region, a promoter region, an intron, 5'UTR, 3'UTR, or polyadenylation signal) is targeted for alteration.

In an embodiment, the method provides an alteration that comprises disrupting the BCL11A gene by the insertion or deletion of one or more nucleotides mediated by Cas9 (e.g., enzymatically active Cas9 (eaCas9), e.g., Cas9 nuclease or Cas9 nickase) as described below. This type of alteration is also referred to as "knocking out" the BCL11A gene.

In another embodiment, the method provides an alteration that does not comprise nucleotide insertion or deletion in the BCL11A gene and is mediated by enzymatically inactive Cas9 (eiCas9) or an eiCas9-fusion protein, as described below. This type of alteration is also referred to as "knocking down" the BCL11A gene.

In an embodiment, the methods and compositions discussed herein may be used to alter the BCL11A gene to treat or prevent SCD by knocking out one or both alleles in the BCL11A gene. In an embodiment, the coding region (e.g., an early coding region) of the BCL11A gene, is targeted to alter the gene. In an embodiment, a non-coding region of the BCL11A gene (e.g., an enhancer region, a promoter region, an intron, 5' UTR, 3'UTR, polyadenylation signal) is targeted to alter the gene. In an embodiment, an enhancer (e.g., a tissue-specific enhancer, e.g., a myeloid enhancer, e.g., an erythroid enhancer) is targeted to alter the gene. BCL11A erythroid enhancer comprises an approximate 12.4 kb fragment of BCL11A intron2, located between approximate +52.0 to +64.4 kilobases (kb) from the Transcription Start Site (TSS+52 kb to TSS+64.4 kb, see FIG. 10). It's also referred to herein as chromosome 2 location 60,716,189-60,728,612 (according to UCSC Genome Browser hg 19 human genome assembly). Three deoxyribonuclese I hypersensitive sites (DHSs), TSS+62 kb, TSS+58 kb and TSS+55 kb are located in this region. Deoxyribonuclease I sensitivity is a marker for gene regulatory elements. While not wishing to be bound by theory, it's believed that deleting the enhancer region (e.g., TSS+52 kb to TSS+64.4 kb) may reduce or eliminate BCL11A expression in erythroid precursors which leads to *gamma* globin derepression while sparing BCL11A expression in nonerythoroid lineages. In an embodiment, the method provides an alteration that comprises a deletion of the enhancer region (e.g., a tissue-specific enhancer, e.g., a myleoid enhancer, e.g., an erythroid enhancer) or a portion of the region resulting in disruption of one or more DNase 1-hypersensitive sites (DHS). In an embodiment, the method provides an alteration that comprises an insertion or deletion of one or more nucleotides. As described herein, in an embodiment, a targeted knockout approach is mediated by non-homologous end joining (NHEJ) using a CRISPR/Cas system comprising an enzymatically active Cas9 (eaCas9). In an embodiment, a targeted knockout approach alters the BCL11A gene. In an embodiment, a targeted knockout approach reduces or eliminates expression of functional BCL11A gene product. In an embodiment, targeting affects one or both alleles of the BCL11A gene. In an embodiment, an enhancer disruption approach reduces or eliminates expression of functional BCL11A gene product in the erythroid lineage.

"SCD target knockout position", as used herein, refers to a position in the BCL11A gene, which if altered, e.g., disrupted by insertion or deletion of one or more nucleotides, e.g., by NHEJ-mediated alteration, results in reduction or elimination of expression of functional BCL11A gene product. In an embodiment, the position is in the BCL11A coding region, e.g., an early coding region. In an embodiment, the position is in the BCL11A non-coding region, e.g., an enhancer region.

In an embodiment, methods and compositions discussed herein, provide for altering (e.g., knocking out) the BCL11A gene. In an embodiment, knocking out the BCL11A gene herein refers to (1) insertion or deletion (e.g., NHEJ-mediated insertion or deletion) of one or more nucleotides in close proximity to or within the early coding region of the BCL11A gene, or (2) deletion (e.g., NHEJ-mediated deletion) of a genomic sequence including the erythroid enhancer of the BCL11A gene, In an embodiment, the SCD target knockout position is altered by genome editing using the CRISPR/Cas9 system. The SCD target knockout position may be targeted by cleaving with either a single nuclease or dual nickases, e.g., to induce insertion or deletion (e.g., NHEJ-mediated insertion or deletion) of one or more nucleotides in close proximity to or within the early coding region of the SCD target knockout position or to delete (e.g., mediated by NHEJ) a genomic sequence including the erythroid enhancer of the BCL11A gene.

In an embodiment, the methods and compositions described herein introduce one or more breaks in close proximity to or within the early coding region in at least one allele of the BCL11A gene. In an embodiment, a single strand break is introduced in close proximity to or within the early coding region in at least one allele of the BCL11A gene. In an embodiment, the single strand break will be accompanied by an additional single strand break, positioned by a second gRNA molecule.

In an embodiment, a double strand break is introduced in close proximity to or within the early coding region in at least one allele of the BCL11A gene. In an embodiment, a double strand break will be accompanied by an additional single strand break positioned by a second gRNA molecule. In an embodiment, a double strand break will be accompanied by two additional single strand breaks positioned by a second gRNA molecule and a third gRNA molecule.

In an embodiment, a pair of single strand breaks is introduced in close proximity to or within the early coding region in at least one allele of the BCL11A gene. In an embodiment, the pair of single strand breaks will be accompanied by an additional double strand break, positioned by a third gRNA molecule. In an embodiment, the pair of single strand breaks will be accompanied by an additional pair of single strand breaks positioned by a third gRNA molecule and a fourth gRNA molecule.

In an embodiment, two double strand breaks are introduced to flank the erythroid enhancer at the in the BCL11A gene (one 5' and the other one 3' to the erythroid enhancer) to remove (e.g., delete) the genomic sequence including the erythroid enhancer. It is contemplated herein that in an embodiment the deletion of the genomic sequence including the erythroid enhancer is mediated by NHEJ. In an embodiment, the breaks (i.e., the two double strand breaks) are positioned to avoid unwanted deletion of certain elements, such as endogenous splice sites. The breaks, i.e., two double strand breaks, can be positioned upstream and downstream of the erythroid enhancer, as discussed herein.

In an embodiment, two sets of breaks (e.g., one double strand break and a pair of single strand breaks) are introduced to flank the erythroid enhancer in the BCL11A gene (one set 5' and the other set 3' to the erythroid enhancer) to remove (e.g., delete) the genomic sequence including the erythroid enhancer. It is contemplated herein that in an embodiment the deletion of the genomic sequence including the erythroid enhancer is mediated by NHEJ. In an embodiment, the breaks (i.e., the double strand break and the pair of single strand breaks) are positioned to avoid unwanted deletion of certain chromosome elements, such as endogenous splice sites. The breaks, e.g., the double strand break and the pair of single strand breaks, can be positioned upstream and downstream of the erythroid enhancer, as discussed herein.

In an embodiment, two sets of breaks (e.g., two pairs of single strand breaks) are introduced to flank the erythroid enhancer at the SCD target position in the BCL11A gene (one set 5' and the other set 3' to the erythroid enhancer) to remove (e.g., delete) the genomic sequence including the erythroid enhancer. It is contemplated herein that in an embodiment the deletion of the genomic sequence including the erythroid enhancer is mediated by NHEJ. In an embodiment, the breaks (i.e., the two pairs of single strand breaks) are positioned to avoid unwanted deletion of certain chromosome elements, such as endogenous splice sites. The breaks, e.g., the two pairs of single strand breaks, can be positioned upstream and downstream of the erythroid enhancer, as discussed herein.

In an embodiment, the methods and compositions discussed herein may be used to alter the BCL11A gene to treat or prevent SCD by knocking down one or both alleles of the BCL11A gene. In one embodiment, the coding region of the BCL11A gene, is targeted to alter the gene. In another embodiment, a non-coding region (e.g., an enhancer region, a promoter region, an intron, 5' UTR, 3'UTR, polyadenylation signal) of the BCL11A gene is targeted to alter the gene. In an embodiment, the promoter region of the BCL11A gene is targeted to knock down the expression of the BCL11A gene. A targeted knockdown approach alters, e.g., reduces or eliminates the expression of the BCL11A gene. As described herein, in an embodiment, a targeted knockdown is mediated by targeting an enzymatically inactive Cas9 (eiCas9) or an eiCas9 fused to a transcription repressor domain or chromatin modifying protein to alter transcription, e.g., to block, reduce, or decrease transcription, of the BCL11A gene.

"SCD target knockdown position", as used herein, refers to a position, e.g., in the BCL11A gene, which if targeted by an eiCas9 or an eiCas9 fusion described herein, results in reduction or elimination of expression of functional BCL11A gene product. In an embodiment, transcription is reduced or eliminated. In an embodiment, the position is in the BCL11A promoter sequence. In an embodiment, a position in the promoter sequence of the BCL11A gene is targeted by an enzymatically inactive Cas9 (eiCas9) or an eiCas9-fusion protein, as described herein.

In an embodiment, one or more gRNA molecule comprising a targeting domain configured to target an enzymatically inactive Cas9 (eiCas9) or an eiCas9 fusion protein (e.g., an eiCas9 fused to a transcription repressor domain), sufficiently close to a SCD target knockdown position to reduce, decrease or repress expression of the BCL11A gene.

"SCD target position", as used herein, refers to any of an SCD target point position, SCD target knockout position, or SCD target knockdown position, as described herein.

In one aspect, disclosed herein is a gRNA molecule, e.g., an isolated or non-naturally occurring gRNA molecule, comprising a targeting domain which is complementary with a target domain from the HBB gene or BCL11A gene.

When two or more gRNAs are used to position two or more cleavage events, e.g., double strand or single strand breaks, in a target nucleic acid, it is contemplated that the two or more cleavage events may be made by the same or different Cas9 proteins. For example, when two gRNAs are used to position two double strand breaks, a single Cas9 nuclease may be used to create both double strand breaks. When two or more gRNAs are used to position two or more single stranded breaks (single strand breaks), a single Cas9 nickase may be used to create the two or more single strand breaks. When two or more gRNAs are used to position at least one double strand break and at least one single strand break, two Cas9 proteins may be used, e.g., one Cas9 nuclease and one Cas9 nickase. It is contemplated that when two or more Cas9 proteins are used that the two or more Cas9 proteins may be delivered sequentially to control specificity of a double strand versus a single strand break at the desired position in the target nucleic acid.

In an embodiment, the targeting domain of the first gRNA molecule and the targeting domain of the second gRNA molecule hybridize to the target domain through complementary base pairing to opposite strands of the target nucleic acid molecule. In an embodiment, the gRNA molecule and the second gRNA molecule are configured such that the PAMs are oriented outward.

In an embodiment, the targeting domain of a gRNA molecule is configured to avoid unwanted target chromosome elements, such as repeat elements, e.g., an Alu repeat, or the endogenous splice sites, in the target domain. The gRNA molecule may be a first, second, third and/or fourth gRNA molecule.

In an embodiment, the targeting domain of a gRNA molecule is configured to position a cleavage event sufficiently far from a preselected nucleotide, e.g., the nucleotide of a coding region, such that the nucleotide is not altered. In an embodiment, the targeting domain of a gRNA molecule is configured to position an intronic cleavage event sufficiently far from an intron/exon border, or naturally occurring splice signal, to avoid alteration of the exonic sequence or unwanted splicing events. The gRNA molecule may be a first, second, third and/or fourth gRNA molecule, as described herein.

In an embodiment, a point mutation in the HBB gene, e.g., at E6, e.g., E6V, is targeted, e.g., for correction. In an embodiment, the targeting domain of a gRNA molecule comprises a sequence that is the same as, or differs by no more than 1, 2, 3, 4, or 5 nucleotides from, a targeting domain sequence from any one of Tables 1A-1D. In an embodiment, the targeting domain is selected from those in Tables 1A-1D. For example, in an embodiment, the targeting domain is:

AAGGUGAACGUGGAUGAAGU; (SEQ ID NO: 387)

GUAACGGCAGACUUCUCCUC; (SEQ ID NO: 388)

-continued

GUGAACGUGGAUGAAGU; (SEQ ID NO: 389)

or

ACGGCAGACUUCUCCUC. (SEQ ID NO: 390)

In an embodiment, when the SCD target point position is E6, e.g., E6V, and two gRNAs are used to position two breaks, e.g., two single stranded breaks, in the target nucleic acid sequence, the targeting domain of each guide RNA is selected from one of Tables 1A-1D.

In an embodiment, a point mutation in the HBB gene, e.g., at E6, e.g., E6V, is targeted, e.g., for correction. In an embodiment, the targeting domain of a gRNA molecule comprises a sequence that is the same as, or differs by no more than 1, 2, 3, 4, or 5 nucleotides from, a targeting domain sequence from any one of Tables 13A-13D. In an embodiment, the targeting domain is selected from those in Tables 13A-13D. For example, in an embodiment, the targeting domain is:

GGUGCACCUGACUCCUG; (SEQ ID NO: 6803)

or

GUAACGGCAGACUUCUCCAC. (SEQ ID NO: 6804)

In an embodiment, when the SCD target point position is E6, e.g., E6V, and two gRNAs are used to position two breaks, e.g., two single stranded breaks, in the target nucleic acid sequence, the targeting domain of each guide RNA is selected from one of Tables 13A-13D.

In an embodiment, a point mutation in the HBB gene, e.g., at E6, e.g., E6V, is targeted, e.g., for correction. In an embodiment, the targeting domain of a gRNA molecule comprises a sequence that is the same as, or differs by no more than 1, 2, 3, 4, or 5 nucleotides from, a targeting domain sequence from any one of Tables 14A-14C. In an embodiment, the targeting domain is selected from those in Tables 14A-14C.

In an embodiment, when the SCD target point position is E6, e.g., E6V, and two gRNAs are used to position two breaks, e.g., two single stranded breaks, in the target nucleic acid sequence, each guide RNA is selected from one of Tables 14A-14C.

In an embodiment, a point mutation in the HBB gene, e.g., at E6, e.g., E6V, is targeted, e.g., for correction. In an embodiment, the targeting domain of a gRNA molecule comprises a sequence that is the same as, or differs by no more than 1, 2, 3, 4, or 5 nucleotides from, a targeting domain sequence from any one of Tables 24A-24D. In an embodiment, the targeting domain is selected from those in Tables 24A-24D.

In an embodiment, when the SCD target point position is E6, e.g., E6V, and two gRNAs are used to position two breaks, e.g., two single stranded breaks, in the target nucleic acid sequence, the targeting domain of each guide RNA is selected from one of Tables 24A-24D.

In an embodiment, a point mutation in the HBB gene, e.g., at E6, e.g., E6V, is targeted, e.g., for correction. In an embodiment, the targeting domain of a gRNA molecule comprises a sequence that is the same as, or differs by no more than 1, 2, 3, 4, or 5 nucleotides from, a targeting domain sequence from any one of Tables 25A-25B. In an embodiment, the targeting domain is selected from those in Tables 25A-25B.

In an embodiment, when the SCD target point position is E6, e.g., E6V, and two gRNAs are used to position two breaks, e.g., two single stranded breaks, in the target nucleic acid sequence, the targeting domain of each guide RNA is selected from one of Tables 25A-25B.

In an embodiment, a point mutation in the HBB gene, e.g., at E6, e.g., E6V, is targeted, e.g., for correction. In an embodiment, the targeting domain of a gRNA molecule comprises a sequence that is the same as, or differs by no more than 1, 2, 3, 4, or 5 nucleotides from, a targeting domain sequence from Table 26. In an embodiment, the targeting domain is selected from those in Table 26.

In an embodiment, when the SCD target point position is E6, e.g., E6V, and two gRNAs are used to position two breaks, e.g., two single stranded breaks, in the target nucleic acid sequence, the targeting domain of each guide RNA is selected from Table 26. In another embodiment, a position in the coding region, e.g., the early coding region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Tables 2A-2F. In an embodiment, the targeting domain is selected from those in Tables 2A-2F. In another embodiment, the targeting domain is:

UGGCAUCCAGGUCACGCCAG; (SEQ ID NO: 486)

GAUGCUUUUUUCAUCUCGAU; (SEQ ID NO: 487)

GCAUCCAAUCCCGUGGAGGU; (SEQ ID NO: 488)

UUUUCAUCUCGAUUGGUGAA; (SEQ ID NO: 489)

CCAGAUGAACUUCCCAUUGG; (SEQ ID NO: 490)

AGGAGGUCAUGAUCCCCUUC; (SEQ ID NO: 491)

CAUCCAGGUCACGCCAG; (SEQ ID NO: 492)

GCUUUUUUCAUCUCGAU; (SEQ ID NO: 493)

UCCAAUCCCGUGGAGGU; (SEQ ID NO: 494)

UCAUCUCGAUUGGUGAA; (SEQ ID NO: 495)

GAUGAACUUCCCAUUGG; (SEQ ID NO: 496)

or

AGGUCAUGAUCCCCUUC. (SEQ ID NO: 497)

In an embodiment, when the SCD target knockout position is the BCL11A coding region, e.g., early coding region, and more than one gRNA is used to position breaks, e.g., two single stranded breaks or two double stranded breaks, or a combination of single strand and double strand breaks, e.g., to create one or more indels, in the target nucleic acid sequence, the targeting domain of each guide RNA is selected from one of Tables 2A-2F.

In another embodiment, a position in the coding region, e.g., the early coding region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Table 4A-4E. In an embodiment, the targeting domain is selected from those in Table 4A-4E. In another embodiment, the targeting domain is:

GAGCUCCAUGUGCAGAACGA; (SEQ ID NO: 3073)

GAGCUCCCAACGGGCCG; (SEQ ID NO: 3074)

GAGUGCAGAAUAUGCCCCGC; (SEQ ID NO: 3075)

GAUAAACAAUCGUCAUCCUC; (SEQ ID NO: 3076)

GAUGCCAACCUCCACGGGAU; (SEQ ID NO: 3077)

GCAGAAUAUGCCCCGCA; (SEQ ID NO: 3078)

GCAUCCAAUCCCGUGGAGGU; (SEQ ID NO: 3079)

GCCAACCUCCACGGGAU; (SEQ ID NO: 3080)

GCUCCCAACGGGCCGUGGUC; (SEQ ID NO: 3081)
or

GGAGCUCUAAUCCCCACGCC. (SEQ ID NO: 3082)

In an embodiment, when the SCD target knockout position is the BCL11A coding region, e.g., early coding region, and more than one gRNA is used to position breaks, e.g., two single strand breaks or two double strand breaks, or a combination of single strand and double strand breaks, e.g., to create one or more indels, in the target nucleic acid sequence, the targeting domain of each guide RNA is selected from one of Table 4A-4E.

In another embodiment, a position in the coding region, e.g., the early coding region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Table 5A-5E. In an embodiment, the targeting domain is selected from those in Table 5A-5E.

In an embodiment, when the SCD target knockout position is the BCL11A coding region, e.g., early coding region, and more than one gRNA is used to position breaks, e.g., two single strand breaks or two double strand breaks, or a combination of single strand and double strand breaks, e.g., to create one or more indels, in the target nucleic acid sequence, the targeting domain of each guide RNA is selected from one of Table 5A-5E.

In another embodiment, a position in the coding region, e.g., the early coding region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Table 6A-6B. In an embodiment, the targeting domain is selected from those in Table 6A-6B.

In an embodiment, when the SCD target knockout position is the BCL11A coding region, e.g., early coding region, and more than one gRNA is used to position breaks, e.g., two single strand breaks or two double strand breaks, or a combination of single strand and double strand breaks, e.g., to create one or more indels, in the target nucleic acid sequence, the targeting domain of each guide RNA is selected from one of Table 6A-6B.

In another embodiment, a position in the coding region, e.g., the early coding region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Table 15A-15D. In an embodiment, the targeting domain is selected from those in Table 15A-15D.

In an embodiment, when the SCD target knockout position is the BCL11A coding region, e.g., early coding region, and more than one gRNA is used to position breaks, e.g., two single strand breaks or two double strand breaks, or a combination of single strand and double strand breaks, e.g., to create one or more indels, in the target nucleic acid sequence, the targeting domain of each guide RNA is selected from one of Table 15A-15D.

In another embodiment, a position in the coding region, e.g., the early coding region, of the BCL11A gene is targeted. e.g., for knockout. In an embodiment, the targeting domain comprises a sequence that is the same as, or differs by no more than 1, 2, 3, 4, or 5 nucleotides from, a targeting domain sequence from any one of Table 16A-16E. In an embodiment, the targeting domain is selected from those in Table 16A-16E.

In an embodiment, when the SCD target knockout position is the BCL11A coding region, e.g., early coding region, and more than one gRNA is used to position breaks, e.g., two single strand breaks or two double strand breaks, or a combination of single strand and double strand breaks, e.g., to create one or more indels, in the target nucleic acid sequence, the targeting domain of each guide RNA is selected from one of Table 16A-16E.

In another embodiment, a position in the coding region, e.g., the early coding region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Table 17A-17B. In an embodiment, the targeting domain is selected from those in Table 17A-17B.

In an embodiment, when the SCD target knockout position is the BCL11A coding region, e.g., early coding region, and more than one gRNA is used to position breaks, e.g., two single strand breaks or two double strand breaks, or a combination of single strand and double strand breaks, e.g., to create one or more indels, in the target nucleic acid sequence, the targeting domain of each guide RNA is selected from one of Table 17A-17B.

In another embodiment, a position in the non-coding region, e.g., the enhancer region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Tables 7A-7D. In an embodiment, the targeting domain is selected from those in Tables 7A-7D. In another embodiment, the targeting domain is:

```
                              (SEQ ID NO: 4835)
GAAAAUACUUACUGUACUGC;

(SEQ ID NO: 4836)
GAAAGCAGUGUAAGGCU;

(SEQ ID NO: 4837)
GGCUGUUUUGGAAUGUAGAG;
or (SEQ ID NO: 4838)
GUGCUACUUAUACAAUUCAC.
```

In an embodiment, when the SCD target knockout position is the non-coding region, e.g., the enhancer region, of the BCL11A gene, and more than one gRNA is used to position breaks, e.g., two single strand breaks or two double strand breaks, or a combination of single and double strand breaks, e.g., to create a deletion, in the target nucleic acid sequence, the targeting domain of each guide RNA is selected from one of Table 7A-7D.

In another embodiment, a position in the non-coding region, e.g., the enhancer region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Tables 8A-8D. In an embodiment, the targeting domain is selected from those in Tables 8A-8D.

In an embodiment, when the SCD target knockout position is the non-coding region, e.g., the enhancer region, of the BCL11A gene, and more than one gRNA is used to position breaks, e.g., two single strand breaks or two double strand breaks, or a combination of single and double strand breaks, e.g., to create a deletion, in the target nucleic acid sequence, the targeting domain of each guide RNA is selected from one of Table 8A-8D.

In another embodiment, a position in the non-coding region, e.g., the enhancer region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from Table 9. In an embodiment, the targeting domain is selected from those in Table 9.

In an embodiment, when the SCD target knockout position is the non-coding region, e.g., the enhancer region, of the BCL11A gene, and more than one gRNA is used to position breaks, e.g., two single strand breaks or two double strand breaks, or a combination of single and double strand breaks, e.g., to create a deletion, in the target nucleic acid sequence, the targeting domain of each guide RNA is selected from one of Table 9.

In another embodiment, a position in the non-coding region, e.g., the enhancer region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Tables 21A-21E. In an embodiment, the targeting domain is selected from those in Tables 21A-21E. In an embodiment, when the SCD target knockout position is the non-coding region, e.g., the enhancer region, of the BCL11A gene, and more than one gRNA is used to position breaks, e.g., two single strand breaks or two double strand breaks, or a combination of single strand and double strand breaks, e.g., to create a deletion, in the target nucleic acid sequence, the targeting domain of each guide RNA is selected from one of Table 21A-21E.

In another embodiment, a position in the non-coding region, e.g., the enhancer region, of the BCL11A gene is targeted. e.g., for knockout. In an embodiment, the targeting domain comprises a sequence that is the same as, or differs by no more than 1, 2, 3, 4, or 5 nucleotides from, a targeting domain sequence from any one of Tables 22A-22E. In an embodiment, the targeting domain is selected from those in Tables 22A-22E. In an embodiment, when the SCD target knockout position is the non-coding region, e.g., the enhancer region, of the BCL11A gene, and more than one gRNA is used to position breaks, e.g., two single strand breaks or two double strand breaks, or a combination of single strand and double strand breaks, e.g., to create a deletion, in the target nucleic acid sequence, the targeting domain of each guide RNA is selected from one of Table 22A-22E.

In another embodiment, a position in the non-coding region, e.g., the enhancer region, of the BCL11A gene is targeted, e.g., for knockout. In an embodiment, the targeting domain comprises a sequence that is the same as, or differs by no more than 1, 2, 3, 4, or 5 nucleotides from, a targeting domain sequence from any one of Tables 23A-23C. In an embodiment, the targeting domain is selected from those in Tables 23A-23C.

In an embodiment, when the SCD target knockout position is the non-coding region, e.g., the enhancer region, of the BCL11A gene, and more than one gRNA is used to position breaks, e.g., two single strand breaks or two double strand breaks, or a combination of single strand and double strand breaks, e.g., to create a deletion, in the target nucleic acid sequence, the targeting domain of each guide RNA is selected from one of Table 23A-23C.

In an embodiment, the targeting domain of the gRNA molecule is configured to target an enzymatically inactive Cas9 (eiCas9) or an eiCas9 fusion protein (e.g., an eiCas9 fused to a transcription repressor domain), sufficiently close to an SCD knockdown target position to reduce, decrease or repress expression of the BCL11A gene. In an embodiment, the targeting domain is configured to target the promoter region of the BCL11A gene to block transcription initiation, binding of one or more transcription enhancers or activators, and/or RNA polymerase. One or more gRNA may be used to target an eiCas9 to the promoter region of the BCL11A gene.

In an embodiment, when the BCL11A promoter region is targeted, e.g., for knockdown, the targeting domain can comprise a sequence that is the same as, or differs by no more than 1, 2, 3, 4, or 5 nucleotides from, a targeting domain sequence from any one of Tables 3A-3C. In an embodiment, the targeting domain is selected from those in Tables 3A-3C.

In an embodiment, when the SCD target knockdown position is the BCL11A promoter region and more than one gRNA is used to position an eiCas9 or an eiCas9-fusion protein (e.g., an eiCas9-transcription repressor domain fusion protein), in the target nucleic acid sequence, the targeting domain of each guide RNA is selected from one of Tables 3A-3C.

In an embodiment, when the BCL11A promoter region is targeted, e.g., for knockdown, the targeting domain can comprise a sequence that is the same as, or differs by no more than 1, 2, 3, 4, or 5 nucleotides from, a targeting domain sequence from any one of Tables 10A-10D. In an embodiment, the targeting domain is selected from those in Tables 10A-10D. In another embodiment, the targeting domain is:

GACGACGGCUCGGUUCACAU; (SEQ ID NO: 4981)

GACGCCAGACGCGGCCCCCG; (SEQ ID NO: 4982)

GCCUUGCUUGCGGCGAGACA; (SEQ ID NO: 4983)

GGCUCCGCGGACGCCAGACG; (SEQ ID NO: 4984)

GACGGCUCGGUUCACAU; (SEQ ID NO: 4985)

GCCGCGUCUGGCGUCCG; (SEQ ID NO: 4986)
or

GCGGGCGGACGACGGCU. (SEQ ID NO: 4987)

In an embodiment, when the SCD target knockdown position is the BCL11A promoter region and more than one gRNA is used to position an eiCas9 or an eiCas9-fusion protein (e.g., an eiCas9-transcription repressor domain fusion protein), in the target nucleic acid sequence, each guide RNA is selected from one of Tables 10A-10D.

In an embodiment, when the BCL11A promoter region is targeted, e.g., for knockdown, the targeting domain can comprise a sequence that is the same as, or differs by no more than 1, 2, 3, 4, or 5 nucleotides from, a targeting domain sequence from any one of Tables 11A-11D. In an embodiment, the targeting domain is selected from those in Tables 11A-11D.

In an embodiment, when the SCD target knockdown position is the BCL11A promoter region and more than one gRNA is used to position an eiCas9 or an eiCas9-fusion protein (e.g., an eiCas9-transcription repressor domain fusion protein), in the target nucleic acid sequence, each guide RNA is selected from one of Tables 11A-11D.

In an embodiment, when the BCL11A promoter region is targeted, e.g., for knockdown, the targeting domain can comprise a sequence that is the same as, or differs by no more than 1, 2, 3, 4, or 5 nucleotides from, a targeting domain sequence from Table 12. In an embodiment, the targeting domain is selected from those in Table 12.

In an embodiment, when the SCD target knockdown position is the BCL11A promoter region and more than one gRNA is used to position an eiCas9 or an eiCas9-fusion protein (e.g., an eiCas9-transcription repressor domain fusion protein), in the target nucleic acid sequence, each guide RNA is selected from Table 12.

In an embodiment, when the BCL11A promoter region is targeted, e.g., for knockdown, the targeting domain can comprise a sequence that is the same as, or differs by no more than 1, 2, 3, 4, or 5 nucleotides from, a targeting domain sequence from any one of Tables 18A-18C. In an embodiment, the targeting domain is selected from those in Tables 18A-18C.

In an embodiment, when the SCD target knockdown position is the BCL11A promoter region and more than one gRNA is used to position an eiCas9 or an eiCas9-fusion protein (e.g., an eiCas9-transcription repressor domain fusion protein), in the target nucleic acid sequence, each guide RNA is selected from one of Tables 18A-18C.

In an embodiment, when the BCL11A promoter region is targeted, e.g., for knockdown, the targeting domain can comprise a sequence that is the same as, or differs by no more than 1, 2, 3, 4, or 5 nucleotides from, a targeting domain sequence from any one of Tables 19A-19E. In an embodiment, the targeting domain is selected from those in Tables 19A-19E.

In an embodiment, when the SCD target knockdown position is the BCL11A promoter region and more than one gRNA is used to position an eiCas9 or an eiCas9-fusion protein (e.g., an eiCas9-transcription repressor domain fusion protein), in the target nucleic acid sequence, each guide RNA is selected from one of Tables 19A-19E.

In an embodiment, when the BCL11A promoter region is targeted, e.g., for knockdown, the targeting domain can comprise a sequence that is the same as, or differs by no more than 1, 2, 3, 4, or 5 nucleotides from, a targeting domain sequence from any one of Tables 20A-20C. In an embodiment, the targeting domain is selected from those in Tables 20A-20C.

In an embodiment, when the SCD target knockdown position is the BCL11A promoter region and more than one gRNA is used to position an eiCas9 or an eiCas9-fusion protein (e.g., an eiCas9-transcription repressor domain fusion protein), in the target nucleic acid sequence, each guide RNA is selected from one of Tables 20A-20C.

In an embodiment, the targeting domain comprises a sequence that is the same as, or differs by no more than 1, 2, 3, 4, or 5 nucleotides from, a targeting domain sequence selected from any one of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. In an embodiment, the targeting domain is selected from those in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31.

In an embodiment, the targeting domain which is complementary with the BCL11A gene is 16 nucleotides or more in length. In an embodiment, the targeting domain is 16 nucleotides in length. In an embodiment, the targeting domain is 17 nucleotides in length. In another embodiment, the targeting domain is 18 nucleotides in length. In still another embodiment, the targeting domain is 19 nucleotides in length. In still another embodiment, the targeting domain is 20 nucleotides in length. In still another embodiment, the targeting domain is 21 nucleotides in length. In still another embodiment, the targeting domain is 22 nucleotides in length. In still another embodiment, the targeting domain is 23 nucleotides in length. In still another embodiment, the targeting domain is 24 nucleotides in length. In still another embodiment, the targeting domain is 25 nucleotides in length. In still another embodiment, the targeting domain is 26 nucleotides in length.

In an embodiment, the targeting domain comprises 16 nucleotides.

In an embodiment, the targeting domain comprises 17 nucleotides.

In an embodiment, the targeting domain comprises 18 nucleotides.

In an embodiment, the targeting domain comprises 19 nucleotides.

In an embodiment, the targeting domain comprises 20 nucleotides.

In an embodiment, the targeting domain comprises 21 nucleotides.

In an embodiment, the targeting domain comprises 22 nucleotides.

In an embodiment, the targeting domain comprises 23 nucleotides.

In an embodiment, the targeting domain comprises 24 nucleotides.

In an embodiment, the targeting domain comprises 25 nucleotides.

In an embodiment, the targeting domain comprises 26 nucleotides.

In an embodiment, the gRNA, e.g., a gRNA comprising a targeting domain, which is complementary with the HBB gene or BCL11A gene, is a modular gRNA. In another embodiment, the gRNA is a unimolecular or chimeric gRNA.

HBB gRNA as described herein may comprise from 5' to 3': a targeting domain (comprising a "core domain", and optionally a "secondary domain"); a first complementarity domain; a linking domain; a second complementarity domain; a proximal domain; and a tail domain. In an embodiment, the proximal domain and tail domain are taken together as a single domain.

In an embodiment, a gRNA comprises a linking domain of no more than 25 nucleotides in length; a proximal and tail domain, that taken together, are at least 20 nucleotides in length; and a targeting domain equal to or greater than 16, 17, 18, 19, 20, 21, 22, 23, 24, 25 or 26 nucleotides in length.

In another embodiment, a gRNA comprises a linking domain of no more than 25 nucleotides in length; a proximal and tail domain, that taken together, are at least 25 nucleotides in length; and a targeting domain equal to or greater than 16, 17, 18, 19, 20, 21, 22, 23, 24, 25 or 26 nucleotides in length.

In another embodiment, a gRNA comprises a linking domain of no more than 25 nucleotides in length; a proximal and tail domain, that taken together, are at least 30 nucleotides in length; and a targeting domain equal to or greater than 16, 17, 18, 19, 20, 21, 22, 23, 24, 25 or 26 nucleotides in length.

In another embodiment, a gRNA comprises a linking domain of no more than 25 nucleotides in length; a proximal and tail domain, that taken together, are at least 40 nucleotides in length; and a targeting domain equal to or greater than 16, 17, 18, 19, 20, 21, 22, 23, 24, 25 or 26 nucleotides in length.

A cleavage event, e.g., a double strand or single strand break, is generated by a Cas9 molecule. The Cas9 molecule may be an enzymatically active Cas9 (eaCas9) molecule, e.g., an eaCas9 molecule that forms a double strand break in a target nucleic acid or an eaCas9 molecule forms a single strand break in a target nucleic acid (e.g., a nickase molecule). Alternatively, in an embodiment, the Cas9 molecule may be an enzymatically inactive Cas9 (eiCas9) molecule or a modified eiCas9 molecule, e.g., the eiCas9 molecule is fused to Krüppel-associated box (KRAB) to generate an eiCas9-KRAB fusion protein molecule.

In an embodiment, the eaCas9 molecule catalyzes a double strand break.

In an embodiment, the eaCas9 molecule comprises HNH-like domain cleavage activity but has no, or no significant, N-terminal RuvC-like domain cleavage activity. In this case, the eaCas9 molecule is an HNH-like domain nickase, e.g., the eaCas9 molecule comprises a mutation at D10, e.g., D10A. In another embodiment, the eaCas9 molecule comprises N-terminal RuvC-like domain cleavage activity but has no, or no significant, HNH-like domain cleavage activity. In an embodiment, the eaCas9 molecule is an N-terminal RuvC-like domain nickase, e.g., the eaCas9 molecule comprises a mutation at H840, e.g., H840A. In an embodiment, the eaCas9 molecule is an N-terminal RuvC-like domain nickase, e.g., the eaCas9 molecule comprises a mutation at N863, e.g., N863A.

In an embodiment, a single strand break is formed in the strand of the target nucleic acid to which the targeting domain of said gRNA is complementary. In another embodiment, a single strand break is formed in the strand of the target nucleic acid other than the strand to which the targeting domain of said gRNA is complementary.

In another aspect, disclosed herein is a nucleic acid, e.g., an isolated or non-naturally occurring nucleic acid, e.g., DNA, that comprises (a) a sequence that encodes a gRNA molecule comprising a targeting domain that is complementary with a target domain, e.g., with an SCD target position, in the HBB gene or BCL11A gene as disclosed herein.

In an embodiment, the nucleic acid encodes a gRNA molecule, e.g., a first gRNA molecule, comprising a targeting domain configured to provide a cleavage event, e.g., a double strand break or a single strand break, sufficiently close to an SCD target position in the HBB gene or BCL11A gene to allow alteration, e.g., alteration associated with HDR or NHEJ, of the an SCD target position in the HBB gene or BCL11A gene.

In an embodiment, the nucleic acid encodes a gRNA molecule, e.g., a first gRNA molecule, comprising a targeting domain configured to target an enzymatically inactive Cas9 (eiCas9) or an eiCas9 fusion protein (e.g., an eiCas9 fused to a transcription repressor domain), sufficiently close to an SCD knockdown target position to reduce, decrease or repress expression of the BCL11A gene.

In an embodiment, the nucleic acid encodes a gRNA molecule, e.g., the first gRNA molecule, comprising a targeting domain comprising a sequence that is the same as, or differs by no more than 1, 2, 3, 4, or 5 nucleotides from, a targeting domain sequence from any one of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. In an embodiment, the nucleic acid encodes a gRNA molecule comprising a targeting domain is selected from those in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31.

In an embodiment, the nucleic acid encodes a modular gRNA, e.g., one or more nucleic acids encode a modular gRNA. In another embodiment, the nucleic acid encodes a chimeric gRNA. The nucleic acid may encode a gRNA, e.g., the first gRNA molecule, comprising a targeting domain comprising 16 nucleotides or more in length. In one embodiment, the nucleic acid encodes a gRNA, e.g., the first gRNA molecule, comprising a targeting domain that is 16 nucleotides in length. In another embodiment, the nucleic acid encodes a gRNA, e.g., the first gRNA molecule, comprising a targeting domain that is 17 nucleotides in length. In still another embodiment, the nucleic acid encodes a gRNA, e.g., the first gRNA molecule, comprising a targeting domain that is 18 nucleotides in length. In still another embodiment, the nucleic acid encodes a gRNA, e.g., the first gRNA molecule, comprising a targeting domain that is 19 nucleotides in length. In still another embodiment, the nucleic acid encodes a gRNA, e.g., the first gRNA molecule, comprising a targeting domain that is 20 nucleotides in length. In still another embodiment, the nucleic acid encodes a gRNA, e.g., the first gRNA molecule, comprising a targeting domain that is 21 nucleotides in length. In still another embodiment, the nucleic acid encodes a gRNA, e.g., the first gRNA molecule, comprising a targeting domain that is 22 nucleotides in length. In still another embodiment, the nucleic acid encodes a gRNA, e.g., the first gRNA molecule, comprising a targeting domain that is 23 nucleotides in length. In still another embodiment, the nucleic acid encodes a gRNA, e.g., the first gRNA molecule, comprising a targeting domain that is 24 nucleotides in length. In still another embodiment, the nucleic acid encodes a gRNA, e.g., the first gRNA molecule, comprising a targeting domain that is 25 nucleotides in length. In still another embodiment, the nucleic acid encodes a gRNA, e.g., the first gRNA molecule, comprising a targeting domain that is 26 nucleotides in length.

In an embodiment, the targeting domain comprises 16 nucleotides.

In an embodiment, the targeting domain comprises 17 nucleotides.

In an embodiment, the targeting domain comprises 18 nucleotides.

In an embodiment, the targeting domain comprises 19 nucleotides.

In an embodiment, the targeting domain comprises 20 nucleotides.

In an embodiment, the targeting domain comprises 21 nucleotides.

In an embodiment, the targeting domain comprises 22 nucleotides.

In an embodiment, the targeting domain comprises 23 nucleotides.

In an embodiment, the targeting domain comprises 24 nucleotides.

In an embodiment, the targeting domain comprises 25 nucleotides.

In an embodiment, the targeting domain comprises 26 nucleotides.

In an embodiment, a nucleic acid encodes a gRNA comprising from 5' to 3': a targeting domain (comprising a "core domain", and optionally a "secondary domain"); a first complementarity domain; a linking domain; a second complementarity domain; a proximal domain; and a tail domain. In an embodiment, the proximal domain and tail domain are taken together as a single domain.

In an embodiment, a nucleic acid encodes a gRNA e.g., the first gRNA molecule, comprising a linking domain of no more than 25 nucleotides in length; a proximal and tail domain, that taken together, are at least 20 nucleotides in length; and a targeting domain equal to or greater than 16, 17, 18, 19, 20, 21, 22, 23, 24, 25 or 26 nucleotides in length.

In an embodiment, a nucleic acid encodes a gRNA e.g., the first gRNA molecule, comprising a linking domain of no more than 25 nucleotides in length; a proximal and tail domain, that taken together, are at least 30 nucleotides in length; and a targeting domain equal to or greater than 16, 17, 18, 19, 20, 21, 22, 23, 24, 25 or 26 nucleotides in length.

In an embodiment, a nucleic acid encodes a gRNA e.g., the first gRNA molecule, comprising a linking domain of no more than 25 nucleotides in length; a proximal and tail domain, that taken together, are at least 30 nucleotides in length; and a targeting domain equal to or greater than 16, 17, 18, 19, 20, 21, 22, 23, 24, 25 or 26 nucleotides in length.

In an embodiment, a nucleic acid encodes a gRNA comprising e.g., the first gRNA molecule, a linking domain of no more than 25 nucleotides in length; a proximal and tail domain, that taken together, are at least 40 nucleotides in length; and a targeting domain equal to or greater than 16, 17, 18, 19, 20, 21, 22, 23, 24, 25 or 26 nucleotides in length.

In an embodiment, a nucleic acid comprises (a) a sequence that encodes a gRNA molecule e.g., the first gRNA molecule, comprising a targeting domain that is complementary with a target domain in the HBB gene or BCL11A gene as disclosed herein, and further comprising (b) a sequence that encodes a Cas9 molecule.

The Cas9 molecule may be an enzymatically active Cas9 (eaCas9) molecule, e.g., an eaCas9 molecule that forms a double strand break in a target nucleic acid or an eaCas9 molecule forms a single strand break in a target nucleic acid (e.g., a nickase molecule). Alternatively, in an embodiment, the Cas9 molecule may be an enzymatically inactive Cas9 (eiCas9) molecule or a modified eiCas9 molecule, e.g., the eiCas9 molecule is fused to Krüppel-associated box (KRAB) to generate an eiCas9-KRAB fusion protein molecule.

A nucleic acid disclosed herein may comprise (a) a sequence that encodes a gRNA molecule comprising a targeting domain that is complementary with a target domain in the HBB gene or BCL11A gene as disclosed herein; (b) a sequence that encodes a Cas9 molecule; and further comprises (c)(i) a sequence that encodes a second gRNA molecule described herein having a targeting domain that is complementary to a second target domain of the HBB gene or BCL11A gene, and optionally, (c)(ii) a sequence that encodes a third gRNA molecule described herein having a targeting domain that is complementary to a third target domain of the HBB gene or BCL11A gene; and optionally, (c)(iii) a sequence that encodes a fourth gRNA molecule described herein having a targeting domain that is complementary to a fourth target domain of the HBB gene or BCL11A gene.

In an embodiment, a nucleic acid encodes a second gRNA molecule comprising a targeting domain configured to provide a cleavage event, e.g., a double strand break or a single strand break, sufficiently close to an SCD target position in the HBB gene or BCL11A gene, to allow alteration, e.g., alteration associated with HDR or NHEJ, of an SCD target position in the HBB gene or BCL11A gene, either alone or in combination with the break positioned by said first gRNA molecule.

In an embodiment, the nucleic acid encodes a second gRNA molecule comprising a targeting domain configured to target an enzymatically inactive Cas9 (eiCas9) or an eiCas9 fusion protein (e.g., an eiCas9 fused to a transcription repressor domain), sufficiently close to an SCD knockdown target position to reduce, decrease or repress expression of the BCL11A gene.

In an embodiment, a nucleic acid encodes a third gRNA molecule comprising a targeting domain configured to provide a cleavage event, e.g., a double strand break or a single strand break, sufficiently close to an SCD target position in the HBB gene or BCL11A gene to allow alteration, e.g., alteration associated with HDR or NHEJ, of an SCD target position in the HBB gene or BCL11A gene, either alone or in combination with the break positioned by the first and/or second gRNA molecule.

In an embodiment, the nucleic acid encodes a third gRNA molecule comprising a targeting domain configured to target an enzymatically inactive Cas9 (eiCas9) or an eiCas9 fusion protein (e.g., an eiCas9 fused to a transcription repressor domain), sufficiently close to an SCD knockdown target position to reduce, decrease or repress expression of the BCL11A gene.

In an embodiment, a nucleic acid encodes a fourth gRNA molecule comprising a targeting domain configured to provide a cleavage event, e.g., a double strand break or a single strand break, sufficiently close to an SCD target position in the HBB gene or BCL11A gene to allow alteration, e.g., alteration associated with HDR or NHEJ, of an SCD target position in the HBB gene or BCL11A gene, either alone or in combination with the break positioned by the first gRNA molecule, the second gRNA molecule and/or the third gRNA molecule.

In an embodiment, the nucleic acid encodes a fourth gRNA molecule comprising a targeting domain configured to target an enzymatically inactive Cas9 (eiCas9) or an eiCas9 fusion protein (e.g., an eiCas9 fused to a transcription repressor domain), sufficiently close to an SCD knockdown target position to reduce, decrease or repress expression of the BCL11A gene.

In an embodiment, the nucleic acid encodes a second gRNA molecule. The second gRNA is selected to target the same SCD target position as the first gRNA molecule. Optionally, the nucleic acid may encode a third gRNA, and further optionally, the nucleic acid may encode a fourth gRNA molecule. The third gRNA molecule and the fourth gRNA molecule are selected to target the same SCD target position as the first and/or second gRNA molecules.

In an embodiment, the nucleic acid encodes a second gRNA molecule comprising a targeting domain comprising a sequence that is the same as, or differs by no more than 1, 2, 3, 4, or 5 nucleotides from, a targeting domain sequence from one of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. In an embodiment, the nucleic acid encodes a second gRNA molecule comprising a targeting domain selected from those in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. In an embodiment, when a third or fourth gRNA molecule are present, the third and fourth gRNA molecules may independently comprise a targeting domain comprising a sequence that is the same as, or differs by no more than 1, 2, 3, 4, or 5 nucleotides from, a targeting domain sequence from one of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. In a further embodiment, when a third or fourth gRNA molecule are present, the third and fourth gRNA molecules may independently comprise a targeting domain selected from those in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31.

In an embodiment, the nucleic acid encodes a second gRNA which is a modular gRNA, e.g., wherein one or more nucleic acid molecules encode a modular gRNA. In another embodiment, the nucleic acid encoding a second gRNA is a chimeric gRNA. In another embodiment, when a nucleic acid encodes a third or fourth gRNA, the third and/or fourth gRNA may be a modular gRNA or a chimeric gRNA. When multiple gRNAs are used, any combination of modular or chimeric gRNAs may be used.

A nucleic acid may encode a second, a third, and/or a fourth gRNA comprising a targeting domain comprising 16 nucleotides or more in length. In an embodiment, the nucleic acid encodes a second gRNA comprising a targeting domain that is 16 nucleotides in length. In another embodiment, the nucleic acid encodes a second gRNA comprising a targeting domain that is 17 nucleotides in length. In still another embodiment, the nucleic acid encodes a second gRNA comprising a targeting domain that is 18 nucleotides in length. In still another embodiment, the nucleic acid encodes a second gRNA comprising a targeting domain that is 19 nucleotides in length. In still another embodiment, the nucleic acid encodes a second gRNA comprising a targeting domain that is 20 nucleotides in length. In still another embodiment, the nucleic acid encodes a second gRNA comprising a targeting domain that is 21 nucleotides in length. In still another embodiment, the nucleic acid encodes a second gRNA comprising a targeting domain that is 22 nucleotides in length. In still another embodiment, the nucleic acid encodes a second gRNA comprising a targeting domain that is 23 nucleotides in length. In still another embodiment, the nucleic acid encodes a second gRNA comprising a targeting domain that is 24 nucleotides in length. In still another embodiment, the nucleic acid encodes a second gRNA comprising a targeting domain that is 25 nucleotides in length. In still another embodiment, the nucleic acid encodes a second gRNA comprising a targeting domain that is 26 nucleotides in length.

In an embodiment, the targeting domain comprises 16 nucleotides.

In an embodiment, the targeting domain comprises 17 nucleotides.

In an embodiment, the targeting domain comprises 18 nucleotides.

In an embodiment, the targeting domain comprises 19 nucleotides.

In an embodiment, the targeting domain comprises 20 nucleotides.

In an embodiment, the targeting domain comprises 21 nucleotides.

In an embodiment, the targeting domain comprises 22 nucleotides.

In an embodiment, the targeting domain comprises 23 nucleotides.

In an embodiment, the targeting domain comprises 24 nucleotides.

In an embodiment, the targeting domain comprises 25 nucleotides.

In an embodiment, the targeting domain comprises 26 nucleotides.

In an embodiment, a nucleic acid encodes a second, a third, and/or a fourth gRNA comprising from 5' to 3': a targeting domain (comprising a "core domain", and optionally a "secondary domain"); a first complementarity domain; a linking domain; a second complementarity domain; a proximal domain; and a tail domain. In an embodiment, the proximal domain and tail domain are taken together as a single domain.

In an embodiment, a nucleic acid encodes a second, a third, and/or a fourth gRNA comprising a linking domain of no more than 25 nucleotides in length; a proximal and tail domain, that taken together, are at least 20 nucleotides in length; and a targeting domain equal to or greater than 16, 17, 18, 19, 20, 21, 22, 23, 24, 25 or 26 nucleotides in length.

In an embodiment, a nucleic acid encodes a second, a third, and/or a fourth gRNA comprising a linking domain of no more than 25 nucleotides in length; a proximal and tail domain, that taken together, are at least 30 nucleotides in length; and a targeting domain equal to or greater than 16, 17, 18, 19, 20, 21, 22, 23, 24, 25 or 26 nucleotides in length.

In an embodiment, a nucleic acid encodes a second, a third, and/or a fourth gRNA comprising a linking domain of no more than 25 nucleotides in length; a proximal and tail domain, that taken together, are at least 35 nucleotides in length; and a targeting domain equal to or greater than 16, 17, 18, 19, 20, 21, 22, 23, 24, 25 or 26 nucleotides in length.

In an embodiment, a nucleic acid encodes a second, a third, and/or a fourth gRNA comprising a linking domain of no more than 25 nucleotides in length; a proximal and tail domain, that taken together, are at least 40 nucleotides in length; and a targeting domain equal to or greater than 16, 17, 18, 19, 20, 21, 22, 23, 24, 25 or 26 nucleotides in length.

In an embodiment, when the HBB gene is corrected, e.g., by HDR, the nucleic acid encodes (a) a sequence that encodes a gRNA molecule comprising a targeting domain that is complementary with a target domain in the HBB gene as disclosed herein; (b) a sequence that encodes a Cas9 molecule; optionally, (c)(i) a sequence that encodes a second gRNA molecule described herein having a targeting domain that is complementary to a second target domain of the HBB gene, and further optionally, (c)(ii) a sequence that encodes a third gRNA molecule described herein having a targeting domain that is complementary to a third target domain of the HBB gene; and still further optionally, (c)(iii) a sequence that encodes a fourth gRNA molecule described herein having a targeting domain that is complementary to a fourth target domain of the HBB gene; and further may comprise (d) a template nucleic acid (in an embodiment where an exogenous template is used).

In an embodiment, a mutation in the HBB gene is corrected, e.g., by HDR, using an exogenously provided template nucleic acid.

In an embodiment, the template nucleic acid is a single stranded nucleic acid. In another embodiment, the template nucleic acid is a double stranded nucleic acid. In an embodiment, the template nucleic acid comprises a nucleotide sequence, e.g., of one or more nucleotides, that will be added to or will template a change in the target nucleic acid. In another embodiment, the template nucleic acid comprises a nucleotide sequence that may be used to modify the target position. In another embodiment, the template nucleic acid comprises a nucleotide sequence, e.g., of one or more nucleotides, that corresponds to wild type sequence of the target nucleic acid, e.g., of the target position.

The template nucleic acid may comprise a replacement sequence, e.g., a replacement sequence from the Table 27. In an embodiment, the template nucleic acid comprises a 5' homology arm, e.g., a 5' homology arm from Table 27. In another embodiment, the template nucleic acid comprises a 3' homology arm, e.g., a 3' homology arm from Table 27.

In another embodiment, a mutation in the HBB gene is corrected, e.g., by HDR, without using an exogenously provided template nucleic acid. While not wishing to be bound by theory, it is believed that an endogenous region of homology can mediate HDR-based correction. In an embodiment, alteration of the target sequence occurs by HDR with an endogenous genomic donor sequence. In an embodiment, the endogenous genomic donor sequence is located on the same chromosome as the target sequence. In another embodiment, the endogenous genomic donor sequence is located on a different chromosome from the target sequence. In an embodiment, the endogenous genomic donor sequence comprises one or more nucleotides derived from the HBD gene. Mutations in the HBB gene that can be corrected (e.g., altered) by HDR with an endogenous genomic donor sequence include, e.g., a point mutation at E6, e.g., E6V.

As described above, a nucleic acid may comprise (a) a sequence encoding a gRNA molecule comprising a targeting domain that is complementary with a target domain in the HBB gene or BCL11A gene, and (b) a sequence encoding a Cas9 molecule.

In an embodiment, (a) and (b) are present on the same nucleic acid molecule, e.g., the same vector, e.g., the same viral vector, e.g., the same adeno-associated virus (AAV) vector. In an embodiment, the nucleic acid molecule is an AAV vector. Exemplary AAV vectors that may be used in any of the described compositions and methods include an AAV2 vector, a modified AAV2 vector, an AAV3 vector, a modified AAV3 vector, an AAV6 vector, a modified AAV6 vector, an AAV8 vector and an AAV9 vector.

In another embodiment, (a) is present on a first nucleic acid molecule, e.g. a first vector, e.g., a first viral vector, e.g., a first AAV vector; and (b) is present on a second nucleic acid molecule, e.g., a second vector, e.g., a second vector, e.g., a second AAV vector. The first and second nucleic acid molecules may be AAV vectors.

In another embodiment, the nucleic acid may further comprise (c) a sequence that encodes a second, third and/or fourth gRNA molecule as described herein. In an embodiment, the nucleic acid comprises (a), (b) and (c). Each of (a) and (c) may be present on the same nucleic acid molecule, e.g., the same vector, e.g., the same viral vector, e.g., the same adeno-associated virus (AAV) vector. In an embodiment, the nucleic acid molecule is an AAV vector.

In another embodiment, (a) and (c) are on different vectors. For example, (a) may be present on a first nucleic acid molecule, e.g. a first vector, e.g., a first viral vector, e.g., a first AAV vector; and (c) may be present on a second nucleic acid molecule, e.g., a second vector. e.g., a second vector, e.g., a second AAV vector. In an embodiment, the first and second nucleic acid molecules are AAV vectors.

In another embodiment, each of (a), (b), and (c) are present on the same nucleic acid molecule, e.g., the same vector, e.g., the same viral vector, e.g., an AAV vector. In an embodiment, the nucleic acid molecule is an AAV vector. In an alternate embodiment, one of (a), (b), and (c) is encoded on a first nucleic acid molecule, e.g., a first vector, e.g., a first viral vector, e.g., a first AAV vector; and a second and third of (a), (b), and (c) is encoded on a second nucleic acid molecule, e.g., a second vector, e.g., a second vector, e.g., a second AAV vector. The first and second nucleic acid molecule may be AAV vectors.

In an embodiment, (a) is present on a first nucleic acid molecule, e.g., a first vector, e.g., a first viral vector, a first AAV vector; and (b) and (c) are present on a second nucleic acid molecule, e.g., a second vector, e.g., a second vector, e.g., a second AAV vector. The first and second nucleic acid molecule may be AAV vectors.

In another embodiment, (b) is present on a first nucleic acid molecule, e.g., a first vector, e.g., a first viral vector, e.g., a first AAV vector; and (a) and (c) are present on a second nucleic acid molecule, e.g., a second vector, e.g., a second vector, e.g., a second AAV vector. The first and second nucleic acid molecule may be AAV vectors.

In another embodiment, (c) is present on a first nucleic acid molecule, e.g., a first vector, e.g., a first viral vector, e.g., a first AAV vector; and (b) and (a) are present on a second nucleic acid molecule, e.g., a second vector, e.g., a second vector, e.g., a second AAV vector. The first and second nucleic acid molecule may be AAV vectors.

In another embodiment, each of (a), (b) and (c) are present on different nucleic acid molecules, e.g., different vectors, e.g., different viral vectors, e.g., different AAV vector. For example, (a) may be on a first nucleic acid molecule, (b) on a second nucleic acid molecule, and (c) on a third nucleic acid molecule. The first, second and third nucleic acid molecule may be AAV vectors.

In another embodiment, when a third and/or fourth gRNA molecule are present, each of (a), (b), (c)(i), (c)(ii) and (c)(iii) may be present on the same nucleic acid molecule, e.g., the same vector, e.g., the same viral vector, e.g., an AAV vector. In an embodiment, the nucleic acid molecule is an AAV vector. In an alternate embodiment, each of (a), (b), (c)(i), (c)(ii) and (c)(iii) may be present on the different nucleic acid molecules, e.g., different vectors, e.g., the different viral vectors, e.g., different AAV vectors. In further embodiments, each of (a), (b), (c)(i), (c)(ii) and (c)(iii) may be present on more than one nucleic acid molecule, but fewer than five nucleic acid molecules, e.g., AAV vectors.

In another embodiment, when (d) a template nucleic acid is present, each of (a), (b), and (d) may be present on the same nucleic acid molecule, e.g., the same vector, e.g., the same viral vector, e.g., an AAV vector. In an embodiment, the nucleic acid molecule is an AAV vector. In an alternate embodiment, each of (a), (b), and (d) may be present on the different nucleic acid molecules, e.g., different vectors, e.g., the different viral vectors, e.g., different AAV vectors. In further embodiments, each of (a), (b), and (d) may be present on more than one nucleic acid molecule, but fewer than three nucleic acid molecules, e.g., AAV vectors.

In another embodiment, when (d) a template nucleic acid is present, each of (a), (b), (c)(i) and (d) may be present on the same nucleic acid molecule, e.g., the same vector, e.g., the same viral vector, e.g., an AAV vector. In an embodiment, the nucleic acid molecule is an AAV vector. In an alternate embodiment, each of (a), (b), (c)(i) and (d) may be present on the different nucleic acid molecules, e.g., different vectors, e.g., the different viral vectors, e.g., different AAV vectors. In further embodiments, each of (a), (b), (c)(i) and (d) may be present on more than one nucleic acid molecule, but fewer than four nucleic acid molecules, e.g., AAV vectors.

In another embodiment, when (d) a template nucleic acid is present, each of (a), (b), (c)(i), (c)(ii) and (d) may be present on the same nucleic acid molecule, e.g., the same vector, e.g., the same viral vector, e.g., an AAV vector. In an embodiment, the nucleic acid molecule is an AAV vector. In an alternate embodiment, each of (a), (b), (c)(i), (c)(ii) and (d) may be present on the different nucleic acid molecules, e.g., different vectors, e.g., the different viral vectors, e.g., different AAV vectors. In further embodiments, each of (a), (b), (c)(i), (c)(ii) and (d) may be present on more than one nucleic acid molecule, but fewer than five nucleic acid molecules, e.g., AAV vectors.

In another embodiment, when (d) a template nucleic acid is present, each of (a), (b), (c)(i), (c)(ii), (c)(iii) and (d) may be present on the same nucleic acid molecule, e.g., the same vector, e.g., the same viral vector, e.g., an AAV vector. In an alternate embodiment, each of (a), (b), (c)(i), (c)(ii), (c)(iii) and (d) may be present on the different nucleic acid molecules, e.g., different vectors, e.g., the different viral vectors. e.g., different AAV vectors. In further embodiments, each of (a), (b), (c)(i), (c)(ii), (c)(iii) and (d) may be present on more than one nucleic acid molecule, but fewer than six nucleic acid molecules, e.g., AAV vectors.

The nucleic acids described herein may comprise a promoter operably linked to the sequence that encodes the gRNA molecule of (a), e.g., a promoter described herein. The nucleic acid may further comprise a second promoter operably linked to the sequence that encodes the second, third and/or fourth gRNA molecule of (c), e.g., a promoter described herein. The promoter and second promoter differ from one another. In an embodiment, the promoter and second promoter are the same.

The nucleic acids described herein may further comprise a promoter operably linked to the sequence that encodes the Cas9 molecule of (b), e.g., a promoter described herein.

In another aspect, disclosed herein is a composition comprising (a) a gRNA molecule comprising a targeting domain that is complementary with a target domain in the HBB gene or BCL11A gene, as described herein. The composition of (a) may further comprise (b) a Cas9 molecule, e.g., a Cas9 molecule as described herein. A composition of (a) and (b) may further comprise (c) a second, third and/or fourth gRNA molecule, e.g., a second, third and/or fourth gRNA molecule described herein. A composition of (a), (b) and (c) may further comprise (d) a template nucleic acid (in an embodiment where an exogenous template is used). In an embodiment, the composition is a pharmaceutical composition. The Compositions described herein, e.g., pharmaceutical compositions described herein, can be used in treating SCD in a subject, e.g., in accordance with a method disclosed herein.

In another aspect, disclosed herein is a method of altering a cell, e.g., altering the structure, e.g., altering the sequence, of a target nucleic acid of a cell, comprising contacting said cell with: (a) a gRNA that targets the HBB gene or BCL11A gene, e.g., a gRNA as described herein; (b) a Cas9 molecule, e.g., a Cas9 molecule as described herein; and optionally, (c) a second, third and/or fourth gRNA that targets HBB gene or BCL11A gene, e.g., a gRNA; and optionally, (d) a template nucleic acid, as described herein.

In an embodiment, the method comprises contacting said cell with (a) and (b).

In an embodiment, the method comprises contacting said cell with (a), (b), and (c).

In an embodiment, the method comprises contacting said cell with (a), (b), (c) and (d).

In an embodiment, the gRNA targets the HBB gene and no exogenous template nucleic acid is contacted with the cell.

The gRNA of (a) and optionally (c) may be selected from any of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, or a gRNA that differs by no more than 1, 2, 3, 4, or 5 nucleotides from, a targeting domain sequence from any of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31.

In an embodiment, the method comprises contacting a cell from a subject suffering from or likely to develop SCD. The cell may be from a subject having a mutation at an SCD target position in the HBB gene or a subject which would benefit from having a mutation at an SCD target position in the BCL11A gene.

In an embodiment, the cell being contacted in the disclosed method is an erythroid cell. The contacting may be performed ex vivo and the contacted cell may be returned to the subject's body after the contacting step. In another embodiment, the contacting step may be performed in vivo.

In an embodiment, the method of altering a cell as described herein comprises acquiring knowledge of the sequence at an SCD target position in said cell, prior to the contacting step. Acquiring knowledge of the sequence at an SCD target position in the cell may be by sequencing the HBB gene or BCL11A gene, or a portion of the HBB gene or BCL11A gene.

In an embodiment, the contacting step of the method comprises contacting the cell with a nucleic acid, e.g., a vector, e.g., an AAV vector, that expresses at least one of (a), (b), and (c). In an embodiment, the contacting step of the method comprises contacting the cell with a nucleic acid, e.g., a vector, e.g., an AAV vector, that expresses each of (a), (b), and (c). In another embodiment, the contacting step of the method comprises delivering to the cell a Cas9 molecule of (b) and a nucleic acid which encodes a gRNA (a) and optionally, a second gRNA (c)(i) (and further optionally, a third gRNA (c)(iv) and/or fourth gRNA (c)(iii).

In an embodiment, the contacting step of the method comprises contacting the cell with a nucleic acid, e.g., a vector, e.g., an AAV vector, that expresses at least one of (a), (b), (c) and (d). In an embodiment, the contacting step of the method comprises contacting the cell with a nucleic acid, e.g., a vector, e.g., an AAV vector, that expresses each of (a), (b), and (c). In another embodiment, the contacting step of the method comprises delivering to the cell a Cas9 molecule of (b), a nucleic acid which encodes a gRNA of (a) and a template nucleic acid of (d), and optionally, a second gRNA (c)(i) (and further optionally, a third gRNA (c)(iv) and/or fourth gRNA (c)(iii).

In an embodiment, contacting comprises contacting the cell with a nucleic acid, e.g., a vector, e.g., an AAV vector, e.g., an AAV2 vector, a modified AAV2 vector, an AAV3 vector, a modified AAV3 vector, an AAV6 vector, a modified AAV6 vector, an AAV8 vector or an AAV9 vector.

In an embodiment, contacting comprises delivering to the cell a Cas9 molecule of (b), as a protein or an mRNA, and a nucleic acid which encodes (a) and optionally a second, third and/or fourth gRNA of (c).

In an embodiment, contacting comprises delivering to the cell a Cas9 molecule of (b), as a protein or an mRNA, said gRNA of (a), as an RNA, and optionally said second, third and/or fourth gRNA of (c), as an RNA.

In an embodiment, contacting comprises delivering to the cell a gRNA of (a) as an RNA, optionally said second, third and/or fourth gRNA of (c) as an RNA, and a nucleic acid that encodes the Cas9 molecule of (b).

In another aspect, disclosed herein is a method of treating or preventing a subject suffering from or likely to develop SCD, e.g., altering the structure, e.g., sequence, of a target nucleic acid of the subject, comprising contacting the subject (or a cell from the subject) with:

(a) a gRNA that targets the HBB gene or BCL11A gene, e.g., a gRNA disclosed herein;

(b) a Cas9 molecule, e.g., a Cas9 molecule disclosed herein; and optionally, (c)(i) a second gRNA that targets the HBB gene or BCL11A gene, e.g., a second gRNA disclosed herein, and further optionally, (c)(ii) a third gRNA, and still further optionally, (c)(iii) a fourth gRNA that target the HBB gene or BCL11A gene, e.g., a third and fourth gRNA disclosed herein.

The method of treating a subject may further comprise contacting the subject (or a cell from the subject) with (d) a template nucleic acid (in an embodiment where an exogenous template is used), e.g., a template nucleic acid disclosed herein.

In an embodiment, a template nucleic acid is used when the method of treating a subject uses HDR to alter the sequence of the target nucleic acid of the subject. In an embodiment, the gRNA targets the HBB gene and no exogenous template nucleic acid is contacted with the subject (or a cell from the subject).

In an embodiment, contacting comprises contacting with (a) and (b).

In an embodiment, contacting comprises contacting with (a), (b), and (c)(i).

In an embodiment, contacting comprises contacting with (a), (b), (c)(i) and (c)(ii).

In an embodiment, contacting comprises contacting with (a), (b), (c)(i), (c)(ii) and (c)(iii).

In an embodiment, contacting comprises contacting with (a), (b), (c)(i) and (d).

In an embodiment, contacting comprises contacting with (a), (b), (c)(i), (c)(ii) and (d).

In an embodiment, contacting comprises contacting with (a), (b), (c)(i), (c)(ii), (c)(iii) and (d).

The gRNA of (a) or (c) (e.g., (c)(i), (c)(ii), or (c)(iii) may be selected from any of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, or a gRNA that differs by no more than 1, 2, 3, 4, or 5 nucleotides from, a targeting domain sequence from any of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31.

In an embodiment, the method comprises acquiring knowledge of the sequence (e.g., a mutation) of an SCD target position in said subject.

In an embodiment, the method comprises acquiring knowledge of the sequence (e.g., a mutation) of an SCD target position in said subject by sequencing the HBB gene or BCL11A gene or a portion of the HBB gene or BCL11A gene.

In an embodiment, the method comprises correcting a mutation at an SCD target position in the HBB gene.

In an embodiment, the method comprises correcting a mutation at an SCD target position in the HBB gene by HDR.

In an embodiment, the method comprises introducing a mutation at an SCD target position in the BCL11A gene.

In an embodiment, the method comprises introducing a mutation at an SCD target position in the BCL11A gene by NHEJ.

When the method comprises correcting the mutation at an SCD target position by HDR, a Cas9 of (b), at least one guide RNA, e.g., a guide RNA of (a) and a template nucleic acid of (d) are included in the contacting step.

In an embodiment, a cell of the subject is contacted ex vivo with (a), (b), (d) and optionally (c)(i), further optionally (c)(ii), and still further optionally (c)(iii). In an embodiment, said cell is returned to the subject's body.

In an embodiment, a cell of the subject is contacted is in vivo with (a), (b) (d) and optionally (c)(i), further optionally (c)(ii), and still further optionally (c)(iii).

In an embodiment, the cell of the subject is contacted in vivo by intravenous delivery of (a), (b), (d) and optionally (c)(i), further optionally (c)(ii), and still further optionally (c)(iii).

In an embodiment, the cell of the subject is contacted in vivo by intramuscular delivery of (a), (b), (d) and optionally (c)(i), further optionally (c)(ii), and still further optionally (c)(iii).

In an embodiment, the cell of the subject is contacted in vivo by subcutaneous delivery of (a), (b), (d) and optionally (c)(i), further optionally (c)(ii), and still further optionally (c)(iii).

In an embodiment, the cell of the subject is contacted in vivo by intra-bone marrow (IBM) delivery of (a), (b), (d) and optionally (c)(i), further optionally (c)(ii), and still further optionally (c)(iii).

In an embodiment, contacting comprises contacting the subject with a nucleic acid, e.g., a vector, e.g., an AAV vector, described herein, e.g., a nucleic acid that encodes at least one of (a), (b), (d) and optionally (c)(i), further optionally (c)(ii), and still further optionally (c)(iii).

In an embodiment, contacting comprises delivering to said subject said Cas9 molecule of (b), as a protein or mRNA, and a nucleic acid which encodes (a), a nucleic acid of (d) and optionally (c)(i), further optionally (c)(ii), and still further optionally (c)(iii).

In an embodiment, contacting comprises delivering to the subject the Cas9 molecule of (b), as a protein or mRNA, the gRNA of (a), as an RNA, a nucleic acid of (d) and optionally the second, third and/or fourth gRNA of (c), as an RNA.

In an embodiment, contacting comprises delivering to the subject the gRNA of (a), as an RNA, optionally said second, third and/or fourth gRNA of (c), as an RNA, a nucleic acid that encodes the Cas9 molecule of (b), and a nucleic acid of (d).

When the method comprises (1) introducing a mutation at an SCD target position by NHEJ or (2) knocking down expression of the BCL11A gene by targeting the promoter region, a Cas9 of (b) and at least one guide RNA, e.g., a guide RNA of (a) are included in the contacting step.

In an embodiment, a cell of the subject is contacted ex vivo with (a), (b) and optionally (c)(i), further optionally (c)(ii), and still further optionally (c)(iii). In an embodiment, said cell is returned to the subject's body.

In an embodiment, a populations of cells from a subject is contacted ex vivo with (a), (b) and optionally (c) to correct the E6V mutation in the HBB gene and a second population of cells from the subject is contacted ex vivo with (a), (b) and optionally (c) to introduce a mutation in the BCL11A gene to knockout the BCL11A gene. A mixture of the two cell populations may be returned to the subject's body to treat or prevent SCD.

In an embodiment, a cell of the subject is contacted is in vivo with (a), (b) and optionally (c)(i), further optionally (c)(ii), and still further optionally (c)(iii). In an embodiment, the cell of the subject is contacted in vivo by intravenous delivery of (a), (b) and optionally (c)(i), further optionally (c)(ii), and still further optionally (c)(iii). In an embodiment, the cell of the subject is contacted in vivo by intramuscular delivery of (a), (b) and optionally (c)(i), further optionally (c)(ii), and still further optionally (c)(iii). In an embodiment, the cell of the subject is contacted in vivo by subcutaneous delivery of (a), (b) and optionally (c)(i), further optionally (c)(ii), and still further optionally (c)(iii). In an embodiment, the cell of the subject is contacted in vivo by intra-bone marrow (IBM) delivery of (a), (b) and optionally (c)(i), further optionally (c)(ii), and still further optionally (c)(iii).

In an embodiment, contacting comprises contacting the subject with a nucleic acid, e.g., a vector, e.g., an AAV vector, described herein. e.g., a nucleic acid that encodes at least one of (a), (b), and optionally (c)(i), further optionally (c)(ii), and still further optionally (c)(iii).

In an embodiment, contacting comprises delivering to said subject said Cas9 molecule of (b), as a protein or mRNA, and a nucleic acid which encodes (a) and optionally (c)(i), further optionally (c)(ii), and still further optionally (c)(iii).

In an embodiment, contacting comprises delivering to the subject the Cas9 molecule of (b), as a protein or mRNA, the gRNA of (a), as an RNA, and optionally the second, third and/or fourth gRNA of (c), as an RNA.

In an embodiment, contacting comprises delivering to the subject the gRNA of (a), as an RNA, optionally said second, third and/or fourth gRNA of (c), as an RNA, and a nucleic acid that encodes the Cas9 molecule of (b).

In another aspect, disclosed herein is a reaction mixture comprising a gRNA, a nucleic acid, or a composition described herein, and a cell, e.g., a cell from a subject having, or likely to develop SCD, or a subject having a mutation at an SCD target position in the HBB gene, or a cell from a subject which would benefit from having a mutation at an SCD target position in the BCL11A gene.

In another aspect, disclosed herein is a kit comprising, (a) gRNA molecule described herein, or nucleic acid that encodes the gRNA, and one or more of the following:

(b) a Cas9 molecule, e.g., a Cas9 molecule described herein, or a nucleic acid or mRNA that encodes the Cas9;

(c)(i) a second gRNA molecule, e.g., a second gRNA molecule described herein or a nucleic acid that encodes (c)(i);

(c)(ii) a third gRNA molecule, e.g., a second gRNA molecule described herein or a nucleic acid that encodes (c)(ii);

(c)(iii) a fourth gRNA molecule, e.g., a second gRNA molecule described herein or a nucleic acid that encodes (c)(iii);

(d) a template nucleic acid (in an embodiment where an exogenous template is used), e.g., a template nucleic acid described herein.

In an embodiment, the kit comprises nucleic acid, e.g., an AAV vector, that encodes one or more of (a), (b), (c)(i), (c)(ii), (c)(iii) and (d).

In an aspect, the disclosure features a gRNA molecule, referred to herein as a governing gRNA molecule, comprising a targeting domain which is complementary to a target domain on a nucleic acid that encodes a component of the CRISPR/Cas system introduced into a cell or subject. In an embodiment, the governing gRNA molecule targets a nucleic acid that encodes a Cas9 molecule or a nucleic acid that encodes a target gene gRNA molecule. In an embodiment, the governing gRNA comprises a targeting domain that is complementary to a target domain in a sequence that encodes a Cas9 component. e.g., a Cas9 molecule or target gene gRNA molecule. In an embodiment, the target domain is designed with, or has, minimal homology to other nucleic acid sequences in the cell, e.g., to minimize off-target cleavage. For example, the targeting domain on the governing gRNA can be selected to reduce or minimize off-target effects. In an embodiment, a target domain for a governing gRNA can be disposed in the control or coding region of a Cas9 molecule or disposed between a control region and a transcribed region. In an embodiment, a target domain for a governing gRNA can be disposed in the control or coding region of a target gene gRNA molecule or disposed between a control region and a transcribed region for a target gene gRNA. While not wishing to be bound by theory, it is believed that altering, e.g., inactivating, a nucleic acid that encodes a Cas9 molecule or a nucleic acid that encodes a target gene gRNA molecule can be effected by cleavage of the targeted nucleic acid sequence or by binding of a Cas9 molecule/governing gRNA molecule complex to the targeted nucleic acid sequence.

The compositions, reaction mixtures and kits, as disclosed herein, can also include a governing gRNA molecule, e.g., a governing gRNA molecule disclosed herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Headings, including numeric and alphabetical headings and subheadings, are for organization and presentation and are not intended to be limiting.

Other features and advantages of the invention will be apparent from the detailed description, drawings, and from the claims.

BRIEF DESCRIPTION OF THE DRAWINGS

FIGS. 1A-1I are representations of several exemplary gRNAs.

FIG. 1A depicts a modular gRNA molecule derived in part (or modeled on a sequence in part) from *Streptococcus pyogenes* (*S. pyogenes*) as a duplexed structure (SEQ ID NOS: 42 and 43, respectively, in order of appearance);

FIG. 1B depicts a unimolecular (or chimeric) gRNA molecule derived in part from *S. pyogenes* as a duplexed structure (SEQ ID NO: 44);

FIG. 1C depicts a unimolecular gRNA molecule derived in part from *S. pyogenes* as a duplexed structure (SEQ ID NO: 45);

FIG. 1D depicts a unimolecular gRNA molecule derived in part from *S. pyogenes* as a duplexed structure (SEQ ID NO: 46);

FIG. 1E depicts a unimolecular gRNA molecule derived in part from *S. pyogenes* as a duplexed structure (SEQ ID NO: 47);

FIG. 1F depicts a modular gRNA molecule derived in part from *Streptococcus thermophilus* (*S. thermophilus*) as a duplexed structure (SEQ ID NOS: 48 and 49, respectively, in order of appearance);

FIG. 1G depicts an alignment of modular gRNA molecules of *S. pyogenes* and *S. thermophilus* (SEQ ID NOS: 50-53, respectively, in order of appearance).

FIGS. 1H-1I depicts additional exemplary structures of unimolecular gRNA molecules.

FIG. 1H shows an exemplary structure of a unimolecular gRNA molecule derived in part from *S. pyogenes* as a duplexed structure (SEQ ID NO: 45).

FIG. 1I shows an exemplary structure of a unimolecular gRNA molecule derived in part from *S. aureus* as a duplexed structure (SEQ ID NO: 40).

Figure 2B:
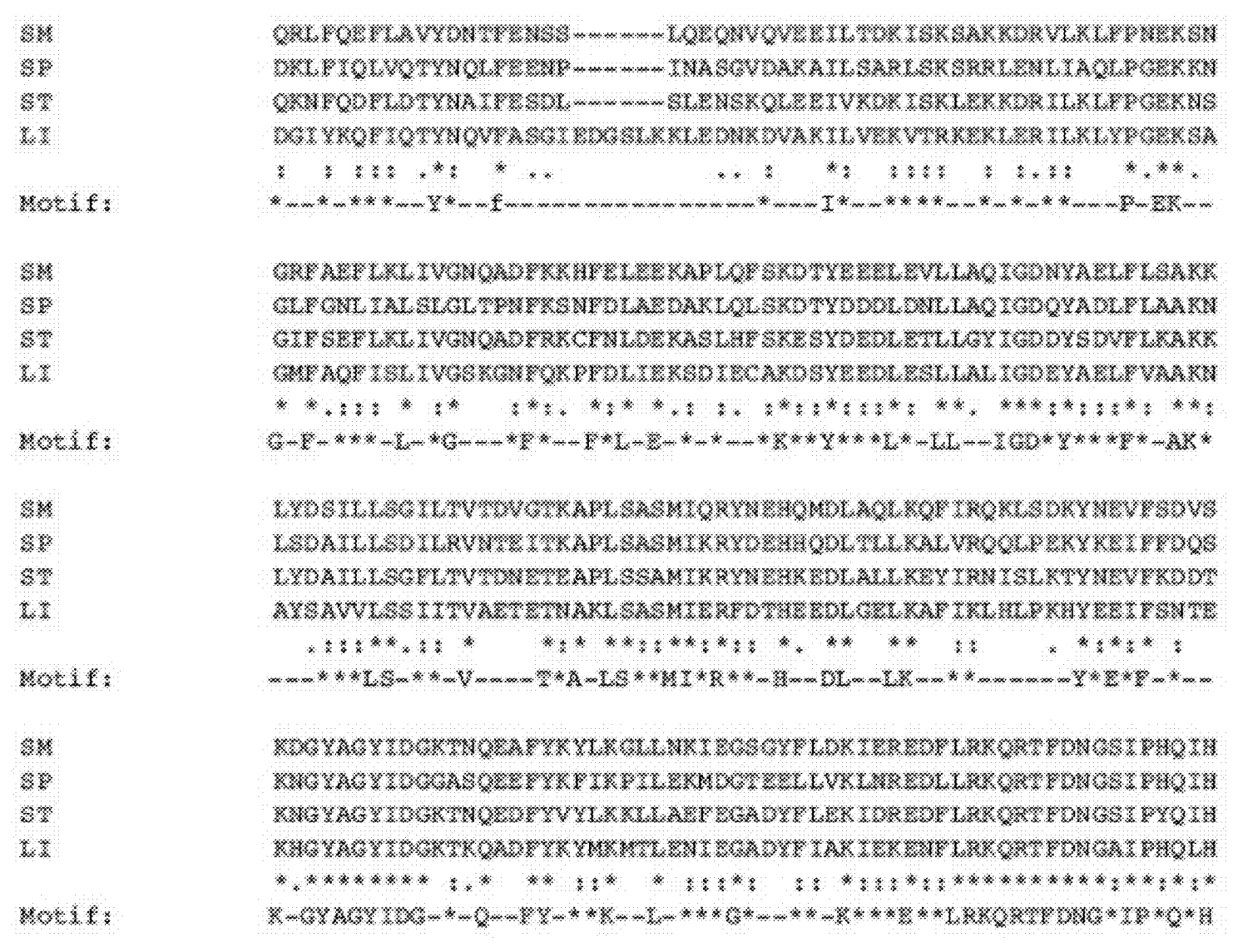
Figure 2E:
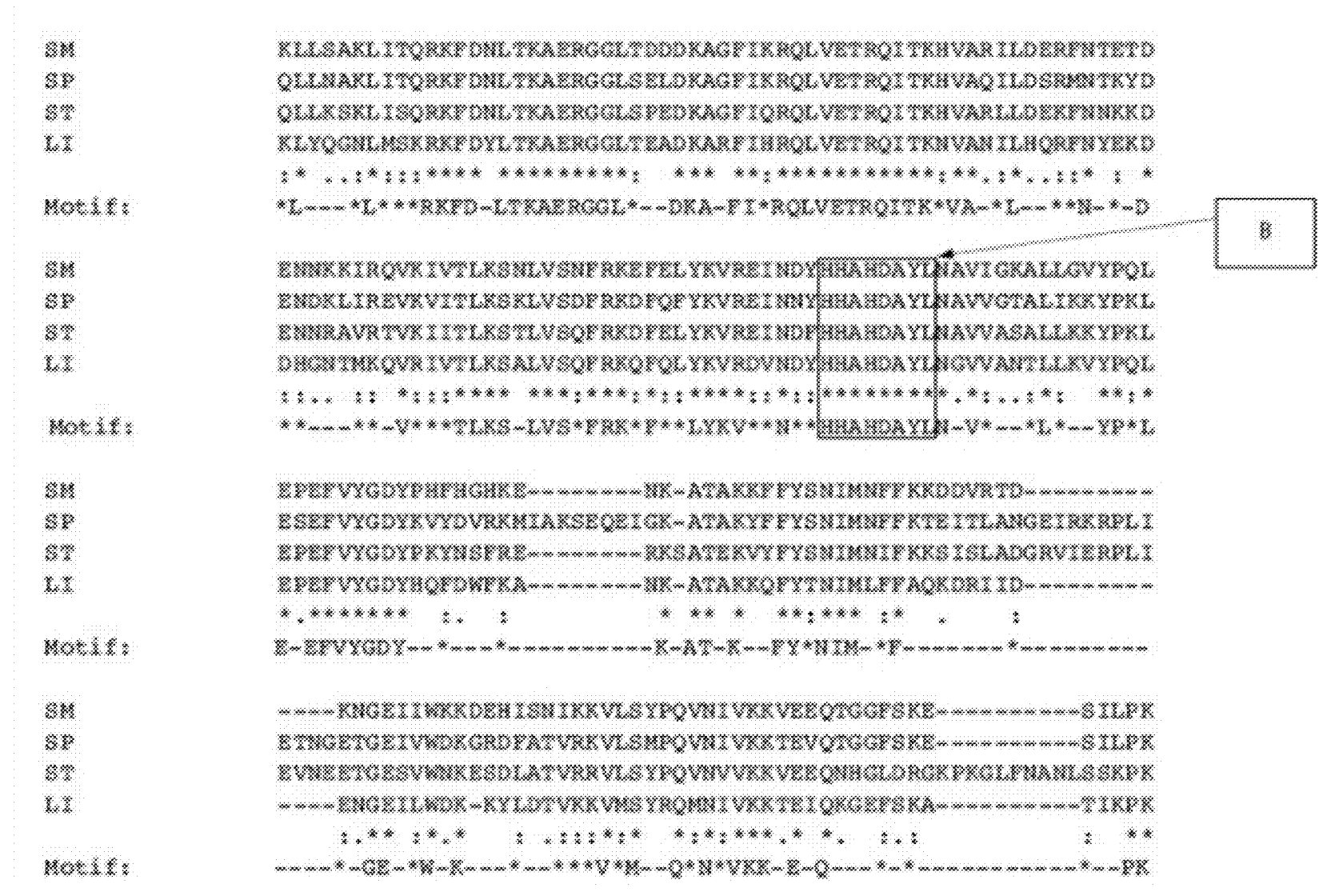

FIGS. 2A-2G depict an alignment of Cas9 sequences from Chylinski et al. (RNA Biol. 2013; 10(5): 726-737). The N-terminal RuvC-like domain is boxed and indicated with a "Y". The other two RuvC-like domains are boxed and indicated with a "B". The HNH-like domain is boxed and indicated by a "G". Sm: *S. mutans* (SEQ ID NO: 1); Sp: *S. pyogenes* (SEQ ID NO: 2); St: *S. thermophilus* (SEQ ID NO: 3); Li: *L. innocua* (SEQ ID NO: 4). Motif: this is a motif based on the four sequences: residues conserved in all four sequences are indicated by single letter amino acid abbreviation; "*" indicates any amino acid found in the corresponding position of any of the four sequences; and "-" indicates any amino acid, e.g., any of the 20 naturally occurring amino acids, or absent.

FIGS. 3A-3B show an alignment of the N-terminal RuvC-like domain from the Cas9 molecules disclosed in Chylinski et al (SEQ ID NOS: 54-103, respectively, in order of appearance). The last line of FIG. 3B identifies 4 highly conserved residues.

Figure 4A:
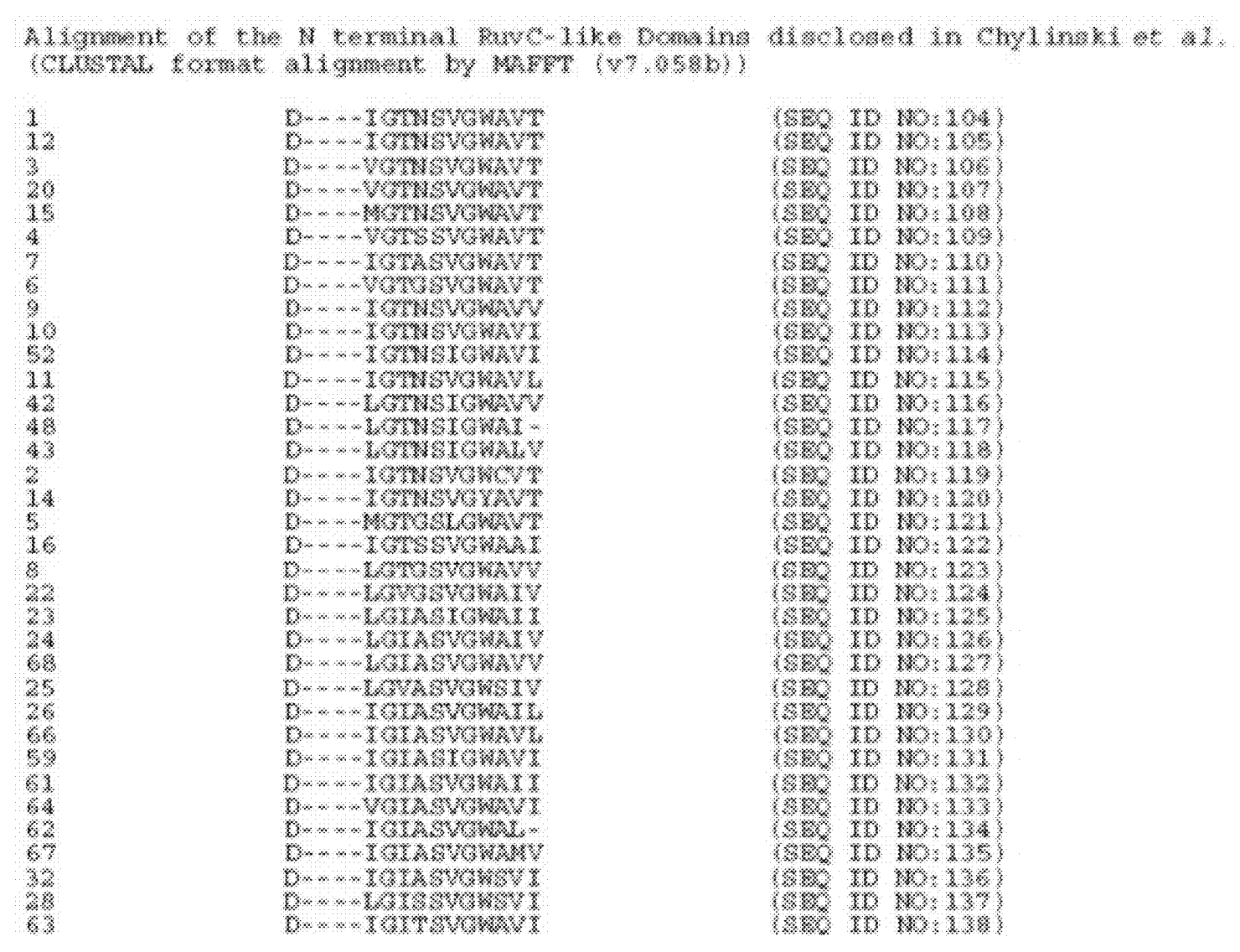

FIGS. 4A-4B show an alignment of the N-terminal RuvC-like domain from the Cas9 molecules disclosed in Chylinski et al. with sequence outliers removed (SEQ ID NOS: 104-177, respectively, in order of appearance). The last line of FIG. 4B identifies 3 highly conserved residues.

FIGS. 5A-5C show an alignment of the HNH-like domain from the Cas9 molecules disclosed in Chylinski et al (SEQ ID NOS: 178-252, respectively, in order of appearance). The last line of FIG. 5C identifies conserved residues.

FIGS. 6A-6B show an alignment of the HNH-like domain from the Cas9 molecules disclosed in Chylinski et al. with sequence outliers removed (SEQ ID NOS: 253-302, respectively, in order of appearance). The last line of FIG. 6B identifies 3 highly conserved residues.

FIGS. 7A-7B depict an alignment of Cas9 sequences from *S. pyogenes* and *Neisseria meningitidis* (*N. meningitidis*). The N-terminal RuvC-like domain is boxed and indicated with a "Y". The other two RuvC-like domains are boxed and indicated with a "B". The HNH-like domain is boxed and indicated with a "G". Sp: *S. pyogenes*; Nm: *N. meningitidis*. Motif: this is a motif based on the two sequences: residues conserved in both sequences are indicated by a single amino acid designation; "*" indicates any amino acid found in the corresponding position of any of the two sequences; "-" indicates any amino acid, e.g., any of the 20 naturally occurring amino acids, and "-" indicates any amino acid, e.g., any of the 20 naturally occurring amino acids, or absent.

FIG. 8 shows a nucleic acid sequence encoding Cas9 of *N. meningitidis* (SEQ ID NO: 303). Sequence indicated by an "R" is an SV40 NLS; sequence indicated as "G" is an HA tag; and sequence indicated by an "O" is a synthetic NLS sequence; the remaining (unmarked) sequence is the open reading frame (ORF).

FIGS. 9A and 9B are schematic representations of the domain organization of *S. pyogenes* Cas 9. FIG. 9A shows the organization of the Cas9 domains, including amino acid positions, in reference to the two lobes of Cas9 (recognition (REC) and nuclease (NUC) lobes). FIG. 9B shows the percent homology of each domain across 83 Cas9 orthologs.

FIGS. 12A-12B depict detected deletion events resulting from co-transfection of exemplary gRNA molecules, BCL11A-2983W and BCL11A-2981W.

FIG. 12A depicts schematic of DNA sequence recognized by BCL11A-2983W and BCL11A-2981W, which flanks the putative erythroid enhancer elements.

FIG. 12B depicts sequenced deletion events from the TOPO cloning of the PCR using primers that flank the enhancer region. A product is obtained when a deletion event has taken place.

FIGS. 13A-13B depicts detected deletion events resulting from co-transfection of the exemplary gRNA molecules, BCL11A-2995W and BCL11A-2984W.

FIG. 13A depicts Schematic of DNA sequence recognized by BCL11A-2995W and BCL11A-2984W, which flanks the putative erythroid enhancer elements.

FIG. 13B depicts sequenced deletion events from the TOPO cloning of the PCR using primers that flank the enhancer region. A product is obtained when a deletion event has taken place.

DETAILED DESCRIPTION

Definitions

Figure 1A:
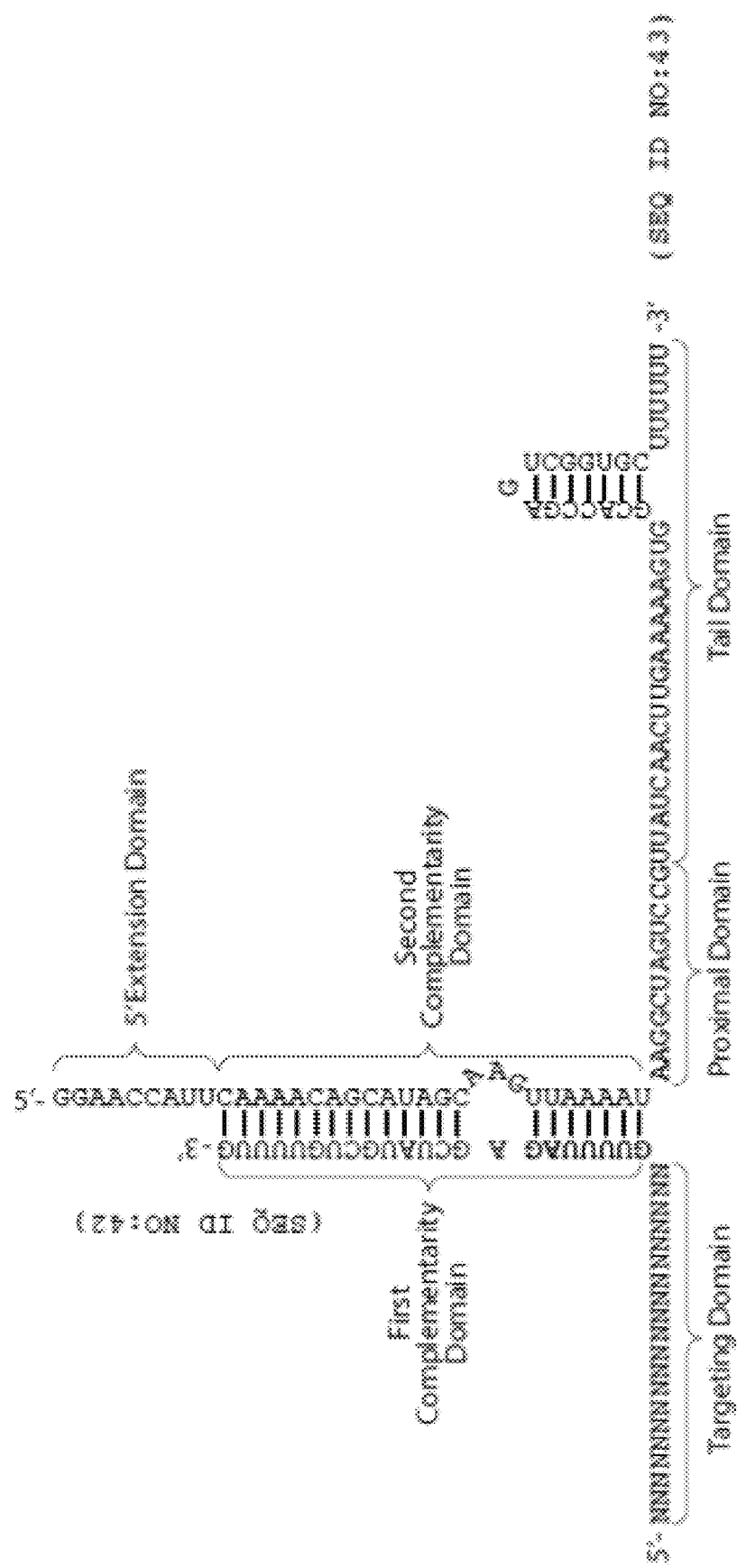

"Alt-HDR" or "alternative HDR", or alternative homology-directed repair, as used herein, refers to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Also, alt-HDR uses a single-stranded or nicked homologous nucleic acid for repair of the break.

"Canonical HDR", or canonical homology-directed repair, as used herein, refers to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, HDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses canonical HDR and alt-HDR.

"Domain", as used herein, is used to describe segments of a protein or nucleic acid. Unless otherwise indicated, a domain is not required to have any specific functional property.

Calculations of homology or sequence identity between two sequences (the terms are used interchangeably herein) are performed as follows. The sequences are aligned for optimal comparison purposes (e.g., gaps can be introduced in one or both of a first and a second amino acid or nucleic acid sequence for optimal alignment and non-homologous sequences can be disregarded for comparison purposes). The optimal alignment is determined as the best score using the GAP program in the GCG software package with a Blossum 62 scoring matrix with a gap penalty of 12, a gap extend penalty of 4, and a frame shift gap penalty of 5. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences.

"Governing gRNA molecule", as used herein, refers to a gRNA molecule that comprises a targeting domain that is complementary to a target domain on a nucleic acid that comprises a sequence that encodes a component of the CRISPR/Cas system that is introduced into a cell or subject. A governing gRNA does not target an endogenous cell or subject sequence. In an embodiment, a governing gRNA molecule comprises a targeting domain that is complementary with a target sequence on: (a) a nucleic acid that encodes a Cas9 molecule; (b) a nucleic acid that encodes a gRNA which comprises a targeting domain that targets the HBB or BCL11A gene (a target gene gRNA); or on more than one nucleic acid that encodes a CRISPR/Cas component, e.g., both (a) and (b). In an embodiment, a nucleic acid molecule that encodes a CRISPR/Cas component, e.g., that encodes a Cas9 molecule or a target gene gRNA, comprises more than one target domain that is complementary with a governing gRNA targeting domain. While not wishing to be bound by theory, it is believed that a governing gRNA molecule complexes with a Cas9 molecule and results in Cas9 mediated inactivation of the targeted nucleic acid, e.g., by cleavage or by binding to the nucleic acid, and results in cessation or reduction of the production of a CRISPR/Cas system component. In an embodiment, the Cas9 molecule forms two complexes: a complex comprising a Cas9 molecule with a target gene gRNA, which complex will alter the HBB or BCL11A gene; and a complex comprising a Cas9 molecule with a governing gRNA molecule, which complex will act to prevent further production of a CRISPR/Cas system component, e.g., a Cas9 molecule or a target gene gRNA molecule. In an embodiment, a governing gRNA molecule/Cas9 molecule complex binds to or promotes cleavage of a control region sequence, e.g., a promoter, operably linked to a sequence that encodes a Cas9 molecule, a sequence that encodes a transcribed region, an exon, or an intron, for the Cas9 molecule. In an embodiment, a governing gRNA molecule/Cas9 molecule complex binds to or promotes cleavage of a control region sequence, e.g., a promoter, operably linked to a gRNA molecule, or a sequence that encodes the gRNA molecule. In an embodiment, the governing gRNA, e.g., a Cas9-targeting governing gRNA molecule, or a target gene gRNA-targeting governing gRNA molecule, limits the effect of the Cas9 molecule/target gene gRNA molecule complex-mediated gene targeting. In an embodiment, a governing gRNA places temporal, level of expression, or other limits, on activity of the Cas9 molecule/target gene gRNA molecule complex. In an embodiment, a governing gRNA reduces off-target or other unwanted activity. In an embodiment, a governing gRNA molecule inhibits, e.g., entirely or substantially entirely inhibits, the production of a component of the Cas9 system and thereby limits, or governs, its activity.

"Modulator", as used herein, refers to an entity, e.g., a drug, that can alter the activity (e.g., enzymatic activity, transcriptional activity, or translational activity), amount, distribution, or structure of a subject molecule or genetic sequence. In an embodiment, modulation comprises cleavage, e.g., breaking of a covalent or non-covalent bond, or the forming of a covalent or non-covalent bond, e.g., the attachment of a moiety, to the subject molecule. In an embodiment, a modulator alters the, three dimensional, secondary, tertiary, or quaternary structure, of a subject molecule. A modulator can increase, decrease, initiate, or eliminate a subject activity.

"Large molecule", as used herein, refers to a molecule having a molecular weight of at least 2, 3, 5, 10, 20, 30, 40, 50, 60, 70, 80, 90, or 100 kD. Large molecules include proteins, polypeptides, nucleic acids, biologics, and carbohydrates.

A "polypeptide", as used herein, refers to a polymer of amino acids having less than 100 amino acid residues. In an embodiment, it has less than 50, 20, or 10 amino acid residues.

"Non-homologous end joining" or "NHEJ", as used herein, refers to ligation mediated repair and/or non-template mediated repair including canonical NHEJ (cNHEJ), alternative NHEJ (altNHEJ), microhomology-mediated end joining (MMEJ), single-strand annealing (SSA), and synthesis-dependent microhomology-mediated end joining (SD-MMEJ).

A "reference molecule", e.g., a reference Cas9 molecule or reference gRNA, as used herein, refers to a molecule to which a subject molecule, e.g., a subject Cas9 molecule of subject gRNA molecule, e.g., a modified or candidate Cas9 molecule is compared. For example, a Cas9 molecule can be characterized as having no more than 10% of the nuclease activity of a reference Cas9 molecule. Examples of reference Cas9 molecules include naturally occurring unmodified Cas9 molecules, e.g., a naturally occurring Cas9 molecule such as a Cas9 molecule of S. pyogenes, S. aureus or S. thermophilus. In an embodiment, the reference Cas9 molecule is the naturally occurring Cas9 molecule having the closest sequence identity or homology with the Cas9 molecule to which it is being compared. In an embodiment, the reference Cas9 molecule is a sequence, e.g., a naturally occurring or known sequence, which is the parental form on which a change, e.g., a mutation has been made.

"Replacement", or "replaced", as used herein with reference to a modification of a molecule does not require a process limitation but merely indicates that the replacement entity is present.

"Small molecule", as used herein, refers to a compound having a molecular weight less than about 2 kD, e.g., less than about 2 kD, less than about 1.5 kD, less than about 1 kD, or less than about 0.75 kD.

"Subject", as used herein, may mean either a human or non-human animal. The term includes, but is not limited to, mammals (e.g., humans, other primates, pigs, rodents (e.g., mice and rats or hamsters), rabbits, guinea pigs, cows, horses, cats, dogs, sheep, and goats). In an embodiment, the subject is a human. In another embodiment, the subject is poultry.

"Treat", "treating" and "treatment", as used herein, mean the treatment of a disease in a mammal, e.g., in a human, including (a) inhibiting the disease, i.e., arresting or preventing its development; (b) relieving the disease, i.e., causing regression of the disease state; and (c) curing the disease.

"Prevent", "preventing" and "prevention", as used herein, means the prevention of a disease in a mammal, e.g., in a human, including (a) avoiding or precluding the disease; (2) affecting the predisposition toward the disease, e.g., preventing at least one symptom of the disease or to delay onset of at least one symptom of the disease.

"X" as used herein in the context of an amino acid sequence, refers to any amino acid (e.g., any of the twenty natural amino acids) unless otherwise specified.

Methods of Repairing Mutation(s) in the HBB Gene

One approach to treat or prevent SCD is to repair (i.e., correct) one or more mutations in the HBB gene, e.g., by HDR. In this approach, mutant HBB allele(s) are corrected and restored to wild type state. While not wishing to be bound by theory, it is believed that correction of the glutamic acid to valine substitution at amino acid 6 in the beta-globin gene restores wild type beta-globin production within erythroid cells. The method described herein can be performed in all cell types. Beta-globin is expressed in cells of erythroid cell lineage. In an embodiment, an erythroid cell is targeted.

In an embodiment, one HBB allele is repaired in the subject. In another embodiment, both HBB alleles are repaired in the subject. In either situation, the subject can be cured of disease. As the disease only displays a phenotype when both alleles are mutated, repair of a single allele is adequate for a cure.

In one aspect, methods and compositions discussed herein, provide for the correction of the underlying genetic cause of SCD, e.g., the correction of a mutation at a target position in the HBB gene, e.g., correction of a mutation at amino acid position 6, e.g., an E6V substitution in the HBB gene.

In an embodiment, the method provides for the correction of a mutation at a target position in the HBB gene, e.g., correction of a mutation at amino acid position 6, e.g., an E6V substitution in the HBB gene. As described herein, in one embodiment, the method comprises the introduction of one or more breaks (e.g., single strand breaks or double strand breaks) sufficiently close to (e.g., either 5' or 3' to) the target position in the HBB gene. e.g., E6V.

In an embodiment, the targeting domain of the gRNA molecule is configured to provide a cleavage event, e.g., a double strand break or a single strand break, sufficiently close to (e.g., either 5' or 3' to) the target position in the HBB gene, e.g., E6V to allow correction, e.g., an alteration in the HBB gene, e.g., an alternation associated with HDR. In an embodiment, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150, 200, 250, 300, 350, 400, 450 or 500 nucleotides of a the target position in the HBB gene, e.g., E6V. The break, e.g., a double strand or single strand break, can be positioned upstream or downstream of the target position in the HBB gene, e.g., E6V.

In an embodiment, a second, third and/or fourth gRNA molecule is configured to provide a cleavage event, e.g., a double strand break or a single strand break, sufficiently close to (e.g., either 5' or 3' to) the target position in the HBB gene, e.g., E6V to allow correction, e.g., an alteration associated with HDR in the HBB gene. In an embodiment, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150, 200, 250, 300, 350, 400, 450 or 500 nucleotides of a the target position in the HBB gene, e.g., E6V. The break, e.g., a double strand or single strand break, can be positioned upstream or downstream of the target position in the HBB gene, e.g., E6V.

In an embodiment, a single strand break is accompanied by an additional single strand break, positioned by a second, third and/or fourth gRNA molecule, as discussed below. For example, The targeting domains bind configured such that a cleavage event, e.g., the two single strand breaks, are positioned within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position in the HBB gene, e.g., E6V. In an embodiment, the first and second gRNA molecules are configured such, that when guiding a Cas9 nickase, a single strand break will be accompanied by an additional single strand break, positioned by a second gRNA, sufficiently close to one another to result in an alteration of the target position in the HBB gene, e.g., E6V. In an embodiment, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In an embodiment, the two gRNA molecules are configured to position cuts at the same position, or within a few nucleotides of one another, on different strands, e.g., essentially mimicking a double strand break.

In an embodiment, a double strand break can be accompanied by an additional double strand break, positioned by a second, third and/or fourth gRNA molecule, as is discussed below. For example, the targeting domain of a first gRNA molecule is configured such that a double strand break is positioned upstream of the target position in the HBB gene, e.g., E6V, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position; and the targeting domain of a second gRNA molecule is configured such that a double strand break is positioned downstream the target position in the HBB gene, e.g., E6V, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position.

In an embodiment, a double strand break can be accompanied by two additional single strand breaks, positioned by a second gRNA molecule and a third gRNA molecule. For example, the targeting domain of a first gRNA molecule is configured such that a double strand break is positioned upstream of the target position in the HBB gene, e.g., E6V, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position; and the targeting domains of a second and third gRNA molecule are configured such that two single strand breaks are positioned downstream of the target position in the HBB gene, e.g., E6V, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position. In an embodiment, the targeting domain of the first, second and third gRNA molecules are configured such that a cleavage event, e.g., a double strand or single strand break, is positioned, independently for each of the gRNA molecules.

In an embodiment, a first and second single strand breaks can be accompanied by two additional single strand breaks positioned by a third gRNA molecule and a fourth gRNA molecule. For example, the targeting domain of a first and second gRNA molecule are configured such that two single strand breaks are positioned upstream of the target position in the HBB gene. e.g., E6V, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position in the HBB gene, e.g., E6V; and the targeting domains of a third and fourth gRNA molecule are configured such that two single strand breaks are positioned downstream of the target position in the HBB gene, e.g., E6V, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position in the HBB gene, e.g., E6V.

In an embodiment, a mutation in the HBB gene, e.g., E6V is corrected using an exogenously provided template nucleic acid, e.g., by HDR. In another embodiment, a mutation in the HBB gene. e.g., E6V is corrected without using an exogenously provided template nucleic acid, e.g., by HDR. In an embodiment, alteration of the target sequence occurs with an endogenous genomic donor sequence, e.g., by HDR. In an embodiment, the endogenous genomic donor sequence comprises one or more nucleotides derived from the HBD gene. In an embodiment, a mutation in the HBB gene, e.g., E6V is corrected by an endogenous genomic donor sequence (e.g, an HBD gene). In an embodiment, an eaCas9 molecule, e.g., an eaCas9 molecule described herein, is used. In an embodiment, the eaCas9 molecule comprises HNH-like domain cleavage activity but has no, or no significant, N-terminal RuvC-like domain cleavage activity. In an embodiment, the eaCas9 molecule is an HNH-like domain nickase. In an embodiment, the eaCas9 molecule comprises a mutation at D10 (e.g., D10A). In an embodiment, the eaCas9 molecule comprises N-terminal RuvC-like domain cleavage activity but has no, or no significant, HNH-like domain cleavage activity. In an embodiment, the eaCas9 molecule is an N-terminal RuvC-like domain nickase. In an embodiment, the eaCas9 molecule comprises a mutation at H840 (e.g., H840A) or N863 (e.g., N863A).

Methods of Altering BCL11A

One approach to increase the expression of HbF involves identification of genes whose products play a role in the regulation of globin gene expression. One such gene is BCL11A. It plays a role in the regulation of γ globin expression. It was first identified because of its role in lymphocyte development. BCL11A encodes a zinc finger protein that is thought to be involved in the stage specific regulation of γ globin expression. The BCL11A gene product is expressed in adult erythroid precursor cells and down-regulation of its expression leads to an increase in γ globin expression. In addition, it appears that the splicing of the BCL11A mRNA is developmentally regulated. In embryonic cells, it appears that the shorter BCL11A mRNA variants, known as BCL11A-S and BCL11A-XS are primary expressed, while in adult cells, the longer BCL11A-L and BCL11A-XL mRNA variants are predominantly expressed. See, Sankaran et al (2008) Science 322 p. 1839. The BCL11A protein appears to interact with the β globin locus to alter its conformation and thus its expression at different developmental stages. Thus, if BCL11A expression is altered e.g., disrupted (e.g., reduced or eliminated), it results in the elevation of γ globin and HbF production.

Disclosed herein are methods for altering the SCD target position in the BCL11A gene. Altering the SCD target position is achieved, e.g., by:
(1) knocking out the BCL11A gene:
  (a) insertion or deletion (e.g., NHEJ-mediated insertion or deletion) of one or more nucleotides in close proximity to or within the early coding region of the BCL11A gene, or
  (b) deletion (e.g., NHEJ-mediated deletion) of a genomic sequence including the erythroid enhancer of the BCL11A gene, or
(2) knocking down the BCL11A gene mediated by enzymatically inactive Cas9 (eiCas9) molecule or an eiCas9-fusion protein by targeting the promoter region of the gene.

All approaches give rise to alteration of the BCL11A gene.

In one embodiment, methods described herein introduce one or more breaks near the early coding region in at least one allele of the BCL11A gene. In another embodiment, methods described herein introduce two or more breaks to flank the erythroid enhancer of SCD target knockout position. The two or more breaks remove (e.g., delete) genomic sequence including the erythorid enhancer. In another embodiment, methods described herein comprises knocking down the BCL11A gene mediated by enzymatically inactive Cas9 (eiCas9) molecule or an eiCas9-fusion protein by targeting the promoter region of SCD target knockdown position. All methods described herein result in alteration of the BCL11A gene.

NHEJ-Mediated Introduction of an Indel in Close Proximity to or within the Early Coding Region of the SCD Knockout Position In an embodiment, the method comprises introducing a NHEJ-mediated insertion or deletion of one more nucleotides in close proximity to the SCD target knockout position (e.g., the early coding region) of the BCL11A gene. As described herein, in one embodiment, the method comprises the introduction of one or more breaks (e.g., single strand breaks or double strand breaks) sufficiently close to (e.g., either 5' or 3' to) the early coding region of the SCD target knockout position, such that the break-induced indel could be reasonably expected to span the SCD target knockout position (e.g., the early coding region). While not wishing to be bound by theory, it is believed that NHEJ-mediated repair of the break(s) allows for the NHEJ-mediated introduction of an indel in close proximity to within the early coding region of the SCD target knockout position.

In an embodiment, the targeting domain of the gRNA molecule is configured to provide a cleavage event, e.g., a double strand break or a single strand break, sufficiently close to the early coding region in the BCL11A gene to allow alteration, e.g., alteration associated with NHEJ in the BCL11A gene. In an embodiment, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150, 200, 250, 300, 350, 400, 450 or 500 nucleotides of a SCD target knockout position. The break, e.g., a double strand or single strand break, can be positioned upstream or downstream of a SCD target knockout position in the BCL11A gene.

In an embodiment, a second gRNA molecule comprising a second targeting domain is configured to provide a cleavage event, e.g., a double strand break or a single strand break, sufficiently close to the early coding region in the BCL11A gene, to allow alteration, e.g., alteration associated with NHEJ in the BCL11A gene, either alone or in combination with the break positioned by said first gRNA molecule. In an embodiment, the targeting domains of the first and second gRNA molecules are configured such that a cleavage event, e.g., a double strand or single strand break, is positioned, independently for each of the gRNA molecules, within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position. In an embodiment, the breaks, e.g., double strand or single strand breaks, are positioned on both sides of a nucleotide of a SCD target knockout position in the BCL11A gene. In an embodiment, the breaks, e.g., double strand or single strand breaks, are positioned on one side, e.g., upstream or downstream, of a nucleotide of a SCD target knockout position in the BCL11A gene.

In an embodiment, a single strand break is accompanied by an additional single strand break, positioned by a second gRNA molecule, as discussed below. For example, The targeting domains bind configured such that a cleavage event, e.g., the two single strand breaks, are positioned within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the early coding region in the BCL11A gene. In an embodiment, the first and second gRNA molecules are configured such, that when guiding a Cas9 nickase, a single strand break will be accompanied by an additional single strand break, positioned by a second gRNA, sufficiently close to one another to result in alteration of the early coding region in the BCL11A gene. In an embodiment, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In an embodiment, the two gRNA molecules are configured to position cuts at the same position, or within a few nucleotides of one another, on different strands, e.g., essentially mimicking a double strand break.

In an embodiment, a double strand break can be accompanied by an additional double strand break, positioned by a second gRNA molecule, as is discussed below. For example, the targeting domain of a first gRNA molecule is configured such that a double strand break is positioned upstream of the early coding region in the BCL11A gene, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position; and the targeting domain of a second gRNA molecule is configured such that a double strand break is positioned downstream of the early coding region in the BCL11A gene, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position.

In an embodiment, a double strand break can be accompanied by two additional single strand breaks, positioned by a second gRNA molecule and a third gRNA molecule. For example, the targeting domain of a first gRNA molecule is configured such that a double strand break is positioned upstream of the early coding region in the BCL11A gene, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position; and the targeting domains of a second and third gRNA molecule are configured such that two single strand breaks are positioned downstream of the early coding region in the BCL11A gene, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the target position. In an embodiment, the targeting domain of the first, second and third gRNA molecules are configured such that a cleavage event, e.g., a double strand or single strand break, is positioned, independently for each of the gRNA molecules.

In an embodiment, a first and second single strand breaks can be accompanied by two additional single strand breaks positioned by a third gRNA molecule and a fourth gRNA molecule. For example, the targeting domain of a first and second gRNA molecule are configured such that two single strand breaks are positioned upstream of the early coding region in the BCL11A gene, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the early coding region in the BCL11A gene; and the targeting domains of a third and fourth gRNA molecule are configured such that two single strand breaks are positioned downstream of a SCD target knockout position in the early coding region in the BCL11A gene, e.g., within 1, 2, 3, 4, 5, 10, 15, 20, 25, 30, 35, 40, 45, 50, 60, 70, 80, 90, 100, 150, 200, 250, 300, 350, 400, 450 or 500 nucleotides of the early coding region in the BCL11A gene.

NHEJ-Mediated Deletion of the Erythroid Enhancer at the SCD Target Position

Figure 10:
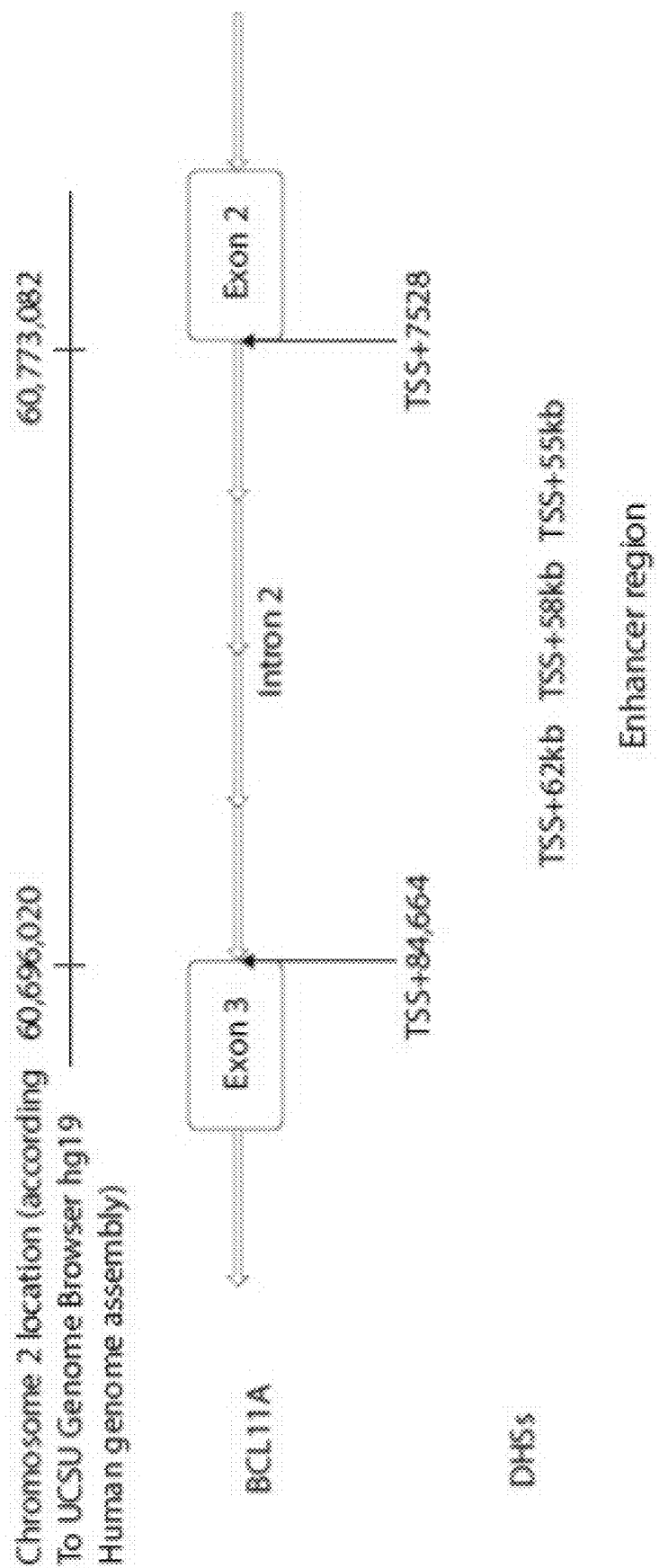
FIG. 10 shows chromosome 2 location (according to UCSC Genome Browser hg 19 human genome assembly) that corresponds to BCL11A intron 2. Three erythroid DHSs are labeled as distance in kilobases from BCL11A TSS (+62, +58 and +55). BCL11A transcription is from right to left.

In an embodiment, the method comprises introducing a NHEJ-mediated deletion of a genomic sequence including the erythroid enhancer. As described herein, in one embodiment, the method comprises the introduction of two double strand breaks—one 5' and the other 3' to (i.e., flanking) the SCD target position (e.g., the erythroid enhancer). Two gRNAs, e.g., unimolecular (or chimeric) or modular gRNA molecules, are configured to position the two double strand breaks on opposite sides of the SCD target knockdown position (e.g., the erythroid enhancer) in the BCL11A gene. In an embodiment, the first double strand break is positioned upstream of the the erythroid enhancer within intron 2 (e.g., between TSS+0.75 kb to TSS+52.0 kb), and the second double strand break is positioned downstream of the the erythroid enhancer within intron 2 (e.g., between TSS+64.4 kb to TSS+84.7 kb) (see FIG. 10). In an embodiment, the two double strand breaks are positioned to remove a portion of the erythroid enhancer resulting in disruption of one or more DHSs. In an embodiment, the breaks (i.e., the two double strand breaks) are positioned to avoid unwanted target chromosome elements, such as repeat elements, e.g., an Alu repeat, or the endogenous splice sites.

The first double strand break may be positioned as follows:

(1) upstream of the 5' end of the erythroid enhancer in intron 2 (e.g., between TSS+0.75 kb to TSS+52.0 kb), or
(2) within the erythroid enhancer provided that a portion of the erythroid enhancer is removed resulting in disruption of one or more DHSs (e.g., between TSS+52.0 kb to TSS+64.4 kb), and the second double strand break to be paired with the first double strand break may be positioned as follows:

(1) downstream the 3' end of the erythroid enhancer in intron 2 (e.g., between TSS+64.4 kb to TSS+84.7 kb), or
(2) within the erythroid enhancer provided that a portion of the erythroid enhancer is removed resulting in disruption of one or more DHSs (e.g., between TSS+52.0 kb to TSS+64.4 kb).

For example, the first double strand break may be positioned in the BCL11A gene:

(1) between TSS+0.75 kb to TSS+10 kb,
(2) between TSS+10 kb to TSS+20 kb,
(3) between TSS+20 kb to TSS+30 kb,
(4) between TSS+30 kb to TSS+40 kb,
(5) between TSS+40 kb to TSS+45 kb,
(6) between TSS+45 kb to TSS+47.5 kb,
(7) between TSS+47.5 kb to TSS+50 kb,
(8) between TSS+50 kb to TSS+51 kb,
(9) between TSS+51 kb to TSS+51.1 kb,
(10) between TSS+51.1 kb to TSS+51.2 kb,
(11) between TSS+51.2 kb to TSS+51.3 kb,
(12) between TSS+51.3 kb to TSS+51.4 kb,
(13) between TSS+51.4 kb to TSS+51.5 kb,
(14) between TSS+51.5 kb to TSS+51.6 kb,
(15) between TSS+51.6 kb to TSS+51.7 kb,
(16) between TSS+51.7 kb to TSS+51.8 kb,
(17) between TSS+51.8 kb to TSS+51.9 kb,
(18) between TSS+51.9 kb to TSS+52 kb,
(19) between TSS+52 kb to TSS+53 kb,
(20) between TSS+53 kb to TSS+54 kb,
(21) between TSS+54 kb to TSS+55 kb,
(22) between TSS+55 kb to TSS+56 kb,
(23) between TSS+56 kb to TSS+57 kb,
(24) between TSS+57 kb to TSS+58 kb,
(25) between TSS+58 kb to TSS+59 kb,
(26) between TSS+59 kb to TSS+60 kb,
(27) between TSS+60 kb to TSS+61 kb,
(28) between TSS+61 kb to TSS+62 kb,
(29) between TSS+62 kb to TSS+63 kb,
(30) between TSS+63 kb to TSS+64 kb, or
(31) between TSS+64 kb to TSS+64.4 kb, and the second double strand break to be paired with the first double strand break may be positioned in the BCL11A gene:

(1) between TSS+52 kb to TSS+53 kb,
(2) between TSS+53 kb to TSS+54 kb,
(3) between TSS+54 kb to TSS+55 kb,
(4) between TSS+55 kb to TSS+56 kb,
(5) between TSS+56 kb to TSS+57 kb,
(6) between TSS+57 kb to TSS+58 kb,
(7) between TSS+58 kb to TSS+59 kb,
(8) between TSS+59 kb to TSS+60 kb,
(9) between TSS+60 kb to TSS+61 kb,
(10) between TSS+61 kb to TSS+62 kb,
(11) between TSS+62 kb to TSS+63 kb,
(12) between TSS+63 kb to TSS+64 kb,
(13) between TSS+64 kb to TSS+64.4 kb,
(14) between TSS+64.4 kb to TSS+65 kb,
(15) between TSS+65 kb to TSS+65.1 kb,
(16) between TSS+65.1 kb to TSS+65.2 kb,

(17) between TSS+65.2 kb to TSS+65.3 kb,
(18) between TSS+65.3 kb to TSS+65.4 kb,
(19) between TSS+65.4 kb to TSS+65.5 kb,
(20) between TSS+65.5 kb to TSS+65.7 kb,
(21) between TSS+65.7 kb to TSS+65.8 kb,
(22) between TSS+65.8 kb to TSS+65.9 kb,
(23) between TSS+65.9 kb to TSS+66 kb,
(24) between TSS+66 kb to TSS+67 kb,
(25) between TSS+67 kb to TSS+68 kb,
(26) between TSS+68 kb to TSS+69 kb,
(27) between TSS+69 kb to TSS+70 kb,
(28) between TSS+70 kb to TSS+75 kb,
(29) between TSS+75 kb to TSS+80 kb, or
(30) between TSS+80 kb to TSS+84.4 kb.

While not wishing to be bound by theory, it is believed that the two double strand breaks allow for NHEJ-mediated deletion of erythroid enhancer in the BCL11A gene.

In an embodiment, the method comprises introducing a NHEJ-mediated deletion of a genomic sequence including the erythroid enhancer. As described herein, in one embodiment, the method comprises the introduction of two sets of breaks (e.g., one double strand break and a pair of single strand breaks)—one 5' and the other 3' to (i.e., flanking) the SCD target position (e.g., the erythroid enhancer). Two gRNAs, e.g., unimolecular (or chimeric) or modular gRNA molecules, are configured to position the two sets of breaks (either the double strand break or the pair of single strand breaks) on opposite sides of the SCD target knockdown position (e.g., the erythroid enhancer) in the BCL11A gene. In an embodiment, the first set of breaks (either the double strand break or the pair of single strand breaks) is positioned upstream of the the erythroid enhancer within intron 2 (e.g., between TSS+0.75 kb to TSS+52.0 kb), and the second set of breaks (either the double strand break or the pair of single strand breaks) is positioned downstream of the the erythroid enhancer within intron 2 (e.g., between TSS+64.4 kb to TSS+84.7 kb) (see FIG. 10). In an embodiment, the two sets of breaks (either the double strand break or the pair of single strand breaks) are positioned to remove a portion of the erythroid enhancer resulting in disruption of one or more DHSs. In an embodiment, the breaks (i.e., the two sets of breaks (either the double strand break or the pair of single strand breaks)) are positioned to avoid unwanted target chromosome elements, such as repeat elements, e.g., an Alu repeat, or the endogenous splice sites.

The first set of breaks (either the double strand break or the pair of single strand breaks) may be positioned as follows:
(1) upstream of the 5' end of the erythroid enhancer in intron 2 (e.g., between TSS+0.75 kb to TSS+52.0 kb), or
(2) within the erythroid enhancer provided that a portion of the erythroid enhancer is removed resulting in disruption of one or more DHSs (e.g., between TSS+52.0 kb to TSS+64.4 kb),
and the second set of breaks (either the double strand break or the pair of single strand breaks) to be paired with the first set of breaks (either the double strand break or the pair of single strand breaks) may be positioned as follows:
(1) downstream the 3' end of the erythroid enhancer in intron 2 (e.g., between TSS+64.4 kb to TSS+84.7 kb), or
(2) within the erythroid enhancer provided that a portion of the erythroid enhancer is removed resulting in disruption of one or more DHSs (e.g., between TSS+52.0 kb to TSS+64.4 kb).

For example, the first set of breaks (either the double strand break or the pair of single strand breaks) may be positioned in the BCL11A gene:
(1) between TSS+0.75 kb to TSS+10 kb,
(2) between TSS+10 kb to TSS+20 kb,
(3) between TSS+20 kb to TSS+30 kb,
(4) between TSS+30 kb to TSS+40 kb,
(5) between TSS+40 kb to TSS+45 kb,
(6) between TSS+45 kb to TSS+47.5 kb,
(7) between TSS+47.5 kb to TSS+50 kb,
(8) between TSS+50 kb to TSS+51 kb,
(9) between TSS+51 kb to TSS+51.1 kb,
(10) between TSS+51.1 kb to TSS+51.2 kb,
(11) between TSS+51.2 kb to TSS+51.3 kb,
(12) between TSS+51.3 kb to TSS+51.4 kb,
(13) between TSS+51.4 kb to TSS+51.5 kb,
(14) between TSS+51.5 kb to TSS+51.6 kb,
(15) between TSS+51.6 kb to TSS+51.7 kb,
(16) between TSS+51.7 kb to TSS+51.8 kb,
(17) between TSS+51.8 kb to TSS+51.9 kb,
(18) between TSS+51.9 kb to TSS+52 kb,
(19) between TSS+52 kb to TSS+53 kb,
(20) between TSS+53 kb to TSS+54 kb,
(21) between TSS+54 kb to TSS+55 kb,
(22) between TSS+55 kb to TSS+56 kb,
(23) between TSS+56 kb to TSS+57 kb,
(24) between TSS+57 kb to TSS+58 kb,
(25) between TSS+58 kb to TSS+59 kb,
(26) between TSS+59 kb to TSS+60 kb,
(27) between TSS+60 kb to TSS+61 kb,
(28) between TSS+61 kb to TSS+62 kb,
(29) between TSS+62 kb to TSS+63 kb,
(30) between TSS+63 kb to TSS+64 kb, or
(31) between TSS+64 kb to TSS+64.4 kb,
and the second set of breaks (either the double strand break or the pair of single strand breaks) to be paired with the first set of breaks (either the double strand break or the pair of single strand breaks) may be positioned in the BCL11A gene:
(1) between TSS+52 kb to TSS+53 kb,
(2) between TSS+53 kb to TSS+54 kb,
(3) between TSS+54 kb to TSS+55 kb,
(4) between TSS+55 kb to TSS+56 kb,
(5) between TSS+56 kb to TSS+57 kb,
(6) between TSS+57 kb to TSS+58 kb,
(7) between TSS+58 kb to TSS+59 kb,
(8) between TSS+59 kb to TSS+60 kb,
(9) between TSS+60 kb to TSS+61 kb,
(10) between TSS+61 kb to TSS+62 kb,
(11) between TSS+62 kb to TSS+63 kb,
(12) between TSS+63 kb to TSS+64 kb,
(13) between TSS+64 kb to TSS+64.4 kb,
(14) between TSS+64.4 kb to TSS+65 kb,
(15) between TSS+65 kb to TSS+65.1 kb,
(16) between TSS+65.1 kb to TSS+65.2 kb,
(17) between TSS+65.2 kb to TSS+65.3 kb,
(18) between TSS+65.3 kb to TSS+65.4 kb,
(19) between TSS+65.4 kb to TSS+65.5 kb,
(20) between TSS+65.5 kb to TSS+65.7 kb,
(21) between TSS+65.7 kb to TSS+65.8 kb,
(22) between TSS+65.8 kb to TSS+65.9 kb,
(23) between TSS+65.9 kb to TSS+66 kb,
(24) between TSS+66 kb to TSS+67 kb,
(25) between TSS+67 kb to TSS+68 kb,
(26) between TSS+68 kb to TSS+69 kb,
(27) between TSS+69 kb to TSS+70 kb,
(28) between TSS+70 kb to TSS+75 kb,

(29) between TSS+75 kb to TSS+80 kb, or
(30) between TSS+80 kb to TSS+84.4 kb.

While not wishing to be bound by theory, it is believed that the two sets of breaks (either the double strand break or the pair of single strand breaks) allow for NHEJ-mediated deletion of erythroid enhancer in the BCL11A gene.

In an embodiment, the method comprises introducing a NHEJ-mediated deletion of a genomic sequence including the erythroid enhancer. As described herein, in one embodiment, the method comprises the introduction of two sets of breaks (e.g., two pairs of single strand breaks)—one 5' and the other 3' to (i.e., flanking) the SCD target position (e.g., the erythroid enhancer). Two gRNAs, e.g., unimolecular (or chimeric) or modular gRNA molecules, are configured to position the two sets of breaks on opposite sides of the SCD target knockdown position (e.g., the erythroid enhancer) in the BCL11A gene. In an embodiment, the first set of breaks (i.e., the first pair of single strand breaks) is positioned upstream of the the erythroid enhancer within intron 2 (e.g., between TSS+0.75 kb to TSS+52.0 kb), and the second set of breaks (i.e., the second pair of single strand breaks) is positioned downstream of the the erythroid enhancer within intron 2 (e.g., between TSS+64.4 kb to TSS+84.7 kb) (see FIG. 10). In an embodiment, the two sets of breaks (e.g., two pairs of single strand breaks)) are positioned to remove a portion of the erythroid enhancer resulting in disruption of one or more DHSs. In an embodiment, the breaks (i.e., the two pairs of single strand breaks) are positioned to avoid unwanted target chromosome elements, such as repeat elements, e.g., an Alu repeat, or the endogenous splice sites.

The first pair of single strand breaks may be positioned as follows:
(1) upstream of the 5' end of the erythroid enhancer in intron 2 (e.g., between TSS+0.75 kb to TSS+52.0 kb), or
(2) within the erythroid enhancer provided that a portion of the erythroid enhancer is removed resulting in disruption of one or more DHSs (e.g., between TSS+52.0 kb to TSS+64.4 kb), and the second pair of single strand breaks to be paired with the first pair of single strand breaks may be positioned as follows:
(1) downstream the 3' end of the erythroid enhancer in intron 2 (e.g., between TSS+64.4 kb to TSS+84.7 kb), or
(2) within the erythroid enhancer provided that a portion of the erythroid enhancer is removed resulting in disruption of one or more DHSs (e.g., between TSS+52.0 kb to TSS+64.4 kb).

For example, the pair of single strand breaks may be positioned in the BCL11A gene:
(1) between TSS+0.75 kb to TSS+10 kb,
(2) between TSS+10 kb to TSS+20 kb,
(3) between TSS+20 kb to TSS+30 kb,
(4) between TSS+30 kb to TSS+40 kb,
(5) between TSS+40 kb to TSS+45 kb,
(6) between TSS+45 kb to TSS+47.5 kb,
(7) between TSS+47.5 kb to TSS+50 kb,
(8) between TSS+50 kb to TSS+51 kb,
(9) between TSS+51 kb to TSS+51.1 kb,
(10) between TSS+51.1 kb to TSS+51.2 kb,
(11) between TSS+51.2 kb to TSS+51.3 kb,
(12) between TSS+51.3 kb to TSS+51.4 kb,
(13) between TSS+51.4 kb to TSS+51.5 kb,
(14) between TSS+51.5 kb to TSS+51.6 kb,
(15) between TSS+51.6 kb to TSS+51.7 kb,
(16) between TSS+51.7 kb to TSS+51.8 kb,
(17) between TSS+51.8 kb to TSS+51.9 kb,
(18) between TSS+51.9 kb to TSS+52 kb,
(19) between TSS+52 kb to TSS+53 kb,
(20) between TSS+53 kb to TSS+54 kb,
(21) between TSS+54 kb to TSS+55 kb,
(22) between TSS+55 kb to TSS+56 kb,
(23) between TSS+56 kb to TSS+57 kb,
(24) between TSS+57 kb to TSS+58 kb,
(25) between TSS+58 kb to TSS+59 kb,
(26) between TSS+59 kb to TSS+60 kb,
(27) between TSS+60 kb to TSS+61 kb,
(28) between TSS+61 kb to TSS+62 kb,
(29) between TSS+62 kb to TSS+63 kb,
(30) between TSS+63 kb to TSS+64 kb, or
(31) between TSS+64 kb to TSS+64.4 kb, and the second pair of single strand breaks to be paired with the first pair of single strand breaks may be positioned in the BCL11A gene:
(1) between TSS+52 kb to TSS+53 kb,
(2) between TSS+53 kb to TSS+54 kb,
(3) between TSS+54 kb to TSS+55 kb,
(4) between TSS+55 kb to TSS+56 kb,
(5) between TSS+56 kb to TSS+57 kb,
(6) between TSS+57 kb to TSS+58 kb,
(7) between TSS+58 kb to TSS+59 kb,
(8) between TSS+59 kb to TSS+60 kb,
(9) between TSS+60 kb to TSS+61 kb,
(10) between TSS+61 kb to TSS+62 kb,
(11) between TSS+62 kb to TSS+63 kb,
(12) between TSS+63 kb to TSS+64 kb,
(13) between TSS+64 kb to TSS+64.4 kb,
(14) between TSS+64.4 kb to TSS+65 kb,
(15) between TSS+65 kb to TSS+65.1 kb,
(16) between TSS+65.1 kb to TSS+65.2 kb,
(17) between TSS+65.2 kb to TSS+65.3 kb,
(18) between TSS+65.3 kb to TSS+65.4 kb,
(19) between TSS+65.4 kb to TSS+65.5 kb,
(20) between TSS+65.5 kb to TSS+65.7 kb,
(21) between TSS+65.7 kb to TSS+65.8 kb,
(22) between TSS+65.8 kb to TSS+65.9 kb,
(23) between TSS+65.9 kb to TSS+66 kb,
(24) between TSS+66 kb to TSS+67 kb,
(25) between TSS+67 kb to TSS+68 kb,
(26) between TSS+68 kb to TSS+69 kb,
(27) between TSS+69 kb to TSS+70 kb,
(28) between TSS+70 kb to TSS+75 kb,
(29) between TSS+75 kb to TSS+80 kb, or
(30) between TSS+80 kb to TSS+84.4 kb.

While not wishing to be bound by theory, it is believed that the two sets of breaks (e.g., the two pair of single strand breaks) allow for NHEJ-mediated deletion of erythroid enhancer in the BCL11A gene.

Knocking Down the BCL11A Gene Mediated by an Enzymatically Inactive Cas9 (eiCas9) Molecule or an eiCas9-Fusion Protein by Targeting the Promoter Region of the Gene.

A targeted knockdown approach reduces or eliminates expression of functional BCL11A gene product. As described herein, a targeted knockdown is mediated by targeting an enzymatically inactive Cas9 (eiCas9) molecule or an eiCas9 fused to a transcription repressor domain or chromatin modifying protein to alter transcription, e.g., to block, reduce, or decrease transcription, of the BCL11A gene. In an embodiment, one or more eiCas9s may be used to block binding of one or more endogenous transcription factors. In another embodiment, an eiCas9 can be fused to a chromatin modifying protein. Altering chromatin status can result in decreased expression of the target gene. One or more eiCas9s fused to one or more chromatin modifying proteins may be used to alter chromatin status.

Methods and compositions discussed herein may be used to alter the expression of the BCL11A gene to treat or prevent SCD by targeting a promoter region of the BCL11A gene. In an embodiment, the promoter region, e.g., at least 2 kb, at least 1.5 kb, at least 1.0 kb, or at least 0.5 kb upstream or downstream of the TSS is targeted to knockdown expression of the BCL11A gene. In an embodiment, the methods and compositions discussed herein may be used to knock down the BCL11A gene to treat or prevent SCD by targeting 0.5 kb upstream or downstream of the TSS. A targeted knockdown approach reduces or eliminates expression of functional BCL11A gene product. As described herein, a targeted knockdown is mediated by targeting an enzymatically inactive Cas9 (eiCas9) molecule or an eiCas9 fused to a transcription repressor domain or chromatin modifying protein to alter transcription, e.g., to block, reduce, or decrease transcription, of the BCL11A gene.

Methods to Treat or Prevent Sickle Cell Disease (SCD)

Disclosed herein are the approaches to treat or prevent SCD, using the compositions and methods described herein.

One approach to treat or prevent SCD is to repair (i.e., correct) one or more mutations in the HBB gene, e.g., by HDR. In this approach, mutant HBB allele(s) are corrected and restored to wild type state. While not wishing to be bound by theory, it is believed that correction of the glutamic acid to valine substitution at amino acid 6 in the beta-globin gene restores wild type beta-globin production within erythroid cells. The method described herein can be performed in all cell types. Beta-globin is expressed in cells of erythroid cell lineage. In an embodiment, an erythroid cell is targeted.

In an embodiment, one HBB allele is repaired in the subject. In another embodiment, both HBB alleles are repaired in the subject. In either situation, the subjects can be cured of disease. As the disease only displays a phenotype when both alleles are mutated, repair of a single allele is adequate for a cure.

In one approach, the BCL11A gene is targeted as a targeted knockout or knockdown, e.g., to increase expression of fetal hemoglobin.

While not wishing to be bound by theory, it is considered that increasing levels of fetal hemoglobin (HbF) in subjects with SCD may ameliorate disease. Fetal hemoglobin can replace beta hemoglobin in the hemoglobin complex, form adequate tetramers with alpha hemoglobin, and effectively carry oxygen to tissues. Subjects with beta-thalassemia who express higher levels of fetal hemoglobin have been found to have a less severe phenotype. Hydroxyurea, often used in the treatment of beta-thalassemia, may exert its mechanism of action via increasing levels of HbF production.

In an embodiment, knockout or knockdown of the BCL11A gene increases fetal hemoglobin levels in beta-thalassemia subjects and improves phenotype and/or reduces or prevents disease progression. BCL11A is a zinc-finger repressor that is involved in the regulation of fetal hemoglobin and acts to repress the synthesis of fetal hemoglobin. Knockout of the BCL11A gene in erythroid cells induces increased fetal hemoglobin (HbF) synthesis and increased HbF can result in more effective oxygen carrying capacity in subjects with beta-thalassemia (HbF will form tetramers with hemoglobin alpha).

In an embodiment, the BCL11A knockout or knockdown is targeted specifically to cells of the erythroid lineage. BCL11A knockout in erythroid cells has been found in in vitro studies to have no effect on erythroid growth, maturation and function. In an embodiment, erythroid cells are preferentially targeted, e.g., at least 90%, 95%, 96%, 97%, 98%, 99%, or 100% of the targeted cells are erythroid cells. For example, in the case of in vivo delivery, erythroid cells are preferentially targeted, and if cells are treated ex vivo and returned to the subject, erythroid cells are preferentially modified.

In an embodiment, the methods described herein result in increased fetal hemoglobin synthesis in beta thalassemia subjects, thereby improving disease phenotype in subjects with SCD. For example, subjects with beta thalassemia major will suffer from less severe anemia and will need fewer blood transfusions. They will therefore have fewer complications arising from transfusions and chelation therapy. In an embodiment, the method described herein increases fetal hemoglobin synthesis and improves the oxygen carrying capacity of erythroid cells. For example, subjects are expected to demonstrate decreased rates of extramedullary erythropoiesis and decreased erythroid hypertrophy within the bone marrow compared to a subject who has not received the therapy. In an embodiment, the method described herein results in reduction of bone fractures, bone abnormalities, splenomegaly, and thrombosis compared to a subject who has not received the therapy.

Knockdown or knockout of one or both BCL11A alleles may be performed prior to disease onset or after disease onset, but preferably early in the disease course.

In an embodiment, the method comprises initiating treatment of a subject prior to disease onset.

In an embodiment, the method comprises initiating treatment of a subject after disease onset.

In an embodiment, the method comprises initiating treatment of a subject well after disease onset, e.g., 1, 2, 3, 4, 5, 6, 7, 8, 9, 10, 12, 16, 24, 36, 48 or more months after onset of SCD. While not wishing to be bound by theory it is believed that this treatment may be effective if subjects present well into the course of illness.

In an embodiment, the method comprises initiating treatment of a subject in an advanced stage of disease.

Overall, initiation of treatment for subjects at all stages of disease is expected to prevent negative consequences of disease and be of benefit to subjects.

In an embodiment, the method comprises initiating treatment of a subject prior to disease expression. In an embodiment, the method comprises initiating treatment of a subject in an early stage of disease, e.g., when a subject has tested positive for beta-thalassemia mutations but has no signs or symptoms associated with beta-thalassemia major, minor or intermedia.

In an embodiment, the method comprises initiating treatment of a subject at the appearance of microcytic anemia, e.g., in an infant, child, adult or young adult.

In an embodiment, the method comprises initiating treatment of a subject who is transfusion-dependent.

In an embodiment, the method comprises initiating treatment of a subject who has tested positive for a mutation in a beta globin gene.

In an embodiment, the method comprises initiating treatment at the appearance of any one or more of the following findings associated or consistent with beta-thalassemia major or beta-thalassemia minor: anemia, diarrhea, fever, failure to thrive, frontal bossing, broken long bones, hepatomegaly, splenomegaly, thrombosis, pulmonary embolus, stroke, leg ulcer, cardiomyopathy, cardiac arrhythmia, and evidence of extramedullary erythropoiesis.

In an embodiment, a cell is treated, e.g., ex vivo. In an embodiment, an ex vivo treated cell is returned to a subject.

In an embodiment, allogenic or autologous bone marrow or erythroid cells are treated ex vivo. In an embodiment, an ex vivo treated allogenic or autologous bone marrow or erythroid cells are administered to the subject. In an embodiment, an erythroid cell, e.g., an autologous erythroid cell, is treated ex vivo and returned to the subject. In an embodiment, an autologous stem cell, is treated ex vivo and returned to the subject. In an embodiment, the modified HSCs are administered to the patient following no myeloablative pre-conditioning. In an embodiment, the modified HSCs are administered to the patient following mild myeloablative pre-conditioning such that following engraftment, some of the hematopoietic cells are devied from the modified HSCs. In other aspects, the HSCs are administered after full myeloablation such that following engraftment, 100% of the hematopoietic cells are derived from the modified HSCs.

In an embodiment, the method comprises delivery of a gRNA molecule and Cas9 molecule by intravenous injection, intramuscular injection, subcutaneous injection, or intra-bone marrow (IBM) injection.

In an embodiment, the method comprises delivery of a gRNA molecule and/or a Cas9 molecule by an AAV. In an embodiment, the method comprises delivery of a gRNA molecule and/or a Cas9 molecule by a lentivirus. In an embodiment, the method comprises delivery of a gRNA molecule and/or a Cas9 molecule by a nanoparticle. In an embodiment, the method comprises delivery of a gRNA molecule by a parvovirus, e.g., a modified parvovirus specifically designed to target bone marrow cells and/or CD4 cells. In an embodiment, two or more gRNA molecules (e.g., a second, third or fourth gRNA molecules) are delivered.

I. gRNA Molecules

A gRNA molecule, as that term is used herein, refers to a nucleic acid that promotes the specific targeting or homing of a gRNA molecule/Cas9 molecule complex to a target nucleic acid. gRNA molecules can be unimolecular (having a single RNA molecule), sometimes referred to herein as "chimeric" gRNAs, or modular (comprising more than one, and typically two, separate RNA molecules). A gRNA molecule comprises a number of domains. The gRNA molecule domains are described in more detail below.

Several exemplary gRNA structures, with domains indicated thereon, are provided in FIGS. 1A-1G. While not wishing to be bound by theory, in an embodiment, with regard to the three dimensional form, or intra- or inter-strand interactions of an active form of a gRNA, regions of high complementarity are sometimes shown as duplexes in FIGS. 1A-1G and other depictions provided herein.

In an embodiment, a unimolecular, or chimeric, gRNA comprises, preferably from 5' to 3':
  a targeting domain (which is complementary to a target nucleic acid in the HBB gene or BCL11A gene, e.g., a targeting domain from any of Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31;
  a first complementarity domain;
  a linking domain;
  a second complementarity domain (which is complementary to the first complementarity domain);
  a proximal domain; and
  optionally, a tail domain.
In an embodiment, a modular gRNA comprises:
  a first strand comprising, preferably from 5' to 3';
  a targeting domain (which is complementary to a target nucleic acid in the HBB gene or BCL11A gene, e.g., a targeting domain from Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31; and
  a first complementarity domain; and
a second strand, comprising, preferably from 5' to 3':
  optionally, a 5' extension domain;
  a second complementarity domain;
  a proximal domain; and
  optionally, a tail domain.
The domains are discussed briefly below.

The Targeting Domain

FIGS. 1A-1G provide examples of the placement of targeting domains.

The targeting domain comprises a nucleotide sequence that is complementary, e.g., at least 80, 85, 90, or 95% complementary, e.g., fully complementary, to the target sequence on the target nucleic acid. The targeting domain is part of an RNA molecule and will therefore comprise the base uracil (U), while any DNA encoding the gRNA molecule will comprise the base thymine (T). While not wishing to be bound by theory, in an embodiment, it is believed that the complementarity of the targeting domain with the target sequence contributes to specificity of the interaction of the gRNA molecule/Cas9 molecule complex with a target nucleic acid. It is understood that in a targeting domain and target sequence pair, the uracil bases in the targeting domain will pair with the adenine bases in the target sequence. In an embodiment, the target domain itself comprises in the 5' to 3' direction, an optional secondary domain, and a core domain. In an embodiment, the core domain is fully complementary with the target sequence. In an embodiment, the targeting domain is 5 to 50 nucleotides in length. The strand of the target nucleic acid with which the targeting domain is complementary is referred to herein as the complementary strand. Some or all of the nucleotides of the domain can have a modification. e.g., a modification found in Section VIII herein.

In an embodiment, the targeting domain is 16 nucleotides in length.

In an embodiment, the targeting domain is 17 nucleotides in length.

In an embodiment, the targeting domain is 18 nucleotides in length.

In an embodiment, the targeting domain is 19 nucleotides in length.

In an embodiment, the targeting domain is 20 nucleotides in length.

In an embodiment, the targeting domain is 21 nucleotides in length.

In an embodiment, the targeting domain is 22 nucleotides in length.

In an embodiment, the targeting domain is 23 nucleotides in length.

In an embodiment, the targeting domain is 24 nucleotides in length.

In an embodiment, the targeting domain is 25 nucleotides in length.

In an embodiment, the targeting domain is 26 nucleotides in length.

In an embodiment, the targeting domain comprises 16 nucleotides.

In an embodiment, the targeting domain comprises 17 nucleotides.

In an embodiment, the targeting domain comprises 18 nucleotides.

In an embodiment, the targeting domain comprises 19 nucleotides.

In an embodiment, the targeting domain comprises 20 nucleotides.

In an embodiment, the targeting domain comprises 21 nucleotides.

In an embodiment, the targeting domain comprises 22 nucleotides.

In an embodiment, the targeting domain comprises 23 nucleotides.

In an embodiment, the targeting domain comprises 24 nucleotides.

In an embodiment, the targeting domain comprises 25 nucleotides.

In an embodiment, the targeting domain comprises 26 nucleotides.

Targeting domains are discussed in more detail below.

The First Complementarity Domain

FIGS. 1A-1G provide examples of first complementarity domains.

The first complementarity domain is complementary with the second complementarity domain, and in an embodiment, has sufficient complementarity to the second complementarity domain to form a duplexed region under at least some physiological conditions. In an embodiment, the first complementarity domain is 5 to 30 nucleotides in length. In an embodiment, the first complementarity domain is 5 to 25 nucleotides in length. In an embodiment, the first complementary domain is 7 to 25 nucleotides in length. In an embodiment, the first complementary domain is 7 to 22 nucleotides in length. In an embodiment, the first complementary domain is 7 to 18 nucleotides in length. In an embodiment, the first complementary domain is 7 to 15 nucleotides in length. In an embodiment, the first complementary domain is 5, 6, 7, 8, 9, 10, 11, 12, 13, 14, 15, 16, 17, 18, 19, 20, 21, 22, 23, 24, or 25 nucleotides in length.

In an embodiment, the first complementarity domain comprises 3 subdomains, which, in the 5' to 3' direction are: a 5' subdomain, a central subdomain, and a 3' subdomain. In an embodiment, the 5' subdomain is 4 to 9, e.g., 4, 5, 6, 7, 8 or 9 nucleotides in length. In an embodiment, the central subdomain is 1, 2, or 3, e.g., 1, nucleotide in length. In an embodiment, the 3' subdomain is 3 to 25, e.g., 4 to 22, 4 to 18, or 4 to 10, or 3, 4, 5, 6, 7, 8, 9, 10, 11, 12, 13, 14, 15, 16, 17, 18, 19, 20, 21, 22, 23, 24, or 25 nucleotides in length.

The first complementarity domain can share homology with, or be derived from, a naturally occurring first complementarity domain. In an embodiment, it has at least 50% homology with a first complementarity domain disclosed herein, e.g., an *S. pyogenes, S. aureus* or *S. thermophilus*, first complementarity domain.

Some or all of the nucleotides of the domain can have a modification, e.g., a modification found in Section VIII herein.

First complementarity domains are discussed in more detail below.

The Linking Domain

FIGS. 1A-1G provide examples of linking domains.

A linking domain serves to link the first complementarity domain with the second complementarity domain of a unimolecular gRNA. The linking domain can link the first and second complementarity domains covalently or non-covalently. In an embodiment, the linkage is covalent. In an embodiment, the linking domain covalently couples the first and second complementarity domains, see, e.g., FIGS. 1B-1E. In an embodiment, the linking domain is, or comprises, a covalent bond interposed between the first complementarity domain and the second complementarity domain. Typically the linking domain comprises one or more, e.g., 2, 3, 4, 5, 6, 7, 8, 9, or 10 nucleotides.

In modular gRNA molecules the two molecules are associated by virtue of the hybridization of the complementarity domains see e.g., FIG. 1A.

A wide variety of linking domains are suitable for use in unimolecular gRNA molecules. Linking domains can consist of a covalent bond, or be as short as one or a few nucleotides, e.g., 1, 2, 3, 4, or 5 nucleotides in length. In an embodiment, a linking domain is 2, 3, 4, 5, 6, 7, 8, 9, 10, 15, 20, or 25 or more nucleotides in length. In an embodiment, a linking domain is 2 to 50, 2 to 40, 2 to 30, 2 to 20, 2 to 10, or 2 to 5 nucleotides in length. In an embodiment, a linking domain shares homology with, or is derived from, a naturally occurring sequence, e.g., the sequence of a tracrRNA that is 5' to the second complementarity domain. In an embodiment, the linking domain has at least 50% homology with a linking domain disclosed herein.

Some or all of the nucleotides of the domain can have a modification, e.g., a modification found in Section VIII herein.

Linking domains are discussed in more detail below.

The 5' Extension Domain

In an embodiment, a modular gRNA can comprise additional sequence, 5' to the second complementarity domain, referred to herein as the 5' extension domain, see, e.g., FIG. 1A. In an embodiment, the 5' extension domain is, 2 to 10, 2 to 9, 2 to 8, 2 to 7, 2 to 6, 2 to 5, 2 to 4 nucleotides in length. In an embodiment, the 5' extension domain is 2, 3, 4, 5, 6, 7, 8, 9, or 10 or more nucleotides in length.

The Second Complementarity Domain

FIGS. 1A-1G provides examples of second complementarity domains.

Figure 1B:
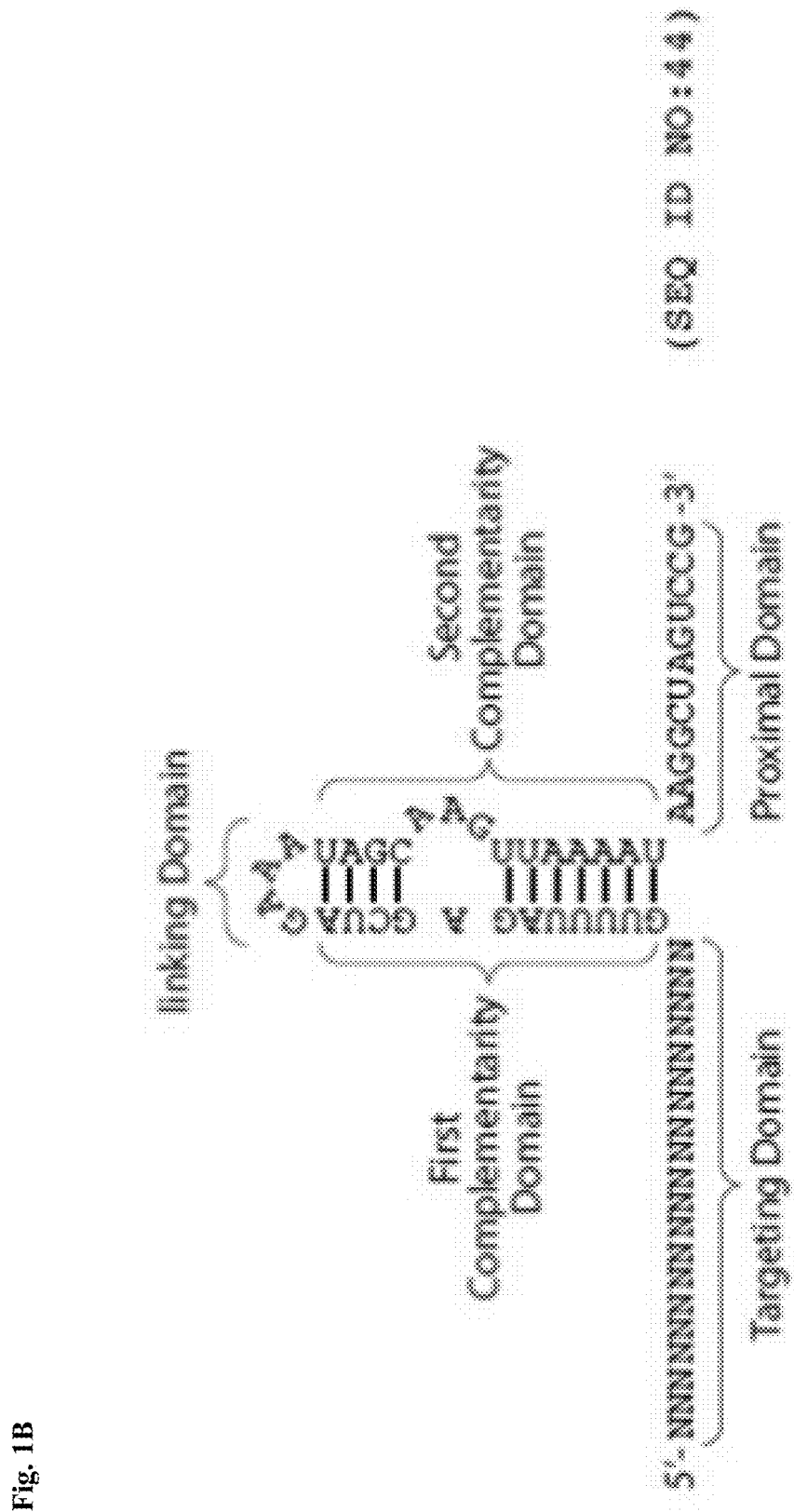
Figure 1C:
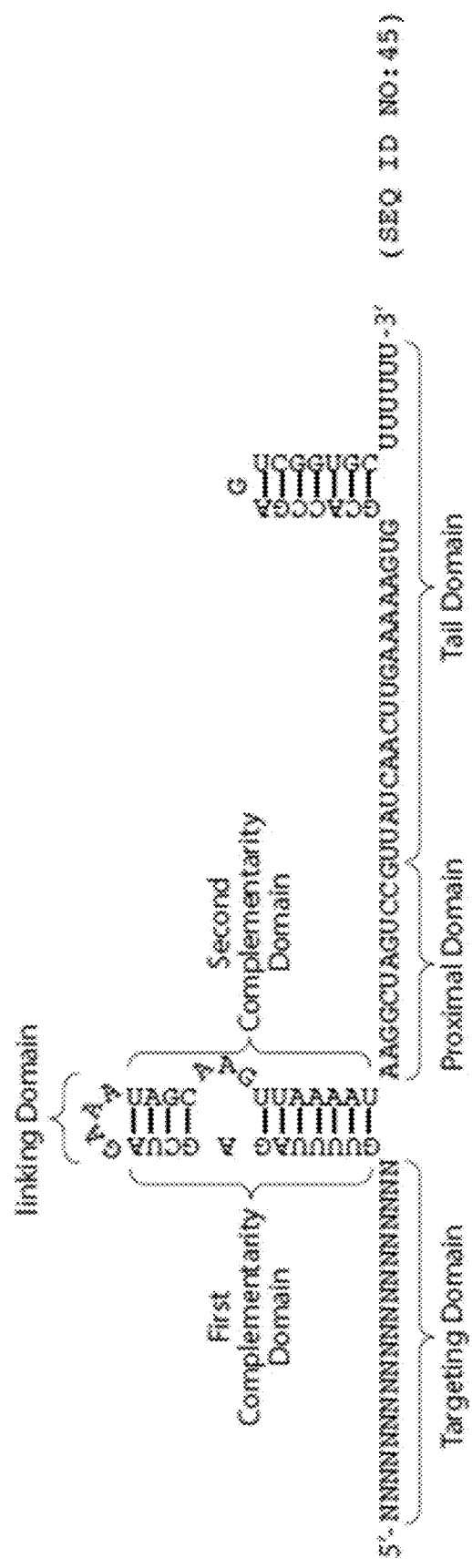
Figure 1D:
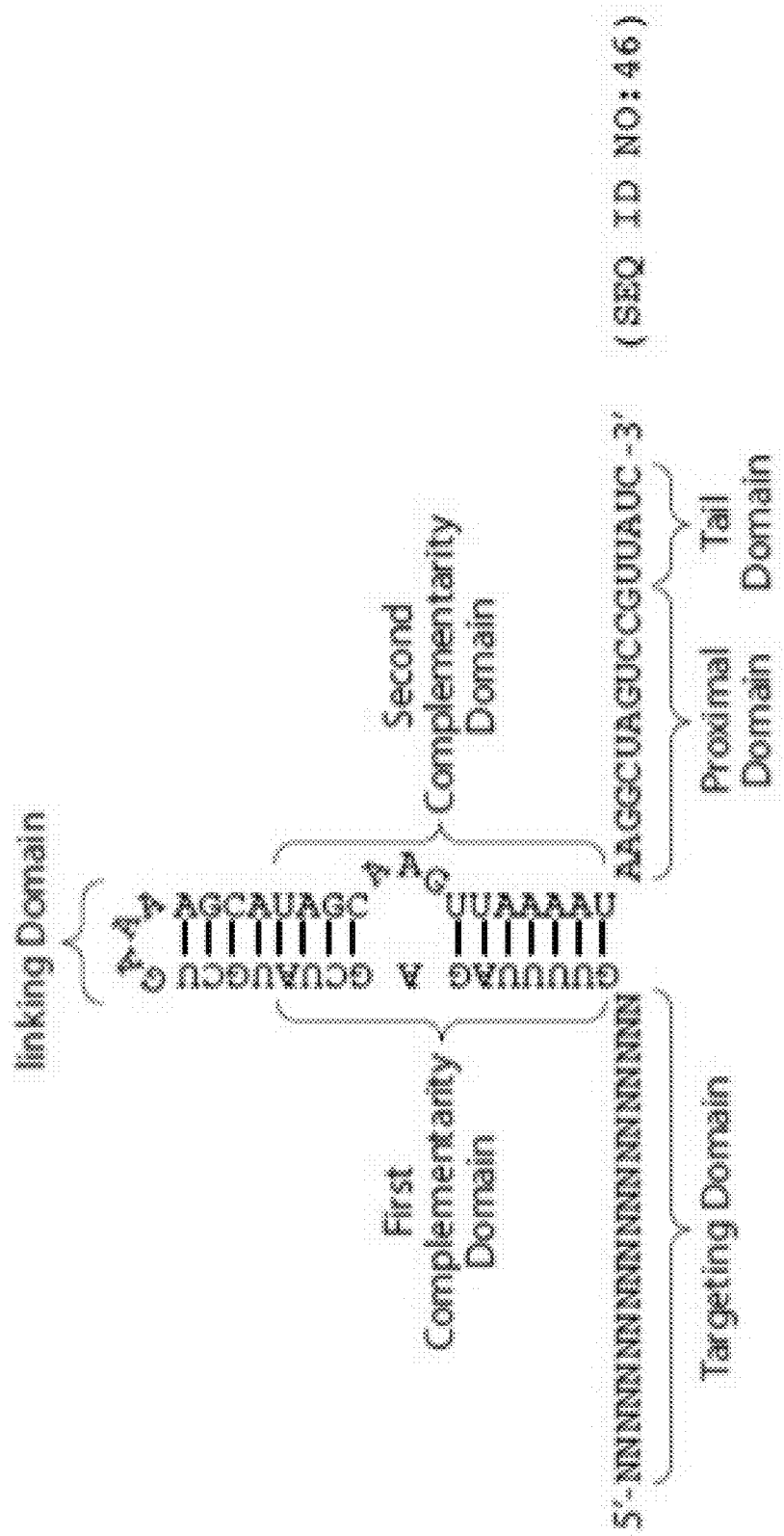
Figure 1E:
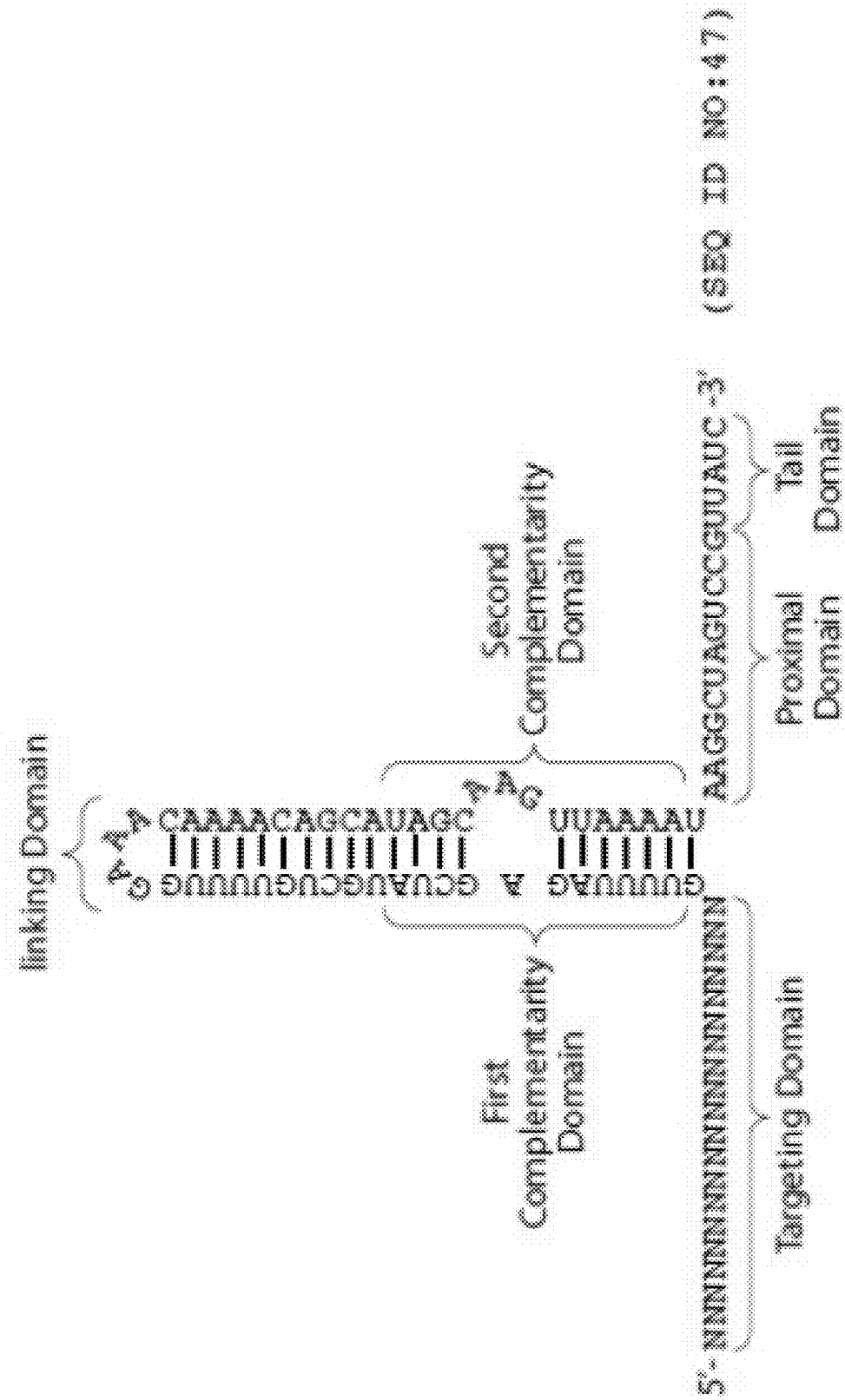
Figure 1F:
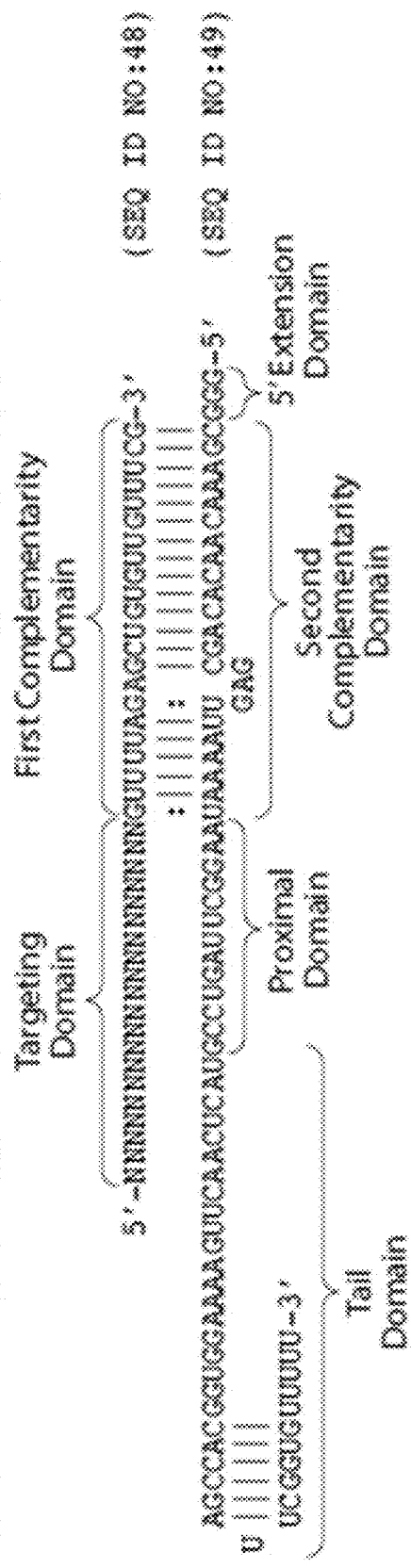

The second complementarity domain is complementary with the first complementarity domain, and in an embodiment, has sufficient complementarity to the second complementarity domain to form a duplexed region under at least some physiological conditions. In an embodiment, e.g., as shown in FIGS. 1A-1B, the second complementarity domain can include sequence that lacks complementarity with the first complementarity domain, e.g., sequence that loops out from the duplexed region.

In an embodiment, the second complementarity domain is 5 to 27 nucleotides in length. In an embodiment, it is longer than the first complementary region. In an embodiment the second complementary domain is 7 to 27 nucleotides in length. In an embodiment, the second complementary domain is 7 to 25 nucleotides in length. In an embodiment, the second complementary domain is 7 to 20 nucleotides in length. In an embodiment, the second complementary domain is 7 to 17 nucleotides in length. In an embodiment, the complementary domain is 5, 6, 7, 8, 9, 10, 11, 12, 13, 14, 15, 16, 17, 18, 19, 20, 21, 22, 23, 24, 25 or 26 nucleotides in length.

In an embodiment, the second complementarity domain comprises 3 subdomains, which, in the 5' to 3' direction are: a 5' subdomain, a central subdomain, and a 3' subdomain. In an embodiment, the 5' subdomain is 3 to 25, e.g., 4 to 22, 4 to 18, or 4 to 10, or 3, 4, 5, 6, 7, 8, 9, 10, 11, 12, 13, 14, 15, 16, 17, 18, 19, 20, 21, 22, 23, 24, or 25 nucleotides in length. In an embodiment, the central subdomain is 1, 2, 3, 4 or 5, e.g., 3, nucleotides in length. In an embodiment, the 3' subdomain is 4 to 9, e.g., 4, 5, 6, 7, 8 or 9 nucleotides in length.

In an embodiment, the 5' subdomain and the 3' subdomain of the first complementarity domain, are respectively, complementary, e.g., fully complementary, with the 3' subdomain and the 5' subdomain of the second complementarity domain.

The second complementarity domain can share homology with or be derived from a naturally occurring second complementarity domain. In an embodiment, it has at least 50% homology with a second complementarity domain disclosed herein, e.g., an *S. pyogenes, S. aureus* or *S. thermophilus*, first complementarity domain.

Some or all of the nucleotides of the domain can have a modification, e.g., a modification found in Section VIII herein.

A Proximal Domain

FIGS. 1A-1G provide examples of proximal domains.

In an embodiment, the proximal domain is 5 to 20 nucleotides in length. In an embodiment, the proximal domain can share homology with or be derived from a naturally occurring proximal domain. In an embodiment, it has at least 50% homology with a proximal domain disclosed herein, e.g., an *S. pyogenes, S. aureus* or *S. thermophilus*, proximal domain.

Some or all of the nucleotides of the domain can have a modification, e.g., modification found in Section VIII herein.

A Tail Domain

FIGS. 1A-1G provide examples of tail domains.

As can be seen by inspection of the tail domains in FIGS. 1A-1E, a broad spectrum of tail domains are suitable for use in gRNA molecules. In an embodiment, the tail domain is 0 (absent), 1, 2, 3, 4, 5, 6, 7, 8, 9, or 10 nucleotides in length. In embodiment, the tail domain nucleotides are from or share homology with sequence from the 5' end of a naturally occurring tail domain, see e.g., panels 4a or 5a of FIG. 1D or FIG. 1E. In an embodiment, the tail domain includes sequences that are complementary to each other and which, under at least some physiological conditions, form a duplexed region.

In an embodiment, the tail domain is absent or is 1 to 50 nucleotides in length. In an embodiment, the tail domain can share homology with or be derived from a naturally occurring proximal tail domain. In an embodiment, it has at least 50% homology with a tail domain disclosed herein, e.g., an *S. pyogenes, S. aureus* or *S. thermophilus*, tail domain.

In an embodiment, the tail domain includes nucleotides at the 3' end that are related to the method of in vitro or in vivo transcription. When a T7 promoter is used for in vitro transcription of the gRNA, these nucleotides may be any nucleotides present before the 3' end of the DNA template. When a U6 promoter is used for in vivo transcription, these nucleotides may be the sequence UUUUUU. When alternate pol-III promoters are used, these nucleotides may be various numbers or uracil bases or may include alternate bases.

The domains of gRNA molecules are described in more detail below.

The Targeting Domain

The "targeting domain" of the gRNA is complementary to the "target domain" on the target nucleic acid. The strand of the target nucleic acid comprising the nucleotide sequence complementary to the core domain of the gRNA is referred to herein as the "complementary strand" of the target nucleic acid. Guidance on the selection of targeting domains can be found, e.g., in Fu Y et al., Nat Biotechnol 2014 (doi: 10.1038/nbt.2808) and Sternberg S H et al., Nature 2014 (doi: 10.1038/nature13011).

In an embodiment, the targeting domain is 16, 17, 18, 19, 20, 21, 22, 23, 24, 25 or 26 nucleotides in length.

In an embodiment, the targeting domain is 16 nucleotides in length.

In an embodiment, the targeting domain is 17 nucleotides in length.

In an embodiment, the targeting domain is 18 nucleotides in length.

In an embodiment, the targeting domain is 19 nucleotides in length.

In an embodiment, the targeting domain is 20 nucleotides in length.

In an embodiment, the targeting domain is 21 nucleotides in length.

In an embodiment, the targeting domain is 22 nucleotides in length.

In an embodiment, the targeting domain is 23 nucleotides in length.

In an embodiment, the targeting domain is 24 nucleotides in length.

In an embodiment, the targeting domain is 25 nucleotides in length.

In an embodiment, the targeting domain is 26 nucleotides in length.

In an embodiment, the targeting domain comprises 16 nucleotides.

In an embodiment, the targeting domain comprises 17 nucleotides.

In an embodiment, the targeting domain comprises 18 nucleotides.

In an embodiment, the targeting domain comprises 19 nucleotides.

In an embodiment, the targeting domain comprises 20 nucleotides.

In an embodiment, the targeting domain comprises 21 nucleotides.

In an embodiment, the targeting domain comprises 22 nucleotides.

In an embodiment, the targeting domain comprises 23 nucleotides.

In an embodiment, the targeting domain comprises 24 nucleotides.

In an embodiment, the targeting domain comprises 25 nucleotides.

In an embodiment, the targeting domain comprises 26 nucleotides.

In an embodiment, the targeting domain is 10+/−5, 20+/−5, 30+/−5, 40+/−5, 50+/−5, 60+/−5, 70+/−5, 80+/−5, 90+/−5, or 100+/−5 nucleotides, in length.

In an embodiment, the targeting domain is 20+/−5 nucleotides in length.

In an embodiment, the targeting domain is 20+/−10, 30+/−10, 40+/−10, 50+/−10, 60+/−10, 70+/−10, 80+/−10, 90+/−10, or 100+/−10 nucleotides, in length.

In an embodiment, the targeting domain is 30+/−10 nucleotides in length.

In an embodiment, the targeting domain is 10 to 100, 10 to 90, 10 to 80, 10 to 70, 10 to 60, 10 to 50, 10 to 40, 10 to 30, 10 to 20 or 10 to 15 nucleotides in length.

In another embodiment, the targeting domain is 20 to 100, 20 to 90, 20 to 80, 20 to 70, 20 to 60, 20 to 50, 20 to 40, 20 to 30, or 20 to 25 nucleotides in length.

Typically the targeting domain has full complementarity with the target sequence. In an embodiment the targeting domain has or includes 1, 2, 3, 4, 5, 6, 7 or 8 nucleotides that are not complementary with the corresponding nucleotide of the targeting domain.

In an embodiment, the target domain includes 1, 2, 3, 4 or 5 nucleotides that are complementary with the corresponding nucleotide of the targeting domain within 5 nucleotides of its 5' end. In an embodiment, the target domain includes 1, 2, 3, 4 or 5 nucleotides that are complementary with the corresponding nucleotide of the targeting domain within 5 nucleotides of its 3' end.

In an embodiment, the target domain includes 1, 2, 3, or 4 nucleotides that are not complementary with the corresponding nucleotide of the targeting domain within 5 nucleotides of its 5' end. In an embodiment, the target domain includes 1, 2, 3, or 4 nucleotides that are not complementary with the corresponding nucleotide of the targeting domain within 5 nucleotides of its 3' end.

In an embodiment, the degree of complementarity, together with other properties of the gRNA, is sufficient to allow targeting of a Cas9 molecule to the target nucleic acid.

In an embodiment, the targeting domain comprises two consecutive nucleotides that are not complementary to the target domain ("non-complementary nucleotides"), e.g., two consecutive noncomplementary nucleotides that are within 5 nucleotides of the 5' end of the targeting domain, within 5 nucleotides of the 3' end of the targeting domain, or more than 5 nucleotides away from one or both ends of the targeting domain.

In an embodiment, no two consecutive nucleotides within 5 nucleotides of the 5' end of the targeting domain, within 5 nucleotides of the 3' end of the targeting domain, or within a region that is more than 5 nucleotides away from one or both ends of the targeting domain, are not complementary to the targeting domain.

In an embodiment, there are no noncomplementary nucleotides within 5 nucleotides of the 5' end of the targeting domain, within 5 nucleotides of the 3' end of the targeting domain, or within a region that is more than 5 nucleotides away from one or both ends of the targeting domain.

In an embodiment, the targeting domain nucleotides do not comprise modifications, e.g., modifications of the type provided in Section VIII. However, in an embodiment, the targeting domain comprises one or more modifications, e.g., modifications that it render it less susceptible to degradation or more bio-compatible, e.g., less immunogenic. By way of example, the backbone of the targeting domain can be modified with a phosphorothioate, or other modification from Section VIII. In an embodiment, a nucleotide of the targeting domain can comprise a 2' modification (e.g., a modification at the 2' position on ribose), e.g., a 2-acetylation, e.g., a 2' methylation, or other modification(s) from Section VIII.

In an embodiment, the targeting domain includes 1, 2, 3, 4, 5, 6, 7 or 8 or more modifications. In an embodiment, the targeting domain includes 1, 2, 3, or 4 modifications within 5 nucleotides of its 5' end. In an embodiment, the targeting domain comprises as many as 1, 2, 3, or 4 modifications within 5 nucleotides of its 3' end.

In an embodiment, the targeting domain comprises modifications at two consecutive nucleotides, e.g., two consecutive nucleotides that are within 5 nucleotides of the 5' end of the targeting domain, within 5 nucleotides of the 3' end of the targeting domain, or more than 5 nucleotides away from one or both ends of the targeting domain.

In an embodiment, no two consecutive nucleotides are modified within 5 nucleotides of the 5' end of the targeting domain, within 5 nucleotides of the 3' end of the targeting domain, or within a region that is more than 5 nucleotides away from one or both ends of the targeting domain. In an embodiment, no nucleotide is modified within 5 nucleotides of the 5' end of the targeting domain, within 5 nucleotides of the 3' end of the targeting domain, or within a region that is more than 5 nucleotides away from one or both ends of the targeting domain.

Modifications in the targeting domain can be selected to not interfere with targeting efficacy, which can be evaluated by testing a candidate modification in the system described in Section IV. gRNAs having a candidate targeting domain having a selected length, sequence, degree of complementarity, or degree of modification, can be evaluated in a system in Section IV. The candidate targeting domain can be placed, either alone, or with one or more other candidate changes in a gRNA molecule/Cas9 molecule system known to be functional with a selected target and evaluated.

In an embodiment, all of the modified nucleotides are complementary to and capable of hybridizing to corresponding nucleotides present in the target domain. In another embodiment, 1, 2, 3, 4, 5, 6, 7 or 8 or more modified nucleotides are not complementary to or capable of hybridizing to corresponding nucleotides present in the target domain.

In an embodiment, the targeting domain comprises, preferably in the 5'→3' direction: a secondary domain and a core domain. These domains are discussed in more detail below.

The Core Domain and Secondary Domain of the Targeting Domain

The "core domain" of the targeting domain is complementary to the "core domain target" on the target nucleic acid. In an embodiment, the core domain comprises about 8 to about 13 nucleotides from the 3' end of the targeting domain (e.g., the most 3' 8 to 13 nucleotides of the targeting domain).

In an embodiment, the core domain and targeting domain, are independently, 6+/−2, 7+/−2, 8+/−2, 9+/−2, 10+/−2, 11+/−2, 12+/−2, 13+/−2, 14+/−2, 15+/−2, or 16+−2, nucleotides in length.

In an embodiment, the core domain and targeting domain, are independently, 10+/−2 nucleotides in length.

In an embodiment, the core domain and targeting domain, are independently, 10+/−4 nucleotides in length.

In an embodiment, the core domain and targeting domain are independently 6, 7, 8, 9, 10, 11, 12, 13, 14, 15, 16, 17, or 18 nucleotides in length.

In an embodiment, the core domain and targeting domain are independently 3 to 20, 4 to 20, 5 to 20, 6 to 20, 7 to 20, 8 to 20, 9 to 20 10 to 20 or 15 to 20 nucleotides in length.

In an embodiment, the core domain and targeting domain are independently 3 to 15, e.g., 6 to 15, 7 to 14, 7 to 13, 6 to 12, 7 to 12, 7 to 11, 7 to 10, 8 to 14, 8 to 13, 8 to 12, 8 to 11, 8 to 10 or 8 to 9 nucleotides in length.

The core domain is complementary with the core domain target. Typically the core domain has exact complementarity with the core domain target. In an embodiment, the core domain can have 1, 2, 3, 4 or 5 nucleotides that are not complementary with the corresponding nucleotide of the core domain. In an embodiment, the degree of complementarity, together with other properties of the gRNA, is sufficient to allow targeting of a Cas9 molecule to the target nucleic acid.

The "secondary domain" of the targeting domain of the gRNA is complementary to the "secondary domain target" of the target nucleic acid.

In an embodiment, the secondary domain is positioned 5' to the core domain.

In an embodiment, the secondary domain is absent or optional.

In an embodiment, if the targeting domain is 26 nucleotides in length and the core domain (counted from the 3' end of the targeting domain) is 8 to 13 nucleotides in length, the secondary domain is 12 to 17 nucleotides in length.

In an embodiment, if the targeting domain is 25 nucleotides in length and the core domain (counted from the 3' end of the targeting domain) is 8 to 13 nucleotides in length, the secondary domain is 12 to 17 nucleotides in length.

In an embodiment, if the targeting domain is 24 nucleotides in length and the core domain (counted from the 3' end of the targeting domain) is 8 to 13 nucleotides in length, the secondary domain is 11 to 16 nucleotides in length.

In an embodiment, if the targeting domain is 23 nucleotides in length and the core domain (counted from the 3' end of the targeting domain) is 8 to 13 nucleotides in length, the secondary domain is 10 to 15 nucleotides in length.

In an embodiment, if the targeting domain is 22 nucleotides in length and the core domain (counted from the 3' end of the targeting domain) is 8 to 13 nucleotides in length, the secondary domain is 9 to 14 nucleotides in length.

In an embodiment, if the targeting domain is 21 nucleotides in length and the core domain (counted from the 3' end of the targeting domain) is 8 to 13 nucleotides in length, the secondary domain is 8 to 13 nucleotides in length.

In an embodiment, if the targeting domain is 20 nucleotides in length and the core domain (counted from the 3' end of the targeting domain) is 8 to 13 nucleotides in length, the secondary domain is 7 to 12 nucleotides in length.

In an embodiment, if the targeting domain is 19 nucleotides in length and the core domain (counted from the 3' end of the targeting domain) is 8 to 13 nucleotides in length, the secondary domain is 6 to 11 nucleotides in length.

In an embodiment, if the targeting domain is 18 nucleotides in length and the core domain (counted from the 3' end of the targeting domain) is 8 to 13 nucleotides in length, the secondary domain is 5 to 10 nucleotides in length.

In an embodiment, if the targeting domain is 17 nucleotides in length and the core domain (counted from the 3' end of the targeting domain) is 8 to 13 nucleotides in length, the secondary domain is 4 to 9 nucleotides in length.

In an embodiment, if the targeting domain is 16 nucleotides in length and the core domain (counted from the 3' end of the targeting domain) is 8 to 13 nucleotides in length, the secondary domain is 3 to 8 nucleotides in length.

In an embodiment, the secondary domain is 0, 1, 2, 3, 4, 5, 6, 7, 8, 9, 10, 11, 12, 13, 14 or 15 nucleotides in length.

The secondary domain is complementary with the secondary domain target. Typically the secondary domain has exact complementarity with the secondary domain target. In an embodiment the secondary domain can have 1, 2, 3, 4 or 5 nucleotides that are not complementary with the corresponding nucleotide of the secondary domain. In an embodiment, the degree of complementarity, together with other properties of the gRNA, is sufficient to allow targeting of a Cas9 molecule to the target nucleic acid.

In an embodiment, the core domain nucleotides do not comprise modifications, e.g., modifications of the type provided in Section VIII. However, in an embodiment, the core domain comprises one or more modifications, e.g., modifications that it render it less susceptible to degradation or more bio-compatible, e.g., less immunogenic. By way of example, the backbone of the core domain can be modified with a phosphorothioate, or other modification(s) from Section VIII. In an embodiment a nucleotide of the core domain can comprise a 2' modification (e.g., a modification at the 2' position on ribose), e.g., a 2-acetylation, e.g., a 2' methylation, or other modification(s) from Section VIII. Typically, a core domain will contain no more than 1, 2, or 3 modifications.

Modifications in the core domain can be selected to not interfere with targeting efficacy, which can be evaluated by testing a candidate modification in the system described in Section IV. gRNAs having a candidate core domain having a selected length, sequence, degree of complementarity, or degree of modification, can be evaluated in the system described at Section IV. The candidate core domain can be placed, either alone, or with one or more other candidate changes in a gRNA molecule/Cas9 molecule system known to be functional with a selected target and evaluated.

In an embodiment, the secondary domain nucleotides do not comprise modifications, e.g., modifications of the type provided in Section VIII. However, in an embodiment, the secondary domain comprises one or more modifications, e.g., modifications that render it less susceptible to degradation or more bio-compatible, e.g., less immunogenic. By way of example, the backbone of the secondary domain can be modified with a phosphorothioate, or other modification(s) from Section VIII. In an embodiment a nucleotide of the secondary domain can comprise a 2' modification (e.g., a modification at the 2' position on ribose), e.g., a 2-acetylation, e.g., a 2' methylation, or other modification from Section VIII. Typically, a secondary domain will contain no more than 1, 2, or 3 modifications.

Modifications in the secondary domain can be selected to not interfere with targeting efficacy, which can be evaluated by testing a candidate modification in the system described in Section IV. gRNAs having a candidate secondary domain having a selected length, sequence, degree of complementarity, or degree of modification, can be evaluated in the system described at Section IV. The candidate secondary domain can be placed, either alone, or with one or more other candidate changes in a gRNA molecule/Cas9 molecule system known to be functional with a selected target and evaluated.

In an embodiment, (1) the degree of complementarity between the core domain and its target, and (2) the degree of complementarity between the secondary domain and its target, may differ. In an embodiment, (1) may be greater than (2). In an embodiment, (1) may be less than (2). In an embodiment, (1) and (2) are the same, e.g., each may be completely complementary with its target.

In an embodiment, (1) the number of modifications (e.g., modifications from Section VIII) of the nucleotides of the core domain and (2) the number of modification (e.g., modifications from Section VIII) of the nucleotides of the secondary domain, may differ. In an embodiment, (1) may be less than (2). In an embodiment, (1) may be greater than (2). In an embodiment, (1) and (2) may be the same, e.g., each may be free of modifications.

The First and Second Complementarity Domains

The first complementarity domain is complementary with the second complementarity domain.

Typically the first domain does not have exact complementarity with the second complementarity domain target. In an embodiment, the first complementarity domain can have 1, 2, 3, 4 or 5 nucleotides that are not complementary with the corresponding nucleotide of the second complementarity domain. In an embodiment, 1, 2, 3, 4, 5 or 6, e.g., 3 nucleotides, will not pair in the duplex, and, e.g., form a non-duplexed or looped-out region. In an embodiment, an unpaired, or loop-out, region, e.g., a loop-out of 3 nucleotides, is present on the second complementarity domain. In an embodiment, the unpaired region begins 1, 2, 3, 4, 5, or 6, e.g., 4, nucleotides from the 5' end of the second complementarity domain.

In an embodiment, the degree of complementarity, together with other properties of the gRNA, is sufficient to allow targeting of a Cas9 molecule to the target nucleic acid.

In an embodiment, the first and second complementarity domains are:

independently, 6+/−2, 7+/−2, 8+/−2, 9+/−2, 10+/−2, 11+/−2, 12+/−2, 13+/−2, 14+/−2, 15+/−2, 16+/−2, 17+/−2, 18+/−2, 19+/−2, or 20+/−2, 21+/−2, 22+/−2, 23+/−2, or 24+/−2 nucleotides in length;

independently, 6, 7, 8, 9, 10, 11, 12, 13, 14, 14, 16, 17, 18, 19, 20, 21, 22, 23, 24, 25, or 26, nucleotides in length; or independently, 5 to 24, 5 to 23, 5 to 22, 5 to 21, 5 to 20, 7 to 18, 9 to 16, or 10 to 14 nucleotides in length.

In an embodiment, the second complementarity domain is longer than the first complementarity domain, e.g., 2, 3, 4, 5, or 6, e.g., 6, nucleotides longer.

In an embodiment, the first and second complementary domains, independently, do not comprise modifications, e.g., modifications of the type provided in Section VIII.

In an embodiment, the first and second complementary domains, independently, comprise one or more modifications, e.g., modifications that the render the domain less susceptible to degradation or more bio-compatible, e.g., less immunogenic. By way of example, the backbone of the domain can be modified with a phosphorothioate, or other modification(s) from Section VIII. In an embodiment a nucleotide of the domain can comprise a 2' modification (e.g., a modification at the 2' position on ribose), e.g., a 2-acetylation, e.g., a 2' methylation, or other modification(s) from Section VIII.

In an embodiment, the first and second complementary domains, independently, include 1, 2, 3, 4, 5, 6, 7 or 8 or more modifications. In an embodiment, the first and second complementary domains, independently, include 1, 2, 3, or 4 modifications within 5 nucleotides of its 5' end. In an embodiment, the first and second complementary domains, independently, include as many as 1, 2, 3, or 4 modifications within 5 nucleotides of its 3' end.

In an embodiment, the first and second complementary domains, independently, include modifications at two consecutive nucleotides, e.g., two consecutive nucleotides that are within 5 nucleotides of the 5' end of the domain, within 5 nucleotides of the 3' end of the domain, or more than 5 nucleotides away from one or both ends of the domain. In an embodiment, the first and second complementary domains, independently, include no two consecutive nucleotides that are modified, within 5 nucleotides of the 5' end of the domain, within 5 nucleotides of the 3' end of the domain, or within a region that is more than 5 nucleotides away from one or both ends of the domain. In an embodiment, the first and second complementary domains, independently, include no nucleotide that is modified within 5 nucleotides of the 5' end of the domain, within 5 nucleotides of the 3' end of the domain, or within a region that is more than 5 nucleotides away from one or both ends of the domain.

Modifications in a complementarity domain can be selected to not interfere with targeting efficacy, which can be evaluated by testing a candidate modification in the system described in Section IV. gRNAs having a candidate complementarity domain having a selected length, sequence, degree of complementarity, or degree of modification, can be evaluated in the system described in Section IV. The candidate complementarity domain can be placed, either alone, or with one or more other candidate changes in a gRNA molecule/Cas9 molecule system known to be functional with a selected target and evaluated.

In an embodiment, the first complementarity domain has at least 60, 70, 80, 85%, 90% or 95% homology with, or differs by no more than 1, 2, 3, 4, 5, or 6 nucleotides from, a reference first complementarity domain, e.g., a naturally occurring, e.g., an *S. pyogenes, S. aureus* or *S. thermophilus*, first complementarity domain, or a first complementarity domain described herein, e.g., from FIGS. 1A-1G.

In an embodiment, the second complementarity domain has at least 60, 70, 80, 85%, 90%, or 95% homology with, or differs by no more than 1, 2, 3, 4, 5, or 6 nucleotides from, a reference second complementarity domain, e.g., a naturally occurring, e.g., an *S. pyogenes, S. aureus* or *S. thermophilus*, second complementarity domain, or a second complementarity domain described herein, e.g., from FIGS. 1A-1G.

The duplexed region formed by first and second complementarity domains is typically 6, 7, 8, 9, 10, 11, 12, 13, 14, 15, 16, 17, 18, 19, 20, 21 or 22 base pairs in length (excluding any looped out or unpaired nucleotides).

In an embodiment, the first and second complementarity domains, when duplexed, comprise 11 paired nucleotides, for example, in the gRNA sequence (one paired strand underlined, one bolded): NNNNNNNNNNNNNNNNNNNNGUUUUAGA <u>GCUAGAAAUAGCAAGUUAAAAUAAGG</u> CUAGUCCGUUAUCAACUUGAAAAAGUGGCACCGAGUCGGUGC (SEQ ID NO: 5).

In an embodiment, the first and second complementarity domains, when duplexed, comprise 15 paired nucleotides, for example in the gRNA sequence (one paired strand underlined, one bolded): NNNNNNNNNNNNNNNNNNNNGUUUUAGA <u>GCUAUGCUGAAAAGCAUAGCAAGUUA</u> AAAUAAGGCUAGUCCGUUAUCAAC-UUGAAAAAGUGGCACCGAGUCGGUGC (SEQ ID NO: 27).

In an embodiment the first and second complementarity domains, when duplexed, comprise 16 paired nucleotides, for example in the gRNA sequence (one paired strand underlined, one bolded): NNNNNNNNNNNNNNNNNNNNGUUUUAGA <u>GCUAUGCUGGAAACAGCAUAGCAAGU</u> UAAAAUAAGGCUAGUCCGUUAUCAAC-UUGAAAAAGUGGCACCGAGUCGGUGC (SEQ ID NO: 28).

In an embodiment the first and second complementarity domains, when duplexed, comprise 21 paired nucleotides, for example in the gRNA sequence (one paired strand underlined, one bolded): NNNNNNNNNNNNNNNNNNNNGUUUUAGA <u>GCUAUGCUGUUUUGGAAACAAAACAG</u> CAUAGCAAGUUAAAAUAAGGCUAGUCCGUUAUCAACUUGAAAAAGUGGCACCGA GUCGGUGC (SEQ ID NO: 29).

In an embodiment, nucleotides are exchanged to remove poly-U tracts, for example in the gRNA sequences (exchanged nucleotides underlined):

(SEQ ID NO: 30)
NNNNNNNNNNNNNNNNNNNNNGU<u>A</u>UUAGAGCUAGAAAUAGCAAGUUA<u>A</u>UAU

AAGGCUAGUCCGUUAUCAACUUGAAAAAGUGGCACCGAGUCGGUGC;

(SEQ ID NO: 31)
NNNNNNNNNNNNNNNNNNNNNGUUU<u>A</u>AGAGCUAGAAAUAGCAAGUU<u>U</u>AAAU

-continued

AAGGCUAGUCCGUUAUCAACUUGAAAAAGUGGCACCGAGUCGGUGC;
or (SEQ ID NO: 32)
NNNNNNNNNNNNNNNNNNNNNNNNGUAUUAGAGCUAUGCUGUAUUGGAAACAAU

ACAGCAUAGCAAGUUAAUAUAAGGCUAGUCCGUUAUCAACUUGAAAAAGU

GGCACCGAGUCGGUGC.

The 5' Extension Domain

In an embodiment, a modular gRNA can comprise additional sequence, 5' to the second complementarity domain. In an embodiment, the 5' extension domain is 2 to 10, 2 to 9, 2 to 8, 2 to 7, 2 to 6, 2 to 5, or 2 to 4 nucleotides in length. In an embodiment, the 5' extension domain is 2, 3, 4, 5, 6, 7, 8, 9, or 10 or more nucleotides in length.

In an embodiment, the 5' extension domain nucleotides do not comprise modifications, e.g., modifications of the type provided in Section VIII. However, in an embodiment, the 5' extension domain comprises one or more modifications, e.g., modifications that it render it less susceptible to degradation or more bio-compatible, e.g., less immunogenic. By way of example, the backbone of the 5' extension domain can be modified with a phosphorothioate, or other modification(s) from Section VIII. In an embodiment, a nucleotide of the 5' extension domain can comprise a 2' modification (e.g., a modification at the 2' position on ribose), e.g., a 2-acetylation, e.g., a 2' methylation, or other modification(s) from Section VIII.

In an embodiment, the 5' extension domain can comprise as many as 1, 2, 3, 4, 5, 6, 7 or 8 modifications. In an embodiment, the 5' extension domain comprises as many as 1, 2, 3, or 4 modifications within 5 nucleotides of its 5' end, e.g., in a modular gRNA molecule. In an embodiment, the 5' extension domain comprises as many as 1, 2, 3, or 4 modifications within 5 nucleotides of its 3' end, e.g., in a modular gRNA molecule.

In an embodiment, the 5' extension domain comprises modifications at two consecutive nucleotides, e.g., two consecutive nucleotides that are within 5 nucleotides of the 5' end of the 5' extension domain, within 5 nucleotides of the 3' end of the 5' extension domain, or more than 5 nucleotides away from one or both ends of the 5' extension domain. In an embodiment, no two consecutive nucleotides are modified within 5 nucleotides of the 5' end of the 5' extension domain, within 5 nucleotides of the 3' end of the 5' extension domain, or within a region that is more than 5 nucleotides away from one or both ends of the 5' extension domain. In an embodiment, no nucleotide is modified within 5 nucleotides of the 5' end of the 5' extension domain, within 5 nucleotides of the 3' end of the 5' extension domain, or within a region that is more than 5 nucleotides away from one or both ends of the 5' extension domain.

Modifications in the 5' extension domain can be selected so as to not interfere with gRNA molecule efficacy, which can be evaluated by testing a candidate modification in the system described in Section IV. gRNAs having a candidate 5' extension domain having a selected length, sequence, degree of complementarity, or degree of modification, can be evaluated in the system described at Section IV. The candidate 5' extension domain can be placed, either alone, or with one or more other candidate changes in a gRNA molecule/Cas9 molecule system known to be functional with a selected target and evaluated.

In an embodiment, the 5' extension domain has at least 60, 70, 80, 85, 90 or 95% homology with, or differs by no more than 1, 2, 3, 4, 5, or 6 nucleotides from, a reference 5' extension domain, e.g., a naturally occurring, e.g., an *S. pyogenes, S. aureus* or *S. thermophilus,* 5' extension domain, or a 5' extension domain described herein, e.g., from FIGS. 1A-1G.

The Linking Domain

In a unimolecular gRNA molecule the linking domain is disposed between the first and second complementarity domains. In a modular gRNA molecule, the two molecules are associated with one another by the complementarity domains.

In an embodiment, the linking domain is 10+/−5, 20+/−5, 30+/−5, 40+/−5, 50+/−5, 60+/−5, 70+/−5, 80+/−5, 90+/−5, or 100+/−5 nucleotides, in length.

In an embodiment, the linking domain is 20+/−10, 30+/−10, 40+/−10, 50+/−10, 60+/−10, 70+/−10, 80+/−10, 90+/−10, or 100+/−10 nucleotides, in length.

In an embodiment, the linking domain is 10 to 100, 10 to 90, 10 to 80, 10 to 70, 10 to 60, 10 to 50, 10 to 40, 10 to 30, 10 to 20 or 10 to 15 nucleotides in length.

In another embodiment, the linking domain is 20 to 100, 20 to 90, 20 to 80, 20 to 70, 20 to 60, 20 to 50, 20 to 40, 20 to 30, or 20 to 25 nucleotides in length.

In an embodiment, the linking domain is 1, 2, 3, 4, 5, 6, 7, 8, 9, 10, 11, 12, 13, 14, 15, 16 17, 18, 19, or 20 nucleotides in length.

In and embodiment, the linking domain is a covalent bond.

In an embodiment, the linking domain comprises a duplexed region, typically adjacent to or within 1, 2, or 3 nucleotides of the 3' end of the first complementarity domain and/or the S-end of the second complementarity domain. In an embodiment, the duplexed region can be 20+/−10 base pairs in length. In an embodiment, the duplexed region can be 10+/−5, 15+/−5, 20+/−5, or 30+/−5 base pairs in length. In an embodiment, the duplexed region can be 1, 2, 3, 4, 5, 6, 7, 8, 9, 10, 11, 12, 13, 14, or 15 base pairs in length.

Typically the sequences forming the duplexed region have exact complementarity with one another, though in an embodiment as many as 1, 2, 3, 4, 5, 6, 7 or 8 nucleotides are not complementary with the corresponding nucleotides.

In an embodiment, the linking domain nucleotides do not comprise modifications, e.g., modifications of the type provided in Section VIII. However, in an embodiment, the linking domain comprises one or more modifications, e.g., modifications that it render it less susceptible to degradation or more bio-compatible, e.g., less immunogenic. By way of example, the backbone of the linking domain can be modified with a phosphorothioate, or other modification(s) from Section VIII. In an embodiment a nucleotide of the linking domain can comprise a 2' modification (e.g., a modification at the 2' position on ribose), e.g., a 2-acetylation, e.g., a 2' methylation, or other modification(s) from Section VIII. In an embodiment, the linking domain can comprise as many as 1, 2, 3, 4, 5, 6, 7 or 8 modifications.

Modifications in a linking domain can be selected so as to not interfere with targeting efficacy, which can be evaluated by testing a candidate modification in the system described in Section IV. gRNAs having a candidate linking domain having a selected length, sequence, degree of complementarity, or degree of modification, can be evaluated a system described in Section IV. A candidate linking domain can be placed, either alone, or with one or more other candidate changes in a gRNA molecule/Cas9 molecule system known to be functional with a selected target and evaluated.

In an embodiment, the linking domain has at least 60, 70, 80, 85, 90 or 95% homology with, or differs by no more than 1, 2, 3, 4, 5, or 6 nucleotides from, a reference linking domain, e.g., a linking domain described herein, e.g., from FIGS. 1A-1G.

The Proximal Domain

In an embodiment, the proximal domain is 6+/−2, 7+/−2, 8+/−2, 9+/−2, 10+/−2, 11+/−2, 12+/−2, 13+/−2, 14+/−2, 14+/−2, 16+/−2, 17+/−2, 18+/−2, 19+/−2, or 20+/−2 nucleotides in length.

In an embodiment, the proximal domain is 6, 7, 8, 9, 10, 11, 12, 13, 14, 15, 16, 17, 18, 19, 20, 21, 22, 23, 24, 25 or 26 nucleotides in length.

In an embodiment, the proximal domain is 5 to 20, 7, to 18, 9 to 16, or 10 to 14 nucleotides in length.

In an embodiment, the proximal domain nucleotides do not comprise modifications, e.g., modifications of the type provided in Section VIII. However, in an embodiment, the proximal domain comprises one or more modifications, e.g., modifications that it render it less susceptible to degradation or more bio-compatible, e.g., less immunogenic. By way of example, the backbone of the proximal domain can be modified with a phosphorothioate, or other modification(s) from Section VIII. In an embodiment a nucleotide of the proximal domain can comprise a 2' modification (e.g., a modification at the 2' position on ribose), e.g., a 2-acetylation, e.g., a 2' methylation, or other modification(s) from Section VIII.

In an embodiment, the proximal domain can comprise as many as 1, 2, 3, 4, 5, 6, 7 or 8 modifications. In an embodiment, the proximal domain comprises as many as 1, 2, 3, or 4 modifications within 5 nucleotides of its 5' end, e.g., in a modular gRNA molecule. In an embodiment, the target domain comprises as many as 1, 2, 3, or 4 modifications within 5 nucleotides of its 3' end, e.g., in a modular gRNA molecule.

In an embodiment, the proximal domain comprises modifications at two consecutive nucleotides, e.g., two consecutive nucleotides that are within 5 nucleotides of the 5' end of the proximal domain, within 5 nucleotides of the 3' end of the proximal domain, or more than 5 nucleotides away from one or both ends of the proximal domain. In an embodiment, no two consecutive nucleotides are modified within 5 nucleotides of the 5' end of the proximal domain, within 5 nucleotides of the 3' end of the proximal domain, or within a region that is more than 5 nucleotides away from one or both ends of the proximal domain. In an embodiment, no nucleotide is modified within 5 nucleotides of the 5' end of the proximal domain, within 5 nucleotides of the 3' end of the proximal domain, or within a region that is more than 5 nucleotides away from one or both ends of the proximal domain.

Modifications in the proximal domain can be selected so as to not interfere with gRNA molecule efficacy, which can be evaluated by testing a candidate modification in the system described in Section IV. gRNAs having a candidate proximal domain having a selected length, sequence, degree of complementarity, or degree of modification, can be evaluated in the system described at Section IV. The candidate proximal domain can be placed, either alone, or with one or more other candidate changes in a gRNA molecule/Cas9 molecule system known to be functional with a selected target and evaluated.

In an embodiment, the proximal domain has at least 60, 70, 80, 85 90 or 95% homology with, or differs by no more than 1, 2, 3.4, 5, or 6 nucleotides from, a reference proximal domain, e.g., a naturally occurring, e.g., an S. pyogenes, S. aureus or S. thermophilus, proximal domain, or a proximal domain described herein, e.g., from FIGS. 1A-1G.

The Tail Domain

In an embodiment, the tail domain is 10+/−5, 20+/−5, 30+/−5, 40+/−5, 50+/−5, 60+/−5, 70+/−5, 80+/−5, 90+/−5, or 100+/−5 nucleotides, in length.

In an embodiment, the tail domain is 20+/−5 nucleotides in length.

In an embodiment, the tail domain is 20+/−10, 30+/−10, 40+/−10, 50+/−10, 60+/−10, 70+/−10, 80+/−10, 90+/−10, or 100+/−10 nucleotides, in length.

In an embodiment, the tail domain is 25+/−10 nucleotides in length.

In an embodiment, the tail domain is 10 to 100, 10 to 90, 10 to 80, 10 to 70, 10 to 60, 10 to 50, 10 to 40, 10 to 30, 10 to 20 or 10 to 15 nucleotides in length.

In another embodiment, the tail domain is 20 to 100, 20 to 90, 20 to 80, 20 to 70, 20 to 60, 20 to 50, 20 to 40, 20 to 30, or 20 to 25 nucleotides in length.

In an embodiment, the tail domain is 1 to 20, 1 to 15, 1 to 10, or 1 to 5 nucleotides in length.

In an embodiment, the tail domain nucleotides do not comprise modifications, e.g., modifications of the type provided in Section VIII. However, in an embodiment, the tail domain comprises one or more modifications, e.g., modifications that it render it less susceptible to degradation or more bio-compatible, e.g., less immunogenic. By way of example, the backbone of the tail domain can be modified with a phosphorothioate, or other modification(s) from Section VIII. In an embodiment a nucleotide of the tail domain can comprise a 2' modification (e.g., a modification at the 2' position on ribose), e.g., a 2-acetylation, e.g., a 2' methylation, or other modification(s) from Section VIII.

In an embodiment, the tail domain can have as many as 1, 2, 3, 4, 5, 6, 7 or 8 modifications. In an embodiment, the target domain comprises as many as 1, 2, 3, or 4 modifications within 5 nucleotides of its 5' end. In an embodiment, the target domain comprises as many as 1, 2, 3, or 4 modifications within 5 nucleotides of its 3' end.

In an embodiment, the tail domain comprises a tail duplex domain, which can form a tail duplexed region. In an embodiment, the tail duplexed region can be 3, 4, 5, 6, 7, 8, 9, 10, 11, or 12 base pairs in length. In an embodiment, a further single stranded domain, exists 3' to the tail duplexed domain. In an embodiment, this domain is 3, 4, 5, 6, 7, 8, 9, or 10 nucleotides in length. In an embodiment it is 4 to 6 nucleotides in length.

In an embodiment, the tail domain has at least 60, 70, 80, or 90% homology with, or differs by no more than 1, 2, 3, 4, 5, or 6 nucleotides from, a reference tail domain, e.g., a naturally occurring, e.g., an S. pyogenes, S. aureus or S. thermophilus, tail domain, or a tail domain described herein, e.g., from FIGS. 1A-1G.

In an embodiment, the proximal and tail domain, taken together comprise the following sequences:

```
                                          (SEQ ID NO: 33)
AAGGCUAGUCCGUUAUCAACUUGAAAAAGUGGCACCGAGUCGGUGCU,
or
                                          (SEQ ID NO: 34)
AAGGCUAGUCCGUUAUCAACUUGAAAAAGUGGCACCGAGUCGGUGGUGC,
or
                                          (SEQ ID NO: 35)
AAGGCUAGUCCGUUAUCAACUUGAAAAAGUGGCACCGAGUCGGUGCGGA
UC,
or
```

-continued

AAGGCUAGUCCGUUAUCAACUUGAAAAAGUG, (SEQ ID NO: 36)
or

AAGGCUAGUCCGUUAUCA, (SEQ ID NO: 37)
or

AAGGCUAGUCCG. (SEQ ID NO: 38)

In an embodiment, the tail domain comprises the 3' sequence UUUUUU, e.g., if a U6 promoter is used for transcription.

In an embodiment, the tail domain comprises the 3' sequence UUUU, e.g., if an H1 promoter is used for transcription.

In an embodiment, tail domain comprises variable numbers of 3' Us depending, e.g., on the termination signal of the pol-III promoter used.

In an embodiment, the tail domain comprises variable 3' sequence derived from the DNA template if a T7 promoter is used.

In an embodiment, the tail domain comprises variable 3' sequence derived from the DNA template, e.g., if in vitro transcription is used to generate the RNA molecule.

In an embodiment, the tail domain comprises variable 3' sequence derived from the DNA template, e., if a pol-II promoter is used to drive transcription.

Modifications in the tail domain can be selected to not interfere with targeting efficacy, which can be evaluated by testing a candidate modification in the system described in Section IV. gRNAs having a candidate tail domain having a selected length, sequence, degree of complementarity, or degree of modification, can be evaluated in the system described in Section IV. The candidate tail domain can be placed, either alone, or with one or more other candidate changes in a gRNA molecule/Cas9 molecule system known to be functional with a selected target and evaluated.

In an embodiment, the tail domain comprises modifications at two consecutive nucleotides, e.g., two consecutive nucleotides that are within 5 nucleotides of the 5' end of the tail domain, within 5 nucleotides of the 3' end of the tail domain, or more than 5 nucleotides away from one or both ends of the tail domain. In an embodiment, no two consecutive nucleotides are modified within 5 nucleotides of the 5' end of the tail domain, within 5 nucleotides of the 3' end of the tail domain, or within a region that is more than 5 nucleotides away from one or both ends of the tail domain. In an embodiment, no nucleotide is modified within 5 nucleotides of the 5' end of the tail domain, within 5 nucleotides of the 3' end of the tail domain, or within a region that is more than 5 nucleotides away from one or both ends of the tail domain.

In an embodiment a gRNA has the following structure:
5' [targeting domain]-[first complementarity domain]-[linking domain]-[second complementarity domain]-[proximal domain]-[tail domain]-3'
wherein, the targeting domain comprises a core domain and optionally a secondary domain, and is 10 to 50 nucleotides in length;
the first complementarity domain is 5 to 25 nucleotides in length and, In an embodiment has at least 50, 60, 70, 80, 85, 90 or 95% homology with a reference first complementarity domain disclosed herein;
the linking domain is 1 to 5 nucleotides in length;
the second complementarity domain is 5 to 27 nucleotides in length and, in an embodiment has at least 50, 60, 70, 80, 85, 90 or 95% homology with a reference second complementarity domain disclosed herein;
the proximal domain is 5 to 20 nucleotides in length and, in an embodiment has at least 50, 60, 70, 80, 85, 90 or 95% homology with a reference proximal domain disclosed herein; and
the tail domain is absent or a nucleotide sequence is 1 to 50 nucleotides in length and, in an embodiment has at least 50, 60, 70, 80, 85, 90 or 95% homology with a reference tail domain disclosed herein.

Exemplary Chimeric gRNAs

In an embodiment, a unimolecular, or chimeric, gRNA comprises, preferably from 5' to 3':
   a targeting domain (which is complementary to a target nucleic acid);
   a first complementarity domain, e.g., comprising 15, 16, 17, 18, 19, 20, 21, 22, 23, 24, 25, or 26 nucleotides;
   a linking domain;
   a second complementarity domain (which is complementary to the first complementarity domain);
   a proximal domain; and
   a tail domain,
   wherein,
   (a) the proximal and tail domain, when taken together, comprise at least 15, 18, 20, 25, 30, 31, 35, 40, 45, 49, 50, or 53 nucleotides;
   (b) there are at least 15, 18, 20, 25, 30, 31, 35, 40, 45, 49, 50, or 53 nucleotides 3' to the last nucleotide of the second complementarity domain; or
   (c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the sequence from (a), (b), or (c), has at least 60, 75, 80, 85, 90, 95, or 99% homology with the corresponding sequence of a naturally occurring gRNA, or with a gRNA described herein.

In an embodiment, the proximal and tail domain, when taken together, comprise at least 15, 18, 20, 25, 30, 31, 35, 40, 45, 49, 50, or 53 nucleotides.

In an embodiment, there are at least 15, 18, 20, 25, 30, 31, 35, 40, 45, 49, 50, or 53 nucleotides 3' to the last nucleotide of the second complementarity domain.

In an embodiment, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 16, 17, 18, 19, 20, 21, 22, 23, 24, 25 or 26 nucleotides (e.g., 16, 17, 18, 19, 20, 21, 22, 23, 24, 25 or 26 consecutive nucleotides) having complementarity with the target domain, e.g., the targeting domain is 16, 17, 18, 19, 20, 21, 22, 23, 24, 25, or 26 nucleotides in length.

In an embodiment, the targeting domain comprises, has, or consists of, 16 nucleotides (e.g., 16 consecutive nucleotides) having complementarity with the target domain, e.g., the targeting domain is 16 nucleotides in length.

In an embodiment, the targeting domain comprises, has, or consists of, 17 nucleotides (e.g., 17 consecutive nucleotides) having complementarity with the target domain, e.g., the targeting domain is 17 nucleotides in length.

In an embodiment, the targeting domain comprises, has, or consists of, 18 nucleotides (e.g., 18 consecutive nucleo- In an embodiment, the targeting domain comprises, has, or consists of, 19 nucleotides (e.g., 19 consecutive nucleotides) having complementarity with the target domain, e.g., the targeting domain is 19 nucleotides in length.

In an embodiment, the targeting domain comprises, has, or consists of, 20 nucleotides (e.g., 20 consecutive nucleotides) having complementarity with the target domain, e.g., the targeting domain is 20 nucleotides in length.

In an embodiment, the targeting domain comprises, has, or consists of, 21 nucleotides (e.g., 21 consecutive nucleotides) having complementarity with the target domain, e.g., the targeting domain is 21 nucleotides in length.

In an embodiment, the targeting domain comprises, has, or consists of, 22 nucleotides (e.g., 22 consecutive nucleotides) having complementarity with the target domain, e.g., the targeting domain is 22 nucleotides in length.

In an embodiment, the targeting domain comprises, has, or consists of, 23 nucleotides (e.g., 23 consecutive nucleotides) having complementarity with the target domain, e.g., the targeting domain is 23 nucleotides in length.

In an embodiment, the targeting domain comprises, has, or consists of, 24 nucleotides (e.g., 24 consecutive nucleotides) having complementarity with the target domain, e.g., the targeting domain is 24 nucleotides in length.

In an embodiment, the targeting domain comprises, has, or consists of, 25 nucleotides (e.g., 25 consecutive nucleotides) having complementarity with the target domain, e.g., the targeting domain is 25 nucleotides in length.

In an embodiment, the targeting domain comprises, has, or consists of, 26 nucleotides (e.g., 26 consecutive nucleotides) having complementarity with the target domain, e.g., the targeting domain is 26 nucleotides in length.

In an embodiment, the targeting domain comprises, has, or consists of, 16 nucleotides (e.g., 16 consecutive nucleotides) having complementarity with the target domain, e.g., the targeting domain is 16 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 16 nucleotides (e.g., 16 consecutive nucleotides) having complementarity with the target domain, e.g., the targeting domain is 16 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 16 nucleotides (e.g., 16 consecutive nucleotides) having complementarity with the target domain, e.g., the targeting domain is 16 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 17 nucleotides (e.g., 17 consecutive nucleotides) having complementarity with the target domain, e.g., the targeting domain is 17 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 17 nucleotides (e.g., 17 consecutive nucleotides) having complementarity with the target domain, e.g., the targeting domain is 17 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 17 nucleotides (e.g., 17 consecutive nucleotides) having complementarity with the target domain, e.g., the targeting domain is 17 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 18 nucleotides (e.g., 18 consecutive nucleotides) having complementarity with the target domain, e.g., the targeting domain is 18 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 18 nucleotides (e.g., 18 consecutive nucleotides) having complementarity with the target domain, e.g., the targeting domain is 18 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 18 nucleotides (e.g., 18 consecutive nucleotides) having complementarity with the target domain, e.g., the targeting domain is 18 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 20 nucleotides (e.g., 20 consecutive nucleotides) having complementarity with the target domain, e.g., the targeting domain is 20 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 20 nucleotides (e.g., 20 consecutive nucleotides) having complementarity with the target domain, e.g., the targeting domain is 20 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 20 nucleotides (e.g., 20 consecutive nucleotides) having complementarity with the target domain, e.g., the targeting domain is 20 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 21 nucleotides (e.g., 21 consecutive nucleotides) having complementarity with the target domain, e.g., the targeting domain is 21 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 23 nucleotides (e.g., 23 consecutive nucleotides) having complementarity with the target domain, e.g., the targeting domain is 23 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 23 nucleotides (e.g., 23 consecutive nucleotides) having complementarity with the target domain, e.g., the targeting domain is 23 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 23 nucleotides (e.g., 23 consecutive nucleotides) having complementarity with the target domain, e.g., the targeting domain is 23 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 25 nucleotides (e.g., 25 consecutive nucleotides) having complementarity with the target domain, e.g., the targeting domain is 25 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 26 nucleotides (e.g., 26 consecutive nucleotides) having complementarity with the target domain, e.g., the targeting domain is 26 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the unimolecular, or chimeric, gRNA molecule (comprising a targeting domain, a first complementary domain, a linking domain, a second complementary domain, a proximal domain and, optionally, a tail domain) comprises the following sequence in which the targeting domain is depicted as 20 Ns but could be any sequence and range in length from 16 to 26 nucleotides and in which the gRNA sequence is followed by 6 Us, which serve as a termination signal for the U6 promoter, but which could be either absent or fewer in number: NNNNNNNNNNNNNNNNNNNNGUUUUAGAGCUA-GAAAUAGCAAGUUAAAAUAAGG CUAGU-CCGUUAUCAACUUGAAAAAGUGGCACCGAGUCG-GUGCUUUUUU (SEQ ID NO: 45). In an embodiment, the unimolecular, or chimeric, gRNA molecule is a S. pyogenes gRNA molecule.

In some embodiments, the unimolecular, or chimeric, gRNA molecule (comprising a targeting domain, a first complementary domain, a linking domain, a second complementary domain, a proximal domain and, optionally, a tail domain) comprises the following sequence in which the targeting domain is depicted as 20 Ns but could be any sequence and range in length from 16 to 26 nucleotides and in which the gRNA sequence is followed by 6 Us, which serve as a termination signal for the U6 promoter, but which could be either absent or fewer in number: NNNNNNNNNNNNNNNNNNNNGUUUUAGUACU-CUGGAAACAGAAUCUACUAAAAC AAGGCAAAAUGCCGUGUUUAUCUCGUCAACUU-GUUGGCGAGAUUUUUU (SEQ ID NO: 40). In an embodiment, the unimolecular, or chimeric, gRNA molecule is a S. aureus gRNA molecule.

Figure 1H:
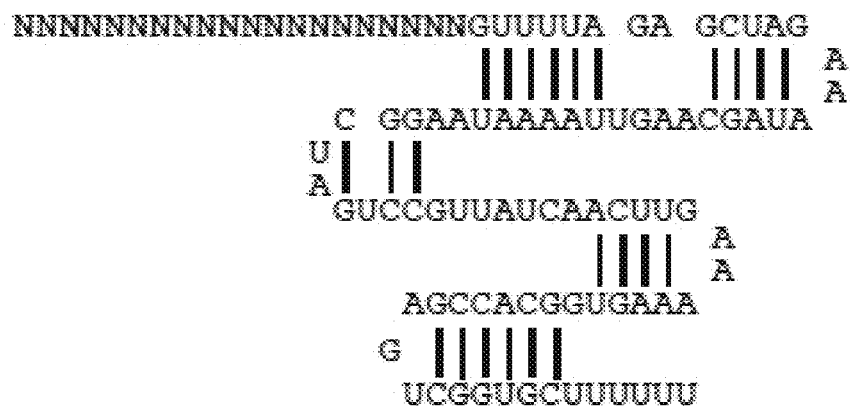
Figure 1I:
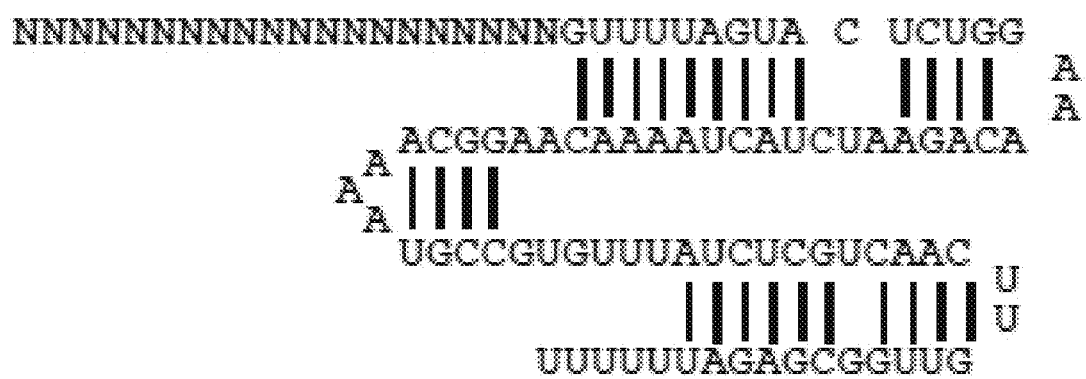
Figure 2D:
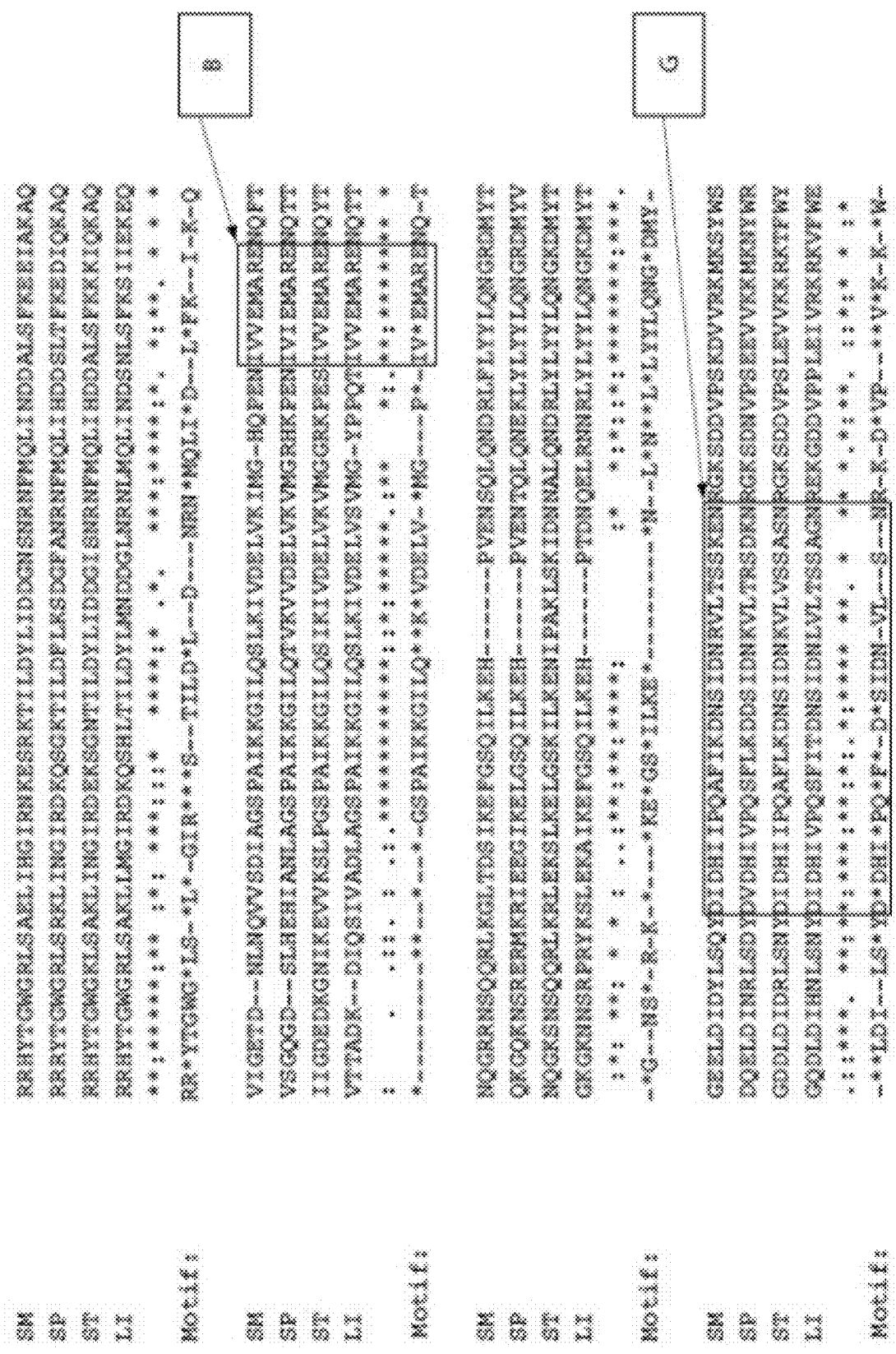
Figure 3B:
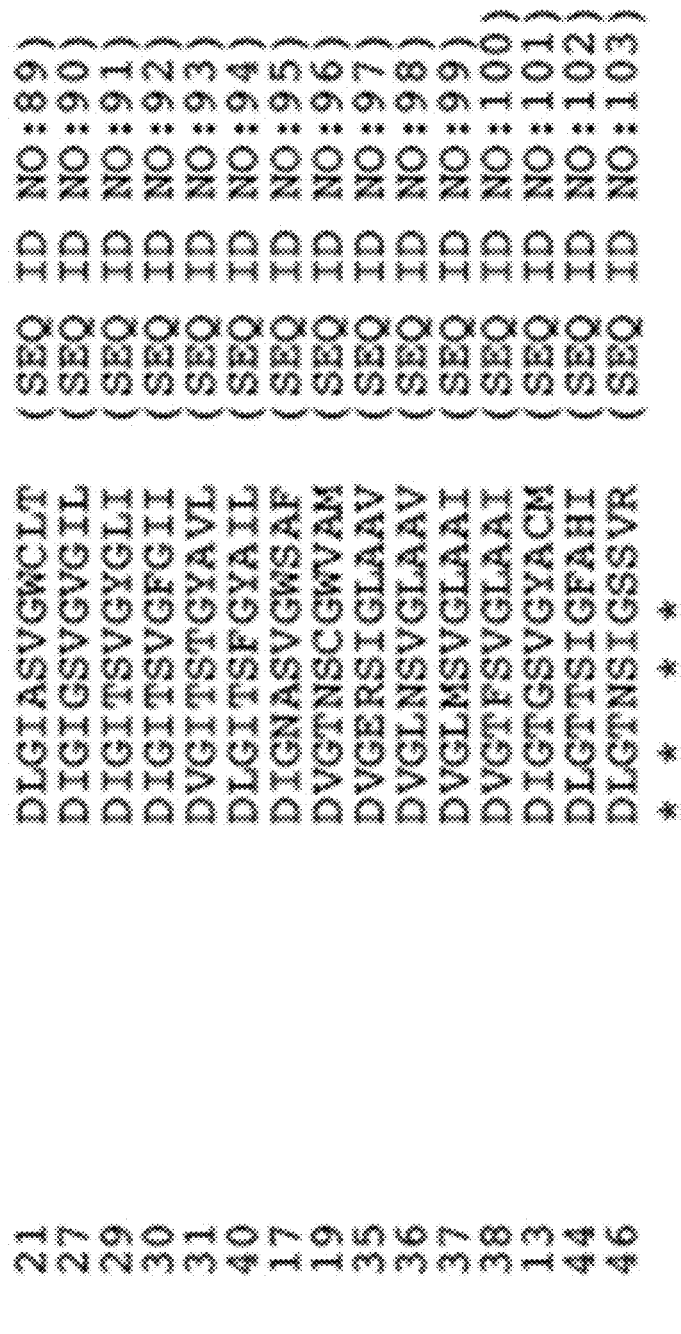
Figure 4B:
Figure 5B:
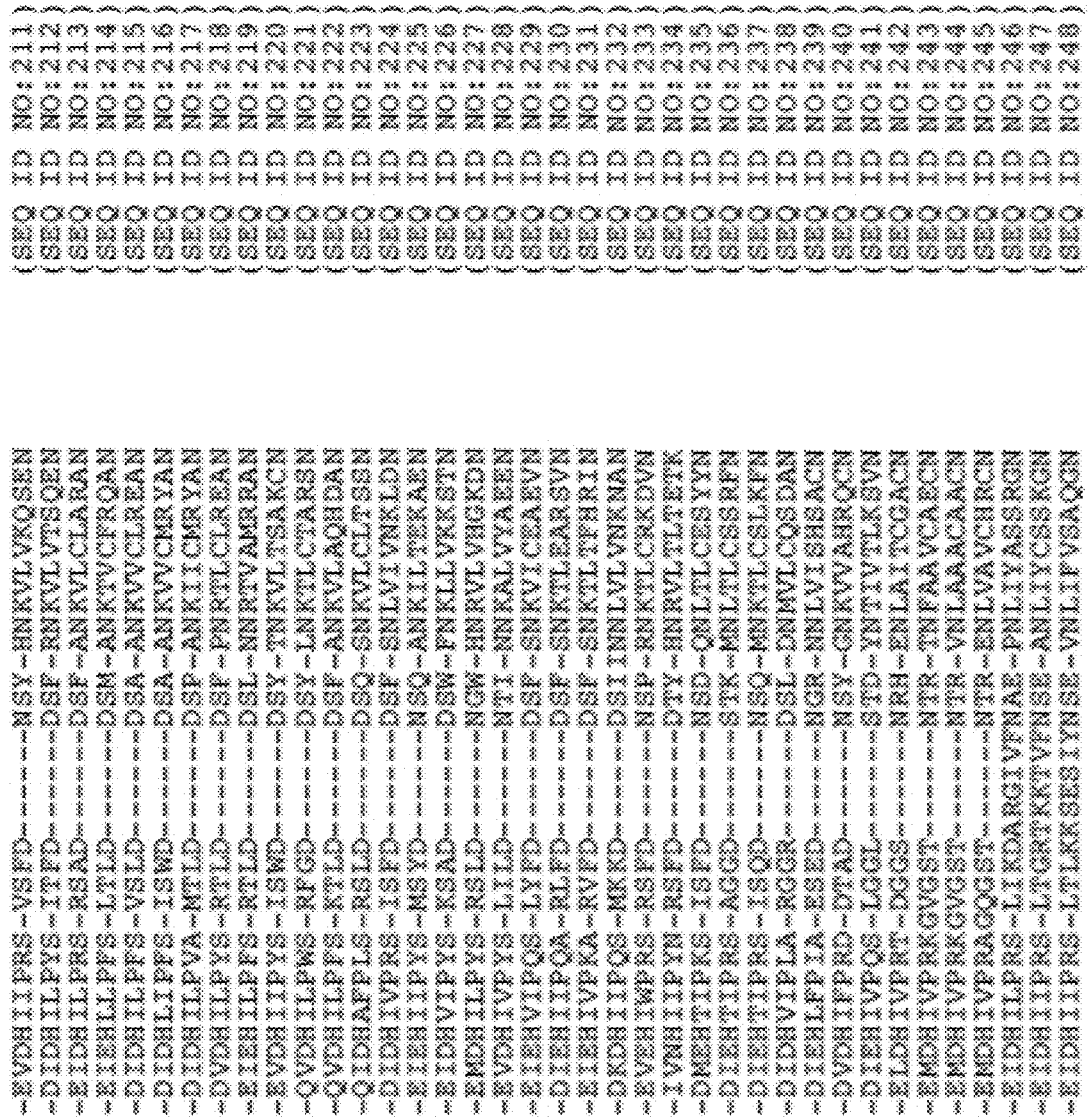

The sequences and structures of exemplary chimeric gRNAs are also shown in FIGS. 1H-1I.

Exemplary Modular gRNAs

In an embodiment, a modular gRNA comprises:
a first strand comprising, preferably from 5' to 3';
   a targeting domain, e.g., comprising 15, 16, 17, 18, 19, 20, 21, 22, 23, 24, 25, or 26 nucleotides;
   a first complementarity domain; and
a second strand, comprising, preferably from 5' to 3':
   optionally a 5' extension domain;
   a second complementarity domain;
   a proximal domain; and
   a tail domain,
wherein:
(a) the proximal and tail domain, when taken together, comprise at least 15, 18, 20, 25, 30, 31, 35, 40, 45, 49, 50, or 53 nucleotides;
(b) there are at least 15, 18, 20, 25, 30, 31, 35, 40, 45, 49, 50, or 53 nucleotides 3' to the last nucleotide of the second complementarity domain; or
(c) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the sequence from (a), (b), or (c), has at least 60, 75, 80, 85, 90, 95, or 99% homology with the corresponding sequence of a naturally occurring gRNA, or with a gRNA described herein.

In an embodiment, the proximal and tail domain, when taken together, comprise at least 15, 18, 20, 25, 30, 31, 35, 40, 45, 49, 50, or 53 nucleotides.

In an embodiment, there are at least 15, 18, 20, 25, 30, 31, 35, 40, 45, 49, 50, or 53 nucleotides 3' to the last nucleotide of the second complementarity domain.

In an embodiment, there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 16, 17, 18, 19, 20, 21, 22, 23, 24, 25 or 26 nucleotides (e.g., 16, 17, 18, 19, 20, 21, 22, 23, 24, 25 or 26 consecutive nucleotides) having complementarity with the target domain, e.g., the targeting domain is 16, 17, 18, 19, 20, 21, 22, 23, 24, 25 or 26 nucleotides in length. In an embodiment, the targeting domain comprises, has, or consists of, 16 nucleotides (e.g., 16 consecutive nucleotides) having complementarity with the target domain, e.g., the targeting domain is 16 nucleotides in length.

In an embodiment, the targeting domain has, or consists of, 17 nucleotides (e.g., 17 consecutive nucleotides) having complementarity with the target domain, e.g., the targeting domain is 17 nucleotides in length.

In an embodiment, the targeting domain has, or consists of, 18 nucleotides (e.g., 18 consecutive nucleotides) having complementarity with the target domain, e.g., the targeting domain is 18 nucleotides in length.

In an embodiment, the targeting domain comprises, has, or consists of, 19 nucleotides (e.g., 19 consecutive nucleotides) having complementarity with the target domain, e.g., the targeting domain is 19 nucleotides in length.

In an embodiment, the targeting domain comprises, has, or consists of, 20 nucleotides (e.g., 20 consecutive nucleotides) having complementarity with the target domain, e.g., the targeting domain is 20 nucleotides in length.

In an embodiment, the targeting domain comprises, has, or consists of, 21 nucleotides (e.g., 21 consecutive nucleotides) having complementarity with the target domain, e.g., the targeting domain is 21 nucleotides in length.

In an embodiment, the targeting domain comprises, has, or consists of, 22 nucleotides (e.g., 22 consecutive nucleotides) having complementarity with the target domain, e.g., the targeting domain is 22 nucleotides in length.

In an embodiment, the targeting domain comprises, has, or consists of, 23 nucleotides (e.g., 23 consecutive nucleotides) having complementarity with the target domain, e.g., the targeting domain is 23 nucleotides in length.

In an embodiment, the targeting domain comprises, has, or consists of, 24 nucleotides (e.g., 24 consecutive nucleotides) having complementarity with the target domain, e.g., the targeting domain is 24 nucleotides in length.

In an embodiment, the targeting domain comprises, has, or consists of, 25 nucleotides (e.g., 25 consecutive nucleotides) having complementarity with the target domain, e.g., the targeting domain is 5 nucleotides in length.

In an embodiment, the targeting domain comprises, has, or consists of, 26 nucleotides (e.g., 26 consecutive nucleotides) having complementarity with the target domain, e.g., the targeting domain is 26 nucleotides in length.

In an embodiment, the targeting domain comprises, has, or consists of, 16 nucleotides (e.g., 16 consecutive nucleotides) having complementarity with the target domain, e.g., the targeting domain is 16 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 16 nucleotides (e.g., 16 consecutive nucleotides) having complementarity with the target domain, e.g., the targeting domain is 16 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 16 nucleotides (e.g., 16 consecutive nucleotides) having complementarity with the target domain, e.g., the targeting domain is 16 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain has, or consists of, 17 nucleotides (e.g., 17 consecutive nucleotides) having complementarity with the target domain, e.g., the targeting domain is 17 nucleotides in length; and the proximal and tail domain, when taken together, comprise at least 15, 18, 20, 25, 30, 31, 35, 40, 45, 49, 50, or 53 nucleotides.

In an embodiment, the targeting domain has, or consists of, 17 nucleotides (e.g., 17 consecutive nucleotides) having complementarity with the target domain, e.g., the targeting domain is 17 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain has, or consists of, 17 nucleotides (e.g., 17 consecutive nucleotides) having complementarity with the target domain, e.g., the targeting domain is 17 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain has, or consists of, 18 nucleotides (e.g., 18 consecutive nucleotides) having complementarity with the target domain, e.g., the targeting domain is 18 nucleotides in length; and the proximal and tail domain, when taken together, comprise at least 15, 18, 20, 25, 30, 31, 35, 40, 45, 49, 50, or 53 nucleotides.

In an embodiment, the targeting domain has, or consists of, 18 nucleotides (e.g., 18 consecutive nucleotides) having complementarity with the target domain, e.g., the targeting domain is 18 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain has, or consists of, 18 nucleotides (e.g., 18 consecutive nucleotides) having complementarity with the target domain, e.g., the targeting domain is 18 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 19 nucleotides (e.g., 19 consecutive nucleotides) having complementarity with the target domain, e.g., the targeting domain is 19 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 20 nucleotides (e.g., 20 consecutive nucleotides) having complementarity with the target domain, e.g., the targeting domain is 20 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 20 nucleotides (e.g., 20 consecutive nucleotides) having complementarity with the target domain, e.g., the targeting domain is 20 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 20 nucleotides (e.g., 20 consecutive nucleotides) having complementarity with the target domain, e.g., the targeting domain is 20 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 21 nucleotides (e.g., 21 consecutive nucleotides) having complementarity with the target domain, e.g., the targeting domain is 21 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 21 nucleotides (e.g., 21 consecutive nucleotides) having complementarity with the target domain, e.g., the targeting domain is 21 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 22 nucleotides (e.g., 22 consecutive nucleotides) having complementarity with the target domain, e.g., the targeting domain is 22 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 23 nucleotides (e.g., 23 consecutive nucleotides) having complementarity with the target domain, e.g., the targeting domain is 23 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 23 nucleotides (e.g., 23 consecutive nucleotides) having complementarity with the target domain, e.g., the targeting domain is 23 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 23 nucleotides (e.g., 23 consecutive nucleotides) having complementarity with the target domain, e.g., the targeting domain is 23 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 24 nucleotides (e.g., 24 consecutive nucleotides) having complementarity with the target domain, e.g., the targeting domain is 24 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 25 nucleotides (e.g., 25 consecutive nucleotides) having complementarity with the target domain, e.g., the targeting domain is 25 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 25 nucleotides (e.g., 25 consecutive nucleotides) having complementarity with the target domain, e.g., the targeting domain is 25 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and the proximal and tail domain, when taken together, comprise at least 15, 18, 20, 25, 30, 31, 35, 40, 45, 49, 50, or 53 nucleotides.

In an embodiment, the targeting domain comprises, has, or consists of, 26 nucleotides (e.g., 26 consecutive nucleotides) having complementarity with the target domain, e.g., the targeting domain is 26 nucleotides in length; and there are at least 15, 18, 20, 25, 30, 31, 35, 40, 45, 49, 50, or 53 nucleotides 3' to the last nucleotide of the second complementarity domain.

In an embodiment, the targeting domain comprises, has, or consists of, 26 nucleotides (e.g., 26 consecutive nucleotides) having complementarity with the target domain, e.g., the targeting domain is 26 nucleotides in length; and there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain.

II. Methods for Designing gRNAs

Methods for designing gRNAs are described herein, including methods for selecting, designing and validating target domains. Exemplary targeting domains are also provided herein. Targeting Domains discussed herein can be incorporated into the gRNAs described herein.

Methods for selection and validation of target sequences as well as off-target analyses are described, e.g., in Mali et al., 2013 Science 339(6121): 823-826; Hsu et al. Nat Biotechnol, 31(9): 827-32; Fu et al., 2014 Nat Biotechnol. doi: 10.1038/nbt.2808. PubMed PMID: 24463574; Heigwer et al., 2014 Nat Methods 11(2):122-3. doi: 10.1038/nmeth.2812. PubMed PMID: 24481216; Bae et al., 2014 Bioinformatics PubMed PMID: 24463181; Xiao A et al., 2014 Bioinformatics PubMed PMID: 24389662.

For example, a software tool can be used to optimize the choice of gRNA within a user's target sequence, e.g., to minimize total off-target activity across the genome. Off target activity may be other than cleavage. For each possible gRNA choice using *S. pyogenes* Cas9, software tools can identify all potential off-target sequences (preceding either NAG or NGG PAMs) across the genome that contain up to a certain number (e.g., 1, 2, 3, 4, 5, 6, 7, 8, 9, or 10) of mismatched base-pairs. The cleavage efficiency at each off-target sequence can be predicted, e.g., using an experimentally-derived weighting scheme. Each possible gRNA can then ranked according to its total predicted off-target cleavage; the top-ranked gRNAs represent those that are likely to have the greatest on-target and the least off-target cleavage. Other functions, e.g., automated reagent design for gRNA vector construction, primer design for the on-target Surveyor assay, and primer design for high-throughput detection and quantification of off-target cleavage via next-generation sequencing, can also be included in the tool. Candidate gRNA molecules can be evaluated by art-known methods or as described in Section IV herein.

Guide RNAs (gRNAs) for use with *S. pyogenes, S. aureus* and *N. meningitidis* Cas9s were identified using a DNA sequence searching algorithm. Guide RNA design was carried out using a custom guide RNA design software based on the public tool cas-offinder (reference: Cas-OFFinder: a fast and versatile algorithm that searches for potential off-target sites of Cas9 RNA-guided endonucleases, Bioinformatics. 2014 Feb. 17. Bae S, Park J, Kim J S. PMID:24463181). Said custom guide RNA design software scores guides after calculating their genomewide off-target propensity. Typically matches ranging from perfect matches to 7 mismatches are considered for guides ranging in length from 17 to 24. Once the off-target sites are computationally determined, an aggregate score is calculated for each guide and summarized in a tabular output using a web-interface. In addition to identifying potential gRNA sites adjacent to PAM sequences, the software also identifies all PAM adjacent sequences that differ by 1, 2, 3 or more nucleotides from the selected gRNA sites. Genomic DNA sequence for each gene was obtained from the UCSC Genome browser and sequences were screened for repeat elements using the publically available RepeatMasker program. RepeatMasker searches input DNA sequences for repeated elements and regions of low complexity. The output is a detailed annotation of the repeats present in a given query sequence.

Following identification, gRNAs were ranked into tiers based on their distance to the target site, their orthogonality or presence of a 5' G (based on identification of close matches in the human genome containing a relevant PAM (e.g., in the case of *S. pyogenes*, a NGG PAM, in the case of *S. aureus*, a NNGRRT or NNGRRV PAM, and in the case of *N. meningitidis*, a NNNNGATT or NNNNGCTT PAM). Orthogonality refers to the number of sequences in the human genome that contain a minimum number of mismatches to the target sequence. A "high level of orthogonality" or "good orthogonality" may, for example, refer to 20-mer gRNAs that have no identical sequences in the human genome besides the intended target, nor any sequences that contain one or two mismatches in the target sequence. Targeting domains with good orthogonality are selected to minimize off-target DNA cleavage.

As an example, for *S. pyogenes* and *N. meningitidis* targets, 17-mer, or 20-mer gRNAs were designed. As another example, for *S. aureus* targets, 18-mer, 19-mer, 20-mer, 21-mer, 22-mer, 23-mer and 24-mer gRNAs were designed. Targeting domains, disclosed herein, may comprise the 17-mer described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 18 or more nucleotides may comprise the 17-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. Targeting domains, disclosed herein, may comprises the 18-mer described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 19 or more nucleotides may comprise the 18-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. Targeting domains, disclosed herein, may comprises the 19-mer described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 20 or more nucleotides may comprise the 19-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. Targeting domains, disclosed herein, may comprises the 20-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 21 or more nucleotides may comprise the 20-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. Targeting domains, disclosed herein, may comprises the 21-mer described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 22 or more nucleotides may comprise the 21-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. Targeting domains, disclosed herein, may comprises the 22-mer described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 23 or more nucleotides may comprise the 22-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. Targeting domains, disclosed herein, may comprises the 23-mer described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 24 or more nucleotides may comprise the 23-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31. Targeting domains, disclosed herein, may comprises the 24-mer described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31, e.g., the targeting domains of 25 or more nucleotides may comprise the 24-mer gRNAs described in Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31.

gRNAs were identified for both single-gRNA nuclease cleavage and for a dual-gRNA paired "nickase" strategy. Criteria for selecting gRNAs and the determination for which gRNAs can be used for the dual-gRNA paired "nickase" strategy is based on two considerations:

1. gRNA pairs should be oriented on the DNA such that PAMs are facing out and cutting with the D10A Cas9 nickase will result in 5' overhangs.
2. An assumption that cleaving with dual nickase pairs will result in deletion of the entire intervening sequence at a reasonable frequency. However, cleaving with dual nickase pairs can also result in indel mutations at the site of only one of the gRNAs. Candidate pair members can be tested for how efficiently they remove the entire sequence versus causing indel mutations at the site of one gRNA.

The targeting domains discussed herein can be incorporated into the gRNAs described herein.

Strategies to Identify gRNAs for *S. pyogenes*, *S. aureus*, and *N. meningitidis* to Correct a Mutation in the HBB Gene gRNAs were designed for use with *S. pyogenes*, and *S. aureus* Cas9 enzymes to target the E6V mutation in the HBB gene. As an example, three strategies were utilized to identify gRNAs for use with *S. pyogenes*, *S. aureus* and *N. meningitidis* Cas9 enzymes.

In one strategy, the gRNAs were identified and ranked into 3 tiers for *S. pyogenes* (Tables 1A-1C). The targeting domains for tier 1 gRNA molecules for use with the *S. pyogenes* Cas9 to target the E6V mutation in the HBB gene were selected based on (1) a reasonable distance to the target position, and (2) a high level of orthogonality. Tier 2 gRNAs were selected based on (1), a reasonable distance to the target position, and (2) presence of a 5'G. Tier 3 used the same distance restriction, but removed the requirement of good orthogonality and the 5'G. Note that tiers are non-inclusive (each gRNA is listed only once). gRNAs for use with the *S. aureus* (Table 1D), Cas9s were identified manually by scanning genomic DNA sequence for the presence of PAM sequences. These gRNAs were not separated into tiers, but were listed in a single list.

In a second strategy, the gRNAs were identified and ranked into 4 tiers for *S. pyogenes* (Tables 13A-13D) and 5 tiers for *S. aureus* (Tables 14A-14C). The targeting domain for tier 1 gRNA molecules to use with *S. pyogenes* Cas9 were selected based on (1) a short distance to the target position, e.g., within 100 bp upstream and 100 bp downstream of the mutation, (2) a high level of orthogonality, and (3) the presence of a 5' G. For selection of tier 2 gRNAs, a short distance and high orthogonality were required but the presence of a 5'G was not required. Tier 3 uses the same distance restriction and the requirement for a 5'G, but removes the requirement of good orthogonality. Tier 4 uses the same distance restriction but removes the requirement of good orthogonality and the 5'G. The targeting domain for tier 1 gRNA molecules to use with *S. aureus* Cas9 were selected based on (1) a short distance to the target position, e.g., within 100 bp upstream and 100 bp downstream of the mutation, (2) a high level of orthogonality, and (3) the presence of a 5' G. For selection of tier 2 gRNAs, a short distance and high orthogonality were required but the presence of a 5'G was not required. Tier 3 uses the same distance restriction and the requirement for a 5'G, but removes the requirement of good orthogonality. Tier 4 uses the same distance restriction but removes the requirement of good orthogonality and the 5'G. Tier 5 is selected based on (1) a short distance to the target position, e.g., within 100 bp upstream and 100 bp downstream of the mutation and (2) PAM is NNGRRV. Note that tiers are non-inclusive (each gRNA is listed only once for the strategy). In certain instances, no gRNA was identified based on the criteria of the particular tier. In some instances, there are no corresponding exemplary gRNAs in certain tiers.

In a third strategy, the gRNAs were identified and ranked into 3 tiers for *S. pyogenes* (Tables 24A-24D), 4 tiers for *S. aureus* (Tables 25A-25B) and 3 tiers for *N. meningitidis* (Tables 26). The targeting domain for tier 1 gRNA molecules to use with *S. pyogenes* Cas9 were selected based on (1) distance to the target position, e.g., within 200 bp upstream and 200 bp downstream of the mutation and (2) a high level of orthogonality. The targeting domain for tier 2 gRNA molecules to use with *S. pyogenes* Cas9 were selected based on (1) distance to the target position, e.g., within 200 bp upstream and 200 bp downstream of the mutation and (2) the presence of a 5'G. The targeting domain for tier 3 gRNA molecules to use with *S. pyogenes* Cas9 were selected based on distance to the target position, e.g., within 200 bp upstream and 200 bp downstream of the mutation. The targeting domain for tier 1 gRNA molecules to use with *S. aureus* Cas9 were selected based on (1) distance to the target position, e.g., within 200 bp upstream and 200 bp downstream of the mutation, (2) a high level of orthogonality and (3) PAM is NNGRRT. The targeting domain for tier 2 gRNA molecules to use with *S. aureus* Cas9 were selected based on (1) distance to the target position, e.g., within 200 bp upstream and 200 bp downstream of the mutation, (2) the presence of a 5'G, and (3) PAM is NNGRRT. The targeting domain for tier 3 gRNA molecules to use with *S. aureus* Cas9 were selected based on (1) distance to the target position, e.g., within 200 bp upstream and 200 bp downstream of the mutation and (2) PAM is NNGRRT. The targeting domain for tier 4 gRNA molecules to use with *S. aureus* Cas9 were selected based on (1) distance to the target position, e.g., within 200 bp upstream and 200 bp downstream of the mutation and (2) PAM is NNGRRV. The targeting domain for tier 1 gRNA molecules to use with *N. meningitidis* Cas9 were selected based on (1) distance to the target position, e.g., within 200 bp upstream and 200 bp downstream of the mutation and (2) a high level of orthogonality. The targeting domain for tier 2 gRNA molecules to use with *N. meningitidis* Cas9 were selected based on (1) distance to the target position, e.g., within 200 bp upstream and 200 bp downstream of the mutation and (2) the presence of a 5'G. The targeting domain for tier 3 gRNA molecules to use with *N. meningitidis* Cas9 were selected based on distance to the target position, e.g., within 200 bp upstream and 200 bp downstream of the mutation.

In an embodiment, dual targeting (e.g., dual nicking) is used to create two nicks on opposite DNA strands by using *S. pyogenes*, *S. aureus* and *N. meningitidis* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary nickase pairs including selecting a targeting domain from Group A and a second targeting domain from Group B in Table 24D (for *S. pyogenes*). It is contemplated herein that in an embodiment a targeting domain of Group A can be combined with any of the targeting domains of Group B in Table 24D (for *S. pyogenes*). For example, HBB-9, HBB-20 can be combined with HBB-11, HBB-39.

Strategies to Identify gRNAs for *S. pyogenes*, *S. aureus*, and *N. meningitidis* to Knock Out the BCL11A Gene gRNAs were designed for use with *S. pyogenes*, *S. aureus* and *N. meningitidis* Cas9 enzymes to induce an insertion or deletion of one or more nucleotides mediated by NHEJ in close proximity to or within the early coding region. As an example, three strategies were utilized to identify gRNAs for use with *S. pyogenes*, *S. aureus* and *N. meningitidis* Cas9 enzymes.

In one strategy, the gRNAs were identified and ranked into 4 tires for *S. pyogenes* (Tables 2A-2D). The targeting domains for tier 1 gRNA molecules for use with the *S. pyogenes* Cas9 to knockout the BCL11A gene were selected based on (1) a reasonable distance to the target position, and (2) a high level of orthogonality. Tier 2 gRNAs were selected based on (1), a reasonable distance to the target position, and (2) presence of a 5'G. Tier 3 used the same distance restriction, but removed the requirement of good orthogonality and the 5'G. Tier 4 only required the presence in the coding sequence. Note that tiers are non-inclusive (each gRNA is listed only once). gRNAs for use with the *S. aureus* (Table 2E), and *N. meningitidis* (Table 2F) Cas9s were identified manually by scanning genomic DNA sequence for the presence of PAM sequences. These gRNAs were not separated into tiers, but were listed in a single list. Note that tiers are non-inclusive (each gRNA is listed only once for the strategy). In certain instances, no gRNA was identified based on the criteria of the particular tier.

In a second strategy, the gRNAs were identified and ranked into 5 tiers for *S. pyogenes* (Tables 4A-4E), and *S. aureus* (Tables 5A-5E); and 2 tiers for *N. meningitidis* (Tables 6A-6B). For *S. pyogenes*, and *S. aureus*, the targeting domain for tier 1 gRNA molecules were selected based on (1) distance to a target site (e.g., start codon), e.g., within 500 bp (e.g., downstream) of the target site (e.g., start codon), (2) a high level of orthogonality and (3) the presence of 5'G. The targeting domain for tier 2 gRNA molecules were selected based on (1) distance to a target site (e.g., start codon), e.g., within 500 bp (e.g., downstream) of the target site (e.g., start codon) and (2) a high level of orthogonality. The targeting domain for tier 3 gRNA molecules were selected based on (1) distance to a target site (e.g., start codon), e.g., within 500 bp (e.g., downstream) of the target site (e.g., start codon) and (2) the presence of 5'G. The targeting domain for tier 4 gRNA molecules were selected based on distance to a target site (e.g., start codon), e.g., within 500 bp (e.g., downstream) of the target site (e.g., start codon). The targeting domain for tier 5 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon). For *N. meningitidis*, the targeting domain for tier 1 gRNA molecules were selected based on (I) distance to a target site (e.g., start codon), e.g., within 500 bp (e.g., downstream) of the target site (e.g., start codon). The targeting domain for tier 2 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon). Note that tiers are non-inclusive (each gRNA is listed only once for the strategy). In certain instances, no gRNA was identified based on the criteria of the particular tier.

In a third strategy, the gRNAs were identified and ranked into 3 tiers for *S. pyogenes* (Tables 15A-15D), and *N. meningitidis* (Tables 17A-17B); and 5 tiers for *S. aureus* (Tables 16A-16D). The targeting domain to be used with *S. pyogenes* Cas9 enzymes for tier 1 gRNA molecules were selected based on (1) distance to a target site (e.g., start codon), e.g., within 500 bp (e.g., downstream) of the target site (e.g., start codon) and (2) a high level of orthogonality. The targeting domain to be used with *S. pyogenes* Cas9 enzymes for tier 2 gRNA molecules were selected based on (1) distance to the target site (e.g., start codon), e.g., within 500 bp (e.g., downstream) of the target site (e.g., start codon). The targeting domain to be used with *S. pyogenes* Cas9 enzymes for tier 3 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon). The gRNAs were identified and ranked into 5 tiers for *S. aureus*, when the relevant PAM was NNGRRT or NNGRRV. The targeting domain to be used with *S. aureus* Cas9 enzymes for tier 1 gRNA molecules were selected based on (1) distance to the target site (e.g., start codon), e.g., within 500 bp (e.g., downstream) of the target site (e.g., start codon), (2) a high level of orthogonality, and (3) PAM is NNGRRT. The targeting domain to be used with *S. aureus* Cas9 enzymes for tier 2 gRNA molecules were selected based on (1) distance to the target site (e.g., start codon), e.g., within 500 bp (e.g., downstream) of the target site (e.g., start codon), and (2) PAM is NNGRRT. The targeting domain to be used with *S. aureus* Cas9 enzymes for tier 3 gRNA molecules were selected based on (1) distance to a the target site (e.g., start codon) mutation, e.g., within 500 bp (e.g., downstream) of the target site (e.g., start codon), and (2) PAM is NNGRRV. The targeting domain to be used with *S. aureus* Cas9 enzymes for tier 4 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon), and (2) PAM is NNGRRT. The targeting domain to be used with *S. aureus* Cas9 enzymes for tier 5 gRNA molecules were selected based on (1) distance to the target site (e.g., start codon), e.g., within reminder of the coding sequence, e.g., downstream of the first 500 bp of coding sequence (e.g., anywhere from +500 (relative to the start codon) to the stop codon), and (2) PAM is NNGRRV. The gRNAs were identified and ranked into 3 tiers for *N. meningitidis*. The targeting domain to be used with *N. meningitidis* Cas9 enzymes for tier 1 gRNA molecules were selected based on (1) distance to the target site, e.g., within 500 bp (e.g., downstream) of the target site (e.g., start codon) and (2) a high level of orthogonality. The targeting domain to be used with *N. meningitidis* Cas9 enzymes for tier 2 gRNA molecules were selected based on (1) distance to the target site (e.g., start codon), e.g., within 500 bp (e.g., downstream) of the target site (e.g., start codon). The targeting domain to be used with *N.*

*meningitidis* Cas9 enzymes for tier 3 gRNA molecules were selected based on distance to the target site (e.g., start codon), e.g., within reminder of the coding sequence, e.g., downstream of the first 500 bp of coding sequence (e.g., anywhere from +500 (relative to the start codon) to the stop codon). Note that tiers are non-inclusive (each gRNA is listed only once for the strategy). In certain instances, no gRNA was identified based on the criteria of the particular tier.

In an embodiment, when a single gRNA molecule is used to target a Cas9 nickase to create a single strand break in close proximity to the BCL11A target position, e.g., the gRNA is used to target either upstream of (e.g., within 500 bp, e.g., within 200 bp upstream of the BCL11A target position), or downstream of (e.g., within 500 bp, e.g., within 200 bp downstream of the BCL11A target position) in the BCL11A gene.

In an embodiment, when a single gRNA molecule is used to target a Cas9 nuclease to create a double strand break to in close proximity to the BCL11A target position, e.g., the gRNA is used to target either upstream of (e.g., within 500 bp, e.g., within 200 bp upstream of the BCL11A target position), or downstream of (e.g., within 500 bp, e.g., within 200 bp downstream of the BCL11A target position) in the BCL11A gene.

In an embodiment, dual targeting is used to create two double strand breaks to in close proximity to the mutation, e.g., the gRNA is used to target either upstream of (e.g., within 500 bp, e.g., within 200 bp upstream of the BCL11A target position), or downstream of (e.g., within 500 bp, e.g., within 200 bp downstream of the BCL11A target position) in the BCL11A gene. In an embodiment, the first and second gRNAs are used to target two Cas9 nucleases to flank, e.g., the first of gRNA is used to target upstream of (e.g., within 500 bp, e.g., within 200 bp upstream of the BCL11A target position), and the second gRNA is used to target downstream of (e.g., within 500 bp, e.g., within 200 bp downstream of the BCL11A target position) in the BCL11A gene.

In an embodiment, dual targeting is used to create a double strand break and a pair of single strand breaks to delete a genomic sequence including the BCL11A target position. In an embodiment, the first, second and third gRNAs are used to target one Cas9 nuclease and two Cas9 nickases to flank, e.g., the first gRNA that will be used with the Cas9 nuclease is used to target upstream of (e.g., within 500 bp, e.g., within 200 bp upstream of the BCL11A target position) or downstream of (e.g., within 500 bp, e.g., within 200 bp downstream of the BCL11A target position), and the second and third gRNAs that will be used with the Cas9 nickase pair are used to target the opposite side of the mutation (e.g., within 200 bp upstream or downstream of the BCL11A target position) in the BCL11A gene.

In an embodiment, when four gRNAs (e.g., two pairs) are used to target four Cas9 nickases to create four single strand breaks to delete genomic sequence including the mutation, the first pair and second pair of gRNAs are used to target four Cas9 nickases to flank, e.g., the first pair of gRNAs are used to target upstream of (e.g., within 500 bp, e.g., within 200 bp upstream of the BCL11A target position), and the second pair of gRNAs are used to target downstream of (e.g., within 500 bp. e.g., within 200 bp downstream of the BCL11A target position) in the BCL11A gene.

In an embodiment, dual targeting (e.g., dual nicking) is used to create two nicks on opposite DNA strands by using *S. pyogenes, S. aureus* and *N. meningitidis* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary nickase pairs including selecting a targeting domain from Group A and a second targeting domain from Group B, or including selecting a targeting domain from Group C and a second targeting domain from Group D in Table 15D (for *S. pyogenes*). It is contemplated herein that in an embodiment a targeting domain of Group A can be combined with any of the targeting domains of Group B; in an embodiment a targeting domain of Group C can be combined with any of the targeting domains of Group D in Table 15D (for *S. pyogenes*). For example, BCL11A-5355 or BCL11A-5380 can be combined with BCL11A-5321 or BCL11A-5416; or BCL11A-5333, BCL11A-5354, or BCL11A-5329 can be combined with BCL11A-5367 or BCL11A-5341.

Strategies to Identify gRNAs for *S. pyogenes, S. aureus*, and *N. meningitidis* to Knock Down the BCL11A Gene gRNAs were designed for use with *S. pyogenes, S. aureus* and *N. meningitidis* one or more Cas9 molecules, e.g., enzymatically inactive Cas9 (eiCas9) molecules or Cas9 fusion proteins (e.g., an eiCas9 fused to a transcription repressor domain or chromatin modifying protein to alter (e.g., to block, reduce, or decrease) the transcription of the BCL11A gene. As an example, three strategies were utilized to identify gRNAs for use with *S. pyogenes, S. aureus* and *N. meningitidis* one or more Cas9 molecules.

In one strategy, the targeting domains for gRNA molecules to knockdown the BCL11A gene were designed to target the 1 kb of sequence 3' of the start codon. They were listed in a single list for *S. pyogenes* (Table 3A), *S. aureus* (Table 3B) and *N. meningitidis* (Table 3C).

In a second strategy, the gRNAs were identified and ranked into 4 tiers for *S. pyogenes* (Tables 10A-10D), and *S. aureus* (Tables 11A-11D). The gRNAs were identified and listed in a single list for *N. meningitidis* (Table 12). For *S. pyogenes*, and *S. aureus*, the targeting domain for tier 1 gRNA molecules were selected based on (1) distance to a target site (e.g., a transcription start site), e.g., within 500 bp (e.g., upstream or downstream) of the target site (e.g., the transcription start site), (2) a high level of orthogonality and (3) the presence of 5'G. The targeting domain for tier 2 gRNA molecules were selected based on (1) distance to a target site (e.g., the transcription start site), e.g., within 500 bp (e.g., upstream or downstream) of the target site (e.g., the transcription start site) and (2) a high level of orthogonality. The targeting domain for tier 3 gRNA molecules were selected based on (1) distance to a target site (e.g., the transcription start site), e.g., within 500 bp (e.g., upstream or downstream) of the target site (e.g., the transcription start site) and (2) the presence of 5'G. The targeting domain for tier 4 gRNA molecules were selected based on distance to a target site (e.g., the transcription start site), e.g., within 500 bp (e.g., upstream or downstream) of the target site (e.g., the transcription start site).

In a third strategy, gRNAs were designed for use with *S. pyogenes, S. aureus* and *N. meningitidis* Cas9 molecules. The gRNAs were identified and ranked into 3 tiers for *S. pyogenes* (Tables 18A-18C). The targeting domain to be used with *S. pyogenes* Cas9 enzymes for tier 1 gRNA molecules were selected based on (1) distance to a target site (e.g., the transcription start site), e.g., within 500 bp (e.g., upstream or downstream) of the target site (e.g., the transcription start site) and (2) a high level of orthogonality. The targeting domain to be used with *S. pyogenes* Cas9 enzymes for tier 2 gRNA molecules were selected based on (1) distance to the target site (e.g., the transcription start site), e.g., within 500 bp (e.g., upstream or downstream) of the target site (e.g., the transcription start site). The targeting domain to be used with *S. pyogenes* Cas9 enzymes for tier 3 gRNA molecules were selected based on distance to the target site (e.g., the transcription start site), e.g., within the additional 500 bp upstream and downstream of the transcription start site (i.e., extending to 1 kb upstream and downstream of the transcription start site. The gRNAs were identified and ranked into 5 tiers for *S. aureus*, when the relevant PAM was NNGRRT or NNGRRV (Tables 19A-19B). The targeting domain to be used with *S. aureus* Cas9 enzymes for tier 1 gRNA molecules were selected based on (1) distance to the target site (e.g., the transcription start site), e.g., within 500 bp (e.g., upstream or downstream) of the target site (e.g., the transcription start site), (2) a high level of orthogonality, and (3) PAM is NNGRRT. The targeting domain to be used with *S. aureus* Cas9 enzymes for tier 2 gRNA molecules were selected based on (1) distance to the target site (e.g., the transcription start site), e.g., within 500 bp (e.g., upstream or downstream) of the target site (e.g., the transcription start site), and (2) PAM is NNGRRT. The targeting domain to be used with *S. aureus* Cas9 enzymes for tier 3 gRNA molecules were selected based on (1) distance to a target site (e.g., the transcription start site), e.g., within 500 bp (e.g., upstream or downstream) of the target site (e.g., the transcription start site), and (2) PAM is NNGRRV. The targeting domain to be used with *S. aureus* Cas9 enzymes for tier 4 gRNA molecules were selected based on (1) distance to the target site (e.g., the transcription start site), e.g., within the additional 500 bp upstream and downstream of the transcription start site (i.e., extending to 1 kb upstream and downstream of the transcription start site, and (2) PAM is NNGRRT. The targeting domain to be used with *S. aureus* Cas9 enzymes for tier 5 gRNA molecules were selected based on (1) distance to the target site (e.g., the transcription start site), e.g., within the additional 500 bp upstream and downstream of the transcription start site (i.e., extending to 1 kb upstream and downstream of the transcription start site, and (2) PAM is NNGRRV. The gRNAs were identified and ranked into 3 tiers for *N. meningitidis* (Tables 20A-20C). The targeting domain to be used with *N. meningitidis* Cas9 enzymes for tier 1 gRNA molecules were selected based on (1) distance to a target site (e.g., the transcription start site), e.g., within 500 bp (e.g., upstream or downstream) of the target site (e.g., the transcription start site) and (2) a high level of orthogonality. The targeting domain to be used with *N. meningitidis* Cas9 enzymes for tier 2 gRNA molecules were selected based on (1) distance to the target site (e.g., the transcription start site), e.g., within 500 bp (e.g., upstream or downstream) of the target site (e.g., the transcription start site). The targeting domain to be used with *N. meningitidis* Cas9 enzymes for tier 3 gRNA molecules were selected based on distance to the target site (e.g., the transcription start site), e.g., within the additional 500 bp upstream and downstream of the transcription start site (i.e., extending to 1 kb upstream and downstream of the transcription start site. Note that tiers are non-inclusive (each gRNA is listed only once for the strategy). In certain instances, no gRNA was identified based on the criteria of the particular tier.

Strategies to Identify gRNAs for *S. pyogenes. S. aureus*, and *N. meningitidis* to Remove (e.g., Delete) the Enhancer Region the BCL11A Gene gRNAs were designed for use with *S. pyogenes, S. aureus* and *N. meningitidis* Cas9 enzymes to remove (e.g., delete) the enhancer region in the BCL11A gene. As an example, two strategies were utilized to identify gRNAs for use with *S. pyogenes, S. aureus* and *N. meningitidis* one or more Cas9 molecules.

In an strategy, the gRNAs were identified and ranked into 4 tiers for *S. pyogenes* (Tables 7A-7D) and for *S. aureus* (Tables 8A-8D). The gRNAs were identified and listed in a single list for *N. meningitidis* (Table 9). The targeting domains for tier 1 gRNA molecules for use with the *S. pyogenes, S. aureus* Cas9 were selected based on (1) a reasonable distance to the target position, e.g., within a region 5' (51.5 to 51.7 kb downstream of transcription start site, TSS) or 3' (65.1 to 65.3 kb downstream of TSS), (2) a high level of orthogonality and (3) presence of a 5'G. For selection of tier 2 gRNAs, reasonable distance and high orthogonality were required but the presence of a 5'G was not required. Tier 3 uses the same distance restriction and the requirement for a 5'G, but removes the requirement of good orthogonality. Tier 4 uses the same distance restriction but removes the requirement of good orthogonality and the 5'G. Note that tiers are non-inclusive (each gRNA is listed only once for the strategy). In certain instances, no gRNA was identified based on the criteria of the particular tier.

In a second strategy, gRNAs were designed for use with *S. pyogenes, S. aureus* and *N. meningitidis* Cas9 molecules. The gRNAs were identified and ranked into 4 tiers for *S. pyogenes* (Tables 21A-21E). The targeting domain to be used with *S. pyogenes* Cas9 enzymes for tier 1 gRNA molecules were selected based on (1) within a region 5' (51.5 to 51.7 kb downstream of TSS) or 3' (65.1 to 65.3 kb downstream of TSS), (2) a high level of orthogonality and (3) presence of 5'G. The targeting domain to be used with *S. pyogenes* Cas9 enzymes for tier 2 gRNA molecules were selected based on (1) within a region 5' (51.5 to 51.7 kb downstream of TSS) or 3' (65.1 to 65.3 kb downstream of TSS) and (2) a high level of orthogonality. The targeting domain to be used with *S. pyogenes* Cas9 enzymes for tier 3 gRNA molecules were selected based on (1) within a region 5' (51.5 to 51.7 kb downstream of TSS) or 3' (65.1 to 65.3 kb downstream of TSS) and (2) presence of 5'G. The targeting domain to be used with *S. pyogenes* Cas9 enzymes for tier 4 gRNA molecules were selected based on within a region 5' (51.5 to 51.7 kb downstream of TSS) or 3' (65.1 to 65.3 kb downstream of TSS). The gRNAs were identified and ranked into 5 tiers for *S. aureus*, when the relevant PAM was NNGRRT or NNGRRV (Tables 22A-22E). The targeting domain to be used with *S. aureus* Cas9 enzymes for tier 1 gRNA molecules were selected based on (1) within a region 5' (51.5 to 51.7 kb downstream of TSS) or 3' (65.1 to 65.3 kb downstream of TSS), (2) a high level of orthogonality, (3)) presence of 5'G and (4) PAM is NNGRRT. The targeting domain to be used with *S. aureus* Cas9 enzymes for tier 2 gRNA molecules were selected based on (1) within a region 5' (51.5 to 51.7 kb downstream of TSS) or 3' (65.1 to 65.3 kb downstream of TSS), (2) a high level of orthogonality, and (3) PAM is NNGRRT. The targeting domain to be used with *S. aureus* Cas9 enzymes for tier 3 gRNA molecules were selected based on (1) within a region 5' (51.5 to 51.7 kb downstream of TSS) or 3' (65.1 to 65.3 kb downstream of TSS), (2) presence of 5'G and (3) PAM is NNGRRT. The targeting domain to be used with *S. aureus* Cas9 enzymes for tier 4 gRNA molecules were selected based on (1) within a region 5' (51.5 to 51.7 kb downstream of TSS) or 3' (65.1 to 65.3 kb downstream of TSS), and (2) PAM is NNGRRT. The targeting domain to be used with *S. aureus* Cas9 enzymes for tier 5 gRNA molecules were selected based on (1) within a region 5' (51.5 to 51.7 kb downstream of TSS) or 3' (65.1 to 65.3 kb downstream of TSS), and (2) PAM is NNGRRV. The gRNAs were identified and ranked into 3 tiers for *N. meningitidis* (Tables 23A-23C). The targeting domain to be used with *N. meningitidis* Cas9 enzymes for tier 1 gRNA molecules were selected based on (1) within a region 5' (51.5 to 51.7 kb downstream of TSS) or 3' (65.1 to 65.3 kb downstream of TSS), (2) a high level of orthogonality and (3) presence of 5'G. The targeting domain to be used with *N. meningitidis* Cas9 enzymes for tier 2 gRNA molecules were selected based on (1) within a region 5' (51.5 to 51.7 kb downstream of TSS) or 3' (65.1 to 65.3 kb downstream of TSS) and (2) a high level of orthogonality. The targeting domain to be used with *N. meningitidis* Cas9 enzymes for tier 3 gRNA molecules were selected based on (1) within a region 5' (51.5 to 51.7 kb downstream of TSS) or 3' (65.1 to 65.3 kb downstream of TSS) and (2) presence of 5'G. The targeting domain to be used with *N. meningitidis* Cas9 enzymes for tier 4 gRNA molecules were selected based on within a region 5' (51.5 to 51.7 kb downstream of TSS) or 3' (65.1 to 65.3 kb downstream of TSS). Note that tiers are non-inclusive (each gRNA is listed only once for the strategy). In certain instances, no gRNA was identified based on the criteria of the particular tier.

In an embodiment, dual targeting (e.g., dual nicking) is used to create two nicks on opposite DNA strands by using *S. pyogenes*, *S. aureus* and *N. meningitidis* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary nickase pairs including selecting a targeting domain from Group A and a second targeting domain from Group B, or including selecting a targeting domain from Group C and a second targeting domain from Group D in Table 20E (for *S. pyogenes*). It is contemplated herein that in an embodiment a targeting domain of Group A can be combined with any of the targeting domains of Group B; in an embodiment a targeting domain of Group C can be combined with any of the targeting domains of Group D in Table 20E (for *S. pyogenes*). For example, BCL11A-13271 or BCL11A-13264 can be combined with BCL11A-13276; or BCL11A-13262 or BCL11A-13282 can be combined with BCL11A-13290 or BCL11A-13280.

In an embodiment, two or more (e.g., three or four) gRNA molecules are used with one Cas9 molecule. In another embodiment, when two or more (e.g., three or four) gRNAs are used with two or more Cas9 molecules, at least one Cas9 molecule is from a different species than the other Cas9 molecule(s). For example, when two gRNA molecules are used with two Cas9 molecules, one Cas9 molecule can be from one species and the other Cas9 molecule can be from a different species. Both Cas9 species are used to generate a single or double-strand break, as desired.

Any of the targeting domains in the tables described herein can be used with a Cas9 nickase molecule to generate a single strand break.

Any of the targeting domains in the tables described herein can be used with a Cas9 nuclease molecule to generate a double strand break.

When two gRNAs designed for use to target two Cas9 molecules, one Cas9 can be one species, the second Cas9 can be from a different species. Both Cas9 species are used to generate a single or double-strand break, as desired.

It is contemplated herein that any upstream gRNA described herein may be paired with any downstream gRNA described herein. When an upstream gRNA designed for use with one species of Cas9 is paired with a downstream gRNA designed for use from a different species of Cas9, both Cas9 species are used to generate a single or double-strand break, as desired.

Exemplary Targeting Domains

Table 1A provides exemplary targeting domains for the E6V target site in the HBB gene selected according to the first tier parameters, and are selected based on the close proximity and orientation to mutation and orthogonality in the human genome. In an embodiment, the targeting domain is the exact complement of the target domain. Any of the targeting domains in the table can be used with a Cas9 molecule (e.g., a *S. pyogenes* Cas9 molecule) that gives double stranded cleavage. Any of the targeting domains in the table can be used with a Cas9 (e.g., a *S. pyogenes* Cas9 nickase) molecule to generate a single strand break. In an embodiment, dual targeting is used to create two nicks on opposite DNA strands by using Cas9 nickases (e.g., a *S. pyogenes* Cas9 nickase) with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position. In an embodiment, two 20-mer guide RNAs are used to target two Cas9 nucleases (e.g., two *S. pyogenes* Cas9 nucleases) or two Cas9 nickases (e.g., two *S. pyogenes* Cas9 nickases), e.g., HBB-8 and HBB-25 are used. In an embodiment, two 17-mer RNAs are used to target two Cas9 nucleases or two Cas9 nickases, e.g., HBB-35 and HBB-53 are used.

TABLE 1A

1st Tier

| gRNA Name | DNA Strand | Targeting Domain | Target Site Length | SEQ ID NO |
|---|---|---|---|---|
| HBB-8 | − | AAGGUGAACGUGGAUGAAGU | 20 | 387 |
| HBB-25 | + | GUAACGGCAGACUUCUCCUC | 20 | 388 |
| HBB-35 | − | GUGAACGUGGAUGAAGU | 17 | 389 |
| HBB-53 | + | ACGGCAGACUUCUCCUC | 17 | 390 |

Table 1B provides exemplary targeting domains for the E6V target site in the HBB gene selected according to the second tier parameters and are selected based on the presence of a 5' G and reasonable proximity to mutation. In an embodiment, the targeting domain is the exact complement of the target domain. Any of the targeting domains in the table can be used with a *S. pyogenes* Cas9 molecule that gives double stranded cleavage. Any of the targeting domains in the table can be used with *S. pyogenes* single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 1B

2nd Tier

| gRNA Name | DNA Strand | Targeting Domain | Target Site Length | SEQ ID NO |
|---|---|---|---|---|
| HBB-12 | − | GAAGUUGGUGGUGAGGCCCU | 20 | 391 |
| HBB-1 | − | GCAACCUCAAACAGACACCA | 20 | 392 |
| HBB-52 | + | GCCCCACAGGGCAGUAA | 17 | 393 |
| HBB-32 | − | GCCGUUACUGCCCUGUG | 17 | 394 |
| HBB-46 | − | GGAGACCAAUAGAAACU | 17 | 395 |
| HBB-37 | − | GGAUGAAGUUGGUGGUG | 17 | 396 |
| HBB-29 | − | GGUGCAUCUGACUCCUG | 17 | 397 |
| HBB-4 | − | GUCUGCCGUUACUGCCCUGU | 20 | 398 |
| HBB-9 | − | GUGAACGUGGAUGAAGUUGG | 20 | 399 |
| HBB-34 | − | GUGGGGCAAGGUGAACG | 17 | 400 |
| HBB-40 | − | GUGGUGAGGCCCUGGGC | 17 | 401 |
| HBB-44 | − | GUUACAAGACAGGUUUA | 17 | 402 |
| HBB-51 | + | GUUCACCUUGCCCCACA | 17 | 403 |
| HBB-39 | − | GUUGGUGGUGAGGCCCU | 17 | 404 |

Table 1C provides exemplary targeting domains for the E6V target site in the HBB gene selected according to the third tier parameters and are selected based on reasonable proximity to mutation. In an embodiment, the targeting domain is the exact complement of the target domain. Any of the targeting domains in the table can be used with a *S. pyogenes* Cas9 molecule that gives double stranded cleavage. Any of the targeting domains in the table can be used with *S. pyogenes* single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 1C

3rd Tier

| gRNA Name | DNA Strand | Targeting Domain | Target Site Length | SEQ ID NO |
|---|---|---|---|---|
| HBB-36 | − | AACGUGGAUGAAGUUGG | 17 | 405 |
| HBB-17 | − | AAGGUUACAAGACAGGUUUA | 20 | 406 |
| HBB-47 | + | ACAUGCCCAGUUUCUAU | 17 | 407 |
| HBB-55 | + | ACCAUGGUGUCUGUUUG | 17 | 408 |
| HBB-28 | − | ACCUCAAACAGACACCA | 17 | 409 |
| HBB-20 | + | ACCUUGAUACCAACCUGCCC | 20 | 410 |

TABLE 1C-continued

3rd Tier

| gRNA Name | DNA Strand | Targeting Domain | Target Site Length | SEQ ID NO |
|---|---|---|---|---|
| HBB-45 | − | AGGAGACCAAUAGAAAC | 17 | 411 |
| HBB-54 | + | AGGAGUCAGAUGCACCA | 17 | 412 |
| HBB-3 | − | AGUCUGCCGUUACUGCCCUG | 20 | 413 |
| HBB-38 | − | AGUUGGUGGUGAGGCCC | 17 | 414 |
| HBB-23 | + | CACGUUCACCUUGCCCCACA | 20 | 415 |
| HBB-2 | − | CAUGGUGCAUCUGACUCCUG | 20 | 416 |
| HBB-22 | + | CCACGUUCACCUUGCCCCAC | 20 | 417 |
| HBB-15 | − | CCCUGGGCAGGUUGGUAUCA | 20 | 418 |
| HBB-7 | − | CCUGUGGGGCAAGGUGAACG | 20 | 419 |
| HBB-21 | + | CCUUGAUACCAACCUGCCCA | 20 | 420 |
| HBB-10 | − | CGUGGAUGAAGUUGGUGGUG | 20 | 421 |
| HBB-6 | − | CGUUACUGCCCUGUGGGGCA | 20 | 422 |
| HBB-50 | + | CGUUCACCUUGCCCCAC | 17 | 423 |
| HBB-26 | + | CUCAGGAGUCAGAUGCACCA | 20 | 424 |
| HBB-30 | − | CUGCCGUUACUGCCCUG | 17 | 425 |
| HBB-24 | + | CUUGCCCCACAGGGCAGUAA | 20 | 426 |
| HBB-19 | − | UAAGGAGACCAAUAGAAACU | 20 | 427 |
| HBB-33 | − | UACUGCCCUGUGGGGCA | 17 | 428 |
| HBB-43 | − | UAUCAAGGUUACAAGAC | 17 | 429 |
| HBB-5 | − | UCUGCCGUUACUGCCCUGUG | 20 | 430 |
| HBB-11 | − | UGAAGUUGGUGGUGAGGCCC | 20 | 431 |
| HBB-41 | − | UGAGGCCCUGGGCAGGU | 17 | 432 |
| HBB-49 | + | UGAUACCAACCUGCCCA | 17 | 433 |
| HBB-27 | + | UGCACCAUGGUGUCUGUUUG | 20 | 434 |
| HBB-31 | − | UGCCGUUACUGCCCUGU | 17 | 435 |
| HBB-42 | − | UGGGCAGGUUGGUAUCA | 17 | 436 |
| HBB-16 | − | UGGUAUCAAGGUUACAAGAC | 20 | 437 |
| HBB-14 | − | UGGUGAGGCCCUGGGCAGGU | 20 | 438 |
| HBB-18 | − | UUAAGGAGACCAAUAGAAAC | 20 | 439 |
| HBB-48 | + | UUGAUACCAACCUGCCC | 17 | 440 |
| HBB-13 | − | UUGGUGGUGAGGCCCUGGGC | 20 | 441 |

Table 1D provides exemplary targeting domains for the E6V target site in the HBB gene selected based on close proximity to mutation. In an embodiment, the targeting domain is the exact complement of the target domain. Any of the targeting domains in the table can be used with a *S. aureus* Cas9 molecule that gives double stranded cleavage. Any of the targeting domains in the table can be used with *S. aureus* single-stranded break nucleases (nickases). In an embodiment, dual targeting is used to create two nicks.

When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 1D

| gRNA Name | DNA Strand | Targeting Domain | Target Site Length | SEQ ID NO |
|---|---|---|---|---|
| HBB-56 | − | CACCAUGGUGCAUCUGACUC | 20 | 442 |
| HBB-57 | − | CCAUGGUGCAUCUGACUCCU | 20 | 443 |
| HBB-58 | − | CAUGGUGCAUCUGACUCCUG | 20 | 444 |
| HBB-59 | − | UGGUGCAUCUGACUCCUGAG | 20 | 445 |
| HBB-60 | − | AAGUCUGCCGUUACUGCCCU | 20 | 446 |
| HBB-61 | − | AGUCUGCCGUUACUGCCCUG | 20 | 447 |
| HBB-62 | − | UUACUGCCCUGUGGGGCAAG | 20 | 448 |
| HBB-63 | − | CCCUGUGGGGCAAGGUGAAC | 20 | 449 |
| HBB-64 | − | GUGGGGCAAGGUGAACGUGG | 20 | 450 |
| HBB-65 | − | GAACGUGGAUGAAGUUGGUG | 20 | 451 |
| HBB-66 | − | AUGAAGUUGGUGGUGAGGCC | 20 | 452 |
| HBB-67 | − | CAAGGUUACAAGACAGGUUU | 20 | 453 |
| HBB-68 | − | AAGGUUACAAGACAGGUUUA | 20 | 454 |
| HBB-69 | − | GACAGGUUUAAGGAGACCAA | 20 | 455 |
| HBB-70 | − | UUUAAGGAGACCAAUAGAAA | 20 | 456 |
| HBB-71 | − | CAUGGUGCAUCUGACUC | 17 | 457 |
| HBB-72 | − | UGGUGCAUCUGACUCCU | 17 | 458 |
| HBB-73 | − | GGUGCAUCUGACUCCUG | 17 | 459 |
| HBB-74 | − | UGCAUCUGACUCCUGAG | 17 | 460 |
| HBB-75 | − | UCUGCCGUUACUGCCCU | 17 | 461 |
| HBB-76 | − | CUGCCGUUACUGCCCUG | 17 | 462 |
| HBB-77 | − | CUGCCCUGUGGGGCAAG | 17 | 463 |
| HBB-78 | − | UGUGGGGCAAGGUGAAC | 17 | 464 |
| HBB-79 | − | GGGCAAGGUGAACGUGG | 17 | 465 |
| HBB-80 | − | CGUGGAUGAAGUUGGUG | 17 | 466 |
| HBB-81 | − | AAGUUGGUGGUGAGGCC | 17 | 467 |
| HBB-82 | − | GGUUACAAGACAGGUUU | 17 | 468 |
| HBB-83 | − | GUUACAAGACAGGUUUA | 17 | 469 |
| HBB-84 | − | AGGUUUAAGGAGACCAA | 17 | 470 |
| HBB-85 | − | AAGGAGACCAAUAGAAA | 17 | 471 |
| HBB-86 | + | GCUAGUGAACACAGUUGUGU | 20 | 472 |
| HBB-87 | + | GUGUCUGUUUGAGGUUGCUA | 20 | 473 |
| HBB-88 | + | AGAUGCACCAUGGUGUCUGU | 20 | 474 |
| HBB-89 | + | GUAACGGCAGACUUCUCCUC | 20 | 475 |

TABLE 1D-continued

| gRNA Name | DNA Strand | Targeting Domain | Target Site Length | SEQ ID NO |
|---|---|---|---|---|
| HBB-90 | + | AGUAACGGCAGACUUCUCCU | 20 | 476 |
| HBB-91 | + | UCCACGUUCACCUUGCCCCA | 20 | 477 |
| HBB-92 | + | AACCUUGAUACCAACCUGCC | 20 | 478 |
| HBB-93 | + | AGUGAACACAGUUGUGU | 17 | 479 |
| HBB-94 | + | UCUGUUUGAGGUUGCUA | 17 | 480 |
| HBB-95 | + | UGCACCAUGGUGUCUGU | 17 | 481 |
| HBB-96 | + | ACGGCAGACUUCUCCUC | 17 | 482 |
| HBB-97 | + | AACGGCAGACUUCUCCU | 17 | 483 |
| HBB-98 | + | ACGUUCACCUUGCCCCA | 17 | 484 |
| HBB-99 | + | CUUGAUACCAACCUGCC | 17 | 485 |

Table 2A provides exemplary targeting domains for knocking out the BCL11A gene selected according to first tier parameters, and are selected based on close proximity to start of the coding sequence and orthogonality in the human genome. In an embodiment, the targeting domain is the exact complement of the target domain. Any of the targeting domains in the table can be used with a *S. pyogenes* Cas9 molecule that gives double stranded cleavage. Any of the targeting domains in the table can be used with a *S. pyogenes* Cas9 single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position. In an embodiment, two 20-mer guide RNAs are used to target two *S. pyogenes* Cas9 nucleases or two *S. pyogenes* Cas9 nickases, e.g., BCL11A-31 and BCL11A-40 BCL11A-30 and BCL11A-42, or BCL11A-24 and BCL11A-53 are used. In an embodiment, two 17-mer RNAs are used to target two Cas9 nucleases or two Cas9 nickases, e.g., BCL11A-79 and BCL11A-90, BCL11A-77 and BCL11A-92, or BCL11A-71 and BCL11A-103 are used.

TABLE 2A

1st Tier

| gRNA Name | DNA Strand | Targeting Domain | Target Site Length | SEQ ID NO |
|---|---|---|---|---|
| BCL11A-32 | − | UGGCAUCCAGGUCACGCCAG | 20 | 486 |
| BCL11A-40 | + | GAUGCUUUUUUCAUCUCGAU | 20 | 487 |
| BCL11A-30 | − | GCAUCCAAUCCCGUGGAGGU | 20 | 488 |
| BCL11A-42 | + | UUUUCAUCUCGAUUGGUGAA | 20 | 489 |
| BCL11A-24 | − | CCAGAUGAACUUCCCAUUGG | 20 | 490 |
| BCL11A-53 | + | AGGAGGUCAUGAUCCCCUUC | 20 | 491 |
| BCL11A-79 | − | CAUCCAGGUCACGCCAG | 17 | 492 |

TABLE 2A-continued

1st Tier

| gRNA Name | DNA Strand | Targeting Domain | Target Site Length | SEQ ID NO |
|---|---|---|---|---|
| BCL11A-90 | + | GCUUUUUCAUCUCGAU | 17 | 493 |
| BCL11A-77 | - | UCCAAUCCCGUGGAGGU | 17 | 494 |
| BCL11A-92 | + | UCAUCUCGAUUGGUGAA | 17 | 495 |
| BCL11A-71 | - | GAUGAACUUCCCAUUGG | 17 | 496 |
| BCL11A-103 | + | AGGUCAUGAUCCCCUUC | 17 | 497 |

Table 2B provides exemplary targeting domains for knocking out the BCL11A gene selected according to the second tier parameters and are selected based on close proximity to start of the coding sequence and presence of a 5' G. In an embodiment, the targeting domain is the exact complement of the target domain. Any of the targeting domains in the table can be used with a *S. pyogenes* Cas9 molecule that gives double stranded cleavage. Any of the targeting domains in the table can be used with a *S. pyogenes* Cas9 single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 2B

2nd Tier

| gRNA Name | DNA Strand | Targeting Domain | Target Site Length | SEQ ID NO |
|---|---|---|---|---|
| BCL11A-28 | - | GAAAAAAGCAUCCAAUCCCG | 20 | 498 |
| BCL11A-15 | - | GAACCAGACCACGGCCCGUU | 20 | 499 |
| BCL11A-37 | + | GACCUGGAUGCCAACCUCCA | 20 | 500 |
| BCL11A-120 | + | GAGCUCCAUGUGCAGAACGA | 20 | 501 |
| BCL11A-106 | + | GAGCUCCCAACGGGCCG | 17 | 502 |
| BCL11A-112 | - | GAGCUCUAAUCCCCACGCCU | 20 | 503 |
| BCL11A-113 | - | GAGUGCAGAAUAUGCCCCGC | 20 | 504 |
| BCL11A-35 | + | GAUAAACAAUCGUCAUCCUC | 20 | 505 |
| BCL11A-19 | - | GAUCAUGACCUCCUCACCUG | 20 | 506 |
| BCL11A-60 | - | GAUGAUGAACCAGACCA | 17 | 507 |
| BCL11A-39 | + | GAUGCCAACCUCCACGGGAU | 20 | 508 |
| BCL11A-133 | + | GCACUCAUCCCAGGCGU | 17 | 509 |
| BCL11A-130 | - | GCAGAAUAUGCCCCGCA | 17 | 510 |
| BCL11A-115 | + | GCAUAUUCUGCACUCAUCCC | 20 | 511 |
| BCL11A-89 | + | GCCAACCUCCACGGGAU | 17 | 512 |
| BCL11A-23 | - | GCCAGAUGAACUUCCCAUUG | 20 | 513 |

TABLE 2B-continued

2nd Tier

| gRNA Name | DNA Strand | Targeting Domain | Target Site Length | SEQ ID NO |
|---|---|---|---|---|
| BCL11A-17 | - | GCCCGUUGGGAGCUCCAGAA | 20 | 514 |
| BCL11A-83 | + | GCUAUGUGUUCCUGUUU | 17 | 515 |
| BCL11A-135 | + | GCUCCAUGUGCAGAACG | 17 | 516 |
| BCL11A-57 | + | GCUCCCAACGGGCCGUGGUC | 20 | 517 |
| BCL11A-127 | - | GCUCUAAUCCCCACGCC | 17 | 518 |
| BCL11A-6 | + | GCUGGGGUUUGCCUUGCUUG | 20 | 519 |
| BCL11A-111 | - | GGAGCUCUAAUCCCCACGCC | 20 | 520 |
| BCL11A-101 | + | GGCACUGCCCACAGGUG | 17 | 521 |
| BCL11A-52 | + | GGCACUGCCCACAGGUGAGG | 20 | 522 |
| BCL11A-16 | - | GGCCCGUUGGGAGCUCCAGA | 20 | 523 |
| BCL11A-12 | + | GGGGUUUGCCUUGCUUG | 17 | 524 |
| BCL11A-109 | + | GUAAGAAUGGCUUCAAG | 17 | 525 |
| BCL11A-123 | + | GUGCAGAACGAGGGGAGGAG | 20 | 526 |
| BCL11A-21 | - | GUGCCAGAUGAACUUCCCAU | 20 | 527 |
| BCL11A-50 | + | GUUCAUCUGGCACUGCCCAC | 20 | 528 |
| BCL11A-65 | - | GUUGGGAGCUCCAGAAG | 17 | 529 |

Table 2C provides exemplary targeting domains for knocking out the BCL11A gene selected according to the third tier parameters and are selected based on close proximity to start of the coding sequence. In an embodiment, the targeting domain is the exact complement of the target domain. Any of the targeting domains in the table can be used with a *S. pyogenes* Cas9 molecule that gives double stranded cleavage. Any of the targeting domains in the table can be used with a *S. pyogenes* Cas9 single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 2C

3rd Tier

| gRNA Name | DNA Strand | Targeting Domain | Target Site Length | SEQ ID NO |
|---|---|---|---|---|
| BCL11A-75 | - | AAAAGCAUCCAAUCCCG | 17 | 530 |
| BCL11A-29 | - | AAAAGCAUCCAAUCCCGUGG | 20 | 531 |
| BCL11A-47 | + | AAAAUAAGAAUGUCCCCCAA | 20 | 532 |
| BCL11A-85 | + | AAACAAUCGUCAUCCUC | 17 | 533 |
| BCL11A-73 | - | AAACGGAAACAAUGCAA | 17 | 534 |

TABLE 2C-continued

3rd Tier

| gRNA Name | DNA Strand | Targeting Domain | Target Site Length | SEQ ID NO |
|---|---|---|---|---|
| BCL11A-125 | − | AAACUUCUGCACUGGAG | 17 | 535 |
| BCL11A-48 | + | AAAUAAGAAUGUCCCCCAAU | 20 | 536 |
| BCL11A-1 | − | AACCCCAGCACUUAAGCAAA | 20 | 537 |
| BCL11A-13 | − | ACAGAUGAUGAACCAGACCA | 20 | 538 |
| BCL11A-61 | − | ACCAGACCACGGCCCGU | 17 | 539 |
| BCL11A-2 | − | ACCCCAGCACUUAAGCAAAC | 20 | 540 |
| BCL11A-38 | + | ACCUGGAUGCCAACCUCCAC | 20 | 541 |
| BCL11A-102 | + | ACUGCCCACAGGUGAGG | 17 | 542 |
| BCL11A-119 | + | AGAGCUCCAUGUGCAGAACG | 20 | 543 |
| BCL11A-70 | − | AGAUGAACUUCCCAUUG | 17 | 544 |
| BCL11A-76 | − | AGCAUCCAAUCCCGUGG | 17 | 545 |
| BCL11A-121 | + | AGCUCCAUGUGCAGAACGAG | 20 | 546 |
| BCL11A-81 | − | AGGAAUUUGCCCCAAAC | 17 | 547 |
| BCL11A-114 | − | AGUGCAGAAUAUGCCCCGCA | 20 | 548 |
| BCL11A-97 | + | AUAAGAAUGUCCCCCAA | 17 | 549 |
| BCL11A-20 | − | AUCAUGACCUCCUCACCUGU | 20 | 550 |
| BCL11A-44 | + | AUCUCGAUUGGUGAAGGGGA | 20 | 551 |
| BCL11A-67 | − | AUGACCUCCUCACCUGU | 17 | 552 |
| BCL11A-138 | + | AUGUGCAGAACGAGGGG | 17 | 553 |
| BCL11A-3 | + | AUUCCCGUUUGCUUAAGUGC | 20 | 554 |
| BCL11A-95 | + | AUUGGUGAAGGGGAAGG | 17 | 555 |
| BCL11A-26 | − | CACAAACGGAAACAAUGCAA | 20 | 556 |
| BCL11A-134 | + | CACUCAUCCCAGGCGUG | 17 | 557 |
| BCL11A-139 | + | CAGAACGAGGGGAGGAG | 17 | 558 |
| BCL11A-69 | − | CAGAUGAACUUCCCAUU | 17 | 559 |
| BCL11A-96 | + | CAGCUUUUCUAAGCAG | 17 | 560 |
| BCL11A-86 | + | CAUCCUCUGGCGUGACC | 17 | 561 |
| BCL11A-93 | + | CAUCUCGAUUGGUGAAG | 17 | 562 |
| BCL11A-100 | + | CAUCUGGCACUGCCCAC | 17 | 563 |
| BCL11A-66 | − | CAUGACCUCCUCACCUG | 17 | 564 |
| BCL11A-99 | + | CCAAUGGGAAGUUCAUC | 17 | 565 |
| BCL11A-46 | + | CCACAGCUUUUCUAAGCAG | 20 | 566 |
| BCL11A-62 | − | CCAGACCACGGCCCGUU | 17 | 567 |
| BCL11A-68 | − | CCAGAUGAACUUCCCAU | 17 | 568 |
| BCL11A-8 | − | CCAGCACUUAAGCAAAC | 17 | 569 |
| BCL11A-107 | + | CCCAACGGGCCGUGGUC | 17 | 570 |
| BCL11A-7 | − | CCCAGCACUUAAGCAAA | 17 | 571 |
| BCL11A-49 | + | CCCCCAAUGGGAAGUUCAUC | 20 | 572 |
| BCL11A-55 | + | CCCCUUCUGGAGCUCCCAAC | 20 | 573 |
| BCL11A-18 | − | CCCGUUGGGAGCUCCAGAAG | 20 | 574 |
| BCL11A-9 | + | CCCGUUUGCUUAAGUGC | 17 | 575 |
| BCL11A-63 | − | CCGUUGGGAGCUCCAGA | 17 | 576 |
| BCL11A-10 | + | CCGUUUGCUUAAGUGCU | 17 | 577 |
| BCL11A-27 | − | CCUCUGCUUAGAAAAGCUG | 20 | 578 |
| BCL11A-104 | + | CCUUCUGGAGCUCCCAA | 17 | 579 |
| BCL11A-36 | + | CGUCAUCCUCUGGCGUGACC | 20 | 580 |
| BCL11A-78 | − | CGUGGAGGUUGGCAUCC | 17 | 581 |
| BCL11A-64 | − | CGUUGGGAGCUCCAGAA | 17 | 582 |
| BCL11A-11 | + | CGUUUGCUUAAGUGCUG | 17 | 583 |
| BCL11A-84 | + | CUAUGUGUUCCUGUUUG | 17 | 584 |
| BCL11A-136 | + | CUCCAUGUGCAGAACGA | 17 | 585 |
| BCL11A-128 | − | CUCUAAUCCCCACGCCU | 17 | 586 |
| BCL11A-118 | + | CUGCACUCAUCCCAGGCGUG | 20 | 587 |
| BCL11A-74 | − | CUGCUUAGAAAAGCUG | 17 | 588 |
| BCL11A-56 | + | CUGGAGCUCCCAACGGGCCG | 20 | 589 |
| BCL11A-87 | + | CUGGAUGCCAACCUCCA | 17 | 590 |
| BCL11A-105 | + | CUUCUGGAGCUCCCAAC | 17 | 591 |
| BCL11A-124 | − | UAAACUUCUGCACUGGA | 17 | 592 |
| BCL11A-98 | + | UAAGAAUGUCCCCCAAU | 17 | 593 |
| BCL11A-34 | − | UAGAGGAAUUUGCCCCAAAC | 20 | 594 |
| BCL11A-131 | + | UAUUCUGCACUCAUCCC | 17 | 595 |
| BCL11A-137 | + | UCCAUGUGCAGAACGAG | 17 | 596 |
| BCL11A-122 | + | UCCAUGUGCAGAACGAGGGG | 20 | 597 |
| BCL11A-126 | − | UCCCCUCGUUCUGCACA | 17 | 598 |
| BCL11A-54 | + | UCCCCUUCUGGAGCUCCCAA | 20 | 599 |
| BCL11A-31 | − | UCCCGUGGAGGUUGGCAUCC | 20 | 600 |
| BCL11A-5 | + | UCCCGUUUGCUUAAGUGCUG | 20 | 601 |
| BCL11A-110 | − | UCCUCCCCUCGUUCUGCACA | 20 | 602 |
| BCL11A-94 | + | UCGAUUGGUGAAGGGGA | 17 | 603 |
| BCL11A-45 | + | UCGAUUGGUGAAGGGGAAGG | 20 | 604 |
| BCL11A-117 | + | UCUGCACUCAUCCCAGGCGU | 20 | 605 |
| BCL11A-51 | + | UCUGGCACUGCCCACAGGUG | 20 | 606 |
| BCL11A-59 | + | UCUGUAAGAAUGGCUUCAAG | 20 | 607 |
| BCL11A-14 | − | UGAACCAGACCACGGCCCGU | 20 | 608 |

TABLE 2C-continued

3rd Tier

| gRNA Name | DNA Strand | Targeting Domain | Target Site Length | SEQ ID NO |
|---|---|---|---|---|
| BCL11A-132 | + | UGCACUCAUCCCAGGCG | 17 | 609 |
| BCL11A-129 | - | UGCAGAAUAUGCCCCGC | 17 | 610 |
| BCL11A-22 | - | UGCCAGAUGAACUUCCCAUU | 20 | 611 |
| BCL11A-82 | + | UGCUAUGUGUUCCUGUU | 17 | 612 |
| BCL11A-88 | + | UGGAUGCCAACCUCCAC | 17 | 613 |
| BCL11A-58 | + | UGGUUCAUCAUCUGUAAGAA | 20 | 614 |
| BCL11A-33 | - | UGUUUAUCAACGUCAUCUAG | 20 | 615 |
| BCL11A-80 | - | UUAUCAACGUCAUCUAG | 17 | 616 |
| BCL11A-25 | - | UUAUUUUAUCGAGCACAAA | 20 | 617 |
| BCL11A-108 | + | UUCAUCAUCUGUAAGAA | 17 | 618 |
| BCL11A-91 | + | UUCAUCUCGAUUGGUGA | 17 | 619 |
| BCL11A-4 | + | UUCCCGUUUGCUUAAGUGCU | 20 | 620 |
| BCL11A-116 | + | UUCUGCACUCAUCCCAGGCG | 20 | 621 |
| BCL11A-43 | + | UUUCAUCUCGAUUGGUGAAG | 20 | 622 |
| BCL11A-72 | - | UUUUUAUCGAGCACAAA | 17 | 623 |
| BCL11A-41 | + | UUUUUCAUCUCGAUUGGUGA | 20 | 624 |

Table 2D provides exemplary targeting domains for knocking out the BCL11A gene selected according to the fourth tier parameters and are selected based on presence in the coding sequence. In an embodiment, the targeting domain is the exact complement of the target domain. Any of the targeting domains in the table can be used with a *S. pyogenes* Cas9 molecule that gives double stranded cleavage. Any of the targeting domains in the table can be used with a *S. pyogenes* Cas9 single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 2D

4th Tier

| gRNA Name | DNA Strand | Targeting domain | Target Site Length | SEQ ID NO |
|---|---|---|---|---|
| BCL11A-140 | - | AACAGCCAUUCACCAGUGCA | 20 | 625 |
| BCL11A-141 | - | CAACACGCACAGAACACUCA | 20 | 626 |
| BCL11A-142 | - | AUCUACUUAGAAAGCGAACA | 20 | 627 |
| BCL11A-143 | - | ACGGAAGUCCCCUGACCCCG | 20 | 628 |
| BCL11A-144 | - | CGGAAGUCCCCUGACCCCGC | 20 | 629 |
| BCL11A-145 | - | AGUCCCCUGACCCCGCGGGU | 20 | 630 |
| BCL11A-146 | - | CCGCGGGUUGGUAUCCCUUC | 20 | 631 |
| BCL11A-147 | - | GUUGGUAUCCCUUCAGGACU | 20 | 632 |
| BCL11A-148 | - | CCUUCCCAGCCACCUCUCCA | 20 | 633 |
| BCL11A-149 | - | CUUCCCAGCCACCUCUCCAU | 20 | 634 |
| BCL11A-150 | - | UUUAACCUGCUAAGAAUACC | 20 | 635 |
| BCL11A-151 | - | ACCAGGAUCAGUAUCGAGAG | 20 | 636 |
| BCL11A-152 | - | UCAGUAUCGAGAGAGGCUUC | 20 | 637 |
| BCL11A-153 | - | AUCGAGAGAGGCUUCCGGCC | 20 | 638 |
| BCL11A-154 | - | GAGGCUUCCGGCCUGGCAGA | 20 | 639 |
| BCL11A-155 | - | AGGCUUCCGGCCUGGCAGAA | 20 | 640 |
| BCL11A-156 | - | UCCACCACCGAGACAUCACU | 20 | 641 |
| BCL11A-157 | - | CCCCCACCGCAUAGAGCGCC | 20 | 642 |
| BCL11A-158 | - | CCCCACCGCAUAGAGCGCCU | 20 | 643 |
| BCL11A-159 | - | CCCACCGCAUAGAGCGCCUG | 20 | 644 |
| BCL11A-160 | - | CCACCGCAUAGAGCGCCUGG | 20 | 645 |
| BCL11A-161 | - | CCGCAUAGAGCGCCUGGGGG | 20 | 646 |
| BCL11A-162 | - | GCGCCUGGGGGCGGAAGAGA | 20 | 647 |
| BCL11A-163 | - | GGGGGCGGAAGAGAUGGCCC | 20 | 648 |
| BCL11A-164 | - | AUCACCCGAGUGCCUUUGAC | 20 | 649 |
| BCL11A-165 | - | UCACCCGAGUGCCUUUGACA | 20 | 650 |
| BCL11A-166 | - | GUGCCUUUGACAGGGUGCUG | 20 | 651 |
| BCL11A-167 | - | GGUGCUGCGGUUGAAUCCAA | 20 | 652 |
| BCL11A-168 | - | GCGGUUGAAUCCAAUGGCUA | 20 | 653 |
| BCL11A-169 | - | GGCUAUGGAGCCUCCCGCCA | 20 | 654 |
| BCL11A-170 | - | CUCCCGCCAUGGAUUUCUCU | 20 | 655 |
| BCL11A-171 | - | CUCUAGGAGACUUAGAGAGC | 20 | 656 |
| BCL11A-172 | - | AGGAGACUUAGAGAGCUGGC | 20 | 657 |
| BCL11A-173 | - | GGAGACUUAGAGAGCUGGCA | 20 | 658 |
| BCL11A-174 | - | UCUAGCCCACCGCUGUCCCC | 20 | 659 |
| BCL11A-175 | - | GCCCACCGCUGUCCCCAGGC | 20 | 660 |
| BCL11A-176 | - | GCCGGCCCAGCCCUAUGCAA | 20 | 661 |
| BCL11A-177 | - | UUACUGCAACCAUUCCAGCC | 20 | 662 |
| BCL11A-178 | - | AGGUAGCAAGCCGCCCUUCC | 20 | 663 |
| BCL11A-179 | - | CCCUCCUCCCUCCCAGCCCC | 20 | 664 |
| BCL11A-180 | - | UCCAAGUCAUGCGAGUUCUG | 20 | 665 |
| BCL11A-181 | - | GUUCAAAUUUCAGAGCAACC | 20 | 666 |

TABLE 2D-continued

4th Tier

| gRNA Name | DNA Strand | Targeting domain | Target Site Length | SEQ ID NO |
|---|---|---|---|---|
| BCL11A-182 | − | CAAAUUUCAGAGCAACCUGG | 20 | 667 |
| BCL11A-183 | − | AGAGCAACCUGGUGGUGCAC | 20 | 668 |
| BCL11A-184 | − | GGUGCACCGGCGCAGCCACA | 20 | 669 |
| BCL11A-185 | − | GUGCACCGGCGCAGCCACAC | 20 | 670 |
| BCL11A-186 | − | GUGCGACCACGCGUGCACCC | 20 | 671 |
| BCL11A-187 | − | GCACAAAUCGUCCCCCAUGA | 20 | 672 |
| BCL11A-188 | − | AUGACGGUCAAGUCCGACGA | 20 | 673 |
| BCL11A-189 | − | UCUCUCCACCGCCAGCUCCC | 20 | 674 |
| BCL11A-190 | − | ACCGCCAGCUCCCCGGAACC | 20 | 675 |
| BCL11A-191 | − | GGAACCCGGCACCAGCGACU | 20 | 676 |
| BCL11A-192 | − | ACCCGGCACCAGCGACUUGG | 20 | 677 |
| BCL11A-193 | − | CCCGGCACCAGCGACUUGGU | 20 | 678 |
| BCL11A-194 | − | CAGCAGCGCGCUCAAGUCCG | 20 | 679 |
| BCL11A-195 | − | CAGCGCGCUCAAGUCCGUGG | 20 | 680 |
| BCL11A-196 | − | GAACGACCCCAACCUGAUCC | 20 | 681 |
| BCL11A-197 | − | CCCAACCUGAUCCCGGAGAA | 20 | 682 |
| BCL11A-198 | − | CCAACCUGAUCCCGGAGAAC | 20 | 683 |
| BCL11A-199 | − | CAACCUGAUCCCGGAGAACG | 20 | 684 |
| BCL11A-200 | − | GAUCCCGGAGAACGGGACG | 20 | 685 |
| BCL11A-201 | − | CCCGGAGAACGGGACGAGG | 20 | 686 |
| BCL11A-202 | − | GAACGGGACGAGGAGGAAG | 20 | 687 |
| BCL11A-203 | − | CGGGGACGAGGAGGAAGAGG | 20 | 688 |
| BCL11A-204 | − | GGAGGAAGAGGAGGACGACG | 20 | 689 |
| BCL11A-205 | − | AGAGGAGGACGACGAGGAAG | 20 | 690 |
| BCL11A-206 | − | CGACGAGGAAGAGGAAGAAG | 20 | 691 |
| BCL11A-207 | − | CGAGGAAGAGGAAGAAGAGG | 20 | 692 |
| BCL11A-208 | − | AGAGGAAGAAGAGGAGGAAG | 20 | 693 |
| BCL11A-209 | − | GGAAGAAGAGGAGGAAGAGG | 20 | 694 |
| BCL11A-210 | − | AGAAGAGGAGGAAGAGGAGG | 20 | 695 |
| BCL11A-211 | − | AGAGGAGGAAGAGGAGGAGG | 20 | 696 |
| BCL11A-212 | + | UCCUCCUCGUCCCCGUUCUC | 20 | 697 |
| BCL11A-213 | + | CCUCCUCGUCCCCGUUCUCC | 20 | 698 |
| BCL11A-214 | + | CGUCCCCGUUCUCCGGGAUC | 20 | 699 |
| BCL11A-215 | + | CCCGUUCUCCGGGAUCAGGU | 20 | 700 |
| BCL11A-216 | + | CCGUUCUCCGGGAUCAGGUU | 20 | 701 |
| BCL11A-217 | + | CGUUCUCCGGGAUCAGGUUG | 20 | 702 |
| BCL11A-218 | + | GUCGUUCUCGCUCUUGAACU | 20 | 703 |
| BCL11A-219 | + | GCUCUUGAACUUGGCCACCA | 20 | 704 |
| BCL11A-220 | + | CACGGACUUGAGCGCGCUGC | 20 | 705 |
| BCL11A-221 | + | GGCGCUGCCCACCAAGUCGC | 20 | 706 |
| BCL11A-222 | + | GCCCACCAAGUCGCUGGUGC | 20 | 707 |
| BCL11A-223 | + | CCCACCAAGUCGCUGGUGCC | 20 | 708 |
| BCL11A-224 | + | AAGUCGCUGGUGCCGGGUUC | 20 | 709 |
| BCL11A-225 | + | AGUCGCUGGUGCCGGGUUCC | 20 | 710 |
| BCL11A-226 | + | GUCGCUGGUGCCGGGUUCCG | 20 | 711 |
| BCL11A-227 | + | GGUGCCGGGUUCCGGGGAGC | 20 | 712 |
| BCL11A-228 | + | GCCGGGUUCCGGGGAGCUGG | 20 | 713 |
| BCL11A-229 | + | GGGUUCCGGGGAGCUGGCGG | 20 | 714 |
| BCL11A-230 | + | GGCGGUGGAGAGACCGUCGU | 20 | 715 |
| BCL11A-231 | + | GUCGUCGGACUUGACCGUCA | 20 | 716 |
| BCL11A-232 | + | UCGUCGGACUUGACCGUCAU | 20 | 717 |
| BCL11A-233 | + | CGUCGGACUUGACCGUCAUG | 20 | 718 |
| BCL11A-234 | + | GUCGGACUUGACCGUCAUGG | 20 | 719 |
| BCL11A-235 | + | UGUGCAUGUGCGUCUUCAUG | 20 | 720 |
| BCL11A-236 | + | CAUGUGGCGCUUCAGCUUGC | 20 | 721 |
| BCL11A-237 | + | GGCGCUUCAGCUUGCUGGCC | 20 | 722 |
| BCL11A-238 | + | GCGCUUCAGCUUGCUGGCCU | 20 | 723 |
| BCL11A-239 | + | UGCUGGCCUGGGUGCACGCG | 20 | 724 |
| BCL11A-240 | + | GGGUGCACGCGUGGUCGCAC | 20 | 725 |
| BCL11A-241 | + | GUCGCACAGGUUGCACUUGU | 20 | 726 |
| BCL11A-242 | + | UCGCACAGGUUGCACUUGUA | 20 | 727 |
| BCL11A-243 | + | UGUAGGGCUUCUCGCCCGUG | 20 | 728 |
| BCL11A-244 | + | UCUCGCCCGUGUGGCUGCGC | 20 | 729 |
| BCL11A-245 | + | GGCUGCGCCGGUGCACCACC | 20 | 730 |
| BCL11A-246 | + | GCCGCAGAACUCGCAUGACU | 20 | 731 |
| BCL11A-247 | + | UCGCAUGACUUGGACUUGAC | 20 | 732 |
| BCL11A-248 | + | CGCAUGACUUGGACUUGACC | 20 | 733 |
| BCL11A-249 | + | GCAUGACUUGGACUUGACCG | 20 | 734 |
| BCL11A-250 | + | CAUGACUUGGACUUGACCGG | 20 | 735 |
| BCL11A-251 | + | ACUUGGACUUGACCGGGGGC | 20 | 736 |
| BCL11A-252 | + | CUUGGACUUGACCGGGGGCU | 20 | 737 |
| BCL11A-253 | + | GGACUUGACCGGGGGCUGGG | 20 | 738 |
| BCL11A-254 | + | GACUUGACCGGGGGCUGGGA | 20 | 739 |
| BCL11A-255 | + | UUGACCGGGGGCUGGGAGGG | 20 | 740 |

TABLE 2D-continued

4th Tier

| gRNA Name | DNA Strand | Targeting domain | Target Site Length | SEQ ID NO |
|---|---|---|---|---|
| BCL11A-256 | + | ACCGGGGCUGGGAGGGAGG | 20 | 741 |
| BCL11A-257 | + | CCGGGGGCUGGGAGGGAGGA | 20 | 742 |
| BCL11A-258 | + | CGGGGGCUGGGAGGGAGGAG | 20 | 743 |
| BCL11A-259 | + | GGGCUGGGAGGGAGGAGGGG | 20 | 744 |
| BCL11A-260 | + | GGAGGAGGGCGGAUUGCAG | 20 | 745 |
| BCL11A-261 | + | GGAGGGGCGGAUUGCAGAGG | 20 | 746 |
| BCL11A-262 | + | GAGGGGCGGAUUGCAGAGGA | 20 | 747 |
| BCL11A-263 | + | GGGCGGAUUGCAGAGGAGGG | 20 | 748 |
| BCL11A-264 | + | GGCGGAUUGCAGAGGAGGGA | 20 | 749 |
| BCL11A-265 | + | GCGGAUUGCAGAGGAGGGAG | 20 | 750 |
| BCL11A-266 | + | CGGAUUGCAGAGGAGGGAGG | 20 | 751 |
| BCL11A-267 | + | GGAUUGCAGAGGAGGGAGGG | 20 | 752 |
| BCL11A-268 | + | GAUUGCAGAGGAGGGAGGGG | 20 | 753 |
| BCL11A-269 | + | GAGGGAGGGGGGCGUCGCC | 20 | 754 |
| BCL11A-270 | + | GAGGGGGGGCGUCGCCAGGA | 20 | 755 |
| BCL11A-271 | + | AGGGGGGGCGUCGCCAGGAA | 20 | 756 |
| BCL11A-272 | + | GGGGGCGUCGCCAGGAAGGG | 20 | 757 |
| BCL11A-273 | + | AGGAAGGGCGGCUUGCUACC | 20 | 758 |
| BCL11A-274 | + | AGGGCGGCUUGCUACCUGGC | 20 | 759 |
| BCL11A-275 | + | GGCUUGCUACCUGGCUGGAA | 20 | 760 |
| BCL11A-276 | + | GGUUGCAGUAACCUUUGCAU | 20 | 761 |
| BCL11A-277 | + | GUUGCAGUAACCUUUGCAUA | 20 | 762 |
| BCL11A-278 | + | CAGUAACCUUUGCAUAGGGC | 20 | 763 |
| BCL11A-279 | + | AGUAACCUUUGCAUAGGGCU | 20 | 764 |
| BCL11A-280 | + | ACCUUUGCAUAGGGCUGGGC | 20 | 765 |
| BCL11A-281 | + | UGCAUAGGGCUGGGCCGGCC | 20 | 766 |
| BCL11A-282 | + | GCAUAGGGCUGGGCCGGCCU | 20 | 767 |
| BCL11A-283 | + | CAUAGGGCUGGGCCGGCCUG | 20 | 768 |
| BCL11A-284 | + | CUGGGCCGGCCUGGGGACAG | 20 | 769 |
| BCL11A-285 | + | GGCCGGCCUGGGGACAGCGG | 20 | 770 |
| BCL11A-286 | + | GCCGGCCUGGGGACAGCGGU | 20 | 771 |
| BCL11A-287 | + | AAGUCUCCAGAGAAAUCCA | 20 | 772 |
| BCL11A-288 | + | UCUCCAGAGAAAUCCAUGG | 20 | 773 |
| BCL11A-289 | + | CUCCAGAGAAAUCCAUGGC | 20 | 774 |
| BCL11A-290 | + | CUAGAGAAAUCCAUGGCGGG | 20 | 775 |
| BCL11A-291 | + | GCGGGAGGCUCCAUAGCCAU | 20 | 776 |
| BCL11A-292 | + | CAACCGCAGCACCCUGUCAA | 20 | 777 |
| BCL11A-293 | + | AGCACCCUGUCAAAGGCACU | 20 | 778 |
| BCL11A-294 | + | GCACCCUGUCAAAGGCACUC | 20 | 779 |
| BCL11A-295 | + | UGUCAAAGGCACUCGGGUGA | 20 | 780 |
| BCL11A-296 | + | GUCAAAGGCACUCGGGUGAU | 20 | 781 |
| BCL11A-297 | + | AAAGGCACUCGGGUGAUGGG | 20 | 782 |
| BCL11A-298 | + | CACUCGGGUGAUGGGUGGCC | 20 | 783 |
| BCL11A-299 | + | ACUCGGGUGAUGGGUGGCCA | 20 | 784 |
| BCL11A-300 | + | GGGCCAUCUCUUCCGCCCCC | 20 | 785 |
| BCL11A-301 | + | CCGCCCCCAGGCGCUCUAUG | 20 | 786 |
| BCL11A-302 | + | CCCCCAGGCGCUCUAUGCGG | 20 | 787 |
| BCL11A-303 | + | CCCCAGGCGCUCUAUGCGGU | 20 | 788 |
| BCL11A-304 | + | CCCAGGCGCUCUAUGCGGUG | 20 | 789 |
| BCL11A-305 | + | CCAGGCGCUCUAUGCGGUGG | 20 | 790 |
| BCL11A-306 | + | UGGGGGUCCAAGUGAUGUCU | 20 | 791 |
| BCL11A-307 | + | GGGUCCAAGUGAUGUCUCGG | 20 | 792 |
| BCL11A-308 | + | UCCAAGUGAUGUCUCGGUGG | 20 | 793 |
| BCL11A-309 | + | GUCUCGGUGGUGGACUAAAC | 20 | 794 |
| BCL11A-310 | + | UCUCGGUGGUGGACUAAACA | 20 | 795 |
| BCL11A-311 | + | CUCGGUGGUGGACUAAACAG | 20 | 796 |
| BCL11A-312 | + | UCGGUGGUGGACUAAACAGG | 20 | 797 |
| BCL11A-313 | + | CGGUGGUGGACUAAACAGGG | 20 | 798 |
| BCL11A-314 | + | GGUGGUGGACUAAACAGGGG | 20 | 799 |
| BCL11A-315 | + | UGGACUAAACAGGGGGGGAG | 20 | 800 |
| BCL11A-316 | + | GGACUAAACAGGGGGGGAGU | 20 | 801 |
| BCL11A-317 | + | CUAAACAGGGGGGAGUGGG | 20 | 802 |
| BCL11A-318 | + | GUGGAAAGCGCCCUUCUGCC | 20 | 803 |
| BCL11A-319 | + | AAAGCGCCCUUCUGCCAGGC | 20 | 804 |
| BCL11A-320 | + | GCCUCUCUCGAUACUGAUCC | 20 | 805 |
| BCL11A-321 | + | CUGAUCCUGGUAUUCUUAGC | 20 | 806 |
| BCL11A-322 | + | UGGUAUUCUUAGCAGGUUAA | 20 | 807 |
| BCL11A-323 | + | GGUAUUCUUAGCAGGUUAAA | 20 | 808 |
| BCL11A-324 | + | GUAUUCUUAGCAGGUUAAAG | 20 | 809 |
| BCL11A-325 | + | UGUCUGCAAUAUGAAUCCCA | 20 | 810 |
| BCL11A-326 | + | GCAAUAUGAAUCCCAUGGAG | 20 | 811 |
| BCL11A-327 | + | AUAUGAAUCCCAUGGAGAGG | 20 | 812 |
| BCL11A-328 | + | GAAUCCCAUGGAGAGGUGGC | 20 | 813 |
| BCL11A-329 | + | AAUCCCAUGGAGAGGUGGCU | 20 | 814 |

TABLE 2D-continued

4th Tier

| gRNA Name | DNA Strand | Targeting domain | Target Site Length | SEQ ID NO |
|---|---|---|---|---|
| BCL11A-330 | + | CCAUGGAGAGGUGGCUGGGA | 20 | 815 |
| BCL11A-331 | + | CAUUCUGCACCUAGUCCUGA | 20 | 816 |
| BCL11A-332 | + | AUUCUGCACCUAGUCCUGAA | 20 | 817 |
| BCL11A-333 | + | CCUGAAGGGAUACCAACCCG | 20 | 818 |
| BCL11A-334 | + | CUGAAGGGAUACCAACCCGC | 20 | 819 |
| BCL11A-335 | + | UGAAGGGAUACCAACCCGCG | 20 | 820 |
| BCL11A-336 | + | GGAUACCAACCCGCGGGGUC | 20 | 821 |
| BCL11A-337 | + | GAUACCAACCCGCGGGGUCA | 20 | 822 |
| BCL11A-338 | + | AUACCAACCCGCGGGGUCAG | 20 | 823 |
| BCL11A-339 | + | UUGCAAGAGAAACCAUGCAC | 20 | 824 |
| BCL11A-340 | + | AGAAACCAUGCACUGGUGAA | 20 | 825 |
| BCL11A-341 | + | AGUUGUACAUGUGUAGCUGC | 20 | 826 |
| BCL11A-342 | + | GUUGUACAUGUGUAGCUGCU | 20 | 827 |
| BCL11A-343 | − | AGCCAUUCACCAGUGCA | 17 | 828 |
| BCL11A-344 | − | CACGCACAGAACACUCA | 17 | 829 |
| BCL11A-345 | − | UACUUAGAAAGCGAACA | 17 | 830 |
| BCL11A-346 | − | GAAGUCCCUGACCCCG | 17 | 831 |
| BCL11A-347 | − | AAGUCCCUGACCCCGC | 17 | 832 |
| BCL11A-348 | − | CCCCUGACCCCGCGGGU | 17 | 833 |
| BCL11A-349 | − | CGGGUUGGUAUCCCUUC | 17 | 834 |
| BCL11A-350 | − | GGUAUCCCUUCAGGACU | 17 | 835 |
| BCL11A-351 | − | UCCCAGCCACCUCUCCA | 17 | 836 |
| BCL11A-352 | − | CCCAGCCACCUCUCCAU | 17 | 837 |
| BCL11A-353 | − | AACCUGCUAAGAAUACC | 17 | 838 |
| BCL11A-354 | − | AGGAUCAGUAUCGAGAG | 17 | 839 |
| BCL11A-355 | − | GUAUCGAGAGAGGCUUC | 17 | 840 |
| BCL11A-356 | − | GAGAGAGGCUUCCGGCC | 17 | 841 |
| BCL11A-357 | − | GCUUCCGGCCUGGCAGA | 17 | 842 |
| BCL11A-358 | − | CUUCCGGCCUGGCAGAA | 17 | 843 |
| BCL11A-359 | − | ACCACCGAGACAUCACU | 17 | 844 |
| BCL11A-360 | − | CCACCGCAUAGAGCGCC | 17 | 845 |
| BCL11A-361 | − | CACCGCAUAGAGCGCCU | 17 | 846 |
| BCL11A-362 | − | ACCGCAUAGAGCGCCUG | 17 | 847 |
| BCL11A-363 | − | CCGCAUAGAGCGCCUGG | 17 | 848 |
| BCL11A-364 | − | CAUAGAGCGCCUGGGGG | 17 | 849 |
| BCL11A-365 | − | CCUGGGGGCGGAAGAGA | 17 | 850 |
| BCL11A-366 | − | GGCGGAAGAGAUGGCCC | 17 | 851 |
| BCL11A-367 | − | ACCCGAGUGCCUUUGAC | 17 | 852 |
| BCL11A-368 | − | CCCGAGUGCCUUUGACA | 17 | 853 |
| BCL11A-369 | − | CCUUUGACAGGGUGCUG | 17 | 854 |
| BCL11A-370 | − | GCUGCGGUUGAAUCCAA | 17 | 855 |
| BCL11A-371 | − | GUUGAAUCCAAUGGCUA | 17 | 856 |
| BCL11A-372 | − | UAUGGAGCCUCCCGCCA | 17 | 857 |
| BCL11A-373 | − | CCGCCAUGGAUUUCUCU | 17 | 858 |
| BCL11A-374 | − | UAGGAGACUUAGAGAGC | 17 | 859 |
| BCL11A-375 | − | AGACUUAGAGAGCUGGC | 17 | 860 |
| BCL11A-376 | − | GACUUAGAGAGCUGGCA | 17 | 861 |
| BCL11A-377 | − | AGCCCACCGCUGUCCCC | 17 | 862 |
| BCL11A-378 | − | CACCGCUGUCCCCAGGC | 17 | 863 |
| BCL11A-379 | − | GGCCCAGCCCUAUGCAA | 17 | 864 |
| BCL11A-380 | − | CUGCAACCAUUCCAGCC | 17 | 865 |
| BCL11A-381 | − | UAGCAAGCCGCCCUUCC | 17 | 866 |
| BCL11A-382 | − | UCCUCCCUCCCAGCCCC | 17 | 867 |
| BCL11A-383 | − | AAGUCAUGCGAGUUCUG | 17 | 868 |
| BCL11A-384 | − | CAAAUUUCAGAGCAACC | 17 | 869 |
| BCL11A-385 | − | AUUUCAGAGCAACCUGG | 17 | 870 |
| BCL11A-386 | − | GCAACCUGGUGGUGCAC | 17 | 871 |
| BCL11A-387 | − | GCACCGGCGCAGCCACA | 17 | 872 |
| BCL11A-388 | − | CACCGGCGCAGCCACAC | 17 | 873 |
| BCL11A-389 | − | CGACCACGCGUGCACCC | 17 | 874 |
| BCL11A-390 | − | CAAAUCGUCCCCAUGA | 17 | 875 |
| BCL11A-391 | − | ACGGUCAAGUCCGACGA | 17 | 876 |
| BCL11A-392 | − | CUCCACCGCCAGCUCCC | 17 | 877 |
| BCL11A-393 | − | GCCAGCUCCCCGGAACC | 17 | 878 |
| BCL11A-394 | − | ACCCGGCACCAGCGACU | 17 | 879 |
| BCL11A-395 | − | CGGCACCAGCGACUUGG | 17 | 880 |
| BCL11A-396 | − | GGCACCAGCGACUUGGU | 17 | 881 |
| BCL11A-397 | − | CAGCGCGCUCAAGUCCG | 17 | 882 |
| BCL11A-398 | − | CGCGCUCAAGUCCGUGG | 17 | 883 |
| BCL11A-399 | − | CGACCCCAACCUGAUCC | 17 | 884 |
| BCL11A-400 | − | AACCUGAUCCCGGAGAA | 17 | 885 |
| BCL11A-401 | − | ACCUGAUCCCGGAGAAC | 17 | 886 |
| BCL11A-402 | − | CCUGAUCCCGGAGAACG | 17 | 887 |
| BCL11A-403 | − | CCCGGAGAACGGGGACG | 17 | 888 |

TABLE 2D-continued

4th Tier

| gRNA Name | DNA Strand | Targeting domain | Target Site Length | SEQ ID NO |
|---|---|---|---|---|
| BCL11A-404 | - | GGAGAACGGGGACGAGG | 17 | 889 |
| BCL11A-405 | - | CGGGGACGAGGAGGAAG | 17 | 890 |
| BCL11A-406 | - | GGACGAGGAGGAAGAGG | 17 | 891 |
| BCL11A-407 | - | GGAAGAGGAGGACGACG | 17 | 892 |
| BCL11A-408 | - | GGAGGACGACGAGGAAG | 17 | 893 |
| BCL11A-409 | - | CGAGGAAGAGGAAGAAG | 17 | 894 |
| BCL11A-410 | - | GGAAGAGGAAGAAGAGG | 17 | 895 |
| BCL11A-411 | - | GGAAGAAGAGGAGGAAG | 17 | 896 |
| BCL11A-412 | - | AGAAGAGGAGGAAGAGG | 17 | 897 |
| BCL11A-413 | - | AGAGGAGGAAGAGGAGG | 17 | 898 |
| BCL11A-414 | - | GGAGGAAGAGGAGGAGG | 17 | 899 |
| BCL11A-415 | + | UCCUCGUCCCCGUUCUC | 17 | 900 |
| BCL11A-416 | + | CCUCGUCCCCGUUCUCC | 17 | 901 |
| BCL11A-417 | + | CCCCGUUCUCCGGGAUC | 17 | 902 |
| BCL11A-418 | + | GUUCUCCGGGAUCAGGU | 17 | 903 |
| BCL11A-419 | + | UUCUCCGGGAUCAGGUU | 17 | 904 |
| BCL11A-420 | + | UCUCCGGGAUCAGGUUG | 17 | 905 |
| BCL11A-421 | + | GUUCUCGCUCUUGAACU | 17 | 906 |
| BCL11A-422 | + | CUUGAACUUGGCCACCA | 17 | 907 |
| BCL11A-423 | + | GGACUUGAGCGCGCUGC | 17 | 908 |
| BCL11A-424 | + | GCUGCCCACCAAGUCGC | 17 | 909 |
| BCL11A-425 | + | CACCAAGUCGCUGGUGC | 17 | 910 |
| BCL11A-426 | + | ACCAAGUCGCUGGUGCC | 17 | 911 |
| BCL11A-427 | + | UCGCUGGUGCCGGGUUC | 17 | 912 |
| BCL11A-428 | + | CGCUGGUGCCGGGUUCC | 17 | 913 |
| BCL11A-429 | + | GCUGGUGCCGGGUUCCG | 17 | 914 |
| BCL11A-430 | + | GCCGGGUUCCGGGGAGC | 17 | 915 |
| BCL11A-431 | + | GGGUUCCGGGGAGCUGG | 17 | 916 |
| BCL11A-432 | + | UUCCGGGGAGCUGGCGG | 17 | 917 |
| BCL11A-433 | + | GGUGGAGAGACCGUCGU | 17 | 918 |
| BCL11A-434 | + | GUCGGACUUGACCGUCA | 17 | 919 |
| BCL11A-435 | + | UCGGACUUGACCGUCAU | 17 | 920 |
| BCL11A-436 | + | CGGACUUGACCGUCAUG | 17 | 921 |
| BCL11A-437 | + | GGACUUGACCGUCAUGG | 17 | 922 |
| BCL11A-438 | + | GCAUGUGCGUCUUCAUG | 17 | 923 |
| BCL11A-439 | + | GUGGCGCUUCAGCUUGC | 17 | 924 |
| BCL11A-440 | + | GCUUCAGCUUGCUGGCC | 17 | 925 |
| BCL11A-441 | + | CUUCAGCUUGCUGGCCU | 17 | 926 |
| BCL11A-442 | + | UGGCCUGGGUGCACGCG | 17 | 927 |
| BCL11A-443 | + | UGCACGCGUGGUCGCAC | 17 | 928 |
| BCL11A-444 | + | GCACAGGUUGCACUUGU | 17 | 929 |
| BCL11A-445 | + | CACAGGUUGCACUUGUA | 17 | 930 |
| BCL11A-446 | + | AGGGCUUCUCGCCCGUG | 17 | 931 |
| BCL11A-447 | + | CGCCCGUGUGGCUGCGC | 17 | 932 |
| BCL11A-448 | + | UGCGCCGGUGCACCACC | 17 | 933 |
| BCL11A-449 | + | GCAGAACUCGCAUGACU | 17 | 934 |
| BCL11A-450 | + | CAUGACUUGGACUUGAC | 17 | 935 |
| BCL11A-451 | + | AUGACUUGGACUUGACC | 17 | 936 |
| BCL11A-452 | + | UGACUUGGACUUGACCG | 17 | 937 |
| BCL11A-453 | + | GACUUGGACUUGACCGG | 17 | 938 |
| BCL11A-454 | + | UGGACUUGACCGGGGGC | 17 | 939 |
| BCL11A-455 | + | GGACUUGACCGGGGGCU | 17 | 940 |
| BCL11A-456 | + | CUUGACCGGGGCUGGG | 17 | 941 |
| BCL11A-457 | + | UUGACCGGGGCUGGGA | 17 | 942 |
| BCL11A-458 | + | ACCGGGGCUGGGAGGG | 17 | 943 |
| BCL11A-459 | + | GGGGGCUGGGAGGGAGG | 17 | 944 |
| BCL11A-460 | + | GGGGCUGGGAGGGAGGA | 17 | 945 |
| BCL11A-461 | + | GGGCUGGGAGGGAGGAG | 17 | 946 |
| BCL11A-462 | + | CUGGGAGGGAGGAGGGG | 17 | 947 |
| BCL11A-463 | + | GGAGGGGCGGAUUGCAG | 17 | 948 |
| BCL11A-464 | + | GGGGCGGAUUGCAGAGG | 17 | 949 |
| BCL11A-465 | + | GGGCGGAUUGCAGAGGA | 17 | 950 |
| BCL11A-466 | + | CGGAUUGCAGAGGAGGG | 17 | 951 |
| BCL11A-467 | + | GGAUUGCAGAGGAGGGA | 17 | 952 |
| BCL11A-468 | + | GAUUGCAGAGGAGGGAG | 17 | 953 |
| BCL11A-469 | + | AUUGCAGAGGAGGGAGG | 17 | 954 |
| BCL11A-470 | + | UUGCAGAGGAGGGAGGG | 17 | 955 |
| BCL11A-471 | + | UGCAGAGGAGGGAGGGG | 17 | 956 |
| BCL11A-472 | + | GGAGGGGGGCGUCGCC | 17 | 957 |
| BCL11A-473 | + | GGGGGCGUCGCCAGGA | 17 | 958 |
| BCL11A-474 | + | GGGGGCGUCGCCAGGAA | 17 | 959 |
| BCL11A-475 | + | GGCGUCGCCAGGAAGGG | 17 | 960 |
| BCL11A-476 | + | AAGGGCGGCUUGCUACC | 17 | 961 |
| BCL11A-477 | + | GCGGCUUGCUACCUGGC | 17 | 962 |

TABLE 2D-continued

4th Tier

| gRNA Name | DNA Strand | Targeting domain | Target Site Length | SEQ ID NO |
|---|---|---|---|---|
| BCL11A-478 | + | UUGCUACCUGGCUGGAA | 17 | 963 |
| BCL11A-479 | + | UGCAGUAACCUUUGCAU | 17 | 964 |
| BCL11A-480 | + | GCAGUAACCUUUGCAUA | 17 | 965 |
| BCL11A-481 | + | UAACCUUUGCAUAGGGC | 17 | 966 |
| BCL11A-482 | + | AACCUUUGCAUAGGGCU | 17 | 967 |
| BCL11A-483 | + | UUUGCAUAGGGCUGGGC | 17 | 968 |
| BCL11A-484 | + | AUAGGGCUGGGCCGGCC | 17 | 969 |
| BCL11A-485 | + | UAGGGCUGGGCCGGCCU | 17 | 970 |
| BCL11A-486 | + | AGGGCUGGGCCGGCCUG | 17 | 971 |
| BCL11A-487 | + | GGCCGGCCUGGGGACAG | 17 | 972 |
| BCL11A-488 | + | CGGCCUGGGGACAGCGG | 17 | 973 |
| BCL11A-489 | + | GGCCUGGGGACAGCGGU | 17 | 974 |
| BCL11A-490 | + | UCUCCUAGAGAAAUCCA | 17 | 975 |
| BCL11A-491 | + | CCUAGAGAAAUCCAUGG | 17 | 976 |
| BCL11A-492 | + | CUAGAGAAAUCCAUGGC | 17 | 977 |
| BCL11A-493 | + | GAGAAAUCCAUGGCGGG | 17 | 978 |
| BCL11A-494 | + | GGAGGCUCCAUAGCCAU | 17 | 979 |
| BCL11A-495 | + | CCGCAGCACCCUGUCAA | 17 | 980 |
| BCL11A-496 | + | ACCCUGUCAAAGGCACU | 17 | 981 |
| BCL11A-497 | + | CCCUGUCAAAGGCACUC | 17 | 982 |
| BCL11A-498 | + | CAAAGGCACUCGGGUGA | 17 | 983 |
| BCL11A-499 | + | AAAGGCACUCGGGUGAU | 17 | 984 |
| BCL11A-500 | + | GGCACUCGGGUGAUGGG | 17 | 985 |
| BCL11A-501 | + | UCGGGUGAUGGGUGGCC | 17 | 986 |
| BCL11A-502 | + | CGGGUGAUGGGUGGCCA | 17 | 987 |
| BCL11A-503 | + | CCAUCUCUUCCGCCCCC | 17 | 988 |
| BCL11A-504 | + | CCCCCAGGCGCUCUAUG | 17 | 989 |
| BCL11A-505 | + | CCAGGCGCUCUAUGCGG | 17 | 990 |
| BCL11A-506 | + | CAGGCGCUCUAUGCGGU | 17 | 991 |
| BCL11A-507 | + | AGGCGCUCUAUGCGGUG | 17 | 992 |
| BCL11A-508 | + | GGCGCUCUAUGCGGUGG | 17 | 993 |
| BCL11A-509 | + | GGGUCCAAGUGAUGUCU | 17 | 994 |
| BCL11A-510 | + | UCCAAGUGAUGUCUCGG | 17 | 995 |
| BCL11A-511 | + | AAGUGAUGUCUCGGUGG | 17 | 996 |
| BCL11A-512 | + | UCGGUGGUGGACUAAAC | 17 | 997 |
| BCL11A-513 | + | CGGUGGUGGACUAAACA | 17 | 998 |
| BCL11A-514 | + | GGUGGUGGACUAAACAG | 17 | 999 |
| BCL11A-515 | + | GUGGUGGACUAAACAGG | 17 | 1000 |
| BCL11A-516 | + | UGGUGGACUAAACAGGG | 17 | 1001 |
| BCL11A-517 | + | GGUGGACUAAACAGGGG | 17 | 1002 |
| BCL11A-518 | + | ACUAAACAGGGGGGGAG | 17 | 1003 |
| BCL11A-519 | + | CUAAACAGGGGGGGAGU | 17 | 1004 |
| BCL11A-520 | + | AACAGGGGGGGAGUGGG | 17 | 1005 |
| BCL11A-521 | + | GAAAGCGCCCUUCUGCC | 17 | 1006 |
| BCL11A-522 | + | GCGCCCUUCUGCCAGGC | 17 | 1007 |
| BCL11A-523 | + | UCUCUCGAUACUGAUCC | 17 | 1008 |
| BCL11A-524 | + | AUCCUGGUAUUCUUAGC | 17 | 1009 |
| BCL11A-525 | + | UAUUCUUAGCAGGUUAA | 17 | 1010 |
| BCL11A-526 | + | AUUCUUAGCAGGUUAAA | 17 | 1011 |
| BCL11A-527 | + | UUCUUAGCAGGUUAAAG | 17 | 1012 |
| BCL11A-528 | + | CUGCAAUAUGAAUCCCA | 17 | 1013 |
| BCL11A-529 | + | AUAUGAAUCCCAUGGAG | 17 | 1014 |
| BCL11A-530 | + | UGAAUCCCAUGGAGAGG | 17 | 1015 |
| BCL11A-531 | + | UCCCAUGGAGAGGUGGC | 17 | 1016 |
| BCL11A-532 | + | CCCAUGGAGAGGUGGCU | 17 | 1017 |
| BCL11A-533 | + | UGGAGAGGUGGCUGGGA | 17 | 1018 |
| BCL11A-534 | + | UCUGCACCUAGUCCUGA | 17 | 1019 |
| BCL11A-535 | + | CUGCACCUAGUCCUGAA | 17 | 1020 |
| BCL11A-536 | + | GAAGGGAUACCAACCCG | 17 | 1021 |
| BCL11A-537 | + | AAGGGAUACCAACCCGC | 17 | 1022 |
| BCL11A-538 | + | AGGGAUACCAACCCGCG | 17 | 1023 |
| BCL11A-539 | + | UACCAACCCGCGGGGUC | 17 | 1024 |
| BCL11A-540 | + | ACCAACCCGCGGGGUCA | 17 | 1025 |
| BCL11A-541 | + | CCAACCCGCGGGGUCAG | 17 | 1026 |
| BCL11A-542 | + | CAAGAGAAACCAUGCAC | 17 | 1027 |
| BCL11A-543 | + | AACCAUGCACUGGUGAA | 17 | 1028 |
| BCL11A-544 | + | UGUACAUGUGUAGCUGC | 17 | 1029 |
| BCL11A-545 | + | GUACAUGUGUAGCUGCU | 17 | 1030 |
| BCL11A-546 | − | AGAGGAGGAGGAGGAGCUGA | 20 | 1031 |
| BCL11A-547 | − | AGGAGCUGACGGAGAGCGAG | 20 | 1032 |
| BCL11A-548 | − | GGAGCUGACGGAGAGCGAGA | 20 | 1033 |
| BCL11A-549 | − | GCUGACGGAGAGCGAGGGG | 20 | 1034 |
| BCL11A-550 | − | GAGAGCGAGGGUGGACUA | 20 | 1035 |
| BCL11A-551 | − | GAGAGGGUGGACUACGGCUU | 20 | 1036 |

TABLE 2D-continued

4th Tier

| gRNA Name | DNA Strand | Targeting domain | Target Site Length | SEQ ID NO |
|---|---|---|---|---|
| BCL11A-552 | − | AGAGGGUGGACUACGGCUUC | 20 | 1037 |
| BCL11A-553 | − | CUACGGCUUCGGGCUGAGCC | 20 | 1038 |
| BCL11A-554 | − | CGGCUUCGGGCUGAGCCUGG | 20 | 1039 |
| BCL11A-555 | − | CUUCGGGCUGAGCCUGGAGG | 20 | 1040 |
| BCL11A-556 | − | GCCACCACGAGAACAGCUCG | 20 | 1041 |
| BCL11A-557 | − | CCACCACGAGAACAGCUCGC | 20 | 1042 |
| BCL11A-558 | − | CACCACGAGAACAGCUCGCG | 20 | 1043 |
| BCL11A-559 | − | CGAGAACAGCUCGCGGGGCG | 20 | 1044 |
| BCL11A-560 | − | CAGCUCGCGGGGCGCGGUCG | 20 | 1045 |
| BCL11A-561 | − | AGCUCGCGGGGCGCGGUCGU | 20 | 1046 |
| BCL11A-562 | − | GCGGGGCGCGGUCGUGGGCG | 20 | 1047 |
| BCL11A-563 | − | CGGGGCGCGGUCGUGGGCGU | 20 | 1048 |
| BCL11A-564 | − | CGCCCUGCCCGACGUCAUGC | 20 | 1049 |
| BCL11A-565 | − | GCCCUGCCCGACGUCAUGCA | 20 | 1050 |
| BCL11A-566 | − | GCCCGACGUCAUGCAGGGCA | 20 | 1051 |
| BCL11A-567 | − | CUCCAUGCAGCACUUCAGCG | 20 | 1052 |
| BCL11A-568 | − | CUUCAGCGAGGCCUUCCACC | 20 | 1053 |
| BCL11A-569 | − | CGAGGCCUUCCACCAGGUCC | 20 | 1054 |
| BCL11A-570 | − | GAGGCCUUCCACCAGGUCCU | 20 | 1055 |
| BCL11A-571 | − | CUGGGCGAGAAGCAUAAGCG | 20 | 1056 |
| BCL11A-572 | − | GAAGCAUAAGCGCGGCCACC | 20 | 1057 |
| BCL11A-573 | − | UAAGCGCGGCCACCUGGCCG | 20 | 1058 |
| BCL11A-574 | − | CGGCCACCUGGCCGAGGCCG | 20 | 1059 |
| BCL11A-575 | − | GGCCACCUGGCCGAGGCCGA | 20 | 1060 |
| BCL11A-576 | − | UGGCCGAGGCCGAGGGCCAC | 20 | 1061 |
| BCL11A-577 | − | GGCCGAGGCCGAGGGCCACA | 20 | 1062 |
| BCL11A-578 | − | GGACACUUGCGACGAAGACU | 20 | 1063 |
| BCL11A-579 | − | CACUUGCGACGAAGACUCGG | 20 | 1064 |
| BCL11A-580 | − | UGCGACGAAGACUCGGUGGC | 20 | 1065 |
| BCL11A-581 | − | AGACUCGGUGGCCGGCGAGU | 20 | 1066 |
| BCL11A-582 | − | GAGUCGGACCGCAUAGACGA | 20 | 1067 |
| BCL11A-583 | − | AUAGACGAUGGCACUGUUAA | 20 | 1068 |
| BCL11A-584 | − | GAUGGCACUGUUAAUGGCCG | 20 | 1069 |
| BCL11A-585 | − | UAAUGGCCGCGGCUGCUCCC | 20 | 1070 |
| BCL11A-586 | − | AAUGGCCGCGGCUGCUCCCC | 20 | 1071 |
| BCL11A-587 | − | CGGCUGCUCCCCGGGCGAGU | 20 | 1072 |
| BCL11A-588 | − | CUCCCCGGGCGAGUCGGCCU | 20 | 1073 |
| BCL11A-589 | − | UCCCCGGGCGAGUCGGCCUC | 20 | 1074 |
| BCL11A-590 | − | CCCCGGGCGAGUCGGCCUCG | 20 | 1075 |
| BCL11A-591 | − | CCCGGGCGAGUCGGCCUCGG | 20 | 1076 |
| BCL11A-592 | − | CCGGGCGAGUCGGCCUCGGG | 20 | 1077 |
| BCL11A-593 | − | CCUGUCCAAAAGCUGCUGC | 20 | 1078 |
| BCL11A-594 | − | CUGUCCAAAAGCUGCUGCU | 20 | 1079 |
| BCL11A-595 | − | UAAGCGCAUCAAGCUCGAGA | 20 | 1080 |
| BCL11A-596 | − | GAAGGAGUUCGACCUGCCCC | 20 | 1081 |
| BCL11A-597 | − | CCCGGCCGCGAUGCCCAACA | 20 | 1082 |
| BCL11A-598 | − | CGGAGAACGUGUACUCGCAG | 20 | 1083 |
| BCL11A-599 | − | GUGUACUCGCAGUGGCUCGC | 20 | 1084 |
| BCL11A-600 | − | GCAGUGGCUCGCCGGCUACG | 20 | 1085 |
| BCL11A-601 | − | UCGCCGGCUACGCGGCCUCC | 20 | 1086 |
| BCL11A-602 | − | AAAGAUCCCUUCCUUAGCUU | 20 | 1087 |
| BCL11A-603 | − | AUCGCCUUUUGCCUCCUCGU | 20 | 1088 |
| BCL11A-604 | − | CUCCUCGUCGGAGCACUCCU | 20 | 1089 |
| BCL11A-605 | − | UCGGAGCACUCCUCGGAGAA | 20 | 1090 |
| BCL11A-606 | − | CGGAGCACUCCUCGGAGAAC | 20 | 1091 |
| BCL11A-607 | − | UUGCGCUUCUCCACACCGCC | 20 | 1092 |
| BCL11A-608 | − | UGCGCUUCUCCACACCGCCC | 20 | 1093 |
| BCL11A-609 | − | GCGCUUCUCCACACCGCCCG | 20 | 1094 |
| BCL11A-610 | − | CUCCACACCGCCCGGGGAGC | 20 | 1095 |
| BCL11A-611 | − | ACACCGCCCGGGGAGCUGGA | 20 | 1096 |
| BCL11A-612 | − | CCGCCCGGGGAGCUGGACGG | 20 | 1097 |
| BCL11A-613 | − | CGCCCGGGGAGCUGGACGGA | 20 | 1098 |
| BCL11A-614 | − | GGAGCUGGACGGAGGGAUCU | 20 | 1099 |
| BCL11A-615 | − | GAGCUGGACGGAGGGAUCUC | 20 | 1100 |
| BCL11A-616 | − | AGCUGGACGGAGGGAUCUCG | 20 | 1101 |
| BCL11A-617 | − | GGAGGGAUCUCGGGGCGCAG | 20 | 1102 |
| BCL11A-618 | − | GAUCUCGGGGCGCAGCGGCA | 20 | 1103 |
| BCL11A-619 | − | AUCUCGGGGCGCAGCGGCAC | 20 | 1104 |
| BCL11A-620 | − | GGGCGCAGCGGCACGGGAAG | 20 | 1105 |
| BCL11A-621 | − | CGCAGCGGCACGGGAAGUGG | 20 | 1106 |
| BCL11A-622 | − | GCAGCGGCACGGGAAGUGGA | 20 | 1107 |
| BCL11A-623 | − | GGGAGCACGCCCCAUAUUAG | 20 | 1108 |
| BCL11A-624 | − | CACGCCCCAUAUUAGUGGUC | 20 | 1109 |
| BCL11A-625 | − | ACGCCCCAUAUUAGUGGUCC | 20 | 1110 |

TABLE 2D-continued

4th Tier

| gRNA Name | DNA Strand | Targeting domain | Target Site Length | SEQ ID NO |
|---|---|---|---|---|
| BCL11A-626 | - | CCAUAUUAGUGGUCCGGGCC | 20 | 1111 |
| BCL11A-627 | - | CAUAUUAGUGGUCCGGGCCC | 20 | 1112 |
| BCL11A-628 | - | UUAGUGGUCCGGGCCCGGGC | 20 | 1113 |
| BCL11A-629 | - | GGGCAGGCCCAGCUCAAAAG | 20 | 1114 |
| BCL11A-630 | - | GGCAGGCCCAGCUCAAAAGA | 20 | 1115 |
| BCL11A-631 | + | GCGUCUGCCCUCUUUUGAGC | 20 | 1116 |
| BCL11A-632 | + | CGUCUGCCCUCUUUUGAGCU | 20 | 1117 |
| BCL11A-633 | + | UCUUUUGAGCUGGGCCUGCC | 20 | 1118 |
| BCL11A-634 | + | CUUUUGAGCUGGGCCUGCCC | 20 | 1119 |
| BCL11A-635 | + | GAGCUGGGCCUGCCCGGGCC | 20 | 1120 |
| BCL11A-636 | + | CCGGGCCCGGACCACUAAUA | 20 | 1121 |
| BCL11A-637 | + | CGGGCCCGGACCACUAAUAU | 20 | 1122 |
| BCL11A-638 | + | GGGCCCGGACCACUAAUAUG | 20 | 1123 |
| BCL11A-639 | + | GAUCCCUCCGUCCAGCUCCC | 20 | 1124 |
| BCL11A-640 | + | AUCCCUCCGUCCAGCUCCCC | 20 | 1125 |
| BCL11A-641 | + | CCUCCGUCCAGCUCCCCGGG | 20 | 1126 |
| BCL11A-642 | + | GUCCAGCUCCCCGGGCGGUG | 20 | 1127 |
| BCL11A-643 | + | GCGCAAACUCCCGUUCUCCG | 20 | 1128 |
| BCL11A-644 | + | CUCCGAGGAGUGCUCCGACG | 20 | 1129 |
| BCL11A-645 | + | CGAGGAGUGCUCCGACGAGG | 20 | 1130 |
| BCL11A-646 | + | UGCUCCGACGAGGAGGCAAA | 20 | 1131 |
| BCL11A-647 | + | GGAGGCAAAAGGCGAUUGUC | 20 | 1132 |
| BCL11A-648 | + | GUCUGGAGUCUCCGAAGCUA | 20 | 1133 |
| BCL11A-649 | + | GGAGUCUCCGAAGCUAAGGA | 20 | 1134 |
| BCL11A-650 | + | GAGUCUCCGAAGCUAAGGAA | 20 | 1135 |
| BCL11A-651 | + | GAAGGGAUCUUUGAGCUGCC | 20 | 1136 |
| BCL11A-652 | + | GGGAUCUUUGAGCUGCCUGG | 20 | 1137 |
| BCL11A-653 | + | CUGCCUGGAGGCCGCGUAGC | 20 | 1138 |
| BCL11A-654 | + | CGAGUACACGUUCUCCGUGU | 20 | 1139 |
| BCL11A-655 | + | GAGUACACGUUCUCCGUGUU | 20 | 1140 |
| BCL11A-656 | + | GUUCUCCGUGUUGGGCAUCG | 20 | 1141 |
| BCL11A-657 | + | UCCGUGUUGGGCAUCGCGGC | 20 | 1142 |
| BCL11A-658 | + | CCGUGUUGGGCAUCGCGGCC | 20 | 1143 |
| BCL11A-659 | + | CGUGUUGGGCAUCGCGGCCG | 20 | 1144 |
| BCL11A-660 | + | GUGUUGGGCAUCGCGGCCGG | 20 | 1145 |
| BCL11A-661 | + | UGGGCAUCGCGGCCGGGGGC | 20 | 1146 |
| BCL11A-662 | + | GAGCUUGAUGCGCUUAGAGA | 20 | 1147 |
| BCL11A-663 | + | AGCUUGAUGCGCUUAGAGAA | 20 | 1148 |
| BCL11A-664 | + | GCUUGAUGCGCUUAGAGAAG | 20 | 1149 |
| BCL11A-665 | + | AGAGAAGGGGCUCAGCGAGC | 20 | 1150 |
| BCL11A-666 | + | GAGAAGGGGCUCAGCGAGCU | 20 | 1151 |
| BCL11A-667 | + | AGAAGGGGCUCAGCGAGCUG | 20 | 1152 |
| BCL11A-668 | + | GCUGCCCAGCAGCAGCUUUU | 20 | 1153 |
| BCL11A-669 | + | CCAGCAGCAGCUUUUUGGAC | 20 | 1154 |
| BCL11A-670 | + | CUUUUUGGACAGGCCCCCCG | 20 | 1155 |
| BCL11A-671 | + | CCCCCCGAGGCCGACUCGCC | 20 | 1156 |
| BCL11A-672 | + | CCCCCGAGGCCGACUCGCCC | 20 | 1157 |
| BCL11A-673 | + | CCCCGAGGCCGACUCGCCCG | 20 | 1158 |
| BCL11A-674 | + | ACUCGCCCGGGGAGCAGCCG | 20 | 1159 |
| BCL11A-675 | + | UAACAGUGCCAUCGUCUAUG | 20 | 1160 |
| BCL11A-676 | + | GUCUAUGCGGUCCGACUCGC | 20 | 1161 |
| BCL11A-677 | + | CUUCGUCGCAAGUGUCCCUG | 20 | 1162 |
| BCL11A-678 | + | GCAAGUGUCCCUGUGGCCCU | 20 | 1163 |
| BCL11A-679 | + | GUCCCUGUGGCCCUCGGCCU | 20 | 1164 |
| BCL11A-680 | + | UGUGGCCCUCGGCCUCGGCC | 20 | 1165 |
| BCL11A-681 | + | GGCCCUCGGCCUCGGCCAGG | 20 | 1166 |
| BCL11A-682 | + | CGCGCUUAUGCUUCUCGCCC | 20 | 1167 |
| BCL11A-683 | + | UAUGCUUCUCGCCCAGGACC | 20 | 1168 |
| BCL11A-684 | + | GCUUCUCGCCCAGGACCUGG | 20 | 1169 |
| BCL11A-685 | + | CUCGCCCAGGACCUGGUGGA | 20 | 1170 |
| BCL11A-686 | + | GGCCUCGCUGAAGUGCUGCA | 20 | 1171 |
| BCL11A-687 | + | CACCAUGCCCUGCAUGACGU | 20 | 1172 |
| BCL11A-688 | + | ACCAUGCCCUGCAUGACGUC | 20 | 1173 |
| BCL11A-689 | + | UGCCCUGCAUGACGUCGGGC | 20 | 1174 |
| BCL11A-690 | + | GCCCUGCAUGACGUCGGGCA | 20 | 1175 |
| BCL11A-691 | + | GCAUGACGUCGGGCAGGGCG | 20 | 1176 |
| BCL11A-692 | + | CGCCCCGCGAGCUGUUCUCG | 20 | 1177 |
| BCL11A-693 | + | CCCGCGAGCUGUUCUCGUGG | 20 | 1178 |
| BCL11A-694 | + | CGUGGUGGCGCGCCGCCUCC | 20 | 1179 |
| BCL11A-695 | - | GGAGGAAGAGGAGGAGG | 17 | 1180 |
| BCL11A-696 | - | GGAGGAGGAGGAGCUGA | 17 | 1181 |
| BCL11A-697 | - | AGCUGACGGAGAGCGAG | 17 | 1182 |
| BCL11A-698 | - | GCUGACGGAGAGCGAGA | 17 | 1183 |
| BCL11A-699 | - | GACGGAGAGCGAGAGGG | 17 | 1184 |

TABLE 2D-continued

4th Tier

| gRNA Name | DNA Strand | Targeting domain | Target Site Length | SEQ ID NO |
|---|---|---|---|---|
| BCL11A-700 | - | AGCGAGAGGGUGGACUA | 17 | 1185 |
| BCL11A-701 | - | AGGGUGGACUACGGCUU | 17 | 1186 |
| BCL11A-702 | - | GGGUGGACUACGGCUUC | 17 | 1187 |
| BCL11A-703 | - | CGGCUUCGGGCUGAGCC | 17 | 1188 |
| BCL11A-704 | - | CUUCGGGCUGAGCCUGG | 17 | 1189 |
| BCL11A-705 | - | CGGGCUGAGCCUGGAGG | 17 | 1190 |
| BCL11A-706 | - | ACCACGAGAACAGCUCG | 17 | 1191 |
| BCL11A-707 | - | CCACGAGAACAGCUCGC | 17 | 1192 |
| BCL11A-708 | - | CACGAGAACAGCUCGCG | 17 | 1193 |
| BCL11A-709 | - | GAACAGCUCGCGGGGCG | 17 | 1194 |
| BCL11A-710 | - | CUCGCGGGGCGCGGUCG | 17 | 1195 |
| BCL11A-711 | - | UCGCGGGGCGCGGUCGU | 17 | 1196 |
| BCL11A-712 | - | GGGCGCGGUCGUGGGCG | 17 | 1197 |
| BCL11A-713 | - | GGCGCGGUCGUGGGCGU | 17 | 1198 |
| BCL11A-714 | - | CCUGCCCGACGUCAUGC | 17 | 1199 |
| BCL11A-715 | - | CUGCCCGACGUCAUGCA | 17 | 1200 |
| BCL11A-716 | - | CGACGUCAUGCAGGGCA | 17 | 1201 |
| BCL11A-717 | - | CAUGCAGCACUUCAGCG | 17 | 1202 |
| BCL11A-718 | - | CAGCGAGGCCUUCCACC | 17 | 1203 |
| BCL11A-719 | - | GGCCUUCCACCAGGUCC | 17 | 1204 |
| BCL11A-720 | - | GCCUUCCACCAGGUCCU | 17 | 1205 |
| BCL11A-721 | - | GGCGAGAAGCAUAAGCG | 17 | 1206 |
| BCL11A-722 | - | GCAUAAGCGCGGCCACC | 17 | 1207 |
| BCL11A-723 | - | GCGCGGCCACCUGGCCG | 17 | 1208 |
| BCL11A-724 | - | CCACCUGGCCGAGGCCG | 17 | 1209 |
| BCL11A-725 | - | CACCUGGCCGAGGCCGA | 17 | 1210 |
| BCL11A-726 | - | CCGAGGCCGAGGGCCAC | 17 | 1211 |
| BCL11A-727 | - | CGAGGCCGAGGGCCACA | 17 | 1212 |
| BCL11A-728 | - | CACUUGCGACGAAGACU | 17 | 1213 |
| BCL11A-729 | - | UUGCGACGAAGACUCGG | 17 | 1214 |
| BCL11A-730 | - | GACGAAGACUCGGUGGC | 17 | 1215 |
| BCL11A-731 | - | CUCGGUGGCCGGCGAGU | 17 | 1216 |
| BCL11A-732 | - | UCGGACCGCAUAGACGA | 17 | 1217 |
| BCL11A-733 | - | GACGAUGGCACUGUUAA | 17 | 1218 |
| BCL11A-734 | - | GGCACUGUUAAUGGCCG | 17 | 1219 |
| BCL11A-735 | - | UGGCCGCGGCUGCUCCC | 17 | 1220 |
| BCL11A-736 | - | GGCCGCGGCUGCUCCCC | 17 | 1221 |
| BCL11A-737 | - | CUGCUCCCCGGGCGAGU | 17 | 1222 |
| BCL11A-738 | - | CCCGGGCGAGUCGGCCU | 17 | 1223 |
| BCL11A-739 | - | CCGGGCGAGUCGGCCUC | 17 | 1224 |
| BCL11A-740 | - | CGGGCGAGUCGGCCUCG | 17 | 1225 |
| BCL11A-741 | - | GGGCGAGUCGGCCUCGG | 17 | 1226 |
| BCL11A-742 | - | GGCGAGUCGGCCUCGGG | 17 | 1227 |
| BCL11A-743 | - | GUCCAAAAAGCUGCUGC | 17 | 1228 |
| BCL11A-744 | - | UCCAAAAAGCUGCUGCU | 17 | 1229 |
| BCL11A-745 | - | GCGCAUCAAGCUCGAGA | 17 | 1230 |
| BCL11A-746 | - | GGAGUUCGACCUGCCCC | 17 | 1231 |
| BCL11A-747 | - | GGCCGCGAUGCCCAACA | 17 | 1232 |
| BCL11A-748 | - | AGAACGUGUACUCGCAG | 17 | 1233 |
| BCL11A-749 | - | UACUCGCAGUGGCUCGC | 17 | 1234 |
| BCL11A-750 | - | GUGGCUCGCCGGCUACG | 17 | 1235 |
| BCL11A-751 | - | CCGGCUACGCGGCCUCC | 17 | 1236 |
| BCL11A-752 | - | GAUCCCUUCCUUAGCUU | 17 | 1237 |
| BCL11A-753 | - | GCCUUUUGCCUCCUCGU | 17 | 1238 |
| BCL11A-754 | - | CUCGUCGGAGCACUCCU | 17 | 1239 |
| BCL11A-755 | - | GAGCACUCCUCGGAGAA | 17 | 1240 |
| BCL11A-756 | - | AGCACUCCUCGGAGAAC | 17 | 1241 |
| BCL11A-757 | - | CGCUUCUCCACACCGCC | 17 | 1242 |
| BCL11A-758 | - | GCUUCUCCACACCGCCC | 17 | 1243 |
| BCL11A-759 | - | CUUCUCCACACCGCCCG | 17 | 1244 |
| BCL11A-760 | - | CACACCGCCCGGGGAGC | 17 | 1245 |
| BCL11A-761 | - | CCGCCCGGGGAGCUGGA | 17 | 1246 |
| BCL11A-762 | - | CCCGGGGAGCUGGACGG | 17 | 1247 |
| BCL11A-763 | - | CCGGGGAGCUGGACGGA | 17 | 1248 |
| BCL11A-764 | - | GCUGGACGGAGGGAUCU | 17 | 1249 |
| BCL11A-765 | - | CUGGACGGAGGGAUCUC | 17 | 1250 |
| BCL11A-766 | - | UGGACGGAGGGAUCUCG | 17 | 1251 |
| BCL11A-767 | - | GGGAUCUCGGGGCGCAG | 17 | 1252 |
| BCL11A-768 | - | CUCGGGGCGCAGCGGCA | 17 | 1253 |
| BCL11A-769 | - | UCGGGGCGCAGCGGCAC | 17 | 1254 |
| BCL11A-770 | - | CGCAGCGGCACGGGAAG | 17 | 1255 |
| BCL11A-771 | - | AGCGGCACGGGAAGUGG | 17 | 1256 |
| BCL11A-772 | - | GCGGCACGGGAAGUGGA | 17 | 1257 |
| BCL11A-773 | - | AGCACGCCCCAUAUUAG | 17 | 1258 |

TABLE 2D-continued

4th Tier

| gRNA Name | DNA Strand | Targeting domain | Target Site Length | SEQ ID NO |
|---|---|---|---|---|
| BCL11A-774 | − | GCCCCAUAUUAGUGGUC | 17 | 1259 |
| BCL11A-775 | − | CCCCAUAUUAGUGGUCC | 17 | 1260 |
| BCL11A-776 | − | UAUUAGUGGUCCGGGCC | 17 | 1261 |
| BCL11A-777 | − | AUUAGUGGUCCGGGCCC | 17 | 1262 |
| BCL11A-778 | − | GUGGUCCGGGCCCGGGC | 17 | 1263 |
| BCL11A-779 | − | CAGGCCCAGCUCAAAAG | 17 | 1264 |
| BCL11A-780 | − | AGGCCCAGCUCAAAAGA | 17 | 1265 |
| BCL11A-781 | + | UCUGCCCUCUUUUGAGC | 17 | 1266 |
| BCL11A-782 | + | CUGCCCUCUUUUGAGCU | 17 | 1267 |
| BCL11A-783 | + | UUUGAGCUGGGCCUGCC | 17 | 1268 |
| BCL11A-784 | + | UUGAGCUGGGCCUGCCC | 17 | 1269 |
| BCL11A-785 | + | CUGGGCCUGCCCGGGCC | 17 | 1270 |
| BCL11A-786 | + | GGCCCGGACCACUAAUA | 17 | 1271 |
| BCL11A-787 | + | GCCCGGACCACUAAUAU | 17 | 1272 |
| BCL11A-788 | + | CCCGGACCACUAAUAUG | 17 | 1273 |
| BCL11A-789 | + | CCCUCCGUCCAGCUCCC | 17 | 1274 |
| BCL11A-790 | + | CCUCCGUCCAGCUCCCC | 17 | 1275 |
| BCL11A-791 | + | CCGUCCAGCUCCCCGGG | 17 | 1276 |
| BCL11A-792 | + | CAGCUCCCCGGCGGUG | 17 | 1277 |
| BCL11A-793 | + | CAAACUCCCGUUCUCCG | 17 | 1278 |
| BCL11A-794 | + | CGAGGAGUGCUCCGACG | 17 | 1279 |
| BCL11A-795 | + | GGAGUGCUCCGACGAGG | 17 | 1280 |
| BCL11A-796 | + | UCCGACGAGGAGGCAAA | 17 | 1281 |
| BCL11A-797 | + | GGCAAAAGGCGAUUGUC | 17 | 1282 |
| BCL11A-798 | + | UGGAGUCUCCGAAGCUA | 17 | 1283 |
| BCL11A-799 | + | GUCUCCGAAGCUAAGGA | 17 | 1284 |
| BCL11A-800 | + | UCUCCGAAGCUAAGGAA | 17 | 1285 |
| BCL11A-801 | + | GGGAUCUUUGAGCUGCC | 17 | 1286 |
| BCL11A-802 | + | AUCUUUGAGCUGCCUGG | 17 | 1287 |
| BCL11A-803 | + | CCUGGAGGCCGCGUAGC | 17 | 1288 |
| BCL11A-804 | + | GUACACGUUCUCCGUGU | 17 | 1289 |
| BCL11A-805 | + | UACACGUUCUCCGUGUU | 17 | 1290 |
| BCL11A-806 | + | CUCCGUGUUGGGCAUCG | 17 | 1291 |
| BCL11A-807 | + | GUGUUGGGCAUCGCGGC | 17 | 1292 |
| BCL11A-808 | + | UGUUGGGCAUCGCGGCC | 17 | 1293 |
| BCL11A-809 | + | GUUGGGCAUCGCGGCCG | 17 | 1294 |
| BCL11A-810 | + | UUGGGCAUCGCGGCCGG | 17 | 1295 |
| BCL11A-811 | + | GCAUCGCGGCCGGGGGC | 17 | 1296 |
| BCL11A-812 | + | CUUGAUGCGCUUAGAGA | 17 | 1297 |
| BCL11A-813 | + | UUGAUGCGCUUAGAGAA | 17 | 1298 |
| BCL11A-814 | + | UGAUGCGCUUAGAGAAG | 17 | 1299 |
| BCL11A-815 | + | GAAGGGGCUCAGCGAGC | 17 | 1300 |
| BCL11A-816 | + | AAGGGGCUCAGCGAGCU | 17 | 1301 |
| BCL11A-817 | + | AGGGGCUCAGCGAGCUG | 17 | 1302 |
| BCL11A-818 | + | GCCCAGCAGCAGCUUUU | 17 | 1303 |
| BCL11A-819 | + | GCAGCAGCUUUUUGGAC | 17 | 1304 |
| BCL11A-820 | + | UUUGGACAGGCCCCCCG | 17 | 1305 |
| BCL11A-821 | + | CCCGAGGCCGACUCGCC | 17 | 1306 |
| BCL11A-822 | + | CCGAGGCCGACUCGCCC | 17 | 1307 |
| BCL11A-823 | + | CGAGGCCGACUCGCCCG | 17 | 1308 |
| BCL11A-824 | + | CGCCCGGGGAGCAGCCG | 17 | 1309 |
| BCL11A-825 | + | CAGUGCCAUCGUCUAUG | 17 | 1310 |
| BCL11A-826 | + | UAUGCGGUCCGACUCGC | 17 | 1311 |
| BCL11A-827 | + | CGUCGCAAGUGUCCCUG | 17 | 1312 |
| BCL11A-828 | + | AGUGUCCCUGUGGCCCU | 17 | 1313 |
| BCL11A-829 | + | CCUGUGGCCCUCGGCCU | 17 | 1314 |
| BCL11A-830 | + | GGCCCUCGGCCUCGGCC | 17 | 1315 |
| BCL11A-831 | + | CCUCGGCCUCGGCCAGG | 17 | 1316 |
| BCL11A-832 | + | GCUUAUGCUUCUCGCCC | 17 | 1317 |
| BCL11A-833 | + | GCUUCUCGCCCAGGACC | 17 | 1318 |
| BCL11A-834 | + | UCUCGCCCAGGACCUGG | 17 | 1319 |
| BCL11A-835 | + | GCCCAGGACCUGGUGGA | 17 | 1320 |
| BCL11A-836 | + | CUCGCUGAAGUGCUGCA | 17 | 1321 |
| BCL11A-837 | + | CAUGCCCUGCAUGACGU | 17 | 1322 |
| BCL11A-838 | + | AUGCCCUGCAUGACGUC | 17 | 1323 |
| BCL11A-839 | + | CCUGCAUGACGUCGGGC | 17 | 1324 |
| BCL11A-840 | + | CUGCAUGACGUCGGGCA | 17 | 1325 |
| BCL11A-841 | + | UGACGUCGGGCAGGGCG | 17 | 1326 |
| BCL11A-842 | + | CCCGCGAGCUGUUCUCG | 17 | 1327 |
| BCL11A-843 | + | GCGAGCUGUUCUCGUGG | 17 | 1328 |
| BCL11A-844 | + | GGUGGCGCCGCCGCUCC | 17 | 1329 |
| BCL11A-845 | − | CCCAGAGAGCUCAAGAUGUG | 20 | 1330 |
| BCL11A-846 | − | UCAAGAUGUGUGGCAGUUUU | 20 | 1331 |
| BCL11A-847 | − | GAUGUGUGGCAGUUUUCGGA | 20 | 1332 |

TABLE 2D-continued

4th Tier

| gRNA Name | DNA Strand | Targeting domain | Target Site Length | SEQ ID NO |
|---|---|---|---|---|
| BCL11A-848 | + | GCCACACAUCUUGAGCUCUC | 20 | 1333 |
| BCL11A-849 | + | CCACACAUCUUGAGCUCUCU | 20 | 1334 |
| BCL11A-850 | + | UCUCUGGGUACUACGCCGAA | 20 | 1335 |
| BCL11A-851 | + | CUCUGGGUACUACGCCGAAU | 20 | 1336 |
| BCL11A-852 | + | UCUGGGUACUACGCCGAAUG | 20 | 1337 |
| BCL11A-853 | + | CUGGGUACUACGCCGAAUGG | 20 | 1338 |
| BCL11A-854 | − | CUUCACACACCCCCAUU | 17 | 1339 |
| BCL11A-855 | − | AGAGAGCUCAAGAUGUG | 17 | 1340 |
| BCL11A-856 | − | AGAUGUGUGGCAGUUUU | 17 | 1341 |
| BCL11A-857 | − | GUGUGGCAGUUUUCGGA | 17 | 1342 |
| BCL11A-858 | + | ACACAUCUUGAGCUCUC | 17 | 1343 |
| BCL11A-859 | + | CACAUCUUGAGCUCUCU | 17 | 1344 |
| BCL11A-860 | + | CUGGGUACUACGCCGAA | 17 | 1345 |
| BCL11A-861 | + | UGGGUACUACGCCGAAU | 17 | 1346 |
| BCL11A-862 | + | GGGUACUACGCCGAAUG | 17 | 1347 |
| BCL11A-863 | + | GGUACUACGCCGAAUGG | 17 | 1348 |

Table 2E provides exemplary targeting domains for knocking out the BCL11A gene. In an embodiment, the targeting domain is the exact complement of the target domain. Any of the targeting domains in the table can be used with a S. aureus Cas9 molecule that gives double stranded cleavage. Any of the targeting domains in the table can be used with a S. aureus Cas9 single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 2E

S. aureus gRNA targets for BCL11A knockout

| gRNA Name | DNA Strand | Targeting Domain | Target Site Length | SEQ ID NO |
|---|---|---|---|---|
| BCL11A-864 | − | AAACCCCAGCACUUAAGCAA | 20 | 1349 |
| BCL11A-865 | − | AACCCCAGCACUUAAGCAAA | 20 | 1350 |
| BCL11A-866 | − | ACCCCAGCACUUAAGCAAAC | 20 | 1351 |
| BCL11A-867 | − | CCCCAGCACUUAAGCAA | 17 | 1352 |
| BCL11A-868 | − | CCCAGCACUUAAGCAAA | 17 | 1353 |
| BCL11A-869 | − | CCAGCACUUAAGCAAAC | 17 | 1354 |
| BCL11A-870 | + | UGGGGUUUGCCUUGCUUGCG | 20 | 1355 |
| BCL11A-871 | + | AUUCCCGUUUGCUUAAGUGC | 20 | 1356 |
| BCL11A-872 | + | AAUUCCCGUUUGCUUAAGUG | 20 | 1357 |
| BCL11A-873 | + | GGUUUGCCUUGCUUGCG | 17 | 1358 |
| BCL11A-874 | + | CCCGUUUGCUUAAGUGC | 17 | 1359 |
| BCL11A-875 | + | UCCCGUUUGCUUAAGUG | 17 | 1360 |
| BCL11A-876 | − | UGAAGCCAUUCUUACAGAUG | 20 | 1361 |
| BCL11A-877 | − | AUGAACCAGACCACGGCCCG | 20 | 1362 |
| BCL11A-878 | − | UGAACCAGACCACGGCCCGU | 20 | 1363 |
| BCL11A-879 | − | GAACCAGACCACGGCCCGUU | 20 | 1364 |
| BCL11A-880 | − | CCACGGCCCGUUGGGAGCUC | 20 | 1365 |
| BCL11A-881 | − | CGGCCCGUUGGGAGCUCCAG | 20 | 1366 |
| BCL11A-882 | − | GGCCCGUUGGGAGCUCCAGA | 20 | 1367 |
| BCL11A-883 | − | GCCCGUUGGGAGCUCCAGAA | 20 | 1368 |
| BCL11A-884 | − | GGAUCAUGACCUCCUCACCU | 20 | 1369 |
| BCL11A-885 | − | UCACCUGUGGGCAGUGCCAG | 20 | 1370 |
| BCL11A-886 | − | AGUGCCAGAUGAACUUCCCA | 20 | 1371 |
| BCL11A-887 | − | GUGCCAGAUGAACUUCCCAU | 20 | 1372 |
| BCL11A-888 | − | UGCCAGAUGAACUUCCCAUU | 20 | 1373 |
| BCL11A-889 | − | GCCAGAUGAACUUCCCAUUG | 20 | 1374 |
| BCL11A-890 | − | GGGGGACAUUCUUAUUUUUA | 20 | 1375 |
| BCL11A-891 | − | CUUAUUUUUAUCGAGCACAA | 20 | 1376 |
| BCL11A-892 | − | UUAUUUUUAUCGAGCACAAA | 20 | 1377 |
| BCL11A-893 | − | AUGCAAUGGCAGCCUCUGCU | 20 | 1378 |
| BCL11A-894 | − | GCCUCUGCUUAGAAAAGCU | 20 | 1379 |
| BCL11A-895 | − | GCCACCUUCCCCUUCACCAA | 20 | 1380 |
| BCL11A-896 | − | CUUCCCCUUCACCAAUCGAG | 20 | 1381 |
| BCL11A-897 | − | UGAAAAAGCAUCCAAUCCC | 20 | 1382 |
| BCL11A-898 | − | GAAAAAGCAUCCAAUCCCG | 20 | 1383 |
| BCL11A-899 | − | GGUUGGCAUCCAGGUCACGC | 20 | 1384 |
| BCL11A-900 | − | UUGGCAUCCAGGUCACGCCA | 20 | 1385 |
| BCL11A-901 | − | GAUUGUUUAUCAACGUCAUC | 20 | 1386 |
| BCL11A-902 | − | UUGUUUAUCAACGUCAUCUA | 20 | 1387 |
| BCL11A-903 | − | UGUUUAUCAACGUCAUCUAG | 20 | 1388 |
| BCL11A-904 | − | CUAGAGGAAUUUGCCCCAAA | 20 | 1389 |
| BCL11A-905 | − | UAGAGGAAUUUGCCCCAAAC | 20 | 1390 |
| BCL11A-906 | − | AGCCAUUCUUACAGAUG | 17 | 1391 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-907 | − | AACCAGACCACGGCCCG | 17 | 1392 |
| BCL11A-908 | − | ACCAGACCACGGCCCGU | 17 | 1393 |
| BCL11A-909 | − | CCAGACCACGGCCCGUU | 17 | 1394 |
| BCL11A-910 | − | CGGCCCGUUGGGAGCUC | 17 | 1395 |
| BCL11A-911 | − | CCCGUUGGGAGCUCCAG | 17 | 1396 |
| BCL11A-912 | − | CCGUUGGGAGCUCCAGA | 17 | 1397 |
| BCL11A-913 | − | CGUUGGGAGCUCCAGAA | 17 | 1398 |
| BCL11A-914 | − | UCAUGACCUCCUCACCU | 17 | 1399 |
| BCL11A-915 | − | CCUGUGGGCAGUGCCAG | 17 | 1400 |
| BCL11A-916 | − | GCCAGAUGAACUUCCCA | 17 | 1401 |
| BCL11A-917 | − | CCAGAUGAACUUCCCAU | 17 | 1402 |
| BCL11A-918 | − | CAGAUGAACUUCCCAUU | 17 | 1403 |
| BCL11A-919 | − | AGAUGAACUUCCCAUUG | 17 | 1404 |
| BCL11A-920 | − | GGACAUUCUUAUUUUUA | 17 | 1405 |
| BCL11A-921 | − | AUUUUUAUCGAGCACAA | 17 | 1406 |
| BCL11A-922 | − | UUUUUAUCGAGCACAAA | 17 | 1407 |
| BCL11A-923 | − | CAAUGGCAGCCUCUGCU | 17 | 1408 |
| BCL11A-924 | − | UCUGCUUAGAAAAAGCU | 17 | 1409 |
| BCL11A-925 | − | ACCUUCCCCUUCACCAA | 17 | 1410 |
| BCL11A-926 | − | CCCCUUCACCAAUCGAG | 17 | 1411 |
| BCL11A-927 | − | AAAAAGCAUCCAAUCCC | 17 | 1412 |
| BCL11A-928 | − | AAAAGCAUCCAAUCCCG | 17 | 1413 |
| BCL11A-929 | − | UGGCAUCCAGGUCACGC | 17 | 1414 |
| BCL11A-930 | − | GCAUCCAGGUCACGCCA | 17 | 1415 |
| BCL11A-931 | − | UGUUUAUCAACGUCAUC | 17 | 1416 |
| BCL11A-932 | − | UUUAUCAACGUCAUCUA | 17 | 1417 |
| BCL11A-933 | − | UUAUCAACGUCAUCUAG | 17 | 1418 |
| BCL11A-934 | − | GAGGAAUUUGCCCCAAA | 17 | 1419 |
| BCL11A-935 | − | AGGAAUUUGCCCCAAAC | 17 | 1420 |
| BCL11A-936 | + | UCAUCGUAAGAAUGGCUUC | 20 | 1421 |
| BCL11A-937 | + | UGGUCUGGUUCAUCAUCUGU | 20 | 1422 |
| BCL11A-938 | + | AUCCCCUUCUGGAGCUCCCA | 20 | 1423 |
| BCL11A-939 | + | AGGAGGUCAUGAUCCCCUUC | 20 | 1424 |
| BCL11A-940 | + | GAGGAGGUCAUGAUCCCCUU | 20 | 1425 |
| BCL11A-941 | + | UCUGGCACUGCCCACAGGUG | 20 | 1426 |
| BCL11A-942 | + | AUCUGGCACUGCCCACAGGU | 20 | 1427 |
| BCL11A-943 | + | UCAUCUGGCACUGCCCACAG | 20 | 1428 |
| BCL11A-944 | + | AAAUAAGAAUGUCCCCCAAU | 20 | 1429 |
| BCL11A-945 | + | AAAAUAAGAAUGUCCCCCAA | 20 | 1430 |
| BCL11A-946 | + | AAAAAUAAGAAUGUCCCCCA | 20 | 1431 |
| BCL11A-947 | + | CGUUUGUGCUCGAUAAAAAU | 20 | 1432 |
| BCL11A-948 | + | UAUCCACAGCUUUUUCUAAG | 20 | 1433 |
| BCL11A-949 | + | UUUCAUCUCGAUUGGUGAAG | 20 | 1434 |
| BCL11A-950 | + | UUUUCAUCUCGAUUGGUGAA | 20 | 1435 |
| BCL11A-951 | + | UUUUUCAUCUCGAUUGGUGA | 20 | 1436 |
| BCL11A-952 | + | UUUUUUCAUCUCGAUUGGUG | 20 | 1437 |
| BCL11A-953 | + | UGCUUUUUCAUCUCGAUUG | 20 | 1438 |
| BCL11A-954 | + | GGAUGCCAACCUCCACGGGA | 20 | 1439 |
| BCL11A-955 | + | GACCUGGAUGCCAACCUCCA | 20 | 1440 |
| BCL11A-956 | + | UGACCUGGAUGCCAACCUCC | 20 | 1441 |
| BCL11A-957 | + | UCGUCAUCCUCUGGCGUGAC | 20 | 1442 |
| BCL11A-958 | + | CUGCUAUGUGUUCCUGUUUG | 20 | 1443 |
| BCL11A-959 | + | CUGCUAUGUGUUCCUGUUUG | 20 | 1444 |
| BCL11A-960 | + | UCUGUAAGAAUGGCUUC | 17 | 1445 |
| BCL11A-961 | + | UCUGGUUCAUCAUCUGU | 17 | 1446 |
| BCL11A-962 | + | CCCUUCUGGAGCUCCCA | 17 | 1447 |
| BCL11A-963 | + | AGGUCAUGAUCCCCUUC | 17 | 1448 |
| BCL11A-964 | + | GAGGUCAUGAUCCCCUU | 17 | 1449 |
| BCL11A-965 | + | GGCACUGCCCACAGGUG | 17 | 1450 |
| BCL11A-966 | + | UGGCACUGCCCACAGGU | 17 | 1451 |
| BCL11A-967 | + | UCUGGCACUGCCCACAG | 17 | 1452 |
| BCL11A-968 | + | UAAGAAUGUCCCCCAAU | 17 | 1453 |
| BCL11A-969 | + | AUAAGAAUGUCCCCCAA | 17 | 1454 |
| BCL11A-970 | + | AAUAAGAAUGUCCCCCA | 17 | 1455 |
| BCL11A-971 | + | UUGUGCUCGAUAAAAAU | 17 | 1456 |
| BCL11A-972 | + | CCACAGCUUUUUCUAAG | 17 | 1457 |
| BCL11A-973 | + | CAUCUCGAUUGGUGAAG | 17 | 1458 |
| BCL11A-974 | + | UCAUCUCGAUUGGUGAA | 17 | 1459 |
| BCL11A-975 | + | UUCAUCUCGAUUGGUGA | 17 | 1460 |
| BCL11A-976 | + | UUUCAUCUCGAUUGGUG | 17 | 1461 |
| BCL11A-977 | + | UUUUUCAUCUCGAUUG | 17 | 1462 |
| BCL11A-978 | + | UGCCAACCUCCACGGGA | 17 | 1463 |
| BCL11A-979 | + | CUGGAUGCCAACCUCCA | 17 | 1464 |
| BCL11A-980 | + | CCUGGAUGCCAACCUCC | 17 | 1465 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-981 | + | UCAUCCUCUGGCGUGAC | 17 | 1466 |
| BCL11A-982 | + | UGCUAUGUGUUCCUGUU | 17 | 1467 |
| BCL11A-983 | + | CUGCUAUGUGUUCCUGU | 17 | 1468 |
| BCL11A-984 | - | CUCCUCCCCUCGUUCUGCAC | 20 | 1469 |
| BCL11A-985 | - | UCCUCCCCUCGUUCUGCACA | 20 | 1470 |
| BCL11A-986 | - | UGGAGCUCUAAUCCCCACGC | 20 | 1471 |
| BCL11A-987 | - | GGAGCUCUAAUCCCCACGCC | 20 | 1472 |
| BCL11A-988 | - | CUCUAAUCCCCACGCCUGGG | 20 | 1473 |
| BCL11A-989 | - | CCCCACGCCUGGGAUGAGUG | 20 | 1474 |
| BCL11A-990 | - | UGAGUGCAGAAUAUGCCCCG | 20 | 1475 |
| BCL11A-991 | - | CUCCCCUCGUUCUGCAC | 17 | 1476 |
| BCL11A-992 | - | UCCCCUCGUUCUGCACA | 17 | 1477 |
| BCL11A-993 | - | AGCUCUAAUCCCCACGC | 17 | 1478 |
| BCL11A-994 | - | GCUCUAAUCCCCACGCC | 17 | 1479 |
| BCL11A-995 | - | UAAUCCCCACGCCUGGG | 17 | 1480 |
| BCL11A-996 | - | CACGCCUGGGAUGAGUG | 17 | 1481 |
| BCL11A-997 | - | GUGCAGAAUAUGCCCCG | 17 | 1482 |
| BCL11A-998 | + | GAGGAGAGGCCCCUCCAGUG | 20 | 1483 |
| BCL11A-999 | + | CAUGUGCAGAACGAGGGGAG | 20 | 1484 |
| BCL11A-1000 | + | UCCAUGUGCAGAACGAGGGG | 20 | 1485 |
| BCL11A-1001 | + | CUCCAUGUGCAGAACGAGGG | 20 | 1486 |
| BCL11A-1002 | + | AGCUCCAUGUGCAGAACGAG | 20 | 1487 |
| BCL11A-1003 | + | GAGCUCCAUGUGCAGAACGA | 20 | 1488 |
| BCL11A-1004 | + | AGAGCUCCAUGUGCAGAACG | 20 | 1489 |
| BCL11A-1005 | + | UAGAGCUCCAUGUGCAGAAC | 20 | 1490 |
| BCL11A-1006 | + | AUUAGAGCUCCAUGUGCAGA | 20 | 1491 |
| BCL11A-1007 | + | GGGGAUUAGAGCUCCAUGUG | 20 | 1492 |
| BCL11A-1008 | + | CUCAUCCCAGGCGUGGGGAU | 20 | 1493 |
| BCL11A-1009 | + | UCUGCACUCAUCCCAGGCGU | 20 | 1494 |
| BCL11A-1010 | + | UUCUGCACUCAUCCCAGGCG | 20 | 1495 |
| BCL11A-1011 | + | AUUCUGCACUCAUCCCAGGC | 20 | 1496 |
| BCL11A-1012 | + | GAGAGGCCCCUCCAGUG | 17 | 1497 |
| BCL11A-1013 | + | GUGCAGAACGAGGGGAG | 17 | 1498 |
| BCL11A-1014 | + | AUGUGCAGAACGAGGGG | 17 | 1499 |
| BCL11A-1015 | + | CAUGUGCAGAACGAGGG | 17 | 1500 |
| BCL11A-1016 | + | UCCAUGUGCAGAACGAG | 17 | 1501 |
| BCL11A-1017 | + | CUCCAUGUGCAGAACGA | 17 | 1502 |
| BCL11A-1018 | + | GCUCCAUGUGCAGAACG | 17 | 1503 |
| BCL11A-1019 | + | AGCUCCAUGUGCAGAAC | 17 | 1504 |
| BCL11A-1020 | + | AGAGCUCCAUGUGCAGA | 17 | 1505 |
| BCL11A-1021 | + | GAUUAGAGCUCCAUGUG | 17 | 1506 |
| BCL11A-1022 | + | AUCCCAGGCGUGGGGAU | 17 | 1507 |
| BCL11A-1023 | + | GCACUCAUCCCAGGCGU | 17 | 1508 |
| BCL11A-1024 | + | UGCACUCAUCCCAGGCG | 17 | 1509 |
| BCL11A-1025 | + | CUGCACUCAUCCCAGGC | 17 | 1510 |
| BCL11A-1026 | - | GGUUUCUCUUGCAACACGCA | 20 | 1511 |
| BCL11A-1027 | - | GCAACACGCACAGAACACUC | 20 | 1512 |
| BCL11A-1028 | - | GCACAGAACACUCAUGGAUU | 20 | 1513 |
| BCL11A-1029 | - | UCAUGGAUUAAGAAUCUACU | 20 | 1514 |
| BCL11A-1030 | - | AUUAAGAAUCUACUUAGAAA | 20 | 1515 |
| BCL11A-1031 | - | AAUCUACUUAGAAAGCGAAC | 20 | 1516 |
| BCL11A-1032 | - | AUCUACUUAGAAAGCGAACA | 20 | 1517 |
| BCL11A-1033 | - | CACGGAAGUCCCCUGACCCC | 20 | 1518 |
| BCL11A-1034 | - | CCCGCGGGUUGGUAUCCCUU | 20 | 1519 |
| BCL11A-1035 | - | UAUCCCUUCAGGACUAGGUG | 20 | 1520 |
| BCL11A-1036 | - | UCCUUCCCAGCCACCUCUCC | 20 | 1521 |
| BCL11A-1037 | - | CCUUCCCAGCCACCUCUCCA | 20 | 1522 |
| BCL11A-1038 | - | AAUAACCCCUUUAACCUGCU | 20 | 1523 |
| BCL11A-1039 | - | CUUUAACCUGCUAAGAAUAC | 20 | 1524 |
| BCL11A-1040 | - | UAAGAAUACCAGGAUCAGUA | 20 | 1525 |
| BCL11A-1041 | - | AGAAUACCAGGAUCAGUAUC | 20 | 1526 |
| BCL11A-1042 | - | AAUACCAGGAUCAGUAUCGA | 20 | 1527 |
| BCL11A-1043 | - | GAGAGAGGCUUCCGGCCUGG | 20 | 1528 |
| BCL11A-1044 | - | AGAGGCUUCCGGCCUGGCAG | 20 | 1529 |
| BCL11A-1045 | - | CCCCCCUGUUUAGUCCACCA | 20 | 1530 |
| BCL11A-1046 | - | GUCCACCACCGAGACAUCAC | 20 | 1531 |
| BCL11A-1047 | - | UCACUGGACCCCCACCGCA | 20 | 1532 |
| BCL11A-1048 | - | ACCCCCACCGCAUAGAGCGC | 20 | 1533 |
| BCL11A-1049 | - | CCCCCACCGCAUAGAGCGCC | 20 | 1534 |
| BCL11A-1050 | - | CCCCACCGCAUAGAGCGCCU | 20 | 1535 |
| BCL11A-1051 | - | ACCGCAUAGAGCGCCUGGGG | 20 | 1536 |
| BCL11A-1052 | - | CCGCAUAGAGCGCCUGGGGG | 20 | 1537 |
| BCL11A-1053 | - | CAUAGAGCGCCUGGGGGCGG | 20 | 1538 |
| BCL11A-1054 | - | UGGCCCUGGCCACCCAUCAC | 20 | 1539 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1055 | - | CAUCACCCGAGUGCCUUUGA | 20 | 1540 |
| BCL11A-1056 | - | CCUUUGACAGGGUGCUGCGG | 20 | 1541 |
| BCL11A-1057 | - | UGCGGUUGAAUCCAAUGGCU | 20 | 1542 |
| BCL11A-1058 | - | GCGGUUGAAUCCAAUGGCUA | 20 | 1543 |
| BCL11A-1059 | - | UGGCUAUGGAGCCUCCCGCC | 20 | 1544 |
| BCL11A-1060 | - | CCUCCCGCCAUGGAUUUCUC | 20 | 1545 |
| BCL11A-1061 | - | CUCCCGCCAUGGAUUUCUCU | 20 | 1546 |
| BCL11A-1062 | - | AUGGAUUUCUCUAGGAGACU | 20 | 1547 |
| BCL11A-1063 | - | GGAUUUCUCUAGGAGACUUA | 20 | 1548 |
| BCL11A-1064 | - | UAGGAGACUUAGAGAGCUGG | 20 | 1549 |
| BCL11A-1065 | - | AGGAGACUUAGAGAGCUGGC | 20 | 1550 |
| BCL11A-1066 | - | GGAGACUUAGAGAGCUGGCA | 20 | 1551 |
| BCL11A-1067 | - | CCCGGUCAAGUCCAAGUCAU | 20 | 1552 |
| BCL11A-1068 | - | GCGGCAAGACGUUCAAAUUU | 20 | 1553 |
| BCL11A-1069 | - | UGGUGCACCGGCGCAGCCAC | 20 | 1554 |
| BCL11A-1070 | - | GCACCGGCGCAGCCACACGG | 20 | 1555 |
| BCL11A-1071 | - | ACCGGCGCAGCCACACGGC | 20 | 1556 |
| BCL11A-1072 | - | CGUGCACCCAGGCCAGCAAG | 20 | 1557 |
| BCL11A-1073 | - | CCAGCAAGCUGAAGCGCCAC | 20 | 1558 |
| BCL11A-1074 | - | GUCUCUCCACCGCCAGCUCC | 20 | 1559 |
| BCL11A-1075 | - | UCUCUCCACCGCCAGCUCCC | 20 | 1560 |
| BCL11A-1076 | - | AACCCGGCACCAGCGACUUG | 20 | 1561 |
| BCL11A-1077 | - | AGUCCGUGGUGGCCAAGUUC | 20 | 1562 |
| BCL11A-1078 | - | CGUGGUGGCCAAGUUCAAGA | 20 | 1563 |
| BCL11A-1079 | - | UGGUGGCCAAGUUCAAGAGC | 20 | 1564 |
| BCL11A-1080 | - | AGAACGACCCCAACCUGAUC | 20 | 1565 |
| BCL11A-1081 | - | GAACGACCCCAACCUGAUCC | 20 | 1566 |
| BCL11A-1082 | - | ACGACCCCAACCUGAUCCCG | 20 | 1567 |
| BCL11A-1083 | - | CCCCAACCUGAUCCCGGAGA | 20 | 1568 |
| BCL11A-1084 | - | CCCAACCUGAUCCCGGAGAA | 20 | 1569 |
| BCL11A-1085 | - | CCAACCUGAUCCCGGAGAAC | 20 | 1570 |
| BCL11A-1086 | - | CCUGAUCCCGGAGAACGGGG | 20 | 1571 |
| BCL11A-1087 | - | UGAUCCCGGAGAACGGGGAC | 20 | 1572 |
| BCL11A-1088 | - | GAUCCCGGAGAACGGGGACG | 20 | 1573 |
| BCL11A-1089 | - | UCCCGGAGAACGGGGACGAG | 20 | 1574 |
| BCL11A-1090 | - | CCCGGAGAACGGGGACGAGG | 20 | 1575 |
| BCL11A-1091 | - | GGAGAACGGGGACGAGGAGG | 20 | 1576 |
| BCL11A-1092 | - | AGAACGGGGACGAGGAGGAA | 20 | 1577 |
| BCL11A-1093 | - | GAACGGGGACGAGGAGGAAG | 20 | 1578 |
| BCL11A-1094 | - | ACGGGGACGAGGAGGAAGAG | 20 | 1579 |
| BCL11A-1095 | - | CGAGGAGGAAGAGGAGGACG | 20 | 1580 |
| BCL11A-1096 | - | AGGAGGAAGAGGAGGACGAC | 20 | 1581 |
| BCL11A-1097 | - | GGAGGAAGAGGAGGACGACG | 20 | 1582 |
| BCL11A-1098 | - | GGAAGAGGAGGACGACGAGG | 20 | 1583 |
| BCL11A-1099 | - | AAGAGGAGGACGACGAGGAA | 20 | 1584 |
| BCL11A-1100 | - | AGAGGAGGACGACGAGGAAG | 20 | 1585 |
| BCL11A-1101 | - | GGGGACGACGAGGAAGAGG | 20 | 1586 |
| BCL11A-1102 | - | GGACGACGAGGAAGAGGAAG | 20 | 1587 |
| BCL11A-1103 | - | ACGACGAGGAAGAGGAAGAA | 20 | 1588 |
| BCL11A-1104 | - | CGACGAGGAAGAGGAAGAAG | 20 | 1589 |
| BCL11A-1105 | - | ACGAGGAAGAGGAAGAAGAG | 20 | 1590 |
| BCL11A-1106 | - | CGAGGAAGAGGAAGAAGAGG | 20 | 1591 |
| BCL11A-1107 | - | GGAAGAGGAAGAAGAGGAGG | 20 | 1592 |
| BCL11A-1108 | - | AAGAGGAAGAAGAGGAGGAA | 20 | 1593 |
| BCL11A-1109 | - | AGAGGAAGAAGAGGAGGAAG | 20 | 1594 |
| BCL11A-1110 | - | AGGAAGAAGAGGAGGAAGAG | 20 | 1595 |
| BCL11A-1111 | - | GGAAGAAGAGGAGGAAGAGG | 20 | 1596 |
| BCL11A-1112 | - | AAGAAGAGGAGGAAGAGGAG | 20 | 1597 |
| BCL11A-1113 | - | AGAAGAGGAGGAAGAGGAGG | 20 | 1598 |
| BCL11A-1114 | - | AAGAGGAGGAAGAGGAGGAG | 20 | 1599 |
| BCL11A-1115 | - | AGAGGAGGAAGAGGAGGAGG | 20 | 1600 |
| BCL11A-1116 | - | AAGAGGAGGAGGAGGAGCUG | 20 | 1601 |
| BCL11A-1117 | - | AGAGGAGGAGGAGGAGCUGA | 20 | 1602 |
| BCL11A-1118 | - | AGGAGGAGGAGGAGCUGACG | 20 | 1603 |
| BCL11A-1119 | - | GGAGGAGGAGCUGACGGAGA | 20 | 1604 |
| BCL11A-1120 | - | AGGAGGAGCUGACGGAGAGC | 20 | 1605 |
| BCL11A-1121 | - | GAGGAGCUGACGGAGAGCGA | 20 | 1606 |
| BCL11A-1122 | - | AGCUGACGGAGAGCGAGAGG | 20 | 1607 |
| BCL11A-1123 | - | CGAGAGGUGGACUACGGCU | 20 | 1608 |
| BCL11A-1124 | - | GGGUGGACUACGGCUUCGGG | 20 | 1609 |
| BCL11A-1125 | - | ACUACGGCUUCGGGCUGAGC | 20 | 1610 |
| BCL11A-1126 | - | CUACGGCUUCGGGCUGAGCC | 20 | 1611 |
| BCL11A-1127 | - | CCUGGAGGCGGCGCGCCACC | 20 | 1612 |
| BCL11A-1128 | - | UGGAGGCGGCGCGCCACCAC | 20 | 1613 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1129 | - | CGCCACCACGAGAACAGCUC | 20 | 1614 |
| BCL11A-1130 | - | GCCACCACGAGAACAGCUCG | 20 | 1615 |
| BCL11A-1131 | - | ACAGCUCGCGGGGCGCGGUC | 20 | 1616 |
| BCL11A-1132 | - | CGCGGGGCGCGGUCGUGGGC | 20 | 1617 |
| BCL11A-1133 | - | CGCGGUCGUGGGCGUGGGCG | 20 | 1618 |
| BCL11A-1134 | - | CGGUCGUGGGCGUGGGCGAC | 20 | 1619 |
| BCL11A-1135 | - | GCGCCCUGCCCGACGUCAUG | 20 | 1620 |
| BCL11A-1136 | - | CAGCUCCAUGCAGCACUUCA | 20 | 1621 |
| BCL11A-1137 | - | GCGAGGCCUUCCACCAGGUC | 20 | 1622 |
| BCL11A-1138 | - | GGCCUUCCACCAGGUCCUGG | 20 | 1623 |
| BCL11A-1139 | - | CCUUCCACCAGGUCCUGGGC | 20 | 1624 |
| BCL11A-1140 | - | GCAUAAGCGCGGCCACCUGG | 20 | 1625 |
| BCL11A-1141 | - | GCGCGGCCACCUGGCCGAGG | 20 | 1626 |
| BCL11A-1142 | - | GCGGCCACCUGGCCGAGGCC | 20 | 1627 |
| BCL11A-1143 | - | CUGGCCGAGGCCGAGGGCCA | 20 | 1628 |
| BCL11A-1144 | - | UGGCCGAGGCCGAGGGCCAC | 20 | 1629 |
| BCL11A-1145 | - | GGGCCACAGGGACACUUGCG | 20 | 1630 |
| BCL11A-1146 | - | CGACGAAGACUCGGUGGCCG | 20 | 1631 |
| BCL11A-1147 | - | AAGACUCGGUGGCCGGCGAG | 20 | 1632 |
| BCL11A-1148 | - | UUAAUGGCCGCGGCUGCUCC | 20 | 1633 |
| BCL11A-1149 | - | UGGCCGCGGCUGCUCCCCGG | 20 | 1634 |
| BCL11A-1150 | - | GCUCCCCGGGCGAGUCGGCC | 20 | 1635 |
| BCL11A-1151 | - | CUCCCCGGGCGAGUCGGCCU | 20 | 1636 |
| BCL11A-1152 | - | UCCCCGGGCGAGUCGGCCUC | 20 | 1637 |
| BCL11A-1153 | - | CCCCGGGCGAGUCGGCCUCG | 20 | 1638 |
| BCL11A-1154 | - | GCCUGUCCAAAAAGCUGCUG | 20 | 1639 |
| BCL11A-1155 | - | UGCUGGGCAGCCCCAGCUCG | 20 | 1640 |
| BCL11A-1156 | - | CUUCUCUAAGCGCAUCAAGC | 20 | 1641 |
| BCL11A-1157 | - | UCUCUAAGCGCAUCAAGCUC | 20 | 1642 |
| BCL11A-1158 | - | CUAAGCGCAUCAAGCUCGAG | 20 | 1643 |
| BCL11A-1159 | - | UAAGCGCAUCAAGCUCGAGA | 20 | 1644 |
| BCL11A-1160 | - | CCCCGGCCGCGAUGCCCAAC | 20 | 1645 |
| BCL11A-1161 | - | CCCGGCCGCGAUGCCCAACA | 20 | 1646 |
| BCL11A-1162 | - | CGGCCGCGAUGCCCAACACG | 20 | 1647 |
| BCL11A-1163 | - | CAAAGAUCCCUUCCUUAGCU | 20 | 1648 |
| BCL11A-1164 | - | AAAGAUCCCUUCCUUAGCUU | 20 | 1649 |
| BCL11A-1165 | - | AAUCGCCUUUUGCCUCCUCG | 20 | 1650 |
| BCL11A-1166 | - | AUCGCCUUUUGCCUCCUCGU | 20 | 1651 |
| BCL11A-1167 | - | CCUCCUCGUCGGAGCACUCC | 20 | 1652 |
| BCL11A-1168 | - | CUCCUCGUCGGAGCACUCCU | 20 | 1653 |
| BCL11A-1169 | - | CCUCGUCGGAGCACUCCUCG | 20 | 1654 |
| BCL11A-1170 | - | GUCGGAGCACUCCUCGGAGA | 20 | 1655 |
| BCL11A-1171 | - | UCGGAGCACUCCUCGGAGAA | 20 | 1656 |
| BCL11A-1172 | - | CGGAGCACUCCUCGGAGAAC | 20 | 1657 |
| BCL11A-1173 | - | UUUGCGCUUCUCCACACCGC | 20 | 1658 |
| BCL11A-1174 | - | UUGCGCUUCUCCACACCGCC | 20 | 1659 |
| BCL11A-1175 | - | UGCGCUUCUCCACACCGCCC | 20 | 1660 |
| BCL11A-1176 | - | GCGCUUCUCCACACCGCCCG | 20 | 1661 |
| BCL11A-1177 | - | UCUCCACACCGCCCGGGGAG | 20 | 1662 |
| BCL11A-1178 | - | CACACCGCCCGGGGAGCUGG | 20 | 1663 |
| BCL11A-1179 | - | ACACCGCCCGGGGAGCUGGA | 20 | 1664 |
| BCL11A-1180 | - | ACCGCCCGGGGAGCUGGACG | 20 | 1665 |
| BCL11A-1181 | - | CCGCCCGGGGAGCUGGACGG | 20 | 1666 |
| BCL11A-1182 | - | GGGAGCUGGACGGAGGGAUC | 20 | 1667 |
| BCL11A-1183 | - | GGAGCUGGACGGAGGGAUCU | 20 | 1668 |
| BCL11A-1184 | - | GGAUCUCGGGGCGCAGCGGC | 20 | 1669 |
| BCL11A-1185 | - | GAUCUCGGGGCGCAGCGGCA | 20 | 1670 |
| BCL11A-1186 | - | AUCUCGGGGCGCAGCGGCAC | 20 | 1671 |
| BCL11A-1187 | - | GGGGCGCAGCGGCACGGGAA | 20 | 1672 |
| BCL11A-1188 | - | GGGCGCAGCGGCACGGGAAG | 20 | 1673 |
| BCL11A-1189 | - | GCGCAGCGGCACGGGAAGUG | 20 | 1674 |
| BCL11A-1190 | - | CGCAGCGGCACGGGAAGUGG | 20 | 1675 |
| BCL11A-1191 | - | GCAGCGGCACGGGAAGUGGA | 20 | 1676 |
| BCL11A-1192 | - | GCACGCCCCAUAUUAGUGGU | 20 | 1677 |
| BCL11A-1193 | - | CCCAUAUUAGUGGUCCGGGC | 20 | 1678 |
| BCL11A-1194 | - | CCCGGGCAGGCCCAGCUCAA | 20 | 1679 |
| BCL11A-1195 | - | CGGGCAGGCCCAGCUCAAAA | 20 | 1680 |
| BCL11A-1196 | - | UUCUCUUGCAACACGCA | 17 | 1681 |
| BCL11A-1197 | - | ACACGCACAGAACACUC | 17 | 1682 |
| BCL11A-1198 | - | CAGAACACUCAUGGAUU | 17 | 1683 |
| BCL11A-1199 | - | UGGAUUAAGAAUCUACU | 17 | 1684 |
| BCL11A-1200 | - | AAGAAUCUACUUAGAAA | 17 | 1685 |
| BCL11A-1201 | - | CUACUUAGAAAGCGAAC | 17 | 1686 |
| BCL11A-1202 | - | UACUUAGAAAGCGAACA | 17 | 1687 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1203 | - | GGAAGUCCCCUGACCCC | 17 | 1688 |
| BCL11A-1204 | - | GCGGGUUGGUAUCCCUU | 17 | 1689 |
| BCL11A-1205 | - | CCCUUCAGGACUAGGUG | 17 | 1690 |
| BCL11A-1206 | - | UUCCCAGCCACCUCUCC | 17 | 1691 |
| BCL11A-1207 | - | UCCCAGCCACCUCUCCA | 17 | 1692 |
| BCL11A-1208 | - | AACCCCUUUAACCUGCU | 17 | 1693 |
| BCL11A-1209 | - | UAACCUGCUAAGAAUAC | 17 | 1694 |
| BCL11A-1210 | - | GAAUACCAGGAUCAGUA | 17 | 1695 |
| BCL11A-1211 | - | AUACCAGGAUCAGUAUC | 17 | 1696 |
| BCL11A-1212 | - | ACCAGGAUCAGUAUCGA | 17 | 1697 |
| BCL11A-1213 | - | AGAGGCUUCCGGCCUGG | 17 | 1698 |
| BCL11A-1214 | - | GGCUUCCGGCCUGGCAG | 17 | 1699 |
| BCL11A-1215 | - | CCCUGUUUAGUCCACCA | 17 | 1700 |
| BCL11A-1216 | - | CACCACCGAGACAUCAC | 17 | 1701 |
| BCL11A-1217 | - | CUUGGACCCCCACCGCA | 17 | 1702 |
| BCL11A-1218 | - | CCCACCGCAUAGAGCGC | 17 | 1703 |
| BCL11A-1219 | - | CCACCGCAUAGAGCGCC | 17 | 1704 |
| BCL11A-1220 | - | CACCGCAUAGAGCGCCU | 17 | 1705 |
| BCL11A-1221 | - | GCAUAGAGCGCCUGGGG | 17 | 1706 |
| BCL11A-1222 | - | CAUAGAGCGCCUGGGGG | 17 | 1707 |
| BCL11A-1223 | - | AGAGCGCCUGGGGGCGG | 17 | 1708 |
| BCL11A-1224 | - | CCCUGGCCACCCAUCAC | 17 | 1709 |
| BCL11A-1225 | - | CACCCGAGUGCCUUUGA | 17 | 1710 |
| BCL11A-1226 | - | UUGACAGGGUGCUGCGG | 17 | 1711 |
| BCL11A-1227 | - | GGUUGAAUCCAAUGGCU | 17 | 1712 |
| BCL11A-1228 | - | GUUGAAUCCAAUGGCUA | 17 | 1713 |
| BCL11A-1229 | - | CUAUGGAGCCUCCCGCC | 17 | 1714 |
| BCL11A-1230 | - | CCCGCCAUGGAUUUCUC | 17 | 1715 |
| BCL11A-1231 | - | CCGCCAUGGAUUUCUCU | 17 | 1716 |
| BCL11A-1232 | - | GAUUUCUCUAGGAGACU | 17 | 1717 |
| BCL11A-1233 | - | UUUCUCUAGGAGACUUA | 17 | 1718 |
| BCL11A-1234 | - | GAGACUUAGAGAGCUGG | 17 | 1719 |
| BCL11A-1235 | - | AGACUUAGAGAGCUGGC | 17 | 1720 |
| BCL11A-1236 | - | GACUUAGAGAGCUGGCA | 17 | 1721 |
| BCL11A-1237 | - | GGUCAAGUCCAAGUCAU | 17 | 1722 |
| BCL11A-1238 | - | GCAAGACGUUCAAAUUU | 17 | 1723 |
| BCL11A-1239 | - | UGCACCGGCGCAGCCAC | 17 | 1724 |
| BCL11A-1240 | - | CCGGCGCAGCCACACGG | 17 | 1725 |
| BCL11A-1241 | - | GGCGCAGCCACACGGGC | 17 | 1726 |
| BCL11A-1242 | - | GCACCCAGGCCAGCAAG | 17 | 1727 |
| BCL11A-1243 | - | GCAAGCUGAAGCGCCAC | 17 | 1728 |
| BCL11A-1244 | - | UCUCCACCGCCAGCUCC | 17 | 1729 |
| BCL11A-1245 | - | CUCCACCGCCAGCUCCC | 17 | 1730 |
| BCL11A-1246 | - | CCGGCACCAGCGACUUG | 17 | 1731 |
| BCL11A-1247 | - | CCGUGGUGGCCAAGUUC | 17 | 1732 |
| BCL11A-1248 | - | GGUGGCCAAGUUCAAGA | 17 | 1733 |
| BCL11A-1249 | - | UGGCCAAGUUCAAGAGC | 17 | 1734 |
| BCL11A-1250 | - | ACGACCCCAACCUGAUC | 17 | 1735 |
| BCL11A-1251 | - | CGACCCCAACCUGAUCC | 17 | 1736 |
| BCL11A-1252 | - | ACCCCAACCUGAUCCCG | 17 | 1737 |
| BCL11A-1253 | - | CAACCUGAUCCCGGAGA | 17 | 1738 |
| BCL11A-1254 | - | AACCUGAUCCCGGAGAA | 17 | 1739 |
| BCL11A-1255 | - | ACCUGAUCCCGGAGAAC | 17 | 1740 |
| BCL11A-1256 | - | GAUCCCGGAGAACGGGG | 17 | 1741 |
| BCL11A-1257 | - | UCCCGGAGAACGGGGAC | 17 | 1742 |
| BCL11A-1258 | - | CCCGGAGAACGGGGACG | 17 | 1743 |
| BCL11A-1259 | - | CGGAGAACGGGGACGAG | 17 | 1744 |
| BCL11A-1260 | - | GGAGAACGGGGACGAGG | 17 | 1745 |
| BCL11A-1261 | - | GAACGGGGACGAGGAGG | 17 | 1746 |
| BCL11A-1262 | - | ACGGGGACGAGGAGGAA | 17 | 1747 |
| BCL11A-1263 | - | CGGGGACGAGGAGGAAG | 17 | 1748 |
| BCL11A-1264 | - | GGGACGAGGAGGAAGAG | 17 | 1749 |
| BCL11A-1265 | - | GGAGGAAGAGGAGGACG | 17 | 1750 |
| BCL11A-1266 | - | AGGAAGAGGAGGACGAC | 17 | 1751 |
| BCL11A-1267 | - | GGAAGAGGAGGACGACG | 17 | 1752 |
| BCL11A-1268 | - | AGAGGAGGACGACGAGG | 17 | 1753 |
| BCL11A-1269 | - | AGGAGGACGACGAGGAA | 17 | 1754 |
| BCL11A-1270 | - | GGAGGACGACGAGGAAG | 17 | 1755 |
| BCL11A-1271 | - | GGACGACGAGGAAGAGG | 17 | 1756 |
| BCL11A-1272 | - | CGACGAGGAAGAGGAAG | 17 | 1757 |
| BCL11A-1273 | - | ACGAGGAAGAGGAAGAA | 17 | 1758 |
| BCL11A-1274 | - | CGAGGAAGAGGAAGAAG | 17 | 1759 |
| BCL11A-1275 | - | AGGAAGAGGAAGAAGAG | 17 | 1760 |
| BCL11A-1276 | - | GGAAGAGGAAGAAGAGG | 17 | 1761 |

TABLE 2E-continued

*S. aureus* gRNA targets for BCL11A knockout

| gRNA Name | DNA Strand | Targeting Domain | Target Site Length | SEQ ID NO |
|---|---|---|---|---|
| BCL11A-1277 | - | AGAGGAAGAAGAGGAGG | 17 | 1762 |
| BCL11A-1278 | - | AGGAAGAAGAGGAGGAA | 17 | 1763 |
| BCL11A-1279 | - | GGAAGAAGAGGAGGAAG | 17 | 1764 |
| BCL11A-1280 | - | AAGAAGAGGAGGAAGAG | 17 | 1765 |
| BCL11A-1281 | - | AGAAGAGGAGGAAGAGG | 17 | 1766 |
| BCL11A-1282 | - | AAGAGGAGGAAGAGGAG | 17 | 1767 |
| BCL11A-1283 | - | AGAGGAGGAAGAGGAGG | 17 | 1768 |
| BCL11A-1284 | - | AGGAGGAAGAGGAGGAG | 17 | 1769 |
| BCL11A-1285 | - | GGAGGAAGAGGAGGAGG | 17 | 1770 |
| BCL11A-1286 | - | AGGAGGAGGAGGAGCUG | 17 | 1771 |
| BCL11A-1287 | - | GGAGGAGGAGGAGCUGA | 17 | 1772 |
| BCL11A-1288 | - | AGGAGGAGGAGCUGACG | 17 | 1773 |
| BCL11A-1289 | - | GGAGGAGCUGACGGAGA | 17 | 1774 |
| BCL11A-1290 | - | AGGAGCUGACGGAGAGC | 17 | 1775 |
| BCL11A-1291 | - | GAGCUGACGGAGAGCGA | 17 | 1776 |
| BCL11A-1292 | - | UGACGGAGAGCGAGAGG | 17 | 1777 |
| BCL11A-1293 | - | GAGGGUGGACUACGGCU | 17 | 1778 |
| BCL11A-1294 | - | UGGACUACGGCUUCGGG | 17 | 1779 |
| BCL11A-1295 | - | ACGGCUUCGGGCUGAGC | 17 | 1780 |
| BCL11A-1296 | - | CGGCUUCGGGCUGAGCC | 17 | 1781 |
| BCL11A-1297 | - | GGAGGCGGCGCGCCACC | 17 | 1782 |
| BCL11A-1298 | - | AGGCGGCGCGCCACCAC | 17 | 1783 |
| BCL11A-1299 | - | CACCACGAGAACAGCUC | 17 | 1784 |
| BCL11A-1300 | - | ACCACGAGAACAGCUCG | 17 | 1785 |
| BCL11A-1301 | - | GCUCGCGGGGCGCGGUC | 17 | 1786 |
| BCL11A-1302 | - | GGGGCGCGGUCGUGGGC | 17 | 1787 |
| BCL11A-1303 | - | GGUCGUGGGCGUGGGCG | 17 | 1788 |
| BCL11A-1304 | - | UCGUGGGCGUGGGCGAC | 17 | 1789 |
| BCL11A-1305 | - | CCCUGCCCGACGUCAUG | 17 | 1790 |
| BCL11A-1306 | - | CUCCAUGCAGCACUUCA | 17 | 1791 |
| BCL11A-1307 | - | AGGCCUUCCACCAGGUC | 17 | 1792 |
| BCL11A-1308 | - | CUUCCACCAGGUCCUGG | 17 | 1793 |
| BCL11A-1309 | - | UCCACCAGGUCCUGGGC | 17 | 1794 |
| BCL11A-1310 | - | UAAGCGCGGCCACCUGG | 17 | 1795 |
| BCL11A-1311 | - | CGGCCACCUGGCCGAGG | 17 | 1796 |
| BCL11A-1312 | - | GCCACCUGGCCGAGGCC | 17 | 1797 |
| BCL11A-1313 | - | GCCGAGGCCGAGGGCCA | 17 | 1798 |
| BCL11A-1314 | - | CCGAGGCCGAGGGCCAC | 17 | 1799 |
| BCL11A-1315 | - | CCACAGGGACACUUGCG | 17 | 1800 |
| BCL11A-1316 | - | CGAAGACUCGGUGGCCG | 17 | 1801 |
| BCL11A-1317 | - | ACUCGGUGGCCGGCGAG | 17 | 1802 |
| BCL11A-1318 | - | AUGGCCGCGGCUGCUCC | 17 | 1803 |
| BCL11A-1319 | - | CCGCGGCUGCUCCCCGG | 17 | 1804 |
| BCL11A-1320 | - | CCCCGGGCGAGUCGGCC | 17 | 1805 |
| BCL11A-1321 | - | CCCGGGCGAGUCGGCCU | 17 | 1806 |
| BCL11A-1322 | - | CCGGGCGAGUCGGCCUC | 17 | 1807 |
| BCL11A-1323 | - | CGGGCGAGUCGGCCUCG | 17 | 1808 |
| BCL11A-1324 | - | UGUCCAAAAAGCUGCUG | 17 | 1809 |
| BCL11A-1325 | - | UGGGCAGCCCCAGCUCG | 17 | 1810 |
| BCL11A-1326 | - | CUCUAAGCGCAUCAAGC | 17 | 1811 |
| BCL11A-1327 | - | CUAAGCGCAUCAAGCUC | 17 | 1812 |
| BCL11A-1328 | - | AGCGCAUCAAGCUCGAG | 17 | 1813 |
| BCL11A-1329 | - | GCGCAUCAAGCUCGAGA | 17 | 1814 |
| BCL11A-1330 | - | CGGCCGCGAUGCCCAAC | 17 | 1815 |
| BCL11A-1331 | - | GGCCGCGAUGCCCAACA | 17 | 1816 |
| BCL11A-1332 | - | CCGCGAUGCCCAACACG | 17 | 1817 |
| BCL11A-1333 | - | AGAUCCCUUCCUUAGCU | 17 | 1818 |
| BCL11A-1334 | - | GAUCCCUUCCUUAGCUU | 17 | 1819 |
| BCL11A-1335 | - | CGCCUUUUGCCUCCUCG | 17 | 1820 |
| BCL11A-1336 | - | GCCUUUUGCCUCCUCGU | 17 | 1821 |
| BCL11A-1337 | - | CCUCGUCGGAGCACUCC | 17 | 1822 |
| BCL11A-1338 | - | CUCGUCGGAGCACUCCU | 17 | 1823 |
| BCL11A-1339 | - | CGUCGGAGCACUCCUCG | 17 | 1824 |
| BCL11A-1340 | - | GGAGCACUCCUCGGAGA | 17 | 1825 |
| BCL11A-1341 | - | GAGCACUCCUCGGAGAA | 17 | 1826 |
| BCL11A-1342 | - | AGCACUCCUCGGAGAAC | 17 | 1827 |
| BCL11A-1343 | - | GCGCUUCUCCACACCGC | 17 | 1828 |
| BCL11A-1344 | - | CGCUUCUCCACACCGCC | 17 | 1829 |
| BCL11A-1345 | - | GCUUCUCCACACCGCCC | 17 | 1830 |
| BCL11A-1346 | - | CUUCUCCACACCGCCCG | 17 | 1831 |
| BCL11A-1347 | - | CCACACCGCCCGGGGAG | 17 | 1832 |
| BCL11A-1348 | - | ACCGCCCGGGGAGCUGG | 17 | 1833 |
| BCL11A-1349 | - | CCGCCCGGGGAGCUGGA | 17 | 1834 |
| BCL11A-1350 | - | GCCCGGGGAGCUGGACG | 17 | 1835 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1351 | - | CCCGGGGAGCUGGACGG | 17 | 1836 |
| BCL11A-1352 | - | AGCUGGACGGAGGGAUC | 17 | 1837 |
| BCL11A-1353 | - | GCUGGACGGAGGGAUCU | 17 | 1838 |
| BCL11A-1354 | - | UCUCGGGGCGCAGCGGC | 17 | 1839 |
| BCL11A-1355 | - | CUCGGGGCGCAGCGGCA | 17 | 1840 |
| BCL11A-1356 | - | UCGGGGCGCAGCGGCAC | 17 | 1841 |
| BCL11A-1357 | - | GCGCAGCGGCACGGGAA | 17 | 1842 |
| BCL11A-1358 | - | CGCAGCGGCACGGGAAG | 17 | 1843 |
| BCL11A-1359 | - | CAGCGGCACGGGAAGUG | 17 | 1844 |
| BCL11A-1360 | - | AGCGGCACGGGAAGUGG | 17 | 1845 |
| BCL11A-1361 | - | GCGGCACGGGAAGUGGA | 17 | 1846 |
| BCL11A-1362 | - | CGCCCCAUAUUAGUGGU | 17 | 1847 |
| BCL11A-1363 | - | AUAUUAGUGGUCCGGGC | 17 | 1848 |
| BCL11A-1364 | - | GGGCAGGCCCAGCUCAA | 17 | 1849 |
| BCL11A-1365 | - | GCAGGCCCAGCUCAAAA | 17 | 1850 |
| BCL11A-1366 | + | AAGUUGUACAUGUGUAGCUG | 20 | 1851 |
| BCL11A-1367 | + | GCAAGAGAAACCAUGCACUG | 20 | 1852 |
| BCL11A-1368 | + | GUGUUCUGUGCGUGUUGCAA | 20 | 1853 |
| BCL11A-1369 | + | GAGUGUUCUGUGCGUGUUGC | 20 | 1854 |
| BCL11A-1370 | + | UCUAAGUAGAUUCUUAAUCC | 20 | 1855 |
| BCL11A-1371 | + | GAUACCAACCCGCGGGGUCA | 20 | 1856 |
| BCL11A-1372 | + | GGAUACCAACCCGCGGGGUC | 20 | 1857 |
| BCL11A-1373 | + | GGGAUACCAACCCGCGGGGU | 20 | 1858 |
| BCL11A-1374 | + | CCUGAAGGGAUACCAACCCG | 20 | 1859 |
| BCL11A-1375 | + | UCCUGAAGGGAUACCAACCC | 20 | 1860 |
| BCL11A-1376 | + | CAUUCUGCACCUAGUCCUGA | 20 | 1861 |
| BCL11A-1377 | + | ACAUUCUGCACCUAGUCCUG | 20 | 1862 |
| BCL11A-1378 | + | AGGACAUUCUGCACCUAGUC | 20 | 1863 |
| BCL11A-1379 | + | CCCAUGGAGAGGUGGCUGGG | 20 | 1864 |
| BCL11A-1380 | + | AAUCCCAUGGAGAGGUGGCU | 20 | 1865 |
| BCL11A-1381 | + | GAAUCCCAUGGAGAGGUGGC | 20 | 1866 |
| BCL11A-1382 | + | UGAAUCCCAUGGAGAGGUGG | 20 | 1867 |
| BCL11A-1383 | + | UCUGCAAUAUGAAUCCCAUG | 20 | 1868 |
| BCL11A-1384 | + | UGUCUGCAAUAUGAAUCCCA | 20 | 1869 |
| BCL11A-1385 | + | UUGUCUGCAAUAUGAAUCCC | 20 | 1870 |
| BCL11A-1386 | + | AAGGGUUAUUGUCUGCAAU | 20 | 1871 |
| BCL11A-1387 | + | UGGUAUUCUUAGCAGGUUAA | 20 | 1872 |
| BCL11A-1388 | + | CUGGUAUUCUUAGCAGGUUA | 20 | 1873 |
| BCL11A-1389 | + | AAAGCGCCCUUCUGCCAGGC | 20 | 1874 |
| BCL11A-1390 | + | GAAAGCGCCCUUCUGCCAGG | 20 | 1875 |
| BCL11A-1391 | + | CUAAACAGGGGGGAGUGGG | 20 | 1876 |
| BCL11A-1392 | + | ACUAAACAGGGGGGAGUGG | 20 | 1877 |
| BCL11A-1393 | + | GUGGACUAAACAGGGGGGA | 20 | 1878 |
| BCL11A-1394 | + | GGUGGUGGACUAAACAGGGG | 20 | 1879 |
| BCL11A-1395 | + | CGGUGGUGGACUAAACAGGG | 20 | 1880 |
| BCL11A-1396 | + | UCGGUGGUGGACUAAACAGG | 20 | 1881 |
| BCL11A-1397 | + | CUCGGUGGUGGACUAAACAG | 20 | 1882 |
| BCL11A-1398 | + | UCUCGGUGGUGGACUAAACA | 20 | 1883 |
| BCL11A-1399 | + | GUCUCGGUGGUGGACUAAAC | 20 | 1884 |
| BCL11A-1400 | + | UGUCUCGGUGGUGGACUAAA | 20 | 1885 |
| BCL11A-1401 | + | GUCCAAGUGAUGUCUCGGUG | 20 | 1886 |
| BCL11A-1402 | + | CCCCAGGCGCUCUAUGCGGU | 20 | 1887 |
| BCL11A-1403 | + | CCCCCAGGCGCUCUAUGCGG | 20 | 1888 |
| BCL11A-1404 | + | GCCCCAGGCGCUCUAUGCG | 20 | 1889 |
| BCL11A-1405 | + | GCACUCGGGUGAUGGGUGGC | 20 | 1890 |
| BCL11A-1406 | + | CUGUCAAAGGCACUCGGGUG | 20 | 1891 |
| BCL11A-1407 | + | CAGCACCCUGUCAAAGGCAC | 20 | 1892 |
| BCL11A-1408 | + | GGCGGGAGGCUCCAUAGCCA | 20 | 1893 |
| BCL11A-1409 | + | CUCCUAGAGAAAUCCAUGGC | 20 | 1894 |
| BCL11A-1410 | + | UCUCCUAGAGAAAUCCAUGG | 20 | 1895 |
| BCL11A-1411 | + | GUCUCCUAGAGAAAUCCAUG | 20 | 1896 |
| BCL11A-1412 | + | CCAGCUCUCUAAGUCUCCUA | 20 | 1897 |
| BCL11A-1413 | + | UGCCAGCUCUCUAAGUCUCC | 20 | 1898 |
| BCL11A-1414 | + | GGGCCGGCCUGGGGACAGCG | 20 | 1899 |
| BCL11A-1415 | + | GCAUAGGGCUGGGCCGGCCU | 20 | 1900 |
| BCL11A-1416 | + | UGCAUAGGGCUGGGCCGGCC | 20 | 1901 |
| BCL11A-1417 | + | UUGCAUAGGGCUGGGCCGGC | 20 | 1902 |
| BCL11A-1418 | + | GCAGUAACCUUUGCAUAGGG | 20 | 1903 |
| BCL11A-1419 | + | UGGUUGCAGUAACCUUUGCA | 20 | 1904 |
| BCL11A-1420 | + | AGGGCGGCUUGCUACCUGGC | 20 | 1905 |
| BCL11A-1421 | + | AAGGGCGGCUUGCUACCUGG | 20 | 1906 |
| BCL11A-1422 | + | GGAGGGGGGCGUCGCCAGG | 20 | 1907 |
| BCL11A-1423 | + | GAGGGAGGGGGGCGUCGCC | 20 | 1908 |
| BCL11A-1424 | + | GGAGGGAGGGGGGCGUCGC | 20 | 1909 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1425 | + | CGGAUUGCAGAGGAGGGAGG | 20 | 1910 |
| BCL11A-1426 | + | GCGGAUUGCAGAGGAGGGAG | 20 | 1911 |
| BCL11A-1427 | + | GGCGGAUUGCAGAGGAGGGA | 20 | 1912 |
| BCL11A-1428 | + | GGGCGGAUUGCAGAGGAGGG | 20 | 1913 |
| BCL11A-1429 | + | GGGGCGGAUUGCAGAGGAGG | 20 | 1914 |
| BCL11A-1430 | + | GAGGGGCGGAUUGCAGAGGA | 20 | 1915 |
| BCL11A-1431 | + | GGAGGGGCGGAUUGCAGAGG | 20 | 1916 |
| BCL11A-1432 | + | AGGAGGGGCGGAUUGCAGAG | 20 | 1917 |
| BCL11A-1433 | + | GGAGGAGGGGCGGAUUGCAG | 20 | 1918 |
| BCL11A-1434 | + | GGGAGGAGGGGCGGAUUGCA | 20 | 1919 |
| BCL11A-1435 | + | GAGGGAGGAGGGGCGGAUUG | 20 | 1920 |
| BCL11A-1436 | + | GGGGCUGGGAGGGAGGAGGG | 20 | 1921 |
| BCL11A-1437 | + | ACCGGGGGCUGGGAGGGAGG | 20 | 1922 |
| BCL11A-1438 | + | GACCGGGGGCUGGGAGGGAG | 20 | 1923 |
| BCL11A-1439 | + | UUGACCGGGGGCUGGGAGGG | 20 | 1924 |
| BCL11A-1440 | + | CUUGACCGGGGGCUGGGAGG | 20 | 1925 |
| BCL11A-1441 | + | GACUUGACCGGGGGCUGGGA | 20 | 1926 |
| BCL11A-1442 | + | GGACUUGACCGGGGGCUGGG | 20 | 1927 |
| BCL11A-1443 | + | UGGACUUGACCGGGGGCUGG | 20 | 1928 |
| BCL11A-1444 | + | CUUGGACUUGACCGGGGGCU | 20 | 1929 |
| BCL11A-1445 | + | ACUUGGACUUGACCGGGGGC | 20 | 1930 |
| BCL11A-1446 | + | GACUUGGACUUGACCGGGGG | 20 | 1931 |
| BCL11A-1447 | + | CGCAUGACUUGGACUUGACC | 20 | 1932 |
| BCL11A-1448 | + | UCGCAUGACUUGGACUUGAC | 20 | 1933 |
| BCL11A-1449 | + | CUCGCAUGACUUGGACUUGA | 20 | 1934 |
| BCL11A-1450 | + | UGCCGCAGAACUCGCAUGAC | 20 | 1935 |
| BCL11A-1451 | + | GAAAUUGAACGUCUUGCCG | 20 | 1936 |
| BCL11A-1452 | + | CCACCAGGUUGCUCUGAAAU | 20 | 1937 |
| BCL11A-1453 | + | CGGUGCACCACCAGGUUGCU | 20 | 1938 |
| BCL11A-1454 | + | GGUCGCACAGGUUGCACUUG | 20 | 1939 |
| BCL11A-1455 | + | UGGCGCUUCAGCUUGCUGGC | 20 | 1940 |
| BCL11A-1456 | + | CGUCGGACUUGACCGUCAUG | 20 | 1941 |
| BCL11A-1457 | + | UCGUCGGACUUGACCGUCAU | 20 | 1942 |
| BCL11A-1458 | + | GUCGUCGGACUUGACCGUCA | 20 | 1943 |
| BCL11A-1459 | + | CGUCGUCGGACUUGACCGUC | 20 | 1944 |
| BCL11A-1460 | + | UGGCGGUGGAGAGACCGUCG | 20 | 1945 |
| BCL11A-1461 | + | GUUCCGGGGAGCUGGCGGUG | 20 | 1946 |
| BCL11A-1462 | + | GGGUUCCGGGGAGCUGGCGG | 20 | 1947 |
| BCL11A-1463 | + | CGGGUUCCGGGGAGCUGGCG | 20 | 1948 |
| BCL11A-1464 | + | GUCGCUGGUGCCGGGUUCCG | 20 | 1949 |
| BCL11A-1465 | + | AGUCGCUGGUGCCGGGUUCC | 20 | 1950 |
| BCL11A-1466 | + | AAGUCGCUGGUGCCGGGUUC | 20 | 1951 |
| BCL11A-1467 | + | CAAGUCGCUGGUGCCGGGUU | 20 | 1952 |
| BCL11A-1468 | + | UGCCCACCAAGUCGCUGGUG | 20 | 1953 |
| BCL11A-1469 | + | UGAACUUGGCCACCACGGAC | 20 | 1954 |
| BCL11A-1470 | + | CGCUCUUGAACUUGGCCACC | 20 | 1955 |
| BCL11A-1471 | + | GGUUGGGGUCGUUCUCGCUC | 20 | 1956 |
| BCL11A-1472 | + | CCCGUUCUCCGGGAUCAGGU | 20 | 1957 |
| BCL11A-1473 | + | CCCCGUUCUCCGGGAUCAGG | 20 | 1958 |
| BCL11A-1474 | + | UCCUCCUCGUCCCCGUUCUC | 20 | 1959 |
| BCL11A-1475 | + | UUCCUCCUCGUCCCCGUUCU | 20 | 1960 |
| BCL11A-1476 | + | GCGCCGCCUCCAGGCUCAGC | 20 | 1961 |
| BCL11A-1477 | + | CACGCCCACGACCGCGCCCC | 20 | 1962 |
| BCL11A-1478 | + | AUGCCCUGCAUGACGUCGGG | 20 | 1963 |
| BCL11A-1479 | + | GCACCAUGCCCUGCAUGACG | 20 | 1964 |
| BCL11A-1480 | + | CGCUGAAGUGCUGCAUGGAG | 20 | 1965 |
| BCL11A-1481 | + | GGCCUCGCUGAAGUGCUGCA | 20 | 1966 |
| BCL11A-1482 | + | AGGCCUCGCUGAAGUGCUGC | 20 | 1967 |
| BCL11A-1483 | + | GGACCUGGUGGAAGGCCUCG | 20 | 1968 |
| BCL11A-1484 | + | GCUUCUCGCCCAGGACCUGG | 20 | 1969 |
| BCL11A-1485 | + | UGCUUCUCGCCCAGGACCUG | 20 | 1970 |
| BCL11A-1486 | + | CCGCGCUUAUGCUUCUCGCC | 20 | 1971 |
| BCL11A-1487 | + | GCGGUCCGACUCGCCGGCCA | 20 | 1972 |
| BCL11A-1488 | + | CCCCGAGGCCGACUCGCCCG | 20 | 1973 |
| BCL11A-1489 | + | CCCCCGAGGCCGACUCGCCC | 20 | 1974 |
| BCL11A-1490 | + | CCCCCCGAGGCCGACUCGCC | 20 | 1975 |
| BCL11A-1491 | + | GCCCCCCGAGGCCGACUCGC | 20 | 1976 |
| BCL11A-1492 | + | CAGCUUUUUGGACAGGCCCC | 20 | 1977 |
| BCL11A-1493 | + | GGCUGCCCAGCAGCAGCUUU | 20 | 1978 |
| BCL11A-1494 | + | AGAGAAGGGGCUCAGCGAGC | 20 | 1979 |
| BCL11A-1495 | + | UAGAGAAGGGGCUCAGCGAG | 20 | 1980 |
| BCL11A-1496 | + | GCGCUUAGAGAAGGGGCUCA | 20 | 1981 |
| BCL11A-1497 | + | GAGCUUGAUGCGCUUAGAGA | 20 | 1982 |
| BCL11A-1498 | + | CGAGCUUGAUGCGCUUAGAG | 20 | 1983 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1499 | + | UCUCGAGCUUGAUGCGCUUA | 20 | 1984 |
| BCL11A-1500 | + | CUUCUCGAGCUUGAUGCGCU | 20 | 1985 |
| BCL11A-1501 | + | GGGGCAGGUCGAACUCCUUC | 20 | 1986 |
| BCL11A-1502 | + | GCAUCGCGGCCGGGGCAGG | 20 | 1987 |
| BCL11A-1503 | + | CCGUGUUGGGCAUCGCGGCC | 20 | 1988 |
| BCL11A-1504 | + | UCCGUGUUGGGCAUCGCGGC | 20 | 1989 |
| BCL11A-1505 | + | CUCCGUGUUGGGCAUCGCGG | 20 | 1990 |
| BCL11A-1506 | + | GCGAGUACACGUUCUCCGUG | 20 | 1991 |
| BCL11A-1507 | + | CGCGUAGCCGGCGAGCCACU | 20 | 1992 |
| BCL11A-1508 | + | GCCUGGAGGCCGCGUAGCCG | 20 | 1993 |
| BCL11A-1509 | + | GAAGGGAUCUUUGAGCUGCC | 20 | 1994 |
| BCL11A-1510 | + | GGAAGGGAUCUUUGAGCUGC | 20 | 1995 |
| BCL11A-1511 | + | CGAAGCUAAGGAAGGGAUCU | 20 | 1996 |
| BCL11A-1512 | + | GGAGUCUCCGAAGCUAAGGA | 20 | 1997 |
| BCL11A-1513 | + | UGGAGUCUCCGAAGCUAAGG | 20 | 1998 |
| BCL11A-1514 | + | GUCUGGAGUCUCCGAAGCUA | 20 | 1999 |
| BCL11A-1515 | + | UGUCUGGAGUCUCCGAAGCU | 20 | 2000 |
| BCL11A-1516 | + | AAGGCGAUUGUCUGGAGUCU | 20 | 2001 |
| BCL11A-1517 | + | GGAGGCAAAAGGCGAUUGUC | 20 | 2002 |
| BCL11A-1518 | + | AGGAGGCAAAAGGCGAUUGU | 20 | 2003 |
| BCL11A-1519 | + | CUCCGAGGAGUGCUCCGACG | 20 | 2004 |
| BCL11A-1520 | + | UCUCCGAGGAGUGCUCCGAC | 20 | 2005 |
| BCL11A-1521 | + | GUUCUCCGAGGAGUGCUCCG | 20 | 2006 |
| BCL11A-1522 | + | GCGCAAACUCCCGUUCUCCG | 20 | 2007 |
| BCL11A-1523 | + | AGCGCAAACUCCCGUUCUCC | 20 | 2008 |
| BCL11A-1524 | + | GAAGCGCAAACUCCCGUUCU | 20 | 2009 |
| BCL11A-1525 | + | CCAGCUCCCGGGCGUGUG | 20 | 2010 |
| BCL11A-1526 | + | GUCCAGCUCCCGGGCGGUG | 20 | 2011 |
| BCL11A-1527 | + | CGUCCAGCUCCCCGGGCGGU | 20 | 2012 |
| BCL11A-1528 | + | AGAUCCCUCCGUCCAGCUCC | 20 | 2013 |
| BCL11A-1529 | + | ACUUCCCGUGCCGCUGCGCC | 20 | 2014 |
| BCL11A-1530 | + | CCGGGCCCGGACCACUAAUA | 20 | 2015 |
| BCL11A-1531 | + | CCCGGGCCCGGACCACUAAU | 20 | 2016 |
| BCL11A-1532 | + | UGAGCUGGGCCUGCCCGGGC | 20 | 2017 |
| BCL11A-1533 | + | CUCUUUUGAGCUGGGCCUGC | 20 | 2018 |
| BCL11A-1534 | + | UGCGUCUGCCCUCUUUUGAG | 20 | 2019 |
| BCL11A-1535 | + | GUCGCUGCGUCUGCCCUCUU | 20 | 2020 |
| BCL11A-1536 | + | UUGUACAUGUGUAGCUG | 17 | 2021 |
| BCL11A-1537 | + | AGAGAAACCAUGCACUG | 17 | 2022 |
| BCL11A-1538 | + | UUCUGUGCGUGUUGCAA | 17 | 2023 |
| BCL11A-1539 | + | UGUUCUGUGCGUGUUGC | 17 | 2024 |
| BCL11A-1540 | + | AAGUAGAUUCUUAAUCC | 17 | 2025 |
| BCL11A-1541 | + | ACCAACCCGCGGGGUCA | 17 | 2026 |
| BCL11A-1542 | + | UACCAACCCGCGGGGUC | 17 | 2027 |
| BCL11A-1543 | + | AUACCAACCCGCGGGGU | 17 | 2028 |
| BCL11A-1544 | + | GAAGGGAUACCAACCCG | 17 | 2029 |
| BCL11A-1545 | + | UGAAGGGAUACCAACCC | 17 | 2030 |
| BCL11A-1546 | + | UCUGCACCUAGUCCUGA | 17 | 2031 |
| BCL11A-1547 | + | UUCUGCACCUAGUCCUG | 17 | 2032 |
| BCL11A-1548 | + | ACAUUCUGCACCUAGUC | 17 | 2033 |
| BCL11A-1549 | + | AUGGAGAGGUGGCUGGG | 17 | 2034 |
| BCL11A-1550 | + | CCCAUGGAGAGGUGGCU | 17 | 2035 |
| BCL11A-1551 | + | UCCCAUGGAGAGGUGGC | 17 | 2036 |
| BCL11A-1552 | + | AUCCCAUGGAGAGGUGG | 17 | 2037 |
| BCL11A-1553 | + | GCAAUAUGAAUCCCAUG | 17 | 2038 |
| BCL11A-1554 | + | CUGCAAUAUGAAUCCCA | 17 | 2039 |
| BCL11A-1555 | + | UCUGCAAUAUGAAUCCC | 17 | 2040 |
| BCL11A-1556 | + | GGGUUAUUGUCUGCAAU | 17 | 2041 |
| BCL11A-1557 | + | UAUUCUUAGCAGGUUAA | 17 | 2042 |
| BCL11A-1558 | + | GUAUUCUUAGCAGGUUA | 17 | 2043 |
| BCL11A-1559 | + | GCGCCCUUCUGCCAGGC | 17 | 2044 |
| BCL11A-1560 | + | AGCGCCCUUCUGCCAGG | 17 | 2045 |
| BCL11A-1561 | + | AACAGGGGGGAGUGGG | 17 | 2046 |
| BCL11A-1562 | + | AAACAGGGGGGAGUGG | 17 | 2047 |
| BCL11A-1563 | + | GACUAAACAGGGGGGA | 17 | 2048 |
| BCL11A-1564 | + | GGUGGACUAAACAGGGG | 17 | 2049 |
| BCL11A-1565 | + | UGGUGGACUAAACAGGG | 17 | 2050 |
| BCL11A-1566 | + | GUGGUGGACUAAACAGG | 17 | 2051 |
| BCL11A-1567 | + | GGUGGUGGACUAAACAG | 17 | 2052 |
| BCL11A-1568 | + | CGGUGGUGGACUAAACA | 17 | 2053 |
| BCL11A-1569 | + | UCGGUGGUGGACUAAAC | 17 | 2054 |
| BCL11A-1570 | + | CUCGGUGGUGGACUAAA | 17 | 2055 |
| BCL11A-1571 | + | CAAGUGAUGUCUCGGUG | 17 | 2056 |
| BCL11A-1572 | + | CAGGCGCUCUAUGCGGU | 17 | 2057 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1573 | + | CCAGGCGCUCUAUGCGG | 17 | 2058 |
| BCL11A-1574 | + | CCCAGGCGCUCUAUGCG | 17 | 2059 |
| BCL11A-1575 | + | CUCGGGUGAUGGGUGGC | 17 | 2060 |
| BCL11A-1576 | + | UCAAAGGCACUCGGGUG | 17 | 2061 |
| BCL11A-1577 | + | CACCCUGUCAAAGGCAC | 17 | 2062 |
| BCL11A-1578 | + | GGGAGGCUCCAUAGCCA | 17 | 2063 |
| BCL11A-1579 | + | CUAGAGAAAUCCAUGGC | 17 | 2064 |
| BCL11A-1580 | + | CCUAGAGAAAUCCAUGG | 17 | 2065 |
| BCL11A-1581 | + | UCCUAGAGAAAUCCAUG | 17 | 2066 |
| BCL11A-1582 | + | GCUCUCUAAGUCUCCUA | 17 | 2067 |
| BCL11A-1583 | + | CAGCUCUCUAAGUCUCC | 17 | 2068 |
| BCL11A-1584 | + | CCGGCCUGGGGACAGCG | 17 | 2069 |
| BCL11A-1585 | + | UAGGGCUGGGCCGGCCU | 17 | 2070 |
| BCL11A-1586 | + | AUAGGGCUGGGCCGGCC | 17 | 2071 |
| BCL11A-1587 | + | CAUAGGGCUGGGCCGGC | 17 | 2072 |
| BCL11A-1588 | + | GUAACCUUUGCAUAGGG | 17 | 2073 |
| BCL11A-1589 | + | UUGCAGUAACCUUUGCA | 17 | 2074 |
| BCL11A-1590 | + | GCGGCUUGCUACCUGGC | 17 | 2075 |
| BCL11A-1591 | + | GGCGGCUUGCUACCUGG | 17 | 2076 |
| BCL11A-1592 | + | GGGGGGGCGUCGCCAGG | 17 | 2077 |
| BCL11A-1593 | + | GGAGGGGGGCGUCGCC | 17 | 2078 |
| BCL11A-1594 | + | GGGAGGGGGGCGUCGC | 17 | 2079 |
| BCL11A-1595 | + | AUUGCAGAGGAGGGAGG | 17 | 2080 |
| BCL11A-1596 | + | GAUUGCAGAGGAGGGAG | 17 | 2081 |
| BCL11A-1597 | + | GGAUUGCAGAGGAGGGA | 17 | 2082 |
| BCL11A-1598 | + | CGGAUUGCAGAGGAGGG | 17 | 2083 |
| BCL11A-1599 | + | GCGGAUUGCAGAGGAGG | 17 | 2084 |
| BCL11A-1600 | + | GGGCGGAUUGCAGAGGA | 17 | 2085 |
| BCL11A-1601 | + | GGGGCGGAUUGCAGAGG | 17 | 2086 |
| BCL11A-1602 | + | AGGGGCGGAUUGCAGAG | 17 | 2087 |
| BCL11A-1603 | + | GGAGGGGCGGAUUGCAG | 17 | 2088 |
| BCL11A-1604 | + | AGGAGGGGCGGAUUGCA | 17 | 2089 |
| BCL11A-1605 | + | GGAGGAGGGGCGGAUUG | 17 | 2090 |
| BCL11A-1606 | + | GCUGGGAGGGAGGAGGG | 17 | 2091 |
| BCL11A-1607 | + | GGGGCUGGGAGGGAGGG | 17 | 2092 |
| BCL11A-1608 | + | CGGGGGCUGGGAGGGAG | 17 | 2093 |
| BCL11A-1609 | + | ACCGGGGGCUGGGAGGG | 17 | 2094 |
| BCL11A-1610 | + | GACCGGGGGCUGGGAGG | 17 | 2095 |
| BCL11A-1611 | + | UUGACCGGGGGCUGGGA | 17 | 2096 |
| BCL11A-1612 | + | CUUGACCGGGGGCUGGG | 17 | 2097 |
| BCL11A-1613 | + | ACUUGACCGGGGGCUGG | 17 | 2098 |
| BCL11A-1614 | + | GGACUUGACCGGGGGCU | 17 | 2099 |
| BCL11A-1615 | + | UGGACUUGACCGGGGGC | 17 | 2100 |
| BCL11A-1616 | + | UUGGACUUGACCGGGGG | 17 | 2101 |
| BCL11A-1617 | + | AUGACUUGGACUUGACC | 17 | 2102 |
| BCL11A-1618 | + | CAUGACUUGGACUUGAC | 17 | 2103 |
| BCL11A-1619 | + | GCAUGACUUGGACUUGA | 17 | 2104 |
| BCL11A-1620 | + | CGCAGAACUCGCAUGAC | 17 | 2105 |
| BCL11A-1621 | + | AUUUGAACGUCUUGCCG | 17 | 2106 |
| BCL11A-1622 | + | CCAGGUUGCUCUGAAAU | 17 | 2107 |
| BCL11A-1623 | + | UGCACCACCAGGUUGCU | 17 | 2108 |
| BCL11A-1624 | + | CGCACAGGUUGCACUUG | 17 | 2109 |
| BCL11A-1625 | + | CGCUUCAGCUUGCUGGC | 17 | 2110 |
| BCL11A-1626 | + | CGGACUUGACCGUCAUG | 17 | 2111 |
| BCL11A-1627 | + | UCGGACUUGACCGUCAU | 17 | 2112 |
| BCL11A-1628 | + | GUCGGACUUGACCGUCA | 17 | 2113 |
| BCL11A-1629 | + | CGUCGGACUUGACCGUC | 17 | 2114 |
| BCL11A-1630 | + | CGGUGGAGAGACCGUCG | 17 | 2115 |
| BCL11A-1631 | + | CCGGGGAGCUGGCGGUG | 17 | 2116 |
| BCL11A-1632 | + | UUCCGGGGAGCUGGCGG | 17 | 2117 |
| BCL11A-1633 | + | GUUCCGGGGAGCUGGCG | 17 | 2118 |
| BCL11A-1634 | + | GCUGGUGCCGGGUUCCG | 17 | 2119 |
| BCL11A-1635 | + | CGCUGGUGCCGGGUUCC | 17 | 2120 |
| BCL11A-1636 | + | UCGCUGGUGCCGGGUUC | 17 | 2121 |
| BCL11A-1637 | + | GUCGCUGGUGCCGGGUU | 17 | 2122 |
| BCL11A-1638 | + | CCACCAAGUCGCUGGUG | 17 | 2123 |
| BCL11A-1639 | + | ACUUGGCCACCACGGAC | 17 | 2124 |
| BCL11A-1640 | + | UCUUGAACUUGGCCACC | 17 | 2125 |
| BCL11A-1641 | + | UGGGGUCGUUCUCGCUC | 17 | 2126 |
| BCL11A-1642 | + | GUUCUCCGGGAUCAGGU | 17 | 2127 |
| BCL11A-1643 | + | CGUUCUCCGGGAUCAGG | 17 | 2128 |
| BCL11A-1644 | + | UCCUCGUCCCCGUUCUC | 17 | 2129 |
| BCL11A-1645 | + | CUCCUCGUCCCCGUUCU | 17 | 2130 |
| BCL11A-1646 | + | CCGCCUCCAGGCUCAGC | 17 | 2131 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1647 | + | GCCCACGACCGCGCCCC | 17 | 2132 |
| BCL11A-1648 | + | CCCUGCAUGACGUCGGG | 17 | 2133 |
| BCL11A-1649 | + | CCAUGCCCUGCAUGACG | 17 | 2134 |
| BCL11A-1650 | + | UGAAGUGCUGCAUGGAG | 17 | 2135 |
| BCL11A-1651 | + | CUCGCUGAAGUGCUGCA | 17 | 2136 |
| BCL11A-1652 | + | CCUCGCUGAAGUGCUGC | 17 | 2137 |
| BCL11A-1653 | + | CCUGGUGGAAGGCCUCG | 17 | 2138 |
| BCL11A-1654 | + | UCUCGCCCAGGACCUGG | 17 | 2139 |
| BCL11A-1655 | + | UUCUCGCCCAGGACCUG | 17 | 2140 |
| BCL11A-1656 | + | CGCUUAUGCUUCUCGCC | 17 | 2141 |
| BCL11A-1657 | + | GUCCGACUCGCCGGCCA | 17 | 2142 |
| BCL11A-1658 | + | CGAGGCCGACUCGCCCG | 17 | 2143 |
| BCL11A-1659 | + | CCGAGGCCGACUCGCCC | 17 | 2144 |
| BCL11A-1660 | + | CCCGAGGCCGACUCGCC | 17 | 2145 |
| BCL11A-1661 | + | CCCCGAGGCCGACUCGC | 17 | 2146 |
| BCL11A-1662 | + | CUUUUUGGACAGGCCCC | 17 | 2147 |
| BCL11A-1663 | + | UGCCCAGCAGCAGCUUU | 17 | 2148 |
| BCL11A-1664 | + | GAAGGGGCUCAGCGAGC | 17 | 2149 |
| BCL11A-1665 | + | AGAAGGGGCUCAGCGAG | 17 | 2150 |
| BCL11A-1666 | + | CUUAGAGAAGGGGCUCA | 17 | 2151 |
| BCL11A-1667 | + | CUUGAUGCGCUUAGAGA | 17 | 2152 |
| BCL11A-1668 | + | GCUUGAUGCGCUUAGAG | 17 | 2153 |
| BCL11A-1669 | + | CGAGCUUGAUGCGCUUA | 17 | 2154 |
| BCL11A-1670 | + | CUCGAGCUUGAUGCGCU | 17 | 2155 |
| BCL11A-1671 | + | GCAGGUCGAACUCCUUC | 17 | 2156 |
| BCL11A-1672 | + | UCGCGGCCGGGGGCAGG | 17 | 2157 |
| BCL11A-1673 | + | UGUUGGGCAUCGCGGCC | 17 | 2158 |
| BCL11A-1674 | + | GUGUUGGGCAUCGCGGC | 17 | 2159 |
| BCL11A-1675 | + | CGUGUUGGGCAUCGCGG | 17 | 2160 |
| BCL11A-1676 | + | AGUACACGUUCUCCGUG | 17 | 2161 |
| BCL11A-1677 | + | GUAGCCGGCGAGCCACU | 17 | 2162 |
| BCL11A-1678 | + | UGGAGGCCGCGUAGCCG | 17 | 2163 |
| BCL11A-1679 | + | GGGAUCUUUGAGCUGCC | 17 | 2164 |
| BCL11A-1680 | + | AGGGAUCUUUGAGCUGC | 17 | 2165 |
| BCL11A-1681 | + | AGCUAAGGAAGGGAUCU | 17 | 2166 |
| BCL11A-1682 | + | GUCUCCGAAGCUAAGGA | 17 | 2167 |
| BCL11A-1683 | + | AGUCUCCGAAGCUAAGG | 17 | 2168 |
| BCL11A-1684 | + | UGGAGUCUCCGAAGCUA | 17 | 2169 |
| BCL11A-1685 | + | CUGGAGUCUCCGAAGCU | 17 | 2170 |
| BCL11A-1686 | + | GCGAUUGUCUGGAGUCU | 17 | 2171 |
| BCL11A-1687 | + | GGCAAAAGGCGAUUGUC | 17 | 2172 |
| BCL11A-1688 | + | AGGCAAAAGGCGAUUGU | 17 | 2173 |
| BCL11A-1689 | + | CGAGGAGUGCUCCGACG | 17 | 2174 |
| BCL11A-1690 | + | CCGAGGAGUGCUCCGAC | 17 | 2175 |
| BCL11A-1691 | + | CUCCGAGGAGUGCUCCG | 17 | 2176 |
| BCL11A-1692 | + | CAAACUCCCGUUCUCCG | 17 | 2177 |
| BCL11A-1693 | + | GCAAACUCCCGUUCUCC | 17 | 2178 |
| BCL11A-1694 | + | GCGCAAACUCCCGUUCU | 17 | 2179 |
| BCL11A-1695 | + | GCUCCCCGGGCGGUGUG | 17 | 2180 |
| BCL11A-1696 | + | CAGCUCCCCGGGCGGUG | 17 | 2181 |
| BCL11A-1697 | + | CCAGCUCCCCGGGCGGU | 17 | 2182 |
| BCL11A-1698 | + | UCCCUCCGUCCAGCUCC | 17 | 2183 |
| BCL11A-1699 | + | UCCCGUGCCGCUGCGCC | 17 | 2184 |
| BCL11A-1700 | + | GGCCCGGACCACUAAUA | 17 | 2185 |
| BCL11A-1701 | + | GGGCCCGGACCACUAAU | 17 | 2186 |
| BCL11A-1702 | + | GCUGGGCCUGCCCGGGC | 17 | 2187 |
| BCL11A-1703 | + | UUUUGAGCUGGGCCUGC | 17 | 2188 |
| BCL11A-1704 | + | GUCUGCCCUCUUUUGAG | 17 | 2189 |
| BCL11A-1705 | + | GCUGCGUCUGCCCUCUU | 17 | 2190 |
| BCL11A-1706 | − | CCCCCAUUCGGCGUAGUACC | 20 | 2191 |
| BCL11A-1707 | − | CCCAUUCGGCGUAGUACCCA | 20 | 2192 |
| BCL11A-1708 | − | CUCAAGAUGUGUGGCAGUUU | 20 | 2193 |
| BCL11A-1709 | − | AGAUGUGUGGCAGUUUUCGG | 20 | 2194 |
| BCL11A-1710 | − | GAUGUGUGGCAGUUUUCGGA | 20 | 2195 |
| BCL11A-1711 | − | GGCAGUUUUCGGAUGGAAGC | 20 | 2196 |
| BCL11A-1712 | − | CAGUUUUCGGAUGGAAGCUC | 20 | 2197 |
| BCL11A-1713 | − | CCAUUCGGCGUAGUACC | 17 | 2198 |
| BCL11A-1714 | − | AUUCGGCGUAGUACCCA | 17 | 2199 |
| BCL11A-1715 | − | AAGAUGUGUGGCAGUUU | 17 | 2200 |
| BCL11A-1716 | − | UGUGUGGCAGUUUUCGG | 17 | 2201 |
| BCL11A-1717 | − | GUGUGGCAGUUUUCGGA | 17 | 2202 |
| BCL11A-1718 | − | AGUUUUCGGAUGGAAGC | 17 | 2203 |
| BCL11A-1719 | − | UUUUCGGAUGGAAGCUC | 17 | 2204 |
| BCL11A-1720 | + | ACGCCGAAUGGGGGUGUGUG | 20 | 2205 |

TABLE 2E-continued

S. aureus gRNA targets for BCL11A knockout

| gRNA Name | DNA Strand | Targeting Domain | Target Site Length | SEQ ID NO |
|---|---|---|---|---|
| BCL11A-1721 | + | ACUACGCCGAAUGGGGUGU | 20 | 2206 |
| BCL11A-1722 | + | CUCUGGGUACUACGCCGAAU | 20 | 2207 |
| BCL11A-1723 | + | UCUCUGGGUACUACGCCGAA | 20 | 2208 |
| BCL11A-1724 | + | CUCUCUGGGUACUACGCCGA | 20 | 2209 |
| BCL11A-1725 | + | UGAGCUCUCUGGGUACUACG | 20 | 2210 |
| BCL11A-1726 | + | UGCCACACAUCUUGAGCUCU | 20 | 2211 |
| BCL11A-1727 | + | UCCGAAAACUGCCACACAUC | 20 | 2212 |
| BCL11A-1728 | + | AAGGGCUCUCGAGCUUCCAU | 20 | 2213 |
| BCL11A-1729 | + | CCGAAUGGGGUGUGUG | 17 | 2214 |
| BCL11A-1730 | + | ACGCCGAAUGGGGUGU | 17 | 2215 |
| BCL11A-1731 | + | UGGGUACUACGCCGAAU | 17 | 2216 |
| BCL11A-1732 | + | CUGGGUACUACGCCGAA | 17 | 2217 |
| BCL11A-1733 | + | UCUGGGUACUACGCCGA | 17 | 2218 |
| BCL11A-1734 | + | GCUCUCUGGGUACUACG | 17 | 2219 |
| BCL11A-1735 | + | CACACAUCUUGAGCUCU | 17 | 2220 |
| BCL11A-1736 | + | GAAAACUGCCACACAUC | 17 | 2221 |
| BCL11A-1737 | + | GGCUCUCGAGCUUCCAU | 17 | 2222 |

Table 2F provides exemplary targeting domains for knocking out the BCL11A gene. In an embodiment, the targeting domain is the exact complement of the target domain. Any of the targeting domains in the table can be used with an N. meningitidis Cas9 molecule that gives double stranded cleavage. Any of the targeting domains in the table can be used with an N. meningitidis Cas9 single-stranded break nucleases (nickases). In an embodiment, dual targeting is used to create two nicks. When selecting gRNAs for use in a nickase pair, one gRNA targets a domain in the complementary strand and the second gRNA targets a domain in the non-complementary strand, e.g., a gRNA comprising any minus strand targeting domain may be paired any gRNA comprising a plus strand targeting domain targeting the same target position.

TABLE 2F

N. meningitidis gRNA targets for BCL11A knockout

| gRNA Name | DNA Strand | Targeting Domain | Target Site Length |
|---|---|---|---|
| BCL11A-1738 | − | AUCCAGGUCACGCCAGAGGA | 20 |
| BCL11A-1739 | − | UGCAACACGCACAGAACACU | 20 |
| BCL11A-1740 | − | UCCUUCCCAGCCACCUCUCC | 20 |
| BCL11A-1741 | − | AUGGCUAUGGAGCCUCCCGC | 20 |
| BCL11A-1742 | − | CAGGUCACGCCAGAGGA | 17 |

TABLE 2F-continued

N. meningitidis gRNA targets for BCL11A knockout

| gRNA Name | DNA Strand | Targeting Domain | Target Site Length |
|---|---|---|---|
| BCL11A-1743 | − | AACACGCACAGAACACU | 17 | 2228 |
| BCL11A-1744 | − | UUCCCAGCCACCUCUCC | 17 | 2229 |
| BCL11A-1745 | − | GCUAUGGAGCCUCCCGC | 17 | 2230 |
| BCL11A-1746 | + | UGAAAAAGCAUCCAAUCCC | 20 | 2231 |
| BCL11A-1747 | + | GGAGGUUGGCAUCCAGGUCA | 20 | 2232 |
| BCL11A-1748 | + | CGCCUGGGAUGAGUGCAGAA | 20 | 2233 |
| BCL11A-1749 | + | UAGAAAGCGAACACGGAAGU | 20 | 2234 |
| BCL11A-1750 | + | GGCUAUGGAGCCUCCCGCCA | 20 | 2235 |
| BCL11A-1751 | + | CCUCCUCCCUCCCAGCCCCC | 20 | 2236 |
| BCL11A-1752 | + | CCCAUGACGGUCAAGUCCGA | 20 | 2237 |
| BCL11A-1753 | + | UUUGCCUCCUCGUCGGAGCA | 20 | 2238 |
| BCL11A-1754 | + | UGAAAAAGCAUCCAAU | 17 | 2239 |
| BCL11A-1755 | + | GGAGGUUGGCAUCCAGG | 17 | 2240 |
| BCL11A-1756 | + | CGCCUGGGAUGAGUGCA | 17 | 2241 |
| BCL11A-1757 | + | UAGAAAGCGAACACGGA | 17 | 2242 |
| BCL11A-1758 | + | GGCUAUGGAGCCUCCCG | 17 | 2243 |
| BCL11A-1759 | + | CCUCCUCCCUCCCAGCC | 17 | 2244 |
| BCL11A-1760 | + | CCCAUGACGGUCAAGUC | 17 | 2245 |
| BCL11A-1761 | + | UUUGCCUCCUCGUCGGA | 17 | 2246 |

Table 3A provides exemplary targeting domains for repressing (i.e., knocking down or decreasing) expression of the BCL11A gene. In an embodiment, the targeting domain is the exact complement of the target domain. Any of the targeting domains in the table can be used with a S. pyogenes eiCas9 molecule to cause a steric block at the promoter region to block transcription resulting in the repression of the BCL11A gene. Alternatively, any of the targeting domains in the table can be used with a S. pyogenes eiCas9 fused to a transcriptional repressor to decrease transcription and therefore downregulate gene expression.

TABLE 3A

S. pyogenes gRNA targets for BCL11A knockdown

| gRNA Name | DNA Strand | Targeting Domain | Target Site Length | SEQ ID NO |
|---|---|---|---|---|
| BCL11A-1762 | − | UCUUCUCCUUGCUGCCUCUG | 20 | 2247 |
| BCL11A-1763 | − | UCCUUGCUGCCUCUGAGGUU | 20 | 2248 |
| BCL11A-1764 | − | UGCUGCCUCUGAGGUUCGGU | 20 | 2249 |
| BCL11A-1765 | − | GCUGCCUCUGAGGUUCGGUC | 20 | 2250 |
| BCL11A-1766 | − | GCCUCUGAGGUUCGGUCGGG | 20 | 2251 |
| BCL11A-1767 | − | CCUCUGAGGUUCGGUCGGGA | 20 | 2252 |

TABLE 3A-continued

S. pyogenes gRNA targets for BCL11A knockdown

| gRNA Name | DNA Strand | Targeting Domain | Target Site Length | SEQ ID NO |
|---|---|---|---|---|
| BCL11A-1768 | - | CUCUGAGGUUCGGUCGGGAG | 20 | 2253 |
| BCL11A-1769 | - | UGAGGUUCGGUCGGGAGGGG | 20 | 2254 |
| BCL11A-1770 | - | GAGGUUCGGUCGGGAGGGGA | 20 | 2255 |
| BCL11A-1771 | - | CGGUCGGGAGGGGAGGGCAG | 20 | 2256 |
| BCL11A-1772 | - | GGGGAGGGCAGCGGCAACCC | 20 | 2257 |
| BCL11A-1773 | - | GAGGGCAGCGGCAACCCAGG | 20 | 2258 |
| BCL11A-1774 | - | CAACCCAGGAGGCAGCAGUC | 20 | 2259 |
| BCL11A-1775 | - | AACCCAGGAGGCAGCAGUCC | 20 | 2260 |
| BCL11A-1776 | - | CUCCCUCUCCCGCGUGCCCC | 20 | 2261 |
| BCL11A-1777 | - | CCCCCGGCCGCCUCCUCCCC | 20 | 2262 |
| BCL11A-1778 | - | CGGCCCUAGCUCCUGCCCUU | 20 | 2263 |
| BCL11A-1779 | - | CCCUAGCUCCUGCCCUUCGG | 20 | 2264 |
| BCL11A-1780 | - | UAGCUCCUGCCCUUCGGCGG | 20 | 2265 |
| BCL11A-1781 | - | CUCCUGCCCUUCGGCGGCGG | 20 | 2266 |
| BCL11A-1782 | - | CUGCCCUUCGGCGGCGGCGG | 20 | 2267 |
| BCL11A-1783 | - | CCCUUCGGCGGCGGCGGCGG | 20 | 2268 |
| BCL11A-1784 | - | UUCGGCGGCGGCGGCGGCGG | 20 | 2269 |
| BCL11A-1785 | - | CGGCGGCGGCGGCGGCGGCG | 20 | 2270 |
| BCL11A-1786 | - | GGCGGCGGCGGCGGCGGCGC | 20 | 2271 |
| BCL11A-1787 | - | GGCGGCGGCGGCGGCGCGGG | 20 | 2272 |
| BCL11A-1788 | - | GCGGCGGCGGCGGCGCGGGA | 20 | 2273 |
| BCL11A-1789 | - | GGCGCGGGAGGGCAAGCGCG | 20 | 2274 |
| BCL11A-1790 | - | GGAGGGCAAGCGCGAGGAGC | 20 | 2275 |
| BCL11A-1791 | - | GCGCGAGGAGCCGGCACAAA | 20 | 2276 |
| BCL11A-1792 | - | GGAGCCGGCACAAAAGGCAG | 20 | 2277 |
| BCL11A-1793 | - | GAGCCGGCACAAAAGGCAGC | 20 | 2278 |
| BCL11A-1794 | - | GCGGGACAAACACCCACCUC | 20 | 2279 |
| BCL11A-1795 | - | GACAAACACCCACCUCUGGC | 20 | 2280 |
| BCL11A-1796 | - | CCACCUCUGGCCGGAACAAA | 20 | 2281 |
| BCL11A-1797 | - | CCUCUGGCCGGAACAAAAGG | 20 | 2282 |
| BCL11A-1798 | - | GGAACAAAAGGCGGCAGUGC | 20 | 2283 |
| BCL11A-1799 | - | GCCGCGUCUCCCGUCCUUCC | 20 | 2284 |
| BCL11A-1800 | - | UCCCGUCCUUCCCGGUCCCA | 20 | 2285 |
| BCL11A-1801 | - | CACGGCUCUCCCCGUCGCCG | 20 | 2286 |
| BCL11A-1802 | - | CGGCCCUCUCCCGACUCCG | 20 | 2287 |
| BCL11A-1803 | - | UCUCCCGACUCCGCGGACUC | 20 | 2288 |
| BCL11A-1804 | - | CUCCGCGGACUCAGGAGCGC | 20 | 2289 |
| BCL11A-1805 | - | UCCGCGGACUCAGGAGCGCC | 20 | 2290 |
| BCL11A-1806 | - | CCGCGGACUCAGGAGCGCCG | 20 | 2291 |
| BCL11A-1807 | - | CGCGGACUCAGGAGCGCCGG | 20 | 2292 |
| BCL11A-1808 | - | GUGCCACUUUCUCACUAUUG | 20 | 2293 |
| BCL11A-1809 | - | UGCCACUUUCUCACUAUUGU | 20 | 2294 |
| BCL11A-1810 | - | GCCACUUUCUCACUAUUGUG | 20 | 2295 |
| BCL11A-1811 | - | ACACUUGACCGUGAGCGCGC | 20 | 2296 |
| BCL11A-1812 | - | AGUCUCACCUCUUUUCUCCC | 20 | 2297 |
| BCL11A-1813 | - | GUCUCACCUCUUUUCUCCCC | 20 | 2298 |
| BCL11A-1814 | - | CCUACCCCCCAUUUUCUUA | 20 | 2299 |
| BCL11A-1815 | - | CCCCAUUUUCUUACGGUGAG | 20 | 2300 |
| BCL11A-1816 | - | CCCAUUUUCUUACGGUGAGU | 20 | 2301 |
| BCL11A-1817 | - | CCCCACCAGCUCCCACCCCC | 20 | 2302 |
| BCL11A-1818 | - | UGUUCAUUAUUUGCAAAAC | 20 | 2303 |
| BCL11A-1819 | - | UCAUUAUUUGCAAAACUGG | 20 | 2304 |
| BCL11A-1820 | - | CAUUAUUUGCAAAACUGGC | 20 | 2305 |
| BCL11A-1821 | - | AUUAUUUGCAAAACUGGCG | 20 | 2306 |
| BCL11A-1822 | - | AUUUGCAAAACUGGCGGGG | 20 | 2307 |
| BCL11A-1823 | - | UUUUGCAAAACUGGCGGGGC | 20 | 2308 |
| BCL11A-1824 | - | UUUGCAAAACUGGCGGGGCG | 20 | 2309 |
| BCL11A-1825 | - | UUGCAAAACUGGCGGGGCGG | 20 | 2310 |
| BCL11A-1826 | - | UGCAAAACUGGCGGGGCGGG | 20 | 2311 |
| BCL11A-1827 | - | GCAAAACUGGCGGGGCGGGG | 20 | 2312 |
| BCL11A-1828 | - | CAAAACUGGCGGGGCGGGGG | 20 | 2313 |
| BCL11A-1829 | - | CUGGCGGGGCGGGGGGGAG | 20 | 2314 |
| BCL11A-1830 | - | UUUCGAAAAGAGAAAUAAAG | 20 | 2315 |
| BCL11A-1831 | - | CGAAAAGAGAAAUAAAGCGG | 20 | 2316 |
| BCL11A-1832 | - | AGAGAAAUAAAGCGGCGGAA | 20 | 2317 |
| BCL11A-1833 | - | GAAAUAAAGCGGCGGAAAGG | 20 | 2318 |
| BCL11A-1834 | - | AGCGGCGGAAAGGAGGAAAG | 20 | 2319 |
| BCL11A-1835 | - | GGCGGAAAGGAGGAAAGAGG | 20 | 2320 |
| BCL11A-1836 | - | UAAAAUUAAAUAAAAUUAAA | 20 | 2321 |
| BCL11A-1837 | - | CUGUCUCAAAAGUGCAUACA | 20 | 2322 |
| BCL11A-1838 | - | CAAAAGUGCAUACACGGCAA | 20 | 2323 |
| BCL11A-1839 | - | UACACGGCAAUGGUUCCAGA | 20 | 2324 |
| BCL11A-1840 | - | ACACGGCAAUGGUUCCAGAU | 20 | 2325 |
| BCL11A-1841 | - | CAAUGGUUCCAGAUGGGAUG | 20 | 2326 |

TABLE 3A-continued

S. pyogenes gRNA targets for BCL11A knockdown

| gRNA Name | DNA Strand | Targeting Domain | Target Site Length | SEQ ID NO |
|---|---|---|---|---|
| BCL11A-1842 | − | AAUGGUUCCAGAUGGGAUGA | 20 | 2327 |
| BCL11A-1843 | − | AUCUCUUUUACCUCGACUCU | 20 | 2328 |
| BCL11A-1844 | − | UCUUUUACCUCGACUCUCGG | 20 | 2329 |
| BCL11A-1845 | − | AUAAUUAUUAUUACUAUUAU | 20 | 2330 |
| BCL11A-1846 | − | UAAUUAUUAUUACUAUUAUU | 20 | 2331 |
| BCL11A-1847 | + | UAAUAUCACGAGAGCGCGC | 20 | 2332 |
| BCL11A-1848 | + | CAGGACUAGAAGCAAAAGCG | 20 | 2333 |
| BCL11A-1849 | + | AGGACUAGAAGCAAAAGCGA | 20 | 2334 |
| BCL11A-1850 | + | GGACUAGAAGCAAAAGCGAG | 20 | 2335 |
| BCL11A-1851 | + | GACUAGAAGCAAAAGCGAGG | 20 | 2336 |
| BCL11A-1852 | + | AGCAAAAGCGAGGGGGAGAG | 20 | 2337 |
| BCL11A-1853 | + | GCAAAAGCGAGGGGGAGAGA | 20 | 2338 |
| BCL11A-1854 | + | CAAAAGCGAGGGGGAGAGAG | 20 | 2339 |
| BCL11A-1855 | + | AGAAAAACCUCCGAGAGUCG | 20 | 2340 |
| BCL11A-1856 | + | AGUCGAGGUAAAAGAGAUAA | 20 | 2341 |
| BCL11A-1857 | + | GUCGAGGUAAAAGAGAUAAA | 20 | 2342 |
| BCL11A-1858 | + | UCGAGGUAAAAGAGAUAAAG | 20 | 2343 |
| BCL11A-1859 | + | CGAGGUAAAAGAGAUAAAGG | 20 | 2344 |
| BCL11A-1860 | + | GAAAAAACCCUCAUCCCAUC | 20 | 2345 |
| BCL11A-1861 | + | CUUUAUUUCUCUUUUCGAAA | 20 | 2346 |
| BCL11A-1862 | + | CAAAAUAAUGAACAAUGCUA | 20 | 2347 |
| BCL11A-1863 | + | GAACAACUCACAUGCAAACC | 20 | 2348 |
| BCL11A-1864 | + | AACAACUCACAUGCAAACCU | 20 | 2349 |
| BCL11A-1865 | + | ACAACUCACAUGCAAACCUG | 20 | 2350 |
| BCL11A-1866 | + | CAACUCACAUGCAAACCUGG | 20 | 2351 |
| BCL11A-1867 | + | CUCACAUGCAAACCUGGGGG | 20 | 2352 |
| BCL11A-1868 | + | UCACAUGCAAACCUGGGGGU | 20 | 2353 |
| BCL11A-1869 | + | GCAAACCUGGGGGUGGGAGC | 20 | 2354 |
| BCL11A-1870 | + | AACCUGGGGGUGGGAGCUGG | 20 | 2355 |
| BCL11A-1871 | + | ACCUGGGGGUGGGAGCUGGU | 20 | 2356 |
| BCL11A-1872 | + | CCUGGGGGUGGGAGCUGGUG | 20 | 2357 |
| BCL11A-1873 | + | GGGUGGGAGCUGGUGGGGAA | 20 | 2358 |
| BCL11A-1874 | + | GGUGGGAGCUGGUGGGGAAA | 20 | 2359 |
| BCL11A-1875 | + | GGGAGCUGGUGGGGAAAGGG | 20 | 2360 |
| BCL11A-1876 | + | UCCCACUCACCGUAAGAAAA | 20 | 2361 |
| BCL11A-1877 | + | CCCACUCACCGUAAGAAAAU | 20 | 2362 |
| BCL11A-1878 | + | CCACUCACCGUAAGAAAAUG | 20 | 2363 |
| BCL11A-1879 | + | CACUCACCGUAAGAAAAUGG | 20 | 2364 |
| BCL11A-1880 | + | ACUCACCGUAAGAAAAUGGG | 20 | 2365 |
| BCL11A-1881 | + | CUCACCGUAAGAAAAUGGGG | 20 | 2366 |
| BCL11A-1882 | + | CCGUAAGAAAAUGGGGGGGU | 20 | 2367 |
| BCL11A-1883 | + | CGUAAGAAAAUGGGGGGGUA | 20 | 2368 |
| BCL11A-1884 | + | AAGAAAAUGGGGGGGUAGGG | 20 | 2369 |
| BCL11A-1885 | + | AGAAAAUGGGGGGGUAGGGA | 20 | 2370 |
| BCL11A-1886 | + | CAAGUCUAAAAAACGAUUCC | 20 | 2371 |
| BCL11A-1887 | + | AAGUCUAAAAAACGAUUCCC | 20 | 2372 |
| BCL11A-1888 | + | AGUCUAAAAAACGAUUCCCG | 20 | 2373 |
| BCL11A-1889 | + | ACGAUUCCCGGGGAGAAAAG | 20 | 2374 |
| BCL11A-1890 | + | GGGGAGAAAAGAGGUGAGAC | 20 | 2375 |
| BCL11A-1891 | + | AAAGAGGUGAGACUGGCUUU | 20 | 2376 |
| BCL11A-1892 | + | UUUGGACACCAGCGCGCUCA | 20 | 2377 |
| BCL11A-1893 | + | GCUCACGGUCAAGUGUGCAG | 20 | 2378 |
| BCL11A-1894 | + | CUCACGGUCAAGUGUGCAGC | 20 | 2379 |
| BCL11A-1895 | + | ACGGUCAAGUGUGCAGCGGG | 20 | 2380 |
| BCL11A-1896 | + | UCCCCACAAUAGUGAGAAAG | 20 | 2381 |
| BCL11A-1897 | + | AUAGUGAGAAAGUGGCACUG | 20 | 2382 |
| BCL11A-1898 | + | GAGAAAGUGGCACUGUGGAA | 20 | 2383 |
| BCL11A-1899 | + | AGAAAGUGGCACUGUGGAAA | 20 | 2384 |
| BCL11A-1900 | + | GAAAGUGGCACUGUGGAAAG | 20 | 2385 |
| BCL11A-1901 | + | GCACUGUGGAAAGGGCCCC | 20 | 2386 |
| BCL11A-1902 | + | CCCCGGCGCUCCUGAGUCCG | 20 | 2387 |
| BCL11A-1903 | + | CGCUCCUGAGUCCGCGGAGU | 20 | 2388 |
| BCL11A-1904 | + | GCUCCUGAGUCCGCGGAGUC | 20 | 2389 |
| BCL11A-1905 | + | UGAGUCCGCGGAGUCGGGAG | 20 | 2390 |
| BCL11A-1906 | + | GAGUCCGCGGAGUCGGGAGA | 20 | 2391 |
| BCL11A-1907 | + | AGUCCGCGGAGUCGGGAGAG | 20 | 2392 |
| BCL11A-1908 | + | CGGAGUCGGGAGAGGGGCCG | 20 | 2393 |
| BCL11A-1909 | + | CGGGAGAGGGGCCGCGGCGA | 20 | 2394 |
| BCL11A-1910 | + | GGGAGAGGGGCCGCGGCGAC | 20 | 2395 |
| BCL11A-1911 | + | GGAGAGGGGCCGCGGCGACG | 20 | 2396 |
| BCL11A-1912 | + | CGCGGCGACGGGGAGAGCCG | 20 | 2397 |
| BCL11A-1913 | + | GCGGCGACGGGGAGAGCCGU | 20 | 2398 |
| BCL11A-1914 | + | GACGGGGAGAGCCGUGGGAC | 20 | 2399 |
| BCL11A-1915 | + | ACGGGGAGAGCCGUGGGACC | 20 | 2400 |

TABLE 3A-continued

S. pyogenes gRNA targets for BCL11A knockdown

| gRNA Name | DNA Strand | Targeting Domain | Target Site Length | SEQ ID NO |
|---|---|---|---|---|
| BCL11A-1916 | + | GGAGAGCCGUGGGACCGGGA | 20 | 2401 |
| BCL11A-1917 | + | AGCCGUGGGACCGGGAAGGA | 20 | 2402 |
| BCL11A-1918 | + | GCCGUGGGACCGGGAAGGAC | 20 | 2403 |
| BCL11A-1919 | + | ACCGGGAAGGACGGGAGACG | 20 | 2404 |
| BCL11A-1920 | + | GGAAGGACGGGAGACGCGGC | 20 | 2405 |
| BCL11A-1921 | + | GGCACUGCCGCCUUUUGUUC | 20 | 2406 |
| BCL11A-1922 | + | CCGCCUUUUGUUCCGGCCAG | 20 | 2407 |
| BCL11A-1923 | + | CCUUUUGUUCCGGCCAGAGG | 20 | 2408 |
| BCL11A-1924 | + | CUUUUGUUCCGGCCAGAGGU | 20 | 2409 |
| BCL11A-1925 | + | UGUCCCGCUGCCUUUUGUGC | 20 | 2410 |
| BCL11A-1926 | + | GCCGCCGCCGCCGCCGCCGA | 20 | 2411 |
| BCL11A-1927 | + | CCGCCGCCGCCGCCGCCGAA | 20 | 2412 |
| BCL11A-1928 | + | CGCCGCCGCCGCCGAAGGGC | 20 | 2413 |
| BCL11A-1929 | + | GCCGCCGAAGGGCAGGAGCU | 20 | 2414 |
| BCL11A-1930 | + | CCGCCGAAGGGCAGGAGCUA | 20 | 2415 |
| BCL11A-1931 | + | CGAAGGGCAGGAGCUAGGGC | 20 | 2416 |
| BCL11A-1932 | + | GAAGGGCAGGAGCUAGGGCC | 20 | 2417 |
| BCL11A-1933 | + | AAGGGCAGGAGCUAGGGCCG | 20 | 2418 |
| BCL11A-1934 | + | AGGGCAGGAGCUAGGGCCGG | 20 | 2419 |
| BCL11A-1935 | + | GCAGGAGCUAGGGCCGGGGG | 20 | 2420 |
| BCL11A-1936 | + | GGAGCUAGGGCCGGGGGAGG | 20 | 2421 |
| BCL11A-1937 | + | GCUAGGGCCGGGGGAGGAGG | 20 | 2422 |
| BCL11A-1938 | + | GGGCCGGGGGAGGAGGCGGC | 20 | 2423 |
| BCL11A-1939 | + | GGCCGGGGGAGGAGGCGGCC | 20 | 2424 |
| BCL11A-1940 | + | GCCGGGGGAGGAGGCGGCCG | 20 | 2425 |
| BCL11A-1941 | + | CCGGGGGAGGAGGCGGCCGG | 20 | 2426 |
| BCL11A-1942 | + | AGGAGGCGGCCGGGGGCACG | 20 | 2427 |
| BCL11A-1943 | + | GGAGGCGGCCGGGGGCACGC | 20 | 2428 |
| BCL11A-1944 | + | CGGCCGGGGGCACGCGGGAG | 20 | 2429 |
| BCL11A-1945 | + | GGCCGGGGGCACGCGGGAGA | 20 | 2430 |
| BCL11A-1946 | + | CGGGGGCACGCGGGAGAGGG | 20 | 2431 |
| BCL11A-1947 | + | GGGGGCACGCGGGAGAGGGA | 20 | 2432 |
| BCL11A-1948 | + | GGCACGCGGGAGAGGGAGGG | 20 | 2433 |
| BCL11A-1949 | + | GCACGCGGGAGAGGGAGGGA | 20 | 2434 |
| BCL11A-1950 | + | GGAGAGGGAGGGAGGGAGCC | 20 | 2435 |
| BCL11A-1951 | + | GAGCCCGGACUGCUGCCUCC | 20 | 2436 |
| BCL11A-1952 | + | AGCCCGGACUGCUGCCUCCU | 20 | 2437 |
| BCL11A-1953 | + | CCCUCCCGACCGAACCUCAG | 20 | 2438 |
| BCL11A-1954 | + | ACCGAACCUCAGAGGCAGCA | 20 | 2439 |
| BCL11A-1955 | + | AGAGGCAGCAAGGAGAAGAC | 20 | 2440 |
| BCL11A-1956 | + | AAAAUAAAAUAAAAUAAAACA | 20 | 2441 |
| BCL11A-1957 | − | UCUCCUUGCUGCCUCUG | 17 | 2442 |
| BCL11A-1958 | − | UUGCUGCCUCUGAGGUU | 17 | 2443 |
| BCL11A-1959 | − | UGCCUCUGAGGUUCGGU | 17 | 2444 |
| BCL11A-1960 | − | GCCUCUGAGGUUCGGUC | 17 | 2445 |
| BCL11A-1961 | − | UCUGAGGUUCGGUCGGG | 17 | 2446 |
| BCL11A-1962 | − | CUGAGGUUCGGUCGGGA | 17 | 2447 |
| BCL11A-1963 | − | UGAGGUUCGGUCGGGAG | 17 | 2448 |
| BCL11A-1964 | − | GGUUCGGUCGGGAGGGG | 17 | 2449 |
| BCL11A-1965 | − | GUUCGGUCGGGAGGGGA | 17 | 2450 |
| BCL11A-1966 | − | UCGGGAGGGGAGGGCAG | 17 | 2451 |
| BCL11A-1967 | − | GAGGGCAGCGGCAACCC | 17 | 2452 |
| BCL11A-1968 | − | GGCAGCGGCAACCCAGG | 17 | 2453 |
| BCL11A-1969 | − | CCCAGGAGGCAGCAGUC | 17 | 2454 |
| BCL11A-1970 | − | CCAGGAGGCAGCAGUCC | 17 | 2455 |
| BCL11A-1971 | − | CCUCUCCCGCGUGCCCC | 17 | 2456 |
| BCL11A-1972 | − | CCGGCCGCCUCCUCCCC | 17 | 2457 |
| BCL11A-1973 | − | CCCUAGCUCCUGCCCUU | 17 | 2458 |
| BCL11A-1974 | − | UAGCUCCUGCCCUUCGG | 17 | 2459 |
| BCL11A-1975 | − | CUCCUGCCCUUCGGCGG | 17 | 2460 |
| BCL11A-1976 | − | CUGCCCUUCGGCGGCGG | 17 | 2461 |
| BCL11A-1977 | − | CCCUUCGGCGGCGGCGG | 17 | 2462 |
| BCL11A-1978 | − | UUCGGCGGCGGCGGCGG | 17 | 2463 |
| BCL11A-1979 | − | GGCGGCGCGGCGGCGG | 17 | 2464 |
| BCL11A-1980 | − | CGGCGGCGGCGGCGGCG | 17 | 2465 |
| BCL11A-1981 | − | GGCGGCGGCGGCGGCGC | 17 | 2466 |
| BCL11A-1982 | − | GGCGGCGGCGGCGCGGG | 17 | 2467 |
| BCL11A-1983 | − | GCGGCGGCGGCGCGGGA | 17 | 2468 |
| BCL11A-1984 | − | GCGGGAGGGCAAGCGCG | 17 | 2469 |
| BCL11A-1985 | − | GGGCAAGCGCGAGGAGC | 17 | 2470 |
| BCL11A-1986 | − | CGAGGAGCCGGACACAAA | 17 | 2471 |
| BCL11A-1987 | − | GCCGGCACAAAAGGCAG | 17 | 2472 |
| BCL11A-1988 | − | CCGGCACAAAAGGCAGC | 17 | 2473 |
| BCL11A-1989 | − | GGACAAACACCCACCUC | 17 | 2474 |

TABLE 3A-continued

*S. pyogenes* gRNA targets for BCL11A knockdown

| gRNA Name | DNA Strand | Targeting Domain | Target Site Length | SEQ ID NO |
|---|---|---|---|---|
| BCL11A-1990 | - | AAACACCCACCUCUGGC | 17 | 2475 |
| BCL11A-1991 | - | CCUCUGGCCGGAACAAA | 17 | 2476 |
| BCL11A-1992 | - | CUGGCCGGAACAAAAGG | 17 | 2477 |
| BCL11A-1993 | - | ACAAAAGGCGGCAGUGC | 17 | 2478 |
| BCL11A-1994 | - | GCGUCUCCCGUCCUUCC | 17 | 2479 |
| BCL11A-1995 | - | CGUCCUUCCCGGUCCCA | 17 | 2480 |
| BCL11A-1996 | - | GGCUCUCCCCGUCGCCG | 17 | 2481 |
| BCL11A-1997 | - | CCCCUCUCCCGACUCCG | 17 | 2482 |
| BCL11A-1998 | - | CCCGACUCCGCGGACUC | 17 | 2483 |
| BCL11A-1999 | - | CGCGGACUCAGGAGCGC | 17 | 2484 |
| BCL11A-2000 | - | GCGGACUCAGGAGCGCC | 17 | 2485 |
| BCL11A-2001 | - | CGGACUCAGGAGCGCCG | 17 | 2486 |
| BCL11A-2002 | - | GGACUCAGGAGCGCCGG | 17 | 2487 |
| BCL11A-2003 | - | CCACUUUCUCACUAUUG | 17 | 2488 |
| BCL11A-2004 | - | CACUUUCUCACUAUUGU | 17 | 2489 |
| BCL11A-2005 | - | ACUUUCUCACUAUUGUG | 17 | 2490 |
| BCL11A-2006 | - | CUUGACCGUGAGCGCGC | 17 | 2491 |
| BCL11A-2007 | - | CUCACCUCUUUUCUCCC | 17 | 2492 |
| BCL11A-2008 | - | UCACCUCUUUUCUCCCC | 17 | 2493 |
| BCL11A-2009 | - | ACCCCCCCAUUUUCUUA | 17 | 2494 |
| BCL11A-2010 | - | CAUUUUCUUACGGUGAG | 17 | 2495 |
| BCL11A-2011 | - | AUUUUCUUACGGUGAGU | 17 | 2496 |
| BCL11A-2012 | - | CACCAGCUCCCACCCCC | 17 | 2497 |
| BCL11A-2013 | - | UCAUUAUUUGCAAAAC | 17 | 2498 |
| BCL11A-2014 | - | UUAUUUGCAAAACUGG | 17 | 2499 |
| BCL11A-2015 | - | UAUUUGCAAAACUGGC | 17 | 2500 |
| BCL11A-2016 | - | AUUUGCAAAACUGGCG | 17 | 2501 |
| BCL11A-2017 | - | UUGCAAAACUGGCGGGG | 17 | 2502 |
| BCL11A-2018 | - | UGCAAAACUGGCGGGGC | 17 | 2503 |
| BCL11A-2019 | - | GCAAAACUGGCGGGGCG | 17 | 2504 |
| BCL11A-2020 | - | CAAAACUGGCGGGGCGG | 17 | 2505 |
| BCL11A-2021 | - | AAAACUGGCGGGGCGGG | 17 | 2506 |
| BCL11A-2022 | - | AAACUGGCGGGGCGGGG | 17 | 2507 |
| BCL11A-2023 | - | AACUGGCGGGGCGGGGG | 17 | 2508 |
| BCL11A-2024 | - | GCGGGGCGGGGGGGAG | 17 | 2509 |
| BCL11A-2025 | - | CGAAAAGAGAAAUAAAG | 17 | 2510 |
| BCL11A-2026 | - | AAAGAGAAAUAAAGCGG | 17 | 2511 |
| BCL11A-2027 | - | GAAAUAAAGCGGCGGAA | 17 | 2512 |
| BCL11A-2028 | - | AUAAAGCGGCGGAAAGG | 17 | 2513 |
| BCL11A-2029 | - | GGCGGAAAGGAGGAAAG | 17 | 2514 |
| BCL11A-2030 | - | GGAAAGGAGGAAAGAGG | 17 | 2515 |
| BCL11A-2031 | - | AAUUAAAUAAAAUUAAA | 17 | 2516 |
| BCL11A-2032 | - | UCUCAAAAGUGCAUACA | 17 | 2517 |
| BCL11A-2033 | - | AAGUGCAUACACGGCAA | 17 | 2518 |
| BCL11A-2034 | - | ACGGCAAUGGUUCCAGA | 17 | 2519 |
| BCL11A-2035 | - | CGGCAAUGGUUCCAGAU | 17 | 2520 |
| BCL11A-2036 | - | UGGUUCCAGAUGGGAUG | 17 | 2521 |
| BCL11A-2037 | - | GGUUCCAGAUGGGAUGA | 17 | 2522 |
| BCL11A-2038 | - | UCUUUUACCUCGACUCU | 17 | 2523 |
| BCL11A-2039 | - | UUUACCUCGACUCUCGG | 17 | 2524 |
| BCL11A-2040 | - | AUUAUUAUUACUAUUAU | 17 | 2525 |
| BCL11A-2041 | - | UUAUUAUUACUAUUAUU | 17 | 2526 |
| BCL11A-2042 | + | UAAUCACGAGAGCGCGC | 17 | 2527 |
| BCL11A-2043 | + | GACUAGAAGCAAAAGCG | 17 | 2528 |
| BCL11A-2044 | + | ACUAGAAGCAAAAGCGA | 17 | 2529 |
| BCL11A-2045 | + | CUAGAAGCAAAAGCGAG | 17 | 2530 |
| BCL11A-2046 | + | UAGAAGCAAAAGCGAGG | 17 | 2531 |
| BCL11A-2047 | + | AAAAGCGAGGGGGAGAG | 17 | 2532 |
| BCL11A-2048 | + | AAAGCGAGGGGGAGAGA | 17 | 2533 |
| BCL11A-2049 | + | AAGCGAGGGGGAGAGAG | 17 | 2534 |
| BCL11A-2050 | + | AAAACCUCCGAGAGUCG | 17 | 2535 |
| BCL11A-2051 | + | CGAGGUAAAAGAGAUAA | 17 | 2536 |
| BCL11A-2052 | + | GAGGUAAAAGAGAUAAA | 17 | 2537 |
| BCL11A-2053 | + | AGGUAAAAGAGAUAAAG | 17 | 2538 |
| BCL11A-2054 | + | GGUAAAAGAGAUAAAGG | 17 | 2539 |
| BCL11A-2055 | + | AAAACCCUCAUCCCAUC | 17 | 2540 |
| BCL11A-2056 | + | UAUUUCUCUUUUCGAAA | 17 | 2541 |
| BCL11A-2057 | + | AAUAAUGAACAAUGCUA | 17 | 2542 |
| BCL11A-2058 | + | CAACUCACAUGCAAACC | 17 | 2543 |
| BCL11A-2059 | + | AACUCACAUGCAAACCU | 17 | 2544 |
| BCL11A-2060 | + | ACUCACAUGCAAACCUG | 17 | 2545 |
| BCL11A-2061 | + | CUCACAUGCAAACCUGG | 17 | 2546 |
| BCL11A-2062 | + | ACAUGCAAACCUGGGGG | 17 | 2547 |
| BCL11A-2063 | + | CAUGCAAACCUGGGGGU | 17 | 2548 |

TABLE 3A-continued

S. pyogenes gRNA targets for BCL11A knockdown

| gRNA Name | DNA Strand | Targeting Domain | Target Site Length | SEQ ID NO |
|---|---|---|---|---|
| BCL11A-2064 | + | AACCUGGGGGUGGGAGC | 17 | 2549 |
| BCL11A-2065 | + | CUGGGGGUGGGAGCUGG | 17 | 2550 |
| BCL11A-2066 | + | UGGGGGUGGGAGCUGGU | 17 | 2551 |
| BCL11A-2067 | + | GGGGGUGGGAGCUGGUG | 17 | 2552 |
| BCL11A-2068 | + | UGGGAGCUGGUGGGGAA | 17 | 2553 |
| BCL11A-2069 | + | GGGAGCUGGUGGGGAAA | 17 | 2554 |
| BCL11A-2070 | + | AGCUGGUGGGGAAAGGG | 17 | 2555 |
| BCL11A-2071 | + | CACUCACCGUAAGAAAA | 17 | 2556 |
| BCL11A-2072 | + | ACUCACCGUAAGAAAAU | 17 | 2557 |
| BCL11A-2073 | + | CUCACCGUAAGAAAAUG | 17 | 2558 |
| BCL11A-2074 | + | UCACCGUAAGAAAAUGG | 17 | 2559 |
| BCL11A-2075 | + | CACCGUAAGAAAAUGGG | 17 | 2560 |
| BCL11A-2076 | + | ACCGUAAGAAAAUGGGG | 17 | 2561 |
| BCL11A-2077 | + | UAAGAAAAUGGGGGGU | 17 | 2562 |
| BCL11A-2078 | + | AAGAAAAUGGGGGGUA | 17 | 2563 |
| BCL11A-2079 | + | AAAAUGGGGGGUAGGG | 17 | 2564 |
| BCL11A-2080 | + | AAAUGGGGGGUAGGGA | 17 | 2565 |
| BCL11A-2081 | + | GUCUAAAAACGAUUCC | 17 | 2566 |
| BCL11A-2082 | + | UCUAAAAACGAUUCCC | 17 | 2567 |
| BCL11A-2083 | + | CUAAAAACGAUUCCCG | 17 | 2568 |
| BCL11A-2084 | + | AUUCCGGGGAGAAAAG | 17 | 2569 |
| BCL11A-2085 | + | GAGAAAAGAGGUGAGAC | 17 | 2570 |
| BCL11A-2086 | + | GAGGUGAGACUGGCUUU | 17 | 2571 |
| BCL11A-2087 | + | GGACACCAGCGCGCUCA | 17 | 2572 |
| BCL11A-2088 | + | CACGGUCAAGUGUGCAG | 17 | 2573 |
| BCL11A-2089 | + | ACGGUCAAGUGUGCAGC | 17 | 2574 |
| BCL11A-2090 | + | GUCAAGUGUGCAGCGGG | 17 | 2575 |
| BCL11A-2091 | + | CCACAAUAGUGAGAAAG | 17 | 2576 |
| BCL11A-2092 | + | GUGAGAAAGUGGCACUG | 17 | 2577 |
| BCL11A-2093 | + | AAAGUGGCACUGUGGAA | 17 | 2578 |
| BCL11A-2094 | + | AAGUGGCACUGUGGAAA | 17 | 2579 |
| BCL11A-2095 | + | AGUGGCACUGUGGAAAG | 17 | 2580 |
| BCL11A-2096 | + | CUGUGGAAAGGGGCCCC | 17 | 2581 |
| BCL11A-2097 | + | CGGCGCUCCUGAGUCCG | 17 | 2582 |
| BCL11A-2098 | + | UCCUGAGUCCGCGGAGU | 17 | 2583 |
| BCL11A-2099 | + | CCUGAGUCCGCGGAGUC | 17 | 2584 |
| BCL11A-2100 | + | GUCCGCGGAGUCGGGAG | 17 | 2585 |
| BCL11A-2101 | + | UCCGCGGAGUCGGGAGA | 17 | 2586 |
| BCL11A-2102 | + | CCGCGGAGUCGGGAGAG | 17 | 2587 |
| BCL11A-2103 | + | AGUCGGGAGAGGGGCCG | 17 | 2588 |
| BCL11A-2104 | + | GAGAGGGGCCGCGGCGA | 17 | 2589 |
| BCL11A-2105 | + | AGAGGGGCCGCGGCGAC | 17 | 2590 |
| BCL11A-2106 | + | GAGGGGCCGCGGCGACG | 17 | 2591 |
| BCL11A-2107 | + | GGCGACGGGGAGAGCCG | 17 | 2592 |
| BCL11A-2108 | + | GCGACGGGGAGAGCCGU | 17 | 2593 |
| BCL11A-2109 | + | GGGGAGAGCCGUGGGAC | 17 | 2594 |
| BCL11A-2110 | + | GGGAGAGCCGUGGGACC | 17 | 2595 |
| BCL11A-2111 | + | GAGCCGUGGGACCGGGA | 17 | 2596 |
| BCL11A-2112 | + | CGUGGGACCGGGAAGGA | 17 | 2597 |
| BCL11A-2113 | + | GUGGGACCGGGAAGGAC | 17 | 2598 |
| BCL11A-2114 | + | GGGAAGGACGGGAGACG | 17 | 2599 |
| BCL11A-2115 | + | AGGACGGGAGACGCGGC | 17 | 2600 |
| BCL11A-2116 | + | ACUGCCGCCUUUUGUUC | 17 | 2601 |
| BCL11A-2117 | + | CCUUUUGUUCCGGCCAG | 17 | 2602 |
| BCL11A-2118 | + | UUUGUUCCGGCCAGAGG | 17 | 2603 |
| BCL11A-2119 | + | UUGUUCCGGCCAGAGGU | 17 | 2604 |
| BCL11A-2120 | + | CCCGCUGCCUUUUGUGC | 17 | 2605 |
| BCL11A-2121 | + | GCCGCCGCCGCCGCCGA | 17 | 2606 |
| BCL11A-2122 | + | CCGCCGCCGCCGCCGAA | 17 | 2607 |
| BCL11A-2123 | + | CGCCGCCGCCGAAGGGC | 17 | 2608 |
| BCL11A-2124 | + | GCCGAAGGGCAGGAGCU | 17 | 2609 |
| BCL11A-2125 | + | CCGAAGGGCAGGAGCUA | 17 | 2610 |
| BCL11A-2126 | + | AGGGCAGGAGCUAGGGC | 17 | 2611 |
| BCL11A-2127 | + | GGGCAGGAGCUAGGGCC | 17 | 2612 |
| BCL11A-2128 | + | GGCAGGAGCUAGGGCCG | 17 | 2613 |
| BCL11A-2129 | + | GCAGGAGCUAGGGCCGG | 17 | 2614 |
| BCL11A-2130 | + | GGAGCUAGGGCCGGGGG | 17 | 2615 |
| BCL11A-2131 | + | GCUAGGGCCGGGGAGG | 17 | 2616 |
| BCL11A-2132 | + | AGGGCCGGGGAGGAGG | 17 | 2617 |
| BCL11A-2133 | + | CCGGGGAGGAGGCGGC | 17 | 2618 |
| BCL11A-2134 | + | CGGGGAGGAGGCGGCC | 17 | 2619 |
| BCL11A-2135 | + | GGGGAGGAGGCGGCCG | 17 | 2620 |
| BCL11A-2136 | + | GGGAGGAGGCGGCCGG | 17 | 2621 |
| BCL11A-2137 | + | AGGCGGCCGGGGGCACG | 17 | 2622 |

TABLE 3A-continued

S. pyogenes gRNA targets for BCL11A knockdown

| gRNA Name | DNA Strand | Targeting Domain | Target Site Length | SEQ ID NO |
|---|---|---|---|---|
| BCL11A-2138 | + | GGCGGCCGGGGGCACGC | 17 | 2623 |
| BCL11A-2139 | + | CCGGGGGCACGCGGGAG | 17 | 2624 |
| BCL11A-2140 | + | CGGGGGCACGCGGGAGA | 17 | 2625 |
| BCL11A-2141 | + | GGGCACGCGGGAGAGGG | 17 | 2626 |
| BCL11A-2142 | + | GGCACGCGGGAGAGGGA | 17 | 2627 |
| BCL11A-2143 | + | ACGCGGGAGAGGGAGGG | 17 | 2628 |
| BCL11A-2144 | + | CGCGGGAGAGGGAGGGA | 17 | 2629 |
| BCL11A-2145 | + | GAGGGAGGGAGGGAGCC | 17 | 2630 |
| BCL11A-2146 | + | CCCGGACUGCUGCCUCC | 17 | 2631 |
| BCL11A-2147 | + | CCGGACUGCUGCCUCCU | 17 | 2632 |
| BCL11A-2148 | + | UCCCGACCGAACCUCAG | 17 | 2633 |
| BCL11A-2149 | + | GAACCUCAGAGGCAGCA | 17 | 2634 |
| BCL11A-2150 | + | GGCAGCAAGGAGAAGAC | 17 | 2635 |
| BCL11A-2151 | + | AUAAAAUAAAUAAAACA | 17 | 2636 |

Table 3B provides exemplary targeting domains for repressing (i.e., knocking down or decreasing) expression of the BCL11A gene. Any of the targeting domains in the table can be used with a S. aureus eiCas9 molecule to cause a steric block in the promoter region to block transcription elongation resulting in the repression of the BCL11A gene. Any of the targeting domains in the table can be used with a S. aureus eiCas9 fused to a transcriptional repressor to decrease transcription and therefore downregulate gene expression.

TABLE 3B

S. aureus gRNA targets for BCL11A knockdown

| gRNA Name | DNA Strand | Targeting Domain | Target Site Length | SEQ ID NO |
|---|---|---|---|---|
| BCL11A-2152 | − | CAGUCUUCUCCUUGCUGCCU | 20 | 2637 |
| BCL11A-2153 | − | UUGCUGCCUCUGAGGUUCGG | 20 | 2638 |
| BCL11A-2154 | − | UGCUGCCUCUGAGGUUCGGU | 20 | 2639 |
| BCL11A-2155 | − | GCUGCCUCUGAGGUUCGGUC | 20 | 2640 |
| BCL11A-2156 | − | UGCCUCUGAGGUUCGGUCGG | 20 | 2641 |
| BCL11A-2157 | − | GCCUCUGAGGUUCGGUCGGG | 20 | 2642 |
| BCL11A-2158 | − | CCUCUGAGGUUCGGUCGGGA | 20 | 2643 |
| BCL11A-2159 | − | CUCUGAGGUUCGGUCGGGAG | 20 | 2644 |
| BCL11A-2160 | − | CUGAGGUUCGGUCGGGAGGG | 20 | 2645 |
| BCL11A-2161 | − | AGGGGAGGGCAGCGGCAACC | 20 | 2646 |
| BCL11A-2162 | − | GGGGAGGGCAGCGGCAACCC | 20 | 2647 |
| BCL11A-2163 | − | GCAACCCAGGAGGCAGCAGU | 20 | 2648 |
| BCL11A-2164 | − | GCGGCGGCGGCGGCGGCGGC | 20 | 2649 |
| BCL11A-2165 | − | CGGCGGCGGCGGCGGCGGCG | 20 | 2650 |
| BCL11A-2166 | − | GGCGGCGGCGGCGGCGGCGC | 20 | 2651 |
| BCL11A-2167 | − | CGGCGGCGGCGGCGGCGCGG | 20 | 2652 |
| BCL11A-2168 | − | GGCGGCGCGGGAGGGCAAGC | 20 | 2653 |
| BCL11A-2169 | − | CGGCGCGGGAGGGCAAGCGC | 20 | 2654 |
| BCL11A-2170 | − | GGCGCGGGAGGGCAAGCGCG | 20 | 2655 |
| BCL11A-2171 | − | AGGAGCCGGCACAAAAGGCA | 20 | 2656 |
| BCL11A-2172 | − | GGAGCCGGCACAAAAGGCAG | 20 | 2657 |
| BCL11A-2173 | − | GGACAAACACCCACCUCUGG | 20 | 2658 |
| BCL11A-2174 | − | GACAAACACCCACCUCUGGC | 20 | 2659 |
| BCL11A-2175 | − | GCGGCCCCUCUCCCGACUCC | 20 | 2660 |
| BCL11A-2176 | − | CUCUCCCGACUCCGCGGACU | 20 | 2661 |
| BCL11A-2177 | − | UCUCCCGACUCCGCGGACUC | 20 | 2662 |
| BCL11A-2178 | − | ACUCCGCGGACUCAGGAGCG | 20 | 2663 |
| BCL11A-2179 | − | CUCCGCGGACUCAGGAGCGC | 20 | 2664 |
| BCL11A-2180 | − | UCCGCGGACUCAGGAGCGCC | 20 | 2665 |
| BCL11A-2181 | − | AGUGCCACUUUCUCACUAUU | 20 | 2666 |
| BCL11A-2182 | − | GUGCCACUUUCUCACUAUUG | 20 | 2667 |
| BCL11A-2183 | − | UGCCACUUUCUCACUAUUGU | 20 | 2668 |
| BCL11A-2184 | − | CUCCCGCUGCACACUUGACC | 20 | 2669 |
| BCL11A-2185 | − | CAGUCUCACCUCUUUUCUCC | 20 | 2670 |
| BCL11A-2186 | − | AGUCUCACCUCUUUUCUCCC | 20 | 2671 |
| BCL11A-2187 | − | GUCUCACCUCUUUUCUCCCC | 20 | 2672 |
| BCL11A-2188 | − | UACCCCCCAUUUUCUUACG | 20 | 2673 |
| BCL11A-2189 | − | CCCCCAUUUUCUUACGGUGA | 20 | 2674 |
| BCL11A-2190 | − | CCCCAUUUUCUUACGGUGAG | 20 | 2675 |
| BCL11A-2191 | − | CCCAUUUUCUUACGGUGAGU | 20 | 2676 |
| BCL11A-2192 | − | UCCCACCCCCAGGUUUGCAU | 20 | 2677 |
| BCL11A-2193 | − | UUCAUUAUUUGCAAAACUG | 20 | 2678 |
| BCL11A-2194 | − | UCAUUAUUUGCAAAACUGG | 20 | 2679 |
| BCL11A-2195 | − | UAUUUGCAAAACUGGCGGG | 20 | 2680 |
| BCL11A-2196 | − | AUUUGCAAAACUGGCGGGG | 20 | 2681 |
| BCL11A-2197 | − | UUUUGCAAAACUGGCGGGGC | 20 | 2682 |
| BCL11A-2198 | − | UUUGCAAAACUGGCGGGGCG | 20 | 2683 |
| BCL11A-2199 | − | UUGCAAAACUGGCGGGGCGG | 20 | 2684 |

TABLE 3B-continued

S. aureus gRNA targets for BCL11A knockdown

| gRNA Name | DNA Strand | Targeting Domain | Target Site Length | SEQ ID NO |
|---|---|---|---|---|
| BCL11A-2200 | - | UGCAAAACUGGCGGGGCGGG | 20 | 2685 |
| BCL11A-2201 | - | GCAAAACUGGCGGGGCGGGG | 20 | 2686 |
| BCL11A-2202 | - | CAAAACUGGCGGGGCGGGGG | 20 | 2687 |
| BCL11A-2203 | - | ACUGGCGGGGCGGGGGGGA | 20 | 2688 |
| BCL11A-2204 | - | CUGGCGGGGCGGGGGGGAG | 20 | 2689 |
| BCL11A-2205 | - | UGGAAUCAUUGCAUUCCUUU | 20 | 2690 |
| BCL11A-2206 | - | UCAUUGCAUUCCUUUUCGAA | 20 | 2691 |
| BCL11A-2207 | - | AUUGCAUUCCUUUUCGAAAA | 20 | 2692 |
| BCL11A-2208 | - | UCGAAAGAGAAAUAAAGCG | 20 | 2693 |
| BCL11A-2209 | - | CGAAAAGAGAAAUAAAGCGG | 20 | 2694 |
| BCL11A-2210 | - | AAGAGAAAUAAAGCGGCGGA | 20 | 2695 |
| BCL11A-2211 | - | AGAGAAAUAAAGCGGCGGAA | 20 | 2696 |
| BCL11A-2212 | - | AGAAAUAAAGCGGCGGAAAG | 20 | 2697 |
| BCL11A-2213 | - | GAAAUAAAGCGGCGGAAAGG | 20 | 2698 |
| BCL11A-2214 | - | UAAAGCGGCGGAAAGGAGGA | 20 | 2699 |
| BCL11A-2215 | - | AAGCGGCGGAAAGGAGGAAA | 20 | 2700 |
| BCL11A-2216 | - | AGCGGCGGAAAGGAGGAAAG | 20 | 2701 |
| BCL11A-2217 | - | CGGCGGAAAGGAGGAAAGAG | 20 | 2702 |
| BCL11A-2218 | - | GGCGGAAAGGAGGAAAGAGG | 20 | 2703 |
| BCL11A-2219 | - | AUACACGGCAAUGGUUCCAG | 20 | 2704 |
| BCL11A-2220 | - | UACACGGCAAUGGUUCCAGA | 20 | 2705 |
| BCL11A-2221 | - | CGGCAAUGGUUCCAGAUGGG | 20 | 2706 |
| BCL11A-2222 | - | GCAAUGGUUCCAGAUGGGAU | 20 | 2707 |
| BCL11A-2223 | - | UAUCUCUUUUACCUCGACUC | 20 | 2708 |
| BCL11A-2224 | - | AUCUCUUUUACCUCGACUCU | 20 | 2709 |
| BCL11A-2225 | - | GACUCUCGGAGGUUUUUCUC | 20 | 2710 |
| BCL11A-2226 | - | AAUAAUUAUUAUUACUAUUA | 20 | 2711 |
| BCL11A-2227 | - | ACUAUUAUUGGGUUACUUAC | 20 | 2712 |
| BCL11A-2228 | - | UAUUAUUGGGUUACUUACGC | 20 | 2713 |
| BCL11A-2229 | - | UCUUCUCCUUGCUGCCU | 17 | 2714 |
| BCL11A-2230 | - | CUGCCUCUGAGGUUCGG | 17 | 2715 |
| BCL11A-2231 | - | UGCCUCUGAGGUUCGGU | 17 | 2716 |
| BCL11A-2232 | - | GCCUCUGAGGUUCGGUC | 17 | 2717 |
| BCL11A-2233 | - | CUCUGAGGUUCGGUCGG | 17 | 2718 |
| BCL11A-2234 | - | UCUGAGGUUCGGUCGGG | 17 | 2719 |
| BCL11A-2235 | - | CUGAGGUUCGGUCGGGA | 17 | 2720 |
| BCL11A-2236 | - | UGAGGUUCGGUCGGGAG | 17 | 2721 |
| BCL11A-2237 | - | AGGUUCGGUCGGGAGGG | 17 | 2722 |
| BCL11A-2238 | - | GGAGGGCAGCGGCAACC | 17 | 2723 |
| BCL11A-2239 | - | GAGGGCAGCGGCAACCC | 17 | 2724 |
| BCL11A-2240 | - | ACCCAGGAGGCAGCAGU | 17 | 2725 |
| BCL11A-2241 | - | GCGGCGGCGGCGGCGGC | 17 | 2726 |
| BCL11A-2242 | - | CGGCGGCGGCGGCGGCG | 17 | 2727 |
| BCL11A-2243 | - | GGCGGCGGCGGCGGCGC | 17 | 2728 |
| BCL11A-2244 | - | CGGCGGCGGCGGCGCGG | 17 | 2729 |
| BCL11A-2245 | - | GGCGCGGGAGGGCAAGC | 17 | 2730 |
| BCL11A-2246 | - | CGCGGGAGGGCAAGCGC | 17 | 2731 |
| BCL11A-2247 | - | GCGGGAGGGCAAGCGCG | 17 | 2732 |
| BCL11A-2248 | - | AGCCGGCACAAAAGGCA | 17 | 2733 |
| BCL11A-2249 | - | GCCGGCACAAAAGGCAG | 17 | 2734 |
| BCL11A-2250 | - | CAAACACCCACCUCUGG | 17 | 2735 |
| BCL11A-2251 | - | AAACACCCACCUCUGGC | 17 | 2736 |
| BCL11A-2252 | - | GCCCCUCUCCCGACUCC | 17 | 2737 |
| BCL11A-2253 | - | UCCCGACUCCGCGGACU | 17 | 2738 |
| BCL11A-2254 | - | CCCGACUCCGCGGACUC | 17 | 2739 |
| BCL11A-2255 | - | CCGCGGACUCAGGAGCG | 17 | 2740 |
| BCL11A-2256 | - | CGCGGACUCAGGAGCGC | 17 | 2741 |
| BCL11A-2257 | - | GCGGACUCAGGAGCGCC | 17 | 2742 |
| BCL11A-2258 | - | GCCACUUUCUCACUAUU | 17 | 2743 |
| BCL11A-2259 | - | CCACUUUCUCACUAUUG | 17 | 2744 |
| BCL11A-2260 | - | CACUUUCUCACUAUUGU | 17 | 2745 |
| BCL11A-2261 | - | CCGCUGCACACUUGACC | 17 | 2746 |
| BCL11A-2262 | - | UCUCACCUCUUUUCUCC | 17 | 2747 |
| BCL11A-2263 | - | CUCACCUCUUUUCUCCC | 17 | 2748 |
| BCL11A-2264 | - | UCACCUCUUUUCUCCCC | 17 | 2749 |
| BCL11A-2265 | - | CCCCCCAUUUUCUUACG | 17 | 2750 |
| BCL11A-2266 | - | CCAUUUUCUUACGGUGA | 17 | 2751 |
| BCL11A-2267 | - | CAUUUUCUUACGGUGAG | 17 | 2752 |
| BCL11A-2268 | - | AUUUUCUUACGGUGAGU | 17 | 2753 |
| BCL11A-2269 | - | CACCCCCAGGUUUGCAU | 17 | 2754 |
| BCL11A-2270 | - | AUUAUUUGCAAAACUG | 17 | 2755 |
| BCL11A-2271 | - | UUAUUUGCAAAACUGG | 17 | 2756 |
| BCL11A-2272 | - | UUUGCAAAACUGGCGGG | 17 | 2757 |
| BCL11A-2273 | - | UUGCAAAACUGGCGGGG | 17 | 2758 |

TABLE 3B-continued

*S. aureus* gRNA targets for BCL11A knockdown

| gRNA Name | DNA Strand | Targeting Domain | Target Site Length | SEQ ID NO |
|---|---|---|---|---|
| BCL11A-2274 | − | UGCAAAACUGGCGGGGC | 17 | 2759 |
| BCL11A-2275 | − | GCAAAACUGGCGGGGCG | 17 | 2760 |
| BCL11A-2276 | − | CAAAACUGGCGGGGCGG | 17 | 2761 |
| BCL11A-2277 | − | AAAACUGGCGGGGCGGG | 17 | 2762 |
| BCL11A-2278 | − | AAACUGGCGGGGCGGGG | 17 | 2763 |
| BCL11A-2279 | − | AACUGGCGGGGCGGGGG | 17 | 2764 |
| BCL11A-2280 | − | GGCGGGGCGGGGGGGA | 17 | 2765 |
| BCL11A-2281 | − | GCGGGGCGGGGGGGAG | 17 | 2766 |
| BCL11A-2282 | − | AAUCAUUGCAUUCCUUU | 17 | 2767 |
| BCL11A-2283 | − | UUGCAUUCCUUUUCGAA | 17 | 2768 |
| BCL11A-2284 | − | GCAUUCCUUUUCGAAAA | 17 | 2769 |
| BCL11A-2285 | − | AAAAGAGAAAUAAAGCG | 17 | 2770 |
| BCL11A-2286 | − | AAAGAGAAAUAAAGCGG | 17 | 2771 |
| BCL11A-2287 | − | AGAAAUAAAGCGGCGGA | 17 | 2772 |
| BCL11A-2288 | − | GAAAUAAAGCGGCGGAA | 17 | 2773 |
| BCL11A-2289 | − | AAUAAAGCGGCGGAAAG | 17 | 2774 |
| BCL11A-2290 | − | AUAAAGCGGCGGAAAGG | 17 | 2775 |
| BCL11A-2291 | − | AGCGGCGGAAAGGAGGA | 17 | 2776 |
| BCL11A-2292 | − | CGGCGGAAAGGAGGAAA | 17 | 2777 |
| BCL11A-2293 | − | GGCGGAAAGGAGGAAAG | 17 | 2778 |
| BCL11A-2294 | − | CGGAAAGGAGGAAAGAG | 17 | 2779 |
| BCL11A-2295 | − | GGAAAGGAGGAAAGAGG | 17 | 2780 |
| BCL11A-2296 | − | CACGGCAAUGGUUCCAG | 17 | 2781 |
| BCL11A-2297 | − | ACGGCAAUGGUUCCAGA | 17 | 2782 |
| BCL11A-2298 | − | CAAUGGUUCCAGAUGGG | 17 | 2783 |
| BCL11A-2299 | − | AUGGUUCCAGAUGGGAU | 17 | 2784 |
| BCL11A-2300 | − | CUCUUUUACCUCGACUC | 17 | 2785 |
| BCL11A-2301 | − | UCUUUUACCUCGACUCU | 17 | 2786 |
| BCL11A-2302 | − | UCUCGGAGGUUUUUCUC | 17 | 2787 |
| BCL11A-2303 | − | AAUUAUUAUUACUAUUA | 17 | 2788 |
| BCL11A-2304 | − | AUUAUUGGGUUACUUAC | 17 | 2789 |
| BCL11A-2305 | − | UAUUGGGUUACUUACGC | 17 | 2790 |
| BCL11A-2306 | + | CGAACCUCAGAGGCAGCAAG | 20 | 2791 |
| BCL11A-2307 | + | ACCGAACCUCAGAGGCAGCA | 20 | 2792 |
| BCL11A-2308 | + | GACCGAACCUCAGAGGCAGC | 20 | 2793 |
| BCL11A-2309 | + | CUCCCCUCCCGACCGAACCU | 20 | 2794 |
| BCL11A-2310 | + | CCGCUGCCCUCCCCUCCCGA | 20 | 2795 |
| BCL11A-2311 | + | GGAGCCCGGACUGCUGCCUC | 20 | 2796 |
| BCL11A-2312 | + | GGGAGAGGGAGGGAGGGAGC | 20 | 2797 |
| BCL11A-2313 | + | GCACGCGGGAGAGGGAGGGA | 20 | 2798 |
| BCL11A-2314 | + | GGCACGCGGGAGAGGGAGGG | 20 | 2799 |
| BCL11A-2315 | + | GGGCACGCGGGAGAGGGAGG | 20 | 2800 |
| BCL11A-2316 | + | GGGGGCACGCGGGAGAGGGA | 20 | 2801 |
| BCL11A-2317 | + | CGGGGGCACGCGGGAGAGGG | 20 | 2802 |
| BCL11A-2318 | + | CCGGGGGCACGCGGGAGAGG | 20 | 2803 |
| BCL11A-2319 | + | GGCCGGGGGCACGCGGGAGA | 20 | 2804 |
| BCL11A-2320 | + | CGGCCGGGGGCACGCGGGAG | 20 | 2805 |
| BCL11A-2321 | + | GCGGCCGGGGGCACGCGGGA | 20 | 2806 |
| BCL11A-2322 | + | AGGCGGCCGGGGGCACGCGG | 20 | 2807 |
| BCL11A-2323 | + | GGAGGCGGCCGGGGGCACGC | 20 | 2808 |
| BCL11A-2324 | + | AGGAGGCGGCCGGGGGCACG | 20 | 2809 |
| BCL11A-2325 | + | GAGGAGGCGGCCGGGGGCAC | 20 | 2810 |
| BCL11A-2326 | + | GGCCGGGGAGGAGGCGGCC | 20 | 2811 |
| BCL11A-2327 | + | GGGCCGGGGAGGAGGCGGC | 20 | 2812 |
| BCL11A-2328 | + | AGGGCCGGGGAGGAGGCGG | 20 | 2813 |
| BCL11A-2329 | + | GCAGGAGCUAGGGCCGGGG | 20 | 2814 |
| BCL11A-2330 | + | GGCAGGAGCUAGGGCCGGG | 20 | 2815 |
| BCL11A-2331 | + | AGGGCAGGAGCUAGGGCCGG | 20 | 2816 |
| BCL11A-2332 | + | AAGGGCAGGAGCUAGGGCCG | 20 | 2817 |
| BCL11A-2333 | + | GAAGGGCAGGAGCUAGGGCC | 20 | 2818 |
| BCL11A-2334 | + | CGAAGGGCAGGAGCUAGGGC | 20 | 2819 |
| BCL11A-2335 | + | CCGAAGGGCAGGAGCUAGGG | 20 | 2820 |
| BCL11A-2336 | + | CGCCGCCGAAGGGCAGGAGC | 20 | 2821 |
| BCL11A-2337 | + | CGCCGCCGCCGCCGAAGGGC | 20 | 2822 |
| BCL11A-2338 | + | CCGCCGCCGCCGCCGAAGGG | 20 | 2823 |
| BCL11A-2339 | + | CGCCGCCGCCGCCGCCGCCG | 20 | 2824 |
| BCL11A-2340 | + | CGCCGCCGCCGCCGCCGCCG | 20 | 2825 |
| BCL11A-2341 | + | GCCUUUGUUCCGGCCAGAG | 20 | 2826 |
| BCL11A-2342 | + | CUGCCGCCUUUUGUUCCGGC | 20 | 2827 |
| BCL11A-2343 | + | GCCGUGGGACCGGGAAGGAC | 20 | 2828 |
| BCL11A-2344 | + | AGCCGUGGGACCGGGAAGGA | 20 | 2829 |
| BCL11A-2345 | + | GAGCCGUGGGACCGGGAAGG | 20 | 2830 |
| BCL11A-2346 | + | GGGAGAGCCGUGGGACCGGG | 20 | 2831 |
| BCL11A-2347 | + | ACGGGGAGAGCCGUGGGACC | 20 | 2832 |

TABLE 3B-continued

S. aureus gRNA targets for BCL11A knockdown

| gRNA Name | DNA Strand | Targeting Domain | Target Site Length | SEQ ID NO |
|---|---|---|---|---|
| BCL11A-2348 | + | GACGGGGAGAGCCGUGGGAC | 20 | 2833 |
| BCL11A-2349 | + | CGACGGGGAGAGCCGUGGGA | 20 | 2834 |
| BCL11A-2350 | + | CGCGGCGACGGGGAGAGCCG | 20 | 2835 |
| BCL11A-2351 | + | CCGCGGCGACGGGGAGAGCC | 20 | 2836 |
| BCL11A-2352 | + | AGAGGGCCGCGGCGACGGG | 20 | 2837 |
| BCL11A-2353 | + | GGAGAGGGGCCGCGGCGACG | 20 | 2838 |
| BCL11A-2354 | + | GGGAGAGGGGCCGCGGCGAC | 20 | 2839 |
| BCL11A-2355 | + | CGGGAGAGGGGCCGCGGCGA | 20 | 2840 |
| BCL11A-2356 | + | UCGGGAGAGGGGCCGCGGCG | 20 | 2841 |
| BCL11A-2357 | + | UGAGUCCGCGGAGUCGGGAG | 20 | 2842 |
| BCL11A-2358 | + | CUGAGUCCGCGGAGUCGGGA | 20 | 2843 |
| BCL11A-2359 | + | UCCUGAGUCCGCGGAGUCGG | 20 | 2844 |
| BCL11A-2360 | + | GCUCCUGAGUCCGCGGAGUC | 20 | 2845 |
| BCL11A-2361 | + | CGCUCCUGAGUCCGCGGAGU | 20 | 2846 |
| BCL11A-2362 | + | GCGCUCCUGAGUCCGCGGAG | 20 | 2847 |
| BCL11A-2363 | + | CCCCGGCGCUCCUGAGUCCG | 20 | 2848 |
| BCL11A-2364 | + | CCCCCGGCGCUCCUGAGUCC | 20 | 2849 |
| BCL11A-2365 | + | GAAAGGGGCCCCCGGCGCUC | 20 | 2850 |
| BCL11A-2366 | + | GAGAAAGUGGCACUGUGGAA | 20 | 2851 |
| BCL11A-2367 | + | UGAGAAAGUGGCACUGUGGA | 20 | 2852 |
| BCL11A-2368 | + | AUAGUGAGAAAGUGGCACUG | 20 | 2853 |
| BCL11A-2369 | + | AAUAGUGAGAAAGUGGCACU | 20 | 2854 |
| BCL11A-2370 | + | GUAGUCAUCCCCACAAUAGU | 20 | 2855 |
| BCL11A-2371 | + | AAGUAGUCAUCCCCACAAUA | 20 | 2856 |
| BCL11A-2372 | + | ACGGUCAAGUGUGCAGCGGG | 20 | 2857 |
| BCL11A-2373 | + | CACGGUCAAGUGUGCAGCGG | 20 | 2858 |
| BCL11A-2374 | + | CUCACGGUCAAGUGUGCAGC | 20 | 2859 |
| BCL11A-2375 | + | GCUCACGGUCAAGUGUGCAG | 20 | 2860 |
| BCL11A-2376 | + | CGCUCACGGUCAAGUGUGCA | 20 | 2861 |
| BCL11A-2377 | + | AAAAGAGGUGAGACUGGCUU | 20 | 2862 |
| BCL11A-2378 | + | GAUUCCCGGGGAGAAAAGAG | 20 | 2863 |
| BCL11A-2379 | + | AAAACGAUUCCCGGGGAGAA | 20 | 2864 |
| BCL11A-2380 | + | UCUAAAAACGAUUCCCGGG | 20 | 2865 |
| BCL11A-2381 | + | AGUCUAAAAACGAUUCCCG | 20 | 2866 |
| BCL11A-2382 | + | AAGUCUAAAAACGAUUCCC | 20 | 2867 |
| BCL11A-2383 | + | CAAGUCUAAAAACGAUUCC | 20 | 2868 |
| BCL11A-2384 | + | ACAAGUCUAAAAACGAUUC | 20 | 2869 |
| BCL11A-2385 | + | AAUGGGGGGUAGGGAGGGA | 20 | 2870 |
| BCL11A-2386 | + | AGAAAAUGGGGGGUAGGGA | 20 | 2871 |
| BCL11A-2387 | + | AAGAAAAUGGGGGGUAGGG | 20 | 2872 |
| BCL11A-2388 | + | UAAGAAAAUGGGGGGUAGG | 20 | 2873 |
| BCL11A-2389 | + | CGUAAGAAAAUGGGGGGUA | 20 | 2874 |
| BCL11A-2390 | + | CCGUAAGAAAAUGGGGGGU | 20 | 2875 |
| BCL11A-2391 | + | ACCGUAAGAAAAUGGGGGG | 20 | 2876 |
| BCL11A-2392 | + | CACUCACCGUAAGAAAAUGG | 20 | 2877 |
| BCL11A-2393 | + | CCACUCACCGUAAGAAAAUG | 20 | 2878 |
| BCL11A-2394 | + | CCCACUCACCGUAAGAAAAU | 20 | 2879 |
| BCL11A-2395 | + | UCCCACUCACCGUAAGAAAA | 20 | 2880 |
| BCL11A-2396 | + | UUCCCACUCACCGUAAGAAA | 20 | 2881 |
| BCL11A-2397 | + | GGUUGCUUCCCACUCACCGU | 20 | 2882 |
| BCL11A-2398 | + | GGUGGGAGCUGGUGGGGAAA | 20 | 2883 |
| BCL11A-2399 | + | GGGUGGGAGCUGGUGGGGAA | 20 | 2884 |
| BCL11A-2400 | + | GGGGUGGGAGCUGGUGGGGA | 20 | 2885 |
| BCL11A-2401 | + | CCUGGGGGUGGGAGCUGGUG | 20 | 2886 |
| BCL11A-2402 | + | ACCUGGGGGUGGGAGCUGGU | 20 | 2887 |
| BCL11A-2403 | + | AACCUGGGGGUGGGAGCUGG | 20 | 2888 |
| BCL11A-2404 | + | AAACCUGGGGGUGGGAGCUG | 20 | 2889 |
| BCL11A-2405 | + | UCACAUGCAAACCUGGGGGU | 20 | 2890 |
| BCL11A-2406 | + | CUCACAUGCAAACCUGGGGG | 20 | 2891 |
| BCL11A-2407 | + | ACUCACAUGCAAACCUGGGG | 20 | 2892 |
| BCL11A-2408 | + | AACAACUCACAUGCAAACCU | 20 | 2893 |
| BCL11A-2409 | + | GAACAACUCACAUGCAAACC | 20 | 2894 |
| BCL11A-2410 | + | CGAACAACUCACAUGCAAAC | 20 | 2895 |
| BCL11A-2411 | + | UAAUGAACAAUGCUAAGGUU | 20 | 2896 |
| BCL11A-2412 | + | CCCGCCAGUUUUGCAAAAUA | 20 | 2897 |
| BCL11A-2413 | + | CUUUAUUUCUCUUUUCGAAA | 20 | 2898 |
| BCL11A-2414 | + | GCUUUAUUUCUCUUUUCGAA | 20 | 2899 |
| BCL11A-2415 | + | CCGCCGCUUUAUUUCUCUUU | 20 | 2900 |
| BCL11A-2416 | + | CCAUUGCCGUGUAUGCACUU | 20 | 2901 |
| BCL11A-2417 | + | GAAAAAACCCUCAUCCCAUC | 20 | 2902 |
| BCL11A-2418 | + | GGAAAAAACCCUCAUCCCAU | 20 | 2903 |
| BCL11A-2419 | + | CGAGGUAAAAGAGAUAAAGG | 20 | 2904 |
| BCL11A-2420 | + | UCGAGGUAAAAGAGAUAAAG | 20 | 2905 |
| BCL11A-2421 | + | GUCGAGGUAAAAGAGAUAAA | 20 | 2906 |

TABLE 3B-continued

*S. aureus* gRNA targets for BCL11A knockdown

| gRNA Name | DNA Strand | Targeting Domain | Target Site Length | SEQ ID NO |
|---|---|---|---|---|
| BCL11A-2422 | + | AGUCGAGGUAAAAGAGAUAA | 20 | 2907 |
| BCL11A-2423 | + | GAGUCGAGGUAAAAGAGAUA | 20 | 2908 |
| BCL11A-2424 | + | ACCUCCGAGAGUCGAGGUAA | 20 | 2909 |
| BCL11A-2425 | + | ACGAGAAAAACCUCCGAGAG | 20 | 2910 |
| BCL11A-2426 | + | UUUUCACGAGAAAAACCUCC | 20 | 2911 |
| BCL11A-2427 | + | AUUUUUCACGAGAAAAACCU | 20 | 2912 |
| BCL11A-2428 | + | UGCAUUUUUAAAUUUUUCAC | 20 | 2913 |
| BCL11A-2429 | + | CAUGCAUUUUUAAAUUUUUC | 20 | 2914 |
| BCL11A-2430 | + | AGCAAAAGCGAGGGGGAGAG | 20 | 2915 |
| BCL11A-2431 | + | AAGCAAAAGCGAGGGGGAGA | 20 | 2916 |
| BCL11A-2432 | + | AGAAGCAAAAGCGAGGGGGA | 20 | 2917 |
| BCL11A-2433 | + | CUAGAAGCAAAAGCGAGGGG | 20 | 2918 |
| BCL11A-2434 | + | GACUAGAAGCAAAAGCGAGG | 20 | 2919 |
| BCL11A-2435 | + | GGACUAGAAGCAAAAGCGAG | 20 | 2920 |
| BCL11A-2436 | + | AGGACUAGAAGCAAAAGCGA | 20 | 2921 |
| BCL11A-2437 | + | CAGGACUAGAAGCAAAAGCG | 20 | 2922 |
| BCL11A-2438 | + | GCAGGACUAGAAGCAAAAGC | 20 | 2923 |
| BCL11A-2439 | + | GCGCAGGACUAGAAGCAAAA | 20 | 2924 |
| BCL11A-2440 | + | AUCACGAGAGCGCGCAGGAC | 20 | 2925 |
| BCL11A-2441 | + | UUAAUAAUCACGAGAGCGCG | 20 | 2926 |
| BCL11A-2442 | + | UAAUAAUUAUUAAUAAUCAC | 20 | 2927 |
| BCL11A-2443 | + | AAUAAUAAUUAUUAAUAAUC | 20 | 2928 |
| BCL11A-2444 | + | ACCUCAGAGGCAGCAAG | 17 | 2929 |
| BCL11A-2445 | + | GAACCUCAGAGGCAGCA | 17 | 2930 |
| BCL11A-2446 | + | CGAACCUCAGAGGCAGC | 17 | 2931 |
| BCL11A-2447 | + | CCCUCCCGACCGAACCU | 17 | 2932 |
| BCL11A-2448 | + | CUGCCCUCCCCUCCCGA | 17 | 2933 |
| BCL11A-2449 | + | GCCCGGACUGCUGCCUC | 17 | 2934 |
| BCL11A-2450 | + | AGAGGGAGGGAGGGAGC | 17 | 2935 |
| BCL11A-2451 | + | CGCGGGAGAGGGAGGGA | 17 | 2936 |
| BCL11A-2452 | + | ACGCGGGAGAGGGAGGG | 17 | 2937 |
| BCL11A-2453 | + | CACGCGGGAGAGGGAGG | 17 | 2938 |
| BCL11A-2454 | + | GGCACGCGGGAGAGGGA | 17 | 2939 |
| BCL11A-2455 | + | GGGCACGCGGGAGAGGG | 17 | 2940 |
| BCL11A-2456 | + | GGGGCACGCGGGAGAGG | 17 | 2941 |
| BCL11A-2457 | + | CGGGGCACGCGGGAGA | 17 | 2942 |
| BCL11A-2458 | + | CCGGGGGCACGCGGGAG | 17 | 2943 |
| BCL11A-2459 | + | GCCGGGGCACGCGGGA | 17 | 2944 |
| BCL11A-2460 | + | CGGCCGGGGCACGCGG | 17 | 2945 |
| BCL11A-2461 | + | GGCGGCCGGGGGCACGC | 17 | 2946 |
| BCL11A-2462 | + | AGGCGGCCGGGGGCACG | 17 | 2947 |
| BCL11A-2463 | + | GAGGCGGCCGGGGGCAC | 17 | 2948 |
| BCL11A-2464 | + | CGGGGGAGGAGGCGGCC | 17 | 2949 |
| BCL11A-2465 | + | CCGGGGGAGGAGGCGGC | 17 | 2950 |
| BCL11A-2466 | + | GCCGGGGAGGAGGCGG | 17 | 2951 |
| BCL11A-2467 | + | GGAGCUAGGGCCGGGGG | 17 | 2952 |
| BCL11A-2468 | + | AGGAGCUAGGGCCGGGG | 17 | 2953 |
| BCL11A-2469 | + | GCAGGAGCUAGGGCCGG | 17 | 2954 |
| BCL11A-2470 | + | GGCAGGAGCUAGGGCCG | 17 | 2955 |
| BCL11A-2471 | + | GGGCAGGAGCUAGGGCC | 17 | 2956 |
| BCL11A-2472 | + | AGGGCAGGAGCUAGGGC | 17 | 2957 |
| BCL11A-2473 | + | AAGGGCAGGAGCUAGGG | 17 | 2958 |
| BCL11A-2474 | + | CGCCGAAGGGCAGGAGC | 17 | 2959 |
| BCL11A-2475 | + | CGCCGCCGCCGAAGGGC | 17 | 2960 |
| BCL11A-2476 | + | CCGCCGCCGCCGAAGGG | 17 | 2961 |
| BCL11A-2477 | + | CGCCGCCGCCGCCGCC | 17 | 2962 |
| BCL11A-2478 | + | CGCCGCCGCCGCCGCCG | 17 | 2963 |
| BCL11A-2479 | + | UUUUGUUCCGGCCAGAG | 17 | 2964 |
| BCL11A-2480 | + | CCGCCUUUUGUUCCGGC | 17 | 2965 |
| BCL11A-2481 | + | GUGGGACCGGGAAGGAC | 17 | 2966 |
| BCL11A-2482 | + | CGUGGGACCGGGAAGGA | 17 | 2967 |
| BCL11A-2483 | + | CCGUGGGACCGGGAAGG | 17 | 2968 |
| BCL11A-2484 | + | AGAGCCGUGGGACCGGG | 17 | 2969 |
| BCL11A-2485 | + | GGGAGAGCCGUGGGACC | 17 | 2970 |
| BCL11A-2486 | + | GGGGAGAGCCGUGGGAC | 17 | 2971 |
| BCL11A-2487 | + | CGGGGAGAGCCGUGGGA | 17 | 2972 |
| BCL11A-2488 | + | GGCGACGGGAGAGCCG | 17 | 2973 |
| BCL11A-2489 | + | CGGCGACGGGAGAGCC | 17 | 2974 |
| BCL11A-2490 | + | GGGGCCGCGGCGACGGG | 17 | 2975 |
| BCL11A-2491 | + | GAGGGGCCGCGGCGACG | 17 | 2976 |
| BCL11A-2492 | + | AGAGGGGCCGCGGCGAC | 17 | 2977 |
| BCL11A-2493 | + | GAGAGGGGCCGCGGCGA | 17 | 2978 |
| BCL11A-2494 | + | GGAGAGGGGCCGCGGCG | 17 | 2979 |
| BCL11A-2495 | + | GUCCGCGGAGUCGGGAG | 17 | 2980 |

TABLE 3B-continued

S. aureus gRNA targets for BCL11A knockdown

| gRNA Name | DNA Strand | Targeting Domain | Target Site Length | SEQ ID NO |
|---|---|---|---|---|
| BCL11A-2496 | + | AGUCCGCGGAGUCGGGA | 17 | 2981 |
| BCL11A-2497 | + | UGAGUCCGCGGAGUCGG | 17 | 2982 |
| BCL11A-2498 | + | CCUGAGUCCGCGGAGUC | 17 | 2983 |
| BCL11A-2499 | + | UCCUGAGUCCGCGGAGU | 17 | 2984 |
| BCL11A-2500 | + | CUCCUGAGUCCGCGGAG | 17 | 2985 |
| BCL11A-2501 | + | CGGCGCUCCUGAGUCCG | 17 | 2986 |
| BCL11A-2502 | + | CCGGCGCUCCUGAGUCC | 17 | 2987 |
| BCL11A-2503 | + | AGGGGCCCCCGGCGCUC | 17 | 2988 |
| BCL11A-2504 | + | AAAGUGGCACUGUGGAA | 17 | 2989 |
| BCL11A-2505 | + | GAAAGUGGCACUGUGGA | 17 | 2990 |
| BCL11A-2506 | + | GUGAGAAAGUGGCACUG | 17 | 2991 |
| BCL11A-2507 | + | AGUGAGAAAGUGGCACU | 17 | 2992 |
| BCL11A-2508 | + | GUCAUCCCCACAAUAGU | 17 | 2993 |
| BCL11A-2509 | + | UAGUCAUCCCCACAAUA | 17 | 2994 |
| BCL11A-2510 | + | GUCAAGUGUGCAGCGGG | 17 | 2995 |
| BCL11A-2511 | + | GGUCAAGUGUGCAGCGG | 17 | 2996 |
| BCL11A-2512 | + | ACGGUCAAGUGUGCAGC | 17 | 2997 |
| BCL11A-2513 | + | CACGGUCAAGUGUGCAG | 17 | 2998 |
| BCL11A-2514 | + | UCACGGUCAAGUGUGCA | 17 | 2999 |
| BCL11A-2515 | + | AGAGGUGAGACUGGCUU | 17 | 3000 |
| BCL11A-2516 | + | UCCCGGGGAGAAAAGAG | 17 | 3001 |
| BCL11A-2517 | + | ACGAUUCCGGGGAGAA | 17 | 3002 |
| BCL11A-2518 | + | AAAAAACGAUUCCCGGG | 17 | 3003 |
| BCL11A-2519 | + | CUAAAAACGAUUCCCG | 17 | 3004 |
| BCL11A-2520 | + | UCUAAAAACGAUUCCC | 17 | 3005 |
| BCL11A-2521 | + | GUCUAAAAACGAUUCC | 17 | 3006 |
| BCL11A-2522 | + | AGUCUAAAAACGAUUC | 17 | 3007 |
| BCL11A-2523 | + | GGGGGGGUAGGGAGGGA | 17 | 3008 |
| BCL11A-2524 | + | AAAUGGGGGGUAGGGA | 17 | 3009 |
| BCL11A-2525 | + | AAAAUGGGGGGUAGGG | 17 | 3010 |
| BCL11A-2526 | + | GAAAAUGGGGGGUAGG | 17 | 3011 |
| BCL11A-2527 | + | AAGAAAUGGGGGGUA | 17 | 3012 |
| BCL11A-2528 | + | UAAGAAAUGGGGGGU | 17 | 3013 |
| BCL11A-2529 | + | GUAAGAAAUGGGGGG | 17 | 3014 |
| BCL11A-2530 | + | UCACCGUAAGAAAUGG | 17 | 3015 |
| BCL11A-2531 | + | CUCACCGUAAGAAAUG | 17 | 3016 |
| BCL11A-2532 | + | ACUCACCGUAAGAAAU | 17 | 3017 |
| BCL11A-2533 | + | CACUCACCGUAAGAAAA | 17 | 3018 |
| BCL11A-2534 | + | CCACUCACCGUAAGAAA | 17 | 3019 |
| BCL11A-2535 | + | UGCUUCCCACUCACCGU | 17 | 3020 |
| BCL11A-2536 | + | GGGAGCUGGUGGGAAA | 17 | 3021 |
| BCL11A-2537 | + | UGGGAGCUGGUGGGAA | 17 | 3022 |
| BCL11A-2538 | + | GUGGGAGCUGGUGGGA | 17 | 3023 |
| BCL11A-2539 | + | GGGGGUGGGAGCUGGUG | 17 | 3024 |
| BCL11A-2540 | + | UGGGGGUGGGAGCUGGU | 17 | 3025 |
| BCL11A-2541 | + | CUGGGGGUGGGAGCUGG | 17 | 3026 |
| BCL11A-2542 | + | CCUGGGGGUGGGAGCUG | 17 | 3027 |
| BCL11A-2543 | + | CAUGCAAACCUGGGGGU | 17 | 3028 |
| BCL11A-2544 | + | ACAUGCAAACCUGGGG | 17 | 3029 |
| BCL11A-2545 | + | CACAUGCAAACCUGGGG | 17 | 3030 |
| BCL11A-2546 | + | AACUCACAUGCAAACCU | 17 | 3031 |
| BCL11A-2547 | + | CAACUCACAUGCAAACC | 17 | 3032 |
| BCL11A-2548 | + | ACAACUCACAUGCAAAC | 17 | 3033 |
| BCL11A-2549 | + | UGAACAAUGCUAAGGUU | 17 | 3034 |
| BCL11A-2550 | + | GCCAGUUUUGCAAAAUA | 17 | 3035 |
| BCL11A-2551 | + | UAUUUCUCUUUUCGAAA | 17 | 3036 |
| BCL11A-2552 | + | UUAUUUCUCUUUUCGAA | 17 | 3037 |
| BCL11A-2553 | + | CCGCUUUAUUUCUCUUU | 17 | 3038 |
| BCL11A-2554 | + | UUGCCGUGUAUGCACUU | 17 | 3039 |
| BCL11A-2555 | + | AAAACCCUCAUCCCAUC | 17 | 3040 |
| BCL11A-2556 | + | AAAAACCCUCAUCCCAU | 17 | 3041 |
| BCL11A-2557 | + | GGUAAAGAGAUAAAGG | 17 | 3042 |
| BCL11A-2558 | + | AGGUAAAAGAGAUAAAG | 17 | 3043 |
| BCL11A-2559 | + | GAGGUAAAAGAGAUAAA | 17 | 3044 |
| BCL11A-2560 | + | CGAGGUAAAAGAGAUAA | 17 | 3045 |
| BCL11A-2561 | + | UCGAGGUAAAAGAGAUA | 17 | 3046 |
| BCL11A-2562 | + | UCCGAGAGUCGAGGUAA | 17 | 3047 |
| BCL11A-2563 | + | AGAAAACCUCCGAGAG | 17 | 3048 |
| BCL11A-2564 | + | UCACGAGAAAACCUCC | 17 | 3049 |
| BCL11A-2565 | + | UUUCACGAGAAAACCU | 17 | 3050 |
| BCL11A-2566 | + | AUUUUAAAUUUUCAC | 17 | 3051 |
| BCL11A-2567 | + | GCAUUUUAAAUUUUUC | 17 | 3052 |
| BCL11A-2568 | + | AAAAGCGAGGGGGAGAG | 17 | 3053 |
| BCL11A-2569 | + | CAAAAGCGAGGGGGAGA | 17 | 3054 |

TABLE 3B-continued

S. aureus gRNA targets for BCL11A knockdown

| gRNA Name | DNA Strand | Targeting Domain | Target Site Length | SEQ ID NO |
|---|---|---|---|---|
| BCL11A-2570 | + | AGCAAAAGCGAGGGGA | 17 | 3055 |
| BCL11A-2571 | + | GAAGCAAAAGCGAGGG | 17 | 3056 |
| BCL11A-2572 | + | UAGAAGCAAAAGCGAGG | 17 | 3057 |
| BCL11A-2573 | + | CUAGAAGCAAAAGCGAG | 17 | 3058 |
| BCL11A-2574 | + | ACUAGAAGCAAAAGCGA | 17 | 3059 |
| BCL11A-2575 | + | GACUAGAAGCAAAAGCG | 17 | 3060 |
| BCL11A-2576 | + | GGACUAGAAGCAAAAGC | 17 | 3061 |
| BCL11A-2577 | + | CAGGACUAGAAGCAAAA | 17 | 3062 |
| BCL11A-2578 | + | ACGAGAGCGCGCAGGAC | 17 | 3063 |
| BCL11A-2579 | + | AUAAUCACGAGAGCGCG | 17 | 3064 |
| BCL11A-2580 | + | UAAUUAUUAAUAAUCAC | 17 | 3065 |
| BCL11A-2581 | + | AAUAAUUAUUAAUAAUC | 17 | 3066 |

Table 3C provides exemplary targeting domains for repressing (i.e., knocking down or decreasing) expression of the BCL11A gene. Any of the targeting domains in the table can be used with an N. meningitidis eiCas9 molecule to cause a steric block in the promoter region to block transcription elongation resulting in the repression of the BCL11A gene. Any of the targeting domains in the table can be used with an N. meningitidis eiCas9 fused to a transcriptional repressor to decrease transcription and therefore downregulate gene expression.

TABLE 3C

N. meningitidis gRNA targets for BCL11A knockdown

| gRNA Name | DNA Strand | Targeting Domain | Target Site Length | SEQ ID NO |
|---|---|---|---|---|
| BCL11A-2582 | − | GCUUCUAGUCCUGCGCGCUC | 20 | 3067 |
| BCL11A-2583 | − | UCUAGUCCUGCGCGCUC | 17 | 3068 |
| BCL11A-2584 | + | UUUAGACUUGUACUCACUCC | 20 | 3069 |
| BCL11A-2585 | + | CAUUCCUUUUCGAAAAGAGA | 20 | 3070 |
| BCL11A-2586 | + | UUUAGACUUGUACUCAC | 17 | 3071 |
| BCL11A-2587 | + | CAUUCCUUUUCGAAAAG | 17 | 3072 |

Table 4A provides exemplary targeting domains for knocking out the BCL11A gene by targeting the early coding sequence the BCL11A gene selected according to first tier parameters. The targeting domains bind within first 500 bp of coding sequence downstream of start codon, good orthogonality, start with G. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. pyogenes Cas9 (nickase) molecule to generate a single strand break. In an embodiment, dual targeting is used to create two nicks on opposite DNA strands by using S. pyogenes Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary gRNA pairs are: BCL11A-2607 and BCL11A-2593, BCL11A-2607 and BCL11A-2598. BCL11A-264 and BCL11A-2593, BCL11A-2614 and BCL11A-2598, BCL11A-2589 and BCL11A-2664, BCL11A-2589 and BCL11A-2666, BCL11A-2596 and BCL11A-2664, BCL11A-2596 and BCL11A-2666, BCL11A-2603 and BCL11A-2664, of BCL11A-2603 and BCL11A-2666.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene. For example, gRNA pairs that target upstream (i.e., 5') of the enhancer region in the BCL11A gene (e.g., 2607 and BCL11A-2593, BCL11A-2607 and BCL11A-2598, BCL11A-264 and BCL11A-2593, or BCL11A-2614 and BCL11A-2598) can be paired with gRNA pairs that target downstream (i.e., 3') of the enhancer region in the BCL11A gene (e.g., BCL11A-2589 and BCL11A-2664, BCL11A-2589 and BCL11A-2666, BCL11A-2596 and BCL11A-2664, BCL11A-2596 and BCL11A-2666, BCL11A-2603 and BCL11A-2664, of BCL11A-2603 and BCL11A-2666).

TABLE 4A

1st Tier

| gRNA Name | DNA Strand | Targeting Domain | Target Site Length | SEQ ID NO |
|---|---|---|---|---|
| BCL11A-2588 | + | GAGCUCCAUGUGCAGAACGA | 20 | 3073 |
| BCL11A-2589 | + | GAGCUCCCAACGGGCCG | 17 | 3074 |
| BCL11A-2590 | − | GAGUGCAGAAUAUGCCCCGC | 20 | 3075 |
| BCL11A-2591 | + | GAUAAACAAUCGUCAUCCUC | 20 | 3076 |
| BCL11A-2592 | + | GAUGCCAACCUCCACGGGAU | 20 | 3077 |
| BCL11A-2593 | − | GCAGAAUAUGCCCCGCA | 17 | 3078 |
| BCL11A-2594 | − | GCAUCCAAUCCCGUGGAGGU | 20 | 3079 |
| BCL11A-2595 | + | GCCAACCUCCACGGGAU | 17 | 3080 |
| BCL11A-2596 | + | GCUCCCAACGGGCCGUGGUC | 20 | 3081 |
| BCL11A-2597 | − | GGAGCUCUAAUCCCCACGCC | 20 | 3082 |

Table 4B provides exemplary targeting domains for knocking out the BCL11A gene by targeting the early coding sequence the BCL11A gene selected according to second tier parameters. The targeting domains bind within first 500 bp of coding sequence downstream of start codon, good orthogonality, and do not start with G. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. pyogenes Cas9 (nickase) molecule to generate a single strand break. In an embodiment, dual targeting is used to create two nicks on opposite DNA strands by using S. pyogenes Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 4B

| | 2nd Tier | | | |
|---|---|---|---|---|
| gRNA Name | DNA Strand | Targeting Domain | Target Site Length | SEQ ID NO |
| BCL11A-2598 | − | AGCAUCCAAUCCCGUGG | 17 | 3083 |
| BCL11A-2599 | − | AGUGCAGAAUAUGCCCCGCA | 20 | 3084 |
| BCL11A-2600 | − | AUGUCUCGCCGCAAGCA | 17 | 3085 |
| BCL11A-2601 | + | AUUCCCGUUUGCUUAAGUGC | 20 | 3086 |
| BCL11A-2602 | + | CAUCCUCUGGCGUGACC | 17 | 3087 |
| BCL11A-2603 | + | CCCAACGGGCCGUGGUC | 17 | 3088 |
| BCL11A-2604 | + | CCCCCAAUGGGAAGUUCAUC | 20 | 3089 |
| BCL11A-2605 | + | CCCGUUUGCUUAAGUGC | 17 | 3090 |
| BCL11A-2606 | + | CGUCAUCCUCUGGCGUGACC | 20 | 3091 |
| BCL11A-2607 | + | UCAUCUCGAUUGGUGAA | 17 | 3092 |
| BCL11A-2608 | − | UCCAAUCCCGUGGAGGU | 17 | 3093 |
| BCL11A-2609 | + | UCCCGUUUGCUUAAGUGCUG | 20 | 3094 |
| BCL11A-2610 | − | UGAACCAGACCACGGCCCGU | 20 | 3095 |
| BCL11A-2611 | − | UGCAGAAUAUGCCCCGC | 17 | 3096 |
| BCL11A-2612 | − | UGGCAUCCAGGUCACGCCAG | 20 | 3097 |

TABLE 4B-continued

| | 2nd Tier | | | |
|---|---|---|---|---|
| gRNA Name | DNA Strand | Targeting Domain | Target Site Length | SEQ ID NO |
| BCL11A-2613 | − | UUAUCAACGUCAUCUAG | 17 | 3098 |
| BCL11A-2614 | + | UUCAUCUCGAUUGGUGA | 17 | 3099 |

Table 4C provides exemplary targeting domains for knocking out the BCL11A gene by targeting the early coding sequence the BCL11A gene selected according to third tier parameters. The targeting domains bind within first 500 bp of coding sequence downstream of start codon and start with G. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. pyogenes Cas9 (nickase) molecule to generate a single strand break. In an embodiment, dual targeting is used to create two nicks on opposite DNA strands by using S. pyogenes Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 4C

| | 3rd Tier | | | |
|---|---|---|---|---|
| gRNA Name | DNA Strand | Targeting Domain | Target Site Length | SEQ ID NO |
| BCL11A-2615 | − | GAAAAAGCAUCCAAUCCCG | 20 | 3100 |
| BCL11A-2616 | − | GAACCAGACCACGGCCCGUU | 20 | 3101 |
| BCL11A-2617 | + | GACCUGGAUGCCAACCUCCA | 20 | 3102 |
| BCL11A-2618 | − | GAGCUCUAAUCCCCACGCCU | 20 | 3103 |
| BCL11A-2619 | − | GAUCAUGACCUCCUCACCUG | 20 | 3104 |
| BCL11A-2620 | − | GAUGAACUUCCCAUUGG | 17 | 3105 |
| BCL11A-2621 | − | GAUGAUGAACCAGACCA | 17 | 3106 |
| BCL11A-2622 | + | GAUGCUUUUUCAUCUCGAU | 20 | 3107 |

TABLE 4C-continued

3rd Tier

| gRNA Name | DNA Strand | Targeting Domain | Target Site Length | SEQ ID NO |
|---|---|---|---|---|
| BCL11A-2623 | + | GCACUCAUCCCAGGCGU | 17 | 3108 |
| BCL11A-2624 | + | GCAUAUUCUGCACUCAUCCC | 20 | 3109 |
| BCL11A-2625 | - | GCCAGAUGAACUUCCCAUUG | 20 | 3110 |
| BCL11A-2626 | - | GCCCGUUGGGAGCUCCAGAA | 20 | 3111 |
| BCL11A-2627 | + | GCUAUGUGUUCCUGUUU | 17 | 3112 |
| BCL11A-2628 | + | GCUCCAUGUGCAGAACG | 17 | 3113 |
| BCL11A-2629 | - | GCUCUAAUCCCCACGCC | 17 | 3114 |
| BCL11A-2630 | + | GCUGGGGUUUGCCUUGCUUG | 20 | 3115 |
| BCL11A-2631 | + | GCUUUUUUCAUCUCGAU | 17 | 3116 |
| BCL11A-2632 | + | GGCACUGCCCACAGGUG | 17 | 3117 |
| BCL11A-2633 | + | GGCACUGCCCACAGGUGAGG | 20 | 3118 |
| BCL11A-2634 | - | GGCCCGUUGGGAGCUCCAGA | 20 | 3119 |
| BCL11A-2635 | + | GGGGUUUGCCUUGCUUG | 17 | 3120 |
| BCL11A-2636 | + | GUAAGAAUGGCUUCAAG | 17 | 3121 |
| BCL11A-2637 | + | GUGCAGAACGAGGGGAGGAG | 20 | 3122 |
| BCL11A-2638 | - | GUGCCAGAUGAACUUCCCAU | 20 | 3123 |
| BCL11A-2639 | + | GUUCAUCUGGCACUGCCCAC | 20 | 3124 |
| BCL11A-2640 | - | GUUGGGAGCUCCAGAAG | 17 | 3125 |

Table 4D provides exemplary targeting domains for knocking out the BCL11A gene by targeting the early coding sequence the BCL11A gene selected according to forth tier parameters. The targeting domains bind within first 500 bp of coding sequence downstream of start codon and do not start with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 4D

4th Tier

| gRNA Name | DNA Strand | Targeting Domain | Target Site Length | SEQ ID NO |
|---|---|---|---|---|
| BCL11A-2641 | - | AAAAGCAUCCAAUCCCG | 17 | 3126 |
| BCL11A-2642 | - | AAAAGCAUCCAAUCCCGUGG | 20 | 3127 |
| BCL11A-2643 | + | AAAAUAAGAAUGUCCCCCAA | 20 | 3128 |
| BCL11A-2644 | + | AAACAAUCGUCAUCCUC | 17 | 3129 |
| BCL11A-2645 | - | AAACGGAAACAAUGCAA | 17 | 3130 |
| BCL11A-2646 | - | AAACUUCUGCACUGGAG | 17 | 3131 |
| BCL11A-2647 | + | AAAUAAGAAUGUCCCCCAAU | 20 | 3132 |
| BCL11A-2648 | - | AACCCCAGCACUUAAGCAAA | 20 | 3133 |
| BCL11A-2649 | + | AAGAAUGGCUUCAAGAGGCU | 20 | 3134 |
| BCL11A-2650 | + | AAUGGCUUCAAGAGGCU | 17 | 3135 |
| BCL11A-2651 | - | ACAGAUGAUGAACCAGACCA | 20 | 3136 |
| BCL11A-2652 | - | ACCAGACCACGGCCCGU | 17 | 3137 |
| BCL11A-2653 | - | ACCCCAGCACUUAAGCAAAC | 20 | 3138 |
| BCL11A-2654 | + | ACCUGGAUGCCAACCUCCAC | 20 | 3139 |
| BCL11A-2655 | + | ACUGCCCACAGGUGAGG | 17 | 3140 |
| BCL11A-2656 | + | AGAGCUCCAUGUGCAGAACG | 20 | 3141 |
| BCL11A-2657 | - | AGAUGAACUUCCCAUUG | 17 | 3142 |
| BCL11A-2658 | + | AGCUCCAUGUGCAGAACGAG | 20 | 3143 |
| BCL11A-2659 | - | AGGAAUUUGCCCCAAAC | 17 | 3144 |
| BCL11A-2660 | + | AGGAGGUCAUGAUCCCCUUC | 20 | 3145 |
| BCL11A-2661 | + | AGGUCAUGAUCCCCUUC | 17 | 3146 |
| BCL11A-2662 | - | AUAAACUUCUGCACUGG | 17 | 3147 |
| BCL11A-2663 | + | AUAAGAAUGUCCCCCAA | 17 | 3148 |
| BCL11A-2664 | - | AUCAUGACCUCCUCACCUGU | 20 | 3149 |
| BCL11A-2665 | + | AUCUCGAUUGGUGAAGGGGA | 20 | 3150 |
| BCL11A-2666 | - | AUGACCUCCUCACCUGU | 17 | 3151 |
| BCL11A-2667 | + | AUGUGCAGAACGAGGGG | 17 | 3152 |
| BCL11A-2668 | + | AUUGGUGAAGGGGAAGG | 17 | 3153 |
| BCL11A-2669 | - | CACAAACGGAAACAAUGCAA | 20 | 3154 |
| BCL11A-2670 | + | CACUCAUCCCAGGCGUG | 17 | 3155 |
| BCL11A-2671 | + | CAGAACGAGGGGAGGAG | 17 | 3156 |
| BCL11A-2672 | - | CAGAUGAACUUCCCAUU | 17 | 3157 |
| BCL11A-2673 | + | CAGCUUUUUCUAAGCAG | 17 | 3158 |
| BCL11A-2674 | - | CAUCCAGGUCACGCCAG | 17 | 3159 |

TABLE 4D-continued

4th Tier

| gRNA Name | DNA Strand | Targeting Domain | Target Site Length | SEQ ID NO |
|---|---|---|---|---|
| BCL11A-2675 | + | CAUCUCGAUUGGUGAAG | 17 | 3160 |
| BCL11A-2676 | + | CAUCUGGCACUGCCCAC | 17 | 3161 |
| BCL11A-2677 | - | CAUGACCUCCUCACCUG | 17 | 3162 |
| BCL11A-2678 | + | CCAAUGGGAAGUUCAUC | 17 | 3163 |
| BCL11A-2679 | + | CCACAGCUUUUUCUAAGCAG | 20 | 3164 |
| BCL11A-2680 | - | CCAGACCACGGCCCGUU | 17 | 3165 |
| BCL11A-2681 | - | CCAGAUGAACUUCCCAU | 17 | 3166 |
| BCL11A-2682 | - | CCAGAUGAACUUCCCAUUGG | 20 | 3167 |
| BCL11A-2683 | - | CCAGCACUUAAGCAAAC | 17 | 3168 |
| BCL11A-2684 | - | CCCAGCACUUAAGCAAA | 17 | 3169 |
| BCL11A-2685 | + | CCCCUUCUGGAGCUCCCAAC | 20 | 3170 |
| BCL11A-2686 | - | CCCGUUGGGAGCUCCAGAAG | 20 | 3171 |
| BCL11A-2687 | - | CCGUUGGGAGCUCCAGA | 17 | 3172 |
| BCL11A-2688 | + | CCGUUUGCUUAAGUGCU | 17 | 3173 |
| BCL11A-2689 | - | CCUCUGCUUAGAAAAGCUG | 20 | 3174 |
| BCL11A-2690 | + | CCUUCUGGAGCUCCCAA | 17 | 3175 |
| BCL11A-2691 | - | CGUGGAGGUUGGCAUCC | 17 | 3176 |
| BCL11A-2692 | - | CGUUGGGAGCUCCAGAA | 17 | 3177 |
| BCL11A-2693 | + | CGUUUGCUUAAGUGCUG | 17 | 3178 |
| BCL11A-2694 | + | CUAUGUGUUCCUGUUUG | 17 | 3179 |
| BCL11A-2695 | + | CUCCAUGUGCAGAACGA | 17 | 3180 |
| BCL11A-2696 | - | CUCUAAUCCCCACGCCU | 17 | 3181 |
| BCL11A-2697 | + | CUGCACUCAUCCCAGGCGUG | 20 | 3182 |
| BCL11A-2698 | + | CUGCUAUGUGUUCCUGUUUG | 20 | 3183 |
| BCL11A-2699 | - | CUGCUUAGAAAAGCUG | 17 | 3184 |
| BCL11A-2700 | + | CUGGAGCUCCCAACGGGCCG | 20 | 3185 |
| BCL11A-2701 | + | CUGGAUGCCAACCUCCA | 17 | 3186 |
| BCL11A-2702 | + | CUUCUGGAGCUCCCAAC | 17 | 3187 |
| BCL11A-2703 | - | UAAACUUCUGCACUGGA | 17 | 3188 |
| BCL11A-2704 | + | UAAGAAUGUCCCCCAAU | 17 | 3189 |
| BCL11A-2705 | - | UAGAGGAAUUUGCCCCAAAC | 20 | 3190 |
| BCL11A-2706 | + | UAUUCUGCACUCAUCCC | 17 | 3191 |
| BCL11A-2707 | + | UCCAUGUGCAGAACGAG | 17 | 3192 |
| BCL11A-2708 | + | UCCAUGUGCAGAACGAGGGG | 20 | 3193 |
| BCL11A-2709 | - | UCCCCUCGUUCUGCACA | 17 | 3194 |
| BCL11A-2710 | + | UCCCCUUCUGGAGCUCCCAA | 20 | 3195 |
| BCL11A-2711 | - | UCCCGUGGAGGUUGGCAUCC | 20 | 3196 |
| BCL11A-2712 | - | UCCUCCCCUCGUUCUGCACA | 20 | 3197 |
| BCL11A-2713 | + | UCGAUUGGUGAAGGGGA | 17 | 3198 |
| BCL11A-2714 | + | UCGAUUGGUGAAGGGGAAGG | 20 | 3199 |
| BCL11A-2715 | + | UCUGCACUCAUCCCAGGCGU | 20 | 3200 |
| BCL11A-2716 | + | UCUGGCACUGCCCACAGGUG | 20 | 3201 |
| BCL11A-2717 | + | UCUGUAAGAAUGGCUUCAAG | 20 | 3202 |
| BCL11A-2718 | + | UGCACUCAUCCCAGGCG | 17 | 3203 |
| BCL11A-2719 | - | UGCCAGAUGAACUUCCCAUU | 20 | 3204 |
| BCL11A-2720 | + | UGCUAUGUGUUCCUGUU | 17 | 3205 |
| BCL11A-2721 | + | UGGAUGCCAACCUCCAC | 17 | 3206 |
| BCL11A-2722 | + | UGGUUCAUCAUCUGUAAGAA | 20 | 3207 |
| BCL11A-2723 | - | UGUUUAUCAACGUCAUCUAG | 20 | 3208 |
| BCL11A-2724 | - | UUAUUUUUAUCGAGCACAAA | 20 | 3209 |
| BCL11A-2725 | + | UUCAUCAUCUGUAAGAA | 17 | 3210 |
| BCL11A-2726 | + | UUCCCGUUUGCUUAAGUGCU | 20 | 3211 |
| BCL11A-2727 | + | UUCUGCACUCAUCCCAGGCG | 20 | 3212 |
| BCL11A-2728 | + | UUUCAUCUCGAUUGGUGAAG | 20 | 3213 |
| BCL11A-2729 | + | UUUUCAUCUCGAUUGGUGAA | 20 | 3214 |
| BCL11A-2730 | - | UUUUUAUCGAGCACAAA | 17 | 3215 |
| BCL11A-2731 | + | UUUUUCAUCUCGAUUGGUGA | 20 | 3216 |

Table 4E provides exemplary targeting domains for knocking out the BCL11A gene by targeting the early coding sequence the BCL11A gene selected according to fifth tier parameters. The targeting domains outside the first 500 bp of coding sequence downstream of start codon. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 4E

5th Tier

| gRNA Name | DNA Strand | Targeting Domain | Target Site Length | SEQ ID NO |
|---|---|---|---|---|
| BCL11A-2732 | + | UAUGCGGUCCGACUCGC | 17 | 3217 |
| BCL11A-2733 | - | UCGGACCGCAUAGACGA | 17 | 3218 |
| BCL11A-2734 | + | UGGGUACUACGCCGAAU | 17 | 3219 |
| BCL11A-2735 | + | GGUACUACGCCGAAUGG | 17 | 3220 |
| BCL11A-2736 | - | UUGCGACGAAGACUCGG | 17 | 3221 |
| BCL11A-2737 | + | CUGGGUACUACGCCGAA | 17 | 3222 |
| BCL11A-2738 | + | GGGUACUACGCCGAAUG | 17 | 3223 |
| BCL11A-2739 | + | UCGGACUUGACCGUCAU | 17 | 3224 |
| BCL11A-2740 | + | AGGGAUACCAACCCGCG | 17 | 3225 |
| BCL11A-2741 | - | CGCGCUCAAGUCCGUGG | 17 | 3226 |
| BCL11A-2742 | + | CGAGGAGUGCUCCGACG | 17 | 3227 |
| BCL11A-2743 | + | GUCGGACUUGACCGUCA | 17 | 3228 |
| BCL11A-2744 | + | UGCACGCGUGGUCGCAC | 17 | 3229 |
| BCL11A-2745 | - | CAGCGCGCUCAAGUCCG | 17 | 3230 |
| BCL11A-2746 | + | UACCAACCCGCGGGGUC | 17 | 3231 |
| BCL11A-2747 | - | GUGGCUCGCCGGCUACG | 17 | 3232 |
| BCL11A-2748 | + | CGGACUUGACCGUCAUG | 17 | 3233 |
| BCL11A-2749 | - | CACCGCAUAGAGCGCCU | 17 | 3234 |
| BCL11A-2750 | - | GCGCAUCAAGCUCGAGA | 17 | 3235 |
| BCL11A-2751 | + | GGCCCGGACCACUAAUA | 17 | 3236 |
| BCL11A-2752 | + | GCCCGGACCACUAAUAU | 17 | 3237 |
| BCL11A-2753 | - | GCAUAAGCGCGGCCACC | 17 | 3238 |
| BCL11A-2754 | + | AGGCGCUCUAUGCGGUG | 17 | 3239 |
| BCL11A-2755 | - | ACGGUCAAGUCCGACGA | 17 | 3240 |
| BCL11A-2756 | + | CGAGGCCGACUCGCCCG | 17 | 3241 |
| BCL11A-2757 | - | ACCGCAUAGAGCGCCUG | 17 | 3242 |
| BCL11A-2758 | - | CGACCACGCGUGCACCC | 17 | 3243 |
| BCL11A-2759 | + | GUACACGUUCUCCGUGU | 17 | 3244 |
| BCL11A-2760 | - | CACUUGCGACGAAGACU | 17 | 3245 |
| BCL11A-2761 | - | CGGGUUGGUAUCCCUUC | 17 | 3246 |
| BCL11A-2762 | - | CUCGUCGGAGCACUCCU | 17 | 3247 |
| BCL11A-2763 | + | CCCGGACCACUAAUAUG | 17 | 3248 |

TABLE 4E-continued

5th Tier

| gRNA Name | DNA Strand | Targeting Domain | Target Site Length | SEQ ID NO |
|---|---|---|---|---|
| BCL11A-2764 | + | UCGGUGGUGGACUAAAC | 17 | 3249 |
| BCL11A-2765 | + | CAGGCGCUCUAUGCGGU | 17 | 3250 |
| BCL11A-2766 | + | AAGGGAUACCAACCCGC | 17 | 3251 |
| BCL11A-2767 | + | GGCGCUCUAUGCGGUGG | 17 | 3252 |
| BCL11A-2768 | - | CCACCGCAUAGAGCGCC | 17 | 3253 |
| BCL11A-2769 | - | UACUCGCAGUGGCUCGC | 17 | 3254 |
| BCL11A-2770 | - | CGGGCGAGUCGGCCUCG | 17 | 3255 |
| BCL11A-2771 | + | UACACGUUCUCCGUGUU | 17 | 3256 |
| BCL11A-2772 | - | AGCACGCCCCAUAUUAG | 17 | 3257 |
| BCL11A-2773 | + | GAAGGGAUACCAACCCG | 17 | 3258 |
| BCL11A-2774 | + | UUGGGCAUCGCGGCCGG | 17 | 3259 |
| BCL11A-2775 | - | CCGGGCGAGUCGGCCUC | 17 | 3260 |
| BCL11A-2776 | + | GGUGGAGAGACCGUCGU | 17 | 3261 |
| BCL11A-2777 | + | GUUGGGCAUCGCGGCCG | 17 | 3262 |
| BCL11A-2778 | - | AGAACGUGUACUCGCAG | 17 | 3263 |
| BCL11A-2779 | + | ACCAACCCGCGGGGUCA | 17 | 3264 |
| BCL11A-2780 | - | CACGAGAACAGCUCGCG | 17 | 3265 |
| BCL11A-2781 | - | UAUUAGUGGUCCGGGCC | 17 | 3266 |
| BCL11A-2782 | + | CGUCGCAAGUGUCCCUG | 17 | 3267 |
| BCL11A-2783 | + | CCCGCGAGCUGUUCUCG | 17 | 3268 |
| BCL11A-2784 | + | UGCGCCGGUGCACCACC | 17 | 3269 |
| BCL11A-2785 | - | CUGCCCGACGUCAUGCA | 17 | 3270 |
| BCL11A-2786 | - | GACGAAGACUCGGUGGC | 17 | 3271 |
| BCL11A-2787 | - | CCUGCCCGACGUCAUGC | 17 | 3272 |
| BCL11A-2788 | + | AAGGGCGGCUUGCUACC | 17 | 3273 |
| BCL11A-2789 | - | GGGUGGACUACGGCUUC | 17 | 3274 |
| BCL11A-2790 | + | UCGCUGGUGCCGGGUUC | 17 | 3275 |
| BCL11A-2791 | - | GGCGAGAAGCAUAAGCG | 17 | 3276 |
| BCL11A-2792 | + | GGACUUGAGCGCGCUGC | 17 | 3277 |
| BCL11A-2793 | - | CUCGGUGGCCGGCGAGU | 17 | 3278 |
| BCL11A-2794 | + | CCCGAGGCCGACUCGCC | 17 | 3279 |
| BCL11A-2795 | - | CCCGGGCGAGUCGGCCU | 17 | 3280 |
| BCL11A-2796 | - | CCGCAUAGAGCGCCUGG | 17 | 3281 |
| BCL11A-2797 | + | UGUUGGGCAUCGCGGCC | 17 | 3282 |
| BCL11A-2798 | + | GUGUUGGGCAUCGCGGC | 17 | 3283 |
| BCL11A-2799 | + | UCUCGAUACUGAUCC | 17 | 3284 |
| BCL11A-2800 | - | ACCCGAGUGCCUUUGAC | 17 | 3285 |

TABLE 4E-continued

5th Tier

| gRNA Name | DNA Strand | Targeting Domain | Target Site Length | SEQ ID NO |
|---|---|---|---|---|
| BCL11A-2801 | + | UCCGACGAGGAGGCAAA | 17 | 3286 |
| BCL11A-2802 | − | ACCCGGCACCAGCGACU | 17 | 3287 |
| BCL11A-2803 | + | CCCCGUUCUCCGGGAUC | 17 | 3288 |
| BCL11A-2804 | + | CCGAGGCCGACUCGCCC | 17 | 3289 |
| BCL11A-2805 | − | CCCCAUAUUAGUGGUCC | 17 | 3290 |
| BCL11A-2806 | + | GACUUGGACUUGACCGG | 17 | 3291 |
| BCL11A-2807 | − | GCCCCAUAUUAGUGGUC | 17 | 3292 |
| BCL11A-2808 | − | AGGGUGGACUACGGCUU | 17 | 3293 |
| BCL11A-2809 | − | CAAAUCGUCCCCCAUGA | 17 | 3294 |
| BCL11A-2810 | − | CGACGUCAUGCAGGGCA | 17 | 3295 |
| BCL11A-2811 | − | GGCCGCGAUGCCCAACA | 17 | 3296 |
| BCL11A-2812 | + | CCAGGCGCUCUAUGCGG | 17 | 3297 |
| BCL11A-2813 | − | CCUGAUCCCGGAGAACG | 17 | 3298 |
| BCL11A-2814 | + | CCAACCCGCGGGGUCAG | 17 | 3299 |
| BCL11A-2815 | − | GGCGAGUCGGCCUCGGG | 17 | 3300 |
| BCL11A-2816 | + | GGCAAAAGGCGAUUGUC | 17 | 3301 |
| BCL11A-2817 | + | UUUGGACAGGCCCCCCG | 17 | 3302 |
| BCL11A-2818 | + | GCGGCUUGCUACCUGGC | 17 | 3303 |
| BCL11A-2819 | + | GGACUUGACCGUCAUGG | 17 | 3304 |
| BCL11A-2820 | + | GGAGUGCUCCGACGAGG | 17 | 3305 |
| BCL11A-2821 | − | AUUAGUGGUCCGGGCCC | 17 | 3306 |
| BCL11A-2822 | − | CCACGAGAACAGCUCGC | 17 | 3307 |
| BCL11A-2823 | − | GUAUCGAGAGAGGCUUC | 17 | 3308 |
| BCL11A-2824 | + | CUCCGUGUUGGGCAUCG | 17 | 3309 |
| BCL11A-2825 | + | CAAACUCCCGUUCUCCG | 17 | 3310 |
| BCL11A-2826 | − | ACCUGAUCCCGGAGAAC | 17 | 3311 |
| BCL11A-2827 | − | GGCACUGUUAAUGGCCG | 17 | 3312 |
| BCL11A-2828 | + | UUCUCCGGGAUCAGGUU | 17 | 3313 |
| BCL11A-2829 | − | UAUGGAGCCUCCCGCCA | 17 | 3314 |
| BCL11A-2830 | + | CUUGAUGCGCUUAGAGA | 17 | 3315 |
| BCL11A-2831 | − | UAGCAAGCCGCCCUUCC | 17 | 3316 |
| BCL11A-2832 | − | CCGGCUACGCGGCCUCC | 17 | 3317 |
| BCL11A-2833 | + | UCCAAGUGAUGUCUCGG | 17 | 3318 |
| BCL11A-2834 | − | GAACAGCUCGCGGGGCG | 17 | 3319 |
| BCL11A-2835 | − | GCUGCGGUUGAAUCCAA | 17 | 3320 |
| BCL11A-2836 | + | UGACUUGGACUUGACCG | 17 | 3321 |
| BCL11A-2837 | − | CCCGGAGAACGGGGACG | 17 | 3322 |
| BCL11A-2838 | + | GUGGCGCUUCAGCUUGC | 17 | 3323 |
| BCL11A-2839 | + | GUUCUCCGGGAUCAGGU | 17 | 3324 |
| BCL11A-2840 | + | CAGUGCCAUCGUCUAUG | 17 | 3325 |
| BCL11A-2841 | + | UCUCCGGGAUCAGGUUG | 17 | 3326 |
| BCL11A-2842 | − | GACGAUGGCACUGUUAA | 17 | 3327 |
| BCL11A-2843 | − | CUGCUCCCCGGGCGAGU | 17 | 3328 |
| BCL11A-2844 | + | CGGUGGUGGACUAAACA | 17 | 3329 |
| BCL11A-2845 | − | CUCGCGGGGCGCGGUCG | 17 | 3330 |
| BCL11A-2846 | + | AUGCCCUGCAUGACGUC | 17 | 3331 |
| BCL11A-2847 | + | UGGACUUGACCGGGGGC | 17 | 3332 |
| BCL11A-2848 | − | ACCACGAGAACAUCACU | 17 | 3333 |
| BCL11A-2849 | − | GGAGUUCGACCUGCCCC | 17 | 3334 |
| BCL11A-2850 | + | CCUGCAUGACGUCGGGC | 17 | 3335 |
| BCL11A-2851 | + | CUGCAUGACGUCGGGCA | 17 | 3336 |
| BCL11A-2852 | − | AGGAUCAGUAUCGAGAG | 17 | 3337 |
| BCL11A-2853 | + | GGACUUGACCGGGGGCU | 17 | 3338 |
| BCL11A-2854 | + | AAAGGCACUCGGGUGAU | 17 | 3339 |
| BCL11A-2855 | − | UGGACGGAGGGAUCUCG | 17 | 3340 |
| BCL11A-2856 | + | CCCCCAGGCGCUCUAUG | 17 | 3341 |
| BCL11A-2857 | − | CCGCCAUGGAUUUCUCU | 17 | 3342 |
| BCL11A-2858 | − | GGCGCGGUCGUGGGCGU | 17 | 3343 |
| BCL11A-2859 | − | AACCUGAUCCCGGAGAA | 17 | 3344 |
| BCL11A-2860 | + | CAUGCCCUGCAUGACGU | 17 | 3345 |
| BCL11A-2861 | + | CGCUGGUGCCGGGUUCC | 17 | 3346 |
| BCL11A-2862 | + | CCUGGAGGCCGCGUAGC | 17 | 3347 |
| BCL11A-2863 | − | CCCCGACCCCGCGGGU | 17 | 3348 |
| BCL11A-2864 | + | GCUUAUGCUUCUCGCCC | 17 | 3349 |
| BCL11A-2865 | − | AAGUCAUGCGAGUUCUG | 17 | 3350 |
| BCL11A-2866 | + | CACCAAGUCGCUGGUGC | 17 | 3351 |
| BCL11A-2867 | − | CCCGAGUGCCUUUGACA | 17 | 3352 |
| BCL11A-2868 | + | CAUGACUUGGACUUGAC | 17 | 3353 |
| BCL11A-2869 | − | CGACCCCAACCUGAUCC | 17 | 3354 |
| BCL11A-2870 | + | ACCAAGUCGCUGGUGCC | 17 | 3355 |
| BCL11A-2871 | + | AAGUGAUGUCUCGGUGG | 17 | 3356 |
| BCL11A-2872 | − | CUUCUCCACACCGCCCG | 17 | 3357 |
| BCL11A-2873 | + | UGGAGUCUCCGAAGCUA | 17 | 3358 |
| BCL11A-2874 | − | CGCUUCUCCACACCGCC | 17 | 3359 |

TABLE 4E-continued

5th Tier

| gRNA Name | DNA Strand | Targeting Domain | Target Site Length | SEQ ID NO |
|---|---|---|---|---|
| BCL11A-2875 | + | GCUGGUGCCGGGUUCCG | 17 | 3360 |
| BCL11A-2876 | - | CGCAGCGGCACGGGAAG | 17 | 3361 |
| BCL11A-2877 | + | GCAUCGCGGCCGGGGGC | 17 | 3362 |
| BCL11A-2878 | - | GAGCACUCCUCGGAGAA | 17 | 3363 |
| BCL11A-2879 | + | GGGGGGCGUCGCCAGGA | 17 | 3364 |
| BCL11A-2880 | + | GAAAGCGCCCUUCUGCC | 17 | 3365 |
| BCL11A-2881 | - | CUGGACGGAGGGAUCUC | 17 | 3366 |
| BCL11A-2882 | - | CGGCUUCGGGCUGAGCC | 17 | 3367 |
| BCL11A-2883 | + | GGGGGCGUCGCCAGGAA | 17 | 3368 |
| BCL11A-2884 | + | UAACCUUUGCAUAGGGC | 17 | 3369 |
| BCL11A-2885 | - | GGGCGAGUCGGCCUCGG | 17 | 3370 |
| BCL11A-2886 | - | CACACCGCCCGGGGAGC | 17 | 3371 |
| BCL11A-2887 | - | GGGAUCUCGGGGCGCAG | 17 | 3372 |
| BCL11A-2888 | + | CUCGCUGAAGUGCUGCA | 17 | 3373 |
| BCL11A-2889 | - | UCGGGGCGCAGCGGCAC | 17 | 3374 |
| BCL11A-2890 | - | AAGUCCCUGACCCCGC | 17 | 3375 |
| BCL11A-2891 | - | GCCUUUUGCCUCCUCGU | 17 | 3376 |
| BCL11A-2892 | - | CACCUGGCCGAGGCCGA | 17 | 3377 |
| BCL11A-2893 | - | GGUAUCCCUUCAGGACU | 17 | 3378 |
| BCL11A-2894 | + | GUGGUGGACUAAACAGG | 17 | 3379 |
| BCL11A-2895 | + | GCGAGCUGUUCUCGUGG | 17 | 3380 |
| BCL11A-2896 | - | AGCACUCCUCGGAGAAC | 17 | 3381 |
| BCL11A-2897 | - | CAUGCAGCACUUCAGCG | 17 | 3382 |
| BCL11A-2898 | + | UGGCCUGGGUGCACGCG | 17 | 3383 |
| BCL11A-2899 | - | AGCGAGAGGGUGGACUA | 17 | 3384 |
| BCL11A-2900 | + | GCACAGGUUGCACUUGU | 17 | 3385 |
| BCL11A-2901 | + | GAGAAAUCCAUGGCGGG | 17 | 3386 |
| BCL11A-2902 | + | GCAGAACUCGCAUGACU | 17 | 3387 |
| BCL11A-2903 | + | UCUCCGAAGCUAAGGAA | 17 | 3388 |
| BCL11A-2904 | + | UGACGUCGGGCAGGGCG | 17 | 3389 |
| BCL11A-2905 | + | GGGUCCAAGUGAUGUCU | 17 | 3390 |
| BCL11A-2906 | - | GCAACCUGGUGGUGCAC | 17 | 3391 |
| BCL11A-2907 | + | GGUGGCGCGCCGCCUCC | 17 | 3392 |
| BCL11A-2908 | + | GCUGCCCACCAAGUCGC | 17 | 3393 |
| BCL11A-2909 | + | GUUCUCGCUCUUGAACU | 17 | 3394 |
| BCL11A-2910 | + | CCGCAGCACCCUGUCAA | 17 | 3395 |
| BCL11A-2911 | - | GAAGUCCCUGACCCCG | 17 | 3396 |
| BCL11A-2912 | - | GCGCGGCCACCUGGCCG | 17 | 3397 |
| BCL11A-2913 | + | GGCGUCGCCAGGAAGGG | 17 | 3398 |
| BCL11A-2914 | - | GUUGAAUCCAAUGGCUA | 17 | 3399 |
| BCL11A-2915 | - | CUCGGGGCGCAGCGGCA | 17 | 3400 |
| BCL11A-2916 | - | CCGAGGCCGAGGGCCAC | 17 | 3401 |
| BCL11A-2917 | + | CUAAACAGGGGGGAGU | 17 | 3402 |
| BCL11A-2918 | - | GCGGCACGGGAAGUGGA | 17 | 3403 |
| BCL11A-2919 | + | CACAGGUUGCACUUGUA | 17 | 3404 |
| BCL11A-2920 | - | CAGCGAGGCCUUCCACC | 17 | 3405 |
| BCL11A-2921 | - | AACCUGCUAAGAAUACC | 17 | 3406 |
| BCL11A-2922 | + | AUCCUGGUAUUCUUAGC | 17 | 3407 |
| BCL11A-2923 | + | GGUGGUGGACUAAACAG | 17 | 3408 |
| BCL11A-2924 | - | CGAGGCCGAGGGCCACA | 17 | 3409 |
| BCL11A-2925 | + | GUACAUGUGUAGCUGCU | 17 | 3410 |
| BCL11A-2926 | + | UUGAUGCGCUUAGAGAA | 17 | 3411 |
| BCL11A-2927 | + | UCCUCGUCCCCGUUCUC | 17 | 3412 |
| BCL11A-2928 | + | AUGACUUGGACUUGACC | 17 | 3413 |
| BCL11A-2929 | + | GUCUCCGAAGCUAAGGA | 17 | 3414 |
| BCL11A-2930 | + | GGUGGACUAAACAGGGG | 17 | 3415 |
| BCL11A-2931 | + | GCAUGUGCGUCUUCAUG | 17 | 3416 |
| BCL11A-2932 | + | GGCACUCGGGUGAUGGG | 17 | 3417 |
| BCL11A-2933 | + | AUAGGGCUGGGCCGGCC | 17 | 3418 |
| BCL11A-2934 | + | CCGUCCAGCUCCCCGGG | 17 | 3419 |
| BCL11A-2935 | + | GCAGUAACCUUUGCAUA | 17 | 3420 |
| BCL11A-2936 | - | GAUCCCUUCCUUAGCUU | 17 | 3421 |
| BCL11A-2937 | + | AAGGGCUCAGCGAGCU | 17 | 3422 |
| BCL11A-2938 | - | AGCUGACGGAGAGCGAG | 17 | 3423 |
| BCL11A-2939 | - | UCGCGGGGCGCGUCGU | 17 | 3424 |
| BCL11A-2940 | - | AGCGGCACGGGAAGUGG | 17 | 3425 |
| BCL11A-2941 | + | CAAAGGCACUCGGGUGA | 17 | 3426 |
| BCL11A-2942 | + | CUGCACCUAGUCCUGAA | 17 | 3427 |
| BCL11A-2943 | - | GCUGGACGGAGGGAUCU | 17 | 3428 |
| BCL11A-2944 | + | CCCUGUCAAAGGCACUC | 17 | 3429 |
| BCL11A-2945 | + | AACCUUUGCAUAGGGCU | 17 | 3430 |
| BCL11A-2946 | + | CGCCCGGGGAGCAGCCG | 17 | 3431 |
| BCL11A-2947 | + | UGGUGGACUAAACAGGG | 17 | 3432 |
| BCL11A-2948 | - | GGCCCAGCCCUAUGCAA | 17 | 3433 |

TABLE 4E-continued

5th Tier

| gRNA Name | DNA Strand | Targeting Domain | Target Site Length | SEQ ID NO |
|---|---|---|---|---|
| BCL11A-2949 | + | CCUCGUCCCCGUUCUCC | 17 | 3434 |
| BCL11A-2950 | - | GCCAGCUCCCCGGAACC | 17 | 3435 |
| BCL11A-2951 | + | GCCGGGUUCCGGGGAGC | 17 | 3436 |
| BCL11A-2952 | + | UGCAGUAACCUUUGCAU | 17 | 3437 |
| BCL11A-2953 | + | GCUUCUCGCCCAGGACC | 17 | 3438 |
| BCL11A-2954 | - | CCGCCCGGGGAGCUGGA | 17 | 3439 |
| BCL11A-2955 | - | CCGGGGAGCUGGACGGA | 17 | 3440 |
| BCL11A-2956 | - | CUUCCGGCCUGGCAGAA | 17 | 3441 |
| BCL11A-2957 | + | CCUAGAGAAAUCCAUGG | 17 | 3442 |
| BCL11A-2958 | + | GGAGGGGGGGCGUCGCC | 17 | 3443 |
| BCL11A-2959 | - | UACUUAGAAAGCGAACA | 17 | 3444 |
| BCL11A-2960 | + | GGAGGCUCCAUAGCCAU | 17 | 3445 |
| BCL11A-2961 | + | ACACAUCUUGAGCUCUC | 17 | 3446 |
| BCL11A-2962 | - | GGCACCAGCGACUUGGU | 17 | 3447 |
| BCL11A-2963 | + | GGGAUCUUUGAGCUGCC | 17 | 3448 |
| BCL11A-2964 | + | GCAGCAGCUUUUUGGAC | 17 | 3449 |
| BCL11A-2965 | + | CUGCAAUAUGAAUCCCA | 17 | 3450 |
| BCL11A-2966 | + | UCUGCACCUAGUCCUGA | 17 | 3451 |
| BCL11A-2967 | + | GAAGGGGCUCAGCGAGC | 17 | 3452 |
| BCL11A-2968 | + | UUCCGGGGAGCUGGCGG | 17 | 3453 |
| BCL11A-2969 | - | GCACCGGCGCAGCCACA | 17 | 3454 |
| BCL11A-2970 | + | AUAUGAAUCCCAUGGAG | 17 | 3455 |
| BCL11A-2971 | - | GUGGUCCGGGCCCGGGC | 17 | 3456 |
| BCL11A-2972 | - | CUUCACACACCCCCAUU | 17 | 3457 |
| BCL11A-2973 | - | GUCCAAAAAGCUGCUGC | 17 | 3458 |
| BCL11A-2974 | - | CGGCACCAGCGACUUGG | 17 | 3459 |
| BCL11A-2975 | - | GCUUCUCCACACCGCCC | 17 | 3460 |
| BCL11A-2976 | + | CGCCCGUGUGGCUGCGC | 17 | 3461 |
| BCL11A-2977 | - | CACGCACAGAACACUCA | 17 | 3462 |
| BCL11A-2978 | + | UGUACAUGUGUAGCUGC | 17 | 3463 |
| BCL11A-2979 | - | CACCGGCGCAGCCACAC | 17 | 3464 |
| BCL11A-2980 | + | UUGCUACCUGGCUGGAA | 17 | 3465 |
| BCL11A-2981 | + | ACCCUGUCAAAGGCACU | 17 | 3466 |
| BCL11A-2982 | - | CCACCUGGCCGAGGCCG | 17 | 3467 |
| BCL11A-2983 | + | GGGCGGAUUGCAGAGGA | 17 | 3468 |
| BCL11A-2984 | + | CUAGAGAAAUCCAUGGC | 17 | 3469 |
| BCL11A-2985 | - | GGCGGAAGAGAUGGCCC | 17 | 3470 |
| BCL11A-2986 | + | GGGGCGGAUUGCAGAGG | 17 | 3471 |
| BCL11A-2987 | - | GUGUGGCAGUUUUCGGA | 17 | 3472 |
| BCL11A-2988 | - | GAGAGAGGCUUCCGGCC | 17 | 3473 |
| BCL11A-2989 | + | CGGGUGAUGGGUGGCCA | 17 | 3474 |
| BCL11A-2990 | - | CCCGGGGAGCUGGACGG | 17 | 3475 |
| BCL11A-2991 | - | UAGGAGACUUAGAGAGC | 17 | 3476 |
| BCL11A-2992 | + | CACAUCUUGAGCUCUCU | 17 | 3477 |
| BCL11A-2993 | + | CCUCGGCCUCGGCCAGG | 17 | 3478 |
| BCL11A-2994 | - | GGCCUUCCACCAGGUCC | 17 | 3479 |
| BCL11A-2995 | + | UCUCGCCCAGGACCUGG | 17 | 3480 |
| BCL11A-2996 | + | UCUGCCCUCUUUUGAGC | 17 | 3481 |
| BCL11A-2997 | + | ACUAAACAGGGGGGGAG | 17 | 3482 |
| BCL11A-2998 | + | CUUGACCGGGGCUGGG | 17 | 3483 |
| BCL11A-2999 | + | UUGACCGGGGCUGGGA | 17 | 3484 |
| BCL11A-3000 | - | AGACUUAGAGAGCUGGC | 17 | 3485 |
| BCL11A-3001 | - | AGCCCACCGCUGUCCCC | 17 | 3486 |
| BCL11A-3002 | - | AGCCAUUCACCAGUGCA | 17 | 3487 |
| BCL11A-3003 | - | GCUUCCGGCCUGGCAGA | 17 | 3488 |
| BCL11A-3004 | - | GACUUAGAGAGCUGGCA | 17 | 3489 |
| BCL11A-3005 | - | AGGCCCAGCUCAAAAGA | 17 | 3490 |
| BCL11A-3006 | + | UCGGGUGAUGGGUGGCC | 17 | 3491 |
| BCL11A-3007 | + | CAAGAGAAACCAUGCAC | 17 | 3492 |
| BCL11A-3008 | + | AUCUUUGAGCUGCCUGG | 17 | 3493 |
| BCL11A-3009 | + | UAUUCUUAGCAGGUUAA | 17 | 3494 |
| BCL11A-3010 | + | CUGCCCUCUUUUGAGCU | 17 | 3495 |
| BCL11A-3011 | + | CCAUCUCUUCCGCCCCC | 17 | 3496 |
| BCL11A-3012 | - | UGGCCGCGGCUGCUCCC | 17 | 3497 |
| BCL11A-3013 | + | CCUGUGGCCCUCGGCCU | 17 | 3498 |
| BCL11A-3014 | + | CAGCUCCCCGGGCGGUG | 17 | 3499 |
| BCL11A-3015 | + | UUUGCAUAGGGCUGGGC | 17 | 3500 |
| BCL11A-3016 | + | GGCCCUCGGCCUCGGCC | 17 | 3501 |
| BCL11A-3017 | - | GCUGACGGAGAGCGAGA | 17 | 3502 |
| BCL11A-3018 | - | AGAUGUGUGGCAGUUUU | 17 | 3503 |
| BCL11A-3019 | + | AUUCUUAGCAGGUUAAA | 17 | 3504 |
| BCL11A-3020 | + | UCUCCUAGAGAAAUCCA | 17 | 3505 |
| BCL11A-3021 | - | CCUUUGACAGGGUGCUG | 17 | 3506 |
| BCL11A-3022 | + | GGAGGGGCGGAUUGCAG | 17 | 3507 |

TABLE 4E-continued

5th Tier

| gRNA Name | DNA Strand | Targeting Domain | Target Site Length | SEQ ID NO |
|---|---|---|---|---|
| BCL11A-3023 | + | UUCUUAGCAGGUUAAAG | 17 | 3508 |
| BCL11A-3024 | + | CGGAUUGCAGAGGAGGG | 17 | 3509 |
| BCL11A-3025 | + | UUUGAGCUGGGCCUGCC | 17 | 3510 |
| BCL11A-3026 | + | CUUCAGCUUGCUGGCCU | 17 | 3511 |
| BCL11A-3027 | + | CUUGAACUUGGCCACCA | 17 | 3512 |
| BCL11A-3028 | − | CUGCAACCAUUCCAGCC | 17 | 3513 |
| BCL11A-3029 | − | CAUAGAGCGCCUGGGGG | 17 | 3514 |
| BCL11A-3030 | − | GGGCGCGGUCGUGGGCG | 17 | 3515 |
| BCL11A-3031 | + | UCCCAUGGAGAGGUGGC | 17 | 3516 |
| BCL11A-3032 | − | GGCCGCGGCUGCUCCCC | 17 | 3517 |
| BCL11A-3033 | − | AUUUCAGAGCAACCUGG | 17 | 3518 |
| BCL11A-3034 | − | GCCUUCCACCAGGUCCU | 17 | 3519 |
| BCL11A-3035 | + | UGAAUCCCAUGGAGAGG | 17 | 3520 |
| BCL11A-3036 | + | UUGAGCUGGGCCUGCCC | 17 | 3521 |
| BCL11A-3037 | + | AGGGGCUCAGCGAGCUG | 17 | 3522 |
| BCL11A-3038 | + | AGGGCUUCUCGCCCGUG | 17 | 3523 |
| BCL11A-3039 | − | CACCGCUGUCCCCAGGC | 17 | 3524 |
| BCL11A-3040 | − | CAAAUUUCAGAGCAACC | 17 | 3525 |
| BCL11A-3041 | − | AGAGAGCUCAAGAUGUG | 17 | 3526 |
| BCL11A-3042 | + | AACCAUGCACUGGUGAA | 17 | 3527 |
| BCL11A-3043 | + | CCUCCGUCCAGCUCCCC | 17 | 3528 |
| BCL11A-3044 | + | AGUGUCCCUGUGGCCCU | 17 | 3529 |
| BCL11A-3045 | + | CCCUCCGUCCAGCUCCC | 17 | 3530 |
| BCL11A-3046 | + | GGCCUGGGGACAGCGGU | 17 | 3531 |
| BCL11A-3047 | + | GCCCAGCAGCAGCUUUU | 17 | 3532 |
| BCL11A-3048 | − | CAGGCCCAGCUCAAAAG | 17 | 3533 |
| BCL11A-3049 | − | CUUCGGGCUGAGCCUGG | 17 | 3534 |
| BCL11A-3050 | + | CCCAUGGAGAGGUGGCU | 17 | 3535 |
| BCL11A-3051 | − | CCCAGCCACCUCUCCAU | 17 | 3536 |
| BCL11A-3052 | + | GGGUUCCGGGGAGCUGG | 17 | 3537 |
| BCL11A-3053 | + | UAGGGCUGGGCCGGCCU | 17 | 3538 |
| BCL11A-3054 | − | CCUGGGGGCGGAAGAGA | 17 | 3539 |
| BCL11A-3055 | + | GCCCAGGACCUGGUGGA | 17 | 3540 |
| BCL11A-3056 | − | CGGGCUGAGCCUGGAGG | 17 | 3541 |
| BCL11A-3057 | − | ACCACGAGAACAGCUCG | 17 | 3542 |
| BCL11A-3058 | + | CGGCCUGGGGACAGCGG | 17 | 3543 |
| BCL11A-3059 | − | UCCAAAAGCUGCUGCU | 17 | 3544 |
| BCL11A-3060 | + | GCGCCCUUCUGCCAGGC | 17 | 3545 |
| BCL11A-3061 | − | UCCCAGCCACCUCUCCA | 17 | 3546 |
| BCL11A-3062 | − | CUCCACCGCCAGCUCCC | 17 | 3547 |
| BCL11A-3063 | + | CUGGGCCUGCCCGGGCC | 17 | 3548 |
| BCL11A-3064 | + | AGGGCUGGGCCGGCCUG | 17 | 3549 |
| BCL11A-3065 | + | AACAGGGGGGAGUGGG | 17 | 3550 |
| BCL11A-3066 | − | GGAGAACGGGACGAGG | 17 | 3551 |
| BCL11A-3067 | + | UGAUGCGCUUAGAGAAG | 17 | 3552 |
| BCL11A-3068 | + | GGAUUGCAGAGGAGGGA | 17 | 3553 |
| BCL11A-3069 | + | GGCCGGCCUGGGGACAG | 17 | 3554 |
| BCL11A-3070 | + | GAUUGCAGAGGAGGGAG | 17 | 3555 |
| BCL11A-3071 | + | AUUGCAGAGGAGGGAGG | 17 | 3556 |
| BCL11A-3072 | + | ACCGGGGCUGGGAGGG | 17 | 3557 |
| BCL11A-3073 | + | UGGAGAGGUGGCUGGGA | 17 | 3558 |
| BCL11A-3074 | + | UUGCAGAGGAGGGAGGG | 17 | 3559 |
| BCL11A-3075 | − | CGGGGACGAGGAGGAAG | 17 | 3560 |
| BCL11A-3076 | − | GACGGAGAGCGAGAGGG | 17 | 3561 |
| BCL11A-3077 | − | UCCUCCCUCCCAGCCCC | 17 | 3562 |
| BCL11A-3078 | + | GCUUCAGCUUGCUGGCC | 17 | 3563 |
| BCL11A-3079 | + | UGCAGAGGAGGGAGGGG | 17 | 3564 |
| BCL11A-3080 | + | GGGCUGGGAGGGAGGAG | 17 | 3565 |
| BCL11A-3081 | − | GGAAGAGGAGGACGACG | 17 | 3566 |
| BCL11A-3082 | + | GGGGCUGGGAGGGAGGA | 17 | 3567 |
| BCL11A-3083 | − | GGAGGACGACGAGGAAG | 17 | 3568 |
| BCL11A-3084 | − | GGAGGAGGAGGAGCUGA | 17 | 3569 |
| BCL11A-3085 | + | GGGGGCUGGGAGGGAGG | 17 | 3570 |
| BCL11A-3086 | + | CUGGGAGGGAGGAGGGG | 17 | 3571 |
| BCL11A-3087 | − | CGAGGAAGAGGAAGAAG | 17 | 3572 |
| BCL11A-3088 | − | GGACGAGGAGGAAGAGG | 17 | 3573 |
| BCL11A-3089 | − | GGAAGAAGAGGAGGAAG | 17 | 3574 |
| BCL11A-3090 | − | GGAAGAGGAAGAAGAGG | 17 | 3575 |
| BCL11A-3091 | − | AGAAGAGGAGGAAGAGG | 17 | 3576 |
| BCL11A-3092 | − | AGAGGAGGAAGAGGAGG | 17 | 3577 |
| BCL11A-3093 | − | GGAGGAAGAGGAGGAGG | 17 | 3578 |
| BCL11A-3094 | + | GUCUAUGCGGUCCGACUCGC | 20 | 3579 |
| BCL11A-3095 | + | UCGUCGGACUUGACCGUCAU | 20 | 3580 |
| BCL11A-3096 | + | CGUCGGACUUGACCGUCAUG | 20 | 3581 |

TABLE 4E-continued

5th Tier

| gRNA Name | DNA Strand | Targeting Domain | Target Site Length | SEQ ID NO |
|---|---|---|---|---|
| BCL11A-3097 | − | AUGACGGUCAAGUCCGACGA | 20 | 3582 |
| BCL11A-3098 | − | GAGUCGGACCGCAUAGACGA | 20 | 3583 |
| BCL11A-3099 | + | CGGGCCCGGACCACUAAUAU | 20 | 3584 |
| BCL11A-3100 | + | GUCGUCGGACUUGACCGUCA | 20 | 3585 |
| BCL11A-3101 | + | CUCUGGGUACUACGCCGAAU | 20 | 3586 |
| BCL11A-3102 | + | CUGGGUACUACGCCGAAUGG | 20 | 3587 |
| BCL11A-3103 | + | CCGGGCCCGGACCACUAAUA | 20 | 3588 |
| BCL11A-3104 | − | CCGCGGGUUGGUAUCCCUUC | 20 | 3589 |
| BCL11A-3105 | + | UCUGGGUACUACGCCGAAUG | 20 | 3590 |
| BCL11A-3106 | + | GGAUACCAACCCGCGGGGUC | 20 | 3591 |
| BCL11A-3107 | − | ACGCCCCAUAUUAGUGGUCC | 20 | 3592 |
| BCL11A-3108 | − | CACUUGCGACGAAGACUCGG | 20 | 3593 |
| BCL11A-3109 | + | UCUCGGGUACUACGCCGAA | 20 | 3594 |
| BCL11A-3110 | − | UAAGCGCAUCAAGCUCGAGA | 20 | 3595 |
| BCL11A-3111 | − | UGCGACGAAGACUCGGUGGC | 20 | 3596 |
| BCL11A-3112 | + | CGCGCUUAUGCUUCUCGCCC | 20 | 3597 |
| BCL11A-3113 | + | UGAAGGGAUACCAACCCGCG | 20 | 3598 |
| BCL11A-3114 | + | GGGCCCGGACCACUAAUAUG | 20 | 3599 |
| BCL11A-3115 | + | CGUGUGGGCAUCGCGGCCG | 20 | 3600 |
| BCL11A-3116 | + | UCCGUGUUGGGCAUCGCGGC | 20 | 3601 |
| BCL11A-3117 | + | GUCGGACUUGACCGUCAUGG | 20 | 3602 |
| BCL11A-3118 | + | GCGCAAACUCCCGUUCUCCG | 20 | 3603 |
| BCL11A-3119 | + | CUCCGAGGAGUGCUCCGACG | 20 | 3604 |
| BCL11A-3120 | + | CACGGACUUGAGCGCGCUGC | 20 | 3605 |
| BCL11A-3121 | − | CACGCCCCAUAUUAGUGGUC | 20 | 3606 |
| BCL11A-3122 | + | GAUACCAACCCGCGGGGUCA | 20 | 3607 |
| BCL11A-3123 | − | CAGCGCGCUCAAGUCCGUGG | 20 | 3608 |
| BCL11A-3124 | + | GGGUGCACGCGUGGUCGCAC | 20 | 3609 |
| BCL11A-3125 | − | GAAGCAUAAGCGCGGCCACC | 20 | 3610 |
| BCL11A-3126 | − | GUGCGACCACGCGUGCACCC | 20 | 3611 |
| BCL11A-3127 | + | GAGUACACGUUCUCCGUGUU | 20 | 3612 |
| BCL11A-3128 | + | GUCUCGGUGGUGGACUAAAC | 20 | 3613 |
| BCL11A-3129 | + | CCGUUCUCCGGGAUCAGGUU | 20 | 3614 |
| BCL11A-3130 | + | CGAGUACACGUUCUCCGUGU | 20 | 3615 |
| BCL11A-3131 | − | CGGAGAACGUGUACUCGCAG | 20 | 3616 |
| BCL11A-3132 | − | GGGAGCACGCCCCAUAUUAG | 20 | 3617 |
| BCL11A-3133 | − | CCAUAUUAGUGGUCCGGGCC | 20 | 3618 |
| BCL11A-3134 | + | GCCGCAGAACUCGCAUGACU | 20 | 3619 |
| BCL11A-3135 | + | CGCCCCGCGAGCUGUUCUCG | 20 | 3620 |
| BCL11A-3136 | − | GCAGUGGCUCGCCGGCUACG | 20 | 3621 |
| BCL11A-3137 | − | CAUAUUAGUGGUCCGGGCCC | 20 | 3622 |
| BCL11A-3138 | + | CUGAAGGGAUACCAACCCGC | 20 | 3623 |
| BCL11A-3139 | + | AUACCAACCCGCGGGGUCAG | 20 | 3624 |
| BCL11A-3140 | − | CAGCAGCGCGCUCAAGUCCG | 20 | 3625 |
| BCL11A-3141 | + | CGUCCCCGUUCUCCGGGAUC | 20 | 3626 |
| BCL11A-3142 | − | CACCACGAGAACAGCUCGCG | 20 | 3627 |
| BCL11A-3143 | − | GCGGUUGAAUCCAAUGGCUA | 20 | 3628 |
| BCL11A-3144 | − | GGACUUGCGACGAAGACU | 20 | 3629 |
| BCL11A-3145 | + | GUGUUGGGCAUCGCGGCCGG | 20 | 3630 |
| BCL11A-3146 | + | CUUCGUCGCAAGUGUCCCUG | 20 | 3631 |
| BCL11A-3147 | + | CCCCAGGCGCUCUAUGCGGU | 20 | 3632 |
| BCL11A-3148 | + | CCGUGUUGGGCAUCGCGGCC | 20 | 3633 |
| BCL11A-3149 | + | CGUUCUCCGGGAUCAGGUUG | 20 | 3634 |
| BCL11A-3150 | + | GCCUCUCGAUACUGAUCC | 20 | 3635 |
| BCL11A-3151 | + | UCGCAUGACUUGGACUUGAC | 20 | 3636 |
| BCL11A-3152 | − | AUCACCCGAGUGCCUUUGAC | 20 | 3637 |
| BCL11A-3153 | − | UAAGCGCGGCCACCUGGCCG | 20 | 3638 |
| BCL11A-3154 | − | GCACAAAUCGUCCCCAUGA | 20 | 3639 |
| BCL11A-3155 | − | CGCCCUGCCCGACGUCAUGC | 20 | 3640 |
| BCL11A-3156 | − | CAACCUGAUCCCGGAGAACG | 20 | 3641 |
| BCL11A-3157 | − | CGGAGCACUCCUCGGAGAAC | 20 | 3642 |
| BCL11A-3158 | − | AGACUCGGUGGCCGGCGAGU | 20 | 3643 |
| BCL11A-3159 | + | GGCGGUGGAGAGACCGUCGU | 20 | 3644 |
| BCL11A-3160 | − | GUGUACUCGCAGUGGCUCGC | 20 | 3645 |
| BCL11A-3161 | − | UCGGAGCACUCCUCGGAGAA | 20 | 3646 |
| BCL11A-3162 | − | CCCGGCCGCGAUGCCCAACA | 20 | 3647 |
| BCL11A-3163 | + | CCCGUUCUCCGGGAUCAGGU | 20 | 3648 |
| BCL11A-3164 | + | UCGUGGUGGACUAAACAGG | 20 | 3649 |
| BCL11A-3165 | + | CCUGAAGGGAUACCAACCCG | 20 | 3650 |
| BCL11A-3166 | + | GUCGUUCUCGCUCUUGAACU | 20 | 3651 |
| BCL11A-3167 | − | CCCCACCGCAUAGAGCGCCU | 20 | 3652 |
| BCL11A-3168 | + | GUCGCUGGUGCCGGGUUCCG | 20 | 3653 |
| BCL11A-3169 | − | CGAGAACAGCUCGCGGGGCG | 20 | 3654 |
| BCL11A-3170 | + | CGCAUGACUUGGACUUGACC | 20 | 3655 |

TABLE 4E-continued

5th Tier

| gRNA Name | DNA Strand | Targeting Domain | Target Site Length | SEQ ID NO |
|---|---|---|---|---|
| BCL11A-3171 | - | CCCACCGCAUAGAGCGCCUG | 20 | 3656 |
| BCL11A-3172 | + | AAGUCGCUGGUGCCGGGUUC | 20 | 3657 |
| BCL11A-3173 | + | CGAGGAGUGCUCCGACGAGG | 20 | 3658 |
| BCL11A-3174 | - | UCCCCGGGCGAGUCGGCCUC | 20 | 3659 |
| BCL11A-3175 | - | CUCCCCGGGCGAGUCGGCCU | 20 | 3660 |
| BCL11A-3176 | + | CAUGACUUGGACUUGACCGG | 20 | 3661 |
| BCL11A-3177 | - | AGCUCGCGGGGCGCGGUCGU | 20 | 3662 |
| BCL11A-3178 | + | UGCUCCGACGAGGAGGCAAA | 20 | 3663 |
| BCL11A-3179 | + | CUUUUGGACAGGCCCCCCG | 20 | 3664 |
| BCL11A-3180 | - | CUACGGCUUCGGGCUGAGCC | 20 | 3665 |
| BCL11A-3181 | - | CCCCGGGCGAGUCGGCCUCG | 20 | 3666 |
| BCL11A-3182 | + | UAACAGUGCCAUCGUCUAUG | 20 | 3667 |
| BCL11A-3183 | - | CUCCUCGUCGGAGCACUCCU | 20 | 3668 |
| BCL11A-3184 | - | CCCGGCACCAGCGACUUGGU | 20 | 3669 |
| BCL11A-3185 | - | GCGCUUCUCCACACCGCCCG | 20 | 3670 |
| BCL11A-3186 | + | CUCGGUGGUGGACUAAACAG | 20 | 3671 |
| BCL11A-3187 | - | CCCCCACCGCAUAGAGCGCC | 20 | 3672 |
| BCL11A-3188 | - | GAUCCCGGAGAACGGGGACG | 20 | 3673 |
| BCL11A-3189 | + | CCAGGCGCUCUAUGCGGUGG | 20 | 3674 |
| BCL11A-3190 | - | UUAGUGGUCCGGGCCCGGGC | 20 | 3675 |
| BCL11A-3191 | + | CCCAGGCGCUCUAUGCGGUG | 20 | 3676 |
| BCL11A-3192 | - | CGGCUGCUCCCCGGGCGAGU | 20 | 3677 |
| BCL11A-3193 | - | UCGCCGGCUACGCGGCCUCC | 20 | 3678 |
| BCL11A-3194 | - | AUCGAGAGAGGCUUCCGGCC | 20 | 3679 |
| BCL11A-3195 | + | GGGUCCAAGUGAUGUCUCGG | 20 | 3680 |
| BCL11A-3196 | - | AUCGCCUUUUGCCUCCUCGU | 20 | 3681 |
| BCL11A-3197 | - | AUCUCGGGGCGCAGCGGCAC | 20 | 3682 |
| BCL11A-3198 | + | CGGUGGUGGACUAAACAGGG | 20 | 3683 |
| BCL11A-3199 | - | GAUGGCACUGUUAAUGGCCG | 20 | 3684 |
| BCL11A-3200 | + | UGCCCUGCAUGACGUCGGGC | 20 | 3685 |
| BCL11A-3201 | + | UCUCGGUGGUGGACUAAACA | 20 | 3686 |
| BCL11A-3202 | - | AGAGGGUGGACUACGGCUUC | 20 | 3687 |
| BCL11A-3203 | + | CCCCGAGGCCGACUCGCCCG | 20 | 3688 |
| BCL11A-3204 | - | GAUCUCGGGGCGCAGCGGCA | 20 | 3689 |
| BCL11A-3205 | - | ACGGAAGUCCCCUGACCCCG | 20 | 3690 |
| BCL11A-3206 | + | ACUCGCCCGGGGAGCAGCCG | 20 | 3691 |
| BCL11A-3207 | - | UUGCGCUUCUCCACACCGCC | 20 | 3692 |
| BCL11A-3208 | - | GGAACCCGGCACCAGCGACU | 20 | 3693 |
| BCL11A-3209 | + | GCAUGACUUGGACUUGACCG | 20 | 3694 |
| BCL11A-3210 | - | UAAUGGCCGCGGCUGCUCCC | 20 | 3695 |
| BCL11A-3211 | - | CCGGGCGAGUCGGCCUCGGG | 20 | 3696 |
| BCL11A-3212 | + | GUCAAAGGCACUCGGGUGAU | 20 | 3697 |
| BCL11A-3213 | - | GGUGCUGCGGUUGAAUCCAA | 20 | 3698 |
| BCL11A-3214 | - | CUGGGCGAGAAGCAUAAGCG | 20 | 3699 |
| BCL11A-3215 | + | ACUUGGACUUGACCGGGGC | 20 | 3700 |
| BCL11A-3216 | + | CCCCCGAGGCCGACUCGCC | 20 | 3701 |
| BCL11A-3217 | - | CCACCGCAUAGAGCGCCUGG | 20 | 3702 |
| BCL11A-3218 | + | AGUCGCUGGUGCCGGGUUCC | 20 | 3703 |
| BCL11A-3219 | + | UCGCACAGGUUGCACUUGUA | 20 | 3704 |
| BCL11A-3220 | + | GCCCUGCAUGACGUCGGGCA | 20 | 3705 |
| BCL11A-3221 | + | CCGCCCCAGGCGCUCUAUG | 20 | 3706 |
| BCL11A-3222 | - | GCCCUGCCCGACGUCAUGCA | 20 | 3707 |
| BCL11A-3223 | + | GUCGCACAGGUUGCACUUGU | 20 | 3708 |
| BCL11A-3224 | - | AGGUAGCAAGCCGCCCUUCC | 20 | 3709 |
| BCL11A-3225 | - | CCAACCUGAUCCCGGAGAAC | 20 | 3710 |
| BCL11A-3226 | + | AGGAAGGGCGGCUUGCUACC | 20 | 3711 |
| BCL11A-3227 | - | GAAGGAGUUCGACCUGCCCC | 20 | 3712 |
| BCL11A-3228 | + | CUUGGACUUGACCGGGGCU | 20 | 3713 |
| BCL11A-3229 | - | GAGAGGGUGGACUACGGCUU | 20 | 3714 |
| BCL11A-3230 | - | UCCAAGUCAUGCGAGUUCUG | 20 | 3715 |
| BCL11A-3231 | - | ACCCGGCACCAGCGACUUGG | 20 | 3716 |
| BCL11A-3232 | + | CCCCCAGGCGCUCUAUGCGG | 20 | 3717 |
| BCL11A-3233 | + | GCGUCUGCCCUCUUUUGAGC | 20 | 3718 |
| BCL11A-3234 | - | GCCCGACGUCAUGCAGGGCA | 20 | 3719 |
| BCL11A-3235 | + | GAGCUUGAUGCGCUUAGAGA | 20 | 3720 |
| BCL11A-3236 | - | CAGCUCGCGGGGCGCGGUCG | 20 | 3721 |
| BCL11A-3237 | + | CGUGGUGGCGCGCCGCCUCC | 20 | 3722 |
| BCL11A-3238 | - | UCACCCGAGUGCCUUUGACA | 20 | 3723 |
| BCL11A-3239 | - | GAACGACCCCAACCUGAUCC | 20 | 3724 |
| BCL11A-3240 | + | CAACCGCAGCACCCUGUCAA | 20 | 3725 |
| BCL11A-3241 | + | UCCAAGUGAUGUCUCGGUGG | 20 | 3726 |
| BCL11A-3242 | + | GUUCUCCGUGUUGGGCAUCG | 20 | 3727 |
| BCL11A-3243 | - | CGGAAGUCCCCUGACCCCGC | 20 | 3728 |
| BCL11A-3244 | + | UAUGCUUCUCGCCCAGGACC | 20 | 3729 |

TABLE 4E-continued

5th Tier

| gRNA Name | DNA Strand | Targeting Domain | Target Site Length | SEQ ID NO |
|---|---|---|---|---|
| BCL11A-3245 | − | AGCUGGACGGAGGGAUCUCG | 20 | 3730 |
| BCL11A-3246 | + | GGCUGCGCCGGUGCACCACC | 20 | 3731 |
| BCL11A-3247 | − | GUUGGUAUCCCUUCAGGACU | 20 | 3732 |
| BCL11A-3248 | − | AUAGACGAUGGCACUGUUAA | 20 | 3733 |
| BCL11A-3249 | − | CUCCCGCCAUGGAUUUCUCU | 20 | 3734 |
| BCL11A-3250 | − | ACCAGGAUCAGUAUCGAGAG | 20 | 3735 |
| BCL11A-3251 | − | AGUCCCUGACCCGCGGGU | 20 | 3736 |
| BCL11A-3252 | + | GUCUGGAGUCUCCGAAGCUA | 20 | 3737 |
| BCL11A-3253 | − | GCCGGCCCAGCCCUAUGCAA | 20 | 3738 |
| BCL11A-3254 | − | GAUGUGUGGCAGUUUUCGGA | 20 | 3739 |
| BCL11A-3255 | + | CUAGAGAAAUCCAUGGCGGG | 20 | 3740 |
| BCL11A-3256 | + | GGCGCUGCCCACCAAGUCGC | 20 | 3741 |
| BCL11A-3257 | − | CCCGGGCGAGUCGGCCUCGG | 20 | 3742 |
| BCL11A-3258 | − | ACACCGCCCGGGGAGCUGGA | 20 | 3743 |
| BCL11A-3259 | + | CAGUAACCUUUGCAUAGGGC | 20 | 3744 |
| BCL11A-3260 | − | UCAGUAUCGAGAGAGGCUUC | 20 | 3745 |
| BCL11A-3261 | + | GCAUGACGUCGGGCAGGGCG | 20 | 3746 |
| BCL11A-3262 | − | CCGCAUAGAGCGCCUGGGGG | 20 | 3747 |
| BCL11A-3263 | + | CCCCCGAGGCCGACUCGCCC | 20 | 3748 |
| BCL11A-3264 | + | AGGGCGGCUUGCUACCUGGC | 20 | 3749 |
| BCL11A-3265 | + | GCACCCUGUCAAAGGCACUC | 20 | 3750 |
| BCL11A-3266 | + | CUGAUCCUGGUAUUCUUAGC | 20 | 3751 |
| BCL11A-3267 | + | CAUGUGGCGCUUCAGCUUGC | 20 | 3752 |
| BCL11A-3268 | + | CCCACCAAGUCGCUGGUGCC | 20 | 3753 |
| BCL11A-3269 | + | GGAGGCAAAAGGCGAUUGUC | 20 | 3754 |
| BCL11A-3270 | − | CCCAACCUGAUCCCGGAGAA | 20 | 3755 |
| BCL11A-3271 | + | GAGUCUCCGAAGCUAAGGAA | 20 | 3756 |
| BCL11A-3272 | − | GGCUAUGGAGCCUCCCGCCA | 20 | 3757 |
| BCL11A-3273 | + | CGUCUGCCCUCUUUUGAGCU | 20 | 3758 |
| BCL11A-3274 | − | CGCCCGGGGAGCUGGACGGA | 20 | 3759 |
| BCL11A-3275 | + | AGUAACCUUUGCAUAGGGCU | 20 | 3760 |
| BCL11A-3276 | − | UCCACCACCGAGAACAGCUC | 20 | 3761 |
| BCL11A-3277 | + | GGUUGCAGUAACCUUUGCAU | 20 | 3762 |
| BCL11A-3278 | + | GCAAUAUGAAUCCCAUGGAG | 20 | 3763 |
| BCL11A-3279 | + | ACCAUGCCCUGCAUGACGUC | 20 | 3764 |
| BCL11A-3280 | + | GGCCUCGCUGAAGUGCUGCA | 20 | 3765 |
| BCL11A-3281 | − | AGAGCAACCUGGUGGUGCAC | 20 | 3766 |
| BCL11A-3282 | + | GCCCACCAAGUCGCUGGUGC | 20 | 3767 |
| BCL11A-3283 | + | UGUCAAAGGCACUCGGGUGA | 20 | 3768 |
| BCL11A-3284 | + | AGCUUGAUGCGCUUAGAGAA | 20 | 3769 |
| BCL11A-3285 | + | AGGGGGGGCGUCGCCAGGAA | 20 | 3770 |
| BCL11A-3286 | + | GUGGAAAGCGCCCUUCUGCC | 20 | 3771 |
| BCL11A-3287 | + | UGGGGGUCCAAGUGAUGUCU | 20 | 3772 |
| BCL11A-3288 | − | CUCCAUGCAGCACUUCAGCG | 20 | 3773 |
| BCL11A-3289 | + | GCGCUUCAGCUUGCUGGCCU | 20 | 3774 |
| BCL11A-3290 | − | CUUCAGCGAGGCCUUCCACC | 20 | 3775 |
| BCL11A-3291 | + | GGAGUCUCCGAAGCUAAGGA | 20 | 3776 |
| BCL11A-3292 | + | CACUCGGGUGAUGGGUGGCC | 20 | 3777 |
| BCL11A-3293 | − | UGCGCUUCUCCACACCGCCC | 20 | 3778 |
| BCL11A-3294 | + | GGUGGUGGACUAAACAGGGG | 20 | 3779 |
| BCL11A-3295 | − | CGAGGCCUUCCACCAGGUCC | 20 | 3780 |
| BCL11A-3296 | − | AAUGGCCGCGGCUGCUCCCC | 20 | 3781 |
| BCL11A-3297 | + | GUUGUACAUGUGUAGCUGCU | 20 | 3782 |
| BCL11A-3298 | − | GUUCUUCACACACCCCCAUU | 20 | 3783 |
| BCL11A-3299 | − | CGCAGCGGCACGGGAAGUGG | 20 | 3784 |
| BCL11A-3300 | + | GCGGGAGGCUCCAUAGCCAU | 20 | 3785 |
| BCL11A-3301 | − | GGUGCACCGGCGCAGCCACA | 20 | 3786 |
| BCL11A-3302 | − | CUCCACACCGCCCGGGGAGC | 20 | 3787 |
| BCL11A-3303 | + | AAAGCGCCCUUCUGCCAGGC | 20 | 3788 |
| BCL11A-3304 | + | ACUCGGGUGAUGGGUGGCCA | 20 | 3789 |
| BCL11A-3305 | + | CUGCCUGGAGGCCGCUAGC | 20 | 3790 |
| BCL11A-3306 | + | GUCCAGCUCCCCGGGCGGUG | 20 | 3791 |
| BCL11A-3307 | − | GAGCUGGACGGAGGGAUCUC | 20 | 3792 |
| BCL11A-3308 | − | UCUAGCCCACCGCUGUCCCC | 20 | 3793 |
| BCL11A-3309 | + | AGUUGUACAUGUGUAGCUGC | 20 | 3794 |
| BCL11A-3310 | + | AUUCUGCACCUAGUCCUGAA | 20 | 3795 |
| BCL11A-3311 | − | CCACCACGAGAACAGCUCGC | 20 | 3796 |
| BCL11A-3312 | + | CUCCUAGAGAAAUCCAUGGC | 20 | 3797 |
| BCL11A-3313 | − | UUUAACCUGCUAAGAAUACC | 20 | 3798 |
| BCL11A-3314 | + | GGACUAAACAGGGGGGGAGU | 20 | 3799 |
| BCL11A-3315 | − | GGCCACCGGCCGAGGCCGA | 20 | 3800 |
| BCL11A-3316 | + | GGCUUGCUACCUGGCUGGAA | 20 | 3801 |
| BCL11A-3317 | + | CAUUCUGCACCUAGUCCUGA | 20 | 3802 |
| BCL11A-3318 | + | UGCUGGCCUGGGGUGCACGCG | 20 | 3803 |

TABLE 4E-continued

5th Tier

| gRNA Name | DNA Strand | Targeting Domain | Target Site Length | SEQ ID NO |
|---|---|---|---|---|
| BCL11A-3319 | + | UGUGGCCCUCGGCCUCGGCC | 20 | 3804 |
| BCL11A-3320 | - | CCGCCCGGGGAGCUGGACGG | 20 | 3805 |
| BCL11A-3321 | - | UGGCCGAGGCCGAGGGCCAC | 20 | 3806 |
| BCL11A-3322 | + | UGGGCAUCGCGGCCGGGGGC | 20 | 3807 |
| BCL11A-3323 | + | UCUCCUAGAGAAAUCCAUGG | 20 | 3808 |
| BCL11A-3324 | + | GGGCCAUCUCUUCCGCCCCC | 20 | 3809 |
| BCL11A-3325 | + | GUUGCAGUAACCUUUGCAUA | 20 | 3810 |
| BCL11A-3326 | + | AAAGGCACUCGGGUGAUGGG | 20 | 3811 |
| BCL11A-3327 | + | GAAGGGAUCUUUGAGCUGCC | 20 | 3812 |
| BCL11A-3328 | + | GCCACACAUCUUGAGCUCUC | 20 | 3813 |
| BCL11A-3329 | - | GGAGGGAUCUCGGGGCGCAG | 20 | 3814 |
| BCL11A-3330 | - | CCCGGAGAACGGGGACGAGG | 20 | 3815 |
| BCL11A-3331 | + | UGCAUAGGGCUGGGCCGGCC | 20 | 3816 |
| BCL11A-3332 | - | CGGGGCGCGGUCGUGGGCGU | 20 | 3817 |
| BCL11A-3333 | + | GAGGGGGGCGUCGCCAGGA | 20 | 3818 |
| BCL11A-3334 | - | ACCGCCAGCUCCCCGGAACC | 20 | 3819 |
| BCL11A-3335 | + | GGUAUUCUUAGCAGGUUAAA | 20 | 3820 |
| BCL11A-3336 | - | AGGCUUCCGGCCUGGCAGAA | 20 | 3821 |
| BCL11A-3337 | + | GAUCCCUCCGUCCAGCUCCC | 20 | 3822 |
| BCL11A-3338 | + | UGGUAUUCUUAGCAGGUUAA | 20 | 3823 |
| BCL11A-3339 | - | AUCUACUUAGAAAGCGAACA | 20 | 3824 |
| BCL11A-3340 | - | CGGCCACCUGGCCGAGGCCG | 20 | 3825 |
| BCL11A-3341 | - | CAACACGCACAGAACACUCA | 20 | 3826 |
| BCL11A-3342 | + | GCCGGCCUGGGGACAGCGGU | 20 | 3827 |
| BCL11A-3343 | - | GCCACCACGAGAACAGCUCG | 20 | 3828 |
| BCL11A-3344 | + | GUAUUCUUAGCAGGUUAAAG | 20 | 3829 |
| BCL11A-3345 | - | CUCUAGGAGACUUAGAGAGC | 20 | 3830 |
| BCL11A-3346 | - | AACAGCCAUUCACCAGUGCA | 20 | 3831 |
| BCL11A-3347 | + | UUGCAAGAGAAACCAUGCAC | 20 | 3832 |
| BCL11A-3348 | + | GACUUGACCGGGGCUGGGA | 20 | 3833 |
| BCL11A-3349 | + | ACCUUUGCAUAGGGCUGGGC | 20 | 3834 |
| BCL11A-3350 | + | UCUUUUGAGCUGGGCCUGCC | 20 | 3835 |
| BCL11A-3351 | - | GAGGCCUUCCACCAGGUCCU | 20 | 3836 |
| BCL11A-3352 | + | CUUUUGAGCUGGGCCUGCCC | 20 | 3837 |
| BCL11A-3353 | + | GGGAUCUUUGAGCUGCCUGG | 20 | 3838 |
| BCL11A-3354 | - | GGGCAGGCCCAGCUCAAAAG | 20 | 3839 |
| BCL11A-3355 | + | AGCACCCUGUCAAAGGCACU | 20 | 3840 |
| BCL11A-3356 | + | UGGACUAAACAGGGGGGGAG | 20 | 3841 |
| BCL11A-3357 | + | GCUCUUGAACUUGGCCACCA | 20 | 3842 |
| BCL11A-3358 | + | GAAUCCCAUGGAGAGGUGGC | 20 | 3843 |
| BCL11A-3359 | - | GUGCACCGGCGCAGCCACAC | 20 | 3844 |
| BCL11A-3360 | - | AAAGAUCCCUUCCUUAGCUU | 20 | 3845 |
| BCL11A-3361 | + | UGUCUGCAAUAUGAAUCCCA | 20 | 3846 |
| BCL11A-3362 | - | GGCAGGCCCAGCUCAAAAGA | 20 | 3847 |
| BCL11A-3363 | + | CCUCCGUCCAGCUCCCCGGG | 20 | 3848 |
| BCL11A-3364 | - | CUGUCCAAAAAGCUGCUGCU | 20 | 3849 |
| BCL11A-3365 | + | GCUUGAUGCGCUUAGAGAAG | 20 | 3850 |
| BCL11A-3366 | - | CGGCUUCGGGCUGAGCCUGG | 20 | 3851 |
| BCL11A-3367 | + | CACCAUGCCCUGCAUGACGU | 20 | 3852 |
| BCL11A-3368 | - | UCAAGAUGUGUGGCAGUUUU | 20 | 3853 |
| BCL11A-3369 | - | GUUCAAAUUUCAGAGCAACC | 20 | 3854 |
| BCL11A-3370 | + | GAGAAGGGGCUCAGCGAGCU | 20 | 3855 |
| BCL11A-3371 | - | GCAGCGGCACGGGAAGUGGA | 20 | 3856 |
| BCL11A-3372 | + | AAGUCUCCUAGAGAAAUCCA | 20 | 3857 |
| BCL11A-3373 | + | GGUGCGGGUUCCGGGGAGC | 20 | 3858 |
| BCL11A-3374 | - | CCUGUCCAAAAAGCUGCUGC | 20 | 3859 |
| BCL11A-3375 | + | AUAUGAAUCCCAUGGAGAGG | 20 | 3860 |
| BCL11A-3376 | - | GGGCGCAGCGGCACGGGAAG | 20 | 3861 |
| BCL11A-3377 | - | GGCCGAGGCCGAGGGCCACA | 20 | 3862 |
| BCL11A-3378 | + | GCAAGUGUCCCUGUGGCCCU | 20 | 3863 |
| BCL11A-3379 | + | GGACUUGACCGGGGCUGGG | 20 | 3864 |
| BCL11A-3380 | + | GCUUCUCGCCCAGGACCUGG | 20 | 3865 |
| BCL11A-3381 | - | GCGCCUGGGGCGGAAGAGA | 20 | 3866 |
| BCL11A-3382 | + | GUCCCUGUGGCCCUCGGCCU | 20 | 3867 |
| BCL11A-3383 | + | AUCCCUCCGUCCAGCUCCCC | 20 | 3868 |
| BCL11A-3384 | - | GUGCCUUUGACAGGGUGCUG | 20 | 3869 |
| BCL11A-3385 | - | CCCAGAGAGCUCAAGAUGUG | 20 | 3870 |
| BCL11A-3386 | + | GGCCCUCGGCCUCGCCAGG | 20 | 3871 |
| BCL11A-3387 | - | GAGAGCGAGAGGGUGGACUA | 20 | 3872 |
| BCL11A-3388 | + | GGGGGCGUCGCCAGGAAGGG | 20 | 3873 |
| BCL11A-3389 | + | AGAGAAGGGGCUCAGCGAGC | 20 | 3874 |
| BCL11A-3390 | + | CCACACAUCUUGAGCUCUCU | 20 | 3875 |
| BCL11A-3391 | + | GCUGCCCAGCAGCAGCUUUU | 20 | 3876 |
| BCL11A-3392 | - | GGAGCUGGACGGAGGGAUCU | 20 | 3877 |

TABLE 4E-continued

5th Tier

| gRNA Name | DNA Strand | Targeting Domain | Target Site Length | SEQ ID NO |
|---|---|---|---|---|
| BCL11A-3393 | - | GGGGGCGGAAGAGAUGGCCC | 20 | 3878 |
| BCL11A-3394 | - | AGGAGACUUAGAGAGCUGGC | 20 | 3879 |
| BCL11A-3395 | - | GAGGCUUCCGGCCUGGCAGA | 20 | 3880 |
| BCL11A-3396 | + | AAUCCCAUGGAGAGGUGGCU | 20 | 3881 |
| BCL11A-3397 | + | UGUGCAUGUGCGUCUUCAUG | 20 | 3882 |
| BCL11A-3398 | + | CUCGCCCAGGACCUGGUGGA | 20 | 3883 |
| BCL11A-3399 | + | UCCUCCUCGUCCCGUUCUC | 20 | 3884 |
| BCL11A-3400 | + | AGAAACCAUGCACUGGUGAA | 20 | 3885 |
| BCL11A-3401 | - | CUUCGGGCUGAGCCUGGAGG | 20 | 3886 |
| BCL11A-3402 | + | GCCGGGUUCCGGGGAGCUGG | 20 | 3887 |
| BCL11A-3403 | + | AGAAGGGGCUCAGCGAGCUG | 20 | 3888 |
| BCL11A-3404 | + | CUAAACAGGGGGGGAGUGGG | 20 | 3889 |
| BCL11A-3405 | - | CAAAUUUCAGAGCAACCUGG | 20 | 3890 |
| BCL11A-3406 | + | GAGGGAGGGGGGCGUCGCC | 20 | 3891 |
| BCL11A-3407 | + | CCUCCUCGUCCCCGUUCUCC | 20 | 3892 |
| BCL11A-3408 | + | CCAGCAGCAGCUUUUUGGAC | 20 | 3893 |
| BCL11A-3409 | - | GCCCACCGCUGUCCCCAGGC | 20 | 3894 |
| BCL11A-3410 | - | GGAGACUUAGAGAGCUGGCA | 20 | 3895 |
| BCL11A-3411 | - | AGGAGCUGACGGAGAGCGAG | 20 | 3896 |
| BCL11A-3412 | + | GAGGGGCGGAUUGCAGAGGA | 20 | 3897 |
| BCL11A-3413 | + | CAUAGGGCUGGGCCGGCCUG | 20 | 3898 |
| BCL11A-3414 | + | GGCGGAUUGCAGAGGAGGGA | 20 | 3899 |
| BCL11A-3415 | + | GGAGGGGCGGAUUGCAGAGG | 20 | 3900 |
| BCL11A-3416 | - | UUACUGCAACCAUUCCAGCC | 20 | 3901 |
| BCL11A-3417 | + | GCAUAGGGCUGGGCCGGCCU | 20 | 3902 |
| BCL11A-3418 | + | GGGCGGAUUGCAGAGGAGGG | 20 | 3903 |
| BCL11A-3419 | + | GGGUUCCGGGGAGCUGGCGG | 20 | 3904 |
| BCL11A-3420 | + | UCUCGCCCGUGUGGCUGCGC | 20 | 3905 |
| BCL11A-3421 | - | CUUCCCAGCCACCUCUCCAU | 20 | 3906 |
| BCL11A-3422 | - | GCUGACGGAGAGCGAGAGGG | 20 | 3907 |
| BCL11A-3423 | + | GCGGAUUGCAGAGGAGGGAG | 20 | 3908 |
| BCL11A-3424 | - | GGAGCUGACGGAGAGCGAGA | 20 | 3909 |
| BCL11A-3425 | - | UCUCUCCACCGCCAGCUCCC | 20 | 3910 |
| BCL11A-3426 | + | UUGACCGGGGCUGGGAGGG | 20 | 3911 |
| BCL11A-3427 | + | CGGAUUGCAGAGGAGGGAGG | 20 | 3912 |
| BCL11A-3428 | - | GCGGGGCGCGGUCGUGGGCG | 20 | 3913 |
| BCL11A-3429 | + | GAGCUGGGCCUGCCCGGGCC | 20 | 3914 |
| BCL11A-3430 | + | CUGGGCCGGCCUGGGGACAG | 20 | 3915 |
| BCL11A-3431 | + | UGUAGGGCUUCUCGCCCGUG | 20 | 3916 |
| BCL11A-3432 | + | CCAUGGAGAGGUGGCUGGGA | 20 | 3917 |
| BCL11A-3433 | + | GGAGGAGGGGCGGAUUGCAG | 20 | 3918 |
| BCL11A-3434 | - | CCUUCCCAGCCACCUCUCCA | 20 | 3919 |
| BCL11A-3435 | + | CCCGCGAGCUGUUCUCGUGG | 20 | 3920 |
| BCL11A-3436 | + | GAUUGCAGAGGAGGGAGGGG | 20 | 3921 |
| BCL11A-3437 | + | GGCCGGCCUGGGGACAGCGG | 20 | 3922 |
| BCL11A-3438 | + | GGAUUGCAGAGGAGGGAGGG | 20 | 3923 |
| BCL11A-3439 | + | ACCGGGGCUGGGAGGGAGG | 20 | 3924 |
| BCL11A-3440 | + | CCGGGGGCUGGGAGGGAGGA | 20 | 3925 |
| BCL11A-3441 | - | GAACGGGGACGAGGAGGAAG | 20 | 3926 |
| BCL11A-3442 | - | CCCUCCUCCCUCCCAGCCCC | 20 | 3927 |
| BCL11A-3443 | + | CGGGGGCUGGGAGGGAGGAG | 20 | 3928 |
| BCL11A-3444 | + | GGCGCUUCAGCUUGCUGGCC | 20 | 3929 |
| BCL11A-3445 | - | CGGGGACGAGGAGGAAGAGG | 20 | 3930 |
| BCL11A-3446 | - | AGAGGAGGAGGAGGAGCUGA | 20 | 3931 |
| BCL11A-3447 | + | GGGCUGGGAGGGAGGAGGGG | 20 | 3932 |
| BCL11A-3448 | - | AGAGGAGGACGACGAGGAAG | 20 | 3933 |
| BCL11A-3449 | - | CGACGAGGAAGAGGAAGAAG | 20 | 3934 |
| BCL11A-3450 | - | GGAGGAAGAGGAGGACGACG | 20 | 3935 |
| BCL11A-3451 | - | CGAGGAAGAGGAAGAAGAGG | 20 | 3936 |
| BCL11A-3452 | - | GGAAGAAGAGGAGGAAGAGG | 20 | 3937 |
| BCL11A-3453 | - | AGAGGAAGAAGAGGAGGAAG | 20 | 3938 |
| BCL11A-3454 | - | AGAAGAGGAGGAAGAGGAGG | 20 | 3939 |
| BCL11A-3455 | - | AGAGGAGGAAGAGGAGGAGG | 20 | 3940 |

Table 5A provides exemplary targeting domains for knocking out the BCL11A gene by targeting the early coding sequence the BCL11A gene selected according to first tier parameters. The targeting domains bind within first 500 bp of coding sequence downstream of start codon, good orthogonality, start with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. aureus Cas9 (nickase) molecule to generate a single strand break. In an embodiment, dual targeting is used to create two nicks on opposite DNA strands by using *S. aureus* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 5A

| gRNA Name | DNA Strand | Targeting Domain | Target Site Length | SEQ ID NO |
|---|---|---|---|---|
| BCL11A-3456 | − | GAACCAGACCACGGCCCGUU | 20 | 3941 |
| BCL11A-3457 | + | GACCUGGAUGCCAACCUCCA | 20 | 3942 |
| BCL11A-3458 | + | GAUUAGAGCUCCAUGUG | 17 | 3943 |
| BCL11A-3459 | − | GAUUGUUUAUCAACGUCAUC | 20 | 3944 |
| BCL11A-3460 | + | GCACUCAUCCCAGGCGU | 17 | 3945 |
| BCL11A-3461 | + | GGGGAUUAGAGCUCCAUGUG | 20 | 3946 |
| BCL11A-3462 | − | GUGCAGAAUAUGCCCCG | 17 | 3947 |

Table 5B provides exemplary targeting domains for knocking out the BCL11A gene by targeting the early coding sequence the BCL11A gene selected according to second tier parameters. The targeting domains bind within first 500 bp of coding sequence downstream of start codon, good orthogonality, and do not start with G. It is contemplated herein that the targeting domain hybridizes to the target domain through complementary base pairing. Any of the targeting domains in the table can be used with a *S. aureus* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. aureus* Cas9 (nickase) molecule to generate a single strand break. In an embodiment, dual targeting is used to create two nicks on opposite DNA strands by using *S. aureus* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 5B

2nd Tier

| gRNA Name | DNA Strand | Targeting Domain | Target Site Length | SEQ ID NO |
|---|---|---|---|---|
| BCL11A-3463 | − | AACCAGACCACGGCCCG | 17 | 3948 |
| BCL11A-3464 | + | AAUUCCCGUUUGCUUAAGUG | 20 | 3949 |
| BCL11A-3465 | − | ACCAGACCACGGCCCGU | 17 | 3950 |
| BCL11A-3466 | − | AUGAACCAGACCACGGCCCG | 20 | 3951 |
| BCL11A-3467 | + | AUUCCCGUUUGCUUAAGUGC | 20 | 3952 |
| BCL11A-3468 | − | CCAGACCACGGCCCGUU | 17 | 3953 |
| BCL11A-3469 | + | CCCGUUUGCUUAAGUGC | 17 | 3954 |
| BCL11A-3470 | + | CCUGGAUGCCAACCUCC | 17 | 3955 |
| BCL11A-3471 | + | CUGGAUGCCAACCUCCA | 17 | 3956 |
| BCL11A-3472 | + | UCAUCCUCUGGCGUGAC | 17 | 3957 |
| BCL11A-3473 | + | UCCCGUUUGCUUAAGUG | 17 | 3958 |
| BCL11A-3474 | + | UCGUCAUCCUCUGGCGUGAC | 20 | 3959 |
| BCL11A-3475 | + | UCUGCACUCAUCCCAGGCGU | 20 | 3960 |
| BCL11A-3476 | + | UCUGGUUCAUCAUCUGU | 17 | 3961 |
| BCL11A-3477 | − | UGAACCAGACCACGGCCCGU | 20 | 3962 |
| BCL11A-3478 | + | UGACCUGGAUGCCAACCUCC | 20 | 3963 |
| BCL11A-3479 | − | UGAGUGCAGAAUAUGCCCCG | 20 | 3964 |
| BCL11A-3480 | + | UGCACUCAUCCCAGGCG | 17 | 3965 |
| BCL11A-3481 | + | UGGUCUGGUUCAUCAUCUGU | 20 | 3966 |
| BCL11A-3482 | − | UGUUUAUCAACGUCAUC | 17 | 3967 |
| BCL11A-3483 | − | UGUUUAUCAACGUCAUCUAG | 20 | 3968 |
| BCL11A-3484 | − | UUAUCAACGUCAUCUAG | 17 | 3969 |
| BCL11A-3485 | + | UUCUGCACUCAUCCCAGGCG | 20 | 3970 |
| BCL11A-3486 | − | UUGUUUAUCAACGUCAUCUA | 20 | 3971 |
| BCL11A-3487 | − | UUUAUCAACGUCAUCUA | 17 | 3972 |

Table 5C provides exemplary targeting domains for knocking out the BCL11A gene by targeting the early coding sequence the BCL11A gene selected according to third tier parameters. The targeting domains bind within first 500 bp of coding sequence downstream of start codon and start with G. It is contemplated herein that the targeting domain hybridizes to the target domain through complementary base pairing. Any of the targeting domains in the table can be used with a *S. aureus* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. aureus* Cas9 (nickase) molecule to generate a single strand break. In an embodiment, dual targeting is used to create two nicks on opposite DNA strands by using *S. aureus* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 5C

3rd Tier

| gRNA Name | DNA Strand | Targeting Domain | Target Site Length | SEQ ID NO |
|---|---|---|---|---|
| BCL11A-3488 | − | GAAAAAAGCAUCCAAUCCCG | 20 | 3973 |
| BCL11A-3489 | + | GAGAGGCCCCUCCAGUG | 17 | 3974 |
| BCL11A-3490 | + | GAGCUCCAUGUGCAGAACGA | 20 | 3975 |
| BCL11A-3491 | − | GAGGAAUUUGCCCCAAA | 17 | 3976 |
| BCL11A-3492 | + | GAGGAGAGGCCCCUCCAGUG | 20 | 3977 |
| BCL11A-3493 | + | GAGGAGGUCAUGAUCCCCUU | 20 | 3978 |
| BCL11A-3494 | + | GAGGUCAUGAUCCCCUU | 17 | 3979 |
| BCL11A-3495 | − | GCAUCCAGGUCACGCCA | 17 | 3980 |
| BCL11A-3496 | − | GCCACCUUCCCCUUCACCAA | 20 | 3981 |
| BCL11A-3497 | − | GCCAGAUGAACUUCCCA | 17 | 3982 |
| BCL11A-3498 | − | GCCAGAUGAACUUCCCAUUG | 20 | 3983 |
| BCL11A-3499 | − | GCCCGUUGGGAGCUCCAGAA | 20 | 3984 |
| BCL11A-3500 | − | GCCUCUGCUUAGAAAAAGCU | 20 | 3985 |
| BCL11A-3501 | + | GCUCCAUGUGCAGAACG | 17 | 3986 |
| BCL11A-3502 | − | GCUCUAAUCCCCACGCC | 17 | 3987 |
| BCL11A-3503 | − | GGACAUUCUUAUUUUUA | 17 | 3988 |
| BCL11A-3504 | − | GGAGCUCUAAUCCCCACGCC | 20 | 3989 |
| BCL11A-3505 | − | GGAUCAUGACCUCCUCACCU | 20 | 3990 |
| BCL11A-3506 | + | GGAUGCCAACCUCCACGGGA | 20 | 3991 |
| BCL11A-3507 | + | GGCACUGCCCACAGGUG | 17 | 3992 |
| BCL11A-3508 | − | GGCCCGUUGGGAGCUCCAGA | 20 | 3993 |
| BCL11A-3509 | − | GGGGGACAUUCUUAUUUUUA | 20 | 3994 |
| BCL11A-3510 | − | GGUUGGCAUCCAGGUCACGC | 20 | 3995 |
| BCL11A-3511 | + | GGUUUGCCUUGCUUGCG | 17 | 3996 |

TABLE 5C-continued

3rd Tier

| gRNA Name | DNA Strand | Targeting Domain | Target Site Length | SEQ ID NO |
|---|---|---|---|---|
| BCL11A-3512 | + | GUGCAGAACGAGGGGAG | 17 | 3997 |
| BCL11A-3513 | − | GUGCCAGAUGAACUUCCCAU | 20 | 3998 |

Table 5D provides exemplary targeting domains for knocking out the BCL11A gene by targeting the early coding sequence the BCL11A gene selected according to forth tier parameters. The targeting domains bind within first 500 bp of coding sequence downstream of start codon and do not start with G. It is contemplated herein that the targeting domain hybridizes to the target domain through complementary base pairing. Any of the targeting domains in the table can be used with a *S. aureus* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. aureus* Cas9 (nickase) molecule to generate a single strand break. In an embodiment, dual targeting is used to create two nicks on opposite DNA strands by using *S. aureus* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 5D

4th Tier

| gRNA Name | DNA Strand | Targeting Domain | Target Site Length | SEQ ID NO |
|---|---|---|---|---|
| BCL11A-3514 | − | AAAAAGCAUCCAAUCCC | 17 | 3999 |
| BCL11A-3515 | + | AAAAAUAAGAAUGUCCCCCA | 20 | 4000 |
| BCL11A-3516 | − | AAAAGCAUCCAAUCCCG | 17 | 4001 |
| BCL11A-3517 | + | AAAAUAAGAAUGUCCCCCAA | 20 | 4002 |
| BCL11A-3518 | − | AAACCCCAGCACUUAAGCAA | 20 | 4003 |
| BCL11A-3519 | + | AAAUAAGAAUGUCCCCCAAU | 20 | 4004 |
| BCL11A-3520 | − | AACCCCAGCACUUAAGCAAA | 20 | 4005 |
| BCL11A-3521 | + | AAUAAGAAUGUCCCCCA | 17 | 4006 |
| BCL11A-3522 | − | ACCCCAGCACUUAAGCAAAC | 20 | 4007 |

TABLE 5D-continued

4th Tier

| gRNA Name | DNA Strand | Targeting Domain | Target Site Length | SEQ ID NO |
|---|---|---|---|---|
| BCL11A-3523 | - | ACCUUCCCCUUCACCAA | 17 | 4008 |
| BCL11A-3524 | + | AGAGCUCCAUGUGCAGA | 17 | 4009 |
| BCL11A-3525 | + | AGAGCUCCAUGUGCAGAACG | 20 | 4010 |
| BCL11A-3526 | - | AGAUGAACUUCCCAUUG | 17 | 4011 |
| BCL11A-3527 | - | AGCCAUUCUUACAGAUG | 17 | 4012 |
| BCL11A-3528 | + | AGCUCCAUGUGCAGAAC | 17 | 4013 |
| BCL11A-3529 | + | AGCUCCAUGUGCAGAACGAG | 20 | 4014 |
| BCL11A-3530 | - | AGCUCUAAUCCCCACGC | 17 | 4015 |
| BCL11A-3531 | - | AGGAAUUUGCCCCAAAC | 17 | 4016 |
| BCL11A-3532 | + | AGGAGGUCAUGAUCCCCUUC | 20 | 4017 |
| BCL11A-3533 | + | AGGUCAUGAUCCCCUUC | 17 | 4018 |
| BCL11A-3534 | - | AGUGCCAGAUGAACUUCCCA | 20 | 4019 |
| BCL11A-3535 | + | AUAAGAAUGUCCCCCAA | 17 | 4020 |
| BCL11A-3536 | + | AUCCCAGGCGUGGGGAU | 17 | 4021 |
| BCL11A-3537 | + | AUCCCCUUCUGGAGCUCCCA | 20 | 4022 |
| BCL11A-3538 | + | AUCUGGCACUGCCCACAGGU | 20 | 4023 |
| BCL11A-3539 | - | AUGCAAUGGCAGCCUCUGCU | 20 | 4024 |
| BCL11A-3540 | + | AUGUGCAGAACGAGGGG | 17 | 4025 |
| BCL11A-3541 | + | AUUAGAGCUCCAUGUGCAGA | 20 | 4026 |
| BCL11A-3542 | + | AUUCUGCACUCAUCCCAGGC | 20 | 4027 |
| BCL11A-3543 | - | AUUUUUAUCGAGCACAA | 17 | 4028 |
| BCL11A-3544 | - | CAAUGGCAGCCUCUGCU | 17 | 4029 |
| BCL11A-3545 | - | CACGCCUGGGAUGAGUG | 17 | 4030 |
| BCL11A-3546 | - | CAGAUGAACUUCCCAUU | 17 | 4031 |
| BCL11A-3547 | + | CAUCUCGAUUGGUGAAG | 17 | 4032 |
| BCL11A-3548 | + | CAUGUGCAGAACGAGGG | 17 | 4033 |
| BCL11A-3549 | + | CAUGUGCAGAACGAGGGGAG | 20 | 4034 |
| BCL11A-3550 | + | CCACAGCUUUUUCUAAG | 17 | 4035 |
| BCL11A-3551 | - | CCACGGCCCGUUGGGAGCUC | 20 | 4036 |
| BCL11A-3552 | - | CCAGAUGAACUUCCCAU | 17 | 4037 |
| BCL11A-3553 | - | CCAGCACUUAAGCAAAC | 17 | 4038 |
| BCL11A-3554 | - | CCCAGCACUUAAGCAAA | 17 | 4039 |
| BCL11A-3555 | - | CCCCACGCCUGGGAUGAGUG | 20 | 4040 |
| BCL11A-3556 | - | CCCCAGCACUUAAGCAA | 17 | 4041 |
| BCL11A-3557 | - | CCCCUUCACCAAUCGAG | 17 | 4042 |
| BCL11A-3558 | - | CCCGUUGGGAGCUCCAG | 17 | 4043 |
| BCL11A-3559 | + | CCCUUCUGGAGCUCCCA | 17 | 4044 |
| BCL11A-3560 | - | CCGUUGGGAGCUCCAGA | 17 | 4045 |
| BCL11A-3561 | - | CCUGUGGGCAGUGCCAG | 17 | 4046 |
| BCL11A-3562 | - | CGGCCCGUUGGGAGCUC | 17 | 4047 |
| BCL11A-3563 | - | CGGCCCGUUGGGAGCUCCAG | 20 | 4048 |
| BCL11A-3564 | - | CGUUGGGAGCUCCAGAA | 17 | 4049 |
| BCL11A-3565 | + | CGUUUGUGCUCGAUAAAAAU | 20 | 4050 |
| BCL11A-3566 | - | CUAGAGGAAUUUGCCCCAAA | 20 | 4051 |
| BCL11A-3567 | + | CUCAUCCCAGGCGUGGGGAU | 20 | 4052 |
| BCL11A-3568 | + | CUCCAUGUGCAGAACGA | 17 | 4053 |
| BCL11A-3569 | + | CUCCAUGUGCAGAACGAGGG | 20 | 4054 |
| BCL11A-3570 | - | CUCCCCUCGUUCUGCAC | 17 | 4055 |
| BCL11A-3571 | - | CUCCUCCCCUCGUUCUGCAC | 20 | 4056 |
| BCL11A-3572 | - | CUCUAAUCCCCACGCCUGGG | 20 | 4057 |
| BCL11A-3573 | + | CUGCACUCAUCCCAGGC | 17 | 4058 |
| BCL11A-3574 | - | CUUAUUUUUAUCGAGCACAA | 20 | 4059 |
| BCL11A-3575 | - | CUUCCCCUUCACCAAUCGAG | 20 | 4060 |
| BCL11A-3576 | + | UAAGAAUGUCCCCCAAU | 17 | 4061 |
| BCL11A-3577 | - | UAAUCCCCACGCCUGGG | 17 | 4062 |
| BCL11A-3578 | + | UAGAGCUCCAUGUGCAGAAC | 20 | 4063 |
| BCL11A-3579 | - | UAGAGGAAUUUGCCCCAAAC | 20 | 4064 |
| BCL11A-3580 | + | UAUCCACAGCUUUUUCUAAG | 20 | 4065 |
| BCL11A-3581 | - | UCACCUGUGGGCAGUGCCAG | 20 | 4066 |
| BCL11A-3582 | + | UCAUCUCGAUUGGUGAA | 17 | 4067 |
| BCL11A-3583 | + | UCAUCUGGCACUGCCCACAG | 20 | 4068 |
| BCL11A-3584 | + | UCAUCUGUAAGAAUGGCUUC | 20 | 4069 |
| BCL11A-3585 | - | UCAUGACCUCCUCACCU | 17 | 4070 |
| BCL11A-3586 | + | UCCAUGUGCAGAACGAG | 17 | 4071 |
| BCL11A-3587 | + | UCCAUGUGCAGAACGAGGGG | 20 | 4072 |
| BCL11A-3588 | - | UCCCCUCGUUCUGCACA | 17 | 4073 |
| BCL11A-3589 | - | UCCUCCCCUCGUUCUGCACA | 20 | 4074 |
| BCL11A-3590 | - | UCUGCUUAGAAAAAGCU | 17 | 4075 |
| BCL11A-3591 | + | UCUGGCACUGCCCACAG | 17 | 4076 |
| BCL11A-3592 | + | UCUGGCACUGCCCACAGGUG | 20 | 4077 |
| BCL11A-3593 | + | UCUGUAAGAAUGGCUUC | 17 | 4078 |
| BCL11A-3594 | - | UGAAAAAGCAUCCAAUCCC | 20 | 4079 |
| BCL11A-3595 | - | UGAAGCCAUUCUUACAGAUG | 20 | 4080 |
| BCL11A-3596 | + | UGCCAACCUCCACGGGA | 17 | 4081 |

TABLE 5D-continued

4th Tier

| gRNA Name | DNA Strand | Targeting Domain | Target Site Length | SEQ ID NO |
|---|---|---|---|---|
| BCL11A-3597 | − | UGCCAGAUGAACUUCCCAUU | 20 | 4082 |
| BCL11A-3598 | + | UGCUUUUUUCAUCUCGAUUG | 20 | 4083 |
| BCL11A-3599 | − | UGGAGCUCUAAUCCCCACGC | 20 | 4084 |
| BCL11A-3600 | + | UGGCACUGCCCACAGGU | 17 | 4085 |
| BCL11A-3601 | − | UGGCAUCCAGGUCACGC | 17 | 4086 |
| BCL11A-3602 | + | UGGGGUUUGCCUUGCUUGCG | 20 | 4087 |
| BCL11A-3603 | − | UUAUUUUUAUCGAGCACAAA | 20 | 4088 |
| BCL11A-3604 | + | UUCAUCUCGAUUGGUGA | 17 | 4089 |
| BCL11A-3605 | − | UUGGCAUCCAGGUCACGCCA | 20 | 4090 |
| BCL11A-3606 | + | UUGUGCUCGAUAAAAAU | 17 | 4091 |
| BCL11A-3607 | + | UUUCAUCUCGAUUGGUG | 17 | 4092 |
| BCL11A-3608 | + | UUUCAUCUCGAUUGGUGAAG | 20 | 4093 |
| BCL11A-3609 | + | UUUUCAUCUCGAUUGGUGAA | 20 | 4094 |
| BCL11A-3610 | − | UUUUUAUCGAGCACAAA | 17 | 4095 |
| BCL11A-3611 | + | UUUUUCAUCUCGAUUGGUGA | 20 | 4096 |
| BCL11A-3612 | + | UUUUUUCAUCUCGAUUG | 17 | 4097 |
| BCL11A-3613 | + | UUUUUUCAUCUCGAUUGGUG | 20 | 4098 |

Table 5E provides exemplary targeting domains for knocking out the BCL11A gene by targeting the early coding sequence the BCL11A gene selected according to fifth tier parameters. The targeting domains target outside the first 500 bp of coding sequence downstream of start codon. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 5E

5th Tier

| gRNA Name | DNA Strand | Targeting Domain | Target Site Length | SEQ ID NO |
|---|---|---|---|---|
| BCL11A-3614 | + | UCGUCGGACUUGACCGUCAU | 20 | 4099 |
| BCL11A-3615 | + | GUCGUCGGACUUGACCGUCA | 20 | 4100 |
| BCL11A-3616 | + | CGUCGUCGGACUUGACCGUC | 20 | 4101 |
| BCL11A-3617 | + | CGUCGGACUUGACCGUCAUG | 20 | 4102 |
| BCL11A-3618 | − | CCCAUAUUAGUGGUCCGGGC | 20 | 4103 |
| BCL11A-3619 | + | GCGGUCCGACUCGCCGGCCA | 20 | 4104 |
| BCL11A-3620 | + | CUCCGAGGAGUGCUCCGACG | 20 | 4105 |
| BCL11A-3621 | − | CCCCCAUUCGGCGUAGUACC | 20 | 4106 |
| BCL11A-3622 | + | UCUCCGAGGAGUGCUCCGAC | 20 | 4107 |
| BCL11A-3623 | − | CCCGCGGGUUGGUAUCCCUU | 20 | 4108 |
| BCL11A-3624 | + | GCGAGUACACGUUCUCCGUG | 20 | 4109 |
| BCL11A-3625 | − | CCCAUUCGGCGUAGUACCCA | 20 | 4110 |
| BCL11A-3626 | + | CUCCGUGUUGGGCAUCGCGG | 20 | 4111 |
| BCL11A-3627 | + | CCGCGCUUAUGCUUCUCGCC | 20 | 4112 |
| BCL11A-3628 | − | CGACGAAGACUCGGUGGCCG | 20 | 4113 |
| BCL11A-3629 | − | ACCCCACCGCAUAGAGCGC | 20 | 4114 |
| BCL11A-3630 | + | ACUACGCCGAAUGGGGGUGU | 20 | 4115 |
| BCL11A-3631 | + | CCGGGCCCGGACCACUAAUA | 20 | 4116 |
| BCL11A-3632 | + | CGCGUAGCCGGCGAGCCACU | 20 | 4117 |
| BCL11A-3633 | − | UCGGAGCACUCCUCGGAGAA | 20 | 4118 |
| BCL11A-3634 | − | CGGAGCACUCCUCGGAGAAC | 20 | 4119 |
| BCL11A-3635 | + | UCUCUGGGUACUACGCCGAA | 20 | 4120 |
| BCL11A-3636 | + | UGCCGCAGAACUCGCAUGAC | 20 | 4121 |
| BCL11A-3637 | + | GAUACCAACCCGCGGGGUCA | 20 | 4122 |
| BCL11A-3638 | + | GGAUACCAACCCGCGGGGUC | 20 | 4123 |
| BCL11A-3639 | + | GGGAUACCAACCCGCGGGGU | 20 | 4124 |
| BCL11A-3640 | − | CCCCCACCGCAUAGAGCGCC | 20 | 4125 |
| BCL11A-3641 | + | GGUUGGGUCGUUCUCGCUC | 20 | 4126 |
| BCL11A-3642 | − | GCACGCCCCAUAUUAGUGGU | 20 | 4127 |
| BCL11A-3643 | − | UAAGCGCAUCAAGCUCGAGA | 20 | 4128 |
| BCL11A-3644 | + | GUUCUCCGAGGAGUGCUCCG | 20 | 4129 |
| BCL11A-3645 | + | UCUCGAGCUUGAUGCGCUUA | 20 | 4130 |
| BCL11A-3646 | − | CUAAGCGCAUCAAGCUCGAG | 20 | 4131 |
| BCL11A-3647 | − | GUCGGAGCACUCCUCGGAGA | 20 | 4132 |
| BCL11A-3648 | − | UGGCCGCGGCUGCUCCCCGG | 20 | 4133 |

TABLE 5E-continued

5th Tier

| gRNA Name | DNA Strand | Targeting Domain | Target Site Length | SEQ ID NO |
|---|---|---|---|---|
| BCL11A-3649 | - | CCCCACCGCAUAGAGCGCCU | 20 | 4134 |
| BCL11A-3650 | + | CCUGAAGGGAUACCAACCCG | 20 | 4135 |
| BCL11A-3651 | - | GCGCUUCUCCACACCGCCCG | 20 | 4136 |
| BCL11A-3652 | - | GCGCCCUGCCCGACGUCAUG | 20 | 4137 |
| BCL11A-3653 | - | AACCCGGCACCAGCGACUUG | 20 | 4138 |
| BCL11A-3654 | + | CUCUGGGUACUACGCCGAAU | 20 | 4139 |
| BCL11A-3655 | + | CCCGUUCUCCGGGAUCAGGU | 20 | 4140 |
| BCL11A-3656 | - | GAACGACCCCAACCUGAUCC | 20 | 4141 |
| BCL11A-3657 | + | ACGCCGAAUGGGGUGUGUG | 20 | 4142 |
| BCL11A-3658 | + | GUCGCUGGUGCCGGGUUCCG | 20 | 4143 |
| BCL11A-3659 | - | CCCCGGGCGAGUCGGCCUCG | 20 | 4144 |
| BCL11A-3660 | + | CGGUGCACCACCAGGUUGCU | 20 | 4145 |
| BCL11A-3661 | - | GUCCACCACCGAGACAUCAC | 20 | 4146 |
| BCL11A-3662 | - | UUAAUGGCCGCGGCUGCUCC | 20 | 4147 |
| BCL11A-3663 | + | CUCUCUGGGUACUACGCCGA | 20 | 4148 |
| BCL11A-3664 | + | GCGCAAACUCCCGUUCUCCG | 20 | 4149 |
| BCL11A-3665 | + | CCCGGGCCCGGACCACUAAU | 20 | 4150 |
| BCL11A-3666 | + | GCCCCCAGGCGCUCUAUGCG | 20 | 4151 |
| BCL11A-3667 | - | AUCGCCUUUGCCUCCUCGU | 20 | 4152 |
| BCL11A-3668 | - | CCUCGUCGGAGCACUCCUCG | 20 | 4153 |
| BCL11A-3669 | + | GAGCUUGAUGCGCUUAGAGA | 20 | 4154 |
| BCL11A-3670 | + | CCCCGUUCUCCGGGAUCAGG | 20 | 4155 |
| BCL11A-3671 | - | CGGCCGCGAUGCCCAACACG | 20 | 4156 |
| BCL11A-3672 | + | GCCCCCGAGGCCGACUCGC | 20 | 4157 |
| BCL11A-3673 | - | CCCGGCCGCGAUGCCCAACA | 20 | 4158 |
| BCL11A-3674 | - | CUCCUCGUCGGAGCACUCCU | 20 | 4159 |
| BCL11A-3675 | + | GUCUCGGUGGUGGACUAAAC | 20 | 4160 |
| BCL11A-3676 | + | CCCCAGGCGCUCUAUGCGGU | 20 | 4161 |
| BCL11A-3677 | + | GGUCGCACAGGUUGCACUUG | 20 | 4162 |
| BCL11A-3678 | + | AGUCGCUGGUGCCGGGUUCC | 20 | 4163 |
| BCL11A-3679 | - | CCCGGUCAAGUCCAAGUCAU | 20 | 4164 |
| BCL11A-3680 | - | AGAACGACCCCAACCUGAUC | 20 | 4165 |
| BCL11A-3681 | + | UCCGUGUUGGGCAUCGCGGC | 20 | 4166 |
| BCL11A-3682 | - | CCUCCUCGUCGGAGCACUCC | 20 | 4167 |
| BCL11A-3683 | - | UCACUUGGACCCCACCGCA | 20 | 4168 |
| BCL11A-3684 | - | CCCAACCUGAUCCCGGAGAA | 20 | 4169 |
| BCL11A-3685 | - | ACUACGGCUUCGGGCUGAGC | 20 | 4170 |
| BCL11A-3686 | - | UUUGCGCUUCUCCACACCGC | 20 | 4171 |
| BCL11A-3687 | + | AAGUCGCUGGUGCCGGGUUC | 20 | 4172 |
| BCL11A-3688 | - | CCCCAACCUGAUCCCGGAGA | 20 | 4173 |
| BCL11A-3689 | - | AAGACUCGGUGGCCGGCGAG | 20 | 4174 |
| BCL11A-3690 | - | GCGCGGCCACCUGGCCGAGG | 20 | 4175 |
| BCL11A-3691 | - | AAUCGCCUUUGCCUCCUCG | 20 | 4176 |
| BCL11A-3692 | - | ACGACCCCAACCUGAUCCCG | 20 | 4177 |
| BCL11A-3693 | - | GAUCCCGGAGAACGGGACG | 20 | 4178 |
| BCL11A-3694 | + | GGGGCAGGUCGAACUCCUUC | 20 | 4179 |
| BCL11A-3695 | - | UGGCUAUGGAGCCUCCCGCC | 20 | 4180 |
| BCL11A-3696 | + | CCCCCAGGCGCUCUAUGCGG | 20 | 4181 |
| BCL11A-3697 | - | GCGGUUGAAUCCAAUGGCUA | 20 | 4182 |
| BCL11A-3698 | - | CUACGGCUUCGGGCUGAGCC | 20 | 4183 |
| BCL11A-3699 | - | ACAGCUCGCGGGGCGGUC | 20 | 4184 |
| BCL11A-3700 | - | CCCCCUGUUUAGUCCACCA | 20 | 4185 |
| BCL11A-3701 | + | CGCAUGACUUGGACUUGACC | 20 | 4186 |
| BCL11A-3702 | - | CACGGAAGUCCCCUGACCCC | 20 | 4187 |
| BCL11A-3703 | - | CCUCCCGCCAUGGAUUUCUC | 20 | 4188 |
| BCL11A-3704 | + | UCUCGGUGGUGGACUAAACA | 20 | 4189 |
| BCL11A-3705 | + | UGAACUUGGCCACCACGGAC | 20 | 4190 |
| BCL11A-3706 | - | CUUCUCUAAGCGCAUCAAGC | 20 | 4191 |
| BCL11A-3707 | + | AGCGCAAACUCCCGUUCUCC | 20 | 4192 |
| BCL11A-3708 | + | UCGGUGGUGGACUAAACAGG | 20 | 4193 |
| BCL11A-3709 | - | CGCCACCACGAGAACAGCUC | 20 | 4194 |
| BCL11A-3710 | - | CUCCCGCCAUGGAUUUCUCU | 20 | 4195 |
| BCL11A-3711 | + | CGAGCUUGAUGCGCUUAGAG | 20 | 4196 |
| BCL11A-3712 | + | AUGCCCUGCAUGACGUCGGG | 20 | 4197 |
| BCL11A-3713 | - | UCUCUAAGCGCAUCAAGCUC | 20 | 4198 |
| BCL11A-3714 | + | GUCCAAGUGAUGUCUCGGUG | 20 | 4199 |
| BCL11A-3715 | + | CCCCCGAGGCCGACUCGCCC | 20 | 4200 |
| BCL11A-3716 | + | CCCCGAGGCCGACUCGCCCG | 20 | 4201 |
| BCL11A-3717 | + | GAAAUUUGAACGUCUUGCCG | 20 | 4202 |
| BCL11A-3718 | + | GUCGCUGCGUCUGCCCUCUU | 20 | 4203 |
| BCL11A-3719 | - | UGGAGGCGGCGCGCCACCAC | 20 | 4204 |
| BCL11A-3720 | + | CUUCUCGAGCUUGAUGCGCU | 20 | 4205 |
| BCL11A-3721 | + | GAAGCGCAAACUCCCGUUCU | 20 | 4206 |
| BCL11A-3722 | - | GAGAGAGGCUUCCGGCCUGG | 20 | 4207 |

TABLE 5E-continued

5th Tier

| gRNA Name | DNA Strand | Targeting Domain | Target Site Length | SEQ ID NO |
|---|---|---|---|---|
| BCL11A-3723 | − | UCCCCGGGCGAGUCGGCCUC | 20 | 4208 |
| BCL11A-3724 | + | CAAGUCGCUGGUGCCGGGUU | 20 | 4209 |
| BCL11A-3725 | − | CAUAGAGCGCCUGGGGGCGG | 20 | 4210 |
| BCL11A-3726 | + | CUCGGUGGUGGACUAAACAG | 20 | 4211 |
| BCL11A-3727 | + | CCCCCCGAGGCCGACUCGCC | 20 | 4212 |
| BCL11A-3728 | − | GGUUUCUCUUGCAACACGCA | 20 | 4213 |
| BCL11A-3729 | + | ACUGGACUUGACCGGGGGC | 20 | 4214 |
| BCL11A-3730 | − | UGAUCCCGGAGAACGGGGAC | 20 | 4215 |
| BCL11A-3731 | + | UGUCUGGAGUCUCCGAAGCU | 20 | 4216 |
| BCL11A-3732 | − | AUGGAUUUCUCUAGGAGACU | 20 | 4217 |
| BCL11A-3733 | − | UGCGGUUGAAUCCAAUGGCU | 20 | 4218 |
| BCL11A-3734 | − | CUCCCCGGGCGAGUCGGCCU | 20 | 4219 |
| BCL11A-3735 | − | CCUGAUCCCGGAGAACGGGG | 20 | 4220 |
| BCL11A-3736 | + | UGUCUCGGUGGUGGACUAAA | 20 | 4221 |
| BCL11A-3737 | + | CGGUGGUGGACUAAACAGGG | 20 | 4222 |
| BCL11A-3738 | + | UGCCCACCAAGUCGCUGGUG | 20 | 4223 |
| BCL11A-3739 | − | CGUGGUGGCCAAGUUCAAGA | 20 | 4224 |
| BCL11A-3740 | − | CAUCACCCGAGUGCCUUUGA | 20 | 4225 |
| BCL11A-3741 | − | GCGGCAAGACGUUCAAAUUU | 20 | 4226 |
| BCL11A-3742 | + | AAGGGCUCUCGAGCUUCCAU | 20 | 4227 |
| BCL11A-3743 | + | GUCUGGAGUCUCCGAAGCUA | 20 | 4228 |
| BCL11A-3744 | − | CCCCGGCCGCGAUGCCCAAC | 20 | 4229 |
| BCL11A-3745 | + | CUGUCAAAGGCACUCGGGUG | 20 | 4230 |
| BCL11A-3746 | + | CUUGGACUUGACCGGGGGCU | 20 | 4231 |
| BCL11A-3747 | + | GACUUGGACUUGACCGGGGG | 20 | 4232 |
| BCL11A-3748 | + | UGCGUCUGCCCUCUUUUGAG | 20 | 4233 |
| BCL11A-3749 | + | GGAGGCAAAAGGCGAUUGUC | 20 | 4234 |
| BCL11A-3750 | − | GCAACACGCACAGAACACUC | 20 | 4235 |
| BCL11A-3751 | + | GCAGUAACCUUUGCAUAGGG | 20 | 4236 |
| BCL11A-3752 | − | UGGUGCACCGGCGCAGCCAC | 20 | 4237 |
| BCL11A-3753 | − | UGGUGGCCAAGUUCAAGAGC | 20 | 4238 |
| BCL11A-3754 | − | GCAUAGCGCGGCCACCUGG | 20 | 4239 |
| BCL11A-3755 | + | UUGCAUAGGGCUGGGCCGGC | 20 | 4240 |
| BCL11A-3756 | − | CCAACCUGAUCCCGGAGAAC | 20 | 4241 |
| BCL11A-3757 | − | AGAUGUGGCAGUUUUCGG | 20 | 4242 |
| BCL11A-3758 | − | CAGUUUUCGGAUGGAAGCUC | 20 | 4243 |
| BCL11A-3759 | − | GCUCCCCGGGCGAGUCGGCC | 20 | 4244 |
| BCL11A-3760 | − | GGGUGGACUACGGCUUCGGG | 20 | 4245 |
| BCL11A-3761 | − | UAUCCCUUCAGGACUAGGUG | 20 | 4246 |
| BCL11A-3762 | − | AUCUCGGGGCGCAGCGGCAC | 20 | 4247 |
| BCL11A-3763 | + | CGCUCUUGAACUUGGCCACC | 20 | 4248 |
| BCL11A-3764 | − | GCACCGGCGCAGCCACACGG | 20 | 4249 |
| BCL11A-3765 | + | GCUUCUCGCCCAGGACCUGG | 20 | 4250 |
| BCL11A-3766 | − | UCCCGGAGAACGGGGACGAG | 20 | 4251 |
| BCL11A-3767 | + | CAGCACCCUGUCAAAGGCAC | 20 | 4252 |
| BCL11A-3768 | + | CAUUCUGCACCUAGUCCUGA | 20 | 4253 |
| BCL11A-3769 | − | CUUUAACCUGCUAAGAAUAC | 20 | 4254 |
| BCL11A-3770 | − | GUCUCUCCACCGCCAGCUCC | 20 | 4255 |
| BCL11A-3771 | − | UCUCUCCACCGCCAGCUCCC | 20 | 4256 |
| BCL11A-3772 | + | UGCUUCUCGCCCAGGACCUG | 20 | 4257 |
| BCL11A-3773 | + | GCGCCGCCUCCAGGCUCAGC | 20 | 4258 |
| BCL11A-3774 | + | AGAUCCCUCCGUCCAGCUCC | 20 | 4259 |
| BCL11A-3775 | − | CGAGAGGGUGGACUACGGCU | 20 | 4260 |
| BCL11A-3776 | + | CGUCCAGCUCCCCGGGCGGU | 20 | 4261 |
| BCL11A-3777 | + | CCAGCUCUCUAAGUCUCCUA | 20 | 4262 |
| BCL11A-3778 | + | UCGCAUGACUUGGACUUGAC | 20 | 4263 |
| BCL11A-3779 | + | GCACCAUGCCCUGCAUGACG | 20 | 4264 |
| BCL11A-3780 | + | AAGGCGAUUGUCUGGAGUCU | 20 | 4265 |
| BCL11A-3781 | + | GCCUGGAGGCCGCGUAGCCG | 20 | 4266 |
| BCL11A-3782 | − | GCGGCCACCUGGCCGAGGCC | 20 | 4267 |
| BCL11A-3783 | − | AGAAUACCAGGAUCAGUAUC | 20 | 4268 |
| BCL11A-3784 | − | GAUGUGGCAGUUUUCGGA | 20 | 4269 |
| BCL11A-3785 | − | UCUCCACCGCCCGGGGAG | 20 | 4270 |
| BCL11A-3786 | − | CCUGGAGGCGGCGCGCCACC | 20 | 4271 |
| BCL11A-3787 | + | CUGGUAUUCUUAGCAGGUUA | 20 | 4272 |
| BCL11A-3788 | + | UAGAGAAGGGCUCAGCGAG | 20 | 4273 |
| BCL11A-3789 | + | GAGUGUUCUGUGCGUGUUGC | 20 | 4274 |
| BCL11A-3790 | − | AAUAACCCCUUUAACCUGCU | 20 | 4275 |
| BCL11A-3791 | + | AAAGCGCCCUUCUGCCAGGC | 20 | 4276 |
| BCL11A-3792 | + | GUCCAGCUCCCCGGGCGGUG | 20 | 4277 |
| BCL11A-3793 | + | AAGGGCGGCUUGCUACCUGG | 20 | 4278 |
| BCL11A-3794 | + | GAAAGCGCCCUUCUGCCAGG | 20 | 4279 |
| BCL11A-3795 | + | AGGGCGGCUUGCUACCUGGC | 20 | 4280 |
| BCL11A-3796 | − | CGCGGGGCGCGGUCGUGGGC | 20 | 4281 |

TABLE 5E-continued

5th Tier

| gRNA Name | DNA Strand | Targeting Domain | Target Site Length | SEQ ID NO |
|---|---|---|---|---|
| BCL11A-3797 | - | GCGAGGCCUUCCACCAGGUC | 20 | 4282 |
| BCL11A-3798 | + | ACUUCCCGUGCCGCUGCGCC | 20 | 4283 |
| BCL11A-3799 | - | GCACAGAACACUCAUGGAUU | 20 | 4284 |
| BCL11A-3800 | + | CCAGCUCCCCGGGCGGUGUG | 20 | 4285 |
| BCL11A-3801 | - | ACCGCCCGGGGAGCUGGACG | 20 | 4286 |
| BCL11A-3802 | + | UGGUUGCAGUAACCUUUGCA | 20 | 4287 |
| BCL11A-3803 | - | AGGAGACUUAGAGAGCUGGC | 20 | 4288 |
| BCL11A-3804 | - | ACCGGCGCAGCCACACGGGC | 20 | 4289 |
| BCL11A-3805 | + | ACAUUCUGCACCUAGUCCUG | 20 | 4290 |
| BCL11A-3806 | + | GUGUUCUGUGCGUGUUGCAA | 20 | 4291 |
| BCL11A-3807 | - | UGGCCCUGGCCACCCAUCAC | 20 | 4292 |
| BCL11A-3808 | + | UGCAUAGGGCUGGGCCGGCC | 20 | 4293 |
| BCL11A-3809 | - | AAUACCAGGAUCAGUAUCGA | 20 | 4294 |
| BCL11A-3810 | + | UCCUGAAGGGAUACCAACCC | 20 | 4295 |
| BCL11A-3811 | + | CUCCUAGAGAAAUCCAUGGC | 20 | 4296 |
| BCL11A-3812 | + | UGGCGGUGGAGAGACCGUCG | 20 | 4297 |
| BCL11A-3813 | - | GGAUUUCUCUAGGAGACUUA | 20 | 4298 |
| BCL11A-3814 | + | CUCGCAUGACUUGGACUUGA | 20 | 4299 |
| BCL11A-3815 | - | GAUCUCGGGGCGCAGCGGCA | 20 | 4300 |
| BCL11A-3816 | + | GGUGGUGGACUAAACAGGGG | 20 | 4301 |
| BCL11A-3817 | + | AGGCCUCGCUGAAGUGCUGC | 20 | 4302 |
| BCL11A-3818 | + | CCACCAGGUUGCUCUGAAAU | 20 | 4303 |
| BCL11A-3819 | - | ACCGCAUAGAGCGCCUGGGG | 20 | 4304 |
| BCL11A-3820 | - | CCAGCAAGCUGAAGCGCCAC | 20 | 4305 |
| BCL11A-3821 | + | GGCCUCGCUGAAGUGCUGCA | 20 | 4306 |
| BCL11A-3822 | - | CGUGCACCCAGGCCAGCAAG | 20 | 4307 |
| BCL11A-3823 | + | GGCGGGAGGCUCCAUAGCCA | 20 | 4308 |
| BCL11A-3824 | + | AGGAGGCAAAAGGCGAUUGU | 20 | 4309 |
| BCL11A-3825 | - | AAAGAUCCCUUCCUUAGCUU | 20 | 4310 |
| BCL11A-3826 | + | GGAGUCUCCGAAGCUAAGGA | 20 | 4311 |
| BCL11A-3827 | + | GCGCUUAGAGAAGGGGCUCA | 20 | 4312 |
| BCL11A-3828 | + | CAGCUUUUGGACAGGCCCC | 20 | 4313 |
| BCL11A-3829 | + | GCACUCGGGUGAUGGGUGGC | 20 | 4314 |
| BCL11A-3830 | + | CACGCCCACGACCGCGCCCC | 20 | 4315 |
| BCL11A-3831 | + | AAGUUGUACAUGUGUAGCUG | 20 | 4316 |
| BCL11A-3832 | - | AGUCCGUGGUGGCCAAGUUC | 20 | 4317 |
| BCL11A-3833 | - | CCCGGAGAACGGGGACGAGG | 20 | 4318 |
| BCL11A-3834 | - | CGGGCAGGCCCAGCUCAAAA | 20 | 4319 |
| BCL11A-3835 | + | UGGUAUUCUUAGCAGGUUAA | 20 | 4320 |
| BCL11A-3836 | + | UUGUCUGCAAUAUGAAUCCC | 20 | 4321 |
| BCL11A-3837 | + | GUCUCCUAGAGAAAUCCAUG | 20 | 4322 |
| BCL11A-3838 | + | UGGACUUGACCGGGGCUGG | 20 | 4323 |
| BCL11A-3839 | + | UGGAGUCUCCGAAGCUAAGG | 20 | 4324 |
| BCL11A-3840 | + | UGAGCUGGGCCUGCCCGGGC | 20 | 4325 |
| BCL11A-3841 | - | CAAAGAUCCCUUCCUUAGCU | 20 | 4326 |
| BCL11A-3842 | + | UGCCACACAUCUUGAGCUCU | 20 | 4327 |
| BCL11A-3843 | - | CCGCCCGGGGAGCUGGACGG | 20 | 4328 |
| BCL11A-3844 | + | AGAGAAGGGGCUCAGCGAGC | 20 | 4329 |
| BCL11A-3845 | - | GGAGACUUAGAGAGCUGGCA | 20 | 4330 |
| BCL11A-3846 | + | GAAUCCCAUGGAGAGGUGGC | 20 | 4331 |
| BCL11A-3847 | + | CGCUGAAGUGCUGCAUGGAG | 20 | 4332 |
| BCL11A-3848 | + | AGGACAUUCUGCACCUAGUC | 20 | 4333 |
| BCL11A-3849 | + | AAUCCCAUGGAGAGGUGGCU | 20 | 4334 |
| BCL11A-3850 | + | UGAGCUCUCUGGGUACUACG | 20 | 4335 |
| BCL11A-3851 | - | GGGCCACAGGGACACUUGCG | 20 | 4336 |
| BCL11A-3852 | - | UAGGAGACUUAGAGAGCUGG | 20 | 4337 |
| BCL11A-3853 | - | CCUUUGACAGGGUGCUGCGG | 20 | 4338 |
| BCL11A-3854 | - | UGGCCGAGGCCGAGGGCCAC | 20 | 4339 |
| BCL11A-3855 | + | GGAAGGGAUCUUUGAGCUGC | 20 | 4340 |
| BCL11A-3856 | + | UCUAAGUAGAUUCUUAAUCC | 20 | 4341 |
| BCL11A-3857 | - | GGGGCGCAGCGGCACGGGAA | 20 | 4342 |
| BCL11A-3858 | - | CUGGCCGAGGCCGAGGGCCA | 20 | 4343 |
| BCL11A-3859 | - | CUCAAGAUGUGUGGCAGUUU | 20 | 4344 |
| BCL11A-3860 | - | CGAAGCUAAGGAAGGGAUCU | 20 | 4345 |
| BCL11A-3861 | + | UGCCAGCUCUCUAAGUCUCC | 20 | 4346 |
| BCL11A-3862 | + | UCUCCUAGAGAAAUCCAUGG | 20 | 4347 |
| BCL11A-3863 | - | GCCACCACGAGAACAGCUCG | 20 | 4348 |
| BCL11A-3864 | + | UCUGCAAUAUGAAUCCCAUG | 20 | 4349 |
| BCL11A-3865 | - | CAGCUCCAUGCAGCACUUCA | 20 | 4350 |
| BCL11A-3866 | - | GCCUGUCCAAAAGCUGCUG | 20 | 4351 |
| BCL11A-3867 | - | UAAGAAUACCAGGAUCAGUA | 20 | 4352 |
| BCL11A-3868 | - | GGAUCUCGGGGCGCAGCGGC | 20 | 4353 |
| BCL11A-3869 | - | GGCAGUUUUCGGAUGGAAGC | 20 | 4354 |
| BCL11A-3870 | - | CGGUCGUGGGCGUGGGCGAC | 20 | 4355 |

TABLE 5E-continued

5th Tier

| gRNA Name | DNA Strand | Targeting Domain | Target Site Length | SEQ ID NO |
|---|---|---|---|---|
| BCL11A-3871 | + | GCAUCGCGGCCGGGGGCAGG | 20 | 4356 |
| BCL11A-3872 | - | AAUCUACUUAGAAAGCGAAC | 20 | 4357 |
| BCL11A-3873 | + | AAGGGGUUAUUGUCUGCAAU | 20 | 4358 |
| BCL11A-3874 | + | GGACUUGACCGGGGGCUGGG | 20 | 4359 |
| BCL11A-3875 | - | UCAUGGAUUAAGAAUCUACU | 20 | 4360 |
| BCL11A-3876 | - | AGAGGCUUCCGGCCUGGCAG | 20 | 4361 |
| BCL11A-3877 | - | GGCCUUCCACCAGGUCCUGG | 20 | 4362 |
| BCL11A-3878 | + | UGGCGCUUCAGCUUGCUGGC | 20 | 4363 |
| BCL11A-3879 | - | CCGCAUAGAGCGCUGGGGGG | 20 | 4364 |
| BCL11A-3880 | + | GGACCUGGUGGAAGGCCUCG | 20 | 4365 |
| BCL11A-3881 | - | CCUUCCACCAGGUCCUGGGC | 20 | 4366 |
| BCL11A-3882 | + | UGUCUGCAAUAUGAAUCCCA | 20 | 4367 |
| BCL11A-3883 | - | GGAGCUGGACGGAGGGAUCU | 20 | 4368 |
| BCL11A-3884 | + | GACUUGACCGGGGGCUGGGA | 20 | 4369 |
| BCL11A-3885 | - | UCCUUCCCAGCCACCUCUCC | 20 | 4370 |
| BCL11A-3886 | + | CUCUUUUGAGCUGGGCCUGC | 20 | 4371 |
| BCL11A-3887 | - | UGCGCUUCUCCACACCGCCC | 20 | 4372 |
| BCL11A-3888 | + | GCAAGAGAAACCAUGCACUG | 20 | 4373 |
| BCL11A-3889 | - | GGGAGCUGGACGGAGGGAUC | 20 | 4374 |
| BCL11A-3890 | + | GUUCCGGGGAGCUGGCGGUG | 20 | 4375 |
| BCL11A-3891 | + | UGAAUCCCAUGGAGAGGUGG | 20 | 4376 |
| BCL11A-3892 | + | CGGGUUCCGGGGAGCUGGCG | 20 | 4377 |
| BCL11A-3893 | + | GUGGACUAAACAGGGGGGGA | 20 | 4378 |
| BCL11A-3894 | + | GGCUGCCCAGCAGCAGCUUU | 20 | 4379 |
| BCL11A-3895 | + | GAAGGGAUCUUUGAGCUGCC | 20 | 4380 |
| BCL11A-3896 | - | CCUUCCCAGCCACCUCUCCA | 20 | 4381 |
| BCL11A-3897 | - | GCGCAGCGGCACGGGAAGUG | 20 | 4382 |
| BCL11A-3898 | + | GGGUUCCGGGGAGCUGGCGG | 20 | 4383 |
| BCL11A-3899 | + | UCCUCCUCGUCCCCGUUCUC | 20 | 4384 |
| BCL11A-3900 | - | GCAGCGGCACGGGAAGUGGA | 20 | 4385 |
| BCL11A-3901 | - | UGCUGGGCAGCCCCAGCUCG | 20 | 4386 |
| BCL11A-3902 | - | GGGCGCAGCGGCACGGGAAG | 20 | 4387 |
| BCL11A-3903 | - | ACACCGCCCGGGGAGCUGGA | 20 | 4388 |
| BCL11A-3904 | + | CCCAUGGAGAGGUGGCUGGG | 20 | 4389 |
| BCL11A-3905 | + | UUCCUCCUCGUCCCCGUUCU | 20 | 4390 |
| BCL11A-3906 | - | AUCUACUUAGAAAGCGAACA | 20 | 4391 |
| BCL11A-3907 | - | CCCGGGCAGGCCCAGCUCAA | 20 | 4392 |
| BCL11A-3908 | - | CACACCGCCCGGGGAGCUGG | 20 | 4393 |
| BCL11A-3909 | + | ACUAAACAGGGGGGGAGUGG | 20 | 4394 |
| BCL11A-3910 | + | GACCGGGGCUGGGAGGGAG | 20 | 4395 |
| BCL11A-3911 | + | GGGCCGGCCUGGGGACAGCG | 20 | 4396 |
| BCL11A-3912 | + | GCAUAGGGCUGGGCCGGCCU | 20 | 4397 |
| BCL11A-3913 | - | AUUAAGAAUCUACUUAGAAA | 20 | 4398 |
| BCL11A-3914 | + | CUAAACAGGGGGGAGUGGG | 20 | 4399 |
| BCL11A-3915 | + | UUGACCGGGGCUGGGAGGG | 20 | 4400 |
| BCL11A-3916 | - | CGCGGUCGUGGGCGUGGGCG | 20 | 4401 |
| BCL11A-3917 | + | GAGGGAGGGGGGCGUCGCC | 20 | 4402 |
| BCL11A-3918 | - | GGAGAACGGGGACGAGGAGG | 20 | 4403 |
| BCL11A-3919 | + | CUUGACCGGGGGCUGGGAGG | 20 | 4404 |
| BCL11A-3920 | + | GGAGGGAGGGGGGCGUCGC | 20 | 4405 |
| BCL11A-3921 | + | ACCGGGGCUGGGAGGGAGG | 20 | 4406 |
| BCL11A-3922 | - | CGCAGCGGCACGGGAAGUGG | 20 | 4407 |
| BCL11A-3923 | + | GCGGAUUGCAGAGGAGGGAG | 20 | 4408 |
| BCL11A-3924 | + | GGAGGGGGGCGUCGCCAGG | 20 | 4409 |
| BCL11A-3925 | + | GGCGGAUUGCAGAGGAGGGA | 20 | 4410 |
| BCL11A-3926 | + | GAGGGGCGGAUUGCAGAGGA | 20 | 4411 |
| BCL11A-3927 | + | GGGGCGGAUUGCAGAGGAGG | 20 | 4412 |
| BCL11A-3928 | - | GAGGAGCUGACGGAGAGCGA | 20 | 4413 |
| BCL11A-3929 | + | UCCGAAAACUGCCACACAUC | 20 | 4414 |
| BCL11A-3930 | + | CGGAUUGCAGAGGAGGGAGG | 20 | 4415 |
| BCL11A-3931 | + | GGAGGGGCGGAUUGCAGAGG | 20 | 4416 |
| BCL11A-3932 | + | GGGCGGAUUGCAGAGGAGGG | 20 | 4417 |
| BCL11A-3933 | + | AGGAGGGGCGGAUUGCAGAG | 20 | 4418 |
| BCL11A-3934 | - | AGAACGGGGACGAGGAGGAA | 20 | 4419 |
| BCL11A-3935 | + | GAGGGAGGAGGGGCGGAUUG | 20 | 4420 |
| BCL11A-3936 | - | UUGCGCUUCUCCACACCGCC | 20 | 4421 |
| BCL11A-3937 | - | AGCUGACGGAGAGCGAGAGG | 20 | 4422 |
| BCL11A-3938 | - | AGGAGGAGCUGACGGAGAGC | 20 | 4423 |
| BCL11A-3939 | + | GGGGCUGGGAGGGAGGAGGG | 20 | 4424 |
| BCL11A-3940 | + | GGGAGGAGGGGCGGAUUGCA | 20 | 4425 |
| BCL11A-3941 | + | CCGUGUUGGGCAUCGCGGCC | 20 | 4426 |
| BCL11A-3942 | - | GAACGGGGACGAGGAGGAAG | 20 | 4427 |
| BCL11A-3943 | + | GGAGGAGGGGCGGAUUGCAG | 20 | 4428 |
| BCL11A-3944 | - | GGAGGAGGAGCUGACGGAGA | 20 | 4429 |

TABLE 5E-continued

5th Tier

| gRNA Name | DNA Strand | Targeting Domain | Target Site Length | SEQ ID NO |
|---|---|---|---|---|
| BCL11A-3945 | − | ACGGGGACGAGGAGGAAGAG | 20 | 4430 |
| BCL11A-3946 | − | AGGAGGAGGAGGAGCUGACG | 20 | 4431 |
| BCL11A-3947 | − | ACGACGAGGAAGAGGAAGAA | 20 | 4432 |
| BCL11A-3948 | − | ACGAGGAAGAGGAAGAAGAG | 20 | 4433 |
| BCL11A-3949 | − | AGGAGGAAGAGGAGGACGAC | 20 | 4434 |
| BCL11A-3950 | − | AAGAGGAGGACGACGAGGAA | 20 | 4435 |
| BCL11A-3951 | − | AGAGGAGGAGGAGGAGCUGA | 20 | 4436 |
| BCL11A-3952 | − | GGAGGAAGAGGAGGACGACG | 20 | 4437 |
| BCL11A-3953 | − | CGAGGAGGAAGAGGAGGACG | 20 | 4438 |
| BCL11A-3954 | − | CGAGGAAGAGGAAGAAGAGG | 20 | 4439 |
| BCL11A-3955 | − | AAGAGGAGGAGGAGGAGCUG | 20 | 4440 |
| BCL11A-3956 | − | CGACGAGGAAGAGGAAGAAG | 20 | 4441 |
| BCL11A-3957 | − | GGAGGACGACGAGGAAGAGG | 20 | 4442 |
| BCL11A-3958 | − | AGAGGAGGACGACGAGGAAG | 20 | 4443 |
| BCL11A-3959 | − | GGACGACGAGGAAGAGGAAG | 20 | 4444 |
| BCL11A-3960 | − | GGAAGAGGAGGACGACGAGG | 20 | 4445 |
| BCL11A-3961 | − | AGGAAGAAGAGGAGGAAGAG | 20 | 4446 |
| BCL11A-3962 | − | AAGAGGAAGAAGAGGAGGAA | 20 | 4447 |
| BCL11A-3963 | − | GGAAGAGGAAGAAGAGGAGG | 20 | 4448 |
| BCL11A-3964 | − | AAGAAGAGGAGGAAGAGGAG | 20 | 4449 |
| BCL11A-3965 | − | AAGAGGAGGAAGAGGAGGAG | 20 | 4450 |
| BCL11A-3966 | − | AGAGGAAGAAGAGGAGGAAG | 20 | 4451 |
| BCL11A-3967 | − | GGAAGAGGAGGAGGAAGAGG | 20 | 4452 |
| BCL11A-3968 | − | AGAAGAGGAGGAAGAGGAGG | 20 | 4453 |
| BCL11A-3969 | − | AGAGGAGGAAGAGGAGGAGG | 20 | 4454 |
| BCL11A-3970 | + | UCGGACUUGACCGUCAU | 17 | 4455 |
| BCL11A-3971 | + | GUCGGACUUGACCGUCA | 17 | 4456 |
| BCL11A-3972 | + | CGUCGGACUUGACCGUC | 17 | 4457 |
| BCL11A-3973 | + | CGGACUUGACCGUCAUG | 17 | 4458 |
| BCL11A-3974 | − | AUAUUAGUGGUCCGGGC | 17 | 4459 |
| BCL11A-3975 | + | GUCCGACUCGCCGGCCA | 17 | 4460 |
| BCL11A-3976 | + | CGAGGAGUGCUCCGACG | 17 | 4461 |
| BCL11A-3977 | − | CCAUUCGGCGUAGUACC | 17 | 4462 |
| BCL11A-3978 | + | CCGAGGAGUGCUCCGAC | 17 | 4463 |
| BCL11A-3979 | − | GCGGGUUGGUAUCCCUU | 17 | 4464 |
| BCL11A-3980 | + | AGUACACGUUCUCCGUG | 17 | 4465 |
| BCL11A-3981 | − | AUUCGGCGUAGUACCCA | 17 | 4466 |
| BCL11A-3982 | + | CGUGUUGGGCAUCGCGG | 17 | 4467 |
| BCL11A-3983 | + | CGCUUAUGCUUCUCGCC | 17 | 4468 |
| BCL11A-3984 | − | CGAAGACUCGGUGGCCG | 17 | 4469 |
| BCL11A-3985 | − | CCCACCGCAUAGAGCGC | 17 | 4470 |
| BCL11A-3986 | + | ACGCCGAAUGGGGGUGU | 17 | 4471 |
| BCL11A-3987 | + | GGCCCGGACCACUAAUA | 17 | 4472 |
| BCL11A-3988 | + | GUAGCCGGCGAGCCACU | 17 | 4473 |
| BCL11A-3989 | − | GAGCACUCCUCGGAGAA | 17 | 4474 |
| BCL11A-3990 | − | AGCACUCCUCGGAGAAC | 17 | 4475 |
| BCL11A-3991 | + | CUGGGUACUACGCCGAA | 17 | 4476 |
| BCL11A-3992 | + | CGCAGAACUCGCAUGAC | 17 | 4477 |
| BCL11A-3993 | + | ACCAACCCGCGGGGUCA | 17 | 4478 |
| BCL11A-3994 | + | UACCAACCCGCGGGGUC | 17 | 4479 |
| BCL11A-3995 | + | AUACCAACCCGCGGGGU | 17 | 4480 |
| BCL11A-3996 | − | CCACCGCAUAGAGCGCC | 17 | 4481 |
| BCL11A-3997 | + | UGGGGUCGUUCUCGCUC | 17 | 4482 |
| BCL11A-3998 | − | CGCCCCAUAUUAGUGGU | 17 | 4483 |
| BCL11A-3999 | − | GCGCAUCAAGCUCGAGA | 17 | 4484 |
| BCL11A-4000 | + | CUCCGAGGAGUGCUCCG | 17 | 4485 |
| BCL11A-4001 | + | CGAGCUUGAUGCGCUUA | 17 | 4486 |
| BCL11A-4002 | − | AGCGCAUCAAGCUCGAG | 17 | 4487 |
| BCL11A-4003 | − | GGAGCACUCCUCGGAGA | 17 | 4488 |
| BCL11A-4004 | − | CCGCGGCUGCUCCCCGG | 17 | 4489 |
| BCL11A-4005 | − | CACCGCAUAGAGCGCCU | 17 | 4490 |
| BCL11A-4006 | + | GAAGGGAUACCAACCCG | 17 | 4491 |
| BCL11A-4007 | − | CUUCUCCACACCGCCCG | 17 | 4492 |
| BCL11A-4008 | − | CCCUGCCCGACGUCAUG | 17 | 4493 |
| BCL11A-4009 | − | CCGGCACCAGCGACUUG | 17 | 4494 |
| BCL11A-4010 | + | UGGGUACUACGCCGAAU | 17 | 4495 |
| BCL11A-4011 | + | GUUCUCCGGGAUCAGGU | 17 | 4496 |
| BCL11A-4012 | − | CGACCCCAACCUGAUCC | 17 | 4497 |
| BCL11A-4013 | + | CCGAAUGGGGUGUGUG | 17 | 4498 |
| BCL11A-4014 | + | GCUGGUGCCGGGUUCCG | 17 | 4499 |
| BCL11A-4015 | − | CGGGCGAGUCGGCCUCG | 17 | 4500 |
| BCL11A-4016 | + | UGCACCACCAGGUUGCU | 17 | 4501 |
| BCL11A-4017 | − | CACCACCGAGACAUCAC | 17 | 4502 |
| BCL11A-4018 | − | AUGGCCGCGGCUGCUCC | 17 | 4503 |

TABLE 5E-continued

5th Tier

| gRNA Name | DNA Strand | Targeting Domain | Target Site Length | SEQ ID NO |
|---|---|---|---|---|
| BCL11A-4019 | + | UCUGGGUACUACGCCGA | 17 | 4504 |
| BCL11A-4020 | + | CAAACUCCCGUUCUCCG | 17 | 4505 |
| BCL11A-4021 | + | GGGCCCGGACCACUAAU | 17 | 4506 |
| BCL11A-4022 | + | CCCAGGCGCUCUAUGCG | 17 | 4507 |
| BCL11A-4023 | − | GCCUUUUGCCUCCUCGU | 17 | 4508 |
| BCL11A-4024 | − | CGUCGGAGCACUCCUCG | 17 | 4509 |
| BCL11A-4025 | + | CUUGAUGCGCUUAGAGA | 17 | 4510 |
| BCL11A-4026 | + | CGUUCUCCGGGAUCAGG | 17 | 4511 |
| BCL11A-4027 | − | CCGCGAUGCCCAACACG | 17 | 4512 |
| BCL11A-4028 | + | CCCCGAGGCCGACUCGC | 17 | 4513 |
| BCL11A-4029 | − | GGCCGCGAUGCCCAACA | 17 | 4514 |
| BCL11A-4030 | − | CUCGUCGGAGCACUCCU | 17 | 4515 |
| BCL11A-4031 | + | UCGGUGGUGGACUAAAC | 17 | 4516 |
| BCL11A-4032 | + | CAGGCGCUCUAUGCGGU | 17 | 4517 |
| BCL11A-4033 | + | CGCACAGGUUGCACUUG | 17 | 4518 |
| BCL11A-4034 | + | CGCUGGUGCCGGGUUCC | 17 | 4519 |
| BCL11A-4035 | − | GGUCAAGUCCAAGUCAU | 17 | 4520 |
| BCL11A-4036 | − | ACGACCCCAACCUGAUC | 17 | 4521 |
| BCL11A-4037 | + | GUGUUUGGGCAUCGCGGC | 17 | 4522 |
| BCL11A-4038 | − | CCUCGUCGGAGCACUCC | 17 | 4523 |
| BCL11A-4039 | − | CUUGGACCCCACCGCA | 17 | 4524 |
| BCL11A-4040 | − | AACCUGAUCCCGGAGAA | 17 | 4525 |
| BCL11A-4041 | − | ACGGCUUCGGGCUGAGC | 17 | 4526 |
| BCL11A-4042 | − | GCGCUUCUCCACACCGC | 17 | 4527 |
| BCL11A-4043 | + | UCGCUGGUGCCGGGUUC | 17 | 4528 |
| BCL11A-4044 | − | CAACCUGAUCCCGGAGA | 17 | 4529 |
| BCL11A-4045 | − | ACUCGGUGGCCGGCGAG | 17 | 4530 |
| BCL11A-4046 | − | CGGCCACCUGGCCGAGG | 17 | 4531 |
| BCL11A-4047 | − | CGCCUUUUGCCUCCUCG | 17 | 4532 |
| BCL11A-4048 | − | ACCCCAACCUGAUCCCG | 17 | 4533 |
| BCL11A-4049 | − | CCCGGAGAACGGGGACG | 17 | 4534 |
| BCL11A-4050 | + | GCAGGUCGAACUCCUUC | 17 | 4535 |
| BCL11A-4051 | − | CUAUGGAGCCUCCCGCC | 17 | 4536 |
| BCL11A-4052 | + | CCAGGCGCUCUAUGCGG | 17 | 4537 |
| BCL11A-4053 | − | GUUGAAUCCAAUGGCUA | 17 | 4538 |
| BCL11A-4054 | − | CGGCUUCGGGCUGAGCC | 17 | 4539 |
| BCL11A-4055 | − | GCUCGCGGGGCGCGGUC | 17 | 4540 |
| BCL11A-4056 | − | CCCUGUUUAGUCCACCA | 17 | 4541 |
| BCL11A-4057 | + | AUGACUUGGACUUGACC | 17 | 4542 |
| BCL11A-4058 | − | GGAAGUCCCCUGACCCC | 17 | 4543 |
| BCL11A-4059 | − | CCCGCCAUGGAUUUCUC | 17 | 4544 |
| BCL11A-4060 | + | CGGUGGUGGACUAAACA | 17 | 4545 |
| BCL11A-4061 | + | ACUUGGCCACCACGGAC | 17 | 4546 |
| BCL11A-4062 | − | CUCUAAGCGCAUCAAGC | 17 | 4547 |
| BCL11A-4063 | + | GCAAACUCCCGUUCUCC | 17 | 4548 |
| BCL11A-4064 | + | GUGGUGGACUAAACAGG | 17 | 4549 |
| BCL11A-4065 | − | CACCACGAGAACAGCUC | 17 | 4550 |
| BCL11A-4066 | − | CCGCCAUGGAUUUCUCU | 17 | 4551 |
| BCL11A-4067 | + | GCUUGAUGCGCUUAGAG | 17 | 4552 |
| BCL11A-4068 | + | CCCUGCAUGACGUCGGG | 17 | 4553 |
| BCL11A-4069 | − | CUAAGCGCAUCAAGCUC | 17 | 4554 |
| BCL11A-4070 | + | CAAGUGAUGUCUCGGUG | 17 | 4555 |
| BCL11A-4071 | + | CCGAGGCCGACUCGCCC | 17 | 4556 |
| BCL11A-4072 | + | CGAGGCCGACUCGCCCG | 17 | 4557 |
| BCL11A-4073 | + | AUUUGAACGUCUUGCCG | 17 | 4558 |
| BCL11A-4074 | + | GCUGCGUCUGCCCUCUU | 17 | 4559 |
| BCL11A-4075 | − | AGGCGGCGCGCCACCAC | 17 | 4560 |
| BCL11A-4076 | + | CUCGAGCUUGAUGCGCU | 17 | 4561 |
| BCL11A-4077 | + | GCGCAAACUCCCGUUCU | 17 | 4562 |
| BCL11A-4078 | − | AGAGGCUUCCGGCCUGG | 17 | 4563 |
| BCL11A-4079 | − | CCGGGCGAGUCGGCCUC | 17 | 4564 |
| BCL11A-4080 | + | GUCGCUGGUGCCGGGUU | 17 | 4565 |
| BCL11A-4081 | − | AGAGCGCCUGGGGGCGG | 17 | 4566 |
| BCL11A-4082 | + | GGUGGUGGACUAAACAG | 17 | 4567 |
| BCL11A-4083 | + | CCCGAGGCCGACUCGCC | 17 | 4568 |
| BCL11A-4084 | − | UUCUCUUGCAACACGCA | 17 | 4569 |
| BCL11A-4085 | + | UGGACUUGACCGGGGC | 17 | 4570 |
| BCL11A-4086 | − | UCCCGGAGAACGGGAC | 17 | 4571 |
| BCL11A-4087 | + | CUGGAGUCUCCGAAGCU | 17 | 4572 |
| BCL11A-4088 | − | GAUUUCUCUAGGAGACU | 17 | 4573 |
| BCL11A-4089 | − | GGUUGAAUCCAAUGGCU | 17 | 4574 |
| BCL11A-4090 | − | CCCGGGCGAGUCGGCCU | 17 | 4575 |
| BCL11A-4091 | − | GAUCCCGGAGAACGGGG | 17 | 4576 |
| BCL11A-4092 | + | CUCGGUGGUGGACUAAA | 17 | 4577 |

TABLE 5E-continued

5th Tier

| gRNA Name | DNA Strand | Targeting Domain | Target Site Length | SEQ ID NO |
|---|---|---|---|---|
| BCL11A-4093 | + | UGGUGGACUAAACAGGG | 17 | 4578 |
| BCL11A-4094 | + | CCACCAAGUCGCUGGUG | 17 | 4579 |
| BCL11A-4095 | − | GGUGGCCAAGUUCAAGA | 17 | 4580 |
| BCL11A-4096 | − | CACCCGAGUGCCUUUGA | 17 | 4581 |
| BCL11A-4097 | − | GCAAGACGUUCAAAUUU | 17 | 4582 |
| BCL11A-4098 | + | GGCUCUCGAGCUUCCAU | 17 | 4583 |
| BCL11A-4099 | + | UGGAGUCUCCGAAGCUA | 17 | 4584 |
| BCL11A-4100 | − | CGGCCGCGAUGCCCAAC | 17 | 4585 |
| BCL11A-4101 | + | UCAAAGGCACUCGGGUG | 17 | 4586 |
| BCL11A-4102 | + | GGACUUGACCGGGGCU | 17 | 4587 |
| BCL11A-4103 | + | UUGGACUUGACCGGGGG | 17 | 4588 |
| BCL11A-4104 | + | GUCUGCCCUCUUUUGAG | 17 | 4589 |
| BCL11A-4105 | + | GGCAAAAGGCGAUUGUC | 17 | 4590 |
| BCL11A-4106 | − | ACACGCACAGAACACUC | 17 | 4591 |
| BCL11A-4107 | + | GUAACCUUUGCAUAGGG | 17 | 4592 |
| BCL11A-4108 | − | UGCACCGGCGCAGCCAC | 17 | 4593 |
| BCL11A-4109 | − | UGGCCAAGUUCAAGAGC | 17 | 4594 |
| BCL11A-4110 | − | UAAGCGCGGCCACCUGG | 17 | 4595 |
| BCL11A-4111 | + | CAUAGGGCUGGGCCGGC | 17 | 4596 |
| BCL11A-4112 | − | ACCUGAUCCCGGAGAAC | 17 | 4597 |
| BCL11A-4113 | − | UGUGUGGCAGUUUUCGG | 17 | 4598 |
| BCL11A-4114 | − | UUUUCGGAUGGAAGCUC | 17 | 4599 |
| BCL11A-4115 | − | CCCCGGGCGAGUCGGCC | 17 | 4600 |
| BCL11A-4116 | + | UGGACUACGGCUUCGGG | 17 | 4601 |
| BCL11A-4117 | − | CCCUUCAGGACUAGGUG | 17 | 4602 |
| BCL11A-4118 | − | UCGGGGCGCAGCGGCAC | 17 | 4603 |
| BCL11A-4119 | + | UCUUGAACUUGGCCACC | 17 | 4604 |
| BCL11A-4120 | − | CCGGCGCAGCCACACGG | 17 | 4605 |
| BCL11A-4121 | + | UCUCGCCCAGGACCUGG | 17 | 4606 |
| BCL11A-4122 | − | CGGAGAACGGGGACGAG | 17 | 4607 |
| BCL11A-4123 | + | CACCCUGUCAAAGGCAC | 17 | 4608 |
| BCL11A-4124 | + | UCUGCACCUAGUCCUGA | 17 | 4609 |
| BCL11A-4125 | − | UAACCUGCUAAGAAUAC | 17 | 4610 |
| BCL11A-4126 | − | UCUCCACCGCCAGCUCC | 17 | 4611 |
| BCL11A-4127 | − | CUCCACCGCCAGCUCCC | 17 | 4612 |
| BCL11A-4128 | + | UUCUGCCCAGGACCUG | 17 | 4613 |
| BCL11A-4129 | + | CCGCCUCCAGGCUCAGC | 17 | 4614 |
| BCL11A-4130 | + | UCCCUCCGUCCAGCUCC | 17 | 4615 |
| BCL11A-4131 | − | GAGGGUGGACUACGGCU | 17 | 4616 |
| BCL11A-4132 | + | CCAGCUCCCCGGGCGGU | 17 | 4617 |
| BCL11A-4133 | + | GCUCUCUAAGUCUCCUA | 17 | 4618 |
| BCL11A-4134 | + | CAUGACUUGGACUUGAC | 17 | 4619 |
| BCL11A-4135 | + | CCAUGCCCUGCAUGACG | 17 | 4620 |
| BCL11A-4136 | + | GCGAUUGUCUGGAGUCU | 17 | 4621 |
| BCL11A-4137 | + | UGGAGGCCGCGUAGCCG | 17 | 4622 |
| BCL11A-4138 | − | GCCACCUGGCCGAGGCC | 17 | 4623 |
| BCL11A-4139 | − | AUACCAGGAUCAGUAUC | 17 | 4624 |
| BCL11A-4140 | − | GUGUGGCAGUUUUCGGA | 17 | 4625 |
| BCL11A-4141 | − | CCACACCGCCCGGGGAG | 17 | 4626 |
| BCL11A-4142 | − | GGAGGCGGCGCGCCACC | 17 | 4627 |
| BCL11A-4143 | + | GUAUUCUUAGCAGGUUA | 17 | 4628 |
| BCL11A-4144 | + | AGAAGGGCUCAGCGAG | 17 | 4629 |
| BCL11A-4145 | + | UGUUCUGUGCGUGUUGC | 17 | 4630 |
| BCL11A-4146 | − | AACCCCUUUAACCUGCU | 17 | 4631 |
| BCL11A-4147 | + | GCGCCCUUCUGCCAGGC | 17 | 4632 |
| BCL11A-4148 | + | CAGCUCCCCGGGCGGUG | 17 | 4633 |
| BCL11A-4149 | + | GGCGGCUUGCUACCUGG | 17 | 4634 |
| BCL11A-4150 | + | AGCGCCCUUCUGCCAGG | 17 | 4635 |
| BCL11A-4151 | + | GCGGCUUGCUACCUGGC | 17 | 4636 |
| BCL11A-4152 | − | GGGGCGCGGUCGUGGGC | 17 | 4637 |
| BCL11A-4153 | − | AGGCCUUCCACCAGGUC | 17 | 4638 |
| BCL11A-4154 | + | UCCCGUGCCGCUGCGCC | 17 | 4639 |
| BCL11A-4155 | − | CAGAACACUCAUGGAUU | 17 | 4640 |
| BCL11A-4156 | + | GCUCCCCGGGCGGUGUG | 17 | 4641 |
| BCL11A-4157 | − | GCCCGGGGAGCUGGACG | 17 | 4642 |
| BCL11A-4158 | + | UUGCAGUAACCUUUGCA | 17 | 4643 |
| BCL11A-4159 | − | AGACUUAGAGAGCUGGC | 17 | 4644 |
| BCL11A-4160 | − | GGCGCAGCCACACGGGC | 17 | 4645 |
| BCL11A-4161 | + | UUCUGCACCUAGUCCUG | 17 | 4646 |
| BCL11A-4162 | + | UUCUGUGCGUGUUGCAA | 17 | 4647 |
| BCL11A-4163 | − | CCCUGGCCACCCAUCAC | 17 | 4648 |
| BCL11A-4164 | + | AUAGGGCUGGGCCGGCC | 17 | 4649 |
| BCL11A-4165 | − | ACCAGGAUCAGUAUCGA | 17 | 4650 |
| BCL11A-4166 | + | UGAAGGGAUACCAACCC | 17 | 4651 |

TABLE 5E-continued

5th Tier

| gRNA Name | DNA Strand | Targeting Domain | Target Site Length | SEQ ID NO |
|---|---|---|---|---|
| BCL11A-4167 | + | CUAGAGAAAUCCAUGGC | 17 | 4652 |
| BCL11A-4168 | + | CGGUGGAGAGACCGUCG | 17 | 4653 |
| BCL11A-4169 | − | UUUCUCUAGGAGACUUA | 17 | 4654 |
| BCL11A-4170 | + | GCAUGACUUGGACUUGA | 17 | 4655 |
| BCL11A-4171 | − | CUCGGGCGCAGCGGCA | 17 | 4656 |
| BCL11A-4172 | + | GGUGGACUAAACAGGGG | 17 | 4657 |
| BCL11A-4173 | + | CCUCGCUGAAGUGCUGC | 17 | 4658 |
| BCL11A-4174 | + | CCAGGUUGCUCUGAAAU | 17 | 4659 |
| BCL11A-4175 | − | GCAUAGAGCGCCUGGGG | 17 | 4660 |
| BCL11A-4176 | − | GCAAGCUGAAGCGCCAC | 17 | 4661 |
| BCL11A-4177 | + | CUCGCUGAAGUGCUGCA | 17 | 4662 |
| BCL11A-4178 | − | GCACCCAGGCCAGCAAG | 17 | 4663 |
| BCL11A-4179 | + | GGGAGGCUCCAUAGCCA | 17 | 4664 |
| BCL11A-4180 | + | AGGCAAAAGGCGAUUGU | 17 | 4665 |
| BCL11A-4181 | − | GAUCCCUUCCUUAGCUU | 17 | 4666 |
| BCL11A-4182 | + | GUCUCCGAAGCUAAGGA | 17 | 4667 |
| BCL11A-4183 | + | CUUAGAGAAGGGGCUCA | 17 | 4668 |
| BCL11A-4184 | + | CUUUUUGGACAGGCCCC | 17 | 4669 |
| BCL11A-4185 | + | CUCGGGUGAUGGGUGGC | 17 | 4670 |
| BCL11A-4186 | + | GCCCACGACCGCGCCCC | 17 | 4671 |
| BCL11A-4187 | + | UUGUACAUGUGUAGCUG | 17 | 4672 |
| BCL11A-4188 | − | CCGUGGUGGCCAAGUUC | 17 | 4673 |
| BCL11A-4189 | − | GGAGAACGGGGACGAGG | 17 | 4674 |
| BCL11A-4190 | − | GCAGGCCCAGCUCAAAA | 17 | 4675 |
| BCL11A-4191 | + | UAUUCUUAGCAGGUUAA | 17 | 4676 |
| BCL11A-4192 | + | UCUGCAAUAUGAAUCCC | 17 | 4677 |
| BCL11A-4193 | + | UCCUAGAGAAAUCCAUG | 17 | 4678 |
| BCL11A-4194 | + | ACUUGACCGGGGCUGG | 17 | 4679 |
| BCL11A-4195 | + | AGUCUCCGAAGCUAAGG | 17 | 4680 |
| BCL11A-4196 | + | GCUGGGCCUGCCCGGGC | 17 | 4681 |
| BCL11A-4197 | − | AGAUCCCUUCCUUAGCU | 17 | 4682 |
| BCL11A-4198 | + | CACACAUCUUGAGCUCU | 17 | 4683 |
| BCL11A-4199 | − | CCCGGGGAGCUGGACGG | 17 | 4684 |
| BCL11A-4200 | + | GAAGGGGCUCAGCGAGC | 17 | 4685 |
| BCL11A-4201 | − | GACUUAGAGAGCUGGCA | 17 | 4686 |
| BCL11A-4202 | + | UCCCAUGGAGAGGUGGC | 17 | 4687 |
| BCL11A-4203 | + | UGAAGUGCUGCAUGGAG | 17 | 4688 |
| BCL11A-4204 | + | ACAUUCUGCACCUAGUC | 17 | 4689 |
| BCL11A-4205 | + | CCCAUGGAGAGGUGGCU | 17 | 4690 |
| BCL11A-4206 | + | GCUCUCUGGGUACUACG | 17 | 4691 |
| BCL11A-4207 | − | CCACAGGGACACUUGCG | 17 | 4692 |
| BCL11A-4208 | − | GAGACUUAGAGAGCUGG | 17 | 4693 |
| BCL11A-4209 | − | UUGACAGGGUGCUGCGG | 17 | 4694 |
| BCL11A-4210 | − | CCGAGGCCGAGGGCCAC | 17 | 4695 |
| BCL11A-4211 | + | AGGGAUCUUUGAGCUGC | 17 | 4696 |
| BCL11A-4212 | + | AAGUAGAUUCUUAAUCC | 17 | 4697 |
| BCL11A-4213 | − | GCGCAGCGGCACGGGAA | 17 | 4698 |
| BCL11A-4214 | − | GCCGAGGCCGAGGGCCA | 17 | 4699 |
| BCL11A-4215 | − | AAGAUGUGUGGCAGUUU | 17 | 4700 |
| BCL11A-4216 | + | AGCUAAGGAAGGGAUCU | 17 | 4701 |
| BCL11A-4217 | + | CAGCUCUCUAAGUCUCC | 17 | 4702 |
| BCL11A-4218 | + | CCUAGAGAAAUCCAUGG | 17 | 4703 |
| BCL11A-4219 | − | ACCACGAGAACAGCUCG | 17 | 4704 |
| BCL11A-4220 | + | GCAAUAUGAAUCCCAUG | 17 | 4705 |
| BCL11A-4221 | − | CUCCAUGCAGCACUUCA | 17 | 4706 |
| BCL11A-4222 | − | UGUCCAAAAAGCUGCUG | 17 | 4707 |
| BCL11A-4223 | − | GAAUACCAGGAUCAGUA | 17 | 4708 |
| BCL11A-4224 | − | UCUCGGGCGCAGCGGC | 17 | 4709 |
| BCL11A-4225 | − | AGUUUCGGAUGGAAGC | 17 | 4710 |
| BCL11A-4226 | − | UCGUGGGCGUGGGCGAC | 17 | 4711 |
| BCL11A-4227 | + | UCGCGCCGGGGCAGG | 17 | 4712 |
| BCL11A-4228 | − | CUACUUAGAAAGCGAAC | 17 | 4713 |
| BCL11A-4229 | + | GGGUUAUUGUCUGCAAU | 17 | 4714 |
| BCL11A-4230 | + | CUUGACCGGGGCUGGG | 17 | 4715 |
| BCL11A-4231 | − | UGGAUUAAGAAUCUACU | 17 | 4716 |
| BCL11A-4232 | − | GGCUUCCGGCCUGGCAG | 17 | 4717 |
| BCL11A-4233 | − | CUUCCACCAGGUCCUGG | 17 | 4718 |
| BCL11A-4234 | + | CGCUUCAGCUUGCUGGC | 17 | 4719 |
| BCL11A-4235 | − | CAUAGAGCGCCUGGGGG | 17 | 4720 |
| BCL11A-4236 | + | CCUGGUGGAAGGCCUCG | 17 | 4721 |
| BCL11A-4237 | − | UCCACCAGGUCCUGGGC | 17 | 4722 |
| BCL11A-4238 | + | CUGCAAUAUGAAUCCCA | 17 | 4723 |
| BCL11A-4239 | − | GCUGGACGGAGGGAUCU | 17 | 4724 |
| BCL11A-4240 | + | UUGACCGGGGCUGGGA | 17 | 4725 |

TABLE 5E-continued

5th Tier

| gRNA Name | DNA Strand | Targeting Domain | Target Site Length | SEQ ID NO |
|---|---|---|---|---|
| BCL11A-4241 | - | UUCCCAGCCACCUCUCC | 17 | 4726 |
| BCL11A-4242 | + | UUUUGAGCUGGGCCUGC | 17 | 4727 |
| BCL11A-4243 | - | GCUUCUCCACACCGCCC | 17 | 4728 |
| BCL11A-4244 | + | AGAGAAACCAUGCACUG | 17 | 4729 |
| BCL11A-4245 | - | AGCUGGACGGAGGGAUC | 17 | 4730 |
| BCL11A-4246 | + | CCGGGGAGCUGGCGGUG | 17 | 4731 |
| BCL11A-4247 | + | AUCCCAUGGAGAGGUGG | 17 | 4732 |
| BCL11A-4248 | + | GUUCCGGGGAGCUGGCG | 17 | 4733 |
| BCL11A-4249 | + | GACUAAACAGGGGGGGA | 17 | 4734 |
| BCL11A-4250 | + | UGCCCAGCAGCAGCUUU | 17 | 4735 |
| BCL11A-4251 | + | GGGAUCUUUGAGCUGCC | 17 | 4736 |
| BCL11A-4252 | - | UCCCAGCCACCUCUCCA | 17 | 4737 |
| BCL11A-4253 | - | CAGCGGCACGGGAAGUG | 17 | 4738 |
| BCL11A-4254 | + | UUCCGGGGAGCUGGCGG | 17 | 4739 |
| BCL11A-4255 | + | UCCUCGUCCCCGUUCUC | 17 | 4740 |
| BCL11A-4256 | - | GCGGCACGGGAAGUGGA | 17 | 4741 |
| BCL11A-4257 | - | UGGGCAGCCCCAGCUCG | 17 | 4742 |
| BCL11A-4258 | - | CGCAGCGGCACGGGAAG | 17 | 4743 |
| BCL11A-4259 | - | CCGCCCGGGGAGCUGGA | 17 | 4744 |
| BCL11A-4260 | + | AUGGAGAGGUGGCUGGG | 17 | 4745 |
| BCL11A-4261 | + | CUCCUCGUCCCCGUUCU | 17 | 4746 |
| BCL11A-4262 | - | UACUUAGAAAGCGAACA | 17 | 4747 |
| BCL11A-4263 | - | GGGCAGGCCCAGCUCAA | 17 | 4748 |
| BCL11A-4264 | - | ACCGCCCGGGGAGCUGG | 17 | 4749 |
| BCL11A-4265 | + | AAACAGGGGGGGAGUGG | 17 | 4750 |
| BCL11A-4266 | + | CGGGGGCUGGGAGGGAG | 17 | 4751 |
| BCL11A-4267 | + | CCGGCCUGGGGACAGCG | 17 | 4752 |
| BCL11A-4268 | + | UAGGGCUGGGCCGGCCU | 17 | 4753 |
| BCL11A-4269 | - | AAGAAUCUACUUAGAAA | 17 | 4754 |
| BCL11A-4270 | + | AACAGGGGGGGAGUGGG | 17 | 4755 |
| BCL11A-4271 | + | ACCGGGGGCUGGGAGGG | 17 | 4756 |
| BCL11A-4272 | - | GGUCGUGGGCGUGGGCG | 17 | 4757 |
| BCL11A-4273 | + | GGAGGGGGGGCGUCGCC | 17 | 4758 |
| BCL11A-4274 | - | GAACGGGACGAGGAGG | 17 | 4759 |
| BCL11A-4275 | + | GACCGGGGGCUGGGAGG | 17 | 4760 |
| BCL11A-4276 | + | GGGAGGGGGGGCGUCGC | 17 | 4761 |
| BCL11A-4277 | + | GGGGGCUGGGAGGGAGG | 17 | 4762 |
| BCL11A-4278 | - | AGCGGCACGGGAAGUGG | 17 | 4763 |
| BCL11A-4279 | + | GAUUGCAGAGGAGGGAG | 17 | 4764 |
| BCL11A-4280 | + | GGGGGGGCGUCGCCAGG | 17 | 4765 |
| BCL11A-4281 | + | GGAUUGCAGAGGAGGGA | 17 | 4766 |
| BCL11A-4282 | + | GGGCGGAUUGCAGAGGA | 17 | 4767 |
| BCL11A-4283 | + | GCGGAUUGCAGAGGAGG | 17 | 4768 |
| BCL11A-4284 | - | GAGCUGACGGAGAGCGA | 17 | 4769 |
| BCL11A-4285 | + | GAAAACUGCCACACAUC | 17 | 4770 |
| BCL11A-4286 | + | AUUGCAGAGGAGGGAGG | 17 | 4771 |
| BCL11A-4287 | + | GGGGCGGAUUGCAGAGG | 17 | 4772 |
| BCL11A-4288 | + | CGGAUUGCAGAGGAGGG | 17 | 4773 |
| BCL11A-4289 | + | AGGGGCGGAUUGCAGAG | 17 | 4774 |
| BCL11A-4290 | - | ACGGGACGAGGAGGAA | 17 | 4775 |
| BCL11A-4291 | + | GGAGGAGGGGCGGAUUG | 17 | 4776 |
| BCL11A-4292 | - | CGCUUCUCCACACCGCC | 17 | 4777 |
| BCL11A-4293 | - | UGACGGAGAGCGAGAGG | 17 | 4778 |
| BCL11A-4294 | - | AGGAGCUGACGGAGAGC | 17 | 4779 |
| BCL11A-4295 | + | GCUGGGAGGGAGGAGGG | 17 | 4780 |
| BCL11A-4296 | + | AGGAGGGGCGGAUUGCA | 17 | 4781 |
| BCL11A-4297 | + | UGUUGGGCAUCGCGGCC | 17 | 4782 |
| BCL11A-4298 | - | CGGGGACGAGGAGGAAG | 17 | 4783 |
| BCL11A-4299 | + | GGAGGGGCGGAUUGCAG | 17 | 4784 |
| BCL11A-4300 | - | GGAGGAGCUGACGGAGA | 17 | 4785 |
| BCL11A-4301 | - | GGGACGAGGAGGAAGAG | 17 | 4786 |
| BCL11A-4302 | - | AGGAGGAGGAGCUGACG | 17 | 4787 |
| BCL11A-4303 | - | ACGAGGAAGAGGAAGAA | 17 | 4788 |
| BCL11A-4304 | - | AGGAAGAGGAAGAAGAG | 17 | 4789 |
| BCL11A-4305 | - | AGGAAGAGGAGGACGAC | 17 | 4790 |
| BCL11A-4306 | - | AGGAGGACGACGAGGAA | 17 | 4791 |
| BCL11A-4307 | - | GGAGGAGGAGGAGCUGA | 17 | 4792 |
| BCL11A-4308 | - | GGAAGAGGAGGACGACG | 17 | 4793 |
| BCL11A-4309 | - | GGAGGAAGAGGAGGACG | 17 | 4794 |
| BCL11A-4310 | - | GGAAGAGGAAGAAGAGG | 17 | 4795 |
| BCL11A-4311 | - | AGGAGGAGGAGGAGCUG | 17 | 4796 |
| BCL11A-4312 | - | CGAGGAAGAGGAAGAAG | 17 | 4797 |
| BCL11A-4313 | - | GGACGACGAGGAAGAGG | 17 | 4798 |
| BCL11A-4314 | - | GGAGGACGACGAGGAAG | 17 | 4799 |

TABLE 5E-continued

5th Tier

| gRNA Name | DNA Strand | Targeting Domain | Target Site Length | SEQ ID NO |
|---|---|---|---|---|
| BCL11A-4315 | - | CGACGAGGAAGAGGAAG | 17 | 4800 |
| BCL11A-4316 | - | AGAGGAGGACGACGAGG | 17 | 4801 |
| BCL11A-4317 | - | AAGAAGAGGAGGAAGAG | 17 | 4802 |
| BCL11A-4318 | - | AGGAAGAAGAGGAGGAA | 17 | 4803 |
| BCL11A-4319 | - | AGAGGAAGAAGAGGAGG | 17 | 4804 |
| BCL11A-4320 | - | AAGAGGAGGAAGAGGAG | 17 | 4805 |
| BCL11A-4321 | - | AGGAGGAAGAGGAGGAG | 17 | 4806 |
| BCL11A-4322 | - | GGAAGAAGAGGAGGAAG | 17 | 4807 |
| BCL11A-4323 | - | AGAAGAGGAGGAAGAGG | 17 | 4808 |
| BCL11A-4324 | - | AGAGGAGGAAGAGGAGG | 17 | 4809 |
| BCL11A-4325 | - | GGAGGAAGAGGAGGAGG | 17 | 4810 |

Table 6A provides exemplary targeting domains for knocking out the BCL11A gene by targeting the early coding sequence the BCL11A gene selected according to first tier parameters. The targeting domains bind within first 500 bp of coding sequence downstream of start codon, good orthogonality, start with G. It is contemplated herein that the targeting domain hybridizes to the target domain through complementary base pairing. Any of the targeting domains in the table can be used with a *N. meningitidis* Cas9 molecule that generates a double strand break (Cas9 nuclease) or a single-strand break (Cas9 nickase). In an embodiment, dual targeting is used to create two double strand breaks to remove the enhancer region in the BCL11A gene. e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *N. meningitidis* Cas9 (nickase) molecule to generate a single strand break. In an embodiment, dual targeting is used to create two nicks on opposite DNA strands by using *N. meningitidis* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 6A

1st Tier

| gRNA Name | DNA Strand | Targeting Domain | Target Site Length | SEQ ID NO |
|---|---|---|---|---|
| BCL11A-4326 | + | UUCUGCACUCAUCCCAGGCG | 20 | 4811 |
| BCL11A-4327 | - | AUCCAGGUCACGCCAGAGGA | 20 | 4812 |
| BCL11A-4328 | + | UGACCUGGAUGCCAACCUCC | 20 | 4813 |
| BCL11A-4329 | + | GGGAUUGGAUGCUUUUUUCA | 20 | 4814 |
| BCL11A-4330 | + | UGCACUCAUCCCAGGCG | 17 | 4815 |
| BCL11A-4331 | - | CAGGUCACGCCAGAGGA | 17 | 4816 |
| BCL11A-4332 | + | CCUGGAUGCCAACCUCC | 17 | 4817 |
| BCL11A-4333 | + | AUUGGAUGCUUUUUUCA | 17 | 4818 |

Table 6B provides exemplary targeting domains for knocking out the BCL11A gene by targeting the early coding sequence the BCL11A gene. The targeting domains target outside the first 500 bp of coding sequence downstream of start codon. It is contemplated herein that the targeting domain hybridizes to the target domain through complementary base pairing. Any of the targeting domains in the table can be used with a *N. meningitidis* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *N. meningitidis* Cas9 (nickase) molecule to generate a single strand break. In an embodiment, dual targeting is used to create two nicks on opposite DNA strands by using *N. meningitidis* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 6B

| gRNA Name | DNA Strand | Targeting Domain | Target Site Length | SEQ ID NO |
|---|---|---|---|---|
| BCL11A-4334 | - | GCUAUGGAGCCUCCCGC | 17 | 4819 |
| BCL11A-4335 | + | GACUUGACCGUCAUGGG | 17 | 4820 |
| BCL11A-4336 | + | UCCGACGAGGAGGCAAA | 17 | 4821 |
| BCL11A-4337 | + | CGGGAGGCUCCAUAGCC | 17 | 4822 |

TABLE 6B-continued

| gRNA Name | DNA Strand | Targeting Domain | Target Site Length | SEQ ID NO |
|---|---|---|---|---|
| BCL11A-4338 | + | UCCGUGUUCGCUUUCUA | 17 | 4823 |
| BCL11A-4339 | - | AACACGCACAGAACACU | 17 | 4824 |
| BCL11A-4340 | - | UUCCCAGCCACCUCUCC | 17 | 4825 |
| BCL11A-4341 | + | GGCUGGGAGGGAGGAGG | 17 | 4826 |
| BCL11A-4342 | + | UCGGACUUGACCGUCAUGGG | 20 | 4827 |
| BCL11A-4343 | - | AUGGCUAUGGAGCCUCCCGC | 20 | 4828 |
| BCL11A-4344 | + | UGCUCCGACGAGGAGGCAAA | 20 | 4829 |
| BCL11A-4345 | + | UGGCGGGAGGCUCCAUAGCC | 20 | 4830 |
| BCL11A-4346 | - | UGCAACACGCACAGAACACU | 20 | 4831 |
| BCL11A-4347 | + | ACUUCCGUGUUCGCUUUCUA | 20 | 4832 |
| BCL11A-4348 | - | UCCUUCCCAGCCACCUCUCC | 20 | 4833 |
| BCL11A-4349 | + | GGGGGCUGGGAGGGAGGAGG | 20 | 4834 | paired any gRNA comprising a plus strand targeting domain provided that the two gRNAs are oriented on the DNA such that PAMs face outward and the distance between the 5' ends of the gRNAs is 0-50 bp. Exemplary gRNA pairs are: BCL11A-5210 and BCL11A-5204, BCL11A-5211 and BCL11A-5204, BCL11A-5172 and BCL11A-5176, BCL11A-5172 and BCL11A-5186, BCL11A-5179 and BCL11A-5176, or BCL11A-5179 and BCL11A-5186.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene. For example, gRNA pairs that target upstream (i.e., 5') of the enhancer region in the BCL11A gene (e.g., BCL11A-5210 and BCL11A-5204, or BCL11A-5211 and BCL11A-5204) can be paired with gRNA pairs that target downstream (i.e., 3') of the enhancer region in the BCL11A gene (e.g., BCL11A-5172 and BCL11A-5176, BCL11A-5172 and BCL11A-5186, BCL11A-5179 and BCL11A-5176, or BCL11A-5179 and BCL11A-5186).

TABLE 7A

1st Tier

| gRNA Name | DNA Strand | Targeting Domain | Target Site Length | 5' or 3' of repeats | SEQ ID NO |
|---|---|---|---|---|---|
| BCL11A-5172 | + | GAAAAUACUUACUGUACUGC | 20 | 3' | 4835 |
| BCL11A-5173 | - | GAAAGCAGUGUAAGGCU | 17 | 5' | 4836 |
| BCL11A-5174 | - | GGCUGUUUUGGAAUGUAGAG | 20 | 5' | 4837 |
| BCL11A-5175 | + | GUGCUACUUAUACAAUUCAC | 20 | 3' | 4838 |

Table 7A provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be Table 7B provides exemplary targeting domains for removing (e.g., deleting) the enhancer region in the BCL11A gene selected according to second tier parameters. The targeting domains bind within a region 5' (51.5 to 51.7 kb downstream of transcription start site, TSS) or 3' (65.1 to 65.3 kb downstream of TSS) of enhancer, good orthogonality, and do not start with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. The table provides exemplary targeting domains for removing (e.g., deleting) the enhancer region in the BCL11A gene selected according to first tier parameters. The targeting domains bind within a region 5'

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 7B

2nd Tier

| gRNA Name | DNA Strand | Targeting Domain | Target Site Length | 5' or 3' of repeats | SEQ ID NO |
|---|---|---|---|---|---|
| BCL11A-5176 | − | AAACUAUUUACAGCCAUAAC | 20 | 3' | 4839 |
| BCL11A-5177 | + | AAAUACUUACUGUACUGCAG | 20 | 3' | 4840 |
| BCL11A-5178 | − | AACUAUUUACAGCCAUAACA | 20 | 3' | 4841 |
| BCL11A-5179 | + | AAUACUUACUGUACUGC | 17 | 3' | 4842 |
| BCL11A-5180 | + | ACAACUUGUGUUGCACU | 17 | 5' | 4843 |
| BCL11A-5181 | + | AUACUUACUGUACUGCA | 17 | 3' | 4844 |
| BCL11A-5182 | + | AUUCACUGGAAACCCUGUUA | 20 | 3' | 4845 |
| BCL11A-5183 | + | AUUUAAGACGGGAAAAC | 17 | 5' | 4846 |
| BCL11A-5184 | + | CACUGGAAACCCUGUUA | 17 | 3' | 4847 |
| BCL11A-5185 | + | CUACUUAUACAAUUCAC | 17 | 3' | 4848 |
| BCL11A-5186 | − | CUAUUUACAGCCAUAAC | 17 | 3' | 4849 |
| BCL11A-5187 | − | UAAGAAAGCAGUGUAAGGCU | 20 | 5' | 4850 |
| BCL11A-5188 | + | UACACAACUUGUGUUGCACU | 20 | 5' | 4851 |
| BCL11A-5189 | + | UACUGUACUGCAGGGGAAUU | 20 | 3' | 4852 |
| BCL11A-5190 | + | UACUUACUGUACUGCAG | 17 | 3' | 4853 |
| BCL11A-5191 | + | UGUACUGCAGGGGAAUU | 17 | 3' | 4854 |

(51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. pyogenes Cas9 (nickase) molecule to generate a single strand break. In an embodiment, dual targeting is used to create two nicks on opposite DNA strands by using S. pyogenes Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

Table 7C provides exemplary targeting domains for removing (e.g., deleting) the enhancer region in the BCL11A gene selected according to third tier parameters. The targeting domains bind within a region 5' (51.5 to 51.7 kb downstream of transcription start site, TSS) or 3' (65.1 to 65.3 kb downstream of TSS) of enhancer and start with G. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. pyogenes Cas9 (nickase) molecule to generate a single strand break. In an embodiment, dual targeting is used to create two nicks on opposite DNA strands by using S. pyogenes Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. The table provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. The table provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are

TABLE 7C

3rd Tier

| gRNA Name | DNA Strand | Targeting Domain | Target Site Length | 5' or 3' repeats | of SEQ ID NO |
|---|---|---|---|---|---|
| BCL11A-5192 | – | GAAUGUAGAGAGGCAGA | 17 | 5' | 4855 |
| BCL11A-5193 | – | GGAAUGUAGAGAGGCAG | 17 | 5' | 4856 |
| BCL11A-5194 | – | GUAAGUAUUUUCUUUCAUUG | 20 | 3' | 4857 |
| BCL11A-5195 | – | GUAAUUAAGAAAGCAGUGUA | 20 | 5' | 4858 |
| BCL11A-5196 | – | GUAUUUUCUUUCAUUGG | 17 | 3' | 4859 |

Table 7D provides exemplary targeting domains for removing (e.g., deleting) the enhancer region in the BCL11A gene selected according to forth tier parameters. The targeting domains bind within a region 5' (51.5 to 51.7 kb downstream of transcription start site, TSS) or 3' (65.1 to 65.3 kb downstream of TSS) of enhancer and do not start with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase). In an embodiment, dual targeting is used to create two double strand breaks to remove the enhancer complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 7D

4th Tier

| gRNA Name | DNA Strand | Targeting Domain | Target Site Length | 5' or 3' of repeats | SEQ ID NO |
|---|---|---|---|---|---|
| BCL11A-5197 | − | AAAAUAAUUAGAAUAAA | 17 | 5' | 4860 |
| BCL11A-5198 | + | AAAAUACUUACUGUACUGCA | 20 | 3' | 4861 |
| BCL11A-5199 | + | AAAAUUUAAGACGGGAAAAC | 20 | 5' | 4862 |
| BCL11A-5200 | − | AAGUAUUUCUUUCAUU | 17 | 3' | 4863 |
| BCL11A-5201 | − | AAUGUAGAGAGGCAGAG | 17 | 5' | 4864 |
| BCL11A-5202 | + | ACAUAAAAAUUUAAGAC | 17 | 5' | 4865 |
| BCL11A-5203 | − | AGAAAGCAGUGUAAGGC | 17 | 5' | 4866 |
| BCL11A-5204 | − | AGAAUAAAAGGCUGUUU | 17 | 5' | 4867 |
| BCL11A-5205 | − | AGUAAAAUAAUUAGAAUAAA | 20 | 5' | 4868 |
| BCL11A-5206 | − | AGUAAGUAUUUCUUUCAUU | 20 | 3' | 4869 |
| BCL11A-5207 | − | AGUAUUUCUUUCAUUG | 17 | 3' | 4870 |
| BCL11A-5208 | − | AUUAAGAAAGCAGUGUA | 17 | 5' | 4871 |
| BCL11A-5209 | − | AUUAGAAUAAAAGGCUGUUU | 20 | 5' | 4872 |
| BCL11A-5210 | + | AUUAUUUUACUAGUGAAUUA | 20 | 5' | 4873 |
| BCL11A-5211 | + | AUUUUACUAGUGAAUUA | 17 | 5' | 4874 |
| BCL11A-5212 | + | CACAUAAAAAUUUAAGA | 17 | 5' | 4875 |
| BCL11A-5213 | − | CAGUAAGUAUUUCUUUCAU | 20 | 3' | 4876 |
| BCL11A-5214 | + | CUCACAUAAAAAUUUAAGAC | 20 | 5' | 4877 |
| BCL11A-5215 | − | UAAGUAUUUCUUUCAU | 17 | 3' | 4878 |
| BCL11A-5216 | − | UAAGUAUUUCUUUCAUUGG | 20 | 3' | 4879 |
| BCL11A-5217 | − | UAUUUACAGCCAUAACA | 17 | 3' | 4880 |
| BCL11A-5218 | + | UCUCACAUAAAAAUUUAAGA | 20 | 5' | 4881 |
| BCL11A-5219 | − | UGGAAUGUAGAGAGGCAGAG | 20 | 5' | 4882 |
| BCL11A-5220 | − | UGUUUUGGAAUGUAGAG | 17 | 5' | 4883 |
| BCL11A-5221 | − | UUAAGAAAGCAGUGUAAGGC | 20 | 5' | 4884 |
| BCL11A-5222 | − | UUGGAAUGUAGAGAGGCAGA | 20 | 5' | 4885 |
| BCL11A-5223 | − | UUUGGAAUGUAGAGAGGCAG | 20 | 5' | 4886 |

Table 8A provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 8A

1st Tier

| gRNA Name | DNA Strand | Targeting Domain | Target Site Length | 5' or 3' of repeats | SEQ ID NO |
|---|---|---|---|---|---|
| BCL11A-5224 | − | GAGGGGCUGAUAUAACUUCU | 20 | 5' | 4887 |
| BCL11A-5225 | + | GCUACUUAUACAAUUCA | 17 | 3' | 4888 |
| BCL11A-5226 | − | GGGCUGAUAUAACUUCU | 17 | 5' | 4889 |
| BCL11A-5227 | − | GUCUUAAAUUUUUAUGUGAG | 20 | 5' | 4890 |
| BCL11A-5228 | + | GUGCUACUUAUACAAUUCAC | 20 | 3' | 4891 |

Table 8B provides exemplary targeting domains for removing (e.g., deleting) the enhancer region in the BCL11A gene selected according to second tier parameters. The targeting domains bind within a region 5' (51.5 to 51.7 kb downstream of transcription start site, TSS) or 3' (65.1 to 65.3 kb downstream of TSS) of enhancer, good orthogonality, and do not start with G. It is contemplated herein that the targeting domain hybridizes to the target domain through complementary base pairing. Any of the targeting domains in the table can be used with a *S. aureus* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. aureus* Cas9 (nickase) molecule to generate a single strand break. In an embodiment, dual targeting is used to create two nicks on opposite DNA strands by using *S. aureus* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. The table provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a *S. aureus* Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a *S. aureus* Cas9 (nickase) molecule to generate a single strand break. In an embodiment, dual targeting is used to create two nicks on opposite DNA strands by using *S. aureus* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 8B

2nd Tier

| gRNA Name | DNA Strand | Targeting Domain | Target Site Length | 5' or 3' of repeats | SEQ ID NO |
|---|---|---|---|---|---|
| BCL11A-5229 | − | AACACAAGUUGUGUAGA | 17 | 5' | 4892 |
| BCL11A-5230 | − | ACUAUUUACAGCCAUAA | 17 | 3' | 4893 |
| BCL11A-5231 | − | AGCACACUGCUGUAAUU | 17 | 5' | 4894 |
| BCL11A-5232 | + | AGUGCUACUUAUACAAUUCA | 20 | 3' | 4895 |
| BCL11A-5233 | + | AUAGUUUGCUUCCCCCA | 17 | 3' | 4896 |

TABLE 8B-continued

2nd Tier

| gRNA Name | DNA Strand | Targeting Domain | Target Site Length | 5' or 3' of repeats | SEQ ID NO |
|---|---|---|---|---|---|
| BCL11A-5234 | − | AUGAGCACACUGCUGUAAUU | 20 | 5' | 4897 |
| BCL11A-5235 | − | CAAACUAUUUACAGCCAUAA | 20 | 3' | 4898 |
| BCL11A-5236 | − | CAGCCAUAACAGGGUUUCCA | 20 | 3' | 4899 |
| BCL11A-5237 | − | CCAUAACAGGGUUUCCA | 17 | 3' | 4900 |
| BCL11A-5238 | + | CUACUUAUACAAUUCAC | 17 | 3' | 4901 |
| BCL11A-5239 | − | CUUUGGCUAUUGAUACUGAU | 20 | 3' | 4902 |
| BCL11A-5240 | + | UAAAUAGUUUGCUUCCCCCA | 20 | 3' | 4903 |
| BCL11A-5241 | + | UAGUUUGCUUCCCCCAAUGA | 20 | 3' | 4904 |
| BCL11A-5242 | − | UGCAACACAAGUUGUGUAGA | 20 | 5' | 4905 |
| BCL11A-5243 | − | UGGAAUGUAGAGAGGCA | 17 | 5' | 4906 |
| BCL11A-5244 | − | UGGCUAUUGAUACUGAU | 17 | 3' | 4907 |
| BCL11A-5245 | + | UUUGCUUCCCCCAAUGA | 17 | 3' | 4908 |
| BCL11A-5246 | − | UUUUGGAAUGUAGAGAGGCA | 20 | 5' | 4909 |

Table 8C provides exemplary targeting domains for removing (e.g., deleting) the enhancer region in the BCL11A gene selected according to third tier parameters. The targeting domains bind within a region 5' (51.5 to 51.7 kb downstream of transcription start site, TSS) or 3' (65.1 to 65.3 kb downstream of TSS) of enhancer and start with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. The table provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 8C

3rd Tier

| gRNA Name | DNA Strand | Targeting Domain | Target Site Length | 5' or 3' of repeats | SEQ ID NO |
|---|---|---|---|---|---|
| BCL11A-5247 | + | GAAAAUACUUACUGUACUGC | 20 | 3' | 4910 |
| BCL11A-5248 | − | GAAUUGUAUAAGUAGCA | 17 | 3' | 4911 |
| BCL11A-5249 | − | GAGUUCUGUGUCAGCAAAAA | 20 | 3' | 4912 |
| BCL11A-5250 | + | GGAAAACAGGAAGAUGCAUU | 20 | 5' | 4913 |
| BCL11A-5251 | − | GGAAUGUAGAGAGGCAG | 17 | 5' | 4914 |
| BCL11A-5252 | − | GGCUGUUUUGGAAUGUA | 17 | 5' | 4915 |
| BCL11A-5253 | − | GUAAGUAUUUUCUUUCA | 17 | 3' | 4916 |
| BCL11A-5254 | − | GUAAGUAUUUUCUUUCAUUG | 20 | 3' | 4917 |
| BCL11A-5255 | − | GUAUUUUCUUUCAUUGG | 17 | 3' | 4918 |

Table 8D provides exemplary targeting domains for removing (e.g., deleting) the enhancer region in the BCL11A gene selected according to forth tier parameters. The targeting domains bind within a region 5' (51.5 to 51.7 kb downstream of transcription start site, TSS) or 3' (65.1 to 65.3 kb downstream of TSS) of enhancer and do not start with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. The table provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 8D

4th Tier

| gRNA Name | DNA Strand | Targeting Domain | Target Site Length | 5' or 3' of repeats | SEQ ID NO |
|---|---|---|---|---|---|
| BCL11A-5256 | + | AAAAAUUUAAGACGGGAAAA | 20 | 5' | 4919 |
| BCL11A-5257 | + | AAAACAGGAAGAUGCAUUCU | 20 | 5' | 4920 |
| BCL11A-5258 | − | AAAACUAGAAAGUUUUA | 17 | 3' | 4921 |

TABLE 8D-continued

4th Tier

| gRNA Name | DNA Strand | Targeting Domain | Target Site Length | 5' or 3' of repeats | SEQ ID NO |
|---|---|---|---|---|---|
| BCL11A-5259 | + | AAAAUACUUACUGUACUGCA | 20 | 3' | 4922 |
| BCL11A-5260 | + | AAAAUUUAAGACGGGAAAAC | 20 | 5' | 4923 |
| BCL11A-5261 | + | AAACAGGAAGAUGCAUU | 17 | 5' | 4924 |
| BCL11A-5262 | − | AAAGGCUGUUUUGGAAUGUA | 20 | 5' | 4925 |
| BCL11A-5263 | + | AAAUACUUACUGUACUG | 17 | 3' | 4926 |
| BCL11A-5264 | + | AAAUACUUACUGUACUGCAG | 20 | 3' | 4927 |
| BCL11A-5265 | − | AAGAAAGCAGUGUAAGG | 17 | 5' | 4928 |
| BCL11A-5266 | − | AAGGCUGUUUUGGAAUG | 17 | 5' | 4929 |
| BCL11A-5267 | − | AAGUAUUUUCUUUCAUU | 17 | 3' | 4930 |
| BCL11A-5268 | + | AAUACUUACUGUACUGC | 17 | 3' | 4931 |
| BCL11A-5269 | − | AAUUAGAAUAAAAGGCUGUU | 20 | 5' | 4932 |
| BCL11A-5270 | + | AAUUAUUUUACUAGUGAAUU | 20 | 5' | 4933 |
| BCL11A-5271 | + | AAUUUAAGACGGGAAAA | 17 | 5' | 4934 |
| BCL11A-5272 | + | ACAGGAAGAUGCAUUCU | 17 | 5' | 4935 |
| BCL11A-5273 | − | ACAGUAAGUAUUUUCUUUCA | 20 | 3' | 4936 |
| BCL11A-5274 | + | ACAUAAAAAUUUAAGAC | 17 | 5' | 4937 |
| BCL11A-5275 | + | ACUUUCUAGUUUUGCUUAAC | 20 | 3' | 4938 |
| BCL11A-5276 | + | AGAAAAUACUUACUGUACUG | 20 | 3' | 4939 |
| BCL11A-5277 | − | AGAAUAAAAGGCUGUUU | 17 | 5' | 4940 |
| BCL11A-5278 | − | AGCAAAACUAGAAAGUUUUA | 20 | 3' | 4941 |
| BCL11A-5279 | − | AGUAAGUAUUUUCUUUCAUU | 20 | 3' | 4942 |
| BCL11A-5280 | − | AGUAUUUUCUUUCAUUG | 17 | 3' | 4943 |
| BCL11A-5281 | − | AGUGAAUUGUAUAAGUAGCA | 20 | 3' | 4944 |
| BCL11A-5282 | + | AUACUUACUGUACUGCA | 17 | 3' | 4945 |
| BCL11A-5283 | + | AUCUCACAUAAAAAUUUAAG | 20 | 5' | 4946 |
| BCL11A-5284 | − | AUUAAGAAAGCAGUGUAAGG | 20 | 5' | 4947 |
| BCL11A-5285 | − | AUUAGAAUAAAAGGCUGUUU | 20 | 5' | 4948 |
| BCL11A-5286 | + | AUUAUUUUACUAGUGAAUUA | 20 | 5' | 4949 |
| BCL11A-5287 | + | AUUUAAGACGGGAAAAC | 17 | 5' | 4950 |
| BCL11A-5288 | + | AUUUUACUAGUGAAUUA | 17 | 5' | 4951 |
| BCL11A-5289 | − | AUUUUCAUGUUAAGCAAAAC | 20 | 3' | 4952 |
| BCL11A-5290 | + | CACAUAAAAAUUUAAGA | 17 | 5' | 4953 |
| BCL11A-5291 | − | CAGUAAGUAUUUUCUUUCAU | 20 | 3' | 4954 |
| BCL11A-5292 | − | CCGUCUUAAAUUUUUAU | 17 | 5' | 4955 |
| BCL11A-5293 | + | CUCACAUAAAAAUUUAAGAC | 20 | 5' | 4956 |
| BCL11A-5294 | − | UAAAAGGCUGUUUUGGAAUG | 20 | 5' | 4957 |
| BCL11A-5295 | − | UAAGUAUUUUCUUUCAU | 17 | 3' | 4958 |

TABLE 8D-continued

4th Tier

| gRNA Name | DNA Strand | Targeting Domain | Target Site Length | 5' or 3' of repeats | SEQ ID NO |
|---|---|---|---|---|---|
| BCL11A-5296 | − | UAAGUAUUUCUUUCAUUGG | 20 | 3' | 4959 |
| BCL11A-5297 | − | UAAUUCACUAGUAAAAUAAU | 20 | 5' | 4960 |
| BCL11A-5298 | + | UACUUACUGUACUGCAG | 17 | 3' | 4961 |
| BCL11A-5299 | − | UAGAAUAAAAGGCUGUU | 17 | 5' | 4962 |
| BCL11A-5300 | + | UAUUUUACUAGUGAAUU | 17 | 5' | 4963 |
| BCL11A-5301 | + | UCACAUAAAAAUUUAAG | 17 | 5' | 4964 |
| BCL11A-5302 | + | UCUCACAUAAAAAUUUAAGA | 20 | 5' | 4965 |
| BCL11A-5303 | + | UGUUUCAUUUUUUGCUGACA | 20 | 3' | 4966 |
| BCL11A-5304 | − | UGUUUUGGAAUGUAGAGAGG | 20 | 5' | 4967 |
| BCL11A-5305 | − | UUAAAUUUUUAUGUGAG | 17 | 5' | 4968 |
| BCL11A-5306 | + | UUAUUCUAAUUAUUUUACUA | 20 | 5' | 4969 |
| BCL11A-5307 | − | UUCACUAGUAAAAUAAU | 17 | 5' | 4970 |
| BCL11A-5308 | − | UUCAUGUUAAGCAAAAC | 17 | 3' | 4971 |
| BCL11A-5309 | + | UUCAUUUUUUGCUGACA | 17 | 3' | 4972 |
| BCL11A-5310 | − | UUCCCGUCUUAAAUUUUUAU | 20 | 5' | 4973 |
| BCL11A-5311 | + | UUCUAAUUAUUUUACUA | 17 | 5' | 4974 |
| BCL11A-5312 | + | UUCUAGUUUUGCUUAAC | 17 | 3' | 4975 |
| BCL11A-5313 | − | UUCUGUGUCAGCAAAAA | 17 | 3' | 4976 |
| BCL11A-5314 | − | UUUGGAAUGUAGAGAGG | 17 | 5' | 4977 |
| BCL11A-5315 | − | UUUGGAAUGUAGAGAGGCAG | 20 | 5' | 4978 |

Table 9 provides exemplary targeting domains for removing (e.g., deleting) the enhancer region in the BCL11A gene selected according to first tier parameters. The targeting domains bind within a region 5' (51.5 to 51.7 kb downstream of transcription start site, TSS) or 3' (65.1 to 65.3 kb downstream of TSS) of enhancer, good orthogonality, starts with G. It is contemplated herein that the targeting domain hybridizes to the target domain through complementary base pairing. Any of the targeting domains in the table can be used with a N. meningitidis Cas9 molecule that generates a double strand break (Cas9 nuclease) or a single-strand break (Cas9 nickase). In an embodiment, dual targeting is used to create two double strand breaks to remove the enhancer region in the BCL11A gene, e.g., the first gRNA is used to target upstream (i.e., 5') of the enhancer region in the BCL11A gene and the second gRNA is used to target downstream (i.e., 3') of the enhancer region in the BCL11A gene.

Any of the targeting domains in the table can be used with a N. meningitidis Cas9 (nickase) molecule to generate a single strand break. In an embodiment, dual targeting is used to create two nicks on opposite DNA strands by using N. meningitidis Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

In an embodiment, four gRNAs (e.g., two pairs) are used to target four Cas9 nickases to create four nicks to remove the enhancer region in the BCL11A gene, e.g., the first pair of gRNAs are used to target upstream (i.e., 5') of the enhancer region in the BCL11A gene and the second pair of gRNAs are used to target downstream (i.e., 3') of the enhancer region in the BCL11A gene.

TABLE 9

1st Tier

| gRNA Name | DNA Strand | Targeting Domain | Target Site Length | 5' or 3' of repeats | SEQ ID NO |
|---|---|---|---|---|---|
| BCL11A-5316 | − | UUUGGAUCUUUGGCUAUUGA | 20 | 3' | 4979 |
| BCL11A-5317 | − | GGAUCUUUGGCUAUUGA | 17 | 3' | 4980 |

Table 10A provides exemplary targeting domains for knocking down expression of the BCL11A gene according to first tier parameters. The targeting domains bind between 500 bp upstream and 500 bp downstream of transcription start site, good orthogonality, starts with G. It is contemplated herein that the targeting domain hybridizes to the target domain through complementary base pairing. Any of the targeting domains in the table can be used with a S. pyogenes eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a S. pyogenes eiCas9 fused to a transcriptional repressor to decrease transcription and therefore downregulate gene expression.

TABLE 10A

1st Tier

| gRNA Name | DNA Strand | Targeting Domain | Target Site Length | SEQ ID NO |
|---|---|---|---|---|
| BCL11A-4350 | + | GACGACGGCUCGGUUCACAU | 20 | 4981 |
| BCL11A-4351 | + | GACGCCAGACGCGGCCCCG | 20 | 4982 |
| BCL11A-4352 | + | GCCUUGCUUGCGGCGAGACA | 20 | 4983 |
| BCL11A-4353 | + | GGCUCCGCGGACGCCAGACG | 20 | 4984 |
| BCL11A-4354 | + | GACGGCUCGGUUCACAU | 17 | 4985 |
| BCL11A-4355 | − | GCCGCGUCUGGCGUCCG | 17 | 4986 |
| BCL11A-4356 | + | GCGGGCGGACGACGGCU | 17 | 4987 |

Table 10B provides exemplary targeting domains for knocking down expression of the BCL11A gene according to second tier parameters. The targeting domains bind between 500 bp upstream and 500 bp downstream of transcription start site, good orthogonality and do not start with G. It is contemplated herein that the targeting domain hybridizes to the target domain through complementary base pairing. Any of the targeting domains in the table can be used with a S. pyogenes eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a S. pyogenes eiCas9 fused to a transcriptional repressor to decrease transcription and therefore downregulate gene expression.

TABLE 10B

2nd Tier

| gRNA Name | DNA Strand | Targeting Domain | Target Site Length | SEQ ID NO |
|---|---|---|---|---|
| BCL11A-4357 | + | ACACGGCAAUGGUUCCAGAU | 20 | 4988 |
| BCL11A-4358 | − | ACCAUGUCUCGCCGCAAGCA | 20 | 4989 |
| BCL11A-4359 | + | ACGACGGCUCGGUUCACAUC | 20 | 4990 |
| BCL11A-4360 | + | AUUCCCGUUUGCUUAAGUGC | 20 | 4991 |
| BCL11A-4361 | − | CAUUUUAGAGUCCGCGUGUG | 20 | 4992 |
| BCL11A-4362 | + | CGGACGCCAGACGCGGCCCC | 20 | 4993 |
| BCL11A-4363 | + | CGGUUCACAUCGGGAGAGCC | 20 | 4994 |
| BCL11A-4364 | − | CUCCUGACGUUCAAGUUCGC | 20 | 4995 |
| BCL11A-4365 | − | UAAUAAUCACGAGAGCGCGC | 20 | 4996 |
| BCL11A-4366 | − | UCCUGACGUUCAAGUUCGCA | 20 | 4997 |
| BCL11A-4367 | + | UCGGUUCACAUCGGGAGAGC | 20 | 4998 |
| BCL11A-4368 | + | UCUUUUACCUCGACUCUCGG | 20 | 4999 |
| BCL11A-4369 | + | UGCUUGCGGCGAGACAUGGU | 20 | 5000 |
| BCL11A-4370 | − | UUUAGAGUCCGCGUGUGUGG | 20 | 5001 |
| BCL11A-4371 | + | ACGGCUCGGUUCACAUC | 17 | 5002 |
| BCL11A-4372 | − | AUGUCUCGCCGCAAGCA | 17 | 5003 |
| BCL11A-4373 | − | CUGACGUUCAAGUUCGC | 17 | 5004 |
| BCL11A-4374 | − | UAAUCACGAGAGCGCGC | 17 | 5005 |
| BCL11A-4375 | + | UCCGCGGACGCCAGACG | 17 | 5006 |
| BCL11A-4376 | − | UGACGUUCAAGUUCGCA | 17 | 5007 |
| BCL11A-4377 | − | UUAGAGUCCGCGUGUGU | 17 | 5008 |
| BCL11A-4378 | + | UUGCGGCGAGACAUGGU | 17 | 5009 |
| BCL11A-4379 | + | UUGCUUGCGGCGAGACA | 17 | 5010 |
| BCL11A-4380 | + | UUUACCUCGACUCUCGG | 17 | 5011 |
| BCL11A-4381 | − | UUUAGAGUCCGCGUGUG | 17 | 5012 |

Table 10C provides exemplary targeting domains for knocking down expression of the BCL11A gene according to third tier parameters. The targeting domains bind between 500 bp upstream and 500 bp downstream of transcription start site and start with G. It is contemplated herein that the targeting domain hybridizes to the target domain through complementary base pairing. Any of the targeting domains in the table can be used with a S. pyogenes eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a *S. pyogenes* eiCas9 fused to a transcriptional repressor to decrease transcription and therefore downregulate gene expression.

TABLE 10C

3rd Tier

| gRNA Name | DNA Strand | Targeting Domain | Target Site Length | SEQ ID NO |
|---|---|---|---|---|
| BCL11A-4382 | − | GAAAAAACCCUCAUCCCAUC | 20 | 5013 |
| BCL11A-4383 | + | GAAAGGGGUGGCAGGGG | 17 | 5014 |
| BCL11A-4384 | + | GAACUUGAACGUCAGGAGUC | 20 | 5015 |
| BCL11A-4385 | − | GAACUUGCAGCUCAGGG | 17 | 5016 |
| BCL11A-4386 | + | GAAGAAAGGGGUGGCAG | 17 | 5017 |
| BCL11A-4387 | + | GAAGAAAGGGGUGGCAGGGG | 20 | 5018 |
| BCL11A-4388 | + | GAAGGGGAAGCUCACACCAA | 20 | 5019 |
| BCL11A-4389 | + | GAAGGGGAGGAGGGAAG | 17 | 5020 |
| BCL11A-4390 | + | GAAUUGUGGGAGAGCCGUCA | 20 | 5021 |
| BCL11A-4391 | + | GACAAGCCAAUGGCCAGUGC | 20 | 5022 |
| BCL11A-4392 | + | GACAGAGACACACAAAACAU | 20 | 5023 |
| BCL11A-4393 | + | GACAUGAAAAAGAGACC | 17 | 5024 |
| BCL11A-4394 | + | GACAUGGUGGGCUGCGGGGC | 20 | 5025 |
| BCL11A-4395 | + | GACGCGGCCCCCGGGGG | 17 | 5026 |
| BCL11A-4396 | − | GACUAGAAGCAAAAGCG | 17 | 5027 |
| BCL11A-4397 | − | GACUAGAAGCAAAAGCGAGG | 20 | 5028 |
| BCL11A-4398 | + | GAGAAGAAAGGGGUGGC | 17 | 5029 |
| BCL11A-4399 | + | GAGAAGGGGAGGAGGGA | 17 | 5030 |
| BCL11A-4400 | + | GAGACACACAAAACAUGGGC | 20 | 5031 |
| BCL11A-4401 | + | GAGACAUGGUGGGCUGC | 17 | 5032 |
| BCL11A-4402 | + | GAGAGAAGAAAGGGGUGGCA | 20 | 5033 |
| BCL11A-4403 | + | GAGAGAAGAGAGAUAGA | 17 | 5034 |
| BCL11A-4404 | + | GAGAGAAGGGGAGGAGGGAA | 20 | 5035 |
| BCL11A-4405 | + | GAGAGAGAGAAGAGAGAUAG | 20 | 5036 |
| BCL11A-4406 | + | GAGAGAGAUGAAAAAAA | 17 | 5037 |
| BCL11A-4407 | + | GAGCAGGAGAGAAGGGG | 17 | 5038 |
| BCL11A-4408 | + | GAGCAGGAGAGAAGGGGAGG | 20 | 5039 |
| BCL11A-4409 | + | GAGCCGGGUUAGAAAGA | 17 | 5040 |
| BCL11A-4410 | + | GAGGGGAGGGGCGCUG | 17 | 5041 |
| BCL11A-4411 | + | GAGGGGCGGGCCGAGGGGAG | 20 | 5042 |
| BCL11A-4412 | + | GAGGGGAGGUGCGGGG | 17 | 5043 |
| BCL11A-4413 | + | GAGGGGAGGUGCGGGCGG | 20 | 5044 |

TABLE 10C-continued

3rd Tier

| gRNA Name | DNA Strand | Targeting Domain | Target Site Length | SEQ ID NO |
|---|---|---|---|---|
| BCL11A-4414 | − | GAGGUAAAAGAGAUAAA | 17 | 5045 |
| BCL11A-4415 | − | GAGUCCGCGUGUGUGGG | 17 | 5046 |
| BCL11A-4416 | − | GAGUCUCCUUCUUUCUAACC | 20 | 5047 |
| BCL11A-4417 | − | GAUGAAGAUAUUUUCUC | 17 | 5048 |
| BCL11A-4418 | − | GCAAAAGCGAGGGGGAGAGA | 20 | 5049 |
| BCL11A-4419 | − | GCACCUCCCCCUCCCCGCAC | 20 | 5050 |
| BCL11A-4420 | − | GCACUUGAACUUGCAGCUCA | 20 | 5051 |
| BCL11A-4421 | + | GCAGGGAAGAUGAAUUG | 17 | 5052 |
| BCL11A-4422 | + | GCAGGGCGAGCAGGAGAGAA | 20 | 5053 |
| BCL11A-4423 | + | GCAGGGGUGGGAGGAAA | 17 | 5054 |
| BCL11A-4424 | + | GCAGGGGUGGGAGGAAAGGG | 20 | 5055 |
| BCL11A-4425 | + | GCCAAUGGCCAGUGCGGGGA | 20 | 5056 |
| BCL11A-4426 | − | GCCACCCCUUUCUUCUCUCC | 20 | 5057 |
| BCL11A-4427 | + | GCCAGACGCGGCCCCCG | 17 | 5058 |
| BCL11A-4428 | − | GCCCCAGCGCCCCCUCCCCU | 20 | 5059 |
| BCL11A-4429 | + | GCCCCCGGGGAGGGGC | 17 | 5060 |
| BCL11A-4430 | − | GCCCGCCCCUCCCCCGG | 17 | 5061 |
| BCL11A-4431 | + | GCCGAGGGGAGGGGCGCUG | 20 | 5062 |
| BCL11A-4432 | + | GCCGCGGCGGUGGCGUGGCC | 20 | 5063 |
| BCL11A-4433 | + | GCCGGGAGAGAAGAAAG | 17 | 5064 |
| BCL11A-4434 | + | GCCGGGAGAGAAGAAAGGGG | 20 | 5065 |
| BCL11A-4435 | + | GCGAGACAUGGUGGGCUGCG | 20 | 5066 |
| BCL11A-4436 | + | GCGCAGGGAAGAUGAAUUGU | 20 | 5067 |
| BCL11A-4437 | + | GCGCCGCGGCGGUGGCG | 17 | 5068 |
| BCL11A-4438 | − | GCGCUCGCUGCGGCCAC | 17 | 5069 |
| BCL11A-4439 | + | GCGGCCCCGGGGAGGGGC | 20 | 5070 |
| BCL11A-4440 | − | GCGGCGCUCGCUGCGGCCAC | 20 | 5071 |
| BCL11A-4441 | + | GCGGCGGCGGCGGCGGC | 17 | 5072 |
| BCL11A-4442 | + | GCGGCGGCGGCGGCGGCGGC | 20 | 5073 |
| BCL11A-4443 | + | GCGGCGGCGGCGGCGGCGGG | 20 | 5074 |
| BCL11A-4444 | + | GCGGCGGCGGCGGCGGG | 17 | 5075 |
| BCL11A-4445 | + | GCGGCGGGCGGACGACGGCU | 20 | 5076 |
| BCL11A-4446 | + | GCGGCGGUGGCGUGGCC | 17 | 5077 |
| BCL11A-4447 | + | GCGGGCGGCGGCGGCGG | 17 | 5078 |
| BCL11A-4448 | + | GCGGGCGGCGGCGGCGGCGG | 20 | 5079 |
| BCL11A-4449 | + | GCGGGAGGGGAGGUG | 17 | 5080 |
| BCL11A-4450 | + | GCGUGGCCGGGAGAGAAGAA | 20 | 5081 |

TABLE 10C-continued

3rd Tier

| gRNA Name | DNA Strand | Targeting Domain | Target Site Length | SEQ ID NO |
|---|---|---|---|---|
| BCL11A-4451 | + | GCUCCCCCCACACACG | 17 | 5082 |
| BCL11A-4452 | + | GCUGGGGUUUGCCUUGCUUG | 20 | 5083 |
| BCL11A-4453 | + | GGACAAGCCAAUGGCCAGUG | 20 | 5084 |
| BCL11A-4454 | + | GGACACACAUCAGGGGC | 17 | 5085 |
| BCL11A-4455 | + | GGACAGAGACACACAAAACA | 20 | 5086 |
| BCL11A-4456 | + | GGACGCCAGACGCGGCCCCC | 20 | 5087 |
| BCL11A-4457 | − | GGACUAGAAGCAAAAGCGAG | 20 | 5088 |
| BCL11A-4458 | + | GGAGAGAAGAAAGGGGUGGC | 20 | 5089 |
| BCL11A-4459 | + | GGAGAGAAGGGAGGAGGGA | 20 | 5090 |
| BCL11A-4460 | + | GGAGAGCCGGGUUAGAAAGA | 20 | 5091 |
| BCL11A-4461 | + | GGAGGGGCGGGCCGAGGGA | 20 | 5092 |
| BCL11A-4462 | + | GGAGGGGGAGGUGCGGGGCG | 20 | 5093 |
| BCL11A-4463 | + | GGAGGGGGCGCUGGGGCCGC | 20 | 5094 |
| BCL11A-4464 | + | GGCAGGGCGAGCAGGAGAGA | 20 | 5095 |
| BCL11A-4465 | + | GGCAGGGGUGGGAGGAA | 17 | 5096 |
| BCL11A-4466 | − | GGCCACUGGUGAGCCCG | 17 | 5097 |
| BCL11A-4467 | + | GGCCCCCGGGGAGGGG | 17 | 5098 |
| BCL11A-4468 | − | GGCCCGCCCCUCCCCCG | 17 | 5099 |
| BCL11A-4469 | + | GGCCGAGGGGAGGGGCGCU | 20 | 5100 |
| BCL11A-4470 | + | GGCCGCAGCGAGCGCCG | 17 | 5101 |
| BCL11A-4471 | + | GGCCGCAGCGAGCGCCGCGG | 20 | 5102 |
| BCL11A-4472 | + | GGCCGCGGGCUCACCAG | 17 | 5103 |
| BCL11A-4473 | + | GGCCGGGAGAAGAAA | 17 | 5104 |
| BCL11A-4474 | + | GGCGAGACAUGGUGGGCUGC | 20 | 5105 |
| BCL11A-4475 | + | GGCGAGCAGGAGAGAAG | 17 | 5106 |
| BCL11A-4476 | + | GGCGAGCAGGAGAGAAGGGG | 20 | 5107 |
| BCL11A-4477 | + | GGCGCAGGGAAGAUGAAUUG | 20 | 5108 |
| BCL11A-4478 | + | GGCGGCGGCGGCGGCGG | 17 | 5109 |
| BCL11A-4479 | + | GGCGGCGGCGGCGGCGGCGG | 20 | 5110 |
| BCL11A-4480 | + | GGCGGGCCGAGGGGAGG | 17 | 5111 |
| BCL11A-4481 | + | GGCUGCGGGGCGGGCGG | 17 | 5112 |
| BCL11A-4482 | + | GGCUGCGGGGCGGGCGGCGG | 20 | 5113 |
| BCL11A-4483 | + | GGGAGAGAAGAAAGGGG | 17 | 5114 |
| BCL11A-4484 | + | GGGAGGAAAGGGUGGGG | 17 | 5115 |
| BCL11A-4485 | + | GGGAGGGGCGGGCCGAG | 17 | 5116 |
| BCL11A-4486 | + | GGGAGGGGCGGGCCGAGGGG | 20 | 5117 |
| BCL11A-4487 | + | GGGAGGGGGAGGUGCGGGGC | 20 | 5118 |
| BCL11A-4488 | + | GGGAGGGGGCGCUGGGGCCG | 20 | 5119 |
| BCL11A-4489 | + | GGGAGGUGCGGGGCGGG | 17 | 5120 |
| BCL11A-4490 | + | GGGCCGAGGGGAGGGGCGC | 20 | 5121 |
| BCL11A-4491 | + | GGGCGAGCAGGAGAGAA | 17 | 5122 |
| BCL11A-4492 | + | GGGCGGGCCGAGGGGAG | 17 | 5123 |
| BCL11A-4493 | + | GGGGAAGCUCACACCAA | 17 | 5124 |
| BCL11A-4494 | + | GGGGAGGGGCGGGCCGA | 17 | 5125 |
| BCL11A-4495 | + | GGGGAGGGGGAGGUGCG | 17 | 5126 |
| BCL11A-4496 | + | GGGGAGGGGGAGGUGCGGGG | 20 | 5127 |
| BCL11A-4497 | + | GGGGAGGUGCGGGGCGG | 17 | 5128 |
| BCL11A-4498 | − | GGGGCCGCGUCUGGCGUCCG | 20 | 5129 |
| BCL11A-4499 | + | GGGGCGGGCCGAGGGGA | 17 | 5130 |
| BCL11A-4500 | + | GGGGCGGGCGGCGGCGG | 17 | 5131 |
| BCL11A-4501 | + | GGGGCGGGCGGCGGCGGCGG | 20 | 5132 |
| BCL11A-4502 | + | GGGGGAGGGGCGGGCCG | 17 | 5133 |
| BCL11A-4503 | + | GGGGGAGGUGCGGGGCG | 17 | 5134 |
| BCL11A-4504 | + | GGGGGCGCUGGGGCCGC | 17 | 5135 |
| BCL11A-4505 | + | GGGGUGGCAGGGGUGGG | 17 | 5136 |
| BCL11A-4506 | + | GGGGUGGGAGGAAAGGG | 17 | 5137 |
| BCL11A-4507 | + | GGGGUGGGAGGAAAGGGUGG | 20 | 5138 |
| BCL11A-4508 | + | GGGGUUUGCCUUGCUUG | 17 | 5139 |
| BCL11A-4509 | + | GGGUGGGAGGAAAGGGU | 17 | 5140 |
| BCL11A-4510 | + | GGGUGGGAGGAAAGGGUGGG | 20 | 5141 |
| BCL11A-4511 | − | GGUAAAAGAGAUAAAGG | 17 | 5142 |
| BCL11A-4512 | + | GGUGGCAGGGGUGGGAGGAA | 20 | 5143 |
| BCL11A-4513 | + | GGUGGGAGGAAAGGGUG | 17 | 5144 |
| BCL11A-4514 | + | GGUGGGAGGAAAGGGUGGGG | 20 | 5145 |
| BCL11A-4515 | + | GGUUCCAGAUGGGAUGA | 17 | 5146 |
| BCL11A-4516 | − | GUAUUAUUUCUAAUUUAUUU | 20 | 5147 |
| BCL11A-4517 | − | GUCGAGGUAAAAGAGAUAAA | 20 | 5148 |
| BCL11A-4518 | + | GUGCGGGAGGGGGAGGUGC | 20 | 5149 |
| BCL11A-4519 | + | GUGCGGGCGGGGGCUCCG | 20 | 5150 |
| BCL11A-4520 | + | GUGGCAGGGGUGGGAGGAAA | 20 | 5151 |
| BCL11A-4521 | + | GUGGCCGGGAGAAGAAAG | 20 | 5152 |
| BCL11A-4522 | + | GUGGGAGGAAAGGGUGG | 17 | 5153 |
| BCL11A-4523 | + | GUGGGCUGCGGGGCGGG | 17 | 5154 |

TABLE 10C-continued

3rd Tier

| gRNA Name | DNA Strand | Targeting Domain | Target Site Length | SEQ ID NO |
|---|---|---|---|---|
| BCL11A-4524 | + | GUGGGCUGCGGGGCGGGCGG | 20 | 5155 |
| BCL11A-4525 | − | GUGUGUGGGGGGGAGCA | 17 | 5156 |

Table 10D provides exemplary targeting domains for knocking down expression of the BCL11A gene according to forth tier parameters. The targeting domains bind between 500 bp upstream and 500 bp downstream of transcription start site and do not start with G. It is contemplated herein that the targeting domain hybridizes to the target domain through complementary base pairing. Any of the targeting domains in the table can be used with a *S. pyogenes* eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a *S. pyogenes* eiCas9 fused to a transcriptional repressor to decrease transcription and therefore downregulate gene expression.

TABLE 10D

4th Tier

| gRNA Name | DNA Strand | Targeting Domain | Target Site Length | SEQ ID NO |
|---|---|---|---|---|
| BCL11A-4526 | + | AAAAAAAAAAAAAAAAAAAG | 20 | 5157 |
| BCL11A-4527 | + | AAAAAAAAAAAAAAAAAAGA | 20 | 5158 |
| BCL11A-4528 | + | AAAAAAAAAAAAAAAG | 17 | 5159 |
| BCL11A-4529 | + | AAAAAAAAAAAAAAGA | 17 | 5160 |
| BCL11A-4530 | + | AAAACAUGGGCAGGGCGAGC | 20 | 5161 |
| BCL11A-4531 | − | AAAACCCUCAUCCCAUC | 17 | 5162 |
| BCL11A-4532 | − | AAAACCUCCGAGAGUCG | 17 | 5163 |
| BCL11A-4533 | − | AAAAGCGAGGGGGAGAG | 17 | 5164 |
| BCL11A-4534 | − | AAAGCGAGGGGGAGAGA | 17 | 5165 |
| BCL11A-4535 | + | AAAGGGGUGGCAGGGGU | 17 | 5166 |
| BCL11A-4536 | + | AAAGGGGUGGCAGGGGUGGG | 20 | 5167 |
| BCL11A-4537 | + | AAAUAAUACAAAGAUGGCGC | 20 | 5168 |
| BCL11A-4538 | − | AACCCCAGCACUUAAGCAAA | 20 | 5169 |
| BCL11A-4539 | + | AACGUCAGGAGUCUGGA | 17 | 5170 |
| BCL11A-4540 | + | AAGAAAGGGUGGCAGGGGU | 20 | 5171 |
| BCL11A-4541 | + | AAGAGACCAGGACAAGCCAA | 20 | 5172 |
| BCL11A-4542 | + | AAGCCAAUGGCCAGUGC | 17 | 5173 |
| BCL11A-4543 | − | AAGCGAGGGGGAGAGAG | 17 | 5174 |
| BCL11A-4544 | + | AAGUGCAUACACGGCAA | 17 | 5175 |
| BCL11A-4545 | + | AAUAAUACAAAGAUGGCGCA | 20 | 5176 |

TABLE 10D-continued

4th Tier

| gRNA Name | DNA Strand | Targeting Domain | Target Site Length | SEQ ID NO |
|---|---|---|---|---|
| BCL11A-4546 | + | AAUACAAAGAUGGCGCA | 17 | 5177 |
| BCL11A-4547 | + | AAUGGACACACAUCAGGGGC | 20 | 5178 |
| BCL11A-4548 | + | AAUGGCCAGUGCGGGGA | 17 | 5179 |
| BCL11A-4549 | + | AAUGGUUCCAGAUGGGAUGA | 20 | 5180 |
| BCL11A-4550 | + | AAUUAAUAAAAUUAAA | 17 | 5181 |
| BCL11A-4551 | + | AAUUAGAAAUAAUACAAAGA | 20 | 5182 |
| BCL11A-4552 | − | AAUUUAUUUUGGAUGUCAAA | 20 | 5183 |
| BCL11A-4553 | + | ACAAGCCAAUGGCCAGUGCG | 20 | 5184 |
| BCL11A-4554 | + | ACACACAAAACAUGGGC | 17 | 5185 |
| BCL11A-4555 | + | ACACCAAUGGACACACAUCA | 20 | 5186 |
| BCL11A-4556 | + | ACAUGGGCAGGGCGAGC | 17 | 5187 |
| BCL11A-4557 | + | ACCAAUGGACACACAUC | 17 | 5188 |
| BCL11A-4558 | − | ACCCCAGCACUUAAGCAAAC | 20 | 5189 |
| BCL11A-4559 | − | ACCCCUUUCUUCUCUCC | 17 | 5190 |
| BCL11A-4560 | + | ACGCCAGACGCGGCCCC | 17 | 5191 |
| BCL11A-4561 | + | ACGCCAGACGCGGCCCCCGG | 20 | 5192 |
| BCL11A-4562 | + | ACGCGGCCCCCGGGGA | 17 | 5193 |
| BCL11A-4563 | + | ACGGCAAUGGUUCCAGA | 17 | 5194 |
| BCL11A-4564 | − | ACUAGAAGCAAAAGCGA | 17 | 5195 |
| BCL11A-4565 | − | ACUGAUGAAGAUAUUUUCUC | 20 | 5196 |
| BCL11A-4566 | − | ACUUGAACUUGCAGCUC | 17 | 5197 |
| BCL11A-4567 | − | ACUUGAACUUGCAGCUCAGG | 20 | 5198 |
| BCL11A-4568 | − | AGAAAACCUCCGAGAGUCG | 20 | 5199 |
| BCL11A-4569 | + | AGAAGAAAGGGGUGGCA | 17 | 5200 |
| BCL11A-4570 | + | AGAAGGGGAGGAGGGAA | 17 | 5201 |
| BCL11A-4571 | + | AGACACACAAAACAUGGCA | 20 | 5202 |
| BCL11A-4572 | + | AGACAUGGUGGGCUGCG | 17 | 5203 |
| BCL11A-4573 | + | AGACAUGGUGGGCUGCGGGG | 20 | 5204 |
| BCL11A-4574 | + | AGACCAGGACAAGCCAA | 17 | 5205 |
| BCL11A-4575 | + | AGACGCGGCCCCCGGGGAG | 20 | 5206 |
| BCL11A-4576 | + | AGAGAAGAAAGGGGUGGCAG | 20 | 5207 |
| BCL11A-4577 | + | AGAGAAGGGGAGGAGGGAAG | 20 | 5208 |
| BCL11A-4578 | + | AGAGACACACAAAACAU | 17 | 5209 |
| BCL11A-4579 | + | AGAGAGAAGAGAGAUAG | 17 | 5210 |
| BCL11A-4580 | + | AGAGAGAAGAGAGAUAGA | 20 | 5211 |
| BCL11A-4581 | + | AGAGAGAGAUGAAAAAAA | 20 | 5212 |
| BCL11A-4582 | − | AGAGUCCGCGUGUGUGG | 17 | 5213 |

TABLE 10D-continued

4th Tier

| gRNA Name | DNA Strand | Targeting Domain | Target Site Length | SEQ ID NO |
|---|---|---|---|---|
| BCL11A-4583 | - | AGCAAAAGCGAGGGGGAGAG | 20 | 5214 |
| BCL11A-4584 | + | AGCAGGAGAGAAGGGGAGGA | 20 | 5215 |
| BCL11A-4585 | + | AGCCAAUGGCCAGUGCG | 17 | 5216 |
| BCL11A-4586 | + | AGCCAAUGGCCAGUGCGGGG | 20 | 5217 |
| BCL11A-4587 | - | AGCCCCUGAUGUGUGUCCAU | 20 | 5218 |
| BCL11A-4588 | + | AGCGAGCGCCGCGGCGG | 17 | 5219 |
| BCL11A-4589 | + | AGCUGCAAGUUCAAGUG | 17 | 5220 |
| BCL11A-4590 | - | AGGACUAGAAGCAAAAGCGA | 20 | 5221 |
| BCL11A-4591 | + | AGGAGAGAAGGGGAGGA | 17 | 5222 |
| BCL11A-4592 | + | AGGGCGAGCAGGAGAGA | 17 | 5223 |
| BCL11A-4593 | + | AGGGGCGGGCCGAGGGG | 17 | 5224 |
| BCL11A-4594 | + | AGGGGCGGGCCGAGGGGAGG | 20 | 5225 |
| BCL11A-4595 | + | AGGGGGAGGUGCGGGGC | 17 | 5226 |
| BCL11A-4596 | + | AGGGGGAGGUGCGGGGCGGG | 20 | 5227 |
| BCL11A-4597 | + | AGGGGGCGCUGGGGCCG | 17 | 5228 |
| BCL11A-4598 | + | AGGGGUGGGAGGAAAGGGUG | 20 | 5229 |
| BCL11A-4599 | - | AGGUAAAAGAGAUAAAG | 17 | 5230 |
| BCL11A-4600 | - | AGUCCGCGUGUGUGGGG | 17 | 5231 |
| BCL11A-4601 | - | AGUCGAGGUAAAAGAGAUAA | 20 | 5232 |
| BCL11A-4602 | + | AGUGCGGGGAGGGGAGGUG | 20 | 5233 |
| BCL11A-4603 | + | AGUGGCCGCAGCGAGCGCCG | 20 | 5234 |
| BCL11A-4604 | + | AUAAUUAUUAUUACUAUUAU | 20 | 5235 |
| BCL11A-4605 | + | AUCUCUUUUACCUCGACUCU | 20 | 5236 |
| BCL11A-4606 | + | AUGGCCAGUGCGGGGAG | 17 | 5237 |
| BCL11A-4607 | + | AUGGUGGGCUGCGGGGC | 17 | 5238 |
| BCL11A-4608 | + | AUGGUGGGCUGCGGGGCGGG | 20 | 5239 |
| BCL11A-4609 | + | AUUAUUAUUACUAUUAU | 17 | 5240 |
| BCL11A-4610 | - | AUUUUAGAGUCCGCGUGUGU | 20 | 5241 |
| BCL11A-4611 | - | CAAAAGCGAGGGGGAGAGAG | 20 | 5242 |
| BCL11A-4612 | + | CAAAAGUGCAUACACGGCAA | 20 | 5243 |
| BCL11A-4613 | + | CAAGCCAAUGGCCAGUG | 17 | 5244 |
| BCL11A-4614 | + | CAAUGGACACACAUCAG | 17 | 5245 |
| BCL11A-4615 | + | CAAUGGCCAGUGCGGGG | 17 | 5246 |
| BCL11A-4616 | + | CAAUGGCCAGUGCGGGGAGG | 20 | 5247 |
| BCL11A-4617 | + | CAAUGGUUCCAGAUGGGAUG | 20 | 5248 |
| BCL11A-4618 | + | CACACAAAACAUGGGCA | 17 | 5249 |
| BCL11A-4619 | + | CACACCAAUGGACACACAUC | 20 | 5250 |
| BCL11A-4620 | + | CACCAAUGGACACACAUCAG | 20 | 5251 |
| BCL11A-4621 | - | CACCGCCGCGGCGCUCGCUG | 20 | 5252 |
| BCL11A-4622 | - | CACUGGCCAUUGGCUUGUCC | 20 | 5253 |
| BCL11A-4623 | - | CACUUGAACUUGCAGCUCAG | 20 | 5254 |
| BCL11A-4624 | + | CAGACGCGGCCCCCGGGGA | 20 | 5255 |
| BCL11A-4625 | + | CAGAGACACACAAAACA | 17 | 5256 |
| BCL11A-4626 | - | CAGGACUAGAAGCAAAAGCG | 20 | 5257 |
| BCL11A-4627 | + | CAGGAGAGAAGGGGAGG | 17 | 5258 |
| BCL11A-4628 | + | CAGGGAAGAUGAAUUGU | 17 | 5259 |
| BCL11A-4629 | + | CAGGGCGAGCAGGAGAGAAG | 20 | 5260 |
| BCL11A-4630 | + | CAGGGGUGGGAGGAAAGGGU | 20 | 5261 |
| BCL11A-4631 | + | CAUGGUGGGCUGCGGGG | 17 | 5262 |
| BCL11A-4632 | + | CCAAUGGACACACAUCA | 17 | 5263 |
| BCL11A-4633 | + | CCAAUGGCCAGUGCGGGGAG | 20 | 5264 |
| BCL11A-4634 | + | CCAGACGCGGCCCCCGG | 17 | 5265 |
| BCL11A-4635 | + | CCAGACGCGGCCCCCGGGGG | 20 | 5266 |
| BCL11A-4636 | - | CCAGCACUUAAGCAAAC | 17 | 5267 |
| BCL11A-4637 | - | CCAGCGCCCCCUCCCCU | 17 | 5268 |
| BCL11A-4638 | + | CCAGUGCGGGGAGGGGG | 17 | 5269 |
| BCL11A-4639 | - | CCCAGCACUUAAGCAAA | 17 | 5270 |
| BCL11A-4640 | - | CCCCCGGGGGCCGCGUC | 17 | 5271 |
| BCL11A-4641 | - | CCCCUCCCCGCACUGGCCAU | 20 | 5272 |
| BCL11A-4642 | + | CCCGGGGGAGGGGCGGGCCG | 20 | 5273 |
| BCL11A-4643 | + | CCCGUUUGCUUAAGUGC | 17 | 5274 |
| BCL11A-4644 | - | CCCUCGGCCCGCCCCUCCCC | 20 | 5275 |
| BCL11A-4645 | - | CCCUGAUGUGUGUCCAU | 17 | 5276 |
| BCL11A-4646 | + | CCGAGGGGAGGGGCGC | 17 | 5277 |
| BCL11A-4647 | - | CCGCGUGUGUGGGGGGAGC | 20 | 5278 |
| BCL11A-4648 | + | CCGGGGGAGGGGCGGGCCGA | 20 | 5279 |
| BCL11A-4649 | + | CCGUUUGCUUAAGUGCU | 17 | 5280 |
| BCL11A-4650 | - | CCUCCCCCGGGGGCCGCGUC | 20 | 5281 |
| BCL11A-4651 | - | CCUCCCCCUCCCCGCAC | 17 | 5282 |
| BCL11A-4652 | - | CCUCGGCCCGCCCCUCCCCC | 20 | 5283 |
| BCL11A-4653 | + | CCUGCUCCCCCCCACACACG | 20 | 5284 |
| BCL11A-4654 | + | CGAGACAUGGUGGGCUG | 17 | 5285 |
| BCL11A-4655 | + | CGAGCGCCGCGGCGGUGGCG | 20 | 5286 |
| BCL11A-4656 | + | CGAGGGGAGGGGCGCU | 17 | 5287 |

TABLE 10D-continued

4th Tier

| gRNA Name | DNA Strand | Targeting Domain | Target Site Length | SEQ ID NO |
|---|---|---|---|---|
| BCL11A-4657 | - | CGAGGUAAAAGAGAUAA | 17 | 5288 |
| BCL11A-4658 | - | CGAGGUAAAAGAGAUAAAGG | 20 | 5289 |
| BCL11A-4659 | - | CGCACUUGAACUUGCAGCUC | 20 | 5290 |
| BCL11A-4660 | + | CGCAGCGAGCGCCGCGG | 17 | 5291 |
| BCL11A-4661 | + | CGCAGCGAGCGCCGCGGCGG | 20 | 5292 |
| BCL11A-4662 | + | CGCCAGACGCGGCCCCC | 17 | 5293 |
| BCL11A-4663 | - | CGCCGCGGCGCUCGCUG | 17 | 5294 |
| BCL11A-4664 | + | CGCCGCGGCGGUGGCGUGGC | 20 | 5295 |
| BCL11A-4665 | + | CGCGGCCCCCGGGGGAG | 17 | 5296 |
| BCL11A-4666 | + | CGCGGCCCCCGGGGAGGGG | 20 | 5297 |
| BCL11A-4667 | + | CGCGGCGGUGGCGUGGC | 17 | 5298 |
| BCL11A-4668 | - | CGCGUGUGUGGGGGGGAGCA | 20 | 5299 |
| BCL11A-4669 | + | CGGCAAUGGUUCCAGAU | 17 | 5300 |
| BCL11A-4670 | - | CGGCCACGCCACCGCCG | 17 | 5301 |
| BCL11A-4671 | - | CGGCCCGCCCCUCCCCC | 17 | 5302 |
| BCL11A-4672 | + | CGGCGAGACAUGGUGGGCUG | 20 | 5303 |
| BCL11A-4673 | + | CGGCGGCGGCGGGCGGACGA | 20 | 5304 |
| BCL11A-4674 | + | CGGCGGCGGGCGGACGA | 17 | 5305 |
| BCL11A-4675 | + | CGGGGAGGGGGAGGUGC | 17 | 5306 |
| BCL11A-4676 | + | CGGGGCGGGGGGCUCCG | 17 | 5307 |
| BCL11A-4677 | + | CGGGGGAGGGGCGGGCCGAG | 20 | 5308 |
| BCL11A-4678 | + | CGUGGCCGGGAGAGAAGAAA | 20 | 5309 |
| BCL11A-4679 | - | CGUGUGUGGGGGGGAGC | 17 | 5310 |
| BCL11A-4680 | + | CGUUUGCUUAAGUGCUG | 17 | 5311 |
| BCL11A-4681 | - | CUAGAAGCAAAAGCGAG | 17 | 5312 |
| BCL11A-4682 | - | CUCCCCGCACUGGCCAU | 17 | 5313 |
| BCL11A-4683 | - | CUCGGCCCGCCCCUCCCCCG | 20 | 5314 |
| BCL11A-4684 | + | CUGAGCUGCAAGUUCAAGUG | 20 | 5315 |
| BCL11A-4685 | + | CUGCGAACUUGAACGUC | 17 | 5316 |
| BCL11A-4686 | + | CUGGACAUGAAAAGAGACC | 20 | 5317 |
| BCL11A-4687 | + | CUGUCUCAAAAGUGCAUACA | 20 | 5318 |
| BCL11A-4688 | + | CUUGAACGUCAGGAGUC | 17 | 5319 |
| BCL11A-4689 | - | CUUGAACUUGCAGCUCA | 17 | 5320 |
| BCL11A-4690 | - | CUUGAACUUGCAGCUCAGGG | 20 | 5321 |
| BCL11A-4691 | + | CUUGCGGCGAGACAUGG | 17 | 5322 |
| BCL11A-4692 | + | GUUCACAUCGGGAGAGC | 17 | 5323 |
| BCL11A-4693 | + | UAAUACAAAGAUGGCGC | 17 | 5324 |
| BCL11A-4694 | + | UAAUUAUUAUUACUAUUAUU | 20 | 5325 |
| BCL11A-4695 | + | UACACGGCAAUGGUUCCAGA | 20 | 5326 |
| BCL11A-4696 | + | UAGAAAUAAUACAAAGA | 17 | 5327 |
| BCL11A-4697 | - | UAGAAGCAAAAGCGAGG | 17 | 5328 |
| BCL11A-4698 | - | UAGAGUCCGCGUGUGUG | 17 | 5329 |
| BCL11A-4699 | - | UAGAGUCCGCGUGUGUGGGG | 20 | 5330 |
| BCL11A-4700 | - | UCCCGGCCACGCCACCGCCG | 20 | 5331 |
| BCL11A-4701 | + | UCCCGUUUGCUUAAGUGCUG | 20 | 5332 |
| BCL11A-4702 | + | UCCCUGCGAACUUGAACGUC | 20 | 5333 |
| BCL11A-4703 | - | UCGAGGUAAAAGAGAUAAAG | 20 | 5334 |
| BCL11A-4704 | - | UCGGCCCGCCCCUCCCC | 17 | 5335 |
| BCL11A-4705 | - | UCGGCCCGCCCCUCCCCCGG | 20 | 5336 |
| BCL11A-4706 | + | UCUCAAAAGUGCAUACA | 17 | 5337 |
| BCL11A-4707 | - | UCUCCUUCUUUCUAACC | 17 | 5338 |
| BCL11A-4708 | + | UCUUUUACCUCGACUCU | 17 | 5339 |
| BCL11A-4709 | - | UGAACUUGCAGCUCAGG | 17 | 5340 |
| BCL11A-4710 | - | UGCGGCCACUGGUGAGCCCG | 20 | 5341 |
| BCL11A-4711 | + | UGCGGGGAGGGGGAGGUGCG | 20 | 5342 |
| BCL11A-4712 | + | UGCGGGGCGGGCGGCGG | 17 | 5343 |
| BCL11A-4713 | + | UGCGGGGCGGGCGGCGGCGG | 20 | 5344 |
| BCL11A-4714 | - | UGCUUAAAAAAAGCCAUGA | 20 | 5345 |
| BCL11A-4715 | + | UGGCCAGUGCGGGGAGG | 17 | 5346 |
| BCL11A-4716 | + | UGGCCAGUGCGGGGAGGGGG | 20 | 5347 |
| BCL11A-4717 | - | UGGCCAUUGGCUUGUCC | 17 | 5348 |
| BCL11A-4718 | + | UGGCCGGGAGAGAAGAA | 17 | 5349 |
| BCL11A-4719 | + | UGGGAGGAAAGGGUGGG | 17 | 5350 |
| BCL11A-4720 | + | UGGGGCCGCGGGCUCACCAG | 20 | 5351 |
| BCL11A-4721 | + | UGGUUCCAGAUGGGAUG | 17 | 5352 |
| BCL11A-4722 | - | UUAAAAAAAGCCAUGA | 17 | 5353 |
| BCL11A-4723 | - | UUAGAGUCCGCGUGUGUGGG | 20 | 5354 |
| BCL11A-4724 | + | UUAUUAUUACUAUUAUU | 17 | 5355 |
| BCL11A-4725 | - | UUAUUUCUAAUUUAUUU | 17 | 5356 |
| BCL11A-4726 | - | UUAUUUUGGAUGUCAAA | 17 | 5357 |
| BCL11A-4727 | + | UUCACAUCGGGAGAGCC | 17 | 5358 |
| BCL11A-4728 | + | UUCCCGUUUGCUUAAGUGCU | 20 | 5359 |
| BCL11A-4729 | + | UUGAACGUCAGGAGUCGGA | 20 | 5360 |
| BCL11A-4730 | - | UUGAACUUGCAGCUCAG | 17 | 5361 |

TABLE 10D-continued

4th Tier

| gRNA Name | DNA Strand | Targeting Domain | Target Site Length | SEQ ID NO |
|---|---|---|---|---|
| BCL11A-4731 | + | UUGCUUGCGGCGAGACAUGG | 20 | 5362 |
| BCL11A-4732 | + | UUGUGGGAGAGCCGUCA | 17 | 5363 |
| BCL11A-4733 | − | UUUUAGAGUCCGCGUGUGUG | 20 | 5364 |

Table 11A provides exemplary targeting domains for knocking down expression of the BCL11A gene according to first tier parameters. The targeting domains bind between 500 bp upstream and 500 bp downstream of transcription start site, good orthogonality, starts with G. It is contemplated herein that the targeting domain hybridizes to the target domain through complementary base pairing. Any of the targeting domains in the table can be used with a S. aureus eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a S. aureus eiCas9 fused to a transcriptional repressor to decrease transcription and therefore downregulate gene expression.

TABLE 11A

1st Tier

| gRNA Name | DNA Strand | Targeting Domain | Target Site Length | SEQ ID NO |
|---|---|---|---|---|
| BCL11A-4734 | + | GACGACGGCUCGGUUCACAU | 20 | 6365 |
| BCL11A-4735 | + | GACGGCUCGGUUCACAU | 17 | 6366 |
| BCL11A-4736 | + | GACGGCUCGGUUCACAUCGG | 20 | 6367 |
| BCL11A-4737 | + | GACGUGACGUCCCUGCGAAC | 20 | 6368 |
| BCL11A-4738 | + | GCGGACGUGACGUCCCU | 17 | 6369 |
| BCL11A-4739 | + | GGACGACGGCUCGGUUCACA | 20 | 6370 |
| BCL11A-4740 | − | GGACGUCACGUCCGCAC | 17 | 6371 |
| BCL11A-4741 | + | GGCUCGGUUCACAUCGG | 17 | 6372 |
| BCL11A-4742 | − | GGCUCUCCCGAUGUGAA | 17 | 6373 |
| BCL11A-4743 | + | GGUUCACAUCGGGAGAG | 17 | 6374 |
| BCL11A-4744 | + | GUCCCUGCGAACUUGAACGU | 20 | 6375 |
| BCL11A-4745 | + | GUGACGUCCCUGCGAAC | 17 | 6376 |

Table 11B provides exemplary targeting domains for knocking down expression of the BCL11A gene according to second tier parameters. The targeting domains bind between 500 bp upstream and 500 bp downstream of transcription start site, good orthogonality and do not start with G. It is contemplated herein that the targeting domain hybridizes to the target domain through complementary base pairing. Any of the targeting domains in the table can be used with a S. aureus eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a S. aureus eiCas9 fused to a transcriptional repressor to decrease transcription and therefore downregulate gene expression.

TABLE 11B

2nd Tier

| gRNA Name | DNA Strand | Targeting Domain | Target Site Length | SEQ ID NO |
|---|---|---|---|---|
| BCL11A-4746 | + | ACGACGGCUCGGUUCACAUC | 20 | 6377 |
| BCL11A-4747 | − | ACGAGAGCGCGCAGGAC | 17 | 6378 |
| BCL11A-4748 | + | ACGGCUCGGUUCACAUC | 17 | 6379 |
| BCL11A-4749 | + | AGUGCGGACGUGACGUCCCU | 20 | 6380 |
| BCL11A-4750 | − | AUCACGAGAGCGCGCAGGAC | 20 | 6381 |
| BCL11A-4751 | − | CAGGGACGUCACGUCCGCAC | 20 | 6382 |
| BCL11A-4752 | + | CAUCGGGAGAGCCGGGU | 17 | 6383 |
| BCL11A-4753 | − | CCCGGCUCUCCCGAUGUGAA | 20 | 6384 |
| BCL11A-4754 | + | CCUGCGAACUUGAACGU | 17 | 6385 |
| BCL11A-4755 | + | CGACGGCUCGGUUCACA | 17 | 6386 |
| BCL11A-4756 | + | CUCGGUUCACAUCGGGAGAG | 20 | 6387 |
| BCL11A-4757 | + | CUGCGAACUUGAACGUC | 17 | 6388 |
| BCL11A-4758 | + | UCACAUCGGGAGAGCCGGGU | 20 | 6389 |
| BCL11A-4759 | + | UCCCUGCGAACUUGAACGUC | 20 | 6390 |

Table 11C provides exemplary targeting domains for knocking down expression of the BCL11A gene according to third tier parameters. The targeting domains bind between 500 bp upstream and 500 bp downstream of transcription start site and start with G. It is contemplated herein that the targeting domain hybridizes to the target domain through complementary base pairing. Any of the targeting domains in the table can be used with a S. aureus eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a S. aureus eiCas9 fused to a transcriptional repressor to decrease transcription and therefore downregulate gene expression.

TABLE 11C

3rd Tier

| gRNA Name | DNA Strand | Targeting Domain | Target Site Length | SEQ ID NO |
|---|---|---|---|---|
| BCL11A-4760 | − | GAAAAAACCCUCAUCCCAUC | 20 | 6391 |
| BCL11A-4761 | + | GAAAGAAGGAGACUCCA | 17 | 6392 |
| BCL11A-4762 | + | GAAAGGGUGGCAGGGG | 17 | 6393 |
| BCL11A-4763 | + | GAAAGGGUGGCAGGGGUGG | 20 | 6394 |
| BCL11A-4764 | + | GAAAUAAUACAAAGAUGGCG | 20 | 6395 |

TABLE 11C-continued

3rd Tier

| gRNA Name | DNA Strand | Targeting Domain | Target Site Length | SEQ ID NO |
|---|---|---|---|---|
| BCL11A-4765 | + | GAACGUCAGGAGUCUGG | 17 | 6396 |
| BCL11A-4766 | + | GAAGAAGGGGUGGCAGGGG | 20 | 6397 |
| BCL11A-4767 | + | GAAGAGAGAUAGAGGGA | 17 | 6398 |
| BCL11A-4768 | − | GAAGCAAAAGCGAGGGG | 17 | 6399 |
| BCL11A-4769 | + | GAAGGGGAGGAGGGAAG | 17 | 6400 |
| BCL11A-4770 | + | GACAAGCCAAUGGCCAGUGC | 20 | 6401 |
| BCL11A-4771 | + | GACACACAAAACAUGGG | 17 | 6402 |
| BCL11A-4772 | + | GACGCCAGACGCGGCCC | 17 | 6403 |
| BCL11A-4773 | + | GACGCCAGACGCGGCCCCCG | 20 | 6404 |
| BCL11A-4774 | + | GACGCGGCCCCCGGGGG | 17 | 6405 |
| BCL11A-4775 | − | GACUAGAAGCAAAAGCG | 17 | 6406 |
| BCL11A-4776 | − | GACUAGAAGCAAAAGCGAGG | 20 | 6407 |
| BCL11A-4777 | + | GACUCUCGGAGGUUUUUCUC | 20 | 6408 |
| BCL11A-4778 | + | GAGAAGAAAGGGGUGGC | 17 | 6409 |
| BCL11A-4779 | + | GAGAAGAGAGAUAGAGG | 17 | 6410 |
| BCL11A-4780 | + | GAGAAGGGGAGGAGGGA | 17 | 6411 |
| BCL11A-4781 | + | GAGACAUGGUGGGCUGCGGG | 20 | 6412 |
| BCL11A-4782 | + | GAGAGAAGAGAGAUAGA | 17 | 6413 |
| BCL11A-4783 | + | GAGAGAAGGGGAGGAGGGAA | 20 | 6414 |
| BCL11A-4784 | + | GAGAGAGAAGAGAGAUA | 17 | 6415 |
| BCL11A-4785 | + | GAGAGAGAGAAGAGAGA | 17 | 6416 |
| BCL11A-4786 | + | GAGAGAGAGAAGAGAGAUAG | 20 | 6417 |
| BCL11A-4787 | + | GAGAGAGAGAGAGAGAG | 17 | 6418 |
| BCL11A-4788 | + | GAGAGAUAGAGGGAGAGAGA | 20 | 6419 |
| BCL11A-4789 | + | GAGAUAGAGGGAGAGAGA | 20 | 6420 |
| BCL11A-4790 | + | GAGCAGGAGAGAAGGGG | 17 | 6421 |
| BCL11A-4791 | + | GAGCAGGAGAGAAGGGGAGG | 20 | 6422 |
| BCL11A-4792 | + | GAGCCGGGUUAGAAAGA | 17 | 6423 |
| BCL11A-4793 | + | GAGCUGCAAGUUCAAGU | 17 | 6424 |
| BCL11A-4794 | + | GAGGGAGAGAGAGAGAA | 17 | 6425 |
| BCL11A-4795 | + | GAGGGGCGGGCCGAGGG | 17 | 6426 |
| BCL11A-4796 | + | GAGGGGGAGGUGCGGGG | 17 | 6427 |
| BCL11A-4797 | + | GAGGGGGCGCUGGGGCC | 17 | 6428 |
| BCL11A-4798 | − | GAGGUAAAAGAGAUAAA | 17 | 6429 |
| BCL11A-4799 | − | GAGUCCGCGUGUGUGGG | 17 | 6430 |
| BCL11A-4800 | − | GAGUCGAGGUAAAAGAGAUA | 20 | 6431 |
| BCL11A-4801 | + | GAUAGAGGGAGAGAGAGAGA | 20 | 6432 |
| BCL11A-4802 | − | GAUGAAGAUAUUUCUC | 17 | 6433 |
| BCL11A-4803 | − | GAUGUCAAAAGGCACUG | 17 | 6434 |
| BCL11A-4804 | − | GAUGUGUGUCCAUUGGU | 17 | 6435 |
| BCL11A-4805 | + | GCAAUGGUUCCAGAUGGGAU | 20 | 6436 |
| BCL11A-4806 | − | GCACUUGAACUUGCAGCUCA | 20 | 6437 |
| BCL11A-4807 | − | GCAGGACUAGAAGCAAAAGC | 20 | 6438 |
| BCL11A-4808 | + | GCAGGAGAGAAGGGGAG | 17 | 6439 |
| BCL11A-4809 | + | GCAGGGAAGAUGAAUUG | 17 | 6440 |
| BCL11A-4810 | + | GCAGGGAAGAUGAAUUGUGG | 20 | 6441 |
| BCL11A-4811 | + | GCAGGGCGAGCAGGAGAGAA | 20 | 6442 |
| BCL11A-4812 | + | GCAGGGGUGGGAGGAAAGGG | 20 | 6443 |
| BCL11A-4813 | − | GCAUUUUUAAAUUUUUC | 17 | 6444 |
| BCL11A-4814 | + | GCCAAUGGCCAGUGCGGGGA | 20 | 6445 |
| BCL11A-4815 | + | GCCAGACGCGGCCCCCG | 17 | 6446 |
| BCL11A-4816 | + | GCCAGACGCGGCCCCCGGGG | 20 | 6447 |
| BCL11A-4817 | + | GCCCCCGGGGAGGGGCGGG | 20 | 6448 |
| BCL11A-4818 | + | GCCGAGGGGAGGGGCG | 17 | 6449 |
| BCL11A-4819 | + | GCCGCGGCGGUGGCGUGGCC | 20 | 6450 |
| BCL11A-4820 | − | GCCGCGUCUGGCGUCCG | 17 | 6451 |
| BCL11A-4821 | + | GCGAGACAUGGUGGGCU | 17 | 6452 |
| BCL11A-4822 | − | GCGCAGGACUAGAAGCAAAA | 20 | 6453 |
| BCL11A-4823 | + | GCGCAGGGAAGAUGAAUUGU | 20 | 6454 |
| BCL11A-4824 | + | GCGCCGCGGCGGUGGCGUGG | 20 | 6455 |
| BCL11A-4825 | + | GCGGACGCCAGACGCGGCCC | 20 | 6456 |
| BCL11A-4826 | + | GCGGCGAGACAUGGUGGGCU | 20 | 6457 |
| BCL11A-4827 | + | GCGGCGGUGGCGUGGCC | 17 | 6458 |
| BCL11A-4828 | + | GCGGGGAGGGGAGGUG | 17 | 6459 |
| BCL11A-4829 | + | GCGGGCGGGGGCUCC | 17 | 6460 |
| BCL11A-4830 | + | GCGUGGCCGGGAGAGAAGAA | 20 | 6461 |
| BCL11A-4831 | − | GCGUGUGGGGGGGAG | 17 | 6462 |
| BCL11A-4832 | + | GCUCACCAGUGGCCGCA | 17 | 6463 |
| BCL11A-4833 | − | GCUCGCUGCGGCCACUG | 17 | 6464 |
| BCL11A-4834 | + | GCUGGACAUGAAAAGAGAC | 20 | 6465 |
| BCL11A-4835 | + | GCUUGCGGCGAGACAUG | 17 | 6466 |
| BCL11A-4836 | − | GGAAAAACCCUCAUCCCAU | 20 | 6467 |
| BCL11A-4837 | + | GGAAGGGGAAGCUCACACCA | 20 | 6468 |
| BCL11A-4838 | + | GGACAAGCCAAUGGCCAGUG | 20 | 6469 |

TABLE 11C-continued

3rd Tier

| gRNA Name | DNA Strand | Targeting Domain | Target Site Length | SEQ ID NO |
|---|---|---|---|---|
| BCL11A-4839 | + | GGACAUGAAAAAGAGAC | 17 | 6470 |
| BCL11A-4840 | + | GGACGCCAGACGCGGCCCCC | 20 | 6471 |
| BCL11A-4841 | - | GGACUAGAAGCAAAAGC | 17 | 6472 |
| BCL11A-4842 | - | GGACUAGAAGCAAAAGCGAG | 20 | 6473 |
| BCL11A-4843 | + | GGAGAGAAGAAAGGGGUGGC | 20 | 6474 |
| BCL11A-4844 | + | GGAGAGAAGGGGAGGAGGGA | 20 | 6475 |
| BCL11A-4845 | + | GGAGAGAGAGAAGAGAGA | 20 | 6476 |
| BCL11A-4846 | + | GGAGAGCCGGGUUAGAAAGA | 20 | 6477 |
| BCL11A-4847 | + | GGAGGGGCGGGCCGAGGGGA | 20 | 6478 |
| BCL11A-4848 | + | GGAGGGGGAGGUGCGGG | 17 | 6479 |
| BCL11A-4849 | + | GGAGGGGGAGGUGCGGGGCG | 20 | 6480 |
| BCL11A-4850 | + | GGCAGGGCGAGCAGGAGAGA | 20 | 6481 |
| BCL11A-4851 | + | GGCAGGGGUGGGAGGAAAGG | 20 | 6482 |
| BCL11A-4852 | - | GGCCGCGUCUGGCGUCC | 17 | 6483 |
| BCL11A-4853 | + | GGCGAGCAGGAGAGAAG | 17 | 6484 |
| BCL11A-4854 | + | GGCGAGCAGGAGAGAAGGGG | 20 | 6485 |
| BCL11A-4855 | + | GGCGCAGGGAAGAUGAAUUG | 20 | 6486 |
| BCL11A-4856 | - | GGCGCUCGCUGCGGCCACUG | 20 | 6487 |
| BCL11A-4857 | + | GGCGGCGGCGGCGGCGG | 17 | 6488 |
| BCL11A-4858 | + | GGCGGCGGCGGCGGCGGCGG | 20 | 6489 |
| BCL11A-4859 | + | GGCGGUGGCGUGGCCGG | 17 | 6490 |
| BCL11A-4860 | + | GGCGUGGCCGGGAGAGAAGA | 20 | 6491 |
| BCL11A-4861 | + | GGGAAGAUGAAUUGUGG | 17 | 6492 |
| BCL11A-4862 | + | GGGAGAGAAGAAAGGGGUGG | 20 | 6493 |
| BCL11A-4863 | + | GGGAGAGCCGGGUUAGA | 17 | 6494 |
| BCL11A-4864 | + | GGGAGAGCCGGGUUAGAAAG | 20 | 6495 |
| BCL11A-4865 | + | GGGAGGAAAGGGUGGGG | 17 | 6496 |
| BCL11A-4866 | + | GGGAGGGGCGGGCCGAG | 17 | 6497 |
| BCL11A-4867 | + | GGGAGGGGCGGGCCGAGGGG | 20 | 6498 |
| BCL11A-4868 | + | GGGAGGGGGAGGUGCGGGGC | 20 | 6499 |
| BCL11A-4869 | + | GGGCAGGGCGAGCAGGA | 17 | 6500 |
| BCL11A-4870 | + | GGGCAGGGCGAGCAGGAGAG | 20 | 6501 |
| BCL11A-4871 | + | GGGCCGAGGGGAGGGGCGC | 20 | 6502 |
| BCL11A-4872 | + | GGGCGAGCAGGAGAGAA | 17 | 6503 |
| BCL11A-4873 | + | GGGCGAGCAGGAGAGAAGGG | 20 | 6504 |
| BCL11A-4874 | + | GGGGAGGGGCGGGCCGA | 17 | 6505 |
| BCL11A-4875 | + | GGGGAGGGGCGGGCCGAGGG | 20 | 6506 |
| BCL11A-4876 | + | GGGGAGGGGGAGGUGCGGGG | 20 | 6507 |
| BCL11A-4877 | + | GGGGAGGGGGCGCUGGGGCC | 20 | 6508 |
| BCL11A-4878 | - | GGGGCCGCGUCUGGCGUCCG | 20 | 6509 |
| BCL11A-4879 | + | GGGGCGGGCCGAGGGGA | 17 | 6510 |
| BCL11A-4880 | + | GGGGGAGGGGCGGGCCG | 17 | 6511 |
| BCL11A-4881 | + | GGGGGAGGUGCGGGGCG | 17 | 6512 |
| BCL11A-4882 | - | GGGGGCCGCGUCUGGCGUCC | 20 | 6513 |
| BCL11A-4883 | + | GGGGUGGCAGGGGUGGG | 17 | 6514 |
| BCL11A-4884 | + | GGGGUGGGAGGAAAGGG | 17 | 6515 |
| BCL11A-4885 | + | GGGGUGGGAGGAAAGGGUGG | 20 | 6516 |
| BCL11A-4886 | + | GGGUGGCAGGGGUGGGAGGA | 20 | 6517 |
| BCL11A-4887 | + | GGGUGGGAGGAAAGGGU | 17 | 6518 |
| BCL11A-4888 | + | GGGUGGGAGGAAAGGGUGGG | 20 | 6519 |
| BCL11A-4889 | - | GGUAAAAGAGAUAAAGG | 17 | 6520 |
| BCL11A-4890 | + | GGUGCGGGCGGGGGCUCC | 20 | 6521 |
| BCL11A-4891 | + | GGUGGGAGGAAAGGGUG | 17 | 6522 |
| BCL11A-4892 | + | GGUGGGAGGAAAGGGUGGGG | 20 | 6523 |
| BCL11A-4893 | + | GGUUAGAAAGAAGGAGACUC | 20 | 6524 |
| BCL11A-4894 | + | GGUUUGCCUUGCUUGCG | 17 | 6525 |
| BCL11A-4895 | - | GUCGAGGUAAAAGAGAUAAA | 20 | 6526 |
| BCL11A-4896 | + | GUGGCCGGGAGAGAAGA | 17 | 6527 |
| BCL11A-4897 | + | GUGGGAGGAAAGGGUGG | 17 | 6528 |

Table 11D provides exemplary targeting domains for knocking down expression of the BCL11A gene according to forth tier parameters. The targeting domains bind between 500 bp upstream and 500 bp downstream of transcription start site and do not start with G. It is contemplated herein that the targeting domain hybridizes to the target domain through complementary base pairing. Any of the targeting domains in the table can be used with a S. aureus eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a S. aureus eiCas9 fused to a transcriptional repressor to decrease transcription and therefore downregulate gene expression.

TABLE 11D

4th Tier

| gRNA Name | DNA Strand | Targeting Domain | Target Site Length | SEQ ID NO |
|---|---|---|---|---|
| BCL11A-4898 | + | AAAAAAAAAAAAAAAAA | 17 | 6529 |
| BCL11A-4899 | + | AAAAAAAAAAAAAAAAAAAA | 20 | 6530 |

TABLE 11D-continued

4th Tier

| gRNA Name | DNA Strand | Targeting Domain | Target Site Length | SEQ ID NO |
|---|---|---|---|---|
| BCL11A-4900 | + | AAAAAAAAAAAAAAAAAAAG | 20 | 6531 |
| BCL11A-4901 | + | AAAAAAAAAAAAAAAAAAGA | 20 | 6532 |
| BCL11A-4902 | + | AAAAAAAAAAAAAAAAG | 17 | 6533 |
| BCL11A-4903 | + | AAAAAAAAAAAAAAAGAGG | 20 | 6534 |
| BCL11A-4904 | + | AAAAAAAAAAAAAAGA | 17 | 6535 |
| BCL11A-4905 | + | AAAAAAAAAAAAGAGGGA | 20 | 6536 |
| BCL11A-4906 | + | AAAAAAAAAAAGAGG | 17 | 6537 |
| BCL11A-4907 | + | AAAAAAAAAAGAGGGAGA | 20 | 6538 |
| BCL11A-4908 | + | AAAAAAAAAAGAGGGA | 17 | 6539 |
| BCL11A-4909 | + | AAAAAAAAAGAGGGAGAGA | 20 | 6540 |
| BCL11A-4910 | + | AAAAAAAAGAGGGAGA | 17 | 6541 |
| BCL11A-4911 | + | AAAAAAAGAGGGAGAGAGA | 20 | 6542 |
| BCL11A-4912 | + | AAAAAAGAGGGAGAGA | 17 | 6543 |
| BCL11A-4913 | + | AAAAAUGGCAAAAGCCCCC | 20 | 6544 |
| BCL11A-4914 | − | AAAAACCCUCAUCCCAU | 17 | 6545 |
| BCL11A-4915 | + | AAAAAGAGGGAGAGAGA | 17 | 6546 |
| BCL11A-4916 | + | AAAAAGAGGGAGAGAGAGAG | 20 | 6547 |
| BCL11A-4917 | + | AAAACAUGGGCAGGGCGAGC | 20 | 6548 |
| BCL11A-4918 | − | AAAACCCUCAUCCCAUC | 17 | 6549 |
| BCL11A-4919 | − | AAAAGCGAGGGGGAGAG | 17 | 6550 |
| BCL11A-4920 | − | AAACCCCAGCACUUAAGCAA | 20 | 6551 |
| BCL11A-4921 | + | AAAGAGGGAGAGAGAGAGAA | 20 | 6552 |
| BCL11A-4922 | + | AAAGGGGUGGCAGGGGU | 17 | 6553 |
| BCL11A-4923 | + | AAAGGGGUGGCAGGGUGGG | 20 | 6554 |
| BCL11A-4924 | + | AAAUAAUACAAAGAUGGCGC | 20 | 6555 |
| BCL11A-4925 | + | AAAUGGCAAAAGCCCCC | 17 | 6556 |
| BCL11A-4926 | + | AACAUGGGCAGGGCGAG | 17 | 6557 |
| BCL11A-4927 | + | AACAUGGGCAGGGCGAGCAG | 20 | 6558 |
| BCL11A-4928 | − | AACCCCAGCACUUAAGCAAA | 20 | 6559 |
| BCL11A-4929 | − | AACCCGGCUCUCCCGAU | 17 | 6560 |
| BCL11A-4930 | + | AAGAAAGGGUGGCAGGGGU | 20 | 6561 |
| BCL11A-4931 | + | AAGAGAGAUAGAGGGAGAGA | 20 | 6562 |
| BCL11A-4932 | + | AAGAGGGAGAGAGAG | 17 | 6563 |
| BCL11A-4933 | + | AAGAUGGCGCAGGGAAG | 17 | 6564 |
| BCL11A-4934 | − | AAGCAAAGCGAGGGGAGA | 20 | 6565 |
| BCL11A-4935 | + | AAGCCAUGGCCAGUGC | 17 | 6566 |
| BCL11A-4936 | + | AAGCCAUGGCCAGUGCGGG | 20 | 6567 |
| BCL11A-4937 | − | AAUAAUAAUUAUUAAUAAUC | 20 | 6568 |
| BCL11A-4938 | + | AAUAAUACAAAGAUGGCGCA | 20 | 6569 |
| BCL11A-4939 | − | AAUAAUUAUUAAUAAUC | 17 | 6570 |
| BCL11A-4940 | + | AAUAAUUAUUAUUACUAUUA | 20 | 6571 |
| BCL11A-4941 | + | AAUACAAAGAUGGCGCA | 17 | 6572 |
| BCL11A-4942 | + | AAUGGCCAGUGCGGGA | 17 | 6573 |
| BCL11A-4943 | + | AAUUAUUAUUACUAUUA | 17 | 6574 |
| BCL11A-4944 | + | AAUUCCCGUUUGCUUAAGUG | 20 | 6575 |
| BCL11A-4945 | + | ACAAAGAUGGCGCAGGGAAG | 20 | 6576 |
| BCL11A-4946 | + | ACAAGCCAUGGCCAGU | 17 | 6577 |
| BCL11A-4947 | + | ACAAGCCAUGGCCAGUGCG | 20 | 6578 |
| BCL11A-4948 | + | ACACACAAAACAUGGGCAGG | 20 | 6579 |
| BCL11A-4949 | + | ACACACAUCAGGGGCUGGAC | 20 | 6580 |
| BCL11A-4950 | + | ACAGAGACACACAAAAC | 17 | 6581 |
| BCL11A-4951 | + | ACAUGGGCAGGGCGAGC | 17 | 6582 |
| BCL11A-4952 | + | ACAUGGUGGGCUGCGGG | 17 | 6583 |
| BCL11A-4953 | + | ACCAAUGGACACACAUC | 17 | 6584 |
| BCL11A-4954 | − | ACCCCAGCACUUAAGCAAAC | 20 | 6585 |
| BCL11A-4955 | − | ACCUCCGAGAUCGAGGUAA | 20 | 6586 |
| BCL11A-4956 | − | ACGAGAAAAACCUCCGAGAG | 20 | 6587 |
| BCL11A-4957 | + | ACGCCAGACGCGGCCCC | 17 | 6588 |
| BCL11A-4958 | + | ACGCCAGACGCGGCCCCGG | 20 | 6589 |
| BCL11A-4959 | + | ACGCGGCCCCGGGGAGGG | 20 | 6590 |
| BCL11A-4960 | + | ACGGCAAUGGUUCCAGA | 17 | 6591 |
| BCL11A-4961 | + | ACGUCAGGAGUCUGGAUGGA | 20 | 6592 |
| BCL11A-4962 | − | ACUAGAAGCAAAAGCGA | 17 | 6593 |
| BCL11A-4963 | + | ACUAUUAUUGGGUUACUUAC | 20 | 6594 |
| BCL11A-4964 | − | ACUCCUGACGUUCAAGUUCG | 20 | 6595 |
| BCL11A-4965 | − | ACUGAUGAAGAUAUUUCUC | 20 | 6596 |
| BCL11A-4966 | + | ACUUGAACGUCAGGAGU | 17 | 6597 |
| BCL11A-4967 | − | ACUUGAACUUGCAGCUC | 17 | 6598 |
| BCL11A-4968 | − | AGAAAACCUCCGAGAG | 17 | 6599 |
| BCL11A-4969 | + | AGAAAGGGUGGCAGGG | 17 | 6600 |
| BCL11A-4970 | + | AGAAGAAAGGGUGGCAGGG | 20 | 6601 |
| BCL11A-4971 | + | AGAAGAGAGAUAGAGGGAGA | 20 | 6602 |
| BCL11A-4972 | − | AGAAGCAAAAGCGAGGGGA | 20 | 6603 |
| BCL11A-4973 | + | AGAAGGGGAGGAGGGAA | 17 | 6604 |

TABLE 11D-continued

4th Tier

| gRNA Name | DNA Strand | Targeting Domain | Target Site Length | SEQ ID NO |
|---|---|---|---|---|
| BCL11A-4974 | + | AGACGCGGCCCCCGGGG | 17 | 6605 |
| BCL11A-4975 | + | AGAGAAGAAAGGGUGG | 17 | 6606 |
| BCL11A-4976 | + | AGAGAAGAGAGAUAGAGGGA | 20 | 6607 |
| BCL11A-4977 | + | AGAGAAGGGGAGGAGGG | 17 | 6608 |
| BCL11A-4978 | + | AGAGAAGGGGAGGAGGGAAG | 20 | 6609 |
| BCL11A-4979 | + | AGAGACACACAAAACAUGGG | 20 | 6610 |
| BCL11A-4980 | + | AGAGAGAAGAGAGAUAG | 17 | 6611 |
| BCL11A-4981 | + | AGAGAGAAGAGAGAUAGAGG | 20 | 6612 |
| BCL11A-4982 | + | AGAGAGAGAAGAGAGAUAGA | 20 | 6613 |
| BCL11A-4983 | + | AGAGAGAGAGAAGAGAGAUA | 20 | 6614 |
| BCL11A-4984 | + | AGAGAGAUAGAGGGAGA | 17 | 6615 |
| BCL11A-4985 | + | AGAGAUAGAGGGAGAGA | 17 | 6616 |
| BCL11A-4986 | + | AGAGCCGGGUUAGAAAG | 17 | 6617 |
| BCL11A-4987 | + | AGAGGGAGAGAGAGAGA | 17 | 6618 |
| BCL11A-4988 | − | AGAGUCCGCGUGUGUGG | 17 | 6619 |
| BCL11A-4989 | + | AGAUAGAGGGAGAGAGA | 17 | 6620 |
| BCL11A-4990 | − | AGCAAAAGCGAGGGGGA | 17 | 6621 |
| BCL11A-4991 | − | AGCAAAAGCGAGGGGGAGAG | 20 | 6622 |
| BCL11A-4992 | + | AGCAGGAGAGAAGGGGAGGA | 20 | 6623 |
| BCL11A-4993 | + | AGCCAAUGGCCAGUGCG | 17 | 6624 |
| BCL11A-4994 | + | AGCCAAUGGCCAGUGCGGGG | 20 | 6625 |
| BCL11A-4995 | + | AGGACAAGCCAAUGGCCAGU | 20 | 6626 |
| BCL11A-4996 | − | AGGACUAGAAGCAAAAGCGA | 20 | 6627 |
| BCL11A-4997 | + | AGGAGAAGGGGAGGA | 17 | 6628 |
| BCL11A-4998 | + | AGGAGAGAAGGGGAGGAGGG | 20 | 6629 |
| BCL11A-4999 | + | AGGGAGAGAGAGAGAGAGAG | 20 | 6630 |
| BCL11A-5000 | + | AGGGCGAGCAGGAGAGA | 17 | 6631 |
| BCL11A-5001 | + | AGGGGAAGCUCACACCA | 17 | 6632 |
| BCL11A-5002 | + | AGGGGCGGGCCGAGGGG | 17 | 6633 |
| BCL11A-5003 | + | AGGGGCUGGACAUGAAA | 17 | 6634 |
| BCL11A-5004 | + | AGGGGGAGGUGCGGGGC | 17 | 6635 |
| BCL11A-5005 | + | AGGGGUGGCAGGGGUGG | 17 | 6636 |
| BCL11A-5006 | + | AGGGGUGGGAGGAAAGG | 17 | 6637 |
| BCL11A-5007 | + | AGGGGUGGGAGGAAAGGGUG | 20 | 6638 |
| BCL11A-5008 | − | AGGUAAAAGAGAUAAAG | 17 | 6639 |
| BCL11A-5009 | − | AGUCCGCGUGUGUGGGG | 17 | 6640 |
| BCL11A-5010 | − | AGUCGAGGUAAAAGAGAUAA | 20 | 6641 |
| BCL11A-5011 | + | AGUGCGGGGAGGGGGAGGUG | 20 | 6642 |
| BCL11A-5012 | + | AUAAUACAAAGAUGGCG | 17 | 6643 |
| BCL11A-5013 | − | AUAAUCACGAGAGCGCG | 17 | 6644 |
| BCL11A-5014 | + | AUACACGGCAAUGGUUCCAG | 20 | 6645 |
| BCL11A-5015 | + | AUAGAGGGAGAGAGAGA | 17 | 6646 |
| BCL11A-5016 | + | AUCAGGGGCUGGACAUGAAA | 20 | 6647 |
| BCL11A-5017 | + | AUCGGGAGAGCCGGGUUAGA | 20 | 6648 |
| BCL11A-5018 | + | AUCUCUUUUACCUCGACUCU | 20 | 6649 |
| BCL11A-5019 | + | AUGGCCAGUGCGGGGAG | 17 | 6650 |
| BCL11A-5020 | + | AUGGGCAGGGCGAGCAG | 17 | 6651 |
| BCL11A-5021 | + | AUGGUUCCAGAUGGGAU | 17 | 6652 |
| BCL11A-5022 | + | AUUAUUGGGUUACUUAC | 17 | 6653 |
| BCL11A-5023 | − | AUUAUUUCUAAUUUAUU | 17 | 6654 |
| BCL11A-5024 | + | AUUCCCGUUUGCUUAAGUGC | 20 | 6655 |
| BCL11A-5025 | − | AUUUUAGAGUCCGCGUGUGU | 20 | 6656 |
| BCL11A-5026 | − | AUUUUAAAAUUUUUCAC | 17 | 6657 |
| BCL11A-5027 | − | AUUUUUCACGAGAAAAACCU | 20 | 6658 |
| BCL11A-5028 | + | CAAAACAUGGGCAGGGCGAG | 20 | 6659 |
| BCL11A-5029 | − | CAAAAGCGAGGGGGAGA | 17 | 6660 |
| BCL11A-5030 | + | CAAGCCAAUGGCCAGUG | 17 | 6661 |
| BCL11A-5031 | + | CAAUGGACACACAUCAGGGG | 20 | 6662 |
| BCL11A-5032 | + | CAAUGGCCAGUGCGGGG | 17 | 6663 |
| BCL11A-5033 | + | CAAUGGCCAGUGCGGGGAGG | 20 | 6664 |
| BCL11A-5034 | + | CAAUGGUUCCAGAUGGG | 17 | 6665 |
| BCL11A-5035 | + | CACAAAACAUGGGCAGG | 17 | 6666 |
| BCL11A-5036 | + | CACACCAAUGGACACACAUC | 20 | 6667 |
| BCL11A-5037 | + | CACACGCGGACUCUAAA | 17 | 6668 |
| BCL11A-5038 | + | CACAUCAGGGGCUGGAC | 17 | 6669 |
| BCL11A-5039 | + | CACCAAUGGACACACAU | 17 | 6670 |
| BCL11A-5040 | + | CACGGCAAUGGUUCCAG | 17 | 6671 |
| BCL11A-5041 | − | CACUGAUGAAGAUAUUUUCU | 20 | 6672 |
| BCL11A-5042 | − | CACUUGAACUUGCAGCU | 17 | 6673 |
| BCL11A-5043 | − | CACUUGAACUUGCAGCUCAG | 20 | 6674 |
| BCL11A-5044 | − | CAGGACUAGAAGCAAAA | 17 | 6675 |
| BCL11A-5045 | − | CAGGACUAGAAGCAAAAGCG | 20 | 6676 |
| BCL11A-5046 | + | CAGGAGAGAAGGGGAGG | 17 | 6677 |
| BCL11A-5047 | + | CAGGGAAGAUGAAUUGU | 17 | 6678 |

TABLE 11D-continued

4th Tier

| gRNA Name | DNA Strand | Targeting Domain | Target Site Length | SEQ ID NO |
|---|---|---|---|---|
| BCL11A-5048 | + | CAGGGCGAGCAGGAGAG | 17 | 6679 |
| BCL11A-5049 | + | CAGGGCGAGCAGGAGAAG | 20 | 6680 |
| BCL11A-5050 | + | CAGGGGUGGGAGGAAAGGGU | 20 | 6681 |
| BCL11A-5051 | + | CAGUGCGGGGAGGGGGAGGU | 20 | 6682 |
| BCL11A-5052 | − | CAUGCAUUUUAAAUUUUUC | 20 | 6683 |
| BCL11A-5053 | + | CAUGGGCAGGGCGAGCAGGA | 20 | 6684 |
| BCL11A-5054 | − | CAUUUUAGAGUCCGCGUGUG | 20 | 6685 |
| BCL11A-5055 | + | CCAAUGGCCAGUGCGGG | 17 | 6686 |
| BCL11A-5056 | + | CCAAUGGCCAGUGCGGGGAG | 20 | 6687 |
| BCL11A-5057 | + | CCACACACGCGGACUCUAAA | 20 | 6688 |
| BCL11A-5058 | + | CCAGACGCGGCCCCCGG | 17 | 6689 |
| BCL11A-5059 | + | CCAGACGCGGCCCCCGGGG | 20 | 6690 |
| BCL11A-5060 | − | CCAGCACUUAAGCAAAC | 17 | 6691 |
| BCL11A-5061 | − | CCAUUGCCGUGUAUGCACUU | 20 | 6692 |
| BCL11A-5062 | − | CCCAGCACUUAAGCAAA | 17 | 6693 |
| BCL11A-5063 | − | CCCCAGCACUUAAGCAA | 17 | 6694 |
| BCL11A-5064 | + | CCCCGGGGAGGGGCGGCC | 20 | 6695 |
| BCL11A-5065 | − | CCCCUCGGCCCGCCCCUCCC | 20 | 6696 |
| BCL11A-5066 | + | CCCGGGGAGGGGCGGG | 17 | 6697 |
| BCL11A-5067 | + | CCCGGGGAGGGGCGGGCCG | 20 | 6698 |
| BCL11A-5068 | + | CCCGUUUGCUUAAGUGC | 17 | 6699 |
| BCL11A-5069 | − | CCCUCGGCCCGCCCCUCCCC | 20 | 6700 |
| BCL11A-5070 | + | CCCUGCUCCCCCCCACACAC | 20 | 6701 |
| BCL11A-5071 | + | CCGAGGGGAGGGGCGC | 17 | 6702 |
| BCL11A-5072 | − | CCGCACUUAACUUGCAGCU | 20 | 6703 |
| BCL11A-5073 | + | CCGCGGCGGUGGCGUGG | 17 | 6704 |
| BCL11A-5074 | + | CCGGGGAGGGGCGGGCCGA | 20 | 6705 |
| BCL11A-5075 | − | CCUCGGCCCGCCCCUCCCCC | 20 | 6706 |
| BCL11A-5076 | − | CCUGACGUUCAAGUUCG | 17 | 6707 |
| BCL11A-5077 | + | CCUGAGCUGCAAGUUCAAGU | 20 | 6708 |
| BCL11A-5078 | − | CCUGAUGUGUGUCCAUUGGU | 20 | 6709 |
| BCL11A-5079 | + | CGAACUUGAACGUCAGGAGU | 20 | 6710 |
| BCL11A-5080 | + | CGAGACAUGGUGGGCUG | 17 | 6711 |
| BCL11A-5081 | + | CGAGCAGGAGAGAAGGG | 17 | 6712 |
| BCL11A-5082 | + | CGAGCAGGAGAGAAGGGGAG | 20 | 6713 |
| BCL11A-5083 | − | CGAGGUAAAAGAGAUAA | 17 | 6714 |
| BCL11A-5084 | − | CGAGGUAAAAGAGAUAAAGG | 20 | 6715 |
| BCL11A-5085 | − | CGCACUUGAACUUGCAGCUC | 20 | 6716 |
| BCL11A-5086 | + | CGCAGGGAAGAUGAAUU | 17 | 6717 |
| BCL11A-5087 | + | CGCCAGACGCGGCCCCC | 17 | 6718 |
| BCL11A-5088 | + | CGCCGCGGCGGUGGCGUGGC | 20 | 6719 |
| BCL11A-5089 | + | CGCGGCGGUGGCGUGGC | 17 | 6720 |
| BCL11A-5090 | + | CGCGGCGGUGGCGUGGCCGG | 20 | 6721 |
| BCL11A-5091 | + | CGGACGCCAGACGCGGCCCC | 20 | 6722 |
| BCL11A-5092 | + | CGGCAAUGGUUCCAGAUGGG | 20 | 6723 |
| BCL11A-5093 | + | CGGCCCCGGGGAGGG | 17 | 6724 |
| BCL11A-5094 | − | CGGCCCGCCCCUCCCCC | 17 | 6725 |
| BCL11A-5095 | + | CGGCGAGACAUGGUGGGCUG | 20 | 6726 |
| BCL11A-5096 | + | CGGCGGCGGCGGCGGCG | 17 | 6727 |
| BCL11A-5097 | + | CGGCGGCGGCGGCGGCGCG | 20 | 6728 |
| BCL11A-5098 | + | CGGCGGUGGCGUGGCCGGGA | 20 | 6729 |
| BCL11A-5099 | + | CGGGCCGAGGGGAGGGGCG | 20 | 6730 |
| BCL11A-5100 | + | CGGGCUCACCAGUGGCCGCA | 20 | 6731 |
| BCL11A-5101 | + | CGGGGAGGGGAGGUGCGGG | 20 | 6732 |
| BCL11A-5102 | + | CGGGGGAGGGGCGGGCC | 17 | 6733 |
| BCL11A-5103 | + | CGGGGGAGGGGCGGGCCGAG | 20 | 6734 |
| BCL11A-5104 | + | CGGUGGCGUGGCCGGGA | 17 | 6735 |
| BCL11A-5105 | + | CGGUGGCGUGGCCGGGAGAG | 20 | 6736 |
| BCL11A-5106 | − | CUAGAAGCAAAAGCGAG | 17 | 6737 |
| BCL11A-5107 | − | CUAGAAGCAAAAGCGAGGGG | 20 | 6738 |
| BCL11A-5108 | − | CUCCUGACGUUCAAGUUCGC | 20 | 6739 |
| BCL11A-5109 | − | CUCGGCCCGCCCCUCCC | 17 | 6740 |
| BCL11A-5110 | + | CUCUUUUACCUCGACUC | 17 | 6741 |
| BCL11A-5111 | − | CUGACGUUCAAGUUCGC | 17 | 6742 |
| BCL11A-5112 | + | CUUGAACGUCAGGAGUCUGG | 20 | 6743 |
| BCL11A-5113 | − | CUUGAACUUGCAGCUCA | 17 | 6744 |
| BCL11A-5114 | + | CUUGCUUGCGGCGAGACAUG | 20 | 6745 |
| BCL11A-5115 | − | UAAUAAUUAUUAAUAAUCAC | 20 | 6746 |
| BCL11A-5116 | + | UAAUACAAAGAUGGCGC | 17 | 6747 |
| BCL11A-5117 | − | UAAUUAUUAAUAAUCAC | 17 | 6748 |
| BCL11A-5118 | + | UACACGGCAAUGGUUCCAGA | 20 | 6749 |
| BCL11A-5119 | + | UAGAAGAAGGAGACUC | 17 | 6750 |
| BCL11A-5120 | − | UAGAAGCAAAAGCGAGG | 17 | 6751 |
| BCL11A-5121 | − | UAGAGUCCGCGUGUGUG | 17 | 6752 |

TABLE 11D-continued

4th Tier

| gRNA Name | DNA Strand | Targeting Domain | Target Site Length | SEQ ID NO |
|---|---|---|---|---|
| BCL11A-5122 | - | UAGAGUCCGCGUGUGUGGGG | 20 | 6753 |
| BCL11A-5123 | + | UAUCUCUUUUACCUCGACUC | 20 | 6754 |
| BCL11A-5124 | + | UAUUAUUGGGUUACUUACGC | 20 | 6755 |
| BCL11A-5125 | + | UAUUGGGUUACUUACGC | 17 | 6756 |
| BCL11A-5126 | + | UCACACCAAUGGACACACAU | 20 | 6757 |
| BCL11A-5127 | - | UCACGAGAAAAACCUCC | 17 | 6758 |
| BCL11A-5128 | + | UCAGGAGUCUGGAUGGA | 17 | 6759 |
| BCL11A-5129 | - | UCAUUUUAGAGUCCGCGUGU | 20 | 6760 |
| BCL11A-5130 | + | UCCCGUUUGCUUAAGUG | 17 | 6761 |
| BCL11A-5131 | - | UCCGAGAGUCGAGGUAA | 17 | 6762 |
| BCL11A-5132 | - | UCCGCGUGUGUGGGGGGGAG | 20 | 6763 |
| BCL11A-5133 | - | UCGAGGUAAAAGAGAUA | 17 | 6764 |
| BCL11A-5134 | - | UCGAGGUAAAAGAGAUAAAG | 20 | 6765 |
| BCL11A-5135 | - | UCGGCCCGCCCCUCCCC | 17 | 6766 |
| BCL11A-5136 | - | UCUAACCCGGCUCUCCCGAU | 20 | 6767 |
| BCL11A-5137 | + | UCUCGGAGGUUUUUCUC | 17 | 6768 |
| BCL11A-5138 | + | UCUUUUACCUCGACUCU | 17 | 6769 |
| BCL11A-5139 | + | UGACAUCCAAAAUAAAU | 17 | 6770 |
| BCL11A-5140 | - | UGAUGAAGAUAUUUUCU | 17 | 6771 |
| BCL11A-5141 | - | UGCAUUUUAAAUUUUUCAC | 20 | 6772 |
| BCL11A-5142 | + | UGCGGGGAGGGGGAGGU | 17 | 6773 |
| BCL11A-5143 | + | UGCUCCCCCCCACACAC | 17 | 6774 |
| BCL11A-5144 | + | UGGACACACAUCAGGGG | 17 | 6775 |
| BCL11A-5145 | + | UGGACAGAGACACACAAAAC | 20 | 6776 |
| BCL11A-5146 | + | UGGCAGGGGUGGGAGGA | 17 | 6777 |
| BCL11A-5147 | + | UGGCCAGUGCGGGGAGG | 17 | 6778 |
| BCL11A-5148 | + | UGGCCGGGAGAGAAGAA | 17 | 6779 |
| BCL11A-5149 | + | UGGCGCAGGGAAGAUGAAUU | 20 | 6780 |
| BCL11A-5150 | + | UGGCGUGGCCGGGAGAG | 17 | 6781 |
| BCL11A-5151 | + | UGGGAGGAAAGGGUGGG | 17 | 6782 |
| BCL11A-5152 | + | UGGGGUUUGCCUUGCUUGCG | 20 | 6783 |
| BCL11A-5153 | - | UGUAUUAUUUCUAAUUUAUU | 20 | 6784 |
| BCL11A-5154 | - | UUAAUAAUCACGAGAGCGCG | 20 | 6785 |
| BCL11A-5155 | + | UUAGAAAGAAGGAGACUCCA | 20 | 6786 |
| BCL11A-5156 | - | UUAGAGUCCGCGUGUGU | 17 | 6787 |
| BCL11A-5157 | - | UUAGAGUCCGCGUGUGUGGG | 20 | 6788 |
| BCL11A-5158 | - | UUGAACUUGCAGCUCAG | 17 | 6789 |
| BCL11A-5159 | - | UUGCCGUGUAUGCACUU | 17 | 6790 |
| BCL11A-5160 | - | UUGGAUGUCAAAAGGCACUG | 20 | 6791 |
| BCL11A-5161 | - | UUUAGAGUCCGCGUGUG | 17 | 6792 |
| BCL11A-5162 | - | UUUAGAGUCCGCGUGUGUGG | 20 | 6793 |
| BCL11A-5163 | - | UUUCACGAGAAAAACCU | 17 | 6794 |
| BCL11A-5164 | - | UUUUAGAGUCCGCGUGU | 17 | 6795 |
| BCL11A-5165 | - | UUUUAGAGUCCGCGUGUGUG | 20 | 6796 |
| BCL11A-5166 | - | UUUUCACGAGAAAAACCUCC | 20 | 6797 |
| BCL11A-5167 | + | UUUUGACAUCCAAAAUAAAU | 20 | 6798 |

Table 12 provides exemplary targeting domains for knocking down expression of the BCL11A gene. The targeting domains bind between 500 bp upstream and 500 bp downstream of transcription start site. It is contemplated herein that the targeting domain hybridizes to the target domain through complementary base pairing. Any of the targeting domains in the table can be used with a N. meningitidis meningitidis eiCas9 molecule to cause a steric block at the target region, e.g., between 500 bp upstream and 500 bp downstream of transcription start site to block transcription resulting in the repression of the BCL11A gene. Alternatively, any of the targeting domains in the table can be used with a N. meningitidis meningitidis eiCas9 fused to a transcriptional repressor to decrease transcription and therefore downregulate gene expression.

TABLE 12

| gRNA Name | DNA Strand | Targeting Domain | Target Site Length | SEQ ID NO |
|---|---|---|---|---|
| BCL11A-5168 | + | GCUUCUAGUCCUGCGCGCUC | 20 | 6799 |
| BCL11A-5169 | + | ACACACGCGGACUCUAAAAU | 20 | 6800 |
| BCL11A-5170 | + | UCUAGUCCUGCGCGCUC | 17 | 6801 |
| BCL11A-5171 | + | CACGCGGACUCUAAAAU | 17 | 6802 |

Table 13A provides exemplary targeting domains for the E6V target site in the HBB gene selected according to the first tier parameters. The targeting domains bind within 100 bp upstream and 100 bp downstream of the target position, good orthogonality and start with G. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase).

Any of the targeting domains in the table can be used with a S. pyogenes Cas9 (nickase) molecule to generate a single strand break. In an embodiment, dual targeting is used to create two nicks on opposite DNA strands by using S. pyogenes Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary gRNA pairs are: HBB-9 and HBB-11, HBB-9 and HBB-39, HBB-20 and HBB-11 and HBB-20 and HBB-39.

TABLE 13A

1st Tier

| gRNA Name | DNA Strand | Targeting Domain | Target Site Length | SEQ ID NO |
|---|---|---|---|---|
| HBB-1 | − | GGUGCACCUGACUCCUG | 17 | 6803 |
| HBB-2 | + | GUAACGGCAGACUUCUCCAC | 20 | 6804 |

Table 13B provides exemplary targeting domains for the E6V target site in the HBB gene selected according to the second tier parameters. The targeting domains bind within 100 bp upstream and 100 bp downstream of the target position, good orthogonality and do not start with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase).

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

TABLE 13B

2nd Tier

| gRNA Name | DNA Strand | Targeting Domain | Target Site Length | SEQ ID NO |
|---|---|---|---|---|
| HBB-3 | + | ACGGCAGACUUCUCCAC | 17 | 6805 |
| HBB-4 | + | ACUUCUCCACAGGAGUC | 17 | 6806 |
| HBB-5 | + | AGGAGUCAGGUGCACCA | 17 | 6807 |
| HBB-6 | − | CAUGGUGCACCUGACUCCUG | 20 | 6808 |
| HBB-7 | + | CACAGGAGUCAGGUGCACCA | 20 | 6809 |
| HBB-8 | + | CAGACUUCUCCACAGGAGUC | 20 | 6810 |

Table 13C provides exemplary targeting domains for the E6V target site in the HBB gene selected according to the third tier parameters. The targeting domains bind within 100 bp upstream and 100 bp downstream of the target position, and start with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase).

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

TABLE 13C

3rd Tier

| gRNA Name | DNA Strand | Targeting Domain | Target Site Length | SEQ ID NO |
|---|---|---|---|---|
| HBB-9 | − | GAAGUUGGUGGUGAGGCCCU | 20 | 6811 |
| HBB-10 | − | GCAACCUCAAACAGACACCA | 20 | 6812 |
| HBB-11 | + | GCCCCACAGGGCAGUAA | 17 | 6813 |
| HBB-12 | − | GCCGUUACUGCCCUGUG | 17 | 6814 |
| HBB-13 | − | GGAUGAAGUUGGUGGUG | 17 | 6815 |
| HBB-14 | − | GUCUGCCGUUACUGCCCUGU | 20 | 6816 |
| HBB-15 | − | GUGAACGUGGAUGAAGU | 17 | 6817 |
| HBB-16 | − | GUGAACGUGGAUGAAGUUGG | 20 | 6818 |
| HBB-17 | − | GUGGGGCAAGGUGAACG | 17 | 6819 |
| HBB-18 | − | GUGGUGAGGCCCUGGGC | 17 | 6820 |
| HBB-19 | + | GUUCACCUUGCCCCACA | 17 | 6821 |
| HBB-20 | − | GUUGGUGGUGAGGCCCU | 17 | 6822 |

Table 13D provides exemplary targeting domains for the E6V target site in the HBB gene selected according to the fourth tier parameters. The targeting domains bind within 100 bp upstream and 100 bp downstream of the target position, and do not start with G. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase).

Any of the targeting domains in the table can be used with a *S. pyogenes* Cas9 (nickase) molecule to generate a single strand break. In an embodiment, dual targeting is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

TABLE 13D

4th Tier

| gRNA Name | DNA Strand | Targeting Domain | Target Site Length | SEQ ID NO |
|---|---|---|---|---|
| HBB-21 | - | AACGUGGAUGAAGUUGG | 17 | 6823 |
| HBB-22 | + | AAGCAAAUGUAAGCAAUAGA | 20 | 6824 |
| HBB-23 | - | AAGGUGAACGUGGAUGAAGU | 20 | 6825 |
| HBB-24 | + | ACCAUGGUGUCUGUUUG | 17 | 6826 |
| HBB-25 | - | ACCUCAAACAGACACCA | 17 | 6827 |
| HBB-26 | + | ACCUUGAUACCAACCUGCCC | 20 | 6828 |
| HBB-27 | - | AGUCUGCCGUUACUGCCCUG | 20 | 6829 |
| HBB-28 | - | AGUUGGUGGUGAGGCCC | 17 | 6830 |
| HBB-29 | + | CAAAUGUAAGCAAUAGA | 17 | 6831 |
| HBB-30 | + | CACGUUCACCUUGCCCCACA | 20 | 6832 |
| HBB-31 | + | CCACGUUCACCUUGCCCCAC | 20 | 6833 |
| HBB-32 | - | CCCUGGGCAGGUUGGUAUCA | 20 | 6834 |
| HBB-33 | - | CCUGUGGGGCAAGGUGAACG | 20 | 6835 |
| HBB-34 | + | CCUUGAUACCAACCUGCCCA | 20 | 6836 |
| HBB-35 | - | CGUGGAUGAAGUUGGUGGUG | 20 | 6837 |
| HBB-36 | - | CGUUACUGCCCUGUGGGGCA | 20 | 6838 |
| HBB-37 | + | CGUUCACCUUGCCCCAC | 17 | 6839 |
| HBB-38 | - | CUGCCGUUACUGCCCUG | 17 | 6840 |
| HBB-39 | + | CUUGCCCCACAGGGCAGUAA | 20 | 6841 |
| HBB-40 | - | UACUGCCCUGUGGGGCA | 17 | 6842 |
| HBB-41 | - | UAUCAAGGUUACAAGAC | 17 | 6843 |
| HBB-42 | - | UCUGCCGUUACUGCCCUGUG | 20 | 6844 |
| HBB-43 | - | UGAAGUUGGUGGUGAGGCCC | 20 | 6845 |
| HBB-44 | - | UGAGGCCCUGGGCAGGU | 17 | 6846 |
| HBB-45 | + | UGAUACCAACCUGCCCA | 17 | 6847 |
| HBB-46 | + | UGCACCAUGGUGUCUGUUUG | 20 | 6848 |
| HBB-47 | - | UGCCGUUACUGCCCUGU | 17 | 6849 |
| HBB-48 | - | UGGGCAGGUUGGUAUCA | 17 | 6850 |
| HBB-49 | - | UGGUAUCAAGGUUACAAGAC | 20 | 6851 |
| HBB-50 | - | UGGUGAGGCCCUGGGCAGGU | 20 | 6852 |
| HBB-51 | + | UUGAUACCAACCUGCCC | 17 | 6853 |
| HBB-52 | - | UUGGUGGUGAGGCCCUGGGC | 20 | 6854 |

Table 14A provides exemplary targeting domains for the E6V target site in the HBB gene selected according to the first tier parameters. The targeting domains bind within 100 bp upstream and 100 bp downstream of the target position, good orthogonality and start with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase).

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary gRNA pairs are: HBB-9 and HBB-11, HBB-9 and HBB-39, HBB-20 and HBB-11 and HBB-20 and HBB-39.

TABLE 14A

1st Tier

| gRNA Name | DNA Strand | Targeting Domain | Target Site Length | SEQ ID NO |
|---|---|---|---|---|
| HBB-53 | + | GUAACGGCAGACUUCUCCAC | 20 | 6855 |

Table 14B provides exemplary targeting domains for the E6V target site in the HBB gene selected according to the second tier parameters. The targeting domains bind within 100 bp upstream and 100 bp downstream of the target position, good orthogonality and do not start with G. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase).

Any of the targeting domains in the table can be used with a S. aureus Cas9 (nickase) molecule to generate a single strand break. In an embodiment, dual targeting is used to create two nicks on opposite DNA strands by using S. aureus Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

TABLE 14B

2nd Tier

| gRNA Name | DNA Strand | Targeting Domain | Target Site Length | SEQ ID NO |
|---|---|---|---|---|
| HBB-54 | - | CCCUGUGGGGCAAGGUGGAC | 20 | 6856 |

Table 14C provides exemplary targeting domains for the E6V target site in the HBB gene selected according to the fifth tier parameters. The targeting domains bind within 100 bp upstream and 100 bp downstream of the target position and PAM is NNGRRV. It is contemplated herein that the targeting domain hybridizes to the target domain through complementary base pairing. Any of the targeting domains in the table can be used with a S. aureus Cas9 molecule that generates a double strand break (Cas9 nuclease) or a single-strand break (Cas9 nickase).

Any of the targeting domains in the table can be used with a *S. aureus* Cas9 (nickase) molecule to generate a single strand break. In an embodiment, dual targeting is used to create two nicks on opposite DNA strands by using *S. aureus* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp.

TABLE 14C

5th Tier

| gRNA Name | DNA Strand | Targeting Domain | Target Site Length | SEQ ID NO |
|---|---|---|---|---|
| HBB-55 | − | AGUCUGCCGUUACUGCCCUG | 20 | 6857 |
| HBB-56 | − | AAGUCUGCCGUUACUGCCCU | 20 | 6858 |
| HBB-57 | + | AACCUUGAUACCAACCUGCC | 20 | 6859 |
| HBB-58 | + | UCCACGUUCACCUUGCCCCA | 20 | 6860 |
| HBB-59 | + | GCUAGUGAACACAGUUGUGU | 20 | 6861 |
| HBB-60 | − | CCAUGGUGCACCUGACUCCU | 20 | 6862 |
| HBB-61 | − | CAUGGUGCACCUGACUCCUG | 20 | 6863 |
| HBB-62 | + | AGGUGCACCAUGGUGUCUGU | 20 | 6864 |
| HBB-63 | − | UGGUGCACCUGACUCCUGUG | 20 | 6865 |
| HBB-64 | − | GAACGUGGAUGAAGUUGGUG | 20 | 6866 |
| HBB-65 | − | UUACUGCCCUGUGGGGCAAG | 20 | 6867 |
| HBB-66 | + | GUGUCUGUUUGAGGUUGCUA | 20 | 6868 |
| HBB-67 | − | GUGGGGCAAGGUGAACGUGG | 20 | 6869 |
| HBB-68 | − | AUGAAGUUGGUGGUGAGGCC | 20 | 6870 |
| HBB-69 | + | AGUAACGGCAGACUUCUCCA | 20 | 6871 |

Table 15A provides exemplary targeting domains for knocking out the BCL11A gene selected according to the first tier parameters. The targeting domains bind within the first 500 bp of the coding sequence (e.g., within 500 bp downstream from the start codon) and have a high level of orthogonality. It is contemplated herein that in an embodiment the targeting domain hybridizes to the target domain through complementary base pairing. Any of the targeting domains in the table can be used with a *S. pyogenes* Cas9 molecule that generates a double stranded break (Cas9 nuclease) or a single-stranded break (Cas9 nickase).

TABLE 15A

1st Tier

| gRNA Name | DNA Strand | Targeting Domain | Target Site Length | SEQ ID NO: |
|---|---|---|---|---|
| BCL11A-5318 | + | UCAUCUCGAUUGGUGAA | 17 | 6872 |
| BCL11A-5319 | + | UUGCUUGCGGCGAGACA | 17 | 6873 |
| BCL11A-5320 | − | AUGUCUCGCCGCAAGCA | 17 | 6874 |

TABLE 15A-continued

1st Tier

| gRNA Name | DNA Strand | Targeting Domain | Target Site Length | SEQ ID NO: |
|---|---|---|---|---|
| BCL11A-5321 | − | GCAGAAUAUGCCCCGCA | 17 | 6875 |
| BCL11A-5322 | − | CCGUUGGGAGCUCCAGA | 17 | 6876 |
| BCL11A-5323 | + | CUCCAUGUGCAGAACGA | 17 | 6877 |
| BCL11A-5324 | + | UCGAUUGGUGAAGGGGA | 17 | 6878 |
| BCL11A-5325 | + | CAUCCUCUGGCGUGACC | 17 | 6879 |
| BCL11A-5326 | − | GCUCUAAUCCCCACGCC | 17 | 6880 |
| BCL11A-5327 | + | CCCGUUUGCUUAAGUGC | 17 | 6881 |
| BCL11A-5328 | + | AAACAAUCGUCAUCCUC | 17 | 6882 |
| BCL11A-5329 | + | CCCAACGGGCCGUGGUC | 17 | 6883 |
| BCL11A-5330 | + | CAUCUCGAUUGGUGAAG | 17 | 6884 |
| BCL11A-5331 | − | CAUCCAGGUCACGCCAG | 17 | 6885 |
| BCL11A-5332 | − | UUAUCAACGUCAUCUAG | 17 | 6886 |
| BCL11A-5333 | + | GAGCUCCCAACGGGCCG | 17 | 6887 |
| BCL11A-5334 | + | UGCACUCAUCCCAGGCG | 17 | 6888 |
| BCL11A-5335 | + | AGACAUGGUGGGCUGCG | 17 | 6889 |
| BCL11A-5336 | + | CGUUUGCUUAAGUGCUG | 17 | 6890 |
| BCL11A-5337 | + | GCUUUUUCAUCUCGAU | 17 | 6891 |
| BCL11A-5338 | + | CCGUUUGCUUAAGUGCU | 17 | 6892 |
| BCL11A-5339 | − | UCCAAUCCCGUGGAGGU | 17 | 6893 |
| BCL11A-5340 | + | UUGCGGCGAGACAUGGU | 17 | 6894 |
| BCL11A-5341 | − | AUGACCUCCUCACCUGU | 17 | 6895 |
| BCL11A-5342 | − | UUAUUUUAUCGAGCACAAA | 20 | 6896 |
| BCL11A-5343 | + | UCCCCUUCUGGAGCUCCCAA | 20 | 6897 |
| BCL11A-5344 | + | UUUUCAUCUCGAUUGGUGAA | 20 | 6898 |
| BCL11A-5345 | + | GCCUUGCUUGCGGCGAGACA | 20 | 6899 |
| BCL11A-5346 | − | ACCAUGUCUCGCCGCAAGCA | 20 | 6900 |
| BCL11A-5347 | + | GAGCUCCAUGUGCAGAACGA | 20 | 6901 |
| BCL11A-5348 | − | UCACAGAUAAACUUCUGCAC | 20 | 6902 |
| BCL11A-5349 | + | CGUCAUCCUCUGGCGUGACC | 20 | 6903 |
| BCL11A-5350 | − | GGAGCUCUAAUCCCCACGCC | 20 | 6904 |
| BCL11A-5351 | − | UCCCGUGGAGGUUGGCAUCC | 20 | 6905 |
| BCL11A-5352 | + | AUUCCCGUUUGCUUAAGUGC | 20 | 6906 |
| BCL11A-5353 | + | CCCCCAAUGGGAAGUUCAUC | 20 | 6907 |
| BCL11A-5354 | + | GCUCCCAACGGGCCGUGGUC | 20 | 6908 |
| BCL11A-5355 | + | UUUCAUCUCGAUUGGUGAAG | 20 | 6909 |
| BCL11A-5356 | − | UGUUUAUCAACGUCAUCUAG | 20 | 6910 |
| BCL11A-5357 | + | AGAGCUCCAUGUGCAGAACG | 20 | 6911 |

TABLE 15A-continued

1st Tier

| gRNA Name | DNA Strand | Targeting Domain | Target Site Length | SEQ ID NO: |
|---|---|---|---|---|
| BCL11A-5358 | − | GAAAAAAGCAUCCAAUCCCG | 20 | 6912 |
| BCL11A-5359 | + | GCGAGACAUGGUGGGCUGCG | 20 | 6913 |
| BCL11A-5360 | − | CAGAUAAACUUCUGCACUGG | 20 | 6914 |
| BCL11A-5361 | + | CGGCGAGACAUGGUGGGCUG | 20 | 6915 |
| BCL11A-5362 | + | CUGCACUCAUCCCAGGCGUG | 20 | 6916 |
| BCL11A-5363 | − | UGAACCAGACCACGGCCCGU | 20 | 6917 |
| BCL11A-5364 | − | GCAUCCAAUCCCGUGGAGGU | 20 | 6918 |
| BCL11A-5365 | + | UGCUUGCGGCGAGACAUGGU | 20 | 6919 |
| BCL11A-5366 | + | UCAAGAGGCUCGGCUGUGGU | 20 | 6920 |
| BCL11A-5367 | − | AUCAUGACCUCCUCACCUGU | 20 | 6921 |

Table 15B provides exemplary targeting domains for knocking out the BCL11A gene selected according to the second tier parameters. The targeting domains bind within the first 500 bp of the coding sequence (e.g., within 500 bp downstream from the start codon). It is contemplated herein that in an embodiment the targeting domain hybridizes to the target domain through complementary base pairing. Any of the targeting domains in the table can be used with a *S. pyogenes* Cas9 molecule that generates a double stranded break (Cas9 nuclease) or a single-stranded break (Cas9 nickase).

TABLE 15B

2nd Tier

| gRNA Name | DNA Strand | Targeting Domain | Target Site Length | SEQ ID NO: |
|---|---|---|---|---|
| BCL11A-5368 | − | UUUUUAUCGAGCACAAA | 17 | 6922 |
| BCL11A-5369 | − | CCCAGCACUUAAGCAAA | 17 | 6923 |
| BCL11A-5370 | + | AUAAGAAUGUCCCCCAA | 17 | 6924 |
| BCL11A-5371 | + | CCUUCUGGAGCUCCCAA | 17 | 6925 |
| BCL11A-5372 | − | AAACGGAAACAAUGCAA | 17 | 6926 |
| BCL11A-5373 | + | UUCAUCAUCUGUAAGAA | 17 | 6927 |
| BCL11A-5374 | − | CGUUGGGAGCUCCAGAA | 17 | 6928 |
| BCL11A-5375 | − | UCCCCUCGUUCUGCACA | 17 | 6929 |
| BCL11A-5376 | − | GAUGAUGAACCAGACCA | 17 | 6930 |
| BCL11A-5377 | + | CUGGAUGCCAACCUCCA | 17 | 6931 |
| BCL11A-5378 | − | CAGGUAAAUGAGAAGCA | 17 | 6932 |
| BCL11A-5379 | − | UAAACUUCUGCACUGGA | 17 | 6933 |
| BCL11A-5380 | + | UUCAUCUCGAUUGGUGA | 17 | 6934 |
| BCL11A-5381 | + | CAUUUGUAGAAGAAAUA | 17 | 6935 |
| BCL11A-5382 | − | AGGAAUUUGCCCCAAAC | 17 | 6936 |

TABLE 15B-continued

2nd Tier

| gRNA Name | DNA Strand | Targeting Domain | Target Site Length | SEQ ID NO: |
|---|---|---|---|---|
| BCL11A-5383 | − | CCAGCACUUAAGCAAAC | 17 | 6937 |
| BCL11A-5384 | + | CUUCUGGAGCUCCCAAC | 17 | 6938 |
| BCL11A-5385 | + | CAUCUGGCACUGCCCAC | 17 | 6939 |
| BCL11A-5386 | + | UGGAUGCCAACCUCCAC | 17 | 6940 |
| BCL11A-5387 | − | CAGAUAAACUUCUGCAC | 17 | 6941 |
| BCL11A-5388 | + | UAUUCUGCACUCAUCCC | 17 | 6942 |
| BCL11A-5389 | − | CGUGGAGGUUGGCAUCC | 17 | 6943 |
| BCL11A-5390 | − | AAACAGGAACACAUAGC | 17 | 6944 |
| BCL11A-5391 | − | UGCAGAAUAUGCCCCGC | 17 | 6945 |
| BCL11A-5392 | + | AUGGUGGGCUGCGGGGC | 17 | 6946 |
| BCL11A-5393 | + | ACUUACAAAUACCCUGC | 17 | 6947 |
| BCL11A-5394 | + | UGUACAUGUGUAGCUGC | 17 | 6948 |
| BCL11A-5395 | + | GAGACAUGGUGGGCUGC | 17 | 6949 |
| BCL11A-5396 | − | GUGUUGUAUUAUUUGC | 17 | 6950 |
| BCL11A-5397 | + | CCAAUGGGAAGUUCAUC | 17 | 6951 |
| BCL11A-5398 | + | AGGUCAUGAUCCCCUUC | 17 | 6952 |
| BCL11A-5399 | + | GUAAGAAUGGCUUCAAG | 17 | 6953 |
| BCL11A-5400 | − | GUUGGGAGCUCCAGAAG | 17 | 6954 |
| BCL11A-5401 | + | CAGCUUUUUCUAAGCAG | 17 | 6955 |
| BCL11A-5402 | + | UCCAUGUGCAGAACGAG | 17 | 6956 |
| BCL11A-2671 | + | CAGAACGAGGGGAGGAG | 17 | 6957 |
| BCL11A-5403 | − | AAACUUCUGCACUGGAG | 17 | 6958 |
| BCL11A-5404 | + | GCUCCAUGUGCAGAACG | 17 | 6959 |
| BCL11A-5405 | − | AAAAGCAUCCAAUCCCG | 17 | 6960 |
| BCL11A-5406 | + | CUUACAAAUACCCUGCG | 17 | 6961 |
| BCL11A-5407 | + | AUUGGUGAAGGGGAAGG | 17 | 6962 |
| BCL11A-5408 | + | ACUGCCCACAGGUGAGG | 17 | 6963 |
| BCL11A-4500 | + | GGGGCGGGCGGCGGCGG | 17 | 6964 |
| BCL11A-5409 | + | UGCGGGGCGGGCGGCGG | 17 | 6965 |
| BCL11A-5410 | + | GGCUGCGGGGCGGGCGG | 17 | 6966 |
| BCL11A-5411 | + | GUGGGCUGCGGGGCGGG | 17 | 6967 |
| BCL11A-5412 | + | AUGUGCAGAACGAGGGG | 17 | 6968 |
| BCL11A-5413 | + | CAUGGUGGGCUGCGGGG | 17 | 6969 |
| BCL11A-5414 | + | CUUGCGGCGAGACAUGG | 17 | 6970 |
| BCL11A-5415 | − | AUAAACUUCUGCACUGG | 17 | 6971 |
| BCL11A-5416 | − | AGCAUCCAAUCCCGUGG | 17 | 6972 |
| BCL11A-5417 | − | GAUGAACUUCCCAUUGG | 17 | 6973 |

TABLE 15B-continued

2nd Tier

| gRNA Name | DNA Strand | Targeting Domain | Target Site Length | SEQ ID NO: |
|---|---|---|---|---|
| BCL11A-5418 | - | CAUGACCUCCUCACCUG | 17 | 6974 |
| BCL11A-5419 | + | AACUUACAAAUACCCUG | 17 | 6975 |
| BCL11A-5420 | - | CUGCUUAGAAAAAGCUG | 17 | 6976 |
| BCL11A-5421 | + | UUCAAGAGGCUCGGCUG | 17 | 6977 |
| BCL11A-5422 | + | CGAGACAUGGUGGGCUG | 17 | 6978 |
| BCL11A-5423 | + | CACUCAUCCCAGGCGUG | 17 | 6979 |
| BCL11A-5424 | + | GGCACUGCCCACAGGUG | 17 | 6980 |
| BCL11A-5425 | - | AGAUGAACUUCCCAUUG | 17 | 6981 |
| BCL11A-5426 | + | GGGGUUUGCCUUGCUUG | 17 | 6982 |
| BCL11A-5427 | + | CUAUGUGUUCCUGUUUG | 17 | 6983 |
| BCL11A-5428 | + | UAAGAAUGUCCCCCAAU | 17 | 6984 |
| BCL11A-5429 | - | CCAGAUGAACUUCCCAU | 17 | 6985 |
| BCL11A-5430 | + | GCCAACCUCCACGGGAU | 17 | 6986 |
| BCL11A-5431 | + | AUUAUUAUUACUAUUAU | 17 | 6987 |
| BCL11A-5432 | - | CUCUAAUCCCCACGCCU | 17 | 6988 |
| BCL11A-5433 | + | AAUGGCUUCAAGAGGCU | 17 | 6989 |
| BCL11A-5434 | + | GUACAUGUGUAGCUGCU | 17 | 6990 |
| BCL11A-5435 | - | ACCAGACCACGGCCCGU | 17 | 6991 |
| BCL11A-5436 | + | GCACUCAUCCCAGGCGU | 17 | 6992 |
| BCL11A-5437 | + | AGAGGCUCGGCUGUGGU | 17 | 6993 |
| BCL11A-5438 | - | CAGAUGAACUUCCCAUU | 17 | 6994 |
| BCL11A-5439 | + | UUAUUAUUACUAUUAUU | 17 | 6995 |
| BCL11A-5440 | - | CCAGACCACGGCCCGUU | 17 | 6996 |
| BCL11A-5441 | + | UGCUAUGUGUUCCUGUU | 17 | 6997 |
| BCL11A-5442 | + | GCUAUGUGUUCCUGUUU | 17 | 6998 |
| BCL11A-5443 | - | AACCCCAGCACUUAAGCAAA | 20 | 6999 |
| BCL11A-5444 | + | AAAAUAAGAAUGUCCCCCAA | 20 | 7000 |
| BCL11A-5445 | - | CACAAACGGAAACAAUGCAA | 20 | 7001 |
| BCL11A-5446 | + | UGGUUCAUCAUCGUAAGAA | 20 | 7002 |
| BCL11A-5447 | - | GCCCGUUGGGAGCUCCAGAA | 20 | 7003 |
| BCL11A-5448 | - | UCCUCCCCUCGUUCUGCACA | 20 | 7004 |
| BCL11A-5449 | - | ACAGAUGAUGAACCAGACCA | 20 | 7005 |
| BCL11A-5450 | + | GACCUGGAUGCCAACCUCCA | 20 | 7006 |
| BCL11A-5451 | - | UAGCAGGUAAAUGAGAAGCA | 20 | 7007 |
| BCL11A-5452 | - | AGUGCAGAAUAUGCCCCGCA | 20 | 7008 |
| BCL11A-5453 | + | GGCCCGUUGGGAGCUCCAGA | 20 | 7009 |
| BCL11A-5454 | + | AUCUCGAUUGGUGAAGGGA | 20 | 7010 |
| BCL11A-5455 | - | AGAUAAACUUCUGCACUGGA | 20 | 7011 |
| BCL11A-5456 | + | UUUUUCAUCUCGAUUGGUGA | 20 | 7012 |
| BCL11A-5457 | - | UAGAGGAAUUUGCCCCAAAC | 20 | 7013 |
| BCL11A-5458 | - | ACCCCAGCACUUAAGCAAAC | 20 | 7014 |
| BCL11A-5459 | + | CCCCUUCUGGAGCUCCCAAC | 20 | 7015 |
| BCL11A-5460 | + | GUUCAUCUGGCACUGCCCAC | 20 | 7016 |
| BCL11A-5461 | + | ACCUGGAUGCCAACCUCCAC | 20 | 7017 |
| BCL11A-5462 | + | GCAUAUUCUGCACUCAUCCC | 20 | 7018 |
| BCL11A-5463 | - | CCCAAACAGGAACACAUAGC | 20 | 7019 |
| BCL11A-5464 | - | GAGUGCAGAAUAUGCCCCGC | 20 | 7020 |
| BCL11A-5465 | + | GACAUGGUGGGCUGCGGGGC | 20 | 7021 |
| BCL11A-5466 | + | UCAACUUACAAAUACCCUGC | 20 | 7022 |
| BCL11A-5467 | + | AGUUGUACAUGUGUAGCUGC | 20 | 7023 |
| BCL11A-5468 | + | GGCGAGACAUGGUGGGCUGC | 20 | 7024 |
| BCL11A-5469 | - | UUGGUGUUGUAUUAUUUGC | 20 | 7025 |
| BCL11A-5470 | + | GAUAAACAAUCGUCAUCCUC | 20 | 7026 |
| BCL11A-5471 | + | AGGAGGUCAUGAUCCCCUUC | 20 | 7027 |
| BCL11A-5472 | + | UCUGUAAGAAUGGCUUCAAG | 20 | 7028 |
| BCL11A-5473 | - | CCCGUUGGGAGCUCCAGAAG | 20 | 7029 |
| BCL11A-5474 | - | UGGCAUCCAGGUCACGCCAG | 20 | 7030 |
| BCL11A-5475 | + | CCACAGCUUUUUCUAAGCAG | 20 | 7031 |
| BCL11A-5476 | + | AGCUCCAUGUGCAGAACGAG | 20 | 7032 |
| BCL11A-5477 | + | GUGCAGAACGAGGGGAGGAG | 20 | 7033 |
| BCL11A-5478 | - | GAUAAACUUCUGCACUGGAG | 20 | 7034 |
| BCL11A-5479 | + | CUGGAGCUCCAACGGGCCG | 20 | 7035 |
| BCL11A-5480 | + | UUCUGCACUCAUCCCAGGCG | 20 | 7036 |
| BCL11A-5481 | + | CAACUUACAAAUACCCUGCG | 20 | 7037 |
| BCL11A-5482 | + | UCGAUUGGUGAAGGGAAGG | 20 | 7038 |
| BCL11A-5483 | + | GGCACUGCCCACAGGUGAGG | 20 | 7039 |
| BCL11A-5484 | + | UGCGGGGCGGGCGGCGGCGG | 20 | 7040 |
| BCL11A-5485 | + | GGCUGCGGGGCGGGCGGCGG | 20 | 7041 |
| BCL11A-5486 | + | GUGGGCUGCGGGGCGGGCGG | 20 | 7042 |
| BCL11A-5487 | + | AUGGUGGGCUGCGGGGCGGG | 20 | 7043 |
| BCL11A-5488 | + | UCCAUGUGCAGAACGAGGGG | 20 | 7044 |
| BCL11A-5489 | + | AGACAUGGUGGGCUGCGGGG | 20 | 7045 |
| BCL11A-5490 | + | UUGCUUGCGGCGAGACAUGG | 20 | 7046 |
| BCL11A-5491 | - | AAAAGCAUCCAAUCCCGUGG | 20 | 7047 |

TABLE 15B-continued

2nd Tier

| gRNA Name | DNA Strand | Targeting Domain | Target Site Length | SEQ ID NO: |
|---|---|---|---|---|
| BCL11A-5492 | - | CCAGAUGAACUUCCCAUUGG | 20 | 7048 |
| BCL11A-5493 | - | GAUCAUGACCUCCUCACCUG | 20 | 7049 |
| BCL11A-5494 | + | CUCAACUUACAAAUACCCUG | 20 | 7050 |
| BCL11A-5495 | - | CCUCUGCUUAGAAAAAGCUG | 20 | 7051 |
| BCL11A-5496 | + | GGCUUCAAGAGGCUCGGCUG | 20 | 7052 |
| BCL11A-5497 | + | UCCCGUUUGCUUAAGUGCUG | 20 | 7053 |
| BCL11A-5498 | + | UCUGGCACUGCCCACAGGUG | 20 | 7054 |
| BCL11A-5499 | - | GCCAGAUGAACUUCCCAUUG | 20 | 7055 |
| BCL11A-5500 | + | GCUGGGGUUUGCCUUGCUUG | 20 | 7056 |
| BCL11A-5501 | + | CUGCUAUGUGUUCCUGUUUG | 20 | 7057 |
| BCL11A-5502 | + | AAAUAAGAAUGUCCCCCAAU | 20 | 7058 |
| BCL11A-5503 | - | GUGCCAGAUGAACUUCCCAU | 20 | 7059 |
| BCL11A-5504 | + | GAUGCUUUUUUCAUCUCGAU | 20 | 7060 |
| BCL11A-5505 | + | GAUGCCAACCUCCACGGGAU | 20 | 7061 |
| BCL11A-5506 | - | GAGCUCUAAUCCCCACGCCU | 20 | 7062 |
| BCL11A-5507 | + | AAGAAUGGCUUCAAGAGGCU | 20 | 7063 |
| BCL11A-5508 | + | GUUGUACAUGUGUAGCUGCU | 20 | 7064 |
| BCL11A-5509 | + | UUCCCGUUUGCUUAAGUGCU | 20 | 7065 |
| BCL11A-5510 | + | UCUGCACUCAUCCCAGGCGU | 20 | 7066 |
| BCL11A-5511 | - | UGCCAGAUGAACUUCCCAUU | 20 | 7067 |
| BCL11A-5512 | - | GAACCAGACCACGGCCCGUU | 20 | 7068 |
| BCL11A-5513 | + | ACCUGCUAUGUGUUCCUGUU | 20 | 7069 |
| BCL11A-5514 | + | CCUGCUAUGUGUUCCUGUUU | 20 | 7070 |

Table 15C provides exemplary targeting domains for knocking out the BCL11A gene selected according to the third tier parameters. The targeting domains fall in the coding sequence of the gene, downstream of the first 500 bp of coding sequence (e.g., anywhere from +500 (relative to the start codon) to the stop codon of the gene). It is contemplated herein that in an embodiment the targeting domain hybridizes to the target domain through complementary base pairing. Any of the targeting domains in the table can be used with a *S. pyogenes* Cas9 molecule that generates a double stranded break (Cas9 nuclease) or a single-stranded break (Cas9 nickase).

TABLE 15C

3rd Tier

| gRNA Name | DNA Strand | Targeting Domain | Target Site Length | SEQ ID NO: |
|---|---|---|---|---|
| BCL11A-5515 | + | UCCGACGAGGAGGCAAA | 17 | 7071 |
| BCL11A-5516 | + | AUUCUUAGCAGGUUAAA | 17 | 7072 |
| BCL11A-5517 | - | GCUGCGGUUGAAUCCAA | 17 | 7073 |
| BCL11A-5518 | - | GGCCCAGCCCUAUGCAA | 17 | 7074 |
| BCL11A-5519 | + | CCGCAGCACCCUGUCAA | 17 | 7075 |
| BCL11A-5520 | - | CUUCCGGCCUGGCAGAA | 17 | 7076 |
| BCL11A-5521 | + | UUGAUGCGCUUAGAGAA | 17 | 7077 |
| BCL11A-5522 | - | AACCUGAUCCCGGAGAA | 17 | 7078 |
| BCL11A-5523 | - | GAGCACUCCUCGGAGAA | 17 | 7079 |
| BCL11A-5524 | + | CUGGGUACUACGCCGAA | 17 | 7080 |
| BCL11A-5525 | + | UCUCCGAAGCUAAGGAA | 17 | 7081 |
| BCL11A-5526 | + | GGGGGCGUCGCCAGGAA | 17 | 7082 |
| BCL11A-5527 | + | UUGCUACCGGCUGGAA | 17 | 7083 |
| BCL11A-5528 | + | CUGCACCUAGUCCUGAA | 17 | 7084 |
| BCL11A-5529 | + | AACCAUGCACUGGUGAA | 17 | 7085 |
| BCL11A-5530 | + | AUUUCUCAGAACUUAA | 17 | 7086 |
| BCL11A-5531 | + | UAUUCUUAGCAGGUUAA | 17 | 7087 |

TABLE 15C-continued

3rd Tier

| gRNA Name | DNA Strand | Targeting Domain | Target Site Length | SEQ ID NO: |
|---|---|---|---|---|
| BCL11A-5532 | − | GACGAUGGCACUGUUAA | 17 | 7088 |
| BCL11A-5533 | + | CGGUGGUGGACUAAACA | 17 | 7089 |
| BCL11A-5534 | − | GGCCGCGAUGCCCAACA | 17 | 7090 |
| BCL11A-5535 | − | UACUUAGAAAGCGAACA | 17 | 7091 |
| BCL11A-2969 | − | GCACCGGCGCAGCCACA | 17 | 7092 |
| BCL11A-2924 | − | CGAGGCCGAGGGCCACA | 17 | 7093 |
| BCL11A-5536 | − | CCCGAGUGCCUUUGACA | 17 | 7094 |
| BCL11A-5537 | + | CUUGAACUUGGCCACCA | 17 | 7095 |
| BCL11A-5538 | − | AAAAUUUGAAGCCCCCA | 17 | 7096 |
| BCL11A-5539 | + | CUGCAAUAUGAAUCCCA | 17 | 7097 |
| BCL11A-5540 | − | UAUGGAGCCUCCCGCCA | 17 | 7098 |
| BCL11A-5541 | + | CGGGUGAUGGGUGGCCA | 17 | 7099 |
| BCL11A-5542 | + | UCUCCUAGAGAAAUCCA | 17 | 7100 |
| BCL11A-5543 | − | UCCCAGCCACCUCUCCA | 17 | 7101 |
| BCL11A-5544 | − | CUCGGGGCGCAGCGGCA | 17 | 7102 |
| BCL11A-5545 | − | CGACGUCAUGCAGGGCA | 17 | 7103 |
| BCL11A-5546 | + | CUGCAUGACGUCGGGCA | 17 | 7104 |
| BCL11A-5547 | − | GACUUAGAGAGCUGGCA | 17 | 7105 |
| BCL11A-5548 | − | CUGCCCGACGUCAUGCA | 17 | 7106 |
| BCL11A-5549 | + | CUCGCUGAAGUGCUGCA | 17 | 7107 |
| BCL11A-5550 | − | AGCCAUUCACCAGUGCA | 17 | 7108 |
| BCL11A-5551 | − | CACGCACAGAACACUCA | 17 | 7109 |
| BCL11A-5552 | + | GUCGGACUUGACCGUCA | 17 | 7110 |
| BCL11A-5553 | + | ACCAACCCGCGGGUCA | 17 | 7111 |
| BCL11A-5554 | − | AGGCCCAGCUCAAAAGA | 17 | 7112 |
| BCL11A-5555 | − | GCUUCCGGCCUGGCAGA | 17 | 7113 |
| BCL11A-5556 | − | CCUGGGGGCGGAAGAGA | 17 | 7114 |
| BCL11A-5557 | + | CUUGAUGCGCUUAGAGA | 17 | 7115 |
| BCL11A-5558 | − | GCUGACGGAGAGCGAGA | 17 | 7116 |
| BCL11A-5559 | − | GCGCAUCAAGCUCGAGA | 17 | 7117 |
| BCL11A-5560 | − | UCGGACCGCAUAGACGA | 17 | 7118 |
| BCL11A-5561 | − | ACGGUCAAGUCCGACGA | 17 | 7119 |
| BCL11A-5562 | − | CACCUGGCCGAGGCCGA | 17 | 7120 |
| BCL11A-5563 | + | GUCUCCGAAGCUAAGGA | 17 | 7121 |
| BCL11A-5564 | + | GGGGGGCGUCGCCAGGA | 17 | 7122 |
| BCL11A-5565 | + | AGGUUGGAGACAGAGGA | 17 | 7123 |
| BCL11A-5566 | + | GGGCGGAUUGCAGAGGA | 17 | 7124 |

TABLE 15C-continued

3rd Tier

| gRNA Name | DNA Strand | Targeting Domain | Target Site Length | SEQ ID NO: |
|---|---|---|---|---|
| BCL11A-5567 | + | GGGGCUGGGAGGGAGGA | 17 | 7125 |
| BCL11A-5568 | − | CCGGGGAGCUGGACGGA | 17 | 7126 |
| BCL11A-5569 | − | GUGUGGCAGUUUUCGGA | 17 | 7127 |
| BCL11A-5570 | + | GGAUUGCAGAGGAGGGA | 17 | 7128 |
| BCL11A-5571 | + | UUGACCGGGGCUGGGA | 17 | 7129 |
| BCL11A-5572 | + | UGGAGAGGUGGCUGGGA | 17 | 7130 |
| BCL11A-5573 | − | CCGCCCGGGGAGCUGGA | 17 | 7131 |
| BCL11A-5574 | − | GCGGCACGGGAAGUGGA | 17 | 7132 |
| BCL11A-5575 | + | GCCCAGGACCUGGUGGA | 17 | 7133 |
| BCL11A-5576 | − | CAAAUCGUCCCCCAUGA | 17 | 7134 |
| BCL11A-5577 | + | UCUGCACCUAGUCCUGA | 17 | 7135 |
| BCL11A-5578 | − | GGAGGAGGAGGAGCUGA | 17 | 7136 |
| BCL11A-5579 | + | CAAAGGCACUCGGGUGA | 17 | 7137 |
| BCL11A-5580 | + | GGCCCGGACCACUAAUA | 17 | 7138 |
| BCL11A-5581 | + | GCAGUAACCUUUGCAUA | 17 | 7139 |
| BCL11A-5582 | − | AGCGAGAGGGUGGACUA | 17 | 7140 |
| BCL11A-5583 | + | UGGAGUCUCCGAAGCUA | 17 | 7141 |
| BCL11A-5584 | − | GUUGAAUCCAAUGGCUA | 17 | 7142 |
| BCL11A-5585 | + | CACAGGUUGCACUUGUA | 17 | 7143 |
| BCL11A-5586 | + | AAUUUCUCAGAACUUA | 17 | 7144 |
| BCL11A-5587 | + | UCGGUGGUGGACUAAAC | 17 | 7145 |
| BCL11A-5588 | − | ACCUGAUCCCGGAGAAC | 17 | 7146 |
| BCL11A-5589 | − | AGCACUCCUCGGAGAAC | 17 | 7147 |
| BCL11A-2979 | − | CACCGGCGCAGCCACAC | 17 | 7148 |
| BCL11A-2916 | − | CCGAGGCCGAGGGCCAC | 17 | 7149 |
| BCL11A-5590 | + | UGCACGCGUGGUCGCAC | 17 | 7150 |
| BCL11A-5591 | − | UCGGGGCGCAGCGGCAC | 17 | 7151 |
| BCL11A-5592 | + | CAAGAGAAACCAUGCAC | 17 | 7152 |
| BCL11A-5593 | − | GCAACCUGGUGGUGCAC | 17 | 7153 |
| BCL11A-5594 | + | GCAGCAGCUUUUUGGAC | 17 | 7154 |
| BCL11A-5595 | + | CAUGACUUGGACUUGAC | 17 | 7155 |
| BCL11A-5596 | − | ACCCGAGUGCCUUUGAC | 17 | 7156 |
| BCL11A-5597 | − | CAAAUUUCAGAGCAACC | 17 | 7157 |
| BCL11A-5598 | − | GCCAGCUCCCCGGAACC | 17 | 7158 |
| BCL11A-5599 | + | UGCGCCGGUGCACCACC | 17 | 7159 |
| BCL11A-5600 | − | GCAUAAGCGCGGCCACC | 17 | 7160 |
| BCL11A-5601 | − | CAGCGAGGCCUUCCACC | 17 | 7161 |
| BCL11A-5602 | + | GCUUCUCGCCCAGGACC | 17 | 7162 |

TABLE 15C-continued

3rd Tier

| gRNA Name | DNA Strand | Targeting Domain | Target Site Length | SEQ ID NO: |
|---|---|---|---|---|
| BCL11A-5603 | + | AUGACUUGGACUUGACC | 17 | 7163 |
| BCL11A-5604 | − | AACCUGCUAAGAAUACC | 17 | 7164 |
| BCL11A-5605 | + | AAGGGCGGCUUGCUACC | 17 | 7165 |
| BCL11A-5606 | − | CGACCACGCGUGCACCC | 17 | 7166 |
| BCL11A-5607 | − | GAAAAUUUGAAGCCCCC | 17 | 7167 |
| BCL11A-5608 | + | CCAUCUCUUCCGCCCCC | 17 | 7168 |
| BCL11A-5609 | − | UCCUCCCUCCCAGCCCC | 17 | 7169 |
| BCL11A-5610 | − | GGAGUUCGACCUGCCCC | 17 | 7170 |
| BCL11A-5611 | + | CCUCCGUCCAGCUCCCC | 17 | 7171 |
| BCL11A-5612 | − | GGCCGCGGCUGCUCCCC | 17 | 7172 |
| BCL11A-5613 | − | AGCCCACCGCUGUCCCC | 17 | 7173 |
| BCL11A-5614 | − | GCUUCUCCACACCGCCC | 17 | 7174 |
| BCL11A-5615 | + | CCGAGGCCGACUCGCCC | 17 | 7175 |
| BCL11A-5616 | + | GCUUAUGCUUCUCGCCC | 17 | 7176 |
| BCL11A-5617 | − | AUUAGUGGUCCGGGCCC | 17 | 7177 |
| BCL11A-5618 | − | GGCGGAAGAGAUGGCCC | 17 | 7178 |
| BCL11A-5619 | + | UUGAGCUGGGCCUGCCC | 17 | 7179 |
| BCL11A-5620 | − | CUCCACCGCCAGCUCCC | 17 | 7180 |
| BCL11A-5621 | + | CCCUCCGUCCAGCUCCC | 17 | 7181 |
| BCL11A-5622 | − | UGGCCGCGGCUGCUCCC | 17 | 7182 |
| BCL11A-5623 | − | CUGCAACCAUUCCAGCC | 17 | 7183 |
| BCL11A-5624 | − | CGGCUUCGGGCUGAGCC | 17 | 7184 |
| BCL11A-5625 | − | CGCUUCUCCACACCGCC | 17 | 7185 |
| BCL11A-5626 | − | CCACCGCAUAGAGCGCC | 17 | 7186 |
| BCL11A-5627 | + | CCCGAGGCCGACUCGCC | 17 | 7187 |
| BCL11A-5628 | + | GGAGGGGGGCGUCGCC | 17 | 7188 |
| BCL11A-5629 | + | AUAGGGCUGGGCCGGCC | 17 | 7189 |
| BCL11A-5630 | − | GAGAGAGGCUUCCGGCC | 17 | 7190 |
| BCL11A-5631 | + | UGUUGGGCAUCGCGGCC | 17 | 7191 |
| BCL11A-5632 | + | GGCCCUCGGCCUCGGCC | 17 | 7192 |
| BCL11A-5633 | + | CUGGGCCUGCCCGGGCC | 17 | 7193 |
| BCL11A-5634 | − | UAUUAGUGGUCCGGGCC | 17 | 7194 |
| BCL11A-5635 | + | GCUUCAGCUUGCUGGCC | 17 | 7195 |
| BCL11A-5636 | + | UCGGGUGAUGGGUGGCC | 17 | 7196 |
| BCL11A-5637 | + | UUUGAGCUGGGCCUGCC | 17 | 7197 |
| BCL11A-5638 | + | GGGAUCUUUGAGCUGCC | 17 | 7198 |
| BCL11A-5639 | + | GAAAGCGCCCUUCUGCC | 17 | 7199 |

TABLE 15C-continued

3rd Tier

| gRNA Name | DNA Strand | Targeting Domain | Target Site Length | SEQ ID NO: |
|---|---|---|---|---|
| BCL11A-5640 | + | ACCAAGUCGCUGGUGCC | 17 | 7200 |
| BCL11A-5641 | + | UCUCUCGAUACUGAUCC | 17 | 7201 |
| BCL11A-5642 | − | CGACCCCAACCUGAUCC | 17 | 7202 |
| BCL11A-5643 | + | GGUGGCGCGCCGCCUCC | 17 | 7203 |
| BCL11A-5644 | − | CCGGCUACGCGGCCUCC | 17 | 7204 |
| BCL11A-5645 | + | CCUCGUCCCCGUUCUCC | 17 | 7205 |
| BCL11A-5646 | − | GGCCUUCCACCAGGUCC | 17 | 7206 |
| BCL11A-5647 | − | CCCCAUAUUAGUGGUCC | 17 | 7207 |
| BCL11A-5648 | − | UAGCAAGCCGCCCUUCC | 17 | 7208 |
| BCL11A-5649 | + | CGCUGGUGCCGGGUUCC | 17 | 7209 |
| BCL11A-5650 | − | UAGGAGACUUAGAGAGC | 17 | 7210 |
| BCL11A-5651 | + | GAAGGGCUCAGCGAGC | 17 | 7211 |
| BCL11A-2886 | − | CACACCGCCCGGGGAGC | 17 | 7212 |
| BCL11A-5652 | + | GCCGGGUUCCGGGGAGC | 17 | 7213 |
| BCL11A-5653 | + | UCUGCCCUCUUUUGAGC | 17 | 7214 |
| BCL11A-5654 | + | CCUGGAGGCCGCGUAGC | 17 | 7215 |
| BCL11A-5655 | + | AUCCUGGUAUUCUUAGC | 17 | 7216 |
| BCL11A-5656 | + | AAGGGAUACCAACCCGC | 17 | 7217 |
| BCL11A-5657 | − | AAGUCCCUGACCCCGC | 17 | 7218 |
| BCL11A-5658 | + | CGCCCGUGUGGCUGCGC | 17 | 7219 |
| BCL11A-5659 | + | UAUGCGGUCCGACUCGC | 17 | 7220 |
| BCL11A-5660 | − | CCACGAGAACAGCUCGC | 17 | 7221 |
| BCL11A-5661 | − | UACUCGCAGUGGCUCGC | 17 | 7222 |
| BCL11A-5662 | + | GCUGCCCACCAAGUCGC | 17 | 7223 |
| BCL11A-5663 | − | CACCGCUGUCCCCAGGC | 17 | 7224 |
| BCL11A-5664 | + | GCGCCCUUCUGCCAGGC | 17 | 7225 |
| BCL11A-5665 | + | GUGUUGGGCAUCGCGGC | 17 | 7226 |
| BCL11A-5666 | + | UAACCUUUGCAUAGGGC | 17 | 7227 |
| BCL11A-5667 | − | GUGGUCCGGGCCCGGGC | 17 | 7228 |
| BCL11A-5668 | + | CCUGCAUGACGUCGGGC | 17 | 7229 |
| BCL11A-5669 | + | UGGACUUGACCGGGGGC | 17 | 7230 |
| BCL11A-5670 | + | GCAUCGCGGCCGGGGGC | 17 | 7231 |
| BCL11A-5671 | + | UUUGCAUAGGGCUGGGC | 17 | 7232 |
| BCL11A-5672 | + | CUAGAGAAAUCCAUGGC | 17 | 7233 |
| BCL11A-5673 | + | GCGGCUUGCUACCUGGC | 17 | 7234 |
| BCL11A-5674 | − | AGACUUAGAGAGCUGGC | 17 | 7235 |
| BCL11A-5675 | + | UCCCAUGGAGAGGUGGC | 17 | 7236 |
| BCL11A-5676 | − | GACGAAGACUCGGUGGC | 17 | 7237 |

TABLE 15C-continued

3rd Tier

| gRNA Name | DNA Strand | Targeting Domain | Target Site Length | SEQ ID NO: |
|---|---|---|---|---|
| BCL11A-5677 | − | CCUGCCCGACGUCAUGC | 17 | 7238 |
| BCL11A-5394 | + | UGUACAUGUGUAGCUGC | 17 | 7239 |
| BCL11A-5678 | + | GGACUUGAGCGCGCUGC | 17 | 7240 |
| BCL11A-5679 | − | GUCCAAAAAGCUGCUGC | 17 | 7241 |
| BCL11A-5680 | + | CACCAAGUCGCUGGUGC | 17 | 7242 |
| BCL11A-5681 | + | GUGGCGCUUCAGCUUGC | 17 | 7243 |
| BCL11A-5682 | + | CCCCGUUCUCCGGGAUC | 17 | 7244 |
| BCL11A-5683 | + | CCCUGUCAAAGGCACUC | 17 | 7245 |
| BCL11A-5684 | − | CCGGGCGAGUCGGCCUC | 17 | 7246 |
| BCL11A-5685 | − | CUGGACGGAGGGAUCUC | 17 | 7247 |
| BCL11A-5686 | + | ACACAUCUUGAGCUCUC | 17 | 7248 |
| BCL11A-5687 | + | UCCUCGUCCCCGUUCUC | 17 | 7249 |
| BCL11A-5688 | + | AUGCCCUGCAUGACGUC | 17 | 7250 |
| BCL11A-5689 | + | UACCAACCCGCGGGGUC | 17 | 7251 |
| BCL11A-5690 | − | GCCCCAUAUUAGUGGUC | 17 | 7252 |
| BCL11A-5691 | + | GGCAAAAGGCGAUUGUC | 17 | 7253 |
| BCL11A-5692 | − | CGGGUUGGUAUCCCUUC | 17 | 7254 |
| BCL11A-5693 | − | GUAUCGAGAGAGGCUUC | 17 | 7255 |
| BCL11A-5694 | − | GGGUGGACUACGGCUUC | 17 | 7256 |
| BCL11A-5695 | + | UCGCUGGUGCCGGGUUC | 17 | 7257 |
| BCL11A-5696 | − | CAGGCCCAGCUCAAAAG | 17 | 7258 |
| BCL11A-5697 | + | GUGAAGAACCUAGAAAG | 17 | 7259 |
| BCL11A-5698 | + | UUCUUAGCAGGUUAAAG | 17 | 7260 |
| BCL11A-3087 | − | CGAGGAAGAGGAAGAAG | 17 | 7261 |
| BCL11A-5699 | + | UGAUGCGCUUAGAGAAG | 17 | 7262 |
| BCL11A-3083 | − | GGAGGACGACGAGGAAG | 17 | 7263 |
| BCL11A-3089 | − | GGAAGAAGAGGAGGAAG | 17 | 7264 |
| BCL11A-3075 | − | CGGGGACGAGGAGGAAG | 17 | 7265 |
| BCL11A-2876 | − | CGCAGCGGCACGGGAAG | 17 | 7266 |
| BCL11A-5700 | + | GGUGGUGGACUAAACAG | 17 | 7267 |
| BCL11A-5701 | + | AAAGAGGUUGGAGACAG | 17 | 7268 |
| BCL11A-5702 | + | GGCCGGCCUGGGGACAG | 17 | 7269 |
| BCL11A-5703 | − | AAAUUUGAAGCCCCCAG | 17 | 7270 |
| BCL11A-5704 | − | GGGAUCUCGGGGCGCAG | 17 | 7271 |
| BCL11A-5705 | − | AGAACGUGUACUCGCAG | 17 | 7272 |
| BCL11A-5706 | + | GGAGGGGCGGAUUGCAG | 17 | 7273 |
| BCL11A-5707 | + | CCAACCCGCGGGGUCAG | 17 | 7274 |

TABLE 15C-continued

3rd Tier

| gRNA Name | DNA Strand | Targeting Domain | Target Site Length | SEQ ID NO: |
|---|---|---|---|---|
| BCL11A-5708 | − | AGGAUCAGUAUCGAGAG | 17 | 7275 |
| BCL11A-5709 | − | AGCUGACGGAGAGCGAG | 17 | 7276 |
| BCL11A-5710 | + | GGUUGGAGACAGAGGAG | 17 | 7277 |
| BCL11A-5711 | + | GGGCUGGGAGGGAGGAG | 17 | 7278 |
| BCL11A-5712 | + | GAUUGCAGAGGAGGGAG | 17 | 7279 |
| BCL11A-5713 | + | ACUAAACAGGGGGGGAG | 17 | 7280 |
| BCL11A-5714 | + | AUAUGAAUCCCAUGGAG | 17 | 7281 |
| BCL11A-5715 | − | AGCACGCCCCAUAUUAG | 17 | 7282 |
| BCL11A-5716 | − | CCUGAUCCCGGAGAACG | 17 | 7283 |
| BCL11A-3081 | − | GGAAGAGGAGGACGACG | 17 | 7284 |
| BCL11A-5717 | + | CGAGGAGUGCUCCGACG | 17 | 7285 |
| BCL11A-2837 | − | CCCGGAGAACGGGGACG | 17 | 7286 |
| BCL11A-5718 | − | GUGGCUCGCCGGCUACG | 17 | 7287 |
| BCL11A-5719 | + | UGACUUGGACUUGACCG | 17 | 7288 |
| BCL11A-5720 | + | GAAGGGAUACCAACCCG | 17 | 7289 |
| BCL11A-5721 | − | GAAGUCCCUGACCCCG | 17 | 7290 |
| BCL11A-5722 | + | UUUGGACAGGCCCCCCG | 17 | 7291 |
| BCL11A-5723 | − | CUUCUCCACACCGCCCG | 17 | 7292 |
| BCL11A-5724 | + | CGAGGCCGACUCGCCCG | 17 | 7293 |
| BCL11A-2946 | + | CGCCCGGGGAGCAGCCG | 17 | 7294 |
| BCL11A-5725 | − | CCACCUGGCCGAGGCCG | 17 | 7295 |
| BCL11A-5726 | + | GUUGGGCAUCGCGGCCG | 17 | 7296 |
| BCL11A-5727 | − | GGCACUGUUAAUGGCCG | 17 | 7297 |
| BCL11A-5728 | − | GCGCGGCCACCUGGCCG | 17 | 7298 |
| BCL11A-5729 | + | CAAACUCCCGUUCUCCG | 17 | 7299 |
| BCL11A-5730 | − | CAGCGCGCUCAAGUCCG | 17 | 7300 |
| BCL11A-5731 | + | GCUGGUGCCGGGUUCCG | 17 | 7301 |
| BCL11A-5732 | − | GGCGAGAAGCAUAAGCG | 17 | 7302 |
| BCL11A-5733 | − | CAUGCAGCACUUCAGCG | 17 | 7303 |
| BCL11A-5734 | + | UGGCCUGGGUGCACGCG | 17 | 7304 |
| BCL11A-5735 | + | AGGGAUACCAACCCGCG | 17 | 7305 |
| BCL11A-5736 | − | CACGAGAACAGCUCGCG | 17 | 7306 |
| BCL11A-5737 | + | UGACGUCGGGCAGGGCG | 17 | 7307 |
| BCL11A-5738 | − | GAACAGCUCGCGGGGCG | 17 | 7308 |
| BCL11A-5739 | − | GGGCGCGGUCGUGGGCG | 17 | 7309 |
| BCL11A-5740 | + | CUCCGUGUUGGGCAUCG | 17 | 7310 |
| BCL11A-5741 | − | CGGGCGAGUCGGCCUCG | 17 | 7311 |
| BCL11A-5742 | − | ACCACGAGAACAGCUCG | 17 | 7312 |

TABLE 15C-continued

3rd Tier

| gRNA Name | DNA Strand | Targeting Domain | Target Site Length | SEQ ID NO: |
|---|---|---|---|---|
| BCL11A-5743 | - | UGGACGGAGGGAUCUCG | 17 | 7313 |
| BCL11A-5744 | + | CCCGCGAGCUGUUCUCG | 17 | 7314 |
| BCL11A-5745 | - | CUCGCGGGGCGCGGUCG | 17 | 7315 |
| BCL11A-5746 | + | GUGGUGGACUAAACAGG | 17 | 7316 |
| BCL11A-5747 | + | CCUCGGCCUCGGCCAGG | 17 | 7317 |
| BCL11A-3090 | - | GGAAGAGGAAGAAGAGG | 17 | 7318 |
| BCL11A-3091 | - | AGAAGAGGAGGAAGAGG | 17 | 7319 |
| BCL11A-3088 | - | GGACGAGGAGGAAGAGG | 17 | 7320 |
| BCL11A-5748 | + | GAGGUUGGAGACAGAGG | 17 | 7321 |
| BCL11A-5749 | + | GGGGCGGAUUGCAGAGG | 17 | 7322 |
| BCL11A-5750 | + | UGAAUCCCAUGGAGAGG | 17 | 7323 |
| BCL11A-5751 | + | GGAGUGCUCCGACGAGG | 17 | 7324 |
| BCL11A-3066 | - | GGAGAACGGGGACGAGG | 17 | 7325 |
| BCL11A-3092 | - | AGAGGAGGAAGAGGAGG | 17 | 7326 |
| BCL11A-5752 | + | GUUGGAGACAGAGGAGG | 17 | 7327 |
| BCL11A-3093 | - | GGAGGAAGAGGAGGAGG | 17 | 7328 |
| BCL11A-5753 | + | AUUGCAGAGGAGGGAGG | 17 | 7329 |
| BCL11A-5754 | + | GGGGGCUGGGAGGGAGG | 17 | 7330 |
| BCL11A-5755 | - | CGGGCUGAGCCUGGAGG | 17 | 7331 |
| BCL11A-5756 | - | CCCGGGGAGCUGGACGG | 17 | 7332 |
| BCL11A-5757 | + | GACUUGGACUUGACCGG | 17 | 7333 |
| BCL11A-5758 | + | UUGGGCAUCGCGGCCGG | 17 | 7334 |
| BCL11A-5759 | + | CGGCCUGGGGACAGCGG | 17 | 7335 |
| BCL11A-5760 | + | UUCCGGGGAGCUGGCGG | 17 | 7336 |
| BCL11A-5761 | + | CCAGGCGCUCUAUGCGG | 17 | 7337 |
| BCL11A-5762 | - | UUGCGACGAAGACUCGG | 17 | 7338 |
| BCL11A-5763 | - | GGGCGAGUCGGCCUCGG | 17 | 7339 |
| BCL11A-5764 | + | UCCAAGUGAUGUCUCGG | 17 | 7340 |
| BCL11A-5765 | + | GGCGUCGCCAGGAAGGG | 17 | 7341 |
| BCL11A-5766 | + | UGGUGGACUAAACAGGG | 17 | 7342 |
| BCL11A-3076 | - | GACGGAGAGCGAGAGGG | 17 | 7343 |
| BCL11A-5767 | + | CGGAUUGCAGAGGAGGG | 17 | 7344 |
| BCL11A-5768 | + | UUGCAGAGGAGGGAGGG | 17 | 7345 |
| BCL11A-5769 | + | ACCGGGGGCUGGGAGGG | 17 | 7346 |
| BCL11A-5770 | + | CCGUCCAGCUCCCCGGG | 17 | 7347 |
| BCL11A-5771 | + | GAGAAAUCCAUGGCGGG | 17 | 7348 |
| BCL11A-5772 | - | GGCGAGUCGGCCUCGGG | 17 | 7349 |

TABLE 15C-continued

3rd Tier

| gRNA Name | DNA Strand | Targeting Domain | Target Site Length | SEQ ID NO: |
|---|---|---|---|---|
| BCL11A-5773 | + | GGUGGACUAAACAGGGG | 17 | 7350 |
| BCL11A-5774 | − | UUUGAAGCCCCCAGGGG | 17 | 7351 |
| BCL11A-5775 | + | CUGGGAGGGAGGAGGGG | 17 | 7352 |
| BCL11A-5776 | + | UGCAGAGGAGGGAGGGG | 17 | 7353 |
| BCL11A-5777 | − | CAUAGAGCGCCUGGGGG | 17 | 7354 |
| BCL11A-5778 | − | AGCCCCCAGGGGUGGGG | 17 | 7355 |
| BCL11A-5779 | + | GGCACUCGGGUGAUGGG | 17 | 7356 |
| BCL11A-5780 | + | CUUGACCGGGGCUGGG | 17 | 7357 |
| BCL11A-5781 | + | AACAGGGGGGAGUGGG | 17 | 7358 |
| BCL11A-5782 | + | GGUACUACGCCGAAUGG | 17 | 7359 |
| BCL11A-5783 | + | CCUAGAGAAAUCCAUGG | 17 | 7360 |
| BCL11A-5784 | + | GGACUUGACCGUCAUGG | 17 | 7361 |
| BCL11A-5785 | − | AUUUCAGAGCAACCUGG | 17 | 7362 |
| BCL11A-5786 | + | UCUCGCCCAGGACCUGG | 17 | 7363 |
| BCL11A-5787 | − | CUUCGGGCUGAGCCUGG | 17 | 7364 |
| BCL11A-5788 | − | CCGCAUAGAGCGCCUGG | 17 | 7365 |
| BCL11A-5789 | + | AUCUUUGAGCUGCCUGG | 17 | 7366 |
| BCL11A-5790 | + | GGGUUCCGGGGAGCUGG | 17 | 7367 |
| BCL11A-5791 | − | AGCGGCACGGGAAGUGG | 17 | 7368 |
| BCL11A-5792 | − | CGCGCUCAAGUCCGUGG | 17 | 7369 |
| BCL11A-5793 | + | GCGAGCUGUUCUCGUGG | 17 | 7370 |
| BCL11A-5794 | + | GGCGCUCUAUGCGGUGG | 17 | 7371 |
| BCL11A-5795 | + | AAGUGAUGUCUCGGUGG | 17 | 7372 |
| BCL11A-5796 | − | CGGCACCAGCGACUUGG | 17 | 7373 |
| BCL11A-5797 | + | GGGUACUACGCCGAAUG | 17 | 7374 |
| BCL11A-5798 | + | CGGACUUGACCGUCAUG | 17 | 7375 |
| BCL11A-5799 | + | GCAUGUGCGUCUUCAUG | 17 | 7376 |
| BCL11A-5800 | + | CCCGGACCACUAAUAUG | 17 | 7377 |
| BCL11A-5801 | + | CCCCCAGGCGCUCUAUG | 17 | 7378 |
| BCL11A-5802 | + | CAGUGCCAUCGUCUAUG | 17 | 7379 |
| BCL11A-5803 | − | GACACUUGUGAGUACUG | 17 | 7380 |
| BCL11A-5804 | + | CGUCGCAAGUGUCCCUG | 17 | 7381 |
| BCL11A-5805 | − | ACCGCAUAGAGCGCCUG | 17 | 7382 |
| BCL11A-5806 | + | AGGGCUGGGCCGGCCUG | 17 | 7383 |
| BCL11A-5807 | + | AGGGGCUCAGCGAGCUG | 17 | 7384 |
| BCL11A-5808 | − | CCUUUGACAGGGUGCUG | 17 | 7385 |
| BCL11A-5809 | − | AAGUCAUGCGAGUUCUG | 17 | 7386 |
| BCL11A-5810 | + | AGGGCUUCUCGCCCGUG | 17 | 7387 |

TABLE 15C-continued

3rd Tier

| gRNA Name | DNA Strand | Targeting Domain | Target Site Length | SEQ ID NO: |
|---|---|---|---|---|
| BCL11A-5811 | + | CAGCUCCCCGGGCGGUG | 17 | 7388 |
| BCL11A-5812 | + | AGGCGCUCUAUGCGGUG | 17 | 7389 |
| BCL11A-5813 | − | UGAAGCCCCCAGGGGUG | 17 | 7390 |
| BCL11A-5814 | − | AGAGAGCUCAAGAUGUG | 17 | 7391 |
| BCL11A-5815 | + | UCUCCGGGAUCAGGUUG | 17 | 7392 |
| BCL11A-5816 | + | UGGGUACUACGCCGAAU | 17 | 7393 |
| BCL11A-5817 | + | GGAGGCUCCAUAGCCAU | 17 | 7394 |
| BCL11A-5818 | − | CCCAGCCACCUCUCCAU | 17 | 7395 |
| BCL11A-5819 | + | UGCAGUAACCUUUGCAU | 17 | 7396 |
| BCL11A-5820 | + | UCGGACUUGACCGUCAU | 17 | 7397 |
| BCL11A-5821 | + | AAAGGCACUCGGGUGAU | 17 | 7398 |
| BCL11A-5822 | + | GCCCGGACCACUAAUAU | 17 | 7399 |
| BCL11A-5823 | + | GUUCUCGCUCUUGAACU | 17 | 7400 |
| BCL11A-5824 | + | ACCCUGUCAAAGGCACU | 17 | 7401 |
| BCL11A-5825 | − | ACCACCGAGACAUCACU | 17 | 7402 |
| BCL11A-5826 | − | CACUUGCGACGAAGACU | 17 | 7403 |
| BCL11A-5827 | − | ACCCGGCACCAGCGACU | 17 | 7404 |
| BCL11A-5828 | − | GGUAUCCCUUCAGGACU | 17 | 7405 |
| BCL11A-5829 | + | GCAGAACUCGCAUGACU | 17 | 7406 |
| BCL11A-5830 | + | AGUGUCCCUGUGGCCCU | 17 | 7407 |
| BCL11A-5831 | − | CACCGCAUAGAGCGCCU | 17 | 7408 |
| BCL11A-5832 | + | UAGGGCUGGGCCGGCCU | 17 | 7409 |
| BCL11A-5833 | + | CCUGUGGCCCUCGGCCU | 17 | 7410 |
| BCL11A-5834 | − | CCCGGGCGAGUCGGCCU | 17 | 7411 |
| BCL11A-5835 | + | CUUCAGCUUGCUGGCCU | 17 | 7412 |
| BCL11A-5836 | − | CUCGUCGGAGCACUCCU | 17 | 7413 |
| BCL11A-5837 | − | GCCUUCCACCAGGUCCU | 17 | 7414 |
| BCL11A-5838 | + | AAGGGGCUCAGCGAGCU | 17 | 7415 |
| BCL11A-5839 | + | CUGCCCUCUUUUGAGCU | 17 | 7416 |
| BCL11A-5840 | + | AACCUUUGCAUAGGGCU | 17 | 7417 |
| BCL11A-5841 | + | GGACUUGACCGGGGCU | 17 | 7418 |
| BCL11A-5842 | + | CCCAUGGAGAGGUGGCU | 17 | 7419 |
| BCL11A-5434 | + | GUACAUGUGUAGCUGCU | 17 | 7420 |
| BCL11A-5843 | − | UCCAAAAAGCUGCUGCU | 17 | 7421 |
| BCL11A-5844 | − | GCUGGACGGAGGGAUCU | 17 | 7422 |
| BCL11A-5845 | + | CACAUCUUGAGCUCUCU | 17 | 7423 |
| BCL11A-5846 | − | CCGCCAUGGAUUUCUCU | 17 | 7424 |

TABLE 15C-continued

| | | 3rd Tier | | |
|---|---|---|---|---|
| gRNA Name | DNA Strand | Targeting Domain | Target Site Length | SEQ ID NO: |
| BCL11A-5847 | + | GGGUCCAAGUGAUGUCU | 17 | 7425 |
| BCL11A-5848 | - | GUCUCCAACCUCUUUCU | 17 | 7426 |
| BCL11A-5849 | - | CUCGGUGGCCGGCGAGU | 17 | 7427 |
| BCL11A-5850 | - | CUGCUCCCCGGGCGAGU | 17 | 7428 |
| BCL11A-5851 | + | CUAAACAGGGGGGGAGU | 17 | 7429 |
| BCL11A-5852 | + | CAUGCCCUGCAUGACGU | 17 | 7430 |
| BCL11A-5853 | - | GGCGCGGUCGUGGGCGU | 17 | 7431 |
| BCL11A-5854 | - | GCCUUUUGCCUCCUCGU | 17 | 7432 |
| BCL11A-5855 | + | GGUGGAGAGACCGUCGU | 17 | 7433 |
| BCL11A-5856 | - | UCGCGGGGCGCGGUCGU | 17 | 7434 |
| BCL11A-5857 | + | GUUCUCCGGGAUCAGGU | 17 | 7435 |
| BCL11A-5858 | + | AGAACCUAGAAAGAGGU | 17 | 7436 |
| BCL11A-5859 | + | GGCCUGGGGACAGCGGU | 17 | 7437 |
| BCL11A-5860 | + | CAGGCGCUCUAUGCGGU | 17 | 7438 |
| BCL11A-5861 | - | CCCCUGACCCCGCGGGU | 17 | 7439 |
| BCL11A-5862 | - | UUGAAGCCCCCAGGGGU | 17 | 7440 |
| BCL11A-5863 | - | GGCACCAGCGACUUGGU | 17 | 7441 |
| BCL11A-5864 | - | ACACUUGUGAGUACUGU | 17 | 7442 |
| BCL11A-5865 | + | GUACACGUUCUCCGUGU | 17 | 7443 |
| BCL11A-5866 | + | GCACAGGUUGCACUUGU | 17 | 7444 |
| BCL11A-5867 | - | CUUCACACACCCCCAUU | 17 | 7445 |
| BCL11A-5868 | - | GAUCCCUUCCUUAGCUU | 17 | 7446 |
| BCL11A-5869 | - | AGGGUGGACUACGGCUU | 17 | 7447 |
| BCL11A-5870 | + | UUCUCCGGGAUCAGGUU | 17 | 7448 |
| BCL11A-5871 | + | UACACGUUCUCCGUGUU | 17 | 7449 |
| BCL11A-5872 | + | GCCCAGCAGCAGCUUUU | 17 | 7450 |
| BCL11A-5873 | - | AGAUGUGUGGCAGUUUU | 17 | 7451 |
| BCL11A-5874 | + | UGCUCCGACGAGGAGGCAAA | 20 | 7452 |
| BCL11A-5875 | + | GGUAUUCUUAGCAGGUUAAA | 20 | 7453 |
| BCL11A-5876 | - | GGUGCUGCGGUUGAAUCCAA | 20 | 7454 |
| BCL11A-5877 | - | GCCGGCCCAGCCCUAUGCAA | 20 | 7455 |
| BCL11A-5878 | + | CAACCGCAGCACCCUGUCAA | 20 | 7456 |
| BCL11A-5879 | - | AGGCUUCCGGCCUGGCAGAA | 20 | 7457 |
| BCL11A-5880 | + | AGCUUGAUGCGCUUAGAGAA | 20 | 7458 |
| BCL11A-5881 | - | CCCAACCUGAUCCCGGAGAA | 20 | 7459 |
| BCL11A-5882 | - | UCGGAGCACUCCUCGGAGAA | 20 | 7460 |
| BCL11A-5883 | + | UCUCUGGGUACUACGCCGAA | 20 | 7461 |
| BCL11A-5884 | + | GAGUCUCCGAAGCUAAGGAA | 20 | 7462 |

TABLE 15C-continued

| gRNA Name | DNA Strand | Targeting Domain | Target Site Length | SEQ ID NO: |
|---|---|---|---|---|
| | | 3rd Tier | | |
| BCL11A-5885 | + | AGGGGGGGCGUCGCCAGGAA | 20 | 7463 |
| BCL11A-5886 | + | GGCUUGCUACCUGGCUGGAA | 20 | 7464 |
| BCL11A-5887 | + | AUUCUGCACCUAGUCCUGAA | 20 | 7465 |
| BCL11A-5888 | + | AGAAACCAUGCACUGGUGAA | 20 | 7466 |
| BCL11A-5889 | + | CAAAUUUCUCAGAACUUAA | 20 | 7467 |
| BCL11A-5890 | + | UGGUAUUCUUAGCAGGUUAA | 20 | 7468 |
| BCL11A-5891 | − | AUAGACGAUGGCACUGUUAA | 20 | 7469 |
| BCL11A-5892 | + | UCUCGGUGGUGGACUAAACA | 20 | 7470 |
| BCL11A-5893 | − | CCCGGCCGCGAUGCCCAACA | 20 | 7471 |
| BCL11A-5894 | − | AUCUACUUAGAAAGCGAACA | 20 | 7472 |
| BCL11A-5895 | − | GGUGCACCGGCGCAGCCACA | 20 | 7473 |
| BCL11A-3377 | − | GGCCGAGGCCGAGGGCCACA | 20 | 7474 |
| BCL11A-5896 | − | UCACCCGAGUGCCUUUGACA | 20 | 7475 |
| BCL11A-5897 | + | GCUCUUGAACUUGGCCACCA | 20 | 7476 |
| BCL11A-5898 | − | GAGAAAAUUUGAAGCCCCCA | 20 | 7477 |
| BCL11A-5899 | + | UGUCUGCAAUAUGAAUCCCA | 20 | 7478 |
| BCL11A-5900 | − | GGCUAUGGAGCCUCCCGCCA | 20 | 7479 |
| BCL11A-5901 | + | ACUCGGGUGAUGGGUGGCCA | 20 | 7480 |
| BCL11A-5902 | + | AAGUCUCCUAGAGAAAUCCA | 20 | 7481 |
| BCL11A-5903 | − | CCUUCCCAGCCACCUCUCCA | 20 | 7482 |
| BCL11A-5904 | − | GAUCUCGGGGCGCAGCGGCA | 20 | 7483 |
| BCL11A-5905 | − | GCCCGACGUCAUGCAGGGCA | 20 | 7484 |
| BCL11A-5906 | + | GCCCUGCAUGACGUCGGGCA | 20 | 7485 |
| BCL11A-5907 | − | GGAGACUUAGAGAGCUGGCA | 20 | 7486 |
| BCL11A-5908 | − | GCCCUGCCCGACGUCAUGCA | 20 | 7487 |
| BCL11A-5909 | + | GGCCUCGCUGAAGUGCUGCA | 20 | 7488 |
| BCL11A-5910 | − | AACAGCCAUUCACCAGUGCA | 20 | 7489 |
| BCL11A-5911 | − | CAACACGCACAGAACACUCA | 20 | 7490 |
| BCL11A-5912 | + | GUCGUCGGACUUGACCGUCA | 20 | 7491 |
| BCL11A-5913 | + | GAUACCAACCCGCGGGGUCA | 20 | 7492 |
| BCL11A-5914 | − | GGCAGGCCCAGCUCAAAAGA | 20 | 7493 |
| BCL11A-5915 | − | GAGGCUUCCGGCCUGGCAGA | 20 | 7494 |
| BCL11A-5916 | − | GCGCCUGGGGCGGAAGAGA | 20 | 7495 |
| BCL11A-5917 | + | GAGCUUGAUGCGCUUAGAGA | 20 | 7496 |
| BCL11A-5918 | − | GGAGCUGACGGAGAGCGAGA | 20 | 7497 |
| BCL11A-5919 | − | UAAGCGCAUCAAGCUCGAGA | 20 | 7498 |
| BCL11A-5920 | − | GAGUCGGACCGCAUAGACGA | 20 | 7499 |

TABLE 15C-continued

3rd Tier

| gRNA Name | DNA Strand | Targeting Domain | Target Site Length | SEQ ID NO: |
|---|---|---|---|---|
| BCL11A-5921 | - | AUGACGGUCAAGUCCGACGA | 20 | 7500 |
| BCL11A-5922 | - | GGCCACCUGGCCGAGGCCGA | 20 | 7501 |
| BCL11A-5923 | + | GGAGUCUCCGAAGCUAAGGA | 20 | 7502 |
| BCL11A-5924 | + | GAGGGGGGCGUCGCCAGGA | 20 | 7503 |
| BCL11A-5925 | + | AAGAGGUUGGAGACAGAGGA | 20 | 7504 |
| BCL11A-5926 | + | GAGGGGCGGAUUGCAGAGGA | 20 | 7505 |
| BCL11A-5927 | + | CCGGGGGCUGGGAGGGAGGA | 20 | 7506 |
| BCL11A-5928 | - | CGCCCGGGGAGCUGGACGGA | 20 | 7507 |
| BCL11A-5929 | - | GAUGUGUGGCAGUUUUCGGA | 20 | 7508 |
| BCL11A-5930 | + | GGCGGAUUGCAGAGGAGGGA | 20 | 7509 |
| BCL11A-5931 | + | GACUUGACCGGGGCUGGGA | 20 | 7510 |
| BCL11A-5932 | + | CCAUGGAGAGGUGGCUGGGA | 20 | 7511 |
| BCL11A-5933 | - | ACACCGCCCGGGGAGCUGGA | 20 | 7512 |
| BCL11A-5934 | - | GCAGCGGCACGGGAAGUGGA | 20 | 7513 |
| BCL11A-5935 | + | CUCGCCCAGGACCUGGUGGA | 20 | 7514 |
| BCL11A-5936 | - | GCACAAAUCGUCCCCAUGA | 20 | 7515 |
| BCL11A-5937 | + | CAUUCUGCACCUAGUCCUGA | 20 | 7516 |
| BCL11A-5938 | - | AGAGGAGGAGGAGGAGCUGA | 20 | 7517 |
| BCL11A-5939 | + | UGUCAAAGGCACUCGGGUGA | 20 | 7518 |
| BCL11A-5940 | + | CCGGGCCCGGACCACUAAUA | 20 | 7519 |
| BCL11A-5941 | + | GUUGCAGUAACCUUUGCAUA | 20 | 7520 |
| BCL11A-5942 | - | GAGAGCGAGAGGGUGGACUA | 20 | 7521 |
| BCL11A-5943 | + | GUCUGGAGUCUCCGAAGCUA | 20 | 7522 |
| BCL11A-5944 | - | GCGGUUGAAUCCAAUGGCUA | 20 | 7523 |
| BCL11A-5945 | + | UCGCACAGGUUGCACUUGUA | 20 | 7524 |
| BCL11A-5946 | + | UCAAAUUUCUCAGAACUUA | 20 | 7525 |
| BCL11A-5947 | + | GUCUCGGUGGUGGACUAAAC | 20 | 7526 |
| BCL11A-5948 | - | CCAACCUGAUCCCGGAGAAC | 20 | 7527 |
| BCL11A-5949 | - | CGGAGCACUCCUCGGAGAAC | 20 | 7528 |
| BCL11A-5950 | - | GUGCACCGGCGCAGCCACAC | 20 | 7529 |
| BCL11A-5951 | - | UGGCCGAGGCCGAGGGCCAC | 20 | 7530 |
| BCL11A-5952 | + | GGGUGCACGCGUGGUCGCAC | 20 | 7531 |
| BCL11A-5953 | - | AUCUCGGGGCGCAGCGGCAC | 20 | 7532 |
| BCL11A-5954 | + | UUGCAAGAGAAACCAUGCAC | 20 | 7533 |
| BCL11A-5955 | - | AGAGCAACCUGGUGGUGCAC | 20 | 7534 |
| BCL11A-5956 | + | CCAGCAGCAGCUUUUUGGAC | 20 | 7535 |
| BCL11A-5957 | + | UCGCAUGACUUGGACUUGAC | 20 | 7536 |
| BCL11A-5958 | - | AUCACCCGAGUGCCUUUGAC | 20 | 7537 |

TABLE 15C-continued

3rd Tier

| gRNA Name | DNA Strand | Targeting Domain | Target Site Length | SEQ ID NO: |
|---|---|---|---|---|
| BCL11A-5959 | − | GUUCAAAUUUCAGAGCAACC | 20 | 7538 |
| BCL11A-5960 | − | ACCGCCAGCUCCCCGGAACC | 20 | 7539 |
| BCL11A-5961 | + | GGCUGCGCCGGUGCACCACC | 20 | 7540 |
| BCL11A-5962 | − | GAAGCAUAAGCGCGGCCACC | 20 | 7541 |
| BCL11A-5963 | − | CUUCAGCGAGGCCUUCCACC | 20 | 7542 |
| BCL11A-5964 | + | UAUGCUUCUCGCCCAGGACC | 20 | 7543 |
| BCL11A-5965 | + | CGCAUGACUUGGACUUGACC | 20 | 7544 |
| BCL11A-5966 | − | UUUAACCUGCUAAGAAUACC | 20 | 7545 |
| BCL11A-5967 | + | AGGAAGGGCGGCUUGCUACC | 20 | 7546 |
| BCL11A-5968 | − | GUGCGACCACGCGUGCACCC | 20 | 7547 |
| BCL11A-5969 | − | UGAGAAAAUUUGAAGCCCCC | 20 | 7548 |
| BCL11A-5970 | + | GGGCCAUCUCUUCCGCCCCC | 20 | 7549 |
| BCL11A-5971 | − | CCCUCCUCCCUCCCAGCCCC | 20 | 7550 |
| BCL11A-5972 | − | GAAGGAGUUCGACCUGCCCC | 20 | 7551 |
| BCL11A-5973 | + | AUCCCUCCGUCCAGCUCCCC | 20 | 7552 |
| BCL11A-5974 | − | AAUGGCCGCGGCUGCUCCCC | 20 | 7553 |
| BCL11A-5975 | − | UCUAGCCCACCGCUGUCCCC | 20 | 7554 |
| BCL11A-5976 | − | UGCGCUUCUCCACACCGCCC | 20 | 7555 |
| BCL11A-5977 | + | CCCCCGAGGCCGACUCGCCC | 20 | 7556 |
| BCL11A-5978 | + | CGCGCUUAUGCUUCUCGCCC | 20 | 7557 |
| BCL11A-5979 | − | CAUAUUAGUGGUCCGGGCCC | 20 | 7558 |
| BCL11A-5980 | − | GGGGGCGGAAGAGAUGGCCC | 20 | 7559 |
| BCL11A-5981 | + | CUUUUGAGCUGGGCCUGCCC | 20 | 7560 |
| BCL11A-5982 | − | UCUCUCCACCGCCAGCUCCC | 20 | 7561 |
| BCL11A-5983 | + | GAUCCCUCCGUCCAGCUCCC | 20 | 7562 |
| BCL11A-5984 | − | UAAUGGCCGCGGCUGCUCCC | 20 | 7563 |
| BCL11A-5985 | − | UUACUGCAACCAUUCCAGCC | 20 | 7564 |
| BCL11A-5986 | − | CUACGGCUUCGGGCUGAGCC | 20 | 7565 |
| BCL11A-5987 | − | UUGCGCUUCUCCACACCGCC | 20 | 7566 |
| BCL11A-5988 | − | CCCCCACCGCAUAGAGCGCC | 20 | 7567 |
| BCL11A-5989 | + | CCCCCCGAGGCCGACUCGCC | 20 | 7568 |
| BCL11A-5990 | + | GAGGGAGGGGGGCGUCGCC | 20 | 7569 |
| BCL11A-5991 | + | UGCAUAGGGCUGGGCCGGCC | 20 | 7570 |
| BCL11A-5992 | − | AUCGAGAGAGGCUUCCGGCC | 20 | 7571 |
| BCL11A-5993 | + | CCGUGUUGGGCAUCGCGGCC | 20 | 7572 |
| BCL11A-5994 | + | UGUGGCCCUCGGCCUCGGCC | 20 | 7573 |
| BCL11A-5995 | + | GAGCUGGGCCUGCCCGGGCC | 20 | 7574 |

TABLE 15C-continued

3rd Tier

| gRNA Name | DNA Strand | Targeting Domain | Target Site Length | SEQ ID NO: |
|---|---|---|---|---|
| BCL11A-5996 | − | CCAUAUUAGUGGUCCGGGCC | 20 | 7575 |
| BCL11A-5997 | + | GGCGCUUCAGCUUGCUGGCC | 20 | 7576 |
| BCL11A-5998 | + | CACUCGGGUGAUGGGUGGCC | 20 | 7577 |
| BCL11A-5999 | + | UCUUUUGAGCUGGGCCUGCC | 20 | 7578 |
| BCL11A-6000 | + | GAAGGGAUCUUUGAGCUGCC | 20 | 7579 |
| BCL11A-6001 | + | GUGGAAAGCGCCCUUCUGCC | 20 | 7580 |
| BCL11A-6002 | + | CCCACCAAGUCGCUGGUGCC | 20 | 7581 |
| BCL11A-6003 | + | GCCUCUCUCGAUACUGAUCC | 20 | 7582 |
| BCL11A-6004 | − | GAACGACCCCAACCUGAUCC | 20 | 7583 |
| BCL11A-6005 | + | CGUGGUGGCGCGCCGCCUCC | 20 | 7584 |
| BCL11A-6006 | − | UCGCCGGCUACGCGGCCUCC | 20 | 7585 |
| BCL11A-6007 | + | CCUCCUCGUCCCCGUUCUCC | 20 | 7586 |
| BCL11A-6008 | − | CGAGGCCUUCCACCAGGUCC | 20 | 7587 |
| BCL11A-6009 | − | ACGCCCCAUAUUAGUGGUCC | 20 | 7588 |
| BCL11A-6010 | − | AGGUAGCAAGCCGCCCUUCC | 20 | 7589 |
| BCL11A-6011 | + | AGUCGCUGGUGCCGGGUUCC | 20 | 7590 |
| BCL11A-6012 | − | CUCUAGGAGACUUAGAGAGC | 20 | 7591 |
| BCL11A-6013 | + | AGAGAAGGGGCUCAGCGAGC | 20 | 7592 |
| BCL11A-6014 | − | CUCCACACCGCCCGGGGAGC | 20 | 7593 |
| BCL11A-6015 | + | GGUGCCGGGUUCCGGGGAGC | 20 | 7594 |
| BCL11A-6016 | + | GCGUCUGCCCUCUUUUGAGC | 20 | 7595 |
| BCL11A-6017 | + | CUGCCUGGAGGCCGCGUAGC | 20 | 7596 |
| BCL11A-6018 | + | CUGAUCCUGGUAUUCUUAGC | 20 | 7597 |
| BCL11A-6019 | + | CUGAAGGGAUACCAACCCGC | 20 | 7598 |
| BCL11A-6020 | − | CGGAAGUCCCCUGACCCCGC | 20 | 7599 |
| BCL11A-6021 | + | UCUCGCCCGUGUGGCUGCGC | 20 | 7600 |
| BCL11A-6022 | + | GUCUAUGCGGUCCGACUCGC | 20 | 7601 |
| BCL11A-6023 | − | CCACCACGAGAACAGCUCGC | 20 | 7602 |
| BCL11A-6024 | − | GUGUACUCGCAGUGGCUCGC | 20 | 7603 |
| BCL11A-6025 | + | GGCGCUGCCCACCAAGUCGC | 20 | 7604 |
| BCL11A-6026 | − | GCCCACCGCUGUCCCCAGGC | 20 | 7605 |
| BCL11A-6027 | + | AAAGCGCCCUUCUGCCAGGC | 20 | 7606 |
| BCL11A-6028 | + | UCCGUGUUGGGCAUCGCGGC | 20 | 7607 |
| BCL11A-6029 | + | CAGUAACCUUUGCAUAGGGC | 20 | 7608 |
| BCL11A-6030 | − | UUAGUGGUCCGGGCCCGGGC | 20 | 7609 |
| BCL11A-6031 | + | UGCCCUGCAUGACGUCGGGC | 20 | 7610 |
| BCL11A-6032 | + | ACUUGGACUUGACCGGGGGC | 20 | 7611 |
| BCL11A-6033 | + | UGGGCAUCGCGGCCGGGGGC | 20 | 7612 |

TABLE 15C-continued

| | | 3rd Tier | | |
|---|---|---|---|---|
| gRNA Name | DNA Strand | Targeting Domain | Target Site Length | SEQ ID NO: |
| BCL11A-6034 | + | ACCUUUGCAUAGGGCUGGGC | 20 | 7613 |
| BCL11A-6035 | + | CUCCUAGAGAAAUCCAUGGC | 20 | 7614 |
| BCL11A-6036 | + | AGGGCGGCUUGCUACCUGGC | 20 | 7615 |
| BCL11A-6037 | − | AGGAGACUUAGAGAGCUGGC | 20 | 7616 |
| BCL11A-6038 | + | GAAUCCCAUGGAGAGGUGGC | 20 | 7617 |
| BCL11A-6039 | − | UGCGACGAAGACUCGGUGGC | 20 | 7618 |
| BCL11A-6040 | − | CGCCCUGCCCGACGUCAUGC | 20 | 7619 |
| BCL11A-5467 | + | AGUUGUACAUGUGUAGCUGC | 20 | 7620 |
| BCL11A-6041 | + | CACGGACUUGAGCGCGCUGC | 20 | 7621 |
| BCL11A-6042 | − | CCUGUCCAAAAGCUGCUGC | 20 | 7622 |
| BCL11A-6043 | + | GCCCACCAAGUCGCUGGUGC | 20 | 7623 |
| BCL11A-6044 | + | CAUGUGGCGCUUCAGCUUGC | 20 | 7624 |
| BCL11A-6045 | + | CGUCCCCGUUCUCCGGGAUC | 20 | 7625 |
| BCL11A-6046 | + | GCACCCUGUCAAAGGCACUC | 20 | 7626 |
| BCL11A-6047 | − | UCCCCGGGCGAGUCGGCCUC | 20 | 7627 |
| BCL11A-6048 | − | GAGCUGGACGGAGGGAUCUC | 20 | 7628 |
| BCL11A-6049 | + | GCCACACAUCUUGAGCUCUC | 20 | 7629 |
| BCL11A-6050 | + | UCCUCCUCGUCCCCGUUCUC | 20 | 7630 |
| BCL11A-6051 | + | ACCAUGCCCUGCAUGACGUC | 20 | 7631 |
| BCL11A-6052 | + | GGAUACCAACCCGCGGGGUC | 20 | 7632 |
| BCL11A-6053 | − | CACGCCCCAUAUUAGUGGUC | 20 | 7633 |
| BCL11A-6054 | + | GGAGGCAAAAGGCGAUUGUC | 20 | 7634 |
| BCL11A-6055 | − | CCGCGGGUUGGUAUCCCUUC | 20 | 7635 |
| BCL11A-6056 | − | UCAGUAUCGAGAGAGGCUUC | 20 | 7636 |
| BCL11A-6057 | − | AGAGGGUGGACUACGGCUUC | 20 | 7637 |
| BCL11A-6058 | + | AAGUCGCUGGUGCCGGGUUC | 20 | 7638 |
| BCL11A-6059 | − | GGGCAGGCCCAGCUCAAAAG | 20 | 7639 |
| BCL11A-6060 | + | UGUGUGAAGAACCUAGAAAG | 20 | 7640 |
| BCL11A-6061 | + | GUAUUCUUAGCAGGUUAAAG | 20 | 7641 |
| BCL11A-3449 | − | CGACGAGGAAGAGGAAGAAG | 20 | 7642 |
| BCL11A-6062 | + | GCUUGAUGCGCUUAGAGAAG | 20 | 7643 |
| BCL11A-3448 | − | AGAGGAGGACGACGAGGAAG | 20 | 7644 |
| BCL11A-3453 | − | AGAGGAAGAAGAGGAGGAAG | 20 | 7645 |
| BCL11A-3441 | − | GAACGGGACGAGGAGGAAG | 20 | 7646 |
| BCL11A-3376 | − | GGGCGCAGCGGCACGGGAAG | 20 | 7647 |
| BCL11A-6063 | + | CUCGGUGGUGGACUAAACAG | 20 | 7648 |
| BCL11A-6064 | + | UAGAAAGAGGUUGGAGACAG | 20 | 7649 |

TABLE 15C-continued

3rd Tier

| gRNA Name | DNA Strand | Targeting Domain | Target Site Length | SEQ ID NO: |
|---|---|---|---|---|
| BCL11A-6065 | + | CUGGGCCGGCCUGGGGACAG | 20 | 7650 |
| BCL11A-6066 | – | AGAAAAUUUGAAGCCCCCAG | 20 | 7651 |
| BCL11A-6067 | – | GGAGGGAUCUCGGGGCGCAG | 20 | 7652 |
| BCL11A-6068 | – | CGGAGAACGUGUACUCGCAG | 20 | 7653 |
| BCL11A-6069 | + | GGAGGAGGGGCGGAUUGCAG | 20 | 7654 |
| BCL11A-6070 | + | AUACCAACCCGCGGGGUCAG | 20 | 7655 |
| BCL11A-6071 | – | ACCAGGAUCAGUAUCGAGAG | 20 | 7656 |
| BCL11A-6072 | – | AGGAGCUGACGGAGAGCGAG | 20 | 7657 |
| BCL11A-6073 | + | AGAGGUUGGAGACAGAGGAG | 20 | 7658 |
| BCL11A-6074 | + | CGGGGGCUGGGAGGGAGGAG | 20 | 7659 |
| BCL11A-6075 | + | GCGGAUUGCAGAGGAGGGAG | 20 | 7660 |
| BCL11A-6076 | + | UGGACUAAACAGGGGGGGAG | 20 | 7661 |
| BCL11A-6077 | + | GCAAUAUGAAUCCCAUGGAG | 20 | 7662 |
| BCL11A-6078 | – | GGGAGCACGCCCCAUAUUAG | 20 | 7663 |
| BCL11A-6079 | – | CAACCUGAUCCCGGAGAACG | 20 | 7664 |
| BCL11A-3450 | – | GGAGGAAGAGGAGGACGACG | 20 | 7665 |
| BCL11A-6080 | + | CUCCGAGGAGUGCUCCGACG | 20 | 7666 |
| BCL11A-6081 | – | GAUCCCGGAGAACGGGGACG | 20 | 7667 |
| BCL11A-6082 | – | GCAGUGGCUCGCCGGCUACG | 20 | 7668 |
| BCL11A-6083 | + | GCAUGACUUGGACUUGACCG | 20 | 7669 |
| BCL11A-6084 | + | CCUGAAGGGAUACCAACCCG | 20 | 7670 |
| BCL11A-6085 | – | ACGGAAGUCCCCUGACCCCG | 20 | 7671 |
| BCL11A-6086 | + | CUUUUUGGACAGGCCCCCCG | 20 | 7672 |
| BCL11A-6087 | – | GCGCUUCUCCACACCGCCCG | 20 | 7673 |
| BCL11A-6088 | + | CCCCGAGGCCGACUCGCCCG | 20 | 7674 |
| BCL11A-6089 | + | ACUCGCCCGGGGAGCAGCCG | 20 | 7675 |
| BCL11A-6090 | – | CGGCCACCUGGCCGAGGCCG | 20 | 7676 |
| BCL11A-6091 | + | CGUGUUGGGCAUCGCGGCCG | 20 | 7677 |
| BCL11A-6092 | – | GAUGGCACUGUUAAUGGCCG | 20 | 7678 |
| BCL11A-6093 | – | UAAGCGCGGCCACCUGGCCG | 20 | 7679 |
| BCL11A-6094 | + | GCGCAAACUCCCGUUCUCCG | 20 | 7680 |
| BCL11A-6095 | – | CAGCAGCGCGCUCAAGUCCG | 20 | 7681 |
| BCL11A-6096 | + | GUCGCUGGUGCCGGGUUCCG | 20 | 7682 |
| BCL11A-6097 | – | CUGGGCGAGAAGCAUAAGCG | 20 | 7683 |
| BCL11A-6098 | – | CUCCAUGCAGCACUUCAGCG | 20 | 7684 |
| BCL11A-6099 | + | UGCUGGCCUGGGUGCACGCG | 20 | 7685 |
| BCL11A-6100 | + | UGAAGGGAUACCAACCCGCG | 20 | 7686 |
| BCL11A-6101 | – | CACCACGAGAACAGCUCGCG | 20 | 7687 |

TABLE 15C-continued

3rd Tier

| gRNA Name | DNA Strand | Targeting Domain | Target Site Length | SEQ ID NO: |
|---|---|---|---|---|
| BCL11A-6102 | + | GCAUGACGUCGGGCAGGGCG | 20 | 7688 |
| BCL11A-6103 | - | CGAGAACAGCUCGCGGGGCG | 20 | 7689 |
| BCL11A-6104 | - | GCGGGCGCGGUCGUGGGCG | 20 | 7690 |
| BCL11A-6105 | + | GUUCUCCGUGUUGGGCAUCG | 20 | 7691 |
| BCL11A-6106 | - | CCCCGGGCGAGUCGGCCUCG | 20 | 7692 |
| BCL11A-6107 | - | GCCACCACGAGAACAGCUCG | 20 | 7693 |
| BCL11A-6108 | - | AGCUGGACGGAGGGAUCUCG | 20 | 7694 |
| BCL11A-6109 | + | CGCCCCGCGAGCUGUUCUCG | 20 | 7695 |
| BCL11A-6110 | - | CAGCUCGCGGGGCGCGGUCG | 20 | 7696 |
| BCL11A-6111 | + | UCGGUGGUGGACUAAACAGG | 20 | 7697 |
| BCL11A-6112 | + | GGCCCUCGGCCUCGGCCAGG | 20 | 7698 |
| BCL11A-3451 | - | CGAGGAAGAGGAAGAAGAGG | 20 | 7699 |
| BCL11A-3452 | - | GGAAGAAGAGGAGGAAGAGG | 20 | 7700 |
| BCL11A-3445 | - | CGGGGACGAGGAGGAAGAGG | 20 | 7701 |
| BCL11A-6113 | + | AAAGAGGUUGGAGACAGAGG | 20 | 7702 |
| BCL11A-6114 | + | GGAGGGGCGGAUUGCAGAGG | 20 | 7703 |
| BCL11A-6115 | + | AUAUGAAUCCCAUGGAGAGG | 20 | 7704 |
| BCL11A-6116 | + | CGAGGAGUGCUCCGACGAGG | 20 | 7705 |
| BCL11A-3330 | - | CCCGGAGAACGGGACGAGG | 20 | 7706 |
| BCL11A-3454 | - | AGAAGAGGAGGAAGAGGAGG | 20 | 7707 |
| BCL11A-6117 | + | GAGGUUGGAGACAGAGGAGG | 20 | 7708 |
| BCL11A-3455 | - | AGAGGAGGAAGAGGAGGAGG | 20 | 7709 |
| BCL11A-6118 | + | CGGAUUGCAGAGGAGGGAGG | 20 | 7710 |
| BCL11A-6119 | + | ACCGGGGGCUGGGAGGGAGG | 20 | 7711 |
| BCL11A-6120 | - | CUUCGGGCUGAGCCUGGAGG | 20 | 7712 |
| BCL11A-6121 | - | CCGCCCGGGGAGCUGGACGG | 20 | 7713 |
| BCL11A-6122 | + | CAUGACUUGGACUUGACCGG | 20 | 7714 |
| BCL11A-6123 | + | GUGUUGGGCAUCGCGGCCGG | 20 | 7715 |
| BCL11A-6124 | + | GGCCGGCCUGGGGACAGCGG | 20 | 7716 |
| BCL11A-6125 | + | GGGUUCCGGGGAGCUGGCGG | 20 | 7717 |
| BCL11A-6126 | + | CCCCCAGGCGCUCUAUGCGG | 20 | 7718 |
| BCL11A-6127 | - | CACUUGCGACGAAGACUCGG | 20 | 7719 |
| BCL11A-6128 | - | CCCGGGCGAGUCGGCCUCGG | 20 | 7720 |
| BCL11A-6129 | + | GGGUCCAAGUGAUGUCUCGG | 20 | 7721 |
| BCL11A-6130 | + | GGGGGCGUCGCCAGGAAGGG | 20 | 7722 |
| BCL11A-6131 | + | CGGUGGUGGACUAAACAGGG | 20 | 7723 |
| BCL11A-6132 | - | GCUGACGGAGAGCGAGAGGG | 20 | 7724 |

TABLE 15C-continued

3rd Tier

| gRNA Name | DNA Strand | Targeting Domain | Target Site Length | SEQ ID NO: |
|---|---|---|---|---|
| BCL11A-6133 | + | GGGCGGAUUGCAGAGGAGGG | 20 | 7725 |
| BCL11A-6134 | + | GGAUUGCAGAGGAGGGAGGG | 20 | 7726 |
| BCL11A-6135 | + | UUGACCGGGGCUGGGAGGG | 20 | 7727 |
| BCL11A-6136 | + | CCUCCGUCCAGCUCCCCGGG | 20 | 7728 |
| BCL11A-6137 | + | CUAGAGAAAUCCAUGGCGGG | 20 | 7729 |
| BCL11A-6138 | − | CCGGGCGAGUCGGCCUCGGG | 20 | 7730 |
| BCL11A-6139 | + | GGUGGUGGACUAAACAGGGG | 20 | 7731 |
| BCL11A-6140 | − | AAAUUUGAAGCCCCCAGGGG | 20 | 7732 |
| BCL11A-6141 | + | GGGCUGGGAGGGAGGAGGGG | 20 | 7733 |
| BCL11A-6142 | + | GAUUGCAGAGGAGGGAGGGG | 20 | 7734 |
| BCL11A-6143 | − | CCGCAUAGAGCGCCUGGGGG | 20 | 7735 |
| BCL11A-6144 | − | UGAAGCCCCCAGGGGUGGGG | 20 | 7736 |
| BCL11A-6145 | + | AAAGGCACUCGGGUGAUGGG | 20 | 7737 |
| BCL11A-6146 | + | GGACUUGACCGGGGCUGGG | 20 | 7738 |
| BCL11A-6147 | + | CUAAACAGGGGGGAGUGGG | 20 | 7739 |
| BCL11A-6148 | + | CUGGGUACUACGCCGAAUGG | 20 | 7740 |
| BCL11A-6149 | + | UCUCCUAGAGAAAUCCAUGG | 20 | 7741 |
| BCL11A-6150 | + | GUCGGACUUGACCGUCAUGG | 20 | 7742 |
| BCL11A-6151 | − | CAAAUUUCAGAGCAACCUGG | 20 | 7743 |
| BCL11A-6152 | + | GCUUCUCGCCCAGGACCUGG | 20 | 7744 |
| BCL11A-6153 | − | CGGCUUCGGGCUGAGCCUGG | 20 | 7745 |
| BCL11A-6154 | − | CCACCGCAUAGAGCGCCUGG | 20 | 7746 |
| BCL11A-6155 | + | GGGAUCUUUGAGCUGCCUGG | 20 | 7747 |
| BCL11A-6156 | + | GCCGGGUUCCGGGGAGCUGG | 20 | 7748 |
| BCL11A-6157 | − | CGCAGCGGCACGGGAAGUGG | 20 | 7749 |
| BCL11A-6158 | − | CAGCGCGCUCAAGUCCGUGG | 20 | 7750 |
| BCL11A-6159 | + | CCCGCGAGCUGUUCUCGUGG | 20 | 7751 |
| BCL11A-6160 | + | CCAGGCGCUCUAUGCGGUGG | 20 | 7752 |
| BCL11A-6161 | + | UCCAAGUGAUGUCUCGGUGG | 20 | 7753 |
| BCL11A-6162 | − | ACCCGGCACCAGCGACUUGG | 20 | 7754 |
| BCL11A-6163 | + | UCUGGGUACUACGCCGAAUG | 20 | 7755 |
| BCL11A-6164 | + | CGUCGGACUUGACCGUCAUG | 20 | 7756 |
| BCL11A-6165 | + | UGUGCAUGUGCGUCUUCAUG | 20 | 7757 |
| BCL11A-6166 | + | GGGCCCGGACCACUAAUAUG | 20 | 7758 |
| BCL11A-6167 | + | CCGCCCCAGGCGCUCUAUG | 20 | 7759 |
| BCL11A-6168 | + | UAACAGUGCCAUCGUCUAUG | 20 | 7760 |
| BCL11A-6169 | − | AGCGACACUUGUGAGUACUG | 20 | 7761 |
| BCL11A-6170 | + | CUUCGUCGCAAGUGUCCCUG | 20 | 7762 |

TABLE 15C-continued

3rd Tier

| gRNA Name | DNA Strand | Targeting Domain | Target Site Length | SEQ ID NO: |
|---|---|---|---|---|
| BCL11A-6171 | - | CCCACCGCAUAGAGCGCCUG | 20 | 7763 |
| BCL11A-6172 | + | CAUAGGGCUGGGCCGGCCUG | 20 | 7764 |
| BCL11A-6173 | + | AGAAGGGGCUCAGCGAGCUG | 20 | 7765 |
| BCL11A-6174 | - | GUGCCUUUGACAGGGUGCUG | 20 | 7766 |
| BCL11A-6175 | - | UCCAAGUCAUGCGAGUUCUG | 20 | 7767 |
| BCL11A-6176 | + | UGUAGGGCUUCUCGCCCGUG | 20 | 7768 |
| BCL11A-6177 | + | GUCCAGCUCCCCGGGCGGUG | 20 | 7769 |
| BCL11A-6178 | + | CCCAGGCGCUCUAUGCGGUG | 20 | 7770 |
| BCL11A-6179 | - | AUUUGAAGCCCCCAGGGGUG | 20 | 7771 |
| BCL11A-6180 | - | CCCAGAGAGCUCAAGAUGUG | 20 | 7772 |
| BCL11A-6181 | + | CGUUCUCCGGGAUCAGGUUG | 20 | 7773 |
| BCL11A-6182 | + | CUCUGGGUACUACGCCGAAU | 20 | 7774 |
| BCL11A-6183 | + | GCGGGAGGCUCCAUAGCCAU | 20 | 7775 |
| BCL11A-6184 | - | CUUCCCAGCCACCUCUCCAU | 20 | 7776 |
| BCL11A-6185 | + | GGUUGCAGUAACCUUUGCAU | 20 | 7777 |
| BCL11A-6186 | + | UCGUCGGACUUGACCGUCAU | 20 | 7778 |
| BCL11A-6187 | + | GUCAAAGGCACUCGGGUGAU | 20 | 7779 |
| BCL11A-6188 | + | CGGGCCCGGACCACUAAUAU | 20 | 7780 |
| BCL11A-6189 | + | GUCGUUCUCGCUCUUGAACU | 20 | 7781 |
| BCL11A-6190 | + | AGCACCCUGUCAAAGGCACU | 20 | 7782 |
| BCL11A-6191 | - | UCCACCACCGAGACAUCACU | 20 | 7783 |
| BCL11A-6192 | - | GGACACUUGCGACGAAGACU | 20 | 7784 |
| BCL11A-6193 | - | GGAACCCGGCACCAGCGACU | 20 | 7785 |
| BCL11A-6194 | - | GUUGGUAUCCCUUCAGGACU | 20 | 7786 |
| BCL11A-6195 | + | GCCGCAGAACUCGCAUGACU | 20 | 7787 |
| BCL11A-6196 | + | GCAAGUGUCCCUGUGGCCCU | 20 | 7788 |
| BCL11A-6197 | - | CCCCACCGCAUAGAGCGCCU | 20 | 7789 |
| BCL11A-6198 | + | GCAUAGGGCUGGGCCGGCCU | 20 | 7790 |
| BCL11A-6199 | + | GUCCCUGUGGCCCUCGGCCU | 20 | 7791 |
| BCL11A-6200 | - | CUCCCCGGGCGAGUCGGCCU | 20 | 7792 |
| BCL11A-6201 | + | GCGCUUCAGCUUGCUGGCCU | 20 | 7793 |
| BCL11A-6202 | - | CUCCUCGUCGGAGCACUCCU | 20 | 7794 |
| BCL11A-6203 | - | GAGGCCUUCCACCAGGUCCU | 20 | 7795 |
| BCL11A-6204 | + | GAGAAGGGGCUCAGCGAGCU | 20 | 7796 |
| BCL11A-6205 | + | CGUCUGCCCUCUUUUGAGCU | 20 | 7797 |
| BCL11A-6206 | + | AGUAACCUUUGCAUAGGGCU | 20 | 7798 |
| BCL11A-6207 | + | CUUGGACUUGACCGGGGCU | 20 | 7799 |

TABLE 15C-continued

3rd Tier

| gRNA Name | DNA Strand | Targeting Domain | Target Site Length | SEQ ID NO: |
|---|---|---|---|---|
| BCL11A-6208 | + | AAUCCCAUGGAGAGGUGGCU | 20 | 7800 |
| BCL11A-5508 | + | GUUGUACAUGUGUAGCUGCU | 20 | 7801 |
| BCL11A-6209 | - | CUGUCCAAAAGCUGCUGCU | 20 | 7802 |
| BCL11A-6210 | - | GGAGCUGGACGGAGGGAUCU | 20 | 7803 |
| BCL11A-6211 | + | CCACACAUCUUGAGCUCUCU | 20 | 7804 |
| BCL11A-6212 | - | CUCCCGCCAUGGAUUUCUCU | 20 | 7805 |
| BCL11A-6213 | + | UGGGGGUCCAAGUGAUGUCU | 20 | 7806 |
| BCL11A-6214 | - | UCUGUCUCCAACCUCUUUCU | 20 | 7807 |
| BCL11A-6215 | - | AGACUCGGUGGCCGGCGAGU | 20 | 7808 |
| BCL11A-6216 | - | CGGCUGCUCCCCGGGCGAGU | 20 | 7809 |
| BCL11A-6217 | + | GGACUAAACAGGGGGGGAGU | 20 | 7810 |
| BCL11A-6218 | + | CACCAUGCCCUGCAUGACGU | 20 | 7811 |
| BCL11A-6219 | - | CGGGGCGCGGUCGUGGGCGU | 20 | 7812 |
| BCL11A-6220 | - | AUCGCCUUUUGCCUCCUCGU | 20 | 7813 |
| BCL11A-6221 | + | GGCGGUGGAGAGACCGUCGU | 20 | 7814 |
| BCL11A-6222 | - | AGCUCGCGGGGCGCGGUCGU | 20 | 7815 |
| BCL11A-6223 | + | CCCGUUCUCCGGGAUCAGGU | 20 | 7816 |
| BCL11A-6224 | + | UGAAGAACCUAGAAAGAGGU | 20 | 7817 |
| BCL11A-6225 | + | GCCGGCCUGGGGACAGCGGU | 20 | 7818 |
| BCL11A-6226 | + | CCCCAGGCGCUCUAUGCGGU | 20 | 7819 |
| BCL11A-6227 | - | AGUCCCUGACCCCGCGGGU | 20 | 7820 |
| BCL11A-6228 | - | AAUUUGAAGCCCCCAGGGGU | 20 | 7821 |
| BCL11A-6229 | - | CCCGGCACCAGCGACUUGGU | 20 | 7822 |
| BCL11A-6230 | - | GCGACACUUGUGAGUACUGU | 20 | 7823 |
| BCL11A-6231 | + | CGAGUACACGUUCUCCGUGU | 20 | 7824 |
| BCL11A-6232 | + | GUCGCACAGGUUGCACUUGU | 20 | 7825 |
| BCL11A-6233 | - | GUUCUUCACACACCCCCAUU | 20 | 7826 |
| BCL11A-6234 | - | AAAGAUCCCUUCCUUAGCUU | 20 | 7827 |
| BCL11A-6235 | - | GAGAGGGUGGACUACGGCUU | 20 | 7828 |
| BCL11A-6236 | + | CCGUUCUCCGGGAUCAGGUU | 20 | 7829 |
| BCL11A-6237 | + | GAGUACACGUUCUCCGUGUU | 20 | 7830 |
| BCL11A-6238 | + | GCUGCCCAGCAGCAGCUUUU | 20 | 7831 |
| BCL11A-6239 | - | UCAAGAUGUGUGGCAGUUUU | 20 | 7832 |

Table 15D provides targeting domains for knocking out the BCL11A gene by dual targeting (e.g., dual single strand cleavages). In an embodiment, dual targeting (e.g., dual nicking) is used to create two nicks on opposite DNA strands by using *S. pyogenes* Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary nickase pairs include a targeting domain from Group A and a second targeting domain from Group B, or include a targeting domain from Group C and a second targeting domain from Group D. It is contemplated herein that in an embodiment a targeting domain of Group A can be combined with any of the targeting domains of Group B; in an embodiment a targeting domain of Group C can be combined with any of the targeting domains of Group D. Exemplary gRNA pairs to be used with *S. pyogenes* Cas9 are shown in Table 15D, e.g., BCL11A-5355 or BCL11A-5380 can be combined with BCL11A-5321 or BCL11A-5416; or BCL11A-5333, BCL11A-5354, or BCL11A-5329 can be combined with BCL11A-5367 or BCL11A-5341.

TABLE 15D

| Group A | Group B |
|---|---|
| BCL11A-5355, BCL11A-5380 | BCL11A-5321, BCL11A-5416 |
| Group C | Group D |
| BCL11A-5333, BCL11A-5354, BCL11A-5329 | BCL11A-5367, BCL11A-5341 |

Table 16A provides exemplary targeting domains for knocking out the BCL11A gene selected according to the first tier parameters. The targeting domains bind within the first 500 bp of the coding sequence (e.g., within 500 bp downstream from the start codon) and have a high level of orthogonality, and the PAM is NNGRRT. It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 16A

1st Tier

| gRNA Name | DNA Strand | Targeting Domain | Target Site Length | SEQ ID NO: |
|---|---|---|---|---|
| BCL11A-6240 | + | UGACCUGGAUGCCAACCUCCA | 21 | 7833 |
| BCL11A-6241 | + | GUGACCUGGAUGCCAACCUCCA | 22 | 7834 |
| BCL11A-6242 | + | CGUGACCUGGAUGCCAACCUCCA | 23 | 7835 |
| BCL11A-6243 | + | GCGUGACCUGGAUGCCAACCUCCA | 24 | 7836 |
| BCL11A-6244 | + | AUGCCAACCUCCACGGGA | 18 | 7837 |
| BCL11A-6245 | + | GAUGCCAACCUCCACGGGA | 19 | 7838 |
| BCL11A-6246 | + | GGAUGCCAACCUCCACGGGA | 20 | 7839 |
| BCL11A-6247 | + | UGGAUGCCAACCUCCACGGGA | 21 | 7840 |
| BCL11A-6248 | + | CUGGAUGCCAACCUCCACGGGA | 22 | 7841 |
| BCL11A-6249 | + | CCUGGAUGCCAACCUCCACGGGA | 23 | 7842 |
| BCL11A-6250 | + | ACCUGGAUGCCAACCUCCACGGGA | 24 | 7843 |
| BCL11A-6251 | + | GUCAUCCUCUGGCGUGAC | 18 | 7844 |
| BCL11A-6252 | + | CGUCAUCCUCUGGCGUGAC | 19 | 7845 |
| BCL11A-6253 | + | UCGUCAUCCUCUGGCGUGAC | 20 | 7846 |
| BCL11A-6254 | + | AUCGUCAUCCUCUGGCGUGAC | 21 | 7847 |
| BCL11A-6255 | + | AAUCGUCAUCCUCUGGCGUGAC | 22 | 7848 |
| BCL11A-6256 | + | CAAUCGUCAUCCUCUGGCGUGAC | 23 | 7849 |
| BCL11A-6257 | + | ACAAUCGUCAUCCUCUGGCGUGAC | 24 | 7850 |
| BCL11A-6258 | + | UUAUUGGGUUACUUACGC | 18 | 7851 |
| BCL11A-6259 | + | AUUAUUGGGUUACUUACGC | 19 | 7852 |
| BCL11A-6260 | + | UAUUAUUGGGUUACUUACGC | 20 | 7853 |
| BCL11A-6261 | + | CUAUUAUUGGGUUACUUACGC | 21 | 7854 |
| BCL11A-6262 | + | ACUAUUAUUGGGUUACUUACGC | 22 | 7855 |

TABLE 16A-continued

1st Tier

| gRNA Name | DNA Strand | Targeting Domain | Target Site Length | SEQ ID NO: |
|---|---|---|---|---|
| BCL11A-6263 | + | UACUAUUAUUGGGUUACUUACGC | 23 | 7856 |
| BCL11A-6264 | + | UUACUAUUAUUGGGUUACUUACGC | 24 | 7857 |
| BCL11A-6265 | + | UCCCGUUUGCUUAAGUGC | 18 | 7858 |
| BCL11A-6266 | + | UUCCCGUUUGCUUAAGUGC | 19 | 7859 |
| BCL11A-5352 | + | AUUCCCGUUUGCUUAAGUGC | 20 | 7860 |
| BCL11A-6267 | + | AAUUCCCGUUUGCUUAAGUGC | 21 | 7861 |
| BCL11A-6268 | + | GAAUUCCCGUUUGCUUAAGUGC | 22 | 7862 |
| BCL11A-6269 | + | AGAAUUCCCGUUUGCUUAAGUGC | 23 | 7863 |
| BCL11A-6270 | + | GAGAAUUCCCGUUUGCUUAAGUGC | 24 | 7864 |
| BCL11A-6271 | + | UUUGUGCUCGAUAAAAAU | 18 | 7865 |
| BCL11A-6272 | + | GUUUGUGCUCGAUAAAAAU | 19 | 7866 |
| BCL11A-6273 | + | CGUUUGUGCUCGAUAAAAAU | 20 | 7867 |
| BCL11A-6274 | + | CCGUUUGUGCUCGAUAAAAAU | 21 | 7868 |
| BCL11A-6275 | + | UCCGUUUGUGCUCGAUAAAAAU | 22 | 7869 |
| BCL11A-6276 | + | UUCCGUUUGUGCUCGAUAAAAAU | 23 | 7870 |
| BCL11A-6277 | + | UUUCCGUUUGUGCUCGAUAAAAAU | 24 | 7871 |
| BCL11A-6278 | + | UGCACUCAUCCCAGGCGU | 18 | 7872 |
| BCL11A-6279 | + | CUGCACUCAUCCCAGGCGU | 19 | 7873 |
| BCL11A-5510 | + | UCUGCACUCAUCCCAGGCGU | 20 | 7874 |
| BCL11A-6280 | + | UUCUGCACUCAUCCCAGGCGU | 21 | 7875 |
| BCL11A-6281 | + | AUUCUGCACUCAUCCCAGGCGU | 22 | 7876 |
| BCL11A-6282 | + | UAUUCUGCACUCAUCCCAGGCGU | 23 | 7877 |
| BCL11A-6283 | + | AUAUUCUGCACUCAUCCCAGGCGU | 24 | 7878 |
| BCL11A-6284 | + | GUCUGGUUCAUCAUCUGU | 18 | 7879 |
| BCL11A-6285 | + | GGUCUGGUUCAUCAUCUGU | 19 | 7880 |
| BCL11A-6286 | + | UGGUCUGGUUCAUCAUCUGU | 20 | 7881 |
| BCL11A-6287 | + | GUGGUCUGGUUCAUCAUCUGU | 21 | 7882 |
| BCL11A-6288 | + | CGUGGUCUGGUUCAUCAUCUGU | 22 | 7883 |
| BCL11A-6289 | + | CCGUGGUCUGGUUCAUCAUCUGU | 23 | 7884 |
| BCL11A-6290 | + | GCCGUGGUCUGGUUCAUCAUCUGU | 24 | 7885 |
| BCL11A-6291 | − | CCGUUGGGAGCUCCAGAA | 18 | 7886 |
| BCL11A-6292 | − | CCCGUUGGGAGCUCCAGAA | 19 | 7887 |
| BCL11A-5447 | − | GCCCGUUGGGAGCUCCAGAA | 20 | 7888 |
| BCL11A-6293 | − | GGCCCGUUGGGAGCUCCAGAA | 21 | 7889 |
| BCL11A-6294 | − | CGGCCCGUUGGGAGCUCCAGAA | 22 | 7890 |
| BCL11A-6295 | − | ACGGCCCGUUGGGAGCUCCAGAA | 23 | 7891 |
| BCL11A-6296 | − | CACGGCCCGUUGGGAGCUCCAGAA | 24 | 7892 |

TABLE 16A-continued

1st Tier

| gRNA Name | DNA Strand | Targeting Domain | Target Site Length | SEQ ID NO: |
|---|---|---|---|---|
| BCL11A-6297 | – | GGCAUCCAGGUCACGCCA | 18 | 7893 |
| BCL11A-6298 | – | UGGCAUCCAGGUCACGCCA | 19 | 7894 |
| BCL11A-6299 | – | UUGGCAUCCAGGUCACGCCA | 20 | 7895 |
| BCL11A-6300 | – | GUUGGCAUCCAGGUCACGCCA | 21 | 7896 |
| BCL11A-6301 | – | GGUUGGCAUCCAGGUCACGCCA | 22 | 7897 |
| BCL11A-6302 | – | AGGUUGGCAUCCAGGUCACGCCA | 23 | 7898 |
| BCL11A-6303 | – | GAGGUUGGCAUCCAGGUCACGCCA | 24 | 7899 |
| BCL11A-6304 | – | AACCCCAGCACUUAAGCAAAC | 21 | 7900 |
| BCL11A-6305 | – | AAACCCCAGCACUUAAGCAAAC | 22 | 7901 |
| BCL11A-6306 | – | CAAACCCCAGCACUUAAGCAAAC | 23 | 7902 |
| BCL11A-6307 | – | GCAAACCCCAGCACUUAAGCAAAC | 24 | 7903 |
| BCL11A-6308 | – | AGCUCUAAUCCCCACGCC | 18 | 7904 |
| BCL11A-6309 | – | GAGCUCUAAUCCCCACGCC | 19 | 7905 |
| BCL11A-5350 | – | GGAGCUCUAAUCCCCACGCC | 20 | 7906 |
| BCL11A-6310 | – | UGGAGCUCUAAUCCCCACGCC | 21 | 7907 |
| BCL11A-6311 | – | AUGGAGCUCUAAUCCCCACGCC | 22 | 7908 |
| BCL11A-6312 | – | CAUGGAGCUCUAAUCCCCACGCC | 23 | 7909 |
| BCL11A-6313 | – | ACAUGGAGCUCUAAUCCCCACGCC | 24 | 7910 |
| BCL11A-6314 | – | UUUAUCAACGUCAUCUAG | 18 | 7911 |
| BCL11A-6315 | – | GUUUAUCAACGUCAUCUAG | 19 | 7912 |
| BCL11A-5356 | – | UGUUUAUCAACGUCAUCUAG | 20 | 7913 |
| BCL11A-6316 | – | UUGUUUAUCAACGUCAUCUAG | 21 | 7914 |
| BCL11A-6317 | – | AUUGUUUAUCAACGUCAUCUAG | 22 | 7915 |
| BCL11A-6318 | – | GAUUGUUUAUCAACGUCAUCUAG | 23 | 7916 |
| BCL11A-6319 | – | CGAUUGUUUAUCAACGUCAUCUAG | 24 | 7917 |
| BCL11A-6320 | – | AGUGCAGAAUAUGCCCCG | 18 | 7918 |
| BCL11A-6321 | – | GAGUGCAGAAUAUGCCCCG | 19 | 7919 |
| BCL11A-6322 | – | UGAGUGCAGAAUAUGCCCCG | 20 | 7920 |
| BCL11A-6323 | – | AUGAGUGCAGAAUAUGCCCCG | 21 | 7921 |
| BCL11A-6324 | – | GAUGAGUGCAGAAUAUGCCCCG | 22 | 7922 |
| BCL11A-6325 | – | GGAUGAGUGCAGAAUAUGCCCCG | 23 | 7923 |
| BCL11A-6326 | – | GGGAUGAGUGCAGAAUAUGCCCCG | 24 | 7924 |
| BCL11A-6327 | – | CUAAUCCCCACGCCUGGG | 18 | 7925 |
| BCL11A-6328 | – | UCUAAUCCCCACGCCUGGG | 19 | 7926 |
| BCL11A-6329 | – | CUCUAAUCCCCACGCCUGGG | 20 | 7927 |
| BCL11A-6330 | – | GCUCUAAUCCCCACGCCUGGG | 21 | 7928 |
| BCL11A-6331 | – | AGCUCUAAUCCCCACGCCUGGG | 22 | 7929 |
| BCL11A-6332 | – | GAGCUCUAAUCCCCACGCCUGGG | 23 | 7930 |

TABLE 16A-continued

1st Tier

| gRNA Name | DNA Strand | Targeting Domain | Target Site Length | SEQ ID NO: |
|---|---|---|---|---|
| BCL11A-6333 | - | GGAGCUCUAAUCCCCACGCCUGGG | 24 | 7931 |
| BCL11A-6334 | - | CCACGCCUGGGAUGAGUG | 18 | 7932 |
| BCL11A-6335 | - | CCCACGCCUGGGAUGAGUG | 19 | 7933 |
| BCL11A-6336 | - | CCCCACGCCUGGGAUGAGUG | 20 | 7934 |
| BCL11A-6337 | - | UCCCCACGCCUGGGAUGAGUG | 21 | 7935 |
| BCL11A-6338 | - | AUCCCCACGCCUGGGAUGAGUG | 22 | 7936 |
| BCL11A-6339 | - | AAUCCCCACGCCUGGGAUGAGUG | 23 | 7937 |
| BCL11A-6340 | - | UAAUCCCCACGCCUGGGAUGAGUG | 24 | 7938 |
| BCL11A-6341 | - | CUCUGCUUAGAAAAAGCU | 18 | 7939 |
| BCL11A-6342 | - | CCUCUGCUUAGAAAAAGCU | 19 | 7940 |
| BCL11A-6343 | - | GCCUCUGCUUAGAAAAAGCU | 20 | 7941 |
| BCL11A-6344 | - | AGCCUCUGCUUAGAAAAAGCU | 21 | 7942 |
| BCL11A-6345 | - | CAGCCUCUGCUUAGAAAAAGCU | 22 | 7943 |
| BCL11A-6346 | - | GCAGCCUCUGCUUAGAAAAAGCU | 23 | 7944 |
| BCL11A-6347 | - | GGCAGCCUCUGCUUAGAAAAAGCU | 24 | 7945 |

Table 16B provides exemplary targeting domains for knocking out the BCL11A gene selected according to the second tier parameters. The targeting domains bind within the first 500 bp of the coding sequence (e.g., within 500 bp downstream from the start codon), and the PAM is NNGRRT. It is contemplated herein that in an embodiment the targeting domain hybridizes to the target domain through complementary base pairing. Any of the targeting domains in the table can be used with a S. aureus Cas9 molecule that generates a double stranded break (Cas9 nuclease) or a single-stranded break (Cas9 nickase).

Table 16C provides exemplary targeting domains for knocking out the BCL11A gene selected according to the third tier parameters. The targeting domains bind within the first 500 bp of the coding sequence (e.g., within 500 bp downstream from the start codon), and the PAM is NNGRRV. It is contemplated herein that in an embodiment the targeting domain hybridizes to the target domain through complementary base pairing. Any of the targeting domains in the table can be used with a S. aureus Cas9 molecule that generates a double stranded break (Cas9 nuclease) or a single-stranded break (Cas9 nickase).

TABLE 16B

2nd Tier

| gRNA Name | DNA Strand | Targeting Domain | Target Site Length | SEQ ID NO: |
|---|---|---|---|---|
| BCL11A-6348 | + | CCUGGAUGCCAACCUCCA | 18 | 7946 |
| BCL11A-6349 | + | ACCUGGAUGCCAACCUCCA | 19 | 7947 |
| BCL11A-5450 | + | GACCUGGAUGCCAACCUCCA | 20 | 7948 |
| BCL11A-6350 | - | CCCAGCACUUAAGCAAAC | 18 | 7949 |
| BCL11A-6351 | - | CCCCAGCACUUAAGCAAAC | 19 | 7950 |
| BCL11A-5458 | - | ACCCCAGCACUUAAGCAAAC | 20 | 7951 |

TABLE 16C

| 3rd Tier | | | | |
|---|---|---|---|---|
| gRNA Name | DNA Strand | Targeting Domain | Target Site Length | SEQ ID NO: |
| BCL11A-6352 | + | AAUAAGAAUGUCCCCCAA | 18 | 7952 |
| BCL11A-6353 | + | AAAUAAGAAUGUCCCCCAA | 19 | 7953 |
| BCL11A-5444 | + | AAAAUAAGAAUGUCCCCCAA | 20 | 7954 |
| BCL11A-6354 | + | AAAAAUAAGAAUGUCCCCCAA | 21 | 7955 |
| BCL11A-6355 | + | UAAAAAUAAGAAUGUCCCCCAA | 22 | 7956 |
| BCL11A-6356 | + | AUAAAAAUAAGAAUGUCCCCCAA | 23 | 7957 |
| BCL11A-6357 | + | GAUAAAAAUAAGAAUGUCCCCCAA | 24 | 7958 |
| BCL11A-6358 | + | UUCAUCUCGAUUGGUGAA | 18 | 7959 |
| BCL11A-6359 | + | UUUCAUCUCGAUUGGUGAA | 19 | 7960 |
| BCL11A-5344 | + | UUUUCAUCUCGAUUGGUGAA | 20 | 7961 |
| BCL11A-6360 | + | UUUUUCAUCUCGAUUGGUGAA | 21 | 7962 |
| BCL11A-6361 | + | UUUUUUCAUCUCGAUUGGUGAA | 22 | 7963 |
| BCL11A-6362 | + | CUUUUUUCAUCUCGAUUGGUGAA | 23 | 7964 |
| BCL11A-6363 | + | GCUUUUUUCAUCUCGAUUGGUGAA | 24 | 7965 |
| BCL11A-6364 | + | AAAUAAGAAUGUCCCCA | 18 | 7966 |
| BCL11A-6365 | + | AAAAUAAGAAUGUCCCCA | 19 | 7967 |
| BCL11A-6366 | + | AAAAAUAAGAAUGUCCCCA | 20 | 7968 |
| BCL11A-6367 | + | UAAAAAUAAGAAUGUCCCCA | 21 | 7969 |
| BCL11A-6368 | + | AUAAAAAUAAGAAUGUCCCCA | 22 | 7970 |
| BCL11A-6369 | + | GAUAAAAAUAAGAAUGUCCCCA | 23 | 7971 |
| BCL11A-6370 | + | CGAUAAAAAUAAGAAUGUCCCCA | 24 | 7972 |
| BCL11A-6371 | + | CCCCUUCUGGAGCUCCCA | 18 | 7973 |
| BCL11A-6372 | + | UCCCCUUCUGGAGCUCCCA | 19 | 7974 |
| BCL11A-6373 | + | AUCCCCUUCUGGAGCUCCCA | 20 | 7975 |
| BCL11A-6374 | + | GAUCCCCUUCUGGAGCUCCCA | 21 | 7976 |
| BCL11A-6375 | + | UGAUCCCCUUCUGGAGCUCCCA | 22 | 7977 |
| BCL11A-6376 | + | AUGAUCCCCUUCUGGAGCUCCCA | 23 | 7978 |
| BCL11A-6377 | + | CAUGAUCCCCUUCUGGAGCUCCCA | 24 | 7979 |
| BCL11A-6378 | + | UAGAGCUCCAUGUGCAGA | 18 | 7980 |
| BCL11A-6379 | + | UUAGAGCUCCAUGUGCAGA | 19 | 7981 |
| BCL11A-6380 | + | AUUAGAGCUCCAUGUGCAGA | 20 | 7982 |
| BCL11A-6381 | + | GAUUAGAGCUCCAUGUGCAGA | 21 | 7983 |
| BCL11A-6382 | + | GGAUUAGAGCUCCAUGUGCAGA | 22 | 7984 |
| BCL11A-6383 | + | GGGAUUAGAGCUCCAUGUGCAGA | 23 | 7985 |
| BCL11A-6384 | + | GGGGAUUAGAGCUCCAUGUGCAGA | 24 | 7986 |
| BCL11A-6385 | + | GCUCCAUGUGCAGAACGA | 18 | 7987 |
| BCL11A-6386 | + | AGCUCCAUGUGCAGAACGA | 19 | 7988 |
| BCL11A-5347 | + | GAGCUCCAUGUGCAGAACGA | 20 | 7989 |

TABLE 16C-continued

3rd Tier

| gRNA Name | DNA Strand | Targeting Domain | Target Site Length | SEQ ID NO: |
|---|---|---|---|---|
| BCL11A-6387 | + | AGAGCUCCAUGUGCAGAACGA | 21 | 7990 |
| BCL11A-6388 | + | UAGAGCUCCAUGUGCAGAACGA | 22 | 7991 |
| BCL11A-6389 | + | UUAGAGCUCCAUGUGCAGAACGA | 23 | 7992 |
| BCL11A-6390 | + | AUUAGAGCUCCAUGUGCAGAACGA | 24 | 7993 |
| BCL11A-6391 | + | UUUCAUCUCGAUUGGUGA | 18 | 7994 |
| BCL11A-6392 | + | UUUUCAUCUCGAUUGGUGA | 19 | 7995 |
| BCL11A-5456 | + | UUUUUCAUCUCGAUUGGUGA | 20 | 7996 |
| BCL11A-6393 | + | UUUUUUCAUCUCGAUUGGUGA | 21 | 7997 |
| BCL11A-6394 | + | CUUUUUUCAUCUCGAUUGGUGA | 22 | 7998 |
| BCL11A-6395 | + | GCUUUUUUCAUCUCGAUUGGUGA | 23 | 7999 |
| BCL11A-6396 | + | UGCUUUUUUCAUCUCGAUUGGUGA | 24 | 8000 |
| BCL11A-6397 | + | GCAGAAGUUUAUCUGUGA | 18 | 8001 |
| BCL11A-6398 | + | UGCAGAAGUUUAUCUGUGA | 19 | 8002 |
| BCL11A-6399 | + | GUGCAGAAGUUUAUCUGUGA | 20 | 8003 |
| BCL11A-6400 | + | AGUGCAGAAGUUUAUCUGUGA | 21 | 8004 |
| BCL11A-6401 | + | CAGUGCAGAAGUUUAUCUGUGA | 22 | 8005 |
| BCL11A-6402 | + | CCAGUGCAGAAGUUUAUCUGUGA | 23 | 8006 |
| BCL11A-6403 | + | UCCAGUGCAGAAGUUUAUCUGUGA | 24 | 8007 |
| BCL11A-6404 | + | GAGCUCCAUGUGCAGAAC | 18 | 8008 |
| BCL11A-6405 | + | AGAGCUCCAUGUGCAGAAC | 19 | 8009 |
| BCL11A-6406 | + | UAGAGCUCCAUGUGCAGAAC | 20 | 8010 |
| BCL11A-6407 | + | UUAGAGCUCCAUGUGCAGAAC | 21 | 8011 |
| BCL11A-6408 | + | AUUAGAGCUCCAUGUGCAGAAC | 22 | 8012 |
| BCL11A-6409 | + | GAUUAGAGCUCCAUGUGCAGAAC | 23 | 8013 |
| BCL11A-6410 | + | GGAUUAGAGCUCCAUGUGCAGAAC | 24 | 8014 |
| BCL11A-6411 | + | UAUUAUUGGGUUACUUAC | 18 | 8015 |
| BCL11A-6412 | + | CUAUUAUUGGGUUACUUAC | 19 | 8016 |
| BCL11A-6413 | + | ACUAUUAUUGGGUUACUUAC | 20 | 8017 |
| BCL11A-6414 | + | UACUAUUAUUGGGUUACUUAC | 21 | 8018 |
| BCL11A-6415 | + | UUACUAUUAUUGGGUUACUUAC | 22 | 8019 |
| BCL11A-6416 | + | AUUACUAUUAUUGGGUUACUUAC | 23 | 8020 |
| BCL11A-6417 | + | UAUUACUAUUAUUGGGUUACUUAC | 24 | 8021 |
| BCL11A-6418 | + | ACCUGGAUGCCAACCUCC | 18 | 8022 |
| BCL11A-6419 | + | GACCUGGAUGCCAACCUCC | 19 | 8023 |
| BCL11A-6420 | + | UGACCUGGAUGCCAACCUCC | 20 | 8024 |
| BCL11A-6421 | + | GUGACCUGGAUGCCAACCUCC | 21 | 8025 |
| BCL11A-6422 | + | CGUGACCUGGAUGCCAACCUCC | 22 | 8026 |

TABLE 16C-continued

3rd Tier

| gRNA Name | DNA Strand | Targeting Domain | Target Site Length | SEQ ID NO: |
|---|---|---|---|---|
| BCL11A-6423 | + | GCGUGACCUGGAUGCCAACCUCC | 23 | 8027 |
| BCL11A-6424 | + | GGCGUGACCUGGAUGCCAACCUCC | 24 | 8028 |
| BCL11A-6425 | + | UCUGCACUCAUCCCAGGC | 18 | 8029 |
| BCL11A-6426 | + | UUCUGCACUCAUCCCAGGC | 19 | 8030 |
| BCL11A-6427 | + | AUUCUGCACUCAUCCCAGGC | 20 | 8031 |
| BCL11A-6428 | + | UAUUCUGCACUCAUCCCAGGC | 21 | 8032 |
| BCL11A-6429 | + | AUAUUCUGCACUCAUCCCAGGC | 22 | 8033 |
| BCL11A-6430 | + | CAUAUUCUGCACUCAUCCCAGGC | 23 | 8034 |
| BCL11A-6431 | + | GCAUAUUCUGCACUCAUCCCAGGC | 24 | 8035 |
| BCL11A-6432 | + | GAGGUCAUGAUCCCCUUC | 18 | 8036 |
| BCL11A-6433 | + | GGAGGUCAUGAUCCCCUUC | 19 | 8037 |
| BCL11A-5471 | + | AGGAGGUCAUGAUCCCCUUC | 20 | 8038 |
| BCL11A-6434 | + | GAGGAGGUCAUGAUCCCCUUC | 21 | 8039 |
| BCL11A-6435 | + | UGAGGAGGUCAUGAUCCCCUUC | 22 | 8040 |
| BCL11A-6436 | + | GUGAGGAGGUCAUGAUCCCCUUC | 23 | 8041 |
| BCL11A-6437 | + | GGUGAGGAGGUCAUGAUCCCCUUC | 24 | 8042 |
| BCL11A-6438 | + | AUCUGUAAGAAUGGCUUC | 18 | 8043 |
| BCL11A-6439 | + | CAUCUGUAAGAAUGGCUUC | 19 | 8044 |
| BCL11A-6440 | + | UCAUCUGUAAGAAUGGCUUC | 20 | 8045 |
| BCL11A-6441 | + | AUCAUCUGUAAGAAUGGCUUC | 21 | 8046 |
| BCL11A-6442 | + | CAUCAUCUGUAAGAAUGGCUUC | 22 | 8047 |
| BCL11A-6443 | + | UCAUCAUCUGUAAGAAUGGCUUC | 23 | 8048 |
| BCL11A-6444 | + | UUCAUCAUCUGUAAGAAUGGCUUC | 24 | 8049 |
| BCL11A-6445 | + | UCAUCUCGAUUGGUGAAG | 18 | 8050 |
| BCL11A-6446 | + | UUCAUCUCGAUUGGUGAAG | 19 | 8051 |
| BCL11A-5355 | + | UUUCAUCUCGAUUGGUGAAG | 20 | 8052 |
| BCL11A-6447 | + | UUUUCAUCUCGAUUGGUGAAG | 21 | 8053 |
| BCL11A-6448 | + | UUUUUCAUCUCGAUUGGUGAAG | 22 | 8054 |
| BCL11A-6449 | + | UUUUUUCAUCUCGAUUGGUGAAG | 23 | 8055 |
| BCL11A-6450 | + | CUUUUUUCAUCUCGAUUGGUGAAG | 24 | 8056 |
| BCL11A-6451 | + | UCCACAGCUUUUUCUAAG | 18 | 8057 |
| BCL11A-6452 | + | AUCCACAGCUUUUUCUAAG | 19 | 8058 |
| BCL11A-6453 | + | UAUCCACAGCUUUUUCUAAG | 20 | 8059 |
| BCL11A-6454 | + | UUAUCCACAGCUUUUUCUAAG | 21 | 8060 |
| BCL11A-6455 | + | CUUAUCCACAGCUUUUUCUAAG | 22 | 8061 |
| BCL11A-6456 | + | GCUUAUCCACAGCUUUUUCUAAG | 23 | 8062 |
| BCL11A-6457 | + | GGCUUAUCCACAGCUUUUUCUAAG | 24 | 8063 |
| BCL11A-6458 | + | AUCUGGCACUGCCCACAG | 18 | 8064 |

TABLE 16C-continued

3rd Tier

| gRNA Name | DNA Strand | Targeting Domain | Target Site Length | SEQ ID NO: |
|---|---|---|---|---|
| BCL11A-6459 | + | CAUCUGGCACUGCCCACAG | 19 | 8065 |
| BCL11A-6460 | + | UCAUCUGGCACUGCCCACAG | 20 | 8066 |
| BCL11A-6461 | + | UUCAUCUGGCACUGCCCACAG | 21 | 8067 |
| BCL11A-6462 | + | GUUCAUCUGGCACUGCCCACAG | 22 | 8068 |
| BCL11A-6463 | + | AGUUCAUCUGGCACUGCCCACAG | 23 | 8069 |
| BCL11A-6464 | + | AAGUUCAUCUGGCACUGCCCACAG | 24 | 8070 |
| BCL11A-6465 | + | CUCCAUGUGCAGAACGAG | 18 | 8071 |
| BCL11A-6466 | + | GCUCCAUGUGCAGAACGAG | 19 | 8072 |
| BCL11A-5476 | + | AGCUCCAUGUGCAGAACGAG | 20 | 8073 |
| BCL11A-6467 | + | GAGCUCCAUGUGCAGAACGAG | 21 | 8074 |
| BCL11A-6468 | + | AGAGCUCCAUGUGCAGAACGAG | 22 | 8075 |
| BCL11A-6469 | + | UAGAGCUCCAUGUGCAGAACGAG | 23 | 8076 |
| BCL11A-6470 | + | UUAGAGCUCCAUGUGCAGAACGAG | 24 | 8077 |
| BCL11A-6471 | + | UGUGCAGAACGAGGGGAG | 18 | 8078 |
| BCL11A-6472 | + | AUGUGCAGAACGAGGGGAG | 19 | 8079 |
| BCL11A-6473 | + | CAUGUGCAGAACGAGGGGAG | 20 | 8080 |
| BCL11A-6474 | + | CCAUGUGCAGAACGAGGGGAG | 21 | 8081 |
| BCL11A-6475 | + | UCCAUGUGCAGAACGAGGGGAG | 22 | 8082 |
| BCL11A-6476 | + | CUCCAUGUGCAGAACGAGGGGAG | 23 | 8083 |
| BCL11A-6477 | + | GCUCCAUGUGCAGAACGAGGGGAG | 24 | 8084 |
| BCL11A-6478 | + | AGCUCCAUGUGCAGAACG | 18 | 8085 |
| BCL11A-6479 | + | GAGCUCCAUGUGCAGAACG | 19 | 8086 |
| BCL11A-5357 | + | AGAGCUCCAUGUGCAGAACG | 20 | 8087 |
| BCL11A-6480 | + | UAGAGCUCCAUGUGCAGAACG | 21 | 8088 |
| BCL11A-6481 | + | UUAGAGCUCCAUGUGCAGAACG | 22 | 8089 |
| BCL11A-6482 | + | AUUAGAGCUCCAUGUGCAGAACG | 23 | 8090 |
| BCL11A-6483 | + | GAUUAGAGCUCCAUGUGCAGAACG | 24 | 8091 |
| BCL11A-6484 | + | CUGCACUCAUCCCAGGCG | 18 | 8092 |
| BCL11A-6485 | + | UCUGCACUCAUCCCAGGCG | 19 | 8093 |
| BCL11A-5480 | + | UUCUGCACUCAUCCCAGGCG | 20 | 8094 |
| BCL11A-6486 | + | AUUCUGCACUCAUCCCAGGCG | 21 | 8095 |
| BCL11A-6487 | + | UAUUCUGCACUCAUCCCAGGCG | 22 | 8096 |
| BCL11A-6488 | + | AUAUUCUGCACUCAUCCCAGGCG | 23 | 8097 |
| BCL11A-6489 | + | CAUAUUCUGCACUCAUCCCAGGCG | 24 | 8098 |
| BCL11A-6490 | + | GGGUUUGCCUUGCUUGCG | 18 | 8099 |
| BCL11A-6491 | + | GGGGUUUGCCUUGCUUGCG | 19 | 8100 |
| BCL11A-6492 | + | UGGGGUUUGCCUUGCUUGCG | 20 | 8101 |

TABLE 16C-continued

3rd Tier

| gRNA Name | DNA Strand | Targeting Domain | Target Site Length | SEQ ID NO: |
|---|---|---|---|---|
| BCL11A-6493 | + | CUGGGGUUUGCCUUGCUUGCG | 21 | 8102 |
| BCL11A-6494 | + | GCUGGGGUUUGCCUUGCUUGCG | 22 | 8103 |
| BCL11A-6495 | + | UGCUGGGGUUUGCCUUGCUUGCG | 23 | 8104 |
| BCL11A-6496 | + | GUGCUGGGGUUUGCCUUGCUUGCG | 24 | 8105 |
| BCL11A-6497 | + | CCAUGUGCAGAACGAGGG | 18 | 8106 |
| BCL11A-6498 | + | UCCAUGUGCAGAACGAGGG | 19 | 8107 |
| BCL11A-6499 | + | CUCCAUGUGCAGAACGAGGG | 20 | 8108 |
| BCL11A-6500 | + | GCUCCAUGUGCAGAACGAGGG | 21 | 8109 |
| BCL11A-6501 | + | AGCUCCAUGUGCAGAACGAGGG | 22 | 8110 |
| BCL11A-6502 | + | GAGCUCCAUGUGCAGAACGAGGG | 23 | 8111 |
| BCL11A-6503 | + | AGAGCUCCAUGUGCAGAACGAGGG | 24 | 8112 |
| BCL11A-6504 | + | GACAUGGUGGGCUGCGGG | 18 | 8113 |
| BCL11A-6505 | + | AGACAUGGUGGGCUGCGGG | 19 | 8114 |
| BCL11A-6506 | + | GAGACAUGGUGGGCUGCGGG | 20 | 8115 |
| BCL11A-6507 | + | CGAGACAUGGUGGGCUGCGGG | 21 | 8116 |
| BCL11A-6508 | + | GCGAGACAUGGUGGGCUGCGGG | 22 | 8117 |
| BCL11A-6509 | + | GGCGAGACAUGGUGGGCUGCGGG | 23 | 8118 |
| BCL11A-6510 | + | CGGCGAGACAUGGUGGGCUGCGGG | 24 | 8119 |
| BCL11A-6511 | + | CAUGUGCAGAACGAGGGG | 18 | 8120 |
| BCL11A-6512 | + | CCAUGUGCAGAACGAGGGG | 19 | 8121 |
| BCL11A-5488 | + | UCCAUGUGCAGAACGAGGGG | 20 | 8122 |
| BCL11A-6513 | + | CUCCAUGUGCAGAACGAGGGG | 21 | 8123 |
| BCL11A-6514 | + | GCUCCAUGUGCAGAACGAGGGG | 22 | 8124 |
| BCL11A-6515 | + | AGCUCCAUGUGCAGAACGAGGGG | 23 | 8125 |
| BCL11A-6516 | + | GAGCUCCAUGUGCAGAACGAGGGG | 24 | 8126 |
| BCL11A-6517 | + | CAAGAGGCUCGGCUGUGG | 18 | 8127 |
| BCL11A-6518 | + | UCAAGAGGCUCGGCUGUGG | 19 | 8128 |
| BCL11A-6519 | + | UUCAAGAGGCUCGGCUGUGG | 20 | 8129 |
| BCL11A-6520 | + | CUUCAAGAGGCUCGGCUGUGG | 21 | 8130 |
| BCL11A-6521 | + | GCUUCAAGAGGCUCGGCUGUGG | 22 | 8131 |
| BCL11A-6522 | + | GGCUUCAAGAGGCUCGGCUGUGG | 23 | 8132 |
| BCL11A-6523 | + | UGGCUUCAAGAGGCUCGGCUGUGG | 24 | 8133 |
| BCL11A-6524 | + | UGCUUGCGGCGAGACAUG | 18 | 8134 |
| BCL11A-6525 | + | UUGCUUGCGGCGAGACAUG | 19 | 8135 |
| BCL11A-6526 | + | CUUGCUUGCGGCGAGACAUG | 20 | 8136 |
| BCL11A-6527 | + | CCUUGCUUGCGGCGAGACAUG | 21 | 8137 |
| BCL11A-6528 | + | GCCUUGCUUGCGGCGAGACAUG | 22 | 8138 |
| BCL11A-6529 | + | UGCCUUGCUUGCGGCGAGACAUG | 23 | 8139 |

TABLE 16C-continued

| 3rd Tier | | | | |
|---|---|---|---|---|
| gRNA Name | DNA Strand | Targeting Domain | Target Site Length | SEQ ID NO: |
| BCL11A-6530 | + | UUGCCUUGCUUGCGGCGAGACAUG | 24 | 8140 |
| BCL11A-6531 | + | CAACUUACAAAUACCCUG | 18 | 8141 |
| BCL11A-6532 | + | UCAACUUACAAAUACCCUG | 19 | 8142 |
| BCL11A-5494 | + | CUCAACUUACAAAUACCCUG | 20 | 8143 |
| BCL11A-6533 | + | GCUCAACUUACAAAUACCCUG | 21 | 8144 |
| BCL11A-6534 | + | GGCUCAACUUACAAAUACCCUG | 22 | 8145 |
| BCL11A-6535 | + | AGGCUCAACUUACAAAUACCCUG | 23 | 8146 |
| BCL11A-6536 | + | AAGGCUCAACUUACAAAUACCCUG | 24 | 8147 |
| BCL11A-6537 | + | GUUGUACAUGUGUAGCUG | 18 | 8148 |
| BCL11A-6538 | + | AGUUGUACAUGUGUAGCUG | 19 | 8149 |
| BCL11A-6539 | + | AAGUUGUACAUGUGUAGCUG | 20 | 8150 |
| BCL11A-6540 | + | CAAGUUGUACAUGUGUAGCUG | 21 | 8151 |
| BCL11A-6541 | + | GCAAGUUGUACAUGUGUAGCUG | 22 | 8152 |
| BCL11A-6542 | + | UGCAAGUUGUACAUGUGUAGCUG | 23 | 8153 |
| BCL11A-6543 | + | UUGCAAGUUGUACAUGUGUAGCUG | 24 | 8154 |
| BCL11A-6544 | + | GCGAGACAUGGUGGGCUG | 18 | 8155 |
| BCL11A-6545 | + | GGCGAGACAUGGUGGGCUG | 19 | 8156 |
| BCL11A-5361 | + | CGGCGAGACAUGGUGGGCUG | 20 | 8157 |
| BCL11A-6546 | + | GCGGCGAGACAUGGUGGGCUG | 21 | 8158 |
| BCL11A-6547 | + | UGCGGCGAGACAUGGUGGGCUG | 22 | 8159 |
| BCL11A-6548 | + | UUGCGGCGAGACAUGGUGGGCUG | 23 | 8160 |
| BCL11A-6549 | + | CUUGCGGCGAGACAUGGUGGGCUG | 24 | 8161 |
| BCL11A-6550 | + | UUCCCGUUUGCUUAAGUG | 18 | 8162 |
| BCL11A-6551 | + | AUUCCCGUUUGCUUAAGUG | 19 | 8163 |
| BCL11A-6552 | + | AAUUCCCGUUUGCUUAAGUG | 20 | 8164 |
| BCL11A-6553 | + | GAAUUCCCGUUUGCUUAAGUG | 21 | 8165 |
| BCL11A-6554 | + | AGAAUUCCCGUUUGCUUAAGUG | 22 | 8166 |
| BCL11A-6555 | + | GAGAAUUCCCGUUUGCUUAAGUG | 23 | 8167 |
| BCL11A-6556 | + | CGAGAAUUCCCGUUUGCUUAAGUG | 24 | 8168 |
| BCL11A-6557 | + | GGAGAGGCCCCUCCAGUG | 18 | 8169 |
| BCL11A-6558 | + | AGGAGAGGCCCCUCCAGUG | 19 | 8170 |
| BCL11A-6559 | + | GAGGAGAGGCCCCUCCAGUG | 20 | 8171 |
| BCL11A-6560 | + | GGAGGAGAGGCCCCUCCAGUG | 21 | 8172 |
| BCL11A-6561 | + | GGGAGGAGAGGCCCCUCCAGUG | 22 | 8173 |
| BCL11A-6562 | + | GGGGAGGAGAGGCCCCUCCAGUG | 23 | 8174 |
| BCL11A-6563 | + | AGGGGAGGAGAGGCCCCUCCAGUG | 24 | 8175 |
| BCL11A-6564 | + | UGGCACUGCCCACAGGUG | 18 | 8176 |

TABLE 16C-continued

3rd Tier

| gRNA Name | DNA Strand | Targeting Domain | Target Site Length | SEQ ID NO: |
|---|---|---|---|---|
| BCL11A-6565 | + | CUGGCACUGCCCACAGGUG | 19 | 8177 |
| BCL11A-5498 | + | UCUGGCACUGCCCACAGGUG | 20 | 8178 |
| BCL11A-6566 | + | AUCUGGCACUGCCCACAGGUG | 21 | 8179 |
| BCL11A-6567 | + | CAUCUGGCACUGCCCACAGGUG | 22 | 8180 |
| BCL11A-6568 | + | UCAUCUGGCACUGCCCACAGGUG | 23 | 8181 |
| BCL11A-6569 | + | UUCAUCUGGCACUGCCCACAGGUG | 24 | 8182 |
| BCL11A-6570 | + | UUUUCAUCUCGAUUGGUG | 18 | 8183 |
| BCL11A-6571 | + | UUUUUCAUCUCGAUUGGUG | 19 | 8184 |
| BCL11A-6572 | + | UUUUUUCAUCUCGAUUGGUG | 20 | 8185 |
| BCL11A-6573 | + | CUUUUUUCAUCUCGAUUGGUG | 21 | 8186 |
| BCL11A-6574 | + | GCUUUUUUCAUCUCGAUUGGUG | 22 | 8187 |
| BCL11A-6575 | + | UGCUUUUUUCAUCUCGAUUGGUG | 23 | 8188 |
| BCL11A-6576 | + | AUGCUUUUUUCAUCUCGAUUGGUG | 24 | 8189 |
| BCL11A-6577 | + | GGAUUAGAGCUCCAUGUG | 18 | 8190 |
| BCL11A-6578 | + | GGGAUUAGAGCUCCAUGUG | 19 | 8191 |
| BCL11A-6579 | + | GGGGAUUAGAGCUCCAUGUG | 20 | 8192 |
| BCL11A-6580 | + | UGGGGAUUAGAGCUCCAUGUG | 21 | 8193 |
| BCL11A-6581 | + | GUGGGGAUUAGAGCUCCAUGUG | 22 | 8194 |
| BCL11A-6582 | + | CGUGGGGAUUAGAGCUCCAUGUG | 23 | 8195 |
| BCL11A-6583 | + | GCGUGGGGAUUAGAGCUCCAUGUG | 24 | 8196 |
| BCL11A-6584 | + | CUUUUUUCAUCUCGAUUG | 18 | 8197 |
| BCL11A-6585 | + | GCUUUUUUCAUCUCGAUUG | 19 | 8198 |
| BCL11A-6586 | + | UGCUUUUUUCAUCUCGAUUG | 20 | 8199 |
| BCL11A-6587 | + | AUGCUUUUUUCAUCUCGAUUG | 21 | 8200 |
| BCL11A-6588 | + | GAUGCUUUUUUCAUCUCGAUUG | 22 | 8201 |
| BCL11A-6589 | + | GGAUGCUUUUUUCAUCUCGAUUG | 23 | 8202 |
| BCL11A-6590 | + | UGGAUGCUUUUUUCAUCUCGAUUG | 24 | 8203 |
| BCL11A-6591 | + | GAGGCUCGGCUGUGGUUG | 18 | 8204 |
| BCL11A-6592 | + | AGAGGCUCGGCUGUGGUUG | 19 | 8205 |
| BCL11A-6593 | + | AAGAGGCUCGGCUGUGGUUG | 20 | 8206 |
| BCL11A-6594 | + | CAAGAGGCUCGGCUGUGGUUG | 21 | 8207 |
| BCL11A-6595 | + | UCAAGAGGCUCGGCUGUGGUUG | 22 | 8208 |
| BCL11A-6596 | + | UUCAAGAGGCUCGGCUGUGGUUG | 23 | 8209 |
| BCL11A-6597 | + | CUUCAAGAGGCUCGGCUGUGGUUG | 24 | 8210 |
| BCL11A-6598 | + | AUAAGAAUGUCCCCAAU | 18 | 8211 |
| BCL11A-6599 | + | AAUAAGAAUGUCCCCAAU | 19 | 8212 |
| BCL11A-5502 | + | AAAUAAGAAUGUCCCCAAU | 20 | 8213 |
| BCL11A-6600 | + | AAAAUAAGAAUGUCCCCAAU | 21 | 8214 |

TABLE 16C-continued

3rd Tier

| gRNA Name | DNA Strand | Targeting Domain | Target Site Length | SEQ ID NO: |
|---|---|---|---|---|
| BCL11A-6601 | + | AAAAAUAAGAAUGUCCCCCAAU | 22 | 8215 |
| BCL11A-6602 | + | UAAAAAUAAGAAUGUCCCCCAAU | 23 | 8216 |
| BCL11A-6603 | + | AUAAAAAUAAGAAUGUCCCCCAAU | 24 | 8217 |
| BCL11A-6604 | + | CAUCCCAGGCGUGGGGAU | 18 | 8218 |
| BCL11A-6605 | + | UCAUCCCAGGCGUGGGGAU | 19 | 8219 |
| BCL11A-6606 | + | CUCAUCCCAGGCGUGGGGAU | 20 | 8220 |
| BCL11A-6607 | + | ACUCAUCCCAGGCGUGGGGAU | 21 | 8221 |
| BCL11A-6608 | + | CACUCAUCCCAGGCGUGGGGAU | 22 | 8222 |
| BCL11A-6609 | + | GCACUCAUCCCAGGCGUGGGGAU | 23 | 8223 |
| BCL11A-6610 | + | UGCACUCAUCCCAGGCGUGGGGAU | 24 | 8224 |
| BCL11A-6611 | + | UCAACUUACAAAUACCCU | 18 | 8225 |
| BCL11A-6612 | + | CUCAACUUACAAAUACCCU | 19 | 8226 |
| BCL11A-6613 | + | GCUCAACUUACAAAUACCCU | 20 | 8227 |
| BCL11A-6614 | + | GGCUCAACUUACAAAUACCCU | 21 | 8228 |
| BCL11A-6615 | + | AGGCUCAACUUACAAAUACCCU | 22 | 8229 |
| BCL11A-6616 | + | AAGGCUCAACUUACAAAUACCCU | 23 | 8230 |
| BCL11A-6617 | + | UAAGGCUCAACUUACAAAUACCCU | 24 | 8231 |
| BCL11A-6618 | + | GGCGAGACAUGGUGGGCU | 18 | 8232 |
| BCL11A-6619 | + | CGGCGAGACAUGGUGGGCU | 19 | 8233 |
| BCL11A-6620 | + | GCGGCGAGACAUGGUGGGCU | 20 | 8234 |
| BCL11A-6621 | + | UGCGGCGAGACAUGGUGGGCU | 21 | 8235 |
| BCL11A-6622 | + | UUGCGGCGAGACAUGGUGGGCU | 22 | 8236 |
| BCL11A-6623 | + | CUUGCGGCGAGACAUGGUGGGCU | 23 | 8237 |
| BCL11A-6624 | + | GCUUGCGGCGAGACAUGGUGGGCU | 24 | 8238 |
| BCL11A-6625 | + | CAGUGCAGAAGUUUAUCU | 18 | 8239 |
| BCL11A-6626 | + | CCAGUGCAGAAGUUUAUCU | 19 | 8240 |
| BCL11A-6627 | + | UCCAGUGCAGAAGUUUAUCU | 20 | 8241 |
| BCL11A-6628 | + | CUCCAGUGCAGAAGUUUAUCU | 21 | 8242 |
| BCL11A-6629 | + | CCUCCAGUGCAGAAGUUUAUCU | 22 | 8243 |
| BCL11A-6630 | + | CCCUCCAGUGCAGAAGUUUAUCU | 23 | 8244 |
| BCL11A-6631 | + | CCCCUCCAGUGCAGAAGUUUAUCU | 24 | 8245 |
| BCL11A-6632 | + | CUGGCACUGCCCACAGGU | 18 | 8246 |
| BCL11A-6633 | + | UCUGGCACUGCCCACAGGU | 19 | 8247 |
| BCL11A-6634 | + | AUCUGGCACUGCCCACAGGU | 20 | 8248 |
| BCL11A-6635 | + | CAUCUGGCACUGCCCACAGGU | 21 | 8249 |
| BCL11A-6636 | + | UCAUCUGGCACUGCCCACAGGU | 22 | 8250 |
| BCL11A-6637 | + | UUCAUCUGGCACUGCCCACAGGU | 23 | 8251 |

TABLE 16C-continued

3rd Tier

| gRNA Name | DNA Strand | Targeting Domain | Target Site Length | SEQ ID NO: |
|---|---|---|---|---|
| BCL11A-6638 | + | GUUCAUCUGGCACUGCCCACAGGU | 24 | 8252 |
| BCL11A-6639 | + | AAGAGGCUCGGCUGUGGU | 18 | 8253 |
| BCL11A-6640 | + | CAAGAGGCUCGGCUGUGGU | 19 | 8254 |
| BCL11A-5366 | + | UCAAGAGGCUCGGCUGUGGU | 20 | 8255 |
| BCL11A-6641 | + | UUCAAGAGGCUCGGCUGUGGU | 21 | 8256 |
| BCL11A-6642 | + | CUUCAAGAGGCUCGGCUGUGGU | 22 | 8257 |
| BCL11A-6643 | + | GCUUCAAGAGGCUCGGCUGUGGU | 23 | 8258 |
| BCL11A-6644 | + | GGCUUCAAGAGGCUCGGCUGUGGU | 24 | 8259 |
| BCL11A-6645 | + | CCUGCUAUGUGUUCCUGU | 18 | 8260 |
| BCL11A-6646 | + | ACCUGCUAUGUGUUCCUGU | 19 | 8261 |
| BCL11A-6647 | + | UACCUGCUAUGUGUUCCUGU | 20 | 8262 |
| BCL11A-6648 | + | UUACCUGCUAUGUGUUCCUGU | 21 | 8263 |
| BCL11A-6649 | + | UUUACCUGCUAUGUGUUCCUGU | 22 | 8264 |
| BCL11A-6650 | + | AUUUACCUGCUAUGUGUUCCUGU | 23 | 8265 |
| BCL11A-6651 | + | CAUUUACCUGCUAUGUGUUCCUGU | 24 | 8266 |
| BCL11A-6652 | + | GGAGGUCAUGAUCCCCUU | 18 | 8267 |
| BCL11A-6653 | + | AGGAGGUCAUGAUCCCCUU | 19 | 8268 |
| BCL11A-6654 | + | GAGGAGGUCAUGAUCCCCUU | 20 | 8269 |
| BCL11A-6655 | + | UGAGGAGGUCAUGAUCCCCUU | 21 | 8270 |
| BCL11A-6656 | + | GUGAGGAGGUCAUGAUCCCCUU | 22 | 8271 |
| BCL11A-6657 | + | GGUGAGGAGGUCAUGAUCCCCUU | 23 | 8272 |
| BCL11A-6658 | + | AGGUGAGGAGGUCAUGAUCCCCUU | 24 | 8273 |
| BCL11A-6659 | + | CUGCUAUGUGUUCCUGUU | 18 | 8274 |
| BCL11A-6660 | + | CCUGCUAUGUGUUCCUGUU | 19 | 8275 |
| BCL11A-5513 | + | ACCUGCUAUGUGUUCCUGUU | 20 | 8276 |
| BCL11A-6661 | + | UACCUGCUAUGUGUUCCUGUU | 21 | 8277 |
| BCL11A-6662 | + | UUACCUGCUAUGUGUUCCUGUU | 22 | 8278 |
| BCL11A-6663 | + | UUUACCUGCUAUGUGUUCCUGUU | 23 | 8279 |
| BCL11A-6664 | + | AUUUACCUGCUAUGUGUUCCUGUU | 24 | 8280 |
| BCL11A-6665 | – | AUUUUUAUCGAGCACAAA | 18 | 8281 |
| BCL11A-6666 | – | UAUUUUUAUCGAGCACAAA | 19 | 8282 |
| BCL11A-5342 | – | UUAUUUUUAUCGAGCACAAA | 20 | 8283 |
| BCL11A-6667 | – | CUUAUUUUUAUCGAGCACAAA | 21 | 8284 |
| BCL11A-6668 | – | UCUUAUUUUUAUCGAGCACAAA | 22 | 8285 |
| BCL11A-6669 | – | UUCUUAUUUUUAUCGAGCACAAA | 23 | 8286 |
| BCL11A-6670 | – | AUUCUUAUUUUUAUCGAGCACAAA | 24 | 8287 |
| BCL11A-6671 | – | AGAGGAAUUUGCCCCAAA | 18 | 8288 |
| BCL11A-6672 | – | UAGAGGAAUUUGCCCCAAA | 19 | 8289 |

TABLE 16C-continued

3rd Tier

| gRNA Name | DNA Strand | Targeting Domain | Target Site Length | SEQ ID NO: |
|---|---|---|---|---|
| BCL11A-6673 | − | CUAGAGGAAUUUGCCCCAAA | 20 | 8290 |
| BCL11A-6674 | − | UCUAGAGGAAUUUGCCCCAAA | 21 | 8291 |
| BCL11A-6675 | − | AUCUAGAGGAAUUUGCCCCAAA | 22 | 8292 |
| BCL11A-6676 | − | CAUCUAGAGGAAUUUGCCCCAAA | 23 | 8293 |
| BCL11A-6677 | − | UCAUCUAGAGGAAUUUGCCCCAAA | 24 | 8294 |
| BCL11A-6678 | − | CCCCAGCACUUAAGCAAA | 18 | 8295 |
| BCL11A-6679 | − | ACCCCAGCACUUAAGCAAA | 19 | 8296 |
| BCL11A-5443 | − | AACCCCAGCACUUAAGCAAA | 20 | 8297 |
| BCL11A-6680 | − | AAACCCCAGCACUUAAGCAAA | 21 | 8298 |
| BCL11A-6681 | − | CAAACCCCAGCACUUAAGCAAA | 22 | 8299 |
| BCL11A-6682 | − | GCAAACCCCAGCACUUAAGCAAA | 23 | 8300 |
| BCL11A-6683 | − | GGCAAACCCCAGCACUUAAGCAAA | 24 | 8301 |
| BCL11A-6684 | − | UAUUUUUAUCGAGCACAA | 18 | 8302 |
| BCL11A-6685 | − | UUAUUUUUAUCGAGCACAA | 19 | 8303 |
| BCL11A-6686 | − | CUUAUUUUUAUCGAGCACAA | 20 | 8304 |
| BCL11A-6687 | − | UCUUAUUUUUAUCGAGCACAA | 21 | 8305 |
| BCL11A-6688 | − | UUCUUAUUUUUAUCGAGCACAA | 22 | 8306 |
| BCL11A-6689 | − | AUUCUUAUUUUUAUCGAGCACAA | 23 | 8307 |
| BCL11A-6690 | − | CAUUCUUAUUUUUAUCGAGCACAA | 24 | 8308 |
| BCL11A-6691 | − | CACCUUCCCCUUCACCAA | 18 | 8309 |
| BCL11A-6692 | − | CCACCUUCCCCUUCACCAA | 19 | 8310 |
| BCL11A-6693 | − | GCCACCUUCCCCUUCACCAA | 20 | 8311 |
| BCL11A-6694 | − | AGCCACCUUCCCCUUCACCAA | 21 | 8312 |
| BCL11A-6695 | − | AAGCCACCUUCCCCUUCACCAA | 22 | 8313 |
| BCL11A-6696 | − | UAAGCCACCUUCCCCUUCACCAA | 23 | 8314 |
| BCL11A-6697 | − | AUAAGCCACCUUCCCCUUCACCAA | 24 | 8315 |
| BCL11A-6698 | − | ACCCCAGCACUUAAGCAA | 18 | 8316 |
| BCL11A-6699 | − | AACCCCAGCACUUAAGCAA | 19 | 8317 |
| BCL11A-6700 | − | AAACCCCAGCACUUAAGCAA | 20 | 8318 |
| BCL11A-6701 | − | CAAACCCCAGCACUUAAGCAA | 21 | 8319 |
| BCL11A-6702 | − | GCAAACCCCAGCACUUAAGCAA | 22 | 8320 |
| BCL11A-6703 | − | GGCAAACCCCAGCACUUAAGCAA | 23 | 8321 |
| BCL11A-6704 | − | AGGCAAACCCCAGCACUUAAGCAA | 24 | 8322 |
| BCL11A-6705 | − | GGAACACAUAGCAGGUAA | 18 | 8323 |
| BCL11A-6706 | − | AGGAACACAUAGCAGGUAA | 19 | 8324 |
| BCL11A-6707 | − | CAGGAACACAUAGCAGGUAA | 20 | 8325 |
| BCL11A-6708 | − | ACAGGAACACAUAGCAGGUAA | 21 | 8326 |

TABLE 16C-continued

3rd Tier

| gRNA Name | DNA Strand | Targeting Domain | Target Site Length | SEQ ID NO: |
|---|---|---|---|---|
| BCL11A-6709 | - | AACAGGAACACAUAGCAGGUAA | 22 | 8327 |
| BCL11A-6710 | - | AAACAGGAACACAUAGCAGGUAA | 23 | 8328 |
| BCL11A-6711 | - | CAAACAGGAACACAUAGCAGGUAA | 24 | 8329 |
| BCL11A-6712 | - | CUCCCCUCGUUCUGCACA | 18 | 8330 |
| BCL11A-6713 | - | CCUCCCCUCGUUCUGCACA | 19 | 8331 |
| BCL11A-5448 | - | UCCUCCCCUCGUUCUGCACA | 20 | 8332 |
| BCL11A-6714 | - | CUCCUCCCCUCGUUCUGCACA | 21 | 8333 |
| BCL11A-6715 | - | UCUCCUCCCCUCGUUCUGCACA | 22 | 8334 |
| BCL11A-6716 | - | CUCUCCUCCCCUCGUUCUGCACA | 23 | 8335 |
| BCL11A-6717 | - | CCUCUCCUCCCCUCGUUCUGCACA | 24 | 8336 |
| BCL11A-6718 | - | UGCCAGAUGAACUUCCCA | 18 | 8337 |
| BCL11A-6719 | - | GUGCCAGAUGAACUUCCCA | 19 | 8338 |
| BCL11A-6720 | - | AGUGCCAGAUGAACUUCCCA | 20 | 8339 |
| BCL11A-6721 | - | CAGUGCCAGAUGAACUUCCCA | 21 | 8340 |
| BCL11A-6722 | - | GCAGUGCCAGAUGAACUUCCCA | 22 | 8341 |
| BCL11A-6723 | - | GGCAGUGCCAGAUGAACUUCCCA | 23 | 8342 |
| BCL11A-6724 | - | GGGCAGUGCCAGAUGAACUUCCCA | 24 | 8343 |
| BCL11A-6725 | - | GCAGGUAAAUGAGAAGCA | 18 | 8344 |
| BCL11A-6726 | - | AGCAGGUAAAUGAGAAGCA | 19 | 8345 |
| BCL11A-5451 | - | UAGCAGGUAAAUGAGAAGCA | 20 | 8346 |
| BCL11A-6727 | - | AUAGCAGGUAAAUGAGAAGCA | 21 | 8347 |
| BCL11A-6728 | - | CAUAGCAGGUAAAUGAGAAGCA | 22 | 8348 |
| BCL11A-6729 | - | ACAUAGCAGGUAAAUGAGAAGCA | 23 | 8349 |
| BCL11A-6730 | - | CACAUAGCAGGUAAAUGAGAAGCA | 24 | 8350 |
| BCL11A-6731 | - | CACAGAUAAACUUCUGCA | 18 | 8351 |
| BCL11A-6732 | - | UCACAGAUAAACUUCUGCA | 19 | 8352 |
| BCL11A-6733 | - | UUCACAGAUAAACUUCUGCA | 20 | 8353 |
| BCL11A-6734 | - | UUUCACAGAUAAACUUCUGCA | 21 | 8354 |
| BCL11A-6735 | - | CUUUCACAGAUAAACUUCUGCA | 22 | 8355 |
| BCL11A-6736 | - | UCUUUCACAGAUAAACUUCUGCA | 23 | 8356 |
| BCL11A-6737 | - | UUCUUUCACAGAUAAACUUCUGCA | 24 | 8357 |
| BCL11A-6738 | - | CCCGUUGGGAGCUCCAGA | 18 | 8358 |
| BCL11A-6739 | - | GCCCGUUGGGAGCUCCAGA | 19 | 8359 |
| BCL11A-5453 | - | GGCCCGUUGGGAGCUCCAGA | 20 | 8360 |
| BCL11A-6740 | - | CGGCCCGUUGGGAGCUCCAGA | 21 | 8361 |
| BCL11A-6741 | - | ACGGCCCGUUGGGAGCUCCAGA | 22 | 8362 |
| BCL11A-6742 | - | CACGGCCCGUUGGGAGCUCCAGA | 23 | 8363 |
| BCL11A-6743 | - | CCACGGCCCGUUGGGAGCUCCAGA | 24 | 8364 |

TABLE 16C-continued

3rd Tier

| gRNA Name | DNA Strand | Targeting Domain | Target Site Length | SEQ ID NO: |
|---|---|---|---|---|
| BCL11A-6744 | - | GUUUAUCAACGUCAUCUA | 18 | 8365 |
| BCL11A-6745 | - | UGUUUAUCAACGUCAUCUA | 19 | 8366 |
| BCL11A-6746 | - | UUGUUUAUCAACGUCAUCUA | 20 | 8367 |
| BCL11A-6747 | - | AUUGUUUAUCAACGUCAUCUA | 21 | 8368 |
| BCL11A-6748 | - | GAUUGUUUAUCAACGUCAUCUA | 22 | 8369 |
| BCL11A-6749 | - | CGAUUGUUUAUCAACGUCAUCUA | 23 | 8370 |
| BCL11A-6750 | - | ACGAUUGUUUAUCAACGUCAUCUA | 24 | 8371 |
| BCL11A-6751 | - | GGGACAUUCUUAUUUUUA | 18 | 8372 |
| BCL11A-6752 | - | GGGGACAUUCUUAUUUUUA | 19 | 8373 |
| BCL11A-6753 | - | GGGGGACAUUCUUAUUUUUA | 20 | 8374 |
| BCL11A-6754 | - | UGGGGGACAUUCUUAUUUUUA | 21 | 8375 |
| BCL11A-6755 | - | UUGGGGGACAUUCUUAUUUUUA | 22 | 8376 |
| BCL11A-6756 | - | AUUGGGGGACAUUCUUAUUUUUA | 23 | 8377 |
| BCL11A-6757 | - | CAUUGGGGGACAUUCUUAUUUUUA | 24 | 8378 |
| BCL11A-6758 | - | GAGGAAUUUGCCCCAAAC | 18 | 8379 |
| BCL11A-6759 | - | AGAGGAAUUUGCCCCAAAC | 19 | 8380 |
| BCL11A-5457 | - | UAGAGGAAUUUGCCCCAAAC | 20 | 8381 |
| BCL11A-6760 | - | CUAGAGGAAUUUGCCCCAAAC | 21 | 8382 |
| BCL11A-6761 | - | UCUAGAGGAAUUUGCCCCAAAC | 22 | 8383 |
| BCL11A-6762 | - | AUCUAGAGGAAUUUGCCCCAAAC | 23 | 8384 |
| BCL11A-6763 | - | CAUCUAGAGGAAUUUGCCCCAAAC | 24 | 8385 |
| BCL11A-6764 | - | ACAGAUAAACUUCUGCAC | 18 | 8386 |
| BCL11A-6765 | - | CACAGAUAAACUUCUGCAC | 19 | 8387 |
| BCL11A-5348 | - | UCACAGAUAAACUUCUGCAC | 20 | 8388 |
| BCL11A-6766 | - | UUCACAGAUAAACUUCUGCAC | 21 | 8389 |
| BCL11A-6767 | - | UUUCACAGAUAAACUUCUGCAC | 22 | 8390 |
| BCL11A-6768 | - | CUUUCACAGAUAAACUUCUGCAC | 23 | 8391 |
| BCL11A-6769 | - | UCUUUCACAGAUAAACUUCUGCAC | 24 | 8392 |
| BCL11A-6770 | - | CCUCCCCUCGUUCUGCAC | 18 | 8393 |
| BCL11A-6771 | - | UCCUCCCCUCGUUCUGCAC | 19 | 8394 |
| BCL11A-6772 | - | CUCCUCCCCUCGUUCUGCAC | 20 | 8395 |
| BCL11A-6773 | - | UCUCCUCCCCUCGUUCUGCAC | 21 | 8396 |
| BCL11A-6774 | - | CUCUCCUCCCCUCGUUCUGCAC | 22 | 8397 |
| BCL11A-6775 | - | CCUCUCCUCCCCUCGUUCUGCAC | 23 | 8398 |
| BCL11A-6776 | - | GCCUCUCCUCCCCUCGUUCUGCAC | 24 | 8399 |
| BCL11A-6777 | - | AAAAAGCAUCCAAUCCC | 18 | 8400 |
| BCL11A-6778 | - | GAAAAAGCAUCCAAUCCC | 19 | 8401 |

TABLE 16C-continued

3rd Tier

| gRNA Name | DNA Strand | Targeting Domain | Target Site Length | SEQ ID NO: |
|---|---|---|---|---|
| BCL11A-6779 | - | UGAAAAAAGCAUCCAAUCCC | 20 | 8402 |
| BCL11A-6780 | - | AUGAAAAAAGCAUCCAAUCCC | 21 | 8403 |
| BCL11A-6781 | - | GAUGAAAAAAGCAUCCAAUCCC | 22 | 8404 |
| BCL11A-6782 | - | AGAUGAAAAAAGCAUCCAAUCCC | 23 | 8405 |
| BCL11A-6783 | - | GAGAUGAAAAAAGCAUCCAAUCCC | 24 | 8406 |
| BCL11A-6784 | - | AGCAGGUAAAUGAGAAGC | 18 | 8407 |
| BCL11A-6785 | - | UAGCAGGUAAAUGAGAAGC | 19 | 8408 |
| BCL11A-6786 | - | AUAGCAGGUAAAUGAGAAGC | 20 | 8409 |
| BCL11A-6787 | - | CAUAGCAGGUAAAUGAGAAGC | 21 | 8410 |
| BCL11A-6788 | - | ACAUAGCAGGUAAAUGAGAAGC | 22 | 8411 |
| BCL11A-6789 | - | CACAUAGCAGGUAAAUGAGAAGC | 23 | 8412 |
| BCL11A-6790 | - | ACACAUAGCAGGUAAAUGAGAAGC | 24 | 8413 |
| BCL11A-6791 | - | GAGCUCUAAUCCCCACGC | 18 | 8414 |
| BCL11A-6792 | - | GGAGCUCUAAUCCCCACGC | 19 | 8415 |
| BCL11A-6793 | - | UGGAGCUCUAAUCCCCACGC | 20 | 8416 |
| BCL11A-6794 | - | AUGGAGCUCUAAUCCCCACGC | 21 | 8417 |
| BCL11A-6795 | - | CAUGGAGCUCUAAUCCCCACGC | 22 | 8418 |
| BCL11A-6796 | - | ACAUGGAGCUCUAAUCCCCACGC | 23 | 8419 |
| BCL11A-6797 | - | CACAUGGAGCUCUAAUCCCCACGC | 24 | 8420 |
| BCL11A-6798 | - | UUGGCAUCCAGGUCACGC | 18 | 8421 |
| BCL11A-6799 | - | GUUGGCAUCCAGGUCACGC | 19 | 8422 |
| BCL11A-6800 | - | GGUUGGCAUCCAGGUCACGC | 20 | 8423 |
| BCL11A-6801 | - | AGGUUGGCAUCCAGGUCACGC | 21 | 8424 |
| BCL11A-6802 | - | GAGGUUGGCAUCCAGGUCACGC | 22 | 8425 |
| BCL11A-6803 | - | GGAGGUUGGCAUCCAGGUCACGC | 23 | 8426 |
| BCL11A-6804 | - | UGGAGGUUGGCAUCCAGGUCACGC | 24 | 8427 |
| BCL11A-6805 | - | UUGUUUAUCAACGUCAUC | 18 | 8428 |
| BCL11A-6806 | - | AUUGUUUAUCAACGUCAUC | 19 | 8429 |
| BCL11A-6807 | - | GAUUGUUUAUCAACGUCAUC | 20 | 8430 |
| BCL11A-6808 | - | CGAUUGUUUAUCAACGUCAUC | 21 | 8431 |
| BCL11A-6809 | - | ACGAUUGUUUAUCAACGUCAUC | 22 | 8432 |
| BCL11A-6810 | - | GACGAUUGUUUAUCAACGUCAUC | 23 | 8433 |
| BCL11A-6811 | - | UGACGAUUGUUUAUCAACGUCAUC | 24 | 8434 |
| BCL11A-6812 | - | CAACCACAGCCGAGCCUC | 18 | 8435 |
| BCL11A-6813 | - | CCAACCACAGCCGAGCCUC | 19 | 8436 |
| BCL11A-6814 | - | UCCAACCACAGCCGAGCCUC | 20 | 8437 |
| BCL11A-6815 | - | CUCCAACCACAGCCGAGCCUC | 21 | 8438 |
| BCL11A-6816 | - | UCUCCAACCACAGCCGAGCCUC | 22 | 8439 |

TABLE 16C-continued

| | | 3rd Tier | | |
|---|---|---|---|---|
| gRNA Name | DNA Strand | Targeting Domain | Target Site Length | SEQ ID NO: |
| BCL11A-6817 | - | UUCUCCAACCACAGCCGAGCCUC | 23 | 8440 |
| BCL11A-6818 | - | UUUCUCCAACCACAGCCGAGCCUC | 24 | 8441 |
| BCL11A-6819 | - | ACGGCCCGUUGGGAGCUC | 18 | 8442 |
| BCL11A-6820 | - | CACGGCCCGUUGGGAGCUC | 19 | 8443 |
| BCL11A-6821 | - | CCACGGCCCGUUGGGAGCUC | 20 | 8444 |
| BCL11A-6822 | - | ACCACGGCCCGUUGGGAGCUC | 21 | 8445 |
| BCL11A-6823 | - | GACCACGGCCCGUUGGGAGCUC | 22 | 8446 |
| BCL11A-6824 | - | AGACCACGGCCCGUUGGGAGCUC | 23 | 8447 |
| BCL11A-6825 | - | CAGACCACGGCCCGUUGGGAGCUC | 24 | 8448 |
| BCL11A-6826 | - | AUUAUUUGCAGGUAAAG | 18 | 8449 |
| BCL11A-6827 | - | UAUUAUUUGCAGGUAAAG | 19 | 8450 |
| BCL11A-6828 | - | GUAUUAUUUGCAGGUAAAG | 20 | 8451 |
| BCL11A-6829 | - | UGUAUUAUUUGCAGGUAAAG | 21 | 8452 |
| BCL11A-6830 | - | UUGUAUUAUUUGCAGGUAAAG | 22 | 8453 |
| BCL11A-6831 | - | GUUGUAUUAUUUGCAGGUAAAG | 23 | 8454 |
| BCL11A-6832 | - | UGUUGUAUUAUUUGCAGGUAAAG | 24 | 8455 |
| BCL11A-6833 | - | AGGUAAAUGAGAAGCAAG | 18 | 8456 |
| BCL11A-6834 | - | CAGGUAAAUGAGAAGCAAG | 19 | 8457 |
| BCL11A-6835 | - | GCAGGUAAAUGAGAAGCAAG | 20 | 8458 |
| BCL11A-6836 | - | AGCAGGUAAAUGAGAAGCAAG | 21 | 8459 |
| BCL11A-6837 | - | UAGCAGGUAAAUGAGAAGCAAG | 22 | 8460 |
| BCL11A-6838 | - | AUAGCAGGUAAAUGAGAAGCAAG | 23 | 8461 |
| BCL11A-6839 | - | CAUAGCAGGUAAAUGAGAAGCAAG | 24 | 8462 |
| BCL11A-6840 | - | CCGCAGGGUAUUUGUAAG | 18 | 8463 |
| BCL11A-6841 | - | CCCGCAGGGUAUUUGUAAG | 19 | 8464 |
| BCL11A-6842 | - | CCCCGCAGGGUAUUUGUAAG | 20 | 8465 |
| BCL11A-6843 | - | GCCCCGCAGGGUAUUUGUAAG | 21 | 8466 |
| BCL11A-6844 | - | UGCCCCGCAGGGUAUUUGUAAG | 22 | 8467 |
| BCL11A-6845 | - | AUGCCCCGCAGGGUAUUUGUAAG | 23 | 8468 |
| BCL11A-6846 | - | UAUGCCCCGCAGGGUAUUUGUAAG | 24 | 8469 |
| BCL11A-6847 | - | UUGUUUCUCCAACCACAG | 18 | 8470 |
| BCL11A-6848 | - | UUUGUUUCUCCAACCACAG | 19 | 8471 |
| BCL11A-6849 | - | UUUUGUUUCUCCAACCACAG | 20 | 8472 |
| BCL11A-6850 | - | CUUUUGUUUCUCCAACCACAG | 21 | 8473 |
| BCL11A-6851 | - | GCUUUUGUUUCUCCAACCACAG | 22 | 8474 |
| BCL11A-6852 | - | UGCUUUUGUUUCUCCAACCACAG | 23 | 8475 |
| BCL11A-6853 | - | GUGCUUUUGUUUCUCCAACCACAG | 24 | 8476 |

TABLE 16C-continued

3rd Tier

| gRNA Name | DNA Strand | Targeting Domain | Target Site Length | SEQ ID NO: |
|---|---|---|---|---|
| BCL11A-6854 | - | ACCUGUGGGCAGUGCCAG | 18 | 8477 |
| BCL11A-6855 | - | CACCUGUGGGCAGUGCCAG | 19 | 8478 |
| BCL11A-6856 | - | UCACCUGUGGGCAGUGCCAG | 20 | 8479 |
| BCL11A-6857 | - | CUCACCUGUGGGCAGUGCCAG | 21 | 8480 |
| BCL11A-6858 | - | CCUCACCUGUGGGCAGUGCCAG | 22 | 8481 |
| BCL11A-6859 | - | UCCUCACCUGUGGGCAGUGCCAG | 23 | 8482 |
| BCL11A-6860 | - | CUCCUCACCUGUGGGCAGUGCCAG | 24 | 8483 |
| BCL11A-6861 | - | GCCCGUUGGGAGCUCCAG | 18 | 8484 |
| BCL11A-6862 | - | GGCCCGUUGGGAGCUCCAG | 19 | 8485 |
| BCL11A-6863 | - | CGGCCCGUUGGGAGCUCCAG | 20 | 8486 |
| BCL11A-6864 | - | ACGGCCCGUUGGGAGCUCCAG | 21 | 8487 |
| BCL11A-6865 | - | CACGGCCCGUUGGGAGCUCCAG | 22 | 8488 |
| BCL11A-6866 | - | CCACGGCCCGUUGGGAGCUCCAG | 23 | 8489 |
| BCL11A-6867 | - | ACCACGGCCCGUUGGGAGCUCCAG | 24 | 8490 |
| BCL11A-6868 | - | UCCCCUUCACCAAUCGAG | 18 | 8491 |
| BCL11A-6869 | - | UUCCCCUUCACCAAUCGAG | 19 | 8492 |
| BCL11A-6870 | - | CUUCCCCUUCACCAAUCGAG | 20 | 8493 |
| BCL11A-6871 | - | CCUUCCCCUUCACCAAUCGAG | 21 | 8494 |
| BCL11A-6872 | - | ACCUUCCCCUUCACCAAUCGAG | 22 | 8495 |
| BCL11A-6873 | - | CACCUUCCCCUUCACCAAUCGAG | 23 | 8496 |
| BCL11A-6874 | - | CCACCUUCCCCUUCACCAAUCGAG | 24 | 8497 |
| BCL11A-6875 | - | GAACCAGACCACGGCCCG | 18 | 8498 |
| BCL11A-6876 | - | UGAACCAGACCACGGCCCG | 19 | 8499 |
| BCL11A-6877 | - | AUGAACCAGACCACGGCCCG | 20 | 8500 |
| BCL11A-6878 | - | GAUGAACCAGACCACGGCCCG | 21 | 8501 |
| BCL11A-6879 | - | UGAUGAACCAGACCACGGCCCG | 22 | 8502 |
| BCL11A-6880 | - | AUGAUGAACCAGACCACGGCCCG | 23 | 8503 |
| BCL11A-6881 | - | GAUGAUGAACCAGACCACGGCCCG | 24 | 8504 |
| BCL11A-6882 | - | AAAAGCAUCCAAUCCCG | 18 | 8505 |
| BCL11A-6883 | - | AAAAAGCAUCCAAUCCCG | 19 | 8506 |
| BCL11A-5358 | - | GAAAAAGCAUCCAAUCCCG | 20 | 8507 |
| BCL11A-6884 | - | UGAAAAAGCAUCCAAUCCCG | 21 | 8508 |
| BCL11A-6885 | - | AUGAAAAAGCAUCCAAUCCCG | 22 | 8509 |
| BCL11A-6886 | - | GAUGAAAAAGCAUCCAAUCCCG | 23 | 8510 |
| BCL11A-6887 | - | AGAUGAAAAAGCAUCCAAUCCCG | 24 | 8511 |
| BCL11A-6888 | - | GAUAAACUUCUGCACUGG | 18 | 8512 |
| BCL11A-6889 | - | AGAUAAACUUCUGCACUGG | 19 | 8513 |
| BCL11A-5360 | - | CAGAUAAACUUCUGCACUGG | 20 | 8514 |

TABLE 16C-continued

3rd Tier

| gRNA Name | DNA Strand | Targeting Domain | Target Site Length | SEQ ID NO: |
|---|---|---|---|---|
| BCL11A-6890 | - | ACAGAUAAACUUCUGCACUGG | 21 | 8515 |
| BCL11A-6891 | - | CACAGAUAAACUUCUGCACUGG | 22 | 8516 |
| BCL11A-6892 | - | UCACAGAUAAACUUCUGCACUGG | 23 | 8517 |
| BCL11A-6893 | - | UUCACAGAUAAACUUCUGCACUGG | 24 | 8518 |
| BCL11A-6894 | - | AAGCCAUUCUUACAGAUG | 18 | 8519 |
| BCL11A-6895 | - | GAAGCCAUUCUUACAGAUG | 19 | 8520 |
| BCL11A-6896 | - | UGAAGCCAUUCUUACAGAUG | 20 | 8521 |
| BCL11A-6897 | - | UUGAAGCCAUUCUUACAGAUG | 21 | 8522 |
| BCL11A-6898 | - | CUUGAAGCCAUUCUUACAGAUG | 22 | 8523 |
| BCL11A-6899 | - | UCUUGAAGCCAUUCUUACAGAUG | 23 | 8524 |
| BCL11A-6900 | - | CUCUUGAAGCCAUUCUUACAGAUG | 24 | 8525 |
| BCL11A-6901 | - | AGAUAAACUUCUGCACUG | 18 | 8526 |
| BCL11A-6902 | - | CAGAUAAACUUCUGCACUG | 19 | 8527 |
| BCL11A-6903 | - | ACAGAUAAACUUCUGCACUG | 20 | 8528 |
| BCL11A-6904 | - | CACAGAUAAACUUCUGCACUG | 21 | 8529 |
| BCL11A-6905 | - | UCACAGAUAAACUUCUGCACUG | 22 | 8530 |
| BCL11A-6906 | - | UUCACAGAUAAACUUCUGCACUG | 23 | 8531 |
| BCL11A-6907 | - | UUUCACAGAUAAACUUCUGCACUG | 24 | 8532 |
| BCL11A-6908 | - | CAGAUGAACUUCCCAUUG | 18 | 8533 |
| BCL11A-6909 | - | CCAGAUGAACUUCCCAUUG | 19 | 8534 |
| BCL11A-5499 | - | GCCAGAUGAACUUCCCAUUG | 20 | 8535 |
| BCL11A-6910 | - | UGCCAGAUGAACUUCCCAUUG | 21 | 8536 |
| BCL11A-6911 | - | GUGCCAGAUGAACUUCCCAUUG | 22 | 8537 |
| BCL11A-6912 | - | AGUGCCAGAUGAACUUCCCAUUG | 23 | 8538 |
| BCL11A-6913 | - | CAGUGCCAGAUGAACUUCCCAUUG | 24 | 8539 |
| BCL11A-6914 | - | AACACAUAGCAGGUAAAU | 18 | 8540 |
| BCL11A-6915 | - | GAACACAUAGCAGGUAAAU | 19 | 8541 |
| BCL11A-6916 | - | GGAACACAUAGCAGGUAAAU | 20 | 8542 |
| BCL11A-6917 | - | AGGAACACAUAGCAGGUAAAU | 21 | 8543 |
| BCL11A-6918 | - | CAGGAACACAUAGCAGGUAAAU | 22 | 8544 |
| BCL11A-6919 | - | ACAGGAACACAUAGCAGGUAAAU | 23 | 8545 |
| BCL11A-6920 | - | AACAGGAACACAUAGCAGGUAAAU | 24 | 8546 |
| BCL11A-6921 | - | GCCAGAUGAACUUCCCAU | 18 | 8547 |
| BCL11A-6922 | - | UGCCAGAUGAACUUCCCAU | 19 | 8548 |
| BCL11A-5503 | - | GUGCCAGAUGAACUUCCCAU | 20 | 8549 |
| BCL11A-6923 | - | AGUGCCAGAUGAACUUCCCAU | 21 | 8550 |
| BCL11A-6924 | - | CAGUGCCAGAUGAACUUCCCAU | 22 | 8551 |

TABLE 16C-continued

3rd Tier

| gRNA Name | DNA Strand | Targeting Domain | Target Site Length | SEQ ID NO: |
|---|---|---|---|---|
| BCL11A-6925 | - | GCAGUGCCAGAUGAACUUCCCAU | 23 | 8552 |
| BCL11A-6926 | - | GGCAGUGCCAGAUGAACUUCCCAU | 24 | 8553 |
| BCL11A-6927 | - | AUCAUGACCUCCUCACCU | 18 | 8554 |
| BCL11A-6928 | - | GAUCAUGACCUCCUCACCU | 19 | 8555 |
| BCL11A-6929 | - | GGAUCAUGACCUCCUCACCU | 20 | 8556 |
| BCL11A-6930 | - | GGGAUCAUGACCUCCUCACCU | 21 | 8557 |
| BCL11A-6931 | - | GGGGAUCAUGACCUCCUCACCU | 22 | 8558 |
| BCL11A-6932 | - | AGGGGAUCAUGACCUCCUCACCU | 23 | 8559 |
| BCL11A-6933 | - | AAGGGGAUCAUGACCUCCUCACCU | 24 | 8560 |
| BCL11A-6934 | - | GCAAUGGCAGCCUCUGCU | 18 | 8561 |
| BCL11A-6935 | - | UGCAAUGGCAGCCUCUGCU | 19 | 8562 |
| BCL11A-6936 | - | AUGCAAUGGCAGCCUCUGCU | 20 | 8563 |
| BCL11A-6937 | - | AAUGCAAUGGCAGCCUCUGCU | 21 | 8564 |
| BCL11A-6938 | - | CAAUGCAAUGGCAGCCUCUGCU | 22 | 8565 |
| BCL11A-6939 | - | ACAAUGCAAUGGCAGCCUCUGCU | 23 | 8566 |
| BCL11A-6940 | - | AACAAUGCAAUGGCAGCCUCUGCU | 24 | 8567 |
| BCL11A-6941 | - | AACCAGACCACGGCCCGU | 18 | 8568 |
| BCL11A-6942 | - | GAACCAGACCACGGCCCGU | 19 | 8569 |
| BCL11A-5363 | - | UGAACCAGACCACGGCCCGU | 20 | 8570 |
| BCL11A-6943 | - | AUGAACCAGACCACGGCCCGU | 21 | 8571 |
| BCL11A-6944 | - | GAUGAACCAGACCACGGCCCGU | 22 | 8572 |
| BCL11A-6945 | - | UGAUGAACCAGACCACGGCCCGU | 23 | 8573 |
| BCL11A-6946 | - | AUGAUGAACCAGACCACGGCCCGU | 24 | 8574 |
| BCL11A-6947 | - | CCAGAUGAACUUCCCAUU | 18 | 8575 |
| BCL11A-6948 | - | GCCAGAUGAACUUCCCAUU | 19 | 8576 |
| BCL11A-5511 | - | UGCCAGAUGAACUUCCCAUU | 20 | 8577 |
| BCL11A-6949 | - | GUGCCAGAUGAACUUCCCAUU | 21 | 8578 |
| BCL11A-6950 | - | AGUGCCAGAUGAACUUCCCAUU | 22 | 8579 |
| BCL11A-6951 | - | CAGUGCCAGAUGAACUUCCCAUU | 23 | 8580 |
| BCL11A-6952 | - | GCAGUGCCAGAUGAACUUCCCAUU | 24 | 8581 |
| BCL11A-6953 | - | ACCAGACCACGGCCCGUU | 18 | 8582 |
| BCL11A-6954 | - | AACCAGACCACGGCCCGUU | 19 | 8583 |
| BCL11A-5512 | - | GAACCAGACCACGGCCCGUU | 20 | 8584 |
| BCL11A-6955 | - | UGAACCAGACCACGGCCCGUU | 21 | 8585 |
| BCL11A-6956 | - | AUGAACCAGACCACGGCCCGUU | 22 | 8586 |
| BCL11A-6957 | - | GAUGAACCAGACCACGGCCCGUU | 23 | 8587 |
| BCL11A-6958 | - | UGAUGAACCAGACCACGGCCCGUU | 24 | 8588 |

Table 16D provides exemplary targeting domains for knocking out the BCL11A gene selected according to the fourth tier parameters. The targeting domains fall in the coding sequence of the gene, downstream of the first 500 bp of coding sequence (e.g., anywhere from +500 (relative to the start codon) to the stop codon of the gene), and the PAM is NNGRRT. It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 16D

4th Tier

| gRNA Name | DNA Strand | Targeting Domain | Target Site Length | SEQ ID NO: |
|---|---|---|---|---|
| BCL11A-6959 | + | GUAUUCUUAGCAGGUUAA | 18 | 8589 |
| BCL11A-6960 | + | GGUAUUCUUAGCAGGUUAA | 19 | 8590 |
| BCL11A-5890 | + | UGGUAUUCUUAGCAGGUUAA | 20 | 8591 |
| BCL11A-6961 | + | CUGGUAUUCUUAGCAGGUUAA | 21 | 8592 |
| BCL11A-6962 | + | CCUGGUAUUCUUAGCAGGUUAA | 22 | 8593 |
| BCL11A-6963 | + | UCCUGGUAUUCUUAGCAGGUUAA | 23 | 8594 |
| BCL11A-6964 | + | AUCCUGGUAUUCUUAGCAGGUUAA | 24 | 8595 |
| BCL11A-6965 | + | CGGGAGGCUCCAUAGCCA | 18 | 8596 |
| BCL11A-6966 | + | GCGGGAGGCUCCAUAGCCA | 19 | 8597 |
| BCL11A-6967 | + | GGCGGGAGGCUCCAUAGCCA | 20 | 8598 |
| BCL11A-6968 | + | UGGCGGGAGGCUCCAUAGCCA | 21 | 8599 |
| BCL11A-6969 | + | AUGGCGGGAGGCUCCAUAGCCA | 22 | 8600 |
| BCL11A-6970 | + | CAUGGCGGGAGGCUCCAUAGCCA | 23 | 8601 |
| BCL11A-6971 | + | CCAUGGCGGGAGGCUCCAUAGCCA | 24 | 8602 |
| BCL11A-6972 | + | GGUCCGACUCGCCGGCCA | 18 | 8603 |
| BCL11A-6973 | + | CGGUCCGACUCGCCGGCCA | 19 | 8604 |
| BCL11A-6974 | + | GCGGUCCGACUCGCCGGCCA | 20 | 8605 |
| BCL11A-6975 | + | UGCGGUCCGACUCGCCGGCCA | 21 | 8606 |
| BCL11A-6976 | + | AUGCGGUCCGACUCGCCGGCCA | 22 | 8607 |
| BCL11A-6977 | + | UAUGCGGUCCGACUCGCCGGCCA | 23 | 8608 |
| BCL11A-6978 | + | CUAUGCGGUCCGACUCGCCGGCCA | 24 | 8609 |
| BCL11A-6979 | + | AGUCUCCGAAGCUAAGGA | 18 | 8610 |
| BCL11A-6980 | + | GAGUCUCCGAAGCUAAGGA | 19 | 8611 |
| BCL11A-5923 | + | GGAGUCUCCGAAGCUAAGGA | 20 | 8612 |
| BCL11A-6981 | + | UGGAGUCUCCGAAGCUAAGGA | 21 | 8613 |
| BCL11A-6982 | + | CUGGAGUCUCCGAAGCUAAGGA | 22 | 8614 |
| BCL11A-6983 | + | UCUGGAGUCUCCGAAGCUAAGGA | 23 | 8615 |
| BCL11A-6984 | + | GUCUGGAGUCUCCGAAGCUAAGGA | 24 | 8616 |
| BCL11A-6985 | + | GGACUAAACAGGGGGGA | 18 | 8617 |
| BCL11A-6986 | + | UGGACUAAACAGGGGGGA | 19 | 8618 |
| BCL11A-6987 | + | GUGGACUAAACAGGGGGGA | 20 | 8619 |
| BCL11A-6988 | + | GGUGGACUAAACAGGGGGGA | 21 | 8620 |
| BCL11A-6989 | + | UGGUGGACUAAACAGGGGGGA | 22 | 8621 |
| BCL11A-6990 | + | GUGGUGGACUAAACAGGGGGGA | 23 | 8622 |

TABLE 16D-continued

4th Tier

| gRNA Name | DNA Strand | Targeting Domain | Target Site Length | SEQ ID NO: |
|---|---|---|---|---|
| BCL11A-6991 | + | GGUGGUGGACUAAACAGGGGGGA | 24 | 8623 |
| BCL11A-6992 | + | UUCUGCACCUAGUCCUGA | 18 | 8624 |
| BCL11A-6993 | + | AUUCUGCACCUAGUCCUGA | 19 | 8625 |
| BCL11A-5937 | + | CAUUCUGCACCUAGUCCUGA | 20 | 8626 |
| BCL11A-6994 | + | ACAUUCUGCACCUAGUCCUGA | 21 | 8627 |
| BCL11A-6995 | + | GACAUUCUGCACCUAGUCCUGA | 22 | 8628 |
| BCL11A-6996 | + | GGACAUUCUGCACCUAGUCCUGA | 23 | 8629 |
| BCL11A-6997 | + | AGGACAUUCUGCACCUAGUCCUGA | 24 | 8630 |
| BCL11A-6998 | + | GCACCCUGUCAAAGGCAC | 18 | 8631 |
| BCL11A-6999 | + | AGCACCCUGUCAAAGGCAC | 19 | 8632 |
| BCL11A-7000 | + | CAGCACCCUGUCAAAGGCAC | 20 | 8633 |
| BCL11A-7001 | + | GCAGCACCCUGUCAAAGGCAC | 21 | 8634 |
| BCL11A-7002 | + | CGCAGCACCCUGUCAAAGGCAC | 22 | 8635 |
| BCL11A-7003 | + | CCGCAGCACCCUGUCAAAGGCAC | 23 | 8636 |
| BCL11A-7004 | + | ACCGCAGCACCCUGUCAAAGGCAC | 24 | 8637 |
| BCL11A-7005 | + | UAAGUAGAUUCUUAAUCC | 18 | 8638 |
| BCL11A-7006 | + | CUAAGUAGAUUCUUAAUCC | 19 | 8639 |
| BCL11A-7007 | + | UCUAAGUAGAUUCUUAAUCC | 20 | 8640 |
| BCL11A-7008 | + | UUCUAAGUAGAUUCUUAAUCC | 21 | 8641 |
| BCL11A-7009 | + | UUUCUAAGUAGAUUCUUAAUCC | 22 | 8642 |
| BCL11A-7010 | + | CUUUCUAAGUAGAUUCUUAAUCC | 23 | 8643 |
| BCL11A-7011 | + | GCUUUCUAAGUAGAUUCUUAAUCC | 24 | 8644 |
| BCL11A-7012 | + | GGCGGCUUGCUACCUGGC | 18 | 8645 |
| BCL11A-7013 | + | GGGCGGCUUGCUACCUGGC | 19 | 8646 |
| BCL11A-6036 | + | AGGGCGGCUUGCUACCUGGC | 20 | 8647 |
| BCL11A-7014 | + | AAGGGCGGCUUGCUACCUGGC | 21 | 8648 |
| BCL11A-7015 | + | GAAGGGCGGCUUGCUACCUGGC | 22 | 8649 |
| BCL11A-7016 | + | GGAAGGGCGGCUUGCUACCUGGC | 23 | 8650 |
| BCL11A-7017 | + | AGGAAGGGCGGCUUGCUACCUGGC | 24 | 8651 |
| BCL11A-7018 | + | GCGCUUCAGCUUGCUGGC | 18 | 8652 |
| BCL11A-7019 | + | GGCGCUUCAGCUUGCUGGC | 19 | 8653 |
| BCL11A-7020 | + | UGGCGCUUCAGCUUGCUGGC | 20 | 8654 |
| BCL11A-7021 | + | GUGGCGCUUCAGCUUGCUGGC | 21 | 8655 |
| BCL11A-7022 | + | UGUGGCGCUUCAGCUUGCUGGC | 22 | 8656 |
| BCL11A-7023 | + | AUGUGGCGCUUCAGCUUGCUGGC | 23 | 8657 |
| BCL11A-7024 | + | CAUGUGGCGCUUCAGCUUGCUGGC | 24 | 8658 |
| BCL11A-7025 | + | CUCCUCGUCCCCGUUCUC | 18 | 8659 |

TABLE 16D-continued

4th Tier

| gRNA Name | DNA Strand | Targeting Domain | Target Site Length | SEQ ID NO: |
|---|---|---|---|---|
| BCL11A-7026 | + | CCUCCUCGUCCCCGUUCUC | 19 | 8660 |
| BCL11A-6050 | + | UCCUCCUCGUCCCCGUUCUC | 20 | 8661 |
| BCL11A-7027 | + | UUCCUCCUCGUCCCCGUUCUC | 21 | 8662 |
| BCL11A-7028 | + | CUUCCUCCUCGUCCCCGUUCUC | 22 | 8663 |
| BCL11A-7029 | + | UCUUCCUCCUCGUCCCCGUUCUC | 23 | 8664 |
| BCL11A-7030 | + | CUCUUCCUCCUCGUCCCCGUUCUC | 24 | 8665 |
| BCL11A-7031 | + | AGGCAAAAGGCGAUUGUC | 18 | 8666 |
| BCL11A-7032 | + | GAGGCAAAAGGCGAUUGUC | 19 | 8667 |
| BCL11A-6054 | + | GGAGGCAAAAGGCGAUUGUC | 20 | 8668 |
| BCL11A-7033 | + | AGGAGGCAAAAGGCGAUUGUC | 21 | 8669 |
| BCL11A-7034 | + | GAGGAGGCAAAAGGCGAUUGUC | 22 | 8670 |
| BCL11A-7035 | + | CGAGGAGGCAAAAGGCGAUUGUC | 23 | 8671 |
| BCL11A-7036 | + | ACGAGGAGGCAAAAGGCGAUUGUC | 24 | 8672 |
| BCL11A-7037 | + | AGCUCUCUGGGUACUACG | 18 | 8673 |
| BCL11A-7038 | + | GAGCUCUCUGGGUACUACG | 19 | 8674 |
| BCL11A-7039 | + | UGAGCUCUCUGGGUACUACG | 20 | 8675 |
| BCL11A-7040 | + | UUGAGCUCUCUGGGUACUACG | 21 | 8676 |
| BCL11A-7041 | + | CUUGAGCUCUCUGGGUACUACG | 22 | 8677 |
| BCL11A-7042 | + | UCUUGAGCUCUCUGGGUACUACG | 23 | 8678 |
| BCL11A-7043 | + | AUCUUGAGCUCUCUGGGUACUACG | 24 | 8679 |
| BCL11A-7044 | + | UGAAGGGAUACCAACCCG | 18 | 8680 |
| BCL11A-7045 | + | CUGAAGGGAUACCAACCCG | 19 | 8681 |
| BCL11A-6084 | + | CCUGAAGGGAUACCAACCCG | 20 | 8682 |
| BCL11A-7046 | + | UCCUGAAGGGAUACCAACCCG | 21 | 8683 |
| BCL11A-7047 | + | GUCCUGAAGGGAUACCAACCCG | 22 | 8684 |
| BCL11A-7048 | + | AGUCCUGAAGGGAUACCAACCCG | 23 | 8685 |
| BCL11A-7049 | + | UAGUCCUGAAGGGAUACCAACCCG | 24 | 8686 |
| BCL11A-7050 | + | GCAAACUCCCGUUCUCCG | 18 | 8687 |
| BCL11A-7051 | + | CGCAAACUCCCGUUCUCCG | 19 | 8688 |
| BCL11A-6094 | + | GCGCAAACUCCCGUUCUCCG | 20 | 8689 |
| BCL11A-7052 | + | AGCGCAAACUCCCGUUCUCCG | 21 | 8690 |
| BCL11A-7053 | + | AAGCGCAAACUCCCGUUCUCCG | 22 | 8691 |
| BCL11A-7054 | + | GAAGCGCAAACUCCCGUUCUCCG | 23 | 8692 |
| BCL11A-7055 | + | AGAAGCGCAAACUCCCGUUCUCCG | 24 | 8693 |
| BCL11A-7056 | + | GGCUGGGAGGGAGGAGGG | 18 | 8694 |
| BCL11A-7057 | + | GGGCUGGGAGGGAGGAGGG | 19 | 8695 |
| BCL11A-7058 | + | GGGGCUGGGAGGGAGGAGGG | 20 | 8696 |
| BCL11A-7059 | + | GGGGGCUGGGAGGGAGGAGGG | 21 | 8697 |

TABLE 16D-continued

4th Tier

| gRNA Name | DNA Strand | Targeting Domain | Target Site Length | SEQ ID NO: |
|---|---|---|---|---|
| BCL11A-7060 | + | CGGGGGCUGGGAGGGAGGAGGG | 22 | 8698 |
| BCL11A-7061 | + | CCGGGGGCUGGGAGGGAGGAGGG | 23 | 8699 |
| BCL11A-7062 | + | ACCGGGGGCUGGGAGGGAGGAGGG | 24 | 8700 |
| BCL11A-7063 | + | UGGUGGACUAAACAGGGG | 18 | 8701 |
| BCL11A-7064 | + | GUGGUGGACUAAACAGGGG | 19 | 8702 |
| BCL11A-6139 | + | GGUGGUGGACUAAACAGGGG | 20 | 8703 |
| BCL11A-7065 | + | CGGUGGUGGACUAAACAGGGG | 21 | 8704 |
| BCL11A-7066 | + | UCGGUGGUGGACUAAACAGGGG | 22 | 8705 |
| BCL11A-7067 | + | CUCGGUGGUGGACUAAACAGGGG | 23 | 8706 |
| BCL11A-7068 | + | UCUCGGUGGUGGACUAAACAGGGG | 24 | 8707 |
| BCL11A-7069 | + | AAGAGAAACCAUGCACUG | 18 | 8708 |
| BCL11A-7070 | + | CAAGAGAAACCAUGCACUG | 19 | 8709 |
| BCL11A-7071 | + | GCAAGAGAAACCAUGCACUG | 20 | 8710 |
| BCL11A-7072 | + | UGCAAGAGAAACCAUGCACUG | 21 | 8711 |
| BCL11A-7073 | + | UUGCAAGAGAAACCAUGCACUG | 22 | 8712 |
| BCL11A-7074 | + | GUUGCAAGAGAAACCAUGCACUG | 23 | 8713 |
| BCL11A-7075 | + | UGUUGCAAGAGAAACCAUGCACUG | 24 | 8714 |
| BCL11A-7076 | + | GUCAAAGGCACUCGGGUG | 18 | 8715 |
| BCL11A-7077 | + | UGUCAAAGGCACUCGGGUG | 19 | 8716 |
| BCL11A-7078 | + | CUGUCAAAGGCACUCGGGUG | 20 | 8717 |
| BCL11A-7079 | + | CCUGUCAAAGGCACUCGGGUG | 21 | 8718 |
| BCL11A-7080 | + | CCCUGUCAAAGGCACUCGGGUG | 22 | 8719 |
| BCL11A-7081 | + | ACCCUGUCAAAGGCACUCGGGUG | 23 | 8720 |
| BCL11A-7082 | + | CACCCUGUCAAAGGCACUCGGGUG | 24 | 8721 |
| BCL11A-7083 | + | CCCACCAAGUCGCUGGUG | 18 | 8722 |
| BCL11A-7084 | + | GCCCACCAAGUCGCUGGUG | 19 | 8723 |
| BCL11A-7085 | + | UGCCCACCAAGUCGCUGGUG | 20 | 8724 |
| BCL11A-7086 | + | CUGCCCACCAAGUCGCUGGUG | 21 | 8725 |
| BCL11A-7087 | + | GCUGCCCACCAAGUCGCUGGUG | 22 | 8726 |
| BCL11A-7088 | + | CGCUGCCCACCAAGUCGCUGGUG | 23 | 8727 |
| BCL11A-7089 | + | GCGCUGCCCACCAAGUCGCUGGUG | 24 | 8728 |
| BCL11A-7090 | + | GGGGUUAUUGUCUGCAAU | 18 | 8729 |
| BCL11A-7091 | + | AGGGGUUAUUGUCUGCAAU | 19 | 8730 |
| BCL11A-7092 | + | AAGGGGUUAUUGUCUGCAAU | 20 | 8731 |
| BCL11A-7093 | + | AAAGGGGUUAUUGUCUGCAAU | 21 | 8732 |
| BCL11A-7094 | + | UAAAGGGGUUAUUGUCUGCAAU | 22 | 8733 |
| BCL11A-7095 | + | UUAAAGGGGUUAUUGUCUGCAAU | 23 | 8734 |

TABLE 16D-continued

4th Tier

| gRNA Name | DNA Strand | Targeting Domain | Target Site Length | SEQ ID NO: |
|---|---|---|---|---|
| BCL11A-7096 | + | GUUAAGGGGUUAUUGUCUGCAAU | 24 | 8735 |
| BCL11A-7097 | + | CUGGGUACUACGCCGAAU | 18 | 8736 |
| BCL11A-7098 | + | UCUGGGUACUACGCCGAAU | 19 | 8737 |
| BCL11A-6182 | + | CUCUGGGUACUACGCCGAAU | 20 | 8738 |
| BCL11A-7099 | + | UCUCUGGGUACUACGCCGAAU | 21 | 8739 |
| BCL11A-7100 | + | CUCUCUGGGUACUACGCCGAAU | 22 | 8740 |
| BCL11A-7101 | + | GCUCUCUGGGUACUACGCCGAAU | 23 | 8741 |
| BCL11A-7102 | + | AGCUCUCUGGGUACUACGCCGAAU | 24 | 8742 |
| BCL11A-7103 | + | CGUAGCCGGCGAGCCACU | 18 | 8743 |
| BCL11A-7104 | + | GCGUAGCCGGCGAGCCACU | 19 | 8744 |
| BCL11A-7105 | + | CGCGUAGCCGGCGAGCCACU | 20 | 8745 |
| BCL11A-7106 | + | CCGCGUAGCCGGCGAGCCACU | 21 | 8746 |
| BCL11A-7107 | + | GCCGCGUAGCCGGCGAGCCACU | 22 | 8747 |
| BCL11A-7108 | + | GGCCGCGUAGCCGGCGAGCCACU | 23 | 8748 |
| BCL11A-7109 | + | AGGCCGCGUAGCCGGCGAGCCACU | 24 | 8749 |
| BCL11A-7110 | + | CCACACAUCUUGAGCUCU | 18 | 8750 |
| BCL11A-7111 | + | GCCACACAUCUUGAGCUCU | 19 | 8751 |
| BCL11A-7112 | + | UGCCACACAUCUUGAGCUCU | 20 | 8752 |
| BCL11A-7113 | + | CUGCCACACAUCUUGAGCUCU | 21 | 8753 |
| BCL11A-7114 | + | ACUGCCACACAUCUUGAGCUCU | 22 | 8754 |
| BCL11A-7115 | + | AACUGCCACACAUCUUGAGCUCU | 23 | 8755 |
| BCL11A-7116 | + | AAACUGCCACACAUCUUGAGCUCU | 24 | 8756 |
| BCL11A-7117 | + | CGUUCUCCGGGAUCAGGU | 18 | 8757 |
| BCL11A-7118 | + | CCGUUCUCCGGGAUCAGGU | 19 | 8758 |
| BCL11A-6223 | + | CCCGUUCUCCGGGAUCAGGU | 20 | 8759 |
| BCL11A-7119 | + | CCCCGUUCUCCGGGAUCAGGU | 21 | 8760 |
| BCL11A-7120 | + | UCCCCGUUCUCCGGGAUCAGGU | 22 | 8761 |
| BCL11A-7121 | + | GUCCCCGUUCUCCGGGAUCAGGU | 23 | 8762 |
| BCL11A-7122 | + | CGUCCCCGUUCUCCGGGAUCAGGU | 24 | 8763 |
| BCL11A-7123 | + | CCAGGCGCUCUAUGCGGU | 18 | 8764 |
| BCL11A-7124 | + | CCCAGGCGCUCUAUGCGGU | 19 | 8765 |
| BCL11A-6226 | + | CCCCAGGCGCUCUAUGCGGU | 20 | 8766 |
| BCL11A-7125 | + | CCCCCAGGCGCUCUAUGCGGU | 21 | 8767 |
| BCL11A-7126 | + | GCCCCCAGGCGCUCUAUGCGGU | 22 | 8768 |
| BCL11A-7127 | + | CGCCCCCAGGCGCUCUAUGCGGU | 23 | 8769 |
| BCL11A-7128 | + | CCGCCCCCAGGCGCUCUAUGCGGU | 24 | 8770 |
| BCL11A-7129 | - | UUCCCAGCCACCUCUCCA | 18 | 8771 |
| BCL11A-7130 | - | CUUCCCAGCCACCUCUCCA | 19 | 8772 |

TABLE 16D-continued

4th Tier

| gRNA Name | DNA Strand | Targeting Domain | Target Site Length | SEQ ID NO: |
|---|---|---|---|---|
| BCL11A-5903 | - | CCUUCCCAGCCACCUCUCCA | 20 | 8773 |
| BCL11A-7131 | - | UCCUUCCCAGCCACCUCUCCA | 21 | 8774 |
| BCL11A-7132 | - | GUCCUUCCCAGCCACCUCUCCA | 22 | 8775 |
| BCL11A-7133 | - | UGUCCUUCCCAGCCACCUCUCCA | 23 | 8776 |
| BCL11A-7134 | - | AUGUCCUUCCCAGCCACCUCUCCA | 24 | 8777 |
| BCL11A-7135 | - | AGCGCAUCAAGCUCGAGA | 18 | 8778 |
| BCL11A-7136 | - | AAGCGCAUCAAGCUCGAGA | 19 | 8779 |
| BCL11A-5919 | - | UAAGCGCAUCAAGCUCGAGA | 20 | 8780 |
| BCL11A-7137 | - | CUAAGCGCAUCAAGCUCGAGA | 21 | 8781 |
| BCL11A-7138 | - | UCUAAGCGCAUCAAGCUCGAGA | 22 | 8782 |
| BCL11A-7139 | - | CUCUAAGCGCAUCAAGCUCGAGA | 23 | 8783 |
| BCL11A-7140 | - | UCUCUAAGCGCAUCAAGCUCGAGA | 24 | 8784 |
| BCL11A-7141 | - | GGAGCUGACGGAGAGCGA | 18 | 8785 |
| BCL11A-7142 | - | AGGAGCUGACGGAGAGCGA | 19 | 8786 |
| BCL11A-7143 | - | GAGGAGCUGACGGAGAGCGA | 20 | 8787 |
| BCL11A-7144 | - | GGAGGAGCUGACGGAGAGCGA | 21 | 8788 |
| BCL11A-7145 | - | AGGAGGAGCUGACGGAGAGCGA | 22 | 8789 |
| BCL11A-7146 | - | GAGGAGGAGCUGACGGAGAGCGA | 23 | 8790 |
| BCL11A-7147 | - | GGAGGAGGAGCUGACGGAGAGCGA | 24 | 8791 |
| BCL11A-7148 | - | UCACCCGAGUGCCUUUGA | 18 | 8792 |
| BCL11A-7149 | - | AUCACCCGAGUGCCUUUGA | 19 | 8793 |
| BCL11A-7150 | - | CAUCACCCGAGUGCCUUUGA | 20 | 8794 |
| BCL11A-7151 | - | CCAUCACCCGAGUGCCUUUGA | 21 | 8795 |
| BCL11A-7152 | - | CCCAUCACCCGAGUGCCUUUGA | 22 | 8796 |
| BCL11A-7153 | - | ACCCAUCACCCGAGUGCCUUUGA | 23 | 8797 |
| BCL11A-7154 | - | CACCCAUCACCCGAGUGCCUUUGA | 24 | 8798 |
| BCL11A-7155 | - | GAGCACUCCUCGGAGAAC | 18 | 8799 |
| BCL11A-7156 | - | GGAGCACUCCUCGGAGAAC | 19 | 8800 |
| BCL11A-5949 | - | CGGAGCACUCCUCGGAGAAC | 20 | 8801 |
| BCL11A-7157 | - | UCGGAGCACUCCUCGGAGAAC | 21 | 8802 |
| BCL11A-7158 | - | GUCGGAGCACUCCUCGGAGAAC | 22 | 8803 |
| BCL11A-7159 | - | CGUCGGAGCACUCCUCGGAGAAC | 23 | 8804 |
| BCL11A-7160 | - | UCGUCGGAGCACUCCUCGGAGAAC | 24 | 8805 |
| BCL11A-7161 | - | GCCCUGGCCACCCAUCAC | 18 | 8806 |
| BCL11A-7162 | - | GGCCCUGGCCACCCAUCAC | 19 | 8807 |
| BCL11A-7163 | - | UGGCCCUGGCCACCCAUCAC | 20 | 8808 |
| BCL11A-7164 | - | AUGGCCCUGGCCACCCAUCAC | 21 | 8809 |

TABLE 16D-continued

4th Tier

| gRNA Name | DNA Strand | Targeting Domain | Target Site Length | SEQ ID NO: |
|---|---|---|---|---|
| BCL11A-7165 | - | GAUGGCCCUGGCCACCCAUCAC | 22 | 8810 |
| BCL11A-7166 | - | AGAUGGCCCUGGCCACCCAUCAC | 23 | 8811 |
| BCL11A-7167 | - | GAGAUGGCCCUGGCCACCCAUCAC | 24 | 8812 |
| BCL11A-7168 | - | UUAACCUGCUAAGAAUAC | 18 | 8813 |
| BCL11A-7169 | - | UUUAACCUGCUAAGAAUAC | 19 | 8814 |
| BCL11A-7170 | - | CUUUAACCUGCUAAGAAUAC | 20 | 8815 |
| BCL11A-7171 | - | CCUUUAACCUGCUAAGAAUAC | 21 | 8816 |
| BCL11A-7172 | - | CCCUUUAACCUGCUAAGAAUAC | 22 | 8817 |
| BCL11A-7173 | - | CCCCUUUAACCUGCUAAGAAUAC | 23 | 8818 |
| BCL11A-7174 | - | ACCCCUUUAACCUGCUAAGAAUAC | 24 | 8819 |
| BCL11A-7175 | - | CGGAAGUCCCUGACCCC | 18 | 8820 |
| BCL11A-7176 | - | ACGGAAGUCCCCUGACCCC | 19 | 8821 |
| BCL11A-7177 | - | CACGGAAGUCCCCUGACCCC | 20 | 8822 |
| BCL11A-7178 | - | ACACGGAAGUCCCCUGACCCC | 21 | 8823 |
| BCL11A-7179 | - | AACACGGAAGUCCCCUGACCCC | 22 | 8824 |
| BCL11A-7180 | - | GAACACGGAAGUCCCCUGACCCC | 23 | 8825 |
| BCL11A-7181 | - | CGAACACGGAAGUCCCCUGACCCC | 24 | 8826 |
| BCL11A-7182 | - | AGAAAAUUUGAAGCCCCC | 18 | 8827 |
| BCL11A-7183 | - | GAGAAAAUUUGAAGCCCCC | 19 | 8828 |
| BCL11A-5969 | - | UGAGAAAAUUUGAAGCCCCC | 20 | 8829 |
| BCL11A-7184 | - | CUGAGAAAAUUUGAAGCCCCC | 21 | 8830 |
| BCL11A-7185 | - | UCUGAGAAAAUUUGAAGCCCCC | 22 | 8831 |
| BCL11A-7186 | - | UUCUGAGAAAAUUUGAAGCCCCC | 23 | 8832 |
| BCL11A-7187 | - | GUUCUGAGAAAAUUUGAAGCCCCC | 24 | 8833 |
| BCL11A-7188 | - | GCUAUGGAGCCUCCCGCC | 18 | 8834 |
| BCL11A-7189 | - | GGCUAUGGAGCCUCCCGCC | 19 | 8835 |
| BCL11A-7190 | - | UGGCUAUGGAGCCUCCCGCC | 20 | 8836 |
| BCL11A-7191 | - | AUGGCUAUGGAGCCUCCCGCC | 21 | 8837 |
| BCL11A-7192 | - | AAUGGCUAUGGAGCCUCCCGCC | 22 | 8838 |
| BCL11A-7193 | - | CAAUGGCUAUGGAGCCUCCCGCC | 23 | 8839 |
| BCL11A-7194 | - | CCAAUGGCUAUGGAGCCUCCCGCC | 24 | 8840 |
| BCL11A-7195 | - | AACACGCACAGAACACUC | 18 | 8841 |
| BCL11A-7196 | - | CAACACGCACAGAACACUC | 19 | 8842 |
| BCL11A-7197 | - | GCAACACGCACAGAACACUC | 20 | 8843 |
| BCL11A-7198 | - | UGCAACACGCACAGAACACUC | 21 | 8844 |
| BCL11A-7199 | - | UUGCAACACGCACAGAACACUC | 22 | 8845 |
| BCL11A-7200 | - | CUUGCAACACGCACAGAACACUC | 23 | 8846 |
| BCL11A-7201 | - | UCUUGCAACACGCACAGAACACUC | 24 | 8847 |

TABLE 16D-continued

| | 4th Tier | | | |
|---|---|---|---|---|
| gRNA Name | DNA Strand | Targeting Domain | Target Site Length | SEQ ID NO: |
| BCL11A-7202 | − | ACGAAGACUCGGUGGCCG | 18 | 8848 |
| BCL11A-7203 | − | GACGAAGACUCGGUGGCCG | 19 | 8849 |
| BCL11A-7204 | − | CGACGAAGACUCGGUGGCCG | 20 | 8850 |
| BCL11A-7205 | − | GCGACGAAGACUCGGUGGCCG | 21 | 8851 |
| BCL11A-7206 | − | UGCGACGAAGACUCGGUGGCCG | 22 | 8852 |
| BCL11A-7207 | − | UUGCGACGAAGACUCGGUGGCCG | 23 | 8853 |
| BCL11A-7208 | − | CUUGCGACGAAGACUCGGUGGCCG | 24 | 8854 |
| BCL11A-7209 | − | GCCCGGGGAGCUGGACGG | 18 | 8855 |
| BCL11A-7210 | − | CGCCCGGGGAGCUGGACGG | 19 | 8856 |
| BCL11A-6121 | − | CCGCCCGGGGAGCUGGACGG | 20 | 8857 |
| BCL11A-7211 | − | ACCGCCCGGGGAGCUGGACGG | 21 | 8858 |
| BCL11A-7212 | − | CACCGCCCGGGGAGCUGGACGG | 22 | 8859 |
| BCL11A-7213 | − | ACACCGCCCGGGGAGCUGGACGG | 23 | 8860 |
| BCL11A-7214 | − | CACACCGCCCGGGGAGCUGGACGG | 24 | 8861 |
| BCL11A-7215 | − | GCCGCGGCUGCUCCCCGG | 18 | 8862 |
| BCL11A-7216 | − | GGCCGCGGCUGCUCCCCGG | 19 | 8863 |
| BCL11A-7217 | − | UGGCCGCGGCUGCUCCCCGG | 20 | 8864 |
| BCL11A-7218 | − | AUGGCCGCGGCUGCUCCCCGG | 21 | 8865 |
| BCL11A-7219 | − | AAUGGCCGCGGCUGCUCCCCGG | 22 | 8866 |
| BCL11A-7220 | − | UAAUGGCCGCGGCUGCUCCCCGG | 23 | 8867 |
| BCL11A-7221 | − | UUAAUGGCCGCGGCUGCUCCCCGG | 24 | 8868 |
| BCL11A-7222 | − | UUUGACAGGGUGCUGCGG | 18 | 8869 |
| BCL11A-7223 | − | CUUUGACAGGGUGCUGCGG | 19 | 8870 |
| BCL11A-7224 | − | CCUUUGACAGGGUGCUGCGG | 20 | 8871 |
| BCL11A-7225 | − | GCCUUUGACAGGGUGCUGCGG | 21 | 8872 |
| BCL11A-7226 | − | UGCCUUUGACAGGGUGCUGCGG | 22 | 8873 |
| BCL11A-7227 | − | GUGCCUUUGACAGGGUGCUGCGG | 23 | 8874 |
| BCL11A-7228 | − | AGUGCCUUUGACAGGGUGCUGCGG | 24 | 8875 |
| BCL11A-7229 | − | AUUUGAAGCCCCCAGGGG | 18 | 8876 |
| BCL11A-7230 | − | AAUUUGAAGCCCCCAGGGG | 19 | 8877 |
| BCL11A-6140 | − | AAAUUUGAAGCCCCCAGGGG | 20 | 8878 |
| BCL11A-7231 | − | AAAAUUUGAAGCCCCCAGGGG | 21 | 8879 |
| BCL11A-7232 | − | GAAAAUUUGAAGCCCCCAGGGG | 22 | 8880 |
| BCL11A-7233 | − | AGAAAAUUUGAAGCCCCCAGGGG | 23 | 8881 |
| BCL11A-7234 | − | GAGAAAAUUUGAAGCCCCCAGGGG | 24 | 8882 |
| BCL11A-7235 | − | UCCCUUCAGGACUAGGUG | 18 | 8883 |
| BCL11A-7236 | − | AUCCCUUCAGGACUAGGUG | 19 | 8884 |

TABLE 16D-continued

4th Tier

| gRNA Name | DNA Strand | Targeting Domain | Target Site Length | SEQ ID NO: |
|---|---|---|---|---|
| BCL11A-7237 | - | UAUCCCUUCAGGACUAGGUG | 20 | 8885 |
| BCL11A-7238 | - | GUAUCCCUUCAGGACUAGGUG | 21 | 8886 |
| BCL11A-7239 | - | GGUAUCCCUUCAGGACUAGGUG | 22 | 8887 |
| BCL11A-7240 | - | UGGUAUCCCUUCAGGACUAGGUG | 23 | 8888 |
| BCL11A-7241 | - | UUGGUAUCCCUUCAGGACUAGGUG | 24 | 8889 |
| BCL11A-7242 | - | CGGUCAAGUCCAAGUCAU | 18 | 8890 |
| BCL11A-7243 | - | CCGGUCAAGUCCAAGUCAU | 19 | 8891 |
| BCL11A-7244 | - | CCCGGUCAAGUCCAAGUCAU | 20 | 8892 |
| BCL11A-7245 | - | CCCCGGUCAAGUCCAAGUCAU | 21 | 8893 |
| BCL11A-7246 | - | CCCCCGGUCAAGUCCAAGUCAU | 22 | 8894 |
| BCL11A-7247 | - | GCCCCCGGUCAAGUCCAAGUCAU | 23 | 8895 |
| BCL11A-7248 | - | AGCCCCCGGUCAAGUCCAAGUCAU | 24 | 8896 |
| BCL11A-7249 | - | UAACCCCUUUAACCUGCU | 18 | 8897 |
| BCL11A-7250 | - | AUAACCCCUUUAACCUGCU | 19 | 8898 |
| BCL11A-7251 | - | AAUAACCCCUUUAACCUGCU | 20 | 8899 |
| BCL11A-7252 | - | CAAUAACCCCUUUAACCUGCU | 21 | 8900 |
| BCL11A-7253 | - | ACAAUAACCCCUUUAACCUGCU | 22 | 8901 |
| BCL11A-7254 | - | GACAAUAACCCCUUUAACCUGCU | 23 | 8902 |
| BCL11A-7255 | - | AGACAAUAACCCCUUUAACCUGCU | 24 | 8903 |
| BCL11A-7256 | - | ACAGAACACUCAUGGAUU | 18 | 8904 |
| BCL11A-7257 | - | CACAGAACACUCAUGGAUU | 19 | 8905 |
| BCL11A-7258 | - | GCACAGAACACUCAUGGAUU | 20 | 8906 |
| BCL11A-7259 | - | CGCACAGAACACUCAUGGAUU | 21 | 8907 |
| BCL11A-7260 | - | ACGCACAGAACACUCAUGGAUU | 22 | 8908 |
| BCL11A-7261 | - | CACGCACAGAACACUCAUGGAUU | 23 | 8909 |
| BCL11A-7262 | - | ACACGCACAGAACACUCAUGGAUU | 24 | 8910 |
| BCL11A-7263 | - | GCAGACGCAGCGACACUU | 18 | 8911 |
| BCL11A-7264 | - | GGCAGACGCAGCGACACUU | 19 | 8912 |
| BCL11A-7265 | - | GGGCAGACGCAGCGACACUU | 20 | 8913 |
| BCL11A-7266 | - | AGGGCAGACGCAGCGACACUU | 21 | 8914 |
| BCL11A-7267 | - | GAGGGCAGACGCAGCGACACUU | 22 | 8915 |
| BCL11A-7268 | - | AGAGGGCAGACGCAGCGACACUU | 23 | 8916 |
| BCL11A-7269 | - | AAGAGGGCAGACGCAGCGACACUU | 24 | 8917 |
| BCL11A-7270 | - | CAAGAUGUGUGGCAGUUU | 18 | 8918 |
| BCL11A-7271 | - | UCAAGAUGUGUGGCAGUUU | 19 | 8919 |
| BCL11A-7272 | - | CUCAAGAUGUGUGGCAGUUU | 20 | 8920 |
| BCL11A-7273 | - | GCUCAAGAUGUGUGGCAGUUU | 21 | 8921 |
| BCL11A-7274 | - | AGCUCAAGAUGUGUGGCAGUUU | 22 | 8922 |

TABLE 16D-continued

| | | 4th Tier | | |
|---|---|---|---|---|
| gRNA Name | DNA Strand | Targeting Domain | Target Site Length | SEQ ID NO: |
| BCL11A-7275 | - | GAGCUCAAGAUGUGUGGCAGUUU | 23 | 8923 |
| BCL11A-7276 | - | AGAGCUCAAGAUGUGUGGCAGUUU | 24 | 8924 |

Table 16E provides exemplary targeting domains for knocking out the BCL11A gene selected according to the fifth tier parameters. The targeting domains fall in the coding sequence of the gene, downstream of the first 500 bp of coding sequence (e.g., anywhere from +500 (relative to the start codon) to the stop codon of the gene), and the PAM is NNGRRV. It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 16E

| | | 5th Tier | | |
|---|---|---|---|---|
| gRNA Name | DNA Strand | Targeting Domain | Target Site Length | SEQ ID NO: |
| BCL11A-7277 | + | UCUCGGUGGUGGACUAAA | 18 | 8925 |
| BCL11A-7278 | + | GUCUCGGUGGUGGACUAAA | 19 | 8926 |
| BCL11A-7279 | + | UGUCUCGGUGGUGGACUAAA | 20 | 8927 |
| BCL11A-7280 | + | AUGUCUCGGUGGUGGACUAAA | 21 | 8928 |
| BCL11A-7281 | + | GAUGUCUCGGUGGUGGACUAAA | 22 | 8929 |
| BCL11A-7282 | + | UGAUGUCUCGGUGGUGGACUAAA | 23 | 8930 |
| BCL11A-7283 | + | GUGAUGUCUCGGUGGUGGACUAAA | 24 | 8931 |
| BCL11A-7284 | + | GUUCUGUGCGUGUUGCAA | 18 | 8932 |
| BCL11A-7285 | + | UGUUCUGUGCGUGUUGCAA | 19 | 8933 |
| BCL11A-7286 | + | GUGUUCUGUGCGUGUUGCAA | 20 | 8934 |
| BCL11A-7287 | + | AGUGUUCUGUGCGUGUUGCAA | 21 | 8935 |
| BCL11A-7288 | + | GAGUGUUCUGUGCGUGUUGCAA | 22 | 8936 |
| BCL11A-7289 | + | UGAGUGUUCUGUGCGUGUUGCAA | 23 | 8937 |
| BCL11A-7290 | + | AUGAGUGUUCUGUGCGUGUUGCAA | 24 | 8938 |
| BCL11A-7291 | + | UCUGGGUACUACGCCGAA | 18 | 8939 |
| BCL11A-7292 | + | CUCUGGGUACUACGCCGAA | 19 | 8940 |
| BCL11A-5883 | + | UCUCUGGGUACUACGCCGAA | 20 | 8941 |
| BCL11A-7293 | + | CUCUCUGGGUACUACGCCGAA | 21 | 8942 |
| BCL11A-7294 | + | GCUCUCUGGGUACUACGCCGAA | 22 | 8943 |
| BCL11A-7295 | + | AGCUCUCUGGGUACUACGCCGAA | 23 | 8944 |
| BCL11A-7296 | + | GAGCUCUCUGGGUACUACGCCGAA | 24 | 8945 |
| BCL11A-7297 | + | UCGGUGGUGGACUAAACA | 18 | 8946 |
| BCL11A-7298 | + | CUCGGUGGUGGACUAAACA | 19 | 8947 |
| BCL11A-5892 | + | UCUCGGUGGUGGACUAAACA | 20 | 8948 |
| BCL11A-7299 | + | GUCUCGGUGGUGGACUAAACA | 21 | 8949 |
| BCL11A-7300 | + | UGUCUCGGUGGUGGACUAAACA | 22 | 8950 |

TABLE 16E-continued

5th Tier

| gRNA Name | DNA Strand | Targeting Domain | Target Site Length | SEQ ID NO: |
|---|---|---|---|---|
| BCL11A-7301 | + | AUGUCUCGGUGGUGGACUAAACA | 23 | 8951 |
| BCL11A-7342 | + | UGAUGCGCUUAGAGAAGGGGCUCA | 24 | 8994 |
| BCL11A-7343 | + | CGUCGGACUUGACCGUCA | 18 | 8995 |
| BCL11A-7344 | + | UCGUCGGACUUGACCGUCA | 19 | 8996 |
| BCL11A-5912 | + | GUCGUCGGACUUGACCGUCA | 20 | 8997 |
| BCL11A-7345 | + | CGUCGUCGGACUUGACCGUCA | 21 | 8998 |
| BCL11A-7346 | + | CCGUCGUCGGACUUGACCGUCA | 22 | 8999 |
| BCL11A-7347 | + | ACCGUCGUCGGACUUGACCGUCA | 23 | 9000 |
| BCL11A-7348 | + | GACCGUCGUCGGACUUGACCGUCA | 24 | 9001 |
| BCL11A-7349 | + | UACCAACCCGCGGGGUCA | 18 | 9002 |
| BCL11A-7350 | + | AUACCAACCCGCGGGGUCA | 19 | 9003 |
| BCL11A-5913 | + | GAUACCAACCCGCGGGGUCA | 20 | 9004 |
| BCL11A-7351 | + | GGAUACCAACCCGCGGGGUCA | 21 | 9005 |
| BCL11A-7352 | + | GGGAUACCAACCCGCGGGGUCA | 22 | 9006 |
| BCL11A-7353 | + | AGGGAUACCAACCCGCGGGGUCA | 23 | 9007 |
| BCL11A-7354 | + | AAGGGAUACCAACCCGCGGGGUCA | 24 | 9008 |
| BCL11A-7355 | + | GCUUGAUGCGCUUAGAGA | 18 | 9009 |
| BCL11A-7356 | + | AGCUUGAUGCGCUUAGAGA | 19 | 9010 |
| BCL11A-5917 | + | GAGCUUGAUGCGCUUAGAGA | 20 | 9011 |
| BCL11A-7357 | + | CGAGCUUGAUGCGCUUAGAGA | 21 | 9012 |
| BCL11A-7358 | + | UCGAGCUUGAUGCGCUUAGAGA | 22 | 9013 |
| BCL11A-7359 | + | CUCGAGCUUGAUGCGCUUAGAGA | 23 | 9014 |
| BCL11A-7360 | + | UCUCGAGCUUGAUGCGCUUAGAGA | 24 | 9015 |
| BCL11A-7361 | + | CUAGAAAGAGGUUGGAGA | 18 | 9016 |
| BCL11A-7362 | + | CCUAGAAAGAGGUUGGAGA | 19 | 9017 |
| BCL11A-7363 | + | ACCUAGAAAGAGGUUGGAGA | 20 | 9018 |
| BCL11A-7364 | + | AACCUAGAAAGAGGUUGGAGA | 21 | 9019 |
| BCL11A-7365 | + | GAACCUAGAAAGAGGUUGGAGA | 22 | 9020 |
| BCL11A-7366 | + | AGAACCUAGAAAGAGGUUGGAGA | 23 | 9021 |
| BCL11A-7367 | + | AAGAACCUAGAAAGAGGUUGGAGA | 24 | 9022 |
| BCL11A-7368 | + | GUGUGUGAAGAACCUAGA | 18 | 9023 |
| BCL11A-7369 | + | GGUGUGUGAAGAACCUAGA | 19 | 9024 |
| BCL11A-7370 | + | GGGUGUGUGAAGAACCUAGA | 20 | 9025 |
| BCL11A-7371 | + | GGGGUGUGUGAAGAACCUAGA | 21 | 9026 |
| BCL11A-7372 | + | GGGGGUGUGUGAAGAACCUAGA | 22 | 9027 |
| BCL11A-7373 | + | UGGGGGUGUGUGAAGAACCUAGA | 23 | 9028 |
| BCL11A-7374 | + | AUGGGGGUGUGUGAAGAACCUAGA | 24 | 9029 |
| BCL11A-7375 | + | CUCUGGGUACUACGCCGA | 18 | 9030 |

TABLE 16E-continued

5th Tier

| gRNA Name | DNA Strand | Targeting Domain | Target Site Length | SEQ ID NO: |
|---|---|---|---|---|
| BCL11A-7376 | + | UCUCUGGGUACUACGCCGA | 19 | 9031 |
| BCL11A-7377 | + | CUCUCUGGGUACUACGCCGA | 20 | 9032 |
| BCL11A-7378 | + | GCUCUCUGGGUACUACGCCGA | 21 | 9033 |
| BCL11A-7379 | + | AGCUCUCUGGGUACUACGCCGA | 22 | 9034 |
| BCL11A-7380 | + | GAGCUCUCUGGGUACUACGCCGA | 23 | 9035 |
| BCL11A-7381 | + | UGAGCUCUCUGGGUACUACGCCGA | 24 | 9036 |
| BCL11A-7382 | + | GAGGUUGGAGACAGAGGA | 18 | 9037 |
| BCL11A-7383 | + | AGAGGUUGGAGACAGAGGA | 19 | 9038 |
| BCL11A-5925 | + | AAGAGGUUGGAGACAGAGGA | 20 | 9039 |
| BCL11A-7384 | + | AAAGAGGUUGGAGACAGAGGA | 21 | 9040 |
| BCL11A-7385 | + | GAAAGAGGUUGGAGACAGAGGA | 22 | 9041 |
| BCL11A-7386 | + | AGAAAGAGGUUGGAGACAGAGGA | 23 | 9042 |
| BCL11A-7387 | + | UAGAAAGAGGUUGGAGACAGAGGA | 24 | 9043 |
| BCL11A-7388 | + | GGGGCGGAUUGCAGAGGA | 18 | 9044 |
| BCL11A-7389 | + | AGGGGCGGAUUGCAGAGGA | 19 | 9045 |
| BCL11A-5926 | + | GAGGGGCGGAUUGCAGAGGA | 20 | 9046 |
| BCL11A-7390 | + | GGAGGGGCGGAUUGCAGAGGA | 21 | 9047 |
| BCL11A-7391 | + | AGGAGGGGCGGAUUGCAGAGGA | 22 | 9048 |
| BCL11A-7392 | + | GAGGAGGGGCGGAUUGCAGAGGA | 23 | 9049 |
| BCL11A-7393 | + | GGAGGAGGGGCGGAUUGCAGAGGA | 24 | 9050 |
| BCL11A-7394 | + | CGGAUUGCAGAGGAGGGA | 18 | 9051 |
| BCL11A-7395 | + | GCGGAUUGCAGAGGAGGGA | 19 | 9052 |
| BCL11A-5930 | + | GGCGGAUUGCAGAGGAGGGA | 20 | 9053 |
| BCL11A-7396 | + | GGGCGGAUUGCAGAGGAGGGA | 21 | 9054 |
| BCL11A-7397 | + | GGGGCGGAUUGCAGAGGAGGGA | 22 | 9055 |
| BCL11A-7398 | + | AGGGGCGGAUUGCAGAGGAGGGA | 23 | 9056 |
| BCL11A-7399 | + | GAGGGGCGGAUUGCAGAGGAGGGA | 24 | 9057 |
| BCL11A-7400 | + | CUUGACCGGGGCUGGGA | 18 | 9058 |
| BCL11A-7401 | + | ACUUGACCGGGGCUGGGA | 19 | 9059 |
| BCL11A-5931 | + | GACUUGACCGGGGCUGGGA | 20 | 9060 |
| BCL11A-7402 | + | GGACUUGACCGGGGCUGGGA | 21 | 9061 |
| BCL11A-7403 | + | UGGACUUGACCGGGGCUGGGA | 22 | 9062 |
| BCL11A-7404 | + | UUGGACUUGACCGGGGCUGGGA | 23 | 9063 |
| BCL11A-7405 | + | CUUGGACUUGACCGGGGCUGGGA | 24 | 9064 |
| BCL11A-7406 | + | CGCAUGACUUGGACUUGA | 18 | 9065 |
| BCL11A-7407 | + | UCGCAUGACUUGGACUUGA | 19 | 9066 |
| BCL11A-7408 | + | CUCGCAUGACUUGGACUUGA | 20 | 9067 |

TABLE 16E-continued

5th Tier

| gRNA Name | DNA Strand | Targeting Domain | Target Site Length | SEQ ID NO: |
|---|---|---|---|---|
| BCL11A-7409 | + | ACUCGCAUGACUUGGACUUGA | 21 | 9068 |
| BCL11A-7410 | + | AACUCGCAUGACUUGGACUUGA | 22 | 9069 |
| BCL11A-7411 | + | GAACUCGCAUGACUUGGACUUGA | 23 | 9070 |
| BCL11A-7412 | + | AGAACUCGCAUGACUUGGACUUGA | 24 | 9071 |
| BCL11A-7413 | + | GGGCCCGGACCACUAAUA | 18 | 9072 |
| BCL11A-7414 | + | CGGGCCCGGACCACUAAUA | 19 | 9073 |
| BCL11A-5940 | + | CCGGGCCCGGACCACUAAUA | 20 | 9074 |
| BCL11A-7415 | + | CCCGGGCCCGGACCACUAAUA | 21 | 9075 |
| BCL11A-7416 | + | GCCCGGGCCCGGACCACUAAUA | 22 | 9076 |
| BCL11A-7417 | + | UGCCCGGGCCCGGACCACUAAUA | 23 | 9077 |
| BCL11A-7418 | + | CUGCCCGGGCCCGGACCACUAAUA | 24 | 9078 |
| BCL11A-7419 | + | AGCUCUCUAAGUCUCCUA | 18 | 9079 |
| BCL11A-7420 | + | CAGCUCUCUAAGUCUCCUA | 19 | 9080 |
| BCL11A-7421 | + | CCAGCUCUCUAAGUCUCCUA | 20 | 9081 |
| BCL11A-7422 | + | GCCAGCUCUCUAAGUCUCCUA | 21 | 9082 |
| BCL11A-7423 | + | UGCCAGCUCUCUAAGUCUCCUA | 22 | 9083 |
| BCL11A-7424 | + | CUGCCAGCUCUCUAAGUCUCCUA | 23 | 9084 |
| BCL11A-7425 | + | CCUGCCAGCUCUCUAAGUCUCCUA | 24 | 9085 |
| BCL11A-7426 | + | CUGGAGUCUCCGAAGCUA | 18 | 9086 |
| BCL11A-7427 | + | UCUGGAGUCUCCGAAGCUA | 19 | 9087 |
| BCL11A-5943 | + | GUCUGGAGUCUCCGAAGCUA | 20 | 9088 |
| BCL11A-7428 | + | UGUCUGGAGUCUCCGAAGCUA | 21 | 9089 |
| BCL11A-7429 | + | UUGUCUGGAGUCUCCGAAGCUA | 22 | 9090 |
| BCL11A-7430 | + | AUUGUCUGGAGUCUCCGAAGCUA | 23 | 9091 |
| BCL11A-7431 | + | GAUUGUCUGGAGUCUCCGAAGCUA | 24 | 9092 |
| BCL11A-7432 | + | UCGAGCUUGAUGCGCUUA | 18 | 9093 |
| BCL11A-7433 | + | CUCGAGCUUGAUGCGCUUA | 19 | 9094 |
| BCL11A-7434 | + | UCUCGAGCUUGAUGCGCUUA | 20 | 9095 |
| BCL11A-7435 | + | UUCUCGAGCUUGAUGCGCUUA | 21 | 9096 |
| BCL11A-7436 | + | CUUCUCGAGCUUGAUGCGCUUA | 22 | 9097 |
| BCL11A-7437 | + | CCUUCUCGAGCUUGAUGCGCUUA | 23 | 9098 |
| BCL11A-7438 | + | UCCUUCUCGAGCUUGAUGCGCUUA | 24 | 9099 |
| BCL11A-7439 | + | GGUAUUCUUAGCAGGUUA | 18 | 9100 |
| BCL11A-7440 | + | UGGUAUUCUUAGCAGGUUA | 19 | 9101 |
| BCL11A-7441 | + | CUGGUAUUCUUAGCAGGUUA | 20 | 9102 |
| BCL11A-7442 | + | CCUGGUAUUCUUAGCAGGUUA | 21 | 9103 |
| BCL11A-7443 | + | UCCUGGUAUUCUUAGCAGGUUA | 22 | 9104 |
| BCL11A-7444 | + | AUCCUGGUAUUCUUAGCAGGUUA | 23 | 9105 |

TABLE 16E-continued

5th Tier

| gRNA Name | DNA Strand | Targeting Domain | Target Site Length | SEQ ID NO: |
|---|---|---|---|---|
| BCL11A-7445 | + | GAUCCUGGUAUUCUUAGCAGGUUA | 24 | 9106 |
| BCL11A-7446 | + | CUCGGUGGUGGACUAAAC | 18 | 9107 |
| BCL11A-7447 | + | UCUCGGUGGUGGACUAAAC | 19 | 9108 |
| BCL11A-5947 | + | GUCUCGGUGGUGGACUAAAC | 20 | 9109 |
| BCL11A-7448 | + | UGUCUCGGUGGUGGACUAAAC | 21 | 9110 |
| BCL11A-7449 | + | AUGUCUCGGUGGUGGACUAAAC | 22 | 9111 |
| BCL11A-7450 | + | GAUGUCUCGGUGGUGGACUAAAC | 23 | 9112 |
| BCL11A-7451 | + | UGAUGUCUCGGUGGUGGACUAAAC | 24 | 9113 |
| BCL11A-7452 | + | UCCGAGGAGUGCUCCGAC | 18 | 9114 |
| BCL11A-7453 | + | CUCCGAGGAGUGCUCCGAC | 19 | 9115 |
| BCL11A-7454 | + | UCUCCGAGGAGUGCUCCGAC | 20 | 9116 |
| BCL11A-7455 | + | UUCUCCGAGGAGUGCUCCGAC | 21 | 9117 |
| BCL11A-7456 | + | GUUCUCCGAGGAGUGCUCCGAC | 22 | 9118 |
| BCL11A-7457 | + | CGUUCUCCGAGGAGUGCUCCGAC | 23 | 9119 |
| BCL11A-7458 | + | CCGUUCUCCGAGGAGUGCUCCGAC | 24 | 9120 |
| BCL11A-7459 | + | AACUUGGCCACCACGGAC | 18 | 9121 |
| BCL11A-7460 | + | GAACUUGGCCACCACGGAC | 19 | 9122 |
| BCL11A-7461 | + | UGAACUUGGCCACCACGGAC | 20 | 9123 |
| BCL11A-7462 | + | UUGAACUUGGCCACCACGGAC | 21 | 9124 |
| BCL11A-7463 | + | CUUGAACUUGGCCACCACGGAC | 22 | 9125 |
| BCL11A-7464 | + | UCUUGAACUUGGCCACCACGGAC | 23 | 9126 |
| BCL11A-7465 | + | CUCUUGAACUUGGCCACCACGGAC | 24 | 9127 |
| BCL11A-7466 | + | CCGCAGAACUCGCAUGAC | 18 | 9128 |
| BCL11A-7467 | + | GCCGCAGAACUCGCAUGAC | 19 | 9129 |
| BCL11A-7468 | + | UGCCGCAGAACUCGCAUGAC | 20 | 9130 |
| BCL11A-7469 | + | UUGCCGCAGAACUCGCAUGAC | 21 | 9131 |
| BCL11A-7470 | + | CUUGCCGCAGAACUCGCAUGAC | 22 | 9132 |
| BCL11A-7471 | + | UCUUGCCGCAGAACUCGCAUGAC | 23 | 9133 |
| BCL11A-7472 | + | GUCUUGCCGCAGAACUCGCAUGAC | 24 | 9134 |
| BCL11A-7473 | + | GCAUGACUUGGACUUGAC | 18 | 9135 |
| BCL11A-7474 | + | CGCAUGACUUGGACUUGAC | 19 | 9136 |
| BCL11A-5957 | + | UCGCAUGACUUGGACUUGAC | 20 | 9137 |
| BCL11A-7475 | + | CUCGCAUGACUUGGACUUGAC | 21 | 9138 |
| BCL11A-7476 | + | ACUCGCAUGACUUGGACUUGAC | 22 | 9139 |
| BCL11A-7477 | + | AACUCGCAUGACUUGGACUUGAC | 23 | 9140 |
| BCL11A-7478 | + | GAACUCGCAUGACUUGGACUUGAC | 24 | 9141 |
| BCL11A-7479 | + | GGGGGUGUGUGAAGAACC | 18 | 9142 |

TABLE 16E-continued

5th Tier

| gRNA Name | DNA Strand | Targeting Domain | Target Site Length | SEQ ID NO: |
|---|---|---|---|---|
| BCL11A-7480 | + | UGGGGGUGUGUGAAGAACC | 19 | 9143 |
| BCL11A-7481 | + | AUGGGGGUGUGUGAAGAACC | 20 | 9144 |
| BCL11A-7482 | + | AAUGGGGGUGUGUGAAGAACC | 21 | 9145 |
| BCL11A-7483 | + | GAAUGGGGGUGUGUGAAGAACC | 22 | 9146 |
| BCL11A-7484 | + | CGAAUGGGGGUGUGUGAAGAACC | 23 | 9147 |
| BCL11A-7485 | + | CCGAAUGGGGGUGUGUGAAGAACC | 24 | 9148 |
| BCL11A-7486 | + | CUCUUGAACUUGGCCACC | 18 | 9149 |
| BCL11A-7487 | + | GCUCUUGAACUUGGCCACC | 19 | 9150 |
| BCL11A-7488 | + | CGCUCUUGAACUUGGCCACC | 20 | 9151 |
| BCL11A-7489 | + | UCGCUCUUGAACUUGGCCACC | 21 | 9152 |
| BCL11A-7490 | + | CUCGCUCUUGAACUUGGCCACC | 22 | 9153 |
| BCL11A-7491 | + | UCUCGCUCUUGAACUUGGCCACC | 23 | 9154 |
| BCL11A-7492 | + | UUCUCGCUCUUGAACUUGGCCACC | 24 | 9155 |
| BCL11A-7493 | + | CAUGACUUGGACUUGACC | 18 | 9156 |
| BCL11A-7494 | + | GCAUGACUUGGACUUGACC | 19 | 9157 |
| BCL11A-5965 | + | CGCAUGACUUGGACUUGACC | 20 | 9158 |
| BCL11A-7495 | + | UCGCAUGACUUGGACUUGACC | 21 | 9159 |
| BCL11A-7496 | + | CUCGCAUGACUUGGACUUGACC | 22 | 9160 |
| BCL11A-7497 | + | ACUCGCAUGACUUGGACUUGACC | 23 | 9161 |
| BCL11A-7498 | + | AACUCGCAUGACUUGGACUUGACC | 24 | 9162 |
| BCL11A-7499 | + | CUGAAGGGAUACCAACCC | 18 | 9163 |
| BCL11A-7500 | + | CCUGAAGGGAUACCAACCC | 19 | 9164 |
| BCL11A-7501 | + | UCCUGAAGGGAUACCAACCC | 20 | 9165 |
| BCL11A-7502 | + | GUCCUGAAGGGAUACCAACCC | 21 | 9166 |
| BCL11A-7503 | + | AGUCCUGAAGGGAUACCAACCC | 22 | 9167 |
| BCL11A-7504 | + | UAGUCCUGAAGGGAUACCAACCC | 23 | 9168 |
| BCL11A-7505 | + | CUAGUCCUGAAGGGAUACCAACCC | 24 | 9169 |
| BCL11A-7506 | + | CGCCCACGACCGCGCCCC | 18 | 9170 |
| BCL11A-7507 | + | ACGCCCACGACCGCGCCCC | 19 | 9171 |
| BCL11A-3830 | + | CACGCCCACGACCGCGCCCC | 20 | 9172 |
| BCL11A-7508 | + | CCACGCCCACGACCGCGCCCC | 21 | 9173 |
| BCL11A-7509 | + | CCCACGCCCACGACCGCGCCCC | 22 | 9174 |
| BCL11A-7510 | + | GCCCACGCCCACGACCGCGCCCC | 23 | 9175 |
| BCL11A-7511 | + | CGCCCACGCCCACGACCGCGCCCC | 24 | 9176 |
| BCL11A-7512 | + | GCUUUUUGGACAGGCCCC | 18 | 9177 |
| BCL11A-7513 | + | AGCUUUUUGGACAGGCCCC | 19 | 9178 |
| BCL11A-7514 | + | CAGCUUUUUGGACAGGCCCC | 20 | 9179 |
| BCL11A-7515 | + | GCAGCUUUUUGGACAGGCCCC | 21 | 9180 |

TABLE 16E-continued

5th Tier

| gRNA Name | DNA Strand | Targeting Domain | Target Site Length | SEQ ID NO: |
|---|---|---|---|---|
| BCL11A-7516 | + | AGCAGCUUUUUGGACAGGCCCC | 22 | 9181 |
| BCL11A-7517 | + | CAGCAGCUUUUUGGACAGGCCCC | 23 | 9182 |
| BCL11A-7518 | + | GCAGCAGCUUUUUGGACAGGCCCC | 24 | 9183 |
| BCL11A-7519 | + | CCCGAGGCCGACUCGCCC | 18 | 9184 |
| BCL11A-7520 | + | CCCCGAGGCCGACUCGCCC | 19 | 9185 |
| BCL11A-5977 | + | CCCCCGAGGCCGACUCGCCC | 20 | 9186 |
| BCL11A-7521 | + | CCCCCCGAGGCCGACUCGCCC | 21 | 9187 |
| BCL11A-7522 | + | GCCCCCCGAGGCCGACUCGCCC | 22 | 9188 |
| BCL11A-7523 | + | GGCCCCCCGAGGCCGACUCGCCC | 23 | 9189 |
| BCL11A-7524 | + | AGGCCCCCCGAGGCCGACUCGCCC | 24 | 9190 |
| BCL11A-7525 | + | GUCUGCAAUAUGAAUCCC | 18 | 9191 |
| BCL11A-7526 | + | UGUCUGCAAUAUGAAUCCC | 19 | 9192 |
| BCL11A-7527 | + | UUGUCUGCAAUAUGAAUCCC | 20 | 9193 |
| BCL11A-7528 | + | AUUGUCUGCAAUAUGAAUCCC | 21 | 9194 |
| BCL11A-7529 | + | UAUUGUCUGCAAUAUGAAUCCC | 22 | 9195 |
| BCL11A-7530 | + | UUAUUGUCUGCAAUAUGAAUCCC | 23 | 9196 |
| BCL11A-7531 | + | GUUAUUGUCUGCAAUAUGAAUCCC | 24 | 9197 |
| BCL11A-7532 | + | UUCCCGUGCCGCUGCGCC | 18 | 9198 |
| BCL11A-7533 | + | CUUCCCGUGCCGCUGCGCC | 19 | 9199 |
| BCL11A-7534 | + | ACUUCCCGUGCCGCUGCGCC | 20 | 9200 |
| BCL11A-7535 | + | CACUUCCCGUGCCGCUGCGCC | 21 | 9201 |
| BCL11A-7536 | + | CCACUUCCCGUGCCGCUGCGCC | 22 | 9202 |
| BCL11A-7537 | + | UCCACUUCCCGUGCCGCUGCGCC | 23 | 9203 |
| BCL11A-7538 | + | CUCCACUUCCCGUGCCGCUGCGCC | 24 | 9204 |
| BCL11A-7539 | + | CCCCGAGGCCGACUCGCC | 18 | 9205 |
| BCL11A-7540 | + | CCCCCGAGGCCGACUCGCC | 19 | 9206 |
| BCL11A-5989 | + | CCCCCCGAGGCCGACUCGCC | 20 | 9207 |
| BCL11A-7541 | + | GCCCCCCGAGGCCGACUCGCC | 21 | 9208 |
| BCL11A-7542 | + | GGCCCCCCGAGGCCGACUCGCC | 22 | 9209 |
| BCL11A-7543 | + | AGGCCCCCCGAGGCCGACUCGCC | 23 | 9210 |
| BCL11A-7544 | + | CAGGCCCCCCGAGGCCGACUCGCC | 24 | 9211 |
| BCL11A-7545 | + | GCGCUUAUGCUUCUCGCC | 18 | 9212 |
| BCL11A-7546 | + | CGCGCUUAUGCUUCUCGCC | 19 | 9213 |
| BCL11A-7547 | + | CCGCGCUUAUGCUUCUCGCC | 20 | 9214 |
| BCL11A-7548 | + | GCCGCGCUUAUGCUUCUCGCC | 21 | 9215 |
| BCL11A-7549 | + | GGCCGCGCUUAUGCUUCUCGCC | 22 | 9216 |
| BCL11A-7550 | + | UGGCCGCGCUUAUGCUUCUCGCC | 23 | 9217 |

TABLE 16E-continued

5th Tier

| gRNA Name | DNA Strand | Targeting Domain | Target Site Length | SEQ ID NO: |
|---|---|---|---|---|
| BCL11A-7551 | + | GUGGCCGCGCUUAUGCUUCUCGCC | 24 | 9218 |
| BCL11A-7552 | + | GGGAGGGGGGCGUCGCC | 18 | 9219 |
| BCL11A-7553 | + | AGGGAGGGGGGCGUCGCC | 19 | 9220 |
| BCL11A-5990 | + | GAGGGAGGGGGGCGUCGCC | 20 | 9221 |
| BCL11A-7554 | + | GGAGGGAGGGGGGCGUCGCC | 21 | 9222 |
| BCL11A-7555 | + | AGGAGGGAGGGGGGCGUCGCC | 22 | 9223 |
| BCL11A-7556 | + | GAGGAGGGAGGGGGGCGUCGCC | 23 | 9224 |
| BCL11A-7557 | + | AGAGGAGGGAGGGGGGCGUCGCC | 24 | 9225 |
| BCL11A-7558 | + | CAUAGGGCUGGGCCGGCC | 18 | 9226 |
| BCL11A-7559 | + | GCAUAGGGCUGGGCCGGCC | 19 | 9227 |
| BCL11A-5991 | + | UGCAUAGGGCUGGGCCGGCC | 20 | 9228 |
| BCL11A-7560 | + | UUGCAUAGGGCUGGGCCGGCC | 21 | 9229 |
| BCL11A-7561 | + | UUUGCAUAGGGCUGGGCCGGCC | 22 | 9230 |
| BCL11A-7562 | + | CUUUGCAUAGGGCUGGGCCGGCC | 23 | 9231 |
| BCL11A-7563 | + | CCUUUGCAUAGGGCUGGGCCGGCC | 24 | 9232 |
| BCL11A-7564 | + | GUGUUGGGCAUCGCGGCC | 18 | 9233 |
| BCL11A-7565 | + | CGUGUUGGGCAUCGCGGCC | 19 | 9234 |
| BCL11A-5993 | + | CCGUGUUGGGCAUCGCGGCC | 20 | 9235 |
| BCL11A-7566 | + | UCCGUGUUGGGCAUCGCGGCC | 21 | 9236 |
| BCL11A-7567 | + | CUCCGUGUUGGGCAUCGCGGCC | 22 | 9237 |
| BCL11A-7568 | + | UCUCCGUGUUGGGCAUCGCGGCC | 23 | 9238 |
| BCL11A-7569 | + | UUCUCCGUGUUGGGCAUCGCGGCC | 24 | 9239 |
| BCL11A-7570 | + | AGGGAUCUUUGAGCUGCC | 18 | 9240 |
| BCL11A-7571 | + | AAGGGAUCUUUGAGCUGCC | 19 | 9241 |
| BCL11A-6000 | + | GAAGGGAUCUUUGAGCUGCC | 20 | 9242 |
| BCL11A-7572 | + | GGAAGGGAUCUUUGAGCUGCC | 21 | 9243 |
| BCL11A-7573 | + | AGGAAGGGAUCUUUGAGCUGCC | 22 | 9244 |
| BCL11A-7574 | + | AAGGAAGGGAUCUUUGAGCUGCC | 23 | 9245 |
| BCL11A-7575 | + | UAAGGAAGGGAUCUUUGAGCUGCC | 24 | 9246 |
| BCL11A-7576 | + | AUCCCUCCGUCCAGCUCC | 18 | 9247 |
| BCL11A-7577 | + | GAUCCCUCCGUCCAGCUCC | 19 | 9248 |
| BCL11A-7578 | + | AGAUCCCUCCGUCCAGCUCC | 20 | 9249 |
| BCL11A-7579 | + | GAGAUCCCUCCGUCCAGCUCC | 21 | 9250 |
| BCL11A-7580 | + | CGAGAUCCCUCCGUCCAGCUCC | 22 | 9251 |
| BCL11A-7581 | + | CCGAGAUCCCUCCGUCCAGCUCC | 23 | 9252 |
| BCL11A-7582 | + | CCCGAGAUCCCUCCGUCCAGCUCC | 24 | 9253 |
| BCL11A-7583 | + | CCAGCUCUCUAAGUCCC | 18 | 9254 |
| BCL11A-7584 | + | GCCAGCUCUCUAAGUCUCC | 19 | 9255 |

TABLE 16E-continued

5th Tier

| gRNA Name | DNA Strand | Targeting Domain | Target Site Length | SEQ ID NO: |
|---|---|---|---|---|
| BCL11A-7585 | + | UGCCAGCUCUCUAAGUCUCC | 20 | 9256 |
| BCL11A-7586 | + | CUGCCAGCUCUCUAAGUCUCC | 21 | 9257 |
| BCL11A-7587 | + | CCUGCCAGCUCUCUAAGUCUCC | 22 | 9258 |
| BCL11A-7588 | + | CCCUGCCAGCUCUCUAAGUCUCC | 23 | 9259 |
| BCL11A-7589 | + | UCCCUGCCAGCUCUCUAAGUCUCC | 24 | 9260 |
| BCL11A-7590 | + | CGCAAACUCCCGUUCUCC | 18 | 9261 |
| BCL11A-7591 | + | GCGCAAACUCCCGUUCUCC | 19 | 9262 |
| BCL11A-7592 | + | AGCGCAAACUCCCGUUCUCC | 20 | 9263 |
| BCL11A-7593 | + | AAGCGCAAACUCCCGUUCUCC | 21 | 9264 |
| BCL11A-7594 | + | GAAGCGCAAACUCCCGUUCUCC | 22 | 9265 |
| BCL11A-7595 | + | AGAAGCGCAAACUCCCGUUCUCC | 23 | 9266 |
| BCL11A-7596 | + | GAGAAGCGCAAACUCCCGUUCUCC | 24 | 9267 |
| BCL11A-7597 | + | UCGCUGGUGCCGGGUUCC | 18 | 9268 |
| BCL11A-7598 | + | GUCGCUGGUGCCGGGUUCC | 19 | 9269 |
| BCL11A-6011 | + | AGUCGCUGGUGCCGGGUUCC | 20 | 9270 |
| BCL11A-7599 | + | AAGUCGCUGGUGCCGGGUUCC | 21 | 9271 |
| BCL11A-7600 | + | CAAGUCGCUGGUGCCGGGUUCC | 22 | 9272 |
| BCL11A-7601 | + | CCAAGUCGCUGGUGCCGGGUUCC | 23 | 9273 |
| BCL11A-7602 | + | ACCAAGUCGCUGGUGCCGGGUUCC | 24 | 9274 |
| BCL11A-7603 | + | GCCGCCUCCAGGCUCAGC | 18 | 9275 |
| BCL11A-7604 | + | CGCCGCCUCCAGGCUCAGC | 19 | 9276 |
| BCL11A-7605 | + | GCGCCGCCUCCAGGCUCAGC | 20 | 9277 |
| BCL11A-7606 | + | CGCGCCGCCUCCAGGCUCAGC | 21 | 9278 |
| BCL11A-7607 | + | GCGCGCCGCCUCCAGGCUCAGC | 22 | 9279 |
| BCL11A-7608 | + | GGCGCGCCGCCUCCAGGCUCAGC | 23 | 9280 |
| BCL11A-7609 | + | UGGCGCGCCGCCUCCAGGCUCAGC | 24 | 9281 |
| BCL11A-7610 | + | AGAAGGGGCUCAGCGAGC | 18 | 9282 |
| BCL11A-7611 | + | GAGAAGGGGCUCAGCGAGC | 19 | 9283 |
| BCL11A-6013 | + | AGAGAAGGGGCUCAGCGAGC | 20 | 9284 |
| BCL11A-7612 | + | UAGAGAAGGGGCUCAGCGAGC | 21 | 9285 |
| BCL11A-7613 | + | UUAGAGAAGGGGCUCAGCGAGC | 22 | 9286 |
| BCL11A-7614 | + | CUUAGAGAAGGGGCUCAGCGAGC | 23 | 9287 |
| BCL11A-7615 | + | GCUUAGAGAAGGGGCUCAGCGAGC | 24 | 9288 |
| BCL11A-7616 | + | CCCCCGAGGCCGACUCGC | 18 | 9289 |
| BCL11A-7617 | + | CCCCCCGAGGCCGACUCGC | 19 | 9290 |
| BCL11A-7618 | + | GCCCCCCGAGGCCGACUCGC | 20 | 9291 |
| BCL11A-7619 | + | GGCCCCCCGAGGCCGACUCGC | 21 | 9292 |

TABLE 16E-continued

5th Tier

| gRNA Name | DNA Strand | Targeting Domain | Target Site Length | SEQ ID NO: |
|---|---|---|---|---|
| BCL11A-7620 | + | AGGCCCCCCGAGGCCGACUCGC | 22 | 9293 |
| BCL11A-7621 | + | CAGGCCCCCCGAGGCCGACUCGC | 23 | 9294 |
| BCL11A-7622 | + | ACAGGCCCCCCGAGGCCGACUCGC | 24 | 9295 |
| BCL11A-7623 | + | AGGGAGGGGGGGCGUCGC | 18 | 9296 |
| BCL11A-7624 | + | GAGGGAGGGGGGGCGUCGC | 19 | 9297 |
| BCL11A-7625 | + | GGAGGGAGGGGGGGCGUCGC | 20 | 9298 |
| BCL11A-7626 | + | AGGAGGGAGGGGGGGCGUCGC | 21 | 9299 |
| BCL11A-7627 | + | GAGGAGGGAGGGGGGGCGUCGC | 22 | 9300 |
| BCL11A-7628 | + | AGAGGAGGGAGGGGGGGCGUCGC | 23 | 9301 |
| BCL11A-7629 | + | CAGAGGAGGGAGGGGGGGCGUCGC | 24 | 9302 |
| BCL11A-7630 | + | AGCGCCCUUCUGCCAGGC | 18 | 9303 |
| BCL11A-7631 | + | AAGCGCCCUUCUGCCAGGC | 19 | 9304 |
| BCL11A-6027 | + | AAAGCGCCCUUCUGCCAGGC | 20 | 9305 |
| BCL11A-7632 | + | GAAAGCGCCCUUCUGCCAGGC | 21 | 9306 |
| BCL11A-7633 | + | GGAAAGCGCCCUUCUGCCAGGC | 22 | 9307 |
| BCL11A-7634 | + | UGGAAAGCGCCCUUCUGCCAGGC | 23 | 9308 |
| BCL11A-7635 | + | GUGGAAAGCGCCCUUCUGCCAGGC | 24 | 9309 |
| BCL11A-7636 | + | GCAUAGGGCUGGGCCGGC | 18 | 9310 |
| BCL11A-7637 | + | UGCAUAGGGCUGGGCCGGC | 19 | 9311 |
| BCL11A-7638 | + | UUGCAUAGGGCUGGGCCGGC | 20 | 9312 |
| BCL11A-7639 | + | UUUGCAUAGGGCUGGGCCGGC | 21 | 9313 |
| BCL11A-7640 | + | CUUUGCAUAGGGCUGGGCCGGC | 22 | 9314 |
| BCL11A-7641 | + | CCUUUGCAUAGGGCUGGGCCGGC | 23 | 9315 |
| BCL11A-7642 | + | ACCUUUGCAUAGGGCUGGGCCGGC | 24 | 9316 |
| BCL11A-7643 | + | CGUGUUGGGCAUCGCGGC | 18 | 9317 |
| BCL11A-7644 | + | CCGUGUUGGGCAUCGCGGC | 19 | 9318 |
| BCL11A-6028 | + | UCCGUGUUGGGCAUCGCGGC | 20 | 9319 |
| BCL11A-7645 | + | CUCCGUGUUGGGCAUCGCGGC | 21 | 9320 |
| BCL11A-7646 | + | UCUCCGUGUUGGGCAUCGCGGC | 22 | 9321 |
| BCL11A-7647 | + | UUCUCCGUGUUGGGCAUCGCGGC | 23 | 9322 |
| BCL11A-7648 | + | GUUCUCCGUGUUGGGCAUCGCGGC | 24 | 9323 |
| BCL11A-7649 | + | AGCUGGGCCUGCCCGGGC | 18 | 9324 |
| BCL11A-7650 | + | GAGCUGGGCCUGCCCGGGC | 19 | 9325 |
| BCL11A-7651 | + | UGAGCUGGGCCUGCCCGGGC | 20 | 9326 |
| BCL11A-7652 | + | UUGAGCUGGGCCUGCCCGGGC | 21 | 9327 |
| BCL11A-7653 | + | UUUGAGCUGGGCCUGCCCGGGC | 22 | 9328 |
| BCL11A-7654 | + | UUUUGAGCUGGGCCUGCCCGGGC | 23 | 9329 |
| BCL11A-7655 | + | CUUUUGAGCUGGGCCUGCCCGGGC | 24 | 9330 |

TABLE 16E-continued

5th Tier

| gRNA Name | DNA Strand | Targeting Domain | Target Site Length | SEQ ID NO: |
|---|---|---|---|---|
| BCL11A-7656 | + | UUGGACUUGACCGGGGC | 18 | 9331 |
| BCL11A-7657 | + | CUUGGACUUGACCGGGGC | 19 | 9332 |
| BCL11A-6032 | + | ACUUGGACUUGACCGGGGC | 20 | 9333 |
| BCL11A-7658 | + | GACUUGGACUUGACCGGGGC | 21 | 9334 |
| BCL11A-7659 | + | UGACUUGGACUUGACCGGGGC | 22 | 9335 |
| BCL11A-7660 | + | AUGACUUGGACUUGACCGGGGC | 23 | 9336 |
| BCL11A-7661 | + | CAUGACUUGGACUUGACCGGGGC | 24 | 9337 |
| BCL11A-7662 | + | CCUAGAGAAAUCCAUGGC | 18 | 9338 |
| BCL11A-7663 | + | UCCUAGAGAAAUCCAUGGC | 19 | 9339 |
| BCL11A-6035 | + | CUCCUAGAGAAAUCCAUGGC | 20 | 9340 |
| BCL11A-7664 | + | UCUCCUAGAGAAAUCCAUGGC | 21 | 9341 |
| BCL11A-7665 | + | GUCUCCUAGAGAAAUCCAUGGC | 22 | 9342 |
| BCL11A-7666 | + | AGUCUCCUAGAGAAAUCCAUGGC | 23 | 9343 |
| BCL11A-7667 | + | AAGUCUCCUAGAGAAAUCCAUGGC | 24 | 9344 |
| BCL11A-7668 | + | AUCCCAUGGAGAGGUGGC | 18 | 9345 |
| BCL11A-7669 | + | AAUCCCAUGGAGAGGUGGC | 19 | 9346 |
| BCL11A-6038 | + | GAAUCCCAUGGAGAGGUGGC | 20 | 9347 |
| BCL11A-7670 | + | UGAAUCCCAUGGAGAGGUGGC | 21 | 9348 |
| BCL11A-7671 | + | AUGAAUCCCAUGGAGAGGUGGC | 22 | 9349 |
| BCL11A-7672 | + | UAUGAAUCCCAUGGAGAGGUGGC | 23 | 9350 |
| BCL11A-7673 | + | AUAUGAAUCCCAUGGAGAGGUGGC | 24 | 9351 |
| BCL11A-7674 | + | ACUCGGGUGAUGGGUGGC | 18 | 9352 |
| BCL11A-7675 | + | CACUCGGGUGAUGGGUGGC | 19 | 9353 |
| BCL11A-7676 | + | GCACUCGGGUGAUGGGUGGC | 20 | 9354 |
| BCL11A-7677 | + | GGCACUCGGGUGAUGGGUGGC | 21 | 9355 |
| BCL11A-7678 | + | AGGCACUCGGGUGAUGGGUGGC | 22 | 9356 |
| BCL11A-7679 | + | AAGGCACUCGGGUGAUGGGUGGC | 23 | 9357 |
| BCL11A-7680 | + | AAAGGCACUCGGGUGAUGGGUGGC | 24 | 9358 |
| BCL11A-7681 | + | CUUUUGAGCUGGGCCUGC | 18 | 9359 |
| BCL11A-7682 | + | UCUUUUGAGCUGGGCCUGC | 19 | 9360 |
| BCL11A-7683 | + | CUCUUUUGAGCUGGGCCUGC | 20 | 9361 |
| BCL11A-7684 | + | CCUCUUUUGAGCUGGGCCUGC | 21 | 9362 |
| BCL11A-7685 | + | CCCUCUUUUGAGCUGGGCCUGC | 22 | 9363 |
| BCL11A-7686 | + | GCCCUCUUUUGAGCUGGGCCUGC | 23 | 9364 |
| BCL11A-7687 | + | UGCCCUCUUUUGAGCUGGGCCUGC | 24 | 9365 |
| BCL11A-7688 | + | AAGGGAUCUUUGAGCUGC | 18 | 9366 |
| BCL11A-7689 | + | GAAGGGAUCUUUGAGCUGC | 19 | 9367 |

TABLE 16E-continued

5th Tier

| gRNA Name | DNA Strand | Targeting Domain | Target Site Length | SEQ ID NO: |
|---|---|---|---|---|
| BCL11A-7690 | + | GGAAGGGAUCUUUGAGCUGC | 20 | 9368 |
| BCL11A-7691 | + | AGGAAGGGAUCUUUGAGCUGC | 21 | 9369 |
| BCL11A-7692 | + | AAGGAAGGGAUCUUUGAGCUGC | 22 | 9370 |
| BCL11A-7693 | + | UAAGGAAGGGAUCUUUGAGCUGC | 23 | 9371 |
| BCL11A-7694 | + | CUAAGGAAGGGAUCUUUGAGCUGC | 24 | 9372 |
| BCL11A-7695 | + | GCCUCGCUGAAGUGCUGC | 18 | 9373 |
| BCL11A-7696 | + | GGCCUCGCUGAAGUGCUGC | 19 | 9374 |
| BCL11A-7697 | + | AGGCCUCGCUGAAGUGCUGC | 20 | 9375 |
| BCL11A-7698 | + | AAGGCCUCGCUGAAGUGCUGC | 21 | 9376 |
| BCL11A-7699 | + | GAAGGCCUCGCUGAAGUGCUGC | 22 | 9377 |
| BCL11A-7700 | + | GGAAGGCCUCGCUGAAGUGCUGC | 23 | 9378 |
| BCL11A-7701 | + | UGGAAGGCCUCGCUGAAGUGCUGC | 24 | 9379 |
| BCL11A-7702 | + | GUGUUCUGUGCGUGUUGC | 18 | 9380 |
| BCL11A-7703 | + | AGUGUUCUGUGCGUGUUGC | 19 | 9381 |
| BCL11A-7704 | + | GAGUGUUCUGUGCGUGUUGC | 20 | 9382 |
| BCL11A-7705 | + | UGAGUGUUCUGUGCGUGUUGC | 21 | 9383 |
| BCL11A-7706 | + | AUGAGUGUUCUGUGCGUGUUGC | 22 | 9384 |
| BCL11A-7707 | + | CAUGAGUGUUCUGUGCGUGUUGC | 23 | 9385 |
| BCL11A-7708 | + | CCAUGAGUGUUCUGUGCGUGUUGC | 24 | 9386 |
| BCL11A-7709 | + | CGAAAACUGCCACACAUC | 18 | 9387 |
| BCL11A-7710 | + | CCGAAAACUGCCACACAUC | 19 | 9388 |
| BCL11A-7711 | + | UCCGAAAACUGCCACACAUC | 20 | 9389 |
| BCL11A-7712 | + | AUCCGAAAACUGCCACACAUC | 21 | 9390 |
| BCL11A-7713 | + | CAUCCGAAAACUGCCACACAUC | 22 | 9391 |
| BCL11A-7714 | + | CCAUCCGAAAACUGCCACACAUC | 23 | 9392 |
| BCL11A-7715 | + | UCCAUCCGAAAACUGCCACACAUC | 24 | 9393 |
| BCL11A-7716 | + | UUGGGGUCGUUCUCGCUC | 18 | 9394 |
| BCL11A-7717 | + | GUUGGGGUCGUUCUCGCUC | 19 | 9395 |
| BCL11A-7718 | + | GGUUGGGGUCGUUCUCGCUC | 20 | 9396 |
| BCL11A-7719 | + | AGGUUGGGGUCGUUCUCGCUC | 21 | 9397 |
| BCL11A-7720 | + | CAGGUUGGGGUCGUUCUCGCUC | 22 | 9398 |
| BCL11A-7721 | + | UCAGGUUGGGGUCGUUCUCGCUC | 23 | 9399 |
| BCL11A-7722 | + | AUCAGGUUGGGGUCGUUCUCGCUC | 24 | 9400 |
| BCL11A-7723 | + | CUCAGAACUUAAGGGCUC | 18 | 9401 |
| BCL11A-7724 | + | UCUCAGAACUUAAGGGCUC | 19 | 9402 |
| BCL11A-7725 | + | UUCUCAGAACUUAAGGGCUC | 20 | 9403 |
| BCL11A-7726 | + | UUUCUCAGAACUUAAGGGCUC | 21 | 9404 |
| BCL11A-7727 | + | UUUUCUCAGAACUUAAGGGCUC | 22 | 9405 |

TABLE 16E-continued

5th Tier

| gRNA Name | DNA Strand | Targeting Domain | Target Site Length | SEQ ID NO: |
|---|---|---|---|---|
| BCL11A-7728 | + | AUUUUCUCAGAACUUAAGGGCUC | 23 | 9406 |
| BCL11A-7729 | + | AAUUUUCUCAGAACUUAAGGGCUC | 24 | 9407 |
| BCL11A-7730 | + | GACAUUCUGCACCUAGUC | 18 | 9408 |
| BCL11A-7731 | + | GGACAUUCUGCACCUAGUC | 19 | 9409 |
| BCL11A-7732 | + | AGGACAUUCUGCACCUAGUC | 20 | 9410 |
| BCL11A-7733 | + | AAGGACAUUCUGCACCUAGUC | 21 | 9411 |
| BCL11A-7734 | + | GAAGGACAUUCUGCACCUAGUC | 22 | 9412 |
| BCL11A-7735 | + | GGAAGGACAUUCUGCACCUAGUC | 23 | 9413 |
| BCL11A-7736 | + | GGGAAGGACAUUCUGCACCUAGUC | 24 | 9414 |
| BCL11A-7737 | + | UCGUCGGACUUGACCGUC | 18 | 9415 |
| BCL11A-7738 | + | GUCGUCGGACUUGACCGUC | 19 | 9416 |
| BCL11A-7739 | + | CGUCGUCGGACUUGACCGUC | 20 | 9417 |
| BCL11A-7740 | + | CCGUCGUCGGACUUGACCGUC | 21 | 9418 |
| BCL11A-7741 | + | ACCGUCGUCGGACUUGACCGUC | 22 | 9419 |
| BCL11A-7742 | + | GACCGUCGUCGGACUUGACCGUC | 23 | 9420 |
| BCL11A-7743 | + | AGACCGUCGUCGGACUUGACCGUC | 24 | 9421 |
| BCL11A-7744 | + | AUACCAACCCGCGGGUC | 18 | 9422 |
| BCL11A-7745 | + | GAUACCAACCCGCGGGUC | 19 | 9423 |
| BCL11A-6052 | + | GGAUACCAACCCGCGGGUC | 20 | 9424 |
| BCL11A-7746 | + | GGGAUACCAACCCGCGGGUC | 21 | 9425 |
| BCL11A-7747 | + | AGGGAUACCAACCCGCGGGUC | 22 | 9426 |
| BCL11A-7748 | + | AAGGGAUACCAACCCGCGGGUC | 23 | 9427 |
| BCL11A-7749 | + | GAAGGGAUACCAACCCGCGGGUC | 24 | 9428 |
| BCL11A-7750 | + | GGCAGGUCGAACUCCUUC | 18 | 9429 |
| BCL11A-7751 | + | GGGCAGGUCGAACUCCUUC | 19 | 9430 |
| BCL11A-7752 | + | GGGGCAGGUCGAACUCCUUC | 20 | 9431 |
| BCL11A-7753 | + | GGGGGCAGGUCGAACUCCUUC | 21 | 9432 |
| BCL11A-7754 | + | CGGGGGCAGGUCGAACUCCUUC | 22 | 9433 |
| BCL11A-7755 | + | CCGGGGGCAGGUCGAACUCCUUC | 23 | 9434 |
| BCL11A-7756 | + | GCCGGGGGCAGGUCGAACUCCUUC | 24 | 9435 |
| BCL11A-7757 | + | GUCGCUGGUGCCGGGUUC | 18 | 9436 |
| BCL11A-7758 | + | AGUCGCUGGUGCCGGGUUC | 19 | 9437 |
| BCL11A-6058 | + | AAGUCGCUGGUGCCGGGUUC | 20 | 9438 |
| BCL11A-7759 | + | CAAGUCGCUGGUGCCGGGUUC | 21 | 9439 |
| BCL11A-7760 | + | CCAAGUCGCUGGUGCCGGGUUC | 22 | 9440 |
| BCL11A-7761 | + | ACCAAGUCGCUGGUGCCGGGUUC | 23 | 9441 |
| BCL11A-7762 | + | CACCAAGUCGCUGGUGCCGGGUUC | 24 | 9442 |

TABLE 16E-continued

5th Tier

| gRNA Name | DNA Strand | Targeting Domain | Target Site Length | SEQ ID NO: |
|---|---|---|---|---|
| BCL11A-7763 | + | CGGUGGUGGACUAAACAG | 18 | 9443 |
| BCL11A-7764 | + | UCGGUGGUGGACUAAACAG | 19 | 9444 |
| BCL11A-6063 | + | CUCGGUGGUGGACUAAACAG | 20 | 9445 |
| BCL11A-7765 | + | UCUCGGUGGUGGACUAAACAG | 21 | 9446 |
| BCL11A-7766 | + | GUCUCGGUGGUGGACUAAACAG | 22 | 9447 |
| BCL11A-7767 | + | UGUCUCGGUGGUGGACUAAACAG | 23 | 9448 |
| BCL11A-7768 | + | AUGUCUCGGUGGUGGACUAAACAG | 24 | 9449 |
| BCL11A-7769 | + | GAAAGAGGUUGGAGACAG | 18 | 9450 |
| BCL11A-7770 | + | AGAAAGAGGUUGGAGACAG | 19 | 9451 |
| BCL11A-6064 | + | UAGAAAGAGGUUGGAGACAG | 20 | 9452 |
| BCL11A-7771 | + | CUAGAAAGAGGUUGGAGACAG | 21 | 9453 |
| BCL11A-7772 | + | CCUAGAAAGAGGUUGGAGACAG | 22 | 9454 |
| BCL11A-7773 | + | ACCUAGAAAGAGGUUGGAGACAG | 23 | 9455 |
| BCL11A-7774 | + | AACCUAGAAAGAGGUUGGAGACAG | 24 | 9456 |
| BCL11A-7775 | + | AGGAGGGGCGGAUUGCAG | 18 | 9457 |
| BCL11A-7776 | + | GAGGAGGGGCGGAUUGCAG | 19 | 9458 |
| BCL11A-6069 | + | GGAGGAGGGGCGGAUUGCAG | 20 | 9459 |
| BCL11A-7777 | + | GGGAGGAGGGGCGGAUUGCAG | 21 | 9460 |
| BCL11A-7778 | + | AGGGAGGAGGGGCGGAUUGCAG | 22 | 9461 |
| BCL11A-7779 | + | GAGGGAGGAGGGGCGGAUUGCAG | 23 | 9462 |
| BCL11A-7780 | + | GGAGGGAGGAGGGGCGGAUUGCAG | 24 | 9463 |
| BCL11A-7781 | + | AAGAGGUUGGAGACAGAG | 18 | 9464 |
| BCL11A-7782 | + | AAAGAGGUUGGAGACAGAG | 19 | 9465 |
| BCL11A-7783 | + | GAAAGAGGUUGGAGACAGAG | 20 | 9466 |
| BCL11A-7784 | + | AGAAAGAGGUUGGAGACAGAG | 21 | 9467 |
| BCL11A-7785 | + | UAGAAAGAGGUUGGAGACAGAG | 22 | 9468 |
| BCL11A-7786 | + | CUAGAAAGAGGUUGGAGACAGAG | 23 | 9469 |
| BCL11A-7787 | + | CCUAGAAAGAGGUUGGAGACAGAG | 24 | 9470 |
| BCL11A-7788 | + | GAGGGGCGGAUUGCAGAG | 18 | 9471 |
| BCL11A-7789 | + | GGAGGGGCGGAUUGCAGAG | 19 | 9472 |
| BCL11A-7790 | + | AGGAGGGGCGGAUUGCAGAG | 20 | 9473 |
| BCL11A-7791 | + | GAGGAGGGGCGGAUUGCAGAG | 21 | 9474 |
| BCL11A-7792 | + | GGAGGAGGGGCGGAUUGCAGAG | 22 | 9475 |
| BCL11A-7793 | + | GGGAGGAGGGGCGGAUUGCAGAG | 23 | 9476 |
| BCL11A-7794 | + | AGGGAGGAGGGGCGGAUUGCAGAG | 24 | 9477 |
| BCL11A-7795 | + | AGCUUGAUGCGCUUAGAG | 18 | 9478 |
| BCL11A-7796 | + | GAGCUUGAUGCGCUUAGAG | 19 | 9479 |
| BCL11A-7797 | + | CGAGCUUGAUGCGCUUAGAG | 20 | 9480 |

TABLE 16E-continued

5th Tier

| gRNA Name | DNA Strand | Targeting Domain | Target Site Length | SEQ ID NO: |
|---|---|---|---|---|
| BCL11A-7798 | + | UCGAGCUUGAUGCGCUUAGAG | 21 | 9481 |
| BCL11A-7799 | + | CUCGAGCUUGAUGCGCUUAGAG | 22 | 9482 |
| BCL11A-7800 | + | UCUCGAGCUUGAUGCGCUUAGAG | 23 | 9483 |
| BCL11A-7801 | + | UUCUCGAGCUUGAUGCGCUUAGAG | 24 | 9484 |
| BCL11A-7802 | + | GAGAAGGGGCUCAGCGAG | 18 | 9485 |
| BCL11A-7803 | + | AGAGAAGGGGCUCAGCGAG | 19 | 9486 |
| BCL11A-7804 | + | UAGAGAAGGGGCUCAGCGAG | 20 | 9487 |
| BCL11A-7805 | + | UUAGAGAAGGGGCUCAGCGAG | 21 | 9488 |
| BCL11A-7806 | + | CUUAGAGAAGGGGCUCAGCGAG | 22 | 9489 |
| BCL11A-7807 | + | GCUUAGAGAAGGGGCUCAGCGAG | 23 | 9490 |
| BCL11A-7808 | + | CGCUUAGAGAAGGGGCUCAGCGAG | 24 | 9491 |
| BCL11A-7809 | + | GGAUUGCAGAGGAGGGAG | 18 | 9492 |
| BCL11A-7810 | + | CGGAUUGCAGAGGAGGGAG | 19 | 9493 |
| BCL11A-6075 | + | GCGGAUUGCAGAGGAGGGAG | 20 | 9494 |
| BCL11A-7811 | + | GGCGGAUUGCAGAGGAGGGAG | 21 | 9495 |
| BCL11A-7812 | + | GGGCGGAUUGCAGAGGAGGGAG | 22 | 9496 |
| BCL11A-7813 | + | GGGGCGGAUUGCAGAGGAGGGAG | 23 | 9497 |
| BCL11A-7814 | + | AGGGGCGGAUUGCAGAGGAGGGAG | 24 | 9498 |
| BCL11A-7815 | + | CCGGGGGCUGGGAGGGAG | 18 | 9499 |
| BCL11A-7816 | + | ACCGGGGGCUGGGAGGGAG | 19 | 9500 |
| BCL11A-7817 | + | GACCGGGGGCUGGGAGGGAG | 20 | 9501 |
| BCL11A-7818 | + | UGACCGGGGGCUGGGAGGGAG | 21 | 9502 |
| BCL11A-7819 | + | UUGACCGGGGGCUGGGAGGGAG | 22 | 9503 |
| BCL11A-7820 | + | CUUGACCGGGGGCUGGGAGGGAG | 23 | 9504 |
| BCL11A-7821 | + | ACUUGACCGGGGGCUGGGAGGGAG | 24 | 9505 |
| BCL11A-7822 | + | CUGAAGUGCUGCAUGGAG | 18 | 9506 |
| BCL11A-7823 | + | GCUGAAGUGCUGCAUGGAG | 19 | 9507 |
| BCL11A-7824 | + | CGCUGAAGUGCUGCAUGGAG | 20 | 9508 |
| BCL11A-7825 | + | UCGCUGAAGUGCUGCAUGGAG | 21 | 9509 |
| BCL11A-7826 | + | CUCGCUGAAGUGCUGCAUGGAG | 22 | 9510 |
| BCL11A-7827 | + | CCUCGCUGAAGUGCUGCAUGGAG | 23 | 9511 |
| BCL11A-7828 | + | GCCUCGCUGAAGUGCUGCAUGGAG | 24 | 9512 |
| BCL11A-7829 | + | CGUCUGCCCUCUUUUGAG | 18 | 9513 |
| BCL11A-7830 | + | GCGUCUGCCCUCUUUUGAG | 19 | 9514 |
| BCL11A-7831 | + | UGCGUCUGCCCUCUUUUGAG | 20 | 9515 |
| BCL11A-7832 | + | CUGCGUCUGCCCUCUUUUGAG | 21 | 9516 |
| BCL11A-7833 | + | GCUGCGUCUGCCCUCUUUUGAG | 22 | 9517 |

TABLE 16E-continued

5th Tier

| gRNA Name | DNA Strand | Targeting Domain | Target Site Length | SEQ ID NO: |
|---|---|---|---|---|
| BCL11A-7834 | + | CGCUGCGUCUGCCCUCUUUUGAG | 23 | 9518 |
| BCL11A-7835 | + | UCGCUGCGUCUGCCCUCUUUUGAG | 24 | 9519 |
| BCL11A-7836 | + | CCGAGGAGUGCUCCGACG | 18 | 9520 |
| BCL11A-7837 | + | UCCGAGGAGUGCUCCGACG | 19 | 9521 |
| BCL11A-6080 | + | CUCCGAGGAGUGCUCCGACG | 20 | 9522 |
| BCL11A-7838 | + | UCUCCGAGGAGUGCUCCGACG | 21 | 9523 |
| BCL11A-7839 | + | UUCUCCGAGGAGUGCUCCGACG | 22 | 9524 |
| BCL11A-7840 | + | GUUCUCCGAGGAGUGCUCCGACG | 23 | 9525 |
| BCL11A-7841 | + | CGUUCUCCGAGGAGUGCUCCGACG | 24 | 9526 |
| BCL11A-7842 | + | ACCAUGCCCUGCAUGACG | 18 | 9527 |
| BCL11A-7843 | + | CACCAUGCCCUGCAUGACG | 19 | 9528 |
| BCL11A-7844 | + | GCACCAUGCCCUGCAUGACG | 20 | 9529 |
| BCL11A-7845 | + | AGCACCAUGCCCUGCAUGACG | 21 | 9530 |
| BCL11A-7846 | + | GAGCACCAUGCCCUGCAUGACG | 22 | 9531 |
| BCL11A-7847 | + | UGAGCACCAUGCCCUGCAUGACG | 23 | 9532 |
| BCL11A-7848 | + | CUGAGCACCAUGCCCUGCAUGACG | 24 | 9533 |
| BCL11A-7849 | + | CCGAGGCCGACUCGCCCG | 18 | 9534 |
| BCL11A-7850 | + | CCCGAGGCCGACUCGCCCG | 19 | 9535 |
| BCL11A-6088 | + | CCCCGAGGCCGACUCGCCCG | 20 | 9536 |
| BCL11A-7851 | + | CCCCCGAGGCCGACUCGCCCG | 21 | 9537 |
| BCL11A-7852 | + | CCCCCCGAGGCCGACUCGCCCG | 22 | 9538 |
| BCL11A-7853 | + | GCCCCCCGAGGCCGACUCGCCCG | 23 | 9539 |
| BCL11A-7854 | + | GGCCCCCCGAGGCCGACUCGCCCG | 24 | 9540 |
| BCL11A-7855 | + | CUGGAGGCCGCGUAGCCG | 18 | 9541 |
| BCL11A-7856 | + | CCUGGAGGCCGCGUAGCCG | 19 | 9542 |
| BCL11A-7857 | + | GCCUGGAGGCCGCGUAGCCG | 20 | 9543 |
| BCL11A-7858 | + | UGCCUGGAGGCCGCGUAGCCG | 21 | 9544 |
| BCL11A-7859 | + | CUGCCUGGAGGCCGCGUAGCCG | 22 | 9545 |
| BCL11A-7860 | + | GCUGCCUGGAGGCCGCGUAGCCG | 23 | 9546 |
| BCL11A-7861 | + | AGCUGCCUGGAGGCCGCGUAGCCG | 24 | 9547 |
| BCL11A-7862 | + | AAUUUGAACGUCUUGCCG | 18 | 9548 |
| BCL11A-7863 | + | AAAUUUGAACGUCUUGCCG | 19 | 9549 |
| BCL11A-7864 | + | GAAAUUUGAACGUCUUGCCG | 20 | 9550 |
| BCL11A-7865 | + | UGAAAUUUGAACGUCUUGCCG | 21 | 9551 |
| BCL11A-7866 | + | CUGAAAUUUGAACGUCUUGCCG | 22 | 9552 |
| BCL11A-7867 | + | UCUGAAAUUUGAACGUCUUGCCG | 23 | 9553 |
| BCL11A-7868 | + | CUCUGAAAUUUGAACGUCUUGCCG | 24 | 9554 |
| BCL11A-7869 | + | UCUCCGAGGAGUGCUCCG | 18 | 9555 |

TABLE 16E-continued

| | 5th Tier | | | |
|---|---|---|---|---|
| gRNA Name | DNA Strand | Targeting Domain | Target Site Length | SEQ ID NO: |
| BCL11A-7870 | + | UUCUCCGAGGAGUGCUCCG | 19 | 9556 |
| BCL11A-7871 | + | GUUCUCCGAGGAGUGCUCCG | 20 | 9557 |
| BCL11A-7872 | + | CGUUCUCCGAGGAGUGCUCCG | 21 | 9558 |
| BCL11A-7873 | + | CCGUUCUCCGAGGAGUGCUCCG | 22 | 9559 |
| BCL11A-7874 | + | CCCGUUCUCCGAGGAGUGCUCCG | 23 | 9560 |
| BCL11A-7875 | + | UCCCGUUCUCCGAGGAGUGCUCCG | 24 | 9561 |
| BCL11A-7876 | + | CGCUGGUGCCGGGUUCCG | 18 | 9562 |
| BCL11A-7877 | + | UCGCUGGUGCCGGGUUCCG | 19 | 9563 |
| BCL11A-6096 | + | GUCGCUGGUGCCGGGUUCCG | 20 | 9564 |
| BCL11A-7878 | + | AGUCGCUGGUGCCGGGUUCCG | 21 | 9565 |
| BCL11A-7879 | + | AAGUCGCUGGUGCCGGGUUCCG | 22 | 9566 |
| BCL11A-7880 | + | CAAGUCGCUGGUGCCGGGUUCCG | 23 | 9567 |
| BCL11A-7881 | + | CCAAGUCGCUGGUGCCGGGUUCCG | 24 | 9568 |
| BCL11A-7882 | + | GCCGGCCUGGGGACAGCG | 18 | 9569 |
| BCL11A-7883 | + | GGCCGGCCUGGGGACAGCG | 19 | 9570 |
| BCL11A-7884 | + | GGGCCGGCCUGGGGACAGCG | 20 | 9571 |
| BCL11A-7885 | + | UGGGCCGGCCUGGGGACAGCG | 21 | 9572 |
| BCL11A-7886 | + | CUGGGCCGGCCUGGGGACAGCG | 22 | 9573 |
| BCL11A-7887 | + | GCUGGGCCGGCCUGGGGACAGCG | 23 | 9574 |
| BCL11A-7888 | + | GGCUGGGCCGGCCUGGGGACAGCG | 24 | 9575 |
| BCL11A-7889 | + | GGUUCCGGGGAGCUGGCG | 18 | 9576 |
| BCL11A-7890 | + | GGGUUCCGGGGAGCUGGCG | 19 | 9577 |
| BCL11A-7891 | + | CGGGUUCCGGGGAGCUGGCG | 20 | 9578 |
| BCL11A-7892 | + | CCGGGUUCCGGGGAGCUGGCG | 21 | 9579 |
| BCL11A-7893 | + | GCCGGGUUCCGGGGAGCUGGCG | 22 | 9580 |
| BCL11A-7894 | + | UGCCGGGUUCCGGGGAGCUGGCG | 23 | 9581 |
| BCL11A-7895 | + | GUGCCGGGUUCCGGGGAGCUGGCG | 24 | 9582 |
| BCL11A-7896 | + | CCCCAGGCGCUCUAUGCG | 18 | 9583 |
| BCL11A-7897 | + | CCCCCAGGCGCUCUAUGCG | 19 | 9584 |
| BCL11A-7898 | + | GCCCCCAGGCGCUCUAUGCG | 20 | 9585 |
| BCL11A-7899 | + | CGCCCCCAGGCGCUCUAUGCG | 21 | 9586 |
| BCL11A-7900 | + | CCGCCCCCAGGCGCUCUAUGCG | 22 | 9587 |
| BCL11A-7901 | + | UCCGCCCCCAGGCGCUCUAUGCG | 23 | 9588 |
| BCL11A-7902 | + | UUCCGCCCCCAGGCGCUCUAUGCG | 24 | 9589 |
| BCL11A-7903 | + | ACCUGGUGGAAGGCCUCG | 18 | 9590 |
| BCL11A-7904 | + | GACCUGGUGGAAGGCCUCG | 19 | 9591 |
| BCL11A-7905 | + | GGACCUGGUGGAAGGCCUCG | 20 | 9592 |

TABLE 16E-continued

5th Tier

| gRNA Name | DNA Strand | Targeting Domain | Target Site Length | SEQ ID NO: |
|---|---|---|---|---|
| BCL11A-7906 | + | AGGACCUGGUGGAAGGCCUCG | 21 | 9593 |
| BCL11A-7907 | + | CAGGACCUGGUGGAAGGCCUCG | 22 | 9594 |
| BCL11A-7908 | + | CCAGGACCUGGUGGAAGGCCUCG | 23 | 9595 |
| BCL11A-7909 | + | CCCAGGACCUGGUGGAAGGCCUCG | 24 | 9596 |
| BCL11A-7910 | + | GCGGUGGAGAGACCGUCG | 18 | 9597 |
| BCL11A-7911 | + | GGCGGUGGAGAGACCGUCG | 19 | 9598 |
| BCL11A-7912 | + | UGGCGGUGGAGAGACCGUCG | 20 | 9599 |
| BCL11A-7913 | + | CUGGCGGUGGAGAGACCGUCG | 21 | 9600 |
| BCL11A-7914 | + | GCUGGCGGUGGAGAGACCGUCG | 22 | 9601 |
| BCL11A-7915 | + | AGCUGGCGGUGGAGAGACCGUCG | 23 | 9602 |
| BCL11A-7916 | + | GAGCUGGCGGUGGAGAGACCGUCG | 24 | 9603 |
| BCL11A-7917 | + | GAGUCUCCGAAGCUAAGG | 18 | 9604 |
| BCL11A-7918 | + | GGAGUCUCCGAAGCUAAGG | 19 | 9605 |
| BCL11A-7919 | + | UGGAGUCUCCGAAGCUAAGG | 20 | 9606 |
| BCL11A-7920 | + | CUGGAGUCUCCGAAGCUAAGG | 21 | 9607 |
| BCL11A-7921 | + | UCUGGAGUCUCCGAAGCUAAGG | 22 | 9608 |
| BCL11A-7922 | + | GUCUGGAGUCUCCGAAGCUAAGG | 23 | 9609 |
| BCL11A-7923 | + | UGUCUGGAGUCUCCGAAGCUAAGG | 24 | 9610 |
| BCL11A-7924 | + | GGUGGUGGACUAAACAGG | 18 | 9611 |
| BCL11A-7925 | + | CGGUGGUGGACUAAACAGG | 19 | 9612 |
| BCL11A-6111 | + | UCGGUGGUGGACUAAACAGG | 20 | 9613 |
| BCL11A-7926 | + | CUCGGUGGUGGACUAAACAGG | 21 | 9614 |
| BCL11A-7927 | + | UCUCGGUGGUGGACUAAACAGG | 22 | 9615 |
| BCL11A-7928 | + | GUCUCGGUGGUGGACUAAACAGG | 23 | 9616 |
| BCL11A-7929 | + | UGUCUCGGUGGUGGACUAAACAGG | 24 | 9617 |
| BCL11A-7930 | + | AGGGGGGGCGUCGCCAGG | 18 | 9618 |
| BCL11A-7931 | + | GAGGGGGGGCGUCGCCAGG | 19 | 9619 |
| BCL11A-7932 | + | GGAGGGGGGGCGUCGCCAGG | 20 | 9620 |
| BCL11A-7933 | + | GGGAGGGGGGGCGUCGCCAGG | 21 | 9621 |
| BCL11A-7934 | + | AGGGAGGGGGGGCGUCGCCAGG | 22 | 9622 |
| BCL11A-7935 | + | GAGGGAGGGGGGGCGUCGCCAGG | 23 | 9623 |
| BCL11A-7936 | + | GGAGGGAGGGGGGGCGUCGCCAGG | 24 | 9624 |
| BCL11A-7937 | + | AAGCGCCCUUCUGCCAGG | 18 | 9625 |
| BCL11A-7938 | + | AAAGCGCCCUUCUGCCAGG | 19 | 9626 |
| BCL11A-7939 | + | GAAAGCGCCCUUCUGCCAGG | 20 | 9627 |
| BCL11A-7940 | + | GGAAAGCGCCCUUCUGCCAGG | 21 | 9628 |
| BCL11A-7941 | + | UGGAAAGCGCCCUUCUGCCAGG | 22 | 9629 |
| BCL11A-7942 | + | GUGGAAAGCGCCCUUCUGCCAGG | 23 | 9630 |

TABLE 16E-continued

5th Tier

| gRNA Name | DNA Strand | Targeting Domain | Target Site Length | SEQ ID NO: |
|---|---|---|---|---|
| BCL11A-7943 | + | GGUGGAAAGCGCCCUUCUGCCAGG | 24 | 9631 |
| BCL11A-7944 | + | AUCGCGGCCGGGGGCAGG | 18 | 9632 |
| BCL11A-7945 | + | CAUCGCGGCCGGGGGCAGG | 19 | 9633 |
| BCL11A-7946 | + | GCAUCGCGGCCGGGGGCAGG | 20 | 9634 |
| BCL11A-7947 | + | GGCAUCGCGGCCGGGGGCAGG | 21 | 9635 |
| BCL11A-7948 | + | GGGCAUCGCGGCCGGGGGCAGG | 22 | 9636 |
| BCL11A-7949 | + | UGGGCAUCGCGGCCGGGGGCAGG | 23 | 9637 |
| BCL11A-7950 | + | UUGGGCAUCGCGGCCGGGGGCAGG | 24 | 9638 |
| BCL11A-7951 | + | CCGUUCUCCGGGAUCAGG | 18 | 9639 |
| BCL11A-7952 | + | CCCGUUCUCCGGGAUCAGG | 19 | 9640 |
| BCL11A-7953 | + | CCCCGUUCUCCGGGAUCAGG | 20 | 9641 |
| BCL11A-7954 | + | UCCCCGUUCUCCGGGAUCAGG | 21 | 9642 |
| BCL11A-7955 | + | GUCCCCGUUCUCCGGGAUCAGG | 22 | 9643 |
| BCL11A-7956 | + | CGUCCCCGUUCUCCGGGAUCAGG | 23 | 9644 |
| BCL11A-7957 | + | UCGUCCCCGUUCUCCGGGAUCAGG | 24 | 9645 |
| BCL11A-7958 | + | GAAGAACCUAGAAAGAGG | 18 | 9646 |
| BCL11A-7959 | + | UGAAGAACCUAGAAAGAGG | 19 | 9647 |
| BCL11A-7960 | + | GUGAAGAACCUAGAAAGAGG | 20 | 9648 |
| BCL11A-7961 | + | UGUGAAGAACCUAGAAAGAGG | 21 | 9649 |
| BCL11A-7962 | + | GUGUGAAGAACCUAGAAAGAGG | 22 | 9650 |
| BCL11A-7963 | + | UGUGUGAAGAACCUAGAAAGAGG | 23 | 9651 |
| BCL11A-7964 | + | GUGUGUGAAGAACCUAGAAAGAGG | 24 | 9652 |
| BCL11A-7965 | + | AGAGGUUGGAGACAGAGG | 18 | 9653 |
| BCL11A-7966 | + | AAGAGGUUGGAGACAGAGG | 19 | 9654 |
| BCL11A-6113 | + | AAAGAGGUUGGAGACAGAGG | 20 | 9655 |
| BCL11A-7967 | + | GAAAGAGGUUGGAGACAGAGG | 21 | 9656 |
| BCL11A-7968 | + | AGAAAGAGGUUGGAGACAGAGG | 22 | 9657 |
| BCL11A-7969 | + | UAGAAAGAGGUUGGAGACAGAGG | 23 | 9658 |
| BCL11A-7970 | + | CUAGAAAGAGGUUGGAGACAGAGG | 24 | 9659 |
| BCL11A-7971 | + | AGGGGCGGAUUGCAGAGG | 18 | 9660 |
| BCL11A-7972 | + | GAGGGGCGGAUUGCAGAGG | 19 | 9661 |
| BCL11A-6114 | + | GGAGGGGCGGAUUGCAGAGG | 20 | 9662 |
| BCL11A-7973 | + | AGGAGGGGCGGAUUGCAGAGG | 21 | 9663 |
| BCL11A-7974 | + | GAGGAGGGGCGGAUUGCAGAGG | 22 | 9664 |
| BCL11A-7975 | + | GGAGGAGGGGCGGAUUGCAGAGG | 23 | 9665 |
| BCL11A-7976 | + | GGGAGGAGGGGCGGAUUGCAGAGG | 24 | 9666 |
| BCL11A-7977 | + | GGCGGAUUGCAGAGGAGG | 18 | 9667 |

TABLE 16E-continued

5th Tier

| gRNA Name | DNA Strand | Targeting Domain | Target Site Length | SEQ ID NO: |
|---|---|---|---|---|
| BCL11A-7978 | + | GGGCGGAUUGCAGAGGAGG | 19 | 9668 |
| BCL11A-7979 | + | GGGGCGGAUUGCAGAGGAGG | 20 | 9669 |
| BCL11A-7980 | + | AGGGGCGGAUUGCAGAGGAGG | 21 | 9670 |
| BCL11A-7981 | + | GAGGGGCGGAUUGCAGAGGAGG | 22 | 9671 |
| BCL11A-7982 | + | GGAGGGGCGGAUUGCAGAGGAGG | 23 | 9672 |
| BCL11A-7983 | + | AGGAGGGGCGGAUUGCAGAGGAGG | 24 | 9673 |
| BCL11A-7984 | + | GAUUGCAGAGGAGGGAGG | 18 | 9674 |
| BCL11A-7985 | + | GGAUUGCAGAGGAGGGAGG | 19 | 9675 |
| BCL11A-6118 | + | CGGAUUGCAGAGGAGGGAGG | 20 | 9676 |
| BCL11A-7986 | + | GCGGAUUGCAGAGGAGGGAGG | 21 | 9677 |
| BCL11A-7987 | + | GGCGGAUUGCAGAGGAGGGAGG | 22 | 9678 |
| BCL11A-7988 | + | GGGCGGAUUGCAGAGGAGGGAGG | 23 | 9679 |
| BCL11A-7989 | + | GGGGCGGAUUGCAGAGGAGGGAGG | 24 | 9680 |
| BCL11A-7990 | + | CGGGGGCUGGGAGGGAGG | 18 | 9681 |
| BCL11A-7991 | + | CCGGGGGCUGGGAGGGAGG | 19 | 9682 |
| BCL11A-6119 | + | ACCGGGGGCUGGGAGGGAGG | 20 | 9683 |
| BCL11A-7992 | + | GACCGGGGGCUGGGAGGGAGG | 21 | 9684 |
| BCL11A-7993 | + | UGACCGGGGGCUGGGAGGGAGG | 22 | 9685 |
| BCL11A-7994 | + | UUGACCGGGGGCUGGGAGGGAGG | 23 | 9686 |
| BCL11A-7995 | + | CUUGACCGGGGGCUGGGAGGGAGG | 24 | 9687 |
| BCL11A-7996 | + | UGACCGGGGGCUGGGAGG | 18 | 9688 |
| BCL11A-7997 | + | UUGACCGGGGGCUGGGAGG | 19 | 9689 |
| BCL11A-7998 | + | CUUGACCGGGGGCUGGGAGG | 20 | 9690 |
| BCL11A-7999 | + | ACUUGACCGGGGGCUGGGAGG | 21 | 9691 |
| BCL11A-8000 | + | GACUUGACCGGGGGCUGGGAGG | 22 | 9692 |
| BCL11A-8001 | + | GGACUUGACCGGGGGCUGGGAGG | 23 | 9693 |
| BCL11A-8002 | + | UGGACUUGACCGGGGGCUGGGAGG | 24 | 9694 |
| BCL11A-8003 | + | CCGUGUUGGGCAUCGCGG | 18 | 9695 |
| BCL11A-8004 | + | UCCGUGUUGGGCAUCGCGG | 19 | 9696 |
| BCL11A-8005 | + | CUCCGUGUUGGGCAUCGCGG | 20 | 9697 |
| BCL11A-8006 | + | UCUCCGUGUUGGGCAUCGCGG | 21 | 9698 |
| BCL11A-8007 | + | UUCUCCGUGUUGGGCAUCGCGG | 22 | 9699 |
| BCL11A-8008 | + | GUUCUCCGUGUUGGGCAUCGCGG | 23 | 9700 |
| BCL11A-8009 | + | CGUUCUCCGUGUUGGGCAUCGCGG | 24 | 9701 |
| BCL11A-8010 | + | GUUCCGGGGAGCUGGCGG | 18 | 9702 |
| BCL11A-8011 | + | GGUUCCGGGGAGCUGGCGG | 19 | 9703 |
| BCL11A-6125 | + | GGGUUCCGGGGAGCUGGCGG | 20 | 9704 |
| BCL11A-8012 | + | CGGGUUCCGGGGAGCUGGCGG | 21 | 9705 |

TABLE 16E-continued

5th Tier

| gRNA Name | DNA Strand | Targeting Domain | Target Site Length | SEQ ID NO: |
|---|---|---|---|---|
| BCL11A-8013 | + | CCGGGUUCCGGGGAGCUGGCGG | 22 | 9706 |
| BCL11A-8014 | + | GCCGGGUUCCGGGGAGCUGGCGG | 23 | 9707 |
| BCL11A-8015 | + | UGCCGGGUUCCGGGGAGCUGGCGG | 24 | 9708 |
| BCL11A-8016 | + | CCCAGGCGCUCUAUGCGG | 18 | 9709 |
| BCL11A-8017 | + | CCCCAGGCGCUCUAUGCGG | 19 | 9710 |
| BCL11A-6126 | + | CCCCCAGGCGCUCUAUGCGG | 20 | 9711 |
| BCL11A-8018 | + | GCCCCCAGGCGCUCUAUGCGG | 21 | 9712 |
| BCL11A-8019 | + | CGCCCCCAGGCGCUCUAUGCGG | 22 | 9713 |
| BCL11A-8020 | + | CCGCCCCCAGGCGCUCUAUGCGG | 23 | 9714 |
| BCL11A-8021 | + | UCCGCCCCCAGGCGCUCUAUGCGG | 24 | 9715 |
| BCL11A-8022 | + | GUGGUGGACUAAACAGGG | 18 | 9716 |
| BCL11A-8023 | + | GGUGGUGGACUAAACAGGG | 19 | 9717 |
| BCL11A-6131 | + | CGGUGGUGGACUAAACAGGG | 20 | 9718 |
| BCL11A-8024 | + | UCGGUGGUGGACUAAACAGGG | 21 | 9719 |
| BCL11A-8025 | + | CUCGGUGGUGGACUAAACAGGG | 22 | 9720 |
| BCL11A-8026 | + | UCUCGGUGGUGGACUAAACAGGG | 23 | 9721 |
| BCL11A-8027 | + | GUCUCGGUGGUGGACUAAACAGGG | 24 | 9722 |
| BCL11A-8028 | + | GCGGAUUGCAGAGGAGGG | 18 | 9723 |
| BCL11A-8029 | + | GGCGGAUUGCAGAGGAGGG | 19 | 9724 |
| BCL11A-6133 | + | GGGCGGAUUGCAGAGGAGGG | 20 | 9725 |
| BCL11A-8030 | + | GGGGCGGAUUGCAGAGGAGGG | 21 | 9726 |
| BCL11A-8031 | + | AGGGGCGGAUUGCAGAGGAGGG | 22 | 9727 |
| BCL11A-8032 | + | GAGGGGCGGAUUGCAGAGGAGGG | 23 | 9728 |
| BCL11A-8033 | + | GGAGGGGCGGAUUGCAGAGGAGGG | 24 | 9729 |
| BCL11A-8034 | + | GACCGGGGCUGGGAGGG | 18 | 9730 |
| BCL11A-8035 | + | UGACCGGGGCUGGGAGGG | 19 | 9731 |
| BCL11A-6135 | + | UUGACCGGGGCUGGGAGGG | 20 | 9732 |
| BCL11A-8036 | + | CUUGACCGGGGCUGGGAGGG | 21 | 9733 |
| BCL11A-8037 | + | ACUUGACCGGGGCUGGGAGGG | 22 | 9734 |
| BCL11A-8038 | + | GACUUGACCGGGGCUGGGAGGG | 23 | 9735 |
| BCL11A-8039 | + | GGACUUGACCGGGGCUGGGAGGG | 24 | 9736 |
| BCL11A-8040 | + | AGUAACCUUUGCAUAGGG | 18 | 9737 |
| BCL11A-8041 | + | CAGUAACCUUUGCAUAGGG | 19 | 9738 |
| BCL11A-8042 | + | GCAGUAACCUUUGCAUAGGG | 20 | 9739 |
| BCL11A-8043 | + | UGCAGUAACCUUUGCAUAGGG | 21 | 9740 |
| BCL11A-8044 | + | UUGCAGUAACCUUUGCAUAGGG | 22 | 9741 |
| BCL11A-8045 | + | GUUGCAGUAACCUUUGCAUAGGG | 23 | 9742 |

TABLE 16E-continued

5th Tier

| gRNA Name | DNA Strand | Targeting Domain | Target Site Length | SEQ ID NO: |
|---|---|---|---|---|
| BCL11A-8046 | + | GGUUGCAGUAACCUUUGCAUAGGG | 24 | 9743 |
| BCL11A-8047 | + | GCCCUGCAUGACGUCGGG | 18 | 9744 |
| BCL11A-8048 | + | UGCCCUGCAUGACGUCGGG | 19 | 9745 |
| BCL11A-8049 | + | AUGCCCUGCAUGACGUCGGG | 20 | 9746 |
| BCL11A-8050 | + | CAUGCCCUGCAUGACGUCGGG | 21 | 9747 |
| BCL11A-8051 | + | CCAUGCCCUGCAUGACGUCGGG | 22 | 9748 |
| BCL11A-8052 | + | ACCAUGCCCUGCAUGACGUCGGG | 23 | 9749 |
| BCL11A-8053 | + | CACCAUGCCCUGCAUGACGUCGGG | 24 | 9750 |
| BCL11A-8054 | + | CUUGGACUUGACCGGGGG | 18 | 9751 |
| BCL11A-8055 | + | ACUUGGACUUGACCGGGGG | 19 | 9752 |
| BCL11A-8056 | + | GACUUGGACUUGACCGGGGG | 20 | 9753 |
| BCL11A-8057 | + | UGACUUGGACUUGACCGGGGG | 21 | 9754 |
| BCL11A-8058 | + | AUGACUUGGACUUGACCGGGGG | 22 | 9755 |
| BCL11A-8059 | + | CAUGACUUGGACUUGACCGGGGG | 23 | 9756 |
| BCL11A-8060 | + | GCAUGACUUGGACUUGACCGGGGG | 24 | 9757 |
| BCL11A-8061 | + | ACUUGACCGGGGGCUGGG | 18 | 9758 |
| BCL11A-8062 | + | GACUUGACCGGGGGCUGGG | 19 | 9759 |
| BCL11A-6146 | + | GGACUUGACCGGGGGCUGGG | 20 | 9760 |
| BCL11A-8063 | + | UGGACUUGACCGGGGGCUGGG | 21 | 9761 |
| BCL11A-8064 | + | UUGGACUUGACCGGGGGCUGGG | 22 | 9762 |
| BCL11A-8065 | + | CUUGGACUUGACCGGGGGCUGGG | 23 | 9763 |
| BCL11A-8066 | + | ACUUGGACUUGACCGGGGGCUGGG | 24 | 9764 |
| BCL11A-8067 | + | CAUGGAGAGGUGGCUGGG | 18 | 9765 |
| BCL11A-8068 | + | CCAUGGAGAGGUGGCUGGG | 19 | 9766 |
| BCL11A-8069 | + | CCCAUGGAGAGGUGGCUGGG | 20 | 9767 |
| BCL11A-8070 | + | UCCCAUGGAGAGGUGGCUGGG | 21 | 9768 |
| BCL11A-8071 | + | AUCCCAUGGAGAGGUGGCUGGG | 22 | 9769 |
| BCL11A-8072 | + | AAUCCCAUGGAGAGGUGGCUGGG | 23 | 9770 |
| BCL11A-8073 | + | GAAUCCCAUGGAGAGGUGGCUGGG | 24 | 9771 |
| BCL11A-8074 | + | AAACAGGGGGGAGUGGG | 18 | 9772 |
| BCL11A-8075 | + | UAAACAGGGGGGAGUGGG | 19 | 9773 |
| BCL11A-6147 | + | CUAAACAGGGGGGAGUGGG | 20 | 9774 |
| BCL11A-8076 | + | ACUAAACAGGGGGGAGUGGG | 21 | 9775 |
| BCL11A-8077 | + | GACUAAACAGGGGGGAGUGGG | 22 | 9776 |
| BCL11A-8078 | + | GGACUAAACAGGGGGGAGUGGG | 23 | 9777 |
| BCL11A-8079 | + | UGGACUAAACAGGGGGGAGUGGG | 24 | 9778 |
| BCL11A-8080 | + | UCCUAGAGAAAUCCAUGG | 18 | 9779 |
| BCL11A-8081 | + | CUCCUAGAGAAAUCCAUGG | 19 | 9780 |

TABLE 16E-continued

5th Tier

| gRNA Name | DNA Strand | Targeting Domain | Target Site Length | SEQ ID NO: |
|---|---|---|---|---|
| BCL11A-6149 | + | UCUCCUAGAGAAAUCCAUGG | 20 | 9781 |
| BCL11A-8082 | + | GUCUCCUAGAGAAAUCCAUGG | 21 | 9782 |
| BCL11A-8083 | + | AGUCUCCUAGAGAAAUCCAUGG | 22 | 9783 |
| BCL11A-8084 | + | AAGUCUCCUAGAGAAAUCCAUGG | 23 | 9784 |
| BCL11A-8085 | + | UAAGUCUCCUAGAGAAAUCCAUGG | 24 | 9785 |
| BCL11A-8086 | + | UUCUCGCCCAGGACCUGG | 18 | 9786 |
| BCL11A-8087 | + | CUUCUCGCCCAGGACCUGG | 19 | 9787 |
| BCL11A-6152 | + | GCUUCUCGCCCAGGACCUGG | 20 | 9788 |
| BCL11A-8088 | + | UGCUUCUCGCCCAGGACCUGG | 21 | 9789 |
| BCL11A-8089 | + | AUGCUUCUCGCCCAGGACCUGG | 22 | 9790 |
| BCL11A-8090 | + | UAUGCUUCUCGCCCAGGACCUGG | 23 | 9791 |
| BCL11A-8091 | + | UUAUGCUUCUCGCCCAGGACCUGG | 24 | 9792 |
| BCL11A-8092 | + | GGGCGGCUUGCUACCUGG | 18 | 9793 |
| BCL11A-8093 | + | AGGGCGGCUUGCUACCUGG | 19 | 9794 |
| BCL11A-8094 | + | AAGGGCGGCUUGCUACCUGG | 20 | 9795 |
| BCL11A-8095 | + | GAAGGGCGGCUUGCUACCUGG | 21 | 9796 |
| BCL11A-8096 | + | GGAAGGGCGGCUUGCUACCUGG | 22 | 9797 |
| BCL11A-8097 | + | AGGAAGGGCGGCUUGCUACCUGG | 23 | 9798 |
| BCL11A-8098 | + | CAGGAAGGGCGGCUUGCUACCUGG | 24 | 9799 |
| BCL11A-8099 | + | GACUUGACCGGGGCUGG | 18 | 9800 |
| BCL11A-8100 | + | GGACUUGACCGGGGCUGG | 19 | 9801 |
| BCL11A-8101 | + | UGGACUUGACCGGGGCUGG | 20 | 9802 |
| BCL11A-8102 | + | UUGGACUUGACCGGGGCUGG | 21 | 9803 |
| BCL11A-8103 | + | CUUGGACUUGACCGGGGCUGG | 22 | 9804 |
| BCL11A-8104 | + | ACUUGGACUUGACCGGGGCUGG | 23 | 9805 |
| BCL11A-8105 | + | GACUUGGACUUGACCGGGGCUGG | 24 | 9806 |
| BCL11A-8106 | + | UAAACAGGGGGGAGUGG | 18 | 9807 |
| BCL11A-8107 | + | CUAAACAGGGGGGAGUGG | 19 | 9808 |
| BCL11A-8108 | + | ACUAAACAGGGGGGAGUGG | 20 | 9809 |
| BCL11A-8109 | + | GACUAAACAGGGGGGAGUGG | 21 | 9810 |
| BCL11A-8110 | + | GGACUAAACAGGGGGGAGUGG | 22 | 9811 |
| BCL11A-8111 | + | UGGACUAAACAGGGGGGAGUGG | 23 | 9812 |
| BCL11A-8112 | + | GUGGACUAAACAGGGGGGAGUGG | 24 | 9813 |
| BCL11A-8113 | + | AAUCCCAUGGAGAGGUGG | 18 | 9814 |
| BCL11A-8114 | + | GAAUCCCAUGGAGAGGUGG | 19 | 9815 |
| BCL11A-8115 | + | UGAAUCCCAUGGAGAGGUGG | 20 | 9816 |
| BCL11A-8116 | + | AUGAAUCCCAUGGAGAGGUGG | 21 | 9817 |

TABLE 16E-continued

5th Tier

| gRNA Name | DNA Strand | Targeting Domain | Target Site Length | SEQ ID NO: |
|---|---|---|---|---|
| BCL11A-8117 | + | UAUGAAUCCCAUGGAGAGGUGG | 22 | 9818 |
| BCL11A-8118 | + | AUAUGAAUCCCAUGGAGAGGUGG | 23 | 9819 |
| BCL11A-8119 | + | AAUAUGAAUCCCAUGGAGAGGUGG | 24 | 9820 |
| BCL11A-8120 | + | UGCAAUAUGAAUCCCAUG | 18 | 9821 |
| BCL11A-8121 | + | CUGCAAUAUGAAUCCCAUG | 19 | 9822 |
| BCL11A-8122 | + | UCUGCAAUAUGAAUCCCAUG | 20 | 9823 |
| BCL11A-8123 | + | GUCUGCAAUAUGAAUCCCAUG | 21 | 9824 |
| BCL11A-8124 | + | UGUCUGCAAUAUGAAUCCCAUG | 22 | 9825 |
| BCL11A-8125 | + | UUGUCUGCAAUAUGAAUCCCAUG | 23 | 9826 |
| BCL11A-8126 | + | AUUGUCUGCAAUAUGAAUCCCAUG | 24 | 9827 |
| BCL11A-8127 | + | CUCCUAGAGAAAUCCAUG | 18 | 9828 |
| BCL11A-8128 | + | UCUCCUAGAGAAAUCCAUG | 19 | 9829 |
| BCL11A-8129 | + | GUCUCCUAGAGAAAUCCAUG | 20 | 9830 |
| BCL11A-8130 | + | AGUCUCCUAGAGAAAUCCAUG | 21 | 9831 |
| BCL11A-8131 | + | AAGUCUCCUAGAGAAAUCCAUG | 22 | 9832 |
| BCL11A-8132 | + | UAAGUCUCCUAGAGAAAUCCAUG | 23 | 9833 |
| BCL11A-8133 | + | CUAAGUCUCCUAGAGAAAUCCAUG | 24 | 9834 |
| BCL11A-8134 | + | UCGGACUUGACCGUCAUG | 18 | 9835 |
| BCL11A-8135 | + | GUCGGACUUGACCGUCAUG | 19 | 9836 |
| BCL11A-6164 | + | CGUCGGACUUGACCGUCAUG | 20 | 9837 |
| BCL11A-8136 | + | UCGUCGGACUUGACCGUCAUG | 21 | 9838 |
| BCL11A-8137 | + | GUCGUCGGACUUGACCGUCAUG | 22 | 9839 |
| BCL11A-8138 | + | CGUCGUCGGACUUGACCGUCAUG | 23 | 9840 |
| BCL11A-8139 | + | CCGUCGUCGGACUUGACCGUCAUG | 24 | 9841 |
| BCL11A-8140 | + | CUUCUCGCCCAGGACCUG | 18 | 9842 |
| BCL11A-8141 | + | GCUUCUCGCCCAGGACCUG | 19 | 9843 |
| BCL11A-8142 | + | UGCUUCUCGCCCAGGACCUG | 20 | 9844 |
| BCL11A-8143 | + | AUGCUUCUCGCCCAGGACCUG | 21 | 9845 |
| BCL11A-8144 | + | UAUGCUUCUCGCCCAGGACCUG | 22 | 9846 |
| BCL11A-8145 | + | UUAUGCUUCUCGCCCAGGACCUG | 23 | 9847 |
| BCL11A-8146 | + | CUUAUGCUUCUCGCCCAGGACCUG | 24 | 9848 |
| BCL11A-8147 | + | AUUCUGCACCUAGUCCUG | 18 | 9849 |
| BCL11A-8148 | + | CAUUCUGCACCUAGUCCUG | 19 | 9850 |
| BCL11A-8149 | + | ACAUUCUGCACCUAGUCCUG | 20 | 9851 |
| BCL11A-8150 | + | GACAUUCUGCACCUAGUCCUG | 21 | 9852 |
| BCL11A-8151 | + | GGACAUUCUGCACCUAGUCCUG | 22 | 9853 |
| BCL11A-8152 | + | AGGACAUUCUGCACCUAGUCCUG | 23 | 9854 |
| BCL11A-8153 | + | AAGGACAUUCUGCACCUAGUCCUG | 24 | 9855 |

TABLE 16E-continued

| | | 5th Tier | | |
|---|---|---|---|---|
| gRNA Name | DNA Strand | Targeting Domain | Target Site Length | SEQ ID NO: |
| BCL11A-6537 | + | GUUGUACAUGUGUAGCUG | 18 | 9856 |
| BCL11A-6538 | + | AGUUGUACAUGUGUAGCUG | 19 | 9857 |
| BCL11A-6539 | + | AAGUUGUACAUGUGUAGCUG | 20 | 9858 |
| BCL11A-6540 | + | CAAGUUGUACAUGUGUAGCUG | 21 | 9859 |
| BCL11A-6541 | + | GCAAGUUGUACAUGUGUAGCUG | 22 | 9860 |
| BCL11A-6542 | + | UGCAAGUUGUACAUGUGUAGCUG | 23 | 9861 |
| BCL11A-6543 | + | UUGCAAGUUGUACAUGUGUAGCUG | 24 | 9862 |
| BCL11A-8154 | + | GAGUACACGUUCUCCGUG | 18 | 9863 |
| BCL11A-8155 | + | CGAGUACACGUUCUCCGUG | 19 | 9864 |
| BCL11A-8156 | + | GCGAGUACACGUUCUCCGUG | 20 | 9865 |
| BCL11A-8157 | + | UGCGAGUACACGUUCUCCGUG | 21 | 9866 |
| BCL11A-8158 | + | CUGCGAGUACACGUUCUCCGUG | 22 | 9867 |
| BCL11A-8159 | + | ACUGCGAGUACACGUUCUCCGUG | 23 | 9868 |
| BCL11A-8160 | + | CACUGCGAGUACACGUUCUCCGUG | 24 | 9869 |
| BCL11A-8161 | + | CCAGCUCCCCGGGCGGUG | 18 | 9870 |
| BCL11A-8162 | + | UCCAGCUCCCCGGGCGGUG | 19 | 9871 |
| BCL11A-6177 | + | GUCCAGCUCCCCGGGCGGUG | 20 | 9872 |
| BCL11A-8163 | + | CGUCCAGCUCCCCGGGCGGUG | 21 | 9873 |
| BCL11A-8164 | + | CCGUCCAGCUCCCCGGGCGGUG | 22 | 9874 |
| BCL11A-8165 | + | UCCGUCCAGCUCCCCGGGCGGUG | 23 | 9875 |
| BCL11A-8166 | + | CUCCGUCCAGCUCCCCGGGCGGUG | 24 | 9876 |
| BCL11A-8167 | + | UCCGGGGAGCUGGCGGUG | 18 | 9877 |
| BCL11A-8168 | + | UUCCGGGGAGCUGGCGGUG | 19 | 9878 |
| BCL11A-8169 | + | GUUCCGGGGAGCUGGCGGUG | 20 | 9879 |
| BCL11A-8170 | + | GGUUCCGGGGAGCUGGCGGUG | 21 | 9880 |
| BCL11A-8171 | + | GGGUUCCGGGGAGCUGGCGGUG | 22 | 9881 |
| BCL11A-8172 | + | CGGGUUCCGGGGAGCUGGCGGUG | 23 | 9882 |
| BCL11A-8173 | + | CCGGGUUCCGGGGAGCUGGCGGUG | 24 | 9883 |
| BCL11A-8174 | + | CCAAGUGAUGUCUCGGUG | 18 | 9884 |
| BCL11A-8175 | + | UCCAAGUGAUGUCUCGGUG | 19 | 9885 |
| BCL11A-8176 | + | GUCCAAGUGAUGUCUCGGUG | 20 | 9886 |
| BCL11A-8177 | + | GGUCCAAGUGAUGUCUCGGUG | 21 | 9887 |
| BCL11A-8178 | + | GGGUCCAAGUGAUGUCUCGGUG | 22 | 9888 |
| BCL11A-8179 | + | GGGGUCCAAGUGAUGUCUCGGUG | 23 | 9889 |
| BCL11A-8180 | + | GGGGGUCCAAGUGAUGUCUCGGUG | 24 | 9890 |
| BCL11A-8181 | + | AGCUCCCCGGGCGGUGUG | 18 | 9891 |
| BCL11A-8182 | + | CAGCUCCCCGGGCGGUGUG | 19 | 9892 |

TABLE 16E-continued

5th Tier

| gRNA Name | DNA Strand | Targeting Domain | Target Site Length | SEQ ID NO: |
|---|---|---|---|---|
| BCL11A-8183 | + | CCAGCUCCCCGGGCGGUGUG | 20 | 9893 |
| BCL11A-8184 | + | UCCAGCUCCCCGGGCGGUGUG | 21 | 9894 |
| BCL11A-8185 | + | GUCCAGCUCCCCGGGCGGUGUG | 22 | 9895 |
| BCL11A-8186 | + | CGUCCAGCUCCCCGGGCGGUGUG | 23 | 9896 |
| BCL11A-8187 | + | CCGUCCAGCUCCCCGGGCGGUGUG | 24 | 9897 |
| BCL11A-8188 | + | GCCGAAUGGGGUGUGUG | 18 | 9898 |
| BCL11A-8189 | + | CGCCGAAUGGGGUGUGUG | 19 | 9899 |
| BCL11A-8190 | + | ACGCCGAAUGGGGUGUGUG | 20 | 9900 |
| BCL11A-8191 | + | UACGCCGAAUGGGGUGUGUG | 21 | 9901 |
| BCL11A-8192 | + | CUACGCCGAAUGGGGUGUGUG | 22 | 9902 |
| BCL11A-8193 | + | ACUACGCCGAAUGGGGUGUGUG | 23 | 9903 |
| BCL11A-8194 | + | UACUACGCCGAAUGGGGUGUGUG | 24 | 9904 |
| BCL11A-8195 | + | GGGAGGAGGGGCGGAUUG | 18 | 9905 |
| BCL11A-8196 | + | AGGGAGGAGGGGCGGAUUG | 19 | 9906 |
| BCL11A-8197 | + | GAGGGAGGAGGGGCGGAUUG | 20 | 9907 |
| BCL11A-8198 | + | GGAGGGAGGAGGGGCGGAUUG | 21 | 9908 |
| BCL11A-8199 | + | GGGAGGGAGGAGGGGCGGAUUG | 22 | 9909 |
| BCL11A-8200 | + | UGGGAGGGAGGAGGGGCGGAUUG | 23 | 9910 |
| BCL11A-8201 | + | CUGGGAGGGAGGAGGGGCGGAUUG | 24 | 9911 |
| BCL11A-8202 | + | UCGCACAGGUUGCACUUG | 18 | 9912 |
| BCL11A-8203 | + | GUCGCACAGGUUGCACUUG | 19 | 9913 |
| BCL11A-8204 | + | GGUCGCACAGGUUGCACUUG | 20 | 9914 |
| BCL11A-8205 | + | UGGUCGCACAGGUUGCACUUG | 21 | 9915 |
| BCL11A-8206 | + | GUGGUCGCACAGGUUGCACUUG | 22 | 9916 |
| BCL11A-8207 | + | CGUGGUCGCACAGGUUGCACUUG | 23 | 9917 |
| BCL11A-8208 | + | GCGUGGUCGCACAGGUUGCACUUG | 24 | 9918 |
| BCL11A-8209 | + | ACCAGGUUGCUCUGAAAU | 18 | 9919 |
| BCL11A-8210 | + | CACCAGGUUGCUCUGAAAU | 19 | 9920 |
| BCL11A-8211 | + | CCACCAGGUUGCUCUGAAAU | 20 | 9921 |
| BCL11A-8212 | + | ACCACCAGGUUGCUCUGAAAU | 21 | 9922 |
| BCL11A-8213 | + | CACCACCAGGUUGCUCUGAAAU | 22 | 9923 |
| BCL11A-8214 | + | GCACCACCAGGUUGCUCUGAAAU | 23 | 9924 |
| BCL11A-8215 | + | UGCACCACCAGGUUGCUCUGAAAU | 24 | 9925 |
| BCL11A-8216 | + | CGGGCCCGGACCACUAAU | 18 | 9926 |
| BCL11A-8217 | + | CCGGGCCCGGACCACUAAU | 19 | 9927 |
| BCL11A-8218 | + | CCCGGGCCCGGACCACUAAU | 20 | 9928 |
| BCL11A-8219 | + | GCCCGGGCCCGGACCACUAAU | 21 | 9929 |
| BCL11A-8220 | + | UGCCCGGGCCCGGACCACUAAU | 22 | 9930 |

TABLE 16E-continued

5th Tier

| gRNA Name | DNA Strand | Targeting Domain | Target Site Length | SEQ ID NO: |
|---|---|---|---|---|
| BCL11A-8221 | + | CUGCCCGGGCCCGGACCACUAAU | 23 | 9931 |
| BCL11A-8222 | + | CCUGCCCGGGCCCGGACCACUAAU | 24 | 9932 |
| BCL11A-8223 | + | GGGCUCUCGAGCUUCCAU | 18 | 9933 |
| BCL11A-8224 | + | AGGGCUCUCGAGCUUCCAU | 19 | 9934 |
| BCL11A-8225 | + | AAGGGCUCUCGAGCUUCCAU | 20 | 9935 |
| BCL11A-8226 | + | UAAGGGCUCUCGAGCUUCCAU | 21 | 9936 |
| BCL11A-8227 | + | UUAAGGGCUCUCGAGCUUCCAU | 22 | 9937 |
| BCL11A-8228 | + | CUUAAGGGCUCUCGAGCUUCCAU | 23 | 9938 |
| BCL11A-8229 | + | ACUUAAGGGCUCUCGAGCUUCCAU | 24 | 9939 |
| BCL11A-8230 | + | GUCGGACUUGACCGUCAU | 18 | 9940 |
| BCL11A-8231 | + | CGUCGGACUUGACCGUCAU | 19 | 9941 |
| BCL11A-6186 | + | UCGUCGGACUUGACCGUCAU | 20 | 9942 |
| BCL11A-8232 | + | GUCGUCGGACUUGACCGUCAU | 21 | 9943 |
| BCL11A-8233 | + | CGUCGUCGGACUUGACCGUCAU | 22 | 9944 |
| BCL11A-8234 | + | CCGUCGUCGGACUUGACCGUCAU | 23 | 9945 |
| BCL11A-8235 | + | ACCGUCGUCGGACUUGACCGUCAU | 24 | 9946 |
| BCL11A-8236 | + | AUAGGGCUGGGCCGGCCU | 18 | 9947 |
| BCL11A-8237 | + | CAUAGGGCUGGGCCGGCCU | 19 | 9948 |
| BCL11A-6198 | + | GCAUAGGGCUGGGCCGGCCU | 20 | 9949 |
| BCL11A-8238 | + | UGCAUAGGGCUGGGCCGGCCU | 21 | 9950 |
| BCL11A-8239 | + | UUGCAUAGGGCUGGGCCGGCCU | 22 | 9951 |
| BCL11A-8240 | + | UUUGCAUAGGGCUGGGCCGGCCU | 23 | 9952 |
| BCL11A-8241 | + | CUUUGCAUAGGGCUGGGCCGGCCU | 24 | 9953 |
| BCL11A-8242 | + | UCUGGAGUCUCCGAAGCU | 18 | 9954 |
| BCL11A-8243 | + | GUCUGGAGUCUCCGAAGCU | 19 | 9955 |
| BCL11A-8244 | + | UGUCUGGAGUCUCCGAAGCU | 20 | 9956 |
| BCL11A-8245 | + | UUGUCUGGAGUCUCCGAAGCU | 21 | 9957 |
| BCL11A-8246 | + | AUUGUCUGGAGUCUCCGAAGCU | 22 | 9958 |
| BCL11A-8247 | + | GAUUGUCUGGAGUCUCCGAAGCU | 23 | 9959 |
| BCL11A-8248 | + | CGAUUGUCUGGAGUCUCCGAAGCU | 24 | 9960 |
| BCL11A-8249 | + | UCUCGAGCUUGAUGCGCU | 18 | 9961 |
| BCL11A-8250 | + | UUCUCGAGCUUGAUGCGCU | 19 | 9962 |
| BCL11A-8251 | + | CUUCUCGAGCUUGAUGCGCU | 20 | 9963 |
| BCL11A-8252 | + | CCUUCUCGAGCUUGAUGCGCU | 21 | 9964 |
| BCL11A-8253 | + | UCCUUCUCGAGCUUGAUGCGCU | 22 | 9965 |
| BCL11A-8254 | + | CUCCUUCUCGAGCUUGAUGCGCU | 23 | 9966 |
| BCL11A-8255 | + | ACUCCUUCUCGAGCUUGAUGCGCU | 24 | 9967 |

TABLE 16E-continued

5th Tier

| gRNA Name | DNA Strand | Targeting Domain | Target Site Length | SEQ ID NO: |
|---|---|---|---|---|
| BCL11A-8256 | + | UGGACUUGACCGGGGCU | 18 | 9968 |
| BCL11A-8257 | + | UUGGACUUGACCGGGGCU | 19 | 9969 |
| BCL11A-6207 | + | CUUGGACUUGACCGGGGCU | 20 | 9970 |
| BCL11A-8258 | + | ACUUGGACUUGACCGGGGCU | 21 | 9971 |
| BCL11A-8259 | + | GACUUGGACUUGACCGGGGCU | 22 | 9972 |
| BCL11A-8260 | + | UGACUUGGACUUGACCGGGGCU | 23 | 9973 |
| BCL11A-8261 | + | AUGACUUGGACUUGACCGGGGCU | 24 | 9974 |
| BCL11A-8262 | + | UCCCAUGGAGAGGUGGCU | 18 | 9975 |
| BCL11A-8263 | + | AUCCCAUGGAGAGGUGGCU | 19 | 9976 |
| BCL11A-6208 | + | AAUCCCAUGGAGAGGUGGCU | 20 | 9977 |
| BCL11A-8264 | + | GAAUCCCAUGGAGAGGUGGCU | 21 | 9978 |
| BCL11A-8265 | + | UGAAUCCCAUGGAGAGGUGGCU | 22 | 9979 |
| BCL11A-8266 | + | AUGAAUCCCAUGGAGAGGUGGCU | 23 | 9980 |
| BCL11A-8267 | + | UAUGAAUCCCAUGGAGAGGUGGCU | 24 | 9981 |
| BCL11A-8268 | + | GUGCACCACCAGGUUGCU | 18 | 9982 |
| BCL11A-8269 | + | GGUGCACCACCAGGUUGCU | 19 | 9983 |
| BCL11A-8270 | + | CGGUGCACCACCAGGUUGCU | 20 | 9984 |
| BCL11A-8271 | + | CCGGUGCACCACCAGGUUGCU | 21 | 9985 |
| BCL11A-8272 | + | GCCGGUGCACCACCAGGUUGCU | 22 | 9986 |
| BCL11A-8273 | + | CGCCGGUGCACCACCAGGUUGCU | 23 | 9987 |
| BCL11A-8274 | + | GCGCCGGUGCACCACCAGGUUGCU | 24 | 9988 |
| BCL11A-8275 | + | AAGCUAAGGAAGGGAUCU | 18 | 9989 |
| BCL11A-8276 | + | GAAGCUAAGGAAGGGAUCU | 19 | 9990 |
| BCL11A-8277 | + | CGAAGCUAAGGAAGGGAUCU | 20 | 9991 |
| BCL11A-8278 | + | CCGAAGCUAAGGAAGGGAUCU | 21 | 9992 |
| BCL11A-8279 | + | UCCGAAGCUAAGGAAGGGAUCU | 22 | 9993 |
| BCL11A-8280 | + | CUCCGAAGCUAAGGAAGGGAUCU | 23 | 9994 |
| BCL11A-8281 | + | UCUCCGAAGCUAAGGAAGGGAUCU | 24 | 9995 |
| BCL11A-8282 | + | GGCGAUUGUCUGGAGUCU | 18 | 9996 |
| BCL11A-8283 | + | AGGCGAUUGUCUGGAGUCU | 19 | 9997 |
| BCL11A-8284 | + | AAGGCGAUUGUCUGGAGUCU | 20 | 9998 |
| BCL11A-8285 | + | AAAGGCGAUUGUCUGGAGUCU | 21 | 9999 |
| BCL11A-8286 | + | AAAAGGCGAUUGUCUGGAGUCU | 22 | 10000 |
| BCL11A-8287 | + | CAAAAGGCGAUUGUCUGGAGUCU | 23 | 10001 |
| BCL11A-8288 | + | GCAAAAGGCGAUUGUCUGGAGUCU | 24 | 10002 |
| BCL11A-8289 | + | CCUCCUCGUCCCCGUUCU | 18 | 10003 |
| BCL11A-8290 | + | UCCUCCUCGUCCCCGUUCU | 19 | 10004 |
| BCL11A-8291 | + | UUCCUCCUCGUCCCCGUUCU | 20 | 10005 |

TABLE 16E-continued

5th Tier

| gRNA Name | DNA Strand | Targeting Domain | Target Site Length | SEQ ID NO: |
|---|---|---|---|---|
| BCL11A-8292 | + | CUUCCUCCUCGUCCCCGUUCU | 21 | 10006 |
| BCL11A-8293 | + | UCUUCCUCCUCGUCCCCGUUCU | 22 | 10007 |
| BCL11A-8294 | + | CUCUUCCUCCUCGUCCCCGUUCU | 23 | 10008 |
| BCL11A-8295 | + | CCUCUUCCUCCUCGUCCCCGUUCU | 24 | 10009 |
| BCL11A-8296 | + | AGCGCAAACUCCCGUUCU | 18 | 10010 |
| BCL11A-8297 | + | AAGCGCAAACUCCCGUUCU | 19 | 10011 |
| BCL11A-8298 | + | GAAGCGCAAACUCCCGUUCU | 20 | 10012 |
| BCL11A-8299 | + | AGAAGCGCAAACUCCCGUUCU | 21 | 10013 |
| BCL11A-8300 | + | GAGAAGCGCAAACUCCCGUUCU | 22 | 10014 |
| BCL11A-8301 | + | GGAGAAGCGCAAACUCCCGUUCU | 23 | 10015 |
| BCL11A-8302 | + | UGGAGAAGCGCAAACUCCCGUUCU | 24 | 10016 |
| BCL11A-8303 | + | GGGGGCUUCAAAUUUUCU | 18 | 10017 |
| BCL11A-8304 | + | UGGGGGCUUCAAAUUUUCU | 19 | 10018 |
| BCL11A-8305 | + | CUGGGGGCUUCAAAUUUUCU | 20 | 10019 |
| BCL11A-8306 | + | CCUGGGGGCUUCAAAUUUUCU | 21 | 10020 |
| BCL11A-8307 | + | CCCUGGGGGCUUCAAAUUUUCU | 22 | 10021 |
| BCL11A-8308 | + | CCCCUGGGGGCUUCAAAUUUUCU | 23 | 10022 |
| BCL11A-8309 | + | ACCCCUGGGGGCUUCAAAUUUUCU | 24 | 10023 |
| BCL11A-8310 | + | AAGAACCUAGAAAGAGGU | 18 | 10024 |
| BCL11A-8311 | + | GAAGAACCUAGAAAGAGGU | 19 | 10025 |
| BCL11A-6224 | + | UGAAGAACCUAGAAAGAGGU | 20 | 10026 |
| BCL11A-8312 | + | GUGAAGAACCUAGAAAGAGGU | 21 | 10027 |
| BCL11A-8313 | + | UGUGAAGAACCUAGAAAGAGGU | 22 | 10028 |
| BCL11A-8314 | + | GUGUGAAGAACCUAGAAAGAGGU | 23 | 10029 |
| BCL11A-8315 | + | UGUGUGAAGAACCUAGAAAGAGGU | 24 | 10030 |
| BCL11A-8316 | + | UCCAGCUCCCCGGGCGGU | 18 | 10031 |
| BCL11A-8317 | + | GUCCAGCUCCCCGGGCGGU | 19 | 10032 |
| BCL11A-8318 | + | CGUCCAGCUCCCCGGGCGGU | 20 | 10033 |
| BCL11A-8319 | + | CCGUCCAGCUCCCCGGGCGGU | 21 | 10034 |
| BCL11A-8320 | + | UCCGUCCAGCUCCCCGGGCGGU | 22 | 10035 |
| BCL11A-8321 | + | CUCCGUCCAGCUCCCCGGGCGGU | 23 | 10036 |
| BCL11A-8322 | + | CCUCCGUCCAGCUCCCCGGGCGGU | 24 | 10037 |
| BCL11A-8323 | + | GAUACCAACCCGCGGGGU | 18 | 10038 |
| BCL11A-8324 | + | GGAUACCAACCCGCGGGGU | 19 | 10039 |
| BCL11A-8325 | + | GGGAUACCAACCCGCGGGGU | 20 | 10040 |
| BCL11A-8326 | + | AGGGAUACCAACCCGCGGGGU | 21 | 10041 |
| BCL11A-8327 | + | AAGGGAUACCAACCCGCGGGGU | 22 | 10042 |

TABLE 16E-continued

5th Tier

| gRNA Name | DNA Strand | Targeting Domain | Target Site Length | SEQ ID NO: |
|---|---|---|---|---|
| BCL11A-8328 | + | GAAGGGAUACCAACCCGCGGGGU | 23 | 10043 |
| BCL11A-8329 | + | UGAAGGGAUACCAACCCGCGGGGU | 24 | 10044 |
| BCL11A-8330 | + | UACGCCGAAUGGGGGUGU | 18 | 10045 |
| BCL11A-8331 | + | CUACGCCGAAUGGGGGUGU | 19 | 10046 |
| BCL11A-8332 | + | ACUACGCCGAAUGGGGGUGU | 20 | 10047 |
| BCL11A-8333 | + | UACUACGCCGAAUGGGGGUGU | 21 | 10048 |
| BCL11A-8334 | + | GUACUACGCCGAAUGGGGGUGU | 22 | 10049 |
| BCL11A-8335 | + | GGUACUACGCCGAAUGGGGGUGU | 23 | 10050 |
| BCL11A-8336 | + | GGGUACUACGCCGAAUGGGGGUGU | 24 | 10051 |
| BCL11A-8337 | + | GAGGCAAAAGGCGAUUGU | 18 | 10052 |
| BCL11A-8338 | + | GGAGGCAAAAGGCGAUUGU | 19 | 10053 |
| BCL11A-8339 | + | AGGAGGCAAAAGGCGAUUGU | 20 | 10054 |
| BCL11A-8340 | + | GAGGAGGCAAAAGGCGAUUGU | 21 | 10055 |
| BCL11A-8341 | + | CGAGGAGGCAAAAGGCGAUUGU | 22 | 10056 |
| BCL11A-8342 | + | ACGAGGAGGCAAAAGGCGAUUGU | 23 | 10057 |
| BCL11A-8343 | + | GACGAGGAGGCAAAAGGCGAUUGU | 24 | 10058 |
| BCL11A-8344 | + | CAAAUUUCUCAGAACUU | 18 | 10059 |
| BCL11A-8345 | + | UCAAAUUUCUCAGAACUU | 19 | 10060 |
| BCL11A-8346 | + | UUCAAAUUUCUCAGAACUU | 20 | 10061 |
| BCL11A-8347 | + | CUUCAAAUUUCUCAGAACUU | 21 | 10062 |
| BCL11A-8348 | + | GCUUCAAAUUUCUCAGAACUU | 22 | 10063 |
| BCL11A-8349 | + | GGCUUCAAAUUUCUCAGAACUU | 23 | 10064 |
| BCL11A-8350 | + | GGGCUUCAAAUUUCUCAGAACUU | 24 | 10065 |
| BCL11A-8351 | + | CGCUGCGUCUGCCCUCUU | 18 | 10066 |
| BCL11A-8352 | + | UCGCUGCGUCUGCCCUCUU | 19 | 10067 |
| BCL11A-8353 | + | GUCGCUGCGUCUGCCCUCUU | 20 | 10068 |
| BCL11A-8354 | + | UGUCGCUGCGUCUGCCCUCUU | 21 | 10069 |
| BCL11A-8355 | + | GUGUCGCUGCGUCUGCCCUCUU | 22 | 10070 |
| BCL11A-8356 | + | AGUGUCGCUGCGUCUGCCCUCUU | 23 | 10071 |
| BCL11A-8357 | + | AAGUGUCGCUGCGUCUGCCCUCUU | 24 | 10072 |
| BCL11A-8358 | + | AGUCGCUGGUGCCGGGUU | 18 | 10073 |
| BCL11A-8359 | + | AAGUCGCUGGUGCCGGGUU | 19 | 10074 |
| BCL11A-8360 | + | CAAGUCGCUGGUGCCGGGUU | 20 | 10075 |
| BCL11A-8361 | + | CCAAGUCGCUGGUGCCGGGUU | 21 | 10076 |
| BCL11A-8362 | + | ACCAAGUCGCUGGUGCCGGGUU | 22 | 10077 |
| BCL11A-8363 | + | CACCAAGUCGCUGGUGCCGGGUU | 23 | 10078 |
| BCL11A-8364 | + | CCACCAAGUCGCUGGUGCCGGGUU | 24 | 10079 |
| BCL11A-8365 | + | CUGCCCAGCAGCAGCUUU | 18 | 10080 |

TABLE 16E-continued

5th Tier

| gRNA Name | DNA Strand | Targeting Domain | Target Site Length | SEQ ID NO: |
|---|---|---|---|---|
| BCL11A-8366 | + | GCUGCCCAGCAGCAGCUUU | 19 | 10081 |
| BCL11A-8367 | + | GGCUGCCCAGCAGCAGCUUU | 20 | 10082 |
| BCL11A-8368 | + | GGGCUGCCCAGCAGCAGCUUU | 21 | 10083 |
| BCL11A-8369 | + | GGGGCUGCCCAGCAGCAGCUUU | 22 | 10084 |
| BCL11A-8370 | + | UGGGGCUGCCCAGCAGCAGCUUU | 23 | 10085 |
| BCL11A-8371 | + | CUGGGGCUGCCCAGCAGCAGCUUU | 24 | 10086 |
| BCL11A-8372 | − | GGCAGGCCCAGCUCAAAA | 18 | 10087 |
| BCL11A-8373 | − | GGGCAGGCCCAGCUCAAAA | 19 | 10088 |
| BCL11A-8374 | − | CGGGCAGGCCCAGCUCAAAA | 20 | 10089 |
| BCL11A-8375 | − | CCGGGCAGGCCCAGCUCAAAA | 21 | 10090 |
| BCL11A-8376 | − | CCCGGGCAGGCCCAGCUCAAAA | 22 | 10091 |
| BCL11A-8377 | − | GCCCGGGCAGGCCCAGCUCAAAA | 23 | 10092 |
| BCL11A-8378 | − | GGCCCGGGCAGGCCCAGCUCAAAA | 24 | 10093 |
| BCL11A-8379 | − | UAAGAAUCUACUUAGAAA | 18 | 10094 |
| BCL11A-8380 | − | UUAAGAAUCUACUUAGAAA | 19 | 10095 |
| BCL11A-8381 | − | AUUAAGAAUCUACUUAGAAA | 20 | 10096 |
| BCL11A-8382 | − | GAUUAAGAAUCUACUUAGAAA | 21 | 10097 |
| BCL11A-8383 | − | GGAUUAAGAAUCUACUUAGAAA | 22 | 10098 |
| BCL11A-8384 | − | UGGAUUAAGAAUCUACUUAGAAA | 23 | 10099 |
| BCL11A-8385 | − | AUGGAUUAAGAAUCUACUUAGAAA | 24 | 10100 |
| BCL11A-8386 | − | CGGGCAGGCCCAGCUCAA | 18 | 10101 |
| BCL11A-8387 | − | CCGGGCAGGCCCAGCUCAA | 19 | 10102 |
| BCL11A-8388 | − | CCCGGGCAGGCCCAGCUCAA | 20 | 10103 |
| BCL11A-8389 | − | GCCCGGGCAGGCCCAGCUCAA | 21 | 10104 |
| BCL11A-8390 | − | GGCCCGGGCAGGCCCAGCUCAA | 22 | 10105 |
| BCL11A-8391 | − | GGGCCCGGGCAGGCCCAGCUCAA | 23 | 10106 |
| BCL11A-8392 | − | CGGGCCCGGGCAGGCCCAGCUCAA | 24 | 10107 |
| BCL11A-8393 | − | GACGAGGAAGAGGAAGAA | 18 | 10108 |
| BCL11A-8394 | − | CGACGAGGAAGAGGAAGAA | 19 | 10109 |
| BCL11A-3947 | − | ACGACGAGGAAGAGGAAGAA | 20 | 10110 |
| BCL11A-8395 | − | GACGACGAGGAAGAGGAAGAA | 21 | 10111 |
| BCL11A-8396 | − | GGACGACGAGGAAGAGGAAGAA | 22 | 10112 |
| BCL11A-8397 | − | AGGACGACGAGGAAGAGGAAGAA | 23 | 10113 |
| BCL11A-8398 | − | GAGGACGACGAGGAAGAGGAAGAA | 24 | 10114 |
| BCL11A-8399 | − | CAACCUGAUCCCGGAGAA | 18 | 10115 |
| BCL11A-8400 | − | CCAACCUGAUCCCGGAGAA | 19 | 10116 |
| BCL11A-5881 | − | CCCAACCUGAUCCCGGAGAA | 20 | 10117 |

TABLE 16E-continued

5th Tier

| gRNA Name | DNA Strand | Targeting Domain | Target Site Length | SEQ ID NO: |
|---|---|---|---|---|
| BCL11A-8401 | − | CCCCAACCUGAUCCCGGAGAA | 21 | 10118 |
| BCL11A-8402 | − | ACCCCAACCUGAUCCCGGAGAA | 22 | 10119 |
| BCL11A-8403 | − | GACCCCAACCUGAUCCCGGAGAA | 23 | 10120 |
| BCL11A-8404 | − | CGACCCCAACCUGAUCCCGGAGAA | 24 | 10121 |
| BCL11A-8405 | − | GGAGCACUCCUCGGAGAA | 18 | 10122 |
| BCL11A-8406 | − | CGGAGCACUCCUCGGAGAA | 19 | 10123 |
| BCL11A-5882 | − | UCGGAGCACUCCUCGGAGAA | 20 | 10124 |
| BCL11A-8407 | − | GUCGGAGCACUCCUCGGAGAA | 21 | 10125 |
| BCL11A-8408 | − | CGUCGGAGCACUCCUCGGAGAA | 22 | 10126 |
| BCL11A-8409 | − | UCGUCGGAGCACUCCUCGGAGAA | 23 | 10127 |
| BCL11A-8410 | − | CUCGUCGGAGCACUCCUCGGAGAA | 24 | 10128 |
| BCL11A-8411 | − | GAGGAGGACGACGAGGAA | 18 | 10129 |
| BCL11A-8412 | − | AGAGGAGGACGACGAGGAA | 19 | 10130 |
| BCL11A-3950 | − | AAGAGGAGGACGACGAGGAA | 20 | 10131 |
| BCL11A-8413 | − | GAAGAGGAGGACGACGAGGAA | 21 | 10132 |
| BCL11A-8414 | − | GGAAGAGGAGGACGACGAGGAA | 22 | 10133 |
| BCL11A-8415 | − | AGGAAGAGGAGGACGACGAGGAA | 23 | 10134 |
| BCL11A-8416 | − | GAGGAAGAGGAGGACGACGAGGAA | 24 | 10135 |
| BCL11A-8417 | − | GAGGAAGAAGAGGAGGAA | 18 | 10136 |
| BCL11A-8418 | − | AGAGGAAGAAGAGGAGGAA | 19 | 10137 |
| BCL11A-3962 | − | AAGAGGAAGAAGAGGAGGAA | 20 | 10138 |
| BCL11A-8419 | − | GAAGAGGAAGAAGAGGAGGAA | 21 | 10139 |
| BCL11A-8420 | − | GGAAGAGGAAGAAGAGGAGGAA | 22 | 10140 |
| BCL11A-8421 | − | AGGAAGAGGAAGAAGAGGAGGAA | 23 | 10141 |
| BCL11A-8422 | − | GAGGAAGAGGAAGAAGAGGAGGAA | 24 | 10142 |
| BCL11A-8423 | − | AACGGGGACGAGGAGGAA | 18 | 10143 |
| BCL11A-8424 | − | GAACGGGGACGAGGAGGAA | 19 | 10144 |
| BCL11A-3934 | − | AGAACGGGGACGAGGAGGAA | 20 | 10145 |
| BCL11A-8425 | − | GAGAACGGGGACGAGGAGGAA | 21 | 10146 |
| BCL11A-8426 | − | GGAGAACGGGGACGAGGAGGAA | 22 | 10147 |
| BCL11A-8427 | − | CGGAGAACGGGGACGAGGAGGAA | 23 | 10148 |
| BCL11A-8428 | − | CCGGAGAACGGGGACGAGGAGGAA | 24 | 10149 |
| BCL11A-8429 | − | GGCGCAGCGGCACGGGAA | 18 | 10150 |
| BCL11A-8430 | − | GGGCGCAGCGGCACGGGAA | 19 | 10151 |
| BCL11A-3857 | − | GGGGCGCAGCGGCACGGGAA | 20 | 10152 |
| BCL11A-8431 | − | CGGGGCGCAGCGGCACGGGAA | 21 | 10153 |
| BCL11A-8432 | − | UCGGGGCGCAGCGGCACGGGAA | 22 | 10154 |
| BCL11A-8433 | − | CUCGGGGCGCAGCGGCACGGGAA | 23 | 10155 |

TABLE 16E-continued

5th Tier

| gRNA Name | DNA Strand | Targeting Domain | Target Site Length | SEQ ID NO: |
|---|---|---|---|---|
| BCL11A-8434 | - | UCUCGGGGCGCAGCGGCACGGGAA | 24 | 10156 |
| BCL11A-8435 | - | CGGCCGCGAUGCCCAACA | 18 | 10157 |
| BCL11A-8436 | - | CCGGCCGCGAUGCCCAACA | 19 | 10158 |
| BCL11A-5893 | - | CCCGGCCGCGAUGCCCAACA | 20 | 10159 |
| BCL11A-8437 | - | CCCCGGCCGCGAUGCCCAACA | 21 | 10160 |
| BCL11A-8438 | - | CCCCCGGCCGCGAUGCCCAACA | 22 | 10161 |
| BCL11A-8439 | - | GCCCCCGGCCGCGAUGCCCAACA | 23 | 10162 |
| BCL11A-8440 | - | UGCCCCCGGCCGCGAUGCCCAACA | 24 | 10163 |
| BCL11A-8441 | - | CUACUUAGAAAGCGAACA | 18 | 10164 |
| BCL11A-8442 | - | UCUACUUAGAAAGCGAACA | 19 | 10165 |
| BCL11A-5894 | - | AUCUACUUAGAAAGCGAACA | 20 | 10166 |
| BCL11A-8443 | - | AAUCUACUUAGAAAGCGAACA | 21 | 10167 |
| BCL11A-8444 | - | GAAUCUACUUAGAAAGCGAACA | 22 | 10168 |
| BCL11A-8445 | - | AGAAUCUACUUAGAAAGCGAACA | 23 | 10169 |
| BCL11A-8446 | - | AAGAAUCUACUUAGAAAGCGAACA | 24 | 10170 |
| BCL11A-8447 | - | CCCCUGUUUAGUCCACCA | 18 | 10171 |
| BCL11A-8448 | - | CCCCCUGUUUAGUCCACCA | 19 | 10172 |
| BCL11A-8449 | - | CCCCCCUGUUUAGUCCACCA | 20 | 10173 |
| BCL11A-8450 | - | CCCCCCCUGUUUAGUCCACCA | 21 | 10174 |
| BCL11A-8451 | - | UCCCCCCCUGUUUAGUCCACCA | 22 | 10175 |
| BCL11A-8452 | - | CUCCCCCCCUGUUUAGUCCACCA | 23 | 10176 |
| BCL11A-8453 | - | ACUCCCCCCCUGUUUAGUCCACCA | 24 | 10177 |
| BCL11A-8454 | - | CAUUCGGCGUAGUACCCA | 18 | 10178 |
| BCL11A-8455 | - | CCAUUCGGCGUAGUACCCA | 19 | 10179 |
| BCL11A-8456 | - | CCCAUUCGGCGUAGUACCCA | 20 | 10180 |
| BCL11A-8457 | - | CCCCAUUCGGCGUAGUACCCA | 21 | 10181 |
| BCL11A-8458 | - | CCCCCAUUCGGCGUAGUACCCA | 22 | 10182 |
| BCL11A-8459 | - | ACCCCCAUUCGGCGUAGUACCCA | 23 | 10183 |
| BCL11A-8460 | - | CACCCCCAUUCGGCGUAGUACCCA | 24 | 10184 |
| BCL11A-8461 | - | GGCCGAGGCCGAGGGCCA | 18 | 10185 |
| BCL11A-8462 | - | UGGCCGAGGCCGAGGGCCA | 19 | 10186 |
| BCL11A-8463 | - | CUGGCCGAGGCCGAGGGCCA | 20 | 10187 |
| BCL11A-8464 | - | CCUGGCCGAGGCCGAGGGCCA | 21 | 10188 |
| BCL11A-8465 | - | ACCUGGCCGAGGCCGAGGGCCA | 22 | 10189 |
| BCL11A-8466 | - | CACCUGGCCGAGGCCGAGGGCCA | 23 | 10190 |
| BCL11A-8467 | - | CCACCUGGCCGAGGCCGAGGGCCA | 24 | 10191 |
| BCL11A-8468 | - | UUUCUCUUGCAACACGCA | 18 | 10192 |

TABLE 16E-continued

5th Tier

| gRNA Name | DNA Strand | Targeting Domain | Target Site Length | SEQ ID NO: |
|---|---|---|---|---|
| BCL11A-8469 | − | GUUUCUCUUGCAACACGCA | 19 | 10193 |
| BCL11A-8470 | − | GGUUUCUCUUGCAACACGCA | 20 | 10194 |
| BCL11A-8471 | − | UGGUUUCUCUUGCAACACGCA | 21 | 10195 |
| BCL11A-8472 | − | AUGGUUUCUCUUGCAACACGCA | 22 | 10196 |
| BCL11A-8473 | − | CAUGGUUUCUCUUGCAACACGCA | 23 | 10197 |
| BCL11A-8474 | − | GCAUGGUUUCUCUUGCAACACGCA | 24 | 10198 |
| BCL11A-8475 | − | ACUUGGACCCCCACCGCA | 18 | 10199 |
| BCL11A-8476 | − | CACUUGGACCCCCACCGCA | 19 | 10200 |
| BCL11A-8477 | − | UCACUUGGACCCCCACCGCA | 20 | 10201 |
| BCL11A-8478 | − | AUCACUUGGACCCCCACCGCA | 21 | 10202 |
| BCL11A-8479 | − | CAUCACUUGGACCCCCACCGCA | 22 | 10203 |
| BCL11A-8480 | − | ACAUCACUUGGACCCCCACCGCA | 23 | 10204 |
| BCL11A-8481 | − | GACAUCACUUGGACCCCCACCGCA | 24 | 10205 |
| BCL11A-8482 | − | UCUCGGGGCGCAGCGGCA | 18 | 10206 |
| BCL11A-8483 | − | AUCUCGGGGCGCAGCGGCA | 19 | 10207 |
| BCL11A-5904 | − | GAUCUCGGGGCGCAGCGGCA | 20 | 10208 |
| BCL11A-8484 | − | GGAUCUCGGGGCGCAGCGGCA | 21 | 10209 |
| BCL11A-8485 | − | GGGAUCUCGGGGCGCAGCGGCA | 22 | 10210 |
| BCL11A-8486 | − | AGGGAUCUCGGGGCGCAGCGGCA | 23 | 10211 |
| BCL11A-8487 | − | GAGGGAUCUCGGGGCGCAGCGGCA | 24 | 10212 |
| BCL11A-8488 | − | AGACUUAGAGAGCUGGCA | 18 | 10213 |
| BCL11A-8489 | − | GAGACUUAGAGAGCUGGCA | 19 | 10214 |
| BCL11A-5907 | − | GGAGACUUAGAGAGCUGGCA | 20 | 10215 |
| BCL11A-8490 | − | AGGAGACUUAGAGAGCUGGCA | 21 | 10216 |
| BCL11A-8491 | − | UAGGAGACUUAGAGAGCUGGCA | 22 | 10217 |
| BCL11A-8492 | − | CUAGGAGACUUAGAGAGCUGGCA | 23 | 10218 |
| BCL11A-8493 | − | UCUAGGAGACUUAGAGAGCUGGCA | 24 | 10219 |
| BCL11A-8494 | − | GCUCCAUGCAGCACUUCA | 18 | 10220 |
| BCL11A-8495 | − | AGCUCCAUGCAGCACUUCA | 19 | 10221 |
| BCL11A-8496 | − | CAGCUCCAUGCAGCACUUCA | 20 | 10222 |
| BCL11A-8497 | − | UCAGCUCCAUGCAGCACUUCA | 21 | 10223 |
| BCL11A-8498 | − | CUCAGCUCCAUGCAGCACUUCA | 22 | 10224 |
| BCL11A-8499 | − | GCUCAGCUCCAUGCAGCACUUCA | 23 | 10225 |
| BCL11A-8500 | − | UGCUCAGCUCCAUGCAGCACUUCA | 24 | 10226 |
| BCL11A-8501 | − | UGGUGGCCAAGUUCAAGA | 18 | 10227 |
| BCL11A-8502 | − | GUGGUGGCCAAGUUCAAGA | 19 | 10228 |
| BCL11A-8503 | − | CGUGGUGGCCAAGUUCAAGA | 20 | 10229 |
| BCL11A-8504 | − | CCGUGGUGGCCAAGUUCAAGA | 21 | 10230 |

TABLE 16E-continued

5th Tier

| gRNA Name | DNA Strand | Targeting Domain | Target Site Length | SEQ ID NO: |
|---|---|---|---|---|
| BCL11A-8505 | - | UCCGUGGUGGCCAAGUUCAAGA | 22 | 10231 |
| BCL11A-8506 | - | GUCCGUGGUGGCCAAGUUCAAGA | 23 | 10232 |
| BCL11A-8507 | - | AGUCCGUGGUGGCCAAGUUCAAGA | 24 | 10233 |
| BCL11A-8508 | - | AGGAGGAGCUGACGGAGA | 18 | 10234 |
| BCL11A-8509 | - | GAGGAGGAGCUGACGGAGA | 19 | 10235 |
| BCL11A-8510 | - | GGAGGAGGAGCUGACGGAGA | 20 | 10236 |
| BCL11A-8511 | - | AGGAGGAGGAGCUGACGGAGA | 21 | 10237 |
| BCL11A-8512 | - | GAGGAGGAGGAGCUGACGGAGA | 22 | 10238 |
| BCL11A-8513 | - | GGAGGAGGAGGAGCUGACGGAGA | 23 | 10239 |
| BCL11A-8514 | - | AGGAGGAGGAGGAGCUGACGGAGA | 24 | 10240 |
| BCL11A-8515 | - | CCAACCUGAUCCCGGAGA | 18 | 10241 |
| BCL11A-8516 | - | CCCAACCUGAUCCCGGAGA | 19 | 10242 |
| BCL11A-8517 | - | CCCCAACCUGAUCCCGGAGA | 20 | 10243 |
| BCL11A-8518 | - | ACCCCAACCUGAUCCCGGAGA | 21 | 10244 |
| BCL11A-8519 | - | GACCCCAACCUGAUCCCGGAGA | 22 | 10245 |
| BCL11A-8520 | - | CGACCCCAACCUGAUCCCGGAGA | 23 | 10246 |
| BCL11A-8521 | - | ACGACCCCAACCUGAUCCCGGAGA | 24 | 10247 |
| BCL11A-8522 | - | CGGAGCACUCCUCGGAGA | 18 | 10248 |
| BCL11A-8523 | - | UCGGAGCACUCCUCGGAGA | 19 | 10249 |
| BCL11A-8524 | - | GUCGGAGCACUCCUCGGAGA | 20 | 10250 |
| BCL11A-8525 | - | CGUCGGAGCACUCCUCGGAGA | 21 | 10251 |
| BCL11A-8526 | - | UCGUCGGAGCACUCCUCGGAGA | 22 | 10252 |
| BCL11A-8527 | - | CUCGUCGGAGCACUCCUCGGAGA | 23 | 10253 |
| BCL11A-8528 | - | CCUCGUCGGAGCACUCCUCGGAGA | 24 | 10254 |
| BCL11A-8529 | - | UACCAGGAUCAGUAUCGA | 18 | 10255 |
| BCL11A-8530 | - | AUACCAGGAUCAGUAUCGA | 19 | 10256 |
| BCL11A-8531 | - | AAUACCAGGAUCAGUAUCGA | 20 | 10257 |
| BCL11A-8532 | - | GAAUACCAGGAUCAGUAUCGA | 21 | 10258 |
| BCL11A-8533 | - | AGAAUACCAGGAUCAGUAUCGA | 22 | 10259 |
| BCL11A-8534 | - | AAGAAUACCAGGAUCAGUAUCGA | 23 | 10260 |
| BCL11A-8535 | - | UAAGAAUACCAGGAUCAGUAUCGA | 24 | 10261 |
| BCL11A-8536 | - | UGUGUGGCAGUUUUCGGA | 18 | 10262 |
| BCL11A-8537 | - | AUGUGUGGCAGUUUUCGGA | 19 | 10263 |
| BCL11A-5929 | - | GAUGUGUGGCAGUUUUCGGA | 20 | 10264 |
| BCL11A-8538 | - | AGAUGUGUGGCAGUUUUCGGA | 21 | 10265 |
| BCL11A-8539 | - | AAGAUGUGUGGCAGUUUUCGGA | 22 | 10266 |
| BCL11A-8540 | - | CAAGAUGUGUGGCAGUUUUCGGA | 23 | 10267 |

TABLE 16E-continued

5th Tier

| gRNA Name | DNA Strand | Targeting Domain | Target Site Length | SEQ ID NO: |
|---|---|---|---|---|
| BCL11A-8541 | - | UCAAGAUGUGUGGCAGUUUUCGGA | 24 | 10268 |
| BCL11A-8542 | - | ACCGCCCGGGGAGCUGGA | 18 | 10269 |
| BCL11A-8543 | - | CACCGCCCGGGGAGCUGGA | 19 | 10270 |
| BCL11A-5933 | - | ACACCGCCCGGGGAGCUGGA | 20 | 10271 |
| BCL11A-8544 | - | CACACCGCCCGGGGAGCUGGA | 21 | 10272 |
| BCL11A-8545 | - | CCACACCGCCCGGGGAGCUGGA | 22 | 10273 |
| BCL11A-8546 | - | UCCACACCGCCCGGGGAGCUGGA | 23 | 10274 |
| BCL11A-8547 | - | CUCCACACCGCCCGGGGAGCUGGA | 24 | 10275 |
| BCL11A-8548 | - | AGCGGCACGGGAAGUGGA | 18 | 10276 |
| BCL11A-8549 | - | CAGCGGCACGGGAAGUGGA | 19 | 10277 |
| BCL11A-5934 | - | GCAGCGGCACGGGAAGUGGA | 20 | 10278 |
| BCL11A-8550 | - | CGCAGCGGCACGGGAAGUGGA | 21 | 10279 |
| BCL11A-8551 | - | GCGCAGCGGCACGGGAAGUGGA | 22 | 10280 |
| BCL11A-8552 | - | GGCGCAGCGGCACGGGAAGUGGA | 23 | 10281 |
| BCL11A-8553 | - | GGGCGCAGCGGCACGGGAAGUGGA | 24 | 10282 |
| BCL11A-8554 | - | AGGAGGAGGAGGAGCUGA | 18 | 10283 |
| BCL11A-8555 | - | GAGGAGGAGGAGGAGCUGA | 19 | 10284 |
| BCL11A-5938 | - | AGAGGAGGAGGAGGAGCUGA | 20 | 10285 |
| BCL11A-8556 | - | AAGAGGAGGAGGAGGAGCUGA | 21 | 10286 |
| BCL11A-8557 | - | GAAGAGGAGGAGGAGGAGCUGA | 22 | 10287 |
| BCL11A-8558 | - | GGAAGAGGAGGAGGAGGAGCUGA | 23 | 10288 |
| BCL11A-8559 | - | AGGAAGAGGAGGAGGAGGAGCUGA | 24 | 10289 |
| BCL11A-8560 | - | GGUUGAAUCCAAUGGCUA | 18 | 10290 |
| BCL11A-8561 | - | CGGUUGAAUCCAAUGGCUA | 19 | 10291 |
| BCL11A-5944 | - | GCGGUUGAAUCCAAUGGCUA | 20 | 10292 |
| BCL11A-8562 | - | UGCGGUUGAAUCCAAUGGCUA | 21 | 10293 |
| BCL11A-8563 | - | CUGCGGUUGAAUCCAAUGGCUA | 22 | 10294 |
| BCL11A-8564 | - | GCUGCGGUUGAAUCCAAUGGCUA | 23 | 10295 |
| BCL11A-8565 | - | UGCUGCGGUUGAAUCCAAUGGCUA | 24 | 10296 |
| BCL11A-8566 | - | AGAAUACCAGGAUCAGUA | 18 | 10297 |
| BCL11A-8567 | - | AAGAAUACCAGGAUCAGUA | 19 | 10298 |
| BCL11A-8568 | - | UAAGAAUACCAGGAUCAGUA | 20 | 10299 |
| BCL11A-8569 | - | CUAAGAAUACCAGGAUCAGUA | 21 | 10300 |
| BCL11A-8570 | - | GCUAAGAAUACCAGGAUCAGUA | 22 | 10301 |
| BCL11A-8571 | - | UGCUAAGAAUACCAGGAUCAGUA | 23 | 10302 |
| BCL11A-8572 | - | CUGCUAAGAAUACCAGGAUCAGUA | 24 | 10303 |
| BCL11A-8573 | - | AUUUCUCUAGGAGACUUA | 18 | 10304 |
| BCL11A-8574 | - | GAUUUCUCUAGGAGACUUA | 19 | 10305 |

TABLE 16E-continued

5th Tier

| gRNA Name | DNA Strand | Targeting Domain | Target Site Length | SEQ ID NO: |
|---|---|---|---|---|
| BCL11A-8575 | − | GGAUUUCUCUAGGAGACUUA | 20 | 10306 |
| BCL11A-8576 | − | UGGAUUUCUCUAGGAGACUUA | 21 | 10307 |
| BCL11A-8577 | − | AUGGAUUUCUCUAGGAGACUUA | 22 | 10308 |
| BCL11A-8578 | − | CAUGGAUUUCUCUAGGAGACUUA | 23 | 10309 |
| BCL11A-8579 | − | CCAUGGAUUUCUCUAGGAGACUUA | 24 | 10310 |
| BCL11A-8580 | − | CCGGCCGCGAUGCCCAAC | 18 | 10311 |
| BCL11A-8581 | − | CCCGGCCGCGAUGCCCAAC | 19 | 10312 |
| BCL11A-8582 | − | CCCCGGCCGCGAUGCCCAAC | 20 | 10313 |
| BCL11A-8583 | − | CCCCCGGCCGCGAUGCCCAAC | 21 | 10314 |
| BCL11A-8584 | − | GCCCCCGGCCGCGAUGCCCAAC | 22 | 10315 |
| BCL11A-8585 | − | UGCCCCCGGCCGCGAUGCCCAAC | 23 | 10316 |
| BCL11A-8586 | − | CUGCCCCCGGCCGCGAUGCCCAAC | 24 | 10317 |
| BCL11A-8587 | − | AACCUGAUCCCGGAGAAC | 18 | 10318 |
| BCL11A-8588 | − | CAACCUGAUCCCGGAGAAC | 19 | 10319 |
| BCL11A-5948 | − | CCAACCUGAUCCCGGAGAAC | 20 | 10320 |
| BCL11A-8589 | − | CCCAACCUGAUCCCGGAGAAC | 21 | 10321 |
| BCL11A-8590 | − | CCCCAACCUGAUCCCGGAGAAC | 22 | 10322 |
| BCL11A-8591 | − | ACCCCAACCUGAUCCCGGAGAAC | 23 | 10323 |
| BCL11A-8592 | − | GACCCCAACCUGAUCCCGGAGAAC | 24 | 10324 |
| BCL11A-8593 | − | UCUACUUAGAAAGCGAAC | 18 | 10325 |
| BCL11A-8594 | − | AUCUACUUAGAAAGCGAAC | 19 | 10326 |
| BCL11A-8595 | − | AAUCUACUUAGAAAGCGAAC | 20 | 10327 |
| BCL11A-8596 | − | GAAUCUACUUAGAAAGCGAAC | 21 | 10328 |
| BCL11A-8597 | − | AGAAUCUACUUAGAAAGCGAAC | 22 | 10329 |
| BCL11A-8598 | − | AAGAAUCUACUUAGAAAGCGAAC | 23 | 10330 |
| BCL11A-8599 | − | UAAGAAUCUACUUAGAAAGCGAAC | 24 | 10331 |
| BCL11A-8600 | − | GAGGCGGCGCGCCACCAC | 18 | 10332 |
| BCL11A-8601 | − | GGAGGCGGCGCGCCACCAC | 19 | 10333 |
| BCL11A-8602 | − | UGGAGGCGGCGCGCCACCAC | 20 | 10334 |
| BCL11A-8603 | − | CUGGAGGCGGCGCGCCACCAC | 21 | 10335 |
| BCL11A-8604 | − | CCUGGAGGCGGCGCGCCACCAC | 22 | 10336 |
| BCL11A-8605 | − | GCCUGGAGGCGGCGCGCCACCAC | 23 | 10337 |
| BCL11A-8606 | − | AGCCUGGAGGCGGCGCGCCACCAC | 24 | 10338 |
| BCL11A-8607 | − | GUGCACCGGCGCAGCCAC | 18 | 10339 |
| BCL11A-8608 | − | GGUGCACCGGCGCAGCCAC | 19 | 10340 |
| BCL11A-8609 | − | UGGUGCACCGGCGCAGCCAC | 20 | 10341 |
| BCL11A-8610 | − | GUGGUGCACCGGCGCAGCCAC | 21 | 10342 |

TABLE 16E-continued

5th Tier

| gRNA Name | DNA Strand | Targeting Domain | Target Site Length | SEQ ID NO: |
|---|---|---|---|---|
| BCL11A-8611 | - | GGUGGUGCACCGGCGCAGCCAC | 22 | 10343 |
| BCL11A-8612 | - | UGGUGGUGCACCGGCGCAGCCAC | 23 | 10344 |
| BCL11A-8613 | - | CUGGUGGUGCACCGGCGCAGCCAC | 24 | 10345 |
| BCL11A-8614 | - | AGCAAGCUGAAGCGCCAC | 18 | 10346 |
| BCL11A-8615 | - | CAGCAAGCUGAAGCGCCAC | 19 | 10347 |
| BCL11A-8616 | - | CCAGCAAGCUGAAGCGCCAC | 20 | 10348 |
| BCL11A-8617 | - | GCCAGCAAGCUGAAGCGCCAC | 21 | 10349 |
| BCL11A-8618 | - | GGCCAGCAAGCUGAAGCGCCAC | 22 | 10350 |
| BCL11A-8619 | - | AGGCCAGCAAGCUGAAGCGCCAC | 23 | 10351 |
| BCL11A-8620 | - | CAGGCCAGCAAGCUGAAGCGCCAC | 24 | 10352 |
| BCL11A-8621 | - | GCCGAGGCCGAGGGCCAC | 18 | 10353 |
| BCL11A-8622 | - | GGCCGAGGCCGAGGGCCAC | 19 | 10354 |
| BCL11A-5951 | - | UGGCCGAGGCCGAGGGCCAC | 20 | 10355 |
| BCL11A-8623 | - | CUGGCCGAGGCCGAGGGCCAC | 21 | 10356 |
| BCL11A-8624 | - | CCUGGCCGAGGCCGAGGGCCAC | 22 | 10357 |
| BCL11A-8625 | - | ACCUGGCCGAGGCCGAGGGCCAC | 23 | 10358 |
| BCL11A-8626 | - | CACCUGGCCGAGGCCGAGGGCCAC | 24 | 10359 |
| BCL11A-8627 | - | CUCGGGGCGCAGCGGCAC | 18 | 10360 |
| BCL11A-8628 | - | UCUCGGGGCGCAGCGGCAC | 19 | 10361 |
| BCL11A-5953 | - | AUCUCGGGGCGCAGCGGCAC | 20 | 10362 |
| BCL11A-8629 | - | GAUCUCGGGGCGCAGCGGCAC | 21 | 10363 |
| BCL11A-8630 | - | GGAUCUCGGGGCGCAGCGGCAC | 22 | 10364 |
| BCL11A-8631 | - | GGGAUCUCGGGGCGCAGCGGCAC | 23 | 10365 |
| BCL11A-8632 | - | AGGGAUCUCGGGGCGCAGCGGCAC | 24 | 10366 |
| BCL11A-8633 | - | CCACCACCGAGACAUCAC | 18 | 10367 |
| BCL11A-8634 | - | UCCACCACCGAGACAUCAC | 19 | 10368 |
| BCL11A-8635 | - | GUCCACCACCGAGACAUCAC | 20 | 10369 |
| BCL11A-8636 | - | AGUCCACCACCGAGACAUCAC | 21 | 10370 |
| BCL11A-8637 | - | UAGUCCACCACCGAGACAUCAC | 22 | 10371 |
| BCL11A-8638 | - | UUAGUCCACCACCGAGACAUCAC | 23 | 10372 |
| BCL11A-8639 | - | UUUAGUCCACCACCGAGACAUCAC | 24 | 10373 |
| BCL11A-8640 | - | GAGGAAGAGGAGGACGAC | 18 | 10374 |
| BCL11A-8641 | - | GGAGGAAGAGGAGGACGAC | 19 | 10375 |
| BCL11A-3949 | - | AGGAGGAAGAGGAGGACGAC | 20 | 10376 |
| BCL11A-8642 | - | GAGGAGGAAGAGGAGGACGAC | 21 | 10377 |
| BCL11A-8643 | - | CGAGGAGGAAGAGGAGGACGAC | 22 | 10378 |
| BCL11A-8644 | - | ACGAGGAGGAAGAGGAGGACGAC | 23 | 10379 |
| BCL11A-8645 | - | GACGAGGAGGAAGAGGAGGACGAC | 24 | 10380 |

TABLE 16E-continued

5th Tier

| gRNA Name | DNA Strand | Targeting Domain | Target Site Length | SEQ ID NO: |
|---|---|---|---|---|
| BCL11A-8646 | - | GUCGUGGGCGUGGGCGAC | 18 | 10381 |
| BCL11A-8647 | - | GGUCGUGGGCGUGGGCGAC | 19 | 10382 |
| BCL11A-8648 | - | CGGUCGUGGGCGUGGGCGAC | 20 | 10383 |
| BCL11A-8649 | - | GCGGUCGUGGGCGUGGGCGAC | 21 | 10384 |
| BCL11A-8650 | - | CGCGGUCGUGGGCGUGGGCGAC | 22 | 10385 |
| BCL11A-8651 | - | GCGCGGUCGUGGGCGUGGGCGAC | 23 | 10386 |
| BCL11A-8652 | - | GGCGCGGUCGUGGGCGUGGGCGAC | 24 | 10387 |
| BCL11A-8653 | - | AUCCCGGAGAACGGGAC | 18 | 10388 |
| BCL11A-8654 | - | GAUCCCGGAGAACGGGAC | 19 | 10389 |
| BCL11A-8655 | - | UGAUCCCGGAGAACGGGAC | 20 | 10390 |
| BCL11A-8656 | - | CUGAUCCCGGAGAACGGGAC | 21 | 10391 |
| BCL11A-8657 | - | CCUGAUCCCGGAGAACGGGAC | 22 | 10392 |
| BCL11A-8658 | - | ACCUGAUCCCGGAGAACGGGAC | 23 | 10393 |
| BCL11A-8659 | - | AACCUGAUCCCGGAGAACGGGAC | 24 | 10394 |
| BCL11A-8660 | - | UGGAGGCGGCGCGCCACC | 18 | 10395 |
| BCL11A-8661 | - | CUGGAGGCGGCGCGCCACC | 19 | 10396 |
| BCL11A-8662 | - | CCUGGAGGCGGCGCGCCACC | 20 | 10397 |
| BCL11A-8663 | - | GCCUGGAGGCGGCGCGCCACC | 21 | 10398 |
| BCL11A-8664 | - | AGCCUGGAGGCGGCGCGCCACC | 22 | 10399 |
| BCL11A-8665 | - | GAGCCUGGAGGCGGCGCGCCACC | 23 | 10400 |
| BCL11A-8666 | - | UGAGCCUGGAGGCGGCGCGCCACC | 24 | 10401 |
| BCL11A-8667 | - | CCCAUUCGGCGUAGUACC | 18 | 10402 |
| BCL11A-8668 | - | CCCCAUUCGGCGUAGUACC | 19 | 10403 |
| BCL11A-8669 | - | CCCCCAUUCGGCGUAGUACC | 20 | 10404 |
| BCL11A-8670 | - | ACCCCCAUUCGGCGUAGUACC | 21 | 10405 |
| BCL11A-8671 | - | CACCCCCAUUCGGCGUAGUACC | 22 | 10406 |
| BCL11A-8672 | - | ACACCCCCAUUCGGCGUAGUACC | 23 | 10407 |
| BCL11A-8673 | - | CACACCCCCAUUCGGCGUAGUACC | 24 | 10408 |
| BCL11A-8674 | - | GAGAAAAUUUGAAGCCCC | 18 | 10409 |
| BCL11A-8675 | - | UGAGAAAAUUUGAAGCCCC | 19 | 10410 |
| BCL11A-8676 | - | CUGAGAAAAUUUGAAGCCCC | 20 | 10411 |
| BCL11A-8677 | - | UCUGAGAAAAUUUGAAGCCCC | 21 | 10412 |
| BCL11A-8678 | - | UUCUGAGAAAAUUUGAAGCCCC | 22 | 10413 |
| BCL11A-8679 | - | GUUCUGAGAAAAUUUGAAGCCCC | 23 | 10414 |
| BCL11A-8680 | - | AGUUCUGAGAAAAUUUGAAGCCCC | 24 | 10415 |
| BCL11A-8681 | - | CGCUUCUCCACACCGCCC | 18 | 10416 |
| BCL11A-8682 | - | GCGCUUCUCCACACCGCCC | 19 | 10417 |

TABLE 16E-continued

5th Tier

| gRNA Name | DNA Strand | Targeting Domain | Target Site Length | SEQ ID NO: |
|---|---|---|---|---|
| BCL11A-5976 | - | UGCGCUUCUCCACACCGCCC | 20 | 10418 |
| BCL11A-8683 | - | UUGCGCUUCUCCACACCGCCC | 21 | 10419 |
| BCL11A-8684 | - | UUUGCGCUUCUCCACACCGCCC | 22 | 10420 |
| BCL11A-8685 | - | GUUUGCGCUUCUCCACACCGCCC | 23 | 10421 |
| BCL11A-8686 | - | AGUUUGCGCUUCUCCACACCGCCC | 24 | 10422 |
| BCL11A-8687 | - | UCUCCACCGCCAGCUCCC | 18 | 10423 |
| BCL11A-8688 | - | CUCUCCACCGCCAGCUCCC | 19 | 10424 |
| BCL11A-5982 | - | UCUCUCCACCGCCAGCUCCC | 20 | 10425 |
| BCL11A-8689 | - | GUCUCUCCACCGCCAGCUCCC | 21 | 10426 |
| BCL11A-8690 | - | GGUCUCUCCACCGCCAGCUCCC | 22 | 10427 |
| BCL11A-8691 | - | CGGUCUCUCCACCGCCAGCUCCC | 23 | 10428 |
| BCL11A-8692 | - | ACGGUCUCUCCACCGCCAGCUCCC | 24 | 10429 |
| BCL11A-8693 | - | ACGGCUUCGGGCUGAGCC | 18 | 10430 |
| BCL11A-8694 | - | UACGGCUUCGGGCUGAGCC | 19 | 10431 |
| BCL11A-5986 | - | CUACGGCUUCGGGCUGAGCC | 20 | 10432 |
| BCL11A-8695 | - | ACUACGGCUUCGGGCUGAGCC | 21 | 10433 |
| BCL11A-8696 | - | GACUACGGCUUCGGGCUGAGCC | 22 | 10434 |
| BCL11A-8697 | - | GGACUACGGCUUCGGGCUGAGCC | 23 | 10435 |
| BCL11A-8698 | - | UGGACUACGGCUUCGGGCUGAGCC | 24 | 10436 |
| BCL11A-8699 | - | GCGCUUCUCCACACCGCC | 18 | 10437 |
| BCL11A-8700 | - | UGCGCUUCUCCACACCGCC | 19 | 10438 |
| BCL11A-5987 | - | UUGCGCUUCUCCACACCGCC | 20 | 10439 |
| BCL11A-8701 | - | UUUGCGCUUCUCCACACCGCC | 21 | 10440 |
| BCL11A-8702 | - | GUUUGCGCUUCUCCACACCGCC | 22 | 10441 |
| BCL11A-8703 | - | AGUUUGCGCUUCUCCACACCGCC | 23 | 10442 |
| BCL11A-8704 | - | GAGUUUGCGCUUCUCCACACCGCC | 24 | 10443 |
| BCL11A-8705 | - | CCCACCGCAUAGAGCGCC | 18 | 10444 |
| BCL11A-8706 | - | CCCCACCGCAUAGAGCGCC | 19 | 10445 |
| BCL11A-5988 | - | CCCCCACCGCAUAGAGCGCC | 20 | 10446 |
| BCL11A-8707 | - | ACCCCCACCGCAUAGAGCGCC | 21 | 10447 |
| BCL11A-8708 | - | GACCCCCACCGCAUAGAGCGCC | 22 | 10448 |
| BCL11A-8709 | - | GGACCCCCACCGCAUAGAGCGCC | 23 | 10449 |
| BCL11A-8710 | - | UGGACCCCCACCGCAUAGAGCGCC | 24 | 10450 |
| BCL11A-8711 | - | GGCCACCUGGCCGAGGCC | 18 | 10451 |
| BCL11A-8712 | - | CGGCCACCUGGCCGAGGCC | 19 | 10452 |
| BCL11A-8713 | - | GCGGCCACCUGGCCGAGGCC | 20 | 10453 |
| BCL11A-8714 | - | CGCGGCCACCUGGCCGAGGCC | 21 | 10454 |
| BCL11A-8715 | - | GCGCGGCCACCUGGCCGAGGCC | 22 | 10455 |

TABLE 16E-continued

5th Tier

| gRNA Name | DNA Strand | Targeting Domain | Target Site Length | SEQ ID NO: |
|---|---|---|---|---|
| BCL11A-8716 | - | AGCGCGGCCACCUGGCCGAGGCC | 23 | 10456 |
| BCL11A-8717 | - | AAGCGCGGCCACCUGGCCGAGGCC | 24 | 10457 |
| BCL11A-8718 | - | UCCCCGGGCGAGUCGGCC | 18 | 10458 |
| BCL11A-8719 | - | CUCCCCGGGCGAGUCGGCC | 19 | 10459 |
| BCL11A-8720 | - | GCUCCCCGGGCGAGUCGGCC | 20 | 10460 |
| BCL11A-8721 | - | UGCUCCCCGGGCGAGUCGGCC | 21 | 10461 |
| BCL11A-8722 | - | CUGCUCCCCGGGCGAGUCGGCC | 22 | 10462 |
| BCL11A-8723 | - | GCUGCUCCCCGGGCGAGUCGGCC | 23 | 10463 |
| BCL11A-8724 | - | GGCUGCUCCCCGGGCGAGUCGGCC | 24 | 10464 |
| BCL11A-8725 | - | ACGACCCCAACCUGAUCC | 18 | 10465 |
| BCL11A-8726 | - | AACGACCCCAACCUGAUCC | 19 | 10466 |
| BCL11A-6004 | - | GAACGACCCCAACCUGAUCC | 20 | 10467 |
| BCL11A-8727 | - | AGAACGACCCCAACCUGAUCC | 21 | 10468 |
| BCL11A-8728 | - | GAGAACGACCCCAACCUGAUCC | 22 | 10469 |
| BCL11A-8729 | - | CGAGAACGACCCCAACCUGAUCC | 23 | 10470 |
| BCL11A-8730 | - | GCGAGAACGACCCCAACCUGAUCC | 24 | 10471 |
| BCL11A-8731 | - | UCCUCGUCGGAGCACUCC | 18 | 10472 |
| BCL11A-8732 | - | CUCCUCGUCGGAGCACUCC | 19 | 10473 |
| BCL11A-8733 | - | CCUCCUCGUCGGAGCACUCC | 20 | 10474 |
| BCL11A-8734 | - | GCCUCCUCGUCGGAGCACUCC | 21 | 10475 |
| BCL11A-8735 | - | UGCCUCCUCGUCGGAGCACUCC | 22 | 10476 |
| BCL11A-8736 | - | UUGCCUCCUCGUCGGAGCACUCC | 23 | 10477 |
| BCL11A-8737 | - | UUUGCCUCCUCGUCGGAGCACUCC | 24 | 10478 |
| BCL11A-8738 | - | CUCUCCACCGCCAGCUCC | 18 | 10479 |
| BCL11A-8739 | - | UCUCUCCACCGCCAGCUCC | 19 | 10480 |
| BCL11A-8740 | - | GUCUCUCCACCGCCAGCUCC | 20 | 10481 |
| BCL11A-8741 | - | GGUCUCUCCACCGCCAGCUCC | 21 | 10482 |
| BCL11A-8742 | - | CGGUCUCUCCACCGCCAGCUCC | 22 | 10483 |
| BCL11A-8743 | - | ACGGUCUCUCCACCGCCAGCUCC | 23 | 10484 |
| BCL11A-8744 | - | GACGGUCUCUCCACCGCCAGCUCC | 24 | 10485 |
| BCL11A-8745 | - | AAUGGCCGCGGCUGCUCC | 18 | 10486 |
| BCL11A-8746 | - | UAAUGGCCGCGGCUGCUCC | 19 | 10487 |
| BCL11A-8747 | - | UUAAUGGCCGCGGCUGCUCC | 20 | 10488 |
| BCL11A-8748 | - | GUUAAUGGCCGCGGCUGCUCC | 21 | 10489 |
| BCL11A-8749 | - | UGUUAAUGGCCGCGGCUGCUCC | 22 | 10490 |
| BCL11A-8750 | - | CUGUUAAUGGCCGCGGCUGCUCC | 23 | 10491 |
| BCL11A-8751 | - | ACUGUUAAUGGCCGCGGCUGCUCC | 24 | 10492 |

TABLE 16E-continued

5th Tier

| gRNA Name | DNA Strand | Targeting Domain | Target Site Length | SEQ ID NO: |
|---|---|---|---|---|
| BCL11A-8752 | - | CUUCCCAGCCACCUCUCC | 18 | 10493 |
| BCL11A-8753 | - | CCUUCCCAGCCACCUCUCC | 19 | 10494 |
| BCL11A-8754 | - | UCCUUCCCAGCCACCUCUCC | 20 | 10495 |
| BCL11A-8755 | - | GUCCUUCCCAGCCACCUCUCC | 21 | 10496 |
| BCL11A-8756 | - | UGUCCUUCCCAGCCACCUCUCC | 22 | 10497 |
| BCL11A-8757 | - | AUGUCCUUCCCAGCCACCUCUCC | 23 | 10498 |
| BCL11A-8758 | - | AAUGUCCUUCCCAGCCACCUCUCC | 24 | 10499 |
| BCL11A-8759 | - | UCUCUAAGCGCAUCAAGC | 18 | 10500 |
| BCL11A-8760 | - | UUCUCUAAGCGCAUCAAGC | 19 | 10501 |
| BCL11A-8761 | - | CUUCUCUAAGCGCAUCAAGC | 20 | 10502 |
| BCL11A-8762 | - | CCUUCUCUAAGCGCAUCAAGC | 21 | 10503 |
| BCL11A-8763 | - | CCCUUCUCUAAGCGCAUCAAGC | 22 | 10504 |
| BCL11A-8764 | - | CCCCUUCUCUAAGCGCAUCAAGC | 23 | 10505 |
| BCL11A-8765 | - | GCCCCUUCUCUAAGCGCAUCAAGC | 24 | 10506 |
| BCL11A-8766 | - | CAGUUUUCGGAUGGAAGC | 18 | 10507 |
| BCL11A-8767 | - | GCAGUUUUCGGAUGGAAGC | 19 | 10508 |
| BCL11A-8768 | - | GGCAGUUUUCGGAUGGAAGC | 20 | 10509 |
| BCL11A-8769 | - | UGGCAGUUUUCGGAUGGAAGC | 21 | 10510 |
| BCL11A-8770 | - | GUGGCAGUUUUCGGAUGGAAGC | 22 | 10511 |
| BCL11A-8771 | - | UGUGGCAGUUUUCGGAUGGAAGC | 23 | 10512 |
| BCL11A-8772 | - | GUGUGGCAGUUUUCGGAUGGAAGC | 24 | 10513 |
| BCL11A-8773 | - | GUGGCCAAGUUCAAGAGC | 18 | 10514 |
| BCL11A-8774 | - | GGUGGCCAAGUUCAAGAGC | 19 | 10515 |
| BCL11A-8775 | - | UGGUGGCCAAGUUCAAGAGC | 20 | 10516 |
| BCL11A-8776 | - | GUGGUGGCCAAGUUCAAGAGC | 21 | 10517 |
| BCL11A-8777 | - | CGUGGUGGCCAAGUUCAAGAGC | 22 | 10518 |
| BCL11A-8778 | - | CCGUGGUGGCCAAGUUCAAGAGC | 23 | 10519 |
| BCL11A-8779 | - | UCCGUGGUGGCCAAGUUCAAGAGC | 24 | 10520 |
| BCL11A-8780 | - | GAGGAGCUGACGGAGAGC | 18 | 10521 |
| BCL11A-8781 | - | GGAGGAGCUGACGGAGAGC | 19 | 10522 |
| BCL11A-8782 | - | AGGAGGAGCUGACGGAGAGC | 20 | 10523 |
| BCL11A-8783 | - | GAGGAGGAGCUGACGGAGAGC | 21 | 10524 |
| BCL11A-8784 | - | GGAGGAGGAGCUGACGGAGAGC | 22 | 10525 |
| BCL11A-8785 | - | AGGAGGAGGAGCUGACGGAGAGC | 23 | 10526 |
| BCL11A-8786 | - | GAGGAGGAGGAGCUGACGGAGAGC | 24 | 10527 |
| BCL11A-8787 | - | UACGGCUUCGGGCUGAGC | 18 | 10528 |
| BCL11A-8788 | - | CUACGGCUUCGGGCUGAGC | 19 | 10529 |
| BCL11A-8789 | - | ACUACGGCUUCGGGCUGAGC | 20 | 10530 |

TABLE 16E-continued

5th Tier

| gRNA Name | DNA Strand | Targeting Domain | Target Site Length | SEQ ID NO: |
|---|---|---|---|---|
| BCL11A-8790 | - | GACUACGGCUUCGGGCUGAGC | 21 | 10531 |
| BCL11A-8791 | - | GGACUACGGCUUCGGGCUGAGC | 22 | 10532 |
| BCL11A-8792 | - | UGGACUACGGCUUCGGGCUGAGC | 23 | 10533 |
| BCL11A-8793 | - | GUGGACUACGGCUUCGGGCUGAGC | 24 | 10534 |
| BCL11A-8794 | - | UGCGCUUCUCCACACCGC | 18 | 10535 |
| BCL11A-8795 | - | UUGCGCUUCUCCACACCGC | 19 | 10536 |
| BCL11A-8796 | - | UUUGCGCUUCUCCACACCGC | 20 | 10537 |
| BCL11A-8797 | - | GUUUGCGCUUCUCCACACCGC | 21 | 10538 |
| BCL11A-8798 | - | AGUUUGCGCUUCUCCACACCGC | 22 | 10539 |
| BCL11A-8799 | - | GAGUUUGCGCUUCUCCACACCGC | 23 | 10540 |
| BCL11A-8800 | - | GGAGUUUGCGCUUCUCCACACCGC | 24 | 10541 |
| BCL11A-8801 | - | CCCCACCGCAUAGAGCGC | 18 | 10542 |
| BCL11A-8802 | - | CCCCCACCGCAUAGAGCGC | 19 | 10543 |
| BCL11A-8803 | - | ACCCCCACCGCAUAGAGCGC | 20 | 10544 |
| BCL11A-8804 | - | GACCCCCACCGCAUAGAGCGC | 21 | 10545 |
| BCL11A-8805 | - | GGACCCCCACCGCAUAGAGCGC | 22 | 10546 |
| BCL11A-8806 | - | UGGACCCCCACCGCAUAGAGCGC | 23 | 10547 |
| BCL11A-8807 | - | UUGGACCCCCACCGCAUAGAGCGC | 24 | 10548 |
| BCL11A-8808 | - | AUCUCGGGGCGCAGCGGC | 18 | 10549 |
| BCL11A-8809 | - | GAUCUCGGGGCGCAGCGGC | 19 | 10550 |
| BCL11A-8810 | - | GGAUCUCGGGGCGCAGCGGC | 20 | 10551 |
| BCL11A-8811 | - | GGGAUCUCGGGGCGCAGCGGC | 21 | 10552 |
| BCL11A-8812 | - | AGGGAUCUCGGGGCGCAGCGGC | 22 | 10553 |
| BCL11A-8813 | - | GAGGGAUCUCGGGGCGCAGCGGC | 23 | 10554 |
| BCL11A-8814 | - | GGAGGGAUCUCGGGGCGCAGCGGC | 24 | 10555 |
| BCL11A-8815 | - | CGGCGCAGCCACACGGGC | 18 | 10556 |
| BCL11A-8816 | - | CCGGCGCAGCCACACGGGC | 19 | 10557 |
| BCL11A-3804 | - | ACCGGCGCAGCCACACGGGC | 20 | 10558 |
| BCL11A-8817 | - | CACCGGCGCAGCCACACGGGC | 21 | 10559 |
| BCL11A-8818 | - | GCACCGGCGCAGCCACACGGGC | 22 | 10560 |
| BCL11A-8819 | - | UGCACCGGCGCAGCCACACGGGC | 23 | 10561 |
| BCL11A-8820 | - | GUGCACCGGCGCAGCCACACGGGC | 24 | 10562 |
| BCL11A-8821 | - | CAUAUUAGUGGUCCGGGC | 18 | 10563 |
| BCL11A-8822 | - | CCAUAUUAGUGGUCCGGGC | 19 | 10564 |
| BCL11A-8823 | - | CCCAUAUUAGUGGUCCGGGC | 20 | 10565 |
| BCL11A-8824 | - | CCCCAUAUUAGUGGUCCGGGC | 21 | 10566 |
| BCL11A-8825 | - | GCCCCAUAUUAGUGGUCCGGGC | 22 | 10567 |

TABLE 16E-continued

5th Tier

| gRNA Name | DNA Strand | Targeting Domain | Target Site Length | SEQ ID NO: |
|---|---|---|---|---|
| BCL11A-8826 | - | CGCCCCAUAUUAGUGGUCCGGGC | 23 | 10568 |
| BCL11A-8827 | - | ACGCCCCAUAUUAGUGGUCCGGGC | 24 | 10569 |
| BCL11A-8828 | - | UUCCACCAGGUCCUGGGC | 18 | 10570 |
| BCL11A-8829 | - | CUUCCACCAGGUCCUGGGC | 19 | 10571 |
| BCL11A-8830 | - | CCUUCCACCAGGUCCUGGGC | 20 | 10572 |
| BCL11A-8831 | - | GCCUUCCACCAGGUCCUGGGC | 21 | 10573 |
| BCL11A-8832 | - | GGCCUUCCACCAGGUCCUGGGC | 22 | 10574 |
| BCL11A-8833 | - | AGGCCUUCCACCAGGUCCUGGGC | 23 | 10575 |
| BCL11A-8834 | - | GAGGCCUUCCACCAGGUCCUGGGC | 24 | 10576 |
| BCL11A-8835 | - | CGGGGCGCGGUCGUGGGC | 18 | 10577 |
| BCL11A-8836 | - | GCGGGGCGCGGUCGUGGGC | 19 | 10578 |
| BCL11A-8837 | - | CGCGGGGCGCGGUCGUGGGC | 20 | 10579 |
| BCL11A-8838 | - | UCGCGGGGCGCGGUCGUGGGC | 21 | 10580 |
| BCL11A-8839 | - | CUCGCGGGGCGCGGUCGUGGGC | 22 | 10581 |
| BCL11A-8840 | - | GCUCGCGGGGCGCGGUCGUGGGC | 23 | 10582 |
| BCL11A-8841 | - | AGCUCGCGGGGCGCGGUCGUGGGC | 24 | 10583 |
| BCL11A-8842 | - | GAGACUUAGAGAGCUGGC | 18 | 10584 |
| BCL11A-8843 | - | GGAGACUUAGAGAGCUGGC | 19 | 10585 |
| BCL11A-6037 | - | AGGAGACUUAGAGAGCUGGC | 20 | 10586 |
| BCL11A-8844 | - | UAGGAGACUUAGAGAGCUGGC | 21 | 10587 |
| BCL11A-8845 | - | CUAGGAGACUUAGAGAGCUGGC | 22 | 10588 |
| BCL11A-8846 | - | UCUAGGAGACUUAGAGAGCUGGC | 23 | 10589 |
| BCL11A-8847 | - | CUCUAGGAGACUUAGAGAGCUGGC | 24 | 10590 |
| BCL11A-8848 | - | GAGCUGGACGGAGGGAUC | 18 | 10591 |
| BCL11A-8849 | - | GGAGCUGGACGGAGGGAUC | 19 | 10592 |
| BCL11A-8850 | - | GGGAGCUGGACGGAGGGAUC | 20 | 10593 |
| BCL11A-8851 | - | GGGGAGCUGGACGGAGGGAUC | 21 | 10594 |
| BCL11A-8852 | - | CGGGGAGCUGGACGGAGGGAUC | 22 | 10595 |
| BCL11A-8853 | - | CCGGGGAGCUGGACGGAGGGAUC | 23 | 10596 |
| BCL11A-8854 | - | CCCGGGGAGCUGGACGGAGGGAUC | 24 | 10597 |
| BCL11A-8855 | - | AACGACCCCAACCUGAUC | 18 | 10598 |
| BCL11A-8856 | - | GAACGACCCCAACCUGAUC | 19 | 10599 |
| BCL11A-8857 | - | AGAACGACCCCAACCUGAUC | 20 | 10600 |
| BCL11A-8858 | - | GAGAACGACCCCAACCUGAUC | 21 | 10601 |
| BCL11A-8859 | - | CGAGAACGACCCCAACCUGAUC | 22 | 10602 |
| BCL11A-8860 | - | GCGAGAACGACCCCAACCUGAUC | 23 | 10603 |
| BCL11A-8861 | - | AGCGAGAACGACCCCAACCUGAUC | 24 | 10604 |
| BCL11A-8862 | - | AAUACCAGGAUCAGUAUC | 18 | 10605 |

TABLE 16E-continued

5th Tier

| gRNA Name | DNA Strand | Targeting Domain | Target Site Length | SEQ ID NO: |
|---|---|---|---|---|
| BCL11A-8863 | - | GAAUACCAGGAUCAGUAUC | 19 | 10606 |
| BCL11A-8864 | - | AGAAUACCAGGAUCAGUAUC | 20 | 10607 |
| BCL11A-8865 | - | AAGAAUACCAGGAUCAGUAUC | 21 | 10608 |
| BCL11A-8866 | - | UAAGAAUACCAGGAUCAGUAUC | 22 | 10609 |
| BCL11A-8867 | - | CUAAGAAUACCAGGAUCAGUAUC | 23 | 10610 |
| BCL11A-8868 | - | GCUAAGAAUACCAGGAUCAGUAUC | 24 | 10611 |
| BCL11A-8869 | - | CCCGGGCGAGUCGGCCUC | 18 | 10612 |
| BCL11A-8870 | - | CCCCGGGCGAGUCGGCCUC | 19 | 10613 |
| BCL11A-6047 | - | UCCCCGGGCGAGUCGGCCUC | 20 | 10614 |
| BCL11A-8871 | - | CUCCCCGGGCGAGUCGGCCUC | 21 | 10615 |
| BCL11A-8872 | - | GCUCCCCGGGCGAGUCGGCCUC | 22 | 10616 |
| BCL11A-8873 | - | UGCUCCCCGGGCGAGUCGGCCUC | 23 | 10617 |
| BCL11A-8874 | - | CUGCUCCCCGGGCGAGUCGGCCUC | 24 | 10618 |
| BCL11A-8875 | - | UCUAAGCGCAUCAAGCUC | 18 | 10619 |
| BCL11A-8876 | - | CUCUAAGCGCAUCAAGCUC | 19 | 10620 |
| BCL11A-8877 | - | UCUCUAAGCGCAUCAAGCUC | 20 | 10621 |
| BCL11A-8878 | - | UUCUCUAAGCGCAUCAAGCUC | 21 | 10622 |
| BCL11A-8879 | - | CUUCUCUAAGCGCAUCAAGCUC | 22 | 10623 |
| BCL11A-8880 | - | CCUUCUCUAAGCGCAUCAAGCUC | 23 | 10624 |
| BCL11A-8881 | - | CCCUUCUCUAAGCGCAUCAAGCUC | 24 | 10625 |
| BCL11A-8882 | - | GUUUUCGGAUGGAAGCUC | 18 | 10626 |
| BCL11A-8883 | - | AGUUUUCGGAUGGAAGCUC | 19 | 10627 |
| BCL11A-8884 | - | CAGUUUUCGGAUGGAAGCUC | 20 | 10628 |
| BCL11A-8885 | - | GCAGUUUUCGGAUGGAAGCUC | 21 | 10629 |
| BCL11A-8886 | - | GGCAGUUUUCGGAUGGAAGCUC | 22 | 10630 |
| BCL11A-8887 | - | UGGCAGUUUUCGGAUGGAAGCUC | 23 | 10631 |
| BCL11A-8888 | - | GUGGCAGUUUUCGGAUGGAAGCUC | 24 | 10632 |
| BCL11A-8889 | - | CCACCACGAGAACAGCUC | 18 | 10633 |
| BCL11A-8890 | - | GCCACCACGAGAACAGCUC | 19 | 10634 |
| BCL11A-8891 | - | CGCCACCACGAGAACAGCUC | 20 | 10635 |
| BCL11A-8892 | - | GCGCCACCACGAGAACAGCUC | 21 | 10636 |
| BCL11A-8893 | - | CGCGCCACCACGAGAACAGCUC | 22 | 10637 |
| BCL11A-8894 | - | GCGCGCCACCACGAGAACAGCUC | 23 | 10638 |
| BCL11A-8895 | - | GGCGCGCCACCACGAGAACAGCUC | 24 | 10639 |
| BCL11A-8896 | - | UCCCGCCAUGGAUUUCUC | 18 | 10640 |
| BCL11A-8897 | - | CUCCCGCCAUGGAUUUCUC | 19 | 10641 |
| BCL11A-8898 | - | CCUCCCGCCAUGGAUUUCUC | 20 | 10642 |

TABLE 16E-continued

5th Tier

| gRNA Name | DNA Strand | Targeting Domain | Target Site Length | SEQ ID NO: |
|---|---|---|---|---|
| BCL11A-8899 | - | GCCUCCCGCCAUGGAUUUCUC | 21 | 10643 |
| BCL11A-8900 | - | AGCCUCCCGCCAUGGAUUUCUC | 22 | 10644 |
| BCL11A-8901 | - | GAGCCUCCCGCCAUGGAUUUCUC | 23 | 10645 |
| BCL11A-8902 | - | GGAGCCUCCCGCCAUGGAUUUCUC | 24 | 10646 |
| BCL11A-8903 | - | GAGGCCUUCCACCAGGUC | 18 | 10647 |
| BCL11A-8904 | - | CGAGGCCUUCCACCAGGUC | 19 | 10648 |
| BCL11A-8905 | - | GCGAGGCCUUCCACCAGGUC | 20 | 10649 |
| BCL11A-8906 | - | AGCGAGGCCUUCCACCAGGUC | 21 | 10650 |
| BCL11A-8907 | - | CAGCGAGGCCUUCCACCAGGUC | 22 | 10651 |
| BCL11A-8908 | - | UCAGCGAGGCCUUCCACCAGGUC | 23 | 10652 |
| BCL11A-8909 | - | UUCAGCGAGGCCUUCCACCAGGUC | 24 | 10653 |
| BCL11A-8910 | - | AGCUCGCGGGGCGCGGUC | 18 | 10654 |
| BCL11A-8911 | - | CAGCUCGCGGGGCGCGGUC | 19 | 10655 |
| BCL11A-8912 | - | ACAGCUCGCGGGGCGCGGUC | 20 | 10656 |
| BCL11A-8913 | - | AACAGCUCGCGGGGCGCGGUC | 21 | 10657 |
| BCL11A-8914 | - | GAACAGCUCGCGGGGCGCGGUC | 22 | 10658 |
| BCL11A-8915 | - | AGAACAGCUCGCGGGGCGCGGUC | 23 | 10659 |
| BCL11A-8916 | - | GAGAACAGCUCGCGGGGCGCGGUC | 24 | 10660 |
| BCL11A-8917 | - | UACUGUGGGAAAGUCUUC | 18 | 10661 |
| BCL11A-8918 | - | GUACUGUGGGAAAGUCUUC | 19 | 10662 |
| BCL11A-8919 | - | AGUACUGUGGGAAAGUCUUC | 20 | 10663 |
| BCL11A-8920 | - | GAGUACUGUGGGAAAGUCUUC | 21 | 10664 |
| BCL11A-8921 | - | UGAGUACUGUGGGAAAGUCUUC | 22 | 10665 |
| BCL11A-8922 | - | GUGAGUACUGUGGGAAAGUCUUC | 23 | 10666 |
| BCL11A-8923 | - | UGUGAGUACUGUGGGAAAGUCUUC | 24 | 10667 |
| BCL11A-8924 | - | UCCGUGGUGGCCAAGUUC | 18 | 10668 |
| BCL11A-8925 | - | GUCCGUGGUGGCCAAGUUC | 19 | 10669 |
| BCL11A-8926 | - | AGUCCGUGGUGGCCAAGUUC | 20 | 10670 |
| BCL11A-8927 | - | AAGUCCGUGGUGGCCAAGUUC | 21 | 10671 |
| BCL11A-8928 | - | CAAGUCCGUGGUGGCCAAGUUC | 22 | 10672 |
| BCL11A-8929 | - | UCAAGUCCGUGGUGGCCAAGUUC | 23 | 10673 |
| BCL11A-8930 | - | CUCAAGUCCGUGGUGGCCAAGUUC | 24 | 10674 |
| BCL11A-6826 | - | AUUAUUUUGCAGGUAAAG | 18 | 10675 |
| BCL11A-6827 | - | UAUUAUUUUGCAGGUAAAG | 19 | 10676 |
| BCL11A-6828 | - | GUAUUAUUUUGCAGGUAAAG | 20 | 10677 |
| BCL11A-8931 | - | UGCACCCAGGCCAGCAAG | 18 | 10678 |
| BCL11A-8932 | - | GUGCACCCAGGCCAGCAAG | 19 | 10679 |
| BCL11A-8933 | - | CGUGCACCCAGGCCAGCAAG | 20 | 10680 |

TABLE 16E-continued

5th Tier

| gRNA Name | DNA Strand | Targeting Domain | Target Site Length | SEQ ID NO: |
|---|---|---|---|---|
| BCL11A-8934 | - | GCGUGCACCCAGGCCAGCAAG | 21 | 10681 |
| BCL11A-8935 | - | CGCGUGCACCCAGGCCAGCAAG | 22 | 10682 |
| BCL11A-8936 | - | ACGCGUGCACCCAGGCCAGCAAG | 23 | 10683 |
| BCL11A-8937 | - | CACGCGUGCACCCAGGCCAGCAAG | 24 | 10684 |
| BCL11A-8938 | - | ACGAGGAAGAGGAAGAAG | 18 | 10685 |
| BCL11A-8939 | - | GACGAGGAAGAGGAAGAAG | 19 | 10686 |
| BCL11A-3449 | - | CGACGAGGAAGAGGAAGAAG | 20 | 10687 |
| BCL11A-8940 | - | ACGACGAGGAAGAGGAAGAAG | 21 | 10688 |
| BCL11A-8941 | - | GACGACGAGGAAGAGGAAGAAG | 22 | 10689 |
| BCL11A-8942 | - | GGACGACGAGGAAGAGGAAGAAG | 23 | 10690 |
| BCL11A-8943 | - | AGGACGACGAGGAAGAGGAAGAAG | 24 | 10691 |
| BCL11A-8944 | - | ACGACGAGGAAGAGGAAG | 18 | 10692 |
| BCL11A-8945 | - | GACGACGAGGAAGAGGAAG | 19 | 10693 |
| BCL11A-3959 | - | GGACGACGAGGAAGAGGAAG | 20 | 10694 |
| BCL11A-8946 | - | AGGACGACGAGGAAGAGGAAG | 21 | 10695 |
| BCL11A-8947 | - | GAGGACGACGAGGAAGAGGAAG | 22 | 10696 |
| BCL11A-8948 | - | GGAGGACGACGAGGAAGAGGAAG | 23 | 10697 |
| BCL11A-8949 | - | AGGAGGACGACGAGGAAGAGGAAG | 24 | 10698 |
| BCL11A-8950 | - | AGGAGGACGACGAGGAAG | 18 | 10699 |
| BCL11A-8951 | - | GAGGAGGACGACGAGGAAG | 19 | 10700 |
| BCL11A-3448 | - | AGAGGAGGACGACGAGGAAG | 20 | 10701 |
| BCL11A-8952 | - | AAGAGGAGGACGACGAGGAAG | 21 | 10702 |
| BCL11A-8953 | - | GAAGAGGAGGACGACGAGGAAG | 22 | 10703 |
| BCL11A-8954 | - | GGAAGAGGAGGACGACGAGGAAG | 23 | 10704 |
| BCL11A-8955 | - | AGGAAGAGGAGGACGACGAGGAAG | 24 | 10705 |
| BCL11A-8956 | - | AGGAAGAAGAGGAGGAAG | 18 | 10706 |
| BCL11A-8957 | - | GAGGAAGAAGAGGAGGAAG | 19 | 10707 |
| BCL11A-3453 | - | AGAGGAAGAAGAGGAGGAAG | 20 | 10708 |
| BCL11A-8958 | - | AAGAGGAAGAAGAGGAGGAAG | 21 | 10709 |
| BCL11A-8959 | - | GAAGAGGAAGAAGAGGAGGAAG | 22 | 10710 |
| BCL11A-8960 | - | GGAAGAGGAAGAAGAGGAGGAAG | 23 | 10711 |
| BCL11A-8961 | - | AGGAAGAGGAAGAAGAGGAGGAAG | 24 | 10712 |
| BCL11A-8962 | - | ACGGGGACGAGGAGGAAG | 18 | 10713 |
| BCL11A-8963 | - | AACGGGGACGAGGAGGAAG | 19 | 10714 |
| BCL11A-3441 | - | GAACGGGGACGAGGAGGAAG | 20 | 10715 |
| BCL11A-8964 | - | AGAACGGGGACGAGGAGGAAG | 21 | 10716 |
| BCL11A-8965 | - | GAGAACGGGGACGAGGAGGAAG | 22 | 10717 |

TABLE 16E-continued

5th Tier

| gRNA Name | DNA Strand | Targeting Domain | Target Site Length | SEQ ID NO: |
|---|---|---|---|---|
| BCL11A-8966 | - | GGAGAACGGGGACGAGGAGGAAG | 23 | 10718 |
| BCL11A-8967 | - | CGGAGAACGGGGACGAGGAGGAAG | 24 | 10719 |
| BCL11A-8968 | - | GCGCAGCGGCACGGGAAG | 18 | 10720 |
| BCL11A-8969 | - | GGCGCAGCGGCACGGGAAG | 19 | 10721 |
| BCL11A-3376 | - | GGGCGCAGCGGCACGGGAAG | 20 | 10722 |
| BCL11A-8970 | - | GGGGCGCAGCGGCACGGGAAG | 21 | 10723 |
| BCL11A-8971 | - | CGGGGCGCAGCGGCACGGGAAG | 22 | 10724 |
| BCL11A-8972 | - | UCGGGGCGCAGCGGCACGGGAAG | 23 | 10725 |
| BCL11A-8973 | - | CUCGGGGCGCAGCGGCACGGGAAG | 24 | 10726 |
| BCL11A-8974 | - | AGGCUUCCGGCCUGGCAG | 18 | 10727 |
| BCL11A-8975 | - | GAGGCUUCCGGCCUGGCAG | 19 | 10728 |
| BCL11A-8976 | - | AGAGGCUUCCGGCCUGGCAG | 20 | 10729 |
| BCL11A-8977 | - | GAGAGGCUUCCGGCCUGGCAG | 21 | 10730 |
| BCL11A-8978 | - | AGAGAGGCUUCCGGCCUGGCAG | 22 | 10731 |
| BCL11A-8979 | - | GAGAGAGGCUUCCGGCCUGGCAG | 23 | 10732 |
| BCL11A-8980 | - | CGAGAGAGGCUUCCGGCCUGGCAG | 24 | 10733 |
| BCL11A-8981 | - | GAGGAAGAGGAAGAAGAG | 18 | 10734 |
| BCL11A-8982 | - | CGAGGAAGAGGAAGAAGAG | 19 | 10735 |
| BCL11A-3948 | - | ACGAGGAAGAGGAAGAAGAG | 20 | 10736 |
| BCL11A-8983 | - | GACGAGGAAGAGGAAGAAGAG | 21 | 10737 |
| BCL11A-8984 | - | CGACGAGGAAGAGGAAGAAGAG | 22 | 10738 |
| BCL11A-8985 | - | ACGACGAGGAAGAGGAAGAAGAG | 23 | 10739 |
| BCL11A-8986 | - | GACGACGAGGAAGAGGAAGAAGAG | 24 | 10740 |
| BCL11A-8987 | - | GAAGAAGAGGAGGAAGAG | 18 | 10741 |
| BCL11A-8988 | - | GGAAGAAGAGGAGGAAGAG | 19 | 10742 |
| BCL11A-3961 | - | AGGAAGAAGAGGAGGAAGAG | 20 | 10743 |
| BCL11A-8989 | - | GAGGAAGAAGAGGAGGAAGAG | 21 | 10744 |
| BCL11A-8990 | - | AGAGGAAGAAGAGGAGGAAGAG | 22 | 10745 |
| BCL11A-8991 | - | AAGAGGAAGAAGAGGAGGAAGAG | 23 | 10746 |
| BCL11A-8992 | - | GAAGAGGAAGAAGAGGAGGAAGAG | 24 | 10747 |
| BCL11A-8993 | - | GGGGACGAGGAGGAAGAG | 18 | 10748 |
| BCL11A-8994 | - | CGGGGACGAGGAGGAAGAG | 19 | 10749 |
| BCL11A-3945 | - | ACGGGGACGAGGAGGAAGAG | 20 | 10750 |
| BCL11A-8995 | - | AACGGGGACGAGGAGGAAGAG | 21 | 10751 |
| BCL11A-8996 | - | GAACGGGGACGAGGAGGAAGAG | 22 | 10752 |
| BCL11A-8997 | - | AGAACGGGGACGAGGAGGAAGAG | 23 | 10753 |
| BCL11A-8998 | - | GAGAACGGGGACGAGGAGGAAGAG | 24 | 10754 |
| BCL11A-8999 | - | CCGGAGAACGGGGACGAG | 18 | 10755 |

TABLE 16E-continued

5th Tier

| gRNA Name | DNA Strand | Targeting Domain | Target Site Length | SEQ ID NO: |
|---|---|---|---|---|
| BCL11A-9000 | − | CCCGGAGAACGGGGACGAG | 19 | 10756 |
| BCL11A-9001 | − | UCCCGGAGAACGGGGACGAG | 20 | 10757 |
| BCL11A-9002 | − | AUCCCGGAGAACGGGGACGAG | 21 | 10758 |
| BCL11A-9003 | − | GAUCCCGGAGAACGGGGACGAG | 22 | 10759 |
| BCL11A-9004 | − | UGAUCCCGGAGAACGGGGACGAG | 23 | 10760 |
| BCL11A-9005 | − | CUGAUCCCGGAGAACGGGGACGAG | 24 | 10761 |
| BCL11A-9006 | − | GACUCGGUGGCCGGCGAG | 18 | 10762 |
| BCL11A-9007 | − | AGACUCGGUGGCCGGCGAG | 19 | 10763 |
| BCL11A-9008 | − | AAGACUCGGUGGCCGGCGAG | 20 | 10764 |
| BCL11A-9009 | − | GAAGACUCGGUGGCCGGCGAG | 21 | 10765 |
| BCL11A-9010 | − | CGAAGACUCGGUGGCCGGCGAG | 22 | 10766 |
| BCL11A-9011 | − | ACGAAGACUCGGUGGCCGGCGAG | 23 | 10767 |
| BCL11A-9012 | − | GACGAAGACUCGGUGGCCGGCGAG | 24 | 10768 |
| BCL11A-9013 | − | AAGCGCAUCAAGCUCGAG | 18 | 10769 |
| BCL11A-9014 | − | UAAGCGCAUCAAGCUCGAG | 19 | 10770 |
| BCL11A-9015 | − | CUAAGCGCAUCAAGCUCGAG | 20 | 10771 |
| BCL11A-9016 | − | UCUAAGCGCAUCAAGCUCGAG | 21 | 10772 |
| BCL11A-9017 | − | CUCUAAGCGCAUCAAGCUCGAG | 22 | 10773 |
| BCL11A-9018 | − | UCUCUAAGCGCAUCAAGCUCGAG | 23 | 10774 |
| BCL11A-9019 | − | UUCUCUAAGCGCAUCAAGCUCGAG | 24 | 10775 |
| BCL11A-9020 | − | GAAGAGGAGGAAGAGGAG | 18 | 10776 |
| BCL11A-9021 | − | AGAAGAGGAGGAAGAGGAG | 19 | 10777 |
| BCL11A-3964 | − | AAGAAGAGGAGGAAGAGGAG | 20 | 10778 |
| BCL11A-9022 | − | GAAGAAGAGGAGGAAGAGGAG | 21 | 10779 |
| BCL11A-9023 | − | GGAAGAAGAGGAGGAAGAGGAG | 22 | 10780 |
| BCL11A-9024 | − | AGGAAGAAGAGGAGGAAGAGGAG | 23 | 10781 |
| BCL11A-9025 | − | GAGGAAGAAGAGGAGGAAGAGGAG | 24 | 10782 |
| BCL11A-9026 | − | GAGGAGGAAGAGGAGGAG | 18 | 10783 |
| BCL11A-9027 | − | AGAGGAGGAAGAGGAGGAG | 19 | 10784 |
| BCL11A-3965 | − | AAGAGGAGGAAGAGGAGGAG | 20 | 10785 |
| BCL11A-9028 | − | GAAGAGGAGGAAGAGGAGGAG | 21 | 10786 |
| BCL11A-9029 | − | AGAAGAGGAGGAAGAGGAGGAG | 22 | 10787 |
| BCL11A-9030 | − | AAGAAGAGGAGGAAGAGGAGGAG | 23 | 10788 |
| BCL11A-9031 | − | GAAGAAGAGGAGGAAGAGGAGGAG | 24 | 10789 |
| BCL11A-9032 | − | UCCACACCGCCCGGGAG | 18 | 10790 |
| BCL11A-9033 | − | CUCCACACCGCCCGGGAG | 19 | 10791 |
| BCL11A-9034 | − | UCUCCACACCGCCCGGGAG | 20 | 10792 |

TABLE 16E-continued

5th Tier

| gRNA Name | DNA Strand | Targeting Domain | Target Site Length | SEQ ID NO: |
|---|---|---|---|---|
| BCL11A-9035 | - | UUCUCCACACCGCCCGGGGAG | 21 | 10793 |
| BCL11A-9036 | - | CUUCUCCACACCGCCCGGGGAG | 22 | 10794 |
| BCL11A-9037 | - | GCUUCUCCACACCGCCCGGGGAG | 23 | 10795 |
| BCL11A-9038 | - | CGCUUCUCCACACCGCCCGGGGAG | 24 | 10796 |
| BCL11A-9039 | - | GCCGCGAUGCCCAACACG | 18 | 10797 |
| BCL11A-9040 | - | GGCCGCGAUGCCCAACACG | 19 | 10798 |
| BCL11A-9041 | - | CGGCCGCGAUGCCCAACACG | 20 | 10799 |
| BCL11A-9042 | - | CCGGCCGCGAUGCCCAACACG | 21 | 10800 |
| BCL11A-9043 | - | CCCGGCCGCGAUGCCCAACACG | 22 | 10801 |
| BCL11A-9044 | - | CCCCGGCCGCGAUGCCCAACACG | 23 | 10802 |
| BCL11A-9045 | - | CCCCCGGCCGCGAUGCCCAACACG | 24 | 10803 |
| BCL11A-9046 | - | AGGAAGAGGAGGACGACG | 18 | 10804 |
| BCL11A-9047 | - | GAGGAAGAGGAGGACGACG | 19 | 10805 |
| BCL11A-3450 | - | GGAGGAAGAGGAGGACGACG | 20 | 10806 |
| BCL11A-9048 | - | AGGAGGAAGAGGAGGACGACG | 21 | 10807 |
| BCL11A-9049 | - | GAGGAGGAAGAGGAGGACGACG | 22 | 10808 |
| BCL11A-9050 | - | CGAGGAGGAAGAGGAGGACGACG | 23 | 10809 |
| BCL11A-9051 | - | ACGAGGAGGAAGAGGAGGACGACG | 24 | 10810 |
| BCL11A-9052 | - | AGGAGGAAGAGGAGGACG | 18 | 10811 |
| BCL11A-9053 | - | GAGGAGGAAGAGGAGGACG | 19 | 10812 |
| BCL11A-3953 | - | CGAGGAGGAAGAGGAGGACG | 20 | 10813 |
| BCL11A-9054 | - | ACGAGGAGGAAGAGGAGGACG | 21 | 10814 |
| BCL11A-9055 | - | GACGAGGAGGAAGAGGAGGACG | 22 | 10815 |
| BCL11A-9056 | - | GGACGAGGAGGAAGAGGAGGACG | 23 | 10816 |
| BCL11A-9057 | - | GGGACGAGGAGGAAGAGGAGGACG | 24 | 10817 |
| BCL11A-9058 | - | UCCCGGAGAACGGGGACG | 18 | 10818 |
| BCL11A-9059 | - | AUCCCGGAGAACGGGGACG | 19 | 10819 |
| BCL11A-6081 | - | GAUCCCGGAGAACGGGGACG | 20 | 10820 |
| BCL11A-9060 | - | UGAUCCCGGAGAACGGGGACG | 21 | 10821 |
| BCL11A-9061 | - | CUGAUCCCGGAGAACGGGGACG | 22 | 10822 |
| BCL11A-9062 | - | CCUGAUCCCGGAGAACGGGGACG | 23 | 10823 |
| BCL11A-9063 | - | ACCUGAUCCCGGAGAACGGGGACG | 24 | 10824 |
| BCL11A-9064 | - | CGCCCGGGGAGCUGGACG | 18 | 10825 |
| BCL11A-9065 | - | CCGCCCGGGGAGCUGGACG | 19 | 10826 |
| BCL11A-9066 | - | ACCGCCCGGGGAGCUGGACG | 20 | 10827 |
| BCL11A-9067 | - | CACCGCCCGGGGAGCUGGACG | 21 | 10828 |
| BCL11A-9068 | - | ACACCGCCCGGGGAGCUGGACG | 22 | 10829 |
| BCL11A-9069 | - | CACACCGCCCGGGGAGCUGGACG | 23 | 10830 |

TABLE 16E-continued

5th Tier

| gRNA Name | DNA Strand | Targeting Domain | Target Site Length | SEQ ID NO: |
|---|---|---|---|---|
| BCL11A-9070 | - | CCACACCGCCCGGGGAGCUGGACG | 24 | 10831 |
| BCL11A-9071 | - | GAGGAGGAGGAGCUGACG | 18 | 10832 |
| BCL11A-9072 | - | GGAGGAGGAGGAGCUGACG | 19 | 10833 |
| BCL11A-9073 | - | AGGAGGAGGAGGAGCUGACG | 20 | 10834 |
| BCL11A-9074 | - | GAGGAGGAGGAGGAGCUGACG | 21 | 10835 |
| BCL11A-9075 | - | AGAGGAGGAGGAGGAGCUGACG | 22 | 10836 |
| BCL11A-9076 | - | AAGAGGAGGAGGAGGAGCUGACG | 23 | 10837 |
| BCL11A-9077 | - | GAAGAGGAGGAGGAGGAGCUGACG | 24 | 10838 |
| BCL11A-9078 | - | GCUUCUCCACACCGCCCG | 18 | 10839 |
| BCL11A-9079 | - | CGCUUCUCCACACCGCCCG | 19 | 10840 |
| BCL11A-6087 | - | GCGCUUCUCCACACCGCCCG | 20 | 10841 |
| BCL11A-9080 | - | UGCGCUUCUCCACACCGCCCG | 21 | 10842 |
| BCL11A-9081 | - | UUGCGCUUCUCCACACCGCCCG | 22 | 10843 |
| BCL11A-9082 | - | UUUGCGCUUCUCCACACCGCCCG | 23 | 10844 |
| BCL11A-9083 | - | GUUUGCGCUUCUCCACACCGCCCG | 24 | 10845 |
| BCL11A-9084 | - | GACCCCAACCUGAUCCCG | 18 | 10846 |
| BCL11A-9085 | - | CGACCCCAACCUGAUCCCG | 19 | 10847 |
| BCL11A-9086 | - | ACGACCCCAACCUGAUCCCG | 20 | 10848 |
| BCL11A-9087 | - | AACGACCCCAACCUGAUCCCG | 21 | 10849 |
| BCL11A-9088 | - | GAACGACCCCAACCUGAUCCCG | 22 | 10850 |
| BCL11A-9089 | - | AGAACGACCCCAACCUGAUCCCG | 23 | 10851 |
| BCL11A-9090 | - | GAGAACGACCCCAACCUGAUCCCG | 24 | 10852 |
| BCL11A-9091 | - | CGGUCGUGGGCGUGGGCG | 18 | 10853 |
| BCL11A-9092 | - | GCGGUCGUGGGCGUGGGCG | 19 | 10854 |
| BCL11A-9093 | - | CGCGGUCGUGGGCGUGGGCG | 20 | 10855 |
| BCL11A-9094 | - | GCGCGGUCGUGGGCGUGGGCG | 21 | 10856 |
| BCL11A-9095 | - | GGCGCGGUCGUGGGCGUGGGCG | 22 | 10857 |
| BCL11A-9096 | - | GGGCGCGGUCGUGGGCGUGGGCG | 23 | 10858 |
| BCL11A-9097 | - | GGGGCGCGGUCGUGGGCGUGGGCG | 24 | 10859 |
| BCL11A-9098 | - | GCCACAGGGACACUUGCG | 18 | 10860 |
| BCL11A-9099 | - | GGCCACAGGGACACUUGCG | 19 | 10861 |
| BCL11A-9100 | - | GGGCCACAGGGACACUUGCG | 20 | 10862 |
| BCL11A-9101 | - | AGGGCCACAGGGACACUUGCG | 21 | 10863 |
| BCL11A-9102 | - | GAGGGCCACAGGGACACUUGCG | 22 | 10864 |
| BCL11A-9103 | - | CGAGGGCCACAGGGACACUUGCG | 23 | 10865 |
| BCL11A-9104 | - | CCGAGGGCCACAGGGACACUUGCG | 24 | 10866 |
| BCL11A-9105 | - | CCGGGCGAGUCGGCCUCG | 18 | 10867 |

TABLE 16E-continued

5th Tier

| gRNA Name | DNA Strand | Targeting Domain | Target Site Length | SEQ ID NO: |
|---|---|---|---|---|
| BCL11A-9106 | - | CCCGGGCGAGUCGGCCUCG | 19 | 10868 |
| BCL11A-6106 | - | CCCCGGGCGAGUCGGCCUCG | 20 | 10869 |
| BCL11A-9107 | - | UCCCCGGGCGAGUCGGCCUCG | 21 | 10870 |
| BCL11A-9108 | - | CUCCCCGGGCGAGUCGGCCUCG | 22 | 10871 |
| BCL11A-9109 | - | GCUCCCCGGGCGAGUCGGCCUCG | 23 | 10872 |
| BCL11A-9110 | - | UGCUCCCCGGGCGAGUCGGCCUCG | 24 | 10873 |
| BCL11A-9111 | - | UCGUCGGAGCACUCCUCG | 18 | 10874 |
| BCL11A-9112 | - | CUCGUCGGAGCACUCCUCG | 19 | 10875 |
| BCL11A-9113 | - | CCUCGUCGGAGCACUCCUCG | 20 | 10876 |
| BCL11A-9114 | - | UCCUCGUCGGAGCACUCCUCG | 21 | 10877 |
| BCL11A-9115 | - | CUCCUCGUCGGAGCACUCCUCG | 22 | 10878 |
| BCL11A-9116 | - | CCUCCUCGUCGGAGCACUCCUCG | 23 | 10879 |
| BCL11A-9117 | - | GCCUCCUCGUCGGAGCACUCCUCG | 24 | 10880 |
| BCL11A-9118 | - | UCGCCUUUUGCCUCCUCG | 18 | 10881 |
| BCL11A-9119 | - | AUCGCCUUUUGCCUCCUCG | 19 | 10882 |
| BCL11A-9120 | - | AAUCGCCUUUUGCCUCCUCG | 20 | 10883 |
| BCL11A-9121 | - | CAAUCGCCUUUUGCCUCCUCG | 21 | 10884 |
| BCL11A-9122 | - | ACAAUCGCCUUUUGCCUCCUCG | 22 | 10885 |
| BCL11A-9123 | - | GACAAUCGCCUUUUGCCUCCUCG | 23 | 10886 |
| BCL11A-9124 | - | AGACAAUCGCCUUUUGCCUCCUCG | 24 | 10887 |
| BCL11A-9125 | - | CACCACGAGAACAGCUCG | 18 | 10888 |
| BCL11A-9126 | - | CCACCACGAGAACAGCUCG | 19 | 10889 |
| BCL11A-6107 | - | GCCACCACGAGAACAGCUCG | 20 | 10890 |
| BCL11A-9127 | - | CGCCACCACGAGAACAGCUCG | 21 | 10891 |
| BCL11A-9128 | - | GCGCCACCACGAGAACAGCUCG | 22 | 10892 |
| BCL11A-9129 | - | CGCGCCACCACGAGAACAGCUCG | 23 | 10893 |
| BCL11A-9130 | - | GCGCGCCACCACGAGAACAGCUCG | 24 | 10894 |
| BCL11A-9131 | - | CUGGGCAGCCCCAGCUCG | 18 | 10895 |
| BCL11A-9132 | - | GCUGGGCAGCCCCAGCUCG | 19 | 10896 |
| BCL11A-9133 | - | UGCUGGGCAGCCCCAGCUCG | 20 | 10897 |
| BCL11A-9134 | - | CUGCUGGGCAGCCCCAGCUCG | 21 | 10898 |
| BCL11A-9135 | - | GCUGCUGGGCAGCCCCAGCUCG | 22 | 10899 |
| BCL11A-9136 | - | UGCUGCUGGGCAGCCCCAGCUCG | 23 | 10900 |
| BCL11A-9137 | - | CUGCUGCUGGGCAGCCCCAGCUCG | 24 | 10901 |
| BCL11A-9138 | - | AGGAAGAGGAAGAAGAGG | 18 | 10902 |
| BCL11A-9139 | - | GAGGAAGAGGAAGAAGAGG | 19 | 10903 |
| BCL11A-3451 | - | CGAGGAAGAGGAAGAAGAGG | 20 | 10904 |
| BCL11A-9140 | - | ACGAGGAAGAGGAAGAAGAGG | 21 | 10905 |

TABLE 16E-continued

5th Tier

| gRNA Name | DNA Strand | Targeting Domain | Target Site Length | SEQ ID NO: |
|---|---|---|---|---|
| BCL11A-9141 | - | GACGAGGAAGAGGAAGAAGAGG | 22 | 10906 |
| BCL11A-9142 | - | CGACGAGGAAGAGGAAGAAGAGG | 23 | 10907 |
| BCL11A-9143 | - | ACGACGAGGAAGAGGAAGAAGAGG | 24 | 10908 |
| BCL11A-9144 | - | AGGACGACGAGGAAGAGG | 18 | 10909 |
| BCL11A-9145 | - | GAGGACGACGAGGAAGAGG | 19 | 10910 |
| BCL11A-3957 | - | GGAGGACGACGAGGAAGAGG | 20 | 10911 |
| BCL11A-9146 | - | AGGAGGACGACGAGGAAGAGG | 21 | 10912 |
| BCL11A-9147 | - | GAGGAGGACGACGAGGAAGAGG | 22 | 10913 |
| BCL11A-9148 | - | AGAGGAGGACGACGAGGAAGAGG | 23 | 10914 |
| BCL11A-9149 | - | AAGAGGAGGACGACGAGGAAGAGG | 24 | 10915 |
| BCL11A-9150 | - | AAGAAGAGGAGGAAGAGG | 18 | 10916 |
| BCL11A-9151 | - | GAAGAAGAGGAGGAAGAGG | 19 | 10917 |
| BCL11A-3452 | - | GGAAGAAGAGGAGGAAGAGG | 20 | 10918 |
| BCL11A-9152 | - | AGGAAGAAGAGGAGGAAGAGG | 21 | 10919 |
| BCL11A-9153 | - | GAGGAAGAAGAGGAGGAAGAGG | 22 | 10920 |
| BCL11A-9154 | - | AGAGGAAGAAGAGGAGGAAGAGG | 23 | 10921 |
| BCL11A-9155 | - | AAGAGGAAGAAGAGGAGGAAGAGG | 24 | 10922 |
| BCL11A-9156 | - | CUGACGGAGAGCGAGAGG | 18 | 10923 |
| BCL11A-9157 | - | GCUGACGGAGAGCGAGAGG | 19 | 10924 |
| BCL11A-9158 | - | AGCUGACGGAGAGCGAGAGG | 20 | 10925 |
| BCL11A-9159 | - | GAGCUGACGGAGAGCGAGAGG | 21 | 10926 |
| BCL11A-9160 | - | GGAGCUGACGGAGAGCGAGAGG | 22 | 10927 |
| BCL11A-9161 | - | AGGAGCUGACGGAGAGCGAGAGG | 23 | 10928 |
| BCL11A-9162 | - | GAGGAGCUGACGGAGAGCGAGAGG | 24 | 10929 |
| BCL11A-9163 | - | AAGAGGAGGACGACGAGG | 18 | 10930 |
| BCL11A-9164 | - | GAAGAGGAGGACGACGAGG | 19 | 10931 |
| BCL11A-3960 | - | GGAAGAGGAGGACGACGAGG | 20 | 10932 |
| BCL11A-9165 | - | AGGAAGAGGAGGACGACGAGG | 21 | 10933 |
| BCL11A-9166 | - | GAGGAAGAGGAGGACGACGAGG | 22 | 10934 |
| BCL11A-9167 | - | GGAGGAAGAGGAGGACGACGAGG | 23 | 10935 |
| BCL11A-9168 | - | AGGAGGAAGAGGAGGACGACGAGG | 24 | 10936 |
| BCL11A-9169 | - | CGGAGAACGGGGACGAGG | 18 | 10937 |
| BCL11A-9170 | - | CCGGAGAACGGGGACGAGG | 19 | 10938 |
| BCL11A-3330 | - | CCCGGAGAACGGGGACGAGG | 20 | 10939 |
| BCL11A-9171 | - | UCCCGGAGAACGGGGACGAGG | 21 | 10940 |
| BCL11A-9172 | - | AUCCCGGAGAACGGGGACGAGG | 22 | 10941 |
| BCL11A-9173 | - | GAUCCCGGAGAACGGGGACGAGG | 23 | 10942 |

TABLE 16E-continued

5th Tier

| gRNA Name | DNA Strand | Targeting Domain | Target Site Length | SEQ ID NO: |
|---|---|---|---|---|
| BCL11A-9174 | - | UGAUCCCGGAGAACGGGGACGAGG | 24 | 10943 |
| BCL11A-9175 | - | GCGGCCACCUGGCCGAGG | 18 | 10944 |
| BCL11A-9176 | - | CGCGGCCACCUGGCCGAGG | 19 | 10945 |
| BCL11A-9177 | - | GCGCGGCCACCUGGCCGAGG | 20 | 10946 |
| BCL11A-9178 | - | AGCGCGGCCACCUGGCCGAGG | 21 | 10947 |
| BCL11A-9179 | - | AAGCGCGGCCACCUGGCCGAGG | 22 | 10948 |
| BCL11A-9180 | - | UAAGCGCGGCCACCUGGCCGAGG | 23 | 10949 |
| BCL11A-9181 | - | AUAAGCGCGGCCACCUGGCCGAGG | 24 | 10950 |
| BCL11A-9182 | - | AAGAGGAAGAAGAGGAGG | 18 | 10951 |
| BCL11A-9183 | - | GAAGAGGAAGAAGAGGAGG | 19 | 10952 |
| BCL11A-3963 | - | GGAAGAGGAAGAAGAGGAGG | 20 | 10953 |
| BCL11A-9184 | - | AGGAAGAGGAAGAAGAGGAGG | 21 | 10954 |
| BCL11A-9185 | - | GAGGAAGAGGAAGAAGAGGAGG | 22 | 10955 |
| BCL11A-9186 | - | CGAGGAAGAGGAAGAAGAGGAGG | 23 | 10956 |
| BCL11A-9187 | - | ACGAGGAAGAGGAAGAAGAGGAGG | 24 | 10957 |
| BCL11A-9188 | - | AAGAGGAGGAAGAGGAGG | 18 | 10958 |
| BCL11A-9189 | - | GAAGAGGAGGAAGAGGAGG | 19 | 10959 |
| BCL11A-3454 | - | AGAAGAGGAGGAAGAGGAGG | 20 | 10960 |
| BCL11A-9190 | - | AAGAAGAGGAGGAAGAGGAGG | 21 | 10961 |
| BCL11A-9191 | - | GAAGAAGAGGAGGAAGAGGAGG | 22 | 10962 |
| BCL11A-9192 | - | GGAAGAAGAGGAGGAAGAGGAGG | 23 | 10963 |
| BCL11A-9193 | - | AGGAAGAAGAGGAGGAAGAGGAGG | 24 | 10964 |
| BCL11A-9194 | - | AGAACGGGGACGAGGAGG | 18 | 10965 |
| BCL11A-9195 | - | GAGAACGGGGACGAGGAGG | 19 | 10966 |
| BCL11A-3918 | - | GGAGAACGGGGACGAGGAGG | 20 | 10967 |
| BCL11A-9196 | - | CGGAGAACGGGGACGAGGAGG | 21 | 10968 |
| BCL11A-9197 | - | CCGGAGAACGGGGACGAGGAGG | 22 | 10969 |
| BCL11A-9198 | - | CCCGGAGAACGGGGACGAGGAGG | 23 | 10970 |
| BCL11A-9199 | - | UCCCGGAGAACGGGGACGAGGAGG | 24 | 10971 |
| BCL11A-9200 | - | AGGAGGAAGAGGAGGAGG | 18 | 10972 |
| BCL11A-9201 | - | GAGGAGGAAGAGGAGGAGG | 19 | 10973 |
| BCL11A-3455 | - | AGAGGAGGAAGAGGAGGAGG | 20 | 10974 |
| BCL11A-9202 | - | AAGAGGAGGAAGAGGAGGAGG | 21 | 10975 |
| BCL11A-9203 | - | GAAGAGGAGGAAGAGGAGGAGG | 22 | 10976 |
| BCL11A-9204 | - | AGAAGAGGAGGAAGAGGAGGAGG | 23 | 10977 |
| BCL11A-9205 | - | AAGAAGAGGAGGAAGAGGAGGAGG | 24 | 10978 |
| BCL11A-9206 | - | ACCGGCGCAGCCACACGG | 18 | 10979 |
| BCL11A-9207 | - | CACCGGCGCAGCCACACGG | 19 | 10980 |

TABLE 16E-continued

5th Tier

| gRNA Name | DNA Strand | Targeting Domain | Target Site Length | SEQ ID NO: |
|---|---|---|---|---|
| BCL11A-3764 | - | GCACCGGCGCAGCCACACGG | 20 | 10981 |
| BCL11A-9208 | - | UGCACCGGCGCAGCCACACGG | 21 | 10982 |
| BCL11A-9209 | - | GUGCACCGGCGCAGCCACACGG | 22 | 10983 |
| BCL11A-9210 | - | GGUGCACCGGCGCAGCCACACGG | 23 | 10984 |
| BCL11A-9211 | - | UGGUGCACCGGCGCAGCCACACGG | 24 | 10985 |
| BCL11A-9212 | - | UAGAGCGCCUGGGGCGG | 18 | 10986 |
| BCL11A-9213 | - | AUAGAGCGCCUGGGGCGG | 19 | 10987 |
| BCL11A-9214 | - | CAUAGAGCGCCUGGGGCGG | 20 | 10988 |
| BCL11A-9215 | - | GCAUAGAGCGCCUGGGGCGG | 21 | 10989 |
| BCL11A-9216 | - | CGCAUAGAGCGCCUGGGGCGG | 22 | 10990 |
| BCL11A-9217 | - | CCGCAUAGAGCGCCUGGGGCGG | 23 | 10991 |
| BCL11A-9218 | - | ACCGCAUAGAGCGCCUGGGGCGG | 24 | 10992 |
| BCL11A-9219 | - | AUGUGUGGCAGUUUUCGG | 18 | 10993 |
| BCL11A-9220 | - | GAUGUGUGGCAGUUUUCGG | 19 | 10994 |
| BCL11A-9221 | - | AGAUGUGUGGCAGUUUUCGG | 20 | 10995 |
| BCL11A-9222 | - | AAGAUGUGUGGCAGUUUUCGG | 21 | 10996 |
| BCL11A-9223 | - | CAAGAUGUGUGGCAGUUUUCGG | 22 | 10997 |
| BCL11A-9224 | - | UCAAGAUGUGUGGCAGUUUUCGG | 23 | 10998 |
| BCL11A-9225 | - | CUCAAGAUGUGUGGCAGUUUUCGG | 24 | 10999 |
| BCL11A-9226 | - | AAUUUGAAGCCCCCAGGG | 18 | 11000 |
| BCL11A-9227 | - | AAAUUUGAAGCCCCCAGGG | 19 | 11001 |
| BCL11A-9228 | - | AAAAUUUGAAGCCCCCAGGG | 20 | 11002 |
| BCL11A-9229 | - | GAAAAUUUGAAGCCCCCAGGG | 21 | 11003 |
| BCL11A-9230 | - | AGAAAAUUUGAAGCCCCCAGGG | 22 | 11004 |
| BCL11A-9231 | - | GAGAAAAUUUGAAGCCCCCAGGG | 23 | 11005 |
| BCL11A-9232 | - | UGAGAAAAUUUGAAGCCCCCAGGG | 24 | 11006 |
| BCL11A-9233 | - | GUGGACUACGGCUUCGGG | 18 | 11007 |
| BCL11A-9234 | - | GGUGGACUACGGCUUCGGG | 19 | 11008 |
| BCL11A-9235 | - | GGGUGGACUACGGCUUCGGG | 20 | 11009 |
| BCL11A-9236 | - | AGGGUGGACUACGGCUUCGGG | 21 | 11010 |
| BCL11A-9237 | - | GAGGGUGGACUACGGCUUCGGG | 22 | 11011 |
| BCL11A-9238 | - | AGAGGGUGGACUACGGCUUCGGG | 23 | 11012 |
| BCL11A-9239 | - | GAGAGGGUGGACUACGGCUUCGGG | 24 | 11013 |
| BCL11A-9240 | - | UGAUCCCGGAGAACGGGG | 18 | 11014 |
| BCL11A-9241 | - | CUGAUCCCGGAGAACGGGG | 19 | 11015 |
| BCL11A-9242 | - | CCUGAUCCCGGAGAACGGGG | 20 | 11016 |
| BCL11A-9243 | - | ACCUGAUCCCGGAGAACGGGG | 21 | 11017 |

TABLE 16E-continued

5th Tier

| gRNA Name | DNA Strand | Targeting Domain | Target Site Length | SEQ ID NO: |
|---|---|---|---|---|
| BCL11A-9244 | - | AACCUGAUCCCGGAGAACGGGG | 22 | 11018 |
| BCL11A-9245 | - | CAACCUGAUCCCGGAGAACGGGG | 23 | 11019 |
| BCL11A-9246 | - | CCAACCUGAUCCCGGAGAACGGGG | 24 | 11020 |
| BCL11A-9247 | - | GCAUAGAGCGCCUGGGGG | 18 | 11021 |
| BCL11A-9248 | - | CGCAUAGAGCGCCUGGGGG | 19 | 11022 |
| BCL11A-6143 | - | CCGCAUAGAGCGCCUGGGGG | 20 | 11023 |
| BCL11A-9249 | - | ACCGCAUAGAGCGCCUGGGGG | 21 | 11024 |
| BCL11A-9250 | - | CACCGCAUAGAGCGCCUGGGGG | 22 | 11025 |
| BCL11A-9251 | - | CCACCGCAUAGAGCGCCUGGGGG | 23 | 11026 |
| BCL11A-9252 | - | CCCACCGCAUAGAGCGCCUGGGGG | 24 | 11027 |
| BCL11A-9253 | - | CGCAUAGAGCGCCUGGGG | 18 | 11028 |
| BCL11A-9254 | - | CCGCAUAGAGCGCCUGGGG | 19 | 11029 |
| BCL11A-9255 | - | ACCGCAUAGAGCGCCUGGGG | 20 | 11030 |
| BCL11A-9256 | - | CACCGCAUAGAGCGCCUGGGG | 21 | 11031 |
| BCL11A-9257 | - | CCACCGCAUAGAGCGCCUGGGG | 22 | 11032 |
| BCL11A-9258 | - | CCCACCGCAUAGAGCGCCUGGGG | 23 | 11033 |
| BCL11A-9259 | - | CCCCACCGCAUAGAGCGCCUGGGG | 24 | 11034 |
| BCL11A-9260 | - | AUAAGCGCGGCCACCUGG | 18 | 11035 |
| BCL11A-9261 | - | CAUAAGCGCGGCCACCUGG | 19 | 11036 |
| BCL11A-9262 | - | GCAUAAGCGCGGCCACCUGG | 20 | 11037 |
| BCL11A-9263 | - | AGCAUAAGCGCGGCCACCUGG | 21 | 11038 |
| BCL11A-9264 | - | AAGCAUAAGCGCGGCCACCUGG | 22 | 11039 |
| BCL11A-9265 | - | GAAGCAUAAGCGCGGCCACCUGG | 23 | 11040 |
| BCL11A-9266 | - | AGAAGCAUAAGCGCGGCCACCUGG | 24 | 11041 |
| BCL11A-9267 | - | GAGAGGCUUCCGGCCUGG | 18 | 11042 |
| BCL11A-9268 | - | AGAGAGGCUUCCGGCCUGG | 19 | 11043 |
| BCL11A-9269 | - | GAGAGAGGCUUCCGGCCUGG | 20 | 11044 |
| BCL11A-9270 | - | CGAGAGAGGCUUCCGGCCUGG | 21 | 11045 |
| BCL11A-9271 | - | UCGAGAGAGGCUUCCGGCCUGG | 22 | 11046 |
| BCL11A-9272 | - | AUCGAGAGAGGCUUCCGGCCUGG | 23 | 11047 |
| BCL11A-9273 | - | UAUCGAGAGAGGCUUCCGGCCUGG | 24 | 11048 |
| BCL11A-9274 | - | CCUUCCACCAGGUCCUGG | 18 | 11049 |
| BCL11A-9275 | - | GCCUUCCACCAGGUCCUGG | 19 | 11050 |
| BCL11A-9276 | - | GGCCUUCCACCAGGUCCUGG | 20 | 11051 |
| BCL11A-9277 | - | AGGCCUUCCACCAGGUCCUGG | 21 | 11052 |
| BCL11A-9278 | - | GAGGCCUUCCACCAGGUCCUGG | 22 | 11053 |
| BCL11A-9279 | - | CGAGGCCUUCCACCAGGUCCUGG | 23 | 11054 |
| BCL11A-9280 | - | GCGAGGCCUUCCACCAGGUCCUGG | 24 | 11055 |

TABLE 16E-continued

5th Tier

| gRNA Name | DNA Strand | Targeting Domain | Target Site Length | SEQ ID NO: |
|---|---|---|---|---|
| BCL11A-9281 | − | GGAGACUUAGAGAGCUGG | 18 | 11056 |
| BCL11A-9282 | − | AGGAGACUUAGAGAGCUGG | 19 | 11057 |
| BCL11A-9283 | − | UAGGAGACUUAGAGAGCUGG | 20 | 11058 |
| BCL11A-9284 | − | CUAGGAGACUUAGAGAGCUGG | 21 | 11059 |
| BCL11A-9285 | − | UCUAGGAGACUUAGAGAGCUGG | 22 | 11060 |
| BCL11A-9286 | − | CUCUAGGAGACUUAGAGAGCUGG | 23 | 11061 |
| BCL11A-9287 | − | UCUCUAGGAGACUUAGAGAGCUGG | 24 | 11062 |
| BCL11A-9288 | − | CACCGCCCGGGGAGCUGG | 18 | 11063 |
| BCL11A-9289 | − | ACACCGCCCGGGGAGCUGG | 19 | 11064 |
| BCL11A-9290 | − | CACACCGCCCGGGGAGCUGG | 20 | 11065 |
| BCL11A-9291 | − | CCACACCGCCCGGGGAGCUGG | 21 | 11066 |
| BCL11A-9292 | − | UCCACACCGCCCGGGGAGCUGG | 22 | 11067 |
| BCL11A-9293 | − | CUCCACACCGCCCGGGGAGCUGG | 23 | 11068 |
| BCL11A-9294 | − | UCUCCACACCGCCCGGGGAGCUGG | 24 | 11069 |
| BCL11A-9295 | − | CAGCGGCACGGGAAGUGG | 18 | 11070 |
| BCL11A-9296 | − | GCAGCGGCACGGGAAGUGG | 19 | 11071 |
| BCL11A-6157 | − | CGCAGCGGCACGGGAAGUGG | 20 | 11072 |
| BCL11A-9297 | − | GCGCAGCGGCACGGGAAGUGG | 21 | 11073 |
| BCL11A-9298 | − | GGCGCAGCGGCACGGGAAGUGG | 22 | 11074 |
| BCL11A-9299 | − | GGGCGCAGCGGCACGGGAAGUGG | 23 | 11075 |
| BCL11A-9300 | − | GGGGCGCAGCGGCACGGGAAGUGG | 24 | 11076 |
| BCL11A-9301 | − | GCCCUGCCCGACGUCAUG | 18 | 11077 |
| BCL11A-9302 | − | CGCCCUGCCCGACGUCAUG | 19 | 11078 |
| BCL11A-9303 | − | GCGCCCUGCCCGACGUCAUG | 20 | 11079 |
| BCL11A-9304 | − | CGCGCCCUGCCCGACGUCAUG | 21 | 11080 |
| BCL11A-9305 | − | CCGCGCCCUGCCCGACGUCAUG | 22 | 11081 |
| BCL11A-9306 | − | GCCGCGCCCUGCCCGACGUCAUG | 23 | 11082 |
| BCL11A-9307 | − | AGCCGCGCCCUGCCCGACGUCAUG | 24 | 11083 |
| BCL11A-9308 | − | CGACACUUGUGAGUACUG | 18 | 11084 |
| BCL11A-9309 | − | GCGACACUUGUGAGUACUG | 19 | 11085 |
| BCL11A-6169 | − | AGCGACACUUGUGAGUACUG | 20 | 11086 |
| BCL11A-9310 | − | CAGCGACACUUGUGAGUACUG | 21 | 11087 |
| BCL11A-9311 | − | GCAGCGACACUUGUGAGUACUG | 22 | 11088 |
| BCL11A-9312 | − | CGCAGCGACACUUGUGAGUACUG | 23 | 11089 |
| BCL11A-9313 | − | ACGCAGCGACACUUGUGAGUACUG | 24 | 11090 |
| BCL11A-9314 | − | GAGGAGGAGGAGGAGCUG | 18 | 11091 |
| BCL11A-9315 | − | AGAGGAGGAGGAGGAGCUG | 19 | 11092 |

TABLE 16E-continued

5th Tier

| gRNA Name | DNA Strand | Targeting Domain | Target Site Length | SEQ ID NO: |
|---|---|---|---|---|
| BCL11A-9316 | - | AAGAGGAGGAGGAGGAGCUG | 20 | 11093 |
| BCL11A-9317 | - | GAAGAGGAGGAGGAGGAGCUG | 21 | 11094 |
| BCL11A-9318 | - | GGAAGAGGAGGAGGAGGAGCUG | 22 | 11095 |
| BCL11A-9319 | - | AGGAAGAGGAGGAGGAGGAGCUG | 23 | 11096 |
| BCL11A-9320 | - | GAGGAAGAGGAGGAGGAGGAGCUG | 24 | 11097 |
| BCL11A-9321 | - | CUGUCCAAAAAGCUGCUG | 18 | 11098 |
| BCL11A-9322 | - | CCUGUCCAAAAAGCUGCUG | 19 | 11099 |
| BCL11A-9323 | - | GCCUGUCCAAAAAGCUGCUG | 20 | 11100 |
| BCL11A-9324 | - | GGCCUGUCCAAAAAGCUGCUG | 21 | 11101 |
| BCL11A-9325 | - | GGGCCUGUCCAAAAAGCUGCUG | 22 | 11102 |
| BCL11A-9326 | - | GGGGCCUGUCCAAAAAGCUGCUG | 23 | 11103 |
| BCL11A-9327 | - | GGGGGCCUGUCCAAAAAGCUGCUG | 24 | 11104 |
| BCL11A-9328 | - | GCAGCGGCACGGGAAGUG | 18 | 11105 |
| BCL11A-9329 | - | CGCAGCGGCACGGGAAGUG | 19 | 11106 |
| BCL11A-9330 | - | GCGCAGCGGCACGGGAAGUG | 20 | 11107 |
| BCL11A-9331 | - | GGCGCAGCGGCACGGGAAGUG | 21 | 11108 |
| BCL11A-9332 | - | GGGCGCAGCGGCACGGGAAGUG | 22 | 11109 |
| BCL11A-9333 | - | GGGGCGCAGCGGCACGGGAAGUG | 23 | 11110 |
| BCL11A-9334 | - | CGGGGCGCAGCGGCACGGGAAGUG | 24 | 11111 |
| BCL11A-9335 | - | CCCGGCACCAGCGACUUG | 18 | 11112 |
| BCL11A-9336 | - | ACCCGGCACCAGCGACUUG | 19 | 11113 |
| BCL11A-9337 | - | AACCCGGCACCAGCGACUUG | 20 | 11114 |
| BCL11A-9338 | - | GAACCCGGCACCAGCGACUUG | 21 | 11115 |
| BCL11A-9339 | - | GGAACCCGGCACCAGCGACUUG | 22 | 11116 |
| BCL11A-9340 | - | CGGAACCCGGCACCAGCGACUUG | 23 | 11117 |
| BCL11A-9341 | - | CCGGAACCCGGCACCAGCGACUUG | 24 | 11118 |
| BCL11A-9342 | - | CUUAAGUUCUGAGAAAAU | 18 | 11119 |
| BCL11A-9343 | - | CCUUAAGUUCUGAGAAAAU | 19 | 11120 |
| BCL11A-9344 | - | CCCUUAAGUUCUGAGAAAAU | 20 | 11121 |
| BCL11A-9345 | - | GCCCUUAAGUUCUGAGAAAAU | 21 | 11122 |
| BCL11A-9346 | - | AGCCCUUAAGUUCUGAGAAAAU | 22 | 11123 |
| BCL11A-9347 | - | GAGCCCUUAAGUUCUGAGAAAAU | 23 | 11124 |
| BCL11A-9348 | - | AGAGCCCUUAAGUUCUGAGAAAAU | 24 | 11125 |
| BCL11A-9349 | - | GGAUUUCUCUAGGAGACU | 18 | 11126 |
| BCL11A-9350 | - | UGGAUUUCUCUAGGAGACU | 19 | 11127 |
| BCL11A-9351 | - | AUGGAUUUCUCUAGGAGACU | 20 | 11128 |
| BCL11A-9352 | - | CAUGGAUUUCUCUAGGAGACU | 21 | 11129 |
| BCL11A-9353 | - | CCAUGGAUUUCUCUAGGAGACU | 22 | 11130 |

TABLE 16E-continued

5th Tier

| gRNA Name | DNA Strand | Targeting Domain | Target Site Length | SEQ ID NO: |
|---|---|---|---|---|
| BCL11A-9354 | − | GCCAUGGAUUUCUCUAGGAGACU | 23 | 11131 |
| BCL11A-9355 | − | CGCCAUGGAUUUCUCUAGGAGACU | 24 | 11132 |
| BCL11A-9356 | − | AUGGAUUAAGAAUCUACU | 18 | 11133 |
| BCL11A-9357 | − | CAUGGAUUAAGAAUCUACU | 19 | 11134 |
| BCL11A-9358 | − | UCAUGGAUUAAGAAUCUACU | 20 | 11135 |
| BCL11A-9359 | − | CUCAUGGAUUAAGAAUCUACU | 21 | 11136 |
| BCL11A-9360 | − | ACUCAUGGAUUAAGAAUCUACU | 22 | 11137 |
| BCL11A-9361 | − | CACUCAUGGAUUAAGAAUCUACU | 23 | 11138 |
| BCL11A-9362 | − | ACACUCAUGGAUUAAGAAUCUACU | 24 | 11139 |
| BCL11A-9363 | − | GCGACACUUGUGAGUACU | 18 | 11140 |
| BCL11A-9364 | − | AGCGACACUUGUGAGUACU | 19 | 11141 |
| BCL11A-9365 | − | CAGCGACACUUGUGAGUACU | 20 | 11142 |
| BCL11A-9366 | − | GCAGCGACACUUGUGAGUACU | 21 | 11143 |
| BCL11A-9367 | − | CGCAGCGACACUUGUGAGUACU | 22 | 11144 |
| BCL11A-9368 | − | ACGCAGCGACACUUGUGAGUACU | 23 | 11145 |
| BCL11A-9369 | − | GACGCAGCGACACUUGUGAGUACU | 24 | 11146 |
| BCL11A-9370 | − | CCACCGCAUAGAGCGCCU | 18 | 11147 |
| BCL11A-9371 | − | CCCACCGCAUAGAGCGCCU | 19 | 11148 |
| BCL11A-6197 | − | CCCCACCGCAUAGAGCGCCU | 20 | 11149 |
| BCL11A-9372 | − | CCCCCACCGCAUAGAGCGCCU | 21 | 11150 |
| BCL11A-9373 | − | ACCCCCACCGCAUAGAGCGCCU | 22 | 11151 |
| BCL11A-9374 | − | GACCCCCACCGCAUAGAGCGCCU | 23 | 11152 |
| BCL11A-9375 | − | GGACCCCCACCGCAUAGAGCGCCU | 24 | 11153 |
| BCL11A-9376 | − | CCCCGGGCGAGUCGGCCU | 18 | 11154 |
| BCL11A-9377 | − | UCCCCGGGCGAGUCGGCCU | 19 | 11155 |
| BCL11A-6200 | − | CUCCCCGGGCGAGUCGGCCU | 20 | 11156 |
| BCL11A-9378 | − | GCUCCCCGGGCGAGUCGGCCU | 21 | 11157 |
| BCL11A-9379 | − | UGCUCCCCGGGCGAGUCGGCCU | 22 | 11158 |
| BCL11A-9380 | − | CUGCUCCCCGGGCGAGUCGGCCU | 23 | 11159 |
| BCL11A-9381 | − | GCUGCUCCCCGGGCGAGUCGGCCU | 24 | 11160 |
| BCL11A-9382 | − | CCUCGUCGGAGCACUCCU | 18 | 11161 |
| BCL11A-9383 | − | UCCUCGUCGGAGCACUCCU | 19 | 11162 |
| BCL11A-6202 | − | CUCCUCGUCGGAGCACUCCU | 20 | 11163 |
| BCL11A-9384 | − | CCUCCUCGUCGGAGCACUCCU | 21 | 11164 |
| BCL11A-9385 | − | GCCUCCUCGUCGGAGCACUCCU | 22 | 11165 |
| BCL11A-9386 | − | UGCCUCCUCGUCGGAGCACUCCU | 23 | 11166 |
| BCL11A-9387 | − | UUGCCUCCUCGUCGGAGCACUCCU | 24 | 11167 |

TABLE 16E-continued

5th Tier

| gRNA Name | DNA Strand | Targeting Domain | Target Site Length | SEQ ID NO: |
|---|---|---|---|---|
| BCL11A-9388 | - | AAGAUCCCUUCCUUAGCU | 18 | 11168 |
| BCL11A-9389 | - | AAAGAUCCCUUCCUUAGCU | 19 | 11169 |
| BCL11A-9390 | - | CAAAGAUCCCUUCCUUAGCU | 20 | 11170 |
| BCL11A-9391 | - | UCAAAGAUCCCUUCCUUAGCU | 21 | 11171 |
| BCL11A-9392 | - | CUCAAAGAUCCCUUCCUUAGCU | 22 | 11172 |
| BCL11A-9393 | - | GCUCAAAGAUCCCUUCCUUAGCU | 23 | 11173 |
| BCL11A-9394 | - | AGCUCAAAGAUCCCUUCCUUAGCU | 24 | 11174 |
| BCL11A-9395 | - | AGAGGGUGGACUACGGCU | 18 | 11175 |
| BCL11A-9396 | - | GAGAGGGUGGACUACGGCU | 19 | 11176 |
| BCL11A-9397 | - | CGAGAGGGUGGACUACGGCU | 20 | 11177 |
| BCL11A-9398 | - | GCGAGAGGGUGGACUACGGCU | 21 | 11178 |
| BCL11A-9399 | - | AGCGAGAGGGUGGACUACGGCU | 22 | 11179 |
| BCL11A-9400 | - | GAGCGAGAGGGUGGACUACGGCU | 23 | 11180 |
| BCL11A-9401 | - | AGAGCGAGAGGGUGGACUACGGCU | 24 | 11181 |
| BCL11A-9402 | - | CGGUUGAAUCCAAUGGCU | 18 | 11182 |
| BCL11A-9403 | - | GCGGUUGAAUCCAAUGGCU | 19 | 11183 |
| BCL11A-9404 | - | UGCGGUUGAAUCCAAUGGCU | 20 | 11184 |
| BCL11A-9405 | - | CUGCGGUUGAAUCCAAUGGCU | 21 | 11185 |
| BCL11A-9406 | - | GCUGCGGUUGAAUCCAAUGGCU | 22 | 11186 |
| BCL11A-9407 | - | UGCUGCGGUUGAAUCCAAUGGCU | 23 | 11187 |
| BCL11A-9408 | - | GUGCUGCGGUUGAAUCCAAUGGCU | 24 | 11188 |
| BCL11A-9409 | - | AGCUGGACGGAGGGAUCU | 18 | 11189 |
| BCL11A-9410 | - | GAGCUGGACGGAGGGAUCU | 19 | 11190 |
| BCL11A-6210 | - | GGAGCUGGACGGAGGGAUCU | 20 | 11191 |
| BCL11A-9411 | - | GGGAGCUGGACGGAGGGAUCU | 21 | 11192 |
| BCL11A-9412 | - | GGGGAGCUGGACGGAGGGAUCU | 22 | 11193 |
| BCL11A-9413 | - | CGGGGAGCUGGACGGAGGGAUCU | 23 | 11194 |
| BCL11A-9414 | - | CCGGGGAGCUGGACGGAGGGAUCU | 24 | 11195 |
| BCL11A-9415 | - | CCCGCCAUGGAUUUCUCU | 18 | 11196 |
| BCL11A-9416 | - | UCCCGCCAUGGAUUUCUCU | 19 | 11197 |
| BCL11A-6212 | - | CUCCCGCCAUGGAUUUCUCU | 20 | 11198 |
| BCL11A-9417 | - | CCUCCCGCCAUGGAUUUCUCU | 21 | 11199 |
| BCL11A-9418 | - | GCCUCCCGCCAUGGAUUUCUCU | 22 | 11200 |
| BCL11A-9419 | - | AGCCUCCCGCCAUGGAUUUCUCU | 23 | 11201 |
| BCL11A-9420 | - | GAGCCUCCCGCCAUGGAUUUCUCU | 24 | 11202 |
| BCL11A-9421 | - | CGAGAGCCCUUAAGUUCU | 18 | 11203 |
| BCL11A-9422 | - | UCGAGAGCCCUUAAGUUCU | 19 | 11204 |
| BCL11A-9423 | - | CUCGAGAGCCCUUAAGUUCU | 20 | 11205 |

TABLE 16E-continued

5th Tier

| gRNA Name | DNA Strand | Targeting Domain | Target Site Length | SEQ ID NO: |
|---|---|---|---|---|
| BCL11A-9424 | - | GCUCGAGAGCCCUUAAGUUCU | 21 | 11206 |
| BCL11A-9425 | - | AGCUCGAGAGCCCUUAAGUUCU | 22 | 11207 |
| BCL11A-9426 | - | AAGCUCGAGAGCCCUUAAGUUCU | 23 | 11208 |
| BCL11A-9427 | - | GAAGCUCGAGAGCCCUUAAGUUCU | 24 | 11209 |
| BCL11A-9428 | - | CGCCUUUUGCCUCCUCGU | 18 | 11210 |
| BCL11A-9429 | - | UCGCCUUUUGCCUCCUCGU | 19 | 11211 |
| BCL11A-6220 | - | AUCGCCUUUUGCCUCCUCGU | 20 | 11212 |
| BCL11A-9430 | - | AAUCGCCUUUUGCCUCCUCGU | 21 | 11213 |
| BCL11A-9431 | - | CAAUCGCCUUUUGCCUCCUCGU | 22 | 11214 |
| BCL11A-9432 | - | ACAAUCGCCUUUUGCCUCCUCGU | 23 | 11215 |
| BCL11A-9433 | - | GACAAUCGCCUUUUGCCUCCUCGU | 24 | 11216 |
| BCL11A-9434 | - | ACGCCCCAUAUUAGUGGU | 18 | 11217 |
| BCL11A-9435 | - | CACGCCCCAUAUUAGUGGU | 19 | 11218 |
| BCL11A-9436 | - | GCACGCCCCAUAUUAGUGGU | 20 | 11219 |
| BCL11A-9437 | - | AGCACGCCCCAUAUUAGUGGU | 21 | 11220 |
| BCL11A-9438 | - | GAGCACGCCCCAUAUUAGUGGU | 22 | 11221 |
| BCL11A-9439 | - | GGAGCACGCCCCAUAUUAGUGGU | 23 | 11222 |
| BCL11A-9440 | - | GGGAGCACGCCCCAUAUUAGUGGU | 24 | 11223 |
| BCL11A-9441 | - | GACACUUGUGAGUACUGU | 18 | 11224 |
| BCL11A-9442 | - | CGACACUUGUGAGUACUGU | 19 | 11225 |
| BCL11A-6230 | - | GCGACACUUGUGAGUACUGU | 20 | 11226 |
| BCL11A-9443 | - | AGCGACACUUGUGAGUACUGU | 21 | 11227 |
| BCL11A-9444 | - | CAGCGACACUUGUGAGUACUGU | 22 | 11228 |
| BCL11A-9445 | - | GCAGCGACACUUGUGAGUACUGU | 23 | 11229 |
| BCL11A-9446 | - | CGCAGCGACACUUGUGAGUACUGU | 24 | 11230 |
| BCL11A-9447 | - | CGCGGGUUGGUAUCCCUU | 18 | 11231 |
| BCL11A-9448 | - | CCGCGGGUUGGUAUCCCUU | 19 | 11232 |
| BCL11A-9449 | - | CCCGCGGGUUGGUAUCCCUU | 20 | 11233 |
| BCL11A-9450 | - | CCCCGCGGGUUGGUAUCCCUU | 21 | 11234 |
| BCL11A-9451 | - | ACCCCGCGGGUUGGUAUCCCUU | 22 | 11235 |
| BCL11A-9452 | - | GACCCCGCGGGUUGGUAUCCCUU | 23 | 11236 |
| BCL11A-9453 | - | UGACCCCGCGGGUUGGUAUCCCUU | 24 | 11237 |
| BCL11A-9454 | - | AGAUCCCUUCCUUAGCUU | 18 | 11238 |
| BCL11A-9455 | - | AAGAUCCCUUCCUUAGCUU | 19 | 11239 |
| BCL11A-6234 | - | AAAGAUCCCUUCCUUAGCUU | 20 | 11240 |
| BCL11A-9456 | - | CAAAGAUCCCUUCCUUAGCUU | 21 | 11241 |
| BCL11A-9457 | - | UCAAAGAUCCCUUCCUUAGCUU | 22 | 11242 |

TABLE 16E-continued

5th Tier

| gRNA Name | DNA Strand | Targeting Domain | Target Site Length | SEQ ID NO: |
|---|---|---|---|---|
| BCL11A-9458 | − | CUCAAAGAUCCCUUCCUUAGCUU | 23 | 11243 |
| BCL11A-9459 | − | GCUCAAAGAUCCCUUCCUUAGCUU | 24 | 11244 |
| BCL11A-9460 | − | CUCGAGAGCCCUUAAGUU | 18 | 11245 |
| BCL11A-9461 | − | GCUCGAGAGCCCUUAAGUU | 19 | 11246 |
| BCL11A-9462 | − | AGCUCGAGAGCCCUUAAGUU | 20 | 11247 |
| BCL11A-9463 | − | AAGCUCGAGAGCCCUUAAGUU | 21 | 11248 |
| BCL11A-9464 | − | GAAGCUCGAGAGCCCUUAAGUU | 22 | 11249 |
| BCL11A-9465 | − | GGAAGCUCGAGAGCCCUUAAGUU | 23 | 11250 |
| BCL11A-9466 | − | UGGAAGCUCGAGAGCCCUUAAGUU | 24 | 11251 |
| BCL11A-9467 | − | GGCAAGACGUUCAAAUUU | 18 | 11252 |
| BCL11A-9468 | − | CGGCAAGACGUUCAAAUUU | 19 | 11253 |
| BCL11A-9469 | − | GCGGCAAGACGUUCAAAUUU | 20 | 11254 |
| BCL11A-9470 | − | UGCGGCAAGACGUUCAAAUUU | 21 | 11255 |
| BCL11A-9471 | − | CUGCGGCAAGACGUUCAAAUUU | 22 | 11256 |
| BCL11A-9472 | − | UCUGCGGCAAGACGUUCAAAUUU | 23 | 11257 |
| BCL11A-9473 | − | UUCUGCGGCAAGACGUUCAAAUUU | 24 | 11258 |

Table 17A provides exemplary targeting domains for knocking out the BCL11A gene selected according to the first tier parameters. The targeting domains bind within the first 500 bp of the coding sequence (e.g., within 500 bp downstream from the start codon) and have a high level of orthogonality. It is contemplated herein that in an embodiment the targeting domain hybridizes to the target domain through complementary base pairing. Any of the targeting domains in the table can be used with a *N. meningitidis* Cas9 molecule that generates a double stranded break (Cas9 nuclease) or a single-stranded break (Cas9 nickase).

TABLE 17A

1st Tier

| gRNA Name | DNA Strand | Targeting Domain | Target Site Length | SEQ ID NO: |
|---|---|---|---|---|
| BCL11A-9474 | + | CGAUUGGUGAAGGGGAA | 17 | 11259 |
| BCL11A-9475 | + | AUUGGAUGCUUUUUUCA | 17 | 11260 |
| BCL11A-9476 | − | CAGGUCACGCCAGAGGA | 17 | 11261 |
| BCL11A-9477 | + | CUUACGCGAGAAUUCCC | 17 | 11262 |
| BCL11A-9478 | + | CCUGGAUGCCAACCUCC | 17 | 11263 |
| BCL11A-9479 | − | AACAAUGCAAUGGCAGC | 17 | 11264 |
| BCL11A-9480 | + | GGGGAAGGUGGCUUAUC | 17 | 11265 |
| BCL11A-9481 | + | GGUUCAUCAUCUGUAAG | 17 | 11266 |
| BCL11A-5334 | + | UGCACUCAUCCCAGGCG | 17 | 11267 |

TABLE 17A-continued

1st Tier

| gRNA Name | DNA Strand | Targeting Domain | Target Site Length | SEQ ID NO: |
|---|---|---|---|---|
| BCL11A-9482 | + | UUAAGUGCUGGGGUUUG | 17 | 11268 |
| BCL11A-9483 | + | CCAACCUCCACGGGAUU | 17 | 11269 |
| BCL11A-9484 | + | UCUCGAUUGGUGAAGGGGAA | 20 | 11270 |
| BCL11A-9485 | + | GGGAUUGGAUGCUUUUUUCA | 20 | 11271 |
| BCL11A-9486 | − | AUCCAGGUCACGCCAGAGGA | 20 | 11272 |
| BCL11A-9487 | + | UUACUUACGCGAGAAUUCCC | 20 | 11273 |
| BCL11A-6420 | + | UGACCUGGAUGCCAACCUCC | 20 | 11274 |
| BCL11A-9488 | − | GGAAACAAUGCAAUGGCAGC | 20 | 11275 |
| BCL11A-9489 | + | GAAGGGGAAGGUGGCUUAUC | 20 | 11276 |
| BCL11A-9490 | + | UCUGGUUCAUCAUCUGUAAG | 20 | 11277 |
| BCL11A-5480 | + | UUCUGCACUCAUCCCAGGCG | 20 | 11278 |

TABLE 17A-continued

1st Tier

| gRNA Name | DNA Strand | Targeting Domain | Target Site Length | SEQ ID NO: |
|---|---|---|---|---|
| BCL11A-9491 | + | UGCUUAAGUGCUGGGGUUUG | 20 | 11279 |
| BCL11A-9492 | + | AUGCCAACCUCCACGGGAUU | 20 | 11280 |

Table 17B provides exemplary targeting domains for knocking out the BCL11A gene selected according to the third tier parameters. The targeting domains fall in the coding sequence of the gene, downstream of the first 500 bp of coding sequence (e.g., anywhere from +500 (relative to the start codon) to the stop codon of the gene). It is contemplated herein that in an embodiment the targeting domain hybridizes to the target domain through complementary base pairing. Any of the targeting domains in the table can be used with a *N. meningindis* Cas9 molecule that generates a double stranded break (Cas9 nuclease) or a single-stranded break (Cas9 nickase).

TABLE 17B

3rd Tier

| gRNA Name | DNA Strand | Targeting Domain | Target Site Length | SEQ ID NO: |
|---|---|---|---|---|
| BCL11A-5515 | + | UCCGACGAGGAGGCAAA | 17 | 11281 |
| BCL11A-5520 | − | CUUCCGGCCUGGCAGAA | 17 | 11282 |
| BCL11A-9493 | + | UCCGUGUUCGCUUUCUA | 17 | 11283 |
| BCL11A-9494 | − | AGAGCGAGAGGGUGGAC | 17 | 11284 |
| BCL11A-9495 | + | CGGGAGGCUCCAUAGCC | 17 | 11285 |
| BCL11A-9496 | − | UUCCCAGCCACCUCUCC | 17 | 11286 |
| BCL11A-9497 | + | AGCUGGGGCUGCCCAGC | 17 | 11287 |
| BCL11A-9498 | − | GCUAUGGAGCCUCCCGC | 17 | 11288 |
| BCL11A-9499 | + | CGGCCAGGUGGCCGCGC | 17 | 11289 |
| BCL11A-9500 | + | GCGUCUUCAUGUGGCGC | 17 | 11290 |
| BCL11A-9501 | + | UCAGAACUUAAGGGCUC | 17 | 11291 |
| BCL11A-9502 | − | AGCUCAAAGAUCCCUUC | 17 | 11292 |
| BCL11A-9503 | + | GCAGGUCGAACUCCUUC | 17 | 11293 |
| BCL11A-9504 | + | GGGGCGUCGCCAGGAAG | 17 | 11294 |
| BCL11A-9505 | − | CCAGGAUCAGUAUCGAG | 17 | 11295 |
| BCL11A-9506 | + | GGCUGGGAGGGAGGAGG | 17 | 11296 |
| BCL11A-9507 | + | GACUUGACCGUCAUGGG | 17 | 11297 |
| BCL11A-9508 | + | CGGCCUCGGCCAGGUGG | 17 | 11298 |
| BCL11A-5799 | + | GCAUGUGCGUCUUCAUG | 17 | 11299 |
| BCL11A-9509 | + | CGCACAGGUUGCACUUG | 17 | 11300 |
| BCL11A-9510 | + | ACUCCUUCUCGAGCUUG | 17 | 11301 |

TABLE 17B-continued

3rd Tier

| gRNA Name | DNA Strand | Targeting Domain | Target Site Length | SEQ ID NO: |
|---|---|---|---|---|
| BCL11A-9511 | − | AACACGCACAGAACACU | 17 | 11302 |
| BCL11A-9512 | − | CCUCGGAGAACGGGAGU | 17 | 11303 |
| BCL11A-9513 | + | GGUCAGGGGACUUCCGU | 17 | 11304 |
| BCL11A-5874 | + | UGCUCCGACGAGGAGGCAAA | 20 | 11305 |
| BCL11A-5879 | − | AGGCUUCCGGCCUGGCAGAA | 20 | 11306 |
| BCL11A-9514 | + | ACUUCCGUGUUCGCUUUCUA | 20 | 11307 |
| BCL11A-9515 | − | CGGAGAGCGAGAGGGUGGAC | 20 | 11308 |
| BCL11A-9516 | + | UGGCGGGAGGCUCCAUAGCC | 20 | 11309 |
| BCL11A-8754 | − | UCCUUCCCAGCCACCUCUCC | 20 | 11310 |
| BCL11A-9517 | + | GCGAGCUGGGGCUGCCCAGC | 20 | 11311 |
| BCL11A-9518 | − | AUGGCUAUGGAGCCUCCCGC | 20 | 11312 |
| BCL11A-9519 | + | CCUCGGCCAGGUGGCCGCGC | 20 | 11313 |
| BCL11A-9520 | + | UGUGCGUCUUCAUGUGGCGC | 20 | 11314 |
| BCL11A-7725 | + | UUCUCAGAACUUAAGGGCUC | 20 | 11315 |
| BCL11A-9521 | − | GGCAGCUCAAAGAUCCCUUC | 20 | 11316 |
| BCL11A-7752 | + | GGGGCAGGUCGAACUCCUUC | 20 | 11317 |
| BCL11A-9522 | + | GGGGGGGCGUCGCCAGGAAG | 20 | 11318 |
| BCL11A-9523 | − | AUACCAGGAUCAGUAUCGAG | 20 | 11319 |
| BCL11A-9524 | + | GGGGGCUGGGAGGGAGGAGG | 20 | 11320 |
| BCL11A-9525 | + | UCGGACUUGACCGUCAUGGG | 20 | 11321 |
| BCL11A-9526 | + | CCUCGGCCUCGGCCAGGUGG | 20 | 11322 |
| BCL11A-6165 | + | UGUGCAUGUGCGUCUUCAUG | 20 | 11323 |
| BCL11A-8204 | + | GGUCGCACAGGUUGCACUUG | 20 | 11324 |
| BCL11A-9527 | + | CGAACUCCUUCUCGAGCUUG | 20 | 11325 |
| BCL11A-9528 | − | UGCAACACGCACAGAACACU | 20 | 11326 |
| BCL11A-9529 | − | ACUCCUCGGAGAACGGGAGU | 20 | 11327 |

TABLE 17B-continued

3rd Tier

| gRNA Name | DNA Strand | Targeting Domain | Target Site Length | SEQ ID NO: |
|---|---|---|---|---|
| BCL11A-9530 | + | CGGGGUCAGGGGACUUCCGU | 20 | 11328 |

Table 18A provides exemplary targeting domains for knocking down the BCL11A gene selected according to the first tier parameters. The targeting domains bind within 500 bp (e.g., upstream or downstream) of a transcription start site (TSS) and have a high level of orthogonality. It is contemplated herein that in an embodiment the targeting domain hybridizes to the target domain through complementary base pairing. Any of the targeting domains in the table can be used with a *S. pyogenes* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 18A

1st Tier

| gRNA Name | DNA Strand | Targeting Domain | Target Site Length | SEQ ID NO: |
|---|---|---|---|---|
| BCL11A-9531 | + | AAGUGCAUACACGGCAA | 17 | 11329 |
| BCL11A-5319 | + | UUGCUUGCGGCGAGACA | 17 | 11330 |
| BCL11A-5320 | - | AUGUCUCGCCGCAAGCA | 17 | 11331 |
| BCL11A-9532 | - | UGACGUUCAAGUUCGCA | 17 | 11332 |
| BCL11A-9533 | + | UUGUGGGAGAGCCGUCA | 17 | 11333 |
| BCL11A-9534 | + | ACGGCAAUGGUUCCAGA | 17 | 11334 |
| BCL11A-9535 | - | GCGCUCGCUGCGGCCAC | 17 | 11335 |
| BCL11A-4560 | + | ACGCCAGACGCGGCCCC | 17 | 11336 |
| BCL11A-9536 | + | UUCACAUCGGGAGAGCC | 17 | 11337 |
| BCL11A-9537 | + | GUUCACAUCGGGAGAGC | 17 | 11338 |
| BCL11A-9538 | - | UAAUCACGAGAGCGCGC | 17 | 11339 |
| BCL11A-9539 | - | CUGACGUUCAAGUUCGC | 17 | 11340 |
| BCL11A-5327 | + | CCCGUUUGCUUAAGUGC | 17 | 11341 |
| BCL11A-9540 | + | ACGGCUCGGUUCACAUC | 17 | 11342 |
| BCL11A-9541 | + | CUUGAACGUCAGGAGUC | 17 | 11343 |
| BCL11A-9542 | + | CUGCGAACUUGAACGUC | 17 | 11344 |
| BCL11A-9543 | - | CCCCCGGGGCCGCGUC | 17 | 11345 |
| BCL11A-9544 | + | UCCGCGGACGCCAGACG | 17 | 11346 |
| BCL11A-9545 | - | GACUAGAAGCAAAAGCG | 17 | 11347 |
| BCL11A-5335 | + | AGACAUGGUGGGCUGCG | 17 | 11348 |
| BCL11A-9546 | - | AAAACCUCCGAGAGUCG | 17 | 11349 |

TABLE 18A-continued

1st Tier

| gRNA Name | DNA Strand | Targeting Domain | Target Site Length | SEQ ID NO: |
|---|---|---|---|---|
| BCL11A-9547 | + | UUUACCUCGACUCUCGG | 17 | 11350 |
| BCL11A-9548 | - | AGUCCGCGUGUGUGGGG | 17 | 11351 |
| BCL11A-5336 | + | CGUUUGCUUAAGUGCUG | 17 | 11352 |
| BCL11A-9549 | - | UAGAGUCCGCGUGUGUG | 17 | 11353 |
| BCL11A-9550 | + | GACGGCUCGGUUCACAU | 17 | 11354 |
| BCL11A-9551 | - | CUCCCCGCACUGGCCAU | 17 | 11355 |
| BCL11A-9552 | + | CGGCAAUGGUUCCAGAU | 17 | 11356 |
| BCL11A-9553 | + | GCGGGCGGACGACGGCU | 17 | 11357 |
| BCL11A-5338 | + | CCGUUUGCUUAAGUGCU | 17 | 11358 |
| BCL11A-5340 | + | UUGCGGCGAGACAUGGU | 17 | 11359 |
| BCL11A-9554 | + | CGUGGCCGGGAGAGAAGAAA | 20 | 11360 |
| BCL11A-5345 | + | GCCUUGCUUGCGGCGAGACA | 20 | 11361 |
| BCL11A-5346 | - | ACCAUGUCUCGCCGCAAGCA | 20 | 11362 |
| BCL11A-9555 | - | UCCUGACGUUCAAGUUCGCA | 20 | 11363 |
| BCL11A-9556 | + | ACACCAAUGGACACACAUCA | 20 | 11364 |
| BCL11A-9557 | + | UACACGGCAAUGGUUCCAGA | 20 | 11365 |
| BCL11A-9558 | + | GCCAAUGGCCAGUGCGGGGA | 20 | 11366 |
| BCL11A-9559 | + | AAUGGUUCCAGAUGGGAUGA | 20 | 11367 |
| BCL11A-9560 | - | GAGUCUCCUUCUUUCUAACC | 20 | 11368 |
| BCL11A-9561 | + | CGGUUCACAUCGGGAGAGCC | 20 | 11369 |
| BCL11A-9562 | + | UCGGUUCACAUCGGGAGAGC | 20 | 11370 |
| BCL11A-9563 | - | CCGCGUGUGGGGGGGAGC | 20 | 11371 |
| BCL11A-9564 | - | UAAUAAUCACGAGAGCGCGC | 20 | 11372 |
| BCL11A-9565 | + | AAAUAAUACAAAGAUGGCGC | 20 | 11373 |
| BCL11A-9566 | - | CUCCUGACGUUCAAGUUCGC | 20 | 11374 |
| BCL11A-9567 | + | GAGACACACAAAACAUGGGC | 20 | 11375 |
| BCL11A-5352 | + | AUUCCCGUUUGCUUAAGUGC | 20 | 11376 |
| BCL11A-9568 | + | ACGACGGCUCGGUUCACAUC | 20 | 11377 |

TABLE 18A-continued

1st Tier

| gRNA Name | DNA Strand | Targeting Domain | Target Site Length | SEQ ID NO: |
|---|---|---|---|---|
| BCL11A-9569 | − | CGCACUUGAACUUGCAGCUC | 20 | 11378 |
| BCL11A-9570 | + | UCCCUGCGAACUUGAACGUC | 20 | 11379 |
| BCL11A-9571 | − | UCGAGGUAAAAGAGAUAAAG | 20 | 11380 |
| BCL11A-9572 | + | CCAAUGGCCAGUGCGGGGAG | 20 | 11381 |
| BCL11A-4351 | + | GACGCCAGACGCGGCCCCCG | 20 | 11382 |
| BCL11A-9573 | − | UGCGGCCACUGGUGAGCCCG | 20 | 11383 |
| BCL11A-9574 | − | GGGGCCGCGUCUGGCGUCCG | 20 | 11384 |
| BCL11A-5359 | + | GCGAGACAUGGUGGGCUGCG | 20 | 11385 |
| BCL11A-9575 | − | AGAAAAACCUCCGAGAGUCG | 20 | 11386 |
| BCL11A-4561 | + | ACGCCAGACGCGGCCCCCGG | 20 | 11387 |
| BCL11A-9576 | + | UCUUUUACCUCGACUCUCGG | 20 | 11388 |
| BCL11A-9577 | − | UAGAGUCCGCGUGUGUGGGG | 20 | 11389 |
| BCL11A-9578 | − | UUUAGAGUCCGCGUGUGUGG | 20 | 11390 |
| BCL11A-9579 | + | CAAUGGUUCCAGAUGGGAUG | 20 | 11391 |
| BCL11A-5361 | + | CGGCGAGACAUGGUGGGCUG | 20 | 11392 |
| BCL11A-9580 | + | CUGAGCUGCAAGUUCAAGUG | 20 | 11393 |
| BCL11A-9581 | − | CAUUUUAGAGUCCGCGUGUG | 20 | 11394 |
| BCL11A-9582 | + | GACGACGGCUCGGUUCACAU | 20 | 11395 |
| BCL11A-9583 | − | AGCCCCUGAUGUGUGUCCAU | 20 | 11396 |
| BCL11A-9584 | + | GCGGCGGGCGGACGACGGCU | 20 | 11397 |
| BCL11A-9585 | + | AUCUCUUUUACCUCGACUCU | 20 | 11398 |
| BCL11A-5365 | + | UGCUUGCGGCGAGACAUGGU | 20 | 11399 |
| BCL11A-9586 | − | AUUUUAGAGUCCGCGUGUGU | 20 | 11400 |

Table 18B provides exemplary targeting domains for knocking down the BCL11A gene selected according to the second tier parameters. The targeting domains bind within 500 bp (e.g., upstream or downstream) of a transcription start site (TSS). It is contemplated herein that in an embodiment the targeting domain hybridizes to the target domain through complementary base pairing. Any of the targeting domains in the table can be used with a *S. pyogenes* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 18B

2nd Tier

| gRNA Name | DNA Strand | Targeting Domain | Target Site Length | SEQ ID NO: |
|---|---|---|---|---|
| BCL11A-9587 | + | GAGAGAGAUGAAAAAAA | 17 | 11401 |
| BCL11A-5369 | − | CCCAGCACUUAAGCAAA | 17 | 11402 |
| BCL11A-9588 | − | UUAUUUUGGAUGUCAAA | 17 | 11403 |
| BCL11A-4473 | + | GGCCGGGAGAGAAGAAA | 17 | 11404 |
| BCL11A-9589 | + | GCAGGGGUGGGAGGAAA | 17 | 11405 |
| BCL11A-9590 | − | GAGGUAAAAGAGAUAAA | 17 | 11406 |
| BCL11A-9591 | + | AAUUAAAUAAAAUUAAA | 17 | 11407 |
| BCL11A-9592 | + | GGGGAAGCUCACACCAA | 17 | 11408 |
| BCL11A-4574 | + | AGACCAGGACAAGCCAA | 17 | 11409 |
| BCL11A-9593 | + | UGGCCGGGAGAGAAGAA | 17 | 11410 |
| BCL11A-4491 | + | GGGCGAGCAGGAGAGAA | 17 | 11411 |

TABLE 18B-continued

2nd Tier

| gRNA Name | DNA Strand | Targeting Domain | Target Site Length | SEQ ID NO: |
|---|---|---|---|---|
| BCL11A-9594 | + | GGCAGGGGUGGGAGGAA | 17 | 11412 |
| BCL11A-4570 | + | AGAAGGGGAGGAGGGAA | 17 | 11413 |
| BCL11A-9595 | - | CGAGGUAAAAGAGAUAA | 17 | 11414 |
| BCL11A-4625 | + | CAGAGACACACAAAACA | 17 | 11415 |
| BCL11A-9596 | + | UCUCAAAAGUGCAUACA | 17 | 11416 |
| BCL11A-9597 | - | GUGUGUGGGGGGGAGCA | 17 | 11417 |
| BCL11A-9598 | + | AAUACAAAGAUGGCGCA | 17 | 11418 |
| BCL11A-9599 | + | CACACAAAACAUGGGCA | 17 | 11419 |
| BCL11A-9600 | + | AGAAGAAAGGGGUGGCA | 17 | 11420 |
| BCL11A-9601 | + | CCAAUGGACACACAUCA | 17 | 11421 |
| BCL11A-9602 | - | CUUGAACUUGCAGCUCA | 17 | 11422 |
| BCL11A-4529 | + | AAAAAAAAAAAAAAGA | 17 | 11423 |
| BCL11A-9603 | + | UAGAAAUAAUACAAAGA | 17 | 11424 |
| BCL11A-9604 | + | GAGCCGGGUUAGAAAGA | 17 | 11425 |
| BCL11A-4592 | + | AGGGCGAGCAGGAGAGA | 17 | 11426 |
| BCL11A-4534 | - | AAAGCGAGGGGAGAGA | 17 | 11427 |
| BCL11A-9605 | + | GAGAGAAGAGAGAUAGA | 17 | 11428 |
| BCL11A-4674 | + | CGGCGGCGGGCGGACGA | 17 | 11429 |
| BCL11A-4494 | + | GGGGAGGGGCGGGCCGA | 17 | 11430 |
| BCL11A-9606 | - | ACUAGAAGCAAAAGCGA | 17 | 11431 |
| BCL11A-4591 | + | AGGAGAGAAGGGGAGGA | 17 | 11432 |
| BCL11A-4399 | + | GAGAAGGGGAGGAGGGA | 17 | 11433 |
| BCL11A-4499 | + | GGGGCGGGCCGAGGGGA | 17 | 11434 |
| BCL11A-9607 | + | AAUGGCCAGUGCGGGGA | 17 | 11435 |
| BCL11A-4562 | + | ACGCGGCCCCGGGGGA | 17 | 11436 |
| BCL11A-9608 | + | AACGUCAGGAGUCUGGA | 17 | 11437 |
| BCL11A-9609 | - | UUAAAAAAAAGCCAUGA | 17 | 11438 |
| BCL11A-9610 | + | GGUUCCAGAUGGGAUGA | 17 | 11439 |
| BCL11A-5383 | - | CCAGCACUUAAGCAAAC | 17 | 11440 |
| BCL11A-9611 | - | CCUCCCCCUCCCCGCAC | 17 | 11441 |
| BCL11A-9612 | - | UCUCCUUCUUUCUAACC | 17 | 11442 |
| BCL11A-9613 | + | GACAUGAAAAGAGACC | 17 | 11443 |
| BCL11A-4662 | + | CGCCAGACGCGGCCCCC | 17 | 11444 |
| BCL11A-9614 | - | CGGCCCGCCCCUCCCCC | 17 | 11445 |
| BCL11A-9615 | - | UCGGCCCGCCCCUCCCC | 17 | 11446 |
| BCL11A-9616 | + | GCGGCGGUGGCGUGGCC | 17 | 11447 |
| BCL11A-9617 | - | ACCCCUUUCUUCUCUCC | 17 | 11448 |

TABLE 18B-continued

2nd Tier

| gRNA Name | DNA Strand | Targeting Domain | Target Site Length | SEQ ID NO: |
|---|---|---|---|---|
| BCL11A-9618 | − | UGGCCAUUGGCUUGUCC | 17 | 11449 |
| BCL11A-9619 | + | ACAUGGGCAGGGCGAGC | 17 | 11450 |
| BCL11A-9620 | − | CGUGUGUGGGGGGGAGC | 17 | 11451 |
| BCL11A-9621 | + | GGGGGCGCUGGGGCCGC | 17 | 11452 |
| BCL11A-4646 | + | CCGAGGGGAGGGGCGC | 17 | 11453 |
| BCL11A-9622 | + | UAAUACAAAGAUGGCGC | 17 | 11454 |
| BCL11A-4441 | + | GCGGCGGCGGCGGCGGC | 17 | 11455 |
| BCL11A-9623 | + | GGACACACAUCAGGGGC | 17 | 11456 |
| BCL11A-4429 | + | GCCCCCGGGGGAGGGGC | 17 | 11457 |
| BCL11A-5392 | + | AUGGUGGGCUGCGGGGC | 17 | 11458 |
| BCL11A-9624 | + | AGGGGGAGGUGCGGGGC | 17 | 11459 |
| BCL11A-9625 | + | ACACACAAAACAUGGGC | 17 | 11460 |
| BCL11A-9626 | + | CGCGGCGGUGGCGUGGC | 17 | 11461 |
| BCL11A-9627 | + | GAGAAGAAAGGGGUGGC | 17 | 11462 |
| BCL11A-5395 | + | GAGACAUGGUGGGCUGC | 17 | 11463 |
| BCL11A-9628 | + | AAGCCAAUGGCCAGUGC | 17 | 11464 |
| BCL11A-9629 | + | CGGGGAGGGGGAGGUGC | 17 | 11465 |
| BCL11A-9630 | + | ACCAAUGGACACACAUC | 17 | 11466 |
| BCL11A-9631 | − | AAAACCCUCAUCCCAUC | 17 | 11467 |
| BCL11A-9632 | − | ACUUGAACUUGCAGCUC | 17 | 11468 |
| BCL11A-9633 | − | GAUGAAGAUAUUUUCUC | 17 | 11469 |
| BCL11A-4528 | + | AAAAAAAAAAAAAAAG | 17 | 11470 |
| BCL11A-4433 | + | GCCGGGAGAGAAGAAAG | 17 | 11471 |
| BCL11A-9634 | − | AGGUAAAAGAGAUAAAG | 17 | 11472 |
| BCL11A-4475 | + | GGCGAGCAGGAGAGAAG | 17 | 11473 |
| BCL11A-4389 | + | GAAGGGGAGGAGGGAAG | 17 | 11474 |
| BCL11A-9635 | + | GGCCGCGGGCUCACCAG | 17 | 11475 |
| BCL11A-9636 | + | GAAGAAAGGGGUGGCAG | 17 | 11476 |
| BCL11A-9637 | + | CAAUGGACACACAUCAG | 17 | 11477 |
| BCL11A-9638 | − | UUGAACUUGCAGCUCAG | 17 | 11478 |
| BCL11A-4543 | − | AAGCGAGGGGAGAGAG | 17 | 11479 |
| BCL11A-4533 | − | AAAAGCGAGGGGAGAG | 17 | 11480 |
| BCL11A-4485 | + | GGGAGGGGCGGGCCGAG | 17 | 11481 |
| BCL11A-9639 | − | CUAGAAGCAAAAGCGAG | 17 | 11482 |
| BCL11A-4492 | + | GGGCGGGCCGAGGGGAG | 17 | 11483 |
| BCL11A-9640 | + | AUGGCCAGUGCGGGGAG | 17 | 11484 |
| BCL11A-4665 | + | CGCGGCCCCCGGGGGAG | 17 | 11485 |
| BCL11A-9641 | + | AGAGAGAAGAGAGAUAG | 17 | 11486 |

TABLE 18B-continued

2nd Tier

| gRNA Name | DNA Strand | Targeting Domain | Target Site Length | SEQ ID NO: |
|---|---|---|---|---|
| BCL11A-9642 | + | GCUCCCCCCCACACACG | 17 | 11487 |
| BCL11A-4427 | + | GCCAGACGCGGCCCCCG | 17 | 11488 |
| BCL11A-9643 | - | GGCCCGCCCCUCCCCCG | 17 | 11489 |
| BCL11A-9644 | - | GGCCACUGGUGAGCCCG | 17 | 11490 |
| BCL11A-4670 | - | CGGCCACGCCACCGCCG | 17 | 11491 |
| BCL11A-4470 | + | GGCCGCAGCGAGCGCCG | 17 | 11492 |
| BCL11A-4502 | + | GGGGGAGGGGCGGGCCG | 17 | 11493 |
| BCL11A-9645 | + | AGGGGGCGCUGGGGCCG | 17 | 11494 |
| BCL11A-9646 | + | CGGGGCGGGGGCUCCG | 17 | 11495 |
| BCL11A-9647 | - | GCCGCGUCUGGCGUCCG | 17 | 11496 |
| BCL11A-9648 | + | GGGGGAGGUGCGGGGCG | 17 | 11497 |
| BCL11A-9649 | + | GCGCCGCGGCGGUGGCG | 17 | 11498 |
| BCL11A-9650 | + | AGCCAAUGGCCAGUGCG | 17 | 11499 |
| BCL11A-9651 | + | GGGGAGGGGGAGGUGCG | 17 | 11500 |
| BCL11A-9652 | - | GGUAAAAGAGAUAAAGG | 17 | 11501 |
| BCL11A-9653 | - | UGAACUUGCAGCUCAGG | 17 | 11502 |
| BCL11A-9654 | - | UAGAAGCAAAAGCGAGG | 17 | 11503 |
| BCL11A-4627 | + | CAGGAGAGAAGGGGAGG | 17 | 11504 |
| BCL11A-4480 | + | GGCGGGCCGAGGGGAGG | 17 | 11505 |
| BCL11A-9655 | + | UGGCCAGUGCGGGGAGG | 17 | 11506 |
| BCL11A-4634 | + | CCAGACGCGGCCCCCGG | 17 | 11507 |
| BCL11A-9656 | - | GCCCGCCCCUCCCCCGG | 17 | 11508 |
| BCL11A-4660 | + | CGCAGCGAGCGCCGCGG | 17 | 11509 |
| BCL11A-4588 | + | AGCGAGCGCCGCGGCGG | 17 | 11510 |
| BCL11A-4478 | + | GGCGGCGGCGGCGGCGG | 17 | 11511 |
| BCL11A-4447 | + | GCGGGCGGCGGCGGCGG | 17 | 11512 |
| BCL11A-4500 | + | GGGGCGGGCGGCGGCGG | 17 | 11513 |
| BCL11A-5409 | + | UGCGGGGCGGGCGGCGG | 17 | 11514 |
| BCL11A-5410 | + | GGCUGCGGGGCGGGCGG | 17 | 11515 |
| BCL11A-9657 | + | GGGGAGGUGCGGGGCGG | 17 | 11516 |
| BCL11A-9658 | + | GGGGUGGGAGGAAAGGG | 17 | 11517 |
| BCL11A-9659 | - | GAACUUGCAGCUCAGGG | 17 | 11518 |
| BCL11A-4444 | + | GCGGCGGCGGCGGCGGG | 17 | 11519 |
| BCL11A-5411 | + | GUGGGCUGCGGGGCGGG | 17 | 11520 |
| BCL11A-9660 | + | GGGAGGUGCGGGGCGGG | 17 | 11521 |
| BCL11A-4483 | + | GGGAGAGAAGAAAGGGG | 17 | 11522 |
| BCL11A-4407 | + | GAGCAGGAGAGAAGGGG | 17 | 11523 |

TABLE 18B-continued

2nd Tier

| gRNA Name | DNA Strand | Targeting Domain | Target Site Length | SEQ ID NO: |
|---|---|---|---|---|
| BCL11A-9661 | + | GAAAGGGUGGCAGGGG | 17 | 11524 |
| BCL11A-4593 | + | AGGGGCGGGCCGAGGGG | 17 | 11525 |
| BCL11A-4467 | + | GGCCCCGGGGAGGGG | 17 | 11526 |
| BCL11A-5413 | + | CAUGGUGGGCUGCGGGG | 17 | 11527 |
| BCL11A-9662 | + | CAAUGGCCAGUGCGGGG | 17 | 11528 |
| BCL11A-9663 | + | GAGGGGAGGUGCGGGG | 17 | 11529 |
| BCL11A-9664 | + | CCAGUGCGGGGAGGGGG | 17 | 11530 |
| BCL11A-4395 | + | GACGCGGCCCCCGGGGG | 17 | 11531 |
| BCL11A-9665 | + | GGGAGGAAAGGGUGGGG | 17 | 11532 |
| BCL11A-9666 | + | UGGGAGGAAAGGGUGGG | 17 | 11533 |
| BCL11A-9667 | + | GGGGUGGCAGGGGUGGG | 17 | 11534 |
| BCL11A-9668 | − | GAGUCCGCGUGUGUGGG | 17 | 11535 |
| BCL11A-5414 | + | CUUGCGGCGAGACAUGG | 17 | 11536 |
| BCL11A-9669 | + | GUGGGAGGAAAGGGUGG | 17 | 11537 |
| BCL11A-9670 | − | AGAGUCCGCGUGUGUGG | 17 | 11538 |
| BCL11A-9671 | + | UGGUUCCAGAUGGGAUG | 17 | 11539 |
| BCL11A-9672 | + | GAGGGGAGGGGGCGCUG | 17 | 11540 |
| BCL11A-9673 | − | CGCCGCGGCGCUCGCUG | 17 | 11541 |
| BCL11A-5422 | + | CGAGACAUGGUGGGCUG | 17 | 11542 |
| BCL11A-9674 | + | AGCUGCAAGUUCAAGUG | 17 | 11543 |
| BCL11A-9675 | + | CAAGCCAAUGGCCAGUG | 17 | 11544 |
| BCL11A-9676 | + | GCGGGGAGGGGAGGUG | 17 | 11545 |
| BCL11A-9677 | + | GGUGGGAGGAAAGGGUG | 17 | 11546 |
| BCL11A-9678 | − | UUUAGAGUCCGCGUGUG | 17 | 11547 |
| BCL11A-9679 | + | GCAGGGAAGAUGAAUUG | 17 | 11548 |
| BCL11A-5426 | + | GGGGUUUGCCUUGCUUG | 17 | 11549 |
| BCL11A-9680 | + | AGAGACACACAAAACAU | 17 | 11550 |
| BCL11A-9681 | − | CCCUGAUGUGUGUCCAU | 17 | 11551 |
| BCL11A-5431 | + | AUUAUUAUUACUAUUAU | 17 | 11552 |
| BCL11A-9682 | − | CCAGCGCCCCUCCCCU | 17 | 11553 |
| BCL11A-9683 | + | CGAGGGGAGGGGGCGCU | 17 | 11554 |
| BCL11A-9684 | + | UCUUUUACCUCGACUCU | 17 | 11555 |
| BCL11A-9685 | + | GGGUGGGAGGAAAGGGU | 17 | 11556 |
| BCL11A-9686 | + | AAAGGGGUGGCAGGGGU | 17 | 11557 |
| BCL11A-9687 | − | UUAGAGUCCGCGUGUGU | 17 | 11558 |
| BCL11A-9688 | + | CAGGGAAGAUGAAUUGU | 17 | 11559 |
| BCL11A-5439 | + | UUAUUAUUACUAUUAUU | 17 | 11560 |
| BCL11A-9689 | − | UUAUUUCUAAUUUAUUU | 17 | 11561 |

TABLE 18B-continued

| | | 2nd Tier | | |
|---|---|---|---|---|
| gRNA Name | DNA Strand | Targeting Domain | Target Site Length | SEQ ID NO: |
| BCL11A-9690 | + | AGAGAGAGAGAUGAAAAAAA | 20 | 11562 |
| BCL11A-5443 | − | AACCCCAGCACUUAAGCAAA | 20 | 11563 |
| BCL11A-9691 | − | AAUUUAUUUUGGAUGUCAAA | 20 | 11564 |
| BCL11A-9692 | + | GUGGCAGGGGUGGGAGGAAA | 20 | 11565 |
| BCL11A-9693 | − | GUCGAGGUAAAAGAGAUAAA | 20 | 11566 |
| BCL11A-9694 | + | UAAAAUUAAAUAAAAUUAAA | 20 | 11567 |
| BCL11A-9695 | + | GAAGGGGAAGCUCACACCAA | 20 | 11568 |
| BCL11A-4541 | + | AAGAGACCAGGACAAGCCAA | 20 | 11569 |
| BCL11A-9696 | + | CAAAAGUGCAUACACGGCAA | 20 | 11570 |
| BCL11A-9697 | + | GCGUGGCCGGGAGAGAAGAA | 20 | 11571 |
| BCL11A-4422 | + | GCAGGGCGAGCAGGAGAGAA | 20 | 11572 |
| BCL11A-9698 | + | GGUGGCAGGGGUGGGAGGAA | 20 | 11573 |
| BCL11A-4404 | + | GAGAGAAGGGGAGGAGGGAA | 20 | 11574 |
| BCL11A-9699 | − | AGUCGAGGUAAAAGAGAUAA | 20 | 11575 |
| BCL11A-4455 | + | GGACAGAGACACACAAAACA | 20 | 11576 |
| BCL11A-9700 | + | CUGUCUCAAAAGUGCAUACA | 20 | 11577 |
| BCL11A-9701 | − | CGCGUGUGUGGGGGGGAGCA | 20 | 11578 |
| BCL11A-9702 | + | AAUAAUACAAAGAUGGCGCA | 20 | 11579 |
| BCL11A-9703 | + | AGACACACAAAACAUGGGCA | 20 | 11580 |
| BCL11A-9704 | + | GAGAGAAGAAAGGGGUGGCA | 20 | 11581 |
| BCL11A-9705 | − | GCACUUGAACUUGCAGCUCA | 20 | 11582 |
| BCL11A-9706 | + | GAAUUGUGGGAGAGCCGUCA | 20 | 11583 |
| BCL11A-4527 | + | AAAAAAAAAAAAAAAAAAGA | 20 | 11584 |
| BCL11A-9707 | + | AAUUAGAAAUAAUACAAAGA | 20 | 11585 |
| BCL11A-9708 | + | GGAGAGCCGGGUUAGAAAGA | 20 | 11586 |
| BCL11A-4464 | + | GGCAGGGCGAGCAGGAGAGA | 20 | 11587 |
| BCL11A-4418 | − | GCAAAAGCGAGGGGGAGAGA | 20 | 11588 |
| BCL11A-9709 | + | AGAGAGAGAAGAGAGAUAGA | 20 | 11589 |
| BCL11A-4673 | + | CGGCGGCGGCGGGCGGACGA | 20 | 11590 |
| BCL11A-4648 | + | CCGGGGAGGGGCGGGCCGA | 20 | 11591 |
| BCL11A-9710 | − | AGGACUAGAAGCAAAAGCGA | 20 | 11592 |
| BCL11A-4584 | + | AGCAGGAGAGAAGGGGAGGA | 20 | 11593 |
| BCL11A-4459 | + | GGAGAGAAGGGGAGGAGGGA | 20 | 11594 |
| BCL11A-4461 | + | GGAGGGGCGGGCCGAGGGA | 20 | 11595 |
| BCL11A-4624 | + | CAGACGCGGCCCCCGGGGGA | 20 | 11596 |
| BCL11A-9711 | + | UUGAACGUCAGGAGUCUGGA | 20 | 11597 |
| BCL11A-9712 | − | UGCUUAAAAAAAAGCCAUGA | 20 | 11598 |

TABLE 18B-continued

2nd Tier

| gRNA Name | DNA Strand | Targeting Domain | Target Site Length | SEQ ID NO: |
|---|---|---|---|---|
| BCL11A-5458 | − | ACCCCAGCACUUAAGCAAAC | 20 | 11599 |
| BCL11A-9713 | − | GCGGCGCUCGCUGCGGCCAC | 20 | 11600 |
| BCL11A-9714 | − | GCACCUCCCCUCCCCGCAC | 20 | 11601 |
| BCL11A-9715 | + | CUGGACAUGAAAAGAGACC | 20 | 11602 |
| BCL11A-4456 | + | GGACGCCAGACGCGGCCCCC | 20 | 11603 |
| BCL11A-9716 | − | CCUCGGCCCGCCCCUCCCCC | 20 | 11604 |
| BCL11A-4362 | + | CGGACGCCAGACGCGGCCCC | 20 | 11605 |
| BCL11A-9717 | − | CCCUCGGCCCGCCCCUCCCC | 20 | 11606 |
| BCL11A-9718 | + | GCCGCGGCGGUGGCGUGGCC | 20 | 11607 |
| BCL11A-9719 | − | GCCACCCCUUUCUUCUCUCC | 20 | 11608 |
| BCL11A-9720 | − | CACUGGCCAUUGGCUUGUCC | 20 | 11609 |
| BCL11A-9721 | + | AAAACAUGGGCAGGGCGAGC | 20 | 11610 |
| BCL11A-9722 | + | GGAGGGGCGCUGGGGCCGC | 20 | 11611 |
| BCL11A-4490 | + | GGGCCGAGGGGAGGGGCGC | 20 | 11612 |
| BCL11A-4442 | + | GCGGCGGCGGCGGCGGCGG | 20 | 11613 |
| BCL11A-9723 | + | AAUGGACACACAUCAGGGGC | 20 | 11614 |
| BCL11A-4439 | + | GCGGCCCCGGGGGAGGGGC | 20 | 11615 |
| BCL11A-5465 | + | GACAUGGUGGGCUGCGGGGC | 20 | 11616 |
| BCL11A-9724 | + | GGGAGGGGGAGGUGCGGGGC | 20 | 11617 |
| BCL11A-9725 | + | CGCCGCGGCGGUGGCGUGGC | 20 | 11618 |
| BCL11A-9726 | + | GGAGAGAAGAAAGGGGUGGC | 20 | 11619 |
| BCL11A-5468 | + | GGCGAGACAUGGUGGGCUGC | 20 | 11620 |
| BCL11A-9727 | + | GACAAGCCAAUGGCCAGUGC | 20 | 11621 |
| BCL11A-9728 | + | GUGCGGGGAGGGGAGGUGC | 20 | 11622 |
| BCL11A-9729 | + | CACACCAAUGGACACACAUC | 20 | 11623 |
| BCL11A-9730 | − | GAAAAAACCCUCAUCCCAUC | 20 | 11624 |
| BCL11A-9731 | − | ACUGAUGAAGAUAUUUCUC | 20 | 11625 |
| BCL11A-9732 | + | GAACUUGAACGUCAGGAGUC | 20 | 11626 |
| BCL11A-9733 | − | CCUCCCCCGGGGCCGCGUC | 20 | 11627 |
| BCL11A-4526 | + | AAAAAAAAAAAAAAAAAAG | 20 | 11628 |
| BCL11A-9734 | + | GUGGCCGGGAGAGAAGAAAG | 20 | 11629 |
| BCL11A-4629 | + | CAGGGCGAGCAGGAGAGAAG | 20 | 11630 |
| BCL11A-4577 | + | AGAGAAGGGGAGGAGGGAAG | 20 | 11631 |
| BCL11A-9735 | + | UGGGGCCGCGGGCUCACCAG | 20 | 11632 |
| BCL11A-9736 | + | AGAGAAGAAAGGGGUGGCAG | 20 | 11633 |
| BCL11A-9737 | + | CACCAAUGGACACACAUCAG | 20 | 11634 |
| BCL11A-9738 | − | CACUUGAACUUGCAGCUCAG | 20 | 11635 |
| BCL11A-4611 | − | CAAAAGCGAGGGGAGAGAG | 20 | 11636 |

TABLE 18B-continued

2nd Tier

| gRNA Name | DNA Strand | Targeting Domain | Target Site Length | SEQ ID NO: |
|---|---|---|---|---|
| BCL11A-4583 | − | AGCAAAAGCGAGGGGAGAG | 20 | 11637 |
| BCL11A-4677 | + | CGGGGGAGGGGCGGGCCGAG | 20 | 11638 |
| BCL11A-9739 | − | GGACUAGAAGCAAAAGCGAG | 20 | 11639 |
| BCL11A-4411 | + | GAGGGGCGGGCCGAGGGGAG | 20 | 11640 |
| BCL11A-4575 | + | AGACGCGGCCCCGGGGGAG | 20 | 11641 |
| BCL11A-9740 | + | GAGAGAGAGAAGAGAGAUAG | 20 | 11642 |
| BCL11A-9741 | + | CCUGCUCCCCCCCACACACG | 20 | 11643 |
| BCL11A-9742 | + | GGCUCCGCGGACGCCAGACG | 20 | 11644 |
| BCL11A-9743 | − | CUCGGCCCGCCCCUCCCCCG | 20 | 11645 |
| BCL11A-9744 | − | UCCCGGCCACGCCACCGCCG | 20 | 11646 |
| BCL11A-9745 | + | AGUGGCCGCAGCGAGCGCCG | 20 | 11647 |
| BCL11A-4642 | + | CCCGGGGGAGGGGCGGGCCG | 20 | 11648 |
| BCL11A-9746 | + | GGGAGGGGGCGCUGGGGCCG | 20 | 11649 |
| BCL11A-9747 | + | GUGCGGGGCGGGGGGCUCCG | 20 | 11650 |
| BCL11A-9748 | − | CAGGACUAGAAGCAAAAGCG | 20 | 11651 |
| BCL11A-9749 | + | GGAGGGGGAGGUGCGGGGCG | 20 | 11652 |
| BCL11A-9750 | + | CGAGCGCCGCGGCGGUGGCG | 20 | 11653 |
| BCL11A-9751 | + | ACAAGCCAAUGGCCAGUGCG | 20 | 11654 |
| BCL11A-9752 | + | UGCGGGGAGGGGGAGGUGCG | 20 | 11655 |
| BCL11A-9753 | − | CGAGGUAAAAGAGAUAAAGG | 20 | 11656 |
| BCL11A-9754 | − | ACUUGAACUUGCAGCUCAGG | 20 | 11657 |
| BCL11A-9755 | − | GACUAGAAGCAAAAGCGAGG | 20 | 11658 |
| BCL11A-4408 | + | GAGCAGGAGAGAAGGGGAGG | 20 | 11659 |
| BCL11A-4594 | + | AGGGGCGGGCCGAGGGGAGG | 20 | 11660 |
| BCL11A-9756 | + | CAAUGGCCAGUGCGGGGAGG | 20 | 11661 |
| BCL11A-9757 | − | UCGGCCCGCCCCUCCCCCGG | 20 | 11662 |
| BCL11A-4471 | + | GGCCGCAGCGAGCGCCGCGG | 20 | 11663 |
| BCL11A-4661 | + | CGCAGCGAGCGCCGCGGCGG | 20 | 11664 |
| BCL11A-4479 | + | GGCGGCGGCGGCGGCGGCGG | 20 | 11665 |
| BCL11A-4448 | + | GCGGGCGGCGCGGCGGCGG | 20 | 11666 |
| BCL11A-4501 | + | GGGGCGGGCGGCGGCGGCGG | 20 | 11667 |
| BCL11A-5484 | + | UGCGGGCGGGCGGCGGCGG | 20 | 11668 |
| BCL11A-5485 | + | GGCUGCGGGGCGGGCGGCGG | 20 | 11669 |
| BCL11A-5486 | + | GUGGGCUGCGGGGCGGGCGG | 20 | 11670 |
| BCL11A-9758 | + | GAGGGGGAGGUGCGGGGCGG | 20 | 11671 |
| BCL11A-9759 | + | GCAGGGGUGGGAGGAAAGGG | 20 | 11672 |
| BCL11A-9760 | − | CUUGAACUUGCAGCUCAGGG | 20 | 11673 |
| BCL11A-4443 | + | GCGGCGGCGGCGGCGGCGGG | 20 | 11674 |

TABLE 18B-continued

2nd Tier

| gRNA Name | DNA Strand | Targeting Domain | Target Site Length | SEQ ID NO: |
|---|---|---|---|---|
| BCL11A-5487 | + | AUGGUGGGCUGCGGGGCGGG | 20 | 11675 |
| BCL11A-9761 | + | AGGGGGAGGUGCGGGGCGGG | 20 | 11676 |
| BCL11A-4434 | + | GCCGGGAGAGAAGAAAGGGG | 20 | 11677 |
| BCL11A-4476 | + | GGCGAGCAGGAGAGAAGGGG | 20 | 11678 |
| BCL11A-9762 | + | GAAGAAAGGGGUGGCAGGGG | 20 | 11679 |
| BCL11A-4486 | + | GGGAGGGGCGGGCCGAGGGG | 20 | 11680 |
| BCL11A-4666 | + | CGCGGCCCCCGGGGAGGGG | 20 | 11681 |
| BCL11A-5489 | + | AGACAUGGUGGGCUGCGGGG | 20 | 11682 |
| BCL11A-9763 | + | AGCCAAUGGCCAGUGCGGGG | 20 | 11683 |
| BCL11A-9764 | + | GGGGAGGGGGAGGUGCGGGG | 20 | 11684 |
| BCL11A-9765 | + | UGGCCAGUGCGGGGAGGGGG | 20 | 11685 |
| BCL11A-4635 | + | CCAGACGCGGCCCCCGGGGG | 20 | 11686 |
| BCL11A-9766 | + | GGUGGGAGGAAAGGGUGGGG | 20 | 11687 |
| BCL11A-9767 | + | GGGUGGGAGGAAAGGGUGGG | 20 | 11688 |
| BCL11A-9768 | + | AAAGGGGUGGCAGGGGUGGG | 20 | 11689 |
| BCL11A-9769 | − | UUAGAGUCCGCGUGUGUGGG | 20 | 11690 |
| BCL11A-5490 | + | UUGCUUGCGGCGAGACAUGG | 20 | 11691 |
| BCL11A-9770 | + | GGGGUGGGAGGAAAGGGUGG | 20 | 11692 |
| BCL11A-9771 | + | GCCGAGGGGAGGGGGCGCUG | 20 | 11693 |
| BCL11A-9772 | − | CACCGCCGCGGCGCUCGCUG | 20 | 11694 |
| BCL11A-5497 | + | UCCCGUUUGCUUAAGUGCUG | 20 | 11695 |
| BCL11A-9773 | + | GGACAAGCCAAUGGCCAGUG | 20 | 11696 |
| BCL11A-9774 | + | AGUGCGGGGAGGGGGAGGUG | 20 | 11697 |
| BCL11A-9775 | + | AGGGGUGGGAGGAAAGGGUG | 20 | 11698 |
| BCL11A-9776 | − | UUUUAGAGUCCGCGUGUGUG | 20 | 11699 |
| BCL11A-9777 | + | GGCGCAGGGAAGAUGAAUUG | 20 | 11700 |
| BCL11A-5500 | + | GCUGGGGUUUGCCUUGCUUG | 20 | 11701 |
| BCL11A-9778 | + | GACAGAGACACACAAAACAU | 20 | 11702 |
| BCL11A-9779 | − | CCCCUCCCCGCACUGGCCAU | 20 | 11703 |
| BCL11A-9780 | + | ACACGGCAAUGGUUCCAGAU | 20 | 11704 |
| BCL11A-9781 | + | AUAAUUAUUAUUACUAUUAU | 20 | 11705 |
| BCL11A-9782 | − | GCCCCAGCGCCCCCUCCCCU | 20 | 11706 |
| BCL11A-9783 | + | GGCCGAGGGGAGGGGCGCU | 20 | 11707 |
| BCL11A-5509 | + | UUCCCGUUUGCUUAAGUGCU | 20 | 11708 |
| BCL11A-9784 | + | CAGGGGUGGGAGGAAAGGGU | 20 | 11709 |
| BCL11A-9785 | + | AAGAAAGGGGUGGCAGGGGU | 20 | 11710 |
| BCL11A-9786 | + | GCGCAGGGAAGAUGAAUUGU | 20 | 11711 |

TABLE 18B-continued

2nd Tier

| gRNA Name | DNA Strand | Targeting Domain | Target Site Length | SEQ ID NO: |
|---|---|---|---|---|
| BCL11A-9787 | + | UAAUUAUUAUUACUAUUAUU | 20 | 11712 |
| BCL11A-9788 | − | GUAUUAUUUCUAAUUUAUUU | 20 | 11713 |

Table 18C provides exemplary targeting domains for knocking down the BCL11A gene selected according to the third tier parameters. The targeting domains binds within the additional 500 bp (e.g., upstream or downstream) of a transcription start site (TSS), e.g., extending to 1 kb upstream and downstream of a TSS. It is contemplated herein that in an embodiment the targeting domain hybridizes to the target domain through complementary base pairing. Any of the targeting domains in the table can be used with a *S. pyogenes* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 18C

| gRNA Name | DNA Strand | Targeting Domain | Target Site Length | SEQ ID NO: |
|---|---|---|---|---|
| BCL11A-9789 | − | CACUCACCGUAAGAAAA | 17 | 11714 |
| BCL11A-9790 | + | CCUCUGGCCGGAACAAA | 17 | 11715 |
| BCL11A-9791 | + | CGAGGAGCCGGCACAAA | 17 | 11716 |
| BCL11A-9792 | − | UAUUUCUCUUUUCGAAA | 17 | 11717 |
| BCL11A-9793 | − | GGGAGCUGGUGGGGAAA | 17 | 11718 |
| BCL11A-9794 | − | AAGUGGCACUGUGGAAA | 17 | 11719 |
| BCL11A-9795 | + | GGGCUGCGGGUCCGAA | 17 | 11720 |
| BCL11A-9796 | + | GAAAUAAAGCGGCGGAA | 17 | 11721 |
| BCL11A-9797 | − | UGGGAGCUGGUGGGGAA | 17 | 11722 |
| BCL11A-9798 | − | AAAGUGGCACUGUGGAA | 17 | 11723 |
| BCL11A-9799 | + | GCCCGAGGGCGCCCCCA | 17 | 11724 |
| BCL11A-9800 | + | CGUCCUUCCCGGUCCCA | 17 | 11725 |
| BCL11A-9801 | + | CCCCCAAGGCCGAGCCA | 17 | 11726 |
| BCL11A-9802 | + | CCCGCGUGUGGACGCCA | 17 | 11727 |
| BCL11A-9597 | − | GUGUGUGGGGGGGAGCA | 17 | 11728 |
| BCL11A-9803 | + | AGGUGGGAGGGAGCGCA | 17 | 11729 |
| BCL11A-9804 | − | GGACACCAGCGCGCUCA | 17 | 11730 |
| BCL11A-9805 | + | CGCGCGGCCUGGAAAGA | 17 | 11731 |
| BCL11A-9806 | − | UCCGCGGAGUCGGGAGA | 17 | 11732 |
| BCL11A-9807 | + | CGCAGGCCGGGGCCCGA | 17 | 11733 |
| BCL11A-9808 | − | GAGAGGGCCGCGGCGA | 17 | 11734 |
| BCL11A-9809 | + | AGCUCCGCAGCGGGCGA | 17 | 11735 |
| BCL11A-9810 | − | CGUGGGACCGGGAAGGA | 17 | 11736 |
| BCL11A-9811 | − | GGUGUGCGUACGGAGGA | 17 | 11737 |
| BCL11A-9812 | + | AGGGCUGCGGGUCCGGA | 17 | 11738 |
| BCL11A-9813 | + | GGGGAAGCGCGGGCGGA | 17 | 11739 |
| BCL11A-9814 | − | AAAUGGGGGGGUAGGGA | 17 | 11740 |

TABLE 18C-continued

| gRNA Name | DNA Strand | Targeting Domain | Target Site Length | SEQ ID NO: |
|---|---|---|---|---|
| BCL11A-9815 | − | GAGCCGUGGGACCGGGA | 17 | 11741 |
| BCL11A-9816 | − | CGCGGCGGCGGCGGGGA | 17 | 11742 |
| BCL11A-9817 | + | GGCGAGGGGAGGUGGGA | 17 | 11743 |
| BCL11A-9818 | + | UCCAGCCUAAGUUUGGA | 17 | 11744 |
| BCL11A-9819 | − | AAUAAUGAACAAUGCUA | 17 | 11745 |
| BCL11A-9820 | − | GGAAGUGGGUGUGCGUA | 17 | 11746 |
| BCL11A-9821 | − | AAGAAAAUGGGGGGGUA | 17 | 11747 |
| BCL11A-9822 | + | ACCCCCCCAUUUUCUUA | 17 | 11748 |
| BCL11A-9823 | + | UCAUUAUUUUGCAAAAC | 17 | 11749 |
| BCL11A-9824 | + | AUAGAGCGAGAGUGCAC | 17 | 11750 |
| BCL11A-9825 | − | GAGAAAAGAGGUGAGAC | 17 | 11751 |
| BCL11A-9826 | − | AGAGGGCCGCGGCGAC | 17 | 11752 |
| BCL11A-9827 | − | GUGGGACCGGGAAGGAC | 17 | 11753 |
| BCL11A-9828 | + | AAGGCCGAGCCAGGGAC | 17 | 11754 |
| BCL11A-9829 | + | GCCUGGAAAGAGGGGAC | 17 | 11755 |
| BCL11A-9830 | − | GGGGAGAGCCGUGGGAC | 17 | 11756 |
| BCL11A-9831 | − | CAACUCACAUGCAAACC | 17 | 11757 |
| BCL11A-9832 | + | UAGAGCGAGAGUGCACC | 17 | 11758 |
| BCL11A-9833 | + | AGGCCGAGCCAGGGACC | 17 | 11759 |
| BCL11A-9834 | + | CCUGGAAAGAGGGGACC | 17 | 11760 |
| BCL11A-9835 | − | GGGAGAGCCGUGGGACC | 17 | 11761 |
| BCL11A-9836 | − | CCGGGAGCAACUCUACC | 17 | 11762 |
| BCL11A-9837 | + | CACCAGCUCCCACCCCC | 17 | 11763 |
| BCL11A-9838 | + | CGGGAGGCUGCAGCCCC | 17 | 11764 |
| BCL11A-9839 | − | GCUUUACUUCGGCCCC | 17 | 11765 |
| BCL11A-9840 | − | CUGUGGAAAGGGGCCCC | 17 | 11766 |
| BCL11A-9841 | + | UCACCUCUUUUCUCCCC | 17 | 11767 |
| BCL11A-9842 | − | CCGCGCUUCCCCAGCCC | 17 | 11768 |
| BCL11A-9843 | + | CCGGGAGGCUGCAGCCC | 17 | 11769 |
| BCL11A-9844 | − | GGGGCGCCCUCGGGCCC | 17 | 11770 |
| BCL11A-9845 | − | CGCCGCCUGCCUCUCCC | 17 | 11771 |
| BCL11A-9846 | + | CUCACCUCUUUUCUCCC | 17 | 11772 |
| BCL11A-9847 | − | UCUAAAAACGAUUCCC | 17 | 11773 |
| BCL11A-9848 | + | GCGGGCGGAGGGAAGCC | 17 | 11774 |
| BCL11A-9849 | − | CCCGCGCUUCCCCAGCC | 17 | 11775 |
| BCL11A-9850 | + | GCCCCCAAGGCCGAGCC | 17 | 11776 |
| BCL11A-9851 | + | CCCCGCGUGUGGACGCC | 17 | 11777 |
| BCL11A-9852 | + | GCGGACUCAGGAGCGCC | 17 | 11778 |

TABLE 18C-continued

| gRNA Name | DNA Strand | Targeting Domain | Target Site Length | SEQ ID NO: |
|---|---|---|---|---|
| BCL11A-9853 | + | GGCAGGCGGCGCAGGCC | 17 | 11779 |
| BCL11A-9854 | + | CAGGAGCCCGCGCGGCC | 17 | 11780 |
| BCL11A-9855 | - | CCGGGGCUGCAGCCUCC | 17 | 11781 |
| BCL11A-9856 | - | CAGGCCGCGCGGGCUCC | 17 | 11782 |
| BCL11A-9857 | + | CCAGGUAGAGUUGCUCC | 17 | 11783 |
| BCL11A-9858 | + | GCAGCGCCCAAGUCUCC | 17 | 11784 |
| BCL11A-9859 | - | UACGGAGGAGGGUGUCC | 17 | 11785 |
| BCL11A-9860 | - | GUCUAAAAAACGAUUCC | 17 | 11786 |
| BCL11A-9861 | + | GCGUCUCCCGUCCUUCC | 17 | 11787 |
| BCL11A-9862 | - | CCCGGUCCCCUCUUUCC | 17 | 11788 |
| BCL11A-9863 | + | AGUUACAGCUCCGCAGC | 17 | 11789 |
| BCL11A-9864 | + | CCGGCACAAAAGGCAGC | 17 | 11790 |
| BCL11A-9865 | - | ACGGUCAAGUGUGCAGC | 17 | 11791 |
| BCL11A-9866 | + | GGGCAAGCGCGAGGAGC | 17 | 11792 |
| BCL11A-9620 | - | CGUGUGUGGGGGGGAGC | 17 | 11793 |
| BCL11A-9867 | - | AACCUGGGGUGGGAGC | 17 | 11794 |
| BCL11A-9868 | - | CCCUGGCGUCCACACGC | 17 | 11795 |
| BCL11A-9869 | - | UUCCCGAGCGCAGCCGC | 17 | 11796 |
| BCL11A-9870 | + | CCGGGCUGGGGAAGCGC | 17 | 11797 |
| BCL11A-9871 | + | CGCGGACUCAGGAGCGC | 17 | 11798 |
| BCL11A-9872 | - | CUCUUUCCAGGCCGCGC | 17 | 11799 |
| BCL11A-9873 | + | CUUGACCGUGAGCGCGC | 17 | 11800 |
| BCL11A-9874 | + | GGAGAGGCAGGCGGCGC | 17 | 11801 |
| BCL11A-9875 | + | AGGCAGGCGGCGCAGGC | 17 | 11802 |
| BCL11A-9876 | + | GGGGACCGGGGAGAGGC | 17 | 11803 |
| BCL11A-9877 | - | GCCCUCCAAACUUAGGC | 17 | 11804 |
| BCL11A-9878 | - | AGGACGGGAGACGCGGC | 17 | 11805 |
| BCL11A-9879 | - | GCGAGCGCGGCGGCGGC | 17 | 11806 |
| BCL11A-9880 | + | AGGCUGCAGCCCCGGGC | 17 | 11807 |
| BCL11A-9881 | + | UGCAAAACUGGCGGGGC | 17 | 11808 |
| BCL11A-9882 | + | UAUUUUGCAAAACUGGC | 17 | 11809 |
| BCL11A-9883 | + | AAACACCCACCUCUGGC | 17 | 11810 |
| BCL11A-9884 | + | UAAGUUUGGAGGGCUGC | 17 | 11811 |
| BCL11A-9885 | + | ACAAAAGGCGGCAGUGC | 17 | 11812 |
| BCL11A-9886 | - | CCCGCUGCCUUUUGUGC | 17 | 11813 |
| BCL11A-9887 | + | CCCGACUCCGCGGACUC | 17 | 11814 |
| BCL11A-9888 | + | GGACAAACACCCACCUC | 17 | 11815 |
| BCL11A-9889 | - | GCCUUGGGGGCGCCCUC | 17 | 11816 |
| BCL11A-9890 | - | UUUGCUGUCCUCUCCUC | 17 | 11817 |

TABLE 18C-continued

| gRNA Name | DNA Strand | Targeting Domain | Target Site Length | SEQ ID NO: |
|---|---|---|---|---|
| BCL11A-9891 | + | AGCCCGCGGCUGCGCUC | 17 | 11818 |
| BCL11A-9892 | - | AGCGCAGCCGCGGGCUC | 17 | 11819 |
| BCL11A-9893 | - | CCUGAGUCCGCGGAGUC | 17 | 11820 |
| BCL11A-9894 | + | UUGGAGGGCUGCGGGUC | 17 | 11821 |
| BCL11A-9895 | - | GUACGGAGGAGGGUGUC | 17 | 11822 |
| BCL11A-9896 | - | GCUCAGCUCUCAACUUC | 17 | 11823 |
| BCL11A-9897 | - | CUUGGGCGCUGCCCUUC | 17 | 11824 |
| BCL11A-9898 | - | ACUGCCGCCUUUUGUUC | 17 | 11825 |
| BCL11A-9899 | - | AUUCCCGGGGAGAAAAG | 17 | 11826 |
| BCL11A-9900 | - | CCACAAUAGUGAGAAAG | 17 | 11827 |
| BCL11A-9901 | + | GGCGGAAAGGAGGAAAG | 17 | 11828 |
| BCL11A-9902 | + | CCGCGCGGCCUGGAAAG | 17 | 11829 |
| BCL11A-9903 | - | AGUGGCACUGUGGAAAG | 17 | 11830 |
| BCL11A-9904 | + | CGAAAAGAGAAAUAAAG | 17 | 11831 |
| BCL11A-9905 | - | GCGGCGGGGAGGGGAAG | 17 | 11832 |
| BCL11A-9906 | + | CCGCGUGUGGACGCCAG | 17 | 11833 |
| BCL11A-9907 | - | CCUUUUGUUCCGGCCAG | 17 | 11834 |
| BCL11A-9908 | + | AAGUUACAGCUCCGCAG | 17 | 11835 |
| BCL11A-9909 | + | GCCGGCACAAAAGGCAG | 17 | 11836 |
| BCL11A-9910 | - | CACGGUCAAGUGUGCAG | 17 | 11837 |
| BCL11A-9911 | + | GCGCGGCCUGGAAAGAG | 17 | 11838 |
| BCL11A-9912 | - | CCGCGGAGUCGGGAGAG | 17 | 11839 |
| BCL11A-9913 | + | GCUCCGCAGCGGGCGAG | 17 | 11840 |
| BCL11A-9914 | + | AAACUUUGCCCGAGGAG | 17 | 11841 |
| BCL11A-9915 | - | GUCCGCGGAGUCGGGAG | 17 | 11842 |
| BCL11A-9916 | + | AAGAGGGGACCGGGGAG | 17 | 11843 |
| BCL11A-9917 | - | GCGGCGGCGGCGGGGAG | 17 | 11844 |
| BCL11A-9918 | + | GCGGGGCGGGGGGGGAG | 17 | 11845 |
| BCL11A-9919 | + | CAUUUCUUACGGUGAG | 17 | 11846 |
| BCL11A-9920 | + | GGGAGCGCACGGCAACG | 17 | 11847 |
| BCL11A-9642 | + | GCUCCCCCCACACACG | 17 | 11848 |
| BCL11A-9921 | - | CCCCUGGCGUCCACACG | 17 | 11849 |
| BCL11A-9922 | - | GGGAAGGACGGGAGACG | 17 | 11850 |
| BCL11A-9923 | - | GAGGGGCCGCGGCGACG | 17 | 11851 |
| BCL11A-9924 | + | CUGGAAAGAGGGGACCG | 17 | 11852 |
| BCL11A-9925 | - | CGCGCUUCCCCAGCCCG | 17 | 11853 |
| BCL11A-9926 | + | UAAAAGCCCCGAGCCCG | 17 | 11854 |
| BCL11A-9927 | + | GCGCAGGCCGGGGCCCG | 17 | 11855 |

TABLE 18C-continued

| gRNA Name | DNA Strand | Targeting Domain | Target Site Length | SEQ ID NO: |
|---|---|---|---|---|
| BCL11A-9928 | + | UCGGGAAACUUUGCCCG | 17 | 11856 |
| BCL11A-9929 | - | CUAAAAAACGAUUCCCG | 17 | 11857 |
| BCL11A-9930 | - | UUUCCCGAGCGCAGCCG | 17 | 11858 |
| BCL11A-9931 | - | GGCGACGGGGAGAGCCG | 17 | 11859 |
| BCL11A-9932 | + | CGGACUCAGGAGCGCCG | 17 | 11860 |
| BCL11A-9933 | + | GGCUCUCCCCGUCGCCG | 17 | 11861 |
| BCL11A-9934 | + | GCAGGCGGCGCAGGCCG | 17 | 11862 |
| BCL11A-9935 | - | AGUCGGGAGAGGGGCCG | 17 | 11863 |
| BCL11A-9936 | + | CCCCUCUCCCGACUCCG | 17 | 11864 |
| BCL11A-9937 | - | CGGCGCUCCUGAGUCCG | 17 | 11865 |
| BCL11A-9938 | + | CCCGGGCUGGGGAAGCG | 17 | 11866 |
| BCL11A-9939 | - | CACGCGGGGAGCGAGCG | 17 | 11867 |
| BCL11A-9940 | - | CCUGGCGUCCACACGCG | 17 | 11868 |
| BCL11A-9941 | + | GUCUCCAGGAGCCCGCG | 17 | 11869 |
| BCL11A-9942 | - | CCUCUUUCCAGGCCGCG | 17 | 11870 |
| BCL11A-9943 | + | GCGGGAGGGCAAGCGCG | 17 | 11871 |
| BCL11A-9944 | - | CGAGCGCGGCGGCGGCG | 17 | 11872 |
| BCL11A-9945 | + | CAGCUCCGCAGCGGGCG | 17 | 11873 |
| BCL11A-9946 | + | GCAAAACUGGCGGGGCG | 17 | 11874 |
| BCL11A-9947 | + | AUUUUGCAAAACUGGCG | 17 | 11875 |
| BCL11A-9948 | - | GCGCAGCCGCGGGCUCG | 17 | 11876 |
| BCL11A-9949 | + | CUGGCCGGAACAAAAGG | 17 | 11877 |
| BCL11A-9950 | + | AUAAAGCGGCGGAAAGG | 17 | 11878 |
| BCL11A-9951 | + | GACCGGGGAGAGGCAGG | 17 | 11879 |
| BCL11A-9952 | + | GGAAAGGAGGAAAGAGG | 17 | 11880 |
| BCL11A-9953 | - | UUUGUUCCGGCCAGAGG | 17 | 11881 |
| BCL11A-9954 | - | GGGUGUGCGUACGGAGG | 17 | 11882 |
| BCL11A-9955 | + | CAGCGGGCGAGGGGAGG | 17 | 11883 |
| BCL11A-9956 | - | AGUGGGUGUGCGUACGG | 17 | 11884 |
| BCL11A-9957 | + | GGACUCAGGAGCGCCGG | 17 | 11885 |
| BCL11A-9958 | + | AAAGAGAAAUAAAGCGG | 17 | 11886 |
| BCL11A-9959 | - | GCGGGGAGCGAGCGCGG | 17 | 11887 |
| BCL11A-9960 | - | GGGAGCGAGCGCGGCGG | 17 | 11888 |
| BCL11A-9961 | - | AGCGAGCGCGGCGGCGG | 17 | 11889 |
| BCL11A-9962 | + | UGGGGAAGCGCGGGCGG | 17 | 11890 |
| BCL11A-9963 | + | CAAAACUGGCGGGGCGG | 17 | 11891 |
| BCL11A-9964 | - | AGCUGGUGGGGAAAGGG | 17 | 11892 |
| BCL11A-9965 | - | AAAAUGGGGGGGUAGGG | 17 | 11893 |
| BCL11A-9966 | + | AGCGAGAGUGCACCGGG | 17 | 11894 |

TABLE 18C-continued

| gRNA Name | DNA Strand | Targeting Domain | Target Site Length | SEQ ID NO: |
|---|---|---|---|---|
| BCL11A-9967 | - | GUCAAGUGUGCAGCGGG | 17 | 11895 |
| BCL11A-9968 | + | GGCUGGGGAAGCGCGGG | 17 | 11896 |
| BCL11A-9969 | + | AAAACUGGCGGGGCGGG | 17 | 11897 |
| BCL11A-9970 | + | CCGCAGCGGGCGAGGGG | 17 | 11898 |
| BCL11A-9971 | - | GCGCGGCGGCGGCGGGG | 17 | 11899 |
| BCL11A-9972 | + | AAACUGGCGGGGCGGGG | 17 | 11900 |
| BCL11A-9973 | + | UUGCAAAACUGGCGGGG | 17 | 11901 |
| BCL11A-9974 | + | AACUGGCGGGGCGGGGG | 17 | 11902 |
| BCL11A-9975 | - | ACAUGCAAACCUGGGGG | 17 | 11903 |
| BCL11A-9976 | - | ACCGUAAGAAAAUGGGG | 17 | 11904 |
| BCL11A-9548 | - | AGUCCGCGUGUGUGGGG | 17 | 11905 |
| BCL11A-9977 | - | CACCGUAAGAAAAUGGG | 17 | 11906 |
| BCL11A-9978 | + | GGGCGAGGGGAGGUGGG | 17 | 11907 |
| BCL11A-9668 | - | GAGUCCGCGUGUGUGGG | 17 | 11908 |
| BCL11A-9979 | - | UCACCGUAAGAAAAUGG | 17 | 11909 |
| BCL11A-9980 | + | UUAUUUGCAAAACUGG | 17 | 11910 |
| BCL11A-9981 | - | CUCACAUGCAAACCUGG | 17 | 11911 |
| BCL11A-9982 | - | CUGGGGGUGGGAGCUGG | 17 | 11912 |
| BCL11A-9670 | - | AGAGUCCGCGUGUGUGG | 17 | 11913 |
| BCL11A-9983 | - | GCGGAGCUGUAACUUGG | 17 | 11914 |
| BCL11A-9984 | - | CCCUGGCUCGGCCUUGG | 17 | 11915 |
| BCL11A-9985 | + | AUCCAGCCUAAGUUUGG | 17 | 11916 |
| BCL11A-9986 | - | CUCACCGUAAGAAAAUG | 17 | 11917 |
| BCL11A-9987 | - | GUGAGAAAGUGGCACUG | 17 | 11918 |
| BCL11A-9988 | - | ACUCACAUGCAAACCUG | 17 | 11919 |
| BCL11A-9989 | - | CCUCCCCUCGCCCGCUG | 17 | 11920 |
| BCL11A-9990 | + | CUAAGUUUGGAGGGCUG | 17 | 11921 |
| BCL11A-9991 | + | GCUGCAGCCCCGGGCUG | 17 | 11922 |
| BCL11A-9992 | + | CGCUCGCUCCCCGCGUG | 17 | 11923 |
| BCL11A-9993 | - | GGGGGUGGGAGCUGGUG | 17 | 11924 |
| BCL11A-9678 | - | UUUAGAGUCCGCGUGUG | 17 | 11925 |
| BCL11A-9549 | - | UAGAGUCCGCGUGUGUG | 17 | 11926 |
| BCL11A-9994 | + | ACUUCUCACUAUUGUG | 17 | 11927 |
| BCL11A-9995 | + | CCACUUUCUCACUAUUG | 17 | 11928 |
| BCL11A-9996 | - | UCCCUGGCUCGGCCUUG | 17 | 11929 |
| BCL11A-9997 | - | ACUCACCGUAAGAAAAU | 17 | 11930 |
| BCL11A-9998 | - | GCUGCGGAGCUGUAACU | 17 | 11931 |
| BCL11A-9999 | - | GCGGGCUCCUGGAGACU | 17 | 11932 |

TABLE 18C-continued

| gRNA Name | DNA Strand | Targeting Domain | Target Site Length | SEQ ID NO: |
|---|---|---|---|---|
| BCL11A-10000 | - | AACUCACAUGCAAACCU | 17 | 11933 |
| BCL11A-10001 | - | GGCCUUGGGGGCGCCCU | 17 | 11934 |
| BCL11A-10002 | - | GGUCCCUGGCUCGGCCU | 17 | 11935 |
| BCL11A-10003 | - | CUUUGCUGUCCUCUCCU | 17 | 11936 |
| BCL11A-10004 | + | GAGCCCGCGGCUGCGCU | 17 | 11937 |
| BCL11A-10005 | + | GGCUGCAGCCCCGGGCU | 17 | 11938 |
| BCL11A-10006 | - | GAGCGCAGCCGCGGGCU | 17 | 11939 |
| BCL11A-10007 | - | CGGCGGGGAGGGGAAGU | 17 | 11940 |
| BCL11A-10008 | - | UCCUGAGUCCGCGGAGU | 17 | 11941 |
| BCL11A-10009 | + | AUUUUCUUACGGUGAGU | 17 | 11942 |
| BCL11A-10010 | - | GCGACGGGGAGAGCCGU | 17 | 11943 |
| BCL11A-10011 | - | UUGUUCCGGCCAGAGGU | 17 | 11944 |
| BCL11A-10012 | + | AGCGGGCGAGGGGAGGU | 17 | 11945 |
| BCL11A-10013 | - | UAAGAAAAUGGGGGGGU | 17 | 11946 |
| BCL11A-10014 | - | CAUGCAAACCUGGGGGU | 17 | 11947 |
| BCL11A-10015 | - | UGGGGGUGGGAGCUGGU | 17 | 11948 |
| BCL11A-9687 | - | UUAGAGUCCGCGUGUGU | 17 | 11949 |
| BCL11A-10016 | + | CACUUUCUCACUAUUGU | 17 | 11950 |
| BCL11A-10017 | - | CGCAGCCCUCCAAACUU | 17 | 11951 |
| BCL11A-10018 | - | GGCUCAGCUCUCAACUU | 17 | 11952 |
| BCL11A-10019 | - | CGGGCUCCUGGAGACUU | 17 | 11953 |
| BCL11A-10020 | - | GCUCGGGGCUUUUACUU | 17 | 11954 |
| BCL11A-10021 | - | GUCCCUGGCUCGGCCUU | 17 | 11955 |
| BCL11A-10022 | + | GGAAUCCAGCCUAAGUU | 17 | 11956 |
| BCL11A-10023 | - | GAGGUGAGACUGGCUUU | 17 | 11957 |
| BCL11A-10024 | - | UCCCACUCACCGUAAGAAAA | 20 | 11958 |
| BCL11A-10025 | + | CCACCUCUGGCCGGAACAAA | 20 | 11959 |
| BCL11A-10026 | + | GCGCGAGGAGCCGGCACAAA | 20 | 11960 |
| BCL11A-10027 | - | CUUUAUUUCUCUUUUCGAAA | 20 | 11961 |
| BCL11A-10028 | - | GGUGGGAGCUGGUGGGGAAA | 20 | 11962 |
| BCL11A-10029 | - | AGAAAGUGGCACUGUGGAAA | 20 | 11963 |
| BCL11A-10030 | + | GGAGGGCUGCGGGUCCGGAA | 20 | 11964 |
| BCL11A-10031 | + | AGAGAAAUAAAGCGGCGGAA | 20 | 11965 |
| BCL11A-10032 | - | GGGUGGGAGCUGGUGGGGAA | 20 | 11966 |
| BCL11A-10033 | - | GAGAAAGUGGCACUGUGGAA | 20 | 11967 |
| BCL11A-10034 | + | GGGGCCCGAGGGCGCCCCA | 20 | 11968 |
| BCL11A-10035 | + | UCCCGUCCUUCCCGGUCCA | 20 | 11969 |
| BCL11A-10036 | + | GCGCCCCAAGGCCGAGCCA | 20 | 11970 |
| BCL11A-10037 | + | CUCCCCGCGUGUGGACGCCA | 20 | 11971 |

TABLE 18C-continued

| gRNA Name | DNA Strand | Targeting Domain | Target Site Length | SEQ ID NO: |
|---|---|---|---|---|
| BCL11A-9701 | - | CGCGUGUGUGGGGGGGAGCA | 20 | 11972 |
| BCL11A-10038 | + | GGGAGGUGGGAGGGAGCGCA | 20 | 11973 |
| BCL11A-10039 | - | UUUGGACACCAGCGCGCUCA | 20 | 11974 |
| BCL11A-10040 | + | GCCCGCGCGGCCUGGAAAGA | 20 | 11975 |
| BCL11A-10041 | - | GAGUCCGCGGAGUCGGGAGA | 20 | 11976 |
| BCL11A-10042 | + | CGGCGCAGGCCGGGGCCCGA | 20 | 11977 |
| BCL11A-10043 | - | CGGGAGAGGGGCCGCGGCGA | 20 | 11978 |
| BCL11A-10044 | + | UACAGCUCCGCAGCGGGCGA | 20 | 11979 |
| BCL11A-10045 | - | AGCCGUGGGACCGGGAAGGA | 20 | 11980 |
| BCL11A-10046 | - | GUGGGUGUGCGUACGGAGGA | 20 | 11981 |
| BCL11A-10047 | + | UGGAGGGCUGCGGGUCCGGA | 20 | 11982 |
| BCL11A-10048 | + | GCUGGGGAAGCGCGGGCGGA | 20 | 11983 |
| BCL11A-10049 | - | AGAAAAUGGGGGGGUAGGGA | 20 | 11984 |
| BCL11A-10050 | - | GGAGAGCCGUGGGACCGGGA | 20 | 11985 |
| BCL11A-10051 | - | GAGCGCGGCGGCGGCGGGGA | 20 | 11986 |
| BCL11A-10052 | + | GCGGGCGAGGGGAGGUGGGA | 20 | 11987 |
| BCL11A-10053 | + | GAAUCCAGCCUAAGUUUGGA | 20 | 11988 |
| BCL11A-10054 | - | CAAAAUAAUGAACAAUGCUA | 20 | 11989 |
| BCL11A-10055 | - | AGGGGAAGUGGGUGUGCGUA | 20 | 11990 |
| BCL11A-10056 | - | CGUAAGAAAAUGGGGGGGUA | 20 | 11991 |
| BCL11A-10057 | + | CCUACCCCCCCAUUUUCUUA | 20 | 11992 |
| BCL11A-10058 | + | UGUUCAUUAUUUUGCAAAAC | 20 | 11993 |
| BCL11A-10059 | + | AAAAUAGAGCGAGAGUGCAC | 20 | 11994 |
| BCL11A-10060 | - | GGGGAGAAAAGAGGUGAGAC | 20 | 11995 |
| BCL11A-10061 | - | GGGAGAGGGGCCGCGGCGAC | 20 | 11996 |
| BCL11A-10062 | - | GCCGUGGGACCGGGAAGGAC | 20 | 11997 |
| BCL11A-10063 | + | CCCAAGGCCGAGCCAGGGAC | 20 | 11998 |
| BCL11A-10064 | + | GCGGCCUGGAAAGAGGGGAC | 20 | 11999 |
| BCL11A-10065 | - | GACGGGGAGAGCCGUGGGAC | 20 | 12000 |
| BCL11A-10066 | - | GAACAACUCACAUGCAAACC | 20 | 12001 |
| BCL11A-10067 | + | AAAUAGAGCGAGAGUGCACC | 20 | 12002 |
| BCL11A-10068 | + | CCAAGGCCGAGCCAGGGACC | 20 | 12003 |
| BCL11A-10069 | + | CGGCCUGGAAAGAGGGGACC | 20 | 12004 |
| BCL11A-10070 | - | ACGGGGAGAGCCGUGGGACC | 20 | 12005 |
| BCL11A-10071 | - | UGUCCGGGAGCAACUCUACC | 20 | 12006 |
| BCL11A-10072 | + | CCCCACCAGCUCCCACCCCC | 20 | 12007 |
| BCL11A-10073 | + | CACCGGGAGGCUGCAGCCCC | 20 | 12008 |
| BCL11A-10074 | - | GGGGCUUUUACUUCGGCCCC | 20 | 12009 |

TABLE 18C-continued

| gRNA Name | DNA Strand | Targeting Domain | Target Site Length | SEQ ID NO: |
|---|---|---|---|---|
| BCL11A-10075 | - | GCACUGUGGAAAGGGGCCCC | 20 | 12010 |
| BCL11A-10076 | + | GUCUCACCUCUUUUCUCCCC | 20 | 12011 |
| BCL11A-10077 | - | CGCCCGCGCUUCCCCAGCCC | 20 | 12012 |
| BCL11A-10078 | + | GCACCGGGAGGCUGCAGCCC | 20 | 12013 |
| BCL11A-10079 | - | UUGGGGGCGCCCUCGGGCCC | 20 | 12014 |
| BCL11A-10080 | - | CUGCGCCGCCUGCCUCUCCC | 20 | 12015 |
| BCL11A-10081 | + | AGUCUCACCUCUUUUCUCCC | 20 | 12016 |
| BCL11A-10082 | - | AAGUCUAAAAAACGAUUCCC | 20 | 12017 |
| BCL11A-10083 | + | AGCGCGGGCGGAGGGAAGCC | 20 | 12018 |
| BCL11A-10084 | - | CCGCCCGCGCUUCCCCAGCC | 20 | 12019 |
| BCL11A-10085 | + | GGCGCCCCAAGGCCGAGCC | 20 | 12020 |
| BCL11A-10086 | + | GCUCCCCGCGUGUGGACGCC | 20 | 12021 |
| BCL11A-10087 | + | UCCGCGGACUCAGGAGCGCC | 20 | 12022 |
| BCL11A-10088 | + | AGAGGCAGGCGGCGCAGGCC | 20 | 12023 |
| BCL11A-10089 | + | CUCCAGGAGCCCGCGCGGCC | 20 | 12024 |
| BCL11A-10090 | - | AGCCCGGGGCUGCAGCCUCC | 20 | 12025 |
| BCL11A-10091 | - | UUCCAGGCCGCGCGGGCUCC | 20 | 12026 |
| BCL11A-10092 | + | AAGCCAGGUAGAGUUGCUCC | 20 | 12027 |
| BCL11A-10093 | + | AGGGCAGCGCCCAAGUCUCC | 20 | 12028 |
| BCL11A-10094 | - | GCGUACGGAGGAGGGUGUCC | 20 | 12029 |
| BCL11A-10095 | - | CAAGUCUAAAAAACGAUUCC | 20 | 12030 |
| BCL11A-10096 | + | GCCGCGUCUCCCGUCCUUCC | 20 | 12031 |
| BCL11A-10097 | - | CUCCCCGGUCCCCUCUUUCC | 20 | 12032 |
| BCL11A-10098 | + | CCAAGUUACAGCUCCGCAGC | 20 | 12033 |
| BCL11A-10099 | + | GAGCCGGCACAAAAGGCAGC | 20 | 12034 |
| BCL11A-10100 | - | CUCACGGUCAAGUGUGCAGC | 20 | 12035 |
| BCL11A-10101 | + | GGAGGGCAAGCGCGAGGAGC | 20 | 12036 |
| BCL11A-9563 | - | CCGCGUGUGUGGGGGGGAGC | 20 | 12037 |
| BCL11A-10102 | - | GCAAACCUGGGGGUGGGAGC | 20 | 12038 |
| BCL11A-10103 | - | GGCCCCUGGCGUCCACACGC | 20 | 12039 |
| BCL11A-10104 | - | AGUUUCCCGAGCGCAGCCGC | 20 | 12040 |
| BCL11A-10105 | + | GCCCCGGGCUGGGGAAGCGC | 20 | 12041 |
| BCL11A-10106 | + | CUCCGCGGACUCAGGAGCGC | 20 | 12042 |
| BCL11A-10107 | - | CCCCUCUUUCCAGGCCGCGC | 20 | 12043 |
| BCL11A-10108 | + | ACACUUGACCGUGAGCGCGC | 20 | 12044 |
| BCL11A-10109 | + | CGGGGAGAGGCAGGCGGCGC | 20 | 12045 |
| BCL11A-10110 | + | GAGAGGCAGGCGGCGCAGGC | 20 | 12046 |
| BCL11A-10111 | + | AGAGGGGACCGGGGAGAGGC | 20 | 12047 |
| BCL11A-10112 | - | GCAGCCCUCCAAACUUAGGC | 20 | 12048 |

TABLE 18C-continued

| gRNA Name | DNA Strand | Targeting Domain | Target Site Length | SEQ ID NO: |
|---|---|---|---|---|
| BCL11A-10113 | - | GGAAGGACGGGAGACGCGGC | 20 | 12049 |
| BCL11A-10114 | - | GGAGCGAGCGCGGCGGCGGC | 20 | 12050 |
| BCL11A-10115 | + | GGGAGGCUGCAGCCCCGGGC | 20 | 12051 |
| BCL11A-10116 | + | UUUUGCAAAACUGGCGGGGC | 20 | 12052 |
| BCL11A-10117 | + | CAUUAUUUGCAAAACUGGC | 20 | 12053 |
| BCL11A-10118 | + | GACAAACACCCACCUCUGGC | 20 | 12054 |
| BCL11A-10119 | + | GCCUAAGUUUGGAGGGCUGC | 20 | 12055 |
| BCL11A-10120 | + | GGAACAAAAGGCGGCAGUGC | 20 | 12056 |
| BCL11A-10121 | - | UGUCCCGCUGCCUUUUGUGC | 20 | 12057 |
| BCL11A-10122 | + | UCUCCCGACUCCGCGGACUC | 20 | 12058 |
| BCL11A-10123 | + | GCGGGACAAACACCCACCUC | 20 | 12059 |
| BCL11A-10124 | - | UCGGCCUUGGGGGCGCCCUC | 20 | 12060 |
| BCL11A-10125 | - | UUCUUUGCUGUCCUCUCCUC | 20 | 12061 |
| BCL11A-10126 | + | CCGAGCCCGCGGCUGCGCUC | 20 | 12062 |
| BCL11A-10127 | - | CCGAGCGCAGCCGCGGGCUC | 20 | 12063 |
| BCL11A-10128 | - | GCUCCUGAGUCCGCGGAGUC | 20 | 12064 |
| BCL11A-10129 | + | AGUUUGGAGGGCUGCGGGUC | 20 | 12065 |
| BCL11A-10130 | - | UGCGUACGGAGGAGGGUGUC | 20 | 12066 |
| BCL11A-10131 | - | GAGGCUCAGCUCUCAACUUC | 20 | 12067 |
| BCL11A-10132 | - | AGACUUGGGCGCUGCCCUUC | 20 | 12068 |
| BCL11A-10133 | - | GGCACUGCCGCCUUUUGUUC | 20 | 12069 |
| BCL11A-10134 | - | ACGAUUCCCGGGGAGAAAAG | 20 | 12070 |
| BCL11A-10135 | - | UCCCCACAAUAGUGAGAAAG | 20 | 12071 |
| BCL11A-10136 | + | AGCGGCGGAAAGGAGGAAAG | 20 | 12072 |
| BCL11A-10137 | + | AGCCCGCGCGGCCUGGAAAG | 20 | 12073 |
| BCL11A-10138 | - | GAAAGUGGCACUGUGGAAAG | 20 | 12074 |
| BCL11A-10139 | + | UUUCGAAAAGAGAAAUAAAG | 20 | 12075 |
| BCL11A-10140 | - | GCGGCGGCGGGGAGGGGAAG | 20 | 12076 |
| BCL11A-10141 | + | UCCCCGCGUGUGGACGCCAG | 20 | 12077 |
| BCL11A-10142 | - | CCGCCUUUUGUUCCGGCCAG | 20 | 12078 |
| BCL11A-10143 | + | UCCAAGUUACAGCUCCGCAG | 20 | 12079 |
| BCL11A-10144 | + | GGAGCCGGCACAAAAGGCAG | 20 | 12080 |
| BCL11A-10145 | - | GCUCACGGUCAAGUGUGCAG | 20 | 12081 |
| BCL11A-10146 | + | CCCGCGCGGCCUGGAAAGAG | 20 | 12082 |
| BCL11A-10147 | - | AGUCCGCGGAGUCGGGAGAG | 20 | 12083 |
| BCL11A-10148 | + | ACAGCUCCGCAGCGGGCGAG | 20 | 12084 |
| BCL11A-10149 | + | GGGAAACUUUGCCCGAGGAG | 20 | 12085 |
| BCL11A-10150 | - | UGAGUCCGCGGAGUCGGGAG | 20 | 12086 |

TABLE 18C-continued

| gRNA Name | DNA Strand | Targeting Domain | Target Site Length | SEQ ID NO: |
|---|---|---|---|---|
| BCL11A-10151 | + | GGAAAGAGGGGACCGGGGAG | 20 | 12087 |
| BCL11A-10152 | - | AGCGCGGCGGCGGCGGGGAG | 20 | 12088 |
| BCL11A-10153 | + | CUGGCGGGGCGGGGGGGGAG | 20 | 12089 |
| BCL11A-10154 | + | CCCCAUUUCUUACGGUGAG | 20 | 12090 |
| BCL11A-10155 | + | GGAGGGAGCGCACGGCAACG | 20 | 12091 |
| BCL11A-9741 | + | CCUGCUCCCCCCCACACACG | 20 | 12092 |
| BCL11A-10156 | - | CGGCCCCUGGCGUCCACACG | 20 | 12093 |
| BCL11A-10157 | - | ACCGGGAAGGACGGGAGACG | 20 | 12094 |
| BCL11A-10158 | - | GGAGAGGGGCCGCGGCGACG | 20 | 12095 |
| BCL11A-10159 | + | GGCCUGGAAAGAGGGGACCG | 20 | 12096 |
| BCL11A-10160 | - | GCCCGCGCUUCCCCAGCCCG | 20 | 12097 |
| BCL11A-10161 | + | AAGUAAAAGCCCCGAGCCCG | 20 | 12098 |
| BCL11A-10162 | + | GCGGCGCAGGCCGGGGCCCG | 20 | 12099 |
| BCL11A-10163 | + | CGCUCGGGAAACUUUGCCCG | 20 | 12100 |
| BCL11A-10164 | - | AGUCUAAAAAACGAUUCCCG | 20 | 12101 |
| BCL11A-10165 | - | AAGUUUCCCGAGCGCAGCCG | 20 | 12102 |
| BCL11A-10166 | - | CGCGGCGACGGGGAGAGCCG | 20 | 12103 |
| BCL11A-10167 | + | CCGCGGACUCAGGAGCGCCG | 20 | 12104 |
| BCL11A-10168 | + | CACGGCUCUCCCCGUCGCCG | 20 | 12105 |
| BCL11A-10169 | + | GAGGCAGGCGGCGCAGGCCG | 20 | 12106 |
| BCL11A-10170 | - | CGGAGUCGGGAGAGGGGCCG | 20 | 12107 |
| BCL11A-10171 | + | CGGCCCCUCUCCCGACUCCG | 20 | 12108 |
| BCL11A-10172 | - | CCCCGGCGCUCCUGAGUCCG | 20 | 12109 |
| BCL11A-10173 | + | AGCCCCGGGCUGGGGAAGCG | 20 | 12110 |
| BCL11A-10174 | - | CCACACGCGGGGAGCGAGCG | 20 | 12111 |
| BCL11A-10175 | - | GCCCUGGCGUCCACACGCG | 20 | 12112 |
| BCL11A-10176 | + | CAAGUCUCCAGGAGCCCGCG | 20 | 12113 |
| BCL11A-10177 | - | UCCCCUCUUUCCAGGCCGCG | 20 | 12114 |
| BCL11A-10178 | + | GGCGCGGGAGGGCAAGCGCG | 20 | 12115 |
| BCL11A-10179 | - | GAGCGAGCGCGGCGGCGGCG | 20 | 12116 |
| BCL11A-10180 | + | UUACAGCUCCGCAGCGGGCG | 20 | 12117 |
| BCL11A-10181 | + | UUUGCAAAACUGGCGGGGCG | 20 | 12118 |
| BCL11A-10182 | + | AUUAUUUUGCAAAACUGGCG | 20 | 12119 |
| BCL11A-10183 | - | CGAGCGCAGCCGCGGGCUCG | 20 | 12120 |
| BCL11A-10184 | + | CCUCUGGCCGGAACAAAAGG | 20 | 12121 |
| BCL11A-10185 | + | GAAAUAAAGCGGCGGAAAGG | 20 | 12122 |
| BCL11A-10186 | + | GGGGACCGGGGAGAGGCAGG | 20 | 12123 |
| BCL11A-10187 | + | GGCGGAAAGGAGGAAAGAGG | 20 | 12124 |
| BCL11A-10188 | - | CCUUUUGUUCCGGCCAGAGG | 20 | 12125 |

TABLE 18C-continued

| gRNA Name | DNA Strand | Targeting Domain | Target Site Length | SEQ ID NO: |
|---|---|---|---|---|
| BCL11A-10189 | - | AGUGGGUGUGCGUACGGAGG | 20 | 12126 |
| BCL11A-10190 | + | CCGCAGCGGGCGAGGGGAGG | 20 | 12127 |
| BCL11A-10191 | - | GGAAGUGGGUGUGCGUACGG | 20 | 12128 |
| BCL11A-10192 | + | CGCGGACUCAGGAGCGCCGG | 20 | 12129 |
| BCL11A-10193 | + | CGAAAAGAGAAAUAAAGCGG | 20 | 12130 |
| BCL11A-10194 | - | CACGCGGGGAGCGAGCGCGG | 20 | 12131 |
| BCL11A-10195 | - | GCGGGGAGCGAGCGCGGCGG | 20 | 12132 |
| BCL11A-10196 | - | GGGAGCGAGCGCGGCGGCGG | 20 | 12133 |
| BCL11A-10197 | + | GGCUGGGGAAGCGCGGGCGG | 20 | 12134 |
| BCL11A-10198 | + | UUGCAAAACUGGCGGGGCGG | 20 | 12135 |
| BCL11A-10199 | - | GGGAGCUGGUGGGGAAAGGG | 20 | 12136 |
| BCL11A-10200 | - | AAGAAAAUGGGGGGUAGGG | 20 | 12137 |
| BCL11A-10201 | + | UAGAGCGAGAGUGCACCGGG | 20 | 12138 |
| BCL11A-10202 | - | ACGGUCAAGUGUGCAGCGGG | 20 | 12139 |
| BCL11A-10203 | + | CCGGGCUGGGGAAGCGCGGG | 20 | 12140 |
| BCL11A-10204 | + | UGCAAAACUGGCGGGGCGGG | 20 | 12141 |
| BCL11A-10205 | + | GCUCCGCAGCGGGCGAGGGG | 20 | 12142 |
| BCL11A-10206 | - | CGAGCGCGGCGGCGGCGGGG | 20 | 12143 |
| BCL11A-10207 | + | GCAAAACUGGCGGGGCGGGG | 20 | 12144 |
| BCL11A-10208 | + | AUUUUGCAAAACUGGCGGGG | 20 | 12145 |
| BCL11A-10209 | + | CAAAACUGGCGGGGCGGGGG | 20 | 12146 |
| BCL11A-10210 | - | CUCACAUGCAAACCUGGGGG | 20 | 12147 |
| BCL11A-10211 | - | CUCACCGUAAGAAAAUGGGG | 20 | 12148 |
| BCL11A-9577 | - | UAGAGUCCGCGUGUGUGGGG | 20 | 12149 |
| BCL11A-10212 | - | ACUCACCGUAAGAAAAUGGG | 20 | 12150 |
| BCL11A-10213 | + | AGCGGGCGAGGGGAGGUGGG | 20 | 12151 |
| BCL11A-9769 | - | UUAGAGUCCGCGUGUGUGGG | 20 | 12152 |
| BCL11A-10214 | - | CACUCACCGUAAGAAAAUGG | 20 | 12153 |
| BCL11A-10215 | + | UCAUUAUUUUGCAAAACUGG | 20 | 12154 |
| BCL11A-10216 | - | CAACUCACAUGCAAACCUGG | 20 | 12155 |
| BCL11A-10217 | - | AACCUGGGGUGGGAGCUGG | 20 | 12156 |
| BCL11A-9578 | - | UUUAGAGUCCGCGUGUGUGG | 20 | 12157 |
| BCL11A-10218 | - | GCUGCGGAGCUGUAACUUGG | 20 | 12158 |
| BCL11A-10219 | - | GGUCCCUGGCUCGGCCUUGG | 20 | 12159 |
| BCL11A-10220 | + | GGAAUCCAGCCUAAGUUUGG | 20 | 12160 |
| BCL11A-10221 | - | CCACUCACCGUAAGAAAAUG | 20 | 12161 |
| BCL11A-10222 | - | AUAGUGAGAAAGUGGCACUG | 20 | 12162 |
| BCL11A-10223 | - | ACAACUCACAUGCAAACCUG | 20 | 12163 |

TABLE 18C-continued

| gRNA Name | DNA Strand | Targeting Domain | Target Site Length | SEQ ID NO: |
|---|---|---|---|---|
| BCL11A-10224 | - | CCACCUCCCCUCGCCCGCUG | 20 | 12164 |
| BCL11A-10225 | + | AGCCUAAGUUUGGAGGGCUG | 20 | 12165 |
| BCL11A-10226 | + | GAGGCUGCAGCCCCGGGCUG | 20 | 12166 |
| BCL11A-10227 | + | CCGCGCUCGCUCCCCGCGUG | 20 | 12167 |
| BCL11A-10228 | - | CCUGGGGGUGGGAGCUGGUG | 20 | 12168 |
| BCL11A-9581 | - | CAUUUUAGAGUCCGCGUGUG | 20 | 12169 |
| BCL11A-9776 | - | UUUUAGAGUCCGCGUGUGUG | 20 | 12170 |
| BCL11A-10229 | + | GCCACUUUCUCACUAUUGUG | 20 | 12171 |
| BCL11A-10230 | + | GUGCCACUUUCUCACUAUUG | 20 | 12172 |
| BCL11A-10231 | - | CGGUCCCUGGCUCGGCCUUG | 20 | 12173 |
| BCL11A-10232 | - | CCCACUCACCGUAAGAAAAU | 20 | 12174 |
| BCL11A-10233 | - | CCCGCUGCGGAGCUGUAACU | 20 | 12175 |
| BCL11A-10234 | - | CGCGCGGGCUCCUGGAGACU | 20 | 12176 |
| BCL11A-10235 | - | AACAACUCACAUGCAAACCU | 20 | 12177 |
| BCL11A-10236 | - | CUCGGCCUUGGGGCGCCCU | 20 | 12178 |
| BCL11A-10237 | - | CCCGGUCCCUGGCUCGGCCU | 20 | 12179 |
| BCL11A-10238 | - | UUUCUUUGCUGUCCUCUCCU | 20 | 12180 |
| BCL11A-10239 | + | CCCGAGCCCGCGGCUGCGCU | 20 | 12181 |
| BCL11A-10240 | + | GGAGGCUGCAGCCCCGGGCU | 20 | 12182 |
| BCL11A-10241 | - | CCCGAGCGCAGCCGCGGGCU | 20 | 12183 |
| BCL11A-10242 | - | CGGCGGCGGGGAGGGGAAGU | 20 | 12184 |
| BCL11A-10243 | - | CGCUCCUGAGUCCGCGGAGU | 20 | 12185 |
| BCL11A-10244 | + | CCCAUUUUCUUACGGUGAGU | 20 | 12186 |
| BCL11A-10245 | - | GCGGCGACGGGGAGAGCCGU | 20 | 12187 |
| BCL11A-10246 | - | CUUUUGUUCCGGCCAGAGGU | 20 | 12188 |
| BCL11A-10247 | + | CGCAGCGGGCGAGGGGAGGU | 20 | 12189 |
| BCL11A-10248 | - | CCGUAAGAAAAUGGGGGGGU | 20 | 12190 |
| BCL11A-10249 | - | UCACAUGCAAACCUGGGGGU | 20 | 12191 |
| BCL11A-10250 | - | ACCUGGGGGUGGGAGCUGGU | 20 | 12192 |
| BCL11A-9586 | - | AUUUUAGAGUCCGCGUGUGU | 20 | 12193 |
| BCL11A-10251 | + | UGCCACUUUCUCACUAUUGU | 20 | 12194 |
| BCL11A-10252 | - | ACCCGCAGCCCUCCAAACUU | 20 | 12195 |
| BCL11A-10253 | - | GGAGGCUCAGCUCUCAACUU | 20 | 12196 |
| BCL11A-10254 | - | GCGCGGGCUCCUGGAGACUU | 20 | 12197 |
| BCL11A-10255 | - | CGGGCUCGGGGCUUUUACUU | 20 | 12198 |
| BCL11A-10256 | - | CCGGUCCCUGGCUCGGCCUU | 20 | 12199 |
| BCL11A-10257 | + | CGCGGAAUCCAGCCUAAGUU | 20 | 12200 |
| BCL11A-10258 | - | AAAGAGGUGAGACUGGCUUU | 20 | 12201 |

Table 19A provides exemplary targeting domains for knocking down the BCL11A gene selected according to the first tier parameters. The targeting domains bind within 500 bp (e.g., upstream or downstream) of a transcription start site (TSS) and have a high level of orthogonality, and the PAM is NNGRRT. It is contemplated herein that in an embodiment the targeting domain hybridizes to the target domain through complementary base pairing. Any of the targeting domains in the table can be used with a *S. aureus* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 19A

1st Tier

| gRNA Name | DNA Strand | Targeting Domain | Target Site Length | SEQ ID NO: |
|---|---|---|---|---|
| BCL11A-10259 | + | GGCGUGGCCGGGAGAGAAGAA | 21 | 12202 |
| BCL11A-10260 | + | UGGCGUGGCCGGGAGAGAAGAA | 22 | 12203 |
| BCL11A-10261 | + | GUGGCGUGGCCGGGAGAGAAGAA | 23 | 12204 |
| BCL11A-10262 | + | GGUGGCGUGGCCGGGAGAGAAGAA | 24 | 12205 |
| BCL11A-10263 | + | CACGGCAAUGGUUCCAGA | 18 | 12206 |
| BCL11A-10264 | + | ACACGGCAAUGGUUCCAGA | 19 | 12207 |
| BCL11A-9557 | + | UACACGGCAAUGGUUCCAGA | 20 | 12208 |
| BCL11A-10265 | + | AUACACGGCAAUGGUUCCAGA | 21 | 12209 |
| BCL11A-10266 | + | CAUACACGGCAAUGGUUCCAGA | 22 | 12210 |
| BCL11A-10267 | + | GCAUACACGGCAAUGGUUCCAGA | 23 | 12211 |
| BCL11A-10268 | + | UGCAUACACGGCAAUGGUUCCAGA | 24 | 12212 |
| BCL11A-6258 | + | UUAUUGGGUUACUUACGC | 18 | 12213 |
| BCL11A-6259 | + | AUUAUUGGGUUACUUACGC | 19 | 12214 |
| BCL11A-6260 | + | UAUUAUUGGGUUACUUACGC | 20 | 12215 |
| BCL11A-6261 | + | CUAUUAUUGGGUUACUUACGC | 21 | 12216 |
| BCL11A-6262 | + | ACUAUUAUUGGGUUACUUACGC | 22 | 12217 |
| BCL11A-6263 | + | UACUAUUAUUGGGUUACUUACGC | 23 | 12218 |
| BCL11A-6264 | + | UUACUAUUAUUGGGUUACUUACGC | 24 | 12219 |
| BCL11A-10269 | + | GGGAGAGAAGAAAGGGGUGGC | 21 | 12220 |
| BCL11A-10270 | + | CGGGAGAGAAGAAAGGGGUGGC | 22 | 12221 |
| BCL11A-10271 | + | CCGGGAGAGAAGAAAGGGGUGGC | 23 | 12222 |
| BCL11A-10272 | + | GCCGGGAGAGAAGAAAGGGGUGGC | 24 | 12223 |
| BCL11A-6265 | + | UCCCGUUUGCUUAAGUGC | 18 | 12224 |
| BCL11A-6266 | + | UUCCCGUUUGCUUAAGUGC | 19 | 12225 |
| BCL11A-5352 | + | AUUCCCGUUUGCUUAAGUGC | 20 | 12226 |
| BCL11A-6267 | + | AAUUCCCGUUUGCUUAAGUGC | 21 | 12227 |
| BCL11A-6268 | + | GAAUUCCCGUUUGCUUAAGUGC | 22 | 12228 |
| BCL11A-6269 | + | AGAAUUCCCGUUUGCUUAAGUGC | 23 | 12229 |
| BCL11A-6270 | + | GAGAAUUCCCGUUUGCUUAAGUGC | 24 | 12230 |
| BCL11A-10273 | + | CCUGCGAACUUGAACGUC | 18 | 12231 |
| BCL11A-10274 | + | CCCUGCGAACUUGAACGUC | 19 | 12232 |
| BCL11A-9570 | + | UCCCUGCGAACUUGAACGUC | 20 | 12233 |

TABLE 19A-continued

| | 1st Tier | | | |
|---|---|---|---|---|
| gRNA Name | DNA Strand | Targeting Domain | Target Site Length | SEQ ID NO: |
| BCL11A-10275 | + | GUCCCUGCGAACUUGAACGUC | 21 | 12234 |
| BCL11A-10276 | + | CGUCCCUGCGAACUUGAACGUC | 22 | 12235 |
| BCL11A-10277 | + | ACGUCCCUGCGAACUUGAACGUC | 23 | 12236 |
| BCL11A-10278 | + | GACGUCCCUGCGAACUUGAACGUC | 24 | 12237 |
| BCL11A-10279 | + | UACAAAGAUGGCGCAGGGAAG | 21 | 12238 |
| BCL11A-10280 | + | AUACAAAGAUGGCGCAGGGAAG | 22 | 12239 |
| BCL11A-10281 | + | AAUACAAAGAUGGCGCAGGGAAG | 23 | 12240 |
| BCL11A-10282 | + | UAAUACAAAGAUGGCGCAGGGAAG | 24 | 12241 |
| BCL11A-10283 | + | CGGUUCACAUCGGGAGAG | 18 | 12242 |
| BCL11A-10284 | + | UCGGUUCACAUCGGGAGAG | 19 | 12243 |
| BCL11A-10285 | + | CUCGGUUCACAUCGGGAGAG | 20 | 12244 |
| BCL11A-10286 | + | GCUCGGUUCACAUCGGGAGAG | 21 | 12245 |
| BCL11A-10287 | + | GGCUCGGUUCACAUCGGGAGAG | 22 | 12246 |
| BCL11A-10288 | + | CGGCUCGGUUCACAUCGGGAGAG | 23 | 12247 |
| BCL11A-10289 | + | ACGGCUCGGUUCACAUCGGGAGAG | 24 | 12248 |
| BCL11A-10290 | + | AAUGGUUCCAGAUGGGAU | 18 | 12249 |
| BCL11A-10291 | + | CAAUGGUUCCAGAUGGGAU | 19 | 12250 |
| BCL11A-10292 | + | GCAAUGGUUCCAGAUGGGAU | 20 | 12251 |
| BCL11A-10293 | + | GGCAAUGGUUCCAGAUGGGAU | 21 | 12252 |
| BCL11A-10294 | + | CGGCAAUGGUUCCAGAUGGGAU | 22 | 12253 |
| BCL11A-10295 | + | ACGGCAAUGGUUCCAGAUGGGAU | 23 | 12254 |
| BCL11A-10296 | + | CACGGCAAUGGUUCCAGAUGGGAU | 24 | 12255 |
| BCL11A-10297 | + | AACUUGAACGUCAGGAGU | 18 | 12256 |
| BCL11A-10298 | + | GAACUUGAACGUCAGGAGU | 19 | 12257 |
| BCL11A-10299 | + | CGAACUUGAACGUCAGGAGU | 20 | 12258 |
| BCL11A-10300 | + | GCGAACUUGAACGUCAGGAGU | 21 | 12259 |
| BCL11A-10301 | + | UGCGAACUUGAACGUCAGGAGU | 22 | 12260 |
| BCL11A-10302 | + | CUGCGAACUUGAACGUCAGGAGU | 23 | 12261 |
| BCL11A-10303 | + | CCUGCGAACUUGAACGUCAGGAGU | 24 | 12262 |
| BCL11A-6304 | − | AACCCCAGCACUUAAGCAAAC | 21 | 12263 |
| BCL11A-6305 | − | AAACCCCAGCACUUAAGCAAAC | 22 | 12264 |
| BCL11A-6306 | − | CAAACCCCAGCACUUAAGCAAAC | 23 | 12265 |
| BCL11A-6307 | − | GCAAACCCCAGCACUUAAGCAAAC | 24 | 12266 |
| BCL11A-10304 | − | AAGCAAAAGCGAGGGGGAGAG | 21 | 12267 |
| BCL11A-10305 | − | GAAGCAAAAGCGAGGGGGAGAG | 22 | 12268 |
| BCL11A-10306 | − | AGAAGCAAAAGCGAGGGGGAGAG | 23 | 12269 |
| BCL11A-10307 | − | UAGAAGCAAAAGCGAGGGGGAGAG | 24 | 12270 |

Table 19B provides exemplary targeting domains for knocking down the BCL11A gene selected according to the second tier parameters. The targeting domains bind within 500 bp (e.g., upstream or downstream) of a transcription start site (TSS), and PAM is NNGRRT. It is contemplated herein that in an embodiment the targeting domain hybridizes to the target domain through complementary base pairing. Any of the targeting domains in the table can be used with a *S. aureus* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 19B

2nd Tier

| gRNA Name | DNA Strand | Targeting Domain | Target Site Length | SEQ ID NO: |
|---|---|---|---|---|
| BCL11A-10308 | + | GUGGCCGGGAGAGAAGAA | 18 | 12271 |
| BCL11A-10309 | + | CGUGGCCGGGAGAGAAGAA | 19 | 12272 |
| BCL11A-9697 | + | GCGUGGCCGGGAGAGAAGAA | 20 | 12273 |
| BCL11A-10310 | + | GUGGCAGGGGUGGGAGGA | 18 | 12274 |
| BCL11A-10311 | + | GGUGGCAGGGGUGGGAGGA | 19 | 12275 |
| BCL11A-10312 | + | GGGUGGCAGGGGUGGGAGGA | 20 | 12276 |
| BCL11A-10313 | + | GGGGUGGCAGGGGUGGGAGGA | 21 | 12277 |
| BCL11A-10314 | + | AGGGGUGGCAGGGGUGGGAGGA | 22 | 12278 |
| BCL11A-10315 | + | AAGGGGUGGCAGGGGUGGGAGGA | 23 | 12279 |
| BCL11A-10316 | + | AAAGGGGUGGCAGGGGUGGGAGGA | 24 | 12280 |
| BCL11A-10317 | + | UAAUUAUUAUUACUAUUA | 18 | 12281 |
| BCL11A-10318 | + | AUAAUUAUUAUUACUAUUA | 19 | 12282 |
| BCL11A-10319 | + | AAUAAUUAUUAUUACUAUUA | 20 | 12283 |
| BCL11A-10320 | + | UAAUAAUUAUUAUUACUAUUA | 21 | 12284 |
| BCL11A-10321 | + | UUAAUAAUUAUUAUUACUAUUA | 22 | 12285 |
| BCL11A-10322 | + | AUUAAUAAUUAUUAUUACUAUUA | 23 | 12286 |
| BCL11A-10323 | + | UAUUAAUAAUUAUUAUUACUAUUA | 24 | 12287 |
| BCL11A-10324 | + | AGAGAAGAAAGGGGUGGC | 18 | 12288 |
| BCL11A-10325 | + | GAGAGAAGAAAGGGGUGGC | 19 | 12289 |
| BCL11A-9726 | + | GGAGAGAAGAAAGGGGUGGC | 20 | 12290 |
| BCL11A-10326 | + | AAAGAUGGCGCAGGGAAG | 18 | 12291 |
| BCL11A-10327 | + | CAAAGAUGGCGCAGGGAAG | 19 | 12292 |
| BCL11A-10328 | + | ACAAAGAUGGCGCAGGGAAG | 20 | 12293 |
| BCL11A-6350 | − | CCCAGCACUUAAGCAAAC | 18 | 12294 |
| BCL11A-6351 | − | CCCCAGCACUUAAGCAAAC | 19 | 12295 |
| BCL11A-5458 | − | ACCCCAGCACUUAAGCAAAC | 20 | 12296 |
| BCL11A-10329 | − | UUCACGAGAAAACCUCC | 18 | 12297 |
| BCL11A-10330 | − | UUUCACGAGAAAACCUCC | 19 | 12298 |
| BCL11A-10331 | − | UUUUCACGAGAAAACCUCC | 20 | 12299 |
| BCL11A-10332 | − | UUUUUCACGAGAAAACCUCC | 21 | 12300 |
| BCL11A-10333 | − | AUUUUUCACGAGAAAACCUCC | 22 | 12301 |
| BCL11A-10334 | − | AAUUUUUCACGAGAAAACCUCC | 23 | 12302 |

TABLE 19B-continued

2nd Tier

| gRNA Name | DNA Strand | Targeting Domain | Target Site Length | SEQ ID NO: |
|---|---|---|---|---|
| BCL11A-10335 | − | AAAUUUUCACGAGAAAACCUCC | 24 | 12303 |
| BCL11A-10336 | − | UGAUGAAGAUAUUUUCUC | 18 | 12304 |
| BCL11A-10337 | − | CUGAUGAAGAUAUUUUCUC | 19 | 12305 |
| BCL11A-9731 | − | ACUGAUGAAGAUAUUUUCUC | 20 | 12306 |
| BCL11A-10338 | − | CACUGAUGAAGAUAUUUUCUC | 21 | 12307 |
| BCL11A-10339 | − | GCACUGAUGAAGAUAUUUUCUC | 22 | 12308 |
| BCL11A-10340 | − | GGCACUGAUGAAGAUAUUUUCUC | 23 | 12309 |
| BCL11A-10341 | − | AGGCACUGAUGAAGAUAUUUUCUC | 24 | 12310 |
| BCL11A-10342 | − | CAAAAGCGAGGGGGAGAG | 18 | 12311 |
| BCL11A-10343 | − | GCAAAAGCGAGGGGGAGAG | 19 | 12312 |
| BCL11A-4583 | − | AGCAAAAGCGAGGGGGAGAG | 20 | 12313 |
| BCL11A-10344 | − | UAUUAUUUCUAAUUUAUU | 18 | 12314 |
| BCL11A-10345 | − | GUAUUAUUUCUAAUUUAUU | 19 | 12315 |
| BCL11A-10346 | − | UGUAUUAUUUCUAAUUUAUU | 20 | 12316 |
| BCL11A-10347 | − | UUGUAUUAUUUCUAAUUUAUU | 21 | 12317 |
| BCL11A-10348 | − | UUUGUAUUAUUUCUAAUUUAUU | 22 | 12318 |
| BCL11A-10349 | − | CUUUGUAUUAUUUCUAAUUUAUU | 23 | 12319 |
| BCL11A-10350 | − | UCUUUGUAUUAUUUCUAAUUUAUU | 24 | 12320 |
| BCL11A-10351 | − | UUGAAUAAUCUUUCAUUU | 18 | 12321 |
| BCL11A-10352 | − | UUUGAAUAAUCUUUCAUUU | 19 | 12322 |
| BCL11A-10353 | − | UUUUGAAUAAUCUUUCAUUU | 20 | 12323 |
| BCL11A-10354 | − | UUUUUGAAUAAUCUUUCAUUU | 21 | 12324 |
| BCL11A-10355 | − | UUUUUUGAAUAAUCUUUCAUUU | 22 | 12325 |
| BCL11A-10356 | − | CUUUUUUGAAUAAUCUUUCAUUU | 23 | 12326 |
| BCL11A-10357 | − | UCUUUUUUGAAUAAUCUUUCAUUU | 24 | 12327 |

Table 19C provides exemplary targeting domains for knocking down the BCL11A gene selected according to the third tier parameters. The targeting domains bind within 500 bp (e.g., upstream or downstream) of a transcription start site (TSS), and the PAM is NNGRRV. It is contemplated herein that in an embodiment the targeting domain hybridizes to the target domain through complementary base pairing. Any of the targeting domains in the table can be used with a S. aureus eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used

TABLE 19C

3rd Tier

| gRNA Name | DNA Strand | Targeting Domain | Target Site Length | SEQ ID NO: |
|---|---|---|---|---|
| BCL11A-10358 | + | AAAAAAAAAAAAAAAAAA | 18 | 12328 |
| BCL11A-10359 | + | AAAAAAAAAAAAAAAAAAA | 19 | 12329 |
| BCL11A-4899 | + | AAAAAAAAAAAAAAAAAAAA | 20 | 12330 |

TABLE 19C-continued

| | | 3rd Tier | | |
|---|---|---|---|---|
| gRNA Name | DNA Strand | Targeting Domain | Target Site Length | SEQ ID NO: |
| BCL11A-10360 | + | AAAAAAAAAAAAAAAAAAAAA | 21 | 12331 |
| BCL11A-10361 | + | AAAAAAAAAAAAAAAAAAAAAA | 22 | 12332 |
| BCL11A-10362 | + | AAAAAAAAAAAAAAAAAAAAAAA | 23 | 12333 |
| BCL11A-10363 | + | AAAAAAAAAAAAAAAAAAAAAAAA | 24 | 12334 |
| BCL11A-10364 | + | CAGGGGCUGGACAUGAAA | 18 | 12335 |
| BCL11A-10365 | + | UCAGGGGCUGGACAUGAAA | 19 | 12336 |
| BCL11A-10366 | + | AUCAGGGGCUGGACAUGAAA | 20 | 12337 |
| BCL11A-10367 | + | CAUCAGGGGCUGGACAUGAAA | 21 | 12338 |
| BCL11A-10368 | + | ACAUCAGGGGCUGGACAUGAAA | 22 | 12339 |
| BCL11A-10369 | + | CACAUCAGGGGCUGGACAUGAAA | 23 | 12340 |
| BCL11A-10370 | + | ACACAUCAGGGGCUGGACAUGAAA | 24 | 12341 |
| BCL11A-10371 | + | ACACACGCGGACUCUAAA | 18 | 12342 |
| BCL11A-10372 | + | CACACACGCGGACUCUAAA | 19 | 12343 |
| BCL11A-10373 | + | CCACACACGCGGACUCUAAA | 20 | 12344 |
| BCL11A-10374 | + | CCCACACACGCGGACUCUAAA | 21 | 12345 |
| BCL11A-10375 | + | CCCCACACACGCGGACUCUAAA | 22 | 12346 |
| BCL11A-10376 | + | CCCCCACACACGCGGACUCUAAA | 23 | 12347 |
| BCL11A-10377 | + | CCCCCCACACACGCGGACUCUAAA | 24 | 12348 |
| BCL11A-10378 | + | AGAGGGAGAGAGAGAA | 18 | 12349 |
| BCL11A-10379 | + | AAGAGGGAGAGAGAGAA | 19 | 12350 |
| BCL11A-4921 | + | AAAGAGGGAGAGAGAGAA | 20 | 12351 |
| BCL11A-10380 | + | AAAAGAGGGAGAGAGAGAA | 21 | 12352 |
| BCL11A-10381 | + | AAAAAGAGGGAGAGAGAGAA | 22 | 12353 |
| BCL11A-10382 | + | AAAAAAGAGGGAGAGAGAGAA | 23 | 12354 |
| BCL11A-10383 | + | AAAAAAAGAGGGAGAGAGAGAA | 24 | 12355 |
| BCL11A-10384 | + | AGGGCGAGCAGGAGAGAA | 18 | 12356 |
| BCL11A-10385 | + | CAGGGCGAGCAGGAGAGAA | 19 | 12357 |
| BCL11A-4422 | + | GCAGGGCGAGCAGGAGAGAA | 20 | 12358 |
| BCL11A-10386 | + | GGCAGGGCGAGCAGGAGAGAA | 21 | 12359 |
| BCL11A-10387 | + | GGGCAGGGCGAGCAGGAGAGAA | 22 | 12360 |
| BCL11A-10388 | + | UGGGCAGGGCGAGCAGGAGAGAA | 23 | 12361 |
| BCL11A-10389 | + | AUGGGCAGGGCGAGCAGGAGAGAA | 24 | 12362 |
| BCL11A-10390 | + | GAGAAGGGGAGGAGGGAA | 18 | 12363 |
| BCL11A-10391 | + | AGAGAAGGGGAGGAGGGAA | 19 | 12364 |
| BCL11A-4404 | + | GAGAGAAGGGGAGGAGGGAA | 20 | 12365 |
| BCL11A-10392 | + | GGAGAGAAGGGGAGGAGGGAA | 21 | 12366 |
| BCL11A-10393 | + | AGGAGAGAAGGGGAGGAGGGAA | 22 | 12367 |
| BCL11A-10394 | + | CAGGAGAGAAGGGGAGGAGGGAA | 23 | 12368 |

TABLE 19C-continued

3rd Tier

| gRNA Name | DNA Strand | Targeting Domain | Target Site Length | SEQ ID NO: |
|---|---|---|---|---|
| BCL11A-10395 | + | GCAGGAGAGAAGGGGAGGAGGGAA | 24 | 12369 |
| BCL11A-10396 | + | ACGACGGCUCGGUUCACA | 18 | 12370 |
| BCL11A-10397 | + | GACGACGGCUCGGUUCACA | 19 | 12371 |
| BCL11A-10398 | + | GGACGACGGCUCGGUUCACA | 20 | 12372 |
| BCL11A-10399 | + | CGGACGACGGCUCGGUUCACA | 21 | 12373 |
| BCL11A-10400 | + | GCGGACGACGGCUCGGUUCACA | 22 | 12374 |
| BCL11A-10401 | + | GGCGGACGACGGCUCGGUUCACA | 23 | 12375 |
| BCL11A-10402 | + | GGGCGGACGACGGCUCGGUUCACA | 24 | 12376 |
| BCL11A-10403 | + | AAGGGGAAGCUCACACCA | 18 | 12377 |
| BCL11A-10404 | + | GAAGGGGAAGCUCACACCA | 19 | 12378 |
| BCL11A-10405 | + | GGAAGGGGAAGCUCACACCA | 20 | 12379 |
| BCL11A-10406 | + | GGGAAGGGGAAGCUCACACCA | 21 | 12380 |
| BCL11A-10407 | + | AGGGAAGGGGAAGCUCACACCA | 22 | 12381 |
| BCL11A-10408 | + | GAGGGAAGGGGAAGCUCACACCA | 23 | 12382 |
| BCL11A-10409 | + | GGAGGGAAGGGGAAGCUCACACCA | 24 | 12383 |
| BCL11A-10410 | + | AGAAAGAAGGAGACUCCA | 18 | 12384 |
| BCL11A-10411 | + | UAGAAAGAAGGAGACUCCA | 19 | 12385 |
| BCL11A-10412 | + | UUAGAAAGAAGGAGACUCCA | 20 | 12386 |
| BCL11A-10413 | + | GUUAGAAAGAAGGAGACUCCA | 21 | 12387 |
| BCL11A-10414 | + | GGUUAGAAAGAAGGAGACUCCA | 22 | 12388 |
| BCL11A-10415 | + | GGGUUAGAAAGAAGGAGACUCCA | 23 | 12389 |
| BCL11A-10416 | + | CGGGUUAGAAAGAAGGAGACUCCA | 24 | 12390 |
| BCL11A-10417 | + | GGCUCACCAGUGGCCGCA | 18 | 12391 |
| BCL11A-10418 | + | GGGCUCACCAGUGGCCGCA | 19 | 12392 |
| BCL11A-10419 | + | CGGGCUCACCAGUGGCCGCA | 20 | 12393 |
| BCL11A-10420 | + | GCGGGCUCACCAGUGGCCGCA | 21 | 12394 |
| BCL11A-10421 | + | CGCGGGCUCACCAGUGGCCGCA | 22 | 12395 |
| BCL11A-10422 | + | CCGCGGGCUCACCAGUGGCCGCA | 23 | 12396 |
| BCL11A-10423 | + | GCCGCGGGCUCACCAGUGGCCGCA | 24 | 12397 |
| BCL11A-10424 | + | UAAUACAAAGAUGGCGCA | 18 | 12398 |
| BCL11A-10425 | + | AUAAUACAAAGAUGGCGCA | 19 | 12399 |
| BCL11A-9702 | + | AAUAAUACAAAGAUGGCGCA | 20 | 12400 |
| BCL11A-10426 | + | AAAUAAUACAAAGAUGGCGCA | 21 | 12401 |
| BCL11A-10427 | + | GAAAUAAUACAAAGAUGGCGCA | 22 | 12402 |
| BCL11A-10428 | + | AGAAAUAAUACAAAGAUGGCGCA | 23 | 12403 |
| BCL11A-10429 | + | UAGAAAUAAUACAAAGAUGGCGCA | 24 | 12404 |
| BCL11A-10430 | + | AAAAAAAAAAAAAAGA | 18 | 12405 |

TABLE 19C-continued

3rd Tier

| gRNA Name | DNA Strand | Targeting Domain | Target Site Length | SEQ ID NO: |
|---|---|---|---|---|
| BCL11A-10431 | + | AAAAAAAAAAAAAAAAAGA | 19 | 12406 |
| BCL11A-4527 | + | AAAAAAAAAAAAAAAAAAGA | 20 | 12407 |
| BCL11A-10432 | + | AAAAAAAAAAAAAAAAAAAGA | 21 | 12408 |
| BCL11A-10433 | + | AAAAAAAAAAAAAAAAAAAAGA | 22 | 12409 |
| BCL11A-10434 | + | AAAAAAAAAAAAAAAAAAAAAGA | 23 | 12410 |
| BCL11A-10435 | + | AAAAAAAAAAAAAAAAAAAAAAGA | 24 | 12411 |
| BCL11A-10436 | + | AGAGCCGGGUUAGAAAGA | 18 | 12412 |
| BCL11A-10437 | + | GAGAGCCGGGUUAGAAAGA | 19 | 12413 |
| BCL11A-9708 | + | GGAGAGCCGGGUUAGAAAGA | 20 | 12414 |
| BCL11A-10438 | + | GGGAGAGCCGGGUUAGAAAGA | 21 | 12415 |
| BCL11A-10439 | + | CGGGAGAGCCGGGUUAGAAAGA | 22 | 12416 |
| BCL11A-10440 | + | UCGGGAGAGCCGGGUUAGAAAGA | 23 | 12417 |
| BCL11A-10441 | + | AUCGGGAGAGCCGGGUUAGAAAGA | 24 | 12418 |
| BCL11A-10442 | + | CGUGGCCGGGAGAGAAGA | 18 | 12419 |
| BCL11A-10443 | + | GCGUGGCCGGGAGAGAAGA | 19 | 12420 |
| BCL11A-10444 | + | GGCGUGGCCGGGAGAGAAGA | 20 | 12421 |
| BCL11A-10445 | + | UGGCGUGGCCGGGAGAGAAGA | 21 | 12422 |
| BCL11A-10446 | + | GUGGCGUGGCCGGGAGAGAAGA | 22 | 12423 |
| BCL11A-10447 | + | GGUGGCGUGGCCGGGAGAGAAGA | 23 | 12424 |
| BCL11A-10448 | + | CGGUGGCGUGGCCGGGAGAGAAGA | 24 | 12425 |
| BCL11A-10449 | + | AGAGAGAGAAGAGAGA | 18 | 12426 |
| BCL11A-10450 | + | GAGAGAGAGAAGAGAGA | 19 | 12427 |
| BCL11A-4845 | + | GGAGAGAGAGAAGAGAGA | 20 | 12428 |
| BCL11A-10451 | + | GGGAGAGAGAGAAGAGAGA | 21 | 12429 |
| BCL11A-10452 | + | AGGGAGAGAGAGAAGAGAGA | 22 | 12430 |
| BCL11A-10453 | + | GAGGGAGAGAGAGAAGAGAGA | 23 | 12431 |
| BCL11A-10454 | + | AGAGGGAGAGAGAGAAGAGAGA | 24 | 12432 |
| BCL11A-10455 | + | UAGAGGGAGAGAGAGAGA | 18 | 12433 |
| BCL11A-10456 | + | AUAGAGGGAGAGAGAGAGA | 19 | 12434 |
| BCL11A-10457 | + | GAUAGAGGGAGAGAGAGAGA | 20 | 12435 |
| BCL11A-10458 | + | AGAUAGAGGGAGAGAGAGAGA | 21 | 12436 |
| BCL11A-10459 | + | GAGAUAGAGGGAGAGAGAGAGA | 22 | 12437 |
| BCL11A-10460 | + | AGAGAUAGAGGGAGAGAGAGAGA | 23 | 12438 |
| BCL11A-10461 | + | GAGAGAUAGAGGGAGAGAGAGAGA | 24 | 12439 |
| BCL11A-10462 | + | GAUAGAGGGAGAGAGAGA | 18 | 12440 |
| BCL11A-10463 | + | AGAUAGAGGGAGAGAGAGA | 19 | 12441 |
| BCL11A-10464 | + | GAGAUAGAGGGAGAGAGAGA | 20 | 12442 |
| BCL11A-10465 | + | AGAGAUAGAGGGAGAGAGAGA | 21 | 12443 |

TABLE 19C-continued

3rd Tier

| gRNA Name | DNA Strand | Targeting Domain | Target Site Length | SEQ ID NO: |
|---|---|---|---|---|
| BCL11A-10466 | + | GAGAGAUAGAGGGAGAGAGAGA | 22 | 12444 |
| BCL11A-10467 | + | AGAGAGAUAGAGGGAGAGAGAGA | 23 | 12445 |
| BCL11A-10468 | + | AAGAGAGAUAGAGGGAGAGAGAGA | 24 | 12446 |
| BCL11A-10469 | + | AAAAAAGAGGGAGAGAGA | 18 | 12447 |
| BCL11A-10470 | + | AAAAAAAGAGGGAGAGAGA | 19 | 12448 |
| BCL11A-4911 | + | AAAAAAAAGAGGGAGAGAGA | 20 | 12449 |
| BCL11A-10471 | + | AAAAAAAAAGAGGGAGAGAGA | 21 | 12450 |
| BCL11A-10472 | + | AAAAAAAAAAGAGGGAGAGAGA | 22 | 12451 |
| BCL11A-10473 | + | AAAAAAAAAAAGAGGGAGAGAGA | 23 | 12452 |
| BCL11A-10474 | + | AAAAAAAAAAAAGAGGGAGAGAGA | 24 | 12453 |
| BCL11A-10475 | + | GAGAUAGAGGGAGAGAGA | 18 | 12454 |
| BCL11A-10476 | + | AGAGAUAGAGGGAGAGAGA | 19 | 12455 |
| BCL11A-10477 | + | GAGAGAUAGAGGGAGAGAGA | 20 | 12456 |
| BCL11A-10478 | + | AGAGAGAUAGAGGGAGAGAGA | 21 | 12457 |
| BCL11A-10479 | + | AAGAGAGAUAGAGGGAGAGAGA | 22 | 12458 |
| BCL11A-10480 | + | GAAGAGAGAUAGAGGGAGAGAGA | 23 | 12459 |
| BCL11A-10481 | + | AGAAGAGAGAUAGAGGGAGAGAGA | 24 | 12460 |
| BCL11A-10482 | + | CAGGGCGAGCAGGAGAGA | 18 | 12461 |
| BCL11A-10483 | + | GCAGGGCGAGCAGGAGAGA | 19 | 12462 |
| BCL11A-4464 | + | GGCAGGGCGAGCAGGAGAGA | 20 | 12463 |
| BCL11A-10484 | + | GGGCAGGGCGAGCAGGAGAGA | 21 | 12464 |
| BCL11A-10485 | + | UGGGCAGGGCGAGCAGGAGAGA | 22 | 12465 |
| BCL11A-10486 | + | AUGGGCAGGGCGAGCAGGAGAGA | 23 | 12466 |
| BCL11A-10487 | + | CAUGGGCAGGGCGAGCAGGAGAGA | 24 | 12467 |
| BCL11A-10488 | + | AAAAAAAGAGGGAGAGA | 18 | 12468 |
| BCL11A-10489 | + | AAAAAAAAGAGGGAGAGA | 19 | 12469 |
| BCL11A-4909 | + | AAAAAAAAAGAGGGAGAGA | 20 | 12470 |
| BCL11A-10490 | + | AAAAAAAAAAGAGGGAGAGA | 21 | 12471 |
| BCL11A-10491 | + | AAAAAAAAAAAGAGGGAGAGA | 22 | 12472 |
| BCL11A-10492 | + | AAAAAAAAAAAAGAGGGAGAGA | 23 | 12473 |
| BCL11A-10493 | + | AAAAAAAAAAAAAGAGGGAGAGA | 24 | 12474 |
| BCL11A-10494 | + | GAGAGAUAGAGGGAGAGA | 18 | 12475 |
| BCL11A-10495 | + | AGAGAGAUAGAGGGAGAGA | 19 | 12476 |
| BCL11A-10496 | + | AAGAGAGAUAGAGGGAGAGA | 20 | 12477 |
| BCL11A-10497 | + | GAAGAGAGAUAGAGGGAGAGA | 21 | 12478 |
| BCL11A-10498 | + | AGAAGAGAGAUAGAGGGAGAGA | 22 | 12479 |
| BCL11A-10499 | + | GAGAAGAGAGAUAGAGGGAGAGA | 23 | 12480 |

TABLE 19C-continued

3rd Tier

| gRNA Name | DNA Strand | Targeting Domain | Target Site Length | SEQ ID NO: |
|---|---|---|---|---|
| BCL11A-10500 | + | AGAGAAGAGAGAUAGAGGGAGAGA | 24 | 12481 |
| BCL11A-10501 | + | AAAAAAAAAAGAGGGAGA | 18 | 12482 |
| BCL11A-10502 | + | AAAAAAAAAAAGAGGGAGA | 19 | 12483 |
| BCL11A-4907 | + | AAAAAAAAAAAAGAGGGAGA | 20 | 12484 |
| BCL11A-10503 | + | AAAAAAAAAAAAAGAGGGAGA | 21 | 12485 |
| BCL11A-10504 | + | AAAAAAAAAAAAAAGAGGGAGA | 22 | 12486 |
| BCL11A-10505 | + | AAAAAAAAAAAAAAAGAGGGAGA | 23 | 12487 |
| BCL11A-10506 | + | AAAAAAAAAAAAAAAAGAGGGAGA | 24 | 12488 |
| BCL11A-10507 | + | AAGAGAGAUAGAGGGAGA | 18 | 12489 |
| BCL11A-10508 | + | GAAGAGAGAUAGAGGGAGA | 19 | 12490 |
| BCL11A-10509 | + | AGAAGAGAGAUAGAGGGAGA | 20 | 12491 |
| BCL11A-10510 | + | GAGAAGAGAGAUAGAGGGAGA | 21 | 12492 |
| BCL11A-10511 | + | AGAGAAGAGAGAUAGAGGGAGA | 22 | 12493 |
| BCL11A-10512 | + | GAGAGAAGAGAGAUAGAGGGAGA | 23 | 12494 |
| BCL11A-10513 | + | AGAGAGAAGAGAGAUAGAGGGAGA | 24 | 12495 |
| BCL11A-10514 | + | AGAGAGAAGAGAGAUAGA | 18 | 12496 |
| BCL11A-10515 | + | GAGAGAGAAGAGAGAUAGA | 19 | 12497 |
| BCL11A-9709 | + | AGAGAGAGAAGAGAGAUAGA | 20 | 12498 |
| BCL11A-10516 | + | GAGAGAGAGAAGAGAGAUAGA | 21 | 12499 |
| BCL11A-10517 | + | AGAGAGAGAGAAGAGAGAUAGA | 22 | 12500 |
| BCL11A-10518 | + | GAGAGAGAGAGAAGAGAGAUAGA | 23 | 12501 |
| BCL11A-10519 | + | GGAGAGAGAGAGAAGAGAGAUAGA | 24 | 12502 |
| BCL11A-10520 | + | CGGGAGAGCCGGGUUAGA | 18 | 12503 |
| BCL11A-10521 | + | UCGGGAGAGCCGGGUUAGA | 19 | 12504 |
| BCL11A-10522 | + | AUCGGGAGAGCCGGGUUAGA | 20 | 12505 |
| BCL11A-10523 | + | CAUCGGGAGAGCCGGGUUAGA | 21 | 12506 |
| BCL11A-10524 | + | ACAUCGGGAGAGCCGGGUUAGA | 22 | 12507 |
| BCL11A-10525 | + | CACAUCGGGAGAGCCGGGUUAGA | 23 | 12508 |
| BCL11A-10526 | + | UCACAUCGGGAGAGCCGGGUUAGA | 24 | 12509 |
| BCL11A-10527 | + | GGGGGAGGGGCGGGCCGA | 18 | 12510 |
| BCL11A-10528 | + | CGGGGGAGGGGCGGGCCGA | 19 | 12511 |
| BCL11A-4648 | + | CCGGGGGAGGGGCGGGCCGA | 20 | 12512 |
| BCL11A-10529 | + | CCCGGGGGAGGGGCGGGCCGA | 21 | 12513 |
| BCL11A-10530 | + | CCCCGGGGGAGGGGCGGGCCGA | 22 | 12514 |
| BCL11A-10531 | + | CCCCCGGGGGAGGGGCGGGCCGA | 23 | 12515 |
| BCL11A-10532 | + | GCCCCCGGGGGAGGGGCGGGCCGA | 24 | 12516 |
| BCL11A-10533 | + | UGGGCAGGGCGAGCAGGA | 18 | 12517 |
| BCL11A-10534 | + | AUGGGCAGGGCGAGCAGGA | 19 | 12518 |

TABLE 19C-continued

3rd Tier

| gRNA Name | DNA Strand | Targeting Domain | Target Site Length | SEQ ID NO: |
|---|---|---|---|---|
| BCL11A-10535 | + | CAUGGGCAGGGCGAGCAGGA | 20 | 12519 |
| BCL11A-10536 | + | ACAUGGGCAGGGCGAGCAGGA | 21 | 12520 |
| BCL11A-10537 | + | AACAUGGGCAGGGCGAGCAGGA | 22 | 12521 |
| BCL11A-10538 | + | AAACAUGGGCAGGGCGAGCAGGA | 23 | 12522 |
| BCL11A-10539 | + | AAAACAUGGGCAGGGCGAGCAGGA | 24 | 12523 |
| BCL11A-10540 | + | CAGGAGAGAAGGGGAGGA | 18 | 12524 |
| BCL11A-10541 | + | GCAGGAGAGAAGGGGAGGA | 19 | 12525 |
| BCL11A-4584 | + | AGCAGGAGAGAAGGGGAGGA | 20 | 12526 |
| BCL11A-10542 | + | GAGCAGGAGAGAAGGGGAGGA | 21 | 12527 |
| BCL11A-10543 | + | CGAGCAGGAGAGAAGGGGAGGA | 22 | 12528 |
| BCL11A-10544 | + | GCGAGCAGGAGAGAAGGGGAGGA | 23 | 12529 |
| BCL11A-10545 | + | GGCGAGCAGGAGAGAAGGGGAGGA | 24 | 12530 |
| BCL11A-10546 | + | AAAAAAAAAAAAGAGGGA | 18 | 12531 |
| BCL11A-10547 | + | AAAAAAAAAAAAAGAGGGA | 19 | 12532 |
| BCL11A-4905 | + | AAAAAAAAAAAAAAGAGGGA | 20 | 12533 |
| BCL11A-10548 | + | AAAAAAAAAAAAAAAGAGGGA | 21 | 12534 |
| BCL11A-10549 | + | AAAAAAAAAAAAAAAAGAGGGA | 22 | 12535 |
| BCL11A-10550 | + | AAAAAAAAAAAAAAAAAGAGGGA | 23 | 12536 |
| BCL11A-10551 | + | AAAAAAAAAAAAAAAAAAGAGGGA | 24 | 12537 |
| BCL11A-10552 | + | AGAAGAGAGAUAGAGGGA | 18 | 12538 |
| BCL11A-10553 | + | GAGAAGAGAGAUAGAGGGA | 19 | 12539 |
| BCL11A-10554 | + | AGAGAAGAGAGAUAGAGGGA | 20 | 12540 |
| BCL11A-10555 | + | GAGAGAAGAGAGAUAGAGGGA | 21 | 12541 |
| BCL11A-10556 | + | AGAGAGAAGAGAGAUAGAGGGA | 22 | 12542 |
| BCL11A-10557 | + | GAGAGAGAAGAGAGAUAGAGGGA | 23 | 12543 |
| BCL11A-10558 | + | AGAGAGAGAAGAGAGAUAGAGGGA | 24 | 12544 |
| BCL11A-10559 | + | AGAGAAGGGGAGGAGGGA | 18 | 12545 |
| BCL11A-10560 | + | GAGAGAAGGGGAGGAGGGA | 19 | 12546 |
| BCL11A-4459 | + | GGAGAGAAGGGGAGGAGGGA | 20 | 12547 |
| BCL11A-10561 | + | AGGAGAGAAGGGGAGGAGGGA | 21 | 12548 |
| BCL11A-10562 | + | CAGGAGAGAAGGGGAGGAGGGA | 22 | 12549 |
| BCL11A-10563 | + | GCAGGAGAGAAGGGGAGGAGGGA | 23 | 12550 |
| BCL11A-10564 | + | AGCAGGAGAGAAGGGGAGGAGGGA | 24 | 12551 |
| BCL11A-10565 | + | GCGGUGGCGUGGCCGGGA | 18 | 12552 |
| BCL11A-10566 | + | GGCGGUGGCGUGGCCGGGA | 19 | 12553 |
| BCL11A-10567 | + | CGGCGGUGGCGUGGCCGGGA | 20 | 12554 |
| BCL11A-10568 | + | GCGGCGGUGGCGUGGCCGGGA | 21 | 12555 |

TABLE 19C-continued

3rd Tier

| gRNA Name | DNA Strand | Targeting Domain | Target Site Length | SEQ ID NO: |
|---|---|---|---|---|
| BCL11A-10569 | + | CGCGGCGGUGGCGUGGCCGGGA | 22 | 12556 |
| BCL11A-10570 | + | CCGCGGCGGUGGCGUGGCCGGGA | 23 | 12557 |
| BCL11A-10571 | + | GCCGCGGCGGUGGCGUGGCCGGGA | 24 | 12558 |
| BCL11A-10572 | + | AGGGGCGGGCCGAGGGGA | 18 | 12559 |
| BCL11A-10573 | + | GAGGGGCGGGCCGAGGGGA | 19 | 12560 |
| BCL11A-4461 | + | GGAGGGGCGGGCCGAGGGGA | 20 | 12561 |
| BCL11A-10574 | + | GGGAGGGGCGGGCCGAGGGGA | 21 | 12562 |
| BCL11A-10575 | + | GGGGAGGGGCGGGCCGAGGGGA | 22 | 12563 |
| BCL11A-10576 | + | GGGGGAGGGGCGGGCCGAGGGGA | 23 | 12564 |
| BCL11A-10577 | + | CGGGGGAGGGGCGGGCCGAGGGGA | 24 | 12565 |
| BCL11A-10578 | + | CAAUGGCCAGUGCGGGA | 18 | 12566 |
| BCL11A-10579 | + | CCAAUGGCCAGUGCGGGA | 19 | 12567 |
| BCL11A-9558 | + | GCCAAUGGCCAGUGCGGGA | 20 | 12568 |
| BCL11A-10580 | + | AGCCAAUGGCCAGUGCGGGA | 21 | 12569 |
| BCL11A-10581 | + | AAGCCAAUGGCCAGUGCGGGA | 22 | 12570 |
| BCL11A-10582 | + | CAAGCCAAUGGCCAGUGCGGGA | 23 | 12571 |
| BCL11A-10583 | + | ACAAGCCAAUGGCCAGUGCGGGA | 24 | 12572 |
| BCL11A-10584 | + | GUCAGGAGUCUGGAUGGA | 18 | 12573 |
| BCL11A-10585 | + | CGUCAGGAGUCUGGAUGGA | 19 | 12574 |
| BCL11A-10586 | + | ACGUCAGGAGUCUGGAUGGA | 20 | 12575 |
| BCL11A-10587 | + | AACGUCAGGAGUCUGGAUGGA | 21 | 12576 |
| BCL11A-10588 | + | GAACGUCAGGAGUCUGGAUGGA | 22 | 12577 |
| BCL11A-10589 | + | UGAACGUCAGGAGUCUGGAUGGA | 23 | 12578 |
| BCL11A-10590 | + | UUGAACGUCAGGAGUCUGGAUGGA | 24 | 12579 |
| BCL11A-10591 | + | AGAGAGAGAAGAGAGAUA | 18 | 12580 |
| BCL11A-10592 | + | GAGAGAGAGAAGAGAGAUA | 19 | 12581 |
| BCL11A-10593 | + | AGAGAGAGAGAAGAGAGAUA | 20 | 12582 |
| BCL11A-10594 | + | GAGAGAGAGAGAAGAGAGAUA | 21 | 12583 |
| BCL11A-10595 | + | GGAGAGAGAGAGAAGAGAGAUA | 22 | 12584 |
| BCL11A-10596 | + | GGGAGAGAGAGAGAAGAGAGAUA | 23 | 12585 |
| BCL11A-10597 | + | AGGGAGAGAGAGAGAAGAGAGAUA | 24 | 12586 |
| BCL11A-10598 | + | GACAGAGACACACAAAAC | 18 | 12587 |
| BCL11A-10599 | + | GGACAGAGACACACAAAAC | 19 | 12588 |
| BCL11A-10600 | + | UGGACAGAGACACACAAAAC | 20 | 12589 |
| BCL11A-10601 | + | AUGGACAGAGACACACAAAAC | 21 | 12590 |
| BCL11A-10602 | + | GAUGGACAGAGACACACAAAAC | 22 | 12591 |
| BCL11A-10603 | + | GGAUGGACAGAGACACACAAAAC | 23 | 12592 |
| BCL11A-10604 | + | UGGAUGGACAGAGACACACAAAAC | 24 | 12593 |

TABLE 19C-continued

3rd Tier

| gRNA Name | DNA Strand | Targeting Domain | Target Site Length | SEQ ID NO: |
|---|---|---|---|---|
| BCL11A-10605 | + | CGUGACGUCCCUGCGAAC | 18 | 12594 |
| BCL11A-10606 | + | ACGUGACGUCCCUGCGAAC | 19 | 12595 |
| BCL11A-10607 | + | GACGUGACGUCCCUGCGAAC | 20 | 12596 |
| BCL11A-10608 | + | GGACGUGACGUCCCUGCGAAC | 21 | 12597 |
| BCL11A-10609 | + | CGGACGUGACGUCCCUGCGAAC | 22 | 12598 |
| BCL11A-10610 | + | GCGGACGUGACGUCCCUGCGAAC | 23 | 12599 |
| BCL11A-10611 | + | UGCGGACGUGACGUCCCUGCGAAC | 24 | 12600 |
| BCL11A-10612 | + | CUGCUCCCCCCCACACAC | 18 | 12601 |
| BCL11A-10613 | + | CCUGCUCCCCCCCACACAC | 19 | 12602 |
| BCL11A-10614 | + | CCCUGCUCCCCCCCACACAC | 20 | 12603 |
| BCL11A-10615 | + | GCCCUGCUCCCCCCCACACAC | 21 | 12604 |
| BCL11A-10616 | + | CGCCCUGCUCCCCCCCACACAC | 22 | 12605 |
| BCL11A-10617 | + | GCGCCCUGCUCCCCCCCACACAC | 23 | 12606 |
| BCL11A-10618 | + | UGCGCCCUGCUCCCCCCCACACAC | 24 | 12607 |
| BCL11A-10619 | + | UGGACAUGAAAAAGAGAC | 18 | 12608 |
| BCL11A-10620 | + | CUGGACAUGAAAAAGAGAC | 19 | 12609 |
| BCL11A-10621 | + | GCUGGACAUGAAAAAGAGAC | 20 | 12610 |
| BCL11A-10622 | + | GGCUGGACAUGAAAAAGAGAC | 21 | 12611 |
| BCL11A-10623 | + | GGGCUGGACAUGAAAAAGAGAC | 22 | 12612 |
| BCL11A-10624 | + | GGGGCUGGACAUGAAAAAGAGAC | 23 | 12613 |
| BCL11A-10625 | + | AGGGGCUGGACAUGAAAAAGAGAC | 24 | 12614 |
| BCL11A-10626 | + | ACACAUCAGGGGCUGGAC | 18 | 12615 |
| BCL11A-10627 | + | CACACAUCAGGGGCUGGAC | 19 | 12616 |
| BCL11A-10628 | + | ACACACAUCAGGGGCUGGAC | 20 | 12617 |
| BCL11A-10629 | + | GACACACAUCAGGGGCUGGAC | 21 | 12618 |
| BCL11A-10630 | + | GGACACACAUCAGGGGCUGGAC | 22 | 12619 |
| BCL11A-10631 | + | UGGACACACAUCAGGGGCUGGAC | 23 | 12620 |
| BCL11A-10632 | + | AUGGACACACAUCAGGGGCUGGAC | 24 | 12621 |
| BCL11A-6411 | + | UAUUAUGGGUUACUUAC | 18 | 12622 |
| BCL11A-6412 | + | CUAUUAUGGGUUACUUAC | 19 | 12623 |
| BCL11A-6413 | + | ACUAUUAUGGGUUACUUAC | 20 | 12624 |
| BCL11A-6414 | + | UACUAUUAUGGGUUACUUAC | 21 | 12625 |
| BCL11A-6415 | + | UUACUAUUAUGGGUUACUUAC | 22 | 12626 |
| BCL11A-6416 | + | AUUACUAUUAUGGGUUACUUAC | 23 | 12627 |
| BCL11A-6417 | + | UAUUACUAUUAUGGGUUACUUAC | 24 | 12628 |
| BCL11A-10633 | + | AAAAUGGCAAAAGCCCCC | 18 | 12629 |
| BCL11A-10634 | + | AAAAAUGGCAAAAGCCCCC | 19 | 12630 |

TABLE 19C-continued

3rd Tier

| gRNA Name | DNA Strand | Targeting Domain | Target Site Length | SEQ ID NO: |
|---|---|---|---|---|
| BCL11A-10635 | + | AAAAAAUGGCAAAAGCCCCC | 20 | 12631 |
| BCL11A-10636 | + | AAAAAAAUGGCAAAAGCCCCC | 21 | 12632 |
| BCL11A-10637 | + | GAAAAAAAUGGCAAAAGCCCCC | 22 | 12633 |
| BCL11A-10638 | + | UGAAAAAAAUGGCAAAAGCCCCC | 23 | 12634 |
| BCL11A-10639 | + | AUGAAAAAAAUGGCAAAAGCCCCC | 24 | 12635 |
| BCL11A-10640 | + | ACGCCAGACGCGGCCCCC | 18 | 12636 |
| BCL11A-10641 | + | GACGCCAGACGCGGCCCCC | 19 | 12637 |
| BCL11A-4456 | + | GGACGCCAGACGCGGCCCCC | 20 | 12638 |
| BCL11A-10642 | + | CGGACGCCAGACGCGGCCCCC | 21 | 12639 |
| BCL11A-10643 | + | GCGGACGCCAGACGCGGCCCCC | 22 | 12640 |
| BCL11A-10644 | + | CGCGGACGCCAGACGCGGCCCCC | 23 | 12641 |
| BCL11A-10645 | + | CCGCGGACGCCAGACGCGGCCCCC | 24 | 12642 |
| BCL11A-10646 | + | GACGCCAGACGCGGCCCC | 18 | 12643 |
| BCL11A-10647 | + | GGACGCCAGACGCGGCCCC | 19 | 12644 |
| BCL11A-4362 | + | CGGACGCCAGACGCGGCCCC | 20 | 12645 |
| BCL11A-10648 | + | GCGGACGCCAGACGCGGCCCC | 21 | 12646 |
| BCL11A-10649 | + | CGCGGACGCCAGACGCGGCCCC | 22 | 12647 |
| BCL11A-10650 | + | CCGCGGACGCCAGACGCGGCCCC | 23 | 12648 |
| BCL11A-10651 | + | UCCGCGGACGCCAGACGCGGCCCC | 24 | 12649 |
| BCL11A-10652 | + | GGACGCCAGACGCGGCCC | 18 | 12650 |
| BCL11A-10653 | + | CGGACGCCAGACGCGGCCC | 19 | 12651 |
| BCL11A-4825 | + | GCGGACGCCAGACGCGGCCC | 20 | 12652 |
| BCL11A-10654 | + | CGCGGACGCCAGACGCGGCCC | 21 | 12653 |
| BCL11A-10655 | + | CCGCGGACGCCAGACGCGGCCC | 22 | 12654 |
| BCL11A-10656 | + | UCCGCGGACGCCAGACGCGGCCC | 23 | 12655 |
| BCL11A-10657 | + | CUCCGCGGACGCCAGACGCGGCCC | 24 | 12656 |
| BCL11A-10658 | + | CCGGGGGAGGGGCGGGCC | 18 | 12657 |
| BCL11A-10659 | + | CCCGGGGGAGGGGCGGGCC | 19 | 12658 |
| BCL11A-5064 | + | CCCCGGGGGAGGGGCGGGCC | 20 | 12659 |
| BCL11A-10660 | + | CCCCCGGGGGAGGGGCGGGCC | 21 | 12660 |
| BCL11A-10661 | + | GCCCCCGGGGGAGGGGCGGGCC | 22 | 12661 |
| BCL11A-10662 | + | GGCCCCCGGGGGAGGGGCGGGCC | 23 | 12662 |
| BCL11A-10663 | + | CGGCCCCCGGGGGAGGGGCGGGCC | 24 | 12663 |
| BCL11A-10664 | + | GGAGGGGGCGCUGGGGCC | 18 | 12664 |
| BCL11A-10665 | + | GGGAGGGGGCGCUGGGGCC | 19 | 12665 |
| BCL11A-10666 | + | GGGGAGGGGGCGCUGGGGCC | 20 | 12666 |
| BCL11A-10667 | + | AGGGGAGGGGGCGCUGGGGCC | 21 | 12667 |
| BCL11A-10668 | + | GAGGGGAGGGGGCGCUGGGGCC | 22 | 12668 |

TABLE 19C-continued

3rd Tier

| gRNA Name | DNA Strand | Targeting Domain | Target Site Length | SEQ ID NO: |
|---|---|---|---|---|
| BCL11A-10669 | + | CGAGGGGAGGGGCGCUGGGGCC | 23 | 12669 |
| BCL11A-10670 | + | CCGAGGGGAGGGGCGCUGGGGCC | 24 | 12670 |
| BCL11A-10671 | + | CGCGGCGGUGGCGUGGCC | 18 | 12671 |
| BCL11A-10672 | + | CCGCGGCGGUGGCGUGGCC | 19 | 12672 |
| BCL11A-9718 | + | GCCGCGGCGGUGGCGUGGCC | 20 | 12673 |
| BCL11A-10673 | + | CGCCGCGGCGGUGGCGUGGCC | 21 | 12674 |
| BCL11A-10674 | + | GCGCCGCGGCGGUGGCGUGGCC | 22 | 12675 |
| BCL11A-10675 | + | AGCGCCGCGGCGGUGGCGUGGCC | 23 | 12676 |
| BCL11A-10676 | + | GAGCGCCGCGGCGGUGGCGUGGCC | 24 | 12677 |
| BCL11A-10677 | + | UGCGGGGCGGGGGCUCC | 18 | 12678 |
| BCL11A-10678 | + | GUGCGGGGCGGGGGCUCC | 19 | 12679 |
| BCL11A-10679 | + | GGUGCGGGGCGGGGGCUCC | 20 | 12680 |
| BCL11A-10680 | + | AGGUGCGGGGCGGGGGCUCC | 21 | 12681 |
| BCL11A-10681 | + | GAGGUGCGGGGCGGGGGCUCC | 22 | 12682 |
| BCL11A-10682 | + | GGAGGUGCGGGGCGGGGGCUCC | 23 | 12683 |
| BCL11A-10683 | + | GGGAGGUGCGGGGCGGGGGCUCC | 24 | 12684 |
| BCL11A-10684 | + | AACAUGGGCAGGGCGAGC | 18 | 12685 |
| BCL11A-10685 | + | AAACAUGGGCAGGGCGAGC | 19 | 12686 |
| BCL11A-9721 | + | AAAACAUGGGCAGGGCGAGC | 20 | 12687 |
| BCL11A-10686 | + | CAAAACAUGGGCAGGGCGAGC | 21 | 12688 |
| BCL11A-10687 | + | ACAAAACAUGGGCAGGGCGAGC | 22 | 12689 |
| BCL11A-10688 | + | CACAAAACAUGGGCAGGGCGAGC | 23 | 12690 |
| BCL11A-10689 | + | ACACAAAACAUGGGCAGGGCGAGC | 24 | 12691 |
| BCL11A-10690 | + | GCCGAGGGGAGGGGCGC | 18 | 12692 |
| BCL11A-10691 | + | GGCCGAGGGGAGGGGCGC | 19 | 12693 |
| BCL11A-4490 | + | GGGCCGAGGGGAGGGGCGC | 20 | 12694 |
| BCL11A-10692 | + | CGGGCCGAGGGGAGGGGCGC | 21 | 12695 |
| BCL11A-10693 | + | GCGGGCCGAGGGGAGGGGCGC | 22 | 12696 |
| BCL11A-10694 | + | GGCGGGCCGAGGGGAGGGGCGC | 23 | 12697 |
| BCL11A-10695 | + | GGGCGGGCCGAGGGGAGGGGCGC | 24 | 12698 |
| BCL11A-10696 | + | AUAAUACAAAGAUGGCGC | 18 | 12699 |
| BCL11A-10697 | + | AAUAAUACAAAGAUGGCGC | 19 | 12700 |
| BCL11A-9565 | + | AAAUAAUACAAAGAUGGCGC | 20 | 12701 |
| BCL11A-10698 | + | GAAAUAAUACAAAGAUGGCGC | 21 | 12702 |
| BCL11A-10699 | + | AGAAAUAAUACAAAGAUGGCGC | 22 | 12703 |
| BCL11A-10700 | + | UAGAAAUAAUACAAAGAUGGCGC | 23 | 12704 |
| BCL11A-10701 | + | UUAGAAAUAAUACAAAGAUGGCGC | 24 | 12705 |

TABLE 19C-continued

3rd Tier

| gRNA Name | DNA Strand | Targeting Domain | Target Site Length | SEQ ID NO: |
|---|---|---|---|---|
| BCL11A-10702 | + | GAGGGGGAGGUGCGGGGC | 18 | 12706 |
| BCL11A-10703 | + | GGAGGGGGAGGUGCGGGGC | 19 | 12707 |
| BCL11A-9724 | + | GGGAGGGGGAGGUGCGGGGC | 20 | 12708 |
| BCL11A-10704 | + | GGGGAGGGGGAGGUGCGGGGC | 21 | 12709 |
| BCL11A-10705 | + | CGGGGAGGGGGAGGUGCGGGGC | 22 | 12710 |
| BCL11A-10706 | + | GCGGGGAGGGGGAGGUGCGGGGC | 23 | 12711 |
| BCL11A-10707 | + | UGCGGGGAGGGGGAGGUGCGGGGC | 24 | 12712 |
| BCL11A-10708 | + | CCGCGGCGGUGGCGUGGC | 18 | 12713 |
| BCL11A-10709 | + | GCCGCGGCGGUGGCGUGGC | 19 | 12714 |
| BCL11A-9725 | + | CGCCGCGGCGGUGGCGUGGC | 20 | 12715 |
| BCL11A-10710 | + | GCGCCGCGGCGGUGGCGUGGC | 21 | 12716 |
| BCL11A-10711 | + | AGCGCCGCGGCGGUGGCGUGGC | 22 | 12717 |
| BCL11A-10712 | + | GAGCGCCGCGGCGGUGGCGUGGC | 23 | 12718 |
| BCL11A-10713 | + | CGAGCGCCGCGGCGGUGGCGUGGC | 24 | 12719 |
| BCL11A-10714 | + | CAAGCCAUGGCCAGUGC | 18 | 12720 |
| BCL11A-10715 | + | ACAAGCCAUGGCCAGUGC | 19 | 12721 |
| BCL11A-9727 | + | GACAAGCCAUGGCCAGUGC | 20 | 12722 |
| BCL11A-10716 | + | GGACAAGCCAUGGCCAGUGC | 21 | 12723 |
| BCL11A-10717 | + | AGGACAAGCCAUGGCCAGUGC | 22 | 12724 |
| BCL11A-10718 | + | CAGGACAAGCCAUGGCCAGUGC | 23 | 12725 |
| BCL11A-10719 | + | CCAGGACAAGCCAUGGCCAGUGC | 24 | 12726 |
| BCL11A-10720 | + | CACCAAUGGACACACAUC | 18 | 12727 |
| BCL11A-10721 | + | ACACCAAUGGACACACAUC | 19 | 12728 |
| BCL11A-9729 | + | CACACCAAUGGACACACAUC | 20 | 12729 |
| BCL11A-10722 | + | UCACACCAAUGGACACACAUC | 21 | 12730 |
| BCL11A-10723 | + | CUCACACCAAUGGACACACAUC | 22 | 12731 |
| BCL11A-10724 | + | GCUCACACCAAUGGACACACAUC | 23 | 12732 |
| BCL11A-10725 | + | AGCUCACACCAAUGGACACACAUC | 24 | 12733 |
| BCL11A-10726 | + | GACGGCUCGGUUCACAUC | 18 | 12734 |
| BCL11A-10727 | + | CGACGGCUCGGUUCACAUC | 19 | 12735 |
| BCL11A-9568 | + | ACGACGGCUCGGUUCACAUC | 20 | 12736 |
| BCL11A-10728 | + | GACGACGGCUCGGUUCACAUC | 21 | 12737 |
| BCL11A-10729 | + | GGACGACGGCUCGGUUCACAUC | 22 | 12738 |
| BCL11A-10730 | + | CGGACGACGGCUCGGUUCACAUC | 23 | 12739 |
| BCL11A-10731 | + | GCGGACGACGGCUCGGUUCACAUC | 24 | 12740 |
| BCL11A-10732 | + | UUAGAAAGAAGGAGACUC | 18 | 12741 |
| BCL11A-10733 | + | GUUAGAAAGAAGGAGACUC | 19 | 12742 |
| BCL11A-10734 | + | GGUUAGAAAGAAGGAGACUC | 20 | 12743 |

TABLE 19C-continued

3rd Tier

| gRNA Name | DNA Strand | Targeting Domain | Target Site Length | SEQ ID NO: |
|---|---|---|---|---|
| BCL11A-10735 | + | GGGUUAGAAAGAAGGAGACUC | 21 | 12744 |
| BCL11A-10736 | + | CGGGUUAGAAAGAAGGAGACUC | 22 | 12745 |
| BCL11A-10737 | + | CCGGGUUAGAAAGAAGGAGACUC | 23 | 12746 |
| BCL11A-10738 | + | GCCGGGUUAGAAAGAAGGAGACUC | 24 | 12747 |
| BCL11A-10739 | + | UCUCUUUUACCUCGACUC | 18 | 12748 |
| BCL11A-10740 | + | AUCUCUUUUACCUCGACUC | 19 | 12749 |
| BCL11A-10741 | + | UAUCUCUUUUACCUCGACUC | 20 | 12750 |
| BCL11A-10742 | + | UUAUCUCUUUUACCUCGACUC | 21 | 12751 |
| BCL11A-10743 | + | UUUAUCUCUUUUACCUCGACUC | 22 | 12752 |
| BCL11A-10744 | + | CUUUAUCUCUUUUACCUCGACUC | 23 | 12753 |
| BCL11A-10745 | + | CCUUUAUCUCUUUUACCUCGACUC | 24 | 12754 |
| BCL11A-10746 | + | CUCUCGGAGGUUUUUCUC | 18 | 12755 |
| BCL11A-10747 | + | ACUCUCGGAGGUUUUUCUC | 19 | 12756 |
| BCL11A-10748 | + | GACUCUCGGAGGUUUUUCUC | 20 | 12757 |
| BCL11A-10749 | + | CGACUCUCGGAGGUUUUUCUC | 21 | 12758 |
| BCL11A-10750 | + | UCGACUCUCGGAGGUUUUUCUC | 22 | 12759 |
| BCL11A-10751 | + | CUCGACUCUCGGAGGUUUUUCUC | 23 | 12760 |
| BCL11A-10752 | + | CCUCGACUCUCGGAGGUUUUUCUC | 24 | 12761 |
| BCL11A-10753 | + | AAAAAAAAAAAAAAAAG | 18 | 12762 |
| BCL11A-10754 | + | AAAAAAAAAAAAAAAAAG | 19 | 12763 |
| BCL11A-4526 | + | AAAAAAAAAAAAAAAAAAG | 20 | 12764 |
| BCL11A-10755 | + | AAAAAAAAAAAAAAAAAAAG | 21 | 12765 |
| BCL11A-10756 | + | AAAAAAAAAAAAAAAAAAAAG | 22 | 12766 |
| BCL11A-10757 | + | AAAAAAAAAAAAAAAAAAAAAG | 23 | 12767 |
| BCL11A-10758 | + | AAAAAAAAAAAAAAAAAAAAAAG | 24 | 12768 |
| BCL11A-10759 | + | GAGAGCCGGGUUAGAAAG | 18 | 12769 |
| BCL11A-10760 | + | GGAGAGCCGGGUUAGAAAG | 19 | 12770 |
| BCL11A-10761 | + | GGGAGAGCCGGGUUAGAAAG | 20 | 12771 |
| BCL11A-10762 | + | CGGGAGAGCCGGGUUAGAAAG | 21 | 12772 |
| BCL11A-10763 | + | UCGGGAGAGCCGGGUUAGAAAG | 22 | 12773 |
| BCL11A-10764 | + | AUCGGGAGAGCCGGGUUAGAAAG | 23 | 12774 |
| BCL11A-10765 | + | CAUCGGGAGAGCCGGGUUAGAAAG | 24 | 12775 |
| BCL11A-10766 | + | GGGCGAGCAGGAGAGAAG | 18 | 12776 |
| BCL11A-10767 | + | AGGGCGAGCAGGAGAGAAG | 19 | 12777 |
| BCL11A-4629 | + | CAGGGCGAGCAGGAGAGAAG | 20 | 12778 |
| BCL11A-10768 | + | GCAGGGCGAGCAGGAGAGAAG | 21 | 12779 |
| BCL11A-10769 | + | GGCAGGGCGAGCAGGAGAGAAG | 22 | 12780 |

TABLE 19C-continued

| 3rd Tier | | | | |
|---|---|---|---|---|
| gRNA Name | DNA Strand | Targeting Domain | Target Site Length | SEQ ID NO: |
| BCL11A-10770 | + | GGGCAGGGCGAGCAGGAGAGAAG | 23 | 12781 |
| BCL11A-10771 | + | UGGGCAGGGCGAGCAGGAGAGAAG | 24 | 12782 |
| BCL11A-10772 | + | AGAAGGGGAGGAGGGAAG | 18 | 12783 |
| BCL11A-10773 | + | GAGAAGGGGAGGAGGGAAG | 19 | 12784 |
| BCL11A-4577 | + | AGAGAAGGGGAGGAGGGAAG | 20 | 12785 |
| BCL11A-10774 | + | GAGAGAAGGGGAGGAGGGAAG | 21 | 12786 |
| BCL11A-10775 | + | GGAGAGAAGGGGAGGAGGGAAG | 22 | 12787 |
| BCL11A-10776 | + | AGGAGAGAAGGGGAGGAGGGAAG | 23 | 12788 |
| BCL11A-10777 | + | CAGGAGAGAAGGGGAGGAGGGAAG | 24 | 12789 |
| BCL11A-10778 | + | ACACGGCAAUGGUUCCAG | 18 | 12790 |
| BCL11A-10779 | + | UACACGGCAAUGGUUCCAG | 19 | 12791 |
| BCL11A-10780 | + | AUACACGGCAAUGGUUCCAG | 20 | 12792 |
| BCL11A-10781 | + | CAUACACGGCAAUGGUUCCAG | 21 | 12793 |
| BCL11A-10782 | + | GCAUACACGGCAAUGGUUCCAG | 22 | 12794 |
| BCL11A-10783 | + | UGCAUACACGGCAAUGGUUCCAG | 23 | 12795 |
| BCL11A-10784 | + | GUGCAUACACGGCAAUGGUUCCAG | 24 | 12796 |
| BCL11A-10785 | + | CAUGGGCAGGGCGAGCAG | 18 | 12797 |
| BCL11A-10786 | + | ACAUGGGCAGGGCGAGCAG | 19 | 12798 |
| BCL11A-10787 | + | AACAUGGGCAGGGCGAGCAG | 20 | 12799 |
| BCL11A-10788 | + | AAACAUGGGCAGGGCGAGCAG | 21 | 12800 |
| BCL11A-10789 | + | AAAACAUGGGCAGGGCGAGCAG | 22 | 12801 |
| BCL11A-10790 | + | CAAAACAUGGGCAGGGCGAGCAG | 23 | 12802 |
| BCL11A-10791 | + | ACAAAACAUGGGCAGGGCGAGCAG | 24 | 12803 |
| BCL11A-10792 | + | GGAGAGAGAGAGAGAGAG | 18 | 12804 |
| BCL11A-10793 | + | GGGAGAGAGAGAGAGAGAG | 19 | 12805 |
| BCL11A-4999 | + | AGGGAGAGAGAGAGAGAGAG | 20 | 12806 |
| BCL11A-10794 | + | GAGGGAGAGAGAGAGAGAGAG | 21 | 12807 |
| BCL11A-10795 | + | AGAGGGAGAGAGAGAGAGAGAG | 22 | 12808 |
| BCL11A-10796 | + | UAGAGGGAGAGAGAGAGAGAGAG | 23 | 12809 |
| BCL11A-10797 | + | AUAGAGGGAGAGAGAGAGAGAGAG | 24 | 12810 |
| BCL11A-10798 | + | AAAGAGGGAGAGAGAGAG | 18 | 12811 |
| BCL11A-10799 | + | AAAAGAGGGAGAGAGAGAG | 19 | 12812 |
| BCL11A-4916 | + | AAAAAGAGGGAGAGAGAGAG | 20 | 12813 |
| BCL11A-10800 | + | AAAAAAGAGGGAGAGAGAGAG | 21 | 12814 |
| BCL11A-10801 | + | AAAAAAAGAGGGAGAGAGAGAG | 22 | 12815 |
| BCL11A-10802 | + | AAAAAAAAGAGGGAGAGAGAGAG | 23 | 12816 |
| BCL11A-10803 | + | AAAAAAAAAGAGGGAGAGAGAGAG | 24 | 12817 |
| BCL11A-10804 | + | GCAGGGCGAGCAGGAGAG | 18 | 12818 |

TABLE 19C-continued

3rd Tier

| gRNA Name | DNA Strand | Targeting Domain | Target Site Length | SEQ ID NO: |
|---|---|---|---|---|
| BCL11A-10805 | + | GGCAGGGCGAGCAGGAGAG | 19 | 12819 |
| BCL11A-4870 | + | GGGCAGGGCGAGCAGGAGAG | 20 | 12820 |
| BCL11A-10806 | + | UGGGCAGGGCGAGCAGGAGAG | 21 | 12821 |
| BCL11A-10807 | + | AUGGGCAGGGCGAGCAGGAGAG | 22 | 12822 |
| BCL11A-10808 | + | CAUGGGCAGGGCGAGCAGGAGAG | 23 | 12823 |
| BCL11A-10809 | + | ACAUGGGCAGGGCGAGCAGGAGAG | 24 | 12824 |
| BCL11A-10810 | + | GUGGCGUGGCCGGGAGAG | 18 | 12825 |
| BCL11A-10811 | + | GGUGGCGUGGCCGGGAGAG | 19 | 12826 |
| BCL11A-10812 | + | CGGUGGCGUGGCCGGGAGAG | 20 | 12827 |
| BCL11A-10813 | + | GCGGUGGCGUGGCCGGGAGAG | 21 | 12828 |
| BCL11A-10814 | + | GGCGGUGGCGUGGCCGGGAGAG | 22 | 12829 |
| BCL11A-10815 | + | CGGCGGUGGCGUGGCCGGGAGAG | 23 | 12830 |
| BCL11A-10816 | + | GCGGCGGUGGCGUGGCCGGGAGAG | 24 | 12831 |
| BCL11A-10817 | + | GGGGAGGGGCGGGCCGAG | 18 | 12832 |
| BCL11A-10818 | + | GGGGGAGGGGCGGGCCGAG | 19 | 12833 |
| BCL11A-4677 | + | CGGGGGAGGGGCGGGCCGAG | 20 | 12834 |
| BCL11A-10819 | + | CCGGGGGAGGGGCGGGCCGAG | 21 | 12835 |
| BCL11A-10820 | + | CCCGGGGGAGGGGCGGGCCGAG | 22 | 12836 |
| BCL11A-10821 | + | CCCCGGGGGAGGGGCGGGCCGAG | 23 | 12837 |
| BCL11A-10822 | + | CCCCCGGGGGAGGGGCGGGCCGAG | 24 | 12838 |
| BCL11A-10823 | + | AAACAUGGGCAGGGCGAG | 18 | 12839 |
| BCL11A-10824 | + | AAAACAUGGGCAGGGCGAG | 19 | 12840 |
| BCL11A-10825 | + | CAAAACAUGGGCAGGGCGAG | 20 | 12841 |
| BCL11A-10826 | + | ACAAAACAUGGGCAGGGCGAG | 21 | 12842 |
| BCL11A-10827 | + | CACAAAACAUGGGCAGGGCGAG | 22 | 12843 |
| BCL11A-10828 | + | ACACAAAACAUGGGCAGGGCGAG | 23 | 12844 |
| BCL11A-10829 | + | CACACAAAACAUGGGCAGGGCGAG | 24 | 12845 |
| BCL11A-10830 | + | AGCAGGAGAGAAGGGGAG | 18 | 12846 |
| BCL11A-10831 | + | GAGCAGGAGAGAAGGGGAG | 19 | 12847 |
| BCL11A-5082 | + | CGAGCAGGAGAGAAGGGGAG | 20 | 12848 |
| BCL11A-10832 | + | GCGAGCAGGAGAGAAGGGGAG | 21 | 12849 |
| BCL11A-10833 | + | GGCGAGCAGGAGAGAAGGGGAG | 22 | 12850 |
| BCL11A-10834 | + | GGGCGAGCAGGAGAGAAGGGGAG | 23 | 12851 |
| BCL11A-10835 | + | AGGGCGAGCAGGAGAGAAGGGGAG | 24 | 12852 |
| BCL11A-10836 | + | AAUGGCCAGUGCGGGGAG | 18 | 12853 |
| BCL11A-10837 | + | CAAUGGCCAGUGCGGGGAG | 19 | 12854 |
| BCL11A-9572 | + | CCAAUGGCCAGUGCGGGGAG | 20 | 12855 |

TABLE 19C-continued

3rd Tier

| gRNA Name | DNA Strand | Targeting Domain | Target Site Length | SEQ ID NO: |
|---|---|---|---|---|
| BCL11A-10838 | + | GCCAAUGGCCAGUGCGGGAG | 21 | 12856 |
| BCL11A-10839 | + | AGCCAAUGGCCAGUGCGGGAG | 22 | 12857 |
| BCL11A-10840 | + | AAGCCAAUGGCCAGUGCGGGAG | 23 | 12858 |
| BCL11A-10841 | + | CAAGCCAAUGGCCAGUGCGGGAG | 24 | 12859 |
| BCL11A-10842 | + | GAGAGAGAAGAGAGAUAG | 18 | 12860 |
| BCL11A-10843 | + | AGAGAGAGAAGAGAGAUAG | 19 | 12861 |
| BCL11A-9740 | + | GAGAGAGAGAAGAGAGAUAG | 20 | 12862 |
| BCL11A-10844 | + | AGAGAGAGAGAAGAGAGAUAG | 21 | 12863 |
| BCL11A-10845 | + | GAGAGAGAGAGAAGAGAGAUAG | 22 | 12864 |
| BCL11A-10846 | + | GGAGAGAGAGAGAAGAGAGAUAG | 23 | 12865 |
| BCL11A-10847 | + | GGGAGAGAGAGAGAAGAGAGAUAG | 24 | 12866 |
| BCL11A-10848 | + | CGCCAGACGCGGCCCCCG | 18 | 12867 |
| BCL11A-10849 | + | ACGCCAGACGCGGCCCCCG | 19 | 12868 |
| BCL11A-4351 | + | GACGCCAGACGCGGCCCCCG | 20 | 12869 |
| BCL11A-10850 | + | GGACGCCAGACGCGGCCCCCG | 21 | 12870 |
| BCL11A-10851 | + | CGGACGCCAGACGCGGCCCCCG | 22 | 12871 |
| BCL11A-10852 | + | GCGGACGCCAGACGCGGCCCCCG | 23 | 12872 |
| BCL11A-10853 | + | CGCGGACGCCAGACGCGGCCCCCG | 24 | 12873 |
| BCL11A-10854 | + | CGGGGGAGGGGCGGGCCG | 18 | 12874 |
| BCL11A-10855 | + | CCGGGGGAGGGGCGGGCCG | 19 | 12875 |
| BCL11A-4642 | + | CCCGGGGGAGGGGCGGGCCG | 20 | 12876 |
| BCL11A-10856 | + | CCCCGGGGGAGGGGCGGGCCG | 21 | 12877 |
| BCL11A-10857 | + | CCCCCGGGGGAGGGGCGGGCCG | 22 | 12878 |
| BCL11A-10858 | + | GCCCCCGGGGGAGGGGCGGGCCG | 23 | 12879 |
| BCL11A-10859 | + | GGCCCCCGGGGGAGGGGCGGGCCG | 24 | 12880 |
| BCL11A-10860 | + | GCGGCGGCGGCGGCGGCG | 18 | 12881 |
| BCL11A-10861 | + | GGCGGCGGCGGCGGCGGCG | 19 | 12882 |
| BCL11A-5097 | + | CGGCGGCGGCGGCGGCGGCG | 20 | 12883 |
| BCL11A-10862 | + | GCGGCGGCGGCGGCGGCGGCG | 21 | 12884 |
| BCL11A-10863 | + | GGCGGCGGCGGCGGCGGCGGCG | 22 | 12885 |
| BCL11A-10864 | + | CGGCGGCGGCGGCGGCGGCGGCG | 23 | 12886 |
| BCL11A-10865 | + | GCGGCGGCGGCGGCGGCGGCGGCG | 24 | 12887 |
| BCL11A-10866 | + | AGGGGGAGGUGCGGGGCG | 18 | 12888 |
| BCL11A-10867 | + | GAGGGGGAGGUGCGGGGCG | 19 | 12889 |
| BCL11A-9749 | + | GGAGGGGGAGGUGCGGGGCG | 20 | 12890 |
| BCL11A-10868 | + | GGGAGGGGGAGGUGCGGGGCG | 21 | 12891 |
| BCL11A-10869 | + | GGGGAGGGGGAGGUGCGGGGCG | 22 | 12892 |
| BCL11A-10870 | + | CGGGGAGGGGGAGGUGCGGGGCG | 23 | 12893 |

TABLE 19C-continued

3rd Tier

| gRNA Name | DNA Strand | Targeting Domain | Target Site Length | SEQ ID NO: |
|---|---|---|---|---|
| BCL11A-10871 | + | GCGGGGAGGGGGAGGUGCGGGGCG | 24 | 12894 |
| BCL11A-10872 | + | GGCCGAGGGGAGGGGCG | 18 | 12895 |
| BCL11A-10873 | + | GGGCCGAGGGGAGGGGCG | 19 | 12896 |
| BCL11A-5099 | + | CGGGCCGAGGGGAGGGGCG | 20 | 12897 |
| BCL11A-10874 | + | GCGGGCCGAGGGGAGGGGCG | 21 | 12898 |
| BCL11A-10875 | + | GGCGGGCCGAGGGGAGGGGCG | 22 | 12899 |
| BCL11A-10876 | + | GGGCGGGCCGAGGGGAGGGGCG | 23 | 12900 |
| BCL11A-10877 | + | GGGGCGGGCCGAGGGGAGGGGCG | 24 | 12901 |
| BCL11A-10878 | + | AAUAAUACAAAGAUGGCG | 18 | 12902 |
| BCL11A-10879 | + | AAAUAAUACAAAGAUGGCG | 19 | 12903 |
| BCL11A-10880 | + | GAAAUAAUACAAAGAUGGCG | 20 | 12904 |
| BCL11A-10881 | + | AGAAAUAAUACAAAGAUGGCG | 21 | 12905 |
| BCL11A-10882 | + | UAGAAAUAAUACAAAGAUGGCG | 22 | 12906 |
| BCL11A-10883 | + | UUAGAAAUAAUACAAAGAUGGCG | 23 | 12907 |
| BCL11A-10884 | + | AUUAGAAAUAAUACAAAGAUGGCG | 24 | 12908 |
| BCL11A-10885 | + | AAGCCAAUGGCCAGUGCG | 18 | 12909 |
| BCL11A-10886 | + | CAAGCCAAUGGCCAGUGCG | 19 | 12910 |
| BCL11A-9751 | + | ACAAGCCAAUGGCCAGUGCG | 20 | 12911 |
| BCL11A-10887 | + | GACAAGCCAAUGGCCAGUGCG | 21 | 12912 |
| BCL11A-10888 | + | GGACAAGCCAAUGGCCAGUGCG | 22 | 12913 |
| BCL11A-10889 | + | AGGACAAGCCAAUGGCCAGUGCG | 23 | 12914 |
| BCL11A-10890 | + | CAGGACAAGCCAAUGGCCAGUGCG | 24 | 12915 |
| BCL11A-6490 | + | GGGUUUGCCUUGCUUGCG | 18 | 12916 |
| BCL11A-6491 | + | GGGGUUUGCCUUGCUUGCG | 19 | 12917 |
| BCL11A-6492 | + | UGGGGUUUGCCUUGCUUGCG | 20 | 12918 |
| BCL11A-6493 | + | CUGGGGUUUGCCUUGCUUGCG | 21 | 12919 |
| BCL11A-6494 | + | GCUGGGGUUUGCCUUGCUUGCG | 22 | 12920 |
| BCL11A-6495 | + | UGCUGGGGUUUGCCUUGCUUGCG | 23 | 12921 |
| BCL11A-6496 | + | GUGCUGGGGUUUGCCUUGCUUGCG | 24 | 12922 |
| BCL11A-10891 | + | CAGGGGUGGGAGGAAAGG | 18 | 12923 |
| BCL11A-10892 | + | GCAGGGGUGGGAGGAAAGG | 19 | 12924 |
| BCL11A-10893 | + | GGCAGGGGUGGGAGGAAAGG | 20 | 12925 |
| BCL11A-10894 | + | UGGCAGGGGUGGGAGGAAAGG | 21 | 12926 |
| BCL11A-10895 | + | GUGGCAGGGGUGGGAGGAAAGG | 22 | 12927 |
| BCL11A-10896 | + | GGUGGCAGGGGUGGGAGGAAAGG | 23 | 12928 |
| BCL11A-10897 | + | GGGUGGCAGGGGUGGGAGGAAAGG | 24 | 12929 |
| BCL11A-10898 | + | ACACAAAACAUGGGCAGG | 18 | 12930 |

TABLE 19C-continued

3rd Tier

| gRNA Name | DNA Strand | Targeting Domain | Target Site Length | SEQ ID NO: |
|---|---|---|---|---|
| BCL11A-10899 | + | CACACAAAACAUGGGCAGG | 19 | 12931 |
| BCL11A-10900 | + | ACACACAAAACAUGGGCAGG | 20 | 12932 |
| BCL11A-10901 | + | GACACACAAAACAUGGGCAGG | 21 | 12933 |
| BCL11A-10902 | + | AGACACACAAAACAUGGGCAGG | 22 | 12934 |
| BCL11A-10903 | + | GAGACACACAAAACAUGGGCAGG | 23 | 12935 |
| BCL11A-10904 | + | AGAGACACACAAAACAUGGGCAGG | 24 | 12936 |
| BCL11A-10905 | + | AAAAAAAAAAAAAGAGG | 18 | 12937 |
| BCL11A-10906 | + | AAAAAAAAAAAAAAGAGG | 19 | 12938 |
| BCL11A-4903 | + | AAAAAAAAAAAAAAAGAGG | 20 | 12939 |
| BCL11A-10907 | + | AAAAAAAAAAAAAAAAGAGG | 21 | 12940 |
| BCL11A-10908 | + | AAAAAAAAAAAAAAAAAGAGG | 22 | 12941 |
| BCL11A-10909 | + | AAAAAAAAAAAAAAAAAAGAGG | 23 | 12942 |
| BCL11A-10910 | + | AAAAAAAAAAAAAAAAAAAGAGG | 24 | 12943 |
| BCL11A-10911 | + | AGAGAAGAGAGAUAGAGG | 18 | 12944 |
| BCL11A-10912 | + | GAGAGAAGAGAGAUAGAGG | 19 | 12945 |
| BCL11A-10913 | + | AGAGAGAAGAGAGAUAGAGG | 20 | 12946 |
| BCL11A-10914 | + | GAGAGAGAAGAGAGAUAGAGG | 21 | 12947 |
| BCL11A-10915 | + | AGAGAGAGAAGAGAGAUAGAGG | 22 | 12948 |
| BCL11A-10916 | + | GAGAGAGAGAAGAGAGAUAGAGG | 23 | 12949 |
| BCL11A-10917 | + | AGAGAGAGAGAAGAGAGAUAGAGG | 24 | 12950 |
| BCL11A-10918 | + | GCAGGAGAGAAGGGGAGG | 18 | 12951 |
| BCL11A-10919 | + | AGCAGGAGAGAAGGGGAGG | 19 | 12952 |
| BCL11A-4408 | + | GAGCAGGAGAGAAGGGGAGG | 20 | 12953 |
| BCL11A-10920 | + | CGAGCAGGAGAGAAGGGGAGG | 21 | 12954 |
| BCL11A-10921 | + | GCGAGCAGGAGAGAAGGGGAGG | 22 | 12955 |
| BCL11A-10922 | + | GGCGAGCAGGAGAGAAGGGGAGG | 23 | 12956 |
| BCL11A-10923 | + | GGGCGAGCAGGAGAGAAGGGGAGG | 24 | 12957 |
| BCL11A-10924 | + | AUGGCCAGUGCGGGGAGG | 18 | 12958 |
| BCL11A-10925 | + | AAUGGCCAGUGCGGGGAGG | 19 | 12959 |
| BCL11A-9756 | + | CAAUGGCCAGUGCGGGGAGG | 20 | 12960 |
| BCL11A-10926 | + | CCAAUGGCCAGUGCGGGGAGG | 21 | 12961 |
| BCL11A-10927 | + | GCCAAUGGCCAGUGCGGGGAGG | 22 | 12962 |
| BCL11A-10928 | + | AGCCAAUGGCCAGUGCGGGGAGG | 23 | 12963 |
| BCL11A-10929 | + | AAGCCAAUGGCCAGUGCGGGGAGG | 24 | 12964 |
| BCL11A-10930 | + | GCCAGACGCGGCCCCCGG | 18 | 12965 |
| BCL11A-10931 | + | CGCCAGACGCGGCCCCCGG | 19 | 12966 |
| BCL11A-4561 | + | ACGCCAGACGCGGCCCCCGG | 20 | 12967 |
| BCL11A-10932 | + | GACGCCAGACGCGGCCCCCGG | 21 | 12968 |

TABLE 19C-continued

3rd Tier

| gRNA Name | DNA Strand | Targeting Domain | Target Site Length | SEQ ID NO: |
|---|---|---|---|---|
| BCL11A-10933 | + | GGACGCCAGACGCGGCCCCGG | 22 | 12969 |
| BCL11A-10934 | + | CGGACGCCAGACGCGGCCCCGG | 23 | 12970 |
| BCL11A-10935 | + | GCGGACGCCAGACGCGGCCCCGG | 24 | 12971 |
| BCL11A-10936 | + | CGGCGGUGGCGUGGCCGG | 18 | 12972 |
| BCL11A-10937 | + | GCGGCGGUGGCGUGGCCGG | 19 | 12973 |
| BCL11A-10938 | + | CGCGGCGGUGGCGUGGCCGG | 20 | 12974 |
| BCL11A-10939 | + | CCGCGGCGGUGGCGUGGCCGG | 21 | 12975 |
| BCL11A-10940 | + | GCCGCGGCGGUGGCGUGGCCGG | 22 | 12976 |
| BCL11A-10941 | + | CGCCGCGGCGGUGGCGUGGCCGG | 23 | 12977 |
| BCL11A-10942 | + | GCGCCGCGGCGGUGGCGUGGCCGG | 24 | 12978 |
| BCL11A-10943 | + | CGGCGGCGGCGGCGGCGG | 18 | 12979 |
| BCL11A-10944 | + | GCGGCGGCGGCGGCGGCGG | 19 | 12980 |
| BCL11A-4479 | + | GGCGGCGGCGGCGGCGGCGG | 20 | 12981 |
| BCL11A-10945 | + | CGGCGGCGGCGGCGGCGGCGG | 21 | 12982 |
| BCL11A-10946 | + | GCGGCGGCGGCGGCGGCGGCGG | 22 | 12983 |
| BCL11A-10947 | + | GGCGGCGGCGGCGGCGGCGGCGG | 23 | 12984 |
| BCL11A-10948 | + | CGGCGGCGGCGGCGGCGGCGGCGG | 24 | 12985 |
| BCL11A-10949 | + | CGGCUCGGUUCACAUCGG | 18 | 12986 |
| BCL11A-10950 | + | ACGGCUCGGUUCACAUCGG | 19 | 12987 |
| BCL11A-10951 | + | GACGGCUCGGUUCACAUCGG | 20 | 12988 |
| BCL11A-10952 | + | CGACGGCUCGGUUCACAUCGG | 21 | 12989 |
| BCL11A-10953 | + | ACGACGGCUCGGUUCACAUCGG | 22 | 12990 |
| BCL11A-10954 | + | GACGACGGCUCGGUUCACAUCGG | 23 | 12991 |
| BCL11A-10955 | + | GGACGACGGCUCGGUUCACAUCGG | 24 | 12992 |
| BCL11A-10956 | + | AGGGGUGGGAGGAAAGGG | 18 | 12993 |
| BCL11A-10957 | + | CAGGGGUGGGAGGAAAGGG | 19 | 12994 |
| BCL11A-9759 | + | GCAGGGGUGGGAGGAAAGGG | 20 | 12995 |
| BCL11A-10958 | + | GGCAGGGGUGGGAGGAAAGGG | 21 | 12996 |
| BCL11A-10959 | + | UGGCAGGGGUGGGAGGAAAGGG | 22 | 12997 |
| BCL11A-10960 | + | GUGGCAGGGGUGGGAGGAAAGGG | 23 | 12998 |
| BCL11A-10961 | + | GGUGGCAGGGGUGGGAGGAAAGGG | 24 | 12999 |
| BCL11A-10962 | + | GCGAGCAGGAGAGAAGGG | 18 | 13000 |
| BCL11A-10963 | + | GGCGAGCAGGAGAGAAGGG | 19 | 13001 |
| BCL11A-4873 | + | GGGCGAGCAGGAGAGAAGGG | 20 | 13002 |
| BCL11A-10964 | + | AGGGCGAGCAGGAGAGAAGGG | 21 | 13003 |
| BCL11A-10965 | + | CAGGGCGAGCAGGAGAGAAGGG | 22 | 13004 |
| BCL11A-10966 | + | GCAGGGCGAGCAGGAGAGAAGGG | 23 | 13005 |

TABLE 19C-continued

3rd Tier

| gRNA Name | DNA Strand | Targeting Domain | Target Site Length | SEQ ID NO: |
|---|---|---|---|---|
| BCL11A-10967 | + | GGCAGGGCGAGCAGGAGAGAAGGG | 24 | 13006 |
| BCL11A-10968 | + | AAGAAAGGGUGGCAGGG | 18 | 13007 |
| BCL11A-10969 | + | GAAGAAAGGGUGGCAGGG | 19 | 13008 |
| BCL11A-10970 | + | AGAAGAAAGGGUGGCAGGG | 20 | 13009 |
| BCL11A-10971 | + | GAGAAGAAAGGGUGGCAGGG | 21 | 13010 |
| BCL11A-10972 | + | AGAGAAGAAAGGGUGGCAGGG | 22 | 13011 |
| BCL11A-10973 | + | GAGAGAAGAAAGGGUGGCAGGG | 23 | 13012 |
| BCL11A-10974 | + | GGAGAGAAGAAAGGGUGGCAGGG | 24 | 13013 |
| BCL11A-10975 | + | GGAGGGGCGGGCCGAGGG | 18 | 13014 |
| BCL11A-10976 | + | GGGAGGGGCGGGCCGAGGG | 19 | 13015 |
| BCL11A-4875 | + | GGGGAGGGGCGGGCCGAGGG | 20 | 13016 |
| BCL11A-10977 | + | GGGGGAGGGGCGGGCCGAGGG | 21 | 13017 |
| BCL11A-10978 | + | CGGGGGAGGGGCGGGCCGAGGG | 22 | 13018 |
| BCL11A-10979 | + | CCGGGGGAGGGGCGGGCCGAGGG | 23 | 13019 |
| BCL11A-10980 | + | CCCGGGGGAGGGGCGGGCCGAGGG | 24 | 13020 |
| BCL11A-10981 | + | GAGAGAAGGGGAGGAGGG | 18 | 13021 |
| BCL11A-10982 | + | GGAGAGAAGGGGAGGAGGG | 19 | 13022 |
| BCL11A-4998 | + | AGGAGAGAAGGGGAGGAGGG | 20 | 13023 |
| BCL11A-10983 | + | CAGGAGAGAAGGGGAGGAGGG | 21 | 13024 |
| BCL11A-10984 | + | GCAGGAGAGAAGGGGAGGAGGG | 22 | 13025 |
| BCL11A-10985 | + | AGCAGGAGAGAAGGGGAGGAGGG | 23 | 13026 |
| BCL11A-10986 | + | GAGCAGGAGAGAAGGGGAGGAGGG | 24 | 13027 |
| BCL11A-10987 | + | GCGGCCCCGGGGGAGGG | 18 | 13028 |
| BCL11A-10988 | + | CGCGGCCCCGGGGGAGGG | 19 | 13029 |
| BCL11A-4959 | + | ACGCGGCCCCGGGGGAGGG | 20 | 13030 |
| BCL11A-10989 | + | GACGCGGCCCCGGGGGAGGG | 21 | 13031 |
| BCL11A-10990 | + | AGACGCGGCCCCGGGGGAGGG | 22 | 13032 |
| BCL11A-10991 | + | CAGACGCGGCCCCGGGGGAGGG | 23 | 13033 |
| BCL11A-10992 | + | CCAGACGCGGCCCCGGGGGAGGG | 24 | 13034 |
| BCL11A-10993 | + | CCCCGGGGGAGGGGCGGG | 18 | 13035 |
| BCL11A-10994 | + | CCCCCGGGGGAGGGGCGGG | 19 | 13036 |
| BCL11A-4817 | + | GCCCCCGGGGGAGGGGCGGG | 20 | 13037 |
| BCL11A-10995 | + | GGCCCCCGGGGGAGGGGCGGG | 21 | 13038 |
| BCL11A-10996 | + | CGGCCCCCGGGGGAGGGGCGGG | 22 | 13039 |
| BCL11A-10997 | + | GCGGCCCCCGGGGGAGGGGCGGG | 23 | 13040 |
| BCL11A-10998 | + | CGCGGCCCCCGGGGGAGGGGCGGG | 24 | 13041 |
| BCL11A-6504 | + | GACAUGGUGGGCUGCGGG | 18 | 13042 |
| BCL11A-6505 | + | AGACAUGGUGGGCUGCGGG | 19 | 13043 |

TABLE 19C-continued

3rd Tier

| gRNA Name | DNA Strand | Targeting Domain | Target Site Length | SEQ ID NO: |
|---|---|---|---|---|
| BCL11A-6506 | + | GAGACAUGGUGGGCUGCGGG | 20 | 13044 |
| BCL11A-6507 | + | CGAGACAUGGUGGGCUGCGGG | 21 | 13045 |
| BCL11A-6508 | + | GCGAGACAUGGUGGGCUGCGGG | 22 | 13046 |
| BCL11A-6509 | + | GGCGAGACAUGGUGGGCUGCGGG | 23 | 13047 |
| BCL11A-6510 | + | CGGCGAGACAUGGUGGGCUGCGGG | 24 | 13048 |
| BCL11A-10999 | + | GCCAAUGGCCAGUGCGGG | 18 | 13049 |
| BCL11A-11000 | + | AGCCAAUGGCCAGUGCGGG | 19 | 13050 |
| BCL11A-11001 | + | AAGCCAAUGGCCAGUGCGGG | 20 | 13051 |
| BCL11A-11002 | + | CAAGCCAAUGGCCAGUGCGGG | 21 | 13052 |
| BCL11A-11003 | + | ACAAGCCAAUGGCCAGUGCGGG | 22 | 13053 |
| BCL11A-11004 | + | GACAAGCCAAUGGCCAGUGCGGG | 23 | 13054 |
| BCL11A-11005 | + | GGACAAGCCAAUGGCCAGUGCGGG | 24 | 13055 |
| BCL11A-11006 | + | GGGAGGGGGAGGUGCGGG | 18 | 13056 |
| BCL11A-11007 | + | GGGGAGGGGGAGGUGCGGG | 19 | 13057 |
| BCL11A-11008 | + | CGGGGAGGGGGAGGUGCGGG | 20 | 13058 |
| BCL11A-11009 | + | GCGGGGAGGGGGAGGUGCGGG | 21 | 13059 |
| BCL11A-11010 | + | UGCGGGGAGGGGGAGGUGCGGG | 22 | 13060 |
| BCL11A-11011 | + | GUGCGGGGAGGGGGAGGUGCGGG | 23 | 13061 |
| BCL11A-11012 | + | AGUGCGGGGAGGGGGAGGUGCGGG | 24 | 13062 |
| BCL11A-11013 | + | CGAGCAGGAGAGAAGGGG | 18 | 13063 |
| BCL11A-11014 | + | GCGAGCAGGAGAGAAGGGG | 19 | 13064 |
| BCL11A-4476 | + | GGCGAGCAGGAGAGAAGGGG | 20 | 13065 |
| BCL11A-11015 | + | GGGCGAGCAGGAGAGAAGGGG | 21 | 13066 |
| BCL11A-11016 | + | AGGGCGAGCAGGAGAGAAGGGG | 22 | 13067 |
| BCL11A-11017 | + | CAGGGCGAGCAGGAGAGAAGGGG | 23 | 13068 |
| BCL11A-11018 | + | GCAGGGCGAGCAGGAGAGAAGGGG | 24 | 13069 |
| BCL11A-11019 | + | AGAAAGGGUGGCAGGGG | 18 | 13070 |
| BCL11A-11020 | + | AAGAAAGGGUGGCAGGGG | 19 | 13071 |
| BCL11A-9762 | + | GAAGAAAGGGUGGCAGGGG | 20 | 13072 |
| BCL11A-11021 | + | AGAAGAAAGGGUGGCAGGGG | 21 | 13073 |
| BCL11A-11022 | + | GAGAAGAAAGGGUGGCAGGGG | 22 | 13074 |
| BCL11A-11023 | + | AGAGAAGAAAGGGUGGCAGGGG | 23 | 13075 |
| BCL11A-11024 | + | GAGAGAAGAAAGGGUGGCAGGGG | 24 | 13076 |
| BCL11A-11025 | + | AUGGACACACAUCAGGGG | 18 | 13077 |
| BCL11A-11026 | + | AAUGGACACACAUCAGGGG | 19 | 13078 |
| BCL11A-11027 | + | CAAUGGACACACAUCAGGGG | 20 | 13079 |
| BCL11A-11028 | + | CCAAUGGACACACAUCAGGGG | 21 | 13080 |

TABLE 19C-continued

3rd Tier

| gRNA Name | DNA Strand | Targeting Domain | Target Site Length | SEQ ID NO: |
|---|---|---|---|---|
| BCL11A-11029 | + | ACCAAUGGACACACAUCAGGGG | 22 | 13081 |
| BCL11A-11030 | + | CACCAAUGGACACACAUCAGGGG | 23 | 13082 |
| BCL11A-11031 | + | ACACCAAUGGACACACAUCAGGGG | 24 | 13083 |
| BCL11A-11032 | + | GAGGGGCGGGCCGAGGGG | 18 | 13084 |
| BCL11A-11033 | + | GGAGGGGCGGGCCGAGGGG | 19 | 13085 |
| BCL11A-4486 | + | GGGAGGGGCGGGCCGAGGGG | 20 | 13086 |
| BCL11A-11034 | + | GGGGAGGGGCGGGCCGAGGGG | 21 | 13087 |
| BCL11A-11035 | + | GGGGGAGGGGCGGGCCGAGGGG | 22 | 13088 |
| BCL11A-11036 | + | CGGGGGAGGGGCGGGCCGAGGGG | 23 | 13089 |
| BCL11A-11037 | + | CCGGGGGAGGGGCGGGCCGAGGGG | 24 | 13090 |
| BCL11A-11038 | + | CAGACGCGGCCCCCGGGG | 18 | 13091 |
| BCL11A-11039 | + | CCAGACGCGGCCCCCGGGG | 19 | 13092 |
| BCL11A-4816 | + | GCCAGACGCGGCCCCCGGGG | 20 | 13093 |
| BCL11A-11040 | + | CGCCAGACGCGGCCCCCGGGG | 21 | 13094 |
| BCL11A-11041 | + | ACGCCAGACGCGGCCCCCGGGG | 22 | 13095 |
| BCL11A-11042 | + | GACGCCAGACGCGGCCCCCGGGG | 23 | 13096 |
| BCL11A-11043 | + | GGACGCCAGACGCGGCCCCCGGGG | 24 | 13097 |
| BCL11A-11044 | + | CCAAUGGCCAGUGCGGGG | 18 | 13098 |
| BCL11A-11045 | + | GCCAAUGGCCAGUGCGGGG | 19 | 13099 |
| BCL11A-9763 | + | AGCCAAUGGCCAGUGCGGGG | 20 | 13100 |
| BCL11A-11046 | + | AAGCCAAUGGCCAGUGCGGGG | 21 | 13101 |
| BCL11A-11047 | + | CAAGCCAAUGGCCAGUGCGGGG | 22 | 13102 |
| BCL11A-11048 | + | ACAAGCCAAUGGCCAGUGCGGGG | 23 | 13103 |
| BCL11A-11049 | + | GACAAGCCAAUGGCCAGUGCGGGG | 24 | 13104 |
| BCL11A-11050 | + | GGAGGGGGAGGUGCGGGG | 18 | 13105 |
| BCL11A-11051 | + | GGGAGGGGGAGGUGCGGGG | 19 | 13106 |
| BCL11A-9764 | + | GGGGAGGGGGAGGUGCGGGG | 20 | 13107 |
| BCL11A-11052 | + | CGGGGAGGGGGAGGUGCGGGG | 21 | 13108 |
| BCL11A-11053 | + | GCGGGGAGGGGGAGGUGCGGGG | 22 | 13109 |
| BCL11A-11054 | + | UGCGGGGAGGGGGAGGUGCGGGG | 23 | 13110 |
| BCL11A-11055 | + | GUGCGGGGAGGGGGAGGUGCGGGG | 24 | 13111 |
| BCL11A-11056 | + | AGACGCGGCCCCCGGGG | 18 | 13112 |
| BCL11A-11057 | + | CAGACGCGGCCCCCGGGGG | 19 | 13113 |
| BCL11A-4635 | + | CCAGACGCGGCCCCCGGGGG | 20 | 13114 |
| BCL11A-11058 | + | GCCAGACGCGGCCCCCGGGGG | 21 | 13115 |
| BCL11A-11059 | + | CGCCAGACGCGGCCCCCGGGGG | 22 | 13116 |
| BCL11A-11060 | + | ACGCCAGACGCGGCCCCCGGGGG | 23 | 13117 |
| BCL11A-11061 | + | GACGCCAGACGCGGCCCCCGGGGG | 24 | 13118 |

TABLE 19C-continued

3rd Tier

| gRNA Name | DNA Strand | Targeting Domain | Target Site Length | SEQ ID NO: |
|---|---|---|---|---|
| BCL11A-11062 | + | UGGGAGGAAAGGGUGGGG | 18 | 13119 |
| BCL11A-11063 | + | GUGGGAGGAAAGGGUGGGG | 19 | 13120 |
| BCL11A-9766 | + | GGUGGGAGGAAAGGGUGGGG | 20 | 13121 |
| BCL11A-11064 | + | GGGUGGGAGGAAAGGGUGGGG | 21 | 13122 |
| BCL11A-11065 | + | GGGGUGGGAGGAAAGGGUGGGG | 22 | 13123 |
| BCL11A-11066 | + | AGGGGUGGGAGGAAAGGGUGGGG | 23 | 13124 |
| BCL11A-11067 | + | CAGGGGUGGGAGGAAAGGGUGGGG | 24 | 13125 |
| BCL11A-11068 | + | AGACACACAAAACAUGGG | 18 | 13126 |
| BCL11A-11069 | + | GAGACACACAAAACAUGGG | 19 | 13127 |
| BCL11A-11070 | + | AGAGACACACAAAACAUGGG | 20 | 13128 |
| BCL11A-11071 | + | CAGAGACACACAAAACAUGGG | 21 | 13129 |
| BCL11A-11072 | + | ACAGAGACACACAAAACAUGGG | 22 | 13130 |
| BCL11A-11073 | + | GACAGAGACACACAAAACAUGGG | 23 | 13131 |
| BCL11A-11074 | + | GGACAGAGACACACAAAACAUGGG | 24 | 13132 |
| BCL11A-11075 | + | GCAAUGGUUCCAGAUGGG | 18 | 13133 |
| BCL11A-11076 | + | GGCAAUGGUUCCAGAUGGG | 19 | 13134 |
| BCL11A-11077 | + | CGGCAAUGGUUCCAGAUGGG | 20 | 13135 |
| BCL11A-11078 | + | ACGGCAAUGGUUCCAGAUGGG | 21 | 13136 |
| BCL11A-11079 | + | CACGGCAAUGGUUCCAGAUGGG | 22 | 13137 |
| BCL11A-11080 | + | ACACGGCAAUGGUUCCAGAUGGG | 23 | 13138 |
| BCL11A-11081 | + | UACACGGCAAUGGUUCCAGAUGGG | 24 | 13139 |
| BCL11A-11082 | + | GUGGGAGGAAAGGGUGGG | 18 | 13140 |
| BCL11A-11083 | + | GGUGGGAGGAAAGGGUGGG | 19 | 13141 |
| BCL11A-9767 | + | GGGUGGGAGGAAAGGGUGGG | 20 | 13142 |
| BCL11A-11084 | + | GGGGUGGGAGGAAAGGGUGGG | 21 | 13143 |
| BCL11A-11085 | + | AGGGGUGGGAGGAAAGGGUGGG | 22 | 13144 |
| BCL11A-11086 | + | CAGGGGUGGGAGGAAAGGGUGGG | 23 | 13145 |
| BCL11A-11087 | + | GCAGGGGUGGGAGGAAAGGGUGGG | 24 | 13146 |
| BCL11A-11088 | + | AGGGGUGGCAGGGGUGGG | 18 | 13147 |
| BCL11A-11089 | + | AAGGGGUGGCAGGGGUGGG | 19 | 13148 |
| BCL11A-9768 | + | AAAGGGGUGGCAGGGGUGGG | 20 | 13149 |
| BCL11A-11090 | + | GAAAGGGGUGGCAGGGGUGGG | 21 | 13150 |
| BCL11A-11091 | + | AGAAAGGGGUGGCAGGGGUGGG | 22 | 13151 |
| BCL11A-11092 | + | AAGAAAGGGGUGGCAGGGGUGGG | 23 | 13152 |
| BCL11A-11093 | + | GAAGAAAGGGGUGGCAGGGGUGGG | 24 | 13153 |
| BCL11A-11094 | + | UGAACGUCAGGAGUCUGG | 18 | 13154 |
| BCL11A-11095 | + | UUGAACGUCAGGAGUCUGG | 19 | 13155 |

TABLE 19C-continued

3rd Tier

| gRNA Name | DNA Strand | Targeting Domain | Target Site Length | SEQ ID NO: |
|---|---|---|---|---|
| BCL11A-11096 | + | CUUGAACGUCAGGAGUCUGG | 20 | 13156 |
| BCL11A-11097 | + | ACUUGAACGUCAGGAGUCUGG | 21 | 13157 |
| BCL11A-11098 | + | AACUUGAACGUCAGGAGUCUGG | 22 | 13158 |
| BCL11A-11099 | + | GAACUUGAACGUCAGGAGUCUGG | 23 | 13159 |
| BCL11A-11100 | + | CGAACUUGAACGUCAGGAGUCUGG | 24 | 13160 |
| BCL11A-11101 | + | GCCGCGGCGGUGGCGUGG | 18 | 13161 |
| BCL11A-11102 | + | CGCCGCGGCGGUGGCGUGG | 19 | 13162 |
| BCL11A-11103 | + | GCGCCGCGGCGGUGGCGUGG | 20 | 13163 |
| BCL11A-11104 | + | AGCGCCGCGGCGGUGGCGUGG | 21 | 13164 |
| BCL11A-11105 | + | GAGCGCCGCGGCGGUGGCGUGG | 22 | 13165 |
| BCL11A-11106 | + | CGAGCGCCGCGGCGGUGGCGUGG | 23 | 13166 |
| BCL11A-11107 | + | GCGAGCGCCGCGGCGGUGGCGUGG | 24 | 13167 |
| BCL11A-11108 | + | GGUGGGAGGAAAGGGUGG | 18 | 13168 |
| BCL11A-11109 | + | GGGUGGGAGGAAAGGGUGG | 19 | 13169 |
| BCL11A-9770 | + | GGGGUGGGAGGAAAGGGUGG | 20 | 13170 |
| BCL11A-11110 | + | AGGGGUGGGAGGAAAGGGUGG | 21 | 13171 |
| BCL11A-11111 | + | CAGGGGUGGGAGGAAAGGGUGG | 22 | 13172 |
| BCL11A-11112 | + | GCAGGGGUGGGAGGAAAGGGUGG | 23 | 13173 |
| BCL11A-11113 | + | GGCAGGGGUGGGAGGAAAGGGUGG | 24 | 13174 |
| BCL11A-11114 | + | GAGAGAAGAAAGGGUGG | 18 | 13175 |
| BCL11A-11115 | + | GGAGAGAAGAAAGGGUGG | 19 | 13176 |
| BCL11A-11116 | + | GGGAGAGAAGAAAGGGUGG | 20 | 13177 |
| BCL11A-11117 | + | CGGGAGAGAAGAAAGGGUGG | 21 | 13178 |
| BCL11A-11118 | + | CCGGGAGAGAAGAAAGGGUGG | 22 | 13179 |
| BCL11A-11119 | + | GCCGGGAGAGAAGAAAGGGUGG | 23 | 13180 |
| BCL11A-11120 | + | GGCCGGGAGAGAAGAAAGGGUGG | 24 | 13181 |
| BCL11A-11121 | + | AAGGGGUGGCAGGGGUGG | 18 | 13182 |
| BCL11A-11122 | + | AAAGGGGUGGCAGGGGUGG | 19 | 13183 |
| BCL11A-11123 | + | GAAAGGGGUGGCAGGGGUGG | 20 | 13184 |
| BCL11A-11124 | + | AGAAAGGGGUGGCAGGGGUGG | 21 | 13185 |
| BCL11A-11125 | + | AAGAAAGGGGUGGCAGGGGUGG | 22 | 13186 |
| BCL11A-11126 | + | GAAGAAAGGGGUGGCAGGGGUGG | 23 | 13187 |
| BCL11A-11127 | + | AGAAGAAAGGGGUGGCAGGGGUGG | 24 | 13188 |
| BCL11A-11128 | + | AGGGAAGAUGAAUUGUGG | 18 | 13189 |
| BCL11A-11129 | + | CAGGGAAGAUGAAUUGUGG | 19 | 13190 |
| BCL11A-11130 | + | GCAGGGAAGAUGAAUUGUGG | 20 | 13191 |
| BCL11A-11131 | + | CGCAGGGAAGAUGAAUUGUGG | 21 | 13192 |
| BCL11A-11132 | + | GCGCAGGGAAGAUGAAUUGUGG | 22 | 13193 |

TABLE 19C-continued

3rd Tier

| gRNA Name | DNA Strand | Targeting Domain | Target Site Length | SEQ ID NO: |
|---|---|---|---|---|
| BCL11A-11133 | + | GGCGCAGGGAAGAUGAAUUGUGG | 23 | 13194 |
| BCL11A-11134 | + | UGGCGCAGGGAAGAUGAAUUGUGG | 24 | 13195 |
| BCL11A-6524 | + | UGCUUGCGGCGAGACAUG | 18 | 13196 |
| BCL11A-6525 | + | UUGCUUGCGGCGAGACAUG | 19 | 13197 |
| BCL11A-6526 | + | CUUGCUUGCGGCGAGACAUG | 20 | 13198 |
| BCL11A-6527 | + | CCUUGCUUGCGGCGAGACAUG | 21 | 13199 |
| BCL11A-6528 | + | GCCUUGCUUGCGGCGAGACAUG | 22 | 13200 |
| BCL11A-6529 | + | UGCCUUGCUUGCGGCGAGACAUG | 23 | 13201 |
| BCL11A-6530 | + | UUGCCUUGCUUGCGGCGAGACAUG | 24 | 13202 |
| BCL11A-6544 | + | GCGAGACAUGGUGGGCUG | 18 | 13203 |
| BCL11A-6545 | + | GGCGAGACAUGGUGGGCUG | 19 | 13204 |
| BCL11A-5361 | + | CGGCGAGACAUGGUGGGCUG | 20 | 13205 |
| BCL11A-6546 | + | GCGGCGAGACAUGGUGGGCUG | 21 | 13206 |
| BCL11A-6547 | + | UGCGGCGAGACAUGGUGGGCUG | 22 | 13207 |
| BCL11A-6548 | + | UUGCGGCGAGACAUGGUGGGCUG | 23 | 13208 |
| BCL11A-6549 | + | CUUGCGGCGAGACAUGGUGGGCUG | 24 | 13209 |
| BCL11A-6550 | + | UUCCCGUUUGCUUAAGUG | 18 | 13210 |
| BCL11A-6551 | + | AUUCCCGUUUGCUUAAGUG | 19 | 13211 |
| BCL11A-6552 | + | AAUUCCCGUUUGCUUAAGUG | 20 | 13212 |
| BCL11A-6553 | + | GAAUUCCCGUUUGCUUAAGUG | 21 | 13213 |
| BCL11A-6554 | + | AGAAUUCCCGUUUGCUUAAGUG | 22 | 13214 |
| BCL11A-6555 | + | GAGAAUUCCCGUUUGCUUAAGUG | 23 | 13215 |
| BCL11A-6556 | + | CGAGAAUUCCCGUUUGCUUAAGUG | 24 | 13216 |
| BCL11A-11135 | + | ACAAGCCAAUGGCCAGUG | 18 | 13217 |
| BCL11A-11136 | + | GACAAGCCAAUGGCCAGUG | 19 | 13218 |
| BCL11A-9773 | + | GGACAAGCCAAUGGCCAGUG | 20 | 13219 |
| BCL11A-11137 | + | AGGACAAGCCAAUGGCCAGUG | 21 | 13220 |
| BCL11A-11138 | + | CAGGACAAGCCAAUGGCCAGUG | 22 | 13221 |
| BCL11A-11139 | + | CCAGGACAAGCCAAUGGCCAGUG | 23 | 13222 |
| BCL11A-11140 | + | ACCAGGACAAGCCAAUGGCCAGUG | 24 | 13223 |
| BCL11A-11141 | + | UGCGGGGAGGGGAGGUG | 18 | 13224 |
| BCL11A-11142 | + | GUGCGGGGAGGGGAGGUG | 19 | 13225 |
| BCL11A-9774 | + | AGUGCGGGGAGGGGAGGUG | 20 | 13226 |
| BCL11A-11143 | + | CAGUGCGGGGAGGGGAGGUG | 21 | 13227 |
| BCL11A-11144 | + | CCAGUGCGGGGAGGGGAGGUG | 22 | 13228 |
| BCL11A-11145 | + | GCCAGUGCGGGGAGGGGAGGUG | 23 | 13229 |
| BCL11A-11146 | + | GGCCAGUGCGGGGAGGGGAGGUG | 24 | 13230 |

TABLE 19C-continued

3rd Tier

| gRNA Name | DNA Strand | Targeting Domain | Target Site Length | SEQ ID NO: |
|---|---|---|---|---|
| BCL11A-11147 | + | GGGUGGGAGGAAAGGGUG | 18 | 13231 |
| BCL11A-11148 | + | GGGGUGGGAGGAAAGGGUG | 19 | 13232 |
| BCL11A-9775 | + | AGGGGUGGGAGGAAAGGGUG | 20 | 13233 |
| BCL11A-11149 | + | CAGGGGUGGGAGGAAAGGGUG | 21 | 13234 |
| BCL11A-11150 | + | GCAGGGGUGGGAGGAAAGGGUG | 22 | 13235 |
| BCL11A-11151 | + | GGCAGGGGUGGGAGGAAAGGGUG | 23 | 13236 |
| BCL11A-11152 | + | UGGCAGGGGUGGGAGGAAAGGGUG | 24 | 13237 |
| BCL11A-11153 | + | CGCAGGGAAGAUGAAUUG | 18 | 13238 |
| BCL11A-11154 | + | GCGCAGGGAAGAUGAAUUG | 19 | 13239 |
| BCL11A-9777 | + | GGCGCAGGGAAGAUGAAUUG | 20 | 13240 |
| BCL11A-11155 | + | UGGCGCAGGGAAGAUGAAUUG | 21 | 13241 |
| BCL11A-11156 | + | AUGGCGCAGGGAAGAUGAAUUG | 22 | 13242 |
| BCL11A-11157 | + | GAUGGCGCAGGGAAGAUGAAUUG | 23 | 13243 |
| BCL11A-11158 | + | AGAUGGCGCAGGGAAGAUGAAUUG | 24 | 13244 |
| BCL11A-11159 | + | UUGACAUCCAAAAUAAAU | 18 | 13245 |
| BCL11A-11160 | + | UUUGACAUCCAAAAUAAAU | 19 | 13246 |
| BCL11A-11161 | + | UUUUGACAUCCAAAAUAAAU | 20 | 13247 |
| BCL11A-11162 | + | CUUUUGACAUCCAAAAUAAAU | 21 | 13248 |
| BCL11A-11163 | + | CCUUUUGACAUCCAAAAUAAAU | 22 | 13249 |
| BCL11A-11164 | + | GCCUUUUGACAUCCAAAAUAAAU | 23 | 13250 |
| BCL11A-11165 | + | UGCCUUUUGACAUCCAAAAUAAAU | 24 | 13251 |
| BCL11A-11166 | + | ACACCAAUGGACACACAU | 18 | 13252 |
| BCL11A-11167 | + | CACACCAAUGGACACACAU | 19 | 13253 |
| BCL11A-11168 | + | UCACACCAAUGGACACACAU | 20 | 13254 |
| BCL11A-11169 | + | CUCACACCAAUGGACACACAU | 21 | 13255 |
| BCL11A-11170 | + | GCUCACACCAAUGGACACACAU | 22 | 13256 |
| BCL11A-11171 | + | AGCUCACACCAAUGGACACACAU | 23 | 13257 |
| BCL11A-11172 | + | AAGCUCACACCAAUGGACACACAU | 24 | 13258 |
| BCL11A-11173 | + | CGACGGCUCGGUUCACAU | 18 | 13259 |
| BCL11A-11174 | + | ACGACGGCUCGGUUCACAU | 19 | 13260 |
| BCL11A-9582 | + | GACGACGGCUCGGUUCACAU | 20 | 13261 |
| BCL11A-11175 | + | GGACGACGGCUCGGUUCACAU | 21 | 13262 |
| BCL11A-11176 | + | CGGACGACGGCUCGGUUCACAU | 22 | 13263 |
| BCL11A-11177 | + | GCGGACGACGGCUCGGUUCACAU | 23 | 13264 |
| BCL11A-11178 | + | GGCGGACGACGGCUCGGUUCACAU | 24 | 13265 |
| BCL11A-11179 | + | UGCGGACGUGACGUCCCU | 18 | 13266 |
| BCL11A-11180 | + | GUGCGGACGUGACGUCCCU | 19 | 13267 |
| BCL11A-11181 | + | AGUGCGGACGUGACGUCCCU | 20 | 13268 |

TABLE 19C-continued

3rd Tier

| gRNA Name | DNA Strand | Targeting Domain | Target Site Length | SEQ ID NO: |
|---|---|---|---|---|
| BCL11A-11182 | + | AAGUGCGGACGUGACGUCCCU | 21 | 13269 |
| BCL11A-11183 | + | CAAGUGCGGACGUGACGUCCCU | 22 | 13270 |
| BCL11A-11184 | + | UCAAGUGCGGACGUGACGUCCCU | 23 | 13271 |
| BCL11A-11185 | + | UUCAAGUGCGGACGUGACGUCCCU | 24 | 13272 |
| BCL11A-6618 | + | GGCGAGACAUGGUGGGCU | 18 | 13273 |
| BCL11A-6619 | + | CGGCGAGACAUGGUGGGCU | 19 | 13274 |
| BCL11A-6620 | + | GCGGCGAGACAUGGUGGGCU | 20 | 13275 |
| BCL11A-6621 | + | UGCGGCGAGACAUGGUGGGCU | 21 | 13276 |
| BCL11A-6622 | + | UUGCGGCGAGACAUGGUGGGCU | 22 | 13277 |
| BCL11A-6623 | + | CUUGCGGCGAGACAUGGUGGGCU | 23 | 13278 |
| BCL11A-6624 | + | GCUUGCGGCGAGACAUGGUGGGCU | 24 | 13279 |
| BCL11A-11186 | + | CUCUUUUACCUCGACUCU | 18 | 13280 |
| BCL11A-11187 | + | UCUCUUUUACCUCGACUCU | 19 | 13281 |
| BCL11A-9585 | + | AUCUCUUUUACCUCGACUCU | 20 | 13282 |
| BCL11A-11188 | + | UAUCUCUUUUACCUCGACUCU | 21 | 13283 |
| BCL11A-11189 | + | UUAUCUCUUUUACCUCGACUCU | 22 | 13284 |
| BCL11A-11190 | + | UUUAUCUCUUUUACCUCGACUCU | 23 | 13285 |
| BCL11A-11191 | + | CUUUAUCUCUUUUACCUCGACUCU | 24 | 13286 |
| BCL11A-11192 | + | UGAGCUGCAAGUUCAAGU | 18 | 13287 |
| BCL11A-11193 | + | CUGAGCUGCAAGUUCAAGU | 19 | 13288 |
| BCL11A-11194 | + | CCUGAGCUGCAAGUUCAAGU | 20 | 13289 |
| BCL11A-11195 | + | CCCUGAGCUGCAAGUUCAAGU | 21 | 13290 |
| BCL11A-11196 | + | CCCCUGAGCUGCAAGUUCAAGU | 22 | 13291 |
| BCL11A-11197 | + | CCCCCUGAGCUGCAAGUUCAAGU | 23 | 13292 |
| BCL11A-11198 | + | CCCCCCUGAGCUGCAAGUUCAAGU | 24 | 13293 |
| BCL11A-11199 | + | GACAAGCCAAUGGCCAGU | 18 | 13294 |
| BCL11A-11200 | + | GGACAAGCCAAUGGCCAGU | 19 | 13295 |
| BCL11A-11201 | + | AGGACAAGCCAAUGGCCAGU | 20 | 13296 |
| BCL11A-11202 | + | CAGGACAAGCCAAUGGCCAGU | 21 | 13297 |
| BCL11A-11203 | + | CCAGGACAAGCCAAUGGCCAGU | 22 | 13298 |
| BCL11A-11204 | + | ACCAGGACAAGCCAAUGGCCAGU | 23 | 13299 |
| BCL11A-11205 | + | GACCAGGACAAGCCAAUGGCCAGU | 24 | 13300 |
| BCL11A-11206 | + | CCCUGCGAACUUGAACGU | 18 | 13301 |
| BCL11A-11207 | + | UCCCUGCGAACUUGAACGU | 19 | 13302 |
| BCL11A-11208 | + | GUCCCUGCGAACUUGAACGU | 20 | 13303 |
| BCL11A-11209 | + | CGUCCCUGCGAACUUGAACGU | 21 | 13304 |
| BCL11A-11210 | + | ACGUCCCUGCGAACUUGAACGU | 22 | 13305 |

TABLE 19C-continued

| | | 3rd Tier | | |
|---|---|---|---|---|
| gRNA Name | DNA Strand | Targeting Domain | Target Site Length | SEQ ID NO: |
| BCL11A-11211 | + | GACGUCCCUGCGAACUUGAACGU | 23 | 13306 |
| BCL11A-11212 | + | UGACGUCCCUGCGAACUUGAACGU | 24 | 13307 |
| BCL11A-11213 | + | GUGCGGGGAGGGGAGGU | 18 | 13308 |
| BCL11A-11214 | + | AGUGCGGGGAGGGGAGGU | 19 | 13309 |
| BCL11A-11215 | + | CAGUGCGGGGAGGGGAGGU | 20 | 13310 |
| BCL11A-11216 | + | CCAGUGCGGGGAGGGGAGGU | 21 | 13311 |
| BCL11A-11217 | + | GCCAGUGCGGGGAGGGGAGGU | 22 | 13312 |
| BCL11A-11218 | + | GGCCAGUGCGGGGAGGGGAGGU | 23 | 13313 |
| BCL11A-11219 | + | UGGCCAGUGCGGGGAGGGGAGGU | 24 | 13314 |
| BCL11A-11220 | + | GGGGUGGGAGGAAAGGGU | 18 | 13315 |
| BCL11A-11221 | + | AGGGGUGGGAGGAAAGGGU | 19 | 13316 |
| BCL11A-9784 | + | CAGGGGUGGGAGGAAAGGGU | 20 | 13317 |
| BCL11A-11222 | + | GCAGGGGUGGGAGGAAAGGGU | 21 | 13318 |
| BCL11A-11223 | + | GGCAGGGGUGGGAGGAAAGGGU | 22 | 13319 |
| BCL11A-11224 | + | UGGCAGGGGUGGGAGGAAAGGGU | 23 | 13320 |
| BCL11A-11225 | + | GUGGCAGGGGUGGGAGGAAAGGGU | 24 | 13321 |
| BCL11A-11226 | + | ACAUCGGGAGAGCCGGGU | 18 | 13322 |
| BCL11A-11227 | + | CACAUCGGGAGAGCCGGGU | 19 | 13323 |
| BCL11A-11228 | + | UCACAUCGGGAGAGCCGGGU | 20 | 13324 |
| BCL11A-11229 | + | UUCACAUCGGGAGAGCCGGGU | 21 | 13325 |
| BCL11A-11230 | + | GUUCACAUCGGGAGAGCCGGGU | 22 | 13326 |
| BCL11A-11231 | + | GGUUCACAUCGGGAGAGCCGGGU | 23 | 13327 |
| BCL11A-11232 | + | CGGUUCACAUCGGGAGAGCCGGGU | 24 | 13328 |
| BCL11A-11233 | + | GAAAGGGGUGGCAGGGGU | 18 | 13329 |
| BCL11A-11234 | + | AGAAAGGGGUGGCAGGGGU | 19 | 13330 |
| BCL11A-9785 | + | AAGAAAGGGGUGGCAGGGGU | 20 | 13331 |
| BCL11A-11235 | + | GAAGAAAGGGGUGGCAGGGGU | 21 | 13332 |
| BCL11A-11236 | + | AGAAGAAAGGGGUGGCAGGGGU | 22 | 13333 |
| BCL11A-11237 | + | GAGAAGAAAGGGGUGGCAGGGGU | 23 | 13334 |
| BCL11A-11238 | + | AGAGAAGAAAGGGGUGGCAGGGGU | 24 | 13335 |
| BCL11A-11239 | + | GCAGGGAAGAUGAAUUGU | 18 | 13336 |
| BCL11A-11240 | + | CGCAGGGAAGAUGAAUUGU | 19 | 13337 |
| BCL11A-9786 | + | GCGCAGGGAAGAUGAAUUGU | 20 | 13338 |
| BCL11A-11241 | + | GGCGCAGGGAAGAUGAAUUGU | 21 | 13339 |
| BCL11A-11242 | + | UGGCGCAGGGAAGAUGAAUUGU | 22 | 13340 |
| BCL11A-11243 | + | AUGGCGCAGGGAAGAUGAAUUGU | 23 | 13341 |
| BCL11A-11244 | + | GAUGGCGCAGGGAAGAUGAAUUGU | 24 | 13342 |
| BCL11A-11245 | + | GCGCAGGGAAGAUGAAUU | 18 | 13343 |

TABLE 19C-continued

3rd Tier

| gRNA Name | DNA Strand | Targeting Domain | Target Site Length | SEQ ID NO: |
|---|---|---|---|---|
| BCL11A-11246 | + | GGCGCAGGGAAGAUGAAUU | 19 | 13344 |
| BCL11A-11247 | + | UGGCGCAGGGAAGAUGAAUU | 20 | 13345 |
| BCL11A-11248 | + | AUGGCGCAGGGAAGAUGAAUU | 21 | 13346 |
| BCL11A-11249 | + | GAUGGCGCAGGGAAGAUGAAUU | 22 | 13347 |
| BCL11A-11250 | + | AGAUGGCGCAGGGAAGAUGAAUU | 23 | 13348 |
| BCL11A-11251 | + | AAGAUGGCGCAGGGAAGAUGAAUU | 24 | 13349 |
| BCL11A-11252 | – | GCAGGACUAGAAGCAAAA | 18 | 13350 |
| BCL11A-11253 | – | CGCAGGACUAGAAGCAAAA | 19 | 13351 |
| BCL11A-11254 | – | GCGCAGGACUAGAAGCAAAA | 20 | 13352 |
| BCL11A-11255 | – | CGCGCAGGACUAGAAGCAAAA | 21 | 13353 |
| BCL11A-11256 | – | GCGCGCAGGACUAGAAGCAAAA | 22 | 13354 |
| BCL11A-11257 | – | AGCGCGCAGGACUAGAAGCAAAA | 23 | 13355 |
| BCL11A-11258 | – | GAGCGCGCAGGACUAGAAGCAAAA | 24 | 13356 |
| BCL11A-6678 | – | CCCCAGCACUUAAGCAAA | 18 | 13357 |
| BCL11A-6679 | – | ACCCCAGCACUUAAGCAAA | 19 | 13358 |
| BCL11A-5443 | – | AACCCCAGCACUUAAGCAAA | 20 | 13359 |
| BCL11A-6680 | – | AAACCCCAGCACUUAAGCAAA | 21 | 13360 |
| BCL11A-6681 | – | CAAACCCCAGCACUUAAGCAAA | 22 | 13361 |
| BCL11A-6682 | – | GCAAACCCCAGCACUUAAGCAAA | 23 | 13362 |
| BCL11A-6683 | – | GGCAAACCCCAGCACUUAAGCAAA | 24 | 13363 |
| BCL11A-11259 | – | CGAGGUAAAAGAGAUAAA | 18 | 13364 |
| BCL11A-11260 | – | UCGAGGUAAAAGAGAUAAA | 19 | 13365 |
| BCL11A-9693 | – | GUCGAGGUAAAAGAGAUAAA | 20 | 13366 |
| BCL11A-11261 | – | AGUCGAGGUAAAAGAGAUAAA | 21 | 13367 |
| BCL11A-11262 | – | GAGUCGAGGUAAAAGAGAUAAA | 22 | 13368 |
| BCL11A-11263 | – | AGAGUCGAGGUAAAAGAGAUAAA | 23 | 13369 |
| BCL11A-11264 | – | GAGAGUCGAGGUAAAAGAGAUAAA | 24 | 13370 |
| BCL11A-6698 | – | ACCCCAGCACUUAAGCAA | 18 | 13371 |
| BCL11A-6699 | – | AACCCCAGCACUUAAGCAA | 19 | 13372 |
| BCL11A-6700 | – | AAACCCCAGCACUUAAGCAA | 20 | 13373 |
| BCL11A-6701 | – | CAAACCCCAGCACUUAAGCAA | 21 | 13374 |
| BCL11A-6702 | – | GCAAACCCCAGCACUUAAGCAA | 22 | 13375 |
| BCL11A-6703 | – | GGCAAACCCCAGCACUUAAGCAA | 23 | 13376 |
| BCL11A-6704 | – | AGGCAAACCCCAGCACUUAAGCAA | 24 | 13377 |
| BCL11A-11265 | – | CGGCUCUCCCGAUGUGAA | 18 | 13378 |
| BCL11A-11266 | – | CCGGCUCUCCCGAUGUGAA | 19 | 13379 |
| BCL11A-11267 | – | CCCGGCUCUCCCGAUGUGAA | 20 | 13380 |

TABLE 19C-continued

3rd Tier

| gRNA Name | DNA Strand | Targeting Domain | Target Site Length | SEQ ID NO: |
|---|---|---|---|---|
| BCL11A-11268 | - | ACCCGGCUCUCCCGAUGUGAA | 21 | 13381 |
| BCL11A-11269 | - | AACCCGGCUCUCCCGAUGUGAA | 22 | 13382 |
| BCL11A-11270 | - | UAACCCGGCUCUCCCGAUGUGAA | 23 | 13383 |
| BCL11A-11271 | - | CUAACCCGGCUCUCCCGAUGUGAA | 24 | 13384 |
| BCL11A-11272 | - | UCGAGGUAAAAGAGAUAA | 18 | 13385 |
| BCL11A-11273 | - | GUCGAGGUAAAAGAGAUAA | 19 | 13386 |
| BCL11A-9699 | - | AGUCGAGGUAAAAGAGAUAA | 20 | 13387 |
| BCL11A-11274 | - | GAGUCGAGGUAAAAGAGAUAA | 21 | 13388 |
| BCL11A-11275 | - | AGAGUCGAGGUAAAAGAGAUAA | 22 | 13389 |
| BCL11A-11276 | - | GAGAGUCGAGGUAAAAGAGAUAA | 23 | 13390 |
| BCL11A-11277 | - | CGAGAGUCGAGGUAAAAGAGAUAA | 24 | 13391 |
| BCL11A-11278 | - | CUCCGAGAGUCGAGGUAA | 18 | 13392 |
| BCL11A-11279 | - | CCUCCGAGAGUCGAGGUAA | 19 | 13393 |
| BCL11A-11280 | - | ACCUCCGAGAGUCGAGGUAA | 20 | 13394 |
| BCL11A-11281 | - | AACCUCCGAGAGUCGAGGUAA | 21 | 13395 |
| BCL11A-11282 | - | AAACCUCCGAGAGUCGAGGUAA | 22 | 13396 |
| BCL11A-11283 | - | AAAACCUCCGAGAGUCGAGGUAA | 23 | 13397 |
| BCL11A-11284 | - | AAAAACCUCCGAGAGUCGAGGUAA | 24 | 13398 |
| BCL11A-11285 | - | ACUUGAACUUGCAGCUCA | 18 | 13399 |
| BCL11A-11286 | - | CACUUGAACUUGCAGCUCA | 19 | 13400 |
| BCL11A-9705 | - | GCACUUGAACUUGCAGCUCA | 20 | 13401 |
| BCL11A-11287 | - | CGCACUUGAACUUGCAGCUCA | 21 | 13402 |
| BCL11A-11288 | - | CCGCACUUGAACUUGCAGCUCA | 22 | 13403 |
| BCL11A-11289 | - | UCCGCACUUGAACUUGCAGCUCA | 23 | 13404 |
| BCL11A-11290 | - | GUCCGCACUUGAACUUGCAGCUCA | 24 | 13405 |
| BCL11A-11291 | - | GCAAAAGCGAGGGGAGA | 18 | 13406 |
| BCL11A-11292 | - | AGCAAAAGCGAGGGGAGA | 19 | 13407 |
| BCL11A-4934 | - | AAGCAAAAGCGAGGGGAGA | 20 | 13408 |
| BCL11A-11293 | - | GAAGCAAAAGCGAGGGGAGA | 21 | 13409 |
| BCL11A-11294 | - | AGAAGCAAAAGCGAGGGGAGA | 22 | 13410 |
| BCL11A-11295 | - | UAGAAGCAAAAGCGAGGGGAGA | 23 | 13411 |
| BCL11A-11296 | - | CUAGAAGCAAAAGCGAGGGGAGA | 24 | 13412 |
| BCL11A-11297 | - | GACUAGAAGCAAAAGCGA | 18 | 13413 |
| BCL11A-11298 | - | GGACUAGAAGCAAAAGCGA | 19 | 13414 |
| BCL11A-9710 | - | AGGACUAGAAGCAAAAGCGA | 20 | 13415 |
| BCL11A-11299 | - | CAGGACUAGAAGCAAAAGCGA | 21 | 13416 |
| BCL11A-11300 | - | GCAGGACUAGAAGCAAAAGCGA | 22 | 13417 |
| BCL11A-11301 | - | CGCAGGACUAGAAGCAAAAGCGA | 23 | 13418 |

TABLE 19C-continued

3rd Tier

| gRNA Name | DNA Strand | Targeting Domain | Target Site Length | SEQ ID NO: |
|---|---|---|---|---|
| BCL11A-11302 | - | GCGCAGGACUAGAAGCAAAAGCGA | 24 | 13419 |
| BCL11A-11303 | - | AAGCAAAAGCGAGGGGGA | 18 | 13420 |
| BCL11A-11304 | - | GAAGCAAAAGCGAGGGGGA | 19 | 13421 |
| BCL11A-4972 | - | AGAAGCAAAAGCGAGGGGGA | 20 | 13422 |
| BCL11A-11305 | - | UAGAAGCAAAAGCGAGGGGGA | 21 | 13423 |
| BCL11A-11306 | - | CUAGAAGCAAAAGCGAGGGGGA | 22 | 13424 |
| BCL11A-11307 | - | ACUAGAAGCAAAAGCGAGGGGGA | 23 | 13425 |
| BCL11A-11308 | - | GACUAGAAGCAAAAGCGAGGGGGA | 24 | 13426 |
| BCL11A-11309 | - | GUCGAGGUAAAAGAGAUA | 18 | 13427 |
| BCL11A-11310 | - | AGUCGAGGUAAAAGAGAUA | 19 | 13428 |
| BCL11A-11311 | - | GAGUCGAGGUAAAAGAGAUA | 20 | 13429 |
| BCL11A-11312 | - | AGAGUCGAGGUAAAAGAGAUA | 21 | 13430 |
| BCL11A-11313 | - | GAGAGUCGAGGUAAAAGAGAUA | 22 | 13431 |
| BCL11A-11314 | - | CGAGAGUCGAGGUAAAAGAGAUA | 23 | 13432 |
| BCL11A-11315 | - | CCGAGAGUCGAGGUAAAAGAGAUA | 24 | 13433 |
| BCL11A-11316 | - | GGGACGUCACGUCCGCAC | 18 | 13434 |
| BCL11A-11317 | - | AGGGACGUCACGUCCGCAC | 19 | 13435 |
| BCL11A-11318 | - | CAGGGACGUCACGUCCGCAC | 20 | 13436 |
| BCL11A-11319 | - | GCAGGGACGUCACGUCCGCAC | 21 | 13437 |
| BCL11A-11320 | - | CGCAGGGACGUCACGUCCGCAC | 22 | 13438 |
| BCL11A-11321 | - | UCGCAGGGACGUCACGUCCGCAC | 23 | 13439 |
| BCL11A-11322 | - | UUCGCAGGGACGUCACGUCCGCAC | 24 | 13440 |
| BCL11A-11323 | - | AUAAUUAUUAAUAAUCAC | 18 | 13441 |
| BCL11A-11324 | - | AAUAAUUAUUAAUAAUCAC | 19 | 13442 |
| BCL11A-11325 | - | UAAUAAUUAUUAAUAAUCAC | 20 | 13443 |
| BCL11A-11326 | - | AUAAUAAUUAUUAAUAAUCAC | 21 | 13444 |
| BCL11A-11327 | - | AAUAAUAAUUAUUAAUAAUCAC | 22 | 13445 |
| BCL11A-11328 | - | UAAUAAUAAUUAUUAAUAAUCAC | 23 | 13446 |
| BCL11A-11329 | - | GUAAUAAUAAUUAUUAAUAAUCAC | 24 | 13447 |
| BCL11A-11330 | - | CAUUUUUAAAUUUUUCAC | 18 | 13448 |
| BCL11A-11331 | - | GCAUUUUUAAAUUUUUCAC | 19 | 13449 |
| BCL11A-11332 | - | UGCAUUUUUAAAUUUUUCAC | 20 | 13450 |
| BCL11A-11333 | - | AUGCAUUUUUAAAUUUUUCAC | 21 | 13451 |
| BCL11A-11334 | - | CAUGCAUUUUUAAAUUUUUCAC | 22 | 13452 |
| BCL11A-11335 | - | GCAUGCAUUUUUAAAUUUUUCAC | 23 | 13453 |
| BCL11A-11336 | - | UGCAUGCAUUUUUAAAUUUUUCAC | 24 | 13454 |
| BCL11A-11337 | - | CACGAGAGCGCGCAGGAC | 18 | 13455 |

TABLE 19C-continued

3rd Tier

| gRNA Name | DNA Strand | Targeting Domain | Target Site Length | SEQ ID NO: |
|---|---|---|---|---|
| BCL11A-11338 | − | UCACGAGAGCGCGCAGGAC | 19 | 13456 |
| BCL11A-11339 | − | AUCACGAGAGCGCGCAGGAC | 20 | 13457 |
| BCL11A-11340 | − | AAUCACGAGAGCGCGCAGGAC | 21 | 13458 |
| BCL11A-11341 | − | UAAUCACGAGAGCGCGCAGGAC | 22 | 13459 |
| BCL11A-11342 | − | AUAAUCACGAGAGCGCGCAGGAC | 23 | 13460 |
| BCL11A-11343 | − | AAUAAUCACGAGAGCGCGCAGGAC | 24 | 13461 |
| BCL11A-11344 | − | UCGGCCCGCCCCUCCCCC | 18 | 13462 |
| BCL11A-11345 | − | CUCGGCCCGCCCCUCCCCC | 19 | 13463 |
| BCL11A-9716 | − | CCUCGGCCCGCCCCUCCCCC | 20 | 13464 |
| BCL11A-11346 | − | CCCUCGGCCCGCCCCUCCCCC | 21 | 13465 |
| BCL11A-11347 | − | CCCCUCGGCCCGCCCCUCCCCC | 22 | 13466 |
| BCL11A-11348 | − | UCCCCUCGGCCCGCCCCUCCCCC | 23 | 13467 |
| BCL11A-11349 | − | CUCCCCUCGGCCCGCCCCUCCCCC | 24 | 13468 |
| BCL11A-11350 | − | CUCGGCCCGCCCCUCCCC | 18 | 13469 |
| BCL11A-11351 | − | CCUCGGCCCGCCCCUCCCC | 19 | 13470 |
| BCL11A-9717 | − | CCCUCGGCCCGCCCCUCCCC | 20 | 13471 |
| BCL11A-11352 | − | CCCCUCGGCCCGCCCCUCCCC | 21 | 13472 |
| BCL11A-11353 | − | UCCCCUCGGCCCGCCCCUCCCC | 22 | 13473 |
| BCL11A-11354 | − | CUCCCCUCGGCCCGCCCCUCCCC | 23 | 13474 |
| BCL11A-11355 | − | CCUCCCCUCGGCCCGCCCCUCCCC | 24 | 13475 |
| BCL11A-11356 | − | CCUCGGCCCGCCCCUCCC | 18 | 13476 |
| BCL11A-11357 | − | CCCUCGGCCCGCCCCUCCC | 19 | 13477 |
| BCL11A-11358 | − | CCCCUCGGCCCGCCCCUCCC | 20 | 13478 |
| BCL11A-11359 | − | UCCCCUCGGCCCGCCCCUCCC | 21 | 13479 |
| BCL11A-11360 | − | CUCCCCUCGGCCCGCCCCUCCC | 22 | 13480 |
| BCL11A-11361 | − | CCUCCCCUCGGCCCGCCCCUCCC | 23 | 13481 |
| BCL11A-11362 | − | CCCUCCCCUCGGCCCGCCCCUCCC | 24 | 13482 |
| BCL11A-11363 | − | GGGCCGCGUCUGGCGUCC | 18 | 13483 |
| BCL11A-11364 | − | GGGGCCGCGUCUGGCGUCC | 19 | 13484 |
| BCL11A-11365 | − | GGGGGCCGCGUCUGGCGUCC | 20 | 13485 |
| BCL11A-11366 | − | CGGGGGCCGCGUCUGGCGUCC | 21 | 13486 |
| BCL11A-11367 | − | CCGGGGGCCGCGUCUGGCGUCC | 22 | 13487 |
| BCL11A-11368 | − | CCCGGGGGCCGCGUCUGGCGUCC | 23 | 13488 |
| BCL11A-11369 | − | CCCCGGGGGCCGCGUCUGGCGUCC | 24 | 13489 |
| BCL11A-11370 | − | AGGACUAGAAGCAAAAGC | 18 | 13490 |
| BCL11A-11371 | − | CAGGACUAGAAGCAAAAGC | 19 | 13491 |
| BCL11A-11372 | − | GCAGGACUAGAAGCAAAAGC | 20 | 13492 |
| BCL11A-11373 | − | CGCAGGACUAGAAGCAAAAGC | 21 | 13493 |

TABLE 19C-continued

| | | 3rd Tier | | |
|---|---|---|---|---|
| gRNA Name | DNA Strand | Targeting Domain | Target Site Length | SEQ ID NO: |
| BCL11A-11374 | - | GCGCAGGACUAGAAGCAAAAGC | 22 | 13494 |
| BCL11A-11375 | - | CGCGCAGGACUAGAAGCAAAAGC | 23 | 13495 |
| BCL11A-11376 | - | GCGCGCAGGACUAGAAGCAAAAGC | 24 | 13496 |
| BCL11A-11377 | - | CCUGACGUUCAAGUUCGC | 18 | 13497 |
| BCL11A-11378 | - | UCCUGACGUUCAAGUUCGC | 19 | 13498 |
| BCL11A-9566 | - | CUCCUGACGUUCAAGUUCGC | 20 | 13499 |
| BCL11A-11379 | - | ACUCCUGACGUUCAAGUUCGC | 21 | 13500 |
| BCL11A-11380 | - | GACUCCUGACGUUCAAGUUCGC | 22 | 13501 |
| BCL11A-11381 | - | AGACUCCUGACGUUCAAGUUCGC | 23 | 13502 |
| BCL11A-11382 | - | CAGACUCCUGACGUUCAAGUUCGC | 24 | 13503 |
| BCL11A-11383 | - | UAAUAAUUAUUAAUAAUC | 18 | 13504 |
| BCL11A-11384 | - | AUAAUAAUUAUUAAUAAUC | 19 | 13505 |
| BCL11A-11385 | - | AAUAAUAAUUAUUAAUAAUC | 20 | 13506 |
| BCL11A-11386 | - | UAAUAAUAAUUAUUAAUAAUC | 21 | 13507 |
| BCL11A-11387 | - | GUAAUAAUAAUUAUUAAUAAUC | 22 | 13508 |
| BCL11A-11388 | - | AGUAAUAAUAAUUAUUAAUAAUC | 23 | 13509 |
| BCL11A-11389 | - | UAGUAAUAAUAAUUAUUAAUAAUC | 24 | 13510 |
| BCL11A-11390 | - | AAAAACCCUCAUCCCAUC | 18 | 13511 |
| BCL11A-11391 | - | AAAAAACCCUCAUCCCAUC | 19 | 13512 |
| BCL11A-9730 | - | GAAAAAACCCUCAUCCCAUC | 20 | 13513 |
| BCL11A-11392 | - | GGAAAAAACCCUCAUCCCAUC | 21 | 13514 |
| BCL11A-11393 | - | GGGAAAAAACCCUCAUCCCAUC | 22 | 13515 |
| BCL11A-11394 | - | GGGGAAAAAACCCUCAUCCCAUC | 23 | 13516 |
| BCL11A-11395 | - | GGGGGAAAAAACCCUCAUCCCAUC | 24 | 13517 |
| BCL11A-11396 | - | CACUUGAACUUGCAGCUC | 18 | 13518 |
| BCL11A-11397 | - | GCACUUGAACUUGCAGCUC | 19 | 13519 |
| BCL11A-9569 | - | CGCACUUGAACUUGCAGCUC | 20 | 13520 |
| BCL11A-11398 | - | CCGCACUUGAACUUGCAGCUC | 21 | 13521 |
| BCL11A-11399 | - | UCCGCACUUGAACUUGCAGCUC | 22 | 13522 |
| BCL11A-11400 | - | GUCCGCACUUGAACUUGCAGCUC | 23 | 13523 |
| BCL11A-11401 | - | CGUCCGCACUUGAACUUGCAGCUC | 24 | 13524 |
| BCL11A-11402 | - | UGCAUUUUUAAAUUUUUC | 18 | 13525 |
| BCL11A-11403 | - | AUGCAUUUUUAAAUUUUUC | 19 | 13526 |
| BCL11A-11404 | - | CAUGCAUUUUUAAAUUUUUC | 20 | 13527 |
| BCL11A-11405 | - | GCAUGCAUUUUUAAAUUUUUC | 21 | 13528 |
| BCL11A-11406 | - | UGCAUGCAUUUUUAAAUUUUUC | 22 | 13529 |
| BCL11A-11407 | - | GUGCAUGCAUUUUUAAAUUUUUC | 23 | 13530 |

TABLE 19C-continued

3rd Tier

| gRNA Name | DNA Strand | Targeting Domain | Target Site Length | SEQ ID NO: |
|---|---|---|---|---|
| BCL11A-11408 | - | UGUGCAUGCAUUUUUAAAUUUUUC | 24 | 13531 |
| BCL11A-11409 | - | GAGGUAAAAGAGAUAAAG | 18 | 13532 |
| BCL11A-11410 | - | CGAGGUAAAAGAGAUAAAG | 19 | 13533 |
| BCL11A-9571 | - | UCGAGGUAAAAGAGAUAAAG | 20 | 13534 |
| BCL11A-11411 | - | GUCGAGGUAAAAGAGAUAAAG | 21 | 13535 |
| BCL11A-11412 | - | AGUCGAGGUAAAAGAGAUAAAG | 22 | 13536 |
| BCL11A-11413 | - | GAGUCGAGGUAAAAGAGAUAAAG | 23 | 13537 |
| BCL11A-11414 | - | AGAGUCGAGGUAAAAGAGAUAAAG | 24 | 13538 |
| BCL11A-11415 | - | CUUGAACUUGCAGCUCAG | 18 | 13539 |
| BCL11A-11416 | - | ACUUGAACUUGCAGCUCAG | 19 | 13540 |
| BCL11A-9738 | - | CACUUGAACUUGCAGCUCAG | 20 | 13541 |
| BCL11A-11417 | - | GCACUUGAACUUGCAGCUCAG | 21 | 13542 |
| BCL11A-11418 | - | CGCACUUGAACUUGCAGCUCAG | 22 | 13543 |
| BCL11A-11419 | - | CCGCACUUGAACUUGCAGCUCAG | 23 | 13544 |
| BCL11A-11420 | - | UCCGCACUUGAACUUGCAGCUCAG | 24 | 13545 |
| BCL11A-11421 | - | GAGAAAAACCUCCGAGAG | 18 | 13546 |
| BCL11A-11422 | - | CGAGAAAAACCUCCGAGAG | 19 | 13547 |
| BCL11A-11423 | - | ACGAGAAAAACCUCCGAGAG | 20 | 13548 |
| BCL11A-11424 | - | CACGAGAAAAACCUCCGAGAG | 21 | 13549 |
| BCL11A-11425 | - | UCACGAGAAAAACCUCCGAGAG | 22 | 13550 |
| BCL11A-11426 | - | UUCACGAGAAAAACCUCCGAGAG | 23 | 13551 |
| BCL11A-11427 | - | UUUCACGAGAAAAACCUCCGAGAG | 24 | 13552 |
| BCL11A-11428 | - | ACUAGAAGCAAAAGCGAG | 18 | 13553 |
| BCL11A-11429 | - | GACUAGAAGCAAAAGCGAG | 19 | 13554 |
| BCL11A-9739 | - | GGACUAGAAGCAAAAGCGAG | 20 | 13555 |
| BCL11A-11430 | - | AGGACUAGAAGCAAAAGCGAG | 21 | 13556 |
| BCL11A-11431 | - | CAGGACUAGAAGCAAAAGCGAG | 22 | 13557 |
| BCL11A-11432 | - | GCAGGACUAGAAGCAAAAGCGAG | 23 | 13558 |
| BCL11A-11433 | - | CGCAGGACUAGAAGCAAAAGCGAG | 24 | 13559 |
| BCL11A-11434 | - | CGCGUGUGUGGGGGGAG | 18 | 13560 |
| BCL11A-11435 | - | CCGCGUGUGUGGGGGGAG | 19 | 13561 |
| BCL11A-11436 | - | UCCGCGUGUGUGGGGGGAG | 20 | 13562 |
| BCL11A-11437 | - | GUCCGCGUGUGUGGGGGGAG | 21 | 13563 |
| BCL11A-11438 | - | AGUCCGCGUGUGUGGGGGGAG | 22 | 13564 |
| BCL11A-11439 | - | GAGUCCGCGUGUGUGGGGGGAG | 23 | 13565 |
| BCL11A-11440 | - | AGAGUCCGCGUGUGUGGGGGGAG | 24 | 13566 |
| BCL11A-11441 | - | GGCCGCGUCUGGCGUCCG | 18 | 13567 |
| BCL11A-11442 | - | GGGCCGCGUCUGGCGUCCG | 19 | 13568 |

TABLE 19C-continued

3rd Tier

| gRNA Name | DNA Strand | Targeting Domain | Target Site Length | SEQ ID NO: |
|---|---|---|---|---|
| BCL11A-9574 | - | GGGGCCGCGUCUGGCGUCCG | 20 | 13569 |
| BCL11A-11443 | - | GGGGGCCGCGUCUGGCGUCCG | 21 | 13570 |
| BCL11A-11444 | - | CGGGGGCCGCGUCUGGCGUCCG | 22 | 13571 |
| BCL11A-11445 | - | CCGGGGGCCGCGUCUGGCGUCCG | 23 | 13572 |
| BCL11A-11446 | - | CCCGGGGGCCGCGUCUGGCGUCCG | 24 | 13573 |
| BCL11A-11447 | - | GGACUAGAAGCAAAAGCG | 18 | 13574 |
| BCL11A-11448 | - | AGGACUAGAAGCAAAAGCG | 19 | 13575 |
| BCL11A-9748 | - | CAGGACUAGAAGCAAAAGCG | 20 | 13576 |
| BCL11A-11449 | - | GCAGGACUAGAAGCAAAAGCG | 21 | 13577 |
| BCL11A-11450 | - | CGCAGGACUAGAAGCAAAAGCG | 22 | 13578 |
| BCL11A-11451 | - | GCGCAGGACUAGAAGCAAAAGCG | 23 | 13579 |
| BCL11A-11452 | - | CGCGCAGGACUAGAAGCAAAAGCG | 24 | 13580 |
| BCL11A-11453 | - | AAUAAUCACGAGAGCGCG | 18 | 13581 |
| BCL11A-11454 | - | UAAUAAUCACGAGAGCGCG | 19 | 13582 |
| BCL11A-11455 | - | UUAAUAAUCACGAGAGCGCG | 20 | 13583 |
| BCL11A-11456 | - | AUUAAUAAUCACGAGAGCGCG | 21 | 13584 |
| BCL11A-11457 | - | UAUUAAUAAUCACGAGAGCGCG | 22 | 13585 |
| BCL11A-11458 | - | UUAUUAAUAAUCACGAGAGCGCG | 23 | 13586 |
| BCL11A-11459 | - | AUUAUUAAUAAUCACGAGAGCGCG | 24 | 13587 |
| BCL11A-11460 | - | UCCUGACGUUCAAGUUCG | 18 | 13588 |
| BCL11A-11461 | - | CUCCUGACGUUCAAGUUCG | 19 | 13589 |
| BCL11A-11462 | - | ACUCCUGACGUUCAAGUUCG | 20 | 13590 |
| BCL11A-11463 | - | GACUCCUGACGUUCAAGUUCG | 21 | 13591 |
| BCL11A-11464 | - | AGACUCCUGACGUUCAAGUUCG | 22 | 13592 |
| BCL11A-11465 | - | CAGACUCCUGACGUUCAAGUUCG | 23 | 13593 |
| BCL11A-11466 | - | CCAGACUCCUGACGUUCAAGUUCG | 24 | 13594 |
| BCL11A-11467 | - | AGGUAAAAGAGAUAAAGG | 18 | 13595 |
| BCL11A-11468 | - | GAGGUAAAAGAGAUAAAGG | 19 | 13596 |
| BCL11A-9753 | - | CGAGGUAAAAGAGAUAAAGG | 20 | 13597 |
| BCL11A-11469 | - | UCGAGGUAAAAGAGAUAAAGG | 21 | 13598 |
| BCL11A-11470 | - | GUCGAGGUAAAAGAGAUAAAGG | 22 | 13599 |
| BCL11A-11471 | - | AGUCGAGGUAAAAGAGAUAAAGG | 23 | 13600 |
| BCL11A-11472 | - | GAGUCGAGGUAAAAGAGAUAAAGG | 24 | 13601 |
| BCL11A-11473 | - | CUAGAAGCAAAAGCGAGG | 18 | 13602 |
| BCL11A-11474 | - | ACUAGAAGCAAAAGCGAGG | 19 | 13603 |
| BCL11A-9755 | - | GACUAGAAGCAAAAGCGAGG | 20 | 13604 |
| BCL11A-11475 | - | GGACUAGAAGCAAAAGCGAGG | 21 | 13605 |

TABLE 19C-continued

3rd Tier

| gRNA Name | DNA Strand | Targeting Domain | Target Site Length | SEQ ID NO: |
|---|---|---|---|---|
| BCL11A-11476 | - | AGGACUAGAAGCAAAAGCGAGG | 22 | 13606 |
| BCL11A-11477 | - | CAGGACUAGAAGCAAAAGCGAGG | 23 | 13607 |
| BCL11A-11478 | - | GCAGGACUAGAAGCAAAAGCGAGG | 24 | 13608 |
| BCL11A-11479 | - | AGAAGCAAAAGCGAGGGG | 18 | 13609 |
| BCL11A-11480 | - | UAGAAGCAAAAGCGAGGGG | 19 | 13610 |
| BCL11A-11481 | - | CUAGAAGCAAAAGCGAGGGG | 20 | 13611 |
| BCL11A-11482 | - | ACUAGAAGCAAAAGCGAGGGG | 21 | 13612 |
| BCL11A-11483 | - | GACUAGAAGCAAAAGCGAGGGG | 22 | 13613 |
| BCL11A-11484 | - | GGACUAGAAGCAAAAGCGAGGGG | 23 | 13614 |
| BCL11A-11485 | - | AGGACUAGAAGCAAAAGCGAGGGG | 24 | 13615 |
| BCL11A-11486 | - | GAGUCCGCGUGUGUGGGG | 18 | 13616 |
| BCL11A-11487 | - | AGAGUCCGCGUGUGUGGGG | 19 | 13617 |
| BCL11A-9577 | - | UAGAGUCCGCGUGUGUGGGG | 20 | 13618 |
| BCL11A-11488 | - | UUAGAGUCCGCGUGUGUGGGG | 21 | 13619 |
| BCL11A-11489 | - | UUUAGAGUCCGCGUGUGUGGGG | 22 | 13620 |
| BCL11A-11490 | - | UUUUAGAGUCCGCGUGUGUGGGG | 23 | 13621 |
| BCL11A-11491 | - | AUUUUAGAGUCCGCGUGUGUGGGG | 24 | 13622 |
| BCL11A-11492 | - | AGAGUCCGCGUGUGUGGG | 18 | 13623 |
| BCL11A-11493 | - | UAGAGUCCGCGUGUGUGGG | 19 | 13624 |
| BCL11A-9769 | - | UUAGAGUCCGCGUGUGUGGG | 20 | 13625 |
| BCL11A-11494 | - | UUUAGAGUCCGCGUGUGUGGG | 21 | 13626 |
| BCL11A-11495 | - | UUUUAGAGUCCGCGUGUGUGGG | 22 | 13627 |
| BCL11A-11496 | - | AUUUUAGAGUCCGCGUGUGUGGG | 23 | 13628 |
| BCL11A-11497 | - | CAUUUUAGAGUCCGCGUGUGUGGG | 24 | 13629 |
| BCL11A-11498 | - | UAGAGUCCGCGUGUGUGG | 18 | 13630 |
| BCL11A-11499 | - | UUAGAGUCCGCGUGUGUGG | 19 | 13631 |
| BCL11A-9578 | - | UUUAGAGUCCGCGUGUGUGG | 20 | 13632 |
| BCL11A-11500 | - | UUUUAGAGUCCGCGUGUGUGG | 21 | 13633 |
| BCL11A-11501 | - | AUUUUAGAGUCCGCGUGUGUGG | 22 | 13634 |
| BCL11A-11502 | - | CAUUUUAGAGUCCGCGUGUGUGG | 23 | 13635 |
| BCL11A-11503 | - | UCAUUUUAGAGUCCGCGUGUGUGG | 24 | 13636 |
| BCL11A-11504 | - | CGCUCGCUGCGGCCACUG | 18 | 13637 |
| BCL11A-11505 | - | GCGCUCGCUGCGGCCACUG | 19 | 13638 |
| BCL11A-11506 | - | GGCGCUCGCUGCGGCCACUG | 20 | 13639 |
| BCL11A-11507 | - | CGGCGCUCGCUGCGGCCACUG | 21 | 13640 |
| BCL11A-11508 | - | GCGGCGCUCGCUGCGGCCACUG | 22 | 13641 |
| BCL11A-11509 | - | CGCGGCGCUCGCUGCGGCCACUG | 23 | 13642 |
| BCL11A-11510 | - | CCGCGGCGCUCGCUGCGGCCACUG | 24 | 13643 |

TABLE 19C-continued

| | | 3rd Tier | | |
|---|---|---|---|---|
| gRNA Name | DNA Strand | Targeting Domain | Target Site Length | SEQ ID NO: |
| BCL11A-11511 | − | GGAUGUCAAAAGGCACUG | 18 | 13644 |
| BCL11A-11512 | − | UGGAUGUCAAAAGGCACUG | 19 | 13645 |
| BCL11A-11513 | − | UUGGAUGUCAAAAGGCACUG | 20 | 13646 |
| BCL11A-11514 | − | UUUGGAUGUCAAAAGGCACUG | 21 | 13647 |
| BCL11A-11515 | − | UUUUGGAUGUCAAAAGGCACUG | 22 | 13648 |
| BCL11A-11516 | − | AUUUUGGAUGUCAAAAGGCACUG | 23 | 13649 |
| BCL11A-11517 | − | UAUUUUGGAUGUCAAAAGGCACUG | 24 | 13650 |
| BCL11A-11518 | − | UUUUAGAGUCCGCGUGUG | 18 | 13651 |
| BCL11A-11519 | − | AUUUUAGAGUCCGCGUGUG | 19 | 13652 |
| BCL11A-9581 | − | CAUUUUAGAGUCCGCGUGUG | 20 | 13653 |
| BCL11A-11520 | − | UCAUUUUAGAGUCCGCGUGUG | 21 | 13654 |
| BCL11A-11521 | − | UUCAUUUUAGAGUCCGCGUGUG | 22 | 13655 |
| BCL11A-11522 | − | UUUCAUUUUAGAGUCCGCGUGUG | 23 | 13656 |
| BCL11A-11523 | − | CUUUCAUUUUAGAGUCCGCGUGUG | 24 | 13657 |
| BCL11A-11524 | − | UUAGAGUCCGCGUGUGUG | 18 | 13658 |
| BCL11A-11525 | − | UUUAGAGUCCGCGUGUGUG | 19 | 13659 |
| BCL11A-9776 | − | UUUUAGAGUCCGCGUGUGUG | 20 | 13660 |
| BCL11A-11526 | − | AUUUUAGAGUCCGCGUGUGUG | 21 | 13661 |
| BCL11A-11527 | − | CAUUUUAGAGUCCGCGUGUGUG | 22 | 13662 |
| BCL11A-11528 | − | UCAUUUUAGAGUCCGCGUGUGUG | 23 | 13663 |
| BCL11A-11529 | − | UUCAUUUUAGAGUCCGCGUGUGUG | 24 | 13664 |
| BCL11A-11530 | − | AAAAAACCCUCAUCCCAU | 18 | 13665 |
| BCL11A-11531 | − | GAAAAAACCCUCAUCCCAU | 19 | 13666 |
| BCL11A-11532 | − | GGAAAAAACCCUCAUCCCAU | 20 | 13667 |
| BCL11A-11533 | − | GGGAAAAAACCCUCAUCCCAU | 21 | 13668 |
| BCL11A-11534 | − | GGGGAAAAAACCCUCAUCCCAU | 22 | 13669 |
| BCL11A-11535 | − | GGGGGAAAAAACCCUCAUCCCAU | 23 | 13670 |
| BCL11A-11536 | − | AGGGGGAAAAAACCCUCAUCCCAU | 24 | 13671 |
| BCL11A-11537 | − | UAACCCGGCUCUCCCGAU | 18 | 13672 |
| BCL11A-11538 | − | CUAACCCGGCUCUCCCGAU | 19 | 13673 |
| BCL11A-11539 | − | UCUAACCCGGCUCUCCCGAU | 20 | 13674 |
| BCL11A-11540 | − | UUCUAACCCGGCUCUCCCGAU | 21 | 13675 |
| BCL11A-11541 | − | UUUCUAACCCGGCUCUCCCGAU | 22 | 13676 |
| BCL11A-11542 | − | CUUUCUAACCCGGCUCUCCCGAU | 23 | 13677 |
| BCL11A-11543 | − | UCUUUCUAACCCGGCUCUCCCGAU | 24 | 13678 |
| BCL11A-11544 | − | UUUUCACGAGAAAACCU | 18 | 13679 |
| BCL11A-11545 | − | UUUUUCACGAGAAAACCU | 19 | 13680 |

TABLE 19C-continued

3rd Tier

| gRNA Name | DNA Strand | Targeting Domain | Target Site Length | SEQ ID NO: |
|---|---|---|---|---|
| BCL11A-11546 | - | AUUUUUCACGAGAAAAACCU | 20 | 13681 |
| BCL11A-11547 | - | AAUUUUUCACGAGAAAAACCU | 21 | 13682 |
| BCL11A-11548 | - | AAAUUUUUCACGAGAAAAACCU | 22 | 13683 |
| BCL11A-11549 | - | UAAAUUUUUCACGAGAAAAACCU | 23 | 13684 |
| BCL11A-11550 | - | UUAAAUUUUUCACGAGAAAAACCU | 24 | 13685 |
| BCL11A-11551 | - | GCACUUGAACUUGCAGCU | 18 | 13686 |
| BCL11A-11552 | - | CGCACUUGAACUUGCAGCU | 19 | 13687 |
| BCL11A-11553 | - | CCGCACUUGAACUUGCAGCU | 20 | 13688 |
| BCL11A-11554 | - | UCCGCACUUGAACUUGCAGCU | 21 | 13689 |
| BCL11A-11555 | - | GUCCGCACUUGAACUUGCAGCU | 22 | 13690 |
| BCL11A-11556 | - | CGUCCGCACUUGAACUUGCAGCU | 23 | 13691 |
| BCL11A-11557 | - | ACGUCCGCACUUGAACUUGCAGCU | 24 | 13692 |
| BCL11A-11558 | - | CUGAUGAAGAUAUUUUCU | 18 | 13693 |
| BCL11A-11559 | - | ACUGAUGAAGAUAUUUUCU | 19 | 13694 |
| BCL11A-11560 | - | CACUGAUGAAGAUAUUUUCU | 20 | 13695 |
| BCL11A-11561 | - | GCACUGAUGAAGAUAUUUUCU | 21 | 13696 |
| BCL11A-11562 | - | GGCACUGAUGAAGAUAUUUUCU | 22 | 13697 |
| BCL11A-11563 | - | AGGCACUGAUGAAGAUAUUUUCU | 23 | 13698 |
| BCL11A-11564 | - | AAGGCACUGAUGAAGAUAUUUUCU | 24 | 13699 |
| BCL11A-11565 | - | UGAUGUGUGUCCAUUGGU | 18 | 13700 |
| BCL11A-11566 | - | CUGAUGUGUGUCCAUUGGU | 19 | 13701 |
| BCL11A-11567 | - | CCUGAUGUGUGUCCAUUGGU | 20 | 13702 |
| BCL11A-11568 | - | CCCUGAUGUGUGUCCAUUGGU | 21 | 13703 |
| BCL11A-11569 | - | CCCCUGAUGUGUGUCCAUUGGU | 22 | 13704 |
| BCL11A-11570 | - | GCCCCUGAUGUGUGUCCAUUGGU | 23 | 13705 |
| BCL11A-11571 | - | AGCCCCUGAUGUGUGUCCAUUGGU | 24 | 13706 |
| BCL11A-11572 | - | AUUUUAGAGUCCGCGUGU | 18 | 13707 |
| BCL11A-11573 | - | CAUUUUAGAGUCCGCGUGU | 19 | 13708 |
| BCL11A-11574 | - | UCAUUUUAGAGUCCGCGUGU | 20 | 13709 |
| BCL11A-11575 | - | UUCAUUUUAGAGUCCGCGUGU | 21 | 13710 |
| BCL11A-11576 | - | UUUCAUUUUAGAGUCCGCGUGU | 22 | 13711 |
| BCL11A-11577 | - | CUUUCAUUUUAGAGUCCGCGUGU | 23 | 13712 |
| BCL11A-11578 | - | UCUUUCAUUUUAGAGUCCGCGUGU | 24 | 13713 |
| BCL11A-11579 | - | UUUAGAGUCCGCGUGUGU | 18 | 13714 |
| BCL11A-11580 | - | UUUUAGAGUCCGCGUGUGU | 19 | 13715 |
| BCL11A-9586 | - | AUUUUAGAGUCCGCGUGUGU | 20 | 13716 |
| BCL11A-11581 | - | CAUUUUAGAGUCCGCGUGUGU | 21 | 13717 |
| BCL11A-11582 | - | UCAUUUUAGAGUCCGCGUGUGU | 22 | 13718 |

TABLE 19C-continued

3rd Tier

| gRNA Name | DNA Strand | Targeting Domain | Target Site Length | SEQ ID NO: |
|---|---|---|---|---|
| BCL11A-11583 | - | UUCAUUUUAGAGUCCGCGUGUGU | 23 | 13719 |
| BCL11A-11584 | - | UUUCAUUUUAGAGUCCGCGUGUGU | 24 | 13720 |
| BCL11A-11585 | - | AUUGCCGUGUAUGCACUU | 18 | 13721 |
| BCL11A-11586 | - | CAUUGCCGUGUAUGCACUU | 19 | 13722 |
| BCL11A-11587 | - | CCAUUGCCGUGUAUGCACUU | 20 | 13723 |
| BCL11A-11588 | - | ACCAUUGCCGUGUAUGCACUU | 21 | 13724 |
| BCL11A-11589 | - | AACCAUUGCCGUGUAUGCACUU | 22 | 13725 |
| BCL11A-11590 | - | GAACCAUUGCCGUGUAUGCACUU | 23 | 13726 |
| BCL11A-11591 | - | GGAACCAUUGCCGUGUAUGCACUU | 24 | 13727 |

Table 19D provides exemplary targeting domains for knocking down the BCL11A gene selected according to the fourth tier parameters. The targeting domains bind within the additional 500 bp (e.g., upstream or downstream) of a transcription start site (TSS), e.g., extending to 1 kb upstream and downstream of a TSS, and the PAM is NNGRRT. It is contemplated herein that in an embodiment the targeting domain hybridizes to the target domain through complementary base pairing. Any of the targeting domains in the table can be used with a *S. aureus* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 19D

4th Tier

| gRNA Name | DNA Strand | Targeting Domain | Target Site Length | SEQ ID NO: |
|---|---|---|---|---|
| BCL11A-11592 | + | CUCACCUCUUUUCUCCCC | 18 | 13728 |
| BCL11A-11593 | + | UCUCACCUCUUUUCUCCCC | 19 | 13729 |
| BCL11A-10076 | + | GUCUCACCUCUUUUCUCCCC | 20 | 13730 |
| BCL11A-11594 | + | AGUCUCACCUCUUUUCUCCCC | 21 | 13731 |
| BCL11A-11595 | + | CAGUCUCACCUCUUUUCUCCCC | 22 | 13732 |
| BCL11A-11596 | + | CCAGUCUCACCUCUUUUCUCCCC | 23 | 13733 |
| BCL11A-11597 | + | GCCAGUCUCACCUCUUUUCUCCCC | 24 | 13734 |
| BCL11A-11598 | + | AAAAGAAAAAAUAGAGC | 18 | 13735 |
| BCL11A-11599 | + | AAAAAGAAAAAAUAGAGC | 19 | 13736 |
| BCL11A-11600 | + | AAAAAAGAAAAAAUAGAGC | 20 | 13737 |
| BCL11A-11601 | + | CAAAAAAGAAAAAAUAGAGC | 21 | 13738 |
| BCL11A-11602 | + | UCAAAAAAGAAAAAAUAGAGC | 22 | 13739 |
| BCL11A-11603 | + | UUCAAAAAAGAAAAAAUAGAGC | 23 | 13740 |
| BCL11A-11604 | + | AUUCAAAAAAGAAAAAAUAGAGC | 24 | 13741 |
| BCL11A-11605 | + | GGCGGGGCGGGGGGGAG | 18 | 13742 |
| BCL11A-11606 | + | UGGCGGGGCGGGGGGGAG | 19 | 13743 |
| BCL11A-10153 | + | CUGGCGGGGCGGGGGGGAG | 20 | 13744 |
| BCL11A-11607 | + | ACUGGCGGGGCGGGGGGGAG | 21 | 13745 |

TABLE 19D-continued

4th Tier

| gRNA Name | DNA Strand | Targeting Domain | Target Site Length | SEQ ID NO: |
|---|---|---|---|---|
| BCL11A-11608 | + | AACUGGCGGGGCGGGGGGGAG | 22 | 13746 |
| BCL11A-11609 | + | AAACUGGCGGGGCGGGGGGGAG | 23 | 13747 |
| BCL11A-11610 | + | AAAACUGGCGGGGCGGGGGGGAG | 24 | 13748 |
| BCL11A-11611 | + | AGGGAGCGCACGGCAACG | 18 | 13749 |
| BCL11A-11612 | + | GAGGGAGCGCACGGCAACG | 19 | 13750 |
| BCL11A-10155 | + | GGAGGGAGCGCACGGCAACG | 20 | 13751 |
| BCL11A-11613 | + | GGGAGGGAGCGCACGGCAACG | 21 | 13752 |
| BCL11A-11614 | + | UGGGAGGGAGCGCACGGCAACG | 22 | 13753 |
| BCL11A-11615 | + | GUGGGAGGGAGCGCACGGCAACG | 23 | 13754 |
| BCL11A-11616 | + | GGUGGGAGGGAGCGCACGGCAACG | 24 | 13755 |
| BCL11A-11617 | + | CCCCCCCAUUUUCUUACG | 18 | 13756 |
| BCL11A-11618 | + | ACCCCCCCAUUUUCUUACG | 19 | 13757 |
| BCL11A-11619 | + | UACCCCCCCAUUUUCUUACG | 20 | 13758 |
| BCL11A-11620 | + | CUACCCCCCCAUUUUCUUACG | 21 | 13759 |
| BCL11A-11621 | + | CCUACCCCCCCAUUUUCUUACG | 22 | 13760 |
| BCL11A-11622 | + | CCCUACCCCCCCAUUUUCUUACG | 23 | 13761 |
| BCL11A-11623 | + | UCCCUACCCCCCCAUUUUCUUACG | 24 | 13762 |
| BCL11A-11624 | + | GGGCGGAGGGAAGCCAGG | 18 | 13763 |
| BCL11A-11625 | + | CGGGCGGAGGGAAGCCAGG | 19 | 13764 |
| BCL11A-11626 | + | GCGGGCGGAGGGAAGCCAGG | 20 | 13765 |
| BCL11A-11627 | + | CGCGGGCGGAGGGAAGCCAGG | 21 | 13766 |
| BCL11A-11628 | + | GCGCGGGCGGAGGGAAGCCAGG | 22 | 13767 |
| BCL11A-11629 | + | AGCGCGGGCGGAGGGAAGCCAGG | 23 | 13768 |
| BCL11A-11630 | + | AAGCGCGGGCGGAGGGAAGCCAGG | 24 | 13769 |
| BCL11A-11631 | + | CGGAAAGGAGGAAAGAGG | 18 | 13770 |
| BCL11A-11632 | + | GCGGAAAGGAGGAAAGAGG | 19 | 13771 |
| BCL11A-10187 | + | GGCGGAAAGGAGGAAAGAGG | 20 | 13772 |
| BCL11A-11633 | + | CGGCGGAAAGGAGGAAAGAGG | 21 | 13773 |
| BCL11A-11634 | + | GCGGCGGAAAGGAGGAAAGAGG | 22 | 13774 |
| BCL11A-11635 | + | AGCGGCGGAAAGGAGGAAAGAGG | 23 | 13775 |
| BCL11A-11636 | + | AAGCGGCGGAAAGGAGGAAAGAGG | 24 | 13776 |
| BCL11A-11637 | + | AAACUGGCGGGGCGGGGG | 18 | 13777 |
| BCL11A-11638 | + | AAAACUGGCGGGGCGGGGG | 19 | 13778 |
| BCL11A-10209 | + | CAAAACUGGCGGGGCGGGGG | 20 | 13779 |
| BCL11A-11639 | + | GCAAAACUGGCGGGGCGGGGG | 21 | 13780 |
| BCL11A-11640 | + | UGCAAAACUGGCGGGGCGGGGG | 22 | 13781 |
| BCL11A-11641 | + | UUGCAAAACUGGCGGGGCGGGGG | 23 | 13782 |
| BCL11A-11642 | + | UUUGCAAAACUGGCGGGGCGGGGG | 24 | 13783 |

TABLE 19D-continued

| | 4th Tier | | | |
|---|---|---|---|---|
| gRNA Name | DNA Strand | Targeting Domain | Target Site Length | SEQ ID NO: |
| BCL11A-11643 | + | CCACCCCCAGGUUUGCAU | 18 | 13784 |
| BCL11A-11644 | + | CCCACCCCCAGGUUUGCAU | 19 | 13785 |
| BCL11A-11645 | + | UCCCACCCCCAGGUUUGCAU | 20 | 13786 |
| BCL11A-11646 | + | CUCCCACCCCCAGGUUUGCAU | 21 | 13787 |
| BCL11A-11647 | + | GCUCCCACCCCCAGGUUUGCAU | 22 | 13788 |
| BCL11A-11648 | + | AGCUCCCACCCCCAGGUUUGCAU | 23 | 13789 |
| BCL11A-11649 | + | CAGCUCCCACCCCCAGGUUUGCAU | 24 | 13790 |
| BCL11A-11650 | + | GCCUAAGUUUGGAGGGCU | 18 | 13791 |
| BCL11A-11651 | + | AGCCUAAGUUUGGAGGGCU | 19 | 13792 |
| BCL11A-11652 | + | CAGCCUAAGUUUGGAGGGCU | 20 | 13793 |
| BCL11A-11653 | + | CCAGCCUAAGUUUGGAGGGCU | 21 | 13794 |
| BCL11A-11654 | + | UCCAGCCUAAGUUUGGAGGGCU | 22 | 13795 |
| BCL11A-11655 | + | AUCCAGCCUAAGUUUGGAGGGCU | 23 | 13796 |
| BCL11A-11656 | + | AAUCCAGCCUAAGUUUGGAGGGCU | 24 | 13797 |
| BCL11A-11657 | + | CCACUUUCUCACUAUUGU | 18 | 13798 |
| BCL11A-11658 | + | GCCACUUUCUCACUAUUGU | 19 | 13799 |
| BCL11A-10251 | + | UGCCACUUUCUCACUAUUGU | 20 | 13800 |
| BCL11A-11659 | + | GUGCCACUUUCUCACUAUUGU | 21 | 13801 |
| BCL11A-11660 | + | AGUGCCACUUUCUCACUAUUGU | 22 | 13802 |
| BCL11A-11661 | + | CAGUGCCACUUUCUCACUAUUGU | 23 | 13803 |
| BCL11A-11662 | + | ACAGUGCCACUUUCUCACUAUUGU | 24 | 13804 |
| BCL11A-11663 | − | UUAUUUCUCUUUUCGAAA | 18 | 13805 |
| BCL11A-11664 | − | UUUAUUUCUCUUUUCGAAA | 19 | 13806 |
| BCL11A-10027 | − | CUUUAUUUCUCUUUUCGAAA | 20 | 13807 |
| BCL11A-11665 | − | GCUUUAUUUCUCUUUUCGAAA | 21 | 13808 |
| BCL11A-11666 | − | CGCUUUAUUUCUCUUUUCGAAA | 22 | 13809 |
| BCL11A-11667 | − | CCGCUUUAUUUCUCUUUUCGAAA | 23 | 13810 |
| BCL11A-11668 | − | GCCGCUUUAUUUCUCUUUUCGAAA | 24 | 13811 |
| BCL11A-11669 | − | CGGCGGCGGGGAGGGGAA | 18 | 13812 |
| BCL11A-11670 | − | GCGGCGGCGGGGAGGGGAA | 19 | 13813 |
| BCL11A-11671 | − | GGCGGCGGCGGGGAGGGGAA | 20 | 13814 |
| BCL11A-11672 | − | CGGCGGCGGCGGGGAGGGGAA | 21 | 13815 |
| BCL11A-11673 | − | GCGGCGGCGGCGGGGAGGGGAA | 22 | 13816 |
| BCL11A-11674 | − | CGCGGCGGCGGCGGGGAGGGGAA | 23 | 13817 |
| BCL11A-11675 | − | GCGCGGCGGCGGCGGGGAGGGGAA | 24 | 13818 |
| BCL11A-11676 | − | UGGGGGGGUAGGGAGGGA | 18 | 13819 |
| BCL11A-11677 | − | AUGGGGGGGUAGGGAGGGA | 19 | 13820 |

TABLE 19D-continued

4th Tier

| gRNA Name | DNA Strand | Targeting Domain | Target Site Length | SEQ ID NO: |
|---|---|---|---|---|
| BCL11A-11678 | - | AAUGGGGGGUAGGGAGGGA | 20 | 13821 |
| BCL11A-11679 | - | AAAUGGGGGGUAGGGAGGGA | 21 | 13822 |
| BCL11A-11680 | - | AAAAUGGGGGGUAGGGAGGGA | 22 | 13823 |
| BCL11A-11681 | - | GAAAAUGGGGGGUAGGGAGGGA | 23 | 13824 |
| BCL11A-11682 | - | AGAAAAUGGGGGGUAGGGAGGGA | 24 | 13825 |
| BCL11A-11683 | - | AAAUGGGGGGUAGGGA | 18 | 13826 |
| BCL11A-11684 | - | GAAAAUGGGGGGUAGGGA | 19 | 13827 |
| BCL11A-10049 | - | AGAAAAUGGGGGGUAGGGA | 20 | 13828 |
| BCL11A-11685 | - | AAGAAAAUGGGGGGUAGGGA | 21 | 13829 |
| BCL11A-11686 | - | UAAGAAAAUGGGGGGUAGGGA | 22 | 13830 |
| BCL11A-11687 | - | GUAAGAAAAUGGGGGGUAGGGA | 23 | 13831 |
| BCL11A-11688 | - | CGUAAGAAAAUGGGGGGUAGGGA | 24 | 13832 |
| BCL11A-11689 | - | AAGGGGCCCCCGGCGCUC | 18 | 13833 |
| BCL11A-11690 | - | AAAGGGGCCCCCGGCGCUC | 19 | 13834 |
| BCL11A-11691 | - | GAAAGGGGCCCCCGGCGCUC | 20 | 13835 |
| BCL11A-11692 | - | GGAAAGGGGCCCCCGGCGCUC | 21 | 13836 |
| BCL11A-11693 | - | UGGAAAGGGGCCCCCGGCGCUC | 22 | 13837 |
| BCL11A-11694 | - | GUGGAAAGGGGCCCCCGGCGCUC | 23 | 13838 |
| BCL11A-11695 | - | UGUGGAAAGGGGCCCCCGGCGCUC | 24 | 13839 |
| BCL11A-11696 | - | CUUUUGUUCCGGCCAGAG | 18 | 13840 |
| BCL11A-11697 | - | CCUUUUGUUCCGGCCAGAG | 19 | 13841 |
| BCL11A-11698 | - | GCCUUUUGUUCCGGCCAGAG | 20 | 13842 |
| BCL11A-11699 | - | CGCCUUUUGUUCCGGCCAGAG | 21 | 13843 |
| BCL11A-11700 | - | CCGCCUUUUGUUCCGGCCAGAG | 22 | 13844 |
| BCL11A-11701 | - | GCCGCCUUUUGUUCCGGCCAGAG | 23 | 13845 |
| BCL11A-11702 | - | UGCCGCCUUUUGUUCCGGCCAGAG | 24 | 13846 |
| BCL11A-11703 | - | GUGGGUGUGCGUACGGAG | 18 | 13847 |
| BCL11A-11704 | - | AGUGGGUGUGCGUACGGAG | 19 | 13848 |
| BCL11A-11705 | - | AAGUGGGUGUGCGUACGGAG | 20 | 13849 |
| BCL11A-11706 | - | GAAGUGGGUGUGCGUACGGAG | 21 | 13850 |
| BCL11A-11707 | - | GGAAGUGGGUGUGCGUACGGAG | 22 | 13851 |
| BCL11A-11708 | - | GGGAAGUGGGUGUGCGUACGGAG | 23 | 13852 |
| BCL11A-11709 | - | GGGGAAGUGGGUGUGCGUACGGAG | 24 | 13853 |
| BCL11A-11710 | - | CCGGCGCUCCUGAGUCCG | 18 | 13854 |
| BCL11A-11711 | - | CCCGGCGCUCCUGAGUCCG | 19 | 13855 |
| BCL11A-10172 | - | CCCCGGCGCUCCUGAGUCCG | 20 | 13856 |
| BCL11A-11712 | - | CCCCCGGCGCUCCUGAGUCCG | 21 | 13857 |
| BCL11A-11713 | - | GCCCCCGGCGCUCCUGAGUCCG | 22 | 13858 |

TABLE 19D-continued

4th Tier

| gRNA Name | DNA Strand | Targeting Domain | Target Site Length | SEQ ID NO: |
|---|---|---|---|---|
| BCL11A-11714 | - | GGCCCCCGGCGCUCCUGAGUCCG | 23 | 13859 |
| BCL11A-11715 | - | GGGCCCCCGGCGCUCCUGAGUCCG | 24 | 13860 |
| BCL11A-11716 | - | CAGCCCUCCAAACUUAGG | 18 | 13861 |
| BCL11A-11717 | - | GCAGCCCUCCAAACUUAGG | 19 | 13862 |
| BCL11A-11718 | - | CGCAGCCCUCCAAACUUAGG | 20 | 13863 |
| BCL11A-11719 | - | CCGCAGCCCUCCAAACUUAGG | 21 | 13864 |
| BCL11A-11720 | - | CCCGCAGCCCUCCAAACUUAGG | 22 | 13865 |
| BCL11A-11721 | - | ACCCGCAGCCCUCCAAACUUAGG | 23 | 13866 |
| BCL11A-11722 | - | GACCCGCAGCCCUCCAAACUUAGG | 24 | 13867 |
| BCL11A-11723 | - | CUCACCGUAAGAAAAUGG | 18 | 13868 |
| BCL11A-11724 | - | ACUCACCGUAAGAAAAUGG | 19 | 13869 |
| BCL11A-10214 | - | CACUCACCGUAAGAAAAUGG | 20 | 13870 |
| BCL11A-11725 | - | CCACUCACCGUAAGAAAAUGG | 21 | 13871 |
| BCL11A-11726 | - | CCCACUCACCGUAAGAAAAUGG | 22 | 13872 |
| BCL11A-11727 | - | UCCCACUCACCGUAAGAAAAUGG | 23 | 13873 |
| BCL11A-11728 | - | UUCCCACUCACCGUAAGAAAAUGG | 24 | 13874 |
| BCL11A-11729 | - | GAGGCUCAGCUCUCAACU | 18 | 13875 |
| BCL11A-11730 | - | GGAGGCUCAGCUCUCAACU | 19 | 13876 |
| BCL11A-11731 | - | UGGAGGCUCAGCUCUCAACU | 20 | 13877 |
| BCL11A-11732 | - | UUGGAGGCUCAGCUCUCAACU | 21 | 13878 |
| BCL11A-11733 | - | CUUGGAGGCUCAGCUCUCAACU | 22 | 13879 |
| BCL11A-11734 | - | ACUUGGAGGCUCAGCUCUCAACU | 23 | 13880 |
| BCL11A-11735 | - | AACUUGGAGGCUCAGCUCUCAACU | 24 | 13881 |
| BCL11A-11736 | - | CAACUCACAUGCAAACCU | 18 | 13882 |
| BCL11A-11737 | - | ACAACUCACAUGCAAACCU | 19 | 13883 |
| BCL11A-10235 | - | AACAACUCACAUGCAAACCU | 20 | 13884 |
| BCL11A-11738 | - | GAACAACUCACAUGCAAACCU | 21 | 13885 |
| BCL11A-11739 | - | CGAACAACUCACAUGCAAACCU | 22 | 13886 |
| BCL11A-11740 | - | GCGAACAACUCACAUGCAAACCU | 23 | 13887 |
| BCL11A-11741 | - | UGCGAACAACUCACAUGCAAACCU | 24 | 13888 |
| BCL11A-10351 | - | UUGAAUAAUCUUUCAUUU | 18 | 13889 |
| BCL11A-10352 | - | UUUGAAUAAUCUUUCAUUU | 19 | 13890 |
| BCL11A-10353 | - | UUUUGAAUAAUCUUUCAUUU | 20 | 13891 |
| BCL11A-10354 | - | UUUUUGAAUAAUCUUUCAUUU | 21 | 13892 |
| BCL11A-10355 | - | UUUUUUGAAUAAUCUUUCAUUU | 22 | 13893 |
| BCL11A-10356 | - | CUUUUUUGAAUAAUCUUUCAUUU | 23 | 13894 |
| BCL11A-10357 | - | UCUUUUUUGAAUAAUCUUUCAUUU | 24 | 13895 |

TABLE 19D-continued

4th Tier

| gRNA Name | DNA Strand | Targeting Domain | Target Site Length | SEQ ID NO: |
|---|---|---|---|---|
| BCL11A-11742 | − | GCUCUAUUUUUUCUUUU | 18 | 13896 |
| BCL11A-11743 | − | CGCUCUAUUUUUUCUUUU | 19 | 13897 |
| BCL11A-11744 | − | UCGCUCUAUUUUUUCUUUU | 20 | 13898 |
| BCL11A-11745 | − | CUCGCUCUAUUUUUUCUUUU | 21 | 13899 |
| BCL11A-11746 | − | UCUCGCUCUAUUUUUUCUUUU | 22 | 13900 |
| BCL11A-11747 | − | CUCUCGCUCUAUUUUUUCUUUU | 23 | 13901 |
| BCL11A-11748 | − | ACUCUCGCUCUAUUUUUUCUUUU | 24 | 13902 |

Table 19E provides exemplary targeting domains for knocking down the BCL11A gene selected according to the fifth tier parameters. The targeting domains bind within the additional 500 bp (e.g., upstream or downstream) of a transcription start site (TSS), e.g., extending to 1 kb upstream and downstream of a TSS, and the PAM is NNGRRV. It is contemplated herein that in an embodiment the targeting domain hybridizes to the target domain through complementary base pairing. Any of the targeting domains in the table can be used with a *S. aureus* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 19E

5th Tier

| gRNA Name | DNA Strand | Targeting Domain | Target Site Length | SEQ ID NO: |
|---|---|---|---|---|
| BCL11A-11749 | + | AUUCAAAAAGAAAAAAA | 18 | 13903 |
| BCL11A-11750 | + | UAUUCAAAAAGAAAAAAA | 19 | 13904 |
| BCL11A-11751 | + | UUAUUCAAAAAGAAAAAAA | 20 | 13905 |
| BCL11A-11752 | + | AUUAUUCAAAAAGAAAAAAA | 21 | 13906 |
| BCL11A-11753 | + | GAUUAUUCAAAAAGAAAAAAA | 22 | 13907 |
| BCL11A-11754 | + | AGAUUAUUCAAAAAGAAAAAAA | 23 | 13908 |
| BCL11A-11755 | + | AAGAUUAUUCAAAAAGAAAAAAA | 24 | 13909 |
| BCL11A-11756 | + | AUGAAAGAUUAUUCAAAA | 18 | 13910 |
| BCL11A-11757 | + | AAUGAAAGAUUAUUCAAAA | 19 | 13911 |
| BCL11A-11758 | + | AAAUGAAAGAUUAUUCAAAA | 20 | 13912 |
| BCL11A-11759 | + | AAAAUGAAAGAUUAUUCAAAA | 21 | 13913 |
| BCL11A-11760 | + | UAAAAUGAAAGAUUAUUCAAAA | 22 | 13914 |
| BCL11A-11761 | + | CUAAAAUGAAAGAUUAUUCAAAA | 23 | 13915 |
| BCL11A-11762 | + | UCUAAAAUGAAAGAUUAUUCAAAA | 24 | 13916 |
| BCL11A-11763 | + | UGCAUUCCUUUUCGAAAA | 18 | 13917 |
| BCL11A-11764 | + | UUGCAUUCCUUUUCGAAAA | 19 | 13918 |
| BCL11A-11765 | + | AUUGCAUUCCUUUUCGAAAA | 20 | 13919 |
| BCL11A-11766 | + | CAUUGCAUUCCUUUUCGAAAA | 21 | 13920 |
| BCL11A-11767 | + | UCAUUGCAUUCCUUUUCGAAAA | 22 | 13921 |
| BCL11A-11768 | + | AUCAUUGCAUUCCUUUUCGAAAA | 23 | 13922 |

TABLE 19E-continued

5th Tier

| gRNA Name | DNA Strand | Targeting Domain | Target Site Length | SEQ ID NO: |
|---|---|---|---|---|
| BCL11A-11769 | + | AAUCAUUGCAUUCCUUUUCGAAAA | 24 | 13923 |
| BCL11A-11770 | + | GCGGCGGAAAGGAGGAAA | 18 | 13924 |
| BCL11A-11771 | + | AGCGGCGGAAAGGAGGAAA | 19 | 13925 |
| BCL11A-11772 | + | AAGCGGCGGAAAGGAGGAAA | 20 | 13926 |
| BCL11A-11773 | + | AAAGCGGCGGAAAGGAGGAAA | 21 | 13927 |
| BCL11A-11774 | + | UAAAGCGGCGGAAAGGAGGAAA | 22 | 13928 |
| BCL11A-11775 | + | AUAAAGCGGCGGAAAGGAGGAAA | 23 | 13929 |
| BCL11A-11776 | + | AAUAAAGCGGCGGAAAGGAGGAAA | 24 | 13930 |
| BCL11A-11777 | + | GCCCGCGCGGCCUGGAAA | 18 | 13931 |
| BCL11A-11778 | + | AGCCCGCGCGGCCUGGAAA | 19 | 13932 |
| BCL11A-11779 | + | GAGCCCGCGCGGCCUGGAAA | 20 | 13933 |
| BCL11A-11780 | + | GGAGCCCGCGCGGCCUGGAAA | 21 | 13934 |
| BCL11A-11781 | + | AGGAGCCCGCGCGGCCUGGAAA | 22 | 13935 |
| BCL11A-11782 | + | CAGGAGCCCGCGCGGCCUGGAAA | 23 | 13936 |
| BCL11A-11783 | + | CCAGGAGCCCGCGCGGCCUGGAAA | 24 | 13937 |
| BCL11A-10371 | + | ACACACGCGGACUCUAAA | 18 | 13938 |
| BCL11A-10372 | + | CACACACGCGGACUCUAAA | 19 | 13939 |
| BCL11A-10373 | + | CCACACACGCGGACUCUAAA | 20 | 13940 |
| BCL11A-10374 | + | CCCACACACGCGGACUCUAAA | 21 | 13941 |
| BCL11A-10375 | + | CCCCACACACGCGGACUCUAAA | 22 | 13942 |
| BCL11A-10376 | + | CCCCCACACACGCGGACUCUAAA | 23 | 13943 |
| BCL11A-10377 | + | CCCCCCACACACGCGGACUCUAAA | 24 | 13944 |
| BCL11A-11784 | + | AUUGCAUUCCUUUUCGAA | 18 | 13945 |
| BCL11A-11785 | + | CAUUGCAUUCCUUUUCGAA | 19 | 13946 |
| BCL11A-11786 | + | UCAUUGCAUUCCUUUUCGAA | 20 | 13947 |
| BCL11A-11787 | + | AUCAUUGCAUUCCUUUUCGAA | 21 | 13948 |
| BCL11A-11788 | + | AAUCAUUGCAUUCCUUUUCGAA | 22 | 13949 |
| BCL11A-11789 | + | GAAUCAUUGCAUUCCUUUUCGAA | 23 | 13950 |
| BCL11A-11790 | + | GGAAUCAUUGCAUUCCUUUUCGAA | 24 | 13951 |
| BCL11A-11791 | + | AGAAAUAAAGCGGCGGAA | 18 | 13952 |
| BCL11A-11792 | + | GAGAAAUAAAGCGGCGGAA | 19 | 13953 |
| BCL11A-10031 | + | AGAGAAAUAAAGCGGCGGAA | 20 | 13954 |
| BCL11A-11793 | + | AAGAGAAAUAAAGCGGCGGAA | 21 | 13955 |
| BCL11A-11794 | + | AAAGAGAAAUAAAGCGGCGGAA | 22 | 13956 |
| BCL11A-11795 | + | AAAAGAGAAAUAAAGCGGCGGAA | 23 | 13957 |
| BCL11A-11796 | + | GAAAAGAGAAAUAAAGCGGCGGAA | 24 | 13958 |
| BCL11A-11797 | + | CCCGAGGAGAGGACAGCA | 18 | 13959 |

TABLE 19E-continued

5th Tier

| gRNA Name | DNA Strand | Targeting Domain | Target Site Length | SEQ ID NO: |
|---|---|---|---|---|
| BCL11A-11798 | + | GCCCGAGGAGAGGACAGCA | 19 | 13960 |
| BCL11A-11799 | + | UGCCCGAGGAGAGGACAGCA | 20 | 13961 |
| BCL11A-11800 | + | UUGCCCGAGGAGAGGACAGCA | 21 | 13962 |
| BCL11A-11801 | + | UUUGCCCGAGGAGAGGACAGCA | 22 | 13963 |
| BCL11A-11802 | + | CUUUGCCCGAGGAGAGGACAGCA | 23 | 13964 |
| BCL11A-11803 | + | ACUUUGCCCGAGGAGAGGACAGCA | 24 | 13965 |
| BCL11A-11804 | + | CCAAGUUACAGCUCCGCA | 18 | 13966 |
| BCL11A-11805 | + | UCCAAGUUACAGCUCCGCA | 19 | 13967 |
| BCL11A-11806 | + | CUCCAAGUUACAGCUCCGCA | 20 | 13968 |
| BCL11A-11807 | + | CCUCCAAGUUACAGCUCCGCA | 21 | 13969 |
| BCL11A-11808 | + | GCCUCCAAGUUACAGCUCCGCA | 22 | 13970 |
| BCL11A-11809 | + | AGCCUCCAAGUUACAGCUCCGCA | 23 | 13971 |
| BCL11A-11810 | + | GAGCCUCCAAGUUACAGCUCCGCA | 24 | 13972 |
| BCL11A-11811 | + | GAGCCGGCACAAAAGGCA | 18 | 13973 |
| BCL11A-11812 | + | GGAGCCGGCACAAAAGGCA | 19 | 13974 |
| BCL11A-11813 | + | AGGAGCCGGCACAAAAGGCA | 20 | 13975 |
| BCL11A-11814 | + | GAGGAGCCGGCACAAAAGGCA | 21 | 13976 |
| BCL11A-11815 | + | CGAGGAGCCGGCACAAAAGGCA | 22 | 13977 |
| BCL11A-11816 | + | GCGAGGAGCCGGCACAAAAGGCA | 23 | 13978 |
| BCL11A-11817 | + | CGCGAGGAGCCGGCACAAAAGGCA | 24 | 13979 |
| BCL11A-11818 | + | AAAUAGAGCGAGAGUGCA | 18 | 13980 |
| BCL11A-11819 | + | AAAAUAGAGCGAGAGUGCA | 19 | 13981 |
| BCL11A-11820 | + | AAAAAUAGAGCGAGAGUGCA | 20 | 13982 |
| BCL11A-11821 | + | AAAAAAUAGAGCGAGAGUGCA | 21 | 13983 |
| BCL11A-11822 | + | AAAAAAAUAGAGCGAGAGUGCA | 22 | 13984 |
| BCL11A-11823 | + | GAAAAAAAUAGAGCGAGAGUGCA | 23 | 13985 |
| BCL11A-11824 | + | AGAAAAAAAUAGAGCGAGAGUGCA | 24 | 13986 |
| BCL11A-11825 | + | CCGCGCGGCCUGGAAAGA | 18 | 13987 |
| BCL11A-11826 | + | CCCGCGCGGCCUGGAAAGA | 19 | 13988 |
| BCL11A-10040 | + | GCCCGCGCGGCCUGGAAAGA | 20 | 13989 |
| BCL11A-11827 | + | AGCCCGCGCGGCCUGGAAAGA | 21 | 13990 |
| BCL11A-11828 | + | GAGCCCGCGCGGCCUGGAAAGA | 22 | 13991 |
| BCL11A-11829 | + | GGAGCCCGCGCGGCCUGGAAAGA | 23 | 13992 |
| BCL11A-11830 | + | AGGAGCCCGCGCGGCCUGGAAAGA | 24 | 13993 |
| BCL11A-11831 | + | AAAAAAGAAAAAAAUAGA | 18 | 13994 |
| BCL11A-11832 | + | CAAAAAAGAAAAAAAUAGA | 19 | 13995 |
| BCL11A-11833 | + | UCAAAAAAGAAAAAAAUAGA | 20 | 13996 |

TABLE 19E-continued

5th Tier

| gRNA Name | DNA Strand | Targeting Domain | Target Site Length | SEQ ID NO: |
|---|---|---|---|---|
| BCL11A-11834 | + | UUCAAAAAGAAAAAAUAGA | 21 | 13997 |
| BCL11A-11835 | + | AUUCAAAAAGAAAAAAUAGA | 22 | 13998 |
| BCL11A-11836 | + | UAUUCAAAAAGAAAAAAUAGA | 23 | 13999 |
| BCL11A-11837 | + | UUAUUCAAAAAGAAAAAAUAGA | 24 | 14000 |
| BCL11A-11838 | + | CAGCUCCGCAGCGGGCGA | 18 | 14001 |
| BCL11A-11839 | + | ACAGCUCCGCAGCGGGCGA | 19 | 14002 |
| BCL11A-10044 | + | UACAGCUCCGCAGCGGGCGA | 20 | 14003 |
| BCL11A-11840 | + | UUACAGCUCCGCAGCGGGCGA | 21 | 14004 |
| BCL11A-11841 | + | GUUACAGCUCCGCAGCGGGCGA | 22 | 14005 |
| BCL11A-11842 | + | AGUUACAGCUCCGCAGCGGGCGA | 23 | 14006 |
| BCL11A-11843 | + | AAGUUACAGCUCCGCAGCGGGCGA | 24 | 14007 |
| BCL11A-11844 | + | GGAAACUUUGCCCGAGGA | 18 | 14008 |
| BCL11A-11845 | + | GGGAAACUUUGCCCGAGGA | 19 | 14009 |
| BCL11A-11846 | + | CGGGAAACUUUGCCCGAGGA | 20 | 14010 |
| BCL11A-11847 | + | UCGGGAAACUUUGCCCGAGGA | 21 | 14011 |
| BCL11A-11848 | + | CUCGGGAAACUUUGCCCGAGGA | 22 | 14012 |
| BCL11A-11849 | + | GCUCGGGAAACUUUGCCCGAGGA | 23 | 14013 |
| BCL11A-11850 | + | CGCUCGGGAAACUUUGCCCGAGGA | 24 | 14014 |
| BCL11A-11851 | + | AAGCGGCGGAAAGGAGGA | 18 | 14015 |
| BCL11A-11852 | + | AAAGCGGCGGAAAGGAGGA | 19 | 14016 |
| BCL11A-11853 | + | UAAAGCGGCGGAAAGGAGGA | 20 | 14017 |
| BCL11A-11854 | + | AUAAAGCGGCGGAAAGGAGGA | 21 | 14018 |
| BCL11A-11855 | + | AAUAAAGCGGCGGAAAGGAGGA | 22 | 14019 |
| BCL11A-11856 | + | AAAUAAAGCGGCGGAAAGGAGGA | 23 | 14020 |
| BCL11A-11857 | + | GAAAUAAAGCGGCGGAAAGGAGGA | 24 | 14021 |
| BCL11A-11858 | + | GAGAAAUAAAGCGGCGGA | 18 | 14022 |
| BCL11A-11859 | + | AGAGAAAUAAAGCGGCGGA | 19 | 14023 |
| BCL11A-11860 | + | AAGAGAAAUAAAGCGGCGGA | 20 | 14024 |
| BCL11A-11861 | + | AAAGAGAAAUAAAGCGGCGGA | 21 | 14025 |
| BCL11A-11862 | + | AAAAGAGAAAUAAAGCGGCGGA | 22 | 14026 |
| BCL11A-11863 | + | GAAAAGAGAAAUAAAGCGGCGGA | 23 | 14027 |
| BCL11A-11864 | + | CGAAAAGAGAAAUAAAGCGGCGGA | 24 | 14028 |
| BCL11A-11865 | + | UGGGGAAGCGCGGGCGGA | 18 | 14029 |
| BCL11A-11866 | + | CUGGGGAAGCGCGGGCGGA | 19 | 14030 |
| BCL11A-10048 | + | GCUGGGGAAGCGCGGGCGGA | 20 | 14031 |
| BCL11A-11867 | + | GGCUGGGGAAGCGCGGGCGGA | 21 | 14032 |
| BCL11A-11868 | + | GGGCUGGGGAAGCGCGGGCGGA | 22 | 14033 |

TABLE 19E-continued

5th Tier

| gRNA Name | DNA Strand | Targeting Domain | Target Site Length | SEQ ID NO: |
|---|---|---|---|---|
| BCL11A-11869 | + | CGGGCUGGGGAAGCGCGGGCGGA | 23 | 14034 |
| BCL11A-11870 | + | CCGGGCUGGGGAAGCGCGGGCGGA | 24 | 14035 |
| BCL11A-11871 | + | CCAAGGCCGAGCCAGGGA | 18 | 14036 |
| BCL11A-11872 | + | CCCAAGGCCGAGCCAGGGA | 19 | 14037 |
| BCL11A-11873 | + | CCCCAAGGCCGAGCCAGGGA | 20 | 14038 |
| BCL11A-11874 | + | CCCCCAAGGCCGAGCCAGGGA | 21 | 14039 |
| BCL11A-11875 | + | GCCCCCAAGGCCGAGCCAGGGA | 22 | 14040 |
| BCL11A-11876 | + | CGCCCCCAAGGCCGAGCCAGGGA | 23 | 14041 |
| BCL11A-11877 | + | GCGCCCCCAAGGCCGAGCCAGGGA | 24 | 14042 |
| BCL11A-11878 | + | CGGCCUGGAAAGAGGGGA | 18 | 14043 |
| BCL11A-11879 | + | GCGGCCUGGAAAGAGGGGA | 19 | 14044 |
| BCL11A-11880 | + | CGCGGCCUGGAAAGAGGGGA | 20 | 14045 |
| BCL11A-11881 | + | GCGCGGCCUGGAAAGAGGGGA | 21 | 14046 |
| BCL11A-11882 | + | CGCGCGGCCUGGAAAGAGGGGA | 22 | 14047 |
| BCL11A-11883 | + | CCGCGCGGCCUGGAAAGAGGGGA | 23 | 14048 |
| BCL11A-11884 | + | CCCGCGCGGCCUGGAAAGAGGGGA | 24 | 14049 |
| BCL11A-11885 | + | UGGCGGGGCGGGGGGGA | 18 | 14050 |
| BCL11A-11886 | + | CUGGCGGGGCGGGGGGGA | 19 | 14051 |
| BCL11A-11887 | + | ACUGGCGGGGCGGGGGGGA | 20 | 14052 |
| BCL11A-11888 | + | AACUGGCGGGGCGGGGGGGA | 21 | 14053 |
| BCL11A-11889 | + | AAACUGGCGGGGCGGGGGGGA | 22 | 14054 |
| BCL11A-11890 | + | AAAACUGGCGGGGCGGGGGGGA | 23 | 14055 |
| BCL11A-11891 | + | CAAAACUGGCGGGGCGGGGGGGA | 24 | 14056 |
| BCL11A-11892 | + | GGGCGAGGGGAGGUGGGA | 18 | 14057 |
| BCL11A-11893 | + | CGGGCGAGGGGAGGUGGGA | 19 | 14058 |
| BCL11A-10052 | + | GCGGGCGAGGGGAGGUGGGA | 20 | 14059 |
| BCL11A-11894 | + | AGCGGGCGAGGGGAGGUGGGA | 21 | 14060 |
| BCL11A-11895 | + | CAGCGGGCGAGGGGAGGUGGGA | 22 | 14061 |
| BCL11A-11896 | + | GCAGCGGGCGAGGGGAGGUGGGA | 23 | 14062 |
| BCL11A-11897 | + | CGCAGCGGGCGAGGGGAGGUGGGA | 24 | 14063 |
| BCL11A-11898 | + | GAGCCCGCGCGGCCUGGA | 18 | 14064 |
| BCL11A-11899 | + | GGAGCCCGCGCGGCCUGGA | 19 | 14065 |
| BCL11A-11900 | + | AGGAGCCCGCGCGGCCUGGA | 20 | 14066 |
| BCL11A-11901 | + | CAGGAGCCCGCGCGGCCUGGA | 21 | 14067 |
| BCL11A-11902 | + | CCAGGAGCCCGCGCGGCCUGGA | 22 | 14068 |
| BCL11A-11903 | + | UCCAGGAGCCCGCGCGGCCUGGA | 23 | 14069 |
| BCL11A-11904 | + | CUCCAGGAGCCCGCGCGGCCUGGA | 24 | 14070 |

TABLE 19E-continued

5th Tier

| gRNA Name | DNA Strand | Targeting Domain | Target Site Length | SEQ ID NO: |
|---|---|---|---|---|
| BCL11A-11905 | + | CCCAUUUCUUACGGUGA | 18 | 14071 |
| BCL11A-11906 | + | CCCCAUUUCUUACGGUGA | 19 | 14072 |
| BCL11A-11907 | + | CCCCCAUUUCUUACGGUGA | 20 | 14073 |
| BCL11A-11908 | + | CCCCCCAUUUCUUACGGUGA | 21 | 14074 |
| BCL11A-11909 | + | CCCCCCCAUUUCUUACGGUGA | 22 | 14075 |
| BCL11A-11910 | + | ACCCCCCCAUUUCUUACGGUGA | 23 | 14076 |
| BCL11A-11911 | + | UACCCCCCCAUUUCUUACGGUGA | 24 | 14077 |
| BCL11A-11912 | + | GAGGGAGCGCACGGCAAC | 18 | 14078 |
| BCL11A-11913 | + | GGAGGGAGCGCACGGCAAC | 19 | 14079 |
| BCL11A-11914 | + | GGGAGGGAGCGCACGGCAAC | 20 | 14080 |
| BCL11A-11915 | + | UGGGAGGGAGCGCACGGCAAC | 21 | 14081 |
| BCL11A-11916 | + | GUGGGAGGGAGCGCACGGCAAC | 22 | 14082 |
| BCL11A-11917 | + | GGUGGGAGGGAGCGCACGGCAAC | 23 | 14083 |
| BCL11A-11918 | + | AGGUGGGAGGGAGCGCACGGCAAC | 24 | 14084 |
| BCL11A-10612 | + | CUGCUCCCCCCCACACAC | 18 | 14085 |
| BCL11A-10613 | + | CCUGCUCCCCCCCACACAC | 19 | 14086 |
| BCL11A-10614 | + | CCCUGCUCCCCCCCACACAC | 20 | 14087 |
| BCL11A-10615 | + | GCCCUGCUCCCCCCCACACAC | 21 | 14088 |
| BCL11A-10616 | + | CGCCCUGCUCCCCCCCACACAC | 22 | 14089 |
| BCL11A-10617 | + | GCGCCCUGCUCCCCCCCACACAC | 23 | 14090 |
| BCL11A-10618 | + | UGCGCCCUGCUCCCCCCCACACAC | 24 | 14091 |
| BCL11A-11919 | + | AAUAGAGCGAGAGUGCAC | 18 | 14092 |
| BCL11A-11920 | + | AAAUAGAGCGAGAGUGCAC | 19 | 14093 |
| BCL11A-10059 | + | AAAAUAGAGCGAGAGUGCAC | 20 | 14094 |
| BCL11A-11921 | + | AAAAAUAGAGCGAGAGUGCAC | 21 | 14095 |
| BCL11A-11922 | + | AAAAAAUAGAGCGAGAGUGCAC | 22 | 14096 |
| BCL11A-11923 | + | AAAAAAAUAGAGCGAGAGUGCAC | 23 | 14097 |
| BCL11A-11924 | + | GAAAAAAAUAGAGCGAGAGUGCAC | 24 | 14098 |
| BCL11A-11925 | + | ACAGCAAAGAAAAAUCAC | 18 | 14099 |
| BCL11A-11926 | + | GACAGCAAAGAAAAAUCAC | 19 | 14100 |
| BCL11A-11927 | + | GGACAGCAAAGAAAAAUCAC | 20 | 14101 |
| BCL11A-11928 | + | AGGACAGCAAAGAAAAAUCAC | 21 | 14102 |
| BCL11A-11929 | + | GAGGACAGCAAAGAAAAAUCAC | 22 | 14103 |
| BCL11A-11930 | + | AGAGGACAGCAAAGAAAAAUCAC | 23 | 14104 |
| BCL11A-11931 | + | GAGAGGACAGCAAAGAAAAAUCAC | 24 | 14105 |
| BCL11A-11932 | + | CAAGGCCGAGCCAGGGAC | 18 | 14106 |
| BCL11A-11933 | + | CCAAGGCCGAGCCAGGGAC | 19 | 14107 |

TABLE 19E-continued

5th Tier

| gRNA Name | DNA Strand | Targeting Domain | Target Site Length | SEQ ID NO: |
|---|---|---|---|---|
| BCL11A-10063 | + | CCCAAGGCCGAGCCAGGGAC | 20 | 14108 |
| BCL11A-11934 | + | CCCCAAGGCCGAGCCAGGGAC | 21 | 14109 |
| BCL11A-11935 | + | CCCCCAAGGCCGAGCCAGGGAC | 22 | 14110 |
| BCL11A-11936 | + | GCCCCCAAGGCCGAGCCAGGGAC | 23 | 14111 |
| BCL11A-11937 | + | CGCCCCCAAGGCCGAGCCAGGGAC | 24 | 14112 |
| BCL11A-11938 | + | GGCCUGGAAAGAGGGGAC | 18 | 14113 |
| BCL11A-11939 | + | CGGCCUGGAAAGAGGGGAC | 19 | 14114 |
| BCL11A-10064 | + | GCGGCCUGGAAAGAGGGGAC | 20 | 14115 |
| BCL11A-11940 | + | CGCGGCCUGGAAAGAGGGGAC | 21 | 14116 |
| BCL11A-11941 | + | GCGCGGCCUGGAAAGAGGGGAC | 22 | 14117 |
| BCL11A-11942 | + | CGCGCGGCCUGGAAAGAGGGGAC | 23 | 14118 |
| BCL11A-11943 | + | CCGCGCGGCCUGGAAAGAGGGGAC | 24 | 14119 |
| BCL11A-11944 | + | AUAGAGCGAGAGUGCACC | 18 | 14120 |
| BCL11A-11945 | + | AAUAGAGCGAGAGUGCACC | 19 | 14121 |
| BCL11A-10067 | + | AAAUAGAGCGAGAGUGCACC | 20 | 14122 |
| BCL11A-11946 | + | AAAAUAGAGCGAGAGUGCACC | 21 | 14123 |
| BCL11A-11947 | + | AAAAAUAGAGCGAGAGUGCACC | 22 | 14124 |
| BCL11A-11948 | + | AAAAAAUAGAGCGAGAGUGCACC | 23 | 14125 |
| BCL11A-11949 | + | AAAAAAAUAGAGCGAGAGUGCACC | 24 | 14126 |
| BCL11A-11950 | + | AAGGCCGAGCCAGGGACC | 18 | 14127 |
| BCL11A-11951 | + | CAAGGCCGAGCCAGGGACC | 19 | 14128 |
| BCL11A-10068 | + | CCAAGGCCGAGCCAGGGACC | 20 | 14129 |
| BCL11A-11952 | + | CCCAAGGCCGAGCCAGGGACC | 21 | 14130 |
| BCL11A-11953 | + | CCCCAAGGCCGAGCCAGGGACC | 22 | 14131 |
| BCL11A-11954 | + | CCCCCAAGGCCGAGCCAGGGACC | 23 | 14132 |
| BCL11A-11955 | + | GCCCCCAAGGCCGAGCCAGGGACC | 24 | 14133 |
| BCL11A-11956 | + | GCCUGGAAAGAGGGGACC | 18 | 14134 |
| BCL11A-11957 | + | GGCCUGGAAAGAGGGGACC | 19 | 14135 |
| BCL11A-10069 | + | CGGCCUGGAAAGAGGGGACC | 20 | 14136 |
| BCL11A-11958 | + | GCGGCCUGGAAAGAGGGGACC | 21 | 14137 |
| BCL11A-11959 | + | CGCGGCCUGGAAAGAGGGGACC | 22 | 14138 |
| BCL11A-11960 | + | GCGCGGCCUGGAAAGAGGGGACC | 23 | 14139 |
| BCL11A-11961 | + | CGCGCGGCCUGGAAAGAGGGGACC | 24 | 14140 |
| BCL11A-11962 | + | CCCGCUGCACACUUGACC | 18 | 14141 |
| BCL11A-11963 | + | UCCCGCUGCACACUUGACC | 19 | 14142 |
| BCL11A-11964 | + | CUCCCGCUGCACACUUGACC | 20 | 14143 |
| BCL11A-11965 | + | CCUCCCGCUGCACACUUGACC | 21 | 14144 |

TABLE 19E-continued

5th Tier

| gRNA Name | DNA Strand | Targeting Domain | Target Site Length | SEQ ID NO: |
|---|---|---|---|---|
| BCL11A-11966 | + | UCCUCCCGCUGCACACUUGACC | 22 | 14145 |
| BCL11A-11967 | + | UUCCUCCCGCUGCACACUUGACC | 23 | 14146 |
| BCL11A-11968 | + | UUUCCUCCCGCUGCACACUUGACC | 24 | 14147 |
| BCL11A-11969 | + | CGGCGCAGGCCGGGGCCC | 18 | 14148 |
| BCL11A-11970 | + | GCGGCGCAGGCCGGGGCCC | 19 | 14149 |
| BCL11A-11971 | + | GGCGGCGCAGGCCGGGGCCC | 20 | 14150 |
| BCL11A-11972 | + | AGGCGGCGCAGGCCGGGGCCC | 21 | 14151 |
| BCL11A-11973 | + | CAGGCGGCGCAGGCCGGGGCCC | 22 | 14152 |
| BCL11A-11974 | + | GCAGGCGGCGCAGGCCGGGGCCC | 23 | 14153 |
| BCL11A-11975 | + | GGCAGGCGGCGCAGGCCGGGGCCC | 24 | 14154 |
| BCL11A-11976 | + | GCUCGGGAAACUUUGCCC | 18 | 14155 |
| BCL11A-11977 | + | CGCUCGGGAAACUUUGCCC | 19 | 14156 |
| BCL11A-11978 | + | GCGCUCGGGAAACUUUGCCC | 20 | 14157 |
| BCL11A-11979 | + | UGCGCUCGGGAAACUUUGCCC | 21 | 14158 |
| BCL11A-11980 | + | CUGCGCUCGGGAAACUUUGCCC | 22 | 14159 |
| BCL11A-11981 | + | GCUGCGCUCGGGAAACUUUGCCC | 23 | 14160 |
| BCL11A-11982 | + | GGCUGCGCUCGGGAAACUUUGCCC | 24 | 14161 |
| BCL11A-11983 | + | UCUCACCUCUUUUCUCCC | 18 | 14162 |
| BCL11A-11984 | + | GUCUCACCUCUUUUCUCCC | 19 | 14163 |
| BCL11A-10081 | + | AGUCUCACCUCUUUUCUCCC | 20 | 14164 |
| BCL11A-11985 | + | CAGUCUCACCUCUUUUCUCCC | 21 | 14165 |
| BCL11A-11986 | + | CCAGUCUCACCUCUUUUCUCCC | 22 | 14166 |
| BCL11A-11987 | + | GCCAGUCUCACCUCUUUUCUCCC | 23 | 14167 |
| BCL11A-11988 | + | AGCCAGUCUCACCUCUUUUCUCCC | 24 | 14168 |
| BCL11A-11989 | + | GGGGCCGAAGUAAAAGCC | 18 | 14169 |
| BCL11A-11990 | + | AGGGGCCGAAGUAAAAGCC | 19 | 14170 |
| BCL11A-11991 | + | CAGGGGCCGAAGUAAAAGCC | 20 | 14171 |
| BCL11A-11992 | + | CCAGGGGCCGAAGUAAAAGCC | 21 | 14172 |
| BCL11A-11993 | + | GCCAGGGGCCGAAGUAAAAGCC | 22 | 14173 |
| BCL11A-11994 | + | CGCCAGGGGCCGAAGUAAAAGCC | 23 | 14174 |
| BCL11A-11995 | + | ACGCCAGGGGCCGAAGUAAAAGCC | 24 | 14175 |
| BCL11A-11996 | + | CACCGGGAGGCUGCAGCC | 18 | 14176 |
| BCL11A-11997 | + | GCACCGGGAGGCUGCAGCC | 19 | 14177 |
| BCL11A-11998 | + | UGCACCGGGAGGCUGCAGCC | 20 | 14178 |
| BCL11A-11999 | + | GUGCACCGGGAGGCUGCAGCC | 21 | 14179 |
| BCL11A-12000 | + | AGUGCACCGGGAGGCUGCAGCC | 22 | 14180 |
| BCL11A-12001 | + | GAGUGCACCGGGAGGCUGCAGCC | 23 | 14181 |

TABLE 19E-continued

5th Tier

| gRNA Name | DNA Strand | Targeting Domain | Target Site Length | SEQ ID NO: |
|---|---|---|---|---|
| BCL11A-12002 | + | AGAGUGCACCGGGAGGCUGCAGCC | 24 | 14182 |
| BCL11A-12003 | + | CGCCCCAAGGCCGAGCC | 18 | 14183 |
| BCL11A-12004 | + | GCGCCCCAAGGCCGAGCC | 19 | 14184 |
| BCL11A-10085 | + | GGCGCCCCAAGGCCGAGCC | 20 | 14185 |
| BCL11A-12005 | + | GGGCGCCCCAAGGCCGAGCC | 21 | 14186 |
| BCL11A-12006 | + | AGGGCGCCCCAAGGCCGAGCC | 22 | 14187 |
| BCL11A-12007 | + | GAGGGCGCCCCAAGGCCGAGCC | 23 | 14188 |
| BCL11A-12008 | + | CGAGGGCGCCCCAAGGCCGAGCC | 24 | 14189 |
| BCL11A-12009 | + | UCCCCGCGUGUGGACGCC | 18 | 14190 |
| BCL11A-12010 | + | CUCCCCGCGUGUGGACGCC | 19 | 14191 |
| BCL11A-10086 | + | GCUCCCCGCGUGUGGACGCC | 20 | 14192 |
| BCL11A-12011 | + | CGCUCCCCGCGUGUGGACGCC | 21 | 14193 |
| BCL11A-12012 | + | UCGCUCCCCGCGUGUGGACGCC | 22 | 14194 |
| BCL11A-12013 | + | CUCGCUCCCCGCGUGUGGACGCC | 23 | 14195 |
| BCL11A-12014 | + | GCUCGCUCCCCGCGUGUGGACGCC | 24 | 14196 |
| BCL11A-12015 | + | CGCGGACUCAGGAGCGCC | 18 | 14197 |
| BCL11A-12016 | + | CCGCGGACUCAGGAGCGCC | 19 | 14198 |
| BCL11A-10087 | + | UCCGCGGACUCAGGAGCGCC | 20 | 14199 |
| BCL11A-12017 | + | CUCCGCGGACUCAGGAGCGCC | 21 | 14200 |
| BCL11A-12018 | + | ACUCCGCGGACUCAGGAGCGCC | 22 | 14201 |
| BCL11A-12019 | + | GACUCCGCGGACUCAGGAGCGCC | 23 | 14202 |
| BCL11A-12020 | + | CGACUCCGCGGACUCAGGAGCGCC | 24 | 14203 |
| BCL11A-12021 | + | CCAGGAGCCCGCGCGGCC | 18 | 14204 |
| BCL11A-12022 | + | UCCAGGAGCCCGCGCGGCC | 19 | 14205 |
| BCL11A-10089 | + | CUCCAGGAGCCCGCGCGGCC | 20 | 14206 |
| BCL11A-12023 | + | UCUCCAGGAGCCCGCGCGGCC | 21 | 14207 |
| BCL11A-12024 | + | GUCUCCAGGAGCCCGCGCGGCC | 22 | 14208 |
| BCL11A-12025 | + | AGUCUCCAGGAGCCCGCGCGGCC | 23 | 14209 |
| BCL11A-12026 | + | AAGUCUCCAGGAGCCCGCGCGGCC | 24 | 14210 |
| BCL11A-12027 | + | GGCCCCUCUCCCGACUCC | 18 | 14211 |
| BCL11A-12028 | + | CGGCCCCUCUCCCGACUCC | 19 | 14212 |
| BCL11A-12029 | + | GCGGCCCCUCUCCCGACUCC | 20 | 14213 |
| BCL11A-12030 | + | CGCGGCCCCUCUCCCGACUCC | 21 | 14214 |
| BCL11A-12031 | + | CCGCGGCCCCUCUCCCGACUCC | 22 | 14215 |
| BCL11A-12032 | + | GCCGCGGCCCCUCUCCCGACUCC | 23 | 14216 |
| BCL11A-12033 | + | CGCCGCGGCCCCUCUCCCGACUCC | 24 | 14217 |
| BCL11A-12034 | + | GGCAGCGCCCAAGUCUCC | 18 | 14218 |

TABLE 19E-continued

5th Tier

| gRNA Name | DNA Strand | Targeting Domain | Target Site Length | SEQ ID NO: |
|---|---|---|---|---|
| BCL11A-12035 | + | GGGCAGCGCCCAAGUCUCC | 19 | 14219 |
| BCL11A-10093 | + | AGGGCAGCGCCCAAGUCUCC | 20 | 14220 |
| BCL11A-12036 | + | AAGGGCAGCGCCCAAGUCUCC | 21 | 14221 |
| BCL11A-12037 | + | GAAGGGCAGCGCCCAAGUCUCC | 22 | 14222 |
| BCL11A-12038 | + | GGAAGGGCAGCGCCCAAGUCUCC | 23 | 14223 |
| BCL11A-12039 | + | CGGAAGGGCAGCGCCCAAGUCUCC | 24 | 14224 |
| BCL11A-12040 | + | GUCUCACCUCUUUUCUCC | 18 | 14225 |
| BCL11A-12041 | + | AGUCUCACCUCUUUUCUCC | 19 | 14226 |
| BCL11A-12042 | + | CAGUCUCACCUCUUUUCUCC | 20 | 14227 |
| BCL11A-12043 | + | CCAGUCUCACCUCUUUUCUCC | 21 | 14228 |
| BCL11A-12044 | + | GCCAGUCUCACCUCUUUUCUCC | 22 | 14229 |
| BCL11A-12045 | + | AGCCAGUCUCACCUCUUUUCUCC | 23 | 14230 |
| BCL11A-12046 | + | AAGCCAGUCUCACCUCUUUUCUCC | 24 | 14231 |
| BCL11A-12047 | + | CGGCGCGGGAGGGCAAGC | 18 | 14232 |
| BCL11A-12048 | + | GCGGCGCGGGAGGGCAAGC | 19 | 14233 |
| BCL11A-12049 | + | GGCGGCGCGGGAGGGCAAGC | 20 | 14234 |
| BCL11A-12050 | + | GCCCCGGGCUGGGGAAGC | 18 | 14235 |
| BCL11A-12051 | + | AGCCCCGGGCUGGGGAAGC | 19 | 14236 |
| BCL11A-12052 | + | CAGCCCCGGGCUGGGGAAGC | 20 | 14237 |
| BCL11A-12053 | + | GCAGCCCCGGGCUGGGGAAGC | 21 | 14238 |
| BCL11A-12054 | + | UGCAGCCCCGGGCUGGGGAAGC | 22 | 14239 |
| BCL11A-12055 | + | CUGCAGCCCCGGGCUGGGGAAGC | 23 | 14240 |
| BCL11A-12056 | + | GCUGCAGCCCCGGGCUGGGGAAGC | 24 | 14241 |
| BCL11A-12057 | + | GCGCCCCCAAGGCCGAGC | 18 | 14242 |
| BCL11A-12058 | + | GGCGCCCCCAAGGCCGAGC | 19 | 14243 |
| BCL11A-12059 | + | GGGCGCCCCCAAGGCCGAGC | 20 | 14244 |
| BCL11A-12060 | + | AGGGCGCCCCCAAGGCCGAGC | 21 | 14245 |
| BCL11A-12061 | + | GAGGGCGCCCCCAAGGCCGAGC | 22 | 14246 |
| BCL11A-12062 | + | CGAGGGCGCCCCCAAGGCCGAGC | 23 | 14247 |
| BCL11A-12063 | + | CCGAGGGCGCCCCCAAGGCCGAGC | 24 | 14248 |
| BCL11A-12064 | + | CUCCCCGCGUGUGGACGC | 18 | 14249 |
| BCL11A-12065 | + | GCUCCCCGCGUGUGGACGC | 19 | 14250 |
| BCL11A-12066 | + | CGCUCCCCGCGUGUGGACGC | 20 | 14251 |
| BCL11A-12067 | + | UCGCUCCCCGCGUGUGGACGC | 21 | 14252 |
| BCL11A-12068 | + | CUCGCUCCCCGCGUGUGGACGC | 22 | 14253 |
| BCL11A-12069 | + | GCUCGCUCCCCGCGUGUGGACGC | 23 | 14254 |
| BCL11A-12070 | + | CGCUCGCUCCCCGCGUGUGGACGC | 24 | 14255 |

TABLE 19E-continued

5th Tier

| gRNA Name | DNA Strand | Targeting Domain | Target Site Length | SEQ ID NO: |
|---|---|---|---|---|
| BCL11A-12071 | + | GCGCGGGAGGGCAAGCGC | 18 | 14256 |
| BCL11A-12072 | + | GGCGCGGGAGGGCAAGCGC | 19 | 14257 |
| BCL11A-12073 | + | CGGCGCGGGAGGGCAAGCGC | 20 | 14258 |
| BCL11A-12074 | + | CCGCGGACUCAGGAGCGC | 18 | 14259 |
| BCL11A-12075 | + | UCCGCGGACUCAGGAGCGC | 19 | 14260 |
| BCL11A-10106 | + | CUCCGCGGACUCAGGAGCGC | 20 | 14261 |
| BCL11A-12076 | + | ACUCCGCGGACUCAGGAGCGC | 21 | 14262 |
| BCL11A-12077 | + | GACUCCGCGGACUCAGGAGCGC | 22 | 14263 |
| BCL11A-12078 | + | CGACUCCGCGGACUCAGGAGCGC | 23 | 14264 |
| BCL11A-12079 | + | CCGACUCCGCGGACUCAGGAGCGC | 24 | 14265 |
| BCL11A-12080 | + | CCGAGCCCGCGGCUGCGC | 18 | 14266 |
| BCL11A-12081 | + | CCCGAGCCCGCGGCUGCGC | 19 | 14267 |
| BCL11A-12082 | + | CCCCGAGCCCGCGGCUGCGC | 20 | 14268 |
| BCL11A-12083 | + | GCCCCGAGCCCGCGGCUGCGC | 21 | 14269 |
| BCL11A-12084 | + | AGCCCCGAGCCCGCGGCUGCGC | 22 | 14270 |
| BCL11A-12085 | + | AAGCCCCGAGCCCGCGGCUGCGC | 23 | 14271 |
| BCL11A-12086 | + | AAAGCCCCGAGCCCGCGGCUGCGC | 24 | 14272 |
| BCL11A-12087 | + | GAGGCAGGCGGCGCAGGC | 18 | 14273 |
| BCL11A-12088 | + | AGAGGCAGGCGGCGCAGGC | 19 | 14274 |
| BCL11A-10110 | + | GAGAGGCAGGCGGCGCAGGC | 20 | 14275 |
| BCL11A-12089 | + | GGAGAGGCAGGCGGCGCAGGC | 21 | 14276 |
| BCL11A-12090 | + | GGGAGAGGCAGGCGGCGCAGGC | 22 | 14277 |
| BCL11A-12091 | + | GGGGAGAGGCAGGCGGCGCAGGC | 23 | 14278 |
| BCL11A-12092 | + | CGGGGAGAGGCAGGCGGCGCAGGC | 24 | 14279 |
| BCL11A-12093 | + | UCCAGGAGCCCGCGCGGC | 18 | 14280 |
| BCL11A-12094 | + | CUCCAGGAGCCCGCGCGGC | 19 | 14281 |
| BCL11A-12095 | + | UCUCCAGGAGCCCGCGCGGC | 20 | 14282 |
| BCL11A-12096 | + | GUCUCCAGGAGCCCGCGCGGC | 21 | 14283 |
| BCL11A-12097 | + | AGUCUCCAGGAGCCCGCGCGGC | 22 | 14284 |
| BCL11A-12098 | + | AAGUCUCCAGGAGCCCGCGCGGC | 23 | 14285 |
| BCL11A-12099 | + | CAAGUCUCCAGGAGCCCGCGCGGC | 24 | 14286 |
| BCL11A-12100 | + | GAGGCUGCAGCCCCGGGC | 18 | 14287 |
| BCL11A-12101 | + | GGAGGCUGCAGCCCCGGGC | 19 | 14288 |
| BCL11A-10115 | + | GGGAGGCUGCAGCCCCGGGC | 20 | 14289 |
| BCL11A-12102 | + | CGGGAGGCUGCAGCCCCGGGC | 21 | 14290 |
| BCL11A-12103 | + | CCGGGAGGCUGCAGCCCCGGGC | 22 | 14291 |
| BCL11A-12104 | + | ACCGGGAGGCUGCAGCCCCGGGC | 23 | 14292 |

TABLE 19E-continued

5th Tier

| gRNA Name | DNA Strand | Targeting Domain | Target Site Length | SEQ ID NO: |
|---|---|---|---|---|
| BCL11A-12105 | + | CACCGGGAGGCUGCAGCCCCGGGC | 24 | 14293 |
| BCL11A-12106 | + | UACAGCUCCGCAGCGGGC | 18 | 14294 |
| BCL11A-12107 | + | UUACAGCUCCGCAGCGGGC | 19 | 14295 |
| BCL11A-12108 | + | GUUACAGCUCCGCAGCGGGC | 20 | 14296 |
| BCL11A-12109 | + | AGUUACAGCUCCGCAGCGGGC | 21 | 14297 |
| BCL11A-12110 | + | AAGUUACAGCUCCGCAGCGGGC | 22 | 14298 |
| BCL11A-12111 | + | CAAGUUACAGCUCCGCAGCGGGC | 23 | 14299 |
| BCL11A-12112 | + | CCAAGUUACAGCUCCGCAGCGGGC | 24 | 14300 |
| BCL11A-12113 | + | GGCGGCGCAGGCCGGGGC | 18 | 14301 |
| BCL11A-12114 | + | AGGCGGCGCAGGCCGGGGC | 19 | 14302 |
| BCL11A-12115 | + | CAGGCGGCGCAGGCCGGGGC | 20 | 14303 |
| BCL11A-12116 | + | GCAGGCGGCGCAGGCCGGGGC | 21 | 14304 |
| BCL11A-12117 | + | GGCAGGCGGCGCAGGCCGGGGC | 22 | 14305 |
| BCL11A-12118 | + | AGGCAGGCGGCGCAGGCCGGGGC | 23 | 14306 |
| BCL11A-12119 | + | GAGGCAGGCGGCGCAGGCCGGGGC | 24 | 14307 |
| BCL11A-12120 | + | UUGCAAAACUGGCGGGGC | 18 | 14308 |
| BCL11A-12121 | + | UUUGCAAAACUGGCGGGGC | 19 | 14309 |
| BCL11A-10116 | + | UUUUGCAAAACUGGCGGGGC | 20 | 14310 |
| BCL11A-12122 | + | AUUUUGCAAAACUGGCGGGGC | 21 | 14311 |
| BCL11A-12123 | + | UAUUUUGCAAAACUGGCGGGGC | 22 | 14312 |
| BCL11A-12124 | + | UUAUUUUGCAAAACUGGCGGGGC | 23 | 14313 |
| BCL11A-12125 | + | AUUAUUUUGCAAAACUGGCGGGGC | 24 | 14314 |
| BCL11A-12126 | + | CAAACACCCACCUCUGGC | 18 | 14315 |
| BCL11A-12127 | + | ACAAACACCCACCUCUGGC | 19 | 14316 |
| BCL11A-10118 | + | GACAAACACCCACCUCUGGC | 20 | 14317 |
| BCL11A-12128 | + | GGACAAACACCCACCUCUGGC | 21 | 14318 |
| BCL11A-12129 | + | GGGACAAACACCCACCUCUGGC | 22 | 14319 |
| BCL11A-12130 | + | CGGGACAAACACCCACCUCUGGC | 23 | 14320 |
| BCL11A-12131 | + | GCGGGACAAACACCCACCUCUGGC | 24 | 14321 |
| BCL11A-12132 | + | GCGCUCGGGAAACUUUGC | 18 | 14322 |
| BCL11A-12133 | + | UGCGCUCGGGAAACUUUGC | 19 | 14323 |
| BCL11A-12134 | + | CUGCGCUCGGGAAACUUUGC | 20 | 14324 |
| BCL11A-12135 | + | GCUGCGCUCGGGAAACUUUGC | 21 | 14325 |
| BCL11A-12136 | + | GGCUGCGCUCGGGAAACUUUGC | 22 | 14326 |
| BCL11A-12137 | + | CGGCUGCGCUCGGGAAACUUUGC | 23 | 14327 |
| BCL11A-12138 | + | GCGGCUGCGCUCGGGAAACUUUGC | 24 | 14328 |
| BCL11A-12139 | + | UCCCGACUCCGCGGACUC | 18 | 14329 |

TABLE 19E-continued

5th Tier

| gRNA Name | DNA Strand | Targeting Domain | Target Site Length | SEQ ID NO: |
|---|---|---|---|---|
| BCL11A-12140 | + | CUCCCGACUCCGCGGACUC | 19 | 14330 |
| BCL11A-10122 | + | UCUCCCGACUCCGCGGACUC | 20 | 14331 |
| BCL11A-12141 | + | CUCUCCCGACUCCGCGGACUC | 21 | 14332 |
| BCL11A-12142 | + | CCUCUCCCGACUCCGCGGACUC | 22 | 14333 |
| BCL11A-12143 | + | CCCUCUCCCGACUCCGCGGACUC | 23 | 14334 |
| BCL11A-12144 | + | CCCCUCUCCCGACUCCGCGGACUC | 24 | 14335 |
| BCL11A-12145 | + | GAGCCCGCGGCUGCGCUC | 18 | 14336 |
| BCL11A-12146 | + | CGAGCCCGCGGCUGCGCUC | 19 | 14337 |
| BCL11A-10126 | + | CCGAGCCCGCGGCUGCGCUC | 20 | 14338 |
| BCL11A-12147 | + | CCCGAGCCCGCGGCUGCGCUC | 21 | 14339 |
| BCL11A-12148 | + | CCCCGAGCCCGCGGCUGCGCUC | 22 | 14340 |
| BCL11A-12149 | + | GCCCCGAGCCCGCGGCUGCGCUC | 23 | 14341 |
| BCL11A-12150 | + | AGCCCCGAGCCCGCGGCUGCGCUC | 24 | 14342 |
| BCL11A-12151 | + | AGCCAGGUAGAGUUGCUC | 18 | 14343 |
| BCL11A-12152 | + | AAGCCAGGUAGAGUUGCUC | 19 | 14344 |
| BCL11A-12153 | + | GAAGCCAGGUAGAGUUGCUC | 20 | 14345 |
| BCL11A-12154 | + | GGAAGCCAGGUAGAGUUGCUC | 21 | 14346 |
| BCL11A-12155 | + | GGGAAGCCAGGUAGAGUUGCUC | 22 | 14347 |
| BCL11A-12156 | + | AGGGAAGCCAGGUAGAGUUGCUC | 23 | 14348 |
| BCL11A-12157 | + | GAGGGAAGCCAGGUAGAGUUGCUC | 24 | 14349 |
| BCL11A-12158 | + | GGGCAGCGCCCAAGUCUC | 18 | 14350 |
| BCL11A-12159 | + | AGGGCAGCGCCCAAGUCUC | 19 | 14351 |
| BCL11A-12160 | + | AAGGGCAGCGCCCAAGUCUC | 20 | 14352 |
| BCL11A-12161 | + | GAAGGGCAGCGCCCAAGUCUC | 21 | 14353 |
| BCL11A-12162 | + | GGAAGGGCAGCGCCCAAGUCUC | 22 | 14354 |
| BCL11A-12163 | + | CGGAAGGGCAGCGCCCAAGUCUC | 23 | 14355 |
| BCL11A-12164 | + | CCGGAAGGGCAGCGCCCAAGUCUC | 24 | 14356 |
| BCL11A-12165 | + | UUUGGAGGGCUGCGGGUC | 18 | 14357 |
| BCL11A-12166 | + | GUUUGGAGGGCUGCGGGUC | 19 | 14358 |
| BCL11A-10129 | + | AGUUUGGAGGGCUGCGGGUC | 20 | 14359 |
| BCL11A-12167 | + | AAGUUUGGAGGGCUGCGGGUC | 21 | 14360 |
| BCL11A-12168 | + | UAAGUUUGGAGGGCUGCGGGUC | 22 | 14361 |
| BCL11A-12169 | + | CUAAGUUUGGAGGGCUGCGGGUC | 23 | 14362 |
| BCL11A-12170 | + | CCUAAGUUUGGAGGGCUGCGGGUC | 24 | 14363 |
| BCL11A-12171 | + | CGGCGGAAAGGAGGAAAG | 18 | 14364 |
| BCL11A-12172 | + | GCGGCGGAAAGGAGGAAAG | 19 | 14365 |
| BCL11A-10136 | + | AGCGGCGGAAAGGAGGAAAG | 20 | 14366 |

TABLE 19E-continued

5th Tier

| gRNA Name | DNA Strand | Targeting Domain | Target Site Length | SEQ ID NO: |
|---|---|---|---|---|
| BCL11A-12173 | + | AAGCGGCGGAAAGGAGGAAAG | 21 | 14367 |
| BCL11A-12174 | + | AAAGCGGCGGAAAGGAGGAAAG | 22 | 14368 |
| BCL11A-12175 | + | UAAAGCGGCGGAAAGGAGGAAAG | 23 | 14369 |
| BCL11A-12176 | + | AUAAAGCGGCGGAAAGGAGGAAAG | 24 | 14370 |
| BCL11A-12177 | + | AAAUAAAGCGGCGGAAAG | 18 | 14371 |
| BCL11A-12178 | + | GAAAUAAAGCGGCGGAAAG | 19 | 14372 |
| BCL11A-12179 | + | AGAAAUAAAGCGGCGGAAAG | 20 | 14373 |
| BCL11A-12180 | + | GAGAAAUAAAGCGGCGGAAAG | 21 | 14374 |
| BCL11A-12181 | + | AGAGAAAUAAAGCGGCGGAAAG | 22 | 14375 |
| BCL11A-12182 | + | AAGAGAAAUAAAGCGGCGGAAAG | 23 | 14376 |
| BCL11A-12183 | + | AAAGAGAAAUAAAGCGGCGGAAAG | 24 | 14377 |
| BCL11A-12184 | + | CCCGCGCGGCCUGGAAAG | 18 | 14378 |
| BCL11A-12185 | + | GCCCGCGCGGCCUGGAAAG | 19 | 14379 |
| BCL11A-10137 | + | AGCCCGCGCGGCCUGGAAAG | 20 | 14380 |
| BCL11A-12186 | + | GAGCCCGCGCGGCCUGGAAAG | 21 | 14381 |
| BCL11A-12187 | + | GGAGCCCGCGCGGCCUGGAAAG | 22 | 14382 |
| BCL11A-12188 | + | AGGAGCCCGCGCGGCCUGGAAAG | 23 | 14383 |
| BCL11A-12189 | + | CAGGAGCCCGCGCGGCCUGGAAAG | 24 | 14384 |
| BCL11A-12190 | + | AAGAAAAAUCACCCGAAG | 18 | 14385 |
| BCL11A-12191 | + | AAAGAAAAAUCACCCGAAG | 19 | 14386 |
| BCL11A-12192 | + | CAAAGAAAAAUCACCCGAAG | 20 | 14387 |
| BCL11A-12193 | + | GCAAAGAAAAAUCACCCGAAG | 21 | 14388 |
| BCL11A-12194 | + | AGCAAAGAAAAAUCACCCGAAG | 22 | 14389 |
| BCL11A-12195 | + | CAGCAAAGAAAAAUCACCCGAAG | 23 | 14390 |
| BCL11A-12196 | + | ACAGCAAAGAAAAAUCACCCGAAG | 24 | 14391 |
| BCL11A-12197 | + | AGCCGGCACAAAAGGCAG | 18 | 14392 |
| BCL11A-12198 | + | GAGCCGGCACAAAAGGCAG | 19 | 14393 |
| BCL11A-10144 | + | GGAGCCGGCACAAAAGGCAG | 20 | 14394 |
| BCL11A-12199 | + | AGGAGCCGGCACAAAAGGCAG | 21 | 14395 |
| BCL11A-12200 | + | GAGGAGCCGGCACAAAAGGCAG | 22 | 14396 |
| BCL11A-12201 | + | CGAGGAGCCGGCACAAAAGGCAG | 23 | 14397 |
| BCL11A-12202 | + | GCGAGGAGCCGGCACAAAAGGCAG | 24 | 14398 |
| BCL11A-12203 | + | GCGGAAAGGAGGAAAGAG | 18 | 14399 |
| BCL11A-12204 | + | GGCGGAAAGGAGGAAAGAG | 19 | 14400 |
| BCL11A-12205 | + | CGGCGGAAAGGAGGAAAGAG | 20 | 14401 |
| BCL11A-12206 | + | GCGGCGGAAAGGAGGAAAGAG | 21 | 14402 |
| BCL11A-12207 | + | AGCGGCGGAAAGGAGGAAAGAG | 22 | 14403 |

TABLE 19E-continued

5th Tier

| gRNA Name | DNA Strand | Targeting Domain | Target Site Length | SEQ ID NO: |
|---|---|---|---|---|
| BCL11A-12208 | + | AAGCGGCGGAAAGGAGGAAAGAG | 23 | 14404 |
| BCL11A-12209 | + | AAAGCGGCGGAAAGGAGGAAAGAG | 24 | 14405 |
| BCL11A-12210 | + | AUCACCCGAAGUUGAGAG | 18 | 14406 |
| BCL11A-12211 | + | AAUCACCCGAAGUUGAGAG | 19 | 14407 |
| BCL11A-12212 | + | AAAUCACCCGAAGUUGAGAG | 20 | 14408 |
| BCL11A-12213 | + | AAAAUCACCCGAAGUUGAGAG | 21 | 14409 |
| BCL11A-12214 | + | AAAAAUCACCCGAAGUUGAGAG | 22 | 14410 |
| BCL11A-12215 | + | GAAAAAUCACCCGAAGUUGAGAG | 23 | 14411 |
| BCL11A-12216 | + | AGAAAAAUCACCCGAAGUUGAGAG | 24 | 14412 |
| BCL11A-12217 | + | CGGGAAACUUUGCCCGAG | 18 | 14413 |
| BCL11A-12218 | + | UCGGGAAACUUUGCCCGAG | 19 | 14414 |
| BCL11A-12219 | + | CUCGGGAAACUUUGCCCGAG | 20 | 14415 |
| BCL11A-12220 | + | GCUCGGGAAACUUUGCCCGAG | 21 | 14416 |
| BCL11A-12221 | + | CGCUCGGGAAACUUUGCCCGAG | 22 | 14417 |
| BCL11A-12222 | + | GCGCUCGGGAAACUUUGCCCGAG | 23 | 14418 |
| BCL11A-12223 | + | UGCGCUCGGGAAACUUUGCCCGAG | 24 | 14419 |
| BCL11A-12224 | + | AGCUCCGCAGCGGGCGAG | 18 | 14420 |
| BCL11A-12225 | + | CAGCUCCGCAGCGGGCGAG | 19 | 14421 |
| BCL11A-10148 | + | ACAGCUCCGCAGCGGGCGAG | 20 | 14422 |
| BCL11A-12226 | + | UACAGCUCCGCAGCGGGCGAG | 21 | 14423 |
| BCL11A-12227 | + | UUACAGCUCCGCAGCGGGCGAG | 22 | 14424 |
| BCL11A-12228 | + | GUUACAGCUCCGCAGCGGGCGAG | 23 | 14425 |
| BCL11A-12229 | + | AGUUACAGCUCCGCAGCGGGCGAG | 24 | 14426 |
| BCL11A-12230 | + | CGCAGCGGGCGAGGGGAG | 18 | 14427 |
| BCL11A-12231 | + | CCGCAGCGGGCGAGGGGAG | 19 | 14428 |
| BCL11A-12232 | + | UCCGCAGCGGGCGAGGGGAG | 20 | 14429 |
| BCL11A-12233 | + | CUCCGCAGCGGGCGAGGGGAG | 21 | 14430 |
| BCL11A-12234 | + | GCUCCGCAGCGGGCGAGGGGAG | 22 | 14431 |
| BCL11A-12235 | + | AGCUCCGCAGCGGGCGAGGGGAG | 23 | 14432 |
| BCL11A-12236 | + | CAGCUCCGCAGCGGGCGAGGGGAG | 24 | 14433 |
| BCL11A-12237 | + | CCAUUUUCUUACGGUGAG | 18 | 14434 |
| BCL11A-12238 | + | CCCAUUUUCUUACGGUGAG | 19 | 14435 |
| BCL11A-10154 | + | CCCCAUUUUCUUACGGUGAG | 20 | 14436 |
| BCL11A-12239 | + | CCCCCAUUUUCUUACGGUGAG | 21 | 14437 |
| BCL11A-12240 | + | CCCCCCAUUUUCUUACGGUGAG | 22 | 14438 |
| BCL11A-12241 | + | CCCCCCCAUUUUCUUACGGUGAG | 23 | 14439 |
| BCL11A-12242 | + | ACCCCCCCAUUUUCUUACGGUGAG | 24 | 14440 |

TABLE 19E-continued

5th Tier

| gRNA Name | DNA Strand | Targeting Domain | Target Site Length | SEQ ID NO: |
|---|---|---|---|---|
| BCL11A-12243 | + | CCUGGAAAGAGGGGACCG | 18 | 14441 |
| BCL11A-12244 | + | GCCUGGAAAGAGGGGACCG | 19 | 14442 |
| BCL11A-10159 | + | GGCCUGGAAAGAGGGGACCG | 20 | 14443 |
| BCL11A-12245 | + | CGGCCUGGAAAGAGGGGACCG | 21 | 14444 |
| BCL11A-12246 | + | GCGGCCUGGAAAGAGGGGACCG | 22 | 14445 |
| BCL11A-12247 | + | CGCGGCCUGGAAAGAGGGGACCG | 23 | 14446 |
| BCL11A-12248 | + | GCGCGGCCUGGAAAGAGGGGACCG | 24 | 14447 |
| BCL11A-12249 | + | CUCGGGAAACUUUGCCCG | 18 | 14448 |
| BCL11A-12250 | + | GCUCGGGAAACUUUGCCCG | 19 | 14449 |
| BCL11A-10163 | + | CGCUCGGGAAACUUUGCCCG | 20 | 14450 |
| BCL11A-12251 | + | GCGCUCGGGAAACUUUGCCCG | 21 | 14451 |
| BCL11A-12252 | + | UGCGCUCGGGAAACUUUGCCCG | 22 | 14452 |
| BCL11A-12253 | + | CUGCGCUCGGGAAACUUUGCCCG | 23 | 14453 |
| BCL11A-12254 | + | GCUGCGCUCGGGAAACUUUGCCCG | 24 | 14454 |
| BCL11A-12255 | + | GAAAAGAGAAAUAAAGCG | 18 | 14455 |
| BCL11A-12256 | + | CGAAAAGAGAAAUAAAGCG | 19 | 14456 |
| BCL11A-12257 | + | UCGAAAAGAGAAAUAAAGCG | 20 | 14457 |
| BCL11A-12258 | + | UUCGAAAAGAGAAAUAAAGCG | 21 | 14458 |
| BCL11A-12259 | + | UUUCGAAAAGAGAAAUAAAGCG | 22 | 14459 |
| BCL11A-12260 | + | UUUUCGAAAAGAGAAAUAAAGCG | 23 | 14460 |
| BCL11A-12261 | + | CUUUUCGAAAAGAGAAAUAAAGCG | 24 | 14461 |
| BCL11A-12262 | + | UCCGCGGACUCAGGAGCG | 18 | 14462 |
| BCL11A-12263 | + | CUCCGCGGACUCAGGAGCG | 19 | 14463 |
| BCL11A-12264 | + | ACUCCGCGGACUCAGGAGCG | 20 | 14464 |
| BCL11A-12265 | + | GACUCCGCGGACUCAGGAGCG | 21 | 14465 |
| BCL11A-12266 | + | CGACUCCGCGGACUCAGGAGCG | 22 | 14466 |
| BCL11A-12267 | + | CCGACUCCGCGGACUCAGGAGCG | 23 | 14467 |
| BCL11A-12268 | + | CCCGACUCCGCGGACUCAGGAGCG | 24 | 14468 |
| BCL11A-12269 | + | CGCGGGAGGGCAAGCGCG | 18 | 14469 |
| BCL11A-12270 | + | GCGCGGGAGGGCAAGCGCG | 19 | 14470 |
| BCL11A-10178 | + | GGCGCGGGAGGGCAAGCGCG | 20 | 14471 |
| BCL11A-12271 | + | ACAGCUCCGCAGCGGGCG | 18 | 14472 |
| BCL11A-12272 | + | UACAGCUCCGCAGCGGGCG | 19 | 14473 |
| BCL11A-10180 | + | UUACAGCUCCGCAGCGGGCG | 20 | 14474 |
| BCL11A-12273 | + | GUUACAGCUCCGCAGCGGGCG | 21 | 14475 |
| BCL11A-12274 | + | AGUUACAGCUCCGCAGCGGGCG | 22 | 14476 |
| BCL11A-12275 | + | AAGUUACAGCUCCGCAGCGGGCG | 23 | 14477 |

TABLE 19E-continued

5th Tier

| gRNA Name | DNA Strand | Targeting Domain | Target Site Length | SEQ ID NO: |
|---|---|---|---|---|
| BCL11A-12276 | + | CAAGUUACAGCUCCGCAGCGGGCG | 24 | 14478 |
| BCL11A-12277 | + | GCUGGGGAAGCGCGGGCG | 18 | 14479 |
| BCL11A-12278 | + | GGCUGGGGAAGCGCGGGCG | 19 | 14480 |
| BCL11A-12279 | + | GGGCUGGGGAAGCGCGGGCG | 20 | 14481 |
| BCL11A-12280 | + | CGGGCUGGGGAAGCGCGGGCG | 21 | 14482 |
| BCL11A-12281 | + | CCGGGCUGGGGAAGCGCGGGCG | 22 | 14483 |
| BCL11A-12282 | + | CCCGGGCUGGGGAAGCGCGGGCG | 23 | 14484 |
| BCL11A-12283 | + | CCCCGGGCUGGGGAAGCGCGGGCG | 24 | 14485 |
| BCL11A-12284 | + | UGCAAAACUGGCGGGGCG | 18 | 14486 |
| BCL11A-12285 | + | UUGCAAAACUGGCGGGGCG | 19 | 14487 |
| BCL11A-10181 | + | UUUGCAAAACUGGCGGGGCG | 20 | 14488 |
| BCL11A-12286 | + | UUUUGCAAAACUGGCGGGGCG | 21 | 14489 |
| BCL11A-12287 | + | AUUUUGCAAAACUGGCGGGGCG | 22 | 14490 |
| BCL11A-12288 | + | UAUUUUGCAAAACUGGCGGGGCG | 23 | 14491 |
| BCL11A-12289 | + | UUAUUUUGCAAAACUGGCGGGGCG | 24 | 14492 |
| BCL11A-12290 | + | AAUAAAGCGGCGGAAAGG | 18 | 14493 |
| BCL11A-12291 | + | AAAUAAAGCGGCGGAAAGG | 19 | 14494 |
| BCL11A-10185 | + | GAAAUAAAGCGGCGGAAAGG | 20 | 14495 |
| BCL11A-12292 | + | AGAAAUAAAGCGGCGGAAAGG | 21 | 14496 |
| BCL11A-12293 | + | GAGAAAUAAAGCGGCGGAAAGG | 22 | 14497 |
| BCL11A-12294 | + | AGAGAAAUAAAGCGGCGGAAAGG | 23 | 14498 |
| BCL11A-12295 | + | AAGAGAAAUAAAGCGGCGGAAAGG | 24 | 14499 |
| BCL11A-12296 | + | CCGAGGGCGCCCCCAAGG | 18 | 14500 |
| BCL11A-12297 | + | CCCGAGGGCGCCCCCAAGG | 19 | 14501 |
| BCL11A-12298 | + | GCCCGAGGGCGCCCCCAAGG | 20 | 14502 |
| BCL11A-12299 | + | GGCCCGAGGGCGCCCCCAAGG | 21 | 14503 |
| BCL11A-12300 | + | GGGCCCGAGGGCGCCCCCAAGG | 22 | 14504 |
| BCL11A-12301 | + | GGGGCCCGAGGGCGCCCCCAAGG | 23 | 14505 |
| BCL11A-12302 | + | CGGGGCCCGAGGGCGCCCCCAAGG | 24 | 14506 |
| BCL11A-12303 | + | AGAGGCAGGCGGCGCAGG | 18 | 14507 |
| BCL11A-12304 | + | GAGAGGCAGGCGGCGCAGG | 19 | 14508 |
| BCL11A-12305 | + | GGAGAGGCAGGCGGCGCAGG | 20 | 14509 |
| BCL11A-12306 | + | GGGAGAGGCAGGCGGCGCAGG | 21 | 14510 |
| BCL11A-12307 | + | GGGGAGAGGCAGGCGGCGCAGG | 22 | 14511 |
| BCL11A-12308 | + | CGGGGAGAGGCAGGCGGCGCAGG | 23 | 14512 |
| BCL11A-12309 | + | CCGGGGAGAGGCAGGCGGCGCAGG | 24 | 14513 |
| BCL11A-12310 | + | GCAGCGGGCGAGGGGAGG | 18 | 14514 |

TABLE 19E-continued

5th Tier

| gRNA Name | DNA Strand | Targeting Domain | Target Site Length | SEQ ID NO: |
|---|---|---|---|---|
| BCL11A-12311 | + | CGCAGCGGGCGAGGGGAGG | 19 | 14515 |
| BCL11A-10190 | + | CCGCAGCGGGCGAGGGGAGG | 20 | 14516 |
| BCL11A-12312 | + | UCCGCAGCGGGCGAGGGGAGG | 21 | 14517 |
| BCL11A-12313 | + | CUCCGCAGCGGGCGAGGGGAGG | 22 | 14518 |
| BCL11A-12314 | + | GCUCCGCAGCGGGCGAGGGGAGG | 23 | 14519 |
| BCL11A-12315 | + | AGCUCCGCAGCGGGCGAGGGGAGG | 24 | 14520 |
| BCL11A-12316 | + | GGAGGGCUGCGGGUCCGG | 18 | 14521 |
| BCL11A-12317 | + | UGGAGGGCUGCGGGUCCGG | 19 | 14522 |
| BCL11A-12318 | + | UUGGAGGGCUGCGGGUCCGG | 20 | 14523 |
| BCL11A-12319 | + | UUUGGAGGGCUGCGGGUCCGG | 21 | 14524 |
| BCL11A-12320 | + | GUUUGGAGGGCUGCGGGUCCGG | 22 | 14525 |
| BCL11A-12321 | + | AGUUUGGAGGGCUGCGGGUCCGG | 23 | 14526 |
| BCL11A-12322 | + | AAGUUUGGAGGGCUGCGGGUCCGG | 24 | 14527 |
| BCL11A-12323 | + | AAAAGAGAAAUAAAGCGG | 18 | 14528 |
| BCL11A-12324 | + | GAAAAGAGAAAUAAAGCGG | 19 | 14529 |
| BCL11A-10193 | + | CGAAAAGAGAAAUAAAGCGG | 20 | 14530 |
| BCL11A-12325 | + | UCGAAAAGAGAAAUAAAGCGG | 21 | 14531 |
| BCL11A-12326 | + | UUCGAAAAGAGAAAUAAAGCGG | 22 | 14532 |
| BCL11A-12327 | + | UUUCGAAAAGAGAAAUAAAGCGG | 23 | 14533 |
| BCL11A-12328 | + | UUUUCGAAAAGAGAAAUAAAGCGG | 24 | 14534 |
| BCL11A-12329 | + | GUUACAGCUCCGCAGCGG | 18 | 14535 |
| BCL11A-12330 | + | AGUUACAGCUCCGCAGCGG | 19 | 14536 |
| BCL11A-12331 | + | AAGUUACAGCUCCGCAGCGG | 20 | 14537 |
| BCL11A-12332 | + | CAAGUUACAGCUCCGCAGCGG | 21 | 14538 |
| BCL11A-12333 | + | CCAAGUUACAGCUCCGCAGCGG | 22 | 14539 |
| BCL11A-12334 | + | UCCAAGUUACAGCUCCGCAGCGG | 23 | 14540 |
| BCL11A-12335 | + | CUCCAAGUUACAGCUCCGCAGCGG | 24 | 14541 |
| BCL11A-12336 | + | CGGGCUGGGGAAGCGCGG | 18 | 14542 |
| BCL11A-12337 | + | CCGGGCUGGGGAAGCGCGG | 19 | 14543 |
| BCL11A-12338 | + | CCCGGGCUGGGGAAGCGCGG | 20 | 14544 |
| BCL11A-12339 | + | CCCCGGGCUGGGGAAGCGCGG | 21 | 14545 |
| BCL11A-12340 | + | GCCCCGGGCUGGGGAAGCGCGG | 22 | 14546 |
| BCL11A-12341 | + | AGCCCCGGGCUGGGGAAGCGCGG | 23 | 14547 |
| BCL11A-12342 | + | CAGCCCCGGGCUGGGGAAGCGCGG | 24 | 14548 |
| BCL11A-12343 | + | CUGGGGAAGCGCGGGCGG | 18 | 14549 |
| BCL11A-12344 | + | GCUGGGGAAGCGCGGGCGG | 19 | 14550 |
| BCL11A-10197 | + | GGCUGGGGAAGCGCGGGCGG | 20 | 14551 |

TABLE 19E-continued

5th Tier

| gRNA Name | DNA Strand | Targeting Domain | Target Site Length | SEQ ID NO: |
|---|---|---|---|---|
| BCL11A-12345 | + | GGGCUGGGGAAGCGCGGGCGG | 21 | 14552 |
| BCL11A-12346 | + | CGGGCUGGGGAAGCGCGGGCGG | 22 | 14553 |
| BCL11A-12347 | + | CCGGGCUGGGGAAGCGCGGGCGG | 23 | 14554 |
| BCL11A-12348 | + | CCCGGGCUGGGGAAGCGCGGGCGG | 24 | 14555 |
| BCL11A-12349 | + | GCAAAACUGGCGGGGCGG | 18 | 14556 |
| BCL11A-12350 | + | UGCAAAACUGGCGGGGCGG | 19 | 14557 |
| BCL11A-10198 | + | UUGCAAAACUGGCGGGGCGG | 20 | 14558 |
| BCL11A-12351 | + | UUUGCAAAACUGGCGGGGCGG | 21 | 14559 |
| BCL11A-12352 | + | UUUUGCAAAACUGGCGGGGCGG | 22 | 14560 |
| BCL11A-12353 | + | AUUUUGCAAAACUGGCGGGGCGG | 23 | 14561 |
| BCL11A-12354 | + | UAUUUUGCAAAACUGGCGGGGCGG | 24 | 14562 |
| BCL11A-12355 | + | UGGAAAGAGGGGACCGGG | 18 | 14563 |
| BCL11A-12356 | + | CUGGAAAGAGGGGACCGGG | 19 | 14564 |
| BCL11A-12357 | + | CCUGGAAAGAGGGGACCGGG | 20 | 14565 |
| BCL11A-12358 | + | GCCUGGAAAGAGGGGACCGGG | 21 | 14566 |
| BCL11A-12359 | + | GGCCUGGAAAGAGGGGACCGGG | 22 | 14567 |
| BCL11A-12360 | + | CGGCCUGGAAAGAGGGGACCGGG | 23 | 14568 |
| BCL11A-12361 | + | GCGGCCUGGAAAGAGGGGACCGGG | 24 | 14569 |
| BCL11A-12362 | + | GGAGGCUGCAGCCCCGGG | 18 | 14570 |
| BCL11A-12363 | + | GGGAGGCUGCAGCCCCGGG | 19 | 14571 |
| BCL11A-12364 | + | CGGGAGGCUGCAGCCCCGGG | 20 | 14572 |
| BCL11A-12365 | + | CCGGGAGGCUGCAGCCCCGGG | 21 | 14573 |
| BCL11A-12366 | + | ACCGGGAGGCUGCAGCCCCGGG | 22 | 14574 |
| BCL11A-12367 | + | CACCGGGAGGCUGCAGCCCCGGG | 23 | 14575 |
| BCL11A-12368 | + | GCACCGGGAGGCUGCAGCCCCGGG | 24 | 14576 |
| BCL11A-12369 | + | GGGCUGGGGAAGCGCGGG | 18 | 14577 |
| BCL11A-12370 | + | CGGGCUGGGGAAGCGCGGG | 19 | 14578 |
| BCL11A-10203 | + | CCGGGCUGGGGAAGCGCGGG | 20 | 14579 |
| BCL11A-12371 | + | CCCGGGCUGGGGAAGCGCGGG | 21 | 14580 |
| BCL11A-12372 | + | CCCCGGGCUGGGGAAGCGCGGG | 22 | 14581 |
| BCL11A-12373 | + | GCCCCGGGCUGGGGAAGCGCGGG | 23 | 14582 |
| BCL11A-12374 | + | AGCCCCGGGCUGGGGAAGCGCGGG | 24 | 14583 |
| BCL11A-12375 | + | CAAAACUGGCGGGGCGGG | 18 | 14584 |
| BCL11A-12376 | + | GCAAAACUGGCGGGGCGGG | 19 | 14585 |
| BCL11A-10204 | + | UGCAAAACUGGCGGGGCGGG | 20 | 14586 |
| BCL11A-12377 | + | UUGCAAAACUGGCGGGGCGGG | 21 | 14587 |
| BCL11A-12378 | + | UUUGCAAAACUGGCGGGGCGGG | 22 | 14588 |

TABLE 19E-continued

5th Tier

| gRNA Name | DNA Strand | Targeting Domain | Target Site Length | SEQ ID NO: |
|---|---|---|---|---|
| BCL11A-12379 | + | UUUUGCAAAACUGGCGGGGCGGG | 23 | 14589 |
| BCL11A-12380 | + | AUUUUGCAAAACUGGCGGGGCGGG | 24 | 14590 |
| BCL11A-12381 | + | UUUUGCAAAACUGGCGGG | 18 | 14591 |
| BCL11A-12382 | + | AUUUUGCAAAACUGGCGGG | 19 | 14592 |
| BCL11A-12383 | + | UAUUUUGCAAAACUGGCGGG | 20 | 14593 |
| BCL11A-12384 | + | UUAUUUUGCAAAACUGGCGGG | 21 | 14594 |
| BCL11A-12385 | + | AUUAUUUUGCAAAACUGGCGGG | 22 | 14595 |
| BCL11A-12386 | + | CAUUAUUUUGCAAAACUGGCGGG | 23 | 14596 |
| BCL11A-12387 | + | UCAUUAUUUUGCAAAACUGGCGGG | 24 | 14597 |
| BCL11A-12388 | + | GCGUGUGGACGCCAGGGG | 18 | 14598 |
| BCL11A-12389 | + | CGCGUGUGGACGCCAGGGG | 19 | 14599 |
| BCL11A-12390 | + | CCGCGUGUGGACGCCAGGGG | 20 | 14600 |
| BCL11A-12391 | + | CCCGCGUGUGGACGCCAGGGG | 21 | 14601 |
| BCL11A-12392 | + | CCCCGCGUGUGGACGCCAGGGG | 22 | 14602 |
| BCL11A-12393 | + | UCCCCGCGUGUGGACGCCAGGGG | 23 | 14603 |
| BCL11A-12394 | + | CUCCCCGCGUGUGGACGCCAGGGG | 24 | 14604 |
| BCL11A-12395 | + | AAAACUGGCGGGGCGGGG | 18 | 14605 |
| BCL11A-12396 | + | CAAAACUGGCGGGGCGGGG | 19 | 14606 |
| BCL11A-10207 | + | GCAAAACUGGCGGGGCGGGG | 20 | 14607 |
| BCL11A-12397 | + | UGCAAAACUGGCGGGGCGGGG | 21 | 14608 |
| BCL11A-12398 | + | UUGCAAAACUGGCGGGGCGGGG | 22 | 14609 |
| BCL11A-12399 | + | UUUGCAAAACUGGCGGGGCGGGG | 23 | 14610 |
| BCL11A-12400 | + | UUUUGCAAAACUGGCGGGGCGGGG | 24 | 14611 |
| BCL11A-12401 | + | UUUGCAAAACUGGCGGGG | 18 | 14612 |
| BCL11A-12402 | + | UUUUGCAAAACUGGCGGGG | 19 | 14613 |
| BCL11A-10208 | + | AUUUUGCAAAACUGGCGGGG | 20 | 14614 |
| BCL11A-12403 | + | UAUUUUGCAAAACUGGCGGGG | 21 | 14615 |
| BCL11A-12404 | + | UUAUUUUGCAAAACUGGCGGGG | 22 | 14616 |
| BCL11A-12405 | + | AUUAUUUUGCAAAACUGGCGGGG | 23 | 14617 |
| BCL11A-12406 | + | CAUUAUUUUGCAAAACUGGCGGGG | 24 | 14618 |
| BCL11A-12407 | + | CGGGCGAGGGGAGGUGGG | 18 | 14619 |
| BCL11A-12408 | + | GCGGGCGAGGGGAGGUGGG | 19 | 14620 |
| BCL11A-10213 | + | AGCGGGCGAGGGGAGGUGGG | 20 | 14621 |
| BCL11A-12409 | + | CAGCGGGCGAGGGGAGGUGGG | 21 | 14622 |
| BCL11A-12410 | + | GCAGCGGGCGAGGGGAGGUGGG | 22 | 14623 |
| BCL11A-12411 | + | CGCAGCGGGCGAGGGGAGGUGGG | 23 | 14624 |
| BCL11A-12412 | + | CCGCAGCGGGCGAGGGGAGGUGGG | 24 | 14625 |

TABLE 19E-continued

5th Tier

| gRNA Name | DNA Strand | Targeting Domain | Target Site Length | SEQ ID NO: |
|---|---|---|---|---|
| BCL11A-12413 | + | AUUAUUUUGCAAAACUGG | 18 | 14626 |
| BCL11A-12414 | + | CAUUAUUUUGCAAAACUGG | 19 | 14627 |
| BCL11A-10215 | + | UCAUUAUUUUGCAAAACUGG | 20 | 14628 |
| BCL11A-12415 | + | UUCAUUAUUUUGCAAAACUGG | 21 | 14629 |
| BCL11A-12416 | + | GUUCAUUAUUUUGCAAAACUGG | 22 | 14630 |
| BCL11A-12417 | + | UGUUCAUUAUUUUGCAAAACUGG | 23 | 14631 |
| BCL11A-12418 | + | UUGUUCAUUAUUUUGCAAAACUGG | 24 | 14632 |
| BCL11A-12419 | + | ACAAACACCCACCUCUGG | 18 | 14633 |
| BCL11A-12420 | + | GACAAACACCCACCUCUGG | 19 | 14634 |
| BCL11A-12421 | + | GGACAAACACCCACCUCUGG | 20 | 14635 |
| BCL11A-12422 | + | GGGACAAACACCCACCUCUGG | 21 | 14636 |
| BCL11A-12423 | + | CGGGACAAACACCCACCUCUGG | 22 | 14637 |
| BCL11A-12424 | + | GCGGGACAAACACCCACCUCUGG | 23 | 14638 |
| BCL11A-12425 | + | AGCGGGACAAACACCCACCUCUGG | 24 | 14639 |
| BCL11A-12426 | + | GCGGGCGAGGGGAGGUGG | 18 | 14640 |
| BCL11A-12427 | + | AGCGGGCGAGGGGAGGUGG | 19 | 14641 |
| BCL11A-12428 | + | CAGCGGGCGAGGGGAGGUGG | 20 | 14642 |
| BCL11A-12429 | + | GCAGCGGGCGAGGGGAGGUGG | 21 | 14643 |
| BCL11A-12430 | + | CGCAGCGGGCGAGGGGAGGUGG | 22 | 14644 |
| BCL11A-12431 | + | CCGCAGCGGGCGAGGGGAGGUGG | 23 | 14645 |
| BCL11A-12432 | + | UCCGCAGCGGGCGAGGGGAGGUGG | 24 | 14646 |
| BCL11A-12433 | + | CAUUAUUUUGCAAAACUG | 18 | 14647 |
| BCL11A-12434 | + | UCAUUAUUUUGCAAAACUG | 19 | 14648 |
| BCL11A-12435 | + | UUCAUUAUUUUGCAAAACUG | 20 | 14649 |
| BCL11A-12436 | + | GUUCAUUAUUUUGCAAAACUG | 21 | 14650 |
| BCL11A-12437 | + | UGUUCAUUAUUUUGCAAAACUG | 22 | 14651 |
| BCL11A-12438 | + | UUGUUCAUUAUUUUGCAAAACUG | 23 | 14652 |
| BCL11A-12439 | + | AUUGUUCAUUAUUUUGCAAAACUG | 24 | 14653 |
| BCL11A-12440 | + | GGCUGCAGCCCCGGGCUG | 18 | 14654 |
| BCL11A-12441 | + | AGGCUGCAGCCCCGGGCUG | 19 | 14655 |
| BCL11A-10226 | + | GAGGCUGCAGCCCCGGGCUG | 20 | 14656 |
| BCL11A-12442 | + | GGAGGCUGCAGCCCCGGGCUG | 21 | 14657 |
| BCL11A-12443 | + | GGGAGGCUGCAGCCCCGGGCUG | 22 | 14658 |
| BCL11A-12444 | + | CGGGAGGCUGCAGCCCCGGGCUG | 23 | 14659 |
| BCL11A-12445 | + | CCGGGAGGCUGCAGCCCCGGGCUG | 24 | 14660 |
| BCL11A-12446 | + | GCCACUUUCUCACUAUUG | 18 | 14661 |
| BCL11A-12447 | + | UGCCACUUUCUCACUAUUG | 19 | 14662 |

TABLE 19E-continued

5th Tier

| gRNA Name | DNA Strand | Targeting Domain | Target Site Length | SEQ ID NO: |
|---|---|---|---|---|
| BCL11A-10230 | + | GUGCCACUUUCUCACUAUUG | 20 | 14663 |
| BCL11A-12448 | + | AGUGCCACUUUCUCACUAUUG | 21 | 14664 |
| BCL11A-12449 | + | CAGUGCCACUUUCUCACUAUUG | 22 | 14665 |
| BCL11A-12450 | + | ACAGUGCCACUUUCUCACUAUUG | 23 | 14666 |
| BCL11A-12451 | + | CACAGUGCCACUUUCUCACUAUUG | 24 | 14667 |
| BCL11A-12452 | + | GAAUCCAGCCUAAGUUUG | 18 | 14668 |
| BCL11A-12453 | + | GGAAUCCAGCCUAAGUUUG | 19 | 14669 |
| BCL11A-12454 | + | CGGAAUCCAGCCUAAGUUUG | 20 | 14670 |
| BCL11A-12455 | + | GCGGAAUCCAGCCUAAGUUUG | 21 | 14671 |
| BCL11A-12456 | + | CGCGGAAUCCAGCCUAAGUUUG | 22 | 14672 |
| BCL11A-12457 | + | ACGCGGAAUCCAGCCUAAGUUUG | 23 | 14673 |
| BCL11A-12458 | + | AACGCGGAAUCCAGCCUAAGUUUG | 24 | 14674 |
| BCL11A-12459 | + | CUCCCGACUCCGCGGACU | 18 | 14675 |
| BCL11A-12460 | + | UCUCCCGACUCCGCGGACU | 19 | 14676 |
| BCL11A-12461 | + | CUCUCCCGACUCCGCGGACU | 20 | 14677 |
| BCL11A-12462 | + | CCUCUCCCGACUCCGCGGACU | 21 | 14678 |
| BCL11A-12463 | + | CCCUCUCCCGACUCCGCGGACU | 22 | 14679 |
| BCL11A-12464 | + | CCCCUCUCCCGACUCCGCGGACU | 23 | 14680 |
| BCL11A-12465 | + | GCCCCUCUCCCGACUCCGCGGACU | 24 | 14681 |
| BCL11A-12466 | + | CGAGCCCGCGGCUGCGCU | 18 | 14682 |
| BCL11A-12467 | + | CCGAGCCCGCGGCUGCGCU | 19 | 14683 |
| BCL11A-10239 | + | CCCGAGCCCGCGGCUGCGCU | 20 | 14684 |
| BCL11A-12468 | + | CCCCGAGCCCGCGGCUGCGCU | 21 | 14685 |
| BCL11A-12469 | + | GCCCCGAGCCCGCGGCUGCGCU | 22 | 14686 |
| BCL11A-12470 | + | AGCCCCGAGCCCGCGGCUGCGCU | 23 | 14687 |
| BCL11A-12471 | + | AAGCCCCGAGCCCGCGGCUGCGCU | 24 | 14688 |
| BCL11A-12472 | + | AGGCUGCAGCCCCGGGCU | 18 | 14689 |
| BCL11A-12473 | + | GAGGCUGCAGCCCCGGGCU | 19 | 14690 |
| BCL11A-10240 | + | GGAGGCUGCAGCCCCGGGCU | 20 | 14691 |
| BCL11A-12474 | + | GGGAGGCUGCAGCCCCGGGCU | 21 | 14692 |
| BCL11A-12475 | + | CGGGAGGCUGCAGCCCCGGGCU | 22 | 14693 |
| BCL11A-12476 | + | CCGGGAGGCUGCAGCCCCGGGCU | 23 | 14694 |
| BCL11A-12477 | + | ACCGGGAGGCUGCAGCCCCGGGCU | 24 | 14695 |
| BCL11A-12478 | + | GCGGAAUCCAGCCUAAGU | 18 | 14696 |
| BCL11A-12479 | + | CGCGGAAUCCAGCCUAAGU | 19 | 14697 |
| BCL11A-12480 | + | ACGCGGAAUCCAGCCUAAGU | 20 | 14698 |
| BCL11A-12481 | + | AACGCGGAAUCCAGCCUAAGU | 21 | 14699 |

TABLE 19E-continued

5th Tier

| gRNA Name | DNA Strand | Targeting Domain | Target Site Length | SEQ ID NO: |
|---|---|---|---|---|
| BCL11A-12482 | + | CAACGCGGAAUCCAGCCUAAGU | 22 | 14700 |
| BCL11A-12483 | + | GCAACGCGGAAUCCAGCCUAAGU | 23 | 14701 |
| BCL11A-12484 | + | GGCAACGCGGAAUCCAGCCUAAGU | 24 | 14702 |
| BCL11A-12485 | + | CAUUUUCUUACGGUGAGU | 18 | 14703 |
| BCL11A-12486 | + | CCAUUUUCUUACGGUGAGU | 19 | 14704 |
| BCL11A-10244 | + | CCCAUUUUCUUACGGUGAGU | 20 | 14705 |
| BCL11A-12487 | + | CCCCAUUUUCUUACGGUGAGU | 21 | 14706 |
| BCL11A-12488 | + | CCCCCAUUUUCUUACGGUGAGU | 22 | 14707 |
| BCL11A-12489 | + | CCCCCCAUUUUCUUACGGUGAGU | 23 | 14708 |
| BCL11A-12490 | + | CCCCCCCAUUUUCUUACGGUGAGU | 24 | 14709 |
| BCL11A-12491 | + | CGCGCUCGCUCCCCGCGU | 18 | 14710 |
| BCL11A-12492 | + | CCGCGCUCGCUCCCCGCGU | 19 | 14711 |
| BCL11A-12493 | + | GCCGCGCUCGCUCCCCGCGU | 20 | 14712 |
| BCL11A-12494 | + | CGCCGCGCUCGCUCCCCGCGU | 21 | 14713 |
| BCL11A-12495 | + | CCGCCGCGCUCGCUCCCCGCGU | 22 | 14714 |
| BCL11A-12496 | + | GCCGCCGCGCUCGCUCCCCGCGU | 23 | 14715 |
| BCL11A-12497 | + | CGCCGCCGCGCUCGCUCCCCGCGU | 24 | 14716 |
| BCL11A-12498 | + | CAGCGGGCGAGGGGAGGU | 18 | 14717 |
| BCL11A-12499 | + | GCAGCGGGCGAGGGGAGGU | 19 | 14718 |
| BCL11A-10247 | + | CGCAGCGGGCGAGGGGAGGU | 20 | 14719 |
| BCL11A-12500 | + | CCGCAGCGGGCGAGGGGAGGU | 21 | 14720 |
| BCL11A-12501 | + | UCCGCAGCGGGCGAGGGGAGGU | 22 | 14721 |
| BCL11A-12502 | + | CUCCGCAGCGGGCGAGGGGAGGU | 23 | 14722 |
| BCL11A-12503 | + | GCUCCGCAGCGGGCGAGGGGAGGU | 24 | 14723 |
| BCL11A-12504 | + | GUUUGGAGGGCUGCGGGU | 18 | 14724 |
| BCL11A-12505 | + | AGUUUGGAGGGCUGCGGGU | 19 | 14725 |
| BCL11A-12506 | + | AAGUUUGGAGGGCUGCGGGU | 20 | 14726 |
| BCL11A-12507 | + | UAAGUUUGGAGGGCUGCGGGU | 21 | 14727 |
| BCL11A-12508 | + | CUAAGUUUGGAGGGCUGCGGGU | 22 | 14728 |
| BCL11A-12509 | + | CCUAAGUUUGGAGGGCUGCGGGU | 23 | 14729 |
| BCL11A-12510 | + | GCCUAAGUUUGGAGGGCUGCGGGU | 24 | 14730 |
| BCL11A-12511 | + | UGCCACUUUCUCACUAUU | 18 | 14731 |
| BCL11A-12512 | + | GUGCCACUUUCUCACUAUU | 19 | 14732 |
| BCL11A-12513 | + | AGUGCCACUUUCUCACUAUU | 20 | 14733 |
| BCL11A-12514 | + | CAGUGCCACUUUCUCACUAUU | 21 | 14734 |
| BCL11A-12515 | + | ACAGUGCCACUUUCUCACUAUU | 22 | 14735 |
| BCL11A-12516 | + | CACAGUGCCACUUUCUCACUAUU | 23 | 14736 |

TABLE 19E-continued

5th Tier

| gRNA Name | DNA Strand | Targeting Domain | Target Site Length | SEQ ID NO: |
|---|---|---|---|---|
| BCL11A-12517 | + | CCACAGUGCCACUUUCUCACUAUU | 24 | 14737 |
| BCL11A-12518 | + | GAAAAAUCACCCGAAGUU | 18 | 14738 |
| BCL11A-12519 | + | AGAAAAAUCACCCGAAGUU | 19 | 14739 |
| BCL11A-12520 | + | AAGAAAAAUCACCCGAAGUU | 20 | 14740 |
| BCL11A-12521 | + | AAAGAAAAAUCACCCGAAGUU | 21 | 14741 |
| BCL11A-12522 | + | CAAAGAAAAAUCACCCGAAGUU | 22 | 14742 |
| BCL11A-12523 | + | GCAAAGAAAAAUCACCCGAAGUU | 23 | 14743 |
| BCL11A-12524 | + | AGCAAAGAAAAAUCACCCGAAGUU | 24 | 14744 |
| BCL11A-12525 | + | CGGAAUCCAGCCUAAGUU | 18 | 14745 |
| BCL11A-12526 | + | GCGGAAUCCAGCCUAAGUU | 19 | 14746 |
| BCL11A-10257 | + | CGCGGAAUCCAGCCUAAGUU | 20 | 14747 |
| BCL11A-12527 | + | ACGCGGAAUCCAGCCUAAGUU | 21 | 14748 |
| BCL11A-12528 | + | AACGCGGAAUCCAGCCUAAGUU | 22 | 14749 |
| BCL11A-12529 | + | CAACGCGGAAUCCAGCCUAAGUU | 23 | 14750 |
| BCL11A-12530 | + | GCAACGCGGAAUCCAGCCUAAGUU | 24 | 14751 |
| BCL11A-12531 | + | GAAUCAUUGCAUUCCUUU | 18 | 14752 |
| BCL11A-12532 | + | GGAAUCAUUGCAUUCCUUU | 19 | 14753 |
| BCL11A-12533 | + | UGGAAUCAUUGCAUUCCUUU | 20 | 14754 |
| BCL11A-12534 | + | GUGGAAUCAUUGCAUUCCUUU | 21 | 14755 |
| BCL11A-12535 | + | AGUGGAAUCAUUGCAUUCCUUU | 22 | 14756 |
| BCL11A-12536 | + | GAGUGGAAUCAUUGCAUUCCUUU | 23 | 14757 |
| BCL11A-12537 | + | GGAGUGGAAUCAUUGCAUUCCUUU | 24 | 14758 |
| BCL11A-12538 | − | CCACUCACCGUAAGAAAA | 18 | 14759 |
| BCL11A-12539 | − | CCCACUCACCGUAAGAAAA | 19 | 14760 |
| BCL11A-10024 | − | UCCCACUCACCGUAAGAAAA | 20 | 14761 |
| BCL11A-12540 | − | UUCCCACUCACCGUAAGAAAA | 21 | 14762 |
| BCL11A-12541 | − | CUUCCCACUCACCGUAAGAAAA | 22 | 14763 |
| BCL11A-12542 | − | GCUUCCCACUCACCGUAAGAAAA | 23 | 14764 |
| BCL11A-12543 | − | UGCUUCCCACUCACCGUAAGAAAA | 24 | 14765 |
| BCL11A-12544 | − | CCCACUCACCGUAAGAAA | 18 | 14766 |
| BCL11A-12545 | − | UCCCACUCACCGUAAGAAA | 19 | 14767 |
| BCL11A-12546 | − | UUCCCACUCACCGUAAGAAA | 20 | 14768 |
| BCL11A-12547 | − | CUUCCCACUCACCGUAAGAAA | 21 | 14769 |
| BCL11A-12548 | − | GCUUCCCACUCACCGUAAGAAA | 22 | 14770 |
| BCL11A-12549 | − | UGCUUCCCACUCACCGUAAGAAA | 23 | 14771 |
| BCL11A-12550 | − | UUGCUUCCCACUCACCGUAAGAAA | 24 | 14772 |
| BCL11A-12551 | − | UGGGAGCUGGUGGGGAAA | 18 | 14773 |

TABLE 19E-continued

5th Tier

| gRNA Name | DNA Strand | Targeting Domain | Target Site Length | SEQ ID NO: |
|---|---|---|---|---|
| BCL11A-12552 | - | GUGGGAGCUGGUGGGGAAA | 19 | 14774 |
| BCL11A-10028 | - | GGUGGGAGCUGGUGGGGAAA | 20 | 14775 |
| BCL11A-12553 | - | GGGUGGGAGCUGGUGGGGAAA | 21 | 14776 |
| BCL11A-12554 | - | GGGGUGGGAGCUGGUGGGGAAA | 22 | 14777 |
| BCL11A-12555 | - | GGGGGUGGGAGCUGGUGGGGAAA | 23 | 14778 |
| BCL11A-12556 | - | UGGGGGUGGGAGCUGGUGGGGAAA | 24 | 14779 |
| BCL11A-12557 | - | AACGAUUCCCGGGGAGAA | 18 | 14780 |
| BCL11A-12558 | - | AAACGAUUCCCGGGGAGAA | 19 | 14781 |
| BCL11A-12559 | - | AAAACGAUUCCCGGGGAGAA | 20 | 14782 |
| BCL11A-12560 | - | AAAAACGAUUCCCGGGGAGAA | 21 | 14783 |
| BCL11A-12561 | - | AAAAAACGAUUCCCGGGGAGAA | 22 | 14784 |
| BCL11A-12562 | - | UAAAAAACGAUUCCCGGGGAGAA | 23 | 14785 |
| BCL11A-12563 | - | CUAAAAAACGAUUCCCGGGGAGAA | 24 | 14786 |
| BCL11A-12564 | - | UUUAUUUCUCUUUUCGAA | 18 | 14787 |
| BCL11A-12565 | - | CUUUAUUUCUCUUUUCGAA | 19 | 14788 |
| BCL11A-12566 | - | GCUUUAUUUCUCUUUUCGAA | 20 | 14789 |
| BCL11A-12567 | - | CGCUUUAUUUCUCUUUUCGAA | 21 | 14790 |
| BCL11A-12568 | - | CCGCUUUAUUUCUCUUUUCGAA | 22 | 14791 |
| BCL11A-12569 | - | GCCGCUUUAUUUCUCUUUUCGAA | 23 | 14792 |
| BCL11A-12570 | - | CGCCGCUUUAUUUCUCUUUUCGAA | 24 | 14793 |
| BCL11A-12571 | - | GUGGGAGCUGGUGGGGAA | 18 | 14794 |
| BCL11A-12572 | - | GGUGGGAGCUGGUGGGGAA | 19 | 14795 |
| BCL11A-10032 | - | GGGUGGGAGCUGGUGGGGAA | 20 | 14796 |
| BCL11A-12573 | - | GGGGUGGGAGCUGGUGGGGAA | 21 | 14797 |
| BCL11A-12574 | - | GGGGGUGGGAGCUGGUGGGGAA | 22 | 14798 |
| BCL11A-12575 | - | UGGGGGUGGGAGCUGGUGGGGAA | 23 | 14799 |
| BCL11A-12576 | - | CUGGGGGUGGGAGCUGGUGGGGAA | 24 | 14800 |
| BCL11A-12577 | - | GAAAGUGGCACUGUGGAA | 18 | 14801 |
| BCL11A-12578 | - | AGAAAGUGGCACUGUGGAA | 19 | 14802 |
| BCL11A-10033 | - | GAGAAAGUGGCACUGUGGAA | 20 | 14803 |
| BCL11A-12579 | - | UGAGAAAGUGGCACUGUGGAA | 21 | 14804 |
| BCL11A-12580 | - | GUGAGAAAGUGGCACUGUGGAA | 22 | 14805 |
| BCL11A-12581 | - | AGUGAGAAAGUGGCACUGUGGAA | 23 | 14806 |
| BCL11A-12582 | - | UAGUGAGAAAGUGGCACUGUGGAA | 24 | 14807 |
| BCL11A-12583 | - | CUCACGGUCAAGUGUGCA | 18 | 14808 |
| BCL11A-12584 | - | GCUCACGGUCAAGUGUGCA | 19 | 14809 |
| BCL11A-12585 | - | CGCUCACGGUCAAGUGUGCA | 20 | 14810 |

TABLE 19E-continued

5th Tier

| gRNA Name | DNA Strand | Targeting Domain | Target Site Length | SEQ ID NO: |
|---|---|---|---|---|
| BCL11A-12586 | - | GCGCUCACGGUCAAGUGUGCA | 21 | 14811 |
| BCL11A-12587 | - | CGCGCUCACGGUCAAGUGUGCA | 22 | 14812 |
| BCL11A-12588 | - | GCGCGCUCACGGUCAAGUGUGCA | 23 | 14813 |
| BCL11A-12589 | - | AGCGCGCUCACGGUCAAGUGUGCA | 24 | 14814 |
| BCL11A-12590 | - | GGAGAGGGGCCGCGGCGA | 18 | 14815 |
| BCL11A-12591 | - | GGGAGAGGGGCCGCGGCGA | 19 | 14816 |
| BCL11A-10043 | - | CGGGAGAGGGGCCGCGGCGA | 20 | 14817 |
| BCL11A-12592 | - | UCGGGAGAGGGGCCGCGGCGA | 21 | 14818 |
| BCL11A-12593 | - | GUCGGGAGAGGGGCCGCGGCGA | 22 | 14819 |
| BCL11A-12594 | - | AGUCGGGAGAGGGGCCGCGGCGA | 23 | 14820 |
| BCL11A-12595 | - | GAGUCGGGAGAGGGGCCGCGGCGA | 24 | 14821 |
| BCL11A-12596 | - | CCGUGGGACCGGGAAGGA | 18 | 14822 |
| BCL11A-12597 | - | GCCGUGGGACCGGGAAGGA | 19 | 14823 |
| BCL11A-10045 | - | AGCCGUGGGACCGGGAAGGA | 20 | 14824 |
| BCL11A-12598 | - | GAGCCGUGGGACCGGGAAGGA | 21 | 14825 |
| BCL11A-12599 | - | AGAGCCGUGGGACCGGGAAGGA | 22 | 14826 |
| BCL11A-12600 | - | GAGAGCCGUGGGACCGGGAAGGA | 23 | 14827 |
| BCL11A-12601 | - | GGAGAGCCGUGGGACCGGGAAGGA | 24 | 14828 |
| BCL11A-12602 | - | GAGUCCGCGGAGUCGGGA | 18 | 14829 |
| BCL11A-12603 | - | UGAGUCCGCGGAGUCGGGA | 19 | 14830 |
| BCL11A-12604 | - | CUGAGUCCGCGGAGUCGGGA | 20 | 14831 |
| BCL11A-12605 | - | CCUGAGUCCGCGGAGUCGGGA | 21 | 14832 |
| BCL11A-12606 | - | UCCUGAGUCCGCGGAGUCGGGA | 22 | 14833 |
| BCL11A-12607 | - | CUCCUGAGUCCGCGGAGUCGGGA | 23 | 14834 |
| BCL11A-12608 | - | GCUCCUGAGUCCGCGGAGUCGGGA | 24 | 14835 |
| BCL11A-12609 | - | GGCGUCCACACGCGGGA | 18 | 14836 |
| BCL11A-12610 | - | UGGCGUCCACACGCGGGGA | 19 | 14837 |
| BCL11A-12611 | - | CUGGCGUCCACACGCGGGGA | 20 | 14838 |
| BCL11A-12612 | - | CCUGGCGUCCACACGCGGGGA | 21 | 14839 |
| BCL11A-12613 | - | CCCUGGCGUCCACACGCGGGGA | 22 | 14840 |
| BCL11A-12614 | - | CCCCUGGCGUCCACACGCGGGGA | 23 | 14841 |
| BCL11A-12615 | - | GCCCCUGGCGUCCACACGCGGGGA | 24 | 14842 |
| BCL11A-12616 | - | GCGCGGCGGCGGCGGGGA | 18 | 14843 |
| BCL11A-12617 | - | AGCGCGGCGGCGGCGGGGA | 19 | 14844 |
| BCL11A-10051 | - | GAGCGCGGCGGCGGCGGGGA | 20 | 14845 |
| BCL11A-12618 | - | CGAGCGCGGCGGCGGCGGGGA | 21 | 14846 |
| BCL11A-12619 | - | GCGAGCGCGGCGGCGGCGGGGA | 22 | 14847 |

TABLE 19E-continued

5th Tier

| gRNA Name | DNA Strand | Targeting Domain | Target Site Length | SEQ ID NO: |
|---|---|---|---|---|
| BCL11A-12620 | - | AGCGAGCGCGGCGGCGGCGGGGA | 23 | 14848 |
| BCL11A-12621 | - | GAGCGAGCGCGGCGGCGGCGGGGA | 24 | 14849 |
| BCL11A-12622 | - | GGUGGGAGCUGGUGGGGA | 18 | 14850 |
| BCL11A-12623 | - | GGGUGGGAGCUGGUGGGGA | 19 | 14851 |
| BCL11A-12624 | - | GGGGUGGGAGCUGGUGGGGA | 20 | 14852 |
| BCL11A-12625 | - | GGGGGUGGGAGCUGGUGGGGA | 21 | 14853 |
| BCL11A-12626 | - | UGGGGGUGGGAGCUGGUGGGGA | 22 | 14854 |
| BCL11A-12627 | - | CUGGGGGUGGGAGCUGGUGGGGA | 23 | 14855 |
| BCL11A-12628 | - | CCUGGGGGUGGGAGCUGGUGGGGA | 24 | 14856 |
| BCL11A-12629 | - | ACGGGGAGAGCCGUGGGA | 18 | 14857 |
| BCL11A-12630 | - | GACGGGGAGAGCCGUGGGA | 19 | 14858 |
| BCL11A-12631 | - | CGACGGGGAGAGCCGUGGGA | 20 | 14859 |
| BCL11A-12632 | - | GCGACGGGGAGAGCCGUGGGA | 21 | 14860 |
| BCL11A-12633 | - | GGCGACGGGGAGAGCCGUGGGA | 22 | 14861 |
| BCL11A-12634 | - | CGGCGACGGGGAGAGCCGUGGGA | 23 | 14862 |
| BCL11A-12635 | - | GCGGCGACGGGGAGAGCCGUGGGA | 24 | 14863 |
| BCL11A-12636 | - | AGAAAGUGGCACUGUGGA | 18 | 14864 |
| BCL11A-12637 | - | GAGAAAGUGGCACUGUGGA | 19 | 14865 |
| BCL11A-12638 | - | UGAGAAAGUGGCACUGUGGA | 20 | 14866 |
| BCL11A-12639 | - | GUGAGAAAGUGGCACUGUGGA | 21 | 14867 |
| BCL11A-12640 | - | AGUGAGAAAGUGGCACUGUGGA | 22 | 14868 |
| BCL11A-12641 | - | UAGUGAGAAAGUGGCACUGUGGA | 23 | 14869 |
| BCL11A-12642 | - | AUAGUGAGAAAGUGGCACUGUGGA | 24 | 14870 |
| BCL11A-12643 | - | CGCCAGUUUUGCAAAAUA | 18 | 14871 |
| BCL11A-12644 | - | CCGCCAGUUUUGCAAAAUA | 19 | 14872 |
| BCL11A-12645 | - | CCCGCCAGUUUUGCAAAAUA | 20 | 14873 |
| BCL11A-12646 | - | CCCCGCCAGUUUUGCAAAAUA | 21 | 14874 |
| BCL11A-12647 | - | GCCCCGCCAGUUUUGCAAAAUA | 22 | 14875 |
| BCL11A-12648 | - | CGCCCCGCCAGUUUUGCAAAAUA | 23 | 14876 |
| BCL11A-12649 | - | CCGCCCCGCCAGUUUUGCAAAAUA | 24 | 14877 |
| BCL11A-12650 | - | GUAGUCAUCCCCACAAUA | 18 | 14878 |
| BCL11A-12651 | - | AGUAGUCAUCCCCACAAUA | 19 | 14879 |
| BCL11A-12652 | - | AAGUAGUCAUCCCCACAAUA | 20 | 14880 |
| BCL11A-12653 | - | AAAGUAGUCAUCCCCACAAUA | 21 | 14881 |
| BCL11A-12654 | - | GAAAGUAGUCAUCCCCACAAUA | 22 | 14882 |
| BCL11A-12655 | - | GGAAAGUAGUCAUCCCCACAAUA | 23 | 14883 |
| BCL11A-12656 | - | AGGAAAGUAGUCAUCCCCACAAUA | 24 | 14884 |

TABLE 19E-continued

5th Tier

| gRNA Name | DNA Strand | Targeting Domain | Target Site Length | SEQ ID NO: |
|---|---|---|---|---|
| BCL11A-12657 | - | GGGAAGUGGGUGUGCGUA | 18 | 14885 |
| BCL11A-12658 | - | GGGGAAGUGGGUGUGCGUA | 19 | 14886 |
| BCL11A-10055 | - | AGGGGAAGUGGGUGUGCGUA | 20 | 14887 |
| BCL11A-12659 | - | GAGGGGAAGUGGGUGUGCGUA | 21 | 14888 |
| BCL11A-12660 | - | GGAGGGGAAGUGGGUGUGCGUA | 22 | 14889 |
| BCL11A-12661 | - | GGGAGGGGAAGUGGGUGUGCGUA | 23 | 14890 |
| BCL11A-12662 | - | GGGGAGGGGAAGUGGGUGUGCGUA | 24 | 14891 |
| BCL11A-12663 | - | UAAGAAAAUGGGGGGGUA | 18 | 14892 |
| BCL11A-12664 | - | GUAAGAAAAUGGGGGGGUA | 19 | 14893 |
| BCL11A-10056 | - | CGUAAGAAAAUGGGGGGGUA | 20 | 14894 |
| BCL11A-12665 | - | CCGUAAGAAAAUGGGGGGGUA | 21 | 14895 |
| BCL11A-12666 | - | ACCGUAAGAAAAUGGGGGGGUA | 22 | 14896 |
| BCL11A-12667 | - | CACCGUAAGAAAAUGGGGGGGUA | 23 | 14897 |
| BCL11A-12668 | - | UCACCGUAAGAAAAUGGGGGGGUA | 24 | 14898 |
| BCL11A-12669 | - | AACAACUCACAUGCAAAC | 18 | 14899 |
| BCL11A-12670 | - | GAACAACUCACAUGCAAAC | 19 | 14900 |
| BCL11A-12671 | - | CGAACAACUCACAUGCAAAC | 20 | 14901 |
| BCL11A-12672 | - | GCGAACAACUCACAUGCAAAC | 21 | 14902 |
| BCL11A-12673 | - | UGCGAACAACUCACAUGCAAAC | 22 | 14903 |
| BCL11A-12674 | - | UUGCGAACAACUCACAUGCAAAC | 23 | 14904 |
| BCL11A-12675 | - | GUUGCGAACAACUCACAUGCAAAC | 24 | 14905 |
| BCL11A-12676 | - | CCGCUGCGGAGCUGUAAC | 18 | 14906 |
| BCL11A-12677 | - | CCCGCUGCGGAGCUGUAAC | 19 | 14907 |
| BCL11A-12678 | - | GCCCGCUGCGGAGCUGUAAC | 20 | 14908 |
| BCL11A-12679 | - | CGCCCGCUGCGGAGCUGUAAC | 21 | 14909 |
| BCL11A-12680 | - | UCGCCCGCUGCGGAGCUGUAAC | 22 | 14910 |
| BCL11A-12681 | - | CUCGCCCGCUGCGGAGCUGUAAC | 23 | 14911 |
| BCL11A-12682 | - | CCUCGCCCGCUGCGGAGCUGUAAC | 24 | 14912 |
| BCL11A-12683 | - | GGCCCCUGGCGUCCACAC | 18 | 14913 |
| BCL11A-12684 | - | CGGCCCCUGGCGUCCACAC | 19 | 14914 |
| BCL11A-12685 | - | UCGGCCCCUGGCGUCCACAC | 20 | 14915 |
| BCL11A-12686 | - | UUCGGCCCCUGGCGUCCACAC | 21 | 14916 |
| BCL11A-12687 | - | CUUCGGCCCCUGGCGUCCACAC | 22 | 14917 |
| BCL11A-12688 | - | ACUUCGGCCCCUGGCGUCCACAC | 23 | 14918 |
| BCL11A-12689 | - | UACUUCGGCCCCUGGCGUCCACAC | 24 | 14919 |
| BCL11A-12690 | - | GCGCGGGCUCCUGGAGAC | 18 | 14920 |
| BCL11A-12691 | - | CGCGCGGGCUCCUGGAGAC | 19 | 14921 |

TABLE 19E-continued

| | | 5th Tier | | |
|---|---|---|---|---|
| gRNA Name | DNA Strand | Targeting Domain | Target Site Length | SEQ ID NO: |
| BCL11A-12692 | - | CCGCGCGGGCUCCUGGAGAC | 20 | 14922 |
| BCL11A-12693 | - | GCCGCGCGGGCUCCUGGAGAC | 21 | 14923 |
| BCL11A-12694 | - | GGCCGCGCGGGCUCCUGGAGAC | 22 | 14924 |
| BCL11A-12695 | - | AGGCCGCGCGGGCUCCUGGAGAC | 23 | 14925 |
| BCL11A-12696 | - | CAGGCCGCGCGGGCUCCUGGAGAC | 24 | 14926 |
| BCL11A-12697 | - | GAGAGGGGCCGCGGCGAC | 18 | 14927 |
| BCL11A-12698 | - | GGAGAGGGGCCGCGGCGAC | 19 | 14928 |
| BCL11A-10061 | - | GGGAGAGGGGCCGCGGCGAC | 20 | 14929 |
| BCL11A-12699 | - | CGGGAGAGGGGCCGCGGCGAC | 21 | 14930 |
| BCL11A-12700 | - | UCGGGAGAGGGGCCGCGGCGAC | 22 | 14931 |
| BCL11A-12701 | - | GUCGGGAGAGGGGCCGCGGCGAC | 23 | 14932 |
| BCL11A-12702 | - | AGUCGGGAGAGGGGCCGCGGCGAC | 24 | 14933 |
| BCL11A-12703 | - | CGUGGGACCGGGAAGGAC | 18 | 14934 |
| BCL11A-12704 | - | CCGUGGGACCGGGAAGGAC | 19 | 14935 |
| BCL11A-10062 | - | GCCGUGGGACCGGGAAGGAC | 20 | 14936 |
| BCL11A-12705 | - | AGCCGUGGGACCGGGAAGGAC | 21 | 14937 |
| BCL11A-12706 | - | GAGCCGUGGGACCGGGAAGGAC | 22 | 14938 |
| BCL11A-12707 | - | AGAGCCGUGGGACCGGGAAGGAC | 23 | 14939 |
| BCL11A-12708 | - | GAGAGCCGUGGGACCGGGAAGGAC | 24 | 14940 |
| BCL11A-12709 | - | CGGGGAGAGCCGUGGGAC | 18 | 14941 |
| BCL11A-12710 | - | ACGGGGAGAGCCGUGGGAC | 19 | 14942 |
| BCL11A-10065 | - | GACGGGGAGAGCCGUGGGAC | 20 | 14943 |
| BCL11A-12711 | - | CGACGGGGAGAGCCGUGGGAC | 21 | 14944 |
| BCL11A-12712 | - | GCGACGGGGAGAGCCGUGGGAC | 22 | 14945 |
| BCL11A-12713 | - | GGCGACGGGGAGAGCCGUGGGAC | 23 | 14946 |
| BCL11A-12714 | - | CGGCGACGGGGAGAGCCGUGGGAC | 24 | 14947 |
| BCL11A-12715 | - | ACAACUCACAUGCAAACC | 18 | 14948 |
| BCL11A-12716 | - | AACAACUCACAUGCAAACC | 19 | 14949 |
| BCL11A-10066 | - | GAACAACUCACAUGCAAACC | 20 | 14950 |
| BCL11A-12717 | - | CGAACAACUCACAUGCAAACC | 21 | 14951 |
| BCL11A-12718 | - | GCGAACAACUCACAUGCAAACC | 22 | 14952 |
| BCL11A-12719 | - | UGCGAACAACUCACAUGCAAACC | 23 | 14953 |
| BCL11A-12720 | - | UUGCGAACAACUCACAUGCAAACC | 24 | 14954 |
| BCL11A-12721 | - | GGGGAGAGCCGUGGGACC | 18 | 14955 |
| BCL11A-12722 | - | CGGGGAGAGCCGUGGGACC | 19 | 14956 |
| BCL11A-10070 | - | ACGGGGAGAGCCGUGGGACC | 20 | 14957 |
| BCL11A-12723 | - | GACGGGGAGAGCCGUGGGACC | 21 | 14958 |

TABLE 19E-continued

5th Tier

| gRNA Name | DNA Strand | Targeting Domain | Target Site Length | SEQ ID NO: |
|---|---|---|---|---|
| BCL11A-12724 | - | CGACGGGGAGAGCCGUGGGACC | 22 | 14959 |
| BCL11A-12725 | - | GCGACGGGGAGAGCCGUGGGACC | 23 | 14960 |
| BCL11A-12726 | - | GGCGACGGGGAGAGCCGUGGGACC | 24 | 14961 |
| BCL11A-12727 | - | UCGGCCUUGGGGGCGCCC | 18 | 14962 |
| BCL11A-12728 | - | CUCGGCCUUGGGGGCGCCC | 19 | 14963 |
| BCL11A-12729 | - | GCUCGGCCUUGGGGGCGCCC | 20 | 14964 |
| BCL11A-12730 | - | GGCUCGGCCUUGGGGGCGCCC | 21 | 14965 |
| BCL11A-12731 | - | UGGCUCGGCCUUGGGGGCGCCC | 22 | 14966 |
| BCL11A-12732 | - | CUGGCUCGGCCUUGGGGGCGCCC | 23 | 14967 |
| BCL11A-12733 | - | CCUGGCUCGGCCUUGGGGGCGCCC | 24 | 14968 |
| BCL11A-12734 | - | GUCUAAAAAACGAUUCCC | 18 | 14969 |
| BCL11A-12735 | - | AGUCUAAAAAACGAUUCCC | 19 | 14970 |
| BCL11A-10082 | - | AAGUCUAAAAAACGAUUCCC | 20 | 14971 |
| BCL11A-12736 | - | CAAGUCUAAAAAACGAUUCCC | 21 | 14972 |
| BCL11A-12737 | - | ACAAGUCUAAAAAACGAUUCCC | 22 | 14973 |
| BCL11A-12738 | - | UACAAGUCUAAAAAACGAUUCCC | 23 | 14974 |
| BCL11A-12739 | - | GUACAAGUCUAAAAAACGAUUCCC | 24 | 14975 |
| BCL11A-12740 | - | GCCCGCGCUUCCCCAGCC | 18 | 14976 |
| BCL11A-12741 | - | CGCCCGCGCUUCCCCAGCC | 19 | 14977 |
| BCL11A-10084 | - | CCGCCCGCGCUUCCCCAGCC | 20 | 14978 |
| BCL11A-12742 | - | UCCGCCCGCGCUUCCCCAGCC | 21 | 14979 |
| BCL11A-12743 | - | CUCCGCCCGCGCUUCCCCAGCC | 22 | 14980 |
| BCL11A-12744 | - | CCUCCGCCCGCGCUUCCCCAGCC | 23 | 14981 |
| BCL11A-12745 | - | CCCUCCGCCCGCGCUUCCCCAGCC | 24 | 14982 |
| BCL11A-12746 | - | AGUUUCCCGAGCGCAGCC | 18 | 14983 |
| BCL11A-12747 | - | AAGUUUCCCGAGCGCAGCC | 19 | 14984 |
| BCL11A-12748 | - | AAAGUUUCCCGAGCGCAGCC | 20 | 14985 |
| BCL11A-12749 | - | CAAAGUUUCCCGAGCGCAGCC | 21 | 14986 |
| BCL11A-12750 | - | GCAAAGUUUCCCGAGCGCAGCC | 22 | 14987 |
| BCL11A-12751 | - | GGCAAAGUUUCCCGAGCGCAGCC | 23 | 14988 |
| BCL11A-12752 | - | GGGCAAAGUUUCCCGAGCGCAGCC | 24 | 14989 |
| BCL11A-12753 | - | GCGGCGACGGGGAGAGCC | 18 | 14990 |
| BCL11A-12754 | - | CGCGGCGACGGGGAGAGCC | 19 | 14991 |
| BCL11A-12755 | - | CCGCGGCGACGGGGAGAGCC | 20 | 14992 |
| BCL11A-12756 | - | GCCGCGGCGACGGGGAGAGCC | 21 | 14993 |
| BCL11A-12757 | - | GGCCGCGGCGACGGGGAGAGCC | 22 | 14994 |
| BCL11A-12758 | - | GGGCCGCGGCGACGGGGAGAGCC | 23 | 14995 |

TABLE 19E-continued

| gRNA Name | DNA Strand | Targeting Domain | Target Site Length | SEQ ID NO: |
|---|---|---|---|---|
| | | 5th Tier | | |
| BCL11A-12759 | - | GGGGCCGCGGCGACGGGGAGAGCC | 24 | 14996 |
| BCL11A-12760 | - | CCGGUCCCUGGCUCGGCC | 18 | 14997 |
| BCL11A-12761 | - | CCCGGUCCCUGGCUCGGCC | 19 | 14998 |
| BCL11A-12762 | - | UCCCGGUCCCUGGCUCGGCC | 20 | 14999 |
| BCL11A-12763 | - | CCAGGCCGCGCGGGCUCC | 18 | 15000 |
| BCL11A-12764 | - | UCCAGGCCGCGCGGGCUCC | 19 | 15001 |
| BCL11A-10091 | - | UUCCAGGCCGCGCGGGCUCC | 20 | 15002 |
| BCL11A-12765 | - | UUUCCAGGCCGCGCGGGCUCC | 21 | 15003 |
| BCL11A-12766 | - | CUUUCCAGGCCGCGCGGGCUCC | 22 | 15004 |
| BCL11A-12767 | - | UCUUUCCAGGCCGCGCGGGCUCC | 23 | 15005 |
| BCL11A-12768 | - | CUCUUUCCAGGCCGCGCGGGCUCC | 24 | 15006 |
| BCL11A-12769 | - | UUCUUUGCUGUCCUCUCC | 18 | 15007 |
| BCL11A-12770 | - | UUUCUUUGCUGUCCUCUCC | 19 | 15008 |
| BCL11A-12771 | - | UUUUCUUUGCUGUCCUCUCC | 20 | 15009 |
| BCL11A-12772 | - | UUUUUCUUUGCUGUCCUCUCC | 21 | 15010 |
| BCL11A-12773 | - | AUUUUUCUUUGCUGUCCUCUCC | 22 | 15011 |
| BCL11A-12774 | - | GAUUUUUCUUUGCUGUCCUCUCC | 23 | 15012 |
| BCL11A-12775 | - | UGAUUUUUCUUUGCUGUCCUCUCC | 24 | 15013 |
| BCL11A-12776 | - | CCCGGCGCUCCUGAGUCC | 18 | 15014 |
| BCL11A-12777 | - | CCCCGGCGCUCCUGAGUCC | 19 | 15015 |
| BCL11A-12778 | - | CCCCCGGCGCUCCUGAGUCC | 20 | 15016 |
| BCL11A-12779 | - | GCCCCCGGCGCUCCUGAGUCC | 21 | 15017 |
| BCL11A-12780 | - | GGCCCCCGGCGCUCCUGAGUCC | 22 | 15018 |
| BCL11A-12781 | - | GGGCCCCCGGCGCUCCUGAGUCC | 23 | 15019 |
| BCL11A-12782 | - | GGGGCCCCCGGCGCUCCUGAGUCC | 24 | 15020 |
| BCL11A-12783 | - | GUACGGAGGAGGGUGUCC | 18 | 15021 |
| BCL11A-12784 | - | CGUACGGAGGAGGGUGUCC | 19 | 15022 |
| BCL11A-10094 | - | GCGUACGGAGGAGGGUGUCC | 20 | 15023 |
| BCL11A-12785 | - | UGCGUACGGAGGAGGGUGUCC | 21 | 15024 |
| BCL11A-12786 | - | GUGCGUACGGAGGAGGGUGUCC | 22 | 15025 |
| BCL11A-12787 | - | UGUGCGUACGGAGGAGGGUGUCC | 23 | 15026 |
| BCL11A-12788 | - | GUGUGCGUACGGAGGAGGGUGUCC | 24 | 15027 |
| BCL11A-12789 | - | AGUCUAAAAACGAUUCC | 18 | 15028 |
| BCL11A-12790 | - | AAGUCUAAAAACGAUUCC | 19 | 15029 |
| BCL11A-10095 | - | CAAGUCUAAAAACGAUUCC | 20 | 15030 |
| BCL11A-12791 | - | ACAAGUCUAAAAACGAUUCC | 21 | 15031 |
| BCL11A-12792 | - | UACAAGUCUAAAAACGAUUCC | 22 | 15032 |

TABLE 19E-continued

5th Tier

| gRNA Name | DNA Strand | Targeting Domain | Target Site Length | SEQ ID NO: |
|---|---|---|---|---|
| BCL11A-12793 | - | GUACAAGUCUAAAAAACGAUUCC | 23 | 15033 |
| BCL11A-12794 | - | AGUACAAGUCUAAAAAACGAUUCC | 24 | 15034 |
| BCL11A-12795 | - | CGCCCGCGCUUCCCCAGC | 18 | 15035 |
| BCL11A-12796 | - | CCGCCCGCGCUUCCCCAGC | 19 | 15036 |
| BCL11A-12797 | - | UCCGCCCGCGCUUCCCCAGC | 20 | 15037 |
| BCL11A-12798 | - | CUCCGCCCGCGCUUCCCCAGC | 21 | 15038 |
| BCL11A-12799 | - | CCUCCGCCCGCGCUUCCCCAGC | 22 | 15039 |
| BCL11A-12800 | - | CCCUCCGCCCGCGCUUCCCCAGC | 23 | 15040 |
| BCL11A-12801 | - | UCCCUCCGCCCGCGCUUCCCCAGC | 24 | 15041 |
| BCL11A-12802 | - | CACGGUCAAGUGUGCAGC | 18 | 15042 |
| BCL11A-12803 | - | UCACGGUCAAGUGUGCAGC | 19 | 15043 |
| BCL11A-10100 | - | CUCACGGUCAAGUGUGCAGC | 20 | 15044 |
| BCL11A-12804 | - | GCUCACGGUCAAGUGUGCAGC | 21 | 15045 |
| BCL11A-12805 | - | CGCUCACGGUCAAGUGUGCAGC | 22 | 15046 |
| BCL11A-12806 | - | GCGCUCACGGUCAAGUGUGCAGC | 23 | 15047 |
| BCL11A-12807 | - | CGCGCUCACGGUCAAGUGUGCAGC | 24 | 15048 |
| BCL11A-12808 | - | CCCCUGGCGUCCACACGC | 18 | 15049 |
| BCL11A-12809 | - | GCCCCUGGCGUCCACACGC | 19 | 15050 |
| BCL11A-10103 | - | GGCCCCUGGCGUCCACACGC | 20 | 15051 |
| BCL11A-12810 | - | CGGCCCCUGGCGUCCACACGC | 21 | 15052 |
| BCL11A-12811 | - | UCGGCCCCUGGCGUCCACACGC | 22 | 15053 |
| BCL11A-12812 | - | UUCGGCCCCUGGCGUCCACACGC | 23 | 15054 |
| BCL11A-12813 | - | CUUCGGCCCCUGGCGUCCACACGC | 24 | 15055 |
| BCL11A-12814 | - | CCCCUCUUUCCAGGCCGC | 18 | 15056 |
| BCL11A-12815 | - | UCCCCUCUUUCCAGGCCGC | 19 | 15057 |
| BCL11A-12816 | - | GUCCCCUCUUUCCAGGCCGC | 20 | 15058 |
| BCL11A-12817 | - | GGUCCCCUCUUUCCAGGCCGC | 21 | 15059 |
| BCL11A-12818 | - | CGGUCCCCUCUUUCCAGGCCGC | 22 | 15060 |
| BCL11A-12819 | - | CCGGUCCCCUCUUUCCAGGCCGC | 23 | 15061 |
| BCL11A-12820 | - | CCCGGUCCCCUCUUUCCAGGCCGC | 24 | 15062 |
| BCL11A-12821 | - | GCCGCCUUUUGUUCCGGC | 18 | 15063 |
| BCL11A-12822 | - | UGCCGCCUUUUGUUCCGGC | 19 | 15064 |
| BCL11A-12823 | - | CUGCCGCCUUUUGUUCCGGC | 20 | 15065 |
| BCL11A-12824 | - | ACUGCCGCCUUUUGUUCCGGC | 21 | 15066 |
| BCL11A-12825 | - | CACUGCCGCCUUUUGUUCCGGC | 22 | 15067 |
| BCL11A-12826 | - | GCACUGCCGCCUUUUGUUCCGGC | 23 | 15068 |
| BCL11A-12827 | - | GGCACUGCCGCCUUUUGUUCCGGC | 24 | 15069 |

TABLE 19E-continued

5th Tier

| gRNA Name | DNA Strand | Targeting Domain | Target Site Length | SEQ ID NO: |
|---|---|---|---|---|
| BCL11A-12828 | - | AGCGAGCGCGGCGGCGGC | 18 | 15070 |
| BCL11A-12829 | - | GAGCGAGCGCGGCGGCGGC | 19 | 15071 |
| BCL11A-10114 | - | GGAGCGAGCGCGGCGGCGGC | 20 | 15072 |
| BCL11A-12830 | - | GGGAGCGAGCGCGGCGGCGGC | 21 | 15073 |
| BCL11A-12831 | - | GGGGAGCGAGCGCGGCGGCGGC | 22 | 15074 |
| BCL11A-12832 | - | CGGGGAGCGAGCGCGGCGGCGGC | 23 | 15075 |
| BCL11A-12833 | - | GCGGGGAGCGAGCGCGGCGGCGGC | 24 | 15076 |
| BCL11A-12834 | - | CCGAGCGCAGCCGCGGGC | 18 | 15077 |
| BCL11A-12835 | - | CCCGAGCGCAGCCGCGGGC | 19 | 15078 |
| BCL11A-12836 | - | UCCCGAGCGCAGCCGCGGGC | 20 | 15079 |
| BCL11A-12837 | - | UUCCCGAGCGCAGCCGCGGGC | 21 | 15080 |
| BCL11A-12838 | - | UUUCCCGAGCGCAGCCGCGGGC | 22 | 15081 |
| BCL11A-12839 | - | GUUUCCCGAGCGCAGCCGCGGGC | 23 | 15082 |
| BCL11A-12840 | - | AGUUUCCCGAGCGCAGCCGCGGGC | 24 | 15083 |
| BCL11A-12841 | - | UCCAGGCCGCGCGGGCUC | 18 | 15084 |
| BCL11A-12842 | - | UUCCAGGCCGCGCGGGCUC | 19 | 15085 |
| BCL11A-12843 | - | UUUCCAGGCCGCGCGGGCUC | 20 | 15086 |
| BCL11A-12844 | - | CUUUCCAGGCCGCGCGGGCUC | 21 | 15087 |
| BCL11A-12845 | - | UCUUUCCAGGCCGCGCGGGCUC | 22 | 15088 |
| BCL11A-12846 | - | CUCUUUCCAGGCCGCGCGGGCUC | 23 | 15089 |
| BCL11A-12847 | - | CCUCUUUCCAGGCCGCGCGGGCUC | 24 | 15090 |
| BCL11A-12848 | - | UCCUGAGUCCGCGGAGUC | 18 | 15091 |
| BCL11A-12849 | - | CUCCUGAGUCCGCGGAGUC | 19 | 15092 |
| BCL11A-10128 | - | GCUCCUGAGUCCGCGGAGUC | 20 | 15093 |
| BCL11A-12850 | - | CGCUCCUGAGUCCGCGGAGUC | 21 | 15094 |
| BCL11A-12851 | - | GCGCUCCUGAGUCCGCGGAGUC | 22 | 15095 |
| BCL11A-12852 | - | GGCGCUCCUGAGUCCGCGGAGUC | 23 | 15096 |
| BCL11A-12853 | - | CGGCGCUCCUGAGUCCGCGGAGUC | 24 | 15097 |
| BCL11A-12854 | - | CGUACGGAGGAGGGUGUC | 18 | 15098 |
| BCL11A-12855 | - | GCGUACGGAGGAGGGUGUC | 19 | 15099 |
| BCL11A-10130 | - | UGCGUACGGAGGAGGGUGUC | 20 | 15100 |
| BCL11A-12856 | - | GUGCGUACGGAGGAGGGUGUC | 21 | 15101 |
| BCL11A-12857 | - | UGUGCGUACGGAGGAGGGUGUC | 22 | 15102 |
| BCL11A-12858 | - | GUGUGCGUACGGAGGAGGGUGUC | 23 | 15103 |
| BCL11A-12859 | - | GGUGUGCGUACGGAGGAGGGUGUC | 24 | 15104 |
| BCL11A-12860 | - | AAGUCUAAAAACGAUUC | 18 | 15105 |
| BCL11A-12861 | - | CAAGUCUAAAAACGAUUC | 19 | 15106 |

TABLE 19E-continued

5th Tier

| gRNA Name | DNA Strand | Targeting Domain | Target Site Length | SEQ ID NO: |
|---|---|---|---|---|
| BCL11A-12862 | - | ACAAGUCUAAAAAACGAUUC | 20 | 15107 |
| BCL11A-12863 | - | UACAAGUCUAAAAAACGAUUC | 21 | 15108 |
| BCL11A-12864 | - | GUACAAGUCUAAAAAACGAUUC | 22 | 15109 |
| BCL11A-12865 | - | AGUACAAGUCUAAAAAACGAUUC | 23 | 15110 |
| BCL11A-12866 | - | GAGUACAAGUCUAAAAAACGAUUC | 24 | 15111 |
| BCL11A-12867 | - | CUCCUCGGGCAAAGUUUC | 18 | 15112 |
| BCL11A-12868 | - | UCUCCUCGGGCAAAGUUUC | 19 | 15113 |
| BCL11A-12869 | - | CUCUCCUCGGGCAAAGUUUC | 20 | 15114 |
| BCL11A-12870 | - | CCUCUCCUCGGGCAAAGUUUC | 21 | 15115 |
| BCL11A-12871 | - | UCCUCUCCUCGGGCAAAGUUUC | 22 | 15116 |
| BCL11A-12872 | - | GUCCUCUCCUCGGGCAAAGUUUC | 23 | 15117 |
| BCL11A-12873 | - | UGUCCUCUCCUCGGGCAAAGUUUC | 24 | 15118 |
| BCL11A-12874 | - | UCACGGUCAAGUGUGCAG | 18 | 15119 |
| BCL11A-12875 | - | CUCACGGUCAAGUGUGCAG | 19 | 15120 |
| BCL11A-10145 | - | GCUCACGGUCAAGUGUGCAG | 20 | 15121 |
| BCL11A-12876 | - | CGCUCACGGUCAAGUGUGCAG | 21 | 15122 |
| BCL11A-12877 | - | GCGCUCACGGUCAAGUGUGCAG | 22 | 15123 |
| BCL11A-12878 | - | CGCGCUCACGGUCAAGUGUGCAG | 23 | 15124 |
| BCL11A-12879 | - | GCGCGCUCACGGUCAAGUGUGCAG | 24 | 15125 |
| BCL11A-12880 | - | UUCCCGGGGAGAAAAGAG | 18 | 15126 |
| BCL11A-12881 | - | AUUCCCGGGGAGAAAAGAG | 19 | 15127 |
| BCL11A-12882 | - | GAUUCCCGGGGAGAAAAGAG | 20 | 15128 |
| BCL11A-12883 | - | CGAUUCCCGGGGAGAAAAGAG | 21 | 15129 |
| BCL11A-12884 | - | ACGAUUCCCGGGGAGAAAAGAG | 22 | 15130 |
| BCL11A-12885 | - | AACGAUUCCCGGGGAGAAAAGAG | 23 | 15131 |
| BCL11A-12886 | - | AAACGAUUCCCGGGGAGAAAAGAG | 24 | 15132 |
| BCL11A-12887 | - | GCUCCUGAGUCCGCGGAG | 18 | 15133 |
| BCL11A-12888 | - | CGCUCCUGAGUCCGCGGAG | 19 | 15134 |
| BCL11A-12889 | - | GCGCUCCUGAGUCCGCGGAG | 20 | 15135 |
| BCL11A-12890 | - | GGCGCUCCUGAGUCCGCGGAG | 21 | 15136 |
| BCL11A-12891 | - | CGGCGCUCCUGAGUCCGCGGAG | 22 | 15137 |
| BCL11A-12892 | - | CCGGCGCUCCUGAGUCCGCGGAG | 23 | 15138 |
| BCL11A-12893 | - | CCCGGCGCUCCUGAGUCCGCGGAG | 24 | 15139 |
| BCL11A-12894 | - | AGUCCGCGGAGUCGGGAG | 18 | 15140 |
| BCL11A-12895 | - | GAGUCCGCGGAGUCGGGAG | 19 | 15141 |
| BCL11A-10150 | - | UGAGUCCGCGGAGUCGGGAG | 20 | 15142 |
| BCL11A-12896 | - | CUGAGUCCGCGGAGUCGGGAG | 21 | 15143 |

TABLE 19E-continued

5th Tier

| gRNA Name | DNA Strand | Targeting Domain | Target Site Length | SEQ ID NO: |
|---|---|---|---|---|
| BCL11A-12897 | - | CCUGAGUCCGCGGAGUCGGAG | 22 | 15144 |
| BCL11A-12898 | - | UCCUGAGUCCGCGGAGUCGGGAG | 23 | 15145 |
| BCL11A-12899 | - | CUCCUGAGUCCGCGGAGUCGGGAG | 24 | 15146 |
| BCL11A-12900 | - | CGCGGCGGCGGCGGGGAG | 18 | 15147 |
| BCL11A-12901 | - | GCGCGGCGGCGGCGGGGAG | 19 | 15148 |
| BCL11A-10152 | - | AGCGCGGCGGCGGCGGGGAG | 20 | 15149 |
| BCL11A-12902 | - | GAGCGCGGCGGCGGCGGGGAG | 21 | 15150 |
| BCL11A-12903 | - | CGAGCGCGGCGGCGGCGGGGAG | 22 | 15151 |
| BCL11A-12904 | - | GCGAGCGCGGCGGCGGCGGGGAG | 23 | 15152 |
| BCL11A-12905 | - | AGCGAGCGCGGCGGCGGCGGGGAG | 24 | 15153 |
| BCL11A-11434 | - | CGCGUGUGUGGGGGGGAG | 18 | 15154 |
| BCL11A-11435 | - | CCGCGUGUGUGGGGGGGAG | 19 | 15155 |
| BCL11A-11436 | - | UCCGCGUGUGUGGGGGGGAG | 20 | 15156 |
| BCL11A-11437 | - | GUCCGCGUGUGUGGGGGGGAG | 21 | 15157 |
| BCL11A-11438 | - | AGUCCGCGUGUGUGGGGGGGAG | 22 | 15158 |
| BCL11A-11439 | - | GAGUCCGCGUGUGUGGGGGGGAG | 23 | 15159 |
| BCL11A-11440 | - | AGAGUCCGCGUGUGUGGGGGGGAG | 24 | 15160 |
| BCL11A-12906 | - | GCCCUGGCGUCCACACG | 18 | 15161 |
| BCL11A-12907 | - | GGCCCUGGCGUCCACACG | 19 | 15162 |
| BCL11A-10156 | - | CGGCCCUGGCGUCCACACG | 20 | 15163 |
| BCL11A-12908 | - | UCGGCCCUGGCGUCCACACG | 21 | 15164 |
| BCL11A-12909 | - | UUCGGCCCUGGCGUCCACACG | 22 | 15165 |
| BCL11A-12910 | - | CUUCGGCCCUGGCGUCCACACG | 23 | 15166 |
| BCL11A-12911 | - | ACUUCGGCCCUGGCGUCCACACG | 24 | 15167 |
| BCL11A-12912 | - | AGAGGGGCCGCGGCGACG | 18 | 15168 |
| BCL11A-12913 | - | GAGAGGGGCCGCGGCGACG | 19 | 15169 |
| BCL11A-10158 | - | GGAGAGGGGCCGCGGCGACG | 20 | 15170 |
| BCL11A-12914 | - | GGGAGAGGGGCCGCGGCGACG | 21 | 15171 |
| BCL11A-12915 | - | CGGGAGAGGGGCCGCGGCGACG | 22 | 15172 |
| BCL11A-12916 | - | UCGGGAGAGGGGCCGCGGCGACG | 23 | 15173 |
| BCL11A-12917 | - | GUCGGGAGAGGGGCCGCGGCGACG | 24 | 15174 |
| BCL11A-12918 | - | GAAGUGGGUGUGCGUACG | 18 | 15175 |
| BCL11A-12919 | - | GGAAGUGGGUGUGCGUACG | 19 | 15176 |
| BCL11A-12920 | - | GGGAAGUGGGUGUGCGUACG | 20 | 15177 |
| BCL11A-12921 | - | GGGGAAGUGGGUGUGCGUACG | 21 | 15178 |
| BCL11A-12922 | - | AGGGGAAGUGGGUGUGCGUACG | 22 | 15179 |
| BCL11A-12923 | - | GAGGGGAAGUGGGUGUGCGUACG | 23 | 15180 |

TABLE 19E-continued

5th Tier

| gRNA Name | DNA Strand | Targeting Domain | Target Site Length | SEQ ID NO: |
|---|---|---|---|---|
| BCL11A-12924 | – | GGAGGGGAAGUGGGUGUGCGUACG | 24 | 15181 |
| BCL11A-12925 | – | UCUAAAAAACGAUUCCCG | 18 | 15182 |
| BCL11A-12926 | – | GUCUAAAAAACGAUUCCCG | 19 | 15183 |
| BCL11A-10164 | – | AGUCUAAAAAACGAUUCCCG | 20 | 15184 |
| BCL11A-12927 | – | AAGUCUAAAAAACGAUUCCCG | 21 | 15185 |
| BCL11A-12928 | – | CAAGUCUAAAAAACGAUUCCCG | 22 | 15186 |
| BCL11A-12929 | – | ACAAGUCUAAAAAACGAUUCCCG | 23 | 15187 |
| BCL11A-12930 | – | UACAAGUCUAAAAAACGAUUCCCG | 24 | 15188 |
| BCL11A-12931 | – | CGGCGACGGGGAGAGCCG | 18 | 15189 |
| BCL11A-12932 | – | GCGGCGACGGGGAGAGCCG | 19 | 15190 |
| BCL11A-10166 | – | CGCGGCGACGGGGAGAGCCG | 20 | 15191 |
| BCL11A-12933 | – | CCGCGGCGACGGGGAGAGCCG | 21 | 15192 |
| BCL11A-12934 | – | GCCGCGGCGACGGGGAGAGCCG | 22 | 15193 |
| BCL11A-12935 | – | GGCCGCGGCGACGGGGAGAGCCG | 23 | 15194 |
| BCL11A-12936 | – | GGGCCGCGGCGACGGGGAGAGCCG | 24 | 15195 |
| BCL11A-12937 | – | CCCUGGCGUCCACACGCG | 18 | 15196 |
| BCL11A-12938 | – | CCCCUGGCGUCCACACGCG | 19 | 15197 |
| BCL11A-10175 | – | GCCCCUGGCGUCCACACGCG | 20 | 15198 |
| BCL11A-12939 | – | GGCCCCUGGCGUCCACACGCG | 21 | 15199 |
| BCL11A-12940 | – | CGGCCCCUGGCGUCCACACGCG | 22 | 15200 |
| BCL11A-12941 | – | UCGGCCCCUGGCGUCCACACGCG | 23 | 15201 |
| BCL11A-12942 | – | UUCGGCCCCUGGCGUCCACACGCG | 24 | 15202 |
| BCL11A-12943 | – | GGGAGAGGGGCCGCGGCG | 18 | 15203 |
| BCL11A-12944 | – | CGGGAGAGGGGCCGCGGCG | 19 | 15204 |
| BCL11A-12945 | – | UCGGGAGAGGGGCCGCGGCG | 20 | 15205 |
| BCL11A-12946 | – | GUCGGGAGAGGGGCCGCGGCG | 21 | 15206 |
| BCL11A-12947 | – | AGUCGGGAGAGGGGCCGCGGCG | 22 | 15207 |
| BCL11A-12948 | – | GAGUCGGGAGAGGGGCCGCGGCG | 23 | 15208 |
| BCL11A-12949 | – | GGAGUCGGGAGAGGGGCCGCGGCG | 24 | 15209 |
| BCL11A-12950 | – | GGAGCGAGCGCGGCGGCG | 18 | 15210 |
| BCL11A-12951 | – | GGGAGCGAGCGCGGCGGCG | 19 | 15211 |
| BCL11A-12952 | – | GGGGAGCGAGCGCGGCGGCG | 20 | 15212 |
| BCL11A-12953 | – | CGGGGAGCGAGCGCGGCGGCG | 21 | 15213 |
| BCL11A-12954 | – | GCGGGGAGCGAGCGCGGCGGCG | 22 | 15214 |
| BCL11A-12955 | – | CGCGGGGAGCGAGCGCGGCGGCG | 23 | 15215 |
| BCL11A-12956 | – | ACGCGGGGAGCGAGCGCGGCGGCG | 24 | 15216 |
| BCL11A-12957 | – | GCGAGCGCGGCGGCGGCG | 18 | 15217 |

TABLE 19E-continued

5th Tier

| gRNA Name | DNA Strand | Targeting Domain | Target Site Length | SEQ ID NO: |
|---|---|---|---|---|
| BCL11A-12958 | - | AGCGAGCGCGGCGGCGGCG | 19 | 15218 |
| BCL11A-10179 | - | GAGCGAGCGCGGCGGCGGCG | 20 | 15219 |
| BCL11A-12959 | - | GGAGCGAGCGCGGCGGCGGCG | 21 | 15220 |
| BCL11A-12960 | - | GGGAGCGAGCGCGGCGGCGGCG | 22 | 15221 |
| BCL11A-12961 | - | GGGGAGCGAGCGCGGCGGCGGCG | 23 | 15222 |
| BCL11A-12962 | - | CGGGGAGCGAGCGCGGCGGCGGCG | 24 | 15223 |
| BCL11A-12963 | - | GCCGUGGGACCGGGAAGG | 18 | 15224 |
| BCL11A-12964 | - | AGCCGUGGGACCGGGAAGG | 19 | 15225 |
| BCL11A-12965 | - | GAGCCGUGGGACCGGGAAGG | 20 | 15226 |
| BCL11A-12966 | - | AGAGCCGUGGGACCGGGAAGG | 21 | 15227 |
| BCL11A-12967 | - | GAGAGCCGUGGGACCGGGAAGG | 22 | 15228 |
| BCL11A-12968 | - | GGAGAGCCGUGGGACCGGGAAGG | 23 | 15229 |
| BCL11A-12969 | - | GGGAGAGCCGUGGGACCGGGAAGG | 24 | 15230 |
| BCL11A-12970 | - | AGAAAAUGGGGGGUAGG | 18 | 15231 |
| BCL11A-12971 | - | AAGAAAAUGGGGGGUAGG | 19 | 15232 |
| BCL11A-12972 | - | UAAGAAAAUGGGGGGUAGG | 20 | 15233 |
| BCL11A-12973 | - | GUAAGAAAAUGGGGGGUAGG | 21 | 15234 |
| BCL11A-12974 | - | CGUAAGAAAAUGGGGGGUAGG | 22 | 15235 |
| BCL11A-12975 | - | CCGUAAGAAAAUGGGGGGUAGG | 23 | 15236 |
| BCL11A-12976 | - | ACCGUAAGAAAAUGGGGGGUAGG | 24 | 15237 |
| BCL11A-12977 | - | AAGUGGGUGUGCGUACGG | 18 | 15238 |
| BCL11A-12978 | - | GAAGUGGGUGUGCGUACGG | 19 | 15239 |
| BCL11A-10191 | - | GGAAGUGGGUGUGCGUACGG | 20 | 15240 |
| BCL11A-12979 | - | GGGAAGUGGGUGUGCGUACGG | 21 | 15241 |
| BCL11A-12980 | - | GGGGAAGUGGGUGUGCGUACGG | 22 | 15242 |
| BCL11A-12981 | - | AGGGGAAGUGGGUGUGCGUACGG | 23 | 15243 |
| BCL11A-12982 | - | GAGGGGAAGUGGGUGUGCGUACGG | 24 | 15244 |
| BCL11A-12983 | - | CGGUCAAGUGUGCAGCGG | 18 | 15245 |
| BCL11A-12984 | - | ACGGUCAAGUGUGCAGCGG | 19 | 15246 |
| BCL11A-12985 | - | CACGGUCAAGUGUGCAGCGG | 20 | 15247 |
| BCL11A-12986 | - | UCACGGUCAAGUGUGCAGCGG | 21 | 15248 |
| BCL11A-12987 | - | CUCACGGUCAAGUGUGCAGCGG | 22 | 15249 |
| BCL11A-12988 | - | GCUCACGGUCAAGUGUGCAGCGG | 23 | 15250 |
| BCL11A-12989 | - | CGCUCACGGUCAAGUGUGCAGCGG | 24 | 15251 |
| BCL11A-12990 | - | GAGCGAGCGCGGCGGCGG | 18 | 15252 |
| BCL11A-12991 | - | GGAGCGAGCGCGGCGGCGG | 19 | 15253 |
| BCL11A-10196 | - | GGGAGCGAGCGCGGCGGCGG | 20 | 15254 |

TABLE 19E-continued

5th Tier

| gRNA Name | DNA Strand | Targeting Domain | Target Site Length | SEQ ID NO: |
|---|---|---|---|---|
| BCL11A-12992 | − | GGGGAGCGAGCGCGGCGGCGG | 21 | 15255 |
| BCL11A-12993 | − | CGGGGAGCGAGCGCGGCGGCGG | 22 | 15256 |
| BCL11A-12994 | − | GCGGGGAGCGAGCGCGGCGGCGG | 23 | 15257 |
| BCL11A-12995 | − | CGCGGGGAGCGAGCGCGGCGGCGG | 24 | 15258 |
| BCL11A-12996 | − | CUGAGUCCGCGGAGUCGG | 18 | 15259 |
| BCL11A-12997 | − | CCUGAGUCCGCGGAGUCGG | 19 | 15260 |
| BCL11A-12998 | − | UCCUGAGUCCGCGGAGUCGG | 20 | 15261 |
| BCL11A-12999 | − | CUCCUGAGUCCGCGGAGUCGG | 21 | 15262 |
| BCL11A-13000 | − | GCUCCUGAGUCCGCGGAGUCGG | 22 | 15263 |
| BCL11A-13001 | − | CGCUCCUGAGUCCGCGGAGUCGG | 23 | 15264 |
| BCL11A-13002 | − | GCGCUCCUGAGUCCGCGGAGUCGG | 24 | 15265 |
| BCL11A-13003 | − | GAAAAUGGGGGGUAGGG | 18 | 15266 |
| BCL11A-13004 | − | AGAAAAUGGGGGGUAGGG | 19 | 15267 |
| BCL11A-10200 | − | AAGAAAAUGGGGGGUAGGG | 20 | 15268 |
| BCL11A-13005 | − | UAAGAAAAUGGGGGGUAGGG | 21 | 15269 |
| BCL11A-13006 | − | GUAAGAAAAUGGGGGGUAGGG | 22 | 15270 |
| BCL11A-13007 | − | CGUAAGAAAAUGGGGGGUAGGG | 23 | 15271 |
| BCL11A-13008 | − | CCGUAAGAAAAUGGGGGGUAGGG | 24 | 15272 |
| BCL11A-13009 | − | AGGGGCCGCGGCGACGGG | 18 | 15273 |
| BCL11A-13010 | − | GAGGGGCCGCGGCGACGGG | 19 | 15274 |
| BCL11A-13011 | − | AGAGGGGCCGCGGCGACGGG | 20 | 15275 |
| BCL11A-13012 | − | GAGAGGGGCCGCGGCGACGGG | 21 | 15276 |
| BCL11A-13013 | − | GGAGAGGGGCCGCGGCGACGGG | 22 | 15277 |
| BCL11A-13014 | − | GGGAGAGGGGCCGCGGCGACGGG | 23 | 15278 |
| BCL11A-13015 | − | CGGGAGAGGGGCCGCGGCGACGGG | 24 | 15279 |
| BCL11A-13016 | − | GAGAGCCGUGGGACCGGG | 18 | 15280 |
| BCL11A-13017 | − | GGAGAGCCGUGGGACCGGG | 19 | 15281 |
| BCL11A-13018 | − | GGGAGAGCCGUGGGACCGGG | 20 | 15282 |
| BCL11A-13019 | − | GGGGAGAGCCGUGGGACCGGG | 21 | 15283 |
| BCL11A-13020 | − | CGGGGAGAGCCGUGGGACCGGG | 22 | 15284 |
| BCL11A-13021 | − | ACGGGGAGAGCCGUGGGACCGGG | 23 | 15285 |
| BCL11A-13022 | − | GACGGGGAGAGCCGUGGGACCGGG | 24 | 15286 |
| BCL11A-13023 | − | UAAAAAACGAUUCCCGGG | 18 | 15287 |
| BCL11A-13024 | − | CUAAAAAACGAUUCCCGGG | 19 | 15288 |
| BCL11A-13025 | − | UCUAAAAAACGAUUCCCGGG | 20 | 15289 |
| BCL11A-13026 | − | GUCUAAAAAACGAUUCCCGGG | 21 | 15290 |
| BCL11A-13027 | − | AGUCUAAAAAACGAUUCCCGGG | 22 | 15291 |

TABLE 19E-continued

5th Tier

| gRNA Name | DNA Strand | Targeting Domain | Target Site Length | SEQ ID NO: |
|---|---|---|---|---|
| BCL11A-13028 | - | AAGUCUAAAAAACGAUUCCCGGG | 23 | 15292 |
| BCL11A-13029 | - | CAAGUCUAAAAAACGAUUCCCGGG | 24 | 15293 |
| BCL11A-13030 | - | GGUCAAGUGUGCAGCGGG | 18 | 15294 |
| BCL11A-13031 | - | CGGUCAAGUGUGCAGCGGG | 19 | 15295 |
| BCL11A-10202 | - | ACGGUCAAGUGUGCAGCGGG | 20 | 15296 |
| BCL11A-13032 | - | CACGGUCAAGUGUGCAGCGGG | 21 | 15297 |
| BCL11A-13033 | - | UCACGGUCAAGUGUGCAGCGGG | 22 | 15298 |
| BCL11A-13034 | - | CUCACGGUCAAGUGUGCAGCGGG | 23 | 15299 |
| BCL11A-13035 | - | GCUCACGGUCAAGUGUGCAGCGGG | 24 | 15300 |
| BCL11A-13036 | - | GAGCGCGGCGGCGGCGGG | 18 | 15301 |
| BCL11A-13037 | - | CGAGCGCGGCGGCGGCGGG | 19 | 15302 |
| BCL11A-13038 | - | GCGAGCGCGGCGGCGGCGGG | 20 | 15303 |
| BCL11A-13039 | - | AGCGAGCGCGGCGGCGGCGGG | 21 | 15304 |
| BCL11A-13040 | - | GAGCGAGCGCGGCGGCGGCGGG | 22 | 15305 |
| BCL11A-13041 | - | GGAGCGAGCGCGGCGGCGGCGGG | 23 | 15306 |
| BCL11A-13042 | - | GGGAGCGAGCGCGGCGGCGGCGGG | 24 | 15307 |
| BCL11A-13043 | - | AGCGCGGCGGCGGCGGGG | 18 | 15308 |
| BCL11A-13044 | - | GAGCGCGGCGGCGGCGGGG | 19 | 15309 |
| BCL11A-10206 | - | CGAGCGCGGCGGCGGCGGGG | 20 | 15310 |
| BCL11A-13045 | - | GCGAGCGCGGCGGCGGCGGGG | 21 | 15311 |
| BCL11A-13046 | - | AGCGAGCGCGGCGGCGGCGGGG | 22 | 15312 |
| BCL11A-13047 | - | GAGCGAGCGCGGCGGCGGCGGGG | 23 | 15313 |
| BCL11A-13048 | - | GGAGCGAGCGCGGCGGCGGCGGGG | 24 | 15314 |
| BCL11A-13049 | - | CGUAAGAAAAUGGGGGGG | 18 | 15315 |
| BCL11A-13050 | - | CCGUAAGAAAAUGGGGGGG | 19 | 15316 |
| BCL11A-13051 | - | ACCGUAAGAAAAUGGGGGGG | 20 | 15317 |
| BCL11A-13052 | - | CACCGUAAGAAAAUGGGGGGG | 21 | 15318 |
| BCL11A-13053 | - | UCACCGUAAGAAAAUGGGGGGG | 22 | 15319 |
| BCL11A-13054 | - | CUCACCGUAAGAAAAUGGGGGGG | 23 | 15320 |
| BCL11A-13055 | - | ACUCACCGUAAGAAAAUGGGGGGG | 24 | 15321 |
| BCL11A-13056 | - | CACAUGCAAACCUGGGGG | 18 | 15322 |
| BCL11A-13057 | - | UCACAUGCAAACCUGGGGG | 19 | 15323 |
| BCL11A-10210 | - | CUCACAUGCAAACCUGGGGG | 20 | 15324 |
| BCL11A-13058 | - | ACUCACAUGCAAACCUGGGGG | 21 | 15325 |
| BCL11A-13059 | - | AACUCACAUGCAAACCUGGGGG | 22 | 15326 |
| BCL11A-13060 | - | CAACUCACAUGCAAACCUGGGGG | 23 | 15327 |
| BCL11A-13061 | - | ACAACUCACAUGCAAACCUGGGGG | 24 | 15328 |

TABLE 19E-continued

5th Tier

| gRNA Name | DNA Strand | Targeting Domain | Target Site Length | SEQ ID NO: |
|---|---|---|---|---|
| BCL11A-13062 | - | UCACAUGCAAACCUGGGG | 18 | 15329 |
| BCL11A-13063 | - | CUCACAUGCAAACCUGGGG | 19 | 15330 |
| BCL11A-13064 | - | ACUCACAUGCAAACCUGGGG | 20 | 15331 |
| BCL11A-13065 | - | AACUCACAUGCAAACCUGGGG | 21 | 15332 |
| BCL11A-13066 | - | CAACUCACAUGCAAACCUGGGG | 22 | 15333 |
| BCL11A-13067 | - | ACAACUCACAUGCAAACCUGGGG | 23 | 15334 |
| BCL11A-13068 | - | AACAACUCACAUGCAAACCUGGGG | 24 | 15335 |
| BCL11A-11486 | - | GAGUCCGCGUGUGUGGGG | 18 | 15336 |
| BCL11A-11487 | - | AGAGUCCGCGUGUGUGGGG | 19 | 15337 |
| BCL11A-9577 | - | UAGAGUCCGCGUGUGUGGGG | 20 | 15338 |
| BCL11A-11488 | - | UUAGAGUCCGCGUGUGUGGGG | 21 | 15339 |
| BCL11A-11489 | - | UUUAGAGUCCGCGUGUGUGGGG | 22 | 15340 |
| BCL11A-11490 | - | UUUUAGAGUCCGCGUGUGUGGGG | 23 | 15341 |
| BCL11A-11491 | - | AUUUUAGAGUCCGCGUGUGUGGGG | 24 | 15342 |
| BCL11A-11492 | - | AGAGUCCGCGUGUGUGGG | 18 | 15343 |
| BCL11A-11493 | - | UAGAGUCCGCGUGUGUGGG | 19 | 15344 |
| BCL11A-9769 | - | UUAGAGUCCGCGUGUGUGGG | 20 | 15345 |
| BCL11A-11494 | - | UUUAGAGUCCGCGUGUGUGGG | 21 | 15346 |
| BCL11A-11495 | - | UUUUAGAGUCCGCGUGUGUGGG | 22 | 15347 |
| BCL11A-11496 | - | AUUUUAGAGUCCGCGUGUGUGGG | 23 | 15348 |
| BCL11A-11497 | - | CAUUUUAGAGUCCGCGUGUGUGGG | 24 | 15349 |
| BCL11A-13069 | - | CCUGGGGGUGGGAGCUGG | 18 | 15350 |
| BCL11A-13070 | - | ACCUGGGGGUGGGAGCUGG | 19 | 15351 |
| BCL11A-10217 | - | AACCUGGGGGUGGGAGCUGG | 20 | 15352 |
| BCL11A-13071 | - | AAACCUGGGGGUGGGAGCUGG | 21 | 15353 |
| BCL11A-13072 | - | CAAACCUGGGGGUGGGAGCUGG | 22 | 15354 |
| BCL11A-13073 | - | GCAAACCUGGGGGUGGGAGCUGG | 23 | 15355 |
| BCL11A-13074 | - | UGCAAACCUGGGGGUGGGAGCUGG | 24 | 15356 |
| BCL11A-11498 | - | UAGAGUCCGCGUGUGUGG | 18 | 15357 |
| BCL11A-11499 | - | UUAGAGUCCGCGUGUGUGG | 19 | 15358 |
| BCL11A-9578 | - | UUUAGAGUCCGCGUGUGUGG | 20 | 15359 |
| BCL11A-11500 | - | UUUUAGAGUCCGCGUGUGUGG | 21 | 15360 |
| BCL11A-11501 | - | AUUUUAGAGUCCGCGUGUGUGG | 22 | 15361 |
| BCL11A-11502 | - | CAUUUUAGAGUCCGCGUGUGUGG | 23 | 15362 |
| BCL11A-11503 | - | UCAUUUUAGAGUCCGCGUGUGUGG | 24 | 15363 |
| BCL11A-13075 | - | ACUCACCGUAAGAAAAUG | 18 | 15364 |
| BCL11A-13076 | - | CACUCACCGUAAGAAAAUG | 19 | 15365 |

TABLE 19E-continued

5th Tier

| gRNA Name | DNA Strand | Targeting Domain | Target Site Length | SEQ ID NO: |
|---|---|---|---|---|
| BCL11A-10221 | - | CCACUCACCGUAAGAAAAUG | 20 | 15366 |
| BCL11A-13077 | - | CCCACUCACCGUAAGAAAAUG | 21 | 15367 |
| BCL11A-13078 | - | UCCCACUCACCGUAAGAAAAUG | 22 | 15368 |
| BCL11A-13079 | - | UUCCCACUCACCGUAAGAAAAUG | 23 | 15369 |
| BCL11A-13080 | - | CUUCCCACUCACCGUAAGAAAAUG | 24 | 15370 |
| BCL11A-13081 | - | AGUGAGAAAGUGGCACUG | 18 | 15371 |
| BCL11A-13082 | - | UAGUGAGAAAGUGGCACUG | 19 | 15372 |
| BCL11A-10222 | - | AUAGUGAGAAAGUGGCACUG | 20 | 15373 |
| BCL11A-13083 | - | AAUAGUGAGAAAGUGGCACUG | 21 | 15374 |
| BCL11A-13084 | - | CAAUAGUGAGAAAGUGGCACUG | 22 | 15375 |
| BCL11A-13085 | - | ACAAUAGUGAGAAAGUGGCACUG | 23 | 15376 |
| BCL11A-13086 | - | CACAAUAGUGAGAAAGUGGCACUG | 24 | 15377 |
| BCL11A-13087 | - | ACCUGGGGUGGGAGCUG | 18 | 15378 |
| BCL11A-13088 | - | AACCUGGGGUGGGAGCUG | 19 | 15379 |
| BCL11A-13089 | - | AAACCUGGGGUGGGAGCUG | 20 | 15380 |
| BCL11A-13090 | - | CAAACCUGGGGUGGGAGCUG | 21 | 15381 |
| BCL11A-13091 | - | GCAAACCUGGGGUGGGAGCUG | 22 | 15382 |
| BCL11A-13092 | - | UGCAAACCUGGGGUGGGAGCUG | 23 | 15383 |
| BCL11A-13093 | - | AUGCAAACCUGGGGUGGGAGCUG | 24 | 15384 |
| BCL11A-13094 | - | ACCUCCCCUCGCCCGCUG | 18 | 15385 |
| BCL11A-13095 | - | CACCUCCCCUCGCCCGCUG | 19 | 15386 |
| BCL11A-10224 | - | CCACCUCCCCUCGCCCGCUG | 20 | 15387 |
| BCL11A-13096 | - | CCCACCUCCCCUCGCCCGCUG | 21 | 15388 |
| BCL11A-13097 | - | UCCCACCUCCCCUCGCCCGCUG | 22 | 15389 |
| BCL11A-13098 | - | CUCCCACCUCCCCUCGCCCGCUG | 23 | 15390 |
| BCL11A-13099 | - | CCUCCCACCUCCCCUCGCCCGCUG | 24 | 15391 |
| BCL11A-13100 | - | UGGGGGUGGGAGCUGGUG | 18 | 15392 |
| BCL11A-13101 | - | CUGGGGGUGGGAGCUGGUG | 19 | 15393 |
| BCL11A-10228 | - | CCUGGGGGUGGGAGCUGGUG | 20 | 15394 |
| BCL11A-13102 | - | ACCUGGGGGUGGGAGCUGGUG | 21 | 15395 |
| BCL11A-13103 | - | AACCUGGGGGUGGGAGCUGGUG | 22 | 15396 |
| BCL11A-13104 | - | AAACCUGGGGGUGGGAGCUGGUG | 23 | 15397 |
| BCL11A-13105 | - | CAAACCUGGGGGUGGGAGCUGGUG | 24 | 15398 |
| BCL11A-11518 | - | UUUUAGAGUCCGCGUGUG | 18 | 15399 |
| BCL11A-11519 | - | AUUUUAGAGUCCGCGUGUG | 19 | 15400 |
| BCL11A-9581 | - | CAUUUUAGAGUCCGCGUGUG | 20 | 15401 |
| BCL11A-11520 | - | UCAUUUUAGAGUCCGCGUGUG | 21 | 15402 |

TABLE 19E-continued

5th Tier

| gRNA Name | DNA Strand | Targeting Domain | Target Site Length | SEQ ID NO: |
|---|---|---|---|---|
| BCL11A-11521 | - | UUCAUUUUAGAGUCCGCGUGUG | 22 | 15403 |
| BCL11A-11522 | - | UUUCAUUUUAGAGUCCGCGUGUG | 23 | 15404 |
| BCL11A-11523 | - | CUUUCAUUUUAGAGUCCGCGUGUG | 24 | 15405 |
| BCL11A-11524 | - | UUAGAGUCCGCGUGUGUG | 18 | 15406 |
| BCL11A-11525 | - | UUUAGAGUCCGCGUGUGUG | 19 | 15407 |
| BCL11A-9776 | - | UUUUAGAGUCCGCGUGUGUG | 20 | 15408 |
| BCL11A-11526 | - | AUUUUAGAGUCCGCGUGUGUG | 21 | 15409 |
| BCL11A-11527 | - | CAUUUUAGAGUCCGCGUGUGUG | 22 | 15410 |
| BCL11A-11528 | - | UCAUUUUAGAGUCCGCGUGUGUG | 23 | 15411 |
| BCL11A-11529 | - | UUCAUUUUAGAGUCCGCGUGUGUG | 24 | 15412 |
| BCL11A-13106 | - | CACUCACCGUAAGAAAAU | 18 | 15413 |
| BCL11A-13107 | - | CCACUCACCGUAAGAAAAU | 19 | 15414 |
| BCL11A-10232 | - | CCCACUCACCGUAAGAAAAU | 20 | 15415 |
| BCL11A-13108 | - | UCCCACUCACCGUAAGAAAAU | 21 | 15416 |
| BCL11A-13109 | - | UUCCCACUCACCGUAAGAAAAU | 22 | 15417 |
| BCL11A-13110 | - | CUUCCCACUCACCGUAAGAAAAU | 23 | 15418 |
| BCL11A-13111 | - | GCUUCCCACUCACCGUAAGAAAAU | 24 | 15419 |
| BCL11A-13112 | - | CGCUGCGGAGCUGUAACU | 18 | 15420 |
| BCL11A-13113 | - | CCGCUGCGGAGCUGUAACU | 19 | 15421 |
| BCL11A-10233 | - | CCCGCUGCGGAGCUGUAACU | 20 | 15422 |
| BCL11A-13114 | - | GCCCGCUGCGGAGCUGUAACU | 21 | 15423 |
| BCL11A-13115 | - | CGCCCGCUGCGGAGCUGUAACU | 22 | 15424 |
| BCL11A-13116 | - | UCGCCCGCUGCGGAGCUGUAACU | 23 | 15425 |
| BCL11A-13117 | - | CUCGCCCGCUGCGGAGCUGUAACU | 24 | 15426 |
| BCL11A-13118 | - | UAGUGAGAAAGUGGCACU | 18 | 15427 |
| BCL11A-13119 | - | AUAGUGAGAAAGUGGCACU | 19 | 15428 |
| BCL11A-13120 | - | AAUAGUGAGAAAGUGGCACU | 20 | 15429 |
| BCL11A-13121 | - | CAAUAGUGAGAAAGUGGCACU | 21 | 15430 |
| BCL11A-13122 | - | ACAAUAGUGAGAAAGUGGCACU | 22 | 15431 |
| BCL11A-13123 | - | CACAAUAGUGAGAAAGUGGCACU | 23 | 15432 |
| BCL11A-13124 | - | CCACAAUAGUGAGAAAGUGGCACU | 24 | 15433 |
| BCL11A-13125 | - | CGGUCCCUGGCUCGGCCU | 18 | 15434 |
| BCL11A-13126 | - | CCGGUCCCUGGCUCGGCCU | 19 | 15435 |
| BCL11A-10237 | - | CCCGGUCCCUGGCUCGGCCU | 20 | 15436 |
| BCL11A-13127 | - | CACCUCCCCUCGCCCGCU | 18 | 15437 |
| BCL11A-13128 | - | CCACCUCCCCUCGCCCGCU | 19 | 15438 |
| BCL11A-13129 | - | CCCACCUCCCCUCGCCCGCU | 20 | 15439 |

TABLE 19E-continued

5th Tier

| gRNA Name | DNA Strand | Targeting Domain | Target Site Length | SEQ ID NO: |
|---|---|---|---|---|
| BCL11A-13130 | - | UCCCACCUCCCCUCGCCCGCU | 21 | 15440 |
| BCL11A-13131 | - | CUCCCACCUCCCCUCGCCCGCU | 22 | 15441 |
| BCL11A-13132 | - | CCUCCCACCUCCCCUCGCCCGCU | 23 | 15442 |
| BCL11A-13133 | - | CCCUCCCACCUCCCCUCGCCCGCU | 24 | 15443 |
| BCL11A-13134 | - | CGAGCGCAGCCGCGGGCU | 18 | 15444 |
| BCL11A-13135 | - | CCGAGCGCAGCCGCGGGCU | 19 | 15445 |
| BCL11A-10241 | - | CCCGAGCGCAGCCGCGGGCU | 20 | 15446 |
| BCL11A-13136 | - | UCCCGAGCGCAGCCGCGGGCU | 21 | 15447 |
| BCL11A-13137 | - | UUCCCGAGCGCAGCCGCGGGCU | 22 | 15448 |
| BCL11A-13138 | - | UUUCCCGAGCGCAGCCGCGGGCU | 23 | 15449 |
| BCL11A-13139 | - | GUUUCCCGAGCGCAGCCGCGGGCU | 24 | 15450 |
| BCL11A-13140 | - | CUCCUGAGUCCGCGGAGU | 18 | 15451 |
| BCL11A-13141 | - | GCUCCUGAGUCCGCGGAGU | 19 | 15452 |
| BCL11A-10243 | - | CGCUCCUGAGUCCGCGGAGU | 20 | 15453 |
| BCL11A-13142 | - | GCGCUCCUGAGUCCGCGGAGU | 21 | 15454 |
| BCL11A-13143 | - | GGCGCUCCUGAGUCCGCGGAGU | 22 | 15455 |
| BCL11A-13144 | - | CGGCGCUCCUGAGUCCGCGGAGU | 23 | 15456 |
| BCL11A-13145 | - | CCGGCGCUCCUGAGUCCGCGGAGU | 24 | 15457 |
| BCL11A-13146 | - | AGUCAUCCCCACAAUAGU | 18 | 15458 |
| BCL11A-13147 | - | UAGUCAUCCCCACAAUAGU | 19 | 15459 |
| BCL11A-13148 | - | GUAGUCAUCCCCACAAUAGU | 20 | 15460 |
| BCL11A-13149 | - | AGUAGUCAUCCCCACAAUAGU | 21 | 15461 |
| BCL11A-13150 | - | AAGUAGUCAUCCCCACAAUAGU | 22 | 15462 |
| BCL11A-13151 | - | AAAGUAGUCAUCCCCACAAUAGU | 23 | 15463 |
| BCL11A-13152 | - | GAAAGUAGUCAUCCCCACAAUAGU | 24 | 15464 |
| BCL11A-13153 | - | UUGCUUCCCACUCACCGU | 18 | 15465 |
| BCL11A-13154 | - | GUUGCUUCCCACUCACCGU | 19 | 15466 |
| BCL11A-13155 | - | GGUUGCUUCCCACUCACCGU | 20 | 15467 |
| BCL11A-13156 | - | AGGUUGCUUCCCACUCACCGU | 21 | 15468 |
| BCL11A-13157 | - | GAGGUUGCUUCCCACUCACCGU | 22 | 15469 |
| BCL11A-13158 | - | GGAGGUUGCUUCCCACUCACCGU | 23 | 15470 |
| BCL11A-13159 | - | GGGAGGUUGCUUCCCACUCACCGU | 24 | 15471 |
| BCL11A-13160 | - | GGGGAAGUGGGUGUGCGU | 18 | 15472 |
| BCL11A-13161 | - | AGGGGAAGUGGGUGUGCGU | 19 | 15473 |
| BCL11A-13162 | - | GAGGGGAAGUGGGUGUGCGU | 20 | 15474 |
| BCL11A-13163 | - | GGAGGGGAAGUGGGUGUGCGU | 21 | 15475 |
| BCL11A-13164 | - | GGGAGGGGAAGUGGGUGUGCGU | 22 | 15476 |

TABLE 19E-continued

5th Tier

| gRNA Name | DNA Strand | Targeting Domain | Target Site Length | SEQ ID NO: |
|---|---|---|---|---|
| BCL11A-13165 | - | GGGGAGGGGAAGUGGGUGUGCGU | 23 | 15477 |
| BCL11A-13166 | - | CGGGGAGGGGAAGUGGGUGUGCGU | 24 | 15478 |
| BCL11A-13167 | - | GUAAGAAAAUGGGGGGU | 18 | 15479 |
| BCL11A-13168 | - | CGUAAGAAAAUGGGGGGU | 19 | 15480 |
| BCL11A-10248 | - | CCGUAAGAAAAUGGGGGGU | 20 | 15481 |
| BCL11A-13169 | - | ACCGUAAGAAAAUGGGGGGU | 21 | 15482 |
| BCL11A-13170 | - | CACCGUAAGAAAAUGGGGGGU | 22 | 15483 |
| BCL11A-13171 | - | UCACCGUAAGAAAAUGGGGGGU | 23 | 15484 |
| BCL11A-13172 | - | CUCACCGUAAGAAAAUGGGGGGU | 24 | 15485 |
| BCL11A-13173 | - | ACAUGCAAACCUGGGGU | 18 | 15486 |
| BCL11A-13174 | - | CACAUGCAAACCUGGGGU | 19 | 15487 |
| BCL11A-10249 | - | UCACAUGCAAACCUGGGGU | 20 | 15488 |
| BCL11A-13175 | - | CUCACAUGCAAACCUGGGGU | 21 | 15489 |
| BCL11A-13176 | - | ACUCACAUGCAAACCUGGGGU | 22 | 15490 |
| BCL11A-13177 | - | AACUCACAUGCAAACCUGGGGU | 23 | 15491 |
| BCL11A-13178 | - | CAACUCACAUGCAAACCUGGGGU | 24 | 15492 |
| BCL11A-13179 | - | CUGGGGGUGGGAGCUGGU | 18 | 15493 |
| BCL11A-13180 | - | CCUGGGGGUGGGAGCUGGU | 19 | 15494 |
| BCL11A-10250 | - | ACCUGGGGGUGGGAGCUGGU | 20 | 15495 |
| BCL11A-13181 | - | AACCUGGGGGUGGGAGCUGGU | 21 | 15496 |
| BCL11A-13182 | - | AAACCUGGGGGUGGGAGCUGGU | 22 | 15497 |
| BCL11A-13183 | - | CAAACCUGGGGGUGGGAGCUGGU | 23 | 15498 |
| BCL11A-13184 | - | GCAAACCUGGGGGUGGGAGCUGGU | 24 | 15499 |
| BCL11A-11572 | - | AUUUUAGAGUCCGCGUGU | 18 | 15500 |
| BCL11A-11573 | - | CAUUUUAGAGUCCGCGUGU | 19 | 15501 |
| BCL11A-11574 | - | UCAUUUUAGAGUCCGCGUGU | 20 | 15502 |
| BCL11A-11575 | - | UUCAUUUUAGAGUCCGCGUGU | 21 | 15503 |
| BCL11A-11576 | - | UUUCAUUUUAGAGUCCGCGUGU | 22 | 15504 |
| BCL11A-11577 | - | CUUUCAUUUUAGAGUCCGCGUGU | 23 | 15505 |
| BCL11A-11578 | - | UCUUUCAUUUUAGAGUCCGCGUGU | 24 | 15506 |
| BCL11A-13185 | - | GCGUACGGAGGAGGGUGU | 18 | 15507 |
| BCL11A-13186 | - | UGCGUACGGAGGAGGGUGU | 19 | 15508 |
| BCL11A-13187 | - | GUGCGUACGGAGGAGGGUGU | 20 | 15509 |
| BCL11A-13188 | - | UGUGCGUACGGAGGAGGGUGU | 21 | 15510 |
| BCL11A-13189 | - | GUGUGCGUACGGAGGAGGGUGU | 22 | 15511 |
| BCL11A-13190 | - | GGUGUGCGUACGGAGGAGGGUGU | 23 | 15512 |
| BCL11A-13191 | - | GGGUGUGCGUACGGAGGAGGGUGU | 24 | 15513 |

TABLE 19E-continued

5th Tier

| gRNA Name | DNA Strand | Targeting Domain | Target Site Length | SEQ ID NO: |
|---|---|---|---|---|
| BCL11A-11579 | - | UUUAGAGUCCGCGUGUGU | 18 | 15514 |
| BCL11A-11580 | - | UUUUAGAGUCCGCGUGUGU | 19 | 15515 |
| BCL11A-9586 | - | AUUUUAGAGUCCGCGUGUGU | 20 | 15516 |
| BCL11A-11581 | - | CAUUUUAGAGUCCGCGUGUGU | 21 | 15517 |
| BCL11A-11582 | - | UCAUUUUAGAGUCCGCGUGUGU | 22 | 15518 |
| BCL11A-11583 | - | UUCAUUUUAGAGUCCGCGUGUGU | 23 | 15519 |
| BCL11A-11584 | - | UUUCAUUUUAGAGUCCGCGUGUGU | 24 | 15520 |
| BCL11A-13192 | - | GACUUGGGCGCUGCCCUU | 18 | 15521 |
| BCL11A-13193 | - | AGACUUGGGCGCUGCCCUU | 19 | 15522 |
| BCL11A-13194 | - | GAGACUUGGGCGCUGCCCUU | 20 | 15523 |
| BCL11A-13195 | - | GGAGACUUGGGCGCUGCCCUU | 21 | 15524 |
| BCL11A-13196 | - | UGGAGACUUGGGCGCUGCCCUU | 22 | 15525 |
| BCL11A-13197 | - | CUGGAGACUUGGGCGCUGCCCUU | 23 | 15526 |
| BCL11A-13198 | - | CCUGGAGACUUGGGCGCUGCCCUU | 24 | 15527 |
| BCL11A-13199 | - | GGUCCCUGGCUCGGCCUU | 18 | 15528 |
| BCL11A-13200 | - | CGGUCCCUGGCUCGGCCUU | 19 | 15529 |
| BCL11A-10256 | - | CCGGUCCCUGGCUCGGCCUU | 20 | 15530 |
| BCL11A-13201 | - | AAGAGGUGAGACUGGCUU | 18 | 15531 |
| BCL11A-13202 | - | AAAGAGGUGAGACUGGCUU | 19 | 15532 |
| BCL11A-13203 | - | AAAAGAGGUGAGACUGGCUU | 20 | 15533 |
| BCL11A-13204 | - | GAAAAGAGGUGAGACUGGCUU | 21 | 15534 |
| BCL11A-13205 | - | AGAAAAGAGGUGAGACUGGCUU | 22 | 15535 |
| BCL11A-13206 | - | GAGAAAAGAGGUGAGACUGGCUU | 23 | 15536 |
| BCL11A-13207 | - | GGAGAAAAGAGGUGAGACUGGCUU | 24 | 15537 |
| BCL11A-13208 | - | AUGAACAAUGCUAAGGUU | 18 | 15538 |
| BCL11A-13209 | - | AAUGAACAAUGCUAAGGUU | 19 | 15539 |
| BCL11A-13210 | - | UAAUGAACAAUGCUAAGGUU | 20 | 15540 |
| BCL11A-13211 | - | AUAAUGAACAAUGCUAAGGUU | 21 | 15541 |
| BCL11A-13212 | - | AAUAAUGAACAAUGCUAAGGUU | 22 | 15542 |
| BCL11A-13213 | - | AAAUAAUGAACAAUGCUAAGGUU | 23 | 15543 |
| BCL11A-13214 | - | AAAAUAAUGAACAAUGCUAAGGUU | 24 | 15544 |
| BCL11A-13215 | - | GCCGCUUUAUUUCUCUUU | 18 | 15545 |
| BCL11A-13216 | - | CGCCGCUUUAUUUCUCUUU | 19 | 15546 |
| BCL11A-13217 | - | CCGCCGCUUUAUUUCUCUUU | 20 | 15547 |

TABLE 19E-continued

5th Tier

| gRNA Name | DNA Strand | Targeting Domain | Target Site Length | SEQ ID NO: |
|---|---|---|---|---|
| BCL11A-13218 | − | UCCGCCGCUUUAUUUCUCUUU | 21 | 15548 |
| BCL11A-13219 | − | UUCCGCCGCUUUAUUUCUCUUU | 22 | 15549 |
| BCL11A-13220 | − | UUUCCGCCGCUUUAUUUCUCUUU | 23 | 15550 |
| BCL11A-13221 | − | CUUUCCGCCGCUUUAUUUCUCUUU | 24 | 15551 |

Table 20A provides exemplary targeting domains for knocking down the BCL11A gene selected according to the first tier parameters. The targeting domains bind within 500 bp (e.g., upstream or downstream) of a transcription start site (TSS) and have a high level of orthogonality. It is contemplated herein that in an embodiment the targeting domain hybridizes to the target domain through complementary base pairing. Any of the targeting domains in the table can be used with a N. meningitidis eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

Table 20B provides exemplary targeting domains for knocking down the BCL11A gene selected according to the second tier parameters. The targeting domains bind within 500 bp (e.g., upstream or downstream) of a transcription start site (TSS). It is contemplated herein that in an embodiment the targeting domain hybridizes to the target domain through complementary base pairing. Any of the targeting domains in the table can be used with a N. meningitidis eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or More gRNA may be used to target an eiCas9 to the promoter region of the BCL11A gene.

TABLE 20A

1st Tier

| gRNA Name | DNA Strand | Targeting Domain | Target Site Length | SEQ ID NO: |
|---|---|---|---|---|
| BCL11A-13222 | + | ACACACCCCUCUCUCCC | 17 | 15552 |
| BCL11A-9477 | + | CUUACGCGAGAAUUCCC | 17 | 15553 |
| BCL11A-13223 | + | CCCUCUCUCCCCCUCGC | 17 | 15554 |
| BCL11A-13224 | + | UCUAGUCCUGCGCGCUC | 17 | 15555 |
| BCL11A-9638 | − | UUGAACUUGCAGCUCAG | 17 | 15556 |
| BCL11A-9482 | + | UUAAGUGCUGGGGUUUG | 17 | 15557 |
| BCL11A-13225 | + | CACGCGGACUCUAAAAU | 17 | 15558 |
| BCL11A-13226 | + | AAUUGUGGGAGAGCCGU | 17 | 15559 |
| BCL11A-13227 | − | GAUGUGUGUCCAUUGGU | 17 | 15560 |
| BCL11A-13228 | + | UGCACACACCCCUCUCUCCC | 20 | 15561 |
| BCL11A-9487 | + | UUACUUACGCGAGAAUUCCC | 20 | 15562 |
| BCL11A-13229 | + | CACCCCUCUCUCCCCCUCGC | 20 | 15563 |
| BCL11A-13230 | + | GCUUCUAGUCCUGCGCGCUC | 20 | 15564 |
| BCL11A-9738 | − | CACUUGAACUUGCAGCUCAG | 20 | 15565 |
| BCL11A-9491 | + | UGCUUAAGUGCUGGGGUUUG | 20 | 15566 |
| BCL11A-13231 | + | AUGAAUUGUGGGAGAGCCGU | 20 | 15567 |
| BCL11A-11567 | − | CCUGAUGUGUGUCCAUUGGU | 20 | 15568 |

TABLE 20B

2nd Tier

| gRNA Name | DNA Strand | Targeting Domain | Target Site Length | SEQ ID NO: |
|---|---|---|---|---|
| BCL11A-13232 | − | CCCUCCCCGCACUGGCC | 17 | 15569 |
| BCL11A-13233 | − | UUUUUUUUUUUUUUUU | 17 | 15570 |
| BCL11A-13234 | − | UCCCCCUCCCCGCACUGGCC | 20 | 15571 |
| BCL11A-13235 | + | ACACACGCGGACUCUAAAAU | 20 | 15572 |
| BCL11A-13236 | − | UUUUUUUUUUUUUUUUUUUU | 20 | 15573 |

Table 20C provides exemplary targeting domains for knocking down the BCL11A gene selected according to the third tier parameters. The targeting domains bind within the additional 500 bp (e.g., upstream or downstream) of a transcription start site (TSS), e.g., extending to 1 kb upstream and downstream of a TSS. It is contemplated herein that in an embodiment the targeting domain hybridizes to the target domain through complementary base pairing. Any of the targeting domains in the table can be used with a *N. meningitidis* eiCas9 molecule or eiCas9 fusion protein (e.g., an eiCas9 fused to a transcription repressor domain) to alter the BCL11A gene (e.g., reduce or eliminate BCL11A gene expression, BCL11A protein function, or the level of BCL11A protein). One or more gRNA may be used to target an eiCas9 to the promoter region of the BCL11A gene.

TABLE 20C

3rd Tier

| gRNA Name | DNA Strand | Targeting Domain | Target Site Length | SEQ ID NO: |
|---|---|---|---|---|
| BCL11A-13237 | − | GUGAGUACAAGUCUAAA | 17 | 15574 |
| BCL11A-13238 | − | GCUGGUGGGGAAAGGGA | 17 | 15575 |
| BCL11A-13239 | − | GUCCGGGAGCAACUCUA | 17 | 15576 |
| BCL11A-13240 | − | CCUUUUGUGCCGGCUCC | 17 | 15577 |
| BCL11A-13241 | − | ACCUGGCUUCCCUCCGC | 17 | 15578 |
| BCL11A-9896 | − | GCUCAGCUCUCAACUUC | 17 | 15579 |
| BCL11A-13242 | − | UCCUCUUUCCUCCUUUC | 17 | 15580 |
| BCL11A-13243 | − | GGGAGAAAAGAGGUGAG | 17 | 15581 |
| BCL11A-13244 | − | CAGCCCUCCAAACUUAG | 17 | 15582 |
| BCL11A-13245 | − | CUUUUCGAAAAGGAAUG | 17 | 15583 |
| BCL11A-13225 | + | CACGCGGACUCUAAAAU | 17 | 15584 |
| BCL11A-10006 | − | GAGCGCAGCCGCGGGCU | 17 | 15585 |
| BCL11A-13246 | − | GGAGUGAGUACAAGUCUAAA | 20 | 15586 |
| BCL11A-13247 | − | GGAGCUGGUGGGGAAAGGGA | 20 | 15587 |
| BCL11A-13248 | − | GGUGUCCGGGAGCAACUCUA | 20 | 15588 |
| BCL11A-13249 | − | CUGCCUUUUGUGCCGGCUCC | 20 | 15589 |
| BCL11A-13250 | − | UCUACCUGGCUUCCCUCCGC | 20 | 15590 |
| BCL11A-10131 | − | GAGGCUCAGCUCUCAACUUC | 20 | 15591 |
| BCL11A-13251 | − | UCCUCCUCUUUCCUCCUUUC | 20 | 15592 |
| BCL11A-13252 | − | CCGGGGAGAAAAGAGGUGAG | 20 | 15593 |
| BCL11A-13253 | − | CCGCAGCCCUCCAAACUUAG | 20 | 15594 |
| BCL11A-13254 | − | UCUCUUUUCGAAAAGGAAUG | 20 | 15595 |

TABLE 20C-continued

3rd Tier

| gRNA Name | DNA Strand | Targeting Domain | Target Site Length | SEQ ID NO: |
|---|---|---|---|---|
| BCL11A-13235 | + | ACACACGCGGACUCUAAAAU | 20 | 15596 |
| BCL11A-10241 | − | CCCGAGCGCAGCCGCGGGCU | 20 | 15597 |

Table 21A provides exemplary targeting domains for removing (e.g., deleting) the enhancer region of the BCL11A gene selected according to the first tier parameters. The targeting domains bind within a region 5' (51.5 to 51.7 kb downstream of TSS) or 3' (65.1 to 65.3 kb downstream of TSS), and have a high level of orthogonality and starts with 5'G. It is contemplated herein that in an embodiment the targeting domain hybridizes to the target domain through complementary base pairing. Any of the targeting domains in the table can be used with a S. pyogenes Cas9 molecule that generates a double stranded break (Cas9 nuclease) or a single-stranded break (Cas9 nickase).

TABLE 21A

1st Tier

| gRNA Name | DNA Strand | Targeting Domain | Target Site Length | 5' or 3' | SEQ ID NO: |
|---|---|---|---|---|---|
| BCL11A-13255 | + | GCACUAGGUGAAAUCUC | 17 | 5' | 15598 |
| BCL11A-13256 | − | GAAAGCAGUGUAAGGCU | 17 | 5' | 15599 |
| BCL11A-13257 | − | GUAAUUAAGAAAGCAGUGUA | 20 | 5' | 15600 |
| BCL11A-13258 | + | GUUGCACUAGGUGAAAUCUC | 20 | 5' | 15601 |
| BCL11A-13259 | − | GGCUGUUUUGGAAUGUAGAG | 20 | 5' | 15602 |
| BCL11A-13260 | − | GGCUGUUUUGGAUCUU | 17 | 3' | 15603 |
| BCL11A-13261 | + | GUGCUACUUAUACAAUUCAC | 20 | 3' | 15604 |
| BCL11A-13262 | + | GAAAAUACUUACUGUACUGC | 20 | 3' | 15605 |

Table 21B provides exemplary targeting domains for removing (e.g., deleting) the enhancer region of the BCL11A gene selected according to the second tier parameters. The targeting domains bind within a region 5' (51.5 to 51.7 kb downstream of TSS) or 3' (65.1 to 65.3 kb downstream of TSS) and have a high level of orthogonality. It is contemplated herein that in an embodiment the targeting domain hybridizes to the target domain through complementary base pairing. Any of the targeting domains in the table can be used with a S. pyogenes Cas9 molecule that generates a double stranded break (Cas9 nuclease) or a single-stranded break (Cas9 nickase).

TABLE 21B

2nd Tier

| gRNA Name | DNA Strand | Targeting Domain | Target Site Length | 5' or 3' | SEQ ID NO: |
|---|---|---|---|---|---|
| BCL11A-13263 | − | AUUAAGAAAGCAGUGUA | 17 | 5' | 15606 |
| BCL11A-13264 | + | AUUUUACUAGUGAAUUA | 17 | 5' | 15607 |
| BCL11A-13265 | + | AUUUAAGACGGGAAAAC | 17 | 5' | 15608 |
| BCL11A-13266 | − | AGAAAGCAGUGUAAGGC | 17 | 5' | 15609 |
| BCL11A-13267 | − | UGUUUUGGAAUGUAGAG | 17 | 5' | 15610 |

TABLE 21B-continued

2nd Tier

| gRNA Name | DNA Strand | Targeting Domain | Target Site Length | 5' or 3' | SEQ ID NO: |
|---|---|---|---|---|---|
| BCL11A-13268 | + | ACAACUUGUGUUGCACU | 17 | 5' | 15611 |
| BCL11A-13269 | + | UCUCACAUAAAAAUUUAAGA | 20 | 5' | 15612 |
| BCL11A-13270 | − | UUGGAAUGUAGAGAGGCAGA | 20 | 5' | 15613 |
| BCL11A-13271 | + | AUUAUUUUACUAGUGAAUUA | 20 | 5' | 15614 |
| BCL11A-13272 | + | AAAAUUUAAGACGGGAAAAC | 20 | 5' | 15615 |
| BCL11A-13273 | + | CUCACAUAAAAAUUUAAGAC | 20 | 5' | 15616 |
| BCL11A-13274 | + | UACACAACUUGUGUUGCACU | 20 | 5' | 15617 |
| BCL11A-13275 | − | UAAGAAAGCAGUGUAAGGCU | 20 | 5' | 15618 |
| BCL11A-13276 | − | AUUAGAAUAAAAGGCUGUUU | 20 | 5' | 15619 |
| BCL11A-13277 | − | UAUUUACAGCCAUAACA | 17 | 3' | 15620 |
| BCL11A-13278 | + | AUACUUACUGUACUGCA | 17 | 3' | 15621 |
| BCL11A-13279 | + | CACUGGAAACCCUGUUA | 17 | 3' | 15622 |
| BCL11A-13280 | − | CUAUUUACAGCCAUAAC | 17 | 3' | 15623 |
| BCL11A-13281 | + | CUACUUAUACAAUUCAC | 17 | 3' | 15624 |
| BCL11A-13282 | + | AAUACUUACUGUACUGC | 17 | 3' | 15625 |
| BCL11A-13283 | + | UACUUACUGUACUGCAG | 17 | 3' | 15626 |
| BCL11A-13284 | + | UGUACUGCAGGGGAAUU | 17 | 3' | 15627 |
| BCL11A-13285 | − | UGGGUAGCAGUGGCUUU | 17 | 3' | 15628 |
| BCL11A-13286 | − | UGGCUUUAGGCUGUUUU | 17 | 3' | 15629 |
| BCL11A-13287 | − | AACUAUUUACAGCCAUAACA | 20 | 3' | 15630 |
| BCL11A-13288 | + | AAAAUACUUACUGUACUGCA | 20 | 3' | 15631 |
| BCL11A-13289 | + | AUUCACUGGAAACCCUGUUA | 20 | 3' | 15632 |
| BCL11A-13290 | − | AAACUAUUUACAGCCAUAAC | 20 | 3' | 15633 |
| BCL11A-13291 | + | AAAUACUUACUGUACUGCAG | 20 | 3' | 15634 |
| BCL11A-13292 | + | UACUGUACUGCAGGGGAAUU | 20 | 3' | 15635 |
| BCL11A-13293 | − | UUAGGCUGUUUUUGGAUCUU | 20 | 3' | 15636 |
| BCL11A-13294 | − | CAGUGGCUUUAGGCUGUUUU | 20 | 3' | 15637 |

Table 21C provides exemplary targeting domains for removing (e.g., deleting) the enhancer region of the BCL11A gene selected according to the third tier parameters. The targeting domains bind within a region 5' (51.5 to 51.7 kb downstream of TSS) or 3' (65.1 to 65.3 kb downstream of TSS) and starts with 5'G. It is contemplated herein that in an embodiment the targeting domain hybridizes to the target domain through complementary base pairing. Any of the targeting domains in the table can be used with a *S. pyogenes* Cas9 molecule that generates a double stranded break (Cas9 nuclease) or a single-stranded break (Cas9 nickase).

TABLE 21C

| | | 3rd Tier | | | |
|---|---|---|---|---|---|
| gRNA Name | DNA Strand | Targeting Domain | Target Site Length | 5' or 3' | SEQ ID NO: |
| BCL11A-13295 | − | GAAUGUAGAGAGGCAGA | 17 | 5' | 15638 |
| BCL11A-13296 | − | GGAAUGUAGAGAGGCAG | 17 | 5' | 15639 |
| BCL11A-13297 | − | GUAUUUUCUUUCAUUGG | 17 | 3' | 15640 |
| BCL11A-13298 | − | GUAAGUAUUUUCUUUCAUUG | 20 | 3' | 15641 |

Table 21D provides exemplary targeting domains for removing (e.g., deleting) the enhancer region of the BCL11A gene selected according to the fourth tier parameters. The targeting domains bind within a region 5' (51.5 to 51.7 kb downstream of TSS) or 3' (65.1 to 65.3 kb downstream of TSS). It is contemplated herein that in an embodiment the targeting domain hybridizes to the target domain through complementary base pairing. Any of the targeting domains in the table can be used with a S. pyogenes Cas9 molecule that generates a double stranded break (Cas9 nuclease) or a single-stranded break (Cas9 nickase).

Table 21E provides targeting domains for removing (e.g., deleting) the enhancer region of the BCL11A gene by dual targeting (e.g., dual double strand cleavage). It is contemplated herein that an upstream gRNA can be paired with a downstream gRNA to guide Cas9 nuclease pairs. Exemplary nickase pairs include a targeting domain from Group A and a second targeting domain from Group B, or include a targeting domain from Group C and a second targeting domain from Group D. It is contemplated herein that in an embodiment a targeting domain of Group A can be combined with any of the targeting domains of Group B; in an

TABLE 21D

| | | 4th Tier | | | |
|---|---|---|---|---|---|
| gRNA Name | DNA Strand | Targeting Domain | Target Site Length | 5' or 3' | SEQ ID NO: |
| BCL11A-13299 | − | AAAAUAAUUAGAAUAAA | 17 | 5' | 15642 |
| BCL11A-13300 | + | CACAUAAAAAUUUAAGA | 17 | 5' | 15643 |
| BCL11A-13301 | + | ACAUAAAAAUUUAAGAC | 17 | 5' | 15644 |
| BCL11A-13302 | − | UGUAAGGCUGGGCGCAG | 17 | 5' | 15645 |
| BCL11A-13303 | − | AAUGUAGAGAGGCAGAG | 17 | 5' | 15646 |
| BCL11A-13304 | − | AGAAUAAAAGGCUGUUU | 17 | 5' | 15647 |
| BCL11A-13305 | − | AGUAAAAUAAUUAGAAUAAA | 20 | 5' | 15648 |
| BCL11A-13306 | − | UUAAGAAAGCAGUGUAAGGC | 20 | 5' | 15649 |
| BCL11A-13307 | − | CAGUGUAAGGCUGGGCGCAG | 20 | 5' | 15650 |
| BCL11A-13308 | − | UUUGGAAUGUAGAGAGGCAG | 20 | 5' | 15651 |
| BCL11A-13309 | − | UGGAAUGUAGAGAGGCAGAG | 20 | 5' | 15652 |
| BCL11A-13310 | − | AGUAUUUUCUUUCAUUG | 17 | 3' | 15653 |
| BCL11A-13311 | − | UAAGUAUUUUCUUUCAU | 17 | 3' | 15654 |
| BCL11A-13312 | − | AAGUAUUUUCUUUCAUU | 17 | 3' | 15655 |
| BCL11A-13313 | − | UAAGUAUUUUCUUUCAUUGG | 20 | 3' | 15656 |
| BCL11A-13314 | − | CAGUAAGUAUUUUCUUUCAU | 20 | 3' | 15657 |
| BCL11A-13315 | − | AGUAAGUAUUUUCUUUCAUU | 20 | 3' | 15658 | embodiment a targeting domain of Group C can be combined with any of the targeting domains of Group D. For example, BCL11A-13271 or BCL11A-13264 can be combined with BCL11A-13276; or BCL11A-13262 or BCL11A-13282 can be combined with BCL11A-13290 or BCL11A-13280.

TABLE 21E

| Group A | Group B |
|---|---|
| BCL11A-13271, BCL11A-13264 | BCL11A-13276 |

TABLE 21E-continued

| Group C | Group D |
|---|---|
| BCL11A-13262, BCL11A-13282 | BCL11A-13290, BCL11A-13280 |

Table 22A provides exemplary targeting domains for removing (e.g., deleting) the enhancer region of the BCL11A gene selected according to the first tier parameters. The targeting domains bind within a region 5' (51.5 to 51.7 kb downstream of TSS) or 3' (65.1 to 65.3 kb downstream of TSS), have a high level of orthogonality, and start with 5'G. The PAM is NNGRRT. It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 22A

1st Tier

| gRNA Name | DNA Strand | Targeting Domain | Target Site Length | 5' or 3' | SEQ ID NO: |
|---|---|---|---|---|---|
| BCL11A-13316 | – | GGGGCUGAUAUAACUUCU | 18 | 5' | 15659 |
| BCL11A-13317 | – | GAGGGGCUGAUAUAACUUCU | 20 | 5' | 15660 |
| BCL11A-13318 | – | GCAGAGGGGCUGAUAUAACUUCU | 23 | 5' | 15661 |
| BCL11A-13319 | – | GGCAGAGGGGCUGAUAUAACUUCU | 24 | 5' | 15662 |
| BCL11A-13320 | – | GCAAACUAUUUACAGCCAUAA | 21 | 3' | 15663 |
| BCL11A-13321 | – | GAAGCAAACUAUUUACAGCCAUAA | 24 | 3' | 15664 |
| BCL11A-13322 | – | GCCAUAACAGGGUUUCCA | 18 | 3' | 15665 |
| BCL11A-13323 | – | GUGAAUUGUAUAAGUAGCA | 19 | 3' | 15666 |
| BCL11A-13324 | – | GCAAAACUAGAAAGUUUUA | 19 | 3' | 15667 |
| BCL11A-13325 | – | GCAGUGGCUUUAGGCUGUUU | 20 | 3' | 15668 |
| BCL11A-13326 | – | GUAGCAGUGGCUUUAGGCUGUUU | 23 | 3' | 15669 |
| BCL11A-13327 | – | GGUAGCAGUGGCUUUAGGCUGUUU | 24 | 3' | 15670 |

Table 22B provides exemplary targeting domains for removing (e.g., deleting) the enhancer region of the BCL11A gene selected according to the second tier parameters. The targeting domains bind within a region 5' (51.5 to 51.7 kb downstream of TSS) or 3' (65.1 to 65.3 kb downstream of TSS), and have a high level of orthogonality. The PAM is NNGRRT. It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 22B

2nd Tier

| gRNA Name | DNA Strand | Targeting Domain | Target Site Length | 5' or 3' | SEQ ID NO: |
|---|---|---|---|---|---|
| BCL11A-13328 | + | UUUAUUCUAAUUAUUUACUA | 21 | 5' | 15671 |
| BCL11A-13329 | + | UUUUAUUCUAAUUAUUUACUA | 22 | 5' | 15672 |

TABLE 22B-continued

2nd Tier

| gRNA Name | DNA Strand | Targeting Domain | Target Site Length | 5' or 3' | SEQ ID NO: |
|---|---|---|---|---|---|
| BCL11A-13330 | + | CUUUUAUUCUAAUUAUUUUACUA | 23 | 5' | 15673 |
| BCL11A-13331 | + | CCUUUUAUUCUAAUUAUUUUACUA | 24 | 5' | 15674 |
| BCL11A-13332 | + | UAUUUUACUAGUGAAUUA | 18 | 5' | 15675 |
| BCL11A-13333 | + | UUAUUUUACUAGUGAAUUA | 19 | 5' | 15676 |
| BCL11A-13334 | + | AUUAUUUUACUAGUGAAUUA | 20 | 5' | 15677 |
| BCL11A-13335 | + | AAUUAUUUUACUAGUGAAUUA | 21 | 5' | 15678 |
| BCL11A-13336 | + | UAAUUAUUUUACUAGUGAAUUA | 22 | 5' | 15679 |
| BCL11A-13337 | + | CUAAUUAUUUUACUAGUGAAUUA | 23 | 5' | 15680 |
| BCL11A-13338 | + | UCUAAUUAUUUUACUAGUGAAUUA | 24 | 5' | 15681 |
| BCL11A-13339 | - | AUUCACUAGUAAAAUAAU | 18 | 5' | 15682 |
| BCL11A-13340 | - | AAUUCACUAGUAAAAUAAU | 19 | 5' | 15683 |
| BCL11A-13341 | - | UAAUUCACUAGUAAAAUAAU | 20 | 5' | 15684 |
| BCL11A-13342 | - | AGGGGCUGAUAUAACUUCU | 19 | 5' | 15685 |
| BCL11A-13343 | - | AGAGGGGCUGAUAUAACUUCU | 21 | 5' | 15686 |
| BCL11A-13344 | - | CAGAGGGGCUGAUAUAACUUCU | 22 | 5' | 15687 |
| BCL11A-13345 | - | UAGAAUAAAAGGCUGUUU | 18 | 5' | 15688 |
| BCL11A-13346 | - | UUAGAAUAAAAGGCUGUUU | 19 | 5' | 15689 |
| BCL11A-13347 | - | AUUAGAAUAAAAGGCUGUUU | 20 | 5' | 15690 |
| BCL11A-13348 | - | AAUUAGAAUAAAAGGCUGUUU | 21 | 5' | 15691 |
| BCL11A-13349 | - | UAAUUAGAAUAAAAGGCUGUUU | 22 | 5' | 15692 |
| BCL11A-13350 | - | AUAAUUAGAAUAAAAGGCUGUUU | 23 | 5' | 15693 |
| BCL11A-13351 | - | AAUAAUUAGAAUAAAAGGCUGUUU | 24 | 5' | 15694 |
| BCL11A-13352 | + | AUACUUACUGUACUGCAG | 18 | 3' | 15695 |
| BCL11A-13353 | + | AAUACUUACUGUACUGCAG | 19 | 3' | 15696 |
| BCL11A-13354 | + | AAAUACUUACUGUACUGCAG | 20 | 3' | 15697 |
| BCL11A-13355 | - | AACUAUUUACAGCCAUAA | 18 | 3' | 15698 |
| BCL11A-13356 | - | AAACUAUUUACAGCCAUAA | 19 | 3' | 15699 |
| BCL11A-13357 | - | CAAACUAUUUACAGCCAUAA | 20 | 3' | 15700 |
| BCL11A-13358 | - | AGCAAACUAUUUACAGCCAUAA | 22 | 3' | 15701 |
| BCL11A-13359 | - | AAGCAAACUAUUUACAGCCAUAA | 23 | 3' | 15702 |
| BCL11A-13360 | - | AGCCAUAACAGGGUUUCCA | 19 | 3' | 15703 |
| BCL11A-13361 | - | CAGCCAUAACAGGGUUUCCA | 20 | 3' | 15704 |
| BCL11A-13362 | - | ACAGCCAUAACAGGGUUUCCA | 21 | 3' | 15705 |
| BCL11A-13363 | - | UACAGCCAUAACAGGGUUUCCA | 22 | 3' | 15706 |
| BCL11A-13364 | - | UUACAGCCAUAACAGGGUUUCCA | 23 | 3' | 15707 |
| BCL11A-13365 | - | UUUACAGCCAUAACAGGGUUUCCA | 24 | 3' | 15708 |
| BCL11A-13366 | - | UGAAUUGUAUAAGUAGCA | 18 | 3' | 15709 |

TABLE 22B-continued

2nd Tier

| gRNA Name | DNA Strand | Targeting Domain | Target Site Length | 5' or 3' | SEQ ID NO: |
|---|---|---|---|---|---|
| BCL11A-13367 | − | AGUGAAUUGUAUAAGUAGCA | 20 | 3' | 15710 |
| BCL11A-13368 | − | CAGUGAAUUGUAUAAGUAGCA | 21 | 3' | 15711 |
| BCL11A-13369 | − | CCAGUGAAUUGUAUAAGUAGCA | 22 | 3' | 15712 |
| BCL11A-13370 | − | UCCAGUGAAUUGUAUAAGUAGCA | 23 | 3' | 15713 |
| BCL11A-13371 | − | UUCCAGUGAAUUGUAUAAGUAGCA | 24 | 3' | 15714 |
| BCL11A-13372 | − | CAAAACUAGAAAGUUUUA | 18 | 3' | 15715 |
| BCL11A-13373 | − | AGCAAAACUAGAAAGUUUUA | 20 | 3' | 15716 |
| BCL11A-13374 | − | AGUGGCUUUAGGCUGUUU | 18 | 3' | 15717 |
| BCL11A-13375 | − | CAGUGGCUUUAGGCUGUUU | 19 | 3' | 15718 |
| BCL11A-13376 | − | AGCAGUGGCUUUAGGCUGUUU | 21 | 3' | 15719 |
| BCL11A-13377 | − | UAGCAGUGGCUUUAGGCUGUUU | 22 | 3' | 15720 |

Table 22C provides exemplary targeting domains for removing (e.g., deleting) the enhancer region of the BCL11A gene selected according to the third tier parameters. The targeting domains bind within a region 5' (51.5 to 51.7 kb downstream of TSS) or 3' (65.1 to 65.3 kb downstream of TSS), and start with 5'G. The PAM is NNGRRT.

It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 22C

3rd Tier

| gRNA Name | DNA Strand | Targeting Domain | Target Site Length | 5' or 3' | SEQ ID NO: |
|---|---|---|---|---|---|
| BCL11A-13378 | + | GAAAAUACUUACUGUACUGCAG | 22 | 3' | 15721 |
| BCL11A-13379 | − | GUUAAGCAAAACUAGAAAGUUUUA | 24 | 3' | 15722 |

Table 22D provides exemplary targeting domains for removing (e.g., deleting) the enhancer region of the BCL11A gene selected according to the second tier parameters. The targeting domains bind within a region 5' (51.5 to 51.7 kb downstream of TSS) or 3' (65.1 to 65.3 kb downstream of TSS), and the PAM is NNGRRT. It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 22D

4th Tier

| gRNA Name | DNA Strand | Targeting Domain | Target Site Length | 5' or 3' | SEQ ID NO: |
|---|---|---|---|---|---|
| BCL11A-13380 | + | AUUCUAAUUAUUUUACUA | 18 | 5' | 15723 |
| BCL11A-13381 | + | UAUUCUAAUUAUUUUACUA | 19 | 5' | 15724 |

TABLE 22D-continued

4th Tier

| gRNA Name | DNA Strand | Targeting Domain | Target Site Length | 5' or 3' | SEQ ID NO: |
|---|---|---|---|---|---|
| BCL11A-13382 | + | UUAUUCUAAUUAUUUUACUA | 20 | 5' | 15725 |
| BCL11A-13383 | − | AUAAUUCACUAGUAAAAUAAU | 21 | 5' | 15726 |
| BCL11A-13384 | − | CAUAAUUCACUAGUAAAAUAAU | 22 | 5' | 15727 |
| BCL11A-13385 | − | CCAUAAUUCACUAGUAAAAUAAU | 23 | 5' | 15728 |
| BCL11A-13386 | − | UCCAUAAUUCACUAGUAAAAUAAU | 24 | 5' | 15729 |
| BCL11A-13387 | + | AAAAUACUUACUGUACUGCAG | 21 | 3' | 15730 |
| BCL11A-13388 | + | AGAAAAUACUUACUGUACUGCAG | 23 | 3' | 15731 |
| BCL11A-13389 | + | AAGAAAAUACUUACUGUACUGCAG | 24 | 3' | 15732 |
| BCL11A-13390 | − | AAGCAAAACUAGAAAGUUUUA | 21 | 3' | 15733 |
| BCL11A-13391 | − | UAAGCAAAACUAGAAAGUUUUA | 22 | 3' | 15734 |
| BCL11A-13392 | − | UUAAGCAAAACUAGAAAGUUUUA | 23 | 3' | 15735 |

Table 22E provides exemplary targeting domains for removing (e.g., deleting) the enhancer region of the BCL11A gene selected according to the third tier parameters. The targeting domains bind within a region 5' (51.5 to 51.7 kb downstream of TSS) or 3' (65.1 to 65.3 kb downstream of TSS), and the PAM is NNGRRV. It is contemplated herein that in an embodiment the targeting domain hybridizes to the target domain through complementary base pairing. Any of the targeting domains in the table can be used with a *S. aureus* Cas9 molecule that generates a double stranded break (Cas9 nuclease) or a single-stranded break (Cas9 nickase).

TABLE 22E

5th Tier

| gRNA Name | DNA Strand | Targeting Domain | Target Site Length | 5' or 3' | SEQ ID NO: |
|---|---|---|---|---|---|
| BCL11A-13393 | + | AAAUUUAAGACGGGAAAA | 18 | 5' | 15736 |
| BCL11A-13394 | + | AAAAUUUAAGACGGGAAAA | 19 | 5' | 15737 |
| BCL11A-13395 | + | AAAAAUUUAAGACGGGAAAA | 20 | 5' | 15738 |
| BCL11A-13396 | + | UAAAAAUUUAAGACGGGAAAA | 21 | 5' | 15739 |
| BCL11A-13397 | + | AUAAAAAUUUAAGACGGGAAAA | 22 | 5' | 15740 |
| BCL11A-13398 | + | CAUAAAAAUUUAAGACGGGAAAA | 23 | 5' | 15741 |
| BCL11A-13399 | + | ACAUAAAAAUUUAAGACGGGAAAA | 24 | 5' | 15742 |
| BCL11A-13400 | + | UCACAUAAAAAUUUAAGA | 18 | 5' | 15743 |
| BCL11A-13401 | + | CUCACAUAAAAAUUUAAGA | 19 | 5' | 15744 |
| BCL11A-13402 | + | UCUCACAUAAAAAUUUAAGA | 20 | 5' | 15745 |
| BCL11A-13403 | + | AUCUCACAUAAAAAUUUAAGA | 21 | 5' | 15746 |
| BCL11A-13404 | + | CAUCUCACAUAAAAAUUUAAGA | 22 | 5' | 15747 |
| BCL11A-13405 | + | UCAUCUCACAUAAAAAUUUAAGA | 23 | 5' | 15748 |
| BCL11A-13406 | + | CUCAUCUCACAUAAAAAUUUAAGA | 24 | 5' | 15749 |
| BCL11A-13407 | + | AAUUUAAGACGGGAAAAC | 18 | 5' | 15750 |
| BCL11A-13408 | + | AAAUUUAAGACGGGAAAAC | 19 | 5' | 15751 |

TABLE 22E-continued

5th Tier

| gRNA Name | DNA Strand | Targeting Domain | Target Site Length | 5' or 3' | SEQ ID NO: |
|---|---|---|---|---|---|
| BCL11A-13409 | + | AAAAUUUAAGACGGGAAAAC | 20 | 5' | 15752 |
| BCL11A-13410 | + | AAAAAUUUAAGACGGGAAAAC | 21 | 5' | 15753 |
| BCL11A-13411 | + | UAAAAAUUUAAGACGGGAAAAC | 22 | 5' | 15754 |
| BCL11A-13412 | + | AUAAAAAUUUAAGACGGGAAAAC | 23 | 5' | 15755 |
| BCL11A-13413 | + | CAUAAAAAUUUAAGACGGGAAAAC | 24 | 5' | 15756 |
| BCL11A-13414 | + | CACAUAAAAAUUUAAGAC | 18 | 5' | 15757 |
| BCL11A-13415 | + | UCACAUAAAAAUUUAAGAC | 19 | 5' | 15758 |
| BCL11A-13416 | + | CUCACAUAAAAAUUUAAGAC | 20 | 5' | 15759 |
| BCL11A-13417 | + | UCUCACAUAAAAAUUUAAGAC | 21 | 5' | 15760 |
| BCL11A-13418 | + | AUCUCACAUAAAAAUUUAAGAC | 22 | 5' | 15761 |
| BCL11A-13419 | + | CAUCUCACAUAAAAAUUUAAGAC | 23 | 5' | 15762 |
| BCL11A-13420 | + | UCAUCUCACAUAAAAAUUUAAGAC | 24 | 5' | 15763 |
| BCL11A-13421 | + | CUCACAUAAAAAUUUAAG | 18 | 5' | 15764 |
| BCL11A-13422 | + | UCUCACAUAAAAAUUUAAG | 19 | 5' | 15765 |
| BCL11A-13423 | + | AUCUCACAUAAAAAUUUAAG | 20 | 5' | 15766 |
| BCL11A-13424 | + | CAUCUCACAUAAAAAUUUAAG | 21 | 5' | 15767 |
| BCL11A-13425 | + | UCAUCUCACAUAAAAAUUUAAG | 22 | 5' | 15768 |
| BCL11A-13426 | + | CUCAUCUCACAUAAAAAUUUAAG | 23 | 5' | 15769 |
| BCL11A-13427 | + | GCUCAUCUCACAUAAAAAUUUAAG | 24 | 5' | 15770 |
| BCL11A-13428 | + | CAACUUGUGUUGCACUAG | 18 | 5' | 15771 |
| BCL11A-13429 | + | ACAACUUGUGUUGCACUAG | 19 | 5' | 15772 |
| BCL11A-13430 | + | CACAACUUGUGUUGCACUAG | 20 | 5' | 15773 |
| BCL11A-13431 | + | ACACAACUUGUGUUGCACUAG | 21 | 5' | 15774 |
| BCL11A-13432 | + | UACACAACUUGUGUUGCACUAG | 22 | 5' | 15775 |
| BCL11A-13433 | + | CUACACAACUUGUGUUGCACUAG | 23 | 5' | 15776 |
| BCL11A-13434 | + | UCUACACAACUUGUGUUGCACUAG | 24 | 5' | 15777 |
| BCL11A-13435 | + | AACAGGAAGAUGCAUUCU | 18 | 5' | 15778 |
| BCL11A-13436 | + | AAACAGGAAGAUGCAUUCU | 19 | 5' | 15779 |
| BCL11A-13437 | + | AAAACAGGAAGAUGCAUUCU | 20 | 5' | 15780 |
| BCL11A-13438 | + | GAAAACAGGAAGAUGCAUUCU | 21 | 5' | 15781 |
| BCL11A-13439 | + | GGAAAACAGGAAGAUGCAUUCU | 22 | 5' | 15782 |
| BCL11A-13440 | + | GGGAAAACAGGAAGAUGCAUUCU | 23 | 5' | 15783 |
| BCL11A-13441 | + | CGGGAAAACAGGAAGAUGCAUUCU | 24 | 5' | 15784 |
| BCL11A-13442 | + | UUAUUUUACUAGUGAAUU | 18 | 5' | 15785 |
| BCL11A-13443 | + | AUUAUUUUACUAGUGAAUU | 19 | 5' | 15786 |
| BCL11A-13444 | + | AAUUAUUUUACUAGUGAAUU | 20 | 5' | 15787 |
| BCL11A-13445 | + | UAAUUAUUUUACUAGUGAAUU | 21 | 5' | 15788 |

TABLE 22E-continued

5th Tier

| gRNA Name | DNA Strand | Targeting Domain | Target Site Length | 5' or 3' | SEQ ID NO: |
|---|---|---|---|---|---|
| BCL11A-13446 | + | CUAAUUAUUUUACUAGUGAAUU | 22 | 5' | 15789 |
| BCL11A-13447 | + | UCUAAUUAUUUUACUAGUGAAUU | 23 | 5' | 15790 |
| BCL11A-13448 | + | UUCUAAUUAUUUUACUAGUGAAUU | 24 | 5' | 15791 |
| BCL11A-13449 | + | AAAACAGGAAGAUGCAUU | 18 | 5' | 15792 |
| BCL11A-13450 | + | GAAAACAGGAAGAUGCAUU | 19 | 5' | 15793 |
| BCL11A-13451 | + | GGAAAACAGGAAGAUGCAUU | 20 | 5' | 15794 |
| BCL11A-13452 | + | GGGAAAACAGGAAGAUGCAUU | 21 | 5' | 15795 |
| BCL11A-13453 | + | CGGGAAAACAGGAAGAUGCAUU | 22 | 5' | 15796 |
| BCL11A-13454 | + | ACGGGAAAACAGGAAGAUGCAUU | 23 | 5' | 15797 |
| BCL11A-13455 | + | GACGGGAAAACAGGAAGAUGCAUU | 24 | 5' | 15798 |
| BCL11A-13456 | − | UUGGAAUGUAGAGAGGCA | 18 | 5' | 15799 |
| BCL11A-13457 | − | UUUGGAAUGUAGAGAGGCA | 19 | 5' | 15800 |
| BCL11A-13458 | − | UUUUGGAAUGUAGAGAGGCA | 20 | 5' | 15801 |
| BCL11A-13459 | − | GUUUUGGAAUGUAGAGAGGCA | 21 | 5' | 15802 |
| BCL11A-13460 | − | UGUUUUGGAAUGUAGAGAGGCA | 22 | 5' | 15803 |
| BCL11A-13461 | − | CUGUUUUGGAAUGUAGAGAGGCA | 23 | 5' | 15804 |
| BCL11A-13462 | − | GCUGUUUUGGAAUGUAGAGAGGCA | 24 | 5' | 15805 |
| BCL11A-13463 | − | CAACACAAGUUGUGUAGA | 18 | 5' | 15806 |
| BCL11A-13464 | − | GCAACACAAGUUGUGUAGA | 19 | 5' | 15807 |
| BCL11A-13465 | − | UGCAACACAAGUUGUGUAGA | 20 | 5' | 15808 |
| BCL11A-13466 | − | GUGCAACACAAGUUGUGUAGA | 21 | 5' | 15809 |
| BCL11A-13467 | − | AGUGCAACACAAGUUGUGUAGA | 22 | 5' | 15810 |
| BCL11A-13468 | − | UAGUGCAACACAAGUUGUGUAGA | 23 | 5' | 15811 |
| BCL11A-13469 | − | CUAGUGCAACACAAGUUGUGUAGA | 24 | 5' | 15812 |
| BCL11A-13470 | − | AGGCUGUUUUGGAAUGUA | 18 | 5' | 15813 |
| BCL11A-13471 | − | AAGGCUGUUUUGGAAUGUA | 19 | 5' | 15814 |
| BCL11A-13472 | − | AAAGGCUGUUUUGGAAUGUA | 20 | 5' | 15815 |
| BCL11A-13473 | − | AAAAGGCUGUUUUGGAAUGUA | 21 | 5' | 15816 |
| BCL11A-13474 | − | UAAAAGGCUGUUUUGGAAUGUA | 22 | 5' | 15817 |
| BCL11A-13475 | − | AUAAAAGGCUGUUUUGGAAUGUA | 23 | 5' | 15818 |
| BCL11A-13476 | − | AAUAAAAGGCUGUUUUGGAAUGUA | 24 | 5' | 15819 |
| BCL11A-13477 | − | UGGAAUGUAGAGAGGCAG | 18 | 5' | 15820 |
| BCL11A-13478 | − | UUGGAAUGUAGAGAGGCAG | 19 | 5' | 15821 |
| BCL11A-13479 | − | UUUGGAAUGUAGAGAGGCAG | 20 | 5' | 15822 |
| BCL11A-13480 | − | UUUUGGAAUGUAGAGAGGCAG | 21 | 5' | 15823 |
| BCL11A-13481 | − | GUUUUGGAAUGUAGAGAGGCAG | 22 | 5' | 15824 |
| BCL11A-13482 | − | UGUUUUGGAAUGUAGAGAGGCAG | 23 | 5' | 15825 |

TABLE 22E-continued

5th Tier

| gRNA Name | DNA Strand | Targeting Domain | Target Site Length | 5' or 3' | SEQ ID NO: |
|---|---|---|---|---|---|
| BCL11A-13483 | − | CUGUUUUGGAAUGUAGAGAGGCAG | 24 | 5' | 15826 |
| BCL11A-13484 | − | CUUAAAUUUUUAUGUGAG | 18 | 5' | 15827 |
| BCL11A-13485 | − | UCUUAAAUUUUUAUGUGAG | 19 | 5' | 15828 |
| BCL11A-13486 | − | GUCUUAAAUUUUUAUGUGAG | 20 | 5' | 15829 |
| BCL11A-13487 | − | CGUCUUAAAUUUUUAUGUGAG | 21 | 5' | 15830 |
| BCL11A-13488 | − | CCGUCUUAAAUUUUUAUGUGAG | 22 | 5' | 15831 |
| BCL11A-13489 | − | CCCGUCUUAAAUUUUUAUGUGAG | 23 | 5' | 15832 |
| BCL11A-13490 | − | UCCCGUCUUAAAUUUUUAUGUGAG | 24 | 5' | 15833 |
| BCL11A-13491 | − | UAAGAAAGCAGUGUAAGG | 18 | 5' | 15834 |
| BCL11A-13492 | − | UUAAGAAAGCAGUGUAAGG | 19 | 5' | 15835 |
| BCL11A-13493 | − | AUUAAGAAAGCAGUGUAAGG | 20 | 5' | 15836 |
| BCL11A-13494 | − | AAUUAAGAAAGCAGUGUAAGG | 21 | 5' | 15837 |
| BCL11A-13495 | − | UAAUUAAGAAAGCAGUGUAAGG | 22 | 5' | 15838 |
| BCL11A-13496 | − | GUAAUUAAGAAAGCAGUGUAAGG | 23 | 5' | 15839 |
| BCL11A-13497 | − | UGUAAUUAAGAAAGCAGUGUAAGG | 24 | 5' | 15840 |
| BCL11A-13498 | − | UUUUGGAAUGUAGAGAGG | 18 | 5' | 15841 |
| BCL11A-13499 | − | GUUUUGGAAUGUAGAGAGG | 19 | 5' | 15842 |
| BCL11A-13500 | − | UGUUUUGGAAUGUAGAGAGG | 20 | 5' | 15843 |
| BCL11A-13501 | − | CUGUUUUGGAAUGUAGAGAGG | 21 | 5' | 15844 |
| BCL11A-13502 | − | GCUGUUUUGGAAUGUAGAGAGG | 22 | 5' | 15845 |
| BCL11A-13503 | − | GGCUGUUUUGGAAUGUAGAGAGG | 23 | 5' | 15846 |
| BCL11A-13504 | − | AGGCUGUUUUGGAAUGUAGAGAGG | 24 | 5' | 15847 |
| BCL11A-13505 | − | AAAGGCUGUUUUGGAAUG | 18 | 5' | 15848 |
| BCL11A-13506 | − | AAAAGGCUGUUUUGGAAUG | 19 | 5' | 15849 |
| BCL11A-13507 | − | UAAAAGGCUGUUUUGGAAUG | 20 | 5' | 15850 |
| BCL11A-13508 | − | AUAAAAGGCUGUUUUGGAAUG | 21 | 5' | 15851 |
| BCL11A-13509 | − | AAUAAAAGGCUGUUUUGGAAUG | 22 | 5' | 15852 |
| BCL11A-13510 | − | GAAUAAAAGGCUGUUUUGGAAUG | 23 | 5' | 15853 |
| BCL11A-13511 | − | AGAAUAAAAGGCUGUUUUGGAAUG | 24 | 5' | 15854 |
| BCL11A-13512 | − | AGUGCAACACAAGUUGUG | 18 | 5' | 15855 |
| BCL11A-13513 | − | UAGUGCAACACAAGUUGUG | 19 | 5' | 15856 |
| BCL11A-13514 | − | CUAGUGCAACACAAGUUGUG | 20 | 5' | 15857 |
| BCL11A-13515 | − | CCUAGUGCAACACAAGUUGUG | 21 | 5' | 15858 |
| BCL11A-13516 | − | ACCUAGUGCAACACAAGUUGUG | 22 | 5' | 15859 |
| BCL11A-13517 | − | CACCUAGUGCAACACAAGUUGUG | 23 | 5' | 15860 |
| BCL11A-13518 | − | UCACCUAGUGCAACACAAGUUGUG | 24 | 5' | 15861 |
| BCL11A-13519 | − | CCCGUCUUAAAUUUUUAU | 18 | 5' | 15862 |

TABLE 22E-continued

5th Tier

| gRNA Name | DNA Strand | Targeting Domain | Target Site Length | 5' or 3' | SEQ ID NO: |
|---|---|---|---|---|---|
| BCL11A-13520 | − | UCCCGUCUUAAAUUUUAU | 19 | 5' | 15863 |
| BCL11A-13521 | − | UUCCCGUCUUAAAUUUUAU | 20 | 5' | 15864 |
| BCL11A-13522 | − | UUUCCCGUCUUAAAUUUUAU | 21 | 5' | 15865 |
| BCL11A-13523 | − | UUUUCCCGUCUUAAAUUUUAU | 22 | 5' | 15866 |
| BCL11A-13524 | − | GUUUUCCCGUCUUAAAUUUUAU | 23 | 5' | 15867 |
| BCL11A-13525 | − | UGUUUUCCCGUCUUAAAUUUUAU | 24 | 5' | 15868 |
| BCL11A-13526 | − | GAGCACACUGCUGUAAUU | 18 | 5' | 15869 |
| BCL11A-13527 | − | UGAGCACACUGCUGUAAUU | 19 | 5' | 15870 |
| BCL11A-13528 | − | AUGAGCACACUGCUGUAAUU | 20 | 5' | 15871 |
| BCL11A-13529 | − | GAUGAGCACACUGCUGUAAUU | 21 | 5' | 15872 |
| BCL11A-13530 | − | AGAUGAGCACACUGCUGUAAUU | 22 | 5' | 15873 |
| BCL11A-13531 | − | GAGAUGAGCACACUGCUGUAAUU | 23 | 5' | 15874 |
| BCL11A-13532 | − | UGAGAUGAGCACACUGCUGUAAUU | 24 | 5' | 15875 |
| BCL11A-13533 | − | UUAGAAUAAAAGGCUGUU | 18 | 5' | 15876 |
| BCL11A-13534 | − | AUUAGAAUAAAAGGCUGUU | 19 | 5' | 15877 |
| BCL11A-13535 | − | AAUUAGAAUAAAAGGCUGUU | 20 | 5' | 15878 |
| BCL11A-13536 | − | UAAUUAGAAUAAAAGGCUGUU | 21 | 5' | 15879 |
| BCL11A-13537 | − | AUAAUUAGAAUAAAAGGCUGUU | 22 | 5' | 15880 |
| BCL11A-13538 | − | AAUAAUUAGAAUAAAAGGCUGUU | 23 | 5' | 15881 |
| BCL11A-13539 | − | AAAUAAUUAGAAUAAAAGGCUGUU | 24 | 5' | 15882 |
| BCL11A-13540 | + | UUUCAUUUUUGCUGACA | 18 | 3' | 15883 |
| BCL11A-13541 | + | GUUUCAUUUUUGCUGACA | 19 | 3' | 15884 |
| BCL11A-13542 | + | UGUUUCAUUUUUGCUGACA | 20 | 3' | 15885 |
| BCL11A-13543 | + | UUGUUUCAUUUUUGCUGACA | 21 | 3' | 15886 |
| BCL11A-13544 | + | UUUGUUUCAUUUUUGCUGACA | 22 | 3' | 15887 |
| BCL11A-13545 | + | UUUUGUUUCAUUUUUGCUGACA | 23 | 3' | 15888 |
| BCL11A-13546 | + | UUUUUGUUUCAUUUUUGCUGACA | 24 | 3' | 15889 |
| BCL11A-13547 | + | AAUAGUUUGCUUCCCCA | 18 | 3' | 15890 |
| BCL11A-13548 | + | AAAUAGUUUGCUUCCCCA | 19 | 3' | 15891 |
| BCL11A-13549 | + | UAAAUAGUUUGCUUCCCCA | 20 | 3' | 15892 |
| BCL11A-13550 | + | GUAAAUAGUUUGCUUCCCCA | 21 | 3' | 15893 |
| BCL11A-13551 | + | UGUAAAUAGUUUGCUUCCCCA | 22 | 3' | 15894 |
| BCL11A-13552 | + | CUGUAAAUAGUUUGCUUCCCCA | 23 | 3' | 15895 |
| BCL11A-13553 | + | GCUGUAAAUAGUUUGCUUCCCCA | 24 | 3' | 15896 |
| BCL11A-13554 | + | AAUACUUACUGUACUGCA | 18 | 3' | 15897 |
| BCL11A-13555 | + | AAAUACUUACUGUACUGCA | 19 | 3' | 15898 |
| BCL11A-13556 | + | AAAAUACUUACUGUACUGCA | 20 | 3' | 15899 |

TABLE 22E-continued

5th Tier

| gRNA Name | DNA Strand | Targeting Domain | Target Site Length | 5' or 3' | SEQ ID NO: |
|---|---|---|---|---|---|
| BCL11A-13557 | + | GAAAAUACUUACUGUACUGCA | 21 | 3' | 15900 |
| BCL11A-13558 | + | AGAAAAUACUUACUGUACUGCA | 22 | 3' | 15901 |
| BCL11A-13559 | + | AAGAAAAUACUUACUGUACUGCA | 23 | 3' | 15902 |
| BCL11A-13560 | + | AAAGAAAAUACUUACUGUACUGCA | 24 | 3' | 15903 |
| BCL11A-13561 | + | UGCUACUUAUACAAUUCA | 18 | 3' | 15904 |
| BCL11A-13562 | + | GUGCUACUUAUACAAUUCA | 19 | 3' | 15905 |
| BCL11A-13563 | + | AGUGCUACUUAUACAAUUCA | 20 | 3' | 15906 |
| BCL11A-13564 | + | CAGUGCUACUUAUACAAUUCA | 21 | 3' | 15907 |
| BCL11A-13565 | + | UCAGUGCUACUUAUACAAUUCA | 22 | 3' | 15908 |
| BCL11A-13566 | + | CUCAGUGCUACUUAUACAAUUCA | 23 | 3' | 15909 |
| BCL11A-13567 | + | ACUCAGUGCUACUUAUACAAUUCA | 24 | 3' | 15910 |
| BCL11A-13568 | + | GUUUGCUUCCCCCAAUGA | 18 | 3' | 15911 |
| BCL11A-13569 | + | AGUUUGCUUCCCCCAAUGA | 19 | 3' | 15912 |
| BCL11A-13570 | + | UAGUUUGCUUCCCCCAAUGA | 20 | 3' | 15913 |
| BCL11A-13571 | + | AUAGUUUGCUUCCCCCAAUGA | 21 | 3' | 15914 |
| BCL11A-13572 | + | AAUAGUUUGCUUCCCCCAAUGA | 22 | 3' | 15915 |
| BCL11A-13573 | + | AAAUAGUUUGCUUCCCCCAAUGA | 23 | 3' | 15916 |
| BCL11A-13574 | + | UAAAUAGUUUGCUUCCCCCAAUGA | 24 | 3' | 15917 |
| BCL11A-13575 | + | UUUCUAGUUUUGCUUAAC | 18 | 3' | 15918 |
| BCL11A-13576 | + | CUUUCUAGUUUUGCUUAAC | 19 | 3' | 15919 |
| BCL11A-13577 | + | ACUUUCUAGUUUUGCUUAAC | 20 | 3' | 15920 |
| BCL11A-13578 | + | AACUUUCUAGUUUUGCUUAAC | 21 | 3' | 15921 |
| BCL11A-13579 | + | AAACUUUCUAGUUUUGCUUAAC | 22 | 3' | 15922 |
| BCL11A-13580 | + | AAAACUUUCUAGUUUUGCUUAAC | 23 | 3' | 15923 |
| BCL11A-13581 | + | UAAAACUUUCUAGUUUUGCUUAAC | 24 | 3' | 15924 |
| BCL11A-13582 | + | GCUACUUAUACAAUUCAC | 18 | 3' | 15925 |
| BCL11A-13583 | + | UGCUACUUAUACAAUUCAC | 19 | 3' | 15926 |
| BCL11A-13584 | + | GUGCUACUUAUACAAUUCAC | 20 | 3' | 15927 |
| BCL11A-13585 | + | AGUGCUACUUAUACAAUUCAC | 21 | 3' | 15928 |
| BCL11A-13586 | + | CAGUGCUACUUAUACAAUUCAC | 22 | 3' | 15929 |
| BCL11A-13587 | + | UCAGUGCUACUUAUACAAUUCAC | 23 | 3' | 15930 |
| BCL11A-13588 | + | CUCAGUGCUACUUAUACAAUUCAC | 24 | 3' | 15931 |
| BCL11A-13589 | + | AAAUACUUACUGUACUGC | 18 | 3' | 15932 |
| BCL11A-13590 | + | AAAAUACUUACUGUACUGC | 19 | 3' | 15933 |
| BCL11A-13591 | + | GAAAAUACUUACUGUACUGC | 20 | 3' | 15934 |
| BCL11A-13592 | + | AGAAAAUACUUACUGUACUGC | 21 | 3' | 15935 |
| BCL11A-13593 | + | AAGAAAAUACUUACUGUACUGC | 22 | 3' | 15936 |

TABLE 22E-continued

5th Tier

| gRNA Name | DNA Strand | Targeting Domain | Target Site Length | 5' or 3' | SEQ ID NO: |
|---|---|---|---|---|---|
| BCL11A-13594 | + | AAAGAAAAUACUUACUGUACUGC | 23 | 3' | 15937 |
| BCL11A-13595 | + | GAAAGAAAAUACUUACUGUACUGC | 24 | 3' | 15938 |
| BCL11A-13596 | + | AAAAUACUUACUGUACUG | 18 | 3' | 15939 |
| BCL11A-13597 | + | GAAAAUACUUACUGUACUG | 19 | 3' | 15940 |
| BCL11A-13598 | + | AGAAAAUACUUACUGUACUG | 20 | 3' | 15941 |
| BCL11A-13599 | + | AAGAAAAUACUUACUGUACUG | 21 | 3' | 15942 |
| BCL11A-13600 | + | AAAGAAAAUACUUACUGUACUG | 22 | 3' | 15943 |
| BCL11A-13601 | + | GAAAGAAAAUACUUACUGUACUG | 23 | 3' | 15944 |
| BCL11A-13602 | + | UGAAAGAAAAUACUUACUGUACUG | 24 | 3' | 15945 |
| BCL11A-13603 | − | GUUCUGUGUCAGCAAAAA | 18 | 3' | 15946 |
| BCL11A-13604 | − | AGUUCUGUGUCAGCAAAAA | 19 | 3' | 15947 |
| BCL11A-13605 | − | GAGUUCUGUGUCAGCAAAAA | 20 | 3' | 15948 |
| BCL11A-13606 | − | UGAGUUCUGUGUCAGCAAAAA | 21 | 3' | 15949 |
| BCL11A-13607 | − | CUGAGUUCUGUGUCAGCAAAAA | 22 | 3' | 15950 |
| BCL11A-13608 | − | ACUGAGUUCUGUGUCAGCAAAAA | 23 | 3' | 15951 |
| BCL11A-13609 | − | CACUGAGUUCUGUGUCAGCAAAAA | 24 | 3' | 15952 |
| BCL11A-13610 | − | AGUAAGUAUUUUCUUUCA | 18 | 3' | 15953 |
| BCL11A-13611 | − | CAGUAAGUAUUUUCUUUCA | 19 | 3' | 15954 |
| BCL11A-13612 | − | ACAGUAAGUAUUUUCUUUCA | 20 | 3' | 15955 |
| BCL11A-13613 | − | UACAGUAAGUAUUUUCUUUCA | 21 | 3' | 15956 |
| BCL11A-13614 | − | GUACAGUAAGUAUUUUCUUUCA | 22 | 3' | 15957 |
| BCL11A-13615 | − | AGUACAGUAAGUAUUUUCUUUCA | 23 | 3' | 15958 |
| BCL11A-13616 | − | CAGUACAGUAAGUAUUUUCUUUCA | 24 | 3' | 15959 |
| BCL11A-13617 | − | UUUCAUGUUAAGCAAAAC | 18 | 3' | 15960 |
| BCL11A-13618 | − | UUUUCAUGUUAAGCAAAAC | 19 | 3' | 15961 |
| BCL11A-13619 | − | AUUUUCAUGUUAAGCAAAAC | 20 | 3' | 15962 |
| BCL11A-13620 | − | UAUUUUCAUGUUAAGCAAAAC | 21 | 3' | 15963 |
| BCL11A-13621 | − | UUAUUUUCAUGUUAAGCAAAAC | 22 | 3' | 15964 |
| BCL11A-13622 | − | AUUAUUUUCAUGUUAAGCAAAAC | 23 | 3' | 15965 |
| BCL11A-13623 | − | UAUUAUUUUCAUGUUAAGCAAAAC | 24 | 3' | 15966 |
| BCL11A-13624 | − | AGUAUUUUCUUUCAUUGG | 18 | 3' | 15967 |
| BCL11A-13625 | − | AAGUAUUUUCUUUCAUUGG | 19 | 3' | 15968 |
| BCL11A-13626 | − | UAAGUAUUUUCUUUCAUUGG | 20 | 3' | 15969 |
| BCL11A-13627 | − | GUAAGUAUUUUCUUUCAUUGG | 21 | 3' | 15970 |
| BCL11A-13628 | − | AGUAAGUAUUUUCUUUCAUUGG | 22 | 3' | 15971 |
| BCL11A-13629 | − | CAGUAAGUAUUUUCUUUCAUUGG | 23 | 3' | 15972 |
| BCL11A-13630 | − | ACAGUAAGUAUUUUCUUUCAUUGG | 24 | 3' | 15973 |

TABLE 22E-continued

5th Tier

| gRNA Name | DNA Strand | Targeting Domain | Target Site Length | 5' or 3' | SEQ ID NO: |
|---|---|---|---|---|---|
| BCL11A-13631 | - | AAGUAUUUCUUUCAUUG | 18 | 3' | 15974 |
| BCL11A-13632 | - | UAAGUAUUUCUUUCAUUG | 19 | 3' | 15975 |
| BCL11A-13633 | - | GUAAGUAUUUCUUUCAUUG | 20 | 3' | 15976 |
| BCL11A-13634 | - | AGUAAGUAUUUCUUUCAUUG | 21 | 3' | 15977 |
| BCL11A-13635 | - | CAGUAAGUAUUUCUUUCAUUG | 22 | 3' | 15978 |
| BCL11A-13636 | - | ACAGUAAGUAUUUCUUUCAUUG | 23 | 3' | 15979 |
| BCL11A-13637 | - | UACAGUAAGUAUUUCUUUCAUUG | 24 | 3' | 15980 |
| BCL11A-13638 | - | GUAAGUAUUUCUUUCAU | 18 | 3' | 15981 |
| BCL11A-13639 | - | AGUAAGUAUUUCUUUCAU | 19 | 3' | 15982 |
| BCL11A-13640 | - | CAGUAAGUAUUUCUUUCAU | 20 | 3' | 15983 |
| BCL11A-13641 | - | ACAGUAAGUAUUUCUUUCAU | 21 | 3' | 15984 |
| BCL11A-13642 | - | UACAGUAAGUAUUUCUUUCAU | 22 | 3' | 15985 |
| BCL11A-13643 | - | GUACAGUAAGUAUUUCUUUCAU | 23 | 3' | 15986 |
| BCL11A-13644 | - | AGUACAGUAAGUAUUUCUUUCAU | 24 | 3' | 15987 |
| BCL11A-13645 | - | UUGGCUAUUGAUACUGAU | 18 | 3' | 15988 |
| BCL11A-13646 | - | UUUGGCUAUUGAUACUGAU | 19 | 3' | 15989 |
| BCL11A-13647 | - | CUUUGGCUAUUGAUACUGAU | 20 | 3' | 15990 |
| BCL11A-13648 | - | UCUUUGGCUAUUGAUACUGAU | 21 | 3' | 15991 |
| BCL11A-13649 | - | AUCUUUGGCUAUUGAUACUGAU | 22 | 3' | 15992 |
| BCL11A-13650 | - | GAUCUUUGGCUAUUGAUACUGAU | 23 | 3' | 15993 |
| BCL11A-13651 | - | GGAUCUUUGGCUAUUGAUACUGAU | 24 | 3' | 15994 |
| BCL11A-13652 | - | UAAGUAUUUCUUUCAUU | 18 | 3' | 15995 |
| BCL11A-13653 | - | GUAAGUAUUUCUUUCAUU | 19 | 3' | 15996 |
| BCL11A-13654 | - | AGUAAGUAUUUCUUUCAUU | 20 | 3' | 15997 |
| BCL11A-13655 | - | CAGUAAGUAUUUCUUUCAUU | 21 | 3' | 15998 |
| BCL11A-13656 | - | ACAGUAAGUAUUUCUUUCAUU | 22 | 3' | 15999 |
| BCL11A-13657 | - | UACAGUAAGUAUUUCUUUCAUU | 23 | 3' | 16000 |
| BCL11A-13658 | - | GUACAGUAAGUAUUUCUUUCAUU | 24 | 3' | 16001 |

Table 23A provides exemplary targeting domains for removing (e.g., deleting) the enhancer region of the BCL11A gene selected according to the first tier parameters. The targeting domains bind within a region 5' (51.5 to 51.7 kb downstream of TSS) or 3' (65.1 to 65.3 kb downstream of TSS), have a high level of orthogonality, and start with 5'G. It is contemplated herein that in an embodiment the targeting domain hybridizes to the target domain through complementary base pairing. Any of the targeting domains in the table can be used with a N. meningitidis Cas9 molecule that generates a double stranded break (Cas9 nuclease) or a single-stranded break (Cas9 nickase).

TABLE 23A

1st Tier

| gRNA Name | DNA Strand | Targeting Domain | Target Site Length | 5' or 3' | SEQ ID NO: |
|---|---|---|---|---|---|
| BCL11A-13659 | − | GGAUCUUUGGCUAUUGA | 17 | 3' | 16002 |

Table 23B provides exemplary targeting domains for removing (e.g., deleting) the enhancer region of the BCL11A gene selected according to the second tier parameters. The targeting domains bind within a region 5' (51.5 to 51.7 kb downstream of TSS) or 3' (65.1 to 65.3 kb downstream of TSS) and have a high level of orthogonality. It is contemplated herein that in an embodiment the targeting domain hybridizes to the target domain through complementary base pairing. Any of the targeting domains in the table can be used with a *N. meningitidis* Cas9 molecule that generates a double stranded break (Cas9 nuclease) or a single-stranded break (Cas9 nickase).

TABLE 23B

2nd Tier

| gRNA Name | DNA Strand | Targeting Domain | Target Site Length | 5' or 3' | SEQ ID NO: |
|---|---|---|---|---|---|
| BCL11A-13660 | + | UCGGUAAAACUUUCUAG | 17 | 3' | 16003 |
| BCL11A-13661 | − | UUUGGAUCUUUGGCUAUUGA | 20 | 3' | 16004 |
| BCL11A-13662 | + | CCCUGUUAUGGCUGUAAAUA | 20 | 3' | 16005 |
| BCL11A-13663 | + | AAUUCGGUAAAACUUUCUAG | 20 | 3' | 16006 |

Table 23C provides exemplary targeting domains for removing (e.g., deleting) the enhancer region of the BCL11A gene selected according to the fourth tier parameters. The targeting domains bind within a region 5' (51.5 to 51.7 kb downstream of TSS) or 3' (65.1 to 65.3 kb downstream of TSS). It is contemplated herein that in an embodiment the targeting domain hybridizes to the target domain through complementary base pairing. Any of the targeting domains in the table can be used with a *N. meningitidis* Cas9 molecule that generates a double stranded break (Cas9 nuclease) or a single-stranded break (Cas9 nickase).

TABLE 23C

4th Tier

| gRNA Name | DNA Strand | Targeting Domain | Target Site Length | 5' or 3' | SEQ ID NO: |
|---|---|---|---|---|---|
| BCL11A-13664 | + | CACUGCGCCCAGCCUUA | 17 | 5' | 16007 |
| BCL11A-13665 | + | AGCCACUGCGCCCAGCCUUA | 20 | 5' | 16008 |
| BCL11A-13666 | + | UGUUAUGGCUGUAAAUA | 17 | 3' | 16009 |

Table 24A provides exemplary targeting domains for correcting a mutation (e.g., E6V) in the HBB gene selected according to the first tier parameters. The targeting domains bind within 200 bp to a mutation (e.g., E6V) and have a high level of orthogonality. It is contemplated herein that the targeting domain hybridizes to the target domain through complementary base pairing. Any of the targeting domains in the table can be used with a *S. pyogenes* Cas9 molecule that generates a double strand break (Cas9 nuclease) or a single-strand break (Cas9 nickase).

TABLE 24A

1st Tier

| gRNA Name | DNA Strand | Targeting Domain | Target Site Length | SEQ ID NO: |
|---|---|---|---|---|
| HBB-19 | + | GUUCACCUUGCCCCACA | 17 | 16010 |
| HBB-5 | + | AGGAGUCAGGUGCACCA | 17 | 16011 |

TABLE 24A-continued

1st Tier

| gRNA Name | DNA Strand | Targeting Domain | Target Site Length | SEQ ID NO: |
|---|---|---|---|---|
| HBB-40 | - | UACUGCCCUGUGGGCA | 17 | 16012 |
| HBB-70 | - | GCUGGGCAUAAAAGUCA | 17 | 16013 |
| HBB-71 | - | GUUACAAGACAGGUUUA | 17 | 16014 |
| HBB-72 | - | AGGAGACCAAUAGAAAC | 17 | 16015 |
| HBB-37 | + | CGUUCACCUUGCCCCAC | 17 | 16016 |
| HBB-3 | + | ACGGCAGACUUCUCCAC | 17 | 16017 |
| HBB-41 | - | UAUCAAGGUUACAAGAC | 17 | 16018 |
| HBB-73 | + | ACUUUUAUGCCCAGCCC | 17 | 16019 |
| HBB-74 | - | GGCUGGGCAUAAAAGUC | 17 | 16020 |
| HBB-4 | + | ACUUCUCCACAGGAGUC | 17 | 16021 |
| HBB-75 | - | AAUAGAAACUGGGCAUG | 17 | 16022 |
| HBB-38 | - | CUGCCGUUACUGCCCUG | 17 | 16023 |
| HBB-13 | - | GGAUGAAGUUGGUGGUG | 17 | 16024 |
| HBB-12 | - | GCCGUUACUGCCCUGUG | 17 | 16025 |
| HBB-76 | + | ACAUGCCCAGUUUCUAU | 17 | 16026 |
| HBB-77 | - | GGAGACCAAUAGAAACU | 17 | 16027 |
| HBB-15 | - | GUGAACGUGGAUGAAGU | 17 | 16028 |
| HBB-47 | - | UGCCGUUACUGCCCUGU | 17 | 16029 |
| HBB-39 | + | CUUGCCCACAGGGCAGUAA | 20 | 16030 |
| HBB-30 | + | CACGUUCACCUUGCCCCACA | 20 | 16031 |
| HBB-7 | + | CACAGGAGUCAGGUGCACCA | 20 | 16032 |
| HBB-78 | - | AGCAGGGAGGGCAGGAGCCA | 20 | 16033 |
| HBB-36 | - | CGUUACUGCCCUGUGGGGCA | 20 | 16034 |
| HBB-79 | - | AGGGCUGGGCAUAAAAGUCA | 20 | 16035 |
| HBB-22 | + | AAGCAAAUGUAAGCAAUAGA | 20 | 16036 |
| HBB-80 | - | AAGGUUACAAGACAGGUUUA | 20 | 16037 |
| HBB-81 | - | UUAAGGAGACCAAUAGAAAC | 20 | 16038 |
| HBB-2 | + | GUAACGGCAGACUUCUCCAC | 20 | 16039 |
| HBB-49 | - | UGGUAUCAAGGUUACAAGAC | 20 | 16040 |
| HBB-82 | + | CUGACUUUUAUGCCCAGCCC | 20 | 16041 |
| HBB-43 | - | UGAAGUUGGUGGUGAGGCCC | 20 | 16042 |
| HBB-83 | - | GAGCAGGGAGGGCAGGAGCC | 20 | 16043 |
| HBB-84 | - | CAGGGCUGGGCAUAAAAGUC | 20 | 16044 |
| HBB-8 | + | CAGACUUCUCCACAGGAGUC | 20 | 16045 |
| HBB-16 | - | GUGAACGUGGAUGAAGUUGG | 20 | 16046 |
| HBB-85 | - | ACCAAUAGAAACUGGGCAUG | 20 | 16047 |
| HBB-27 | - | AGUCUGCCGUUACUGCCCUG | 20 | 16048 |
| HBB-35 | - | CGUGGAUGAAGUUGGUGGUG | 20 | 16049 |
| HBB-42 | - | UCUGCCGUUACUGCCCUGUG | 20 | 16050 |
| HBB-86 | - | UAAGGAGACCAAUAGAAACU | 20 | 16051 |
| HBB-9 | - | GAAGUUGGUGGUGAGGCCCU | 20 | 16052 |
| HBB-87 | - | GGAGGGCAGGAGCCAGGGCU | 20 | 16053 |
| HBB-23 | - | AAGGUGAACGUGGAUGAAGU | 20 | 16054 |
| HBB-14 | - | GUCUGCCGUUACUGCCCUGU | 20 | 16055 |

Table 24B provides exemplary targeting domains for correcting a mutation (e.g., E6V) in the HBB gene selected according to the second tier parameters. The targeting domains bind within 200 bp to a mutation (e.g., E6V) and start with a 5'G. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase).

TABLE 24B

2nd Tier

| gRNA Name | DNA Strand | Targeting Domain | Target Site Length | SEQ ID NO: |
|---|---|---|---|---|
| HBB-11 | + | GCCCCACAGGGCAGUAA | 17 | 16056 |
| HBB-18 | - | GUGGUGAGGCCCUGGGC | 17 | 16057 |
| HBB-17 | - | GUGGGGCAAGGUGAACG | 17 | 16058 |
| HBB-1 | - | GGUGCACCUGACUCCUG | 17 | 16059 |
| HBB-20 | - | GUUGGUGGUGAGGCCCU | 17 | 16060 |
| HBB-88 | - | GGGCAGGAGCCAGGGCU | 17 | 16061 |
| HBB-10 | - | GCAACCUCAAACAGACACCA | 20 | 16062 |
| HBB-89 | - | GGGAGGGCAGGAGCCAGGGC | 20 | 16063 |

Table 24C provides exemplary targeting domains for correcting a mutation (e.g., E6V) in the HBB gene selected according to the third tier parameters. The targeting domains bind within 200 bp to a mutation (e.g., E6V). It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase).

TABLE 24C

3rd Tier

| gRNA Name | DNA Strand | Targeting Domain | Target Site Length | SEQ ID NO: |
|---|---|---|---|---|
| HBB-25 | - | ACCUCAAACAGACACCA | 17 | 16064 |
| HBB-45 | + | UGAUACCAACCUGCCCA | 17 | 16065 |
| HBB-90 | - | AGGGAGGGCAGGAGCCA | 17 | 16066 |
| HBB-48 | - | UGGGCAGGUUGGUAUCA | 17 | 16067 |
| HBB-29 | + | CAAAUGUAAGCAAUAGA | 17 | 16068 |
| HBB-28 | - | AGUUGGUGGUGAGGCCC | 17 | 16069 |
| HBB-51 | + | UUGAUACCAACCUGCCC | 17 | 16070 |
| HBB-91 | - | CAGGGAGGGCAGGAGCC | 17 | 16071 |
| HBB-92 | - | AGGGCAGGAGCCAGGGC | 17 | 16072 |
| HBB-21 | - | AACGUGGAUGAAGUUGG | 17 | 16073 |
| HBB-24 | + | ACCAUGGUGUCUGUUUG | 17 | 16074 |
| HBB-44 | - | UGAGGCCCUGGGCAGGU | 17 | 16075 |
| HBB-34 | + | CCUUGAUACCAACCUGCCCA | 20 | 16076 |
| HBB-32 | - | CCCUGGGCAGGUUGGUAUCA | 20 | 16077 |
| HBB-31 | + | CCACGUUCACCUUGCCCCAC | 20 | 16078 |
| HBB-26 | + | ACCUUGAUACCAACCUGCCC | 20 | 16079 |
| HBB-52 | - | UUGGUGGUGAGGCCCUGGGC | 20 | 16080 |
| HBB-33 | - | CCUGUGGGGCAAGGUGAACG | 20 | 16081 |
| HBB-6 | - | CAUGGUGCACCUGACUCCUG | 20 | 16082 |
| HBB-46 | + | UGCACCAUGGUGUCUGUUUG | 20 | 16083 |
| HBB-50 | - | UGGUGAGGCCCUGGGCAGGU | 20 | 16084 |

Table 24D provides targeting domains for correcting a mutation (e.g., E6V) in the HBB gene by dual targeting (e.g., dual single strand cleavages). In an embodiment, dual targeting (e.g., dual nicking) is used to create two nicks on opposite DNA strands by using S. pyogenes Cas9 nickases with two targeting domains that are complementary to opposite DNA strands, e.g., a gRNA comprising any minus strand targeting domain may be paired any gRNA comprising a plus strand targeting domain provided that the two gRNAs are oriented on the DNA such that PAMs face outward and the distance between the 5' ends of the gRNAs is 0-50 bp. Exemplary nickase pairs include a targeting domain from Group A and a second targeting domain from Group B in Table 24D (for S. pyogenes). It is contemplated herein that in an embodiment a targeting domain of Group A can be combined with any of the targeting domains of Group B in Table 24D (for S. pyogenes). For example, HBB-9 or HBB-20 can be combined with HBB-11 or HBB-39.

TABLE 24D

| Group A | Group B |
|---|---|
| HBB-9, HBB-20 | HBB-11, HBB-39 |

Table 25A provides exemplary targeting domains for correcting a mutation (e.g., E6V) in the HBB gene selected according to the first tier parameters. The targeting domains bind within 200 bp to a mutation (e.g., E6V), and have a high level of orthogonality. The PAM is NNGRRT. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase).

TABLE 25A

1st Tier

| gRNA Name | DNA Strand | Targeting Domain | Target Site Length | SEQ ID NO: |
|---|---|---|---|---|
| HBB-93 | + | AACGGCAGACUUCUCCAC | 18 | 16085 |
| HBB-94 | + | UAACGGCAGACUUCUCCAC | 19 | 16086 |
| HBB-2 | + | GUAACGGCAGACUUCUCCAC | 20 | 16087 |
| HBB-95 | + | AGUAACGGCAGACUUCUCCAC | 21 | 16088 |
| HBB-96 | + | CAGUAACGGCAGACUUCUCCAC | 22 | 16089 |
| HBB-97 | + | GCAGUAACGGCAGACUUCUCCAC | 23 | 16090 |
| HBB-98 | + | GGCAGUAACGGCAGACUUCUCCAC | 24 | 16091 |
| HBB-99 | - | CUGUGGGGCAAGGUGAAC | 18 | 16092 |
| HBB-100 | - | CCUGUGGGGCAAGGUGAAC | 19 | 16093 |
| HBB-101 | - | CCCUGUGGGGCAAGGUGAAC | 20 | 16094 |
| HBB-102 | - | GCCCUGUGGGGCAAGGUGAAC | 21 | 16095 |
| HBB-103 | - | UGCCCUGUGGGGCAAGGUGAAC | 22 | 16096 |
| HBB-104 | - | CUGCCCUGUGGGGCAAGGUGAAC | 23 | 16097 |
| HBB-105 | - | ACUGCCCUGUGGGGCAAGGUGAAC | 24 | 16098 |

Table 25B provides exemplary targeting domains for correcting a mutation (e.g., E6V) in the HBB gene selected according to the fourth tier parameters. The targeting domains bind within 200 bp to a mutation (e.g., E6V), and the PAM is NNGRRV. It is contemplated herein that the targeting domain hybridizes to the target domain through complementary base pairing. Any of the targeting domains in the table can be used with a S. pyogenes Cas9 molecule that generates a double strand break (Cas9 nuclease) or a single-strand break (Cas9 nickase).

TABLE 25B

| | | 4th Tier | | |
|---|---|---|---|---|
| gRNA Name | DNA Strand | Targeting Domain | Target Site Length | SEQ ID NO: |
| HBB-106 | + | CACGUUCACCUUGCCCCA | 18 | 16099 |
| HBB-107 | + | CCACGUUCACCUUGCCCCA | 19 | 16100 |
| HBB-58 | + | UCCACGUUCACCUUGCCCCA | 20 | 16101 |
| HBB-108 | + | AUCCACGUUCACCUUGCCCCA | 21 | 16102 |
| HBB-109 | + | CAUCCACGUUCACCUUGCCCCA | 22 | 16103 |
| HBB-110 | + | UCAUCCACGUUCACCUUGCCCCA | 23 | 16104 |
| HBB-111 | + | UUCAUCCACGUUCACCUUGCCCCA | 24 | 16105 |
| HBB-112 | + | UAACGGCAGACUUCUCCA | 18 | 16106 |
| HBB-113 | + | GUAACGGCAGACUUCUCCA | 19 | 16107 |
| HBB-69 | + | AGUAACGGCAGACUUCUCCA | 20 | 16108 |
| HBB-114 | + | CAGUAACGGCAGACUUCUCCA | 21 | 16109 |
| HBB-115 | + | GCAGUAACGGCAGACUUCUCCA | 22 | 16110 |
| HBB-116 | + | GGCAGUAACGGCAGACUUCUCCA | 23 | 16111 |
| HBB-117 | + | GGGCAGUAACGGCAGACUUCUCCA | 24 | 16112 |
| HBB-118 | + | GUCUGUUUGAGGUUGCUA | 18 | 16113 |
| HBB-119 | + | UGUCUGUUUGAGGUUGCUA | 19 | 16114 |
| HBB-66 | + | GUGUCUGUUUGAGGUUGCUA | 20 | 16115 |
| HBB-120 | + | GGUGUCUGUUUGAGGUUGCUA | 21 | 16116 |
| HBB-121 | + | UGGUGUCUGUUUGAGGUUGCUA | 22 | 16117 |
| HBB-122 | + | AUGGUGUCUGUUUGAGGUUGCUA | 23 | 16118 |
| HBB-123 | + | CAUGGUGUCUGUUUGAGGUUGCUA | 24 | 16119 |
| HBB-124 | + | CCUUGAUACCAACCUGCC | 18 | 16120 |
| HBB-125 | + | ACCUUGAUACCAACCUGCC | 19 | 16121 |
| HBB-57 | + | AACCUUGAUACCAACCUGCC | 20 | 16122 |
| HBB-126 | + | UAACCUUGAUACCAACCUGCC | 21 | 16123 |
| HBB-127 | + | GUAACCUUGAUACCAACCUGCC | 22 | 16124 |
| HBB-128 | + | UGUAACCUUGAUACCAACCUGCC | 23 | 16125 |
| HBB-129 | + | UUGUAACCUUGAUACCAACCUGCC | 24 | 16126 |
| HBB-130 | + | GUGCACCAUGGUGUCUGU | 18 | 16127 |
| HBB-131 | + | GGUGCACCAUGGUGUCUGU | 19 | 16128 |
| HBB-62 | + | AGGUGCACCAUGGUGUCUGU | 20 | 16129 |
| HBB-132 | + | CAGGUGCACCAUGGUGUCUGU | 21 | 16130 |
| HBB-133 | + | UCAGGUGCACCAUGGUGUCUGU | 22 | 16131 |
| HBB-134 | + | GUCAGGUGCACCAUGGUGUCUGU | 23 | 16132 |
| HBB-135 | + | AGUCAGGUGCACCAUGGUGUCUGU | 24 | 16133 |
| HBB-136 | + | UAGUGAACACAGUUGUGU | 18 | 16134 |
| HBB-137 | + | CUAGUGAACACAGUUGUGU | 19 | 16135 |
| HBB-59 | + | GCUAGUGAACACAGUUGUGU | 20 | 16136 |

TABLE 25B-continued

4th Tier

| gRNA Name | DNA Strand | Targeting Domain | Target Site Length | SEQ ID NO: |
|---|---|---|---|---|
| HBB-138 | + | UGCUAGUGAACACAGUUGUGU | 21 | 16137 |
| HBB-139 | + | UUGCUAGUGAACACAGUUGUGU | 22 | 16138 |
| HBB-140 | + | GUUGCUAGUGAACACAGUUGUGU | 23 | 16139 |
| HBB-141 | + | GGUUGCUAGUGAACACAGUUGUGU | 24 | 16140 |
| HBB-142 | - | UAAGGAGACCAAUAGAAA | 18 | 16141 |
| HBB-143 | - | UUAAGGAGACCAAUAGAAA | 19 | 16142 |
| HBB-144 | - | UUUAAGGAGACCAAUAGAAA | 20 | 16143 |
| HBB-145 | - | GUUUAAGGAGACCAAUAGAAA | 21 | 16144 |
| HBB-146 | - | GGUUUAAGGAGACCAAUAGAAA | 22 | 16145 |
| HBB-147 | - | AGGUUUAAGGAGACCAAUAGAAA | 23 | 16146 |
| HBB-148 | - | CAGGUUUAAGGAGACCAAUAGAAA | 24 | 16147 |
| HBB-149 | - | CAGGUUUAAGGAGACCAA | 18 | 16148 |
| HBB-150 | - | ACAGGUUUAAGGAGACCAA | 19 | 16149 |
| HBB-151 | - | GACAGGUUUAAGGAGACCAA | 20 | 16150 |
| HBB-152 | - | AGACAGGUUUAAGGAGACCAA | 21 | 16151 |
| HBB-153 | - | AAGACAGGUUUAAGGAGACCAA | 22 | 16152 |
| HBB-154 | - | CAAGACAGGUUUAAGGAGACCAA | 23 | 16153 |
| HBB-155 | - | ACAAGACAGGUUUAAGGAGACCAA | 24 | 16154 |
| HBB-156 | - | GGUUACAAGACAGGUUUA | 18 | 16155 |
| HBB-157 | - | AGGUUACAAGACAGGUUUA | 19 | 16156 |
| HBB-80 | - | AAGGUUACAAGACAGGUUUA | 20 | 16157 |
| HBB-158 | - | CAAGGUUACAAGACAGGUUUA | 21 | 16158 |
| HBB-159 | - | UCAAGGUUACAAGACAGGUUUA | 22 | 16159 |
| HBB-160 | - | AUCAAGGUUACAAGACAGGUUUA | 23 | 16160 |
| HBB-161 | - | UAUCAAGGUUACAAGACAGGUUUA | 24 | 16161 |
| HBB-162 | - | GAAGUUGGUGGUGAGGCC | 18 | 16162 |
| HBB-163 | - | UGAAGUUGGUGGUGAGGCC | 19 | 16163 |
| HBB-68 | - | AUGAAGUUGGUGGUGAGGCC | 20 | 16164 |
| HBB-164 | - | GAUGAAGUUGGUGGUGAGGCC | 21 | 16165 |
| HBB-165 | - | GGAUGAAGUUGGUGGUGAGGCC | 22 | 16166 |
| HBB-166 | - | UGGAUGAAGUUGGUGGUGAGGCC | 23 | 16167 |
| HBB-167 | - | GUGGAUGAAGUUGGUGGUGAGGCC | 24 | 16168 |
| HBB-168 | - | ACUGCCCUGUGGGGCAAG | 18 | 16169 |
| HBB-169 | - | UACUGCCCUGUGGGGCAAG | 19 | 16170 |
| HBB-65 | - | UUACUGCCCUGUGGGGCAAG | 20 | 16171 |
| HBB-170 | - | GUUACUGCCCUGUGGGGCAAG | 21 | 16172 |
| HBB-171 | - | CGUUACUGCCCUGUGGGGCAAG | 22 | 16173 |

TABLE 25B-continued

| 4th Tier | | | | |
|---|---|---|---|---|
| gRNA Name | DNA Strand | Targeting Domain | Target Site Length | SEQ ID NO: |
| HBB-172 | − | CCGUUACUGCCCUGUGGGGCAAG | 23 | 16174 |
| HBB-173 | − | GCCGUUACUGCCCUGUGGGGCAAG | 24 | 16175 |
| HBB-174 | − | GGAGGGCAGGAGCCAGGG | 18 | 16176 |
| HBB-175 | − | GGGAGGGCAGGAGCCAGGG | 19 | 16177 |
| HBB-176 | − | AGGGAGGGCAGGAGCCAGGG | 20 | 16178 |
| HBB-177 | − | CAGGGAGGGCAGGAGCCAGGG | 21 | 16179 |
| HBB-178 | − | GCAGGGAGGGCAGGAGCCAGGG | 22 | 16180 |
| HBB-179 | − | AGCAGGGAGGGCAGGAGCCAGGG | 23 | 16181 |
| HBB-180 | − | GAGCAGGGAGGGCAGGAGCCAGGG | 24 | 16182 |
| HBB-181 | − | UGGGCAUAAAAGUCAGGG | 18 | 16183 |
| HBB-182 | − | CUGGGCAUAAAAGUCAGGG | 19 | 16184 |
| HBB-183 | − | GCUGGGCAUAAAAGUCAGGG | 20 | 16185 |
| HBB-184 | − | GGCUGGGCAUAAAAGUCAGGG | 21 | 16186 |
| HBB-185 | − | GGGCUGGGCAUAAAAGUCAGGG | 22 | 16187 |
| HBB-186 | − | AGGGCUGGGCAUAAAAGUCAGGG | 23 | 16188 |
| HBB-187 | − | CAGGGCUGGGCAUAAAAGUCAGGG | 24 | 16189 |
| HBB-188 | − | GGGGCAAGGUGAACGUGG | 18 | 16190 |
| HBB-189 | − | UGGGGCAAGGUGAACGUGG | 19 | 16191 |
| HBB-67 | − | GUGGGGCAAGGUGAACGUGG | 20 | 16192 |
| HBB-190 | − | UGUGGGGCAAGGUGAACGUGG | 21 | 16193 |
| HBB-191 | − | CUGUGGGGCAAGGUGAACGUGG | 22 | 16194 |
| HBB-192 | − | CCUGUGGGGCAAGGUGAACGUGG | 23 | 16195 |
| HBB-193 | − | CCCUGUGGGGCAAGGUGAACGUGG | 24 | 16196 |
| HBB-194 | − | UCUGCCGUUACUGCCCUG | 18 | 16197 |
| HBB-195 | − | GUCUGCCGUUACUGCCCUG | 19 | 16198 |
| HBB-27 | − | AGUCUGCCGUUACUGCCCUG | 20 | 16199 |
| HBB-196 | − | AAGUCUGCCGUUACUGCCCUG | 21 | 16200 |
| HBB-197 | − | GAAGUCUGCCGUUACUGCCCUG | 22 | 16201 |
| HBB-198 | − | AGAAGUCUGCCGUUACUGCCCUG | 23 | 16202 |
| HBB-199 | − | GAGAAGUCUGCCGUUACUGCCCUG | 24 | 16203 |
| HBB-200 | − | UGGUGCACCUGACUCCUG | 18 | 16204 |
| HBB-201 | − | AUGGUGCACCUGACUCCUG | 19 | 16205 |
| HBB-6 | − | CAUGGUGCACCUGACUCCUG | 20 | 16206 |
| HBB-202 | − | CCAUGGUGCACCUGACUCCUG | 21 | 16207 |
| HBB-203 | − | ACCAUGGUGCACCUGACUCCUG | 22 | 16208 |
| HBB-204 | − | CACCAUGGUGCACCUGACUCCUG | 23 | 16209 |
| HBB-205 | − | ACACCAUGGUGCACCUGACUCCUG | 24 | 16210 |
| HBB-206 | − | ACGUGGAUGAAGUUGGUG | 18 | 16211 |

TABLE 25B-continued

| | 4th Tier | | |
|---|---|---|---|
| gRNA Name | DNA Strand Targeting Domain | Target Site Length | SEQ ID NO: |
| HBB-207 | - AACGUGGAUGAAGUUGGUG | 19 | 16212 |
| HBB-64 | - GAACGUGGAUGAAGUUGGUG | 20 | 16213 |
| HBB-208 | - UGAACGUGGAUGAAGUUGGUG | 21 | 16214 |
| HBB-209 | - GUGAACGUGGAUGAAGUUGGUG | 22 | 16215 |
| HBB-210 | - GGUGAACGUGGAUGAAGUUGGUG | 23 | 16216 |
| HBB-211 | - AGGUGAACGUGGAUGAAGUUGGUG | 24 | 16217 |
| HBB-212 | - GUGCACCUGACUCCUGUG | 18 | 16218 |
| HBB-213 | - GGUGCACCUGACUCCUGUG | 19 | 16219 |
| HBB-63 | - UGGUGCACCUGACUCCUGUG | 20 | 16220 |
| HBB-214 | - AUGGUGCACCUGACUCCUGUG | 21 | 16221 |
| HBB-215 | - CAUGGUGCACCUGACUCCUGUG | 22 | 16222 |
| HBB-216 | - CCAUGGUGCACCUGACUCCUGUG | 23 | 16223 |
| HBB-217 | - ACCAUGGUGCACCUGACUCCUGUG | 24 | 16224 |
| HBB-218 | - GUCUGCCGUUACUGCCCU | 18 | 16225 |
| HBB-219 | - AGUCUGCCGUUACUGCCCU | 19 | 16226 |
| HBB-56 | - AAGUCUGCCGUUACUGCCCU | 20 | 16227 |
| HBB-220 | - GAAGUCUGCCGUUACUGCCCU | 21 | 16228 |
| HBB-221 | - AGAAGUCUGCCGUUACUGCCCU | 22 | 16229 |
| HBB-222 | - GAGAAGUCUGCCGUUACUGCCCU | 23 | 16230 |
| HBB-223 | - GGAGAAGUCUGCCGUUACUGCCCU | 24 | 16231 |
| HBB-224 | - AUGGUGCACCUGACUCCU | 18 | 16232 |
| HBB-225 | - CAUGGUGCACCUGACUCCU | 19 | 16233 |
| HBB-60 | - CCAUGGUGCACCUGACUCCU | 20 | 16234 |
| HBB-226 | - ACCAUGGUGCACCUGACUCCU | 21 | 16235 |
| HBB-227 | - CACCAUGGUGCACCUGACUCCU | 22 | 16236 |
| HBB-228 | - ACACCAUGGUGCACCUGACUCCU | 23 | 16237 |
| HBB-229 | - GACACCAUGGUGCACCUGACUCCU | 24 | 16238 |
| HBB-230 | - AGGGCUGGGCAUAAAAGU | 18 | 16239 |
| HBB-231 | - CAGGGCUGGGCAUAAAAGU | 19 | 16240 |
| HBB-232 | - CCAGGGCUGGGCAUAAAAGU | 20 | 16241 |
| HBB-233 | - GCCAGGGCUGGGCAUAAAAGU | 21 | 16242 |
| HBB-234 | - AGCCAGGGCUGGGCAUAAAAGU | 22 | 16243 |
| HBB-235 | - GAGCCAGGGCUGGGCAUAAAAGU | 23 | 16244 |
| HBB-236 | - GGAGCCAGGGCUGGGCAUAAAAGU | 24 | 16245 |
| HBB-237 | - AGGUUACAAGACAGGUUU | 18 | 16246 |
| HBB-238 | - AAGGUUACAAGACAGGUUU | 19 | 16247 |
| HBB-239 | - CAAGGUUACAAGACAGGUUU | 20 | 16248 |

TABLE 25B-continued

4th Tier

| gRNA Name | DNA Strand | Targeting Domain | Target Site Length | SEQ ID NO: |
|---|---|---|---|---|
| HBB-240 | − | UCAAGGUUACAAGACAGGUUU | 21 | 16249 |
| HBB-241 | − | AUCAAGGUUACAAGACAGGUUU | 22 | 16250 |
| HBB-242 | − | UAUCAAGGUUACAAGACAGGUUU | 23 | 16251 |
| HBB-243 | − | GUAUCAAGGUUACAAGACAGGUUU | 24 | 16252 |

Table 26 provides exemplary targeting domains for correcting a mutation (e.g., E6V) in the HBB gene selected according to the first tier parameters. The targeting domains bind within 200 bp to a mutation (e.g., E6V) and have a high level of orthogonality. It is contemplated herein that the targeting domain hybridizes to the target domain through complementary base pairing. Any of the targeting domains in the table can be used with a *N. meningitidis* Cas9 molecule that generates a double strand break (Cas9 nuclease) or a single-strand break (Cas9 nickase).

TABLE 26

1st Tier

| gRNA Name | DNA Strand | Targeting Domain | Target Site Length | SEQ ID NO: |
|---|---|---|---|---|
| HBB-244 | − | AGCCAUCUAUUGCUUAC | 17 | 16253 |
| HBB-245 | − | GUCAGGGCAGAGCCAUC | 17 | 16254 |
| HBB-246 | − | CAGAGCCAUCUAUUGCUUAC | 20 | 16255 |
| HBB-247 | − | AAAGUCAGGGCAGAGCCAUC | 20 | 16256 |

III. Cas9 Molecules

Cas9 molecules of a variety of species can be used in the methods and compositions described herein. While the *S. pyogenes*, *S. aureus*, and *S. thermophilus* Cas9 molecules are the subject of much of the disclosure herein, Cas9 molecules of, derived from, or based on the Cas9 proteins of other species listed herein can be used as well. In other words, while the much of the description herein uses *S. pyogenes* and *S. thermophilus* Cas9 molecules, Cas9 molecules from the other species can replace them, e.g., *Staphylococcus aureus* and *Neisseria meningitidis* Cas9 molecules. Additional Cas9 species include: *Acidovorax avenue, Actinobacillus pleuropneumoniae, Actinobacillus succinogenes, Actinobacillus suis, Actinomyces sp., Cycliphilus denitrificans, Aminomonas paucivorans, Bacillus cereus, Bacillus smithii, Bacillus thuringiensis, Bacteroides sp., Blastopirellula marina, Bradyrhizobium sp., Brevibacillus laterosporus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, Gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis sp., Methylosinus trichosporium, Mobiluncus mulieris, Neisseria bacilliformis, Neisseria cinerea, Neisseria flavescens, Neisseria lactamica, Neisseria sp., Neisseria wadsworthii, Nitrosomonas sp., Parvibaculum lavamentivorans, Pasteurella multocida, Phascolarciobacterium succinatutens, Ralstonia syzygii, Rhodopseudomonas palustris, Rhodovulum sp., Simonsiella muelleri, Sphingomonas sp., Sporolactobacillus vineae, Staphylococcus lugdunensis, Streptococcus sp., Subdoligranulum sp., Tistrella mobilis, Treponema sp.,* or *Verminephrobacter eiseniae.*

A Cas9 molecule, or Cas9 polypeptide, as that term is used herein, refers to a molecule or a polypeptide that can interact with a guide RNA (gRNA) molecule and, in concert with the gRNA molecule, localizes to a site which comprises a target domain, and in an embodiment, a PAM sequence. Cas9 molecule and Cas9 polypeptide, as those terms are used herein, refer to naturally occurring Cas9 molecules and to engineered, altered, or modified Cas9 molecules or Cas9 polypeptides that differ, e.g., by at least one amino acid residue, from a reference sequence, e.g., the most similar naturally occurring Cas9 molecule or a sequence of Table 28.

Cas9 Domains

Crystal structures have been determined for two different naturally occurring bacterial Cas9 molecules (Jinek et al., Science, 343(6176):1247997, 2014) and for *S. pyogenes* Cas9 with a guide RNA (e.g., a synthetic fusion of crRNA and tracrRNA) (Nishimasu et al., Cell, 156:935-949, 2014; and Anders et al., Nature, 2014, doi: 10.1038/nature13579).

Figures 9A, 9B:
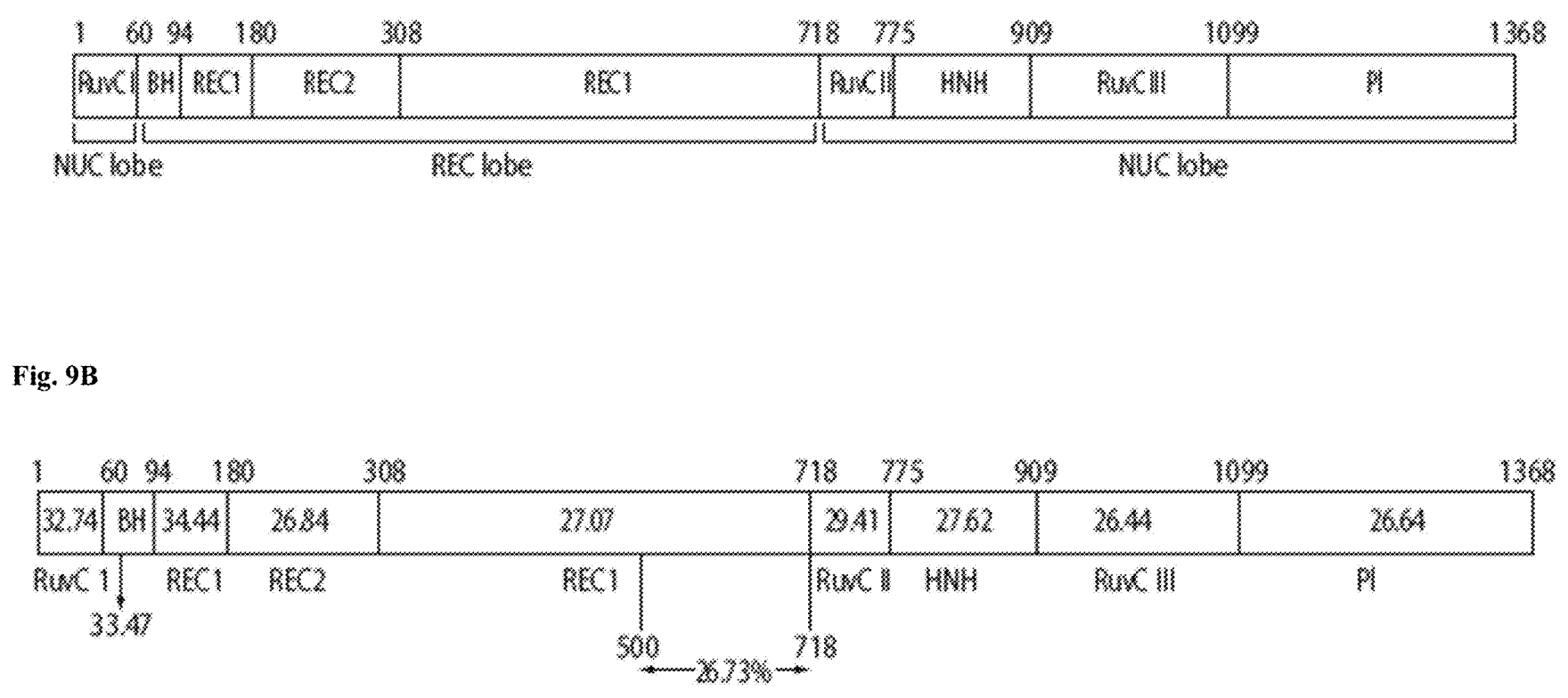

A naturally occurring Cas9 molecule comprises two lobes: a recognition (REC) lobe and a nuclease (NUC) lobe; each of which further comprise domains described herein. FIGS. 9A-9B provide a schematic of the organization of important Cas9 domains in the primary structure. The domain nomenclature and the numbering of the amino acid residues encompassed by each domain used throughout this disclosure is as described in Nishimasu et al. The numbering of the amino acid residues is with reference to Cas9 from *S. pyogenes.*

The REC lobe comprises the arginine-rich bridge helix (BH), the REC1 domain, and the REC2 domain. The REC lobe does not share structural similarity with other known proteins, indicating that it is a Cas9-specific functional domain. The BH domain is a long α helix and arginine rich region and comprises amino acids 60-93 of the sequence of *S. pyogenes* Cas9. The REC1 domain is important for recognition of the repeat:anti-repeat duplex, e.g., of a gRNA or a tracrRNA, and is therefore critical for Cas9 activity by recognizing the target sequence. The REC1 domain comprises two REC1 motifs at amino acids 94 to 179 and 308 to 717 of the sequence of *S. pyogenes* Cas9. These two REC1 domains, though separated by the REC2 domain in the linear primary structure, assemble in the tertiary structure to form the REC1 domain. The REC2 domain, or parts thereof, may also play a role in the recognition of the repeat:anti-repeat duplex. The REC2 domain comprises amino acids 180-307 of the sequence of S. pyogenes Cas9.

The NUC lobe comprises the RuvC domain, the HNH domain, and the PAM-interacting (PI) domain. The RuvC domain shares structural similarity to retroviral integrase superfamily members and cleaves a single strand, e.g., the non-complementary strand of the target nucleic acid molecule. The RuvC domain is assembled from the three split RuvC motifs (RuvC I, RuvCII, and RuvCIII, which are often commonly referred to in the art as RuvCI domain, or N-terminal RuvC domain, RuvCII domain, and RuvCIII domain) at amino acids 1-59, 718-769, and 909-1098, respectively, of the sequence of S. pyogenes Cas9. Similar to the REC1 domain, the three RuvC motifs are linearly separated by other domains in the primary structure, however in the tertiary structure, the three RuvC motifs assemble and form the RuvC domain. The HNH domain shares structural similarity with HNH endonucleases, and cleaves a single strand, e.g., the complementary strand of the target nucleic acid molecule. The HNH domain lies between the RuvC II-III motifs and comprises amino acids 775-908 of the sequence of S. pyogenes Cas9. The PI domain interacts with the PAM of the target nucleic acid molecule, and comprises amino acids 1099-1368 of the sequence of S. pyogenes Cas9.

A RuvC-Like Domain and an HNH-Like Domain

In an embodiment, a Cas9 molecule or Cas9 polypeptide comprises an HNH-like domain and a RuvC-like domain. In an embodiment, cleavage activity is dependent on a RuvC-like domain and an HNH-like domain. A Cas9 molecule or Cas9 polypeptide, e.g., an eaCas9 molecule or eaCas9 polypeptide, can comprise one or more of the following domains: a RuvC-like domain and an HNH-like domain. In an embodiment, a Cas9 molecule or Cas9 polypeptide is an eaCas9 molecule or eaCas9 polypeptide and the eaCas9 molecule or eaCas9 polypeptide comprises a RuvC-like domain, e.g., a RuvC-like domain described below, and/or an HNH-like domain, e.g., an HNH-like domain described below.

RuvC-Like Domains

In an embodiment, a RuvC-like domain cleaves, a single strand, e.g., the non-complementary strand of the target nucleic acid molecule. The Cas9 molecule or Cas9 polypeptide can include more than one RuvC-like domain (e.g., one, two, three or more RuvC-like domains). In an embodiment, a RuvC-like domain is at least 5, 6, 7, 8 amino acids in length but not more than 20, 19, 18, 17, 16 or 15 amino acids in length. In an embodiment, the Cas9 molecule or Cas9 polypeptide comprises an N-terminal RuvC-like domain of about 10 to 20 amino acids, e.g., about 15 amino acids in length.

N-Terminal RuvC-Like Domains

Some naturally occurring Cas9 molecules comprise more than one RuvC-like domain with cleavage being dependent on the N-terminal RuvC-like domain. Accordingly, Cas9 molecules or Cas9 polypeptide can comprise an N-terminal RuvC-like domain. Exemplary N-terminal RuvC-like domains are described below.

In an embodiment, an eaCas9 molecule or eaCas9 polypeptide comprises an N-terminal RuvC-like domain comprising an amino acid sequence of formula I:

D-X1-G-X2-X3-X4-X5-G-X6-X7-X8-X9        (SEQ ID NO: 8), wherein,

X1 is selected from I, V, M, L and T (e.g., selected from I, V, and L);

X2 is selected from T, I, V, S, N, Y, E and L (e.g., selected from T, V, and I);

X3 is selected from N, S, G, A, D, T, R, M and F (e.g., A or N);

X4 is selected from S, Y, N and F (e.g., S);

X5 is selected from V, I, L, C, T and F (e.g., selected from V, I and L);

X6 is selected from W, F, V, Y, S and L (e.g., W);

X7 is selected from A, S, C, V and G (e.g., selected from A and S);

X8 is selected from V, I, L, A, M and H (e.g., selected from V, I, M and L); and X9 is selected from any amino acid or is absent (e.g., selected from T, V, I, L, Δ, F, S, A, Y, M and R, or, e.g., selected from T, V, I, L and Δ).

In an embodiment, the N-terminal RuvC-like domain differs from a sequence of SEQ ID NO:8, by as many as 1 but no more than 2, 3, 4, or 5 residues.

In embodiment, the N-terminal RuvC-like domain is cleavage competent.

In embodiment, the N-terminal RuvC-like domain is cleavage incompetent.

In an embodiment, a eaCas9 molecule or eaCas9 polypeptide comprises an N-terminal RuvC-like domain comprising an amino acid sequence of formula II:

D-X1-G-X2-X3-S-X5-G-X6-X7-X8-X9,        (SEQ ID NO: 9), wherein

X1 is selected from I, V, M, L and T (e.g., selected from I, V, and L);

X2 is selected from T, I, V, S, N, Y, E and L (e.g., selected from T, V, and I);

X3 is selected from N, S, G, A, D, T, R, M and F (e.g., A or N);

X5 is selected from V, I, L, C, T and F (e.g., selected from V, I and L);

X6 is selected from W, F, V, Y, S and L (e.g., W);

X7 is selected from A, S, C, V and G (e.g., selected from A and S);

X8 is selected from V, I, L, A, M and H (e.g., selected from V, I, M and L); and X9 is selected from any amino acid or is absent (e.g., selected from T, V, I, L, Δ, F, S, A, Y, M and R or selected from e.g., T, V, I, L and Δ).

In an embodiment, the N-terminal RuvC-like domain differs from a sequence of SEQ ID NO:9 by as many as 1 but no more than 2, 3, 4, or 5 residues.

In an embodiment, the N-terminal RuvC-like domain comprises an amino acid sequence of formula III:

D-I-G-X2-X3-S-V-G-W-A-X8-X9        (SEQ ID NO: 10), wherein

X2 is selected from T, I, V, S, N, Y, E and L (e.g., selected from T, V, and I);

X3 is selected from N, S, G, A, D, T, R, M and F (e.g., A or N);

X8 is selected from V, I, L, A, M and H (e.g., selected from V, I, M and L); and X9 is selected from any amino acid or is absent (e.g., selected from T, V, I, L, Δ, F, S, A, Y, M and R or selected from e.g., T, V, I, L and Δ).

In an embodiment, the N-terminal RuvC-like domain differs from a sequence of SEQ ID NO:10 by as many as 1 but no more than, 2, 3, 4, or 5 residues.

In an embodiment, the N-terminal RuvC-like domain comprises an amino acid sequence of formula III:

D-I-G-T-N-S-V-G-W-A-V-X, (SEQ ID NO: 11)

wherein

X is a non-polar alkyl amino acid or a hydroxyl amino acid, e.g., X is selected from V, I, L and T (e.g., the eaCas9 molecule can comprise an N-terminal RuvC-like domain shown in FIGS. 2A-2G (is depicted as Y)).

In an embodiment, the N-terminal RuvC-like domain differs from a sequence of SEQ ID NO:11 by as many as 1 but no more than, 2, 3, 4, or 5 residues.

In an embodiment, the N-terminal RuvC-like domain differs from a sequence of an N-terminal RuvC like domain disclosed herein, e.g., in FIGS. 3A-3B or FIGS. 7A-7B, as many as 1 but no more than 2, 3, 4, or 5 residues. In an embodiment, 1, 2, 3 or all of the highly conserved residues identified in FIGS. 3A-3B or FIGS. 7A-7B are present.

In an embodiment, the N-terminal RuvC-like domain differs from a sequence of an N-terminal RuvC-like domain disclosed herein, e.g., in FIGS. 4A-4B or FIGS. 7A-7B, as many as 1 but no more than 2, 3, 4, or 5 residues. In an embodiment, 1, 2, or all of the highly conserved residues identified in FIGS. 4A-4B or FIGS. 7A-7B are present.

Additional RuvC-Like Domains

In addition to the N-terminal RuvC-like domain, the Cas9 molecule or Cas9 polypeptide, e.g., an eaCas9 molecule or eaCas9 polypeptide, can comprise one or more additional RuvC-like domains. In an embodiment, the Cas9 molecule or Cas9 polypeptide can comprise two additional RuvC-like domains. Preferably, the additional RuvC-like domain is at least 5 amino acids in length and, e.g., less than 15 amino acids in length, e.g., 5 to 10 amino acids in length, e.g., 8 amino acids in length.

An additional RuvC-like domain can comprise an amino acid sequence:

I-X1-X2-E-X3-A-R-E (SEQ ID NO:12), wherein

X1 is V or H,
X2 is I, L or V (e.g., I or V); and
X3 is M or T.

In an embodiment, the additional RuvC-like domain comprises the amino acid sequence:

I-V-X2-E-M-A-R-E (SEQ ID NO:13), wherein

X2 is I, L or V (e.g., I or V) (e.g., the eaCas9 molecule or eaCas9 polypeptide can comprise an additional RuvC-like domain shown in FIG. 2A-2G or FIGS. 7A-7B (depicted as B)).

An additional RuvC-like domain can comprise an amino acid sequence:

H-H-A-X1-D-A-X2-X3 (SEQ ID NO: 14), wherein

X1 is H or L;
X2 is R or V; and
X3 is E or V.

In an embodiment, the additional RuvC-like domain comprises the amino acid sequence:

H-H-A-H-D-A-Y-L (SEQ ID NO:15).

In an embodiment, the additional RuvC-like domain differs from a sequence of SEQ ID NO: 12, 13, 14 or 15 by as many as 1 but no more than 2, 3, 4, or 5 residues.

In some embodiments, the sequence flanking the N-terminal RuvC-like domain is a sequences of formula V:

K-X1'-Y-X2'-X3'-X4'-Z-T-D-X9'-Y, (SEQ ID NO: 16).

wherein

X1' is selected from K and P,
X2' is selected from V, L, I, and F (e.g., V, I and L);
X3' is selected from G, A and S (e.g., G),
X4' is selected from L, I, V and F (e.g., L);
X9' is selected from D, E, N and Q; and
Z is an N-terminal RuvC-like domain, e.g., as described above.

HNH-Like Domains

In an embodiment, an HNH-like domain cleaves a single stranded complementary domain, e.g., a complementary strand of a double stranded nucleic acid molecule. In an embodiment, an HNH-like domain is at least 15, 20, 25 amino acids in length but not more than 40, 35 or 30 amino acids in length, e.g., 20 to 35 amino acids in length, e.g., 25 to 30 amino acids in length. Exemplary HNH-like domains are described below.

In an embodiment, an eaCas9 molecule or eaCas9 polypeptide comprises an HNH-like domain having an amino acid sequence of formula VI:

X1-X2-X3-H-X4-X5-P-X6-X7-X8-X9-X10-X11-X12-X13-X14-X15-N-X16-X17-X18-X19-X20-X21-X22-X23-N (SEQ ID NO: 17), wherein X1 is selected from D, E, Q and N (e.g., D and E);
X2 is selected from L, I, R, Q, V, M and K;
X3 is selected from D and E;
X4 is selected from I, V, T, A and L (e.g., A, I and V);
X5 is selected from V, Y, I, L, F and W (e.g., V, I and L);
X6 is selected from Q, H, R, K, Y, I, L, F and W;
X7 is selected from S, A, D, T and K (e.g., S and A);
X8 is selected from F, L, V, K, Y, M, I, R, A, E, D and Q (e.g., F);
X9 is selected from L, R, T, I, V, S, C, Y, K, F and G;
X10 is selected from K, Q, Y, T, F, L, W, M, A, E, G, and S;
X11 is selected from D, S, N, R, L and T (e.g., D);
X12 is selected from D, N and S;
X13 is selected from S, A, T, G and R (e.g., S);
X14 is selected from I, L, F, S, R, Y, Q, W, D, K and H (e.g., I, L and F);
X15 is selected from D, S, I, N, E, A, H, F, L, Q, M, G, Y and V;
X16 is selected from K, L, R, M, T and F (e.g., L, R and K);
X17 is selected from V, L, I, A and T;
X18 is selected from L, I, V and A (e.g., L and I);
X19 is selected from T, V, C, E, S and A (e.g., T and V);
X20 is selected from R, F, T, W, E, L, N, C, K, V, S, Q, I, Y, H and A;
X21 is selected from S, P, R, K, N, A, H, Q, G and L;
X22 is selected from D, G, T, N, S, K, A, I, E, L, Q, R and Y; and
X23 is selected from K, V, A, E, Y, I, C, L, S, T, G, K, M, D and F.

In an embodiment, a HNH-like domain differs from a sequence of SEQ ID NO: 17 by at least one but no more than, 2, 3, 4, or 5 residues.

In an embodiment, the HNH-like domain is cleavage competent.

In an embodiment, the HNH-like domain is cleavage incompetent.

In an embodiment, an eaCas9 molecule or eaCas9 polypeptide comprises an HNH-like domain comprising an amino acid sequence of formula VII:

X1-X2-X3-H-X4-X5-P-X6-S-X8-X9-X10-D-D-S-X14-X15-N-K-V-L-X19-X20-X21-X22-X23-N (SEQ ID NO: 18), wherein
X1 is selected from D and E;
X2 is selected from L, I, R, Q, V, M and K;
X3 is selected from D and E;
X4 is selected from I, V, T, A and L (e.g., A, I and V);
X5 is selected from V, Y, I, L, F and W (e.g., V, I and L);
X6 is selected from Q, H, R, K, Y, I, L, F and W;
X8 is selected from F, L, V, K, Y, M, I, R, A, E, D and Q (e.g., F);
X9 is selected from L, R, T, I, V, S, C, Y, K, F and G;
X10 is selected from K, Q, Y, T, F, L, W, M, A, E, G, and S;
X14 is selected from I, L, F, S, R, Y, Q, W, D, K and H (e.g., I, L and F);
X15 is selected from D, S, I, N, E, A, H, F, L, Q, M, G, Y and V;
X19 is selected from T, V, C, E, S and A (e.g., T and V);
X20 is selected from R, F, T, W, E, L, N, C, K, V, S, Q, I, Y, H and A;
X21 is selected from S, P, R, K, N, A, H, Q, G and L;
X22 is selected from D, G, T, N, S, K, A, I, E, L, Q, R and Y; and
X23 is selected from K, V, A, E, Y, I, C, L, S, T, G, K, M, D and F.

In an embodiment, the HNH-like domain differs from a sequence of SEQ ID NO: 18 by 1, 2, 3, 4, or 5 residues.

In an embodiment, an eaCas9 molecule or eaCas9 polypeptide comprises an HNH-like domain comprising an amino acid sequence of formula VII:

X1-V-X3-H-I-V-P-X6-S-X8-X9-X10-D-D-S-X14-X15-N-K-V-L-T-X20-X21-X22-X23-N (SEQ ID NO:19), wherein
X1 is selected from D and E;
X3 is selected from D and E;
X6 is selected from Q, H, R, K, Y, I, L and W;
X8 is selected from F, L, V, K, Y, M, I, R, A, E, D and Q (e.g., F);
X9 is selected from L, R, T, I, V, S, C, Y, K, F and G;
X10 is selected from K, Q, Y, T, F, L, W, M, A, E, G, and S;
X14 is selected from I, L, F, S, R, Y, Q, W, D, K and H (e.g., I, L and F);
X15 is selected from D, S, I, N, E, A, H, F, L, Q, M, G, Y and V;
X20 is selected from R, F, T, W, E, L, N, C, K, V, S, Q, I, Y, H and A;
X21 is selected from S, P, R, K, N, A, H, Q, G and L;
X22 is selected from D, G, T, N, S, K, A, I, E, L, Q, R and Y; and
X23 is selected from K, V, A, E, Y, I, C, L, S, T, G, K, M, D and F.

In an embodiment, the HNH-like domain differs from a sequence of SEQ ID NO: 19 by 1, 2, 3, 4, or 5 residues.

In an embodiment, an eaCas9 molecule or eaCas9 polypeptide comprises an HNH-like domain having an amino acid sequence of formula VIII:

D-X2-D-H-I-X5-P-Q-X7-F-X9-X10-D-X12-S-I-D-N-X16-V-L-X19-X20-S-X22-X23-N (SEQ ID NO:20), wherein
X2 is selected from I and V;
X5 is selected from I and V;
X7 is selected from A and S;
X9 is selected from I and L;
X10 is selected from K and T;
X12 is selected from D and N;
X16 is selected from R, K and L; X19 is selected from T and V;
X20 is selected from S and R;
X22 is selected from K, D and A; and
X23 is selected from E, K, G and N (e.g., the eaCas9 molecule or eaCas9 polypeptide can comprise an HNH-like domain as described herein).

In an embodiment, the HNH-like domain differs from a sequence of SEQ ID NO: 20 by as many as 1 but no more than 2, 3, 4, or 5 residues.

In an embodiment, an eaCas9 molecule or eaCas9 polypeptide comprises the amino acid sequence of formula IX:

L-Y-Y-L-Q-N-G-X1'-D-M-Y-X2'-X3'-X4'-X5'-L-D-I-X6'-X7'-L-S-X8'-Y-Z-N-R-X9'-K-X10'-D-X11'-V-P (SEQ ID NO: 21), wherein
X1' is selected from K and R;
X2' is selected from V and T;
X3' is selected from G and D;
X4' is selected from E, Q and D;
X5' is selected from E and D;
X6' is selected from D, N and H;
X7' is selected from Y, R and N;
X8' is selected from Q, D and N; X9' is selected from G and E;
X10' is selected from S and G;
X11' is selected from D and N; and
Z is an HNH-like domain, e.g., as described above.

In an embodiment, the eaCas9 molecule or eaCas9 polypeptide comprises an amino acid sequence that differs from a sequence of SEQ ID NO:21 by as many as 1 but no more than 2, 3, 4, or 5 residues.

In an embodiment, the HNH-like domain differs from a sequence of an HNH-like domain disclosed herein, e.g., in FIGS. 5A-5C or FIGS. 7A-7B, as many as 1 but no more than 2, 3, 4, or 5 residues. In an embodiment, 1 or both of the highly conserved residues identified in FIGS. 5A-5C or FIGS. 7A-7B are present.

In an embodiment, the HNH-like domain differs from a sequence of an HNH-like domain disclosed herein, e.g., in FIGS. 6A-6B or FIGS. 7A-7B, as many as 1 but no more than 2, 3, 4, or 5 residues. In an embodiment, 1, 2, all 3 of the highly conserved residues identified in FIGS. 6A-6B or FIGS. 7A-7B are present.

Cas9 Activities

Nuclease and Helicase Activities

In an embodiment, the Cas9 molecule or Cas9 polypeptide is capable of cleaving a target nucleic acid molecule. Typically wild type Cas9 molecules cleave both strands of a target nucleic acid molecule. Cas9 molecules and Cas9 polypeptides can be engineered to alter nuclease cleavage (or other properties), e.g., to provide a Cas9 molecule or Cas9 polypeptide which is a nickase, or which lacks the ability to cleave target nucleic acid. A Cas9 molecule or Cas9 polypeptide that is capable of cleaving a target nucleic acid molecule is referred to herein as an eaCas9 (an enzymatically active Cas9) molecule or eaCas9 polypeptide.

In an embodiment, an eaCas9 molecule or eaCas9 polypeptide comprises one or more of the following enzymatic activities:

a nickase activity, i.e., the ability to cleave a single strand, e.g., the non-complementary strand or the complementary strand, of a nucleic acid molecule;

a double stranded nuclease activity, i.e., the ability to cleave both strands of a double stranded nucleic acid and create a double stranded break, which in an embodiment is the presence of two nickase activities;

an endonuclease activity;

an exonuclease activity; and a helicase activity, i.e., the ability to unwind the helical structure of a double stranded nucleic acid.

In an embodiment, an enzymatically active or an eaCas9 molecule or eaCas9 polypeptide cleaves both DNA strands and results in a double stranded break. In an embodiment, an eaCas9 molecule or eaCas9 polypeptide cleaves only one strand, e.g., the strand to which the gRNA hybridizes to, or the strand complementary to the strand the gRNA hybridizes with. In an embodiment, an eaCas9 molecule or eaCas9 polypeptide comprises cleavage activity associated with an HNH domain. In an embodiment, an eaCas9 molecule or eaCas9 polypeptide comprises cleavage activity associated with a RuvC domain. In an embodiment, an eaCas9 molecule or eaCas9 polypeptide comprises cleavage activity associated with an HNH domain and cleavage activity associated with a RuvC domain. In an embodiment, an eaCas9 molecule or eaCas9 polypeptide comprises an active, or cleavage competent, HNH domain and an inactive, or cleavage incompetent, RuvC domain. In an embodiment, an eaCas9 molecule or eaCas9 polypeptide comprises an inactive, or cleavage incompetent, HNH domain and an active, or cleavage competent, RuvC domain.

Some Cas9 molecules or Cas9 polypeptides have the ability to interact with a gRNA molecule, and in conjunction with the gRNA molecule localize to a core target domain, but are incapable of cleaving the target nucleic acid, or incapable of cleaving at efficient rates. Cas9 molecules having no, or no substantial, cleavage activity are referred to herein as an eiCas9 molecule or eiCas9 polypeptide. For example, an eiCas9 molecule or eiCas9 polypeptide can lack cleavage activity or have substantially less, e.g., less than 20, 10, 5, 1 or 0.1% of the cleavage activity of a reference Cas9 molecule or eiCas9 polypeptide, as measured by an assay described herein.

Targeting and PAMs

A Cas9 molecule or Cas9 polypeptide, is a polypeptide that can interact with a guide RNA (gRNA) molecule and, in concert with the gRNA molecule, localizes to a site which comprises a target domain, and in an embodiment, a PAM sequence.

In an embodiment, the ability of an eaCas9 molecule or eaCas9 polypeptide to interact with and cleave a target nucleic acid is PAM sequence dependent. A PAM sequence is a sequence in the target nucleic acid. In an embodiment, cleavage of the target nucleic acid occurs upstream from the PAM sequence. EaCas9 molecules from different bacterial species can recognize different sequence motifs (e.g., PAM sequences). In an embodiment, an eaCas9 molecule of *S. pyogenes* recognizes the sequence motif NGG and directs cleavage of a target nucleic acid sequence 1 to 10, e.g., 3 to 5, base pairs upstream from that sequence. See, e.g., Mali et al., SCIENCE 2013; 339(6121): 823-826. In an embodiment, an eaCas9 molecule of *S. thermophilus* recognizes the sequence motif NGGNG (SEQ ID NO.: 90) and/or NNAGAAW (W=A or T) (SEQ ID NO.: 91) and directs cleavage of a target nucleic acid sequence 1 to 10, e.g., 3 to 5, base pairs upstream from these sequences. See, e.g., Horvath et al., SCIENCE 2010; 327(5962):167-170, and Deveau et al., J BACTERIOL 2008; 190(4): 1390-1400. In an embodiment, an eaCas9 molecule of *S. mutans* recognizes the sequence motif NGG and/or NAAR (R=A or G) (SEQ ID NO.: 92) and directs cleavage of a target nucleic acid sequence 1 to 10, e.g., 3 to 5 base pairs, upstream from this sequence. See, e.g., Deveau et al., J BACTERIOL 2008; 190(4): 1390-1400. In an embodiment, an eaCas9 molecule of *S. aureus* recognizes the sequence motif NNGRR (R=A or G) (SEQ ID NO.: 93) and directs cleavage of a target nucleic acid sequence 1 to 10, e.g., 3 to 5, base pairs upstream from that sequence. In an embodiment, an eaCas9 molecule of *S. aureus* recognizes the sequence motif NNGRRN (R=A or G) and directs cleavage of a target nucleic acid sequence 1 to 10, e.g., 3 to 5, base pairs upstream from that sequence. In an embodiment, an eaCas9 molecule of *S. aureus* recognizes the sequence motif NNGRRT (R=A or G) and directs cleavage of a target nucleic acid sequence 1 to 10, e.g., 3 to 5, base pairs upstream from that sequence. In an embodiment, an eaCas9 molecule of *S. aureus* recognizes the sequence motif NNGRRV (R=A or G) (SEQ ID NO.:) and directs cleavage of a target nucleic acid sequence 1 to 10, e.g., 3 to 5, base pairs upstream from that sequence. In an embodiment, an eaCas9 molecule of *N. meningitidis* recognizes the sequence motif NNNNGATT (SEQ ID NO.: 94) or NNNGCTT (R=A or G) (SEQ ID NO: 95) and directs cleavage of a target nucleic acid sequence 1 to 10, e.g., 3 to 5, base pairs upstream from that sequence. See, e.g., Hou et al., PNAS 2013; 110(39):15644-15649. The ability of a Cas9 molecule to recognize a PAM sequence can be determined, e.g., using a transformation assay described in Jinek el al., SCIENCE 2012, 337:816. In the aforementioned embodiments, N can be any nucleotide residue, e.g., any of A, G, C or T.

As is discussed herein, Cas9 molecules can be engineered to alter the PAM specificity of the Cas9 molecule.

Exemplary naturally occurring Cas9 molecules are described in Chylinski et al., RNA BIOLOGY 2013 10:5, 727-737. Such Cas9 molecules include Cas9 molecules of a cluster 1 bacterial family, cluster 2 bacterial family, cluster 3 bacterial family, cluster 4 bacterial family, cluster 5 bacterial family, cluster 6 bacterial family, a cluster 7 bacterial family, a cluster 8 bacterial family, a cluster 9 bacterial family, a cluster 10 bacterial family, a cluster 11 bacterial family, a cluster 12 bacterial family, a cluster 13 bacterial family, a cluster 14 bacterial family, a cluster 15 bacterial family, a cluster 16 bacterial family, a cluster 17 bacterial family, a cluster 18 bacterial family, a cluster 19 bacterial family, a cluster 20 bacterial family, a cluster 21 bacterial family, a cluster 22 bacterial family, a cluster 23 bacterial family, a cluster 24 bacterial family, a cluster 25 bacterial family, a cluster 26 bacterial family, a cluster 27 bacterial family, a cluster 28 bacterial family, a cluster 29 bacterial family, a cluster 30 bacterial family, a cluster 31 bacterial family, a cluster 32 bacterial family, a cluster 33 bacterial family, a cluster 34 bacterial family, a cluster 35 bacterial family, a cluster 36 bacterial family, a cluster 37 bacterial family, a cluster 38 bacterial family, a cluster 39 bacterial family, a cluster 40 bacterial family, a cluster 41 bacterial family, a cluster 42 bacterial family, a cluster 43 bacterial family, a cluster 44 bacterial family, a cluster 45 bacterial family, a cluster 46 bacterial family, a cluster 47 bacterial family, a cluster 48 bacterial family, a cluster 49 bacterial family, a cluster 50 bacterial family, a cluster 51 bacterial family, a cluster 52 bacterial family, a cluster 53 bacterial family, a cluster 54 bacterial family, a cluster 55 bacterial family, a cluster 56 bacterial family, a cluster 57 bacterial family, a cluster 58 bacterial family, a cluster 59 bacterial family, a cluster 60 bacterial family, a cluster 61 bacterial family, a cluster 62 bacterial family, a cluster 63 bacterial family, a cluster 64 bacterial family, a cluster 65 bacterial family, a cluster 66 bacterial family, a cluster 67 bacterial family, a cluster 68 bacterial family, a cluster 69 bacterial family, a cluster 70 bacterial family, a cluster 71 bacterial family, a cluster 72 bacterial family, a cluster 73 bacterial family, a cluster 74 bacterial family, a cluster 75 bacterial family, a cluster 76 bacterial family, a cluster 77 bacterial family, or a cluster 78 bacterial family.

Exemplary naturally occurring Cas9 molecules include a Cas9 molecule of a cluster 1 bacterial family. Examples include a Cas9 molecule of: *S. pyogenes* (e.g., strain SF370, MGAS10270, MGAS10750, MGAS2096, MGAS315, MGAS5005, MGAS6180, MGAS9429, NZ131 and SSI-1), *S. thermophilus* (e.g., strain LMD-9), *S. pseudoporcinus* (e.g., strain SPIN 20026), *S. mutans* (e.g., strain UA159, NN2025), *S. macacae* (e.g., strain NCTC11558), *S. gallolyticus* (e.g., strain UCN34, ATCC BAA-2069), *S. equines* (e.g., strain ATCC 9812, MGCS 124), *S. dysdalactiae* (e.g., strain GGS 124), *S. bovis* (e.g., strain ATCC 700338), *S. anginosus* (e.g., strain F0211), *S. agalactiae* (e.g., strain NEM316, A909), *Listeria monocytogenes* (e.g., strain F6854), *Listeria innocua* (*L. innocua*, e.g., strain Clip11262), *Enterococcus italicus* (e.g., strain DSM 15952), or *Enterococcus faecium* (e.g., strain 1,231,408). Additional exemplary Cas9 molecules are a Cas9 molecule of *Neisseria meningitidis* (Hou et al., PNAS Early Edition 2013, 1-6 and a *S. aureus* cas9 molecule.

In an embodiment, a Cas9 molecule or Cas9 polypeptide, e.g., an eaCas9 molecule or eaCas9 polypeptide, comprises an amino acid sequence:

having 60%, 65%, 70%, 75%, 80%, 85%, 90%, 95%, 96%, 97%, 98% or 99% homology with;

differs at no more than, 2, 5, 10, 15, 20, 30, or 40% of the amino acid residues when compared with;

differs by at least 1, 2, 5, 10 or 20 amino acids, but by no more than 100, 80, 70, 60, 50, 40 or 30 amino acids from; or is identical to any Cas9 molecule sequence described herein, or a naturally occurring Cas9 molecule sequence, e.g., a Cas9 molecule from a species listed herein or described in Chylinski et al., RNA BIOLOGY 2013 10:5, 727-737; Hou et al., PNAS Early Edition 2013, 1-6; SEQ ID NO:1-4. In an embodiment, the Cas9 molecule or Cas9 polypeptide comprises one or more of the following activities: a nickase activity; a double stranded cleavage activity (e.g., an endonuclease and/or exonuclease activity); a helicase activity; or the ability, together with a gRNA molecule, to localize to a target nucleic acid.

In an embodiment, a Cas9 molecule or Cas9 polypeptide comprises any of the amino acid sequence of the consensus sequence of FIGS. 2A-2G, wherein "*" indicates any amino acid found in the corresponding position in the amino acid sequence of a Cas9 molecule of *S. pyogenes, S. thermophilus, S. mutans* and *L. innocua*, and "-" indicates any amino acid. In an embodiment, a Cas9 molecule or Cas9 polypeptide differs from the sequence of the consensus sequence disclosed in FIGS. 2A-2G by at least 1, but no more than 2, 3, 4, 5, 6, 7, 8, 9, or 10 amino acid residues. In an embodiment, a Cas9 molecule or Cas9 polypeptide comprises the amino acid sequence of SEQ ID NO:7 of FIGS. 7A-7B, wherein "*" indicates any amino acid found in the corresponding position in the amino acid sequence of a Cas9 molecule of *S. pyogenes*, or *N. meningitidis*, "-" indicates any amino acid, and "-" indicates any amino acid or absent. In an embodiment, a Cas9 molecule or Cas9 polypeptide differs from the sequence of SEQ ID NO:6 or 7 disclosed in FIGS. 7A-7B by at least 1, but no more than 2, 3, 4, 5, 6, 7, 8, 9, or 10 amino acid residues.

A comparison of the sequence of a number of Cas9 molecules indicate that certain regions are conserved. These are identified below as:

region 1 (residues 1 to 180, or in the case of region 1'residues 120 to 180)

region 2 (residues 360 to 480);

region 3 (residues 660 to 720);

region 4 (residues 817 to 900); and region 5 (residues 900 to 960);

In an embodiment, a Cas9 molecule or Cas9 polypeptide comprises regions 1-5, together with sufficient additional Cas9 molecule sequence to provide a biologically active molecule, e.g., a Cas9 molecule having at least one activity described herein. In an embodiment, each of regions 1-5, independently, have 50%, 60%, 70%, 80%, 85%, 90%, 95%, 96%, 97%, 98% or 99% homology with the corresponding residues of a Cas9 molecule or Cas9 polypeptide described herein, e.g., a sequence from FIGS. 2A-2G or from FIGS. 7A-7B.

In an embodiment, a Cas9 molecule or Cas9 polypeptide, e.g., an eaCas9 molecule or eaCas9 polypeptide, comprises an amino acid sequence referred to as region 1:

having 50%, 60%, 70%, 80%, 85%, 90%, 95%, 96%, 97%, 98% or 99% homology with amino acids 1-180 (the numbering is according to the motif sequence in FIG. 2; 52% of residues in the four Cas9 sequences in FIGS. 2A-2G are conserved) of the amino acid sequence of Cas9 of *S. pyogenes;* differs by at least 1, 2, 5, 10 or 20 amino acids but by no more than 90, 80, 70, 60, 50, 40 or 30 amino acids from amino acids 1-180 of the amino acid sequence of Cas9 of *S. pyogenes, S. thermophilus, S. mutans* or *Listeria innocua*; or is identical to 1-180 of the amino acid sequence of Cas9 of *S. pyogenes, S. thermophilus, S. mutans* or *L. innocua*.

In an embodiment, a Cas9 molecule or Cas9 polypeptide, e.g., an eaCas9 molecule or eaCas9 polypeptide, comprises an amino acid sequence referred to as region 1':

having 55%, 60%, 65%, 70%, 75%, 80%, 85%, 90%, 95%, 96%, 97%, 98% or 99% homology with amino acids 120-180 (55% of residues in the four Cas9 sequences in FIG. 2 are conserved) of the amino acid sequence of Cas9 of *S. pyogenes, S. thermophilus, S. mutans* or *L. innocua;* differs by at least 1, 2, or 5 amino acids but by no more than 35, 30, 25, 20 or 10 amino acids from amino acids 120-180 of the amino acid sequence of Cas9 of *S. pyogenes, S. thermophilus, S. mutans* or *L. innocua*; or is identical to 120-180 of the amino acid sequence of Cas9 of *S. pyogenes, S. thermophilus, S. mutans* or *L. innocua*.

In an embodiment, a Cas9 molecule or Cas9 polypeptide, e.g., an eaCas9 molecule or eaCas9 polypeptide, comprises an amino acid sequence referred to as region 2:

having 50%, 55%, 60%, 65%, 70%, 75%, 80%, 85%, 90%, 95%, 96%, 97%, 98% or 99% homology with amino acids 360-480 (52% of residues in the four Cas9 sequences in FIG. 2 are conserved) of the amino acid sequence of Cas9 of *S. pyogenes, S. thermophilus, S. mutans* or *L. innocua;* differs by at least 1, 2, or 5 amino acids but by no more than 35, 30, 25, 20 or 10 amino acids from amino acids 360-480 of the amino acid sequence of Cas9 of *S. pyogenes, S. thermophilus, S. mutans* or *L. innocua*; or is identical to 360-480 of the amino acid sequence of Cas9 of *S. pyogenes, S. thermophilus, S. mutans* or *L. innocua*.

In an embodiment, a Cas9 molecule or Cas9 polypeptide, e.g., an eaCas9 molecule or eaCas9 polypeptide, comprises an amino acid sequence referred to as region 3:

having 55%, 60%, 65%, 70%, 75%, 80%, 85%, 90%, 95%, 96%, 97%, 98%, or 99% homology with amino acids 660-720 (56% of residues in the four Cas9 sequences in FIG. 2 are conserved) of the amino acid sequence of Cas9 of *S. pyogenes, S. thermophilus, S. mutans* or *L. innocua;* differs by at least 1, 2, or 5 amino acids but by no more than 35, 30, 25, 20 or 10 amino acids from amino acids 660-720 of the amino acid sequence of Cas9 of *S. pyogenes, S. thermophilus, S. mutans* or *L. innocua;* or is identical to 660-720 of the amino acid sequence of Cas9 of *S. pyogenes, S. thermophilus, S. mutans* or *L. innocua.*

In an embodiment, a Cas9 molecule or Cas9 polypeptide, e.g., an eaCas9 molecule or eaCas9 polypeptide, comprises an amino acid sequence referred to as region 4:

having 50%, 55%, 60%, 65%, 70%, 75%, 80%, 85%, 90%, 95%, 96%, 97%, 98%, or 99% homology with amino acids 817-900 (55% of residues in the four Cas9 sequences in FIGS. 2A-2G are conserved) of the amino acid sequence of Cas9 of *S. pyogenes, S. thermophilus, S. mutans* or *L. innocua;* differs by at least 1, 2, or 5 amino acids but by no more than 35, 30, 25, 20 or 10 amino acids from amino acids 817-900 of the amino acid sequence of Cas9 of *S. pyogenes, S. thermophilus, S. mutans* or *L. innocua;* or is identical to 817-900 of the amino acid sequence of Cas9 of *S. pyogenes, S. thermophilus, S. mutans* or *L. innocua.*

In an embodiment, a Cas9 molecule or Cas9 polypeptide, e.g., an eaCas9 molecule or eaCas9 polypeptide, comprises an amino acid sequence referred to as region 5:

having 50%, 55%, 60%, 65%, 70%, 75%, 80%, 85%, 90%, 95%, 96%, 97%, 98%, or 99% homology with amino acids 900-960 (60% of residues in the four Cas9 sequences in FIGS. 2A-2G are conserved) of the amino acid sequence of Cas9 of *S. pyogenes, S. thermophilus, S. mutans* or *L. innocua;* differs by at least 1, 2, or 5 amino acids but by no more than 35, 30, 25, 20 or 10 amino acids from amino acids 900-960 of the amino acid sequence of Cas9 of *S. pyogenes, S. thermophilus, S. mutans* or *L. innocua;* or is identical to 900-960 of the amino acid sequence of Cas9 of *S. pyogenes, S. thermophilus, S. mutans* or *L. innocua.*

Engineered or Altered Cas9 Molecules and Cas9 Polypeptides

Cas9 molecules and Cas9 polypeptides described herein, e.g., naturally occurring Cas9 molecules, can possess any of a number of properties, including: nuclease activity (e.g., endonuclease and/or exonuclease activity); helicase activity; the ability to associate functionally with a gRNA molecule; and the ability to target (or localize to) a site on a nucleic acid (e.g., PAM recognition and specificity). In an embodiment, a Cas9 molecule or Cas9 polypeptide can include all or a subset of these properties. In a typical embodiment, a Cas9 molecule or Cas9 polypeptide has the ability to interact with a gRNA molecule and, in concert with the gRNA molecule, localize to a site in a nucleic acid. Other activities, e.g., PAM specificity, cleavage activity, or helicase activity can vary more widely in Cas9 molecules and Cas9 polypeptides.

Cas9 molecules include engineered Cas9 molecules and engineered Cas9 polypeptides (engineered, as used in this context, means merely that the Cas9 molecule or Cas9 polypeptide differs from a reference sequences, and implies no process or origin limitation). An engineered Cas9 molecule or Cas9 polypeptide can comprise altered enzymatic properties, e.g., altered nuclease activity, (as compared with a naturally occurring or other reference Cas9 molecule) or altered helicase activity. As discussed herein, an engineered Cas9 molecule or Cas9 polypeptide can have nickase activity (as opposed to double strand nuclease activity). In an embodiment an engineered Cas9 molecule or Cas9 polypeptide can have an alteration that alters its size, e.g., a deletion of amino acid sequence that reduces its size, e.g., without significant effect on one or more, or any Cas9 activity. In an embodiment, an engineered Cas9 molecule or Cas9 polypeptide can comprise an alteration that affects PAM recognition. E.g., an engineered Cas9 molecule can be altered to recognize a PAM sequence other than that recognized by the endogenous wild-type PI domain. In an embodiment a Cas9 molecule or Cas9 polypeptide can differ in sequence from a naturally occurring Cas9 molecule but not have significant alteration in one or more Cas9 activities.

Cas9 molecules or Cas9 polypeptides with desired properties can be made in a number of ways, e.g., by alteration of a parental, e.g., naturally occurring, Cas9 molecules or Cas9 polypeptides, to provide an altered Cas9 molecule or Cas9 polypeptide having a desired property. For example, one or more mutations or differences relative to a parental Cas9 molecule, e.g., a naturally occurring or engineered Cas9 molecule, can be introduced. Such mutations and differences comprise: substitutions (e.g., conservative substitutions or substitutions of non-essential amino acids); insertions; or deletions. In an embodiment, a Cas9 molecule or Cas9 polypeptide can comprises one or more mutations or differences, e.g., at least 1, 2, 3, 4, 5, 10, 15, 20, 30, 40 or 50 mutations but less than 200, 100, or 80 mutations relative to a reference, e.g., a parental, Cas9 molecule.

In an embodiment, a mutation or mutations do not have a substantial effect on a Cas9 activity, e.g. a Cas9 activity described herein. In an embodiment, a mutation or mutations have a substantial effect on a Cas9 activity, e.g. a Cas9 activity described herein.

Non-Cleaving and Modified-Cleavage Cas9 Molecules and Cas9 Polypeptides

In an embodiment, a Cas9 molecule or Cas9 polypeptide comprises a cleavage property that differs from naturally occurring Cas9 molecules, e.g., that differs from the naturally occurring Cas9 molecule having the closest homology. For example, a Cas9 molecule or Cas9 polypeptide can differ from naturally occurring Cas9 molecules, e.g., a Cas9 molecule of *S. pyogenes*, as follows: its ability to modulate, e.g., decreased or increased, cleavage of a double stranded nucleic acid (endonuclease and/or exonuclease activity), e.g., as compared to a naturally occurring Cas9 molecule (e.g., a Cas9 molecule of *S. pyogenes*); its ability to modulate, e.g., decreased or increased, cleavage of a single strand of a nucleic acid, e.g., a non-complementary strand of a nucleic acid molecule or a complementary strand of a nucleic acid molecule (nickase activity), e.g., as compared to a naturally occurring Cas9 molecule (e.g., a Cas9 molecule of *S. pyogenes*); or the ability to cleave a nucleic acid molecule, e.g., a double stranded or single stranded nucleic acid molecule, can be eliminated.

Modified Cleavage eaCas9 Molecules and eaCas9 Polypeptides

In an embodiment, an eaCas9 molecule or eaCas9 polypeptide comprises one or more of the following activities: cleavage activity associated with an N-terminal RuvC-like domain; cleavage activity associated with an HNH-like domain; cleavage activity associated with an HNH-like domain and cleavage activity associated with an N-terminal RuvC-like domain.

In an embodiment, an eaCas9 molecule or eaCas9 polypeptide comprises an active, or cleavage competent, HNH-like domain (e.g., an HNH-like domain described herein, e.g., SEQ ID NO: 17, SEQ ID NO: 18, SEQ ID NO: 19, SEQ ID NO: 20 or SEQ ID NO: 21) and an inactive, or cleavage incompetent, N-terminal RuvC-like domain. An exemplary inactive, or cleavage incompetent N-terminal RuvC-like domain can have a mutation of an aspartic acid in an N-terminal RuvC-like domain, e.g., an aspartic acid at position 9 of the consensus sequence disclosed in FIGS. 2A-2G or an aspartic acid at position 10 of SEQ ID NO: 7, e.g., can be substituted with an alanine. In an embodiment, the eaCas9 molecule or eaCas9 polypeptide differs from wild type in the N-terminal RuvC-like domain and does not cleave the target nucleic acid, or cleaves with significantly less efficiency, e.g., less than 20, 10, 5, 1 or 1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of S. pyogenes, or S. thermophilus. In an embodiment, the reference Cas9 molecule is the naturally occurring Cas9 molecule having the closest sequence identity or homology.

In an embodiment, an eaCas9 molecule or eaCas9 polypeptide comprises an inactive, or cleavage incompetent, HNH domain and an active, or cleavage competent, N-terminal RuvC-like domain (e.g., a RuvC-like domain described herein, e.g., SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, or SEQ ID NO: 16). Exemplary inactive, or cleavage incompetent HNH-like domains can have a mutation at one or more of: a histidine in an HNH-like domain, e.g., a histidine shown at position 856 of the consensus sequence disclosed in FIGS. 2A-2G, e.g., can be substituted with an alanine; and one or more asparagines in an HNH-like domain, e.g., an asparagine shown at position 870 of the consensus sequence disclosed in FIGS. 2A-2G and/or at position 879 of the consensus sequence disclosed in FIGS. 2A-2G, e.g., can be substituted with an alanine. In an embodiment, the eaCas9 differs from wild type in the HNH-like domain and does not cleave the target nucleic acid, or cleaves with significantly less efficiency, e.g., less than 20, 10, 5, 1 or 0.1% of the cleavage activity of a reference Cas9 molecule, e.g., as measured by an assay described herein. The reference Cas9 molecule can by a naturally occurring unmodified Cas9 molecule, e.g., a naturally occurring Cas9 molecule such as a Cas9 molecule of S. pyogenes, or S. thermophilus. In an embodiment, the reference Cas9 molecule is the naturally occurring Cas9 molecule having the closest sequence identity or homology.

Alterations in the Ability to Cleave One or Both Strands of a Target Nucleic Acid In an embodiment, exemplary Cas9 activities comprise one or more of PAM specificity, cleavage activity, and helicase activity. A mutation(s) can be present, e.g., in: one or more RuvC domains, e.g., an N-terminal RuvC domain; an HNH domain; a region outside the RuvC domains and the HNH domain. In an embodiment, a mutation(s) is present in a RuvC domain. In an embodiment, a mutation(s) is present in an HNH domain. In an embodiment, mutations are present in both a RuvC domain and an HNH domain.

Exemplary mutations that may be made in the RuvC domain or HNH domain with reference to the S. pyogenes sequence include: D10A, E762A, H840A, N854A, N863A and/or D986A.

In an embodiment, a Cas9 molecule is an eiCas9 molecule comprising one or more differences in a RuvC domain and/or in an HNH domain as compared to a reference Cas9 molecule, and the eiCas9 molecule does not cleave a nucleic acid, or cleaves with significantly less efficiency than does wildtype, e.g., when compared with wild type in a cleavage assay, e.g., as described herein, cuts with less than 50, 25, 10, or 1% of a reference Cas9 molecule, as measured by an assay described herein.

Whether or not a particular sequence, e.g., a substitution, may affect one or more activity, such as targeting activity, cleavage activity, etc, can be evaluated or predicted, e.g., by evaluating whether the mutation is conservative. In an embodiment, a "non-essential" amino acid residue, as used in the context of a Cas9 molecule, is a residue that can be altered from the wild-type sequence of a Cas9 molecule, e.g., a naturally occurring Cas9 molecule, e.g., an eaCas9 molecule, without abolishing or more preferably, without substantially altering a Cas9 activity (e.g., cleavage activity), whereas changing an "essential" amino acid residue results in a substantial loss of activity (e.g., cleavage activity).

In an embodiment, a Cas9 molecule comprises a cleavage property that differs from naturally occurring Cas9 molecules, e.g., that differs from the naturally occurring Cas9 molecule having the closest homology. For example, a Cas9 molecule can differ from naturally occurring Cas9 molecules, e.g., a Cas9 molecule of S. aureus, S. pyogenes, or C. jejuni as follows: its ability to modulate, e.g., decreased or increased, cleavage of a double stranded break (endonuclease and/or exonuclease activity), e.g., as compared to a naturally occurring Cas9 molecule (e.g., a Cas9 molecule of S. aureus, S. pyogenes, or C. jejuni); its ability to modulate, e.g., decreased or increased, cleavage of a single strand of a nucleic acid, e.g., a non-complimentary strand of a nucleic acid molecule or a complementary strand of a nucleic acid molecule (nickase activity), e.g., as compared to a naturally occurring Cas9 molecule (e.g., a Cas9 molecule of S. aureus, S. pyogenes, or C. jejuni); or the ability to cleave a nucleic acid molecule, e.g., a double stranded or single stranded nucleic acid molecule, can be eliminated.

In an embodiment, the altered Cas9 molecule is an eaCas9 molecule comprising one or more of the following activities: cleavage activity associated with a RuvC domain; cleavage activity associated with an HNH domain; cleavage activity associated with an HNH domain and cleavage activity associated with a RuvC domain.

In an embodiment, the altered Cas9 molecule is an eiCas9 molecule which does not cleave a nucleic acid molecule (either double stranded or single stranded nucleic acid molecules) or cleaves a nucleic acid molecule with significantly less efficiency, e.g., less than 20, 10, 5, 1 or 0.1% of the cleavage activity of a reference Cas9 molecule, e.g., as measured by an assay described herein. The reference Cas9 molecule can be a naturally occurring unmodified Cas9 molecule, e.g., a naturally occurring Cas9 molecule such as a Cas9 molecule of S. pyogenes, S. thermophilus, S. aureus, C. jejuni or N. meningitidis. In an embodiment, the reference Cas9 molecule is the naturally occurring Cas9 molecule having the closest sequence identity or homology. In an embodiment, the eiCas9 molecule lacks substantial cleavage activity associated with a RuvC domain and cleavage activity associated with an HNH domain.

In an embodiment, the altered Cas9 molecule or Cas9 polypeptide is an eaCas9 molecule or eaCas9 polypeptide comprising the fixed amino acid residues of S. pyogenes shown in the consensus sequence disclosed in FIGS. 2A-2G, and has one or more amino acids that differ from the amino acid sequence of S. pyogenes (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIGS. 2A-2G or SEQ ID NO: 7.

In an embodiment, the altered Cas9 molecule or Cas9 polypeptide comprises a sequence in which:

the sequence corresponding to the fixed sequence of the consensus sequence disclosed in FIGS. 2A-2G differs at no more than 1, 2, 3, 4, 5, 10, 15, or 20% of the fixed residues in the consensus sequence disclosed in FIGS. 2A-2G;

the sequence corresponding to the residues identified by "*" in the consensus sequence disclosed in FIGS. 2A-2G differ at no more than 1, 2, 3, 4, 5, 10, 15, 20, 25, 30, 35, or 40% of the "*" residues from the corresponding sequence of naturally occurring Cas9 molecule, e.g., an S. pyogenes Cas9 molecule; and, the sequence corresponding to the residues identified by "-" in the consensus sequence disclosed in FIGS. 2A-2G differ at no more than 5, 10, 15, 20, 25, 30, 35, 40, 45, 55, or 60% of the "-" residues from the corresponding sequence of naturally occurring Cas9 molecule, e.g., an S. pyogenes Cas9 molecule.

In an embodiment, the altered Cas9 molecule or Cas9 polypeptide is an eaCas9 molecule or eaCas9 polypeptide comprising the fixed amino acid residues of S. thermophilus shown in the consensus sequence disclosed in FIGS. 2A-2G, and has one or more amino acids that differ from the amino acid sequence of S. thermophilus (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIGS. 2A-2G. In an embodiment In an embodiment, the altered Cas9 molecule or Cas9 polypeptide comprises a sequence in which:

the sequence corresponding to the fixed sequence of the consensus sequence disclosed in FIGS. 2A-2G differs at no more than 1, 2, 3, 4, 5, 10, 15, or 20% of the fixed residues in the consensus sequence disclosed in FIGS. 2A-2G;

the sequence corresponding to the residues identified by "*" in the consensus sequence disclosed in FIGS. 2A-2G differ at no more than 1, 2, 3, 4, 5, 10, 15, 20, 25, 30, 35, or 40% of the "*" residues from the corresponding sequence of naturally occurring Cas9 molecule, e.g., an S. thermophilus Cas9 molecule; and, the sequence corresponding to the residues identified by "-" in the consensus sequence disclosed in FIGS. 2A-2G differ at no more than 5, 10, 15, 20, 25, 30, 35, 40, 45, 55, or 60% of the "-" residues from the corresponding sequence of naturally occurring Cas9 molecule, e.g., an S. thermophilus Cas9 molecule.

In an embodiment, the altered Cas9 molecule or Cas9 polypeptide is an eaCas9 molecule or eaCas9 polypeptide comprising the fixed amino acid residues of S. mutans shown in the consensus sequence disclosed in FIGS. 2A-2G, and has one or more amino acids that differ from the amino acid sequence of S. mutans (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIGS. 2A-2G.

In an embodiment, the altered Cas9 molecule or Cas9 polypeptide comprises a sequence in which:

the sequence corresponding to the fixed sequence of the consensus sequence disclosed in FIGS. 2A-2G differs at no more than 1, 2, 3, 4, 5, 10, 15, or 20% of the fixed residues in the consensus sequence disclosed in FIGS. 2A-2G;

the sequence corresponding to the residues identified by "*" in the consensus sequence disclosed in FIGS. 2A-2G differ at no more than 1, 2, 3, 4, 5, 10, 15, 20, 25, 30, 35, or 40% of the "*" residues from the corresponding sequence of naturally occurring Cas9 molecule, e.g., an S. mutans Cas9 molecule; and, the sequence corresponding to the residues identified by "-" in the consensus sequence disclosed in FIGS. 2A-2G differ at no more than 5, 10, 15, 20, 25, 30, 35, 40, 45, 55, or 60% of the "-" residues from the corresponding sequence of naturally occurring Cas9 molecule, e.g., an S. mutans Cas9 molecule.

In an embodiment, the altered Cas9 molecule or Cas9 polypeptide is an eaCas9 molecule or eaCas9 polypeptide comprising the fixed amino acid residues of L. innocula shown in the consensus sequence disclosed in FIGS. 2A-2G, and has one or more amino acids that differ from the amino acid sequence of L. innocula (e.g., has a substitution) at one or more residue (e.g., 2, 3, 5, 10, 15, 20, 30, 50, 70, 80, 90, 100, 200 amino acid residues) represented by an "-" in the consensus sequence disclosed in FIGS. 2A-2G.

In an embodiment, the altered Cas9 molecule or Cas9 polypeptide comprises a sequence in which:

the sequence corresponding to the fixed sequence of the consensus sequence disclosed in FIGS. 2A-2G differs at no more than 1, 2, 3, 4, 5, 10, 15, or 20% of the fixed residues in the consensus sequence disclosed in FIGS. 2A-2G;

the sequence corresponding to the residues identified by "*" in the consensus sequence disclosed in FIGS. 2A-2G differ at no more than 1, 2, 3, 4, 5, 10, 15, 20, 25, 30, 35, or 40% of the "*" residues from the corresponding sequence of naturally occurring Cas9 molecule, e.g., an L. innocula Cas9 molecule; and, the sequence corresponding to the residues identified by "-" in the consensus sequence disclosed in FIGS. 2A-2G differ at no more than 5, 10, 15, 20, 25, 30, 35, 40, 45, 55, or 60% of the "-" residues from the corresponding sequence of naturally occurring Cas9 molecule, e.g., an L. innocula Cas9 molecule.

In an embodiment, the altered Cas9 molecule or Cas9 polypeptide, e.g., an eaCas9 molecule or eaCas9 polypeptide, can be a fusion, e.g., of two of more different Cas9 molecules, e.g., of two or more naturally occurring Cas9 molecules of different species. For example, a fragment of a naturally occurring Cas9 molecule of one species can be fused to a fragment of a Cas9 molecule of a second species. As an example, a fragment of a Cas9 molecule of S. pyogenes comprising an N-terminal RuvC-like domain can be fused to a fragment of Cas9 molecule of a species other than S. pyogenes (e.g., S. thermophilus) comprising an HNH-like domain.

Cas9 Molecules and Cas9 Polypeptides with Altered PAM Recognition or No PAM Recognition Naturally occurring Cas9 molecules can recognize specific PAM sequences, for example the PAM recognition sequences described above for, e.g., S. pyogenes, S. thermophilus, S. mutans, S. aureus and N. meningitidis.

In an embodiment, a Cas9 molecule or Cas9 polypeptide has the same PAM specificities as a naturally occurring Cas9 molecule. In an embodiment, a Cas9 molecule or Cas9 polypeptide has a PAM specificity not associated with a naturally occurring Cas9 molecule, or a PAM specificity not associated with the naturally occurring Cas9 molecule to which it has the closest sequence homology. For example, a naturally occurring Cas9 molecule can be altered, e.g., to alter PAM recognition, e.g., to alter the PAM sequence that the Cas9 molecule or Cas9 polypeptide recognizes to decrease off target sites and/or improve specificity; or eliminate a PAM recognition requirement. In an embodiment, a Cas9 molecule or Cas9 polypeptide can be altered, e.g., to increase length of PAM recognition sequence and/or improve Cas9 specificity to high level of identity (e.g., 98%, 99% or 100% match between gRNA and a PAM sequence), e.g., to decrease off target sites and increase specificity. In an embodiment, the length of the PAM recognition sequence is at least 4, 5, 6, 7, 8, 9, 10 or 15 amino acids in length. In an embodiment, the Cas9 specificity requires at least 90%, 95%, 96%, 97%, 98%, 99% or more homology between the gRNA and the PAM sequence. Cas9 molecules or Cas9 polypeptides that recognize different PAM sequences and/or have reduced off-target activity can be generated using directed evolution. Exemplary methods and systems that can be used for directed evolution of Cas9 molecules are described, e.g., in Esvelt et al. Nature 2011, 472(7344): 499-503. Candidate Cas9 molecules can be evaluated, e.g., by methods described in Section IV.

Alterations of the PI domain, which mediates PAM recognition are discussed below.

Synthetic Cas9 Molecules and Cas9 Polypeptides with Altered PI Domains

Current genome-editing methods are limited in the diversity of target sequences that can be targeted by the PAM sequence that is recognized by the Cas9 molecule utilized. A synthetic Cas9 molecule (or Syn-Cas9 molecule), or synthetic Cas9 polypeptide (or syn-Cas9 polypeptide), as that term is used herein, refers to a Cas9 molecule or Cas9 polypeptide that comprises a Cas9 core domain from one bacterial species and a functional altered PI domain, i.e., a PI domain other than that naturally associated with the Cas9 core domain, e.g., from a different bacterial species.

In an embodiment, the altered PI domain recognizes a PAM sequence that is different from the PAM sequence recognized by the naturally-occurring Cas9 from which the Cas9 core domain is derived. In an embodiment, the altered PI domain recognizes the same PAM sequence recognized by the naturally-occurring Cas9 from which the Cas9 core domain is derived, but with different affinity or specificity. A Syn-Cas9 molecule or Syn-Cas9 polypeptide can be, respectively, a Syn-eaCas9 molecule or Syn-eaCas9 polypeptide or a Syn-eiCas9 molecule Syn-eiCas9 polypeptide.

An exemplary Syn-Cas9 molecule Syn-Cas9 polypeptide comprises:

a) a Cas9 core domain, e.g., a Cas9 core domain from Table 28 or 29, e.g., a *S. aureus*, *S. pyogenes*, or *C. jejuni* Cas9 core domain; and b) an altered PI domain from a species X Cas9 sequence selected from Tables 31 and 32.

In an embodiment, the RKR motif (the PAM binding motif) of said altered PI domain comprises: differences at 1, 2, or 3 amino acid residues; a difference in amino acid sequence at the first, second, or third position; differences in amino acid sequence at the first and second positions, the first and third positions, or the second and third positions; as compared with the sequence of the RKR motif of the native or endogenous PI domain associated with the Cas9 core domain.

In an embodiment, the Cas9 core domain comprises the Cas9 core domain from a species X Cas9 from Table 28 and said altered PI domain comprises a PI domain from a species Y Cas9 from Table 28.

In an embodiment, the RKR motif of the species X Cas9 is other than the RKR motif of the species Y Cas9.

In an embodiment, the RKR motif of the altered PI domain is selected from XXY, XNG, and XNQ.

In an embodiment, the altered PI domain has at least 60, 70, 80, 90, 95, or 100% homology with the amino acid sequence of a naturally occurring PI domain of said species Y from Table 28.

In an embodiment, the altered PI domain differs by no more than 50, 40, 30, 25, 20, 15, 10, 5, 4, 3, 2, or 1 amino acid residue from the amino acid sequence of a naturally occurring PI domain of said second species from Table 28.

In an embodiment, the Cas9 core domain comprises a *S. aureus* core domain and altered PI domain comprises: an *A. denitrificans* PI domain; a *C. jejuni* PI domain; a *H. mustelae* PI domain; or an altered PI domain of species X PI domain, wherein species X is selected from Table 32.

In an embodiment, the Cas9 core domain comprises a *S. pyogenes* core domain and the altered PI domain comprises: an *A. denitrificans* PI domain; a *C. jejuni* PI domain; a *H. mustelae* PI domain; or an altered PI domain of species X PI domain, wherein species X is selected from Table 32.

In an embodiment, the Cas9 core domain comprises a *C. jejuni* core domain and the altered PI domain comprises: an *A. denitrificans* PI domain; a *H. mustelae* PI domain; or an altered PI domain of species X PI domain, wherein species X is selected from Table 32.

In an embodiment, the Cas9 molecule further comprises a linker disposed between said Cas9 core domain and said altered PI domain.

In an embodiment, the linker comprises: a linker described elsewhere herein disposed between the Cas9 core domain and the heterologous PI domain. Suitable linkers are further described in Section V.

Exemplary altered PI domains for use in Syn-Cas9 molecules are described in Tables 31 and 32. The sequences for the 83 Cas9 orthologs referenced in Tables 31 and 32 are provided in Table 28. Table 30 provides the Cas9 orthologs with known PAM sequences and the corresponding RKR motif.

In an embodiment, a Syn-Cas9 molecule may also be size-optimized, e.g., the Syn-Cas9 molecule comprises one or more deletions, and optionally one or more linkers disposed between the amino acid residues flanking the deletions. In an embodiment, a Syn-Cas9 molecule comprises a REC deletion.

Size-Optimized Cas9 Molecules

Engineered Cas9 molecules and engineered Cas9 polypeptides described herein include a Cas9 molecule or Cas9 polypeptide comprising a deletion that reduces the size of the molecule while still retaining desired Cas9 properties, e.g., essentially native conformation, Cas9 nuclease activity, and/or target nucleic acid molecule recognition. Provided herein are Cas9 molecules or Cas9 polypeptides comprising one or more deletions and optionally one or more linkers, wherein a linker is disposed between the amino acid residues that flank the deletion. Methods for identifying suitable deletions in a reference Cas9 molecule, methods for generating Cas9 molecules with a deletion and a linker, and methods for using such Cas9 molecules will be apparent to one of ordinary skill in the art upon review of this document.

A Cas9 molecule, e.g., a *S. aureus*, *S. pyogenes*, or *C. jejuni*, Cas9 molecule, having a deletion is smaller, e.g., has reduced number of amino acids, than the corresponding naturally-occurring Cas9 molecule. The smaller size of the Cas9 molecules allows increased flexibility for delivery methods, and thereby increases utility for genome-editing. A Cas9 molecule can comprise one or more deletions that do not substantially affect or decrease the activity of the resultant Cas9 molecules described herein. Activities that are retained in the Cas9 molecules comprising a deletion as described herein include one or more of the following:

a nickase activity, i.e., the ability to cleave a single strand, e.g., the non-complementary strand or the complementary strand, of a nucleic acid molecule; a double stranded nuclease activity, i.e., the ability to cleave both strands of a double stranded nucleic acid and create a double stranded break, which in an embodiment is the presence of two nickase activities;

an endonuclease activity;

an exonuclease activity;

a helicase activity, i.e., the ability to unwind the helical structure of a double stranded nucleic acid;

and recognition activity of a nucleic acid molecule, e.g., a target nucleic acid or a gRNA.

Activity of the Cas9 molecules described herein can be assessed using the activity assays described herein or in the art.

Identifying Regions Suitable for Deletion

Suitable regions of Cas9 molecules for deletion can be identified by a variety of methods. Naturally-occurring orthologous Cas9 molecules from various bacterial species, e.g., any one of those listed in Table 28, can be modeled onto the crystal structure of S. pyogenes Cas9 (Nishimasu et al., Cell, 156:935-949, 2014) to examine the level of conservation across the selected Cas9 orthologs with respect to the three-dimensional conformation of the protein. Less conserved or unconserved regions that are spatially located distant from regions involved in Cas9 activity, e.g., interface with the target nucleic acid molecule and/or gRNA, represent regions or domains are candidates for deletion without substantially affecting or decreasing Cas9 activity.

REC-Optimized Cas9 Molecules

A REC-optimized Cas9 molecule, as that term is used herein, refers to a Cas9 molecule that comprises a deletion in one or both of the REC2 domain and the RE1$_{CT}$ domain (collectively a REC deletion), wherein the deletion comprises at least 10% of the amino acid residues in the cognate domain. A REC-optimized Cas9 molecule can be an eaCas9 molecule or an eiCas9 molecule. An exemplary REC-optimized Cas9 molecule comprises:

a) a deletion selected from:

i) a REC2 deletion;

ii) a REC1$_{CT}$ deletion; or iii) a REC1$_{SUB}$ deletion.

Optionally, a linker is disposed between the amino acid residues that flank the deletion. In an embodiment a Cas9 molecule includes only one deletion, or only two deletions. A Cas9 molecule can comprise a REC2 deletion and a REC1$_{CT}$ deletion. A Cas9 molecule can comprise a REC2 deletion and a REC1$_{SUB}$ deletion.

Generally, the deletion will contain at least 10% of the amino acids in the cognate domain, e.g., a REC2 deletion will include at least 10% of the amino acids in the REC2 domain.

A deletion can comprise: at least 10, 20, 30, 40, 50, 60, 70, 80, or 90% of the amino acid residues of its cognate domain; all of the amino acid residues of its cognate domain; an amino acid residue outside its cognate domain; a plurality of amino acid residues outside its cognate domain; the amino acid residue immediately N terminal to its cognate domain; the amino acid residue immediately C terminal to its cognate domain; the amino acid residue immediately N terminal to its cognate and the amino acid residue immediately C terminal to its cognate domain; a plurality of, e.g., up to 5, 10, 15, or 20, amino acid residues N terminal to its cognate domain; a plurality of, e.g., up to 5, 10, 15, or 20, amino acid residues C terminal to its cognate domain; a plurality of, e.g., up to 5, 10, 15, or 20, amino acid residues N terminal to to its cognate domain and a plurality of e.g., up to 5, 10, 15, or 20, amino acid residues C terminal to its cognate domain.

In an embodiment, a deletion does not extend beyond: its cognate domain; the N terminal amino acid residue of its cognate domain; the C terminal amino acid residue of its cognate domain.

A REC-optimized Cas9 molecule can include a linker disposed between the amino acid residues that flank the deletion. Suitable linkers for use between the amino acid resides that flank a REC deletion in a REC-optimized Cas9 molecule is disclosed in Section V.

In an embodiment a REC-optimized Cas9 molecule comprises an amino acid sequence that, other than any REC deletion and associated linker, has at least 50, 55, 60, 65, 70, 75, 80, 85, 90, 95, 99, or 100% homology with the amino acid sequence of a naturally occurring Cas 9, e.g., a Cas9 molecule described in Table 28, e.g., a S. aureus Cas9 molecule, a S. pyogenes Cas9 molecule, or a C. jejuni Cas9 molecule.

In an embodiment, a a REC-optimized Cas9 molecule comprises an amino acid sequence that, other than any REC deletion and associated linker, differs by no more than 1, 2, 3, 4, 5, 6, 7, 8, 9, 10, 15, 20, or 25, amino acid residues from the amino acid sequence of a naturally occurring Cas 9, e.g., a Cas9 molecule described in Table 28, e.g., a S. aureus Cas9 molecule, a S. pyogenes Cas9 molecule, or a C. jejuni Cas9 molecule.

In an embodiment, a REC-optimized Cas9 molecule comprises an amino acid sequence that, other than any REC deletion and associate linker, differs by no more than 1, 2, 3, 4, 5, 6, 7, 8, 9, 10, 15, 20, or 25% of the, amino acid residues from the amino acid sequence of a naturally occurring Cas 9, e.g., a Cas9 molecule described in Table 28, e.g., a S. aureus Cas9 molecule, a S. pyogenes Cas9 molecule, or a C. jejuni Cas9 molecule.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology).

Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

The percent identity between two amino acid sequences can also be determined using the algorithm of E. Meyers and W. Miller, (1988) Comput. Appl. Biosci. 4:11-17) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (1970) J. Mol. Biol. 48:444-453) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Sequence information for exemplary REC deletions are provided for 83 naturally-occurring Cas9 orthologs in Table 28.

The amino acid sequences of exemplary Cas9 molecules from different bacterial species are shown below.

TABLE 28

Amino Acid Sequence of Cas9 Orthologs

| | | REC2 | | | REC1$_{CT}$ | | | Rec$_{sub}$ | | |
|---|---|---|---|---|---|---|---|---|---|---|
| Species/Composite ID | Amino acid sequence | start (AA pos) | stop (AA pos) | # AA deleted (n) | start (AA pos) | stop (AA pos) | # AA deleted (n) | start (AA pos) | stop (AA pos) | # AA deleted (n) |
| Staphylococcus Aureus tr\|J7RUA5\|J7RUA5_STAAU | SEQ ID NO: 304 | 126 | 166 | 41 | 296 | 352 | 57 | 296 | 352 | 57 |
| Streptococcus Pyogenes sp\|Q99ZW2\|CAS9_STRP1 | SEQ ID NO: 305 | 176 | 314 | 139 | 511 | 592 | 82 | 511 | 592 | 82 |
| Campylobacter jejuni NCTC 11168 gi\|218563121\|ref\|YP_002344900.1 | SEQ ID NO: 306 | 137 | 181 | 45 | 316 | 360 | 45 | 316 | 360 | 45 |
| Bacteroides fragilis NCTC 9343 gi\|60683389\|ref\|YP_213533.1\| | SEQ ID NO: 307 | 148 | 339 | 192 | 524 | 617 | 84 | 524 | 617 | 84 |
| Bifidobacterium bifidum S17 gi\|310286728\|ref\|YP_003937986. | SEQ ID NO: 308 | 173 | 335 | 163 | 516 | 607 | 87 | 516 | 607 | 87 |
| Veillonella atypica ACS-134-V-Col7a gi\|303229466\|ref\|ZP_07316256.1 | SEQ ID NO: 309 | 185 | 339 | 155 | 574 | 663 | 79 | 574 | 663 | 79 |
| Lactobacillus rhamnosus GG gi\|258509199\|ref\|YP_003171950.1 | SEQ ID NO: 310 | 169 | 320 | 152 | 559 | 645 | 78 | 559 | 645 | 78 |
| Filifactor alocis ATCC 35896 gi\|374307738\|ref\|YP_005054169.1 | SEQ ID NO: 311 | 166 | 314 | 149 | 508 | 592 | 76 | 508 | 592 | 76 |
| Oenococcus kitaharae DSM 17330 gi\|366983953\|gb\|EHN59352.1\| | SEQ ID NO: 312 | 169 | 317 | 149 | 555 | 639 | 80 | 555 | 639 | 80 |
| Fructobacillus fructosus KCTC 3544 gi\|339625081\|ref\|ZP_08660870.1 | SEQ ID NO: 313 | 168 | 314 | 147 | 488 | 571 | 76 | 488 | 571 | 76 |
| Catenibacterium mitsuokai DSM 15897 gi\|224543312\|ref\|ZP_03683851.1 | SEQ ID NO: 314 | 173 | 318 | 146 | 511 | 594 | 78 | 511 | 594 | 78 |
| Finegoldia magna ATCC 29328 gi\|169823755\|ref\|YP_001691366.1 | SEQ ID NO: 315 | 168 | 313 | 146 | 452 | 534 | 77 | 452 | 534 | 77 |
| CoriobacteriumglomeransPW2 gi\|328956315\|ref\|YP_004373648.1 | SEQ ID NO: 316 | 175 | 318 | 144 | 511 | 592 | 82 | 511 | 592 | 82 |
| Eubacterium yurii ATCC 43715 gi\|306821691\|ref\|ZP_07455288.1 | SEQ ID NO: 317 | 169 | 310 | 142 | 552 | 633 | 76 | 552 | 633 | 76 |
| Peptoniphilus duerdenii ATCC BAA-1640 gi\|304438954\|ref\|ZP_07398877.1 | SEQ ID NO: 318 | 171 | 311 | 141 | 535 | 615 | 76 | 535 | 615 | 76 |
| Acidaminococcus sp. D21 gi\|227824983\|ref\|ZP_03989815.1 | SEQ ID NO: 319 | 167 | 306 | 140 | 511 | 591 | 75 | 511 | 591 | 75 |
| Lactobacillus farciminis KCTC 3681 gi\|336394882\|ref\|ZP_08576281.1 | SEQ ID NO: 320 | 171 | 310 | 140 | 542 | 621 | 85 | 542 | 621 | 85 |
| Streptococcus sanguinis SK49 gi\|422884106\|ref\|ZP_16930555.1 | SEQ ID NO: 321 | 185 | 324 | 140 | 411 | 490 | 85 | 411 | 490 | 85 |
| Coprococcus catus GD-7 gi\|291520705\|emb\|CBK78998.1\| | SEQ ID NO: 322 | 172 | 310 | 139 | 556 | 634 | 76 | 556 | 634 | 76 |
| Streptococcus mutans UA159 gi\|24379809\|ref\|NP_721764.1\| | SEQ ID NO: 323 | 176 | 314 | 139 | 392 | 470 | 84 | 392 | 470 | 84 |
| Streptococcus pyogenes M1 GAS gi\|13622193\|gb\|AAK33936.1\| | SEQ ID NO: 324 | 176 | 314 | 139 | 523 | 600 | 82 | 523 | 600 | 82 |
| Streptococcus thermophilus LMD-9 gi\|116628213\|ref\|YP_820832.1\| | SEQ ID NO: 325 | 176 | 314 | 139 | 481 | 558 | 81 | 481 | 558 | 81 |
| Fusobacterium nucleatum ATCC49256 gi\|34762592\|ref\|ZP_00143587.1\| | SEQ ID NO: 326 | 171 | 308 | 138 | 537 | 614 | 76 | 537 | 614 | 76 |
| Planococcus antarcticus DSM 14505 gi\|389815359\|ref\|ZP_10206685.1 | SEQ ID NO: 327 | 162 | 299 | 138 | 538 | 614 | 94 | 538 | 614 | 94 |
| Treponema denticola ATCC 35405 gi\|42525843\|ref\|NP_970941.1\| | SEQ ID NO: 328 | 169 | 305 | 137 | 524 | 600 | 81 | 524 | 600 | 81 |
| Solobacterium moorei F0204 gi\|320528778\|ref\|ZP_08029929.1 | SEQ ID NO: 329 | 179 | 314 | 136 | 544 | 619 | 77 | 544 | 619 | 77 |
| Staphylococcus pseudintermedius ED99 gi\|323463801\|gb\|ADX75954.1\| | SEQ ID NO: 330 | 164 | 299 | 136 | 531 | 606 | 92 | 531 | 606 | 92 |
| Flavobacterium branchiophilum FL-15 gi\|347536497\|ref\|YP_004843922.1 | SEQ ID NO: 331 | 162 | 286 | 125 | 538 | 613 | 63 | 538 | 613 | 63 |
| Ignavibacterium album JCM 16511 gi\|385811609\|ref\|YP_005848005.1 | SEQ ID NO: 332 | 223 | 329 | 107 | 357 | 432 | 90 | 357 | 432 | 90 |

TABLE 28-continued

Amino Acid Sequence of Cas9 Orthologs

| Species/Composite ID | Amino acid sequence | REC2 | | | REC1$_{CT}$ | | | Rec$_{sub}$ | | |
|---|---|---|---|---|---|---|---|---|---|---|
| | | start (AA pos) | stop (AA pos) | # AA deleted (n) | start (AA pos) | stop (AA pos) | # AA deleted (n) | start (AA pos) | stop (AA pos) | # AA deleted (n) |
| *Bergeyella zoohelcum* ATCC 43767 gi\|423317190\|ref\|ZP_17295095.1\| | SEQ ID NO: 333 | 165 | 261 | 97 | 529 | 604 | 56 | 529 | 604 | 56 |
| *Nitrobacter hamburgensis* X14 gi\|92109262\|ref\|YP_571550.1\| | SEQ ID NO: 334 | 169 | 253 | 85 | 536 | 611 | 48 | 536 | 611 | 48 |
| *Odoribacter laneus* YIT 12061 gi\|374384763\|ref\|ZP_09642280.1\| | SEQ ID NO: 335 | 164 | 242 | 79 | 535 | 610 | 63 | 535 | 610 | 63 |
| *Legionella pneumophila* str. Paris gi\|54296138\|ref\|YP_122507.1\| | SEQ ID NO: 336 | 164 | 239 | 76 | 402 | 476 | 67 | 402 | 476 | 67 |
| *Bacteroides* sp. 20 3 gi\|301311869\|ref\|ZP_07721791.1\| | SEQ ID NO: 337 | 198 | 269 | 72 | 530 | 604 | 83 | 530 | 604 | 83 |
| *Akkermansia muciniphila* ATCC BAA-835 gi\|187736489\|ref\|YP_001878601. | SEQ ID NO: 338 | 136 | 202 | 67 | 348 | 418 | 62 | 348 | 418 | 62 |
| *Prevotella* sp. C561 gi\|345885718\|ref\|ZP_08837074.1\| | SEQ ID NO: 339 | 184 | 250 | 67 | 357 | 425 | 78 | 357 | 425 | 78 |
| *Wolinella succinogenes* DSM 1740 gi\|34557932\|ref\|NP_907747.1\| | SEQ ID NO: 340 | 157 | 218 | 36 | 401 | 468 | 60 | 401 | 468 | 60 |
| *Alicyclobacillus hesperidum* URH17-3-68 gi\|403744858\|ref\|ZP_10953934.1\| | SEQ ID NO: 341 | 142 | 196 | 55 | 416 | 482 | 61 | 416 | 482 | 61 |
| *Caenispirillum salinarum* AK4 gi\|427429481\|ref\|ZP_18919511.1\| | SEQ ID NO: 342 | 161 | 214 | 54 | 330 | 393 | 68 | 330 | 393 | 68 |
| *Eubacterium rectale* ATCC 33656 gi\|238924075\|ref\| YP_002937591.1\| | SEQ ID NO: 343 | 133 | 185 | 53 | 322 | 384 | 60 | 322 | 384 | 60 |
| *Mycoplasma synoviae* 53 gi\|71894592\|ref\|YP_278700.1\| | SEQ ID NO: 344 | 187 | 239 | 53 | 319 | 381 | 80 | 319 | 381 | 80 |
| *Porphyromonas* sp. oral taxon 279 str. F0450 gi\|402847315\|ref\|ZP_10895610.1 | SEQ ID NO: 345 | 150 | 202 | 53 | 309 | 371 | 60 | 309 | 371 | 60 |
| *Streptococcus thermophilus* LMD-9 gi\|116627542\|ref\|YP_820161.1\| | SEQ ID NO: 346 | 127 | 178 | 139 | 424 | 486 | 81 | 424 | 486 | 81 |
| *Roseburia inulinivorans* DSM 16841 gi\|225377804\|ref\|ZP_03755025.1\| | SEQ ID NO: 347 | 154 | 204 | 51 | 318 | 380 | 69 | 318 | 380 | 69 |
| *Methylosinus trichosporium* OB3b gi\|296446027\|ref\|ZP_06887976.1\| | SEQ ID NO: 348 | 144 | 193 | 50 | 426 | 488 | 64 | 426 | 488 | 64 |
| *Ruminococcus albus* 8 gi\|325677756\|ref\|ZP_08157403.1\| | SEQ ID NO: 349 | 139 | 187 | 49 | 351 | 412 | 55 | 351 | 412 | 55 |
| *Bifidobacterium longum* DJO10A gi\|189440764\|ref\|YP_001955845. | SEQ ID NO: 350 | 183 | 230 | 48 | 370 | 431 | 44 | 370 | 431 | 44 |
| *Enterococcus faecalis* TX0012 gi\|315149830\|gb\|EFT93846.1\| | SEQ ID NO: 351 | 123 | 170 | 48 | 327 | 387 | 60 | 327 | 387 | 60 |
| *Mycoplasma mobile* 163K gi\|47458868\|ref\|YP_015730.1\| | SEQ ID NO: 352 | 179 | 226 | 48 | 314 | 374 | 79 | 314 | 374 | 79 |
| *Actinomyces coleocanis* DSM 15436 gi\|227494853\|ref\|ZP_03925169.1\| | SEQ ID NO: 353 | 147 | 193 | 47 | 358 | 418 | 40 | 358 | 418 | 40 |
| *Dinoroseobacter shibae* DFL 12 gi\|159042956\|ref\|YP_001531750.1\| | SEQ ID NO: 354 | 138 | 184 | 47 | 338 | 398 | 48 | 338 | 398 | 48 |
| *Actinomyces* sp. oral taxon 180 str. F0310 gi\|315605738\|ref\|ZP_07880770.1\| | SEQ ID NO: 355 | 183 | 228 | 46 | 349 | 409 | 40 | 349 | 409 | 40 |
| *Alcanivorax* sp. W11-5 gi\|407803669\|ref\|ZP_11150502.1\| | SEQ ID NO: 356 | 139 | 183 | 45 | 344 | 404 | 61 | 344 | 404 | 61 |
| *Aminomonas paucivorans* DSM 12260 gi\|312879015\|ref\|ZP_07738815.1\| | SEQ ID NO: 357 | 134 | 178 | 45 | 341 | 401 | 63 | 341 | 401 | 63 |
| *Mycoplasma canis* PG 14 gi\|384393286\|gb\|EIE39736.1\| | SEQ ID NO: 358 | 139 | 183 | 45 | 319 | 379 | 76 | 319 | 379 | 76 |
| *Lactobacillus coryniformis* KCTC 3535 gi\|336393381\|ref\|ZP_08574780.1\| | SEQ ID NO: 359 | 141 | 184 | 44 | 328 | 387 | 61 | 328 | 387 | 61 |
| *Elusimicrobium minutum* Pei191 gi\|187250660\|ref\|YP_001875142.1\| | SEQ ID NO: 360 | 177 | 219 | 43 | 322 | 381 | 47 | 322 | 381 | 47 |
| *Neisseria meningitidis* Z2491 gi\|218767588\|ref\|YP_002342100.1\| | SEQ ID NO: 361 | 147 | 189 | 43 | 360 | 419 | 61 | 360 | 419 | 61 |
| *Pasteurella multocida* str. Pm70 gi\|15602992\|ref\|NP_246064.1\| | SEQ ID NO: 362 | 139 | 181 | 43 | 319 | 378 | 61 | 319 | 378 | 61 |
| *Rhodovulum* sp. PH10 gi\|402849997\|ref\|ZP_10898214.1\| | SEQ ID NO: 363 | 141 | 183 | 43 | 319 | 378 | 48 | 319 | 378 | 48 |
| *Eubacterium dolichum* DSM 3991 gi\|160915782\|ref\|ZP_02077990.1\| | SEQ ID NO: 364 | 131 | 172 | 42 | 303 | 361 | 59 | 303 | 361 | 59 |
| *Nitratifractor salsuginis* DSM 16511 gi\|319957206\|ref\|YP_004168469.1\| | SEQ ID NO: 365 | 143 | 184 | 42 | 347 | 404 | 61 | 347 | 404 | 61 |
| *Rhodospirillum rubrum* ATCC 11170 gi\|83591793\|ref\|YP_425545.1\| | SEQ ID NO: 366 | 139 | 180 | 42 | 314 | 371 | 55 | 314 | 371 | 55 |
| *Clostridium cellulolyticum* H10 gi\|220930482\|ref\|YP_002507391.1\| | SEQ ID NO: 367 | 137 | 176 | 40 | 320 | 376 | 61 | 320 | 376 | 61 |

TABLE 28-continued

Amino Acid Sequence of Cas9 Orthologs

| Species/Composite ID | Amino acid sequence | REC2 start (AA pos) | REC2 stop (AA pos) | REC2 # AA deleted (n) | REC1$_{CT}$ start (AA pos) | REC1$_{CT}$ stop (AA pos) | REC1$_{CT}$ # AA deleted (n) | Rec$_{sub}$ start (AA pos) | Rec$_{sub}$ stop (AA pos) | Rec$_{sub}$ # AA deleted (n) |
|---|---|---|---|---|---|---|---|---|---|---|
| *Helicobacter mustelae* 12198 gi\|291276265\|ref\|YP_003516037.1 | SEQ ID NO: 368 | 148 | 187 | 40 | 298 | 354 | 48 | 298 | 354 | 48 |
| *Ilyobacter polytropus* DSM 2926 gi\|310780384\|ref\|YP_003968716.1 | SEQ ID NO: 369 | 134 | 173 | 40 | 462 | 517 | 63 | 462 | 517 | 63 |
| *Sphaerochaeta globus* str. Buddy gi\|325972003\|ref\|YP_004248194.1 | SEQ ID NO: 370 | 163 | 202 | 40 | 335 | 389 | 45 | 335 | 389 | 45 |
| *Staphylococcus lugdunensis* M23590 gi\|315659848\|ref\|ZP_07912707.1 | SEQ ID NO: 371 | 128 | 167 | 40 | 337 | 391 | 57 | 337 | 391 | 57 |
| *Treponema* sp. JC4 gi\|384109266\|ref\|ZP_10010146.1 | SEQ ID NO: 372 | 144 | 183 | 40 | 328 | 382 | 63 | 328 | 382 | 63 |
| uncultured delta proteobacterium HF0070 07E19 gi\|297182908\|gb\|ADI19058.1\| | SEQ ID NO: 373 | 154 | 193 | 40 | 313 | 365 | 55 | 313 | 365 | 55 |
| *Alicycliphilus denitrificans* K601 gi\|330822845\|ref\|YP_004386148.1 | SEQ ID NO: 374 | 140 | 178 | 39 | 317 | 366 | 48 | 317 | 366 | 48 |
| *Azospirillum* sp. B510 gi\|288957741\|ref\|YP_003448082.1 | SEQ ID NO: 375 | 205 | 243 | 39 | 342 | 389 | 46 | 342 | 389 | 46 |
| *Bradyrhizobium* sp. BTAi1 gi\|148255343\|ref\|YP_001239928.1 | SEQ ID NO: 376 | 143 | 181 | 39 | 323 | 370 | 48 | 323 | 370 | 48 |
| *Parvibaculum lavamentivorans* DS-1 gi\|154250555\|ref\|YP_001411379.1 | SEQ ID NO: 377 | 138 | 176 | 39 | 327 | 374 | 58 | 327 | 374 | 58 |
| *Prevotella timonensis* CRIS 5C-B1 gi\|282880052\|ref\|ZP_06288774.1 | SEQ ID NO: 378 | 170 | 208 | 39 | 328 | 375 | 61 | 328 | 375 | 61 |
| *Bacillus smithii* 7 3 47FAA gi\|365156657\|ref\|ZP_09352959.1 | SEQ ID NO: 379 | 134 | 171 | 38 | 401 | 448 | 63 | 401 | 448 | 63 |
| *Cand. Puniceispirillum marinum* IMCC1322 gi\|294086111\|ref\|YP_003552871.1 | SEQ ID NO: 380 | 135 | 172 | 38 | 344 | 391 | 53 | 344 | 391 | 53 |
| *Barnesiella intestinihominis* YIT 11860 gi\|404487228\|ref\|ZP_11022414.1 | SEQ ID NO: 381 | 140 | 176 | 37 | 371 | 417 | 60 | 371 | 417 | 60 |
| *Ralstonia syzygii* R24 gi\|344171927\|emb\|CCA84553.1\| | SEQ ID NO: 382 | 140 | 176 | 37 | 395 | 440 | 50 | 395 | 440 | 50 |
| *Wolinella succinogenes* DSM 1740 gi\|34557790\|ref\|NP_907605.1\| | SEQ ID NO: 383 | 145 | 180 | 36 | 348 | 392 | 60 | 348 | 392 | 60 |
| *Mycoplasma gallisepticum* str. F gi\|284931710\|gb\|ADC31648.1\| | SEQ ID NO: 384 | 144 | 177 | 34 | 373 | 416 | 71 | 373 | 416 | 71 |
| *Acidothermus cellulolyticus* 11B gi\|117929158\|ref\|YP_873709.1\| | SEQ ID NO: 385 | 150 | 182 | 33 | 341 | 380 | 58 | 341 | 380 | 58 |
| *Mycoplasma ovipneumoniae* SC01 gi\|363542550\|ref\|ZP_09312133.1 | SEQ ID NO: 386 | 156 | 184 | 29 | 381 | 420 | 62 | 381 | 420 | 62 |

TABLE 29

Amino Acid Sequence of Cas9 Core Domains

| Strain Name | Cas9 Start (AA pos) | Cas9 Stop (AA pos) |
|---|---|---|
| | Start and Stop numbers refer to the sequence in Table 28 | |
| *Staphylococcus Aureus* | 1 | 772 |
| *Streptococcus Pyogenes* | 1 | 1099 |
| *Campulobacter Jejuni* | 1 | 741 |

TABLE 30

Identified PAM sequences and corresponding RKR motifs.

| Strain Name | PAM sequence (NA) | RKR motif (AA) |
|---|---|---|
| *Streptococcus pyogenes* | NGG | RKR |
| *Streptococcus mutans* | NGG | RKR |
| *Streptococcus thermophilus* A | NGGNG | RYR |
| *Treponema denticola* | NAAAAN | VAK |
| *Streptococcus thermophilus* B | NNAAAAW | IYK |
| *Campylobacter jejuni* | NNNNACA | NLK |
| *Pasteurella multocida* | GNNNCNNA | KDG |
| *Neisseria meningitidis* | NNNNGATT or | IGK |
| *Staphylococcus aureus* | NNGRRV (R = A or G; V = A, G or C) NNGRRT (R = A or G) | NDK |

PI domains are provided in Tables 31 and 32.

TABLE 31

Altered PI Domains

| Strain Name | PI Start (AA pos) Start and Stop numbers refer to the sequences in Table 28 | PI Stop (AA pos) | Length of PI (AA) | RKR motif (AA) |
|---|---|---|---|---|
| Alicycliphilus denitrificans K601 | 837 | 1029 | 193 | --Y |

TABLE 31-continued

Altered PI Domains

| Strain Name | PI Start (AA pos) Start and Stop numbers refer to the sequences in Table 28 | PI Stop (AA pos) | Length of PI (AA) | RKR motif (AA) |
|---|---|---|---|---|
| Campylobacter jejuni NCTC 11168 | 741 | 984 | 244 | -NG |
| Helicobacter mustelae 12198 | 771 | 1024 | 254 | -NQ |

TABLE 32

Other Altered PI Domains

| Strain Name | PI Start (AA pos) Start and Stop numbers refer to the sequences in Table 28 | PI Stop (AA pos) | Length of PI (AA) | RKR motif (AA) |
|---|---|---|---|---|
| Akkermansia muciniphila ATCC BAA-835 | 871 | 1101 | 231 | ALK |
| Ralstonia syzygii R24 | 821 | 1062 | 242 | APY |
| Cand. Puniceispirillum marinum IMCC1322 | 815 | 1035 | 221 | AYK |
| Fructobacillus fructosus KCTC 3544 | 1074 | 1323 | 250 | DGN |
| Eubacterium yurii ATCC 43715 | 1107 | 1391 | 285 | DGY |
| Eubacterium dolichum DSM 3991 | 779 | 1096 | 318 | DKK |
| Dinoroseobacter shibae DFL 12 | 851 | 1079 | 229 | DPI |
| Clostridium cellulolyticum H10 | 767 | 1021 | 255 | EGK |
| Pasteurella multocida str. Pm70 | 815 | 1056 | 242 | ENN |
| Mycoplasma canis PG 14 | 907 | 1233 | 327 | EPK |
| Porphyromonas sp. oral taxon 279 str. F0450 | 935 | 1197 | 263 | EPT |
| Filifactor alocis ATCC 35896 | 1094 | 1365 | 272 | EVD |
| Aminomonas paucivorans DSM 12260 | 801 | 1052 | 252 | EVY |
| Wolinella succinogenes DSM 1740 | 1034 | 1409 | 376 | EYK |
| Oenococcus kitaharae DSM 17330 | 1119 | 1389 | 271 | GAL |
| Coriobacteriumglomerans PW2 | 1126 | 1384 | 259 | GDR |
| Peptoniphilus duerdenii ATCC BAA-1640 | 1091 | 1364 | 274 | GDS |
| Bifidobacterium bifidum S17 | 1138 | 1420 | 283 | GGL |
| Alicyclobacillus hesperidum URH17-3-68 | 876 | 1146 | 271 | GGR |
| Roseburia inulinivorans DSM 16841 | 895 | 1152 | 258 | GGT |
| Actinomyces coleocanis DSM 15436 | 843 | 1105 | 263 | GKK |
| Odoribacter laneus YIT 12061 | 1103 | 1498 | 396 | GKV |
| Coprococcus catus GD-7 | 1063 | 1338 | 276 | GNQ |
| Enterococcus faecalis TX0012 | 829 | 1150 | 322 | GRK |
| Bacillus smithii 7 3 47FAA | 809 | 1088 | 280 | GSK |
| Legionella pneumophila str. Paris | 1021 | 1372 | 352 | GTM |

TABLE 32-continued

Other Altered PI Domains

| Strain Name | PI Start (AA pos) Start and Stop numbers refer to the sequences in Table 28 | PI Stop (AA pos) | Length of PI (AA) | RKR motif (AA) |
|---|---|---|---|---|
| Bacteroides fragilis NCTC 9343 | 1140 | 1436 | 297 | IPV |
| Mycoplasma ovipneumoniae SC01 | 923 | 1265 | 343 | IRI |
| Actinomyces sp. oral taxon 180 str. F0310 | 895 | 1181 | 287 | KEK |
| Treponema sp. JC4 | 832 | 1062 | 231 | KIS |
| Fusobacteriumnucleatum ATCC49256 | 1073 | 1374 | 302 | KKV |
| Lactobacillus farciminis KCTC 3681 | 1101 | 1356 | 256 | KKV |
| Nitratifractor salsuginis DSM 16511 | 840 | 1132 | 293 | KMR |
| Lactobacillus coryniformis KCTC 3535 | 850 | 1119 | 270 | KNK |
| Mycoplasma mobile 163K | 916 | 1236 | 321 | KNY |
| Flavobacterium branchiophilum FL-15 | 1182 | 1473 | 292 | KQK |
| Prevotella timonensis CRIS 5C-B1 | 957 | 1218 | 262 | KQQ |
| Methylosinus trichosporium OB3b | 830 | 1082 | 253 | KRP |
| Prevotella sp. C561 | 1099 | 1424 | 326 | KRY |
| Mycoplasma gallisepticum str. F | 911 | 1269 | 359 | KTA |
| Lactobacillus rhamnosus GG | 1077 | 1363 | 287 | KYG |
| Wolinella succinogenes DSM 1740 | 811 | 1059 | 249 | LPN |
| Streptococcus thermophilus LMD-9 | 1099 | 1388 | 290 | MLA |
| Treponema denticola ATCC 35405 | 1092 | 1395 | 304 | NDS |
| Bergeyella zoohelcum ATCC 43767 | 1098 | 1415 | 318 | NEK |
| Veillonella atypica ACS-134-V-Col7a | 1107 | 1398 | 292 | NGF |
| Neisseria meningitidis Z2491 | 835 | 1082 | 248 | NHN |
| Ignavibacterium album JCM 16511 | 1296 | 1688 | 393 | NKK |
| Ruminococcus albus 8 | 853 | 1156 | 304 | NNF |
| Streptococcus thermophilus LMD-9 | 811 | 1121 | 311 | NNK |
| Barnesiella intestinihominis YIT 11860 | 871 | 1153 | 283 | NPV |
| Azospirillum sp. B510 | 911 | 1168 | 258 | PFH |
| Rhodospirillum rubrum ATCC 11170 | 863 | 1173 | 311 | PRG |
| Planococcus antarcticus DSM 14505 | 1087 | 1333 | 247 | PYY |
| Staphylococcus pseudintermedius ED99 | 1073 | 1334 | 262 | QIV |
| Alcanivorax sp. W11-5 | 843 | 1113 | 271 | RIE |
| Bradyrhizobium sp. BTAi1 | 811 | 1064 | 254 | RIY |
| Streptococcus pyogenes MI GAS | 1099 | 1368 | 270 | RKR |
| Streptococcus mutans UA159 | 1078 | 1345 | 268 | RKR |
| Streptococcus Pyogenes | 1099 | 1368 | 270 | RKR |
| Bacteroides sp. 20_3 | 1147 | 1517 | 371 | RNI |
| S. aureus | 772 | 1053 | 282 | RNK |

TABLE 32-continued

Other Altered PI Domains

| Strain Name | PI Start (AA pos) Start and Stop numbers refer to the sequences in Table 28 | PI Stop (AA pos) | Length of PI (AA) | RKR motif (AA) |
|---|---|---|---|---|
| Solobacterium moorei F0204 | 1062 | 1327 | 266 | RSG |
| Finegoldia magna ATCC 29328 | 1081 | 1348 | 268 | RTE |
| uncultured delta proteobacterium HF0070 07E19 | 770 | 1011 | 242 | SGG |
| Acidaminococcus sp. D21 | 1064 | 1358 | 295 | SIG |
| Eubacterium rectale ATCC 33656 | 824 | 1114 | 291 | SKK |
| Caenispirillum salinarum AK4 | 1048 | 1442 | 395 | SLV |
| Acidothermus cellulolyticus 11B | 830 | 1138 | 309 | SPS |
| Catenibacterium mitsuokai DSM 15897 | 1068 | 1329 | 262 | SPT |
| Parvibaculum lavamentivorans DS-1 | 827 | 1037 | 211 | TGN |
| Staphylococcus lugdunensis M23590 | 772 | 1054 | 283 | TKK |
| Streptococcus sanguinis SK49 | 1123 | 1421 | 299 | TRM |
| Elusimicrobium minutum Pei191 | 910 | 1195 | 286 | TTG |
| Nitrobacter hamburgensis X14 | 914 | 1166 | 253 | VAY |
| Mycoplasma synoviae 53 | 991 | 1314 | 324 | VGF |
| Sphaerochaeta globus str. Buddy | 877 | 1179 | 303 | VKG |
| Ilyobacter polytropus DSM 2926 | 837 | 1092 | 256 | VNG |
| Rhodovulum sp. PH10 | 821 | 1059 | 239 | VPY |
| Bifidobacterium longum DJO10A | 904 | 1187 | 284 | VRK |

Amino Acid Sequences Described in Table 28:

SEQ ID NO: 304

MKRNYILGLDIGITSVGYGIIDYETRDVIDAGVRLFKEANVENNEGRRSKRGARRLKRRRRHRI
QRVKKLLFDYNLLTDHSELSGINPYEARVKGLSQKLSEEEFSAALLHLAKRRGVHNVNEVEEDT
GNELSTKEQISRNSKALEEKYVAELQLERLKKDGEVRGSINRFKTSDYVKEAKQLLKVQKAYHQ
LDQSFIDTYIDLLETRRTYYEGPGEGSPFGWKDIKEWYEMLMGHCTYFPEELRSVKYAYNADLY
NALNDLNNLVITRDENEKLEYYEKFQIIENVFKQKKKPTLKQIAKEILVNEEDIKGYRVTSTGK
PEFTNLKVYHDIKDITARKEIIENAELLDQIAKILTIYQSSEDIQEELTNLNSELTQEEIEQIS
NLKGYTGTHNLSLKAINLILDELWHTNDNQIAIFNRLKLVPKKVDLSQQKEIPTTLVDDFILSP
VVKRSFIQSIKVINAIIKKYGLPNDIIIELAREKNSKDAQKMINEMQKRNRQTNERIEEIIRTT
GKENAKYLIEKIKLHDMQEGKCLYSLEAIPLEDLLNNPFNYEVDHIIPRSVSFDNSFNNKVLVK
QEENSKKGNRTPFQYLSSSDSKISYETFKKHILNLAKGKGRISKTKKEYLLEERDINRFSVQKD
FINRNLVDTRYATRGLMNLLRSYFRVNNLDVKVKSINGGFTSFLRRKWKFKKERNKGYKHHAED
ALIIANADFIFKEWKKLDKAKKVMENQMFEEKQAESMPEIETEQEYKEIFITPHQIKHIKDFKD
YKYSHRVDKKPNRELINDTLYSTRKDDKGNTLIVNNLNGLYDKDNDKLKKLINKSPEKKLMYHH
DPQTYQKLKLIMEQYGDEKNPLYKYYEETGNYLTKYSKKDNGPVIKKIKYYGNKLNAHLDITDD

-continued

YPNSRNKVVKLSLKPYRFDVYLDNGVYKFVTVKNLDVIKKENYYEVNSKCYEEAKKLKKISNQA

EFIASFYNNDLIKINGELYRVIGVNNDLLNRIEVNMIDITYREYLENMNDKRPPRIIKTIASKT

QSIKKYSTDILGNLYEVKSKKHPQIIKKG

SEQ ID NO: 305

MDKKYSIGLDIGTNSVGWAVITDEYKVPSKKFKVLGNTDRHSIKKNLIGALLFDSGETAEATRL

KRTARRRYTRRKNRICYLQEIFSNEMAKVDDSFFHRLEESFLVEEDKKHERHPIFGNIVDEVAY

HEKYPTIYHLRKKLVDSTDKADLRLIYLALAHMIKFRGHFLIEGDLNPDNSDVDKLFIQLVQTY

NQLFEENPINASGVDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILRVNTEITKAPLSAS

MIKRYDEHHQDLTLLKALVRQQLPEKYKEIFFDQSKNGYAGYIDGGASQEEFYKFIKPILEKMD

GTEELLVKLNREDLLRKQRTFDNGSIPHQIHLGELHAILRRQEDFYPFLKDNREKIEKILTFRI

PYYVGPLARGNSRFAWMTRKSEETITPWNFEEVVDKGASAQSFIERMTNFDKNLPNEKVLPKHS

LLYEYFTVYNELTKVKYVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLTLFEDREMIEERLKTYA

HLFDDKVMKQLKRRRYTGWGRLSRKLINGIRDKQSGKTILDFLKSDGFANRNFMQLIHDDSLTF

KEDIQKAQVSGQGDSLHEHIANLAGSPAIKKGILQTVKVVDELVKVMGRHKPENIVIEMARENQ

TTQKGQKNSRERMKRIEEGIKELGSQILKEHPVENTQLQNEKLYLYYLQNGRDMYVDQELDINR

LSDYDVDHIVPQSFLKDDSIDNKVLTRSDKNRGKSDNVPSEEVVKKMKNYWRQLLNAKLITQRK

FDNLTKAERGGLSELDKAGFIKRQLVETRQITKHVAQILDSRMNTKYDENDKLIREVKVITLKS

KLVSDFRKDFQFYKVREINNYHHAHDAYLNAVVGTALIKKYPKLESEFVYGDYKVYDVRKMIAK

SEQEIGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLAS

AGELQKGNELALPSKYVNFLYLASHYEKLKGSPEDNEQKQLFVEQHKHYLDEIIEQISEFSKRV

ILADANLDKVLSAYNKHRDKPIREQAENIIHLFTLTNLGAPAAFKYFDTTIDRKRYTSTKEVLD

ATLIHQSITGLYETRIDLSQLGGD

SEQ ID NO: 306

MARILAFDIGISSIGWAFSENDELKDCGVRIFTKVENPKTGESLALPRRLARSARKRLARRKAR

LNHLKHLIANEFKLNYEDYQSFDESLAKAYKGSLISPYELRFRALNELLSKQDFARVILHIAKR

RGYDDIKNSDDKEKGAILKAIQNEEKLANYQSVGEYLYKEYFQKFKENSKEFTNVRNKKESYE

RCIAQSFLKDELKLIFKKQREFGFSFSKKFEEEVLSVAFYKRALKDFSHLVGNCSFFTDEKRAP

KNSPLAFMFVALTRIINLLNNLKNTEGILYTKDDLNALLNEVLKNGTLTYKQTKKLLGLSDDYE

FKGEKGTYFIEFKKYKEFIKALGEHNLSQDDLNEIAKDITLIKDEIKLKKALAKYDLNQNQIDS

LSKLEFKDHLNISFKALKLVTPLMLEGKKYDEACNELNLKVAINEDKKDFLPAFNETYYKDEVT

NPVVLRAIKEYRKVLNALLKKYGKVHKINIELAREVGKNHSQRAKIEKEQNENYKAKKDAELEC

EKLGLKINSKNILKLRLFKEQKEFCAYSGEKIKISDLQDEKMLEIDHIYPYSRSFDDSYMNKVL

VFTKQNQEKLNQTPFEAFGNDSAKWQKIEVLAKNLPTKKQKRILDKNYKDKEQKNFKDRNLNDT

RYIARLVLNYTKDYLDFLPLSDDENTKLNDTQKGSKVHVEAKSGMLTSALRHTWGFSAKDRNNH

LHHAIDAVIIAYANNSIVKAFSDFKKEQESNSAELYAKKISELDYKNKRKFFEPFSGFRQKVLD

KIDEIFVSKPERKKPSGALHEETFRKEEEFYQSYGGKEGVLKALELGKIRKVNGKIVKNGDMFR

VDIFKHKKTNKFYAVPIYTMDFALKVLPNKAVARSKKGEIKDWILMDENYEFCFSLYKDSLILI

-continued

QTKDMQEPEFVYYNAFTSSTVSLIVSKHDNKFETLSKNQKILFKNANEKEVIAKSIGIQNLKVF

EKYIVSALGEVTKAEFRQREDFKK

SEQ ID NO: 307

MKRILGLDLGTNSIGWALVNEAENKDERSSIVKLGVRVNPLTVDELTNFEKGKSITTNADRTLK

RGMRRNLQRYKLRRETLTEVLKEHKLITEDTILSENGNRTTFETYRLRAKAVTEEISLEEFARV

LLMINKKRGYKSSRKAKGVEEGTLIDGMDIARELYNNNLTPGELCLQLLDAGKKFLPDFYRSDL

QNELDRIWEKQKEYYPEILTDVLKEELRGKKRDAVWAICAKYFVWKENYTEWNKEKGKTEQQER

EHKLEGIYSKRKRDEAKRENLQWRVNGLKEKLSLEQLVIVFQEMNTQINNSSGYLGAISDRSKE

LYFNKQTVGQYQMEMLDKNPNASLRNMVFYRQDYLDEFNMLWEKQAVYHKELTEELKKEIRDII

IPFYQRRLKSQKGLIGFCEFESRQIEVDIDGKKKIKTVGNRVISRSSPLFQEFKIWQILNNIEVT

VVGKKRKRRKLKENYSALFEELNDAEQLELNGSRRLCQEEKELLAQELFIRDKMTKSEVLKLLF

DNPQELDLNFKTIDGNKTGYALFQAYSKMIEMSGHEPVDFKKPVEKVVEYIKAVFDLLNWNTDI

LGFNSNEELDNQPYYKLWHLLYSFEGDNTPTGNGRLIQKMTELYGFEKEYATILANVSFQDDYG

SLSAKAIHKILPHLKEGNRYDVACVYAGYRHSESSLTREEIANKVLKDRLMLLPKNSLHNPVVE

KILNQMVNVINVIIDIYGKPDEIRVELARELKKNAKEREELTKSIAQTTKAHEEYKTLLQTEFG

LTNVSRTDILRYKLYKELESCGYKTLYSNTYISREKLFSKEFDIEHIIPQARLFDDSFSNKTLE

ARSVNIEKGNKTAYDFVKEKFGESGADNSLEHYLNNIEDLFKSGKISKTKYNKLKMAEQDIPDG

FIERDLRNTQYIAKKALSMLNEISHRVVATSGSVTDKLREDWQLIDVMKELNWEKYKALGLVEY

FEDRDGRQIGRIKDWTKRNDHRHHAMDALTVAFTKDVFIQYFNNKNASLDPNANEHAIKNKYFQ

NGRAIAPMPLREFRAEAKKHLENTLISIKAKNKVITGNINKTRKKGGVNKNMQQTPRGQLHLET

IYGSGKQYLTKEEKVNASFDMRKIGTVSKSAYRDALLKRLYENDNDPKKAFAGKNSLDKQPIWL

DKEQMRKVPEKVKIVTLEAIYTIRKEISPDLKVDKVIDVGVRKILIDRLNEYGNDAKKAFSNLD

KNPIWLNKEKGISIKRVTISGISNAQSLHVKKDKDGKPILDENGRNIPVDFVNTGNNHHVAVYY

RPVIDKRGQLVVDEAGNPKYELEEVVVSFFEAVTRANLGLPIIDKDYKTTEGWQFLFSMKQNEY

FVFPNEKTGFNPKEIDLLDVENYGLISPNLFRVQKFSLKNYVFRHHLETTIKDTSSILRGITWI

DFRSSKGLDTIVKVRVNHIGQIVSVGEY

SEQ ID NO: 308
MSRKNYVDDYAISLDIGNASVGWSAFTPNYRLVRAKGHELIGVRLFDPADTAESRRMARTTRRR

YSRRRWRLRLLDALFDQALSEIDPSFLARRKYSWVHPDDENNADCWYGSVLFDSNEQDKRFYEK

YPTIYHLRKALMEDDSQHDIREIYLAIHHMVKYRGNFLVEGTLESSNAFKEDELLKLLGRITRY

EMSEGEQNSDIEQDDENKLVAPANGQLADALCATRGSRSMRVDNALEALSAVNDLSREQRAIVK

AIFAGLEGNKLDLAKIFVSKEFSSENKKILGIYFNKSDYEEKCVQIVDSGLLDDEEREFLDRMQ

GQYNAIALKQLLGRSTSVSDSKCASYDAHRANWNLIKLQLRTKENEKDINENYGILVGWKIDSG

QRKSVRGESAYENMRKKANVFFKKMIETSDLSETDKNRLIHDIEEDKLFPIQRDSDNGVIPHQL

HQNELKQIIKKQGKYYPFLLDAFEKDGKQINKIEGLLTFRVPYFVGPLVVPEDLQKSDNSENHW

MVRKKKGEITPWNFDEMVDKDASGRKFIERLVGTDSYLLGEPTLPKNSLLYQEYEVLNELNNVR

LSVRTGNHWNDKRRMRLGREEKTLLCQRLFMKGQTVTKRTAENLLRKEYGRTYELSGLSDESKF

TSSLSTYGKMCRIFGEKYVNEHRDLMEKIVELQTVFEDKETLLHQLRQLEGISEADCALLVNTH

YTGWGRLSRKLLTTKAGECKISDDFAPRKHSIIEIMRAEDRNLMEIITDKQLGFSDWIEQENLG

AENGSSLMEVVDDLRVSPKVKRGIIQSIRLIDDISKAVGKRPSRIFLELADDIQPSGRTISRKS

RLQDLYRNANLGKEFKGIADELNACSDKDLQDDRLFLYYTQLGKDMYTGEELDLDRLSSAYDID

-continued

HIIPQAVTQNDSIDNRVLVARAENARKTDSFTYMPQIADRMRNFWQILLDNGLISRVKFERLTR

QNEFSEREKERFVQRSLVETRQIMKNVATLMRQRYGNSAAVIGLNAELTKEMHRYLGFSHKNRD

INDYHHAQDALCVGIAGQFAANRGFFADGEVSDGAQNSYNQYLRDYLRGYREKLSAEDRKQGRA

FGFIVGSMRSQDEQKRVNPRTGEVVWSEEDKDYLRKVMNYRKMLVTQKVGDDFGALYDETRYAA

TDPKGIKGIPFDGAKQDTSLYGGFSSAKPAYAVLIESKGKTRLVNVTMQEYSLLGDRPSDDELR

KVLAKKKSEYAKANILLRHVPKMQLIRYGGGLMVIKSAGELNNAQQLWLPYEEYCYFDDLSQGK

GSLEKDDLKKLLDSILGSVQCLYPWHRFTEEELADLHVAFDKLPEDEKKNVITGIVSALHADAK

TANLSIVGMTGSWRRMNNKSGYTFSDEDEFIFQSPSGLFEKRVTVGELKRKAKKEVNSKYRTNE

KRLPTLSGASQP

SEQ ID NO: 309
METQTSNQLITSHLKDYPKQDYFVGLDIGTNSVGWAVTNTSYELLKFHSHKMWGSRLFEEGESA

VTRRGFRSMRRRLERRKLRLKLLEELFADAMAQVDSTFFIRLHESKYHYEDKTTGHSSKHILFI

DEDYTDQDYFTEYPTIYHLRKDLMENGTDDIRKLFLAVHHILKYRGNFLYEGATFNSNAFTFED

VLKQALVNITFNCFDTNSAISSISNILMESGKTKSDKAKAIERLVDTYTVFDEVNTPDKPQKEQ

VKEDKKTLKAFANLVLGLSANLIDLFGSVEDIDDDLKKLQIVGDTYDEKRDELAKVWGDEIHII

DDCKSVYDAIILMSIKEPGLTISQSKVKAFDKHKEDLVILKSLLKLDRNVYNEMFKSDKKGLHN

YVHYIKQGRTEETSCSREDFYKYTKKIVEGLADSKDKEYILNEIELQTLLPLQRIKDNGVIPYQ

LHLEELKVILDKCGPKFPFLHTVSDGFSVTEKLIKMLEFRIPYYVGPLNTHHNIDNGGFSWAVR

KQAGRVTPWNFEEKIDREKSAAAFIKNLTNKCTYLFGEDVLPKSSLLYSEFMLLNELNNVRIDG

KALAQGVKQHLIDSIFKQDHKKMTKNRIELFLKDNNYITKKHKPEITGLDGEIKNDLTSYRDMV

RILGNNFDVSMAEDIITDITIFGESKKMLRQTLRNKFGSQLNDETIKKLSKLRYRDWGRLSKKL

LKGIDGCDKAGNGAPKTIIELMRNDSYNLMEILGDKFSFMECIEEENAKLAQGQVVNPHDIIDE

LALSPAVKRAVWQALRIVDEVAHIKKALPSRIFVEVARTNKSEKKKKDSRQKRLSDLYSAIKKD

DVLQSGLQDKEFGALKSGLANYDDAALRSKKLYLYYTQMGRCAYTGNIIDLNQLNTDNYDIDHI

YPRSLTKDDSFDNLVLCERTANAKKSDIYPIDNRIQTKQKPFWAFLKHQGLISERKYERLTRIA

PLTADDLSGFIARQLVETNQSVKATTTLLRRLYPDIDVVFVKAENVSDFRHNNNFIKVRSLNHH

HHAKDAYLNIVVGNVYHEKFTRNFRLFFKKNGANRTYNLAKMFNYDVICTNAQDGKAWDVKTSM

NTVKKMMASNDVRVTRRLLEQSGALADATIYKASVAAKAKDGAYIGMKTKYSVFADVTKYGGMT

KIKNAYSIIVQYTGKKGEEIKEIVPLPIYLINRNATDIELIDYVKSVIPKAKDISIKYRLCIN

QLVKVNGFYYYLGGKTNDKIYIDNAIELVVPHDIATYIKLLDKYDLLRKENKTLKASSITTSIY

NINTSTVVSLNKVGIDVFDYFMSKLRTPLYMKMKGNKVDELSSTGRSKFIKMTLEEQSIYLLEV

LNLLTNSKTTFDVKPLGITGSRSTIGVKIHNLDEFKIINESITGLYSNEVTIV

SEQ ID NO: 310
MTKLNQPYGIGLDIGSNSIGFAVVDANSHLLRLKGETAIGARLFREGQSAADRRGSRTTRRRLS

RTRWRLSFLRDFFAPHITKIDPDFFLRQKYSEISPKDKDRFKYEKRLFNDRTDAEFYEDYPSMY

HLRLHLMTHTHKADPREIFLAIHHILKSRGHFLTPGAAKDFNTDKVDLEDIFPALTEAYAQVYP

DLELTFDLAKADDFKAKLLDEQATPSDTQKALVNLLLSSDGEKEIVKKRKQVLTEFAKAITGLK

TKFNLALGTEVDEADASNWQFSMGQLDDKWSNIETSMTDQGTEIFEQIQELYRARLLNGIVPAG

MSLSQAKVADYGQHKEDLELFKTYLKKLNDHELAKTIRGLYDRYINGDDAKPFLREDFVKALTK

EVTAHPNEVSEQLLNRMGQANFMLKQRTKANGAIPIQLQQRELDQIIANQSKYYDWLAAPNPVE

AHRWKMPYQLDELLNFHIPYYVGPLITPKQQAESGENVFAWMVRKDPSGNITPYNFDEKVDREA

SANTFIQRMKTTDTYLIGEDVLPKQSLLYQKYEVLNELNNVRINNECLGTDQKQRLIREVFERH

-continued

SSVTIKQVADNLVAHGDFARRPEIRGLADEKRFLSSLSTYHQLKEILHEAIDDPTKLLDIENII
TWSTVFEDHTIFETKLAEIEWLDPKKINELSGIRYRGWGQFSRKLLDGLKLGNGHTVIQELMLS
NHNLMQILADETLKETMTELNQDKLKTDDIEDVINDAYTSPSNKKALRQVLRVVEDIKHAANGQ
DPSWLFIETADGTGTAGKRTQSRQKQIQTVYANAAQELIDSAVRGELEDKIADKASFTDRLVLY
FMQGGRDIYTGAPLNIDQLSHYDIDHILPQSLIKDDSLDNRVLVNATINREKNNVFASTLFAGK
MKATWRKWHEAGLISGRKLRNLMLRPDEIDKFAKGFVARQLVETRQIIKLTEQIAAAQYPNTKI
IAVKAGLSHQLREELDFPKNRDVNHYHHAFDAFLAARIGTYLLKRYPKLAPFFTYGEFAKVDVK
KFREFNFIGALTHAKKNIIAKDTGEIVWDKERDIRELDRIYNFKRMLITHEVYFETADLFKQTI
YAAKDSKERGGSKQLIPKKQGYPTQVYGGYTQESGSYNALVRVAEADTTAYQVIKISAQNASKI
ASANLKSREKGKQLLNEIVVKQLAKRRKNWKPSANSFKIVIPRFGMGTLFQNAKYGLFMVNSDT
YYRNYQELWLSRENQKLLKKLFSIKYEKTQMNHDALQVYKAIIDQVEKFFKLYDINQFRAKLSD
AIERFEKLPINTDGNKIGKTETLRQILIGLQANGTRSNVKNLGIKTDLGLLQVGSGIKLDKDTQ
IVYQSPSGLFKRRIPLADL

SEQ ID NO: 311

MTKEYYLGLDVGTNSVGWAVTDSQYNLCKFKKKDMWGIRLFESANTAKDRRLQRGNRRRLERKK
QRIDLLQEIFSPEICKIDPTFFIRLNESRLHLEDKSNDFKYPLFIEKDYSDIEYYKEFPTIFHL
RKHLIESEEKQDIRLIYALHNIIKTRGHFLIDGDLQSAKQLRPILDTFLLSLQEEQNLSVSLS
ENQKDEYEEILKNRSIAKSEKVKKLKNLFEISDELEKEEKKAQSAVIENFCKFIVGNKGDVCKF
LRVSKEELEIDSFSFSEGKYEDDIVKNLEEKVPEKVYLFEQMKAMYDWNILVDILETEEYISFA
KVKQYEKHKTNLRLLRDIILKYCTKDEYNRMFNDEKEAGSYTAYVGKLKKNNKKYWIEKKRNPE
EFYKSLGKLLDKIEPLKEDLEVLTMMIEECKNHTLLPIQKNKDNGVIPHQVHEVELKKILENAK
KYYSFLTETDKDGYSVVQKIESIFRFRIPYYVGPLSTRHQEKGSNVWMVRKPGREDRIYPWNME
EIIDFEKSNENFITRMTNKCTYLIGEDVLPKHSLLYSKYMVLNELNNVKVRGKKLPTSLKQKVF
EDLFENKSKVTGKNLLEYLQIQDKDIQIDDLSGFDKDFKTSLKSYLDFKKQIFGEEIEKESIQN
MIEDIIKWITIYGNDKEMLKRVIRANYSNQLTEEQMKKITGFQYSGWGNFSKMFLKGISGSDVS
TGETFDIITAMWETDNNLMQILSKKFTFMDNVEDFNSGKVGKIDKITYDSTVKEMFLSPENKRA
VWQTIQVAEEIKKVMGCEPKKIFIEMARGGEKVKKRTKSRKAQLLELYAACEEDCRELIKEIED
RDERDFNSMKLFLYYTQFGKCMYSGDDIDINELIRGNSKWDRDHIYPQSKIKDDSIDNLVLVNK
TYNAKKSNELLSEDIQKKMHSFWLSLLNKKLITKSKYDRLTRKGDFTDEELSGFIARQLVETRQ
STKAIADIFKQIYSSEVVYVKSSLVSDFRKKPLNYLKSRRVNDYHHAKDAYLNIVVGNVYNKKF
TSNPIQWMKKNRDTNYSLNKVFEHDVVINGEVIWEKCTYHEDTNTYDGGTLDRIRKIVERDNIL
YTEYAYCEKGELFNATIQNKNGNSTVSLKKGLDVKKYGGYFSANTSYFSLIEFEDKKGDRARHI
IGVPIYIANMLEHSPSAFLEYCEQKGYQNVRILVEKIKKNSLLIINGYPLRIRGENEVDTSFKR
AIQLKLDQKNYELVRNIEKFLEKYVEKKGNYPIDENRDHITHEKMNQLYEVLLSKMKKFNKKGM
ADPSDRIEKSKPKFIKLEDLIDKINVINKMLNLLRCDNDTKADLSLIELPKNAGSFVVKKNTIG
KSKIILVNQSVTGLYENRREL

SEQ ID NO: 312

MARDYSVGLDIGTSSVGWAAIDNKYHLIRAKSKNLIGVRLFDSAVTAEKRRGYRTTRRRLSRRH
WRLRLLNDIFAGPLTDFGDENFLARLKYSWVHPQDQSNQAHFAAGLLFDSKEQDKDFYRKYPTI
YHLRLALMNDDQKHDLREVYLAIHHLVKYRGHFLIEGDVKADSAFDVHTFADAIQRYAESNNSD
ENLLGKIDEKKLSAALTDKHGSKSQRAETAETAFDILDLQSKKQIQAILKSVVGNQANLMAIFG

-continued

LDSSAISKDEQKNYKFSFDDADIDEKIADSEALLSDTEFEFLCDLKAAFDGLTLKMLLGDDKTV

SAAMVRRFNEHQKDWEYIKSHIRNAKNAGNGLYEKSKKFDGINAAYLALQSDNEDDRKKAKKIF

QDEISSADIPDDVKADFLKKIDDDQFLPIQRTKNNGTIPHQLHRNELEQIIEKQGIYYPFLKDT

YQENSHELNKITALINFRVPYYVGPLVEEEQKIADDGKNIPDPTNHWMVRKSNDTITPWNLSQV

VDLDKSGRRFIERLTGTDTYLIGEPTLPKNSLLYQKFDVLQELNNIRVSGRRLDIRAKQDAFEH

LFKVQKTVSATNLKDFLVQAGYISEDTQIEGLADVNGKNFNNALTTYNYLVSVLGREFVENPSN

EELLEEITELQTVFEDKKVLRRQLDQLDGLSDHNREKLSRKHYTGWGRISKKLLTTKIVQNADK

IDNQTFDVPRMNQSIIDTLYNTKMNLMEIINNAEDDFGVRAWIDKQNTTDGDEQDVYSLIDELA

GPKEIKRGIVQSFRILDDITKAVGYAPKRVYLEFARKTQESHLTNSRKNQLSTLLKNAGLSELV

TQVSQYDAAALQNDRLYLFLQQGKDMYSGEKLNLDNLSNYDIDHIIPQAYTKDNSLDNRVLVS

NITNRRKSDSSNYLPALIDKMRPFWSVLSKQGLLSKHKFANLTRTRDFDDMEKERFIARSLVET

RQIIKNVASLIDSHFGGETKAVAIRSSLTADMRRYVDIPKNRDINDYHHAFDALLFSTVGQYTE

NSGLMKKGQLSDSAGNQYNRYIKEWIHAARLNAQSQRVNPFGFVVGSMRNAAPGKLNPETGEIT

PEEENADWSIADLDYLHKVMNFRKITVTRRLKDQKGQLYDESRYPSVLHDAKSKASINFDKHKPV

DLYGGFSSAKPAYAALIKFKNKFRLVNVLRQWTYSDKNSEDYILEQIRGKYPKAEMVLSHIPYG

QLVKKDGALVTISSATELHNFEQLWLPLADYKLINTLLKTKEDNLVDILHNRLDLPEMTIESAF

YKAFDSILSFAFNRYALHQNALVKLQAHRDDFNALNYEDKQQTLERILDALHASPASSDLKKIN

LSSGFGRLFSPSHFTLADTDEFIFQSVTGLFSTQKTVAQLYQETK

SEQ ID NO: 313
MVYDVGLDIGTGSVGWVALDENGKLARAKGKNLVGVRLFDTAQTAADRRGFRTTRRRLSRRKWR

LRLLDELFSAEINEIDSSFFQRLKYSYVHPKDEENKAHYYGGYLFPTEEETKKFHRSYPTIYHL

RQELMAQPNKRFDIREIYLAIHHLVKYRGHFLSSQEKITIGSTYNPEDLANAIEVYADEKGLSW

ELNNPEQLTEIISGEAGYGLNKSMKADEALKLFEFDNNQDKVAIKTLLAGLTGNQIDFAKLFGK

DISDKDEAKLWKLKLDDEALEEKSQTILSQLTDEEIELFHAVVQAYDGFVLIGLLNGADSVSAA

MVQLYDQHREDRKLLKSLAQKAGLKHKRFSEIYEQLALATDEATIKNGISTARELVEESNLSKE

VKEDTLRRLDENEFLPKQRTKANSVIPHQLHLAELQKILQNQGQYYPFLLDTFEKEDGQDNKIE

ELLRFRIPYYVGPLVTKKDVEHAGGDADNHWVERNEGFEKSRVTPWNFDKVFNRDKAARDFIER

LTGNDTYLIGEKTLPQNSLRYQLFTVLNELNNVRVNGKKFDSKTKADLINDLFKARKTVSLSAL

KDYLKAQGKGDVTITGLADESKFNSSLSSYNDLKKTFDAEYLENEDNQETLEKIIEIQTVFEDS

KIASRELSKLPLDDDQVKKLSQTHYTGWGRLSEKLLDSKIIDERGQKVSILDKLKSTSQNFMSI

INNDKYGVQAWITEQNTGSSKLTFDEKVNELTTSPANKRGIKQSFAVLNDIKKAMKEEPRRVYL

EFAREDQTSVRSVPRYNQLKEKYQSKSLSEEAKVLKKTLDGNKNKMSDDRYFLYFQQQGKDMYT

GRPINFERLSQDYDIDHIIPQAFTKDDSLDNRVLVSRPENARKSDSFAYTDEVQKQDGSLWTSL

LKSGFINRKKYERLTKAGKYLDGQKTGFIARQLVETRQIIKNVASLIEGEYENSKAVAIRSEIT

ADMRLLVGIKKHREINSFHHAFDALLITAAGQYMQNRYPDRDSTNVYNEFDRYTNDYLKNLRQL

SSRDEVRRLKSFGFVVGTMRKGNEDWSEENTSYLRKVMMFKNILTTKKTEKDRGPLNKETIFSP

KSGKKLIPLNSKRSDTALYGGYSNVYSAYMTLVRANGKNLLIKIPISIANQIEVGNLKINDYIV

NNPAIKKFEKILISKLPLGQLVNEDGNLIYLASNEYRHNAKQLWLSTTDADKIASISENSSDEE

LLEAYDILTSENVKNRFPFFKKDIDKLSQVRDEFLDSDKRIAVIQTILRGLQIDAAYQAPVKII

SKKVSDWHKLQQSGGIKLSDNSEMIYQSATGIFETRVKISDLL

SEQ ID NO: 314
IVDYCIGLDLGTGSVGWAVVDMNHRLMKRNGKHLWGSRLFSNAETAANRRASRSIRRRYNKRRE

-continued

RIRLLRAILQDMVLEKDPTFFIRLEHTSFLDEEDKAKYLGTDYKDNYNLFIDEDFNDYTYYHKY

PTIYHLRKALCESTEKADPRLIYLALHHIVKYRGNFLYEGQKFNMDASNIEDKLSDIFTQFTSF

NNIPYEDDEKKNLEILEILKKPLSKKAKVDEVMTLIAPEKDYKSAFKELVTGIAGNKMNVTKMI

LCEPIKQGDSEIKLKFSDSNYDDQFSEVEKDLGEYVEFVDALHNVYSWVELQTIMGATHTDNAS

ISEAMVSRYNKHHDDLKLLKDCIKNNVPNKYFDMFRNDSEKSKGYYNYINRPSKAPVDEFYKYV

KKCIEKVDTPEAKQILNDIELENFLLKQNSRTNGSVPYQMQLDEMIKIIDNQAEYYPILKEKRE

QLLSILTFRIPYYFGPLNETSEHAWIKRLEGKENQRILPWNYQDIVDVDATAEGFIKRMSYCT

YFPDEEVLPKNSLIVSKYEVYNELNKIRVDDKLLEVDVKNDIYNELFMKNKTVTEKKLKNWLVN

NQCCSKDAEIKGFQKENQFSTSLTPWIDFTNIFGKIDQSNFDLIENIIYDLTVFEDKKIMKRRL

KKKYALPDDKVKQILKLKYKDWSRLSKKLLDGIVADNRFGSSVTVLDVLEMSRLNLMEIINDKD

LGYAQMIEEATSCPEDGKFTYEEVERLAGSPALKRGIWQSLQIVEEITKVMKCRPKYIYIEFER

SEEAKERTESKIKKLENVYKDLDEQTKKEYKSVLEELKGFDNTKKISSDSLFLYFTQLGKCMYS

GKKLDIDSLDKYQIDHIVPQSLVKDDSFDNRVLVVPSENQRKLDDLVVPFDIRDKMYRFWKLLF

DHELISPKKFYSLIKTEYTERDEERFINRQLVETRQITKNVTQIIEDHYSTTKVAAIRANLSHE

FRVKNHIYKNRDINDYHHAHDAYIVALIGGFMRDRYPNMHDSKAVYSEYMKMFRKNKNDQKRWK

DGFVINSMNYPYEVDGKLIWNPDLINEIKKCFYYKDCYCTTKLDQKSGQLFNLTVLSNDAHADK

GVTKAVVPVNKNRSDVHKYGGFSGLQYTIVAIEGQKKKGKKTELVKKISGVPLHLKAASINEKI

NYIEEKEGLSDVRIIKDNIPVNQMIEMDGGEYLLTSPTEYVNARQLVLNEKQCALIADIYNAIY

KQDYDNLDDILMIQLYIELTNKMKVLYPAYRGIAEKFESMNENYVVISKEEKANIIKQMLIVMH

RGPQNGNIVYDDFKISDRIGRLKTKNHNLNNIVFISQSPTGIYTKKYKL

SEQ ID NO: 315
MKSEKKYYIGLDVGTNSVGWAVTDEFYNILRAKGKDLWGVRLFEKADTAANTRIFRSGRRRNDR

KGMRLQILREIFEDEIKKVDKDFYDRLDESKFWAEDKKVSGKYSLFNDKNFSDKQYFEKFPTIF

HLRKYLMEEHGKVDIRYYFLAINQMMKRRGHFLIDGQISHVTDDKPLKEQLILLINDLLKIELE

EELMDSIFEILADVNEKRTDKKNNLKELIKGQDFNKQEGNILNSIFESIVTGKAKIKNIISDED

ILEKIKEDNKEDFVLTGDSYEENLQYFEEVLQENITLFNTLKSTYDFLILQSILKGKSTLSDAQ

VERYDEHKKDLEILKKVIKKYDEDGKLFKQVFKEDNGNGYVSYIGYYLNKNKKITAKKKISNIE

FTKYVKGILEKQCDCEDEDVKYLLGKIEQENFLLKQISSINSVIPHQIHLFELDKILENLAKNY

PSFNNKKEEFTKIEKIRKTFTFRIPYYVGPLNDYHKNNGGNAWIFRNKGEKIRPWNFEKIVDLH

KSEEEFIKRMLNQCTYLPEETVLPKSSILYSEYMVLNELNNLRINGKPLDTDVKLKLIEELFKK

KTKVTLKSIRDYMVRNNFADKEDFDNSEKNLEIASNMKSYIDFNNILEDKFDVEMVEDLIEKIT

IHTGNKKLLKKYIEETYPDLSSSQIQKIINLKYKDWGRLSRKLLDGIKGTKKETEKTDTVINFL

RNSSDNLMQIIGSQNYSFNEYIDKLRKKYIPQEISYEVVENLYVSPSVKKMIWQVIRVTEEITK

VMGYDPDKIFIEMAKSEEEKKTTISRKNKLLDLYKAIKKDERDSQYEKLLTGLNKLDDSDLRSR

KLYLYYTQMGRDMYTGEKIDLDKLFDSTHYDKDHIIPQSMKKDDSIINNLVLVNKNANQTTKGN

IYPVPSSIRNNPKIYNYWKYLMEKEFISKEKYNRLIRNTPLTNEELGGFINRQLVETRQSTKAI

KELFEKFYQKSKIIPVKASLASDLRKDMNTLKSREVNDLHHAHDAFLNIVAGDVWNREFTSNPI

NYVKENREGDKVKYSLSKDFTRPRKSKGKVIWTPEKGRKLIVDTLNKPSVLISNESHVKKGELF

NATIAGKKDYKKGKIYLPLKKDDRLQDVSKYGGYKAINGAFFFLVEHTKSKKRIRSIELFPLHL

LSKFYEDKNTVLDYAINVLQLQDPKIIIDKINYRTEIIIDNFSYLISTKSNDGSITVKPNEQMY

WRVDEISNLKKIENKYKKDAILTEEDRKIMESYIDKIYQQFKAGKYKNRRTTDTIIEKYEIIDL

```
DTLDNKQLYQLLVAFISLSYKTSNNAVDFTVIGLGTECGKPRITNLPDNTYLVYKSITGIYEKR

IRIK
                                                    SEQ ID NO: 316
MKLRGIEDDYSIGLDMGTSSVGWAVTDERGTLAHFKRKPTWGSRLFREAQTAAVARMPRGQRRR

YVRRRWRLDLLQKLFEQQMEQADPDFFIRLRQSRLLRDDRAEEHADYRWPLFNDCKFTERDYYQ

RFPTIYHVRSWLMETDEQADIRLIYLALHNIVKHRGNFLREGQSLSAKSARPDEALNHLRETLR

VWSSERGFECSIADNGSILAMLTHPDLSPSDRRKKIAPLFDVKSDDAAADKKLGIALAGAVIGL

KTEFKNIFGDFPCEDSSIYLSNDEAVDAVRSACPDDCAELFDRLCEVYSAYVLQGLLSYAPGQT

ISANMVEKYRRYGEDLALLKKLVKIYAPDQYRMFFSGATYPGTGIYDAAQARGYTKYNLGPKKS

EYKPSESMQYDDFRKAVEKLFAKTDARADERYRMMMDRFDKQQFLRRLKTSDNGSIYHQLHLEE

LKAIVENQGRFYPFLKRDADKLVSLVSFRIPYYVGPLSTRNARTDQHGENRFAWSERKPGMQDE

PIFPWNWESIIDRSKSAEKFILRMTGMCTYLQQEPVLPKSSLLYEEFCVLNELNGAHWSIDGDD

EHRFDAADREGIIEELFRRKRTVSYGDVAGWMERERNQIGAHVCGGQGEKGFESKLGSYIFFCK

DVFKVERLEQSDYPMIERIILWNTLFEDRKILSQRLKEEYGSRLSAEQIKTICKKRFTGWGRLS

EKFLTGITVQVDEDSVSIMDVLREGCPVSGKRGRAMVMMEILRDEELGFQKKVDDFNRAFFAEN

AQALGVNELPGSPAVRRSLNQSIRIVDEIASIAGKAPANIFIEVTRDEDPKKKGRRTKRRYNDL

KDALEAFKKEDPELWRELCETAPNDMDERLSLYFMQRGKCLYSGRAIDIHQLSNAGIYEVDHII

PRTYVKDDSLENKALVYREENQRKTDMLLIDPEIRRRMSGYWRMLHEAKLIGDKKFRNLLRSRI

DDKALKGFIARQLVETGQMVKLVRSLLEARYPETNIISVKASISHDLRTAAELVKCREANDFHH

AHDAFLACRVGLFIQKRHPCVYENPIGLSQVVRNYVRQQADIFKRCRTIPGSSGFIVNSFMTSG

FDKETGEIFKDDWDAEAEVEGIRRSLNFRQCFISRMPFEDHGVFWDATIYSPRAKKTAALPLKQ

GLNPSRYGSFSREQFAYFFIYKARNPRKEQTLFEFAQVPVRLSAQIRQDENALERYARELAKDQ

GLEFIRIERSKILKNQLIEIDGDRLCITGKEEVRNACELAFAQDEMRVIRMLVSEKPVSRECVI

SLFNRILLHGDQASRRLSKQLKLALLSEAFSEASDNVQRNVVLGLIAIFNGSTNMVNLSDIGGS

KFAGNVRIKYKKELASPKVNVHLIDQSVTGMFERRTKIGL
                                                    SEQ ID NO: 317
MENKQYYIGLDVGTNSVGWAVTDTSYNLLRAKGKDMWGARLFEKANTAAERRTKRTSRRRSERE

KARKAMLKELFADEINRVDPSFFIRLEESKFFLDDRSENNRQRYTLFNDATFTDKDYYEKYKTI

FHLRSALINSDEKFDVRLVFLAILNLFSHRGHFLNASLKGDGDIQGMDVFYNDLVESCEYFEIE

LPRITNIDNFEKILSQKGKSRTKILEELSEELSISKKDKSKYNLIKLISGLEASVVELYNIEDI

QDENKKIKIGFRESDYEESSLKVKEIIGDEYFDLVERAKSVHDMGLLSNIIGNSKYLCEARVEA

YENHHKDLLKIKELLKKYDKKAYNDMFRKMTDKNYSAYVGSVNSNIAKERRSVDKRKIEDLYKY

IEDTALKNIPDDNKDKIEILEKIKLGEFLKKQLTASNGVIPNQLQSRELRAILKKAENYLPFLK

EKGEKNLTVSEMIIQLFEFQIPYYVGPLDKNPKKDNKANSWAKIKQGGRILPWNFEDKVDVKGS

RKEFIEKMVRKCTYISDEHTLPKQSLLYEKFMVLNEINNIKIDGEKISVEAKQKIYNDLFVKGK

KVSQKDIKKELISLNIMDKDSVLSGTDTVCNAYLSSIGKFTGVFKEEINKQSIVDMIEDIIFLK

TVYGDEKRFVKEEIVEKYGDEIDKDKIKRILGFKFSNWGNLSKSFLELEGADVGTGEVRSIIQS

LWETNFNLMELLSSRFTYMDELEKRVKKLEKPLSEWTIEDLDDMYLSSPVKRMIWQSMKIVDEI

QTVIGYAPKRIFVEMTRSEGEKVRTKSRKDRLKELYNGIKEDSKQWVKELDSKDESYFRSKKMY

LYYLQKGRCMYSGEVIELDKLMDDNLYDIDHIYPRSFVKDDSLDNLVLVKKEINNRKQNDPITP

QIQASCQGFWKILHDQGFMSNEKYSRLTRKTQEFSDEEKLSFINRQIVETGQATKCMAQILQKS
```

```
                                                        -continued
MGEDVDVVFSKARLVSEFRHKFELFKSRLINDFHHANDAYLNIVVGNSYFVKFTRNPANFIKDA

RKNPDNPVYKYHMDRFFERDVKSKSEVAWIGQSEGNSGTIVIVKKTMAKNSPLITKKVEEGHGS

ITKETIVGVKEIKFGRNKVEKADTPKKPNLQAYRPIKTSDERLCNILRYGGRTSISISGYCLV

EYVKKRKTIRSLEAIPVYLGRKDSLSEEKLLNYFRYNLNDGGKDSVSDIRLCLPFISTNSLVKI

DGYLYYLGGKNDDRIQLYNAYQLKMKKEEVEYIRKIEKAVSMSKFDEIDREKNPVLTEEKNIEL

YNKIQDKFENTVFSKRMSLVKYNKKDLSFGDFLKNKKSKFEEIDLEKQCKVLYNIIFNLSNLKE

VDLSDIGGSKSTGKCRCKKNITNYKEFKLIQQSITGLYSCEKDLMTI

SEQ ID NO: 318
MKNLKEYYIGLDIGTASVGWAVTDESYNIPKFNGKKMWGVRLFDDAKTAEERRTQRGSRRRLNR

RKERINLLQDLFATEISKVDPNFFLRLDNSDLYREDKDEKLKSKYTLFNDKDFKDRDYHKKYPT

IHHLIMDLIEDEGKKDIRLLYLACHYLLKNRGHFIFEGQKFDTKNSFDKSINDLKIHLRDEYNI

DLEFNNEDLIEIITDTTLNKTNKKKELKNIVGDTKFLKAISAIMIGSSQKLVDLFEDGEFEETT

VKSVDFSTTAFDDKYSEYEEALGDTISLLNILKSIYDSSILENLLKDADKSKDGNKYISKAFVK

KFNKHGKDLKTLKRIIKKYLPSEYANIFRNKSINDNYVAYTKSNITSNKRTKASKFTKQEDFYK

FIKKHLDTIKETKLNSSENEDLKLIDEMLTDIEFKTFIPKLKSSDNGVIPYQLKLMELKKILDN

QSKYYDFLNESDEYGTVKDKVESIMEFRIPYYVGPLNPDSKYAWIKRENTKITPWNFKDIVDLD

SSREEFIDRLIGRCTYLKEEKVLPKASLIYNEFMVLNELNNLKLNEFLITEEMKKAIFEELFKT

KKKVTLKAVSNLLKKEFNLTGDILLSGTDGDFKQGLNSYIDFKNIIGDKVDRDDYRIKIEEIIK

LIVLYEDDKTYLKKKIKSAYKNDFTDDEIKKIAALNYKDWGRLSKRFLTGIEGVDKTTGEKGSI

IYFMREYNLNLMELMSGHYTFTEEVEKLNPVENRELCYEMVDELYLSPSVKRMLWQSLRVVDEI

KRIIGKDPKKIFIEMARAKEAKNSRKESRKNKLLEFYKFGKKAFINEIGEERYNYLLNEINSEE

ESKFRWDNLYLYYTQLGRCMYSLEPIDLADLKSNNIYDQDHIYPKSKIYDDSLENRVLVKKNLN

HEKGNQYPIPEKVLNKNAYGFWKILFDKGLIGQKKYTRLTRRTPFEERELAEFIERQIVETRQA

TKETANLLKNICQDSEIVYSKAENASRFRQEFDIIKCRTVNDLHHMHDAYLNIVVGNVYNTKFT

KNPLNFIKDKDNVRSYNLENMFKYDVVRGSYTAWIADDSEGNVKAATIKKVKRELEGKNYRFTR

MSYIGTGGLYDQNLMRKGKGQIPQKENTNKSNIEKYGGYNKASSAYFALIESDGKAGRERTLET

IPIMVYNQEKYGNTEAVDKYLKDNLELQDPKILKDKIKINSLIKLDGFLYNIKGKTGDSLSIAG

SVQLIVNKEEQKLIKKMDKFLVKKKDNKDIKVTSFDNIKEEELIKLYKTLSDKLNNGIYSNKRN

NQAKNISEALDKFKEISIEEKIDVLNQIILLFQSYNNGCNLKSIGLSAKTGVVFIPKKLNYKEC

KLINQSITGLFENEVDLLNL

SEQ ID NO: 319
MGKMYYLGLDIGTNSVGYAVTDPSYHLLKFKGEPMWGAHVFAAGNQSAERRSFRTSRRRLDRRQ

QRVKLVQEIFAPVISPIDPRFFIRLHESALWRDDVAETDKHIFFNDPTYTDKEYYSDYPTIHHL

IVDLMESSEKHDPRLVYLAVAWLVAHRGHFLNEVDKDNIGDVLSFDAFYPEFLAFLSDNGVSPW

VCESKALQATLLSRNSVNDKYALKSLIFGSQKPEDNFDANISEDGLIQLLAGKKVKVNKLFPQ

ESNDASFTLNDKEDAIEEILGTLTPDECEWIAHIRRLFDWAIMKHALKDGRTISESKVKLYEQH

HHDLTQLKYFVKTYLAKEYDDIFRNVDSETTKNYVAYSYHVKEVKGTLPKNKATQEEFCKYVLG

KVKNIECSEADKVDFDEMIQRLTDNSFMPKQVSGENRVIPYQLYYYELKTILNKAASYLPFLTQ

CGKDAISNQDKLLSIMTFRIPYFVGPLRKDNSEHAWLERKAGKIYPWNFNDKVDLDKSEEAFIR

RMTNTCTYYPGEDVLPLDSLIYEKFMILNEINNIRIDGYPISVDVKQQVFGLFEKKRRVTVKDI

QNLLLSLGALDKHGKLTGIDTTIHSNYNTYHHFKSLMERGVLTRDDVERIVERMTYSDDTKRVR

LWLNNNYGTLTADDVKHISRLRKHDFGRLSKMFLTGLKGVHKETGERASILDFMWNTNDNLMQL
```

-continued

LSECYTFSDEITKLQEAYYAKAQLSLNDFLDSMYISNAVKRPIYRTLAVVNDIRKACGTAPKRI

FIEMARDGESKKKRSVTRREQIKNLYRSIRKDFQQEVDFLEKILENKSDGQLQSDALYLYFAQL

GRDMYTGDPIKLEHIKDQSFYNIDHIYPQSMVKDDSLDNKVLVQSEINGEKSSRYPLDAAIRNK

MKPLWDAYYNHGLISLKKYQRLTRSTPFTDDEKWDFINRQLVETRQSTKALAILLKRKFPDTEI

VYSKAGLSSDFRHEFGLVKSRNINDLHHAKDAFLAIVTGNVYHERFNRRWFMVNQPYSVKTKTL

FTHSIKNGNFVAWNGEEDLGRIVKMLKQNKNTIHFTRFSFDRKEGLFDIQPLKASTGLVPRKAG

LDVVKYGGYDKSTAAYYLLVRFTLEDKKTQHKLMMIPVEGLYKARIDHDKEFLTDYAQTTISEI

LQKDKQKVINIMFPMGTRHIKLNSMISIDGFYLSIGGKSSKGKSVLCHAMVPLIVPHKIECYIK

AMESFARKFKENNKLRIVEKFDKITVEDNLNLYELFLQKLQHNPYNKFFSTQFDVLTNGRSTFT

KLSPEEQVQTLLNILSIFKTCRSSGCDLKSINGSAQAARIMISADLTGLSKKYSDIRLVEQSAS

GLFVSKSQNLLEYL

SEQ ID NO: 320
MTKKEQPYNIGLDIGTSSVGWAVTNDNYDLLNIKKKNLWGVRLFEEAQTAKETRLNRSTRRRYR

RRKNRINWLNEIFSEELAKTDPSFLIRLQNSWVSKKDPDRKRDKYNLFIDGPYTDKEYYREFPT

IFHLRKELILNKDKADIRLIYLALHNILKYRGNFTYEHQKFNISNLNNNLSKELIELNQQLIKY

DISFPDDCDWNHISDILIGRGNATQKSSNILKDFTLDKETKKLLKEVINLILGNVAHLNTIFKT

SLTKDEEKLNFSGKDIESKLDDLDSILDDDQFTVLDAANRIYSTITLNEILNGESYFSMAKVNQ

YENHAIDLCKLRDMWHTTKNEEAVEQSRQAYDDYINKPKYGTKELYTSLKKFLKVALPTNLAKE

AEEKISKGTYLVKPRNSENGVVPYQLNKIEMEKIIDNQSQYYPFLKENKEKLLSILSFRIPYYV

GPLQSAEKNPFAWMERKSNGHARPWNFDEIVDREKSSNKFIRRMTVTDSYLVGEPVLPKNSLIY

QRYEVLNELNNIRITENLKTNPIGSRLTVETKQRIYNELFKKYKKVTVKKLTKWLIAQGYYKNP

ILIGLSQKDEFNSTLTTYLDMKKIFGSSFMEDNKNYDQIEELIEWLTIFEDKQILNEKLHSSKY

SYTPDQIKKISNMRYKGWGRLSKKILMDITTETNTPQLLQLSNYSILDLMWATNNNFISIMSND

KYDFKNYIENHNLNKNEDQNISDLVNDIHVSPALKRGITQSIKIVQEIVKFMGHAPKHIFIEVT

RETKKSEITTSREKRIKRLQSKLLNKANDFKPQLREYLVPNKKIQEELKKHKNDLSSERIMLYF

LQNGKSLYSEESLNINKLSDYQVDHILPRTYIPDDSLENKALVLAKENQRKADDLLLNSNVIDR

NLERWTYMLNNNMIGLKKFKNLTRRVITDKDKLGFIHRQLVQTSQMVKGVANILDNMYKNQGTT

CIQARANLSTAFRKALSGQDDTYHFKHPELVKNRNVNDFHHAQDAYLASFLGTYRLRRFPTNEM

LLMNGEYNKFYGQVKELYSKKKKLPDSRKNGFIISPLVNGTTQYDRNTGEIIWNVGFRDKILKI

FNYHQCNVTRKTEIKTGQFYDQTIYSPKNPKYKKLIAQKKDMDPNIYGGFSGDNKSSITIVKID

NNKIKPVAIPIRLINDLKDKKTLQNWLEENVKHKKSIQIIKNNVPIGQIIYSKKVGLLSLNSDR

EVANRQQLILPPEHSALLRLLQIPDEDLDQILAFYDKNILVEILQELITKMKKFYPFYKGEREF

LIANIENFNQATTSEKVNSLEELITLLHANSTSAHLIFNNIEKKAFGRKTHGLTLNNTDFIYQS

VTGLYETRIHIE

SEQ ID NO: 321
MTKFNKNYSIGLDIGVSSVGYAVVTEDYRVPAFKFKVLGNTEKEKIKKNLIGSTTFVSAQPAKG

TRVFRVNRRRIDRRNHRITYLRDIFQKEIEKVDKNFYRRLDESFRVLGDKSEDLQIKQPFFGDK

ELETAYHKKYPTIYHLRKHLADADKNSPVADIREVYMAISHILKYRGHFLTLDKINPNNINMQN

SWIDFIESCQEVFDLEISDESKNIADIFKSSENRQEKVKKILPYFQQELLKKDKSIFKQLLQLL

FGLKTKFKDCFELEEEPDLNFSKENYDENLENFLGSLEEDFSDVFAKLKVLRDTILLSGMLTYT

GATHARFSATMVERYEEHRKDLQRFKFFIKQNLSEQDYLDIFGRKTQNGFDVDKETKGYVGYIT

-continued

NKMVLTNPQKQKTIQQNFYDYISGKITGIEGAEYFLNKISDGTFLRKLRTSDNGAIPNQIHAYE

LEKIIERQGKDYPFLLENKDKLLSILTFKIPYYVGPLAKGSNSRFAWIKRATSSDILDDNDEDT

RNGKIRPWNYQKLINMDETRDAFITNLIGNDIILLNEKVLPKRSLIYEEVMLQNELTRVKYKDK

YGKAHFFDSELRQNIINGLFKNNSKRVNAKSLIKYLSDNHKDLNAIEIVSGVEKGKSFNSTLKT

YNDLKTIFSEELLDSEIYQKELEEIIKVITVFDDKKSIKNYLTKFFGHLEILDEEKINQLSKLR

YSGWGRYSAKLLLDIRDEDTGFNLLQFLRNDEENRNLTKLISDNTLSFEPKIKDIQSKSTIEDD

IFDEIKKLAGSPAIKRGILNSIKIVDELVQIIGYPPHNIVIEMARENMTTEEGQKKAKTRKTKL

ESALKNIENSLLENGKVPHSDEQLQSEKLYLYYLQNGKDMYTLDKTGSPAPLYLDQLDQYEVDH

IIPYSFLPIDSIDNKVLTHRENNQQKLNNIPDKETVANMKPFWEKLYNAKLISQTKYQRLTTSE

RTPDGVLTESMKAGFIERQLVETRQIIKHVARILDNRFSDTKIITLKSQLITNFRNTFHIAKIR

ELNDYHHAHDAYLAVVVGQTLLKVYPKLAPELIYGHHAHFNRHEENKATLRKHLYSNIMRFFNN

PDSKVSKDIWDCNRDLPIIKDVIYNSQINFVKRTMIKKGAFYNQNPVGKFNKQLAANNRYPLKT

KALCLDTSIYGGYGPMNSALSIIIAERFNEKKGKIETVKEFHDIFIIDYEKFNNNPFQFLNDT

SENGFLKKNNINRVLGFYRIPKYSLMQKIDGTRMLFESKSNLHKATQFKLTKTQNELFFHMKRL

LTKSNLMDLKSKSAIKESQNFILKHKEEFDNISNQLSAFSQKMLGNTTSLKNLIKGYNERKIKE

IDIRDETIKYFYDNFIKMFSFVKSGAPKDINDFFDNKCTVARMRPKPDKKLLNATLIHQSITGL

YETRIDLSKLGED

SEQ ID NO: 322
MKQEYFLGLDMGTGSLGWAVTDSTYQVMRKHGKALWGTRLFESASTAEERRMFRTARRRLDRRN

WRIQVLQEIFSEEISKVDPGFFLRMKESKYYPEDKRDAEGNCPELPYALFVDDNYTDKNYHKDY

PTIYHLRKMLMETTEIPDIRLVYLVLHHMMKHRGHFLLSGDISQIKEFKSTFEQLIQNIQDEEL

EWHISLDDAAIQFVEHVLKDRNLTRSTKKSRLIKQLNAKSACEKAILNLLSGGTVKLSDIFNNK

ELDESERPKVSFADSGYDDYIGIVEAELAEQYYIIASAKAVYDWSVLVEILGNSVSISEAKIKV

YQKHQADLKTLKKIVRQYMTKEDYKRVFVDTEEKLNNYSAYIGMTKKNGKKVDLKSKQCTQADF

YDFLKKNVIKVIDHKEITQEIESEIEKENFLPKQVTKDNGVIPYQVHDYELKKILDNLGTRMPF

IKENAEKIQQLFEFRIPYYVGPLNRVDDGKDGKFTWSVRKSDARIYPWNFTEVIDVEASAEKFI

RRMTNKCTYLVGEDVLPKDSLVYSKFMVLNELNNLRLNGEKISVELKQRIYEELFCKYRKVTRK

KLERYLVIEGIAKKGVEITGIDGDFKASLTAYHDFKERLTDVQLSQRAKEAIVLNVVLFGDDKK

LLKQRLSKMYPNLTTGQLKGICSLSYQGWGRLSKTFLEEITVPAPGTGEVWNIMTALWQTNDNL

MQLLSRNYGFTNEVEEFNTLKKETDLSYKTVDELYVSPAVKRQIWQTLKVVKEIQKVMGNAPKR

VFVEMAREKQEGKRSDSRKKQLVELYRACKNEERDWITELNAQSDQQLRSDKLFLYYIQKGRCM

YSGETIQLDELWDNTKYDIDHIYPQSKTMDDSLNNRVLVKKNYNAIKSDTYPLSLDIQKKMMSF

WKMLQQQGFITKEKYVRLVRSDELSADELAGFIERQIVETRQSTKAVATILKEALPDTEIVYVK

AGNVSNFRQTYELLKVREMNDLHHAKDAYLNIVVGNAYFVKFTKNAAWFIRNNPGRSYNLKRMF

EFDIERSGEIAWKAGNKGSIVTVKKVMQKNNILVTRKAYEVKGGLFDQQIMKKGKGQVPIKGND

ERLADIEKYGGYNKAAGTYFMLVKSLDKKGKEIRTIEFVPLYLKNQIEINHESAIQYLAQERGL

NSPEILLSKIKIDTLFKVDGFKMWLSGRTGNQLIFKGANQLILSHQEAAILKGVVKYVNRKNEN

KDAKLSERDGMTEEKLLQLYDTFLDKLSNTVYSIRLSAQIKTLTEKRAKFIGLSNEDQCIVLNE

ILHMFQCQSGSANLKLIGGPGSAGILVMNNNITACKQISVINQSPTGIYEKEIDLIKL

SEQ ID NO: 323
MKKPYSIGLDIGTNSVGWAVVTDDYKVPAKKMKVLGNTDKSHIEKNLLGALLFDSGNTAEDRRL

KRTARRRYTRRRNRILYLQEIFSEEMGKVDDSFFHRLEDSFLVTEDKRGERHPIFGNLEEEVKY

-continued

HENFPTIYHLRQYLADNPEKVDLRLVYLALAHIIKFRGHFLIEGKFDTRNNDVQRLFQEFLAVY

DNTFENSSLQEQNVQVEEILTDKISKSAKKDRVLKLFPNEKSNGRFAEFLKLIVGNQADFKKHF

ELEEKAPLQFSKDTYEEELEVLLAQIGDNYAELFLSAKKLYDSILLSGILTVTDVGTKAPLSAS

MIQRYNEHQMDLAQLKQFIRQKLSDKYNEVFSDVSKDGYAGYIDGKTNQEAFYKYLKGLLNKIE

GSGYFLDKIEREDFLRKQRTFDNGSIPHQIHLQEMRAIIRRQAEFYPFLADNQDRIEKLLTFRI

PYYVGPLARGKSDFAWLSRKSADKITPWNFDEIVDKESSAEAFINRMTNYDLYLPNQKVLPKHS

LLYEKFTVYNELTKVKYKTEQGKTAFFDANMKQEIFDGVFKVYRKVTKDKLMDFLEKEFDEFRI

VDLTGLDKENKVFNASYGTYHDLCKILDKDFLDNSKNEKILEDIVLTLTLFEDREMIRKRLENY

SDLLTKEQVKKLERRHYTGWGRLSAELIHGIRNKESRKTILDYLIDDGNSNRNFMQLINDDALS

FKEEIAKAQVIGETDNLNQVVSDIAGSPAIKKGILQSLKIVDELVKIMGHQPENIVVEMARENQ

FTNQGRRNSQQRLKGLTDSIKEFGSQILKEHPVENSQLQNDRLFLYYLQNGRDMYTGEELDIDY

LSQYDIDHIIPQAFIKDNSIDNRVLTSSKENRGKSDDVPSKDVVRKMKSYWSKLLSAKLITQRK

FDNLTKAERGGLTDDDKAGFIKRQLVETRQITKHVARILDERFNTETDENNKKIRQVKIVTLKS

NLVSNFRKEFELYKVREINDYHHAHDAYLNAVIGKALLGVYPQLEPEFVYGDYPHFHGHKENKA

TAKKFFYSNIMNFFKKDDVRTDKNGEIIWKKDEHISNIKKVLSYPQVNIVKKVEEQTGGFSKES

ILPKGNSDKLIPRKTKKFYWDTKKYGGFDSPIVAYSILVIADIEKGKSKKLKTVKALVGVTIME

KMTFERDPVAFLERKGYRNVQEENIIKLPKYSLFKLENGRKRLLASARELQKGNEIVLPNHLGT

LLYHAKNIHKVDEPKHLDYVDKHKDEFKELLDVVSNFSKKYTLAEGNLEKIKELYAQNNGEDLK

ELASSFINLLTFTAIGAPATFKFFDKNIDRKRYTSTTEILNATLIHQSITGLYETRIDLNKLGG

D

SEQ ID NO: 324

MDKKYSIGLDIGTNSVGWAVITDEYKVPSKKFKVLGNTDRHSIKKNLIGALLFDSGETAEATRL

KRTARRRYTRRKNRICYLQEIFSNEMAKVDDSFFHRLEESFLVEEDKKHERHPIFGNIVDEAY

HEKYPTIYHLRKKLVDSTDKADLRLIYLALAHMIKFRGHFLIEGDLNPDNSDVDKLFIQLVQTY

NQLFEENPINASGVDAKAILSARLSKSRRLENLIAQLPGEKKNGLFGNLIALSLGLTPNFKSNF

DLAEDAKLQLSKDTYDDDLDNLLAQIGDQYADLFLAAKNLSDAILLSDILRVNTEITKAPLSAS

MIKRYDEHHQDLTLLKALVRQQLPEKYKEIFFDQSKNGYAGYIDGGASQEEFYKFIKPILEKMD

GTEELLVKLNREDLLRKQRTFDNGSIPHQIHLGELHAILRRQEDFYPFLKDNREKIEKILTFRI

PYYVGPLARGNSRFAWMTRKSEETITPWNFEEVVDKGASAQSFIERMTNFDKNLPNEKVLPKHS

LLYEYFTVYNELTKVKYVTEGMRKPAFLSGEQKKAIVDLLFKTNRKVTVKQLKEDYFKKIECFD

SVEISGVEDRFNASLGTYHDLLKIIKDKDFLDNEENEDILEDIVLTLTLFEDREMIEERLKTYA

HLFDDKVMKQLKRRRYTGWGRLSRKLINGIRDKQSGKTILDFLKSDGFANRNFMQLIHDDSLTF

KEDIQKAQVSGQGDSLHEHIANLAGSPAIKKGILQTVKVVDELVKVMGRHKPENIVIEMARENQ

TTQKGQKNSRERMKRIEEGIKELGSQILKEHPVENTQLQNEKLYLYYLQNGRDMYVDQELDINR

LSDYDVDHIVPQSFLKDDSIDNKVLTRSDKNRGKSDNVPSEEVVKKMKNYWRQLLNAKLITQRK

FDNLTKAERGGLSELDKAGFIKRQLVETRQITKHVAQILDSRMNTKYDENDKLIREVKVITLKS

KLVSDFRKDFQFYKVREINNYHHAHDAYLNAVVGTALIKKYPKLESEFVYGDYKVYDVRKMIAK

SEQEIGKATAKYFFYSNIMNFFKTEITLANGEIRKRPLIETNGETGEIVWDKGRDFATVRKVLS

MPQVNIVKKTEVQTGGFSKESILPKRNSDKLIARKKDWDPKKYGGFDSPTVAYSVLVVAKVEKG

KSKKLKSVKELLGITIMERSSFEKNPIDFLEAKGYKEVKKDLIIKLPKYSLFELENGRKRMLAS

AGELQKGNELALPSKYVNFLYLASHYEKLKGSPEDNEQKQLFVEQHKHYLDEIIEQISEFSKRV

ILADANLDKVLSAYNKHRDKPIREQAENIIHLFTLTNLGAPAAFKYFDTTIDRKRYTSTKEVLD

ATLIHQSITGLYETRIDLSQLGGD

SEQ ID NO: 325

MTKPYSIGLDIGTNSVGWAVTTDNYKVPSKKMKVLGNTSKKYIKKNLLGVLLFDSGITAEGRRL

KRTARRRYTRRRNRILYLQEIFSTEMATLDDAFFQRLDDSFLVPDDKRDSKYPIFGNLVEEKAY

HDEFPTIYHLRKYLADSTKKADLRLVYLALAHMIKYRGHFLIEGEFNSKNNDIQKNFQDFLDTY

NAIFESDLSLENSKQLEEIVKDKISKLEKKDRILKLFPGEKNSGIFSEFLKLIVGNQADFRKCF

NLDEKASLHFSKESYDEDLETLLGYIGDDYSDVFLKAKKLYDAILLSGFLTVTDNETEAPLSSA

MIKRYNEHKEDLALLKEYIRNISLKTYNEVFKDDTKNGYAGYIDGKTNQEDFYVYLKKLLAEFE

GADYFLEKIDREDFLRKQRTFDNGSIPYQIHLQEMRAILDKQAKFYPFLAKNKERIEKILTFRI

PYYVGPLARGNSDFAWSIRKRNEKITPWNFEDVIDKESSAEAFINRMTSFDLYLPEEKVLPKHS

LLYETFNVYNELTKVRFIAESMRDYQFLDSKQKKDIVRLYFKDKRKVTDKDIIEYLHAIYGYDG

IELKGIEKQFNSSLSTYHDLLNIINDKEFLDDSSNEAIIEEIIHTLTIFEDREMIKQRLSKFEN

IFDKSVLKKLSRRHYTGWGKLSAKLINGIRDEKSGNTILDYLIDDGISNRNFMQLIHDDALSFK

KKIQKAQIIGDEDKGNIKEVVKSLPGSPAIKKGILQSIKIVDELVKVMGGRKPESIVVEMAREN

QYTNQGKSNSQQRLKRLEKSLKELGSKILKENIPAKLSKIDNNALQNDRLYLYYLQNGKDMYTG

DDLDIDRLSNYDIDHIIPQAFLKDNSIDNKVLVSSASNRGKSDDVPSLEVVKKRKTFWYQLLKS

KLISQRKFDNLTKAERGGLSPEDKAGFIQRQLVETRQITKHVARLLDEKFNNKKDENNRAVRTV

KIITLKSTLVSQFRKDFELYKVREINDFHHAHDAYLNAVVASALLKKYPKLEPEFVYGDYPKYN

SFRERKSATEKVYFYSNIMNIFKKSISLADGRVIERPLIEVNEETGESVWNKESDLATVRRVLS

YPQVNVVKKVEEQNHGLDRGKPKGLFNANLSSKPKPNSNENLVGAKEYLDPKKYGGYAGISNSF

TVLVKGTIEKGAKKKITNVLEFQGISILDRINYRKDKLNFLLEKGYKDIELIIELPKYSLFELS

DGSRRMLASILSTNNKRGEIHKGNQIFLSQKFVKLLYHAKRISNTINENHRKYVENHKKEFEEL

FYYILEFNENYVGAKKNGKLLNSAFQSWQNHSIDELCSSFIGPTGSERKGLFELTSRGSAADFE

FLGVKIPRYRDYTPSSLLKDATLIHQSVTGLYETRIDLAKLGEG

SEQ ID NO: 326

MKKQKFSDYYLGFDIGTNSVGWCVTDLDYNVLRFNKKDMWGSRLFDEAKTAAERRVQRNSRRRL

KRRKWRLNLLEEIFSDEIMKIDSNFFRRLKESSLWLEDKNSKEKFTLFNDDNYKDYDFYKQYPT

IFHLRDELIKNPEKKDIRLIYLALHSIFKSRGHFLFEGQNLKEIKNFETLYNNLISFLEDNGIN

KSIDKDNIEKLEKIICDSGKGLKDKEKEFKGIFNSDKQLVAIFKLSVGSSVSLNDLFDTDEYKK

EEVEKEKISFREQIYEDDKPIYYSILGEKIELLDIAKSFYDFMVLNNILSDSNYISEAKVKLYE

EHKKDLKNLKYIIRKYNKENYDKLFKDKNENNYPAYIGLNKEKDKKEVVEKSRLKIDDLIKVIK

GYLPKPERIEEKDKTIFNEILNKIELKTILPKQRISDNGTLPYQIHEVELEKILENQSKYYDFL

NYEENGVSTKDKLLKTFKFRIPYYVGPLNSYHKDKGGNSWIVRKEEGKILPWNFEQKVDIEKSA

EEFIKRMTNKCTYLNGEDVIPKDSFLYSEYIILNELNKVQVNDEFLNEENKRKIIDELFKENKK

VSEKKFKEYLLVNQIANRTVELKGIKDSFNSNYVSYIKFKDIFGEKLNLDIYKEISEKSILWKC

LYGDDKKIFEKKIKNEYGDILNKDEIKKINSFKFNTWGRLSEKLLTGIEFINLETGECYSSVME

ALRRTNYNLMELLSSKFTLQESIDNENKEMNEVSYRDLIEESYVSPSLKRAILQTLKIYEEIKK

ITGRVPKKVFIEMARGGDESMKNKKIPARQEQLKKLYDSCGNDIANFSIDIKEMKNSLSSYDNN

SLRQKKLYLYYLQFGKCMYTGREIDLDRLLQNNDTYDIDHIYPRSKVIKDDSFDNLVLVLKNEN

AEKSNEYPVKKEIQEKMKSFWRFLKEKNFISDEKYKRLTGKDDFELRGFMARQLVNVRQTTKEV

-continued

GKILQQIEPEIKIVYSKAEIASSFREMFDFIKVRELNDTHHAKDAYLNIVAGNVYNTKFTEKPY

RYLQEIKENYDVKKIYNYDIKNAWDKENSLEIVKKNMEKNTVNITRFIKEEKGELFNLNPIKKG

ETSNEIISIKPKLYDGKDNKLNEKYGYYTSLKAAYFIYVEHEKKNKKVKTFERITRIDSTLIKN

EKNLIKYLVSQKKLLNPKIIKKIYKEQTLIIDSYPYTFTGVDSNKKVELKNKKQLYLEKKYEQI

LKNALKFVEDNQGETEENYKFIYLKKRNNNEKNETIDAVKERYNIEFNEMYDKFLEKLSSKDYK

NYINNKLYTNFLNSKEKFKKLKLWEKSLILREFLKIFNKNTYGKYEIKDSQTKEKLFSFPEDTG

RIRLGQSSLGNNKELLEESVTGLFVKKIKL

SEQ ID NO: 327
MKNYTIGLDIGVASVGWVCIDENYKILNYNNRHAFGVHEFESAESAAGRRLKRGMRRRYNRRKK

RLQLLQSLFDSYITDSGFFSKTDSQHFWKNNNEFENRSLTEVLSSLRISSRKYPTIYHLRSDLI

ESNKKMDLRLVYLALHNLVKYRGHFLQEGNWSEAASAEGMDDQLLELVTRYAELENLSPLDLSE

SQWKAAETLLLNRNLTKTDQSKELTAMFGKEYEPFCKLVAGLGVSLHQLFPSSEQALAYKETKT

KVQLSNENVEEVMELLLEEESALLEAVQPFYQQVVLYELLKGETYVAKAKVSAFKQYQKDMASL

KNLLDKTFGEKVYRSYFISDKNSQREYQKSHKVEVLCKLDQFNKEAKFAETFYKDLKKLLEDKS

KTSIGTTEKDEMLRIIKAIDSNQFLQKQKGIQNAAIPHQNSLYEAEKILRNQQAHYPFITTEWI

EKVKQILAFRIPYYIGPLVKDTTQSPFSWVERKGDAPITPWNFDEQIDKAASAEAFISRMRKTC

TYLKGQEVLPKSSLTYERFEVLNELNGIQLRTTGAESDFRHRLSYEMKCWIIDNVFKQYKTVST

KRLLQELKKSPYADELYDEHTGEIKEVFGTQKENAFATSLSGYISMKSILGAVVDDNPAMTEEL

IYWIAVFEDREILHLKIQEKYPSITDVQRQKLALVKLPGWGRFSRLLIDGLPLDEQGQSVLDHM

EQYSSVFMEVLKNKGFGLEKKIQKMNQHQVDGTKKIRYEDIEELAGSPALKRGIWRSVKIVEEL

VSIFGEPANIVLEVAREDGEKKRTKSRKDQWEELTKTTLKNDPDLKSFIGEIKSQGDQRFNEQR

FWLYVTQQGKCLYTGKALDIQNLSMYEVDHILPQNFVKDDSLDNLALVMPEANQRKNQVGQNKM

PLEIIEANQQYAMRTLWERLHELKLISSGKLGRLKKPSFDEVDKDKFIARQLVETRQIIKHVRD

LLDERFSKSDIHLVKAGIVSKFRRFSEIPKIRDYNNKHHAMDALFAAALIQSILGKYGKNFLAF

DLSKKDRQKQWRSVKGSNKEFFLFKNFGNLRLQSPVTGEEVSGVEYMKHVYFELPWQTTKMTQT

GDGMFYKESIFSPKVKQAKYVSPKTEKFVHDEVKNHSICLVEFTFMKKEKEVQETKFIDLKVIE

HHQFLKEPESQLAKFLAEKETNSPIIHARIIRTIPKYQKIWIEHFPYYFISTRELHNARQFEIS

YELMEKVKQLSERSSVEELKIVFGLLIDQMNDNYPIYTKSSIQDRVQKFVDTQLYDFKSFEIGF

EELKKAVAANAQRSDTFGSRISKKPKPEEVAIGYESITGLKYRKPRSVVGTKR

SEQ ID NO: 328
MKKEIKDYFLGLDVGTGSVGWAVTDTDYKLLKANRKDLWGMRCFETAETAEVRRLHRGARRIE

RRKKRIKLLQELFSQEIAKTDEGFFQRMKESPFYAEDKTILQENTLFNDKDFADKTYHKAYPTI

NHLIKAWIENKVKPDPRLLYLACHNIIKKRGHFLFEGDFDSENQFDTSIQALFEYLREDMEVDI

DADSQKVKEILKDSSLKNSEKQSRLNKILGLKPSDKQKKAITNLISGNKINFADLYDNPDLKDA

EKNSISFSKDDFDALSDDLASILGDSFELLLKAKAVYNCSVLSKVIGDEQYLSFAKVKIYEKHK

TDLTKLKNVIKKHFPKDYKKVFGYNKNEKNNNNYSGYVGVCKTKSKKLIINNSVNQEDFYKFLK

TILSAKSEIKEVNDILTEIETGTFLPKQISKSNAEIPYQLRKMELEKILSNAEKHFSFLKQKDE

KGLSHSEKIIMLLTFKIPYYIGPINDNHKKFFPDRCWVVKKEKSPSGKTTPWNFFDHIDKEKTA

EAFITSRTNFCTYLVGESVLPKSSLLYSEYTVLNEINNLQIIIDGKNICDIKLKQKIYEDLFKK

YKKITQKQISTFIKHEGICNKTDEVIILGIDKECTSSLKSYIELKNIFGKQVDEISTKNMLEEI

IRWATIYDEGEGKTILKTKIKAEYGKYCSDEQIKKILNLKFSGWGRLSRKFLETVTSEMPGFSE

PVNIITAMRETQNNLMELLSSEFTFTENIKKINSGFEDAEKQFSYDGLVKPLFLSPSVKKMLWQ

-continued

```
TLKLVKEISHITQAPPKKIFIEMAKGAELEPARTKTRLKILQDLYNNCKNDADAFSSEIKDLSG

KIENEDNLRLRSDKLYLYYTQLGKCMYCGKPIEIGHVFDTSNYDIDHIYPQSKIKDDSISNRVL

VCSSCNKNKEDKYPLKSEIQSKQRGFWNFLQRNNFISLEKLNRLTRATPISDDETAKFIARQLV

ETRQATKVAAKVLEKMFPETKIVYSKAETVSMFRNKFDIVKCREINDFHHAHDAYLNIVVGNVY

NTKFTNNPWNFIKEKRDNPKIADTYNYYKVFDYDVKRNNITAWEKGKTIITVKDMLKRNTPIYT

RQAACKKGELFNQTIMKKGLGQHPLKKEGPFSNISKYGGYNKVSAAYYTLIEYEEKGNKIRSLE

TIPLYLVKDIQKDQDVLKSYLTDLLGKKEFKILVPKIKINSLLKINGFPCHITGKTNDSFLLRP

AVQFCCSNNEVLYFKKIIRFSEIRSQREKIGKTISPYEDLSFRSYIKENLWKKTKNDEIGEKEF

YDLLQKKNLEIYDMLLTKHKDTIYKKRPNSATIDILVKGKEKFKSLIIENQFEVILEILKLFSA

TRNVSDLQHIGGSKYSGVAKIGNKISSLDNCILIYQSITGIFEKRIDLLKV

SEQ ID NO: 329
MEGQMKNNGNNLQQGNYYLGLDVGTSSVGWAVTDTDYNVLKFRGKSMWGARLFDEASTAEERRT

HRGNRRRLARRKYRLLLLEQLFEKEIRKIDDNFFVRLHESNLWADDKSKPSKFLLFNDTNFTDK

DYLKKYPTIYHLRSDLIHNSTEHDIRLVFLALHHLIKYRGHFIYDNSANGDVKTLDEAVSDFEE

YLNENDIEFNIENKKEFINVLSDKHLTKKEKKISLKKLYGDITDSENINISVLIEMLSGSSISL

SNLFKDIEFDGKQNLSLDSDIEETLNDVVDILGDNIDLLIHAKEVYDIAVLTSSLGKHKYLCDA

KVELFEKNKKDLMILKKYIKKNHPEDYKKIFSSPTEKKNYAAYSQTNSKNVCSQEEFCLFIKPY

IRDMVKSENEDEVRIAKEVEDKSFLTKLKGTNNSVVPYQIHERELNQILKNIVAYLPFMNDEQE

DISVVDKIKLIFKFKIPYYVGPLNTKSTRSWVYRSDEKIYPWNFSNVIDLDKTAHEFMNRLIGR

CTYTNDPVLPMDSLLYSKYNVLNEINPIKVNGKAIPVEVKQAIYTDLFENSKKKVTRKSIYIYL

LKNGYIEKEDIVSGIDIEIKSKLKSHHDFTQIVQENKCTPEEIERIIKGILVYSDDKSMLRRWL

KNNIKGLSENDVKYLAKLNYKEWGRLSKTLLTDIYTINPEDGEACSILDIMWNTNATLMEILSN

EKYQFKQNIENYKAENYDEKQNLHEELDDMYISPAARRSIWQALRIVDEIVDIKKSAPKKIFIE

MAREKKSAMKKKRTESRKDTLLELYKSCKSQADGFYDEELFEKLSNESNSRLRRDQLYLYYTQM

GRSMYTGKRIDFDKLINDKNTYDIDHIYPRSKIKDDSITNRVLVEKDINGEKTDIYPISEDIRQ

KMQPFWKILKEKGLINEEKYKRLTRNYELTDEELSSFVARQLVETQQSTKALATLLKKEYPSAK

IVYSKAGNVSEFRNRKDKELPKFREINDLHHAKDAYLNIVVGNVYDTKFTEKFFNNIRNENYSL

KRVFDFSVPGAWDAKGSTFNTIKKYMAKNNPIIAFAPYEVKGELFDQQIVPKGKGQFPIKQGKD

IEKYGGYNKLSSAFLFAVEYKGKKARERSLETVYIKDVELYLQDPIKYCESVLGLKEPQIIKPK

ILMGSLFSINNKKLVVTGRSGKQYVCHHIYQLSINDEDSQYLKNIAKYLQEEPDGNIERQNILN

ITSVNNIKLFDVLCTKFNSNTYEIILNSLKNDVNEGREKFSELDILEQCNILLQLLKAFKCNRE

SSNLEKLNNKKQAGVIVIPHLFTKCSVFKVIHQSITGLFEKEMDLLK

SEQ ID NO: 330
MGRKPYILSLDIGTGSVGYACMDKGFNVLKYHDKDALGVYLFDGALTAQERRQFRTSRRRKNRR

IKRLGLLQELLAPLVQNPNFYQFRQFAWKNDNMDFKNKSLSEVLSFLGYESKKYPTIYHLQEA

LLLKDEKFDPELIYMALYHLVKYRGHFLFDHLKIENLTNNDNMHDFVELIETYENLNNIKLNLD

YEKTKVIYEILKDNEMTKNDRAKRVKNMEKKLEQFSIMLLGLKFNEGKLFNHADNAEELKGANQ

SHTFADNYEENLTPFLTVEQSEFIERANKIYLSLTLQDILKGKKSMAMSKVAAYDKFRNELKQV

KDIVYKADSTRTQFKKIFVSSKKSLKQYDATPNDQTFSSLCLFDQYLIRPKKQYSLLIKELKKI

IPQDSELYFEAENDTLLKVLNTTDNASIPMQINLYEAETILRNQQKYHAEITDEMIEKVLSLIQ

FRIPYYVGPLVNDHTASKFGWMERKSNESIKPWNFDEVVDRSKSATQFIRRMTNKCSYLINEDV
```

```
LPKNSLLYQEMEVLNELNATQIRLQTDPKNRKYRMMPQIKLFAVEHIFKKYKTVSHSKFLEIML

NSNHRENFMNHGEKLSIFGTQDDKKFASKLSSYQDMTKIFGDIEGKRAQIEEIIQWITIFEDKK

ILVQKLKECYPELTSKQINQLKKLNYSGWGRLSEKLLTHAYQGHSIIELLRHSDENFMEILTND

VYGFQNFIKEENQVQSNKIQHQDIANLTTSPALKKGIWSTIKLVRELTSIFGEPEKIIMEFATE

DQQKGKKQKSRKQLWDDNIKKNKLKSVDEYKYIIDVANKLNNEQLQQEKLWLYLSQNGKCMYSG

QSIDLDALLSPNATKHYEVDHIFPRSFIKDDSIDNKVLVIKKMNQTKGDQVPLQFIQQPYERIA

YWKSLNKAGLISDSKLHKLMKPEFTAMDKEGFIQRQLVETRQISVHVRDFLKEEYPNTKVIPMK

AKMVSEFRKKFDIPKIRQMNDAHHAIDAYLNGVVYHGAQLAYPNVDLFDFNFKWEKVREKWKAL

GEFNTKQKSRELFFFKKLEKMEVSQGERLISKIKLDMNHFKINYSRKLANIPQQFYNQTAVSPK

TAELKYESNKSNEVVYKGLTPYQTYVVAIKSVNKKGKEKMEYQMIDHYVFDFYKFQNGNEKELA

LYLAQRENKDEVLDAQIVYSLNKGDLLYINNHPCYFVSRKEVINAKQFELTVEQQLSLYNVMNN

KETNVEKLLIEYDFIAEKVINEYHHYLNSKLKEKRVRTFFSESNQTHEDFIKALDELFKVVTAS

ATRSDKIGSRKNSMTHRAFLGKGKDVKIAYTSISGLKTTKPKSLFKLAESRNEL

SEQ ID NO: 331
MAKILGLDLGTNSIGWAVVERENIDFSLIDKGVRIFSEGVKSEKGIESSRAAERTGYRSARKIK

YRRKLRKYETLKVLSLNRMCPLSIEEVEEWKKSGFKDYPLNPEFLKWLSTDEESNVNPYFFRDR

ASKHKVSLFELGRAFYHIAQRRGFLSNRLDQSAEGILEEHCPKIEAIVEDLISIDEISTNITDY

FFETGILDSNEKNGYAKDLDEGDKKLVSLYKSLLAILKKNESDFENCKSEIIERLNKKDVLGKV

KGKIKDISQAMLDGNYKTLGQYFYSLYSKEKIRNQYTSREEHYLSEFITICKVQGIDQINEEEK

INEKKFDGLAKDLYKAIFFQRPLKSQKGLIGKCSFEKSKSRCAISHPDFEEYRMWTYLNTIKIG

TQSDKKLRFLTQDEKLKLVPKFYRKNDFNFDVLAKELIEKGSSFGFYKSSKKNDFFYWFNYKPT

DTVAACQVAASLKNAIGEDWKTKSFKYQTINSNKEQVSRTVDYKDLWHLLTVATSDVYLYEFAI

DKLGLDEKNAKAFSKTKLKKDFASLSLSAINKILPYLKEGLLYSHAVFVANIENIVDENIWKDE

KQRDYIKTQISEIIENYTLEKSRFEIINGLLKEYKSENEDGKRVYYSKEAEQSFENDLKKKLVL

FYKSNEIENKEQQETIFNELLPIFIQQLKDYEFIKIQRLDQKVLIFLKGKNETGQIFCTEEKGT

AEEKEKKIKNRLKKLYHPSDIEKFKKKIIKDEFGNEKIVLGSPLTPSIKNPMAMRALHQLRKVL

NALILEGQIDEKTIIHIEMARELNDANKRKGIQDYQNDNKKFREDAIKEIKKLYFEDCKKEVEP

TEDDILRYQLWMEQNRSEIYEEGKNISICDIIGSNPAYDIEHTIPRSRSQDNSQMNKTLCSQRF

NREVKKQSMPIELNNHLEILPRIAHWKEEADNLTREIEIISRSIKAAATKEIKDKKIRRRHYLT

LKRDYLQGKYDRFIWEEPKVGFKNSQIPDTGIITKYAQAYLKSYFKKVESVKGGMVAEFRKIWG

IQESFIDENGMKHYKVKDRSKHTHHTIDAITIACMTKEKYDVLAHAWTLEDQQNKKEARSIIEA

SKPWKTFKEDLLKIEEEILVSHYTPDNVKKQAKKIVRVRGKKQFVAEVERDVNGKAVPKKAASG

KTIYKLDGEGKKLPRLQQGDTIRGSLHQDSIYGAIKNPLNTDEIKYVIRKDLESIKGSDVESIV

DEVVKEKIKEAIANKVLLLSSNAQQKNKLVGTVWMNEEKRIAINKVRIYANSVKNPLHIKEHSL

LSKSKHVHKQKVYGQNDENYAMAIYELDGKRDFELINIFNLAKLIKQGQGFYPLHKKKEIKGKI

VFVPIEKRNKRDVVLKRGQQVVFYDKEVENPKDISEIVDFKGRIYIIEGLSIQRIVRPSGKVDE

YGVIMLRYFKEARKADDIKQDNFKPDGVFKLGENKPTRKMNHQFTAFVEGIDFKVLPSGKFEKI

SEQ ID NO: 332
MEFKKVLGLDIGTNSIGCALLSLPKSIQDYGKGGRLEWLTSRVIPLDADYMKAFIDGKNGLPQV

ITPAGKRRQKRGSRRLKHRYKLRRSRLIRVFKTLNWLPEDFPLDNPKRIKETISTEGKFSFRIS

DYVPISDESYREFYREFGYPENEIEQVIEEINFRRKTKGKNKNPMIKLLPEDWVVYLRKKALI

KPTTKEELIRIIYLFNQRRGFKSSRKDLTETAILDYDEFAKRLAEKEKYSAENYETKFVSITKV
```

KEVVELKTDGRKGKKRFKVILEDSRIEPYEIERKEKPDWEGKEYTFLVTQKLEKGKFKQNKPDL

PKEEDWALCTTALDNRMGSKHPGEFFFDELLKAFKEKRGYKIRQYPVNRWRYKKELEFIWTKQC

QLNPELNNLNINKEILRKLATVLYPSQSKFFGPKIKEFENSDVLHIISEDIIYYQRDLKSQKSL

ISECRYEKRKGIDGEIYGLKCIPKSSPLYQEFRIWQDIHNIKVIRKESEVNGKKKINIDETQLY

INENIKEKLFELFNSKDSLSEKDILELISLNIINSGIKISKKEEETTHRINLFANRKELKGNET

KSRYRKVFKKLGFDGEYILNHPSKLNRLWHSDYSNDYADKEKTEKSILSSLGWKNRNGKWEKSK

NYDVFNLPLEVAKAIANLPPLKKEYGSYSALAIRKMLVVMRDGKYWQHPDQIAKDQENTSLMLF

DKNLIQLTNNQRKVLNKYLLTLAEVQKRSTLIKQKLNEIEHNPYKLELVSDQDLEKQVLKSFLE

KKNESDYLKGLKTYQAGYLIYGKHSEKDVPIVNSPDELGEYIRKKLPNNSLRNPIVEQVIRETI

FIVRDVWKSFGIIDEIHIELGRELKNNSEERKKTSESQEKNFQEKERARKLLKELLNSSNFEHY

DENGNKIFSSFTVNPNPDSPLDIEKFRIWKNQSGLTDEELNKKLKDEKIPTEIEVKKYILWLTQ

KCRSPYTGKIIPLSKLFDSNVYEIEHIIPRSKMKNDSTNNLVICELGVNKAKGDRLAANFISES

NGKCKFGEVEYTLLKYGDYLQYCKDTFKYQKAKYKNLLATEPPEDFIERQINDTRYIGRKLAEL

LTPVVKDSKNIIFTIGSITSELKITWGLNGVWKDILRPRFKRLESIINKKLIFQDEDDPNKYHF

DLSINPQLDKEGLKRLDHRHHALDATIIAATTREHVRYLNSLNAADNDEEKREYFLSLCNHKIR

DFKLPWENFTSEVKSKLLSCVVSYKESKPILSDPFNKYLKWEYKNGKWQKVFAIQIKNDRWKAV

RRSMFKEPIGTVWIKKIKEVSLKEAIKIQAIWEEVKNDPVRKKKEKYIYDDYAQKVIAKIVQEL

GLSSSMRKQDDEKLNKFINEAKVSAGVNKNLNTTNKTIYNLEGRFYEKIKVAEYVLYKAKRMPL

NKKEYIEKLSLQKMFNDLPNFILEKSILDNYPEILKELESDNKYIIEPHKKNNPVNRLLLEHIL

EYHNNPKEAFSTEGLEKLNKKAINKIGKPIKYITRLDGDINEEEIFRGAVFETDKGSNVYFVMY

ENNQTKDREFLKPNPSISVLKAIEHKNKIDFFAPNRLGFSRIILSPGDLVYVPTNDQYVLIKDN

SSNETIINWDDNEFISNRIYQVKKFTGNSCYFLKNDIASLILSYSASNGVGEFGSQNISEYSVD

DPPIRIKDVCIKIRVDRLGNVRPL

SEQ ID NO: 333
MKHILGLDLGTNSIGWALIERNIEEKYGKIIGMGSRIVPMGAELSKFEQGQAQTKNADRRTNRG

ARRLNKRYKQRRNKLIYILQKLDMLPSQIKLKEDFSDPNKIDKITILPISKKQEQLTAFDLVSL

RVKALTEKVGLEDLGKIIYKYNQLRGYAGGSLEPEKEDIFDEEQSKDKKNKSFIAFSKIVFLGE

PQEEIFKNKKLNRRAIIVETEEGNFEGSTFLENIKVGDSLELLINISASKSGDTITIKLPNKTN

WRKKMENIENQLKEKSKEMGREFYISEFLLELLKENRWAKIRNNTILRARYESEFEAIWNEQVK

HYPFLENLDKKTLIEIVSFIFPGEKESQKKYRELGLEKGLKYIIKNQVVFYQRELKDQSHLISD

CRYEPNEKAIAKSHPVFQEYKVWEQINKLIVNTKIEAGTNRKGEKKYKYIDRPIPTALKEWIFE

ELQNKKEITFSAIFKKLKAEFDLREGIDFLNGMSPKDKLKGNETKLQLQKSLGELWDVLGLDSI

NRQIELWNILYNEKGNEYDLTSDRTSKVLEFINKYGNNIVDDNAEETAIRISKIKFARAYSSLS

LKAVERILPLVRAGKYFNNDFSQQLQSKILKLLNENVEDPFAKAAQTYLDNNQSVLSEGGVGNS

IATILVYDKHTAKEYSHDELYKSYKEINLLKQGDLRNPLVEQIINEALVLIRDIWKNYGIKPNE

IRVELARDLKNSAKERATIHKRNKDNQTINNKIKETLVKNKKELSLANIEKVKLWEAQRHLSPY

TGQPIPLSDLFDKEKYDVDHIIPISRYFDDSFTNKVISEKSVNQEKANRTAMEYFEVGSLKYSI

FTKEQFIAHVNEYFSGVKRKNLLATSIPEDPVQRQIKDTQYIAIRVKEELNKIVGNENVKTTTG

SITDYLRNHWGLTDKFKLLLKERYEALLESEKFLEAEYDNYKKDFDSRKKEYEEKEVLFEEQEL

TREEFIKEYKENYIRYKKNKLIIKGWSKRIDHRHHAIDALIVACTEPAHIKRLNDLNKVLQDWL

VEHKSEFMPNFEGSNSELLEEILSLPENERTEIFTQIEKFRAIEMPWKGFPEQVEQKLKEIIIS

-continued

HKPKDKLLLQYNKAGDRQIKLRGQLHEGTLYGISQGKEAYRIPLTKFGGSKFATEKNIQKIVSP

FLSGFIANHLKEYNNKKEEAFSAEGIMDLNNKLAQYRNEKGELKPHTPISTVKIYYKDPSKNKK

KKDEEDLSLQKLDREKAFNEKLYVKTGDNYLFAVLEGEIKTKKTSQIKRLYDIISFFDATNFLK

EEFRNAPDKKTFDKDLLFRQYFEERNKAKLLFTLKQGDFVYLPNENEEVILDKESPLYNQYWGD

LKERGKNIYVVQKFSKKQIYFIKHTIADIIKKDVEFGSQNCYETVEGRSIKENCFKLEIDRLGN

IVKVIKR

SEQ ID NO: 334
MHVEIDFPHFSRGDSHLAMNKNEILRGSSVLYRLGLDLGSNSLGWFVTHLEKRGDRHEPVALGP

GGVRIFPDGRDPQSGTSNAVDRRMARGARKRRDRFVERRKELIAALIKYNLLPDDARERRALEV

LDPYALRKTALTDTLPAHHVGRALFHLNQRRGFQSNRKTDSKQSEDGAIKQAASRLATDKGNET

LGVFFADMHLRKSYEDRQTAIRAELVRLGKDHLTGNARKKIWAKVRKRLFGDEVLPRADAPHGV

RARATITGTKASYDYYPTRDMLRDEFNAIWAGQSAHHATITDEARTEIEHIIFYQRPLKPAIVG

KCTLDPATRPFKEDPEGYRAPWSHPLAQRFRILSEARNLEIRDTGKGSRRLTKEQSDLVVAALL

ANREVKFDKLRTLLKLPAEARFNLESDRRAALDGDQTAARLSDKKGFNKAWRGFPPERQIAIVA

RLEETEDENELIAWLEKECALDGAAAARVANTTLPDGHCRLGLRAIKKIVPIMQDGLDEDGVAG

AGYHIAAKRAGYDHAKLPTGEQLGRLPYYGQWLQDAVVGSGDARDQKEKQYGQFPNPTVHIGLG

QLRRVVNDLIDKYGPPTEISIEFTRALKLSEQQKAERQREQRRNQDKNKARAEELAKFGRPANP

RNLLKMRLWEELAHDPLDRKCVYTGEQISIERLLSDEVDIDHILPVAMTLDDSPANKIICMRYA

NRHKRKQTPSEAFGSSPTLQGHRYNWDDIAARATGLPRNKRWRFDANAREEFDKRGGFLARQLN

ETGWLARLAKQYLGAVTDPNQIWVVPGRLTSMLRGKWGLNGLLPSDNYAGVQDKAEEFLASTDD

MEFSGVKNRADHRHHAIDGLVTALTDRSLLWKMANAYDEEHEKFVIEPPWPTMRDDLKAALEKM

VVSHKPDHGIEGKLHEDSAYGFVKPLDATGLKEEEAGNLVYRKAIESLNENEVDRIRDIQLRTI

VRDHVNVEKTKGVALADALRQLQAPSDDYPQFKHGLRHVRILKKEKGDYLVPIANRASGVAYKA

YSAGENFCVEVFETAGGKWDGEAVRRFDANKKNAGPKIAHAPQWRDANEGAKLVMRIHKGDLIR

LDHEGRARIMVVHRLDAAAGRFKLADHNETGNLDKRHATNNDIDPFRWLMASYNTLKKLAAVPV

RVDELGRVWRVMPN

SEQ ID NO: 335
METTLGIDLGTNSIGLALVDQEEHQILYSGVRIFPEGINKDTIGLGEKEESRNATRRAKRQMRR

QYFRKKLRKAKLLELLIAYDMCPLKPEDVRRWKNWDKQQKSTVRQFPDTPAFREWLKQNPYELR

KQAVTEDVTRPELGRILYQMIQRRGFLSSRKGKEEGKIFTGKDRMVGIDETRKNLQKQTLGAYL

YDIAPKNGEKYRFRTERVRARYTLRDMYIREFEIIWQRQAGHLGLAHEQATRKKNIFLEGSATN

VRNSKLITHLQAKYGRGHVLIEDTRITVTFQLPLKEVLGGKIEIEEEQLKFKSNESVLFWQRPL

RSQKSLLSKCVFEGRNFYDPVHQKWIIAGPTPAPLSHPEFEEFRAYQFINNIIYGKNEHLTAIQ

REAVFELMCTESKDFNFEKIPKHLKLFEKFNFDDTTKVPACTTISQLRKLFPHPVWEEKREEIW

HCFYFYDDNTLLFEKLQKDYALQTNDLEKIKKIRLSESYGNVSLKAIRRINPYLKKGYAYSTAV

LLGGIRNSFGKRFEYFKEYEPEIEKAVCRILKEKNAEGEVIRKIKDYLVHNRFGFAKNDRAFQK

LYHHSQAITTQAQKERLPETGNLRNPIVQQGLNELRRTVNKLLATCREKYGPSFKFDHIHVEMG

RELRSSKTEREKQSRQIRENEKKNEAAKVKLAEYGLKAYRDNIQKYLLYKEIEEKGGTVCCPYT

GKTLNISHTLGSDNSVQIEHIIPYSISLDDSLANKTLCDATFNREKGELTPYDFYQKDPSPEKW

GASSWEEIEDRAFRLLPYAKAQRFIRRKPQESNEFISRQLNDTRYISKKAVEYLSAICSDVKAF

PGQLTAELRHLWGLNNILQSAPDITFPLPVSATENHREYYVITNEQNEVIRLFPKQGETPRTEK

-continued

GELLLTGEVERKVFRCKGMQEFQTDVSDGKYWRRIKLSSSVTWSPLFAPKPISADGQIVLKGRI

EKGVFVCNQLKQKLKTGLPDGSYWISLPVISQTFKEGESVNNSKLTSQQVQLFGRVREGIFRCH

NYQCPASGADGNFWCTLDTDTAQPAFTPIKNAPPGVGGGQIILTGDVDDKGIFHADDDLHYELP

ASLPKGKYYGIFTVESCDPTLIPIELSAPKTSKGENLIEGNIWVDEHTGEVRFDPKKNREDQRH

HAIDAIVIALSSQSLFQRLSTYNARRENKKRGLDSTEHFPSPWPGFAQDVRQSVVPLLVSYKQN

PKTLCKISKTLYKDGKKIHSCGNAVRGQLHKETVYGQRTAPGATEKSYHIRKDIRELKTSKHIG

KVVDITIRQMLLKHLQENYHIDITQEFNIPSNAFFKEGVYRIFLPNKHGEPVPIKKIRMKEELG

NAERLKDNINQYVNPRNNHHVMIYQDADGNLKEEIVSFWSVIERQNQGQPIYQLPREGRNIVSI

LQINDTFLIGLKEEEPEVYRNDLSTLSKHLYRVQKLSGMYYTFRHHLASTLNNEREEFRIQSLE

AWKRANPVKVQIDEIGRITFLNGPLC

SEQ ID NO: 336

MESSQILSPIGIDLGGKFTGVCLSHLEAFAELPNHANTKYSVILIDHNNFQLSQAQRRATRHRV

RNKKRNQFVKRVALQLFQHILSRDLNAKEETALCHYLNNRGYTYVDTDLDEYIKDETTINLLKE

LLPSESEHNFIDWFLQKMQSSEFRKILVSKVEEKKDDKELKNAVKNIKNFITGFEKNSVEGHRH

RKVYFENIKSDITKDNQLDSIKKKIPSVCLSNLLGHLSNLQWKNLHRYLAKNPKQFDEQTFGNE

FLRMLKNFRHLKGSQESLAVRNLIQQLEQSQDYISILEKTPPEITIPPYEARTNTGMEKDQSLL

LNPEKLNNLYPNWRNLIPGIIDAHPFLEKDLEHTKLRDRKRIISPSKQDEKRDSYILQRYLDLN

KKIDKFKIKKQLSFLGQGKQLPANLIETQKEMETHFNSSLVSVLIQIASAYNKEREDAAQGIWF

DNAFSLCELSNINPPRKQKILPLLVGAILSEDFINNKDKWAKFKIFWNTHKIGRTSLKSKCKEI

EEARKNSGNAFKIDYEEALNHPEHSNNKALIKIIQTIPDIIQAIQSHLGHNDSQALIYHNPFSL

SQLYTILETKRDGFHKNCVAVTCENYWRSQKTEIDPEISYASRLPADSVRPFDGVLARMMQRLA

YEIAMAKWEQIKHIPDNSSLLIPIYLEQNRFEFEESFKKIKGSSSDKTLEQAIEKQNIQWEEKF

QRIINASMNICPYKGASIGGQGEIDHIYPRSLSKKHFGVIFNSEVNLIYCSSQGNREKKEEHYL

LEHLSPLYLKHQFGTDNVSDIKNFISQNVANIKKYISFHLLTPEQQKAARHALFLDYDDEAFKT

ITKFLMSQQKARVNGTQKFLGKQIMEFLSTLADSKQLQLEFSIKQITAEEVHDHRELLSKQEPK

LVKSRQQSFPSHAIDATLTMSIGLKEFPQFSQELDNSWFINHLMPDEVHLNPVRSKEKYNKPNI

SSTPLFKDSLYAERFIPVWVKGETFAIGFSEKDLFEIKPSNKEKLFTLLKTYSTKNPGESLQEL

QAKSKAKWLYFPINKTLALEFLHHYFHKEIVTPDDTTVCHFINSLRYYTKKESITVKILKEPMP

VLSVKFESSKKNVLGSFKHTIALPATKDWERLFNHPNFLALKANPAPNPKEFNEFIRKYFLSDN

NPNSDIPNNGHNIKPQKHKAVRKVFSLPVIPGNAGTMMRIRRKDNKGQPLYQLQTIDDTPSMGI

QINEDRLVKQEVLMDAYKTRNLSTIDGINNSEGQAYATFDNWLTLPVSTFKPEIIKLEMKPHSK

TRRYIRITQSLADFIKTIDEALMIKPSDSIDDPLNMPNEIVCKNKLFGNELKPRDGKMKIVSTG

KIVTYEFESDSTPQWIQTLYVTQLKKQP

SEQ ID NO: 337

MKKIVGLDLGTNSIGWALINAYINKEHLYGIEACGSRIIPMDAAILGNFDKGNSISQTADRTSY

RGIRRLRERHLLRRERLHRILDLLGFLPKHYSDSLNRYGKFLNDIECKLPWVKDETGSYKFIFQ

ESFKEMLANFTEHHPILIANNKKVPYDWTIYYLRKKALTQKISKEELAWILLNFNQKRGYYQLR

GEEEETPNKLVEYYSLKVEKVEDSGERKGKDTWYNVHLENGMIYRRTSNIPLDWEGKTKEFIVT

TDLEADGSPKKDKEGNIKRSFRAPKDDDWTLIKKKTEADIDKIKMTVGAYIYDTLLQKPDQKIR

GKLVRTIERKYYKNELYQILKTQSEFHEELRDKQLYIACLNELYPNNEPRRNSISTRDFCHLFI

EDIIFYQRPLKSKKSLIDNCPYEENRYIDKESGEIKHASIKCIAKSHPLYQEFRLWQFIVNLRI

YRKETDVDVTQELLPTEADYVTLFEWLNEKKEIDQKAFFKYPPFGFKKTTSNYRWNYVEDKPYP

-continued

CNETHAQIIARLGKAHIPKAFLSKEKEETLWHILYSIEDKQEIEKALHSFANKNNLSEEFIEQF

KNFPPFKKEYGSYSAKAIKKLLPLMRMGKYWSIENIDNGTRIRINKIIDGEYDENIRERVRQKA

INLTDITHFRALPLWLACYLVYDRHSEVKDIVKWKTPKDIDLYLKSFKQHSLRNPIVEQVITET

LRTVRDIWQQVGHIDEIHIELGREMKNPADKRARMSQQMIKNENTNLRIKALLTEFLNPEFGIE

NVRPYSPSQQDLLRIYEEGVLNSILELPEDIGIILGKFNQTDTLKRPTRSEILRYKLWLEQKYR

SPYTGEMIPLSKLFTPAYEIEHIIPQSRYFDDSLSNKVICESEINKLKDRSLGYEFIKNHHGEK

VELAFDKPVEVLSVEAYEKLVHESYSHNRSKMKKLLMEDIPDQFIERQLNDSRYISKVVKSLLS

NIVREENEQEAISKNVIPCTGGITDRLKKDWGINDVWNKIVLPRFIRLNELTESTRFTSINTNN

TMIPSMPLELQKGFNKKRIDHRHHAMDAIIIACANRNIVNYLNNVSASKNTKITRRDLQTLLCH

KDKTDNNGNYKWVIDKPWETFTQDTLTALQKITVSFKQNLRVINKTTNHYQHYENGKKIVSNQS

KGDSWAIRKSMHKETVHGEVNLRMIKTVSFNEALKKPQAIVEMDLKKKILAMLELGYDTKRIKN

YFEENKDTWQDINPSKIKVYYFTKETKDRYFAVRKPIDTSFDKKKIKESITDTGIQQIMLRHLE

TKDNDPTLAFSPDGIDEMNRNILILNKGKKHQPIYKVRVYEKAEKFTVGQKGNKRTKFVEAAKG

TNLFFAIYETEEIDKDTKKVIRKRSYSTIPLNVVIERQKQGLSSAPEDENGNLPKYILSPNDLV

YVPTQEEINKGEVVMPIDRDRIYKMVDSSGITANFIPASTANLIFALPKATAEIYCNGENCIQN

EYGIGSPQSKNQKAITGEMVKEICFPIKVDRLGNIIQVGSCILTN

SEQ ID NO: 338
MSRSLTFSFDIGYASIGWAVIASASHDDADPSVCGCGTVLFPKDDCQAFKRREYRRLRRNIRSR

RVRIERIGRLLVQAQIITPEMKETSGHPAPFYLASEALKGHRTLAPIELWHVLRWYAHNRGYDN

NASWSNSLSEDGGNGEDTERVKHAQDLMDKHGTATMAETICRELKLEEGKADAPMEVSTPAYKN

LNTAFPRLIVEKEVRRILELSAPLIPGLTAEIIELIAQHHPLTTEQRGVLLQHGIKLARRYRGS

LLFGQLIPRFDNRIISRCPVTWAQVYEAELKKGNSEQSARERAEKLSKVPTANCPEFYEYRMAR

ILCNIRADGEPLSAEIRRELMNQARQEGKLTKASLEKAISSRLGKETETNVSNYFTLHPDSEEA

LYLNPAVEVLQRSGIGQILSPSVYRIAANRLRRGKSVTPNYLLNLLKSRGESGEALEKKIEKES

KKKEADYADTPLKPKYATGRAPYARTVLKKVVEEILDGEDPTRPARGEAHPDGELKAHDGCLYC

LLDTDSSVNQHQKERRLDTMTNNHLVRHRMLILDRLLKDLIQDFADGQKDRISRVCVEVGKELT

TFSAMDSKKIQRELTLRQKSHTDAVNRLKRKLPGKALSANLIRKCRIAMDMNWTCPFTGATYGD

HELENLELEHIVPHSFRQSNALSSLVLTWPGVNRMKGQRTGYDFVEQEQENPVPDKPNLHICSL

NNYRELVEKLDDKKGHEDDRRRKKKRKALLMVRGLSHKHQSQNHEAMKEIGMTEGMMTQSSHLM

KLACKSIKTSLPDAHIDMIPGAVTAEVRKAWDVFGVFKELCPEAADPDSGKILKENLRSLTHLH

HALDACVLGLIPYIIPAHHNGLLRRVLAMRRIPEKLIPQVRPVANQRHYVLNDDGRMMLRDLSA

SLKENIREQLMEQRVIQHVPADMGGALLKETMQRVLSVDGSGEDAMVSLSKKKDGKKEKNQVKA

SKLVGVFPEGPSKLKALKAAIEIDGNYGVALDPKPVVIRHIKVFKRIMALKEQNGGKPVRILKK

GMLIHLTSSKDPKHAGVWRIESIQDSKGGVKLDLQRAHCAVPKNKTHECNWREVDLISLLKKYQ

MKRYPTSYTGTPR

SEQ ID NO: 339
MTQKVLGLDLGTNSIGSAVRNLDLSDDLQWQLEFFSSDIFRSSVNKESNGREYSLAAQRSAHRR

SRGLNEVRRRRLWATLNLLIKHGFCPMSSESLMRWCTYDKRKGLFREYPIDDKDFNAWILLDFN

GDGRPDYSSPYQLRRELVTRQFDFEQPIERYKLGRALYHIAQHRGFKSSKGETLSQQETNSKPS

STDEIPDVAGAMKASEEKLSKGLSTYMKEHNLLTVGAAFAQLEDEGVRVRNNNDYRAIRSQFQH

EIETIFKFQQGLSVESELYERLISEKKNVGTIFYKRPLRSQRGNVGKCTLERSKPRCAIGHPLF

-continued

EKFRAWTLINNIKVRMSVDTLDEQLPMKLRLDLYNECFLAFVRTEFKFEDIRKYLEKRLGIHFS
YNDKTINYKDSTSVAGCPITARFRKMLGEEWESFRVEGQKERQAHSKNNISFHRVSYSIEDIWH
FCYDAEEPEAVLAFAQETLRLERKKAEELVRIWSAMPQGYAMLSQKAIRNINKILMLGLKYSDA
VILAKVPELVDVSDEELLSIAKDYYLVEAQVNYDKRINSIVNGLIAKYKSVSEEYRFADHNYEY
LLDESDEKDIIRQIENSLGARRWSLMDANEQTDILQKVRDRYQDFFRSHERKFVESPKLGESFE
NYLTKKFPMVEREQWKKLYHPSQITIYRPVSVGKDRSVLRLGNPDIGAIKNPTVLRVLNTLRRR
VNQLLDDGVISPDETRVVVETARELNDANRKWALDTYNRIRHDENEKIKKILEEFYPKRDGIST
DDIDKARYVIDQREVDYFTGSKTYNKDIKKYKFWLEQGGQCMYTGRTINLSNLFDPNAFDIEHT
IPESLSFDSSDMNLTLCDAHYNRFIKKNHIPTDMPNYDKAITIDGKEYPAITSQLQRWVERVER
LNRNVEYWKGQARRAQNKDRKDQCMREMHLWKMELEYWKKKLERFTVTEVTDGFKNSQLVDTRV
ITRHAVLYLKSIFPHVDVQRGDVTAKFRKILGIQSVDEKKDRSLHSHHAIDATTLTIIPVSAKR
DRMLELFAKIEEINKMLSFSGSEDRTGLIQELEGLKNKLQMEVKVCRIGHNVSEIGTFINDNII
VNHHIKNQALTPVRRRLRKKGYIVGGVDNPRWQTGDALRGEIHKASYYGAITQFAKDDEGKVLM
KEGRPQVNPTIKFVIRRELKYKKSAADSGFASWDDLGKAIVDKELFALMKGQFPAETSFKDACE
QGIYMIKKGKNGMPDIKLHHIRHVRCEAPQSGLKIKEQTYKSEKEYKRYFYAAVGDLYAMCCYT
NGKIREFRIYSLYDVSCHRKSDIEDIPEFITDKKGNRLMLDYKLRTGDMILLYKDNPAELYDLD
NVNLSRRLYKINRFESQSNLVLMTHHLSTSKERGRSLGKTVDYQNLPESIRSSVKSLNFLIMGE
NRDFVIKNGKIIFNHR

SEQ ID NO: 340
MLVSPISVDLGGKNTGFFSFTDSLDNSQSGTVIYDESFVLSQVGRRSKRHSKRNNLRNKLVKRL
FLLILQEHHGLSIDVLPDEIRGLFNKRGYTYAGFELDEKKKDALESDTLKEFLSEKLQSIDRDS
DVEDFLNQIASNAESFKDYKKGFEAVFASATHSPNKKLELKDELKSEYGENAKELLAGLRVTKE
ILDEFDKQENQGNLPRAKYFEELGEYIATNEKVKSFFDSNSLKLTDMTKLIGNISNYQLKELRR
YFNDKEMEKGDIWIPNKLHKITERFVRSWHPKNDADRQRRAELMKDLKSKEIMELLTTTEPVMT
IPPYDDMNNRGAVKCQTLRLNEEYLDKHLPNWRDIAKRLNHGKFNDDLADSTVKGYSEDSTLLH
RLLDTSKEIDIYELRGKKPNELLVKTLGQSDANRLYGFAQNYYELIRQKVRAGIWVPVKNKDDS
LNLEDNSNMLKRCNHNPPHKKNQIHNLVAGILGVKLDEAKFAEFEKELWSAKVGNKKLSAYCKN
IEELRKTHGNTFKIDIEELRKKDPAELSKEEKAKLRLTDDVILNEWSQKIANFFDIDDKHRQRF
NNLFSMAQLHTVIDTPRSGFSSTCKRCTAENRFRSETAFYNDETGEFHKKATATCQRLPADTQR
PFSGKIERYIDKLGYELAKIKAKELEGMEAKEIKVPIILEQNAFEYEESLRKSKTGSNDRVINS
KKDRDGKKLAKAKENAEDRLKDKDKRIKAFSSGICPYCGDTIGDDGEIDHILPRSHTLKIYGTV
FNPEGNLIYVHQKCNQAKADSIYKLSDIKAGVSAQWIEEQVANIKGYKTFSVLSAEQQKAFRYA
LFLQNDNEAYKKVVDWLRTDQSARVNGTQKYLAKKIQEKLTKMLPNKHLSFEFILADATEVSEL
RRQYARQNPLLAKAEKQAPSSHAIDAVMAFVARYQKVFKDGTPPNADEVAKLAMLDSWNPASNE
PLTKGLSTNQKIEKMIKSGDYGQKNMREVFGKSIFGENAIGERYKPIVVQEGGYYIGYPATVKK
GYELKNCKVVTSKNDIAKLEKIIKNQDLISLKENQYIKIFSINKQTISELSNRYFNMNYKNLVE
RDKEIVGLLEFIVENCRYYTKKVDVKFAPKYIHETKYPFYDDWRRFDEAWRYLQENQNKTSSKD
RFVIDKSSLNEYYQPDKNEYKLDVDTQPIWDDFCRWYFLDRYKTANDKKSIRIKARKTFSLLAE
SGVQGKVFRAKRKIPTGYAYQALPMDNNVIAGDYANILLEANSKTLSLVPKSGISIEKQLDKKL
DVIKKTDVRGLAIDNNSFFNADFDTHGIRLIVENTSVKVGNFPISAIDKSAKRMIFRALFEKEK

GKRKKKTTISFKESGPVQDYLKVFLKKIVKIQLRTDGSISNIVVRKNAADFTLSFRSEHIQKLL
K

SEQ ID NO: 341
MAYRLGLDIGITSVGWAVVALEKDESGLKPVRIQDLGVRIFDKAEDSKTGASLALPRREARSAR
RRTRRRRHRLWRVKRLLEQHGILSMEQIEALYAQRTSSPDVYALRVAGLDRCLIAEEIARVLIH
IAHRRGFQSNRKSEIKDSDAGKLLKAVQENENLMQSKGYRTVAEMLVSEATKTDAEGKLVHGKK
HGYVSNVRNKAGEYRHTVSRQAIVDEVRKIFAAQRALGNDVMSEELEDSYLKILCSQRNFDDGP
GGDSPYGHGSVSPDGVRQSIYERMVGSCTFETGEKRAPRSSYSFERFQLLTKVVNLRIYRQQED
GGRYPCELTQTERARVIDCAYEQTKITYGKLRKLLDMKDTESFAGLTYGLNRSRNKTEDTVFVE
MKFYHEVRKALQRAGVFIQDLSIETLDQIGWILSVWKSDDNRRKKLSTLGLSDNVIEELLPLNG
SKFGHLSLKAIRKILPFLEDGYSYDVACELAGYQFQGKTEYVKQRLLPPLGEGEVTNPVVRRAL
SQAIKVVNAVIRKHGSPESIHIELARELSKNLDERRKIEKAQKENQKNNEQIKDEIREILGSAH
VTGRDIVKYKLFKQQQEFCMYSGEKLDVTRLFEPGYAEVDHIIPYGISFDDSYDNKVLVKTEQN
RQKGNRTPLEYLRDKPEQKAKFIALVESIPLSQKKKNHLLMDKRAIDLEQEGFRERNLSDTRYI
TRALMNHIQAWLLFDETASTRSKRVVCVNGAVTAYMRARWGLTKDRDAGDKHHAADAVVACIG
DSLIQRVTKYDKFKRNALADRNRYVQQVSKSEGITQYVDKETGEVFTWESFDERKFLPNEPLEP
WPFFRDELLARLSDDPSKNIRAIGLLTYSETEQIDPIFVSRMPTRKVTGAAHKETIRSPRIVKV
DDNKGTEIQVVVSKVALTELKLTKDGEIKDYFRPEDDPRLYNTLRERLVQFGGDAKAAFKEPVY
KISKDGSVRTPVRKVKIQEKLTLGVPVHGGRGIAENGGMVRIDVFAKGGKYYFVPIYVADVLKR
ELPNRLATAHKPYSEWRVVDDSYQFKFSLYPNDAVMIKPSREVDITYKDRKEPVGCRIMYFVSA
NIASASISLRTHDNSGELEGLGIQGLEVFEKYVVGPLGDTHPVYKERRMPFRVERKMN

SEQ ID NO: 342
MPVLSPLSPNAAQGRRRWSLALDIGEGSIGWAVAEVDAEGRVLQLTGTGVTLFPSAWSNENGTY
VAHGAADRAVRGQQQRHDSRRRRLAGLARLCAPVLERSPEDLKDLTRTPPKADPRAIFFLRADA
ARRPLDGPELFRVLHHMAAHRGIRLAELQEVDPPPESDADDAAPAATEDEDGTRRAAADERAFR
RLMAEHMRHGTQPTCGEIMAGRLRETPAGAQPVTRARDGLRVGGGVAVPTRALIEQEFDAIRA
IQAPRHPDLPWDSLRRLVLDQAPIAVPPATPCLFLEELRRRGETFQGRTITREAIDRGLTVDPL
IQALRIRETVGNLRLHERITEPDGRQRYVPRAMPELGLSHGELTAPERDTLVRALMHDPDGLAA
KDGRIPYTRLRKLIGYDNSPVCFAQERDTSGGGITVNPTDPLMARWIDGWVDLPLKARSLYVRD
VVARGADSAALARLLAEGAHGVPPVAAAAVPAATAAILESDIMQPGRYSVCPWAAEAILDAWAN
APTEGFYDVTRGLFGFAPGEIVLEDLRRARGALLAHLPRTMAAARTPNRAAQQRGPLPAYESVI
PSQLITSLRRAHKGRAADWSAADPEERNPFLRTWTGNAATDHILNQVRKTANEVITKYGNRRGW
DPLPSRITVELAREAKHGVIRRNEIAKENRENEGRRKKESAALDTFCQDNTVSWQAGGLPKERA
ALRLRLAQRQEFFCPYCAERPKLRATDLFSPAETEIDHVIERRMGGDGPDNLVLAHKDCNNAKG
KKTPHEHAGDLLDSPALAALWQGWRKENADRLKGKGHKARTPREDKDFMDRVGWRFEEDARAKA
EENQERRGRRMLHDTARATRLARLYLAAAVMPEDPAEIGAPPVETPPSPEDPTGYTAIYRTISR
VQPVNGSVTHMLRQRLLQRDKNRDYQTHHAEDACLLLLAGPAVVQAFNTEAAQHGADAPDDRPV
DLMPTSDAYHQQRRARALGRVPLATVDAALADIVMPESDRQDPETGRVHWRLTRAGRGLKRRID
DLTRNCVILSRPRRPSETGTPGALHNATHYGRREITVDGRTDTVVTQRMNARDLVALLDNAKIV
PAARLDAAAPGDTILKEICTEIADRHDRVVDPEGTHARRWISARLAALVPAHAEAVARDIAELA
DLDALADADRTPEQEARRSALRQSPYLGRAISAKKADGRARAREQEILTRALLDPHWGPRGLRH

-continued

LIMREARAPSLVRIRANKTDAFGRPVPDAAVWVKTDGNAVSQLWRLTSVVTDDGRRIPLPKPIE

KRIEISNLEYARLNGLDEGAGVTGNNAPPRPLRQDIDRLTPLWRDHGTAPGGYLGTAVGELEDK

ARSALRGKAMRQTLTDAGITAEAGWRLDSEGAVCDLEVAKGDTVKKDGKTYKVGVITQGIFGMP

VDAAGSAPRTPEDCEKFEEQYGIKPWKAKGIPLA

SEQ ID NO: 343

MNYTEKEKLFMKYILALDIGIASVGWAILDKESETVIEAGSNIFPEASAADNQLRRDMRGAKRN

NRRLKTRINDFIKLWENNNLSIPQFKSTEIVGLKVRAITEEITLDELYLILYSYLKHRGISYLE

DALDDTVSGSSAYANGLKLNAKELETHYPCEIQQERLNTIGKYRGQSQIINENGEVLDLSNVFT

IGAYRKEIQRVFEIQKKYHPELTDEFCDGYMLIFNRKRKYYEGPGNEKSRTDYGRFTTKLDANG

NYITEDNIFEKLIGKCSVYPDELRAAAASYTAQEYNVLNDLNNLTINGRKLEENEKHEIVERIK

SSNTINMRKIISDCMGENIDDFAGARIDKSGKEIFHKFEVYNKMRKALLEIGIDISNYSREELD

EIGYIMTINTDKEAMMEAFQKSWIDLSDDVKQCLINMRKTNGALFNKWQSFSLKIMNELIPEMY

AQPKEQMTLLTEMGVTKGTQEEFAGLKYIPVDVVSEDIFNPVVRRSVRISFKILNAVLKKYKAL

DTIVIEMPRDRNSEEQKKRINDSQKLNEKEMEYIEKKLAVTYGIKLSPSDFSSQKQLSLKLKLW

NEQDGICLYSGKTIDPNDIINNPQLFEIDHIIPRSISFDDARSNKVLVYRSENQKKGNQTPYYY

LTHSHSEWSFEQYKATVMNLSKKKEYAISRKKIQNLLYSEDITKMDVLKGFINRNINDTSYASR

LVLNTIQNFFMANEADTKVKVIKGSYTHQMRCNLKLDKNRDESYSHHAVDAMLIGYSELGYEAY

HKLQGEFIDFETGEILRKDMWDENMSDEVYADYLYGKKWANIRNEVVKAEKNVKYWHYVMRKSN

RGLCNQTIRGTREYDGKQYKINKLDIRTKEGIKVFAKLAFSKKDSDRERLLVYLNDRRTFDDLC

KIYEDYSDAANPFVQYEKETGDIIRKYSKKHNGPRIDKLKYKDGEVGACIDISHKYGFEKGSKK

VILESLVPYRMDVYYKEENHSYYLVGVKQSDIKFEKGRNVIDEEAYARILVNEKMIQPGQSRAD

LENLGFKFKLSFYKNDIIEYEKDGKIYTERLVSRTMPKQRNYIETKPIDKAKFEKQNLVGLGKT

KFIKKYRYDILGNKYSCSEEKFTSFC

SEQ ID NO: 344

MLRLYCANNLVLNNVQNLWKYLLLLIFDKKIIFLFKIKVILIRRYMENNNKEKIVIGFDLGVAS

VGWSIVNAETKEVIDLGVRLFSEPEKADYRRAKRTTRRLLRRKKFKREKFHKLILKNAEIFGLQ

SRNEILNVYKDQSSKYRNILKLKINALKEEIKPSELVWILRDYLQNRGYFYKNEKLTDEFVSNS

FPSKKLHEHYEKYGFFRGSVKLDNKLDNKKDKAKEKDEEEESDAKKESEELIFSNKQWINEIVK

VFENQSYLTESFKEEYLKLFNYVRPFNKGPGSKNSRTAYGVFSTDIDPETNKFKDYSNIWDKTI

GKCSLFEEEIRAPKNLPSALIFNLQNEICTIKNEFTEFKNWWLNAEQKSEILKFVFTELFNWKD

KKYSDKKFNKNLQDKIKKYLLNFALENFNLNEEILKNRDLENDTVLGLKGVKYYEKSNATADAA

LEFSSLKPLYVFIKFLKEKKLDLNYLLGLENTEILYFLDSIYLAISYSSDLKERNEWFKKLLKE

LYPKIKNNNLEIIENVEDIFEITDQEKFESFSKTHSLSREAFNHIIPLLLSNNEGKNYESLKHS

NEELKKRTEKAELKAQQNQKYLKDNFLKEALVPLSVKTSVLQAIKIFNQIIKNFGKKYEISQVV

IEMARELTKPNLEKLLNNATNSNIKILKEKLDQTEKFDDFTKKKFIDKIENSVVFRNKLFLWFE

QDRKDPYTQLDIKINEIEDETEIDHVIPYSKSADDSWFNKLLVKKSTNQLKKNKTVWEYYQNES

DPEAKWNKFVAWAKRIYLVQKSDKESKDNSEKNSIFKNKKPNLKFKNITKKLFDPYKDLGFLAR

NLNDTRYATKVFRDQLNNYSKHHSKDDENKLFKVVCMNGSITSFLRKSMWRKNEEQVYRFNFWK

KDRDQFFHHAVDASIIAIFSLLTKTLYNKLRVYESYDVQRREDGVYLINKETGEVKKADKDYWK

DQHNFLKIRENAIEIKNVLNNVDFQNQVRYSRKANTKLNTQLFNETLYGVKEFENNFYKLEKVN

LFSRKDLRKFILEDLNEESEKNKKNENGSRKRILTEKYIVDEILQILENEEFKDSKSDINALNK

YMDSLPSKFSEFFSQDFINKCKKENSLILTFDAIKHNDPKKVIKIKNLKFFREDATLKNKQAVH

KDSKNQIKSFYESYKCVGFIWLKNKNDLEESIFVPINSRVIHFGDKDKDIFDFDSYNKEKLLNE

INLKRPENKKFNSINEIEFVKFVKPGALLLNFENQQIYYISTLESSSLRAKIKLLNKMDKGKAV

SMKKITNPDEYKIIEHVNPLGINLNWTKKLENNN

SEQ ID NO: 345
MLMSKHVLGLDLGVGSIGWCLIALDAQGDPAEILGMGSRVVPLNNATKAIEAFNAGAAFTASQE

RTARRTMRRGFARYQLRRYRLRRELEKVGMLPDAALIQLPLLELWELRERAATAGRRLTLPELG

RVLCHINQKRGYRHVKSDAAAIVGDEGEKKKDSNSAYLAGIRANDEKLQAEHKTVGQYFAEQLR

QNQSESPTGGISYRIKDQIFSRQCYIDEYDQIMAVQRVHYPDILTDEFIRMLRDEVIFMQRPLK

SCKHLVSLCEFEKQERVMRVQQDDGKGGWQLVERRVKFGPKVAPKSSPLFQLCCIYEAVNNIRL

TRPNGSPCDITPEERAKIVAHLQSSASLSFAALKKLLKEKALIADQLTSKSGLKGNSTRVALAS

ALQPYPQYHHLLDMELETRMMTVQLTDEETGEVTEREVAVVTDSYVRKPLYRLWHILYSIEERE

AMRRALITQLGMKEEDLDGGLLDQLYRLDFVKPGYGNKSAKFICKLLPQLQQGLGYSEACAAVG

YRHSNSPTSEEITERTLLEKIPLLQRNELRQPLVEKILNQMINLVNALKAEYGIDEVRVELARE

LKMSREERERMARNNKDREERNKGVAAKIRECGLYPTKPRIQKYMLWKEAGRQCLYCGRSIEEE

QCLREGGMEVEHIIPKSVLYDDSYGNKTCACRRCNKEKGNRTALEYIRAKGREAEYMKRINDLL

KEKKISYSKHQRLRWLKEDIPSDFLERQLRLTQYISRQAMAILQQGIRRVSASEGGVTARLRSL

WGYGKILHTLNLDRYDSMGETERVSREGEATEELHITNWSKRMDHRHHAIDALVVACTRQSYIQ

RLNRLSSEFGREDKKKEDQEAQEQQATETGRLSNLERWLTQRPHFSVRTVSDKVAEILISYRPG

QRVVTRGRNIYRKKMADGREVSCVQRGVLVPRGELMEASFYGKILSQGRVRIVKRYPLHDLKGE

VVDPHLRELITTYNQELKSREKGAPIPPLCLDKDKKQEVRSVRCYAKTLSLDKAIPMCFDEKGE

PTAFVKSASNHHLALYRTPKGKLVESIVTFWDAVDRARYGIPLVITHPREVMEQVLQRGDIPEQ

VLSLLPPSDWVFVDSLQQDEMVVIGLSDEELQRALEAQNYRKISEHLYRVQKMSSSYYVFRYHL

ETSVADDKNTSGRIPKFHRVQSLKAYEERNIRKVRVDLLGRISLL

SEQ ID NO: 346
MSDLVLGLDIGIGSVGVGILNKVTGEIIHKNSRIFPAAQAENNLVRRTNRQGRRLARRKKHRRV

RLNRLFEESGLITDFTKISINLNPYQLRVKGLTDELSNEELFIALKNMVKHRGISYLDDASDDG

NSSVGDYAQIVKENSKQLETKTPGQIQLERYQTYGQLRGDFTVEKDGKKHRLINVFPTSAYRSE

ALRILQTQQEFNPQITDEFINRYLEILTGKRKYYHGPGNEKSRTDYGRYRTSGETLDNIFGILI

GKCTFYPDEFRAAKASYTAQEFNLLNDLNNLTVPTETKKLSKEQKNQIINYVKNEKAMGPAKLF

KYIAKLLSCDVADIKGYRIDKSGKAEIHTFEAYRKMKTLETLDIEQMDRETLDKLAYVLTLNTE

REGIQEALEHEFADGSFSQKQVDELVQFRKANSSIFGKGWHNFSVKLMMELIPELYETSEEQMT

ILTRLGKQKTTSSSNKTKYIDEKLLTEEIYNPVVAKSVRQAIKIVNAAIKEYGDFDNIVIEMAR

ETNEDDEKKAIQKIQKANKDEKDAAMLKAANQYNGKAELPHSVFHGHKQLATKIRLWHQQGERC

LYTGKTISIHDLINNSNQFEVDHILPLSITFDDSLANKVLVYATANQEKGQRTPYQALDSMDDA

WSFRELKAFVRESKTLSNKKKEYLLTEEDISKFDVRKKFIERNLVDTRYASRVVLNALQEHFRA

HKIDTKVSVVRGQFTSQLRRHWGIEKTRDTYHHHAVDALIIAASSQLNLWKKQKNTLVSYSEDQ

LLDIETGELISDDEYKESVFKAPYQHFVDTLKSKEFEDSILFSYQVDSKFNRKISDATIYATRQ

AKVGKDKADETYVLGKIKDIYTQDGYDAFMKIYKKDKSKFLMYRHDPQTFEKVIEPILENYPNK

QINEKGKEVPCNPFLKYKEEHGYIRKYSKKGNGPEIKSLKYYDSKLGNHIDITPKDSNNKVVLQ

SVSPWRADVYFNKTTGKYEILGLKYADLQFEKGTGTYKISQEKYNDIKKKEGVDSDSEFKFTLY

-continued

KNDLLLVKDTETKEQQLFRFLSRTMPKQKHYVELKPYDKQKFEGGEALIKVLGNVANSGQCKKG

LGKSNISIYKVRTDVLGNQHIIKNEGDKPKLDF

SEQ ID NO: 347
MNAEHGKEGLLIMEENFQYRIGLDIGITSVGWAVLQNNSQDEPVRITDLGVRIFDVAENPKNGD

ALAAPRRDARTTRRRLRRRRHRLERIKFLLQENGLIEMDSFMERYYKGNLPDVYQLRYEGLDRK

LKDEELAQVLIHIAKHRGFRSTRKAETKEKEGGAVLKATTENQKIMQEKGYRTVGEMLYLDEAF

HTECLWNEKGYVLTPRNRPDDYKHTILRSMLVEEVHAIFAAQRAHGNQKATEGLEEAYVEIMTS

QRSFDMGPGLQPDGKPSPYAMEGFGDRVGKCTFEKDEYRAPKATYTAELFVALQKINHTKLIDE

FGTGRFFSEEERKTIIGLLLSSKELKYGTIRKKLNIDPSLKFNSLNYSAKKEGETEEERVLDTE

KAKFASMFWTYEYSKCLKDRTEEMPVGEKADLFDRIGEILTAYKNDDSRSSRLKELGLSGEEID

GLLDLSPAKYQRVSLKAMRKMQPYLEDGLIYDKACEAAGYDFRALNDGNKKHLLKGEEINAIVN

DITNPVVKRSVSQTIKVINAIIQKYGSPQAVNIELAREMSKNFQDRTNLEKEMKKRQQENERAK

QQIIELGKQNPTGQDILKYRLWNDQGGYCLYSGKKIPLEELFDGGYDIDHILPYSITFDDSYRN

KVLVTAQENRQKGNRTPYEYFGADEKRWEDYEASVRLLVRDYKKQQKLLKKNFTEEERKEFKER

NLNDTKYITRVVYNMIRQNLELEPFNHPEKKKQVWAVNGAVTSYLRKRWGLMQKDRSTDRHHAM

DAVVIACCTDGMIHKISRYMQGRELAYSRNFKFPDEETGEILNRDNFTREQWDEKFGVKVPLPW

NSFRDELDIRLLNEDPKNFLLTHADVQRELDYPGWMYGEEESPIEEGRYINYIRPLFVSRMPNH

KVTGSAHDATIRSARDYETRGVVITKVPLTDLKLNKDNEIEGYYDKDSDRLLYQALVRQLLLHG

NDGKKAFAEDFHKPKADGTEGPVVRKVKIEKKQTSGVMVRGGTGIAANGEMVRIDVFRENGKYY

FVPVYTADVVRKVLPNRAATHTKPYSEWRVMDDANFVFSLYSRDLIHVKSKKDIKTNLVNGGLL

LQKEIFAYYTGADIATASIAGFANDSNFKFRGLGIQSLEIFEKCQVDILGNISVVRHENRQEFH

SEQ ID NO: 348
MRVLGLDAGIASLGWALIEIEESNRGELSQGTIIGAGTWMFDAPEEKTQAGAKLKSEQRRTFRG

QRRVVRRRRQRMNEVRRILHSHGLLPSSDRDALKQPGLDPWRIRAEALDRLLGPVELAVALGHI

ARHRGFKSNSKGAKTNDPADDTSKMKRAVNETREKLARFGSAAKMLVEDESFVLRQTPTKNGAS

EIVRRFRNREGDYSRSLLRDDLAAEMRALFTAQARFQSAIATADLQTAFTKAAFFQRPLQDSEK

LVGPCPFEVDEKRAPKRGYSFELFRFLSRLNHVTLRDGKQERTLTRDELALAAADFGAAAKVSF

TALRKKLKLPETTVFVGVKADEESKLDVVARSGKAAEGTARLRSVIVDALGELAWGALLCSPEK

LDKIAEVISFRSDIGRISEGLAQAGCNAPLVDALTAAASDGRFDPFTGAGHISSKAARNILSGL

RQGMTYDKACCAADYDHTASRERGAFDVGGHGREALKRILQEERISRELVGSPTARKALIESIK

QVKAIVERYGVPDRIHVELARDVGKSIEEREEITRGIEKRNRQKDKLRGLFEKEVGRPPQDGAR

GKEELLRFELWSEQMGRCLYTDDYISPSQLVATDDAVQVDHILPWSRFADDSYANKTLCMAKAN

QDKKGRTPYEWFKAEKTDTEWDAFIVRVEALADMKGFKKRNYKLRNAEEAAAKFRNRNLNDTRW

ACRLLAEALKQLYPKGEKDKDGKERRRVFSRPGALTDRLRRAWGLQWMKKSTKGDRIPDDRHHA

LDAIVIAATTESLLQRATREVQEIEDKGLHYDLVKNVTPPWPGFREQAVEAVEKVFVARAERRR

ARGKAHDATIRHIAVREGEQRVYERRKVAELKLADLDRVKDAERNARLIEKLRNWIEAGSPKDD

PPLSPKGDPIFKVRLVTKSKVNIALDTGNPKRPGTVDRGEMARVDVFRKASKKGKYEYYLVPIY

PHDIATMKTPPIRAVQAYKPEDEWPEMDSSYEFCWSLVPMTYLQVISSKGEIFEGYYRGMNRSV

GAIQLSAHSNSSDVVQGIGARTLTEFKKFNVDRFGRKHEVERELRTWRGETWRGKAYI

SEQ ID NO: 349
MGNYYLGLDVGIGSIGWAVINIEKKRIEDFNVRIFKSGEIQEKNRNSRASQQCRRSRGLRRLYR

RKSHRKLRLKNYLSIIGLTTSEKIDYYYETADNNVIQLRNKGLSEKLTPEEIAACLIHICNNRG

-continued

```
YKDFYEVNVEDIEDPDERNEYKEEHDSIVLISNLMNEGGYCTPAEMICNCREFDEPNSVYRKFH

NSAASKNHYLITRHMLVKEVDLILENQSKYYGILDDKTIAKIKDIIFAQRDFEIGPGKNERFRR

FTGYLDSIGKCQFFKDQERGSRFTVIADIYAFVNVLSQYTYTNNRGESVFDTSFANDLINSALK

NGSMDKRELKAIAKSYHIDISDKNSDTSLTKCFKYIKVVKPLFEKYGYDWDKLIENYTDTDNNV

LNRIGIVLSQAQTPKRRREKLKALNIGLDDGLINELTKLKLSGTANVSYKYMQGSIEAFCEGDL

YGKYQAKFNKEIPDIDENAKPQKLPPFKNEDDCEFFKNPVVFRSINETRKLINAIIDKYGYPAA

VNIETADELNKTFEDRAIDTKRNNDNQKENDRIVKEIIECIKCDEVHARHLIEKYKLWEAQEGK

CLYSGETITKEDMLRDKDKLFEVDHIVPYSLILDNTINNKALVYAEENQKKGQRTPLMYMNEAQ

AADYRVRVNTMFKSKKCSKKKYQYLMLPDLNDQELLGGWRSRNLNDTRYICKYLVNYLRKNLRF

DRSYESSDEDDLKIRDHYRVFPVKSRFTSMFRRWWLNEKTWGRYDKAELKKLTYLDHAADAIII

ANCRPEYVVLAGEKLKLNKMYHQAGKRITPEYEQSKKACIDNLYKLFRMDRRTAEKLLSGHGRL

TPIIPNLSEEVDKRLWDKNIYEQFWKDDKDKKSCEELYRENVASLYKGDPKFASSLSMPVISLK

PDHKYRGTITGEEAIRVKEIDGKLIKLKRKSISEITAESINSIYTDDKILIDSLKTIFEQADYK

DVGDYLKKTNQHFFTTSSGKRVNKVTVIEKVPSRWLRKEIDDNNFSLLNDSSYYCIELYKDSKG

DNNLQGIAMSDIVHDRKTKKLYLKPDFNYPDDYYTHVMYIFPGDYLRIKSTSKKSGEQLKFEGY

FISVKNVNENSFRFISDNKPCAKDKRVSITKKDIVIKLAVDLMGKVQGENNGKGISCGEPLSLL

KEKN
```

SEQ ID NO: 350
```
MLSRQLLGASHLARPVSYSYNVQDNDVHCSYGERCFMRGKRYRIGIDVGLNSVGLAAVEVSDEN

SPVRLLNAQSVIHDGGVDPQKNKEAITRKNMSGVARRTRRMRRRKRERLHKLDMLLGKFGYPVI

EPESLDKPFEEWHVRAELATRYIEDDELRRESISIALRHMARHRGWRNPYRQVDSLISDNPYSK

QYGELKEKAKAYNDDATAAEEESTPAQLVVAMLDAGYAEAPRLRWRTGSKKPDAEGYLPVRLMQ

EDNANELKQIFRVQRVPADEWKPLFRSVFYAVSPKGSAEQRVGQDPLAPEQARALKASLAFQEY

RIANVITNLRIKDASAELRKLTVDEKQSIYDQLVSPSSEDITWSDLCDFLGFKRSQLKGVGSLT

EDGEERISSRPPRLTSVQRIYESDNKIRKPLVAWWKSASDNEHEAMIRLLSNTVDIDKVREDVA

YASAIEFIDGLDDDALTKLDSVDLPSGRAAYSVETLQKLTRQMLTTDDDLHEARKTLFNVTDSW

RPPADPIGEPLGNPSVDRVLKNVNRYLMNCQQRWGNPVSVNIEHVRSSFSSVAFARKDKREYEK

NNEKRSIFRSSLSEQLRADEQMEKVRESDLRRLEAIQRQNGQCLYCGRTITFRTCEMDHIVPRK

GVGSTNTRTNFAAVCAECNRMKSNTPFAIWARSEDAQTRGVSLAEAKKRVTMFTFNPKSYAPRE

VKAFKQAVIARLQQTEDDAAIDNRSIESVAWMADELHRRIDWYFNAKQYVNSASIDDAEAETMK

TTVSVFQGRVTASARRAAGIEGKIHFIGQQSKTRLDRRHHAVDASVIAMMNTAAAQTLMERESL

RESQRLIGLMPGERSWKEYPYEGTSRYESFHLWLDNMDVLLELLNDALDNDRIAVMQSQRYVLG

NSIAHDATIHPLEKVPLGSAMSADLIRRASTPALWCALTRLPDYDEKEGLPEDSHREIRVHDTR

YSADDEMGFFASQAAQIAVQEGSADIGSAIHHARVYRCWKTNAKGVRKYFYGMIRVFQTDLLRA

CHDDLFTVPLPPQSISMRYGEPRVVQALQSGNAQYLGSLVVGDEIEMDFSSLDVDGQIGEYLQF

FSQFSGGNLAWKHWVVDGFFNQTQLRIRPRYLAAEGLAKAFSDDVVPDGVQKIVTKQGWLPPVN

TASKTAVRIVRRNAFGEPRLSSAHHMPCSWQWRHE
```

SEQ ID NO: 351
```
MYSIGLDLGISSVGWSVIDERTGNVIDLGVRLFSAKNSEKNLERRTNRGGRRLIRRKTNRLKDA

KKILAAVGFYEDKSLKNSCPYQLRVKGLTEPLSRGEIYKVTLHILKKRGISYLDEVDTEAAKES

QDYKEQVRKNAQLLTKYTPGQIQLQRLKENNRVKTGINAQGNYQLNVFKVSAYANELATILKTQ
```

-continued

QAFYPNELTDDWIALFVQPGIAEEEAGLIYRKRPYYHGPGNEANNSPYGRWSDFQKTGEPATNIF

DKLIGKDFQGELRASGLSLSAQQYNLLNDLTNLKIDGEVPLSSEQKEYILTELMTKEFTRFGVN

DVVKLLGVKKERLSGWRLDKKGKPEIHTLKGYRNWRKIFAEAGIDLATLPTETIDCLAKVLTLN

TEREGIENTLAFELPELSESVKLLVLDRYKELSQSISTQSWHRFSLKTLHLLIPELMNATSEQN

TLLEQFQLKSDVRKRYSEYKKLPTKDVLAEIYNPTVNKTVSQAFKVIDALLVKYGKEQIRYITI

EMPRDDNEEDEKKRIKELHAKNSQRKNDSQSYFMQKSGWSQEKFQTTIQKNRRFLAKLLYYYEQ

DGICAYTGLPISPELLVSDSTEIDHIIPISISLDDSINNKVLVLSKANQVKGQQTPYDAWMDGS

FKKINGKFSNWDDYQKWVESRHFSHKKENNLLETRNIFDSEQVEKFLARNLNDTRYASRLVLNT

LQSFFTNQETKVRVVNGSFTHTLRKKWGADLDKTRETHHHHAVDATLCAVTSFVKVSRYHYAVK

EETGEKVMREIDFETGEIVNEMSYWEFKKSKKYERKTYQVKWPNFREQLKPVNLHPRIKFSHQV

DRKANRKLSDATIYSVREKTEVKTLKSGKQKITTDEYTIGKIKDIYTLDGWEAFKKKQDKLLMK

DLDEKTYERLLSIAETTPDFQEVEEKNGKVKRVKRSPFAVYCEENDIPAIQKYAKKNNGPLIRS

LKYYDGKLNKHINITKDSQGRPVEKTKNGRKVTLQSLKPYRYDIYQDLETKAYYTVQLYYSDLR

FVEGKYGITEKEYMKKVAEQTKGQVVRFCFSLQKNDGLEIEWKDSQRYDVRFYNFQSANSINFK

GLEQEMMPAENQFKQKPYNNGAINLNIAKYGKEGKKLRKFNTDILGKKHYLFYEKEPKNIIK

SEQ ID NO: 352

MYFYKNKENKLNKKVVLGLDLGIASVGWCLTDISQKEDNKFPIILHGVRLFETVDDSDDKLLNE

TRRKKRGQRRRNRRLFTRKRDFIKYLIDNNIIELEFDKNPKILVRNFIEKYINPFSKNLELKYK

SVTNLPIGFHNLRKAAINEKYKLDKSELIVLLYFYLSLRGAFFDNPEDTKSKEMNKNEIEIFDK

NESIKNAEFPIDKIIEFYKISGKIRSTINLKFGHQDYLKEIKQVFEKQNIDFMNYEKFAMEEKS

FFSRIRNYSEGPGNEKSFSKYGLYANENGNPELIINEKGQKIYTKIFKTLWESKIGKCSYDKKL

YRAPKNSFSAKVFDITNKLTDWKHKNEYISERLKRKILLSRFLNKDSKSAVEKILKEENIKFEN

LSEIAYNKDDNKINLPIINAYHSLTTIFKKHLINFENYLISNENDLSKLMSFYKQQSEKLFVPN

EKGSYEINQNNNVLHIFDAISNILNKFSTIQDRIRILEGYFEFSNLKKDVKSSEIYSEIAKLRE

FSGTSSLSFGAYYKFIPNLISEGSKNYSTISYEEKALQNQKNNFSHSNLFEKTWVEDLIASPTV

KRSLRQTMNLLKEIFKYSEKNNLEIEKIVVEVTRSSNNKHERKKIEGINKYRKEKYEELKKVYD

LPNENTTLLKKLWLLRQQQGYDAYSLRKIEANDVINKPWNYDIDHIVPRSISFDDSFSNLVIVN

KLDNAKKSNDLSAKQFIEKIYGIEKLKEAKENWGNWYLRNANGKAFNDKGKFIKLYTIDNLDEF

DNSDFINRNLSDTSYITNALVNHLTFSNSKYKYSVVSVNGKQTSNLRNQIAFVGIKNNKETERE

WKRPEGFKSINSNDFLIREEGKNDVKDDVLIKDRSFNGHHAEDAYFITIISQYFRSFKRIERLN

VNYRKETRELDDLEKNNIKFKEKASFDNFLLINALDELNEKLNQMRFSRMVITKKNTQLFNETL

YSGKYDKGKNTIKKVEKLNLLDNRTDKIKKIEEFFDEDKLKENELTKLHIFNHDKNLYETLKII

WNEVKIEIKNKNLNEKNYFKYFVNKKLQEGKISFNEWVPILDNDFKIIRKIRYIKFSSEEKETD

EIIFSQSNFLKIDQRQNFSFHNTLYWVQIWVYKNQKDQYCFISIDARNSKFEKDEIKINYEKLK

TQKEKLQIINEEPILKINKGDLFENEEKELFYIVGRDEKPQKLEIKYILGKKIKDQKQIQKPVK

KYFPNWKKVNLTYMGEIFKK

SEQ ID NO: 353

MDNKNYRIGIDVGLNSIGFCAVEVDQHDTPLGFLNLSVYRHDAGIDPNGKKTNTTRLAMSGVAR

RTRRLFRKRKRRLAALDRFIEAQGWTLPDHADYKDPYTPWLVRAELAQTPIRDENDLHEKLAIA

VRHIARHRGWRSPWVPVRSLHVEQPPSDQYLALKERVEAKTLLQMPEGATPAEMVVALDLSVDV

NLRPKNREKTDTRPENKKPGFLGGKLMQSDNANELRKIAKIQGLDDALLRELIELVFAADSPKG

ASGELVGYDVLPGQHGKRRAEKAHPAFQRYRIASIVSNLRIRHLGSGADERLDVETQKRVFEYL

-continued

LNAKPTADITWSDVAEEIGVERNLLMGTATQTADGERASAKPPVDVTNVAFATCKIKPLKEWWL

NADYEARCVMVSALSHAEKLTEGTAAEVEVAEFLQNLSDEDNEKLDSFSLPIGRAAYSVDSLER

LTKRMIENGEDLFEARVNEFGVSEDWRPPAEPIGARVGNPAVDRVLKAVNRYLMAAEAEWGAPL

SVNIEHVREGFISKRQAVEIDRENQKRYQRNQAVRSQIADHINATSGVRGSDVTRYLAIQRQNG

ECLYCGTAITFVNSEMDHIVPRAGLGSTNTRDNLVATCERCNKSKSNKPFAVWAAECGIPGVSV

AEALKRVDFWIADGFASSKEHRELQKGVKDRLKRKVSDPEIDNRSMESVAWMARELAHRVQYYF

DEKHTGTKVRVFRGSLTSAARKASGFESRVNFIGGNGKTRLDRRHHAMDAATVAMLRNSVAKTL

VLRGNIRASERAIGAAETWKSFRGENVADRQIFESWSENMRVLVEKFNLALYNDEVSIFSSLRL

QLGNGKAHDDTITKLQMHKVGDAWSLTEIDRASTPALWCALTRQPDFTWKDGLPANEDRTIIVN

GTHYGPLDKVGIFGKAAASLLVRGGSVDIGSAIHHARIYRIAGKKPTYGMVRVFAPDLLRYRNE

DLFNVELPPQSVSMRYAEPKVREAIREGKAEYLGWLVVGDELLLDLSSETSGQIAELQQDFPGT

THWTVAGFFSPSRLRLRPVYLAQEGLGEDVSEGSKSIIAGQGWRPAVNKVFGSAMPEVIRRDGL

GRKRRFSYSGLPVSWQG

SEQ ID NO: 354
MRLGLDIGTSSIGWWLYETDGAGSDARITGVVDGGVRIFSDGRDPKSGASLAVDRRAARAMRRR

RDRYLRRRATLMKVLAETGLMPADPAEAKALEALDPFALRAAGLDEPLPLPHLGRALFHLNQRR

GFKSNRKTDRGDNESGKIKDATARLDMEMMANGARTYGEFLHKRRQKATDPRHVPSVRTRLSIA

NRGGPDGKEEAGYDFYPDRRHLEEEFHKLWAAQGAHHPELTETLRDLLFEKIFFQRPLKEPEVG

LCLFSGHHGVPPKDPRLPKAHPLTQRRVLYETVNQLRVTADGREARPLTREERDQVIHALDNKK

PTKSLSSMVLKLPALAKVLKLRDGERFTLETGVRDAIACDPLRASPAHPDRFGPRWSILDADAQ

WEVISRIRRVQSDAEHAALVDWLTEAHGLDRAHAEATAHAPLPDGYGRLGLTATTRILYQLTAD

VVTYADAVKACGWHHSDGRTGECFDRLPYYGEVLERHVIPGSYHPDDDDITRFGRITNPTVHIG

LNQLRRLVNRIIETHGKPHQIVVELARDLKKSEEQKRADIKRIRDTTEAAKKRSEKLEELEIED

NGRNRMLLRLWEDLNPDDAMRRFCPYTGTRISAAMIFDGSCDVDHILPYSRTLDDSFPNRTLCL

REANRQKRNQTPWQAWGDTPHWHAIAANLKNLPENKRWRFAPDAMTRFEGENGFLDRALKDTQY

LARISRSYLDTLFTKGGHVWVVPGRFTEMLRRHWGLNSLLSDAGRGAVKAKNRTDHRHHAIDAA

VIAATDPGLLNRISRAAGQGEAAGQSAELIARDTPPPWEGFRDDLRVRLDRIIVSHRADHGRID

HAARKQGRDSTAGQLHQETAYSIVDDIHVASRTDLLSLKPAQLLDEPGRSGQVRDPQLRKALRV

ATGGKTGKDFENALRYFASKPGPYQAIRRVRIIKPLQAQARVPVPAQDPIKAYQGGSNHLFEIW

RLPDGEIEAQVITSFEAHTLEGEKRPHPAAKRLLRVHKGDMVALERDGRRVVGHVQKMDIANGL

FIVPHNEANADTRNNDKSDPFKWIQIGARPAIASGIRRVSVDEIGRLRDGGTRPI

SEQ ID NO: 355
MLHCIAVIRVPPSEEPGFFETHADSCALCHHGCMTYAANDKAIRYRVGIDVGLRSIGFCAVEVD

DEDHPIRILNSVVHVHDAGTGGPGETESLRKRSGVAARARRRGRAEKQRLKKLDVLLEELGWGV

SSNELLDSHAPWHIRKRLVSEYIEDETERRQCLSVAMAHIARHRGWRNSFSKVDTLLLEQAPSD

RMQGLKERVEDRTGLQFSEEVTQGELVATLLEHDGDVTIRGFVRKGGKATKVHGVLEGKYMQSD

LVAELRQICRTQRVSETTFEKLVLSIFHSKEPAPSAARQRERVGLDELQLALDPAAKQPRAERA

HPAFQKFKVVATLANMRIREQSAGERSLTSEELNRVARYLLNHTESESPTWDDVARKLEVPRHR

LRGSSRASLETGGGLTYPPVDDTTVRVMSAEVDWLADWWDCANDESRGHMIDAISNGCGSEPDD

VEDEEVNELISSATAEDMLKLELLAKKLPSGRVAYSLKTLREVTAAILETGDDLSQAITRLYGV

DPGWVPTPAPIEAPVGNPSVDRVLKQVARWLKFASKRWGVPQTVNIEHTREGLKSASLLEEERE

-continued

RWERFEARREIRQKEMYKRLGISGPFRRSDQVRYEILDLQDCACLYCGNEINFQTFEVDHIIPR

VDASSDSRRTNLAAVCHSCNSAKGGLAFGQWVKRGDCPSGVSLENAIKRVRSWSKDRLGLTEKA

MGKRKSEVISRLKTEMPYEEFDGRSMESVAWMAIELKKRIEGYFNSDRPEGCAAVQVNAYSGRL

TACARRAAHVDKRVRLIRLKGDDGHHKNRFDRRNHAMDALVIALMTPAIARTIAVREDRREAQQ

LTRAFESWKNFLGSEERMQDRWESWIGDVEYACDRLNELIDADKIPVTENLRLRNSGKLHADQP

ESLKKARRGSKRPRPQRYVLGDALPADVINRVTDPGLWTALVRAPGFDSQLGLPADLNRGLKLR

GKRISADFPIDYFPTDSPALAVQGGYVGLEFHHARLYRIIGPKEKVKYALLRVCAIDLCGIDCD

DLFEVELKPSSISMRTADAKLKEAMGNGSAKQIGWLVLGDEIQIDPTKFPKQSIGKFLKECGPV

SSWRVSALDTPSKITLKPRLLSNEPLLKTSRVGGHESDLVVAECVEKIMKKTGWVVEINALCQS

GLIRVIRRNALGEVRTSPKSGLPISLNLR

SEQ ID NO: 356
MRYRVGLDLGTASVGAAVFSMDEQGNPMELIWHYERLFSEPLVPDMGQLKPKKAARRLARQQRR

QIDRRASRLRRIAIVSRRLGIAPGRNDSGVHGNDVPTLRAMAVNERIELGQLRAVLLRMGKKRG

YGGTFKAVRKVGEAGEVASGASRLEEEMVALASVQNKDSVTVGEYLAARVEHGLPSKLKVAANN

EYYAPEYALFRQYLGLPAIKGRPDCLPNMYALRHQIEHEFERIWATQSQFHDVMKDHGVKEEIR

NAIFFQRPLKSPADKVGRCSLQTNLPRAPRAQIAAQNFRIEKQMADLRWGMGRRAEMLNDHQKA

VIRELLNQQKELSFRKIYKELERAGCPGPEGKGLNMDRAALGGRDDLSGNTTLAAWRKLGLEDR

WQELDEVTQIQVINFLADLGSPEQLDTDDWSCRFMGKNGRPRNFSDEFVAFMNELRMTDGFDRL

SKMGFEGGRSSYSIKALKALTEWMIAPHWRETPETHRVDEEAAIRECYPESLATPAQGGRQSKL

EPPPLTGNEVVDVALRQVRHTINMMIDDLGSVPAQIVVEMAREMKGGVTRRNDIEKQNKRFASE

RKKAAQSIEENGKTPTPARILRYQLWIEQGHQCPYCESNISLEQALSGAYTNFEHILPRTLTQI

GRKRSELVLAHRECNDEKGNRTPYQAFGHDDRRWRIVEQRANALPKKSSRKTRLLLLKDFEGEA

LTDESIDEFADRQLHESSWLAKVTTQWLSSLGSDVYVSRGSLTAELRRRWGLDTVIPQVRFESG

MPVVDEEGAEITPEEFEKFRLQWEGHRVTREMRTDRRPDKRIDHRHHLVDAIVTALTSRSLYQQ

YAKAWKVADEKQRHGRVDVKVELPMPILTIRDIALEAVRSVRISHKPDRYPDGRFFEATAYGIA

QRLDERSGEKVDWLVSRKSLTDLAPEKKSIDVDKVRANISRIVGEAIRLHISNIFEKRVSKGMT

PQQALREPIEFQGNILRKVRCFYSKADDCVRIEHSSRRGHHYKMLLNDGFAYMEVPCKEGILYG

VPNLVRPSEAVGIKRAPESGDFIRFYKGDTVKNIKTGRVYTIKQILGDGGGKLILTPVTETKPA

DLLSAKWGRLKVGGRNIHLLRLCAE

SEQ ID NO: 357
MIGEHVRGGCLFDDHWTPNWGAFRLPNTVRTFTKAENPKDGSSLAEPRRQARGLRRRLRRKTQR

LEDLRRLLAKEGVLSLSDLETLFRETPAKDPYQLRAEGLDRPLSFPEWVRVLYHITKHRGFQSN

RRNPVEDGQERSRQEEEGKLLSGVGENERLLREGGYRTAGEMLARDPKFQDHRRNRAGDYSHTL

SRSLLLEEARRLFQSQRTLGNPHASSNLEEAFLHLVAFQNPFASGEDIRNKAGHCSLEPDQIRA

PRRSASAETFMLLQKTGNLRLIHRRTGEERPLTDKEREQIHLLAWKQEKVTHKTLRRHLEIPEE

WLFTGLPYHRSGDKAEEKLFVHLAGIHEIRKALDKGPDPAVWDTLRSRRDLLDSIADTLTFYKN

EDEILPRLESLGLSPENARALAPLSFSGTAHLSLSALGKLLPHLEEGKSYTQARADAGYAAPPP

DRHPKLPPLEEADWRNPVVFRALTQTRKVVNALVRRYGPPWCIHLETARELSQPAKVRRRIETE

QQANEKKQQAEREFLDIVGTAPGPGDLLKMRLWREQGGFCPYCEEYLNPTRLAEPGYAEMDHI

LPYSRSLDNGWHNRVLVHGKDNRDKGNRTPFEAFGGDTARWDRLVAWVQASHLSAPKKRNLLRE

DFGEEAERELKDRNLTDTRFITKTAATLLRDRLTFHPEAPKDPVMTLNGRLTAFLRKQWGLHKN

RKNGDLHHALDAAVLAVASRSFVYRLSSHNAAWGELPRGREAENGFSLPYPAFRSEVLARLCPT

-continued

REEILLRLDQGGVGYDEAFRNGLRPVFVSRAPSRRLRGKAHMETLRSPKWKDHPEGPRTASRIP

LKDLNLEKLERMVGKDRDRKLYEALRERLAAFGGNGKKAFVAPFRKPCRSGEGPLVRSLRIFDS

GYSGVELRDGGEVYAVADHESMVRVDVYAKKNRFYLVPVYVADVARGIVKNRAIVAHKSEEEWD

LVDGSFDFRFSLFPGDLVEIEKKDGAYLGYYKSCHRGDGRLLLDRHDRMPRESDCGTFYVSTRK

DVLSMSKYQVDPLGEIRLVGSEKPPFVL

SEQ ID NO: 358
MEKKRKVTLGFDLGIASVGWAIVDSETNQVYKLGSRLFDAPDTNLERRTQRGTRRLLRRRKYRN

QKFYNLVKRTEVFGLSSREAIENRFRELSIKYPNIIELKTKALSQEVCPDEIAWILHDYLKNRG

YFYDEKETKEDFDQQTVESMPSYKLNEFYKKYGYFKGALSQPTESEMKDNKDLKEAFFFDFSNK

EWLKEINYFFNVQKNILSETFIEEFKKIFSFTRDISKGPGSDNMPSPYGIFGEFGDNGQGGRYE

HIWDKNIGKCSIFTNEQRAPKYLPSALIFNFLNELANIRLYSTDKKNIQPLWKLSSVDKLNILL

NLFNLPISEKKKKLTSTNINDIVKKESIKSIMISVEDIDMIKDEWAGKEPNVYGVGLSGLNIEE

SAKENKFKFQDLKILNVLINLLDNVGIKFEFKDRNDIIKNLELLDNLYLFLIYQKESNNKDSSI

DLFIAKNESLNIENLKLKLKEFLLGAGNEFENHNSKTHSLSKKAIDEILPKLLDNNEGWNLEAI

KNYDEEIKSQIEDNSSLMAKQDKKYLNDNFLKDAILPPNVKVTFQQAILIFNKIIQKFSKDFEI

DKVVIELAREMTQDQENDALKGIAKAQKSKKSLVEERLEANNIDKSVFNDKYEKLIYKIFLWIS

QDFKDPYTGAQISVNEIVNNKVEIDHIIPYSLCFDDSSANKVLVHKQSNQEKSNSLPYEYIKQG

HSGWNWDEFTKYVKRVFVNNVDSILSKKERLKKSENLLTASYDGYDKLGFLARNLNDTRYATIL

FRDQLNNYAEHHLIDNKKMFKVIAMNGAVTSFIRKNMSYDNKLRLKDRSDFSHHAYDAAIIALF

SNKTKTLYNLIDPSLNGIISKRSEGYWVIEDRYTGEIKELKKEDWTSIKNNVQARKIAKEIEEY

LIDLDDEVFFSRKTKRKTNRQLYNETIYGIATKTDEDGITNYYKKEKFSILDDKDIYLRLLRER

EKFVINQSNPEVIDQIIEIIESYGKENNIPSRDEAINIKYTKNKINYNLYLKQYMRSLTKSLDQ

FSEEFINQMIANKTFVLYNPTKNTTRKIKFLRLVNDVKINDIRKNQVINKFNGKNNEPKAFYEN

INSLGAIVFKNSANNFKTLSINTQIAIFGDKNWDIEDFKTYNMEKIEKYKEIYGIDKTYNFHSF

IFPGTILLDKQNKEFYYISSIQTVRDIIEIKFLNKIEFKDENKNQDTSKTPKRLMFGIKSIMNN

YEQVDISPFGINKKIFE

SEQ ID NO: 359
MGYRIGLDVGITSTGYAVLKTDKNGLPYKILTLDSVIYPRAENPQTGASLAEPRRIKRGLRRRT

RRTKFRKQRTQQLFIHSGLLSKPEIEQILATPQAKYSVYELRVAGLDRRLTNSELFRVLYFFIG

HRGFKSNRKAELNPENEADKKQMGQLLNSIEEIRKAIAEKGYRTVGELYLKDPKYNDHKRNKGY

IDGYLSTPNRQMLVDEIKQILDKQRELGNEKLTDEFYATYLLGDENRAGIFQAQRDFDEGPGAG

PYAGDQIKKMVGKDIFEPTEDRAAKATYTFQYFNLLQKMTSLNYQNTTGDTWHTLNGLDRQAII

DAVFAKAEKPTKTYKPTDFGELRKLLKLPDDARFNLVNYGSLQTQKEIETVEKKTRFVDFKAYH

DLVKVLPEEMWQSRQLLDHIGTALTLYSSDKRRRYFAEELNLPAELIEKLLPLNFSKFGHLSI

KSMQNIIPYLEMGQVYSEATTNTGYDFRKKQISKDTIREEITNPVVRRAVTKTIKIVEQIIRRY

GKPDGINIELARELGRNFKERGDIQKRQDKNRQTNDKIAAELTELGIPVNGQNIIRYKLHKEQN

GVDPYTGDQIPFERAFSEGYEVDHIIPYSISWDDSYTNKVLTSAKCNREKGNRIPMVYLANNEQ

RLNALTNIADNIIRNSRKRQKLLKQKLSDEELKDWKQRNINDTRFITRVLYNYFRQAIEFNPEL

EKKQRVLPLNGEVTSKIRSRWGFLKVREDGDLHHAIDATVIAAITPKFIQQVTKYSQHQEVKNN

QALWHDAEIKDAEYAAEAQRMDADLFNKIFNGFPLPWPEFLDELLARISDNPVEMMKSRSWNTY

TPIEIAKLKPVFVVRLANHKISGPAHLDTIRSAKLFDEKGIVLSRVSITKLKINKKGQVATGDG

-continued

IYDPENSNNGDKVVYSAIRQALEAHNGSGELAFPDGYLEYVDHGTKKLVRKVRVAKKVSLPVRL

KNKAAADNGSMVRIDVFNTGKKFVFVPIYIKDTVEQVLPNKAIARGKSLWYQITESDQFCFSLY

PGDMVHIESKTGIKPKYSNKENNTSVVPIKNFYGYFDGADIATASILVRAHDSSYTARSIGIAG

LLKFEKYQVDYFGRYHKVHEKKRQLFVKRDE

SEQ ID NO: 360

MQKNINTKQNHIYIKQAQKIKEKLGDKPYRIGLDLGVGSIGFAIVSMEENDGNVLLPKEIIMVG

SRIFKASAGAADRKLSRGQRNNHRHTRERMRYLWKVLAEQKLALPVPADLDRKENSSEGETSAK

RFLGDVLQKDIYELRVKSLDERLSLQELGYVLYHIAGHRGSSAIRTFENDSEEAQKENTENKKI

AGNIKRLMAKKNYRTYGEYLYKEFFENKEKHKREKISNAANNHKFSPTRDLVIKEAEAILKKQA

GKDGFHKELTEEYIEKLTKAIGYESEKLIPESGFCPYLKDEKRLPASHKLNEERRLWETLNNAR

YSDPIVDIVTGEITGYYEKQFTKEQKQKLFDYLLTGSELTPAQTKKLLGLKNTNFEDIILQGRD

KKAQKIKGYKLIKLESMPFWARLSEAQQDSFLYDWNSCPDEKLLTEKLSNEYHLTEEEIDNAFN

EIVLSSSYAPLGKSAMLIILEKIKNDLSYTEAVEEALKEGKLTKEKQAIKDRLPYYGAVLQEST

QKIIAKGFSPQFKDKGYKTPHTNKYELEYGRIANPVVHQTLNELRKLVNEIIDILGKKPCEIGL

ETARELKKSAEDRSKLSREQNDNESNRNRIYEIYIRPQQQVIITRRENPRNYILKFELLEEQKS

QCPFCGGQISPNDIINNQADIEHLFPIAESEDNGRNNLVISHSACNADKAKRSPWAAFASAAKD

SKYDYNRILSNVKENIPHKAWRFNQGAFEKFIENKPMAARFKTDNSYISKVAHKYLACLFEKPN

IICVKGSLTAQLRMAWGLQGLMIPFAKQLITEKESESFNKDVNSNKKIRLDNRHHALDAIVIAY

ASRGYGNLLNKMAGKDYKINYSERNWLSKILLPPNNIVWENIDADLESFESSVKTALKNAFISV

KHDHSDNGELVKGTMYKIFYSERGYTLTTYKKLSALKLTDPQKKKTPKDFLETALLKFKGRESE

MKNEKIKSAIENNKRLFDVIQDNLEKAKKLLEEENEKSKAEGKKEKNINDASIYQKAISLSGDK

YVQLSKKEPGKFFAISKPTPTTTGYGYDTGDSLCVDLYYDNKGKLCGEIIRKIDAQQKNPLKYK

EQGFTLFERIYGGDILEVDFDIHSDKNSFRNNTGSAPENRVFIKVGTFTEITNNNIQIWFGNII

KSTGGQDDSFTINSMQQYNPRKLILSSCGFIKYRSPILKNKEG

SEQ ID NO: 361

MAAFKPNPINYILGLDIGIASVGWAMVEIDEDENPICLIDLGVRVFERAEVPKTGDSLAMARRL

ARSVRRLTRRRAHRLLRARRLLKREGVLQAADFDENGLIKSLPNTPWQLRAAALDRKLTPLEWS

AVLLHLIKHRGYLSQRKNEGETADKELGALLKGVADNAHALQTGDFRTPAELALNKFEKESGHI

RNQRGDYSHTFSRKDLQAELILLFEKQKEFGNPHVSGGLKEGIETLLMTQRPALSGDAVQKMLG

HCTFEPAEPKAAKNTYTAERFIWLTKLNNLRILEQGSERPLTDTERATLMDEPYRKSKLTYAQA

RKLLGLEDTAFFKGLRYGKDNAEASTLMEMKAYHAISRALEKEGLKDKKSPLNLSPELQDEIGT

AFSLFKTDEDITGRLKDRIQPEILEALLKHISFDKFVQISLKALRRIVPLMEQGKRYDEACAEI

YGDHYGKKNTEEKIYLPPIPADEIRNPVVLRALSQARKVINGVVRRYGSPARIHIETAREVGKS

FKDRKEIEKRQEENRKDREKAAAKFREYFPNFVGEPKSKDILKLRLYEQQHGKCLYSGKEINLG

RLNEKGYVEIDHALPFSRTWDDSFNNKVLVLGSENQNKGNQTPYEYFNGKDNSREWQEFKARVE

TSRFPRSKKQRILLQKFDEDGFKERNLNDTRYVNRFLCQFVADRMRLTGKGKKRVFASNGQITN

LLRGFWGLRKVRAENDRHHALDAVVVACSTVAMQQKITRFVRYKEMNAFDGKTIDKETGEVLHQ

KTHFPQPWEFFAQEVMIRVFGKPDGKPEFEEADTPEKLRTLLAEKLSSRPEAVHEYVTPLFVSR

APNRKMSGQGHMETVKSAKRLDEGVSVLRVPLTQLKLKDLEKMVNREREPKLYEALKARLEAHK

DDPAKAFAEPFYKYDKAGNRTQQVKAVRVEQVQKTGVWVRNHNGIADNATMVRVDVFEKGDKYY

LVPIYSWQVAKGILPDRAVVQGKDEEDWQLIDDSFNFKFSLHPNDLVEVITKKARMFGYFASCH

RGTGNINIRIHDLDHKIGKNGILEGIGVKTALSFQKYQIDELGKEIRPCRLKKRPPVR

SEQ ID NO: 362

MQTTNLSYILGLDLGIASVGWAVVEINENEDPIGLIDVGVRIFERAEVPKTGESLALSRRLARS

TRRLIRRRAHRLLLAKRFLKREGILSTIDLEKGLPNQAWELRVAGLERRLSAIEWGAVLLHLIK

HRGYLSKRKNESQTNNKELGALLSGVAQNHQLLQSDDYRTPAELALKKFAKEEGHIRNQRGAYT

HTFNRLDLLAELNLLFAQQHQFGNPHCKEHIQQYMTELLMWQKPALSGEAILKMLGKCTHEKNE

FKAAKHTYSAERFVWLTKLNNLRILEDGAERALNEEERQLLINHPYEKSKLTYAQVRKLLGLSE

QAIFKHLRYSKENAESATFMELKAWHAIRKALENQGLKDTWQDLAKKPDLLDEIGTAFSLYKTD

EDIQQYLTNKVPNSVINALLVSLNFDKFIELSLKSLRKILPLMEQGKRYDQACREIYGHHYGEA

NQKTSQLLPAIPAQEIRNPVVLRTLSQARKVINAIIRQYGSPARVHIETGRELGKSFKERREIQ

KQQEDNRTKRESAVQKFKELFSDFSSEPKSKDILKFRLYEQQHGKCLYSGKEINIHRLNEKGYV

EIDHALPFSRTWDDSFNNKVLVLASENQNKGNQTPYEWLQGKINSERWKNFVALVLGSQCSAAK

KQRLLTQVIDDNKFIDRNLNDTRYIARFLSNYIQENLLLVGKNKKNVFTPNGQITALLRSRWGL

IKARENNNRHHALDAIVVACATPSMQQKITRFIRFKEVHPYKIENRYEMVDQESGEIISPHFPE

PWAYFRQEVNIRVFDNHPDTVLKEMLPDRPQANHQFVQPLFVSRAPTRKMSGQGHMETIKSAKR

LAEGISVLRIPLTQLKPNLLENMVNKEREPALYAGLKARLAEFNQDPAKAFATPFYKQGGQQVK

AIRVEQVQKSGVLVRENNGVADNASIVRTDVFIKNNKFFLVPIYTWQVAKGILPNKAIVAHKNE

DEWEEMDEGAKFKFSLFPNDLVELKTKKEYFFGYYIGLDRATGNISLKEHDGEISKGKDGVYRV

GVKLALSFEKYQVDELGKNRQICRPQQRQPVR

SEQ ID NO: 363

MGIRFAFDLGTNSIGWAVWRTGPGVFGEDTAASLDGSGVLIFKDGRNPKDGQSLATMRRVPRQS

RKRRDRFVLRRRDLLAALRKAGLFPVDVEEGRRLAATDPYHLRAKALDESLTPHEMGRVIFHLN

QRRGFRSNRKADRQDREKGKIAEGSKRLAETLAATNCRTLGEFLWSRHRGTPRTRSPTRIRMEG

EGAKALYAFYPTREMVRAEFERLWTAQSRFAPDLLTPERHEEIAGILFRQRDLAPPKIGCCTFE

PSERRLPRALPSVEARGIYERLAHLRITTGPVSDRGLTRPERDVLASALLAGKSLTFKAVRKTL

KILPHALVNFEEAGEKGLDGALTAKLLSKPDHYGAAWHGLSFAEKDTFVGKLLDEADEERLIRR

LVTENRLSEDAARRCASIPLADGYGRLGRTANTEILAALVEETDETGTVVTYAEAVRRAGERTG

RNWHHSDERDGVILDRLPYYGEILQRHVVPGSGEPEEKNEAARWGRLANPTVHIGLNQLRKVVN

RLIAAHGRPDQIVVELARELKLNREQKERLDRENRKNREENERRTAILAEHGQRDTAENKIRLR

LFEEQARANAGIALCPYTGRAIGIAELFTSEVEIDHILPVSLTLDDSLANRVLCRREANREKRR

QTPFQAFGATPAWNDIVARAAKLPPNKRWRFDPAALERFEREGGFLGRQLNETKYLSRLAKIYL

GKICDPDRVYVTPGTLTGLLRARWGLNSILSDSNFKNRSDHRHHAVDAVVIGVLTRGMIQRIAH

DAARAEDQDLDRVFRDVPVPFEDFRDHVRERVSTITVAVKPEHGKGGALHEDTSYGLVPDTDPN

AALGNLVVRKPIRSLTAGEVDRVRDRALRARLGALAAPFRDESGRVRDAKGLAQALEAFGAENG

IRRVRILKPDASVVTIADRRTGVPYRAVAPGENHHVDIVQMRDGSWRGFAASVFEVNRPGWRPE

WEVKKLGGKLVMRLHKGDMVELSDKDGQRRVKVVQQIEISANRVRLSPHNDGGKLQDRHADADD

PFRWDLATIPLLKDRGCVAVRVDPIGVVTLRRSNV

SEQ ID NO: 364

MMEVFMGRLVLGLDIGITSVGFGIIDLDESEIVDYGVRLFKEGTAAENETRRTKRGGRRLKRRR

VTRREDMLHLLKQAGIISTSFHPLNNPYDVRVKGLNERLNGEELATALLHLCKHRGSSVETIED

DEAKAKEAGETKKVLSMNDQLLKSGKYVCEIQKERLRTNGHIRGHENNFKTRAYVDEAFQILSH

QDLSNELKSAIITIISRKRMYYDGPGGPLSPTPYGRYTYFGQKEPIDLIEKMRGKCSLFPNEPR

APKLAYSAELFNLLNDLNNLSIEGEKLTSEQKAMILKIVHEKGKITPKQLAKEVGVSLEQIRGF

-continued

RIDTKGSPLLSELTGYKMIREVLEKSNDEHLEDHVFYDEIAEILTKTKDIEGRKKQISELSSDL
NEESVHQLAGLTKFTAYHSLSFKALRLINEEMLKTELNQMQSITLFGLKQNNELSVKGMKNIQA
DDTAILSPVAKRAQRETFKVVNRLREIYGEFDSIVVEMAREKNSEEQRKAIRERQKFFEMRNKQ
VADIIGDDRKINAKLREKLVLYQEQDGKTAYSLEPIDLKLLIDDPNAYEVDHIIPISISLDDSI
TNKVLVTHRENQEKGNLTPISAFVKGRFTKGSLAQYKAYCLKLKEKNIKTNKGYRKKVEQYLLN
ENDIYKYDIQKEFINRNLVDTSYASRVVLNTLTTYFKQNEIPTKVFTVKGSLTNAFRRKINLKK
DRDEDYGHHAIDALIIASMPKMRLLSTIFSRYKIEDIYDESTGEVFSSGDDSMYYDDRYFAFIA
SLKAIKVRKFSHKIDTKPNRSVADETIYSTRVIDGKEKVVKKYKDIYDPKFTALAEDILNNAYQ
EKYLMALHDPQTFDQIVKVVNYYFEEMSKSEKYFTKDKKGRIKISGMNPLSLYRDEHGMLKKYS
KKGDGPAITQMKYFDGVLGNHIDISAHYQVRDKKVVLQQISPYRTDFYYSKENGYKFVTIRYKD
VRWSEKKKKYVIDQQDYAMKKAEKKIDDTYEFQFSMHRDELIGITKAEGEALIYPDETWHNFNF
FFHAGETPEILKFTATNNDKSNKIEVKPIHCYCKMRLMPTISKKIVRIDKYATDVVGNLYKVKK
NTLKFEFD

SEQ ID NO: 365
MKKILGVDLGITSFGYAILQETGKDLYRCLDNSVVMRNNPYDEKSGESSQSIRSTQKSMRRLIE
KRKKRIRCVAQTMERYGILDYSETMKINDPKNNPIKNRWQLRAVDAWKRPLSPQELFAIFAHMA
KHRGYKSIATEDLIYELELELGLNDPEKESEKKADERRQVYNALRHLEELRKKYGGETIAQTIH
RAVEAGDLRSYRNHDDYEKMIRREDIEEEIEKVLLRQAELGALGLPEEQVSELIDELKACITDQ
EMPTIDESLFGKCTFYKDELAAPAYSYLYDLYRLYKKLADLNIDGYEVTQEDREKVIEWVEKKI
AQGKNLKKITHKDLRKILGLAPEQKIFGVEDERIVKGKKEPRTFVPFFFLADIAKFKELFASIQ
KHPDALQIFRELAEILQRSKTPQEALDRLRALMAGKGIDTDDRELLELFKNKRSGTRELSHRYI
LEALPLFLEGYDEKEVQRILGFDDREDYSRYPKSLRHLHLREGNLFEKEENPINNHAVKSLASW
ALGLIADLSWRYGPFDEIILETTRDALPEKIRKEIDKAMREREKALDKIIGKYKKEFPSIDKRL
ARKIQLWERQKGLDLYSGKVINLSQLLDGSADIEHIVPQSLGGLSTDYNTIVTLKSVNAAKGNR
LPGDWLAGNPDYRERIGMLSEKGLIDWKKRKNLLAQSLDEIYTENTHSKGIRATSYLEALVAQV
LKRYYPFPDPELRKNGIGVRMIPGKVTSKTRSLLGIKSKSRETNFHHAEDALILSTLTRGWQNR
LHRMLRDNYGKSEAELKELWKKYMPHIEGLTLADYIDEAFRRFMSKGEESLFYRDMFDTIRSIS
YWVDKKPLSASSHKETVYSSRHEVPTLRKNILEAFDSLNVIKDRHKLTTEEFMKRYDKEIRQKL
WLHRIGNTNDESYRAVEERATQIAQILTRYQLMDAQNDKEIDEKFQQALKELITSPIEVTGKLL
RKMRFVYDKLNAMQIDRGLVETDKNMLGIHISKGPNEKLIFRRMDVNNAHELQKERSGILCYLN
EMLFIFNKKGLIHYGCLRSYLEKGQGSKYIALFNPRFPANPKAQPSKFTSDSKIKQVGIGSATG
IIKAHLDLDGHVRSYEVFGTLPEGSIEWFKEESGYGRVEDDPHH

SEQ ID NO: 366
MRPIEPWILGLDIGTDSLGWAVFSCEEKGPPTAKELLGGGVRLFDSGRDAKDHTSRQAERGAFR
RARRQTRTWPWRRDRLIALFQAAGLTPPAAETRQIALALRREAVSRPLAPDALWAALLHLAHHR
GFRSNRIDKRERAAAKALAKAKPAKATAKATAPAKEADDEAGFWEGAEAALRQRMAASGAPTVG
ALLADDLDRGQPVRMRYNQSDRDGVVAPTRALIAEELAEIVARQSSAYPGLDWPAVTRLVLDQR
PLRSKGAGPCAFLPGEDRALRALPTVQDFIIRQTLANLRLPSTSADEPRPLTDEEHAKALALLS
TARFVEWPALRRALGLKRGVKFTAETERNGAKQAARGTAGNLTEAILAPLIPGWSGWDLDRKDR
VFSDLWAARQDRSALLALIGDPRGPTRVTEDETAEAVADAIQIVLPTGRASLSAKAARAIAQAM
APGIGYDEAVTLALGLHHSHRPRQERLARLPYYAAALPDVGLDGDPVGPPPAEDDGAAAEAYYG

-continued

RIGNISVHIALNETRKIVNALLHRHGPILRLVMVETTRELKAGADERKRMIAEQAERERENAEI

DVELRKSDRWMANARERRQRVRLARRQNNLCPYTSTPIGHADLLGDAYDIDHVIPLARGGRDSL

DNMVLCQSDANKTKGDKTPWEAFHDKPGWIAQRDDFLARLDPQTAKALAWRFADDAGERVARKS

AEDEDQGFLPRQLTDTGYIARVALRYLSLVTNEPNAVVATNGRLTGLLRLAWDITPGPAPRDLL

PTPRDALRDDTAARRFLDGLTPPPLAKAVEGAVQARLAALGRSRVADAGLADALGLTLASLGGG

GKNRADHRHHFIDAAMIAVTTRGLINQINQASGAGRILDLRKWPRTNFEPPYPTFRAEVMKQWD

HIHPSIRPAHRDGGSLHAATVFGVRNRPDARVLVQRKPVEKLFLDANAKPLPADKIAEIIDGFA

SPRMAKRFKALLARYQAAHPEVPPALAALAVARDPAFGPRGMTANTVIAGRSDGDGEDAGLITP

FRANPKAAVRTMGNAVYEVWEIQVKGRPRWTHRVLTRFDRTQPAPPPPPENARLVMRLRRGDLV

YWPLESGDRLFLVKKMAVDGRLALWPARLATGKATALYAQLSCPNINLNGDQGYCVQSAEGIRK

EKIRTTSCTALGRLRLSKKAT

SEQ ID NO: 367
MKYTLGLDVGIASVGWAVIDKDNNKIIDLGVRCFDKAEESKTGESLATARRIARGMRRRISRRS

QRLRLVKKLFVQYEIIKDSSEFNRIFDTSRDGWKDPWELRYNALSRILKPYELVQVLTHITKRR

GFKSNRKEDLSTTKEGVVITSIKNNSEMLRTKNYRTIGEMIFMETPENSNKRNKVDEYIHTIAR

EDLLNEIKYIFSIQRKLGSPFVTEKLEHDFLNIWEFQRPFASGDSILSKVGKCTLLKEELRAPT

SCYTSEYFGLLQSINNLVLVEDNNTLTLNNDQRAKIIEYAHFKNEIKYSEIRKLLDIEPEILFK

AHNLTHKNPSGNNESKKFYEMKSYHKLKSTLPTDIWGKLHSNKESLDNLFYCLTVYKNDNEIKD

YLQANNLDYLIEYIAKLPTFNKFKHLSLVAMKRIIPFMEKGYKYSDACNMAELDFTGSSKLEKC

NKLTVEPIIENVTNPVVIRALTQARKVINAIIQKYGLPYMVNIELAREAGMTRQDRDNLKKEHE

NNRKAREKISDLIRQNGRVASGLDILKWRLWEDQGGRCAYSGKPIPVCDLLNDSLTQIDHIYPY

SRSMDDSYMNKVLVLTDENQNKRSYTPYEVWGSTEKWEDFEARIYSMHLPQSKEKRLLNRNFIT

KDLDSFISRNLNDTRYISRFLKNYIESYLQFSNDSPKSCVVCVNGQCTAQLRSRWGLNKNREES

DLHHALDAAVIACADRKIIKEITNYYNERENHNYKVKYPLPWHSFRQDLMETLAGVFISRAPRR

KITGPAHDETIRSPKHFNKGLTSVKIPLTTVTLEKLETMVKNTKGGISDKAVYNVLKNRLIEHN

NKPLKAFAEKIYKPLKNGTNGAIIRSIRVETPSYTGVFRNEGKGISDNSLMVRVDVFKKKDKYY

LVPIYVAHMIKKELPSKAIVPLKPESQWELIDSTHEFLFSLYQNDYLVIKTKKGITEGYYRSCH

RGTGSLSLMPHFANNKNVKIDIGVRTAISIEKYNVDILGNKSIVKGEPRRGMEKYNSFKSN

SEQ ID NO: 368
MIRTLGIDIGIASIGWAVIEGEYTDKGLENKEIVASGVRVFTKAENPKNKESLALPRTLARSAR

RRNARKKGRIQQVKHYLSKALGLDLECFVQGEKLATLFQTSKDFLSPWELRERALYRVLDKEEL

ARVILHIAKRRGYDDITYGVEDNDSGKIKKAIAENSKRIKEEQCKTIGEMMYKLYFQKSLNVRN

KKESYNRCVGRSELREELKTIFQIQQELKSPWVNEELIYKLLGNPDAQSKQEREGLIFYQRPLK

GFGDKIGKCSHIKKGENSPYRACKHAPSAEEFVALTKSINFLKNLTNRHGLCFSQEDMCVYLGK

ILQEAQKNEKGLTYSKLKLLLDLPSDFEFLGLDYSGKNPEKAVFLSLPSTFKLNKITQDRKTQD

KIANILGANKDWEAILKELESLQLSKEQIQTIKDAKLNFSKHINLSLEALYHLLPLMREGKRYD

EGVEILQERGIFSKPQPKNRQLLPPLSELAKEESYFDIPNPVLRRALSEFRKVVNALLEKYGGF

HYFHIELTRDVCKAKSARMQLEKINKKNKSENDAASQLLEVLGLPNTYNNRLKCKLWKQQEEYC

LYSGEKITIDHLKDQRALQIDHAFPLSRSLDDSQSNKVLCLTSSNQEKSNKTPYEWLGSDEKKW

DMYVGRVYSSNFSPSKKRKLTQKNFKERNEEDFLARNLDTGYIGRVTKEYIKHSLSFLPLPDG

KKEHIRIISGSMTSTMRSFWGVQEKNRDHHLHHAQDAIIACIEPSMIQKYTTYLKDKETHRLK

SHQKAQILREGDHKLSLRWPMSNFKDKIQESIQNIIPSHHVSHKVTGELHQETVRTKEFYYQAF

-continued

GGEEGVKKALKFGKIREINQGIVDNGAMVRVDIFKSKDKGKFYAVPIYTYDFAIGKLPNKAIVQ

GKKNGIIKDWLEMDENYEFCFSLFKNDCIKIQTKEMQEAVLAIYKSTNSAKATIELEHLSKYAL

KNEDEEKMFTDTDKEKNKTMTRESCGIQGLKVFQKVKLSVLGEVLEHKPRNRQNIALKTTPKHV

SEQ ID NO: 369
MKYSIGLDIGIASVGWSVINKDKERIEDMGVRIFQKAENPKDGSSLASSRREKRGSRRRNRRKK

HRLDRIKNILCESGLVKKNEIEKIYKNAYLKSPWELRAKSLEAKISNKEIAQILLHIAKRRGFK

SFRKTDRNADDTGKLLSGIQENKKIMEEKGYLTIGDMVAKDPKFNTHVRNKAGSYLFSFSRKLL

EDEVRKIQAKQKELGNTHFTDDVLEKYIEVFNSQRNFDEGPSKPSPYYSEIGQIAKMIGNCTFE

SSEKRTAKNTWSGERFVFLQKLNNFRIVGLSGKRPLTEEERDIVEKEVYLKKEVRYEKLRKILY

LKEEERFGDLNYSKDEKQDKKTEKTKFISLIGNYTIKKLNLSEKLKSEIEEDKSKLDKIIEILT

FNKSDKTIESNLKKLELSREDIEILLSEEFSGTLNLSLKAIKKILPYLEKGLSYNEACEKADYD

YKNNGIKFKRGELLPVVDKDLIANPVVLRAISQTRKVVNAIIRKYGTPHTIHVEVARDLAKSYD

DRQTIIKENKKRELENEKTKKFISEEFGIKNVGKLLLKYRLYQEQEGRCAYSRKELSLSEVIL

DESMTDIDHIIPYSRSMDDSYSNKVLVLSGENRKKSNLLPKEYFDRQGRDWDTFVLNVKAMKIH

PRKKSNLLKEKFTREDNKDWKSRALNDTRYISRFVANYLENALEYRDDSPKKRVFMIPGQLTAQ

LRARWRLNKVRENGDLHHALDAAVVAVTDQKAINNISNISRYKELKNCKDVIPSIEYHADEETG

EVYFEEVKDTRFPMPWSGFDLELQKRLESENPREEFYNLLSDKRYLGWFNYEEGFIEKLRPVFV

SRMPNRGVKGQAHQETIRSSKKISNQIAVSKKPLNSIKLKDLEKMQGRDTDRKLYEALKNRLEE

YDDKPEKAFAEPFYKPTNSGKRGPLVRGIKVEEKQNVGVYVNGGQASNGSMVRIDVFRKNGKFY

TVPIYVHQTLLKELPNRAINGKPYKDWDLIDGSFEFLYSFYPNDLIEIEFGKSKSIKNDNKLTK

TEIPEVNLSEVLGYYRGMDTSTGAATIDTQDGKIQMRIGIKTVKNIKKYQVDVLGNVYKVKREK

RQTF

SEQ ID NO: 370
MSKKVSRRYEEQAQEICQRLGSRPYSIGLDLGVGSIGVAVAAYDPIKKQPSDLVFVSSRIFIPS

TGAAERRQKRGQRNSLRHRANRLKFLWKLLAERNLMLSYSEQDVPDPARLRFEDAVVRANPYEL

RLKGLNEQLTLSELGYALYHIANHRGSSSVRTFLDEEKSSDDKKLEEQQAMTEQLAKEKGISTF

IEVLTAFNTNGLIGYRNSESVKSKGVPVPTRDIISNEIDVLLQTQKQFYQEILSDEYCDRIVSA

ILFENEKIVPEAGCCPYFPDEKKLPRCHFLNEERRLWEAINNARIKMPMQEGAAKRYQSASFSD

EQRHILFHIARSGTDITPKLVQKEFPALKTSIIVLQGKEKAIQKIAGFRFRRLEEKSFWKRLSE

EQKDDFFSAWTNTPDDKRLSKYLMKHLLLTENEVVDALKTVSLIGDYGPIGKTATQLLMKHLED

GLTYTEALERGMETGEFQELSVWEQQSLLPYYGQILTGSTQALMGKYWHSAFKEKRDSEGFFKP

NTNSDEEKYGRIANPVVHQTLNELRKLMNELITILGAKPQEITVELARELKVGAEKREDIIKQQ

TKQEKEAVLAYSKYCEPNNLDKRYIERFRLLEDQAFVCPYCLEHISVADIAAGRADVDHIFPRD

DTADNSYGNKVVAHRQCNDIKGKRTPYAAFSNTSAWGPIMHYLDETPGMWRKRRKFETNEEEYA

KYLQSKGFVSRFESDNSYIAKAAKEYLRCLFNPNNVTAVGSLKGMETSILRKAWNLQGIDDLLG

SRHWSKDADTSPTMRKNRDDNRHHGLDAIVALYCSRSLVQMINTMSEQGKRAVEIEAMIPIGY

ASEPNLSFEAQRELFRKKILEFMDLHAFVSMKTDNDANGALLKDTVYSILGADTQGEDLVFVVK

KKIKDIGVKIGDYEEVASAIRGRITDKQPKWYPMEMKDKIEQLQSKNEAALQKYKESLVQAAAV

LEESNRKLIESGKKPIQLSEKTISKKALELVGGYYYLISNNKRTKTFVVKEPSNEVKGFAFDTG

SNLCLDFYHDAQGKLCGEIIRKIQAMNPSYKPAYMKQGYSLYVRLYQGDVCELRASDLTEAESN

-continued

LAKTTHVRLPNAKPGRTFVIIITFTEMGSGYQIYFSNLAKSKKGQDTSFTLTTIKNYDVRKVQL

SSAGLVRYVSPLLVDKIEKDEVALCGE

SEQ ID NO: 371
MNQKFILGLDIGITSVGYGLIDYETKNIIDAGVRLFPEANVENNEGRRSKRGSRRLKRRRIHRL

ERVKKLLEDYNLLDQSQIPQSTNPYAIRVKGLSEALSKDELVIALLHIAKRRGIHKIDVIDSND

DVGNELSTKEQLNKNSKLLKDKFVCQIQLERMNEGQVRGEKNRFKTADIIKEIIQLLNVQKNFH

QLDENFINKYIELVEMRREYFEGPGKGSPYGWEGDPKAWYETLMGHCTYFPDELRSVKYAYSAD

LFNALNDLNNLVIQRDGLSKLEYHEKYHIIENVFKQKKKPTLKQIANEINVNPEDIKGYRITKS

GKPQFTEFKLYHDLKSVLFDQSILENEDVLDQIAEILTIYQDKDSIKSKLTELDILLNEEDKEN

IAQLTGYTGTHRLSLKCIRLVLEEQWYSSRNQMEIFTHLNIKPKKINLTAANKIPKAMIDEFIL

SPVVKRTFGQAINLINKIIEKYGVPEDIIIELARENNSKDKQKFINEMQKKNENTRKRINEIIG

KYGNQNAKRLVEKIRLHDEQEGKCLYSLESIPLEDLLNNPNHYEVDHIIPRSVSFDNSYHNKVL

VKQSENSKKSNLTPYQYFNSGKSKLSYNQFKQHILNLSKSQDRISKKKKEYLLEERDINKFEVQ

KEFINRNLVDTRYATRELTNYLKAYFSANNMNVKVKTINGSFTDYLRKVWKFKKERNHGYKHHA

EDALIIANADFLFKENKKLKAVNSVLEKPEIESKQLDIQVDSEDNYSEMFIIPKQVQDIKDFRN

FKYSHRVDKKPNRQLINDTLYSTRKKDNSTYIVQTIKDIYAKDNTTLKKQFDKSPEKFLMYQHD

PRTFEKLEVIMKQYANEKNPLAKYHEETGEYLTKYSKKNNGPIVKSLKYIGNKLGSHLDVTHQF

KSSTKKLVKLSIKPYRFDVYLTDKGYKFITISYLDVLKKDNYYYIPEQKYDKLKLGKAIDKNAK

FIASFYKNDLIKLDGEIYKIIGVNSDTRNMIELDLPDIRYKEYCELNNIKGEPRIKKTIGKKVN

SIEKLTTDVLGNVFTNTQYTKPQLLFKRGN

SEQ ID NO: 372
MIMKLEKWRLGLDLGTNSIGWSVFSLDKDNSVQDLIDMGVRIFSDGRDPKTKEPLAVARRTARS

QRKLIYRRKLRRKQVFKFLQEQGLFPKTKEECMTLKSLNPYELRIKALDEKLEPYELGRALFNL

AVRRGFKSNRKDGSREEVSEKKSPDEIKTQADMQTHLEKAIKENGCRTITEFLYKNQGENGGIR

FAPGRMTYYPTRKMYEEEFNLIRSKQEKYYPQVDWDDIYKAIFYQRPLKPQQRGYCIYENDKER

TFKAMPCSQKLRILQDIGNLAYYEGGSKKRVELNDNQDKVLYELLNSKDKVTFDQMRKALCLAD

SNSFNLEENRDFLIGNPTAVKMRSKNRFGKLWDEIPLEEQDLIIETIITADEDDAVYEVIKKYD

LTQEQRDFIVKNTILQSGTSMLCKEVSEKLVKRLEEIADLKYHEAVESLGYKFADQTVEKYDLL

PYYGKVLPGSTMEIDLSAPETNPEKHYGKISNPTVHVALNQTRVVVNALIKEYGKPSQIAIELS

RDLKNNVEKKAEIARKQNQRAKENIAINDTISALYHTAFPGKSFYPNRNDRMKYRLWSELGLGN

KCIYCGKGISGAELFTKEIEIEHILPFSRTLLDAESNLTVAHSSCNAFKAERSPFEAFGTNPSG

YSWQEIIQRANQLKNTSKKNKFSPNAMDSFEKDSSFIARQLSDNQYIAKAALRYLKCLVENPSD

VWTTNGSMTKLLRDKWEMDSILCRKFTEKEVALLGLKPEQIGNYKKNRFDHRHHAIDAVVIGLT

DRSMVQKLATKNSHKGNRIEIPEFPILRSDLIEKVKNIVVSFKPDHGAEGKLSKETLLGKIKLH

GKETFVCRENIVSLSEKNLDDIVDEIKSKVKDYVAKHKGQKIEAVLSDFSKENGIKKVRCVNRV

QTPIEITSGKISRYLSPEDYFAAVIWEIPGEKKTFKAQYIRRNEVEKNSKGLNVVKPAVLENGK

PHPAAKQVCLLHKDDYLEFSDKGKMYFCRIAGYAATNNKLDIRPVYAVSYCADWINSTNETMLT

GYWKPTPTQNWVSVNVLFDKQKARLVTVSPIGRVFRK

SEQ ID NO: 373
MSSKAIDSLEQLDLFKPQEYTLGLDLGIKSIGWAILSGERIANAGVYLFETAEELNSTGNKLIS

KAAERGRKRRIRRMLDRKARRGRHIRYLLEREGLPTDELEEVVVHQSNRTLWDVRAEAVERKLT

KQELAAVLFHLVRHRGYFPNTKKLPPDDESDSADEEQGKINRATSRLREELKASDCKTIGQFLA

-continued

QNRDRQRNREGDYSNLMARKLVFEEALQILAFQRKQGHELSKDFEKTYLDVLMGQRSGRSPKLG
NCSLIPSELRAPSSAPSTEWFKFLQNLGNLQISNAYREEWSIDAPRRAQIIDACSQRSTSSYWQ
IRRDFQIPDEYRFNLVNYERRDPDVDLQEYLQQQERKTLANFRNWKQLEKIIGTGHPIQTLDEA
ARLITLIKDDEKLSDQLADLLPEASDKAITQLCELDFTTAAKISLEAMYRILPHMNQGMGFFDA
CQQESLPEIGVPPAGDRVPPFDEMYNPVVNRVLSQSRKLINAVIDEYGMPAKIRVELARDLGKG
RELRERIKLDQLDKSKQNDQRAEDFRAEFQQAPRGDQSLRYRLWKEQNCTCPYSGRMIPVNSVL
SEDTQIDHILPISQSFDNSLSNKVLCFTEENAQKSNRTPFEYLDAADFQRLEAISGNWPEAKRN
KLLHKSFGKVAEEWKSRALNDTRYLTSALADHLRHHLPDSKIQTVNGRITGYLRKQWGLEKDRD
KHTHHAVDAIVVACTTPAIVQQVTLYHQDIRRYKKLGEKRPTPWPETFRQDVLDVEEEIFITRQ
PKKVSGGIQTKDTLRKHRSKPDRQRVALTKVKLADLERLVEKDASNRNLYEHLKQCLEESGDQP
TKAFKAPFYMPSGPEAKQRPILSKVTLLREKPEPPKQLTELSGGRRYDSMAQGRLDIYRYKPGG
KRKDEYRVVLQRMIDLMRGEENVHVFQKGVPYDQGPEIEQNYTFLFSLYFDDLVEFQRSADSEV
IRGYYRTFNIANGQLKISTYLEGRQDFDFFGANRLAHFAKVQVNLLGKVIK

SEQ ID NO: 374
MRSLRYRLALDLGSTSLGWALFRLDACNRPTAVIKAGVRIFSDGRNPKDGSSLAVTRRAARAMR
RRRDRLLKRKTRMQAKLVEHGFFPADAGKRKALEQLNPYALRAKGLQEALLPGEFARALFHINQ
RRGFKSNRKTDKKDNDSGVLKKAIGQLRQQMAEQGSRTVGEYLWTRLQQGQGVRARYREKPYTT
EEGKKRIDKSYDLYIDRAMIEQEFDALWAAQAAFNPTLFHEAARADLKDTLLHQRPLRPVKPGR
CTLLPEEERAPLALPSTQRFRIHQEVNHLRLLDENLREVALTLAQRDAVVTALETKAKLSFEQI
RKLLKLSGSVQFNLEDAKRTELKGNATSAALARKELFGAAWSGFDEALQDEIVWQLVTEEGEGA
LIAWLQTHTGVDEARAQAIVDVSLPEGYGNLSRKALARIVPALRAAVITYDKAVQAAGFDHHSQ
LGFEYDASEVEDLVHPETGEIRSVFKQLPYYGKALQRHVAFGSGKPEDPDEKRYGKIANPTVHI
GLNQVRMVVNALIRRYGRPTEVVIELARDLKQSREQKVEAQRRQADNQRRNARIRRSIAEVLGI
GEERVRGSDIQKWICWEELSFDAADRRCPYSGVQISAAMLLSDEVEVEHILPFSKTLDDSLNNR
TVAMRQANRIKRNRTPWDARAEFEAQGWSYEDILQRAERMPLRKRYRFAPDGYERWLGDDKDFL
ARALNDTRYLSRVAAEYLRLVCPGTRVIPGQLTALLRGKFGLNDVLGLDGEKNRNDHRHHAVDA
CVIGVTDQGLMQRFATASAQARGDGLTRLVDGMPMPWPTYRDHVERAVRHIWVSHRPDHGFEGA
MMEETSYGIRKDGSIKQRRKADGSAGREISNLIRIHEATQPLRHGVSADGQPLAYKGYVGGSNY
CIEITVNDKGKWEGEVISTFRAYGVVRAGGMGRLRNPHEGQNGRKLIMRLVIGDSVRLEVDGAE
RTMRIVKISGSNGQIFMAPIHEANVDARNTDKQDAFTYTSKYAGSLQKAKTRRVTISPIGEVRD
PGFKG

SEQ ID NO: 375
MARPAFRAPRREHVNGWTPDPHRISKPFFILVSWHLLSRVVIDSSSGCFPGTSRDHTDKFAEWE
CAVQPYRLSFDLGTNSIGWGLLNLDRQGKPREIRALGSRIFSDGRDPQDKASLAVARRLARQMR
RRRDRYLTRRTRLMGALVRFGLMPADPAARKRLEVAVDPYLARERATRERLEPFEIGRALFHLN
QRRGYKPVRTATKPDEEAGKVKEAVERLEAAIAAAGAPTLGAWFAWRKTRGETLRARLAGKGKE
AAYPFYPARRMLEAEFDTLWAEQARHHPDLLTAEAREILRHRIFHQRPLKPPPVGRCTLYPDDG
RAPRALPSAQRLRLFQELASLRVIHLDLSERPLTPAERDRIVAFVQGRPPKAGRKPGKVQKSVP
FEKLRGLLELPPGTGFSLESDKRPELLGDETGARIAPAFGPGWTALPLEEQDALVELLLTEAEP
ERAIAALTARWALDEATAAKLAGATLPDFHGRYGRRAVAELLPVLERETRGDPDGRVRPIRLDE
AVKLLRGGKDHSDFSREGALLDALPYYGAVLERHVAFGTGNPADPEEKRVGRVANPTVHIALNQ

-continued

LRHLVNAILARHGRPEEIVIELARDLKRSAEDRRREDKRQADNQKRNEERKRLILSLGERPTPR
NLLKLRLWEEQGPVENRRCPYSGETISMRMLLSEQVDIDHILPFSVSLDDSAANKVVCLREANR
IKRNRSPWEAFGHDSERWAGILARAEALPKNKRWRFAPDALEKLEGEGGLRARHLNDTRHLSRL
AVEYLRCVCPKVRVSPGRLTALLRRRWGIDAILAEADGPPPEVPAETLDPSPAEKNRADHRHHA
LDAVVIGCIDRSMVQRVQLAAASAEREAAAREDNIRRVLEGFKEEPWDGFRAELERRARTIVVS
HRPEHGIGGALHKETAYGPVDPPEEGFNLVVRKPIDGLSKDEINSVRDPRLRRALIDRLAIRRR
DANDPATALAKAAEDLAAQPASRGIRRVRVLKKESNPIRVEHGGNPSGPRSGGPFHKLLLAGEV
HHVDVALRADGRRWVGHWVTLFEAHGGRGADGAAAPPRLGDGERFLMRLHKGDCLKLEHKGRVR
VMQVVKLEPSSNSVVVVEPHQVKTDRSKHVKISCDQLRARGARRVTVDPLGRVRVHAPGARVGI
GGDAGRTAMEPAEDIS

SEQ ID NO: 376
MKRTSLRAYRLGVDLGANSLGWFVVWLDDHGQPEGLGPGGVRIFPDGRNPQSKQSNAAGRRLAR
SARRRRDRYLQRRGKLMGLLVKHGLMPADEPARKRLECLDPYGLRAKALDEVLPLHHVGRALFH
LNQRRGLFANRAIEQGDKDASAIKAAAGRLQTSMQACGARTLGEFLNRRHQLRATVRARSPVGG
DVQARYEFYPTRAMVDAEFEAIWAAQAPHHPTMTAEAHDTIREAIFSQRAMKRPSIGKCSLDPA
TSQDDVDGFRCAWSHPLAQRFRIWQDVRNLAVVETGPTSSRLGKEDQDKVARALLQTDQLSFDE
IRGLLGLPSDARFNLESDRRDHLKGDATGAILSARRHFGPAWHDRSLDRQIDIVALLESALDEA
AIIASLGTTHSLDEAAAQRALSALLPDGYCRLGLRAIKRVLPLMEAGRTYAEAASAAGYDHALL
PGGKLSPTGYLPYYGQWLQNDVVGSDDERDTNERRWGRLPNPTVHIGIGQLRRVVNELIRWHGP
PAEITVELTRDLKLSPRRLAELEREQAENQRKNDKRTSLLRKLGLPASTHNLLKLRLWDEQGDV
ASECPYTGEAIGLERLVSDDVDIDHLIPFSISWDDSAANKVVCMRYANREKGNRTPFEAFGHRQ
GRPYDWADIAERAARLPRGKRWRFGPGARAQFEELGDFQARLLNETSWLARVAKQYLAAVTHPH
RIHVLPGRLTALLRATWELNDLLPGSDDRAAKSRKDHRHHAIDALVAALTDQALLRRMANAHDD
TRRKIEVLLPWPTFRIDLETRLKAMLVSHKPDHGLQARLHEDTAYGTVEHPETEDGANLVYRKT
FVDISEKEIDRIRDRRLRDLVRAHVAGERQQGKTLKAAVLSFAQRRDIAGHPNGIRHVRLTKSI
KPDYLVPIRDKAGRIYKSYNAGENAFVDILQAESGRWIARATTVFQANQANESHDAPAAQPIMR
VFKGDMLRIDHAGAEKFVKIVRLSPSNNLLYLVEHHQAGVFQTRHDDPEDSFRWLFASFDKLRE
WNAELVRIDTLGQPWRRKRGLETGSEDATRIGWTRPKKWP

SEQ ID NO: 377
MERIFGFDIGTTSIGFSVIDYSSTQSAGNIQRLGVRIFPEARDPDGTPLNQQRRQKRMMRRQLR
RRRIRRKALNETLHEAGFLPAYGSADWPVVMADEPYELRRRGLEEGLSAYEFGRAIYHLAQRH
FKGRELEESDTPDPDVDDEKEAANERAATLKALKNEQTTLGAWLARRPPSDRKRGIHAHRNVVA
EEFERLWEVQSKFHPALKSEEMRARISDTIFAQRPVFWRKNTLGECRFMPGEPLCPKGSWLSQQ
RRMLEKLNNLAIAGGNARPLDAEERDAILSKLQQQASMSWPGVRSALKALYKQRGEPGAEKSLK
FNLELGGESKLLGNALEAKLADMFGPDWPAHPRKQEIRHAVHERLWAADYGETPDKKRVIILSE
KDRKAHREAAANSFVADFGITGEQAAQLQALKLPTGWEPYSIPALNLFLAELEKGERFGALVNG
PDWEGWRRTNFPHRNQPTGEILDKLPSPASKEERERISQLRNPTVVRTQNELRKVVNNLIGLYG
KPDRIRIEVGRDVGKSKEREEIQSGIRRNEKQRKKATEDLIKNGIANPSRDDVEKWILWKEGQ
ERCPYTGDQIGFNALFREGRYEVEHIWPRSRSFDNSPRNKTLCRKDVNIEKGNRMPFEAFGHDE
DRWSAIQIRLQGMVSAKGGTGMSPGKVKRFLAKTMPEDFAARQLNDTRYAAKQILAQLKRLWPD
MGPEAPVKVEAVTGQVTAQLRKLWTLNNILADDGEKTRADHRHHAIDALTVACTHPGMTNKLSR
YWQLRDDPRAEKPALTPPWDTIRADAEKAVSEIVVSHRVRKKVSGPLHKETTYGDTGTDIKTKS

-continued

GTYRQFVTRKKIESLSKGELDEIRDPRIKEIVAAHVAGRGGDPKKAFPPYPCVSPGGPEIRKVR

LTSKQQLNLMAQTGNGYADLGSNHHIAIYRLPDGKADFEIVSLFDASRRLAQRNPIVQRTRADG

ASFVMSLAAGEAIMIPEGSKKGIWIVQGVWASGQVVLERDTDADHSTTTRPMPNPILKDDAKKV

SIDPIGRVRPSND

SEQ ID NO: 378

MNKRILGLDTGTNSLGWAVVDWDEHAQSYELIKYGDVIFQEGVKIEKGIESSKAAERSGYKAIR

KQYFRRRLRKIQVLKVLVKYHLCPYLSDDDLRQWHLQKQYPKSDELMLWQRTSDEEGKNPYYDR

HRCLHEKLDLTVEADRYTLGRALYHLTQRRGFLSNRLDTSADNKEDGVVKSGISQLSTEMEEAG

CEYLGDYFYKLYDAQGNKVRIRQRYTDRNKHYQHEFDAICEKQELSSELIEDLQRAIFFQLPLK

SQRHGVGRCTFERGKPRCADSHPDYEEFRMLCFVNNIQVKGPHDLELRPLTYEEREKIEPLFFR

KSKPNFDFEDIAKALAGKKNYAWIHDKEERAYKFNYRMTQGVPGCPTIAQLKSIFGDDWKTGIA

ETYTLIQKKNGSKSLQEMVDDVWNVLYSFSSVEKLKEFAHHKLQLDEESAEKFAKIKLSHSFAA

LSLKAIRKFLPFLRKGMYYTHASFFANIPTIVGKEIWNKEQNRKYIMENVGELVFNYQPKHREV

QGTIEMLIKDFLANNFELPAGATDKLYHPSMIETYPNAQRNEFGILQLGSPRTNAIRNPMAMRS

LHILRRVVNQLLKESIIDENTEVHVEYARELNDANKRRAIADRQKEQDKQHKKYGDEIRKLYKE

ETGKDIEPTQTDVLKFQLWEEQNHHCLYTGEQIGITDFIGSNPKFDIEHTIPQSVGGDSTQMNL

TLCDNRFNREVKKAKLPTELANHEEILTRIEPWKNKYEQLVKERDKQRTFAGMDKAVKDIRIQK

RHKLQMEIDYWRGKYERFTMTEVPEGFSRRQGTGIGLISRYAGLYLKSLFHQADSRNKSNVYVV

KGVATAEFRKMWGLQSEYEKKCRDNHSHHCMDAITIACIGKREYDLMAEYYRMEETFKQGRGSK

PKFSKPWATFTEDVLNIYKNLLVVHDTPNNMPKHTKKYVQTSIGKVLAQGDTARGSLHLDTYYG

AIERDGEIRYVVRRPLSSFTKPEELENIVDETVKRTIKEAIADKNFKQAIAEPIYMNEEKGILI

KKVRCFAKSVKQPINIRQHRDLSKKEYKQQYHVMNENNYLLAIYEGLVKNKVVREFEIVSYIEA

AKYYKRSQDRNIFSSIVPTHSTKYGLPLKTKLLMGQLVLMFEENPDEIQVDNTKDLVKRLYKVV

GIEKDGRIKFKYHQEARKEGLPIFSTPYKNNDDYAPIFRQSINNINILVDGIDFTIDILGKVTL

KE

SEQ ID NO: 379

MNYKMGLDIGIASVGWAVINLDLKRIEDLGVRIFDKAEHPQNGESLALPRRIARSARRRLRRRK

HRLERIRRLLVSENVLTKEEMNLLFKQKKQIDVWQLRVDALERKLNNDELARVLLHLAKRRGFK

SNRKSERNSKESSEFLKNIEENQSILAQYRSVGEMIVKDSKFAYHKRNKLDSYSNMIARDDLER

EIKLIFEKQREFNNPVCTERLEEKYLNIWSSQRPFASKEDIEKKVGFCTFEPKEKRAPKATYTF

QSFIVWEHINKLRLVSPDETRALTEIERNLLYKQAFSKNKMTYYDIRKLLNLSDDIHFKGLLYD

PKSSLKQIENIRFLELDSYHKIRKCIENVYGKDGIRMFNETDIDTFGYALTIFKDDEDIVAYLQ

NEYITKNGKRVSNLANKVYDKSLIDELLNLSFSKFAHLSMKAIRNILPYMEQGEIYSKACELAG

YNFTGPKKKEKALLLPVIPNIANPVVMRALTQSRKVVNAIIKKYGSPVSIHIELARDLSHSFDE

RKKIQKDQTENRKKNETAIKQLIEYELTKNPTGLDIVKFKLWSEQQGRCMYSLKPIELERLLEP

GYVEVDHILPYSRSLDDSYANKVLVLTKENREKGNHTPVEYGLGSERWKKFEKFVLANKQFSK

KKKQNLLRLRYEETEEKEFKERNLNDTRYISKFFANFIKEHLKFADGDGGQKVYTINGKITAHL

RSRWDFNKNREESDLHHAVDAVIVACATQGMIKKITEFYKAREQNKESAKKKEPIFPQPWPHFA

DELKARLSKFPQESIEAFALGNYDRKKLESLRPVFVSRMPKRSVTGAAHQETLRRCVGIDEQSG

KIQTAVKTKLSDIKLDKDGHFPMYQKESDPRTYEAIRQRLLEHNNDPKKAFQEPLYKPKKNGEP

GPVIRTVKIIDTKNKVVHLDGSKTVAYNSNIVRTDVFEKDGKYYCVPVYTMDIMKGTLPNKAIE

-continued

ANKPYSEWKEMTEEYTFQFSLFPNDLVRIVLPREKTIKTSTNEEIIIKDIFAYYKTIDSATGGL

ELISHDRNFSLRGVGSKTLKRFEKYQVDVLGNIHKVKGEKRVGLAAPTNQKKGKTVDSLQSVSD

SEQ ID NO: 380
MRRLGLDLGTNSIGWCLLDLGDDGEPVSIFRTGARIFSDGRDPKSLGSLKATRREARLTRRRD

RFIQRQKNLINALVKYGLMPADEIQRQALAYKDPYPIRKKALDEAIDPYEMGRAIFHINQRRGF

KSNRKSADNEAGVVKQSIADLEMKLGEAGARTIGEFLADRQATNDTVRARRLSGTNALYEFYPD

RYMLEQEFDTLWAKQAAFNPSLYIEAARERLKEIVFFQRKLKPQEVGRCIFLSDEDRISKALPS

FQRFRIYQELSNLAWIDHDGVAHRITASLALRDHLFDELEHKKKLTFKAMRAILRKQGVVDYPV

GFNLESDNRDHLIGNLTSCIMRDAKKMIGSAWDRLDEEEQDSFILMLQDDQKGDDEVRSILTQQ

YGLSDDVAEDCLDVRLPDGHGSLSKKAIDRILPVLRDQGLIYYDAVKEAGLGEANLYDPYAALS

DKLDYYGKALAGHVMGASGKFEDSDEKRYGTISNPTVHIALNQVRAVVNELIRLHGKPDEVVIE

IGRDLPMGADGKRELERFQKEGRAKNERARDELKKLGHIDSRESRQKFQLWEQLAKEPVDRCCP

FTGKMMSISDLFSDKVEIEHLLPFSLTLDDSMANKTVCFRQANRDKGNRAPFDAFGNSPAGYDW

QEILGRSQNLPYAKRWRFLPDAMKRFEADGGFLERQLNDTRYISRYTTEYISTIIPKNKIWVVT

GRLTSLLRGFWGLNSILRGHNTDDGTPAKKSRDDHRHHAIDAIVVGMTSRGLLQKVSKAARRSE

DLDLTRLFEGRIDPWDGFRDEVKKHIDAIIVSHRPRKKSQGALHNDTAYGIVEHAENGASTVVH

RVPITSLGKQSDIEKVRDPLIKSALLNETAGLSGKSFENAVQKWCADNSIKSLRIVETVSIIPI

TDKEGVAYKGYKGDGNAYMDIYQDPTSSKWKGEIVSRFDANQKGFIPSWQSQFPTARLIMRLRI

NDLLKLQDGEIEEIYRVQRLSGSKILMAPHTEANVDARDRDKNDTFKLTSKSPGKLQSASARKV

HISPTGLIREG

SEQ ID NO: 381
MKNILGLDLGLSSIGWSVIRENSEEQELVAMGSRVVSLTAAELSSFTQGNGVSINSQRTQKRTQ

RKGYDRYQLRRTLLRNKLDTLGMLPDDSLSYLPKLQLWGLRAKAVTQRIELNELGRVLLHLNQK

RGYKSIKSDFSGDKKITDYVKTVKTRYDELKEMRLTIGELFFRRLTENAFFRCKEQVYPRQAYV

EEFDCIMNCQRKFYPDILTDETIRCIRDEIIYYQRPLKSCKYLVSRCEFEKRFYLNAAGKKTEA

GPKVSPRTSPLFQVCRLWESINNIVVKDRRNEIVFISAEQRAALFDFLNTHEKLKGSDLLKLLG

LSKTYGYRLGEQFKTGIQGNKTRVEIERALGNYPDKKRLLQFNLQEESSSMVNTETGEIIPMIS

LSFEQEPLYRLWHVLYSIDDREQLQSVLRQKFGIDDDEVLERLSAIDLVKAGFGNKSSKAIRRI

LPFLQLGMNYAEACEAAGYNHSNNYTKAENEARALLDRLPAIKKNELRQPVVEKILNQMVNVVN

ALMEKYGRFDEIRVELARELKQSKEERSNTYKSINKNQRENEQIAKRIVEYGVPTRSRIQKYKM

WEESKHCCIYCGQPVDVGDFLRGFDVEVEHIIPKSLYFDDSFANKVCSCRSCNKEKNNRTAYDY

MKSKGEKALSDYVERVNTMYTNNQISKTKWQNLLTPVDKISIDFIDRQLRESQYIARKAKEILT

SICYNVTATSGSVTSFLRHVWGWDTVLHDLNFDRYKKVGLTEVIEVNHRGSVIRREQIKDWSKR

FDHRHHAIDALTIACTKQAYIQRLNNLRAEEGPDFNKMSLERYIQSQPHFSVAQVREAVDRILV

SFRAGKRAVTPGKRYIRKNRKRISVQSVLIPRGALSEESVYGVIHVWEKDEQGHVIQKQRAVMK

YPITSINREMLDKEKVVDKRIHRILSGRLAQYNDNPKEAFAKPVYIDKECRIPIRTVRCFAKPA

INTLVPLKKDDKGNPVAWVNPGNNHHVAIYRDEDGKYKERTVTFWEAVDRCRVGIPAIVTQPDT

IWDNILQRNDISENVLESLPDVKWQFVLSLQQNEMFILGMNEEDYRYAMDQQDYALLNKYLYRV

QKLSKSDYSFRYHTETSVEDKYDGKPNLKLSMQMGKLKRVSIKSLLGLNPHKVHISVLGEIKEI

S

SEQ ID NO: 382
MAEKQHRWGLDIGTNSIGWAVIALIEGRPAGLVATGSRIFSDGRNPKDGSSLAVERRGPRQMRR

-continued

RRDRYLRRRDRFMQALINVGLMPGDAAARKALVTENPYVLRQRGLDQALTLPEFGRALFHLNQR

RGFQSNRKTDRATAKESGKVKNAIAAFRAGMGNARTVGEALARRLEDGRPVRARMVGQGKDEHY

ELYIAREWIAQEFDALWASQQRFHAEVLADAARDRLRAILLFQRKLLPVPVGKCFLEPNQPRVA

AALPSAQRFRLMQELNHLRVMTLADKRERPLSFQERNDLLAQLVARPKCGFDMLRKIVFGANKE

AYRFTIESERRKELKGCDTAAKLAKVNALGTRWQALSLDEQDRLVCLLLDGENDAVLADALREH

YGLTDAQIDTLLGLSFEDGHMRLGRSALLRVLDALESGRDEQGLPLSYDKAVVAAGYPAHTADL

ENGERDALPYYGELLWRYTQDAPTAKNDAERKFGKIANPTVHIGLNQLRKLVNALIQRYGKPAQ

IVVELARNLKAGLEEKERIKKQQTANLERNERIRQKLQDAGVPDNRENRLRMRLFEELGQGNGL

GTPCIYSGRQISLQRLFSNDVQVDHILPFSKTLDDSFANKVLAQHDANRYKGNRGPFEAFGANR

DGYAWDDIRARAAVLPRNKRNRFAETAMQDWLHNETDFLARQLTDTAYLSRVARQYLTAICSKD

DVYVSPGRLTAMLRAKWGLNRVLDGVMEEQGRPAVKNRDDHRHHAIDAVVIGATDRAMLQQVAT

LAARAREQDAERLIGDMPTPWPNFLEDVRAAVARCVVSHKPDHGPEGGLHNDTAYGIVAGPFED

GRYRVRHRVSLFDLKPGDLSNVRCDAPLQAELEPIFEQDDARAREVALTALAERYRQRKVWLEE

LMSVLPIRPRGEDGKTLPDSAPYKAYKGDSNYCYELFINERGRWDGELISTFRANQAAYRRFRN

DPARFRRYTAGGRPLLMRLCINDYIAVGTAAERTIFRVVKMSENKITLAEHFEGGTLKQRDADK

DDPFKYLTKSPGALRDLGARRIFVDLIGRVLDPGIKGD

SEQ ID NO: 383

MIERILGVDLGISSLGWAIVEYDKDDEAANRIIDCGVRLFTAAETPKKKESPNKARREARGIRR

VLNRRRVRMNMIKKLFLRAGLIQDVDLDGEGGMFYSKANRADVWELRHDGLYRLLKGDELARVL

IHIAKHRGYKFIGDDEADEESGKVKKAGVVLRQNFEAAGCRTVGEWLWRERGANGKKRNKHGDY

EISIHRDLLVEEVEAIFVAQQEMRSTIATDALKAAYREIAFFVRPMQRIEKMVGHCTYFPEERR

APKSAPTAEKFIAISKFFSTVIIDNEGWEQKIIERKTLEELLDFAVSREKVEFRHLRKFLDLSD

NEIFKGLHYKGKPKTAKKREATLFDPNEPTELEFDKVEAEKKAWISLRGAAKLREALGNEFYGR

FVALGKHADEATKILTYYKDEGQKRRELTKLPLEAEMVERLVKIGFSDFLKLSLKAIRDILPAM

ESGARYDEAVLMLGVPHKEKSAILPPLNKTDIDILNPTVIRAFAQFRKVANALVRKYGAFDRVH

FELAREINTKGEIEDIKESQRKNEKERKEAADWIAETSFQVPLTRKNILKKRLYIQQDGRCAYT

GDVIELERLFDEGYCEIDHILPRSRSADDSFANKVLCLARANQQKTDRTPYEWFGHDAARWNAF

ETRTSAPSNRVRTGKGKIDRLLKKNFDENSEMAFKDRNLNDTRYMARAIKTYCEQYWVFKNSHT

KAPVQVRSGKLTSVLRYQWGLESKDRESHTHHAVDAIIIAFSTQGMVQKLSEYYRFKETHREKE

RPKLAVPLANFRDAVEEATRIENTETVKEGVEVKRLLISRPPRARVTGQAHEQTAKPYPRIKQV

KNKKKWRLAPIDEEKFESFKADRVASANQKNFYETSTIPRVDVYHKKGKFHLVPIYLHEMVLNE

LPNLSLGTNPEAMDENFFKFSIFKDDLISIQTQGTPKKPAKIIMGYFKNMHGANMVLSSINNSP

CEGFTCTPVSMDKKHKDKCKLCPEENRIAGRCLQGFLDYWSQEGLRPPRKEFECDQGVKFALDV

KKYQIDPLGYYYEVKQEKRLGTIPQMRSAKKLVKK

SEQ ID NO: 384

MNNSIKSKPEVTIGLDLGVGSVGWAIVDNETNIIHHLGSRLFSQAKTAEDRRSFRGVRRLIRRR

KYKLKRFVNLIWKYNSYFGFKNKEDILNNYQEQQKLHNTVLNLKSEALNAKIDPKALSWILHDY

LKNRGHFYEDNRDFNVYPTKELAKYFDKYGYYKGIIDSKEDNDNKLEEELTKYKFSNKHWLEEV

KKVLSNQTGLPEKFKEEYESLFSYVRNYSEGPGSINSVSPYGIYHLDEKEGKVVQKYNNIWDKT

IGKCNIFPDEYRAPKNSPIAMIFNEINELSTIRSYSIYLTGWFINQEFKKAYLNKLLDLLIKTN

GEKPIDARQFKKLREETIAESIGKETLKDVENEEKLEKEDHKWKLKGLKLNTNGKIQYNDLSSL

AKFVHKLKQHLKLDFLLEDQYATLDKINFLQSLFVYLGKHLRYSNRVDSANLKEFSDSNKLFER

-continued

ILQKQKDGLFKLFEQTDKDDEKILAQTHSLSTKAMLLAITRMTNLDNDEDNQKNNDKGWNFEAI
KNFDQKFIDITKKNNNLSLKQNKRYLDDRFINDAILSPGVKRILREATKVFNAILKQFSEEYDV
TKVVIELARELSEEKELENTKNYKKLIKKNGDKISEGLKALGISEDEIKDILKSPTKSYKFLLW
LQQDHIDPYSLKEIAFDDIFTKTEKFEIDHIIPYSISFDDSSSNKLLVLAESNQAKSNQTPYEF
ISSGNAGIKWEDYEAYCRKFKDGDSSLLDSTQRSKKFAKMMKTDTSSKYDIGFLARNLNDTRYA
TIVFRDALEDYANNHLVEDKPMFKVVCINGSVTSFLRKNFDDSSYAKKDRDKNIHHAVDASIIS
IFSNETKTLFNQLTQFADYKLFKNTDGSWKKIDPKTGVVTEVTDENWKQIRVRNQVSEIAKVIE
KYIQDSNIERKARYSRKIENKTNISLFNDTVYSAKKVGYEDQIKRKNLKTLDIHESAKENKNSK
VKRQFVYRKLVNVSLLNNDKLADLFAEKEDILMYRANPWVINLAEQIFNEYTENKKIKSQNVFE
KYMLDLTKEFPEKFSEFLVKSMLRNKTAIIYDDKKNIVHRIKRLKMLSSELKENKLSNVIIRSK
NQSGTKLSYQDTINSLALMIMRSIDPTAKKQYIRVPLNTLNLHLGDHDFDLHNMDAYLKKPKFV
KYLKANEIGDEYKPWRVLTSGTLLIHKKDKKLMYISSFQNLNDVIEIKNLIETEYKENDDSDSK
KKKKANRFLMTLSTILNDYILLDAKDNFDILGLSKNRIDEILNSKLGLDKIVK

SEQ ID NO: 385
MGGSEVGTVPVTWRLGVDVGERSIGLAAVSYEEDKPKEILAAVSWIHDGGVGDERSGASRLALR
GMARRARRLRRFRRARLRDLDMLLSELGWTPLPDKNVSPVDAWLARKRLAEEYVVDETERRRLL
GYAVSHMARHRGWRNPWTTIKDLKNLPQPSDSWERTRESLEARYSVSLEPGTVGQWAGYLLQRA
PGIRLNPTQQSAGRRAELSNATAFETRLRQEDVLWELRCIADVQGLPEDVVSNVIDAVFCQKRP
SVPAERIGRDPLDPSQLRASRACLEFQEYRIVAAVANLRIRDGSGSRPLSLEERNAVIEALLAQ
TERSLTWSDIALEILKLPNESDLTSVPEEDGPSSLAYSQFAPFDETSARIAEFIAKNRRKIPTF
AQWWQEQDRTSRSDLVAALADNSIAGEEEQELLVHLPDAELEALEGLALPSGRVAYSRLTLSGL
TRVMRDDGVDVHNARKTCFGVDDNWRPPLPALHEATGHPVVDRNLAILRKFLSSATMRWGPPQS
IVVELARGASESRERQAEEEAARRAHRKANDRIRAELRASGLSDPSPADLVRARLLELYDCHCM
YCGAPISWENSELDHIVPRTDGGSNRHENLAITCGACNKEKGRRPFASWAETSNRVQLRDVIDR
VQKLKYSGNMYWTRDEFSRYKKSVVARLKRRTSDPEVIQSIESTGYAAVALRDRLLSYGEKNGV
AQVAVFRGGVTAEARRWLDISIERLFSRVAIFAQSTSTKRLDRRHHAVDAVVLTTLTPGVAKTL
ADARSRRVSAEFWRRPSDVNRHSTEEPQSPAYRQWKESCSGLGDLLISTAARDSIAVAAPLRLR
PTGALHEETLRAFSEHTVGAAWKGAELRRIVEPEVYAAFLALTDPGGRFLKVSPSEDVLPADEN
RHIVLSDRVLGPRDRVKLFPDDRGSIRVRGGAAYIASFHHARVFRWGSSHSPSFALLRVSLADL
AVAGLLRDGVDVFTAELPPWTPAWRYASIALVKAVESGDAKQVGWLVPGDELDFGPEGVTTAAG
DLSMFLKYFPERHWVVTGFEDDKRINLKPAFLSAEQAEVLRTERSDRPDTLTEAGEILAQFFPR
CWRATVAKVLCHPGLTVIRRTALGQPRWRRGHLPYSWRPWSADPWSGGTP

SEQ ID NO: 386
MHNKKNITIGFDLGIASIGWAIIDSTTSKILDWGTRTFEERKTANERRAFRSTRRNIRRKAYRN
QRFINLILKYKDLFELKNISDIQRANKKDTENYEKIISFFTEIYKKCAAKHSNILEVKVKALDS
KIEKLDLIWILHDYLENRGFFYDLEEENVADKYEGIEHPSILLYDFFKKNGFFKSNSSIPKDLG
GYSFSNLQWVNEIKKLFEVQEINPEFSEKFLNLFTSVRDYAKGPGSEHSASEYGIFQKDEKGKV
FKKYDNIWDKTIGKCSFFVEENRSPVNYPSYEIFNLLNQLINLSTDLKTTNKKIWQLSSNDRNE
LLDELLKVKEKAKIISISLKKNEIKKIILKDFGFEKSDIDDQDTIEGRKIIKEEPTTKLEVTKH
LLATIYSHSSDSNWININNILEFLPYLDAICIILDREKSRGQDEVLKKLTEKNIFEVLKIDREK
QLDFVKSIFSNTKFNFKKIGNFSLKAIREFLPKMFEQNKNSEYLKWKDEEIRRKWEEQKSKLGK

-continued

```
TDKKTKYLNPRIFQDEIISPGTKNTFEQAVLVLNQIIKKYSKENIIDAIIIESPREKNDKKTIE

EIKKRNKKGKGKTLEKLFQILNLENKGYKLSDLETKPAKLLDRLRFYHQQDGIDLYTLDKINID

QLINGSQKYEIEHIIPYSMSYDNSQANKILTEKAENLKKGKLIASEYIKRNGDEFYNKYYEKAK

ELFINKYKKNKKLDSYVDLDEDSAKNRFRFLTLQDYDEFQVEFLARNLNDTRYSTKLFYHALVE

HFENNEFFTYIDENSSKHKVKISTIKGHVTKYFRAKPVQKNNGPNENLNNNKPEKIEKNRENNE

HHAVDAAIVAIIGNKNPQIANLLTLADNKTDKKFLLHDENYKENIETGELVKIPKFEVDKLAKV

EDLKKIIQEKYEEAKKHTAIKFSRKTRTILNGGLSDETLYGFKYDEKEDKYFKIIKKKLVTSKN

EELKKYFENPFGKKADGKSEYTVLMAQSHLSEFNKLKEIFEKYNGFSNKTGNAFVEYMNDLALK

EPTLKAEIESAKSVEKLLYYNFKPSDQFTYHDNINNKSFKRFYKNIRIIEYKSIPIKFKILSKH

DGGKSFKDTLFSLYSLVYKVYENGKESYKSIPVTSQMRNFGIDEFDFLDENLYNKEKLDIYKSD

FAKPIPVNCKPVFVLKKGSILKKKSLDIDDFKETKETEEGNYYFISTISKRFNRDTAYGLKPLK

LSVVKPVAEPSTNPIFKEYIPIHLDELGNEYPVKIKEHTDDEKLMCTIK
```

Nucleic Acids Encoding Cas9 Molecules

Nucleic acids encoding the Cas9 molecules or Cas9 polypeptides, e.g., an eaCas9 molecule or eaCas9 polypeptides are provided herein.

Exemplary nucleic acids encoding Cas9 molecules or Cas9 polypeptides are described in Cong et al., SCIENCE 2013, 399(6121):819-823; Wang et al., CELL 2013, 153(4):910-918; Mali et al., SCIENCE 2013, 399(6121):823-826; Jinek el al., SCIENCE 2012, 337(6096):816-821. Another exemplary nucleic acid encoding a Cas9 molecule or Cas9 polypeptide is shown in FIG. 8.

In an embodiment, a nucleic acid encoding a Cas9 molecule or Cas9 polypeptide can be a synthetic nucleic acid sequence. For example, the synthetic nucleic acid molecule can be chemically modified, e.g., as described in Section VIII. In an embodiment, the Cas9 mRNA has one or more (e.g., all of the following properties: it is capped, polyadenylated, substituted with 5-methylcytidine and/or pseudouridine.

In addition, or alternatively, the synthetic nucleic acid sequence can be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein.

In addition, or alternatively, a nucleic acid encoding a Cas9 molecule or Cas9 polypeptide may comprise a nuclear localization sequence (NLS). Nuclear localization sequences are known in the art.

Provided below is an exemplary codon optimized nucleic acid sequence encoding a Cas9 molecule of S. pyogenes.

(SEQ ID NO: 22)
```
ATGGATAAAA AGTACAGCAT CGGGCTGGAC ATCGGTACAA ACTCAGTGGG

GTGGGCCGTG ATTACGGACG AGTACAAGGT ACCCTCCAAA AAATTTAAAG

TGCTGGGTAA CACGGACAGA CACTCTATAA AGAAAAATCT TATTGGAGCC

TTGCTGTTCG ACTCAGGCGA GACAGCCGAA GCCACAAGGT TGAAGCGGAC

CGCCAGGAGG CGGTATACCA GGAGAAAGAA CCGCATATGC TACCTGCAAG

AAATCTTCAG TAACGAGATG GCAAAGGTTG ACGATAGCTT TTTCCATCGC

CTGGAAGAAT CCTTTCTTGT TGAGGAAGAC AAGAAGCACG AACGGCACCC

CATCTTTGGC AATATTGTCG ACGAAGTGGC ATATCACGAA AAGTACCCGA

CTATCTACCA CCTCAGGAAG AAGCTGGTGG ACTCTACCGA TAAGGCGGAC

CTCAGACTTA TTTATTTGGC ACTCGCCCAC ATGATTAAAT TTAGAGGACA

TTTCTTGATC GAGGGCGACC TGAACCCGGA CAACAGTGAC GTCGATAAGC

TGTTCATCCA ACTTGTGCAG ACCTACAATC AACTGTTCGA AGAAAACCCT

ATAAATGCTT CAGGAGTCGA CGCTAAAGCA ATCCTGTCCG CGCGCCTCTC

AAAATCTAGA AGACTTGAGA ATCTGATTGC TCAGTTGCCC GGGGAAAAGA

AAAATGGATT GTTTGGCAAC CTGATCGCCC TCAGTCTCGG ACTGACCCCA

AATTTCAAAA GTAACTTCGA CCTGGCCGAA GACGCTAAGC TCCAGCTGTC

CAAGGACACA TACGATGACG ACCTCGACAA TCTGCTGGCC CAGATTGGGG
```

-continued

```
ATCAGTACGC CGATCTCTTT TTGGCAGCAA AGAACCTGTC CGACGCCATC
CTGTTGAGCG ATATCTTGAG AGTGAACACC GAAATTACTA AAGCACCCCT
TAGCGCATCT ATGATCAAGC GGTACGACGA GCATCATCAG GATCTGACCC
TGCTGAAGGC TCTTGTGAGG CAACAGCTCC CCGAAAAATA CAAGGAAATC
TTCTTTGACC AGAGCAAAAA CGGCTACGCT GGCTATATAG ATGGTGGGGC
CAGTCAGGAG GAATTCTATA AATTCATCAA GCCCATTCTC GAGAAAATGG
ACGGCACAGA GGAGTTGCTG GTCAAACTTA ACAGGGAGGA CCTGCTGCGG
AAGCAGCGGA CCTTTGACAA CGGGTCTATC CCCCACCAGA TTCATCTGGG
CGAACTGCAC GCAATCCTGA GGAGGCAGGA GGATTTTTAT CCTTTTCTTA
AAGATAACCG CGAGAAAATA GAAAAGATTC TTACATTCAG GATCCCGTAC
TACGTGGGAC CTCTCGCCCG GGGCAATTCA CGGTTTGCCT GGATGACAAG
GAAGTCAGAG GAGACTATTA CACCTTGGAA CTTCGAAGAA GTGGTGGACA
AGGGTGCATC TGCCCAGTCT TTCATCGAGC GGATGACAAA TTTTGACAAG
AACCTCCCTA ATGAGAAGGT GCTGCCCAAA CATTCTCTGC TCTACGAGTA
CTTTACCGTC TACAATGAAC TGACTAAAGT CAAGTACGTC ACCGAGGGAA
TGAGGAAGCC GGCATTCCTT AGTGGAGAAC AGAAGAAGGC GATTGTAGAC
CTGTTGTTCA AGACCAACAG GAAGGTGACT GTGAAGCAAC TTAAAGAAGA
CTACTTTAAG AAGATCGAAT GTTTTGACAG TGTGGAAATT TCAGGGGTTG
AAGACCGCTT CAATGCGTCA TTGGGGACTT ACCATGATCT TCTCAAGATC
ATAAAGGACA AAGACTTCCT GGACAACGAA GAAAATGAGG ATATTCTCGA
AGACATCGTC CTCACCCTGA CCCTGTTCGA AGACAGGGAA ATGATAGAAG
AGCGCTTGAA AACCTATGCC CACCTCTTCG ACGATAAAGT TATGAAGCAG
CTGAAGCGCA GGAGATACAC AGGATGGGGA AGATTGTCAA GGAAGCTGAT
CAATGGAATT AGGGATAAAC AGAGTGGCAA GACCATACTG GATTTCCTCA
AATCTGATGG CTTCGCCAAT AGGAACTTCA TGCAACTGAT TCACGATGAC
TCTCTTACCT TCAAGGAGGA CATTCAAAAG GCTCAGGTGA GCGGGCAGGG
AGACTCCCTT CATGAACACA TCGCGAATTT GGCAGGTTCC CCCGCTATTA
AAAAGGGCAT CCTTCAAACT GTCAAGGTGG TGGATGAATT GGTCAAGGTA
ATGGGCAGAC ATAAGCCAGA AAATATTGTG ATCGAGATGG CCCGCGAAAA
CCAGACCACA CAGAAGGGCC AGAAAAATAG TAGAGAGCGG ATGAAGAGGA
TCGAGGAGGG CATCAAAGAG CTGGGATCTC AGATTCTCAA AGAACACCCC
GTAGAAAACA CACAGCTGCA GAACGAAAAA TTGTACTTGT ACTATCTGCA
GAACGGCAGA GACATGTACG TCGACCAAGA ACTTGATATT AATAGACTGT
CCGACTATGA CGTAGACCAT ATCGTGCCCC AGTCCTTCCT GAAGGACGAC
TCCATTGATA ACAAAGTCTT GACAAGAAGC GACAAGAACA GGGGTAAAAG
TGATAATGTG CCTAGCGAGG AGGTGGTGAA AAAAATGAAG AACTACTGGC
GACAGCTGCT TAATGCAAAG CTCATTACAC AACGGAAGTT CGATAATCTG
ACGAAAGCAG AGAGAGGTGG CTTGTCTGAG TTGGACAAGG CAGGGTTTAT
TAAGCGGCAG CTGGTGGAAA CTAGGCAGAT CACAAAGCAC GTGGCGCAGA
TTTTGGACAG CCGGATGAAC ACAAAATACG ACGAAAATGA TAAACTGATA
```

```
                         -continued
CGAGAGGTCA AAGTTATCAC GCTGAAAAGC AAGCTGGTGT CCGATTTTCG

GAAAGACTTC CAGTTCTACA AAGTTCGCGA GATTAATAAC TACCATCATG

CTCACGATGC GTACCTGAAC GCTGTTGTCG GGACCGCCTT GATAAAGAAG

TACCCAAAGC TGGAATCCGA GTTCGTATAC GGGGATTACA AAGTGTACGA

TGTGAGGAAA ATGATAGCCA AGTCCGAGCA GGAGATTGGA AAGGCCACAG

CTAAGTACTT CTTTTATTCT AACATCATGA ATTTTTTAA GACGGAAATT

ACCCTGGCCA ACGGAGAGAT CAGAAAGCGG CCCCTTATAG AGACAAATGG

TGAAACAGGT GAAATCGTCT GGGATAAGGG CAGGGATTTC GCTACTGTGA

GGAAGGTGCT GAGTATGCCA CAGGTAAATA TCGTGAAAAA ACCGAAGTA

CAGACCGGAG GATTTTCCAA GGAAAGCATT TTGCCTAAAA GAAACTCAGA

CAAGCTCATC GCCCGCAAGA AAGATTGGGA CCCTAAGAAA TACGGGGGAT

TTGACTCACC CACCGTAGCC TATTCTGTGC TGGTGGTAGC TAAGGTGGAA

AAAGGAAAGT CTAAGAAGCT GAAGTCCGTG AAGGAACTCT TGGGAATCAC

TATCATGGAA AGATCATCCT TTGAAAAGAA CCCTATCGAT TTCCTGGAGG

CTAAGGGTTA CAAGGAGGTC AAGAAAGACC TCATCATTAA ACTGCCAAAA

TACTCTCTCT TCGAGCTGGA AAATGGCAGG AAGAGAATGT TGGCCAGCGC

CGGAGAGCTG CAAAAGGGAA ACGAGCTTGC TCTGCCCTCC AAATATGTTA

ATTTTCTCTA TCTCGCTTCC CACTATGAAA AGCTGAAAGG GTCTCCCGAA

GATAACGAGC AGAAGCAGCT GTTCGTCGAA CAGCACAAGC ACTATCTGGA

TGAAATAATC GAACAAATAA GCGAGTTCAG CAAAAGGGTT ATCCTGGCGG

ATGCTAATTT GGACAAAGTA CTGTCTGCTT ATAACAAGCA CCGGGATAAG

CCTATTAGGG AACAAGCCGA GAATATAATT CACCTCTTTA CACTCACGAA

TCTCGGAGCC CCCGCCGCCT TCAAATACTT TGATACGACT ATCGACCGGA

AACGGTATAC CAGTACCAAA GAGGTCCTCG ATGCCACCCT CATCCACCAG

TCAATTACTG GCCTGTACGA AACACGGATC GACCTCTCTC AACTGGGCGG

CGACTAG
```

Provided below is the corresponding amino acid sequence of a *S. pyogenes* Cas9 molecule.

```
                                          (SEQ ID NO: 23)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

-continued
LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK
```

```
YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD*
```

Provided below is an exemplary codon optimized nucleic acid sequence encoding a Cas9 molecule of *N. meningitidis*.

```
                                         (SEQ ID NO: 24)
ATGGCCGCCTTCAAGCCCAACCCCATCAACTACATCCTGGGCCTGGACAT

CGGCATCGCCAGCGTGGGCTGGGCCATGGTGGAGATCGACGAGGACGAGA

ACCCCATCTGCCTGATCGACCTGGGTGTGCGCGTGTTCGAGCGCGCTGAG

GTGCCCAAGACTGGTGACAGTCTGGCTATGGCTCGCCGGCTTGCTCGCTC

TGTTCGGCGCCTTACTCGCCGGCGCGCTCACCGCCTTCTGCGCGCTCGCC

GCCTGCTGAAGCGCGAGGGTGTGCTGCAGGCTGCCGACTTCGACGAGAAC

GGCCTGATCAAGAGCCTGCCCAACACTCCTTGGCAGCTGCGCGCTGCCGC

TCTGGACCGCAAGCTGACTCCTCTGGAGTGGAGCGCCGTGCTGCTGCACC

TGATCAAGCACCGCGGCTACCTGAGCCAGCGCAAGAACGAGGGCGAGACC

GCCGACAAGGAGCTGGGTGCTCTGCTGAAGGGCGTGGCCGACAACGCCCA

CGCCCTGCAGACTGGTGACTTCCGCACTCCTGCTGAGCTGGCCCTGAACA

AGTTCGAGAAGGAGAGCGGCCACATCCGCAACCAGCGCGGCGACTACAGC

CACACCTTCAGCCGCAAGGACCTGCAGGCCGAGCTGATCCTGCTGTTCGA

GAAGCAGAAGGAGTTCGGCAACCCCCACGTGAGCGGCGGCCTGAAGGAGG

GCATCGAGACCCTGCTGATGACCCAGCGCCCCGCCCTGAGCGGCGACGCC

GTGCAGAAGATGCTGGGCCACTGCACCTTCGAGCCAGCCGAGCCCAAGGC

CGCCAAGAACACCTACACCGCCGAGCGCTTCATCTGGCTGACCAAGCTGA

ACAACCTGCGCATCCTGGAGCAGGGCAGCGAGCGCCCCCTGACCGACACC

GAGCGCGCCACCCTGATGGACGAGCCCTACCGCAAGAGCAAGCTGACCTA

CGCCCAGGCCCGCAAGCTGCTGGGTCTGGAGGACACCGCCTTCTTCAAGG

GCCTGCGCTACGGCAAGGACAACGCCGAGGCCAGCACCCTGATGGAGATG

AAGGCCTACCACGCCATCAGCCGCGCCCTGGAGAAGGAGGGCCTGAAGGA

CAAGGAGAGTCCTCTGAACCTGAGCCCCGAGCTGCAGGACGAGATCGGCA

CCGCCTTCAGCCTGTTCAAGACCGACGAGGACATCACCGGCCGCCTGAAG

GACCGCATCCAGCCCGAGATCCTGGAGGCCCTGCTGAAGCACATCAGCTT

CGACAAGTTCGTGCAGATCAGCCTGAAGGCCCTGCGCCGCATCGTGCCCC

TGATGGAGCAGGGCAAGCGCTACGACGAGGCCTGCGCCGAGATCTACGGC

GACCACTACGGCAAGAAGAACACCGAGGAGAAGATCTACCTGCCTCCTAT

CCCCGCCGACGAGATCCGCAACCCCGTGGTGCTGCGCGCCCTGAGCCAGG

CCCGCAAGGTGATCAACGGCGTGGTGCGCCGCTACGGCAGCCCCGCCCGC

ATCCACATCGAGACCGCCCGCGAGGTGGGCAAGAGCTTCAAGGACCGCAA

GGAGATCGAGAAGCGCCAGGAGGAGAACCGCAAGGACCGCGAGAAGGCCG

CCGCCAAGTTCCGCGAGTACTTCCCCAACTTCGTGGGCGAGCCCAAGAGC

AAGGACATCCTGAAGCTGCGCCTGTACGAGCAGCAGCACGGCAAGTGCCT

GTACAGCGGCAAGGAGATCAACCTGGGCCGCCTGAACGAGAAGGGCTACG

TGGAGATCGACCACGCCCTGCCCTTCAGCCGCACCTGGGACGACAGCTTC

AACAACAAGGTGCTGGTGCTGGGCAGCGAGAACCAGAACAAGGGCAACCA

GACCCCCTACGAGTACTTCAACGGCAAGGACAACAGCCGCGAGTGGCAGG

AGTTCAAGGCCCGCGTGGAGACCAGCCGCTTCCCCCGCAGCAAGAAGCAG

CGCATCCTGCTGCAGAAGTTCGACGAGGACGGCTTCAAGGAGCGCAACCT

GAACGACACCCGCTACGTGAACCGCTTCCTGTGCCAGTTCGTGGCCGACC

GCATGCGCCTGACCGGCAAGGGCAAGAAGCGCGTGTTCGCCAGCAACGGC

CAGATCACCAACCTGCTGCGCGGCTTCTGGGGCCTGCGCAAGGTGCGCGC

CGAGAACGACCGCCACCACGCCCTGGACGCCGTGGTGGTGGCCTGCAGCA

CCGTGGCCATGCAGCAGAAGATCACCCGCTTCGTGCGCTACAAGGAGATG

AACGCCTTCGACGGTAAAACCATCGACAAGGAGACCGGCGAGGTGCTGCA

CCAGAAGACCCACTTCCCCCAGCCCTGGGAGTTCTTCGCCCAGGAGGTGA

TGATCCGCGTGTTCGGCAAGCCCGACGGCAAGCCCGAGTTCGAGGAGGCC

GACACCCCCGAGAAGCTGCGCACCCTGCTGGCCGAGAAGCTGAGCAGCCG

CCCTGAGGCCGTGCACGAGTACGTGACTCCTCTGTTCGTGAGCCGCGCCC

CCAACCGCAAGATGAGCGGTCAGGGTCACATGGAGACCGTGAAGAGCGCC

AAGCGCCTGGACGAGGGCGTGAGCGTGCTGCGCGTGCCCCTGACCCAGCT

GAAGCTGAAGGACCTGGAGAAGATGGTGAACCGCGAGCGCGAGCCCAAGC

TGTACGAGGCCCTGAAGGCCCGCCTGGAGGCCCACAAGGACGACCCCGCC

AAGGCCTTCGCCGAGCCCTTCTACAAGTACGACAAGGCCGGCAACCGCAC

CCAGCAGGTGAAGGCCGTGCGCGTGGAGCAGGTGCAGAAGACCGGCGTGT

GGGTGCGCAACCACAACGGCATCGCCGACAACGCCACCATGGTGCGCGTG

GACGTGTTCGAGAAGGGCGACAAGTACTACCTGGTGCCCATCTACAGCTG

GCAGGTGGCCAAGGGCATCCTGCCCGACCGCGCCGTGGTGCAGGGCAAGG

ACGAGGAGGACTGGCAGCTGATCGACGACAGCTTCAACTTCAAGTTCAGC

CTGCACCCCAACGACCTGGTGGAGGTGATCACCAAGAAGGCCCGCATGTT

CGGCTACTTCGCCAGCTGCCACCGCGGCACCGGCAACATCAACATCCGCA

TCCACGACCTGGACCACAAGATCGGCAAGAACGGCATCCTGGAGGGCATC

GGCGTGAAGACCGCCCTGAGCTTCCAGAAGTACCAGATCGACGAGCTGGG

CAAGGAGATCCGCCCCTGCCGCCTGAAGAAGCGCCCTCCTGTGCGCTAA
```

Provided below is the corresponding amino acid sequence of a *N. meningitidis* Cas9 molecule.

```
                                         (SEQ ID NO: 25)
MAAFKPNPINYILGLDIGIASVGWAMVEIDEDENPICLIDLGVRVFERAE

VPKTGDSLAMARRLARSVRRLTRRRAHRLLRARRLLKREGVLQAADFDEN

GLIKSLPNTPWQLRAAALDRKLTPLEWSAVLLHLIKHRGYLSQRKNEGET

ADKELGALLKGVADNAHALQTGDFRTPAELALNKFEKESGHIRNQRGDYS

HTFSRKDLQAELILLFEKQKEFGNPHVSGGLKEGIETLLMTQRPALSGDA

VQKMLGHCTFEPAEPKAAKNTYTAERFIWLTKLNNLRILEQGSERPLTDT
```

-continued
ERATLMDEPYRKSKLTYAQARKLLGLEDTAFFKGLRYGKDNAEASTLMEM

KAYHAISRALEKEGLKDKKSPLNLSPELQDEIGTAFSLFKTDEDITGRLK

DRIQPEILEALLKHISFDKFVQISLKALRRIVPLMEQGKRYDEACAEIYG

DHYGKKNTEEKIYLPPIPADEIRNPVVLRALSQARKVINGVVRRYGSPAR

IHIETAREVGKSFKDRKEIEKRQEENRKDREKAAAKFREYFPNFVGEPKS

KDILKLRLYEQQHGKCLYSGKEINLGRLNEKGYVEIDHALPFSRTWDDSF

NNKVLVLGSENQNKGNQTPYEYFNGKDNSREWQEFKARVETSRFPRSKKQ

RILLQKFDEDGFKERNLNDTRYVNRFLCQFVADRMRLTGKGKKRVFASNG

QITNLLRGFWGLRKVRAENDRHHALDAVVVACSTVAMQQKITRFVRYKEM

NAFDGKTIDKETGEVLHQKTHFPQPWEFFAQEVMIRVFGKPDGKPEFEEA

DTPEKLRTLLAEKLSSRPEAVHEYVTPLFVSRAPNRKMSGQGHMETVKSA

KRLDEGVSVLRVPLTQLKLKDLEKMVNREREPKLYEALKARLEAHKDDPA

KAFAEPFYKYDKAGNRTQQVKAVRVEQVQKTGVWVRNHNGIADNATMVRV

DVFEKGDKYYLVPIYSWQVAKGILPDRAVVQGKDEEDWQLIDDSFNFKFS

LHPNDLVEVITKKARMFGYFASCHRGTGNINIRIHDLDHKIGKNGILEGI

GVKTALSFQKYQIDELGKEIRPCRLKKRPPVR*

Provided below is an amino acid sequence of a *S. aureus* Cas9 molecule.

(SEQ ID NO: 26)
MKRNYILGLDIGITSVGYGIIDYETRDVIDAGVRLFKEANVENNEGRRSK

RGARRLKRRRRHRIQRVKKLLFDYNLLTDHSELSGINPYEARVKGLSQKL

SEEEFSAALLHLAKRRGVHNVNEVEEDTGNELSTKEQISRNSKALEEKYV

AELQLERLKKDGEVRGSINRFKTSDYVKEAKQLLKVQKAYHQLDQSFIDT

YIDLLETRRTYYEGPGEGSPFGWKDIKEWYEMLMGHCTYFPEELRSVKYA

YNADLYNALNDLNNLVITRDENEKLEYYEKFQIIENVFKQKKKPTLKQIA

KEILVNEEDIKGYRVTSTGKPEFTNLKVYHDIKDITARKEIIENAELLDQ

IAKILTIYQSSEDIQEELTNLNSELTQEEIEQISNLKGYTGTHNLSLKAI

NLILDELWHTNDNQIAIFNRLKLVPKKVDLSQQKEIPTTLVDDFILSPVV

KRSFIQSIKVINAIIKKYGLPNDIIIELAREKNSKDAQKMINEMQKRNRQ

TNERIEEIIRTTGKENAKYLIEKIKLHDMQEGKCLYSLEAIPLEDLLNNP

FNYEVDHIIPRSVSFDNSFNNKVLVKQEENSKKGNRTPFQYLSSSDSKIS

YETFKKHILNLAKGKGRISKTKKEYLLEERDINRFSVQKDFINRNLVDTR

YATRGLMNLLRSYFRVNNLDVKVKSINGGFTSFLRRKWKFKKERNKGYKH

HAEDALIIANADFIFKEWKKLDKAKKVMENQMFEEKQAESMPEIETEQEY

KEIFITPHQIKHIKDFKDYKYSHRVDKKPNRELINDTLYSTRKDDKGNTL

IVNNLNGLYDKDNDKLKKLINKSPEKLLMYHHDPQTYQKLKLIMEQYGDE

KNPLYKYYEETGNYLTKYSKKDNGPVIKKIKYYGNKLNAHLDITDDYPNS

RNKVVKLSLKPYRFDVYLDNGVYKFVTVKNLDVIKKENYYEVNSKCYEEA

KKLKKISNQAEFIASFYNNDLIKINGELYRVIGVNNDLLNRIEVNMIDIT

YREYLENMNDKRPPRIIKTIASKTQSIKKYSTDILGNLYEVKSKKHPQII

KKG*

Provided below is an exemplary codon optimized nucleic acid sequence encoding a Cas9 molecule of *S. aureus* Cas9.

(SEQ ID NO: 39)
ATGAAAAGGAACTACATTCTGGGGCTGGACATCGGGATTACAAGCGTGGG

GTATGGGATTATTGACTATGAAACAAGGGACGTGATCGACGCAGGCGTCA

GACTGTTCAAGGAGGCCAACGTGGAAAACAATGAGGGACGGAGAAGCAAG

AGGGGAGCCAGGCGCCTGAAACGACGGAGAAGGCACAGAATCCAGAGGGT

GAAGAAACTGCTGTTCGATTACAACCTGCTGACCGACCATTCTGAGCTGA

GTGGAATTAATCCTTATGAAGCCAGGGTGAAAGGCCTGAGTCAGAAGCTG

TCAGAGGAAGAGTTTTCCGCAGCTCTGCTGCACCTGGCTAAGCGCCGAGG

AGTGCATAACGTCAATGAGGTGGAAGAGGACACCGGCAACGAGCTGTCTA

CAAAGGAACAGATCTCACGCAATAGCAAAGCTCTGGAAGAGAAGTATGTC

GCAGAGCTGCAGCTGGAACGGCTGAAGAAAGATGGCGAGGTGAGAGGGTC

AATTAATAGGTTCAAGACAAGCGACTACGTCAAAGAAGCCAAGCAGCTGC

TGAAAGTGCAGAAGGCTTACCACCAGCTGGATCAGAGCTTCATCGATACT

TATATCGACCTGCTGGAGACTCGGAGAACCTACTATGAGGGACCAGGAGA

AGGGGAGCCCCTTCGGATGGAAAGACATCAAGGAATGGTACGAGATGCTGA

TGGGACATTGCACCTATTTTCCAGAAGAGCTGAGAAGCGTCAAGTACGCT

TATAACGCAGATCTGTACAACGCCCTGAATGACCTGAACAACCTGGTCAT

CACCAGGGATGAAAACGAGAAACTGGAATACTATGAGAAGTTCCAGATCA

TCGAAAACGTGTTTAAGCAGAAGAAAAAGCCTACACTGAAACAGATTGCT

AAGGAGATCCTGGTCAACGAAGAGGACATCAAGGGCTACCGGGTGACAAG

CACTGGAAAACCAGAGTTCACCAATCTGAAAGTGTATCACGATATTAAGG

ACATCACAGCACGGAAAGAAATCATTGAGAACGCCGAACTGCTGGATCAG

ATTGCTAAGATCCTGACTATCTACCAGAGCTCCGAGGACATCCAGGAAGA

GCTGACTAACCTGAACAGCGAGCTGACCCAGGAAGAGATCGAACAGATTA

GTAATCTGAAGGGGTACACCGGAACACACAACCTGTCCCTGAAAGCTATC

AATCTGATTCTGGATGAGCTGTGGCATACAAACGACAATCAGATTGCAAT

CTTTAACCGGCTGAAGCTGGTCCCAAAAAAGGTGGACCTGAGTCAGCAGA

AAGAGATCCCAACCACACTGGTGGACGATTTCATTCTGTCACCCGTGGTC

AAGCGGAGCTTCATCCAGAGCATCAAAGTGATCAACGCCATCATCAAGAA

GTACGGCCTGCCCAATGATATCATTATCGAGCTGGCTAGGGAGAAGAACA

GCAAGGACGCACAGAAGATGATCAATGAGATGCAGAAACGAAACCGGCAG

ACCAATGAACGCATTGAAGAGATTATCCGAACTACCGGGAAAGAGAACGC

AAAGTACCTGATTGAAAAAATCAAGCTGCACGATATGCAGGAGGGAAAGT

GTCTGTATTCTCTGGAGGCCATCCCCCTGGAGGACCTGCTGAACAATCCA

TTCAACTACGAGGTCGATCATATTATCCCCAGAAGCGTGTCCTTCGACAA

TTCCTTTAACAACAAGGTGCTGGTCAAGCAGGAAGAGAACTCTAAAAAGG

GCAATAGGACTCCTTTCCAGTACCTGTCTAGTTCAGATTCCAAGATCTCT

TACGAAACCTTTAAAAAGCACATTCTGAATCTGGCCAAAGGAAAGGGCCG

CATCAGCAAGACCAAAAAGGAGTACCTGCTGGAAGAGCGGGACATCAACA

-continued

```
GATTCTCCGTCCAGAAGGATTTTATTAACCGGAATCTGGTGGACACAAGA

TACGCTACTCGCGGCCTGATGAATCTGCTGCGATCCTATTTCCGGGTGAA

CAATCTGGATGTGAAAGTCAAGTCCATCAACGGCGGGTTCACATCTTTTC

TGAGGCGCAAATGGAAGTTTAAAAAGGAGCGCAACAAAGGGTACAAGCAC

CATGCCGAAGATGCTCTGATTATCGCAAATGCCGACTTCATCTTTAAGGA

GTGGAAAAAGCTGGACAAAGCCAAGAAAGTGATGGAGAACCAGATGTTCG

AAGAGAAGCAGGCCGAATCTATGCCCGAAATCGAGACAGAACAGGAGTAC

AAGGAGATTTTCATCACTCCTCACCAGATCAAGCATATCAAGGATTTCAA

GGACTACAAGTACTCTCACCGGGTGGATAAAAAGCCCAACAGAGAGCTGA

TCAATGACACCCTGTATAGTACAAGAAAAGACGATAAGGGGAATACCCTG

ATTGTGAACAATCTGAACGGACTGTACGACAAAGATAATGACAAGCTGAA

AAAGCTGATCAACAAAAGTCCCGAGAAGCTGCTGATGTACCACCATGATC

CTCAGACATATCAGAAACTGAAGCTGATTATGGAGCAGTACGGCGACGAG

AAGAACCCACTGTATAAGTACTATGAAGAGACTGGGAACTACCTGACCAA

GTATAGCAAAAGGATAATGGCCCCGTGATCAAGAAGATCAAGTACTATG

GGAACAAGCTGAATGCCCATCTGGACATCACAGACGATTACCCTAACAGT

CGCAACAAGGTGGTCAAGCTGTCACTGAAGCCATACAGATTCGATGTCTA

TCTGGACAACGGCGTGTATAAATTTGTGACTGTCAAGAATCTGGATGTCA
```

-continued

```
TCAAAAAGGAGAACTACTATGAAGTGAATAGCAAGTGCTACGAAGAGGCT

AAAAAGCTGAAAAAGATTAGCAACCAGGCAGAGTTCATCGCCTCCTTTTA

CAACAACGACCTGATTAAGATCAATGGCGAACTGTATAGGGTCATCGGGG

TGAACAATGATCTGCTGAACCGCATTGAAGTGAATATGATTGACATCACT

TACCGAGAGTATCTGGAAAACATGAATGATAAGCGCCCCCCTCGAATTAT

CAAAACAATTGCCTCTAAGACTCAGAGTATCAAAAAGTACTCAACCGACA

TTCTGGGAAACCTGTATGAGGTGAAGAGCAAAAAGCACCCTCAGATTATC

AAAAAGGGC
```

If any of the above Cas9 sequences are fused with a peptide or polypeptide at the C-terminus, it is understood that the stop codon will be removed.

Other Cas Molecules and Cas Polypeptides

Various types of Cas molecules or Cas polypeptides can be used to practice the inventions disclosed herein. In some embodiments, Cas molecules of Type II Cas systems are used. In other embodiments, Cas molecules of other Cas systems are used. For example, Type I or Type III Cas molecules may be used. Exemplary Cas molecules (and Cas systems) are described, e.g., in Haft et al., PLoS COMPUTATIONAL BIOLOGY 2005, 1(6): e60 and Makarova et al., NATURE REVIEW MICROBIOLOGY 2011, 9:467-477, the contents of both references are incorporated herein by reference in their entirety. Exemplary Cas molecules (and Cas systems) are also shown in Table 33.

TABLE 33

Cas Systems

| Gene name[‡] | System type or subtype | Name from Haft et al.[§] | Structure of encoded protein (PDB accessions)[¶] | Families (and superfamily) of encoded protein[#**] | Representatives |
|---|---|---|---|---|---|
| cas1 | Type I<br>Type II<br>Type III | cas1 | 3GOD, 3LFX and 2YZS | COG1518 | SERP2463, SPy1047 and ygbT |
| cas2 | Type I<br>Type II<br>Type III | cas2 | 2IVY, 2I8E and 3EXC | COG1343 and COG3512 | SERP2462, SPy1048, SPy1723 (N-terminal domain) and ygbF |
| cas3' | Type I[‡‡] | cas3 | NA | COG1203 | APE1232 and ygcB |
| cas3" | Subtype I-A<br>Subtype I-B | NA | NA | COG2254 | APEI231 and BH0336 |
| cas4 | Subtype I-A<br>Subtype I-B<br>Subtype I-C<br>Subtype I-D<br>Subtype II-B | cas4 and csa1 | NA | COG1468 | APE1239 and BH0340 |
| cas5 | Subtype I-A<br>Subtype I-B<br>Subtype I-C<br>Subtype I-E | cas5a, cas5d, cas5e, cas5h, cas5p, cas5t and cmx5 | 3KG4 | COG1688 (RAMP) | APE1234, BH0337, devS and ygcI |
| cas6 | Subtype I-A<br>Subtype I-B<br>Subtype I-D<br>Subtype III-A Subtype III-B | cas6 and cmx6 | 3I4H | COG1583 and COG5551 (RAMP) | PF1131 and slr7014 |
| cas6e | Subtype I-E | cse3 | 1WJ9 | (RAMP) | ygcH |
| cas6f | Subtype I-F | csy4 | 2XLJ | (RAMP) | y1727 |
| cas7 | Subtype I-A<br>Subtype I-B<br>Subtype I-C<br>Subtype I-E | csa2, csd2, cse4, csh2, csp1 and cst2 | NA | COG1857 and COG3649 (RAMP) | devR and ygcJ |
| cas8a1 | Subtype I-A[‡‡] | cmx1, cst1, csx8, csx13 and CXXC-CXXC | NA | BH0338-like | LA3191[§§] and PG2018[§§] |

TABLE 33-continued

Cas Systems

| Gene name‡ | System type or subtype | Name from Haft et al.§ | Structure of encoded protein (PDB accessions)¶ | Families (and superfamily) of encoded protein#** | Representatives |
|---|---|---|---|---|---|
| cas8a2 | Subtype I-A‡‡ | csa4 and csx9 | NA | PH0918 | AF0070, AF1873, MJ0385, PF0637, PH0918 and SSO1401 |
| cas8b | Subtype I-B‡‡ | csh1 and TM1802 | NA | BH0338-like | MTH1090 and TM1802 |
| cas8c | Subtype I-C‡‡ | csd1 and csp2 | NA | BH0338-like | BH0338 |
| cas9 | Type II‡‡ | csn1 and csx12 | NA | COG3513 | FTN_0757 and SPy1046 |
| cas10 | Type III‡‡ | cmr2, csm1 and csx11 | NA | COG1353 | MTH326, Rv2823c§§ and TM1794§§ |
| cas10d | Subtype I-D‡‡ | csc3 | NA | COG1353 | slr7011 |
| csy1 | Subtype I-F‡‡ | csy1 | NA | y1724-like | y1724 |
| csy2 | Subtype I-F | csy2 | NA | (RAMP) | y1725 |
| csy3 | Subtype I-F | csy3 | NA | (RAMP) | y1726 |
| cse1 | Subtype I-E‡‡ | cse1 | NA | YgcL-like | ygcL |
| cse2 | Subtype I-E | cse2 | 2ZCA | YgcK-like | ygcK |
| csc1 | Subtype I-D | csc1 | NA | alr1563-like (RAMP) | alr1563 |
| csc2 | Subtype I-D | csc1 and csc2 | NA | COG1337 (RAMP) | slr7012 |
| csa5 | Subtype I-A | csa5 | NA | AF1870 | AF1870, MJ0380, PF0643 and SSO1398 |
| csn2 | Subtype II-A | csn2 | NA | SPy1049-like | SPy1049 |
| csm2 | Subtype III-A‡‡ | csm2 | NA | COG1421 | MTH1081 and SERP2460 |
| csm3 | Subtype III-A | csc2 and csm3 | NA | COG1337 (RAMP) | MTH1080 and SERP2459 |
| csm4 | Subtype III-A | csm4 | NA | COG1567 (RAMP) | MTH1079 and SERP2458 |
| csm5 | Subtype III-A | csm5 | NA | COG1332 (RAMP) | MTH1078 and SERP2457 |
| csm6 | Subtype III-A | APE2256 and csm6 | 2WTE | COG1517 | APE2256 and SSO1445 |
| cmr1 | Subtype III-B | cmr1 | NA | COG1367 (RAMP) | PF1130 |
| cmr3 | Subtype III-B | cmr3 | NA | COG1769 (RAMP) | PF1128 |
| cmr4 | Subtype III-B | cmr4 | NA | COG1336 (RAMP) | PF1126 |
| cmr5 | Subtype III-B‡‡ | cmr5 | 2ZOP and 2OEB | COG3337 | MTH324 and PF1125 |
| cmr6 | Subtype III-B | cmr6 | NA | COG1604 (RAMP) | PF1124 |
| csb1 | Subtype I-U | GSU0053 | NA | (RAMP) | Balac_1306 and GSU0053 |
| csb2 | Subtype I-U§§ | NA | NA | (RAMP) | Balac_1305 and GSU0054 |
| csb3 | Subtype I-U | NA | NA | (RAMP) | Balac_1303§§ |
| csx17 | Subtype I-U | NA | NA | NA | Btus_2683 |
| csx14 | Subtype I-U | NA | NA | NA | GSU0052 |
| csx10 | Subtype I-U | csx10 | NA | (RAMP) | Caur_2274 |
| csx16 | Subtype III-U | VVA1548 | NA | NA | VVA1548 |
| csaX | Subtype III-U | csaX | NA | NA | SSO1438 |
| csx3 | Subtype III-U | csx3 | NA | NA | AF1864 |
| csx1 | Subtype III-U | csa3, csx1, csx2, DXTHG, NE0113 and TIGR02710 | 1XMX and 2I71 | COG1517 and COG4006 | MJ1666, NE0113, PF1127 and TM1812 |
| csx15 | Unknown | NA | NA | TTE2665 | TTE2665 |
| csf1 | Type U | csf1 | NA | NA | AFE_1038 |
| csf2 | Type U | csf2 | NA | (RAMP) | AFE_1039 |
| csf3 | Type U | csf3 | NA | (RAMP) | AFE_1040 |
| csf4 | Type U | csf4 | NA | NA | AFE_1037 |

IV. Functional Analysis of Candidate Molecules

Candidate Cas9 molecules, candidate gRNA molecules, candidate Cas9 molecule/gRNA molecule complexes, can be evaluated by art-known methods or as described herein. For example, exemplary methods for evaluating the endonuclease activity of Cas9 molecule are described, e.g., in Jinek et al., SCIENCE 2012, 337(6096):816-821.

Binding and Cleavage Assay: Testing the Endonuclease Activity of Cas9 Molecule

The ability of a Cas9 molecule/gRNA molecule complex to bind to and cleave a target nucleic acid can be evaluated in a plasmid cleavage assay. In this assay, synthetic or in vitro-transcribed gRNA molecule is pre-annealed prior to the reaction by heating to 95° C. and slowly cooling down to room temperature. Native or restriction digest-linearized plasmid DNA (300 ng (~8 nM)) is incubated for 60 min at 37° C. with purified Cas9 protein molecule (50-500 nM) and gRNA (50-500 nM, 1:1) in a Cas9 plasmid cleavage buffer (20 mM HEPES pH 7.5, 150 mM KCl, 0.5 mM DTT, 0.1 mM EDTA) with or without 10 mM $MgCl_2$. The reactions are stopped with 5×DNA loading buffer (30% glycerol, 1.2% SDS, 250 mM EDTA), resolved by a 0.8 or 1% agarose gel electrophoresis and visualized by ethidium bromide staining. The resulting cleavage products indicate whether the Cas9 molecule cleaves both DNA strands, or only one of the two strands. For example, linear DNA products indicate the cleavage of both DNA strands. Nicked open circular products indicate that only one of the two strands is cleaved.

Alternatively, the ability of a Cas9 molecule/gRNA molecule complex to bind to and cleave a target nucleic acid can be evaluated in an oligonucleotide DNA cleavage assay. In this assay, DNA oligonucleotides (10 pmol) are radiolabeled by incubating with 5 units T4 polynucleotide kinase and ~3-6 pmol (~20-40 mCi) [γ-32P]-ATP in 1× T4 polynucleotide kinase reaction buffer at 37° C. for 30 min, in a 50 μL reaction. After heat inactivation (65° C. for 20 min), reactions are purified through a column to remove unincorporated label. Duplex substrates (100 nM) are generated by annealing labeled oligonucleotides with equimolar amounts of unlabeled complementary oligonucleotide at 95° C. for 3 min, followed by slow cooling to room temperature. For cleavage assays, gRNA molecules are annealed by heating to 95° C. for 30 s, followed by slow cooling to room temperature. Cas9 (500 nM final concentration) is pre-incubated with the annealed gRNA molecules (500 nM) in cleavage assay buffer (20 mM HEPES pH 7.5, 100 mM KCl, 5 mM MgCl2, 1 mM DTT, 5% glycerol) in a total volume of 9 μl. Reactions are initiated by the addition of 1 μl target DNA (10 nM) and incubated for 1 h at 37° C. Reactions are quenched by the addition of 20 μl of loading dye (5 mM EDTA, 0.025% SDS, 5% glycerol in formamide) and heated to 95° C. for 5 min. Cleavage products are resolved on 12% denaturing polyacrylamide gels containing 7 M urea and visualized by phosphorimaging. The resulting cleavage products indicate that whether the complementary strand, the non-complementary strand, or both, are cleaved.

One or both of these assays can be used to evaluate the suitability of a candidate gRNA molecule or candidate Cas9 molecule.

Binding Assay: Testing the Binding of Cas9 Molecule to Target DNA

Exemplary methods for evaluating the binding of Cas9 molecule to target DNA are described, e.g., in Jinek et al., SCIENCE 2012; 337(6096):816-821.

For example, in an electrophoretic mobility shift assay, target DNA duplexes are formed by mixing of each strand (10 nmol) in deionized water, heating to 95° C. for 3 min and slow cooling to room temperature. All DNAs are purified on 8% native gels containing 1×TBE. DNA bands are visualized by UV shadowing, excised, and eluted by soaking gel pieces in DEPC-treated $H_2O$. Eluted DNA is ethanol precipitated and dissolved in DEPC-treated $H_2O$. DNA samples are 5' end labeled with [γ-32P]-ATP using T4 polynucleotide kinase for 30 min at 37° C. Polynucleotide kinase is heat denatured at 65° C. for 20 min, and unincorporated radiolabel is removed using a column. Binding assays are performed in buffer containing 20 mM HEPES pH 7.5, 100 mM KCl, 5 mM $MgCl_2$, 1 mM DTT and 10% glycerol in a total volume of 10 μl. Cas9 protein molecule is programmed with equimolar amounts of pre-annealed gRNA molecule and titrated from 100 pM to 1 μM. Radiolabeled DNA is added to a final concentration of 20 pM. Samples are incubated for 1 h at 37° C. and resolved at 4° C. on an 8% native polyacrylamide gel containing 1×TBE and 5 mM $MgCl_2$. Gels are dried and DNA visualized by phosphorimaging.

Differential Scanning Flourimetry (DSF)

The thermostability of Cas9-gRNA ribonucleoprotein (RNP) complexes can be measured via DSF. This technique measures the thermostability of a protein, which can increase under favorable conditions such as the addition of a binding RNA molecule, e.g., a gRNA.

The assay is performed using two different protocols, one to test the best stoichiometric ratio of gRNA:Cas9 protein and another to determine the best solution conditions for RNP formation.

To determine the best solution to form RNP complexes, a 2 uM solution of Cas9 in water+10× SYPRO Orange® (Life Techonologies cat #S-6650) and dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

The second assay consists of mixing various concentrations of gRNA with 2 uM Cas9 in optimal buffer from assay 1 above and incubating at RT for 10' in a 384 well plate. An equal volume of optimal buffer +10× SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° increase in temperature every 10 seconds.

V. Genome Editing Approaches

Mutations in the HBB gene may be corrected using one of the approaches discussed herein. In an embodiment, a mutation in the HBB gene is corrected by homology directed repair (HDR) using an exogenously provided template nucleic acid (see Section V.1). In another embodiment, a mutation in the HBB gene is corrected by homology directed repair without using an exogenously provided template nucleic acid (see Section V.1).

Also described herein are methods for targeted knockout of one or both alleles of the BCL11A gene using NHEJ (see Section V.2). In another embodiment, methods are provided for targeted knockdown of the BCL11A gene (see Section V.3).

V.1 HDR Repair and Template Nucleic Acids

As described herein, nuclease-induced homology directed repair (HDR) can be used to alter a target sequence and correct (e.g., repair or edit) a mutation in the genome. While not wishing to be bound by theory, it is believed that alteration of the target sequence occurs by homology-directed repair (HDR) with an exogenously provided donor template or template nucleic acid. For example, the donor template or the template nucleic acid provides for alteration of the target sequence. It is contemplated that a plasmid donor can be used as a template for homologous recombination. It is further contemplated that a single stranded donor template can be used as a template for alteration of the target sequence by alternate methods of homology directed repair (e.g., single strand annealing) between the target sequence and the donor template. Donor template-effected alteration of a target sequence depends on cleavage by a Cas9 molecule. Cleavage by Cas9 can comprise a double strand break or two single strand breaks. As described herein, nuclease-induced homology directed repair (HDR) can be used to alter a target sequence and correct (e.g., repair or edit) a mutation in the genome without the use of an exogenously provided donor template or template nucleic acid. While not wishing to be bound by theory, it is believed that alteration of the target sequence occurs by homology-directed repair (HDR) with endogenous genomic donor sequence. For example, the endogenous genomic donor sequence provides for alteration of the target sequence. It is contemplated that in an embodiment the endogenous genomic donor sequence is located on the same chromosome as the target sequence. It is further contemplated that in another embodiment the endogenous genomic donor sequence is located on a different chromosome from the target sequence. In an embodiment, the endogenous genomic donor sequence comprises one or more nucleotides derived from the HBD gene. Alteration of a target sequence by endogenous genomic donor sequence depends on cleavage by a Cas9 molecule. Cleavage by Cas9 can comprise a double strand break or two single strand breaks.

Mutations that can be corrected by HDR using a template nucleic acid, or using endogenous genomic donor sequence, include point mutations. In an embodiment, a point mutation can be corrected by either a single double-strand break or two single strand breaks. In an embodiment, a point mutation can be corrected by (1) a single double-strand break, (2) two single strand breaks, (3) two double stranded breaks with a break occurring on each side of the target position, (4) one double stranded break and two single strand breaks with the double strand break and two single strand breaks occurring on each side of the target position (5) four single stranded breaks with a pair of single stranded breaks occurring on each side of the target position, or (6) one single stranded break.

In an embodiment where a single-stranded template nucleic acid is used, the target position can be altered by alternative HDR.

Donor template-effected alteration of a target position depends on cleavage by a Cas9 molecule. Cleavage by Cas9 can comprise a nick, a double strand break, or two single strand breaks, e.g., one on each strand of the target nucleic acid. After introduction of the breaks on the target nucleic acid, resection occurs at the break ends resulting in single stranded overhanging DNA regions.

In canonical HDR, a double-stranded donor template is introduced, comprising homologous sequence to the target nucleic acid that will either be directly incorporated into the target nucleic acid or used as a template to correct the sequence of the target nucleic acid. After resection at the break, repair can progress by different pathways, e.g., by the double Holliday junction model (or double strand break repair, DSBR, pathway) or the synthesis-dependent strand annealing (SDSA) pathway. In the double Holliday junction model, strand invasion by the two single stranded overhangs of the target nucleic acid to the homologous sequences in the donor template occurs, resulting in the formation of an intermediate with two Holliday junctions. The junctions migrate as new DNA is synthesized from the ends of the invading strand to fill the gap resulting from the resection. The end of the newly synthesized DNA is ligated to the resected end, and the junctions are resolved, resulting in the correction of the target nucleic acid, e.g., incorporation of the correct sequence of the donor template at the corresponding target position. Crossover with the donor template may occur upon resolution of the junctions. In the SDSA pathway, only one single stranded overhang invades the donor template and new DNA is synthesized from the end of the invading strand to fill the gap resulting from resection. The newly synthesized DNA then anneals to the remaining single stranded overhang, new DNA is synthesized to fill in the gap, and the strands are ligated to produce the corrected DNA duplex.

In alternative HDR, a single strand donor template, e.g., template nucleic acid, is introduced. A nick, single strand break, or double strand break at the target nucleic acid, for altering a desired target position, is mediated by a Cas9 molecule, e.g., described herein, and resection at the break occurs to reveal single stranded overhangs. Incorporation of the sequence of the template nucleic acid to correct or alter the target position of the target nucleic acid typically occurs by the SDSA pathway, as described above.

Methods of promoting HDR pathways, e.g., canonical HDR or alt-HDR, are described herein in Section VI.

Additional details on template nucleic acids are provided in Section IV entitled "Template nucleic acids" in International Application PCT/US2014/057905.

Mutations in the HBB gene that can be corrected (e.g., altered) by HDR with a template nucleic acid or with endogenous genomic donor sequence include, e.g., point mutation at E6, e.g., E6V.

Double Strand Break Mediated Correction

In an embodiment, double strand cleavage is effected by a Cas9 molecule having cleavage activity associated with an HNH-like domain and cleavage activity associated with a RuvC-like domain, e.g., an N-terminal RuvC-like domain, e.g., a wild type Cas9. Such embodiments require only a single gRNA.

Single Strand Break Mediated Correction

In some embodiments, one single strand break, or nick, is effected by a Cas9 molecule having nickase activity, e.g., a Cas9 nickase as described herein. A nicked target nucleic acid can be a substrate for alt-HDR.

In other embodiments, two single strand breaks, or nicks, are effected by a Cas9 molecule having nickase activity, e.g., cleavage activity associated with an HNH-like domain or cleavage activity associated with an N-terminal RuvC-like domain. Such embodiments usually require two gRNAs, one for placement of each single strand break. In an embodiment, the Cas9 molecule having nickase activity cleaves the strand to which the gRNA hybridizes, but not the strand that is complementary to the strand to which the gRNA hybridizes. In an embodiment, the Cas9 molecule having nickase activity does not cleave the strand to which the gRNA hybridizes, but rather cleaves the strand that is complementary to the strand to which the gRNA hybridizes.

In an embodiment, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HNH activity and will cut on the strand to which the gRNA hybridizes (e.g., the complementary strand, which does not have the NGG PAM on it). In other embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA). In other embodiments, a Cas9 molecule having an N863 mutation, e.g., the N863A mutation, mutation can be used as a nickase. N863A inactivates HNH therefore the Cas9 nickase has (only) RuvC activity and cuts on the non-complementary strand (the strand that has the NGG PAM and whose sequence is identical to the gRNA).

In an embodiment, in which a nickase and two gRNAs are used to position two single strand nicks, one nick is on the +strand and one nick is on the −strand of the target nucleic acid. The PAMs can be outwardly facing. The gRNAs can be selected such that the gRNAs are separated by, from about 0-50, 0-100, or 0-200 nucleotides. In an embodiment, there is no overlap between the target sequences that are complementary to the targeting domains of the two gRNAs. In an embodiment, the gRNAs do not overlap and are separated by as much as 50, 100, or 200 nucleotides. In an embodiment, the use of two gRNAs can increase specificity, e.g., by decreasing off-target binding (Ran et al., Cell 2013; 154(6): 1380-1389).

In an embodiment, a single nick can be used to induce HDR, e.g., alt-HDR. It is contemplated herein that a single nick can be used to increase the ratio of HR to NHEJ at a given cleavage site. In an embodiment, a single strand break is formed in the strand of the target nucleic acid to which the targeting domain of said gRNA is complementary. In another embodiment, a single strand break is formed in the strand of the target nucleic acid other than the strand to which the targeting domain of said gRNA is complementary.

Placement of Double Strand or Single Strand Breaks Relative to the Target Position The double strand break or single strand break in one of the strands should be sufficiently close to target position such that an alteration is produced in the desired region, e.g., correction of a mutation occurs. In an embodiment, the distance is not more than 50, 100, 200, 300, 350 or 400 nucleotides. While not wishing to be bound by theory, in some embodiments, it is believed that the break should be sufficiently close to target position such that the target position is within the region that is subject to exonuclease-mediated removal during end resection. If the distance between the target position and a break is too great, the mutation or other sequence desired to be altered may not be included in the end resection and, therefore, may not be corrected, as donor sequence, either exogenously provided donor sequence or endogenous genomic donor sequence, in some embodiments is only used to correct sequence within the end resection region.

In an embodiment, the targeting domain is configured such that a cleavage event, e.g., a double strand or single strand break, is positioned within 1, 2, 3, 4, 5, 10, 15, 20, 25, 30, 35, 40, 45, 50, 60, 70, 80, 90, 100, 150 or 200 nucleotides of the region desired to be altered, e.g., a mutation. The break, e.g., a double strand or single strand break, can be positioned upstream or downstream of the region desired to be altered, e.g., a mutation. In some embodiments, a break is positioned within the region desired to be altered, e.g., within a region defined by at least two mutant nucleotides. In some embodiments, a break is positioned immediately adjacent to the region desired to be altered, e.g., immediately upstream or downstream of a mutation. In an embodiment, a single strand break is accompanied by an additional single strand break, positioned by a second gRNA molecule, as discussed below. For example, the targeting domains bind configured such that a cleavage event, e.g., the two single strand breaks, are positioned within 1, 2, 3, 4, 5, 10, 15, 20, 25, 30, 35, 40, 45, 50, 60, 70, 80, 90, 100, 150 or 200 nucleotides of a target position. In an embodiment, the first and second gRNA molecules are configured such, that when guiding a Cas9 nickase, a single strand break will be accompanied by an additional single strand break, positioned by a second gRNA, sufficiently close to one another to result in alteration of the desired region. In an embodiment, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In an embodiment, the two gRNA molecules are configured to position cuts at the same position, or within a few nucleotides of one another, on different strands, e.g., essentially mimicking a double strand break.

In an embodiment, in which a gRNA (unimolecular (or chimeric) or modular gRNA) and Cas9 nuclease induce a double strand break for the purpose of inducing HDR-mediated correction, the cleavage site is between 0-200 bp (e.g., 0-175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position. In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In embodiments, one can promote HDR by using nickases to generate a break with overhangs. While not wishing to be bound by theory, the single stranded nature of the overhangs can enhance the cell's likelihood of repairing the break by HDR as opposed to, e.g., NHEJ. Specifically, in some embodiments, HDR is promoted by selecting a first gRNA that targets a first nickase to a first target sequence, and a second gRNA that targets a second nickase to a second target sequence which is on the opposite DNA strand from the first target sequence and offset from the first nick.

In an embodiment, the targeting domain of a gRNA molecule is configured to position a cleavage event sufficiently far from a preselected nucleotide, e.g., the nucleotide of a coding region, such that the nucleotide is not altered. In an embodiment, the targeting domain of a gRNA molecule is configured to position an intronic cleavage event sufficiently far from an intron/exon border, or naturally occurring splice signal, to avoid alteration of the exonic sequence or unwanted splicing events. The gRNA molecule may be a first, second, third and/or fourth gRNA molecule, as described herein.

Placement of a First Break and a Second Break Relative to Each Other

In an embodiment, a double strand break can be accompanied by an additional double strand break, positioned by a second gRNA molecule, as is discussed below.

In an embodiment, a double strand break can be accompanied by two additional single strand breaks, positioned by a second gRNA molecule and a third gRNA molecule.

In an embodiment, a first and second single strand breaks can be accompanied by two additional single strand breaks positioned by a third gRNA molecule and a fourth gRNA molecule.

When two or more gRNAs are used to position two or more cleavage events, e.g., double strand or single strand breaks, in a target nucleic acid, it is contemplated that the two or more cleavage events may be made by the same or different Cas9 proteins. For example, when two gRNAs are used to position two double stranded breaks, a single Cas9 nuclease may be used to create both double stranded breaks. When two or more gRNAs are used to position two or more single stranded breaks (nicks), a single Cas9 nickase may be used to create the two or more nicks. When two or more gRNAs are used to position at least one double stranded break and at least one single stranded break, two Cas9 proteins may be used, e.g., one Cas9 nuclease and one Cas9 nickase. It is contemplated that when two or more Cas9 proteins are used that the two or more Cas9 proteins may be delivered sequentially to control specificity of a double stranded versus a single stranded break at the desired position in the target nucleic acid.

In some embodiments, the targeting domain of the first gRNA molecule and the targeting domain of the second gRNA molecules are complementary to opposite strands of the target nucleic acid molecule. In some embodiments, the gRNA molecule and the second gRNA molecule are configured such that the PAMs are oriented outward.

In certain embodiments, two gRNA are selected to direct Cas9-mediated cleavage at two positions that are a preselected distance from each other. In embodiments, the two points of cleavage are on opposite strands of the target nucleic acid. In some embodiments, the two cleavage points form a blunt ended break, and in other embodiments, they are offset so that the DNA ends comprise one or two overhangs (e.g., one or more 5' overhangs and/or one or more 3' overhangs). In some embodiments, each cleavage event is a nick. In embodiments, the nicks are close enough together that they form a break that is recognized by the double stranded break machinery (as opposed to being recognized by, e.g., the SSBr machinery). In embodiments, the nicks are far enough apart that they create an overhang that is a substrate for HDR, i.e., the placement of the breaks mimics a DNA substrate that has experienced some resection. For instance, in some embodiments the nicks are spaced to create an overhang that is a substrate for processive resection. In some embodiments, the two breaks are spaced within 25-65 nucleotides of each other. The two breaks may be, e.g., about 25, 30, 35, 40, 45, 50, 55, 60 or 65 nucleotides of each other. The two breaks may be, e.g., at least about 25, 30, 35, 40, 45, 50, 55, 60 or 65 nucleotides of each other. The two breaks may be, e.g., at most about 30, 35, 40, 45, 50, 55, 60 or 65 nucleotides of each other. In embodiments, the two breaks are about 25-30, 30-35, 35-40. 40-45, 45-50, 50-55, 55-60, or 60-65 nucleotides of each other.

In some embodiments, the break that mimics a resected break comprises a 3' overhang (e.g., generated by a DSB and a nick, where the nick leaves a 3' overhang), a 5' overhang (e.g., generated by a DSB and a nick, where the nick leaves a 5' overhang), a 3' and a 5' overhang (e.g., generated by three cuts), two 3' overhangs (e.g., generated by two nicks that are offset from each other), or two 5' overhangs (e.g., generated by two nicks that are offset from each other).

In an embodiment, in which two gRNAs (independently, unimolecular (or chimeric) or modular gRNA) complexing with Cas9 nickases induce two single strand breaks for the purpose of inducing HDR-mediated correction, the closer nick is between 0-200 bp (e.g., 0-175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, 75 to 100 bp) away from the target position and the two nicks will ideally be within 25-65 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp, 45 to 50 bp, 50 to 55 bp, 55 to 60 bp, 60 to 65 bp) and no more than 100 bp away from each other (e.g., no more than 90, 80, 70, 60, 50, 40, 30, 20, 10 or 5 bp away from each other). In an embodiment, the cleavage site is between 0-100 bp (e.g., 0 to 75, 0 to 50, 0 to 25, 25 to 100, 25 to 75, 25 to 50, 50 to 100, 50 to 75 or 75 to 100 bp) away from the target position.

In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single stranded breaks (i.e., two gRNAs complex with Cas9 nickases) on either side of the target position. In another embodiment, four gRNAs, e.g., independently, unimolecular (or chimeric) or modular gRNA, are configured to generate two pairs of single stranded breaks (i.e., two pairs of two gRNAs complex with Cas9 nickases) on either side of the target position. The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are, in embodiments, within 25-65 bp of each other (e.g., between 25 to 55, 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, 20 or 10 bp).

When two gRNAs are used to target Cas9 molecules to breaks, different combinations of Cas9 molecules are envisioned. In some embodiments, a first gRNA is used to target a first Cas9 molecule to a first target position, and a second gRNA is used to target a second Cas9 molecule to a second target position. In some embodiments, the first Cas9 molecule creates a nick on the first strand of the target nucleic acid, and the second Cas9 molecule creates a nick on the opposite strand, resulting in a double stranded break (e.g., a blunt ended cut or a cut with overhangs).

Different combinations of nickases can be chosen to target one single stranded break to one strand and a second single stranded break to the opposite strand. When choosing a combination, one can take into account that there are nickases having one active RuvC-like domain, and nickases having one active HNH domain. In an embodiment, a RuvC-like domain cleaves the non-complementary strand of the target nucleic acid molecule. In an embodiment, an HNH-like domain cleaves a single stranded complementary domain, e.g., a complementary strand of a double stranded nucleic acid molecule. Generally, if both Cas9 molecules have the same active domain (e.g., both have an active RuvC domain or both have an active HNH domain), one will choose two gRNAs that bind to opposite strands of the target. In more detail, in some embodiments, a first gRNA is complementary with a first strand of the target nucleic acid and binds a nickase having an active RuvC-like domain and causes that nickase to cleave the strand that is non-complementary to that first gRNA, i.e., a second strand of the target nucleic acid; and a second gRNA is complementary with a second strand of the target nucleic acid and binds a nickase having an active RuvC-like domain and causes that nickase to cleave the strand that is non-complementary to that second gRNA, i.e., the first strand of the target nucleic acid. Conversely, in some embodiments, a first gRNA is complementary with a first strand of the target nucleic acid and binds a nickase having an active HNH domain and causes that nickase to cleave the strand that is complementary to that first gRNA, i.e., a first strand of the target nucleic acid; and a second gRNA is complementary with a second strand of the target nucleic acid and binds a nickase having an active HNH domain and causes that nickase to cleave the strand that is complementary to that second gRNA, i.e., the second strand of the target nucleic acid. In another arrangement, if one Cas9 molecule has an active RuvC-like domain and the other Cas9 molecule has an active HNH domain, the gRNAs for both Cas9 molecules can be complementary to the same strand of the target nucleic acid, so that the Cas9 molecule with the active RuvC-like domain will cleave the non-complementary strand and the Cas9 molecule with the HNH domain will cleave the complementary strand, resulting in a double stranded break.

Length of the Homology Arms of the Donor Template

The homology arm should extend at least as far as the region in which end resection may occur, e.g., in order to allow the resected single stranded overhang to find a complementary region within the donor template. The overall length could be limited by parameters such as plasmid size or viral packaging limits. In an embodiment, a homology arm does not extend into repeated elements, e.g., Alu repeats or LINE repeats.

Exemplary homology arm lengths include at least 50, 100, 250, 500, 750, 1000, 2000, 3000, 4000, or 5000 nucleotides. In some embodiments, the homology arm length is 50-100, 100-250, 250-500, 500-750, 750-1000, 1000-2000, 2000-3000, 3000-4000, or 4000-5000 nucleotides.

Target position, as used herein, refers to a site on a target nucleic acid (e.g., the chromosome) that is modified by a Cas9 molecule-dependent process. For example, the target position can be a modified Cas9 molecule cleavage of the target nucleic acid and template nucleic acid directed modification, e.g., correction, of the target position. In an embodiment, a target position can be a site between two nucleotides, e.g., adjacent nucleotides, on the target nucleic acid into which one or more nucleotides is added. The target position may comprise one or more nucleotides that are altered, e.g., corrected, by a template nucleic acid. In an embodiment, the target position is within a target sequence (e.g., the sequence to which the gRNA binds). In an embodiment, a target position is upstream or downstream of a target sequence (e.g., the sequence to which the gRNA binds).

A template nucleic acid, as that term is used herein, refers to a nucleic acid sequence which can be used in conjunction with a Cas9 molecule and a gRNA molecule to alter the structure of a target position. In an embodiment, the target nucleic acid is modified to have the some or all of the sequence of the template nucleic acid, typically at or near cleavage site(s). In an embodiment, the template nucleic acid is single stranded. In an alternate embodiment, the template nucleic acid is double stranded. In an embodiment, the template nucleic acid is DNA, e.g., double stranded DNA. In an alternate embodiment, the template nucleic acid is single stranded DNA. In an embodiment, the template nucleic acid is encoded on the same vector backbone, e.g. AAV genome, plasmid DNA, as the Cas9 and gRNA. In an embodiment, the template nucleic acid is excised from a vector backbone in vivo, e.g., it is flanked by gRNA recognition sequences. In an embodiment, the template nucleic acid comprises endogenous genomic sequence In an embodiment, the template nucleic acid alters the structure of the target position by participating in a homology directed repair event. In an embodiment, the template nucleic acid alters the sequence of the target position. In an embodiment, the template nucleic acid results in the incorporation of a modified, or non-naturally occurring base into the target nucleic acid.

Typically, the template sequence undergoes a breakage mediated or catalyzed recombination with the target sequence. In an embodiment, the template nucleic acid includes sequence that corresponds to a site on the target sequence that is cleaved by an eaCas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in the HBB gene can be used to alter the structure of a target sequence. The template sequence can be used to alter an unwanted structure, e.g., an unwanted or mutant nucleotide.

A template nucleic acid typically comprises the following components:

[5' homology arm]-[replacement sequence]-[3' homology arm].

The homology arms provide for recombination into the chromosome, thus replacing the undesired element, e.g., a mutation or signature, with the replacement sequence. In an embodiment, the homology arms flank the most distal cleavage sites.

In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, 2000, 3000, 4000, or 5000 nucleotides 5' from the 5' end of the replacement sequence.

In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, 2000, 3000, 4000, or 5000 nucleotides 3' from the 3' end of the replacement sequence.

In an embodiment, to correct a mutation, the homology arms, e.g., the 5' and 3' homology arms, may each comprise about 1000 base pairs (bp) of sequence flanking the most distal gRNAs (e.g., 1000 bp of sequence on either side of the mutation).

It is contemplated herein that one or both homology arms may be shortened to avoid including certain sequence repeat elements, e.g., Alu repeats or LINE elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

It is contemplated herein that template nucleic acids for correcting a mutation may be designed for use as a single-stranded oligonucleotide, e.g., a single-stranded oligodeoxynucleotide (ssODN). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made. In some embodiments, a longer homology arm is made by a method other than chemical synthesis, e.g., by denaturing a long double stranded nucleic acid and purifying one of the strands, e.g., by affinity for a strand-specific sequence anchored to a solid substrate.

While not wishing to be bound by theory, in some embodiments alt-HDR proceeds more efficiently when the template nucleic acid has extended homology 5' to the nick (i.e., in the 5' direction of the nicked strand). Accordingly, in some embodiments, the template nucleic acid has a longer homology arm and a shorter homology arm, wherein the longer homology arm can anneal 5' of the nick. In some embodiments, the arm that can anneal 5' to the nick is at least 25, 50, 75, 100, 125, 150, 175, or 200, 300, 400, 500, 600, 700, 800, 900, 1000, 1500, 2000, 3000, 4000, or 5000 nucleotides from the nick or the 5' or 3' end of the replacement sequence. In some embodiments, the arm that can anneal 5' to the nick is at least 10%, 20%, 30%, 40%, or 50% longer than the arm that can anneal 3' to the nick. In some embodiments, the arm that can anneal 5' to the nick is at least 2×, 3×, 4×, or 5× longer than the arm that can anneal 3' to the nick. Depending on whether a ssDNA template can anneal to the intact strand or the nicked strand, the homology arm that anneals 5' to the nick may be at the 5' end of the ssDNA template or the 3' end of the ssDNA template, respectively.

Similarly, in some embodiments, the template nucleic acid has a 5' homology arm, a replacement sequence, and a 3' homology arm, such that the template nucleic acid has extended homology to the 5' of the nick. For example, the 5' homology arm and 3' homology arm may be substantially the same length, but the replacement sequence may extend farther 5' of the nick than 3' of the nick. In some embodiments, the replacement sequence extends at least 10%, 20%, 30%, 40%, 50%, 2×, 3×, 4×, or 5× further to the 5' end of the nick than the 3' end of the nick. While not wishing to be bound by theory, in some embodiments alt-HDR proceeds more efficiently when the template nucleic acid is centered on the nick. Accordingly, in some embodiments, the template nucleic acid has two homology arms that are essentially the same size. For instance, the first homology arm of a template nucleic acid may have a length that is within 10%, 9%, 8%, 7%, 6%, 5%, 4%, 3%, 2%, or 1% of the second homology arm of the template nucleic acid.

Similarly, in some embodiments, the template nucleic acid has a 5' homology arm, a replacement sequence, and a 3' homology arm, such that the template nucleic acid extends substantially the same distance on either side of the nick. For example, the homology arms may have different lengths, but the replacement sequence may be selected to compensate for this. For example, the replacement sequence may extend further 5' from the nick than it does 3' of the nick, but the homology arm 5' of the nick is shorter than the homology arm 3' of the nick, to compensate. The converse is also possible, e.g., that the replacement sequence may extend further 3' from the nick than it does 5' of the nick, but the homology arm 3' of the nick is shorter than the homology arm 5' of the nick, to compensate.

Exemplary Arrangements of Linear Nucleic Acid Template Systems

In an embodiment, the nucleic acid template system is double stranded. In an embodiment, the nucleic acid template system is single stranded. In an embodiment, the nucleic acid template system comprises a single stranded portion and a double stranded portion. In an embodiment, the template nucleic acid comprises about 50 to 100, e.g., 55 to 95, 60 to 90, 65 to 85, or 70 to 80, base pairs, homology on either side of the nick and/or replacement sequence. In an embodiment, the template nucleic acid comprises about 50, 55, 60, 65, 70, 75, 80, 85, 90, 95, or 100 base pairs homology 5' of the nick or replacement sequence, 3' of the nick or replacement sequence, or both 5' and 3' of the nick or replacement sequences.

In an embodiment, the template nucleic acid comprises about 150 to 200, e.g., 155 to 195, 160 to 190, 165 to 185, or 170 to 180, base pairs homology 3' of the nick and/or replacement sequence. In an embodiment, the template nucleic acid comprises about 150, 155, 160, 165, 170, 175, 180, 185, 190, 195, or 200 base pairs homology 3' of the nick or replacement sequence. In an embodiment, the template nucleic acid comprises less than about 100, 90, 80, 70, 60, 50, 40, 30, 20, 15, or 10 base pairs homology 5' of the nick or replacement sequence.

In an embodiment, the template nucleic acid comprises about 150 to 200, e.g., 155 to 195, 160 to 190, 165 to 185, or 170 to 180, base pairs homology 5' of the nick and/or replacement sequence. In an embodiment, the template nucleic acid comprises about 150, 155, 160, 165, 170, 175, 180, 185, 190, 195, or 200 base pairs homology 5' of the nick or replacement sequence. In an embodiment, the template nucleic acid comprises less than about 100, 90, 80, 70, 60, 50, 40, 30, 20, 15, or 10 base pairs homology 3' of the nick or replacement sequence.

Exemplary Template Nucleic Acids

In an embodiment, the template nucleic acid is a single stranded nucleic acid. In another embodiment, the template nucleic acid is a double stranded nucleic acid. In some embodiments, the template nucleic acid comprises a nucleotide sequence, e.g., of one or more nucleotides, that will be added to or will template a change in the target nucleic acid. In other embodiments, the template nucleic acid comprises a nucleotide sequence that may be used to modify the target position. In other embodiments, the template nucleic acid comprises a nucleotide sequence, e.g., of one or more nucleotides, that corresponds to wild type sequence of the target nucleic acid, e.g., of the target position.

The template nucleic acid may comprise a replacement sequence. In some embodiments, the template nucleic acid comprises a 5' homology arm. In other embodiments, the template nucleic acid comprises a 3' homology arm.

In embodiments, the template nucleic acid is linear double stranded DNA. The length may be, e.g., about 150-200 base pairs, e.g., about 150, 160, 170, 180, 190, or 200 base pairs. The length may be, e.g., at least 150, 160, 170, 180, 190, or 200 base pairs. In some embodiments, the length is no greater than 150, 160, 170, 180, 190, or 200 base pairs. In some embodiments, a double stranded template nucleic acid has a length of about 160 base pairs, e.g., about 155-165, 150-170, 140-180, 130-190, 120-200, 110-210, 100-220, 90-230, or 80-240 base pairs.

The template nucleic acid can be linear single stranded DNA. In embodiments, the template nucleic acid is (i) linear single stranded DNA that can anneal to the nicked strand of the target nucleic acid, (ii) linear single stranded DNA that can anneal to the intact strand of the target nucleic acid, (iii) linear single stranded DNA that can anneal to the transcribed strand of the target nucleic acid, (iv) linear single stranded DNA that can anneal to the non-transcribed strand of the target nucleic acid, or more than one of the preceding. The length may be, e.g., about 150-200 nucleotides, e.g., about 150, 160, 170, 180, 190, or 200 nucleotides. The length may be, e.g., at least 150, 160, 170, 180, 190, or 200 nucleotides. In some embodiments, the length is no greater than 150, 160, 170, 180, 190, or 200 nucleotides. In some embodiments, a single stranded template nucleic acid has a length of about 160 nucleotides, e.g., about 155-165, 150-170, 140-180, 130-190, 120-200, 110-210, 100-220, 90-230, or 80-240 nucleotides.

In some embodiments, the template nucleic acid is circular double stranded DNA, e.g., a plasmid. In some embodiments, the template nucleic acid comprises about 500 to 1000 base pairs of homology on either side of the replacement sequence and/or the nick. In some embodiments, the template nucleic acid comprises about 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence.

In some embodiments, the template nucleic acid is an adenovirus vector, e.g., an AAV vector, e.g., a ssDNA molecule of a length and sequence that allows it to be packaged in an AAV capsid. The vector may be, e.g., less than 5 kb and may contain an ITR sequence that promotes packaging into the capsid. The vector may be integration-deficient; In some embodiments, the template nucleic acid comprises about 150 to 1000 nucleotides of homology on either side of the replacement sequence and/or the nick. In some embodiments, the template nucleic acid comprises about 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at least 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence. In some embodiments, the template nucleic acid comprises at most 100, 150, 200, 300, 400, 500, 600, 700, 800, 900, 1000, 1500, or 2000 nucleotides 5' of the nick or replacement sequence, 3' of the nick or replacement sequence, or both 5' and 3' of the nick or replacement sequence.

In some embodiments, the template nucleic acid is a lentiviral vector, e.g., an IDLV (integration deficiency lentivirus). In some embodiments, the template nucleic acid comprises about 500 to 1000 base pairs of homology on either side of the replacement sequence and/or the nick. In some embodiments, the template nucleic acid comprises about 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises at least 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence. In some embodiments, the template nucleic acid comprises no more than 300, 400, 500, 600, 700, 800, 900, 1000, 1500, or 2000 base pairs of homology 5' of the nick or replacement sequence, 3' of the nick or replacement sequence, or both 5' and 3' of the nick or replacement sequence.

In many embodiments, the template nucleic acid comprises one or more mutations, e.g., silent mutations, that prevent Cas9 from recognizing and cleaving the template nucleic acid. The template nucleic acid may comprise, e.g., at least 1, 2, 3, 4, 5, 10, 20, or 30 silent mutations relative to the corresponding sequence in the genome of the cell to be altered. In embodiments, the template nucleic acid comprises at most 2, 3, 4, 5, 10, 20, 30, or 50 silent mutations relative to the corresponding sequence in the genome of the cell to be altered.

In an embodiment, the template nucleic acid alters the structure of the target position by participating in a homology directed repair event. In an embodiment, the template nucleic acid alters the sequence of the target position. In an embodiment, the template nucleic acid results in the incorporation of a modified, or non-naturally occurring base into the target nucleic acid.

Typically, the template sequence undergoes a breakage mediated or catalyzed recombination with the target sequence. In an embodiment, the template nucleic acid includes sequence that corresponds to a site on the target sequence that is cleaved by an eaCas9 mediated cleavage event. In an embodiment, the template nucleic acid includes sequence that corresponds to both, a first site on the target sequence that is cleaved in a first Cas9 mediated event, and a second site on the target sequence that is cleaved in a second Cas9 mediated event.

In an embodiment, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation.

In other embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position can be used to alter the structure of a target sequence. The template sequence can be used to alter an unwanted structure, e.g., an unwanted or mutant nucleotide.

Exemplary template nucleic acids (also referred to herein as donor constructs) to correction a mutation, e.g., at E6, e.g., E6V, in the HBB gene, are provided.

Suitable sequence for the 5' homology arm can be selected from (e.g., includes a portion of) or include the following sequence:

```
                               SEQ ID NO: 16257
ATAGGAACTTGAATCAAGGAAATGATTTTAAAACGCAGTATTCTTAGTGG
ACTAGAGGAAAAAAATAATCTGAGCCAAGTAGAAGACCTTTTCCCCTCCT
ACCCCTACTTTCTAAGTCACAGAGGCTTTTTGTTCCCCCAGACACTCTTG
CAGATTAGTCCAGGCAGAAACAGTTAGATGTCCCCAGTTAACCTCCTATT
TGACACCACTGATTACCCCATTGATAGTCACACTTTGGGTTGTAAGTGAC
TTTTTATTTATTTGTATTTTTGACTGCATTAAGAGGTCTCTAGTTTTTTA
TCTCTTGTTTCCCAAAACCTAATAAGTAACTAATGCACAGAGCACATTGA
TTTGTATTTATTCTATTTTTAGACATAATTTATTAGCATGCATGAGCAAA
TTAAGAAAAACAACAACAAATGAATGCATATATATGTATATGTATGTGTG
TATATATACACACATATATATATATATTTTTTCTTTTCTTACCAGAAGGT
TTTAATCCAAATAAGGAGAAGATATGCTTAGAACCGAGGTAGAGTTTTCA
TCCATTCTGTCCTGTAAGTATTTTGCATATTCTGGAGACGCAGGAAGAGA
TCCATCTACATATCCCAAAGCTGAATTATGGTAGACAAAACTCTTCCACT
TTTAGTGCATCAACTTCTTATTTGTGTAATAAGAAAATTGGGAAAACGAT
CTTCAATATGCTTACCAAGCTGTGATTCCAAATATTACGTAAATACACTT
GCAAAGGAGGATGTTTTTAGTAGCAATTTGTACTGATGGTATGGGCCAA
GAGATATATCTTAGAGGGAGGGCTGAGGGTTTGAAGTCCAACTCCTAAGC
CAGTGCCAGAAGAGCCAAGGACAGGTACGGCTGTCATCACTTAGACCTCA
CCCTGTGGAGCCACACCCTAGGGTTGGCCAATCTACTCCCAGGAGCAGGG
AGGGCAGGAGCCAGGGCTGGGCATAAAAGTCAGGGCAGAGCCATCTATTG
CTTACATTTGCTTCTGACACAACTGTGTTCACTAGCAACCTCAAACAGAC
ACCATGGTGCATCTGACTCCTG (5'H arm)
```

Suitable sequence for the 3' homology arm can be selected from (e.g., includes a portion of) or include the following sequence:

```
                               SEQ ID NO: 16258
GGAGAAGTCTGCCGTTACTGCCCTGTGGGGCAAGGTGAACGTGGATGAAG
TTGGTGGTGAGGCCCTGGGCAGGTTGGTATCAAGGTTACAAGACAGGTTT
AAGGAGACCAATAGAAACTGGGCATGTGGAGACAGAGAAGACTCTTGGGT
TTCTGATAGGCACTGACTCTCTCTGCCTATTGGTCTATTTTCCCACCCTT
AGGCTGCTGGTGGTCTACCCTTGGACCCAGAGGTTCTTTGAGTCCTTTGG
GGATCTGTCCACTCCTGATGCTGTTATGGGCAACCCTAAGGTGAAGGCTC
ATGGCAAGAAAGTGCTCGGTGCCTTTAGTGATGGCCTGGCTCACCTGGAC
AACCTCAAGGGCACCTTTGCCACACTGAGTGAGCTGCACTGTGACAAGCT
GCACGTGGATCCTGAGAACTTCAGGGTGAGTCTATGGGACGCTTGATGTT
TTCTTTCCCCTTCTTTTCTATGGTTAAGTTCATGTCATAGGAAGGGGATA
AGTAACAGGGTACAGTTTAGAATGGGAAACAGACGAATGATTGCATCAGT
GTGGAAGTCTCAGGATCGTTTTAGTTTCTTTTATTTGCTGTTCATAACAA
TTGTTTTCTTTTGTTTAATTCTTGCTTTCTTTTTTTTCTTCTCCGCAAT
TTTTACTATTATACTTAATGCCTTAACATTGTGTATAACAAAAGGAAATA
TCTCTGAGATACATTAAGTAACTTAAAAAAAAACTTTACACAGTCTGCCT
AGTACATTACTATTTGGAATATATGTGTGCTTATTTGCATATTCATAATC
TCCCTACTTTATTTTCTTTTATTTTTAATTGATACATAATCATTATACAT
ATTTATGGGTTAAAGTGTAATGTTTTAATATGTGTACACATATTGACCAA
ATCAGGGTAATTTTGCATTTGTAATTTTAAAAAATGCTTTCTTCTTTTAA
TATACTTTTTTGTTTATCTTATTTCTAATACTTTCCCTAATCTCTTTCTT
TCAGGGCAATAATGATACAATGTATCATGCCTCTTTGCACCATTCTAAAG
AATAACAGTGATAATTTCTGGGTTAAGGCAATAGCAATATCTCTGCATAT
AAATATTTCTGCATATAAATTGTAACTG (3'H arm)
```

In an embodiment, the replacement sequence comprises or consists of an adenine (A) residue to correct the amino acid sequence to a glutamic acid (E) residue.

In an embodiment, to correct a mutation, e.g., at E6, e.g., E6V, in the HBB gene, the homology arms, e.g., the 5' and 3' homology arms, may each comprise about 1000 base pairs (bp) of sequence flanking the most distal gRNAs (e.g., 1100 bp of sequence on either side of the mutation). The 5' homology arm is shown as bold sequence, codon 6 is shown as underlined sequence, the inserted base to correct the mutation at E6, e.g., E6V, is shown as boxed sequence, and the 3' homology arm is shown as no emphasis sequence.

```
                               (Template Construct 1; SEQ ID NO: 16259)
ATAGGAACTTGAATCAAGGAAATGATTTTAAAACGCAGTATTCTTAGTGGACTA

GAG GAAAAAATAATCTGAGCCAAGTAGAAGACCTTTTCCCCTCCTACCCCTAC

TTTCTAAGTCACAGAGGCTTTTTGTTCCCCCAGACACTCTTGCAGATTAGTCCA

GGCAGAAACAGTTAGATGTCCCCAGTTAACCTCCTATTTGACACCACTGATTAC

CCCATTGATAGTCACACTTTGGGTTGTAAGTGACTTTTTATTTATTTGTATTTTT

GACTGCATTAAGAGGTCTCTAGTTTTTTATCTCTTGTTTCCCAAAACCTAATAA

GTAACTAATGCACAGAGCACATTGATTTGTATTTATTCTATTTTTAGACATAATT

TATTAGCATGCATGAGCAAATTAAGAAAAACAACAACAAATGAATGCATATATA
```

-continued

```
TGTATATGTATGTGTATATATACACACATATATATATATATTTTTCTTTTCT

TACCAGAAGGTTTTAATCCAAATAAGGAGAAGATATGCTTAGAACCGAGGTAG

AGTTTTCATCCATTCTGTCCTGTAAGTATTTTGCATATTCTGGAGACGCAGGAA

GAGATCCATCTACATATCCCAAAGCTGAATTATGGTAGACAAAACTCTTCCACT

TTTAGTGCATCAACTTCTTATTTGTGTAATAAGAAAATTGGGAAAACGATCTTC

AATATGCTTACCAAGCTGTGATTCCAAATATTACGTAAATACACTTGCAAAGGA

GGATGTTTTTAGTAGCAATTTGTACTGATGGTATGGGGCCAAGAGATATATCTT

AGAGGGAGGGCTGAGGGTTTGAAGTCCAACTCCTAAGCCAGTGCCAGAAGAGC

CAAGGACAGGTACGGCTGTCATCACTTAGACCTCACCCTGTGGAGCCACACCC

TAGGGTTGGCCAATCTACTCCCAGGAGCAGGGAGGGCAGGAGCCAGGGCTGG

GCATAAAAGTCAGGGCAGAGCCATCTATTGCTTACATTTGCTTCTGACACAACT

GTGTTCACTAGCAACCTCAAACAGACACCATGGTGCATCTGACTCCTG[A]GGAGA

AGTCTGCCGTTACTGCCCTGTGGGGCAAGGTAACGTGGATGAAGTTGGTGGTGAG

GCCCTGGGCAGGTTGGTATCAAGGTTACAAGACAGGTTTAAGGAGACCAATAGAAA

CTGGGCATGTGGAGACAGAGAAGACTCTTGGGTTTCTGATAGGCACTGACTCTCTCT

GCCTATTGGTCTATTTTCCCACCCTTAGGCTGCTGGTGGTCTACCCTTGGACCCAGAG

GTTCTTTGAGTCCTTTGGGGATCTGTCCACTCCTGATGCTGTTATGGGCAACCCTAAG

GTGAAGGCTCATGGCAAGAAAGTGCTCGGTGCCTTTAGTGATGGCCTGGCTCACCTG

GACAACCTCAAGGGCACCTTTGCCACACTGAGTGAGCTGCACTGTGACAAGCTGCA

CGTGGATCCTGAGAACTTCAGGGTGAGTCTATGGGACGCTTGATGTTTTCTTTCCCCT

TCTTTTCTATGGTTAAGTTCATGTCATAGGAAGGGGATAAGTAACAGGGTACAGTTT

AGAATGGGAAACAGACGAATGATTGCATCAGTGTGGAAGTCTCAGGATCGTTTTAG

TTTCTTTTATTTGCTGTTCATAACAATTGTTTTCTTTTGTTTAATTCTTGCTTTCTTTTT

TTTTCTTCTCCGCAATTTTTACTATTATACTTAATGCCTTAACATTGTGTATAACAAA

AGGAAATATCTCTGAGATACATTAAGTAACTTAAAAAAAAACTTTACACAGTCTGCC

TAGTACATTACTATTTGGAATATATGTGTGCTTATTTGCATATTCATAATCTCCCTAC

TTTATTTTCTTTTATTTTTAATTGATACATAATCATTATACATATTTATGGGTTAAAGT

GTAATGTTTTAATATGTGTACACATATTGACCAAATCAGGGTAATTTTGCATTTGTAA

TTTTAAAAAATGCTTTCTTCTTTTAATATACTTTTTTGTTTATCTTATTTCTAATACTTT

CCCTAATCTCTTTCTTTCAGGGCAATAATGATACAATGTATCATGCCTCTTTGCACCA

TTCTAAAGAATAACAGTGATAATTTCTGGGTTAAGGCAATAGCAATATCTCTGCATA

TAAATATTTCTGCATATAAATTGTAACTG
```

As described below in Table 27, shorter homology arms, e.g., 5' and/or 3' homology arms may be used.

It is contemplated herein that one or both homology arms may be shortened to avoid including certain sequence repeat elements, e.g., Alu repeats, LINE elements. For example, a 5' homology arm may be shortened to avoid a sequence repeat element. In another embodiment, a 3' homology arm may be shortened to avoid a sequence repeat element. In an embodiment, both the 5' and the 3' homology arms may be shortened to avoid including certain sequence repeat elements.

It is contemplated herein that template nucleic acids for correcting a mutation may designed for use as a single-stranded oligonucleotide (ssODN). When using a ssODN, 5' and 3' homology arms may range up to about 200 base pairs (bp) in length, e.g., at least 25, 50, 75, 100, 125, 150, 175, or 200 bp in length. Longer homology arms are also contemplated for ssODNs as improvements in oligonucleotide synthesis continue to be made.

In an embodiment, an ssODN may be used to correct a mutation, e.g., E6V in the HBB gene. For example, the ssODN may include 50 bp 5' and 3' homology arms as shown below. The 5' homology arm is shown as bold sequence, codon 6 is shown as underlined sequence, the inserted base to correct the E6V mutation is shown as boxed sequence, and the 3' homology arm is shown as no emphasis sequence.

(Template Construct 2; SEQ ID NO: 16260)
ACTGTGTTCACTAGCAACCTCAAACAGACACCATGGTGCATCTGACTCCT

GGGAGAAGTCTGCCGTTACTGCCCTGTGGGCAAGGTGAACGTGGATGA

AGT

Silent Mutations in Donor Construct

It is contemplated herein that Cas9 could potentially cleave donor constructs either prior to or following homology directed repair (e.g., homologous recombination), resulting in a possible non-homologous-end-joining event and further DNA sequence mutation at the chromosomal locus of interest. Therefore, to avoid cleavage of the donor sequence before and/or after Cas9-mediated homology directed repair, alternate versions of the donor sequence may be used where silent mutations are introduced. These silent mutations may disrupt Cas9 binding and cleavage, but not disrupt the amino acid sequence of the repaired gene. For example, mutations may include those made to a donor sequence to repair the HBB gene, the mutant form of which can cause Sickle Cell Disease. If gRNA HBB-6 with the 20-base target sequence CGUUACUGCCCUGUGGGGCA is used to insert a donor sequence including (SEQ ID NO: 16297)
CTCCTGAGGAGAAGTCTGCCGTTACTGCCCTGTGGGGCAAGgGTGAACGT

GGATGAAGT, where the italic A is the base being corrected and the bracketed bases are those that match the guide RNA, the donor sequence may be changed to (SEQ ID NO:16298),
CTCCTGAGGAGAAGTCTGCCGTTACTGCCCTGTGGGGCAAGaTGAACGTGGAT
GAAGT where the lowercase a has been changed from a G (lower case g in sequence ID xxx) at that position so that codon 15 still codes for the amino acid Arginine but the PAM sequence AGG has been modified to AGA to reduce or eliminate Cas9 cleavage at that locus.

Table 27 below provides exemplary template nucleic acids. In an embodiment, the template nucleic acid includes the 5' homology arm and the 3' homology arm of a row from Table 27. In another embodiment, a 5' homology arm from the first column can be combined with a 3' homology arm from Table 27. In each embodiment, a combination of the 5' and 3' homology arms include a replacement sequence, e.g., an adenine (A) residue.

TABLE 27

| 5' homology arm (the number of nucleotides from SEQ ID NO: 5'H, beginning at the 3' end of SEQ ID NO: 5'H) | Replacement Sequence = A | 3' homology arm (the number of nucleotides from SEQ ID NO: 3'H, beginning at the 5' end of SEQ ID NO: 3'H) |
| --- | --- | --- |
| 10 or more | | 10 or more |
| 20 or more | | 20 or more |
| 50 or more | | 50 or more |
| 100 or more | | 100 or more |

TABLE 27-continued

| 5' homology arm (the number of nucleotides from SEQ ID NO: 5'H, beginning at the 3' end of SEQ ID NO: 5'H) | Replacement Sequence = A | 3' homology arm (the number of nucleotides from SEQ ID NO: 3'H, beginning at the 5' end of SEQ ID NO: 3'H) |
| --- | --- | --- |
| 150 or more | | 150 or more |
| 200 or more | | 200 or more |
| 250 or more | | 250 or more |
| 300 or more | | 300 or more |
| 350 or more | | 350 or more |
| 400 or more | | 400 or more |
| 450 or more | | 450 or more |
| 500 or more | | 500 or more |
| 550 or more | | 550 or more |
| 600 or more | | 600 or more |
| 650 or more | | 650 or more |
| 700 or more | | 700 or more |
| 750 or more | | 750 or more |
| 800 or more | | 800 or more |
| 850 or more | | 850 or more |
| 900 or more | | 900 or more |
| 1000 or more | | 1000 or more |
| 1100 or more | | 1100 or more |
| 1200 or more | | 1200 or more |
| 1300 or more | | 1300 or more |
| 1400 or more | | 1400 or more |
| 1500 or more | | 1500 or more |
| 1600 or more | | 1600 or more |
| 1700 or more | | 1700 or more |
| 1800 or more | | 1800 or more |
| 1900 or more | | 1900 or more |
| 1200 or more | | 1200 or more |
| At least 50 but not long enough to include a repeated element. | | At least 50 but not long enough to include a repeated element. |

TABLE 27-continued

| 5' homology arm (the number of nucleotides from SEQ ID NO: 5'H, beginning at the 3' end of SEQ ID NO: 5'H) | Replacement Sequence = A | 3' homology arm (the number of nucleotides from SEQ ID NO: 3'H, beginning at the 5' end of SEQ ID NO: 3'H) |
| --- | --- | --- |
| At least 100 but not long enough to include a repeated element. | | At least 100 but not long enough to include a repeated element. |
| At least 150 but not long enough to include a repeated element. | | At least 150 but not long enough to include a repeated element. |
| 5 to 100 nucleotides | | 5 to 100 nucleotides |
| 10 to 150 nucleotides | | 10 to 150 nucleotides |
| 20 to 150 nucleotides | | 20 to 150 nucleotides |

Template Construct No. 1
Template Construct No. 2

V.2 NHEJ Approaches for Gene Targeting

As described herein, nuclease-induced non-homologous end-joining (NHEJ) can be used to target gene-specific knockouts. Nuclease-induced NHEJ can also be used to remove (e.g., delete) sequences in a gene of interest.

While not wishing to be bound by theory, it is believed that, in an embodiment, the genomic alterations associated with the methods described herein rely on nuclease-induced NHEJ and the error-prone nature of the NHEJ repair pathway. NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein.

The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can reach greater than 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it can also be used to delete small sequence motifs (e.g., motifs less than or equal to 50 nucleotides in length) as long as the generation of a specific final sequence is not required. If a double-strand break is targeted near to a target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. In this way, DNA segments as large as several hundred kilobases can be deleted. Both of these approaches can be used to delete specific DNA sequences; however, the error-prone nature of NHEJ may still produce indel mutations at the site of repair.

Both double strand cleaving eaCas9 molecules and single strand, or nickase, eaCas9 molecules can be used in the methods and compositions described herein to generate NHEJ-mediated indels. NHEJ-mediated indels targeted to the the gene, e.g., a coding region, e.g., an early coding region of a gene, of interest can be used to knockout (i.e., eliminate expression of) a gene of interest. For example, early coding region of a gene of interest includes sequence immediately following a start codon, within a first exon of the coding sequence, or within 500 bp of the start codon (e.g., less than 500, 450, 400, 350, 300, 250, 200, 150, 100 or 50 bp).

Placement of Double Strand or Single Strand Breaks Relative to the Target Position In an embodiment, in which a gRNA and Cas9 nuclease generate a double strand break for the purpose of inducing NHEJ-mediated indels, a gRNA, e.g., a unimolecular (or chimeric) or modular gRNA molecule, is configured to position one double-strand break in close proximity to a nucleotide of the target position. In an embodiment, the cleavage site is between 0-30 bp away from the target position (e.g., less than 30, 25, 20, 15, 10, 9, 8, 7, 6, 5, 4, 3, 2 or 1 bp from the target position).

In an embodiment, in which two gRNAs complexing with Cas9 nickases induce two single strand breaks for the purpose of inducing NHEJ-mediated indels, two gRNAs, e.g., independently, unimolecular (or chimeric) or modular e.g., RNA, are configured to position two single-strand breaks to provide for NHEJ repair a nucleotide of the target position. In an embodiment, the gRNAs are configured to position cuts at the same position, or within a few nucleotides of one another, on different strands, essentially mimicking a double strand break. In an embodiment, the closer nick is between 0-30 bp away from the target position (e.g., less than 30, 25, 20, 15, 10, 9, 8, 7, 6, 5, 4, 3, 2 or 1 bp from the target position), and the two nicks are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp). In an embodiment, the gRNAs are configured to place a single strand break on either side of a nucleotide of the target position.

Both double strand cleaving eaCas9 molecules and single strand, or nickase, eaCas9 molecules can be used in the methods and compositions described herein to generate breaks both sides of a target position. Double strand or paired single strand breaks may be generated on both sides of a target position to remove the nucleic acid sequence between the two cuts (e.g., the region between the two breaks in deleted). In one embodiment, two gRNAs, e.g., independently, unimolecular (or chimeric) or modular gRNA, are configured to position a double-strand break on both sides of a target position. In an alternate embodiment, three gRNAs, e.g., independently, unimolecular (or chimeric) or modular gRNA, are configured to position a double strand break (i.e., one gRNA complexes with a cas9 nuclease) and two single strand breaks or paired single strand breaks (i.e., two gRNAs complex with Cas9 nickases) on either side of the target position. In another embodiment, four gRNAs, e.g., independently, unimolecular (or chimeric) or modular gRNA, are configured to generate two pairs of single strand breaks (i.e., two pairs of two gRNAs complex with Cas9 nickases) on either side of the target position. The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are within 25-55 bp of each other (e.g., between 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, or 40 to 45 bp) and no more than 100 bp away from each other (e.g., no more than 90, 80, 70, 60, 50, 40, 30, 20 or 10 bp).

V.3 Targeted Knockdown

Unlike CRISPR/Cas-mediated gene knockout, which permanently eliminates expression by mutating the gene at the DNA level, CRISPR/Cas knockdown allows for temporary reduction of gene expression through the use of artificial transcription factors. Mutating key residues in both DNA cleavage domains of the Cas9 protein (e.g. the D10A and H840A mutations) results in the generation of a catalytically inactive Cas9 (eiCas9 which is also known as dead Cas9 or dCas9) molecule. A catalytically inactive Cas9 complexes with a gRNA and localizes to the DNA sequence specified by that gRNA's targeting domain, however, it does not cleave the target DNA. Fusion of the dCas9 to an effector domain, e.g., a transcription repression domain, enables recruitment of the effector to any DNA site specified by the gRNA. Although an enzymatically inactive (eiCas9) Cas9 molecule itself can block transcription when recruited to early regions in the coding sequence, more robust repression can be achieved by fusing a transcriptional repression domain (for example KRAB, SID or ERD) to the Cas9 and recruiting it to the target knockdown position, e.g., within 1000 bp of sequence 3' of the start codon or within 500 bp of a promoter region 5' of the start codon of a gene. It is likely that targeting DNAseI hypersensitive sites (DHSs) of the promoter may yield more efficient gene repression or activation because these regions are more likely to be accessible to the Cas9 protein and are also more likely to harbor sites for endogenous transcription factors. Especially for gene repression, it is contemplated herein that blocking the binding site of an endogenous transcription factor would aid in downregulating gene expression. In an embodiment, one or more eiCas9 molecules may be used to block binding of one or more endogenous transcription factors. In another embodiment, an eiCas9 molecule can be fused to a chromatin modifying protein. Altering chromatin status can result in decreased expression of the target gene. One or more eiCas9 molecules fused to one or more chromatin modifying proteins may be used to alter chromatin status.

In an embodiment, a gRNA molecule can be targeted to a known transcription response elements (e.g., promoters, enhancers, etc.), a known upstream activating sequences (UAS), and/or sequences of unknown or known function that are suspected of being able to control expression of the target DNA.

CRISPR/Cas-mediated gene knockdown can be used to reduce expression of an unwanted allele or transcript. Contemplated herein are scenarios wherein permanent destruction of the gene is not ideal. In these scenarios, site-specific repression may be used to temporarily reduce or eliminate expression. It is also contemplated herein that the off-target effects of a Cas-repressor may be less severe than those of a Cas-nuclease as a nuclease can cleave any DNA sequence and cause mutations whereas a Cas-repressor may only have an effect if it targets the promoter region of an actively transcribed gene. However, while nuclease-mediated knockout is permanent, repression may only persist as long as the Cas-repressor is present in the cells. Once the repressor is no longer present, it is likely that endogenous transcription factors and gene regulatory elements would restore expression to its natural state.

V.4 Single-Strand Annealing

Single strand annealing (SSA) is another DNA repair process that repairs a double-strand break between two repeat sequences present in a target nucleic acid. Repeat sequences utilized by the SSA pathway are generally greater than 30 nucleotides in length. Resection at the break ends occurs to reveal repeat sequences on both strands of the target nucleic acid. After resection, single strand overhangs containing the repeat sequences are coated with RPA protein to prevent the repeats sequences from inappropriate annealing, e.g., to themselves. RAD52 binds to and each of the repeat sequences on the overhangs and aligns the sequences to enable the annealing of the complementary repeat sequences. After annealing, the single-strand flaps of the overhangs are cleaved. New DNA synthesis fills in any gaps, and ligation restores the DNA duplex. As a result of the processing, the DNA sequence between the two repeats is deleted. The length of the deletion can depend on many factors including the location of the two repeats utilized, and the pathway or processivity of the resection.

In contrast to HDR pathways, SSA does not require a template nucleic acid to alter or correct a target nucleic acid sequence. Instead, the complementary repeat sequence is utilized.

V.5 Other DNA Repair Pathways

SSBR (Single Strand Break Repair)

Single-stranded breaks (SSB) in the genome are repaired by the SSBR pathway, which is a distinct mechanism from the DSB repair mechanisms discussed above. The SSBR pathway has four major stages: SSB detection, DNA end processing, DNA gap filling, and DNA ligation. A more detailed explanation is given in Caldecott, Nature Reviews Genetics 9, 619-631 (August 2008), and a summary is given here.

In the first stage, when a SSB forms, PARP1 and/or PARP2 recognize the break and recruit repair machinery. The binding and activity of PARP1 at DNA breaks is transient and it seems to accelerate SSBr by promoting the focal accumulation or stability of SSBr protein complexes at the lesion. Arguably the most important of these SSBr proteins is XRCC1, which functions as a molecular scaffold that interacts with, stabilizes, and stimulates multiple enzymatic components of the SSBr process including the protein responsible for cleaning the DNA 3' and 5' ends. For instance, XRCC1 interacts with several proteins (DNA polymerase beta, PNK, and three nucleases, APE1, APTX, and APLF) that promote end processing. APE1 has endonuclease activity. APLF exhibits endonuclease and 3' to 5' exonuclease activities. APTX has endonuclease and 3' to 5' exonuclease activity.

This end processing is an important stage of SSBR since the 3'- and/or 5'-termini of most, if not all, SSBs are 'damaged'. End processing generally involves restoring a damaged 3'-end to a hydroxylated state and and/or a damaged 5' end to a phosphate moiety, so that the ends become ligation-competent. Enzymes that can process damaged 3' termini include PNKP, APE1, and TDP1. Enzymes that can process damaged 5' termini include PNKP, DNA polymerase beta, and APTX. LIG3 (DNA ligase III) can also participate in end processing. Once the ends are cleaned, gap filling can occur.

At the DNA gap filling stage, the proteins typically present are PARP1, DNA polymerase beta, XRCC1, FEN1 (flap endonculease 1), DNA polymerase delta/epsilon, PCNA, and LIG1. There are two ways of gap filling, the short patch repair and the long patch repair. Short patch repair involves the insertion of a single nucleotide that is missing. At some SSBs, "gap filling" might continue displacing two or more nucleotides (displacement of up to 12 bases have been reported). FEN1 is an endonuclease that removes the displaced 5'-residues. Multiple DNA polymerases, including Pol β, are involved in the repair of SSBs, with the choice of DNA polymerase influenced by the source and type of SSB.

In the fourth stage, a DNA ligase such as LIG1 (Ligase I) or LIG3 (Ligase III) catalyzes joining of the ends. Short patch repair uses Ligase III and long patch repair uses Ligase I.

Sometimes, SSBR is replication-coupled. This pathway can involve one or more of CtIP, MRN, ERCC1, and FEN1. Additional factors that may promote SSBR include: aPARP, PARP1, PARP2, PARG, XRCC1, DNA polymerase b, DNA polymerase d, DNA polymerase e, PCNA, LIG1, PNK, PNKP, APE1, APTX, APLF, TDP1, LIG3, FEN1, CtIP, MRN, and ERCC1.

MMR (Mismatch Repair)

Cells contain three excision repair pathways: MMR, BER, and NER. The excision repair pathways have a common feature in that they typically recognize a lesion on one strand of the DNA, then exo/endonucleaseases remove the lesion and leave a 1-30 nucleotide gap that is sub-sequentially filled in by DNA polymerase and finally sealed with ligase. A more complete picture is given in Li, Cell Research (2008) 18:85-98, and a summary is provided here.

Mismatch repair (MMR) operates on mispaired DNA bases.

The MSH2/6 or MSH2/3 complexes both have ATPases activity that plays an important role in mismatch recognition and the initiation of repair. MSH2/6 preferentially recognizes base-base mismatches and identifies mispairs of 1 or 2 nucleotides, while MSH2/3 preferentially recognizes larger ID mispairs.

hMLH1 heterodimerizes with hPMS2 to form hMutL α which possesses an ATPase activity and is important for multiple steps of MMR. It possesses a PCNA/replication factor C (RFC)-dependent endonuclease activity which plays an important role in 3' nick-directed MMR involving EXO1. (EXO1 is a participant in both HR and MMR.) It regulates termination of mismatch-provoked excision. Ligase I is the relevant ligase for this pathway. Additional factors that may promote MMR include: EXO1, MSH2, MSH3, MSH6, MLH1, PMS2, MLH3, DNA Pol d, RPA, HMGB1, RFC, and DNA ligase I.

Base Excision Repair (BER)

The base excision repair (BER) pathway is active throughout the cell cycle; it is responsible primarily for removing small, non-helix-distorting base lesions from the genome. In contrast, the related Nucleotide Excision Repair pathway (discussed in the next section) repairs bulky helix-distorting lesions. A more detailed explanation is given in Caldecott, Nature Reviews Genetics 9, 619-631 (August 2008), and a summary is given here.

Upon DNA base damage, base excision repair (BER) is initiated and the process can be simplified into five major steps: (a) removal of the damaged DNA base; (b) incision of the subsequent a basic site; (c) clean-up of the DNA ends; (d) insertion of the correct nucleotide into the repair gap; and (e) ligation of the remaining nick in the DNA backbone. These last steps are similar to the SSBR.

In the first step, a damage-specific DNA glycosylase excises the damaged base through cleavage of the N-glycosidic bond linking the base to the sugar phosphate backbone. Then AP endonuclease-1 (APE1) or bifunctional DNA glycosylases with an associated lyase activity incised the phosphodiester backbone to create a DNA single strand break (SSB). The third step of BER involves cleaning-up of the DNA ends. The fourth step in BER is conducted by Pol β that adds a new complementary nucleotide into the repair gap and in the final step XRCC1/Ligase III seals the remaining nick in the DNA backbone. This completes the short-patch BER pathway in which the majority (~80%) of damaged DNA bases are repaired. However, if the 5'-ends in step 3 are resistant to end processing activity, following one nucleotide insertion by Pol β there is then a polymerase switch to the replicative DNA polymerases, Pol δ/ε, which then add ~2-8 more nucleotides into the DNA repair gap. This creates a 5'-flap structure, which is recognized and excised by flap endonuclease-1 (FEN-1) in association with the processivity factor proliferating cell nuclear antigen (PCNA). DNA ligase I then seals the remaining nick in the DNA backbone and completes long-patch BER. Additional factors that may promote the BER pathway include: DNA glycosylase, APE1, Polb, Pold, Pole, XRCC1, Ligase III, FEN-1, PCNA, RECQL4, WRN, MYH, PNKP, and APTX.

Nucleotide Excision Repair (NER)

Nucleotide excision repair (NER) is an important excision mechanism that removes bulky helix-distorting lesions from DNA. Additional details about NER are given in Marteijn et al., Nature Reviews Molecular Cell Biology 15,465-481 (2014), and a summary is given here. NER a broad pathway encompassing two smaller pathways: global genomic NER (GG-NER) and transcription coupled repair NER (TC-NER). GG-NER and TC-NER use different factors for recognizing DNA damage. However, they utilize the same machinery for lesion incision, repair, and ligation.

Once damage is recognized, the cell removes a short single-stranded DNA segment that contains the lesion. Endonucleases XPF/ERCC1 and XPG (encoded by ERCC5) remove the lesion by cutting the damaged strand on either side of the lesion, resulting in a single-strand gap of 22-30 nucleotides. Next, the cell performs DNA gap filling synthesis and ligation. Involved in this process are: PCNA, RFC, DNA Pol δ, DNA Pol ε or DNA Pol κ, and DNA ligase I or XRCC1/Ligase III. Replicating cells tend to use DNA pol ε and DNA ligase I, while non-replicating cells tend to use DNA Pol δ, DNA Pol κ, and the XRCC1/Ligase III complex to perform the ligation step.

NER can involve the following factors: XPA-G, POLH, XPF, ERCC1, XPA-G, and LIG1. Transcription-coupled NER (TC-NER) can involve the following factors: CSA, CSB, XPB, XPD, XPG, ERCC1, and TTDA. Additional factors that may promote the NER repair pathway include XPA-G, POLH, XPF, ERCC1, XPA-G, LIG1, CSA, CSB, XPA, XPB, XPC, XPD, XPF, XPG, TTDA, UVSSA, USP7, CETN2, RAD23B, UV-DDB, CAK subcomplex, RPA, and PCNA.

Interstrand Crosslink (ICL)

A dedicated pathway called the ICL repair pathway repairs interstrand crosslinks. Interstrand crosslinks, or covalent crosslinks between bases in different DNA strand, can occur during replication or transcription. ICL repair involves the coordination of multiple repair processes, in particular, nucleolytic activity, translesion synthesis (TLS), and HDR. Nucleases are recruited to excise the ICL on either side of the crosslinked bases, while TLS and HDR are coordinated to repair the cut strands. ICL repair can involve the following factors: endonucleases, e.g., XPF and RAD51C, endonucleases such as RAD51, translesion polymerases, e.g., DNA polymerase zeta and Rev1), and the Fanconi anemia (FA) proteins, e.g., FancJ.

Other Pathways

Several other DNA repair pathways exist in mammals.

Translesion synthesis (TLS) is a pathway for repairing a single stranded break left after a defective replication event and involves translesion polymerases, e.g., DNA pol☐ and Rev1.

Error-free postreplication repair (PRR) is another pathway for repairing a single stranded break left after a defective replication event.

V.6 Examples of gRNAs in Genome Editing Methods gRNA molecules as described herein can be used with Cas9 molecules that generate a double strand break or a single strand break to alter the sequence of a target nucleic acid, e.g., a target position or target genetic signature. gRNA molecules useful in these methods are described below.

In an embodiment, the gRNA, e.g., a chimeric gRNA, is configured such that it comprises one or more of the following properties;

a) it can position, e.g., when targeting a Cas9 molecule that makes double strand breaks, a double strand break (i) within 50, 100, 150, 200, 250, 300, 350, 400, 450, or 500 nucleotides of a target position, or (ii) sufficiently close that the target position is within the region of end resection;

b) it has a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and c)
  (i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. thermophilus, S. aureus,* or *N. meningitidis* tail and proximal domain, or a sequence that differs by no more than 1, 2, 3, 4, 5; 6, 7, 8, 9 or 10 nucleotides therefrom;
  (ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. thermophilus, S. aureus,* or *N. meningitidis* gRNA, or a sequence that differs by no more than 1, 2, 3, 4, 5; 6, 7, 8, 9 or 10 nucleotides therefrom;
  (iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. thermophilus, S. aureus,* or *N. meningitidis* gRNA, or a sequence that differs by no more than 1, 2, 3, 4, 5; 6, 7, 8, 9 or 10 nucleotides therefrom;
  (iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. thermophilus, S. aureus,* or *N. meningitidis* tail domain, or a sequence that differs by no more than 1, 2, 3, 4, 5; 6, 7, 8, 9 or 10 nucleotides therefrom; or
  (v) the tail domain comprises 15, 20, 25, 30, 35, 40 nucleotides or all of the corresponding portions of a naturally occurring tail domain, e.g., a naturally occurring *S. pyogenes, S. thermophilus, S. aureus,* or *N. meningitidis* tail domain.

In an embodiment, the gRNA is configured such that it comprises properties: a and b(i).
In an embodiment, the gRNA is configured such that it comprises properties: a and b(ii).
In an embodiment, the gRNA is configured such that it comprises properties: a and b(iii).
In an embodiment, the gRNA is configured such that it comprises properties: a and b(iv).
In an embodiment, the gRNA is configured such that it comprises properties: a and b(v).
In an embodiment, the gRNA is configured such that it comprises properties: a and b(vi).
In an embodiment, the gRNA is configured such that it comprises properties: a and b(vii).
In an embodiment, the gRNA is configured such that it comprises properties: a and b(viii).
In an embodiment, the gRNA is configured such that it comprises properties: a and b(ix).
In an embodiment, the gRNA is configured such that it comprises properties: a and b(x).
In an embodiment, the gRNA is configured such that it comprises properties: a and b(xi).
In an embodiment, the gRNA is configured such that it comprises properties: a and c.
In an embodiment, the gRNA is configured such that in comprises properties: a, b, and c.
In an embodiment, the gRNA is configured such that in comprises properties: a(i), b(i), and c(i).
In an embodiment, the gRNA is configured such that in comprises properties: a(i), b(i), and c(ii).
In an embodiment, the gRNA is configured such that in comprises properties: a(i), b(ii), and c(i).
In an embodiment, the gRNA is configured such that in comprises properties: a(i), b(ii), and c(ii).
In an embodiment, the gRNA is configured such that in comprises properties: a(i), b(iii), and c(i).
In an embodiment, the gRNA is configured such that in comprises properties: a(i), b(iii), and c(ii).
In an embodiment, the gRNA is configured such that in comprises properties: a(i), b(iv), and c(i).
In an embodiment, the gRNA is configured such that in comprises properties: a(i), b(iv), and c(ii).
In an embodiment, the gRNA is configured such that in comprises properties: a(i), b(v), and c(i).
In an embodiment, the gRNA is configured such that in comprises properties: a(i), b(v), and c(ii).
In an embodiment, the gRNA is configured such that in comprises properties: a(i), b(vi), and c(i).
In an embodiment, the gRNA is configured such that in comprises properties: a(i), b(vi), and c(ii).
In an embodiment, the gRNA is configured such that in comprises properties: a(i), b(vii), and c(i).
In an embodiment, the gRNA is configured such that in comprises properties: a(i), b(vii), and c(ii).
In an embodiment, the gRNA is configured such that in comprises properties: a(i), b(viii), and c(i).
In an embodiment, the gRNA is configured such that in comprises properties: a(i), b(viii), and c(ii).
In an embodiment, the gRNA is configured such that in comprises properties: a(i), b(ix), and c(i).
In an embodiment, the gRNA is configured such that in comprises properties: a(i), b(ix), and c(ii).
In an embodiment, the gRNA is configured such that in comprises properties: a(i), b(x), and c(i).
In an embodiment, the gRNA is configured such that in comprises properties: a(i), b(x), and c(ii).
In an embodiment, the gRNA is configured such that in comprises properties: a(i), b(xi), and c(i).
In an embodiment, the gRNA is configured such that in comprises properties: a(i), b(xi), and c(ii).

In an embodiment, the gRNA, e.g., a chimeric gRNA, is configured such that it comprises one or more of the following properties;

a) one or both of the gRNAs can position, e.g., when targeting a Cas9 molecule that makes single strand breaks, a single strand break within (i) 50, 100, 150, 200, 250, 300, 350, 400, 450, or 500 nucleotides of a target position, or (ii) sufficiently close that the target position is within the region of end resection;

b) one or both have a targeting domain of at least 16 nucleotides, e.g., a targeting domain of (i) 16, (ii), 17, (iii) 18, (iv) 19, (v) 20, (vi) 21, (vii) 22, (viii) 23, (ix) 24, (x) 25, or (xi) 26 nucleotides; and c)
(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. thermophilus, S. aureus,* or *N. meningitidis* tail and proximal domain, or a sequence that differs by no more than 1, 2, 3, 4, 5; 6, 7, 8, 9 or 10 nucleotides therefrom;
(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. thermophilus, S. aureus,* or *N. meningitidis* gRNA, or a sequence that differs by no more than 1, 2, 3, 4, 5; 6, 7, 8, 9 or 10 nucleotides therefrom;
(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. thermophilus, S. aureus,* or *N. meningitidis* gRNA, or a sequence that differs by no more than 1, 2, 3, 4, 5; 6, 7, 8, 9 or 10 nucleotides therefrom;
(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. thermophilus, S. aureus,* or *N. meningitidis* tail domain, or a sequence that differs by no more than 1, 2, 3, 4, 5; 6, 7, 8, 9 or 10 nucleotides therefrom; or
(v) the tail domain comprises 15, 20, 25, 30, 35, 40 nucleotides or all of the corresponding portions of a naturally occurring tail domain, e.g., a naturally occurring *S. pyogenes, S. thermophilus, S. aureus,* or *N. meningitidis* tail domain.

In an embodiment, the gRNA is configured such that it comprises properties: a and b(i).
In an embodiment, the gRNA is configured such that it comprises properties: a and b(ii).
In an embodiment, the gRNA is configured such that it comprises properties: a and b(iii).
In an embodiment, the gRNA is configured such that it comprises properties: a and b(iv).
In an embodiment, the gRNA is configured such that it comprises properties: a and b(v).
In an embodiment, the gRNA is configured such that it comprises properties: a and b(vi).
In an embodiment, the gRNA is configured such that it comprises properties: a and b(vii).
In an embodiment, the gRNA is configured such that it comprises properties: a and b(viii).
In an embodiment, the gRNA is configured such that it comprises properties: a and b(ix).
In an embodiment, the gRNA is configured such that it comprises properties: a and b(x).
In an embodiment, the gRNA is configured such that it comprises properties: a and b(xi).
In an embodiment, the gRNA is configured such that it comprises properties: a and c.
In an embodiment, the gRNA is configured such that in comprises properties: a, b, and c.
In an embodiment, the gRNA is configured such that in comprises properties: a(i), b(i), and c(i).
In an embodiment, the gRNA is configured such that in comprises properties: a(i), b(i), and c(ii).
In an embodiment, the gRNA is configured such that in comprises properties: a(i), b(ii), and c(i).
In an embodiment, the gRNA is configured such that in comprises properties: a(i), b(ii), and c(ii).
In an embodiment, the gRNA is configured such that in comprises properties: a(i), b(iii), and c(i).
In an embodiment, the gRNA is configured such that in comprises properties: a(i), b(iii), and c(ii).
In an embodiment, the gRNA is configured such that in comprises properties: a(i), b(iv), and c(i).
In an embodiment, the gRNA is configured such that in comprises properties: a(i), b(iv), and c(ii).
In an embodiment, the gRNA is configured such that in comprises properties: a(i), b(v), and c(i).
In an embodiment, the gRNA is configured such that in comprises properties: a(i), b(v), and c(ii).
In an embodiment, the gRNA is configured such that in comprises properties: a(i), b(vi), and c(i).
In an embodiment, the gRNA is configured such that in comprises properties: a(i), b(vi), and c(ii).
In an embodiment, the gRNA is configured such that in comprises properties: a(i), b(vii), and c(i).
In an embodiment, the gRNA is configured such that in comprises properties: a(i), b(vii), and c(ii).
In an embodiment, the gRNA is configured such that in comprises properties: a(i), b(viii), and c(i).
In an embodiment, the gRNA is configured such that in comprises properties: a(i), b(viii), and c(ii).
In an embodiment, the gRNA is configured such that in comprises properties: a(i), b(ix), and c(i).
In an embodiment, the gRNA is configured such that in comprises properties: a(i), b(ix), and c(ii).
In an embodiment, the gRNA is configured such that in comprises properties: a(i), b(x), and c(i).
In an embodiment, the gRNA is configured such that in comprises properties: a(i), b(x), and c(ii).
In an embodiment, the gRNA is configured such that in comprises properties: a(i), b(xi), and c(i).
In an embodiment, the gRNA is configured such that in comprises properties: a(i), b(xi), and c(ii).

In an embodiment, the gRNA is used with a Cas9 nickase molecule having HNH activity, e.g., a Cas9 molecule having the RuvC activity inactivated, e.g., a Cas9 molecule having a mutation at D10, e.g., the D10A mutation.

In an embodiment, the gRNA is used with a Cas9 nickase molecule having RuvC activity, e.g., a Cas9 molecule having the HNH activity inactivated, e.g., a Cas9 molecule having a mutation at 840, e.g., the H840A.

In an embodiment, the gRNAs are used with a Cas9 nickase molecule having RuvC activity, e.g., a Cas9 molecule having the HNH activity inactivated, e.g., a Cas9 molecule having a mutation at N863, e.g., the N863A mutation.

In an embodiment, a pair of gRNAs, e.g., a pair of chimeric gRNAs, comprising a first and a second gRNA, is configured such that they comprises one or more of the following properties;

a) one or both of the gRNAs can position, e.g., when targeting a Cas9 molecule that makes single strand breaks, a single strand break within (i) 50, 100, 150, 200, 250, 300, 350, 400, 450, or 500 nucleotides of a target position, or (ii) sufficiently close that the target position is within the region of end resection;

b) one or both have a targeting domain of at least 16 nucleotides, e.g., a targeting domain of (i) 16, (ii), 17, (iii) 18, (iv) 19, (v) 20, (vi) 21, (vii) 22, (viii) 23. (ix) 24, (x) 25, or (xi) 26 nucleotides;

c) for one or both:
(i) the proximal and tail domain, when taken together, comprise at least 15, 18, 20, 25, 30, 31, 35, 40, 45, 49, 50, or 53 nucleotides, e.g., at least 15, 18, 20, 25, 30, 31, 35, 40, 45, 49, 50, or 53 nucleotides from a naturally occurring *S. pyogenes, S. thermophilus, S. aureus*, or *N. meningitidis* tail and proximal domain, or a sequence that differs by no more than 1, 2, 3, 4, 5; 6, 7, 8, 9 or 10 nucleotides therefrom;
(ii) there are at least 15, 18, 20, 25, 30, 31, 35, 40, 45, 49, 50, or 53 nucleotides 3' to the last nucleotide of the second complementarity domain, e.g., at least 15, 18, 20, 25, 30, 31, 35, 40, 45, 49, 50, or 53 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;
(iii) there are at least 16, 19, 21, 26, 31, 32, 36, 41, 46, 50, 51, or 54 nucleotides 3' to the last nucleotide of the second complementarity domain that is complementary to its corresponding nucleotide of the first complementarity domain, e.g., at least 16, 19, 21, 26, 31, 32, 36, 41, 46, 50, 51, or 54 nucleotides from the corresponding sequence of a naturally occurring *S. pyogenes, S. thermophilus, S. aureus*, or *N. meningitidis* gRNA, or a sequence that differs by no more than 1, 2, 3, 4, 5; 6, 7, 8, 9 or 10 nucleotides therefrom;
(iv) the tail domain is at least 10, 15, 20, 25, 30, 35 or 40 nucleotides in length, e.g., it comprises at least 10, 15, 20, 25, 30, 35 or 40 nucleotides from a naturally occurring *S. pyogenes, S. thermophilus, S. aureus*, or *N. meningitidis* tail domain; or, or a sequence that differs by no more than 1, 2, 3, 4, 5; 6, 7, 8, 9 or 10 nucleotides therefrom; or
(v) the tail domain comprises 15, 20, 25, 30, 35, 40 nucleotides or all of the corresponding portions of a naturally occurring tail domain, e.g., a naturally occurring *S. pyogenes, S. thermophilus, S. aureus*, or *N. meningitidis* tail domain;

d) the gRNAs are configured such that, when hybridized to target nucleic acid, they are separated by 0-50, 0-100, 0-200, at least 10, at least 20, at least 30 or at least 50 nucleotides;

e) the breaks made by the first gRNA and second gRNA are on different strands; and f) the PAMs are facing outwards.

In an embodiment, one or both of the gRNAs is configured such that it comprises properties: a and b(i).

In an embodiment, one or both of the gRNAs is configured such that it comprises properties: a and b(ii).

In an embodiment, one or both of the gRNAs is configured such that it comprises properties: a and b(iii).

In an embodiment, one or both of the gRNAs is configured such that it comprises properties: a and b(iv).

In an embodiment, one or both of the gRNAs is configured such that it comprises properties: a and b(v).

In an embodiment, one or both of the gRNAs is configured such that it comprises properties: a and b(vi).

In an embodiment, one or both of the gRNAs is configured such that it comprises properties: a and b(vii).

In an embodiment, one or both of the gRNAs is configured such that it comprises properties: a and b(viii).

In an embodiment, one or both of the gRNAs is configured such that it comprises properties: a and b(ix).

In an embodiment, one or both of the gRNAs is configured such that it comprises properties: a and b(x).

In an embodiment, one or both of the gRNAs is configured such that it comprises properties: a and b(xi).

In an embodiment, one or both of the gRNAs configured such that it comprises properties: a and c.

In an embodiment, one or both of the gRNAs is configured such that it comprises properties: a, b, and c.

In an embodiment, one or both of the gRNAs is configured such that it comprises properties: a(i), b(i), and c(i).

In an embodiment, one or both of the gRNAs is configured such that it comprises properties: a(i), b(i), and c(ii).

In an embodiment, one or both of the gRNAs is configured such that it comprises properties: a(i), b(i), c, and d.

In an embodiment, one or both of the gRNAs is configured such that it comprises properties: a(i), b(i), c, and e.

In an embodiment, one or both of the gRNAs is configured such that it comprises properties: a(i), b(i), c, d, and e.

In an embodiment, one or both of the gRNAs is configured such that it comprises properties: a(i), b(ii), and c(i).

In an embodiment, one or both of the gRNAs is configured such that it comprises properties: a(i), b(ii), and c(ii).

In an embodiment, one or both of the gRNAs is configured such that it comprises properties: a(i), b(ii), c, and d.

In an embodiment, one or both of the gRNAs is configured such that it comprises properties: a(i), b(ii), c, and e.

In an embodiment, one or both of the gRNAs is configured such that it comprises properties: a(i), b(ii), c, d, and e.

In an embodiment, one or both of the gRNAs is configured such that it comprises properties: a(i), b(iii), and c(i).

In an embodiment, one or both of the gRNAs is configured such that it comprises properties: a(i), b(iii), and c(ii).

In an embodiment, one or both of the gRNAs is configured such that it comprises properties: a(i), b(iii), c, and d.

In an embodiment, one or both of the gRNAs is configured such that it comprises properties: a(i), b(iii), c, and e.

In an embodiment, one or both of the gRNAs is configured such that it comprises properties: a(i), b(iii), c, d, and e.

In an embodiment, one or both of the gRNAs is configured such that it comprises properties: a(i), b(iv), and c(i).

In an embodiment, one or both of the gRNAs is configured such that it comprises properties: a(i), b(iv), and c(ii).

In an embodiment, one or both of the gRNAs is configured such that it comprises properties: a(i), b(iv), c, and d.

In an embodiment, one or both of the gRNAs is configured such that it comprises properties: a(i), b(iv), c, and e.

In an embodiment, one or both of the gRNAs is configured such that it comprises properties: a(i), b(iv), c, d, and e.

In an embodiment, one or both of the gRNAs is configured such that it comprises properties: a(i), b(v), and c(i).

In an embodiment, one or both of the gRNAs is configured such that it comprises properties: a(i), b(v), and c(ii).

In an embodiment, one or both of the gRNAs is configured such that it comprises properties: a(i), b(v), c, and d.

In an embodiment, one or both of the gRNAs is configured such that it comprises properties: a(i), b(v), c, and e.

In an embodiment, one or both of the gRNAs is configured such that it comprises properties: a(i), b(v), c, d, and e.

In an embodiment, one or both of the gRNAs is configured such that it comprises properties: a(i), b(vi), and c(i).

In an embodiment, one or both of the gRNAs is configured such that it comprises properties: a(i), b(vi), and c(ii).

In an embodiment, one or both of the gRNAs is configured such that it comprises properties: a(i), b(vi), c, and d.

In an embodiment, one or both of the gRNAs is configured such that it comprises properties: a(i), b(vi), c, and e.

In an embodiment, one or both of the gRNAs is configured such that it comprises properties: a(i), b(vi), c, d, and e.

In an embodiment, one or both of the gRNAs is configured such that it comprises properties: a(i), b(vii), and c(i).

In an embodiment, one or both of the gRNAs is configured such that it comprises properties: a(i), b(vii), and c(ii).

In an embodiment, one or both of the gRNAs is configured such that it comprises properties: a(i), b(vii), c, and d.

In an embodiment, one or both of the gRNAs is configured such that it comprises properties: a(i), b(vii), c, and e.

In an embodiment, one or both of the gRNAs is configured such that it comprises properties: a(i), b(vii), c, d, and e.

In an embodiment, one or both of the gRNAs is configured such that it comprises properties: a(i), b(viii), and c(i).

In an embodiment, one or both of the gRNAs is configured such that it comprises properties: a(i), b(viii), and c(ii).

In an embodiment, one or both of the gRNAs is configured such that it comprises properties: a(i), b(viii), c, and d.

In an embodiment, one or both of the gRNAs is configured such that it comprises properties: a(i), b(viii), c, and e.

In an embodiment, one or both of the gRNAs is configured such that it comprises properties: a(i), b(viii), c, d, and e.

In an embodiment, one or both of the gRNAs is configured such that it comprises properties: a(i), b(ix), and c(i).

In an embodiment, one or both of the gRNAs is configured such that it comprises properties: a(i), b(ix), and c(ii).

In an embodiment, one or both of the gRNAs is configured such that it comprises properties: a(i), b(ix), c, and d.

In an embodiment, one or both of the gRNAs is configured such that it comprises properties: a(i), b(ix), c, and e.

In an embodiment, one or both of the gRNAs is configured such that it comprises properties: a(i), b(ix), c, d, and e.

In an embodiment, one or both of the gRNAs is configured such that it comprises properties: a(i), b(x), and c(i).

In an embodiment, one or both of the gRNAs is configured such that it comprises properties: a(i), b(x), and c(ii).

In an embodiment, one or both of the gRNAs is configured such that it comprises properties: a(i), b(x), c, and d.

In an embodiment, one or both of the gRNAs is configured such that it comprises properties: a(i), b(x), c, and e.

In an embodiment, one or both of the gRNAs is configured such that it comprises properties: a(i), b(x), c, d, and e.

In an embodiment, one or both of the gRNAs is configured such that it comprises properties: a(i), b(xi), and c(i).

In an embodiment, one or both of the gRNAs is configured such that it comprises properties: a(i), b(xi), and c(ii).

In an embodiment, one or both of the gRNAs is configured such that it comprises properties: a(i), b(xi), c, and d.

In an embodiment, one or both of the gRNAs is configured such that it comprises properties: a(i), b(xi), c, and e.

In an embodiment, one or both of the gRNAs is configured such that it comprises properties: a(i), b(xi), c, d, and e.

In an embodiment, the gRNAs are used with a Cas9 nickase molecule having HNH activity, e.g., a Cas9 molecule having the RuvC activity inactivated, e.g., a Cas9 molecule having a mutation at D10, e.g., the D10A mutation.

In an embodiment, the gRNAs are used with a Cas9 nickase molecule having RuvC activity, e.g., a Cas9 molecule having the HNH activity inactivated, e.g., a Cas9 molecule having a mutation at H840, e.g., the H840A mutation.

In an embodiment, the gRNAs are used with a Cas9 nickase molecule having RuvC activity. e.g., a Cas9 molecule having the HNH activity inactivated, e.g., a Cas9 molecule having a mutation at N863, e.g., the N863A mutation.

VI. Target Cells

Cas9 molecules and gRNA molecules, e.g., a Cas9 molecule/gRNA molecule complex, can be used to manipulate a cell, e.g., to edit a target nucleic acid, in a wide variety of cells.

In an embodiment, a cell is manipulated by editing (e.g., inducing a mutation in) the HBB and/or BCL11A target genes, e.g., as described herein. In an embodiment, the expression of the HBB and/or BCL11A target genes is modulated, e.g., in vivo. In another embodiment, the expression of the HBB and/or BCL11A target genes is modulated, e.g., ex vivo.

The Cas9 and gRNA molecules described herein can be delivered to a target cell. In an embodiment, the target cell is a circulating blood cell. e.g., a reticulocyte, a myeloid progenitor cell, or a hematopoietic stem cell. In an embodiment, the target cell is a bone marrow cell (e.g., a myeloid progenitor cell, an erythroid progenitor cell, a hematopoietic stem cell, or a mesenchymal stem cell). In an embodiment, the target cell is a myeloid progenitor cell (e.g. a common myeloid progenitor (CMP) cell). In an embodiment, the target cell is an erythroid progenitor cell (e.g. a megakaryocyte erythroid progenitor (MEP) cell). In an embodiment, the target cell is a hematopoietic stem cell (e.g. a long term hematopoietic stem cell (LT-HSC), a short term hematopoietic stem cell (ST-HSC), a multipotent progenitor (MPP) cell, a lineage restricted progenitor (LRP) cell).

In an embodiment, the target cell is manipulated ex vivo by editing (e.g., inducing a mutation in) the HBB and/or BCL11A target genes and/or modulating the expression of the HBB and/or BCL11A target genes, and administered to the subject. Sources of target cells for ex vivo manipulation may include, by way of example, the subject's blood, the subject's cord blood, or the subject's bone marrow. Sources of target cells for ex vivo manipulation may also include, by way of example, heterologous donor blood, cord blood, or bone marrow.

In an embodiment, a myeloid progenitor cell is removed from the subject, manipulated ex vivo as described above, and the myeloid progenitor cell is returned to the subject. In an embodiment, an erythroid progenitor cell is removed from the subject, manipulated ex vivo as described above, and the erythroid progenitor cell is returned to the subject. In an embodiment, a hematopoietic stem cell is removed from the subject, manipulated ex vivo as described above, and the hematopoietic stem cell is returned to the subject. In an embodiment, a CD34+ hematopoietic stem cell is removed from the subject, manipulated ex vivo as described above, and the CD34+ hematopoietic stem cell is returned to the subject.

A suitable cell can also include a stem cell such as, by way of example, an embryonic stem cell, an induced pluripotent stem cell, a hematopoietic stem cell, a neuronal stem cell and a mesenchymal stem cell. In an embodiment, the cell is an induced pluripotent stem (iPS) cell or a cell derived from an iPS cell, e.g., an iPS cell generated from the subject, modified to induce a mutation and differentiated into a clinically relevant cell such as a myeloid progenitor cell, an erythroid progenitor cell or a hematopoietic stem cell. In an embodiment, AAV is used to transduce the target cells, e.g., the target cells described herein.

Cells produced by the methods described herein may be used immediately. Alternatively, the cells may be frozen (e.g., in liquid nitrogen) and stored for later use. The cells will usually be frozen in 10% dimethylsulfoxide (DMSO), 50% serum, 40% buffered medium, or some other such solution as is commonly used in the art to preserve cells at such freezing temperature and thawed in such a manner as commonly known in the art for thawing frozen cultured cells.

VII. Delivery, Formulations and Routes of Administration

The components, e.g., a Cas9 molecule and gRNA molecule (e.g., a Cas9 molecule/gRNA molecule complex), and a donor template nucleic acid, can be delivered or formulated in a variety of forms, see, e.g., Tables 34-35. In an embodiment, one Cas9 molecule and two or more (e.g., 2, 3, 4, or more) different gRNA molecules are delivered, e.g., by an AAV vector. In an embodiment, the sequence encoding the Cas9 molecule and the sequence(s) encoding the two or more (e.g., 2, 3, 4, or more) different gRNA molecules are present on the same nucleic acid molecule, e.g., an AAV vector. When a Cas9 or gRNA component is encoded as DNA for delivery, the DNA will typically but not necessarily include a control region, e.g., comprising a promoter, to effect expression. Useful promoters for Cas9 molecule sequences include CMV, EFS, EF-1a, MSCV, PGK, CAG promoters. In an embodiment, the promoter is a constitutive promoter. In another embodiment, the promoter is a tissue specific promoter. Useful promoters for gRNAs include H1, 7SK, tRNA, and U6 promoters. Promoters with similar or dissimilar strengths can be selected to tune the expression of components. Sequences encoding a Cas9 molecule can comprise a nuclear localization signal (NLS), e.g., an SV40 NLS. In an embodiment, the sequence encoding a Cas9 molecule comprises at least two nuclear localization signals. In an embodiment a promoter for a Cas9 molecule or a gRNA molecule can be, independently, inducible, tissue specific, or cell specific.

Table 34 provides examples of how the components can be formulated, delivered, or administered.

TABLE 34

| Cas9 Molecule(s) | gRNA Molecule(s) | Donor Template Nucleic Acid | Comments |
|---|---|---|---|
| DNA | DNA | DNA | In this embodiment, a Cas9 molecule, typically an eaCas9 molecule, and a gRNA are transcribed from DNA. In this embodiment, they are encoded on separate molecules. In this embodiment, the donor template is provided as a separate DNA molecule. |
| DNA | DNA | | In this embodiment, a Cas9 molecule, typically an eaCas9 molecule, and a gRNA are transcribed from DNA. In this embodiment, they are encoded on separate molecules. In this embodiment, the donor template is provided on the same DNA molecule that encodes the gRNA. |
| | DNA | DNA | In this embodiment, a Cas9 molecule, typically an eaCas9 molecule, and a gRNA are transcribed from DNA, here from a single molecule. In this embodiment, the donor template is provided as a separate DNA molecule. |
| DNA | DNA | DNA | In this embodiment, a Cas9 molecule, typically an eaCas9 molecule, and a gRNA are transcribed from DNA. In this embodiment, they are encoded on separate molecules. In this embodiment, the donor template is provided on the same DNA molecule that encodes the Cas9. |
| DNA | RNA | DNA | In this embodiment, a Cas9 molecule, typically an eaCas9 molecule, is transcribed from DNA, and a gRNA is provided as in vitro transcribed or synthesized RNA. In this embodiment, the donor template is provided as a separate DNA molecule. |
| DNA | RNA | DNA | In this embodiment, a Cas9 Molecule, typically an eaCas9 molecule, is transcribed from DNA, and a gRNA is provided as in vitro transcribed or synthesized RNA. In this embodiment, the donor template is provided on the same DNA molecule that encodes the Cas9. |
| mRNA | RNA | DNA | In this embodiment, a Cas9 molecule, typically an eaCas9 molecule, is translated from in vitro transcribed mRNA, and a gRNA is provided as in vitro transcribed or synthesized RNA. In this embodiment, the donor template is provided as a DNA molecule. |
| mRNA | DNA | DNA | In this embodiment, a Cas9 molecule, typically an eaCas9 molecule, is translated from in vitro transcribed mRNA, and a gRNA is transcribed from DNA. In this embodiment, the donor template is provided as a separate DNA molecule. |
| mRNA | | DNA | In this embodiment, a Cas9 molecule, typically an eaCas9 molecule, is translated from in vitro |

TABLE 34-continued

| Elements | | | |
|---|---|---|---|
| Cas9 Molecule(s) | gRNA Molecule(s) | Donor Template Nucleic Acid | Comments |
| | | | transcribed mRNA, and a gRNA is transcribed from DNA. In this embodiment, the donor template is provided on the same DNA molecule that encodes the gRNA. |
| Protein | DNA | DNA | In this embodiment, a Cas9 molecule, typically an eaCas9 molecule, is provided as a protein, and a gRNA is transcribed from DNA. In this embodiment, the donor template is provided as a separate DNA molecule. |
| Protein | DNA | | In this embodiment, a Cas9 molecule, typically an eaCas9 molecule, is provided as a protein, and a gRNA is transcribed from DNA. In this embodiment, the donor template is provided on the same DNA molecule that encodes the gRNA. |
| Protein | RNA | DNA | In this embodiment, an eaCas9 molecule is provided as a protein, and a gRNA is provided as transcribed or synthesized RNA. In this embodiment, the donor template is provided as a DNA molecule. |

Table 35 summarizes various delivery methods for the components of a Cas system, e.g., the Cas9 molecule component and the gRNA molecule component, as described herein.

TABLE 35

| | Delivery Vector/Mode | Delivery into Non-Dividing Cells | Duration of Expression | Genome Integration | Type of Molecule Delivered |
|---|---|---|---|---|---|
| | Physical (eg, electroporation, particle gun, Calcium Phosphate transfection) | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

DNA-Based Delivery of a Cas9 Molecule and/or One or More gRNA Molecule and/or a Donor Template Nucleic acids (e.g., DNA) encoding a Cas9 molecule (e.g., an eaCas9 molecule), a gRNA molecule, a donor template nucleic acid, or any combination (e.g., two or all) thereof, can be administered to subjects or delivered into cells by art-known methods or as described herein. For example, Cas9-encoding and/or gRNA-encoding DNA, as well as donor template nucleic acids, can be delivered, e.g., by vectors (e.g., viral or non-viral vectors), non-vector based methods (e.g., using naked DNA or DNA complexes), or a combination thereof. Donor template molecules can be administered to subjects or delivered into cells by art-known methods or as described herein. For example, donor template molecules can be delivered, e.g., by vectors (e.g., viral or non-viral vectors), non-vector based methods (e.g., using naked DNA or DNA complexes), or a combination thereof.

Nucleic acids (e.g., DNA) encoding Cas9 molecules (e.g., eaCas9 molecules) and/or gRNA molecules can be conjugated to molecules to promote uptake by the target cells (e.g., the target cells describe herein). Donor template molecules can be conjugated to molecules to promote uptake by the target cells (e.g., the target cells describe herein).

In an embodiment, the Cas9- and/or gRNA-encoding DNA is delivered by a vector (e.g., viral vector/virus or plasmid).

A vector can comprise a sequence that encodes a Cas9 molecule and/or a gRNA molecule. A vector can also comprise a sequence encoding a signal peptide (e.g., for nuclear localization, nucleolar localization, mitochondrial localization), fused, e.g., to a Cas9 molecule sequence. For example, a vector can comprise a nuclear localization sequence (e.g., from SV40) fused to the sequence encoding the Cas9 molecule.

One or more regulatory/control elements, e.g., a promoter, an enhancer, an intron, a polyadenylation signal, a Kozak consensus sequence, internal ribosome entry sites (IRES), a 2A sequence, and splice acceptor or donor can be included in the vectors. In an embodiment, the promoter is recognized by RNA polymerase II (e.g., a CMV promoter). In another embodiment, the promoter is recognized by RNA polymerase III (e.g., a U6 promoter). In an embodiment, the promoter is a regulated promoter (e.g., inducible promoter). In another embodiment, the promoter is a constitutive promoter. In an embodiment, the promoter is a tissue specific promoter. In an embodiment, the promoter is a viral promoter. In another embodiment, the promoter is a non-viral promoter.

In an embodiment, the vector or delivery vehicle is a viral vector (e.g., for generation of recombinant viruses). In an embodiment, the virus is a DNA virus (e.g., dsDNA or ssDNA virus). In another embodiment, the virus is an RNA virus (e.g., an ssRNA virus). Exemplary viral vectors/viruses include, e.g., retroviruses, lentiviruses, adenovirus, adeno-associated virus (AAV), vaccinia viruses, poxviruses, and herpes simplex viruses.

In an embodiment, the virus infects dividing cells. In another embodiment, the virus infects non-dividing cells. In an embodiment, the virus infects both dividing and non-dividing cells. In an embodiment, the virus can integrate into the host genome. In an embodiment, the virus is engineered to have reduced immunity, e.g., in human. In an embodiment, the virus is replication-competent. In another embodiment, the virus is replication-defective, e.g., having one or more coding regions for the genes necessary for additional rounds of virion replication and/or packaging replaced with other genes or deleted. In an embodiment, the virus causes transient expression of the Cas9 molecule and/or the gRNA molecule. In another embodiment, the virus causes long-lasting, e.g., at least 1 week, 2 weeks, 1 month, 2 months, 3 months, 6 months, 9 months, 1 year, 2 years, or permanent expression, of the Cas9 molecule and/or the gRNA molecule. The packaging capacity of the viruses may vary, e.g., from at least about 4 kb to at least about 30 kb, e.g., at least about 5 kb, 10 kb, 15 kb, 20 kb, 25 kb, 30 kb, 35 kb, 40 kb, 45 kb, or 50 kb.

In an embodiment, the viral vector recognizes a specific cell type or tissue. For example, the viral vector can be pseudotyped with a different/alternative viral envelope glycoprotein; engineered with a cell type-specific receptor (e.g., genetic modification(s) of one or more viral envelope glycoproteins to incorporate a targeting ligand such as a peptide ligand, a single chain antibody, or a growth factor); and/or engineered to have a molecular bridge with dual specificities with one end recognizing a viral glycoprotein and the other end recognizing a moiety of the target cell surface (e.g., a ligand-receptor, monoclonal antibody, avidin-biotin and chemical conjugation).

Exemplary viral vectors/viruses include, e.g., retroviruses, lentiviruses, adenovirus, adeno-associated virus (AAV), vaccinia viruses, poxviruses, and herpes simplex viruses.

In an embodiment, the Cas9- and/or gRNA-encoding nucleic acid sequence is delivered by a recombinant retrovirus. In an embodiment, the donor template nucleic acid is delivered by a recombinant retrovirus. In an embodiment, the retrovirus (e.g., Moloney murine leukemia virus) comprises a reverse transcriptase, e.g., that allows integration into the host genome. In an embodiment, the retrovirus is replication-competent. In another embodiment, the retrovirus is replication-defective, e.g., having one of more coding regions for the genes necessary for additional rounds of virion replication and packaging replaced with other genes, or deleted.

In an embodiment, the Cas9- and/or gRNA-encoding nucleic acid sequence is delivered by a recombinant lentivirus. In an embodiment, the donor template nucleic acid is delivered by a recombinant lentivirus. For example, the lentivirus is replication-defective, e.g., does not comprise one or more genes required for viral replication.

In an embodiment, the Cas9- and/or gRNA-encoding DNA is delivered by a recombinant adenovirus. In an embodiment, the donor template nucleic acid is delivered by a recombinant adenovirus. In an embodiment, the adenovirus is engineered to have reduced immunity in human.

In an embodiment, the Cas9- and/or gRNA-encoding DNA is delivered by a recombinant AAV. In an embodiment, the donor template nucleic acid is delivered by a recombinant AAV. In some embodiments, the AAV does not incorporate its genome into that of a host cell, e.g., a target cell as describe herein. In an embodiment, the AAV can incorporate its genome into that of a host cell, e.g., a target cell as described herein. In an embodiment, the AAV is a self-complementary adeno-associated virus (scAAV), e.g., a scAAV that packages both strands which anneal together to form double stranded DNA. AAV serotypes that may be used in the disclosed methods, include AAV1, AAV2, modified AAV2 (e.g., modifications at Y444F, Y500F, Y730F and/or S662V), AAV3, modified AAV3 (e.g., modifications at Y705F, Y731F and/or T492V), AAV4, AAV5, AAV6, modified AAV6 (e.g., modifications at S663V and/or T492V), AAV8, AAV 8.2, AAV9, AAV rh 10, and pseudotyped AAV, such as AAV2/8, AAV2/5 and AAV2/6 can also be used in the disclosed methods.

In an embodiment, an AAV capsid that can be used in the methods described herein is a capsid sequence from serotype AAV1, AAV2, AAV3, AAV4, AAV5, AAV6, AAV7, AAV8, AAV9, AAV.rh8, AAV.rh10, AAV.rh32/33, AAV.rh43, AAV.rh64R1, or AAV7m8.

In an embodiment, the Cas9- and/or gRNA-encoding DNA is delivered in a re-engineered AAV capsid, e.g., with 50% or greater, e.g., 60% or greater. 70% or greater, 80% or greater, 90% or greater, or 95% or greater, sequence homology with a capsid sequence from serotypes AAV1, AAV2, AAV3, AAV4, AAV5, AAV6, AAV7, AAV8, AAV9, AAV.rh8, AAV.rh 10, AAV.rh32/33, AAV.rh43, or AAV.rh64R1.

In an embodiment, the Cas9- and/or gRNA-encoding DNA is delivered by a chimeric AAV capsid. In an embodiment, the donor template nucleic acid is delivered by a chimeric AAV capsid. Exemplary chimeric AAV capsids include, but are not limited to, AAV9i1, AAV2i8, AAV-DJ, AAV2G9, AAV2i8G9, or AAV8G9.

In an embodiment, the AAV is a self-complementary adeno-associated virus (scAAV), e.g., a scAAV that packages both strands which anneal together to form double stranded DNA.

In an embodiment, the Cas9- and/or gRNA-encoding DNA is delivered by a hybrid virus, e.g., a hybrid of one or more of the viruses described herein. In an embodiment, the hybrid virus is hybrid of an AAV (e.g., of any AAV serotype), with a Bocavirus, B19 virus, porcine AAV, goose AAV, feline AAV, canine AAV, or MVM.

A Packaging cell is used to form a virus particle that is capable of infecting a target cell. Such a cell includes a 293 cell, which can package adenovirus, and a ψ2 cell or a PA317 cell, which can package retrovirus. A viral vector used in gene therapy is usually generated by a producer cell line that packages a nucleic acid vector into a viral particle. The vector typically contains the minimal viral sequences required for packaging and subsequent integration into a host or target cell (if applicable), with other viral sequences being replaced by an expression cassette encoding the protein to be expressed, eg. Cas9. For example, an AAV vector used in gene therapy typically only possesses inverted terminal repeat (ITR) sequences from the AAV genome which are required for packaging and gene expression in the host or target cell. The missing viral functions can be supplied in trans by the packaging cell line and/or plasmid containing E2A, E4, and VA genes from adenovirus, and plasmid encoding Rep and Cap genes from AAV, as described in "Triple Transfection Protocol." Henceforth, the viral DNA is packaged in a cell line, which contains a helper plasmid encoding the other AAV genes, namely rep and cap, but lacking ITR sequences. In embodiment, the viral DNA is packaged in a producer cell line, which contains E1A and/or E1B genes from adenovirus. The cell line is also infected with adenovirus as a helper. The helper virus (e.g., adenovirus or HSV) or helper plasmid promotes replication of the AAV vector and expression of AAV genes from the helper plasmid with ITRs. The helper plasmid is not packaged in significant amounts due to a lack of ITR sequences. Contamination with adenovirus can be reduced by, e.g., heat treatment to which adenovirus is more sensitive than AAV.

In an embodiment, the viral vector has the ability of cell type and/or tissue type recognition. For example, the viral vector can be pseudotyped with a different/alternative viral envelope glycoprotein; engineered with a cell type-specific receptor (e.g., genetic modification of the viral envelope glycoproteins to incorporate targeting ligands such as a peptide ligand, a single chain antibodie, a growth factor); and/or engineered to have a molecular bridge with dual specificities with one end recognizing a viral glycoprotein and the other end recognizing a moiety of the target cell surface (e.g., ligand-receptor, monoclonal antibody, avidin-biotin and chemical conjugation).

In an embodiment, the viral vector achieves cell type specific expression. For example, a tissue-specific promoter can be constructed to restrict expression of the transgene (Cas 9 and gRNA) in only the target cell. The specificity of the vector can also be mediated by microRNA-dependent control of transgene expression. In an embodiment, the viral vector has increased efficiency of fusion of the viral vector and a target cell membrane. For example, a fusion protein such as fusion-competent hemagglutin (HA) can be incorporated to increase viral uptake into cells. In an embodiment, the viral vector has the ability of nuclear localization. For example, a virus that requires the breakdown of the nuclear envelope (during cell division) and therefore will not infect a non-diving cell can be altered to incorporate a nuclear localization peptide in the matrix protein of the virus thereby enabling the transduction of non-proliferating cells.

In some embodiments, the Cas9- and/or gRNA-encoding DNA is delivered by a non-vector based method (e.g., using naked DNA or DNA complexes). For example, the DNA can be delivered, e.g., by organically modified silica or silicate (Ormosil), electroporation, transient cell compression or squeezing (e.g., as described in Lee, et al., Nano Lett 12: 6322-27), gene gun, sonoporation, magnetofection, lipid-mediated transfection, dendrimers, inorganic nanoparticles, calcium phosphates, or a combination thereof.

In an embodiment, delivery via electroporation comprises mixing the cells with the Cas9- and/or gRNA-encoding DNA in a cartridge, chamber or cuvette and applying one or more electrical impulses of defined duration and amplitude. In an embodiment, delivery via electroporation is performed using a system in which cells are mixed with the Cas9- and/or gRNA-encoding DNA in a vessel connected to a device (eg, a pump) which feeds the mixture into a cartridge, chamber or cuvette wherein one or more electrical impulses of defined duration and amplitude are applied, after which the cells are delivered to a second vessel.

In an embodiment, the Cas9- and/or gRNA-encoding DNA is delivered by a combination of a vector and a non-vector based method. In an embodiment, the donor template nucleic acid is delivered by a combination of a vector and a non-vector based method. For example, a virosome comprises a liposome combined with an inactivated virus (e.g., HIV or influenza virus), which can result in more efficient gene transfer, e.g., in a respiratory epithelial cell than either a viral or a liposomal method alone.

In an embodiment, the delivery vehicle is a non-viral vector. In an embodiment, the non-viral vector is an inorganic nanoparticle. Exemplary inorganic nanoparticles include, e.g., magnetic nanoparticles (e.g., $Fe_3MnO_2$) or silica. The outer surface of the nanoparticle can be conjugated with a positively charged polymer (e.g., polyethylenimine, polylysine, polyserine) which allows for attachment (e.g., conjugation or entrapment) of payload. In an embodiment, the non-viral vector is an organic nanoparticle (e.g., entrapment of the payload inside the nanoparticle). Exemplary organic nanoparticles include, e.g., SNALP liposomes that contain cationic lipids together with neutral helper lipids which are coated with polyethylene glycol (PEG) and protamine and nucleic acid complex coated with lipid coating.

Exemplary lipids for gene transfer are shown below in Table 36.

TABLE 36

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2.3-Dioleyloxy)prophyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |

Exemplary polymers for gene transfer are shown below in Table 37.

TABLE 37

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

In an embodiment, the vehicle has targeting modifications to increase target cell update of nanoparticles and liposomes, e.g., cell specific antigens, monoclonal antibodies, single chain antibodies, aptamers, polymers, sugars, and cell penetrating peptides. In an embodiment, the vehicle uses fusogenic and endosome-destabilizing peptides/polymers. In an embodiment, the vehicle undergoes acid-triggered conformational changes (e.g., to accelerate endosomal escape of the cargo). In an embodiment, a stimuli-cleavable polymer is used, e.g., for release in a cellular compartment. For example, disulfide-based cationic polymers that are cleaved in the reducing cellular environment can be used.

In an embodiment, the delivery vehicle is a biological non-viral delivery vehicle. In an embodiment, the vehicle is an attenuated bacterium (e.g., naturally or artificially engineered to be invasive but attenuated to prevent pathogenesis and expressing the transgene (e.g., *Listeria monocytogenes*, certain *Salmonella* strains, *Bifidobacterium longum*, and modified *Escherichia coli*), bacteria having nutritional and tissue-specific tropism to target specific tissues, bacteria having modified surface proteins to alter target tissue specificity). In an embodiment, the vehicle is a genetically modified bacteriophage (e.g., engineered phages having large packaging capacity, less immunogenic, containing mammalian plasmid maintenance sequences and having incorporated targeting ligands). In an embodiment, the vehicle is a mammalian virus-like particle. For example, modified viral particles can be generated (e.g., by purification of the "empty" particles followed by ex vivo assembly of the virus with the desired cargo). The vehicle can also be engineered to incorporate targeting ligands to alter target tissue specificity. In an embodiment, the vehicle is a biological liposome. For example, the biological liposome is a phospholipid-based particle derived from human cells (e.g., erythrocyte ghosts, which are red blood cells broken down into spherical structures derived from the subject (e.g., tissue targeting can be achieved by attachment of various tissue or cell-specific ligands), or secretory exosomes—subject (i.e., patient) derived membrane-bound nanovescicle (30-100 nm) of endocytic origin (e.g., can be produced from various cell types and can therefore be taken up by cells without the need of for targeting ligands).

In an embodiment, one or more nucleic acid molecules (e.g., DNA molecules) other than the components of a Cas system, e.g., the Cas9 molecule component and/or the gRNA molecule component described herein, are delivered. In an embodiment, the nucleic acid molecule is delivered at the same time as one or more of the components of the Cas system are delivered. In an embodiment, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Cas system are delivered. In an embodiment, the nucleic acid molecule is delivered by a different means than one or more of the components of the Cas system, e.g., the Cas9 molecule component and/or the gRNA molecule component, are delivered. The nucleic acid molecule can be delivered by any of the delivery methods described herein. For example, the nucleic acid molecule can be delivered by a viral vector, e.g., an integration-deficient lentivirus, and the Cas9 molecule component and/or the gRNA molecule component can be delivered by electroporation, e.g., such that the toxicity caused by nucleic acids (e.g., DNAs) can be reduced. In an embodiment, the nucleic acid molecule encodes a therapeutic protein, e.g., a protein described herein. In an embodiment, the nucleic acid molecule encodes an RNA molecule, e.g., an RNA molecule described herein.

Delivery of RNA Encoding a Cas9 Molecule

RNA encoding Cas9 molecules (e.g., eaCas9 molecules or eiCas9 molecules) and/or gRNA molecules, can be delivered into cells, e.g., target cells described herein, by art-known methods or as described herein. For example, Cas9-encoding and/or gRNA-encoding RNA can be delivered, e.g., by microinjection, electroporation, transient cell compression or squeezing (eg, as described in Lee, et al., 2012, *Nano Lett* 12: 6322-27), lipid-mediated transfection, peptide-mediated delivery, or a combination thereof. Cas9-encoding and/or gRNA-encoding RNA can be conjugated to molecules) promoting uptake by the target cells (e.g., target cells described herein).

In an embodiment, delivery via electroporation comprises mixing the cells with the RNA encoding Cas9 molecules (e.g., eaCas9 molecules, eiCas9 molecules or eiCas9 fusion proteins) and/or gRNA molecules, with or without donor template nucleic acid molecules, in a cartridge, chamber or cuvette and applying one or more electrical impulses of defined duration and amplitude. In an embodiment, delivery via electroporation is performed using a system in which cells are mixed with the RNA encoding Cas9 molecules (e.g., eaCas9 molecules, eiCas9 molecules or eiCas9 fusion proteins) and/or gRNA molecules, with or without donor template nucleic acid molecules in a vessel connected to a device (eg, a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells described herein).

Delivery Cas9 Molecule Protein

Cas9 molecules (e.g., eaCas9 molecules or eiCas9 molecules) can be delivered into cells by art-known methods or as described herein. For example, Cas9 protein molecules can be delivered, e.g., by microinjection, electroporation, transient cell compression or squeezing (eg, as described in Lee, et al [2012] *Nano Lett* 12: 6322-27), lipid-mediated transfection, peptide-mediated delivery, or a combination thereof. Delivery can be accompanied by DNA encoding a gRNA or by a gRNA. Cas9 protein can be conjugated to molecules promoting uptake by the target cells (e.g., target cells described herein).

In an embodiment, delivery via electroporation comprises mixing the cells with the Cas9 molecules (e.g., eaCas9 molecules, eiCas9 molecules or eiCas9 fusion proteins) and/or gRNA molecules, with or without donor nucleic acid, in a cartridge, chamber or cuvette and applying one or more electrical impulses of defined duration and amplitude. In an embodiment, delivery via electroporation is performed using a system in which cells are mixed with the Cas9 molecules (e.g., eaCas9 molecules, eiCas9 molecules or eiCas9 fusion proteins) and/or gRNA molecules, with or without donor nucleic acid in a vessel connected to a device (eg, a pump) which feeds the mixture into a cartridge, chamber or cuvette wherein one or more electrical impulses of defined duration and amplitude are applied, after which the cells are delivered to a second vessel. Cas9-encoding and/or gRNA-encoding RNA can be conjugated to molecules to promote uptake by the target cells (e.g., target cells described herein).

Route of Administration

Systemic modes of administration include oral and parenteral routes. Parenteral routes include, by way of example, intravenous, intrarterial, intraosseous, intramuscular, intradermal, subcutaneous, intranasal and intraperitoneal routes. Components administered systemically may be modified or formulated to target the components to cells of the blood and bone marrow.

Local modes of administration include, by way of example, intra-bone marrow, intrathecal, and intra-cerebroventricular routes. In an embodiment, significantly smaller amounts of the components (compared with systemic approaches) may exert an effect when administered locally (for example, intra-bone marrow) compared to when administered systemically (for example, intravenously). Local modes of administration can reduce or eliminate the incidence of potentially toxic side effects that may occur when therapeutically effective amounts of a component are administered systemically.

In an embodiment, components described herein are delivered by intra-bone marrow injection. Injections may be made directly into the bone marrow compartment of one or more than one bone. In an embodiment, nanoparticle or viral, e.g., AAV vector, delivery is via intra-bone marrow injection.

Administration may be provided as a periodic bolus or as continuous infusion from an internal reservoir or from an external reservoir (for example, from an intravenous bag). Components may be administered locally, for example, by continuous release from a sustained release drug delivery device In addition, components may be formulated to permit release over a prolonged period of time. A release system can include a matrix of a biodegradable material or a material which releases the incorporated components by diffusion. The components can be homogeneously or heterogeneously distributed within the release system. A variety of release systems may be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly(caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly(ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly(vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used for injection. Typically the microspheres are composed of a polymer of lactic acid and glycolic acid, which are structured to form hollow spheres. The spheres can be approximately 15-30 microns in diameter and can be loaded with components described herein.

Bi-Modal or Differential Delivery of Components

Separate delivery of the components of a Cas system, e.g., the Cas9 molecule component and the gRNA molecule component, and more particularly, delivery of the components by differing modes, can enhance performance, e.g., by improving tissue specificity and safety.

In an embodiment, the Cas9 molecule and the gRNA molecule are delivered by different modes, or as sometimes referred to herein as differential modes. Different or differential modes, as used herein, refer modes of delivery that confer different pharmacodynamic or pharmacokinetic properties on the subject component molecule, e.g., a Cas9 molecule, gRNA molecule, or template nucleic acid. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., adeno-associated virus or lentivirus, delivery.

By way of example, the components, e.g., a Cas9 molecule and a gRNA molecule, can be delivered by modes that differ in terms of resulting half-life or persistent of the delivered component the body, or in a particular compartment, tissue or organ. In an embodiment, a gRNA molecule can be delivered by such modes. The Cas9 molecule component can be delivered by a mode which results in less persistence or less exposure to the body or a particular compartment or tissue or organ.

More generally, in an embodiment, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In an embodiment, the first pharmacodynamic or pharmacokinetic property, e.g., distribution, persistence or exposure, is more limited than the second pharmacodynamic or pharmacokinetic property.

In an embodiment, the first mode of delivery is selected to optimize, e.g., minimize, a pharmacodynamic or pharmacokinetic property, e.g., distribution, persistence or exposure.

In an embodiment, the second mode of delivery is selected to optimize, e.g., maximize, a pharmacodynamic or pharmcokinetic property, e.g., distribution, persistence or exposure.

In an embodiment, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In an embodiment, the second mode of delivery comprises a relatively transient element, e.g., an RNA or protein.

In an embodiment, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a Cas9 molecule, is delivered in a transient manner, for example as mRNA or as protein, ensuring that the full Cas9 molecule/gRNA molecule complex is only present and active for a short period of time.

Furthermore, the components can be delivered in different molecular form or with different delivery vectors that complement one another to enhance safety and tissue specificity.

Use of differential delivery modes can enhance performance, safety and efficacy. E.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in an embodiment, a first component, e.g., a gRNA molecule is delivered by a first delivery mode that results in a first spatial, e.g., tissue, distribution. A second component, e.g., a Cas9 molecule is delivered by a second delivery mode that results in a second spatial, e.g., tissue, distribution. In an embodiment, the first mode comprises a first element selected from a liposome, nanoparticle, e.g., polymeric nanoparticle, and a nucleic acid, e.g., viral vector. The second mode comprises a second element selected from the group. In an embodiment, the first mode of delivery comprises a first targeting element, e.g., a cell specific receptor or an antibody, and the second mode of delivery does not include that element. In embodiment, the second mode of delivery comprises a second targeting element, e.g., a second cell specific receptor or second antibody.

When the Cas9 molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA molecule and the Cas9 molecule are packaged in separated delivery vehicles with distinct but overlapping tissue tropism, the fully functional complex is only be formed in the tissue that is targeted by both vectors.

Ex Vivo Delivery

In an embodiment, components described in Table 34 are introduced into cells which are then introduced into the subject, e.g., cells are removed from a subject, manipulated ex vivo and then introduced into the subject. Methods of introducing the components can include, e.g., any of the delivery methods described in Table 35.

VIII. Modified Nucleosides, Nucleotides, and Nucleic Acids

Modified nucleosides and modified nucleotides can be present in nucleic acids, e.g., particularly gRNA, but also other forms of RNA, e.g., mRNA, RNAi, or siRNA. As described herein, "nucleoside" is defined as a compound containing a five-carbon sugar molecule (a pentose or ribose) or derivative thereof, and an organic base, purine or pyrimidine, or a derivative thereof. As described herein, "nucleotide" is defined as a nucleoside further comprising a phosphate group.

Modified nucleosides and nucleotides can include one or more of:

(i) alteration, e.g., replacement, of one or both of the non-linking phosphate oxygens and/or of one or more of the linking phosphate oxygens in the phosphodiester backbone linkage;

(ii) alteration, e.g., replacement, of a constituent of the ribose sugar. e.g., of the 2' hydroxyl on the ribose sugar;

(iii) wholesale replacement of the phosphate moiety with "dephospho" linkers;

(iv) modification or replacement of a naturally occurring nucleobase;

(v) replacement or modification of the ribose-phosphate backbone;

(vi) modification of the 3' end or 5' end of the oligonucleotide, e.g., removal, modification or replacement of a terminal phosphate group or conjugation of a moiety; and (vii) modification of the sugar.

The modifications listed above can be combined to provide modified nucleosides and nucleotides that can have two, three, four, or more modifications. For example, a modified nucleoside or nucleotide can have a modified sugar and a modified nucleobase. In an embodiment, every base of a gRNA is modified, e.g., all bases have a modified phosphate group, e.g., all are phosphorothioate groups. In an embodiment, all, or substantially all, of the phosphate groups of a unimolecular or modular gRNA molecule are replaced with phosphorothioate groups.

In an embodiment, modified nucleotides, e.g., nucleotides having modifications as described herein, can be incorporated into a nucleic acid, e.g., a "modified nucleic acid." In an embodiment, the modified nucleic acids comprise one, two, three or more modified nucleotides. In an embodiment, at least 5% (e.g., at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100%) of the positions in a modified nucleic acid are a modified nucleotides.

Unmodified nucleic acids can be prone to degradation by, e.g., cellular nucleases. For example, nucleases can hydrolyze nucleic acid phosphodiester bonds. Accordingly, in one aspect the modified nucleic acids described herein can contain one or more modified nucleosides or nucleotides, e.g., to introduce stability toward nucleases.

In an embodiment, the modified nucleosides, modified nucleotides, and modified nucleic acids described herein can exhibit a reduced innate immune response when introduced into a population of cells, both in vivo and ex vivo. The term "innate immune response" includes a cellular response to exogenous nucleic acids, including single stranded nucleic acids, generally of viral or bacterial origin, which involves the induction of cytokine expression and release, particularly the interferons, and cell death. In an embodiment, the modified nucleosides, modified nucleotides, and modified nucleic acids described herein can disrupt binding of a major groove interacting partner with the nucleic acid. In an embodiment, the modified nucleosides, modified nucleotides, and modified nucleic acids described herein can exhibit a reduced innate immune response when introduced into a population of cells, both in vivo and ex vivo, and also disrupt binding of a major groove interacting partner with the nucleic acid.

Definitions of Chemical Groups

As used herein, "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 20, from 2 to about 20, from 1 to about 12, from 1 to about 8, from 1 to about 6, from 1 to about 4, or from 1 to about 3 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In an embodiment, aryl groups have from 6 to about 20 carbon atoms.

As used herein, "alkenyl" refers to an aliphatic group containing at least one double bond.

As used herein, "alkynyl" refers to a straight or branched hydrocarbon chain containing 2-12 carbon atoms and characterized in having one or more triple bonds. Examples of alkynyl groups include, but are not limited to, ethynyl, propargyl, and 3-hexynyl.

As used herein, "arylalkyl" or "aralkyl" refers to an alkyl moiety in which an alkyl hydrogen atom is replaced by an aryl group. Aralkyl includes groups in which more than one hydrogen atom has been replaced by an aryl group. Examples of "arylalkyl" or "aralkyl" include benzyl, 2-phenylethyl, 3-phenylpropyl, 9-fluorenyl, benzhydryl, and trityl groups.

As used herein, "cycloalkyl" refers to a cyclic, bicyclic, tricyclic, or polycyclic non-aromatic hydrocarbon groups having 3 to 12 carbons. Examples of cycloalkyl moieties include, but are not limited to, cyclopropyl, cyclopentyl, and cyclohexyl.

As used herein, "heterocyclyl" refers to a monovalent radical of a heterocyclic ring system. Representative heterocyclyls include, without limitation, tetrahydrofuranyl, tetrahydrothienyl, pyrrolidinyl, pyrrolidonyl, piperidinyl, pyrrolinyl, piperazinyl, dioxanyl, dioxolanyl, diazepinyl, oxazepinyl, thiazepinyl, and morpholinyl.

As used herein, "heteroaryl" refers to a monovalent radical of a heteroaromatic ring system. Examples of heteroaryl moieties include, but are not limited to, imidazolyl, oxazolyl, thiazolyl, triazolyl, pyrrolyl, furanyl, indolyl, thiophenyl pyrazolyl, pyridinyl, pyrazinyl, pyridazinyl, pyrimidinyl, indolizinyl, purinyl, naphthyridinyl, quinolyl, and pteridinyl.

Phosphate Backbone Modifications

The Phosphate Group

In an embodiment, the phosphate group of a modified nucleotide can be modified by replacing one or more of the oxygens with a different substituent. Further, the modified nucleotide, e.g., modified nucleotide present in a modified nucleic acid, can include the wholesale replacement of an unmodified phosphate moiety with a modified phosphate as described herein. In an embodiment, the modification of the phosphate backbone can include alterations that result in either an uncharged linker or a charged linker with unsymmetrical charge distribution.

Examples of modified phosphate groups include, phosphorothioate, phosphoroselenates, borano phosphates, borano phosphate esters, hydrogen phosphonates, phosphoroamidates, alkyl or aryl phosphonates and phosphotriesters. In an embodiment, one of the non-bridging phosphate oxygen atoms in the phosphate backbone moiety can be replaced by any of the following groups: sulfur (S), selenium (Se), $BR_3$ (wherein R can be, e.g., hydrogen, alkyl, or aryl), C (e.g., an alkyl group, an aryl group, and the like), H, $NR_2$ (wherein R can be, e.g., hydrogen, alkyl, or aryl), or OR (wherein R can be, e.g., alkyl or aryl). The phosphorous atom in an unmodified phosphate group is achiral. However, replacement of one of the non-bridging oxygens with one of the above atoms or groups of atoms can render the phosphorous atom chiral; that is to say that a phosphorous atom in a phosphate group modified in this way is a stereogenic center. The stereogenic phosphorous atom can possess either the "R" configuration (herein Rp) or the "S" configuration (herein Sp).

Phosphorodithioates have both non-bridging oxygens replaced by sulfur. The phosphorus center in the phosphorodithioates is achiral which precludes the formation of oligoribonucleotide diastereomers. In an embodiment, modifications to one or both non-bridging oxygens can also include the replacement of the non-bridging oxygens with a group independently selected from S, Se, B, C, H, N, and OR (R can be, e.g., alkyl or aryl).

The phosphate linker can also be modified by replacement of a bridging oxygen, (i.e., the oxygen that links the phosphate to the nucleoside), with nitrogen (bridged phosphoroamidates), sulfur (bridged phosphorothioates) and carbon (bridged methylenephosphonates). The replacement can occur at either linking oxygen or at both of the linking oxygens.

Replacement of the Phosphate Group

The phosphate group can be replaced by non-phosphorus containing connectors. In an embodiment, the charge phosphate group can be replaced by a neutral moiety.

Examples of moieties which can replace the phosphate group can include, without limitation, e.g., methyl phosphonate, hydroxylamino, siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino.

Replacement of the Ribophosphate Backbone

Scaffolds that can mimic nucleic acids can also be constructed wherein the phosphate linker and ribose sugar are replaced by nuclease resistant nucleoside or nucleotide surrogates. In an embodiment, the nucleobases can be tethered by a surrogate backbone. Examples can include, without limitation, the morpholino, cyclobutyl, pyrrolidine and peptide nucleic acid (PNA) nucleoside surrogates.

Sugar Modifications

The modified nucleosides and modified nucleotides can include one or more modifications to the sugar group. For example, the 2' hydroxyl group (OH) can be modified or replaced with a number of different "oxy" or "deoxy" substituents. In an embodiment, modifications to the 2' hydroxyl group can enhance the stability of the nucleic acid since the hydroxyl can no longer be deprotonated to form a 2'-alkoxide ion. The 2'-alkoxide can catalyze degradation by intramolecular nucleophilic attack on the linker phosphorus atom.

Examples of "oxy"-2' hydroxyl group modifications can include alkoxy or aryloxy (OR, wherein "R" can be, e.g., alkyl, cycloalkyl, aryl, aralkyl, heteroaryl or a sugar); polyethyleneglycols (PEG), $O(CH_2CH_2O)_nCH_2CH_2OR$ wherein R can be, e.g., H or optionally substituted alkyl, and n can be an integer from 0 to 20 (e.g., from 0 to 4, from 0 to 8, from 0 to 10, from 0 to 16, from 1 to 4, from 1 to 8, from 1 to 10, from 1 to 16, from 1 to 20, from 2 to 4, from 2 to 8, from 2 to 10, from 2 to 16, from 2 to 20, from 4 to 8, from 4 to 10, from 4 to 16, and from 4 to 20). In an embodiment, the "oxy"-2' hydroxyl group modification can include "locked" nucleic acids (LNA) in which the 2' hydroxyl can be connected, e.g., by a $C_{1-6}$ alkylene or $C_{1-6}$ heteroalkylene bridge, to the 4' carbon of the same ribose sugar, where exemplary bridges can include methylene, propylene, ether, or amino bridges; O-amino (wherein amino can be, e.g., $NH_2$; alkylamino, dialkylamino, heterocyclyl, arylamino, diarylamino, heteroarylamino, or diheteroarylamino, ethylenediamine, or polyamino) and aminoalkoxy, $O(CH_2)_n$-amino, (wherein amino can be, e.g., $NH_2$; alkylamino, dialkylamino, heterocyclyl, arylamino, diarylamino, heteroarylamino, or diheteroarylamino, ethylenediamine, or polyamino). In an embodiment, the "oxy"-2' hydroxyl group modification can include the methoxyethyl group (MOE), ($OCH_2CH_2OCH_3$, e.g., a PEG derivative).

"Deoxy" modifications can include hydrogen (i.e. deoxyribose sugars, e.g., at the overhang portions of partially ds RNA); halo (e.g., bromo, chloro, fluoro, or iodo); amino (wherein amino can be, e.g., $NH_2$; alkylamino, dialkylamino, heterocyclyl, arylamino, diarylamino, heteroarylamino, diheteroarylamino, or amino acid); $NH(CH_2CH_2NH)_nCH_2CH_2$-amino (wherein amino can be, e.g., as described herein), —NHC(O)R (wherein R can be, e.g., alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino as described herein.

The sugar group can also contain one or more carbons that possess the opposite stereochemical configuration than that of the corresponding carbon in ribose. Thus, a modified nucleic acid can include nucleotides containing e.g., arabinose, as the sugar. The nucleotide "monomer" can have an alpha linkage at the 1' position on the sugar, e.g., alpha-nucleosides. The modified nucleic acids can also include "abasic" sugars, which lack a nucleobase at C-1'. These abasic sugars can also be further modified at one or more of the constituent sugar atoms. The modified nucleic acids can also include one or more sugars that are in the L form, e.g. L-nucleosides.

Generally, RNA includes the sugar group ribose, which is a 5-membered ring having an oxygen. Exemplary modified nucleosides and modified nucleotides can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). In an embodiment, the modified nucleotides can include multicyclic forms (e.g., tricyclo; and "unlocked" forms, such as glycol nucleic acid (GNA) (e.g., R-GNA or S-GNA, where ribose is replaced by glycol units attached to phosphodiester bonds), threose nucleic acid (TNA, where ribose is replaced with α-L-threofuranosyl-(3'→2')).

Modifications on the Nucleobase

The modified nucleosides and modified nucleotides described herein, which can be incorporated into a modified nucleic acid, can include a modified nucleobase. Examples of nucleobases include, but are not limited to, adenine (A), guanine (G), cytosine (C), and uracil (U). These nucleobases can be modified or wholly replaced to provide modified nucleosides and modified nucleotides that can be incorporated into modified nucleic acids. The nucleobase of the nucleotide can be independently selected from a purine, a pyrimidine, a purine or pyrimidine analog. In an embodiment, the nucleobase can include, for example, naturally-occurring and synthetic derivatives of a base.

Uracil

In an embodiment, the modified nucleobase is a modified uracil. Exemplary nucleobases and nucleosides having a modified uracil include without limitation pseudouridine (ψ), pyridin-4-one ribonucleoside, 5-aza-uridine, 6-aza-uridine, 2-thio-5-aza-uridine, 2-thio-uridine (s2U), 4-thio-uridine (s4U), 4-thio-pseudouridine, 2-thio-pseudouridine, 5-hydroxy-uridine (ho$^5$U), 5-aminoallyl-uridine, 5-halo-uridine (e.g., 5-iodo-uridine or 5-bromo-uridine), 3-methyl-uridine (m$^3$U), 5-methoxy-uridine (mo$^5$U), uridine 5-oxyacetic acid (cmo$^5$U), uridine 5-oxyacetic acid methyl ester (mcmo$^5$U), 5-carboxymethyl-uridine (cm$^5$U), 1-carboxymethyl-pseudouridine, 5-carboxyhydroxymethyl-uridine (chm$^5$U), 5-carboxyhydroxymethyl-uridine methyl ester (mchm$^5$U), 5-methoxycarbonylmethyl-uridine (mcm$^5$U), 5-methoxycarbonylmethyl-2-thio-uridine (mcm$^5$s2U), 5-aminomethyl-2-thio-uridine (nm$^5$s2U), 5-methylaminomethyl-uridine (mnm$^5$U), 5-methylaminomethyl-2-thio-uridine (mnm$^5$s2U), 5-methylaminomethyl-2-seleno-uridine (mnm$^5$se2U), 5-carbamoylmethyl-uridine (ncm$^5$U), 5-carboxymethylaminomethyl-uridine (cmnm$^5$U), 5-carboxymethylaminomethyl-2-thio-uridine (cmnm$^5$s2U), 5-propynyl-uridine, 1-propynyl-pseudouridine, 5-taurinomethyl-uridine (τcm$^5$U), 1-taurinomethyl-pseudouridine, 5-taurinomethyl-2-thio-uridine(τm$^5$s2U), 1-taurinomethyl-4-thio-pseudouridine, 5-methyl-uridine (m$^5$U, i.e., having the nucleobase deoxythymine), 1-methyl-pseudouridine (m$^1$ψ), 5-methyl-2-thio-uridine (m$^5$s2U), 1-methyl-4-thio-pseudouridine (m$^1$s$^4$ψ), 4-thio-1-methyl-pseudouridine, 3-methyl-pseudouridine (m$^3$ψ), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine (m$^5$D), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine (acp$^3$U), 1-methyl-3-(3-amino-3-carboxypropyl)pseudouridine (acp$^3$ψ), 5-(isopentenylaminomethyl)uridine (inm$^5$U), 5-(isopentenylaminomethyl)-2-thio-uridine (inm$^5$s2U), α-thio-uridine, 2'-O-methyl-uridine (Um), 5,2'-O-dimethyl-uridine (m$^5$Um), 2'-O-methyl-pseudouridine (ψm), 2-thio-2'-O-methyl-uridine (s2Um), 5-methoxycarbonylmethyl-2'-O-methyl-uridine (mcm$^5$Um), 5-carbamoylmethyl-2'-O-methyl-uridine (ncm$^5$Um), 5-carboxymethylaminomethyl-2'-O-methyl-uridine (cmnm$^5$Um), 3,2'-O-dimethyl-uridine (m$^3$Um), 5-(isopentenylaminomethyl)-2'-O-methyl-uridine (inm$^5$Um), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, pyrazolo[3,4-d]pyrimidines, xanthine, and hypoxanthine.

Cytosine

In an embodiment, the modified nucleobase is a modified cytosine. Exemplary nucleobases and nucleosides having a modified cytosine include without limitation 5-aza-cytidine, 6-aza-cytidine, pseudoisocytidine, 3-methyl-cytidine (m$^3$C), N4-acetyl-cytidine (act), 5-formyl-cytidine (f$^5$C), N4-methyl-cytidine (m$^4$C), 5-methyl-cytidine (m$^5$C), 5-halo-cytidine (e.g., 5-iodo-cytidine), 5-hydroxymethyl-cytidine (hm$^5$C), 1-methyl-pseudoisocytidine, pyrrolo-cytidine, pyrrolo-pseudoisocytidine, 2-thio-cytidine (s2C), 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, lysidine (k$^2$C), α-thio-cytidine, 2'-O-methyl-cytidine (Cm), 5,2'-O-dimethyl-cytidine (m$^5$Cm), N4-acetyl-2'-O-methyl-cytidine (ac⁴Cm), N4,2'-O-dimethyl-cytidine (m⁴Cm), 5-formyl-2'-O-methyl-cytidine (f⁵Cm), N4,N4,2'-O-trimethyl-cytidine (m⁴₂Cm), 1-thio-cytidine, 2'-F-ara-cytidine, 2'-F-cytidine, and 2'-OH-ara-cytidine.

Adenine

In an embodiment, the modified nucleobase is a modified adenine. Exemplary nucleobases and nucleosides having a modified adenine include without limitation 2-amino-purine, 2,6-diaminopurine, 2-amino-6-halo-purine (e.g., 2-amino-6-chloro-purine), 6-halo-purine (e.g., 6-chloro-purine), 2-amino-6-methyl-purine, 8-azido-adenosine, 7-deaza-adenosine, 7-deaza-8-aza-adenosine, 7-deaza-2-amino-purine, 7-deaza-8-aza-2-amino-purine, 7-deaza-2,6-diaminopurine, 7-deaza-8-aza-2,6-diaminopurine, 1-methyl-adenosine (m¹A), 2-methyl-adenosine (m²A), N6-methyl-adenosine (m⁶A), 2-methylthio-N6-methyl-adenosine (ms2m⁶A), N6-isopentenyl-adenosine (i⁶A), 2-methylthio-N6-isopentenyl-adenosine (ms²i⁶A), N6-(cis-hydroxyisopentenyl)adenosine (io⁶A), 2-methylthio-N6-(cis-hydroxyisopentenyl)adenosine (ms2io⁶A), N6-glycinylcarbamoyl-adenosine (g⁶A), N6-threonylcarbamoyl-adenosine (t⁶A), N6-methyl-N6-threonylcarbamoyl-adenosine (m⁶t⁶A), 2-methylthio-N6-threonylcarbamoyl-adenosine (ms²g⁶A), N6,N6-dimethyl-adenosine (m⁶₂A), N6-hydroxynorvalylcarbamoyl-adenosine (hn⁶A), 2-methylthio-N6-hydroxynorvalylcarbamoyl-adenosine (ms2hn⁶A), N6-acetyl-adenosine (ac⁶A), 7-methyl-adenosine, 2-methylthio-adenosine, 2-methoxy-adenosine, α-thio-adenosine, 2'-O-methyl-adenosine (Am), N⁶,2'-O-dimethyl-adenosine (m⁶Am), N⁶-Methyl-2'-deoxyadenosine, N6,N6,2'-O-trimethyl-adenosine (m⁶₂Am), 1,2'-O-dimethyl-adenosine (m¹Am), 2'-O-ribosyladenosine (phosphate) (Ar(p)), 2-amino-N6-methyl-purine, 1-thio-adenosine, 8-azido-adenosine, 2'-F-ara-adenosine, 2'-F-adenosine, 2'-OH-ara-adenosine, and N6-(19-amino-pentaoxanonadecyl)-adenosine.

Guanine

In an embodiment, the modified nucleobase is a modified guanine. Exemplary nucleobases and nucleosides having a modified guanine include without limitation inosine (I), 1-methyl-inosine (m¹I), wyosine (imG), methylwyosine (mimG), 4-demethyl-wyosine (imG-14), isowyosine (imG2), wybutosine (yW), peroxywybutosine (o₂yW), hydroxywybutosine (OHyW), undermodified hydroxywybutosine (OHyW*), 7-deaza-guanosine, queuosine (Q), epoxyqueuosine (oQ), galactosyl-queuosine (galQ), mannosyl-queuosine (manQ), 7-cyano-7-deaza-guanosine (preQ₀), 7-aminomethyl-7-deaza-guanosine (preQ₁), archaeosine (G⁺), 7-deaza-8-aza-guanosine, 6-thio-guanosine, 6-thio-7-deaza-guanosine, 6-thio-7-deaza-8-aza-guanosine, 7-methyl-guanosine (m⁷G), 6-thio-7-methyl-guanosine, 7-methyl-inosine, 6-methoxy-guanosine, 1-methyl-guanosine (m'G), N2-methyl-guanosine (m²G), N2,N2-dimethyl-guanosine (m²₂G), N2,7-dimethyl-guanosine (m²,7G), N2,N2,7-dimethyl-guanosine (m²,2,7G), 8-oxo-guanosine, 7-methyl-8-oxo-guanosine, 1-methyl-6-thio-guanosine, N2-methyl-6-thio-guanosine, N2,N2-dimethyl-6-thio-guanosine, α-thio-guanosine, 2'-O-methyl-guanosine (Gm), N2-methyl-2'-O-methyl-guanosine (m²Gm), N2,N2-dimethyl-2'-O-methyl-guanosine (m²₂Gm), 1-methyl-2'-O-methyl-guanosine (m'Gm), N2,7-dimethyl-2'-O-methyl-guanosine (m²,7Gm), 2'-O-methyl-inosine (Im), 1,2'-O-dimethyl-inosine (m'Im), O⁶-phenyl-2'-deoxyinosine, 2'-O-ribosylguanosine (phosphate) (Gr(p)), 1-thio-guanosine, O⁶-methyl-guanosine, O⁶-Methyl-2'-deoxyguanosine, 2'-F-ara-guanosine, and 2'-F-guanosine.

Exemplary Modified gRNAs

In some embodiments, the modified nucleic acids can be modified gRNAs. It is to be understood that any of the gRNAs described herein can be modified in accordance with this section, including any gRNA that comprises a targeting domain from Tables 1A-1D, 2A-2F, 3A-3C, 4A-4E, 5A-5E, 6A-6B, 7A-7D, 8A-8D, 9, 10A-10D, 11A-11D, 12, 13A-13D, 14A-14C, 15A-15D, 16A-16E, 17A-17B, 18A-18C, 19A-19E, 20A-20C, 21A-21E, 22A-22E, 23A-23C, 24A-24D, 25A-25B, 26, or 31.

As discussed above, transiently expressed or delivered nucleic acids can be prone to degradation by, e.g., cellular nucleases. Accordingly, in one aspect the modified gRNAs described herein can contain one or more modified nucleosides or nucleotides which introduce stability toward nucleases. While not wishing to be bound by theory it is also believed that certain modified gRNAs described herein can exhibit a reduced innate immune response when introduced into a population of cells, particularly the cells of the present invention. As noted above, the term "innate immune response" includes a cellular response to exogenous nucleic acids, including single stranded nucleic acids, generally of viral or bacterial origin, which involves the induction of cytokine expression and release, particularly the interferons, and cell death.

While some of the exemplary modification discussed in this section may be included at any position within the gRNA sequence, in some embodiments, a gRNA comprises a modification at or near its 5' end (e.g., within 1-10, 1-5, or 1-2 nucleotides of its 5' end). In some embodiments, a gRNA comprises a modification at or near its 3' end (e.g., within 1-10, 1-5, or 1-2 nucleotides of its 3' end). In some embodiments, a gRNA comprises both a modification at or near its 5' end and a modification at or near its 3' end.

In an embodiment, the 5' end of a gRNA is modified by the inclusion of a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)). The cap or cap analog can be included during either chemical synthesis or in vitro transcription of the gRNA.

In an embodiment, an in vitro transcribed gRNA is modified by treatment with a phosphatase (e.g., calf intestinal alkaline phosphatase) to remove the 5' triphosphate group.

In an embodiment, the 3' end of a gRNA is modified by the addition of one or more (e.g., 25-200) adenine (A) residues. The polyA tract can be contained in the nucleic acid (e.g., plasmid, PCR product, viral genome) encoding the gRNA, or can be added to the gRNA during chemical synthesis, or following in vitro transcription using a polyadenosine polymerase (e.g., *E. coli* Poly(A)Polymerase).

In an embodiment, in vitro transcribed gRNA contains both a 5' cap structure or cap analog and a 3' polyA tract. In an embodiment, an in vitro transcribed gRNA is modified by treatment with a phosphatase (e.g., calf intestinal alkaline phosphatase) to remove the 5' triphosphate group and comprises a 3' polyA tract.

In some embodiments, gRNAs can be modified at a 3' terminal U ribose. For example, the two terminal hydroxyl groups of the U ribose can be oxidized to aldehyde groups and a concomitant opening of the ribose ring to afford a modified nucleoside as shown below:

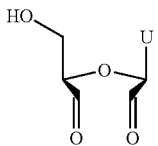

wherein "U" can be an unmodified or modified uridine.

In another embodiment, the 3' terminal U can be modified with a 2'3' cyclic phosphate as shown below:

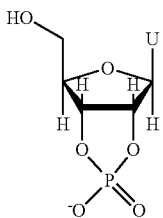

wherein "U" can be an unmodified or modified uridine.

In some embodiments, the gRNA molecules may contain 3' nucleotides which can be stabilized against degradation, e.g., by incorporating one or more of the modified nucleotides described herein. In this embodiment, e.g., uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In some embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH$_2$; alkylamino, dialkylamino, heterocyclyl, arylamino, diarylamino, heteroarylamino, diheteroarylamino, or amino acid); or cyano (—CN). In some embodiments, the phosphate backbone can be modified as described herein, e.g., with a phosphothioate group. In some embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

In some embodiments, a gRNA can include "locked" nucleic acids (LNA) in which the 2' OH-group can be connected, e.g., by a C1-6 alkylene or C1-6 heteroalkylene bridge, to the 4' carbon of the same ribose sugar, where exemplary bridges can include methylene, propylene, ether, or amino bridges; O-amino (wherein amino can be, e.g., NH$_2$; alkylamino, dialkylamino, heterocyclyl, arylamino, diarylamino, heteroarylamino, or diheteroarylamino, ethylenediamine, or polyamino) and aminoalkoxy or O(CH$_2$)$_n$-amino (wherein amino can be, e.g., NH$_2$; alkylamino, dialkylamino, heterocyclyl, arylamino, diarylamino, heteroarylamino, or diheteroarylamino, ethylenediamine, or polyamino).

In some embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNA molecules include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In an embodiment, a gRNA comprises a 4'-S, 4'-Se or a 4'-C-aminomethyl-2'-O-Me modification.

In some embodiments, deaza nucleotides, e.g., 7-deaza-adenosine, can be incorporated into the gRNA. In some embodiments, O- and N-alkylated nucleotides, e.g., N6-methyl adenosine, can be incorporated into the gRNA. In some embodiments, one or more or all of the nucleotides in a gRNA molecule are deoxynucleotides.

miRNA Binding Sites microRNAs (or miRNAs) are naturally occurring cellular 19-25 nucleotide long noncoding RNAs. They bind to nucleic acid molecules having an appropriate miRNA binding site, e.g., in the 3' UTR of an mRNA, and down-regulate gene expression. While not wishing to be bound by theory it is believed that the down regulation is either by reducing nucleic acid molecule stability or by inhibiting translation. An RNA species disclosed herein, e.g., an mRNA encoding Cas9 can comprise an miRNA binding site, e.g., in its 3'UTR. The miRNA binding site can be selected to promote down regulation of expression is a selected cell type. By way of example, the incorporation of a binding site for miR-122, a microRNA abundant in liver, can inhibit the expression of the gene of interest in the liver.

EXAMPLES

The following Examples are merely illustrative and are not intended to limit the scope or content of the invention in any way.

Example 1

Cloning and Initial Screening of gRNAs

The suitability of candidate gRNAs can be evaluated as described in this example. Although described for a chimeric gRNA, the approach can also be used to evaluate modular gRNAs.

Cloning gRNAs into Vectors

For each gRNA, a pair of overlapping oligonucleotides is designed and obtained. Oligonucleotides are annealed and ligated into a digested vector backbone containing an upstream U6 promoter and the remaining sequence of a long chimeric gRNA. Plasmid is sequence-verified and prepped to generate sufficient amounts of transfection-quality DNA. Alternate promoters maybe used to drive in vivo transcription (e.g. H1 promoter) or for in vitro transcription (e.g., a T7 promoter).

Cloning gRNAs in Linear dsDNA Molecule (STITCHR)

For each gRNA, a single oligonucleotide is designed and obtained. The U6 promoter and the gRNA scaffold (e.g. including everything except the targeting domain, e.g., including sequences derived from the crRNA and tracrRNA, e.g., including a first complementarity domain; a linking domain; a second complementarity domain; a proximal domain; and a tail domain) are separately PCR amplified and purified as dsDNA molecules. The gRNA-specific oligonucleotide is used in a PCR reaction to stitch together the U6 and the gRNA scaffold, linked by the targeting domain specified in the oligonucleotide. Resulting dsDNA molecule (STITCHR product) is purified for transfection. Alternate promoters may be used to drive in vivo transcription (e.g., H1 promoter) or for in vitro transcription (e.g., T7 promoter). Any gRNA scaffold may be used to create gRNAs compatible with Cas9s from any bacterial species.

Initial gRNA Screen

Each gRNA to be tested is transfected, along with a plasmid expressing Cas9 and a small amount of a GFP-expressing plasmid into human cells. In preliminary experiments, these cells can be immortalized human cell lines such as 293T, K562 or U2OS. Alternatively, primary human cells may be used. In this case, cells may be relevant to the eventual therapeutic cell target (for example, an erythroid cell). The use of primary cells similar to the potential therapeutic target cell population may provide important information on gene targeting rates in the context of endogenous chromatin and gene expression.

Transfection may be performed using lipid transfection (such as Lipofectamine or Fugene) or by electroporation (such as Lonza Nucleofection). Following transfection, GFP expression can be determined either by fluorescence microscopy or by flow cytometry to confirm consistent and high levels of transfection. These preliminary transfections can comprise different gRNAs and different targeting approaches (17-mers, 20-mers, nuclease, dual-nickase, etc.) to determine which gRNAs/combinations of gRNAs give the greatest activity.

Efficiency of cleavage with each gRNA may be assessed by measuring NHEJ-induced indel formation at the target locus by a T7E1-type assay or by sequencing. Alternatively, other mismatch-sensitive enzymes, such as Cell/Surveyor nuclease, may also be used.

For the T7E1 assay, PCR amplicons are approximately 500-700 bp with the intended cut site placed asymmetrically in the amplicon. Following amplification, purification and size-verification of PCR products, DNA is denatured and re-hybridized by heating to 95° C. and then slowly cooling. Hybridized PCR products are then digested with T7 Endonuclease I (or other mismatch-sensitive enzyme) which recognizes and cleaves non-perfectly matched DNA. If indels are present in the original template DNA, when the amplicons are denatured and re-annealed, this results in the hybridization of DNA strands harboring different indels and therefore lead to double-stranded DNA that is not perfectly matched. Digestion products may be visualized by gel electrophoresis or by capillary electrophoresis. The fraction of DNA that is cleaved (density of cleavage products divided by the density of cleaved and uncleaved) may be used to estimate a percent NHEJ using the following equation: % NHEJ=$(1-(1-\text{fraction cleaved})^{1/2})$. The T7E1 assay is sensitive down to about 2-5% NHEJ.

Sequencing may be used instead of, or in addition to, the T7E1 assay. For Sanger sequencing, purified PCR amplicons are cloned into a plasmid backbone, transformed, miniprepped and sequenced with a single primer. Sanger sequencing may be used for determining the exact nature of indels after determining the NHEJ rate by T7E1.

Sequencing may also be performed using next generation sequencing techniques. When using next generation sequencing, amplicons may be 300-500 bp with the intended cut site placed asymmetrically. Following PCR, next generation sequencing adapters and barcodes (for example Illumina multiplex adapters and indexes) may be added to the ends of the amplicon, e.g., for use in high throughput sequencing (for example on an Illumina MiSeq). This method allows for detection of very low NHEJ rates.

Example 2

Assessment of Gene Targeting by NHEJ

The gRNAs that induce the greatest levels of NHEJ in initial tests can be selected for further evaluation of gene targeting efficiency. In this case, cells are derived from disease subjects and, therefore, harbor the relevant mutation.

Following transfection (usually 2-3 days post-transfection) genomic DNA may be isolated from a bulk population of transfected cells and PCR may be used to amplify the target region. Following PCR, gene targeting efficiency to generate the desired mutations (either knockout of a target gene or removal of a target sequence motif) may be determined by sequencing. For Sanger sequencing, PCR amplicons may be 500-700 bp long. For next generation sequencing, PCR amplicons may be 300-500 bp long. If the goal is to knockout gene function, sequencing may be used to assess what percent of alleles have undergone NHEJ-induced indels that result in a frameshift or large deletion or insertion that would be expected to destroy gene function. If the goal is to remove a specific sequence motif, sequencing may be used to assess what percent of alleles have undergone NHEJ-induced deletions that span this sequence.

Example 3

Assessment of Gene Targeting by HDR

The gRNAs that induce the greatest levels of NHEJ in initial tests can be selected for further evaluation of gene targeting efficiency. In this case, cells are derived from disease subjects and, therefore, harbor the relevant mutation.

Following transfection (usually 2-3 days post-transfection) genomic DNA may be isolated from a bulk population of transfected cells and PCR may be used to amplify the target region. Following PCR, gene targeting efficiency can be determined by several methods.

Determination of gene targeting frequency involves measuring the percentage of alleles that have undergone homologous directed repair (HDR) with the exogenously provided donor template or endogenous genomic donor sequence and which therefore have incorporated the desired correction. If the desired HDR event creates or destroys a restriction enzyme site, the frequency of gene targeting may be determined by a RFLP assay. If no restriction site is created or destroyed, sequencing may be used to determine gene targeting frequency. If a RFLP assay is used, sequencing may still be used to verify the desired HDR event and ensure that no other mutations are present. If an exogenously provided donor template is employed, at least one of the primers is placed in the endogenous gene sequence outside of the region included in the homology arms, which prevents amplification of donor template still present in the cells. Therefore, the length of the homology arms present in the donor template may affect the length of the PCR amplicon. PCR amplicons can either span the entire donor region (both primers placed outside the homology arms) or they can span only part of the donor region and a single junction between donor and endogenous DNA (one internal and one external primer). If the amplicons span less than the entire donor region, two different PCRs should be used to amplify and sequence both the 5' and the 3' junction.

If the PCR amplicon is short (less than 600 bp) it is possible to use next generation sequencing. Following PCR, next generation sequencing adapters and barcodes (for example Illumina multiplex adapters and indexes) may be added to the ends of the amplicon, e.g., for use in high throughput sequencing (for example on an Illumina MiSeq). This method allows for detection of very low gene targeting rates.

If the PCR amplicon is too long for next generation sequencing, Sanger sequencing can be performed. For Sanger sequencing, purified PCR amplicons will be cloned into a plasmid backbone (for example, TOPO cloned using the LifeTech Zero Blunt® TOPO® cloning kit), transformed, miniprepped and sequenced.

The same or similar assays described above can be used to measure the percentage of alleles that have undergone HDR with endogenous genomic donor sequence and which therefore have incorporated the desired correction.

Example 4

Screening of gRNAs for Targeting BCL11A

In order to identify gRNAs with the highest on target NHEJ efficiency, thirty exemplary *S. pyogenes* gRNAs were selected for testing (Table 31). The gRNAs tested target three different regions of the BCL11A locus—5' of a red blood cell enhancer, 3' of a red blood cell enhancer and downstream of the ATG start codon in exon 2 (specified in Table 31).

TABLE 31

| gRNA Name | Targeting Sequence | Size | Gene Region | SEQ ID NO |
|---|---|---|---|---|
| BCL11A-2981W | GUGCUACUUAUACAAUUCAC | 20 | 3' of enhancer | 16261 |
| BCL11A-2982W | GAAAAUACUUACUGUACUGC | 20 | 3' of enhancer | 16262 |
| BCL11A-2983W | GGCUGUUUUGGAAUGUAGAG | 20 | 5' of enhancer | 16263 |
| BCL11A-2984W | AUUCACUGGAAACCCUGUUA | 20 | 3' of enhancer | 16264 |
| BCL11A-2985W | UACUGUACUGCAGGGGAAUU | 20 | 3' of enhancer | 16265 |
| BCL11A-2986W | AAACUAUUUACAGCCAUAAC | 20 | 3' of enhancer | 16266 |
| BCL11A-2987W | AAAUACUUACUGUACUGCAG | 20 | 3' of enhancer | 16267 |
| BCL11A-2988W | CUAUUUACAGCCAUAAC | 17 | 3' of enhancer | 16268 |
| BCL11A-2989W | CUACUUAUACAAUUCAC | 17 | 3' of enhancer | 16269 |
| BCL11A-2990W | CACUGGAAACCCUGUUA | 17 | 3' of enhancer | 16270 |
| BCL11A-2991W | UACUUACUGUACUGCAG | 17 | 3' of enhancer | 16271 |
| BCL11A-2992W | UGUACUGCAGGGGAAUU | 17 | 3' of enhancer | 16272 |
| BCL11A-2993W | AAUACUUACUGUACUGC | 17 | 3' of enhancer | 16273 |
| BCL11A-2994W | AUACUUACUGUACUGCA | 17 | 3' of enhancer | 16274 |
| BCL11A-2995W | GAAUGUAGAGAGGCAGA | 17 | 5' of enhancer | 16275 |
| BCL11A-2996W | GGAAUGUAGAGAGGCAG | 17 | 5' of enhancer | 16276 |
| BCL11A-2997W | GUAAGUAUUUUCUUUCAUUG | 20 | 3' of enhancer | 16277 |
| BCL11A-2998W | GUAAUUAAGAAAGCAGUGUA | 20 | 5' of enhancer | 16278 |
| BCL11A-2999W | GUAUUUUCUUUCAUUGG | 17 | 3' of enhancer | 16279 |
| BCL11A-32W | UGGCAUCCAGGUCACGCCAG | 20 | Exon 2 | 16280 |
| BCL11A-40W | GAUGCUUUUUUCAUCUCGAU | 20 | Exon 2 | 16281 |
| BCL11A-30W | GCAUCCAAUCCCGUGGAGGU | 20 | Exon 2 | 16282 |
| BCL11A-42W | UUUUCAUCUCGAUUGGUGAA | 20 | Exon 2 | 16283 |
| BCL11A-24W | CCAGAUGAACUUCCCAUUGG | 20 | Exon 2 | 16284 |
| BCL11A-53W | AGGAGGUCAUGAUCCCCUUC | 20 | Exon 2 | 16285 |

TABLE 31-continued

| gRNA Name | Targeting Sequence | Size | Gene Region | SEQ ID NO |
|---|---|---|---|---|
| BCL11A-79W | CAUCCAGGUCACGCCAG | 17 | Exon 2 | 16286 |
| BCL11A-90W | GCUUUUUUCAUCUCGAU | 17 | Exon 2 | 16287 |
| BCL11A-77W | UCCAAUCCCGUGGAGGU | 17 | Exon 2 | 16288 |
| BCL11A-92W | UCAUCUCGAUUGGUGAA | 17 | Exon 2 | 16289 |
| BCL11A-71W | GAUGAACUUCCCAUUGG | 17 | Exon 2 | 16290 |

A DNA template comprised of an exemplary gRNA (including the target region and the *S. pyogenes* TRACR sequence) under the control of a U6 promoter was generated by a PCR StitchR reaction. This DNA template was subsequently transfected into 293 cells using Lipofectamine 3000 along with a DNA plasmid encoding the *S. pyogenes* Cas9 downstream of a CMV promoter. Genomic DNA was isolated from the cells 48-72 hours post transfection. To determine the rate of modification at the BCL11A locus, the target region was amplified using a locus PCR with the primers listed in Table 32.

TABLE 32

| Primer Sequence | Exon |
|---|---|
| TGCCTACATCTGATTCAGTGA GG (SEQ ID NO: 16291) | BCL11A exon 2 5' primer |
| TGCCTCATTGACAAATTTGC TC (SEQ ID NO: 16292) | BCL11A exon 2 3' primer |
| AGACCGTCTCTTTGGTGCAG (SEQ ID NO: 16293) | BCL11A 5' enhancer 5' primer |
| GCAGTGGCTTTAGGCTGTTT (SEQ ID NO: 16294) | BCL11A 5' enhancer 3' primer |
| GTGTGATCTCGGCTCACCAC (SEQ ID NO: 16295) | BCL11A 3' enhancer 5' primer |
| CCCTGACTTTGGAGCTCAGC (SEQ ID NO: 16296) | BCL11A 3' enhancer 3' primer |

Figure 11:
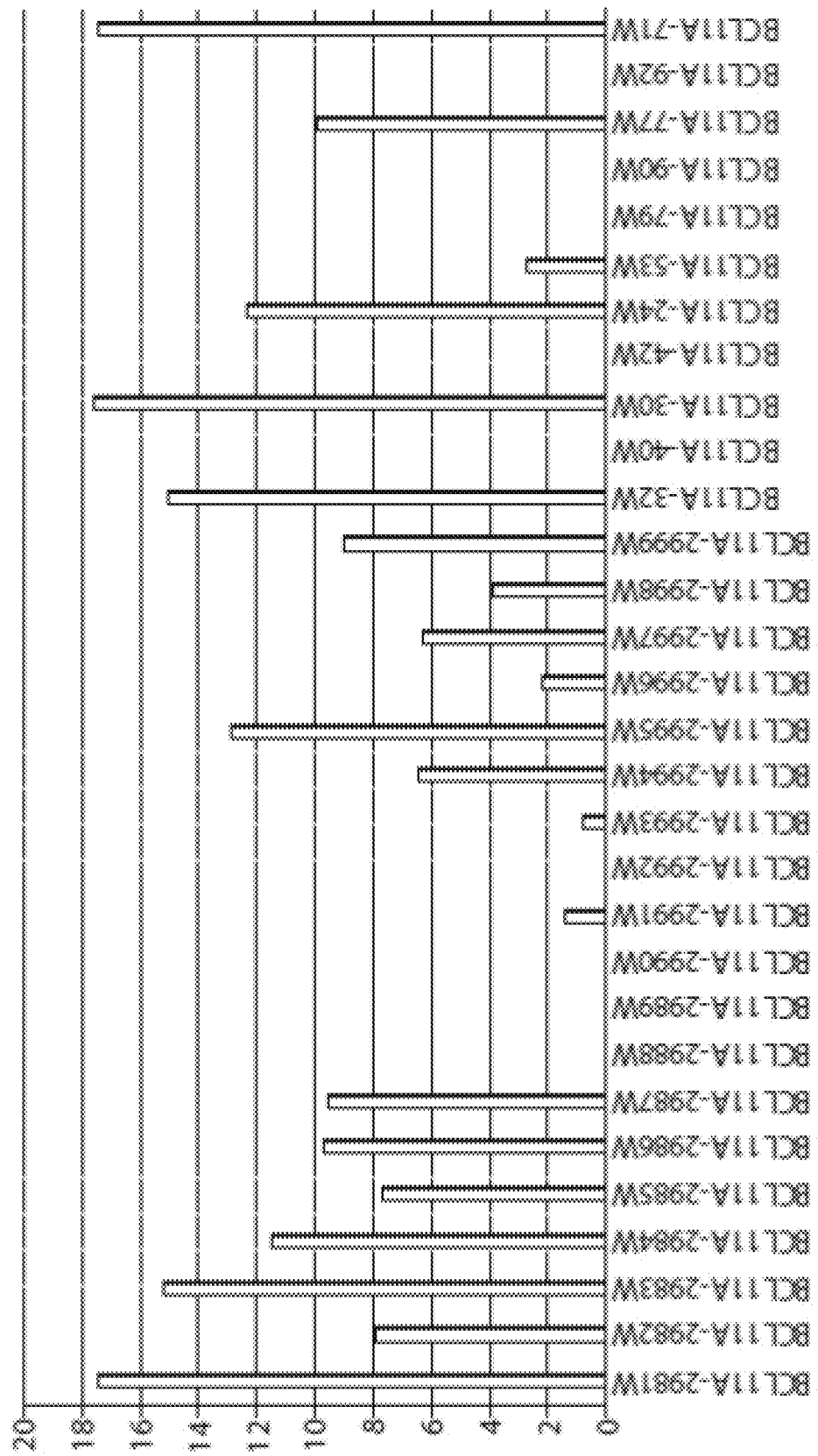
FIG. 11 depicts the efficiency of NHEJ mediated by a Cas9 molecule and exemplary gRNA molecules targeting three different regions of the BCL11A locus.
Figure 12A:
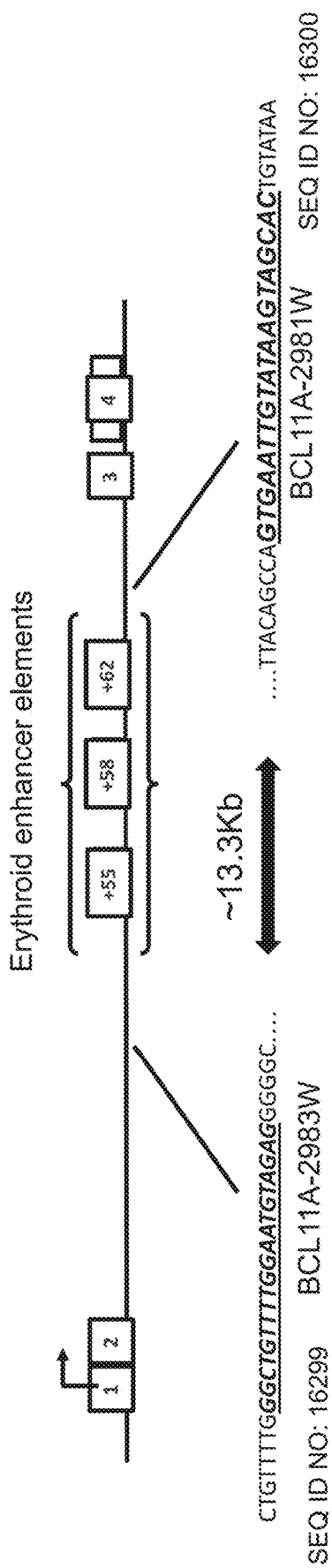
Figure 13A:
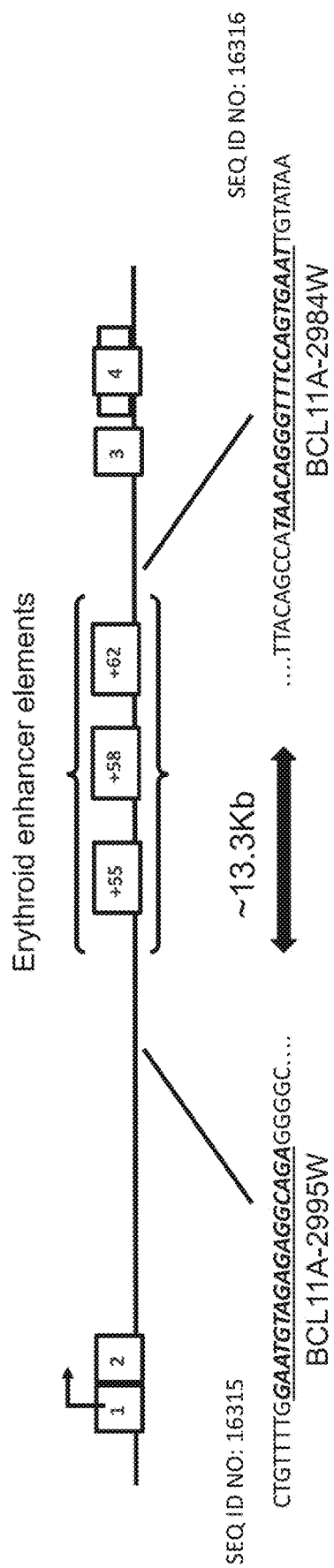

After PCR amplification, a T7E1-directed mismatch cleavage assay was performed on the PCR product. Briefly, this assay involves melting the PCR product followed by a re-annealing step. If gene modification has occurred, there will exist double stranded products that are not perfect matches due to some frequency of insertions or deletions. These double stranded products are sensitive to cleavage by a T7 endonuclease 1 enzyme at the site of mismatch. Therefore, the efficiency of cutting by the Cas9/gRNA complex was determined by analyzing the amount of T7E1 cleavage. The formula that was used to provide a measure of % NHEJ from the T7E1 cutting is the following: 100*(1−(1−(fraction cleaved))^0.5). The results of this analysis are shown in FIG. 11. The top performing gRNAs in this assay were BCL11A-2981, BCL11A-2983, BCL11A-2995, BCL11A-32, BCL11A-30, and BCL11A-71.

Example 5

Deletion of the Erythroid Enhancer Elements Using Two gRNAs Flanking the Sequence In order to test whether the erythroid enhancer sequence can be deleted using a two gRNA approach, two pairs of gRNAs were tested in 293 cells. Pair number 1 comprised BCL11A-2983W and BCL11A-2981W while Pair number 2 comprised BCL11A-2995W and BCL11A-2984W. In this example, a plasmid encoding *S. pyogenes* Cas9 downstream of a CMV promoter was delivered with either gRNA pair 1 or gRNA pair 2. The gRNAs were delivered as separate STITCHR products with each template comprising the U6 promoter, gRNA target sequence and *S. pyogenes* TRACR sequence. The DNA templates were delivered to 293 cells using lipid transfection (Lipofectamine 3000, Life Technologies). 72 hours post transfection, the cells were harvested and gDNA was isolated. To detect the deletion of the enhancer region of BCL11A, PCR primers flanking the enhancer sequences were used to amplify the deletion event. The PCR product was TOPO cloned and sequenced by Sanger sequencing. The results of these analyses are presented in FIG. 12A-13B. As shown in FIG. 12A-13B, the deletion for both gRNA pairs that were delivered to the 293 cells were detected.

Example 6

Gene Targeting of the HBB Locus by CRISPR/Cas9 to Investigate Repair Pathway Choice in Response to Different Types of DNA Lesions The CRISPR/Cas9 system was used to target the human HBB gene in the region of the sickle cell anemia-causing mutation.

To examine how the nature of the targeted break affects the frequency of different DNA repair outcomes, blunt double-strand breaks, single-strand nicks, and dual-nicks in which the nicks are placed on opposite strands and leave either 3' or 5' overhangs of varying lengths, were introduced by utilizing the wild type Cas9 nuclease, as well as two different Cas9 nickases. Several different DNA repair outcomes including indel mutations resulting from non-homologous end-joining, homology-dependent repair (HDR) using the donor as a template, and HDR using the closely related HBD gene as an endogenous template, were characterized using either single-strand oligonucleotide (ssODN) or plasmid DNA donors. The frequency of these various repair outcomes under different conditions offer insight into the mechanisms of DNA repair and how it is impacted by the nature of the DNA break. The data also indicates a therapeutic approach in which correction of the sickle-cell mutation is efficiently mediated through HDR with either a donor template or with the HBD gene.

In this study different gRNA for the HBB region that surrounds the nucleotides encoding the amino acid most commonly mutated in sickle cell disease had been tested in 293T cells with wild type Cas9 molecule. The gRNAs that induced similar high rates of NHEJ and had PAMs facing in opposite orientations were selected to test as pairs with Cas9 D10A and Cas9 N863A nickases.

Figure 14:
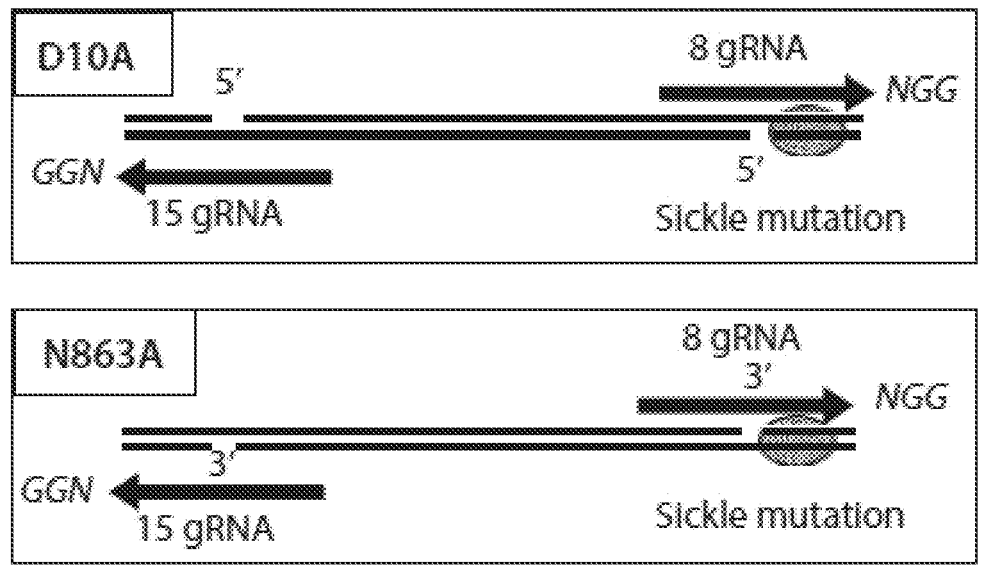
FIG. 14 depicts a scheme of the pair 8/15 of gRNAs surrounding the sickle mutation in combination with a Cas9 nickase (D10A or N863A). The nickases are shown as the grey ovals.

As shown in FIG. 14, the gRNA pair 8/15 ("8gRNA"/"15gRNA" pair) was selected as one of the best pairs of gRNA. "8gRNA" has the targeting domain sequence of GUAACGGCAGACUUCUCCUC (SEQ ID NO: 388) and "15gRNA" has the targeting domain sequence of AAGGUGAACGUGGAUGAAGU (SEQ ID NO: 387). This pair of gRNAs in combination with the mutant Cas9 D10A would generate a 5' overhang of 47 bp, and in combination with the mutant N863A would generate a 3' overhang of 47 bp.

In this Example, U20S cells were electroporated with 200 ng of each gRNA and 750 ng of plasmid that encodes wild type Cas9 or mutant Cas9. Cells were collected 6 days after electroporation and genomic DNA was extracted. PCR amplification of the HBB locus was performed and subcloned into a Topo Blunt Vector. For each condition in each experiment 96 colonies were sequenced with Sanger sequencing. In the experiments assessing HDR efficacy, cells were electroporated with 2.5 ug of single stranded oligo or double stranded oligo in addition to the gRNA and the Cas9-encoding plasmid.

Figure 15:
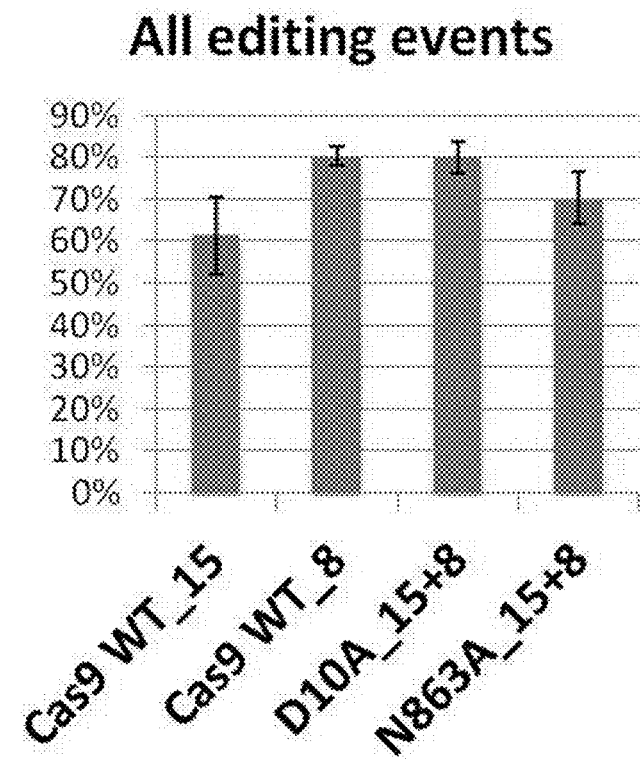
FIG. 15 depicts the percentages of total editing event after a wildtype Cas9 or a Cas9 nickase (D10A or N863A). A prepentation of at least three independent experiments for each condition is shown.

As shown in FIG. 15, the total percentages of all editing events detected by Sanger sequencing of the HBB locus were similar using wild type Cas9 or Cas9 nickases (D10A, N863A).

Figure 16A:
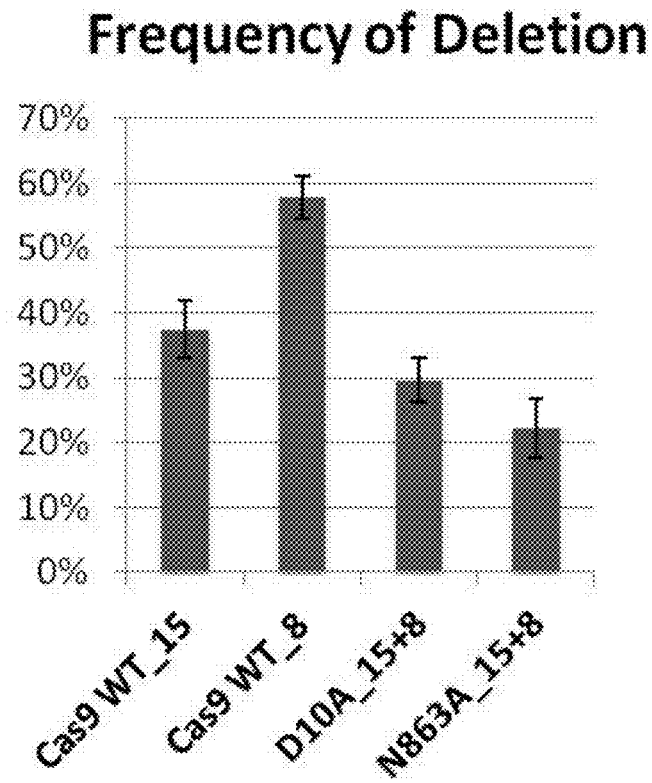
FIG. 16A depicts the frequency of deletions a wildtype Cas9 or a Cas9 nickase (D10A or N863A). A representation of at least 3 independent experiments for each condition is shown.
Figure 16B:
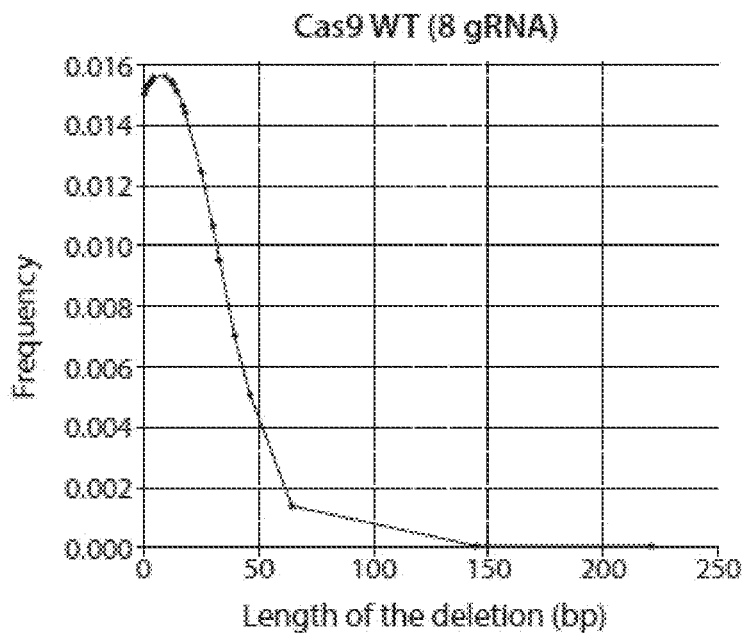
FIG. 16B depicts the frequency distribution of the length of deletions using a wildtype Cas9 and gRNA 8 (similar results have been obtained with gRNA 15).
Figure 16C:
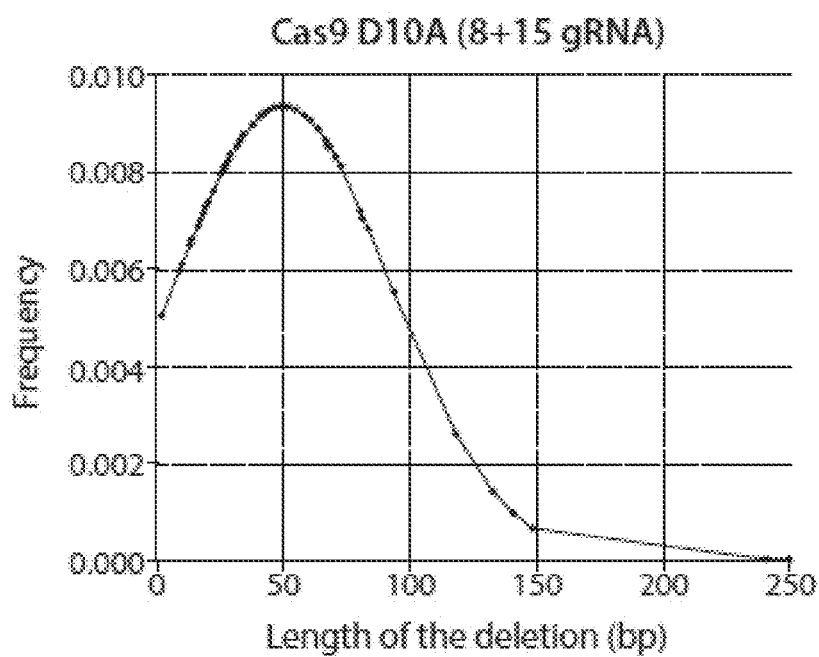
FIG. 16C depicts the frequency distribution of the length of deletions using a Cas9 nickase (D10A) with gRNAs 8/15 (similar results have been obtained using Cas9 N863A).

FIGS. 16A-16B show that a majority of the total gene editing events (about ¾ of the total) were small deletions (<10 bp). This is consistent with the notion that wildtype Cas9 generates a blunt end which are preferentially repaired by canonical NHEJ. In contrast, deletions represented only about a quarter of the total events using either nickase (D10A or N863A). Moreover, larger deletions of ~50 bp that can be mapped to the region between the two nickase sites were observed (FIG. 16A or 16C). The remaining gene-editing events were substantially different between the two nickases.

Figure 17A:
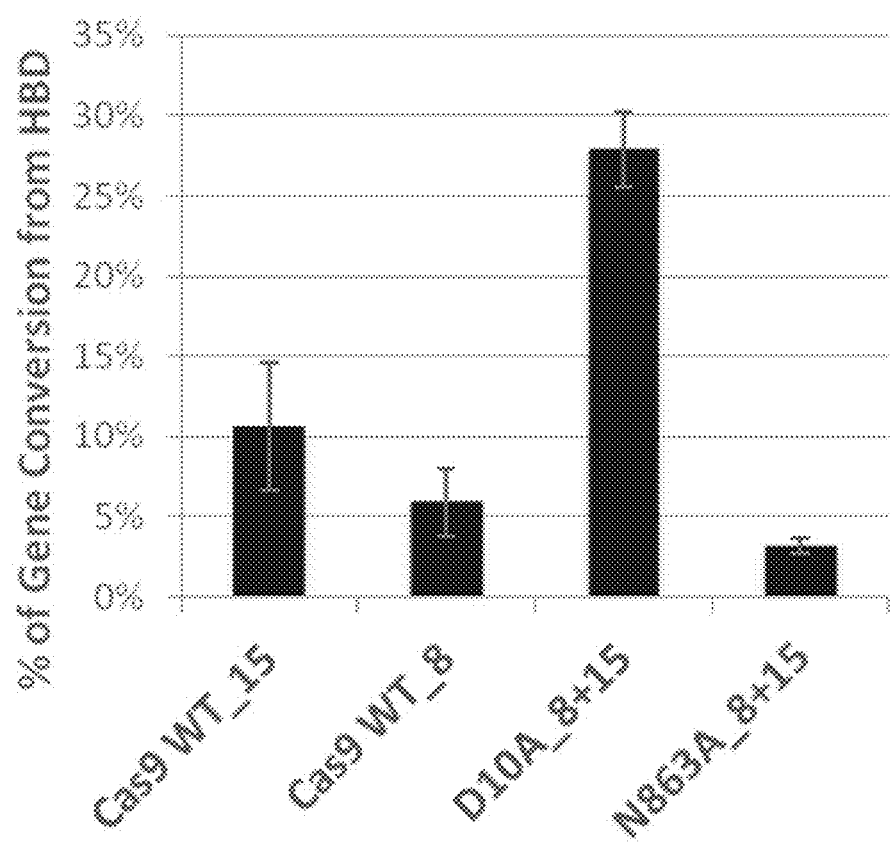
FIG. 17A depicts the frequency of gene conversion a wildtype Cas9 or a Cas9 nickase (D10A or N863A).
Figure 17B:
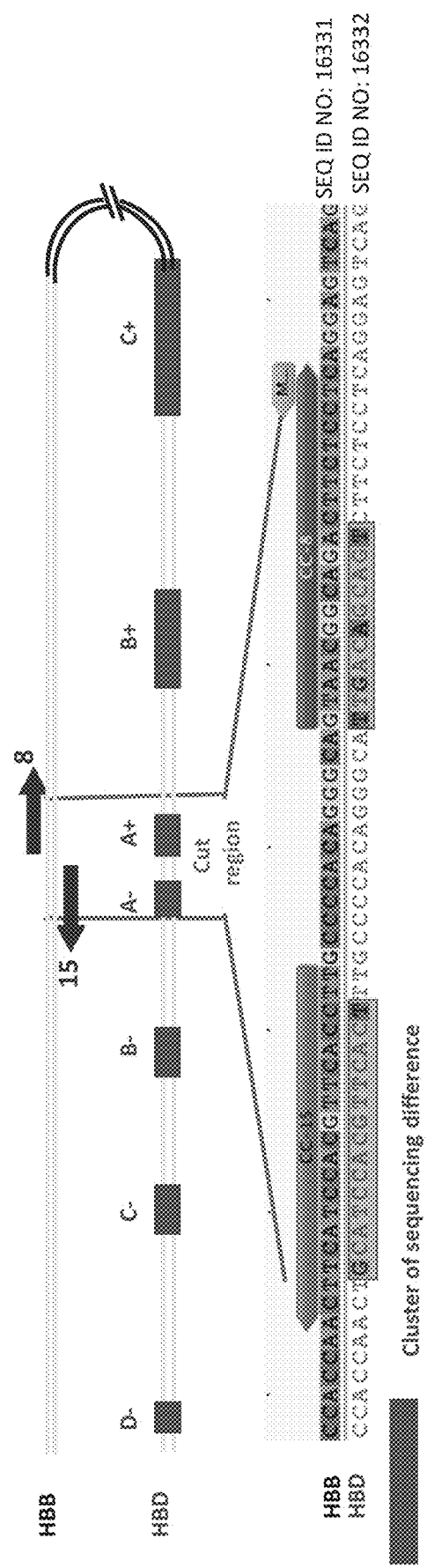
FIG. 17B shows a scheme representing the region of similarity between the HBB and HBD loci.
Figure 18:
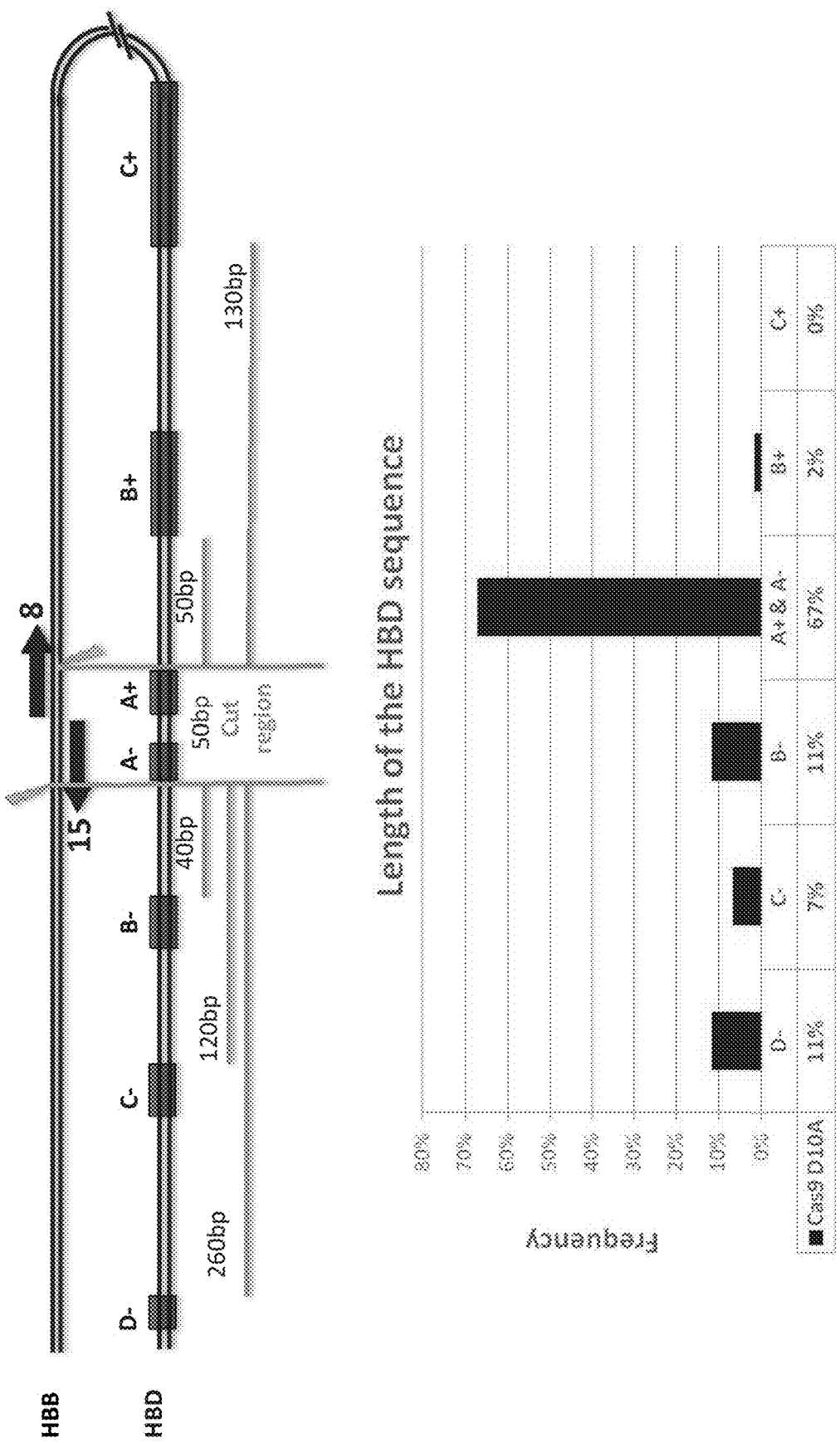
FIG. 18 depicts the frequency of different lengths of HBD sequences that were incorporated into the HBB locus.
Figure 19A:
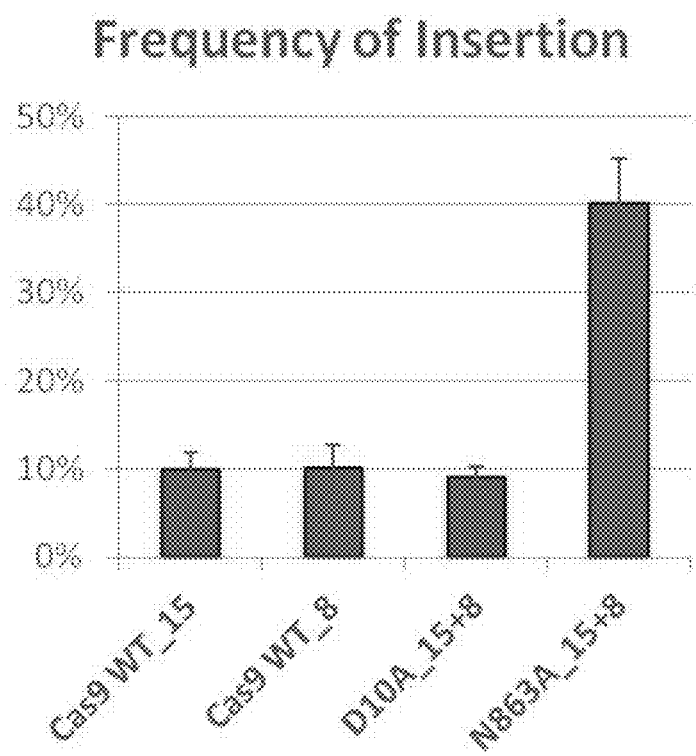
FIG. 19A depicts the frequency of insertions using a wildtype Cas9 or a Cas9 nickase (D10A or N863A). A representation of at least three independent experiments for each condition is shown.
Figure 19B:
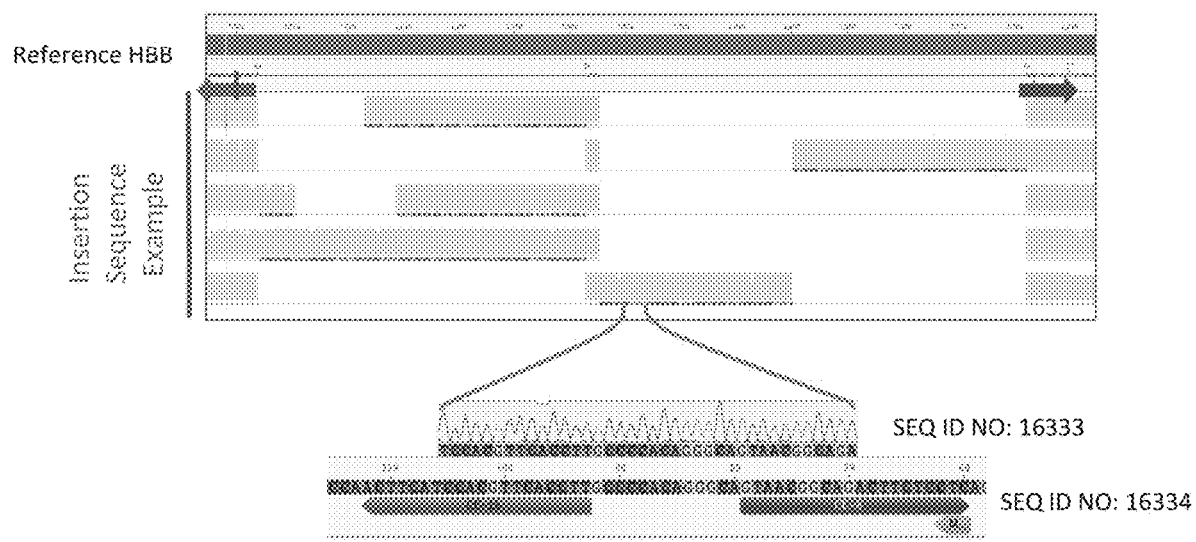
FIG. 19B depicts examples of common reads observed in U2OS cells electroporated with plasmid encoding Cas9 N863 and gRNA 8/15 pair. The HBB reference is shown on the top.

As shown in FIG. 17A, in the case of Cas9 D10A nickase which leaves a 5' protruding end, the lesion is mostly repaired through a mechanism defined as gene conversion. In gene conversion, the HBD locus will serve as a template to repair the HBB gene. HBD is a highly similar gene (92% identity with HBB) that does not carry the sickle-cell mutation (FIG. 17B). FIG. 18 shows that the majority of the HBD sequence that got incorporated in the HBB locus was in the region between the nickase cuts. In contrast, a low frequency of gene conversion was observed when the N863 nicase was used (FIG. 17A). In the case of Cas9 N863A nickase, a majority of the gene editing events were insertions in which the inserted part was a duplication of the overhangs (FIGS. 19A-19B).

Figure 20A:
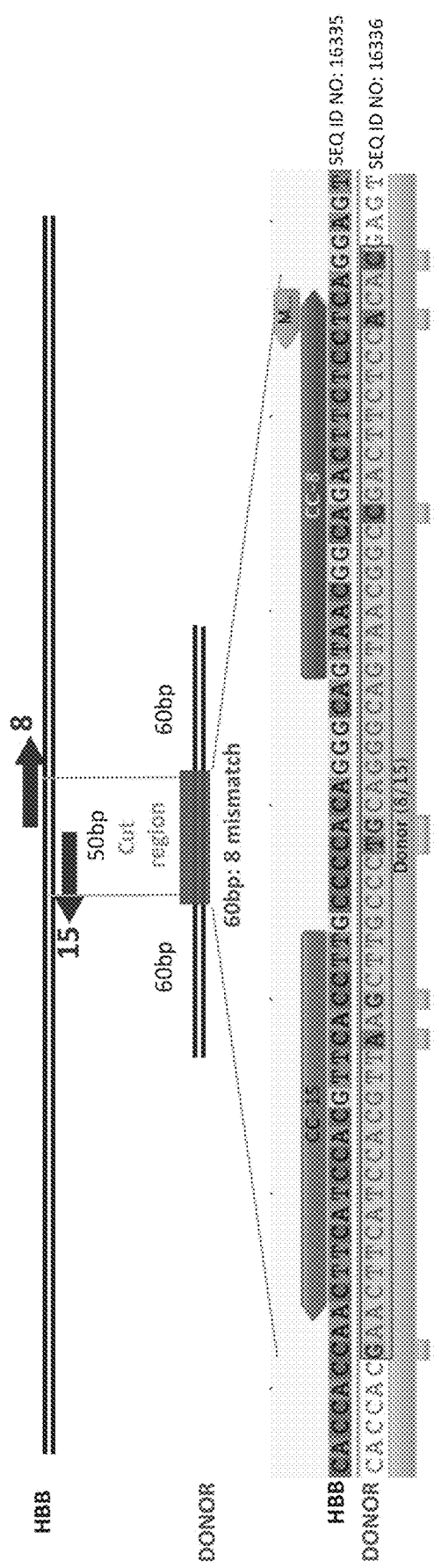
FIG. 20A is a schematic representation of the donor template.
Figure 20B:
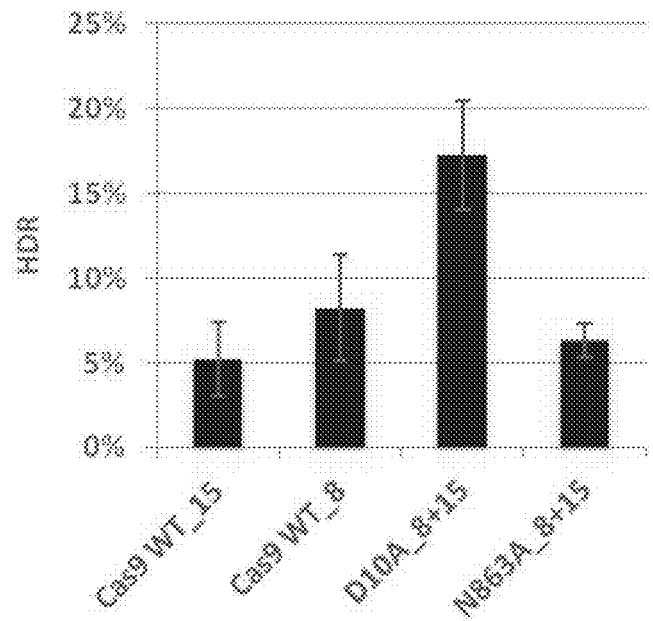
FIG. 20B depicts the frequency of HDR using a wildtype Cas9 or a Cas9 nickase (D10A or N863A).
Figure 20C:
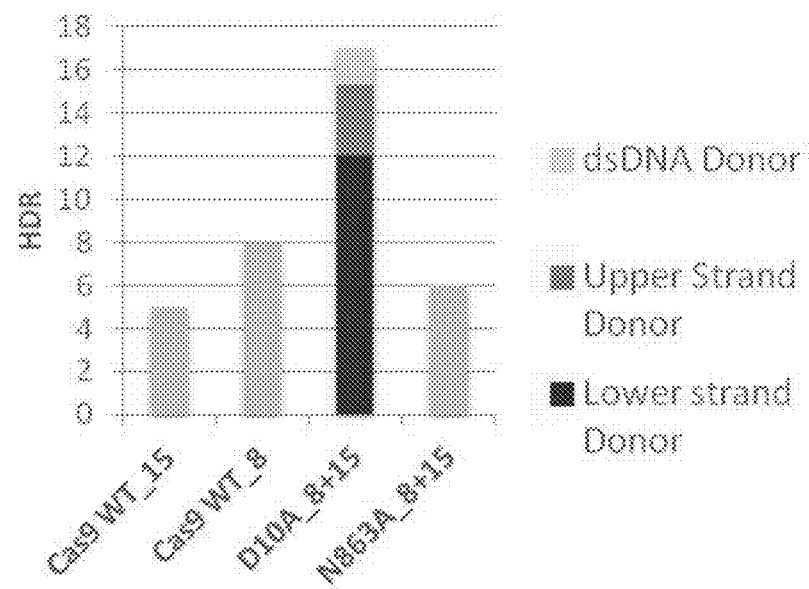
FIG. 20C depicts different forms of nonors and there contribution to HDR.

To test the effect that different lesions had on the engagement of HDR, a donor template was provided as a single strand oligo or as ds DNA donor. In both cases the length of the donor is approximately 170 bp with 60 bp of homology outside the nicks and with 8 mismatches (FIG. 20A). As shown in FIG. 20B, the Cas9 D10A nickase that resulted in a 5' overhang gave a significantly higher rate of HDR, especially when using the upper stand as a single-strand oligo donor. FIG. 20C shows different forms of donors (dsDNA, upper stand, and lower strand) and there contribution to HDR.

In summary, Cas9 nickases (D10A and N863A) showed comparable levels of efficacy compared to wildtype Cas9. Different DNA ends engage different repair pathways. The use of a wildtype Cas9 generates a blunt end, which are preferentially repaired by canonical NHEJ. Use of a Cas9 nickase with two gRNAs generates either 3' or 5' overhangs, which are not suitable substrates to be repaired by canonical NHEJ but can be repaired by alternative pathways.

The 5' protruding end was mostly repaired through a mechanism called gene conversion in which the HBB gene is repaired by using the HBD locus as a template. Use of nickase is advantageous to promote HDR. In the experiments in which a donor was provided, a significantly higher rate of HDR was observed using a nickase compared to the wildtype Cas9. The nature of the donor template also influences the outcome as HDR was preferentially observed when an SS Oligo was used.

Example 7

Assessment of Gene Targeting in Hematopoietic Stem Cells

Transplantation of autologous CD34$^+$ hematopoietic stem cells (HSCs, also known as hematopoietic stem/progenitor cells or HSPCs) genetically modified to correct the Sickle Cell Disease (SCD) mutation in the human β-hemoglobin gene (HBB) would prevent deformability (sickling) after deoxygenation in the erythrocyte progeny of corrected HSCs which could ameliorate symptoms associated with SCD. Genome editing with the CRISPR/Cas9 platform precisely alters endogenous gene targets by creating an indel at the targeted cut site that can lead to knock down of gene expression at the edited locus. In this Example, genome editing in the human K562 bone marrow erythroleukemia cell line, which serve as a proxy for HSCs and which can be predictive of genome editing in HSCs, were electroporated with Cas9 mRNA and gRNA HBB-8 and gRNA HBB-15 to induce gene editing at the human HBB locus.

K562 cells were grown in RPMI media (Life Technologies) containing 10% fetal bovine serum (FBS). For the RNA electroporation, the Maxcyte GT device (maxcyte.com) was used. *S. pyogenes* Cas9 mRNA and gRNA HBB-15 and gRNA HBB-8 were prepared by in vitro transcription using linearized plasmid DNA as templates and the Ambion mMessage mMachine® T7 Ultra Transcription kit (Life Technologies) according to the manufacturer's instructions. In this embodiment, both the Cas9 and gRNA were in vitro transcribed using a T7 polymerase. For example, a 5' ARCA cap was added to both RNA species simultaneous to transcription while a polyA tail was added after transcription to the 3' end of the RNA species by an *E. coli* polyA polymerase. Capped and tailed gRNA HBB-8 and gRNA HBB-15 were complexed at room temperature with *S. pyogenes* H-NLS-Cas9 protein at a molar ratio of ~25:1 (gRNA:Cas9 protein) in a total of 30 μg RNP. Briefly, three million K562 cells were suspended in 100 μL Maxcyte EP buffer and transferred to the RNP solution (13 μL). In addition, K562 cells were electroporated with *S. pyogenes* Cas9 mRNA and each of the gRNA HBB-8 and gRNA HBB-15. For the mRNA/gRNA electroporation with the Maxcyte device, 10 μg of gRNA HBB-8 (or 10 μg of HBB gRNA HBB-15) were mixed with 10 μg of Cas9 mRNA. Four million K562 cells were suspended in 100 μL Maxcyte EP buffer and then transferred to the mRNA/gRNA solution (13 μL). K562 cells mixed with either RNP or RNA were electroporated with the Maxcyte GT device. At 48 hours after electroporation, K562 cells were enumerated by trypan blue exclusion and were determined to have >88% viability in the electroporated cell populations. Genomic DNA was extracted from K562 cells 48 hours after electroporation and HBB locus-specific PCR reactions were performed.

Figure 21:
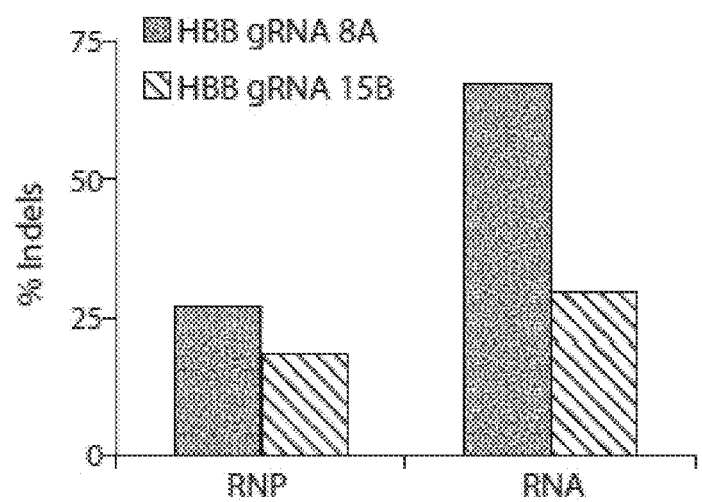
FIG. 21 depicts genome editing of the HBB locus in bone marrow leukemia K562 hematopoietic cells after electroporation of Cas9 protein complexed to HBB gRNAs 8 and 15 (RNP) or Cas9 mRNA co-delivered with HBB gRNAs 8 and 15 (RNA).

In order to detect indels at the HBB locus, T7E1 assays were performed on HBB locus-specific PCR products that were amplified from genomic DNA samples from electroporated K562 cells and the percentage of indels detected at the HBB locus was calculated (FIG. 21).

Co-delivery of 10 µg RNP which contains wild-type *S. pyogenes* Cas9 protein with HBB gRNA 8 or HBB gRNA 15 resulted in 26.8% and 16.1% indels, respectively, at the HBB locus in gDNA from K562 cells (molar ratio protein:gRNA 24:1). Co-delivery of Cas9 mRNA with gRNA HBB-8 or HBB-15 led to 66.9% and 29.5% indels at the HBB locus in gDNA from K562 cells (10 µg of each RNA/4 million cells). This example shows that delivery of Cas9 mRNA/gRNA and Cas9 RNPs leads to editing of the HBB locus in a relevant bone marrow derived hematopoietic cell line (K562 cells). Clinically, transplantation of autologous HSCs in which the HBB locus has been edited to correct the genetic mutation that causes red blood cell sickling could be used to ameliorate symptoms of SCD.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11242525B2). An electronic copy of the "Sequence Listing" will also be available from the USPTO upon request and payment of the fee set forth in 37 CFR 1.19(b)(3).

What is claimed is:

1. A method of altering a cell comprising contacting the cell with:
   (a) a first gRNA molecule comprising a first targeting domain which is complementary with a first target domain located within a BCL11A gene, wherein the first targeting domain is configured to provide a first cleavage event in a region of the BCL11A gene which is complementary to a sequence that is the same as, or differs by no more than 3 nucleotides from, a sequence selected from the group consisting of SEQ ID NOs: 16261 to 16279; and
   (b) a Cas9 molecule.

2. The method of claim 1, wherein the cell is from a subject having a mutation at an SCD target position in the HBB gene or from a subject which would benefit from having an alteration at an SCD target position in the BCL11A gene.

3. The method of claim 1, wherein the cell is selected from the group consisting of an erythroid cell, a bone marrow cell, and a stem cell.

4. The method of claim 2, wherein the contacting step is performed ex vivo.

5. The method of claim 4, wherein the contacted cell is returned to the subject's body.

6. The method of claim 1, wherein the contacting is performed in vivo.

7. The method of claim 1, wherein the cell is from a subject that has SCD.

8. The method of claim 1, further comprising contacting the cell with (c) a second gRNA molecule.

9. The method of claim 8, wherein the second gRNA molecule comprises a second targeting domain that is complementary with a second target domain located within the BCL11A gene, wherein the second targeting domain is configured to provide a second cleavage event in a region of the BCL11A gene which is complementary to a sequence that is the same as, or differs by no more than 3 nucleotides from, a sequence selected from the group consisting of SEQ ID NOs:16261 to 16279.

10. The method of claim 9, wherein the contacting step comprises contacting the cell with a nucleic acid that encodes at least one of (a) the first gRNA molecule, (b) the Cas9 molecule, and (c) the second gRNA molecule.

11. The method of claim 10, wherein the nucleic acid is an AAV vector.

12. A method of altering a cell comprising contacting the cell with:
   (a) a first gRNA molecule comprising a first targeting domain which is complementary with a first target domain located in a BCL11A gene, wherein the first targeting domain is configured to provide a first cleavage event in a region of the BCL11A gene, and wherein the first targeting domain comprises a sequence that is the same as, or differs by no more than 3 nucleotides from, a sequence selected from the group consisting of SEQ ID NOs:16261 to 16279; and
   (b) a Cas9 molecule.

13. The method of claim 12, wherein the cell is selected from the group consisting of an erythroid cell, a bone marrow cell, and a stem cell.

14. The method of claim 12, wherein the cell is from a subject having a mutation at an SCD target position in the HBB gene or from a subject which would benefit from having an alteration at an SCD target position in the BCL11A gene.

15. The method of claim 14, wherein the contacting step is performed ex vivo.

16. The method of claim 15, wherein the contacted cell is returned to the subject's body.

17. The method of claim 12, wherein the contacting is performed in vivo.

18. The method of claim 12, wherein the cell is from a subject that has SCD.

19. The method of claim 12, further comprising contacting the cell with (c) a second gRNA molecule.

20. The method of claim 19, wherein the second gRNA molecule comprises a second targeting domain which is complementary with a second target domain located in a BCL11A gene, wherein the second targeting domain is configured to provide a second cleavage event in a region of the BCL11A gene, and wherein the second targeting domain comprises a sequence that is the same as, or differs by no more than 3 nucleotides from, a sequence selected from the group consisting of SEQ ID NOs:16261 to 16279.

21. The method of claim 20, wherein the contacting step comprises contacting the cell with a nucleic acid that encodes at least one of (a) the first gRNA molecule, (b) the Cas9 molecule, and (c) the second gRNA molecule.

22. The method of claim 20, wherein the contacting step comprises contacting the cell with a nucleic acid that encodes (a) the first gRNA molecule, (b) the Cas9 molecule, and (c) the second gRNA molecule.

23. The method of claim 20, wherein contacting comprises delivering to the cell the Cas9 molecule of (b) and a nucleic acid which encodes (a) and (c).

24. The method of claim 20, wherein contacting comprises delivering to the cell the Cas9 molecule of (b), the first gRNA of (a) and the second gRNA of (c).

25. The method of claim 20, wherein contacting comprises delivering to the cell the first gRNA of (a), the second gRNA of (c) and a nucleic acid that encodes the Cas9 molecule of (b).

26. The method of claim 20, further comprising contacting the cell with a third gRNA molecule.

27. The method of claim 26, further comprising contacting the cell with a fourth gRNA molecule.

28. The method of claim 21, wherein the nucleic acid is an AAV vector.

* * * * *